US011541059B2

(12) United States Patent
Kutok et al.

(10) Patent No.: US 11,541,059 B2
(45) Date of Patent: *Jan. 3, 2023

(54) HETEROCYCLIC COMPOUNDS AND USES THEREOF

(71) Applicant: Infinity Pharmaceuticals, Inc., Cambridge, MA (US)

(72) Inventors: Jeffery L. Kutok, Natick, MA (US); David G. Winkler, Arlington, MA (US); Vito J. Palombella, Needham, MA (US); Alfredo C. Castro, Woburn, MA (US); Catherine A. Evans, Somerville, MA (US); Somarajannair Janardanannair, Woburn, MA (US); Andre Lescarbeau, Somerville, MA (US); Tao Liu, Wellesley, MA (US); Martin R. Tremblay, Melrose, MA (US)

(73) Assignee: Infinity Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/816,132

(22) Filed: Mar. 11, 2020

(65) Prior Publication Data

US 2021/0000837 A1    Jan. 7, 2021

Related U.S. Application Data

(63) Continuation of application No. 15/672,964, filed on Aug. 9, 2017, now Pat. No. 10,675,286, which is a continuation of application No. 14/661,656, filed on Mar. 18, 2015, now Pat. No. 9,775,844.

(60) Provisional application No. 62/101,980, filed on Jan. 9, 2015, provisional application No. 62/075,173, filed on Nov. 4, 2014, provisional application No. 62/059,766, filed on Oct. 3, 2014, provisional application No. 62/033,008, filed on Aug. 4, 2014, provisional application No. 62/000,923, filed on May 20, 2014, provisional application No. 61/980,484, filed on Apr. 16, 2014, provisional application No. 61/955,717, filed on Mar. 19, 2014.

(51) Int. Cl.
| | |
|---|---|
| A61K 31/4725 | (2006.01) |
| A61K 31/519 | (2006.01) |
| A61K 31/337 | (2006.01) |
| A61K 39/395 | (2006.01) |
| A61P 35/00 | (2006.01) |
| A61K 31/5377 | (2006.01) |
| A61K 45/06 | (2006.01) |
| A61K 31/497 | (2006.01) |
| A61K 31/517 | (2006.01) |
| A61K 31/427 | (2006.01) |
| A61K 31/495 | (2006.01) |
| A61K 31/506 | (2006.01) |
| A61K 39/00 | (2006.01) |

(52) U.S. Cl.
CPC ........ *A61K 31/5377* (2013.01); *A61K 31/337* (2013.01); *A61K 31/427* (2013.01); *A61K 31/4725* (2013.01); *A61K 31/495* (2013.01); *A61K 31/497* (2013.01); *A61K 31/506* (2013.01); *A61K 31/517* (2013.01); *A61K 31/519* (2013.01); *A61K 39/0005* (2013.01); *A61K 39/39533* (2013.01); *A61K 39/39566* (2013.01); *A61K 45/06* (2013.01); *A61K 2039/505* (2013.01); *A61K 2300/00* (2013.01)

(58) Field of Classification Search
CPC .............. A61K 31/4725; A61K 31/519; A61K 31/337; A61K 39/395; A61P 35/00
See application file for complete search history.

(56) References Cited

U.S. PATENT DOCUMENTS

| | | | |
|---|---|---|---|
| 4,547,508 | A | 10/1985 | Konz et al. |
| 4,656,159 | A | 4/1987 | McPherson et al. |
| 4,704,381 | A | 11/1987 | Schaumann et al. |
| 4,795,627 | A | 1/1989 | Fisher et al. |
| 4,981,856 | A | 1/1991 | Hughes |
| 5,240,941 | A | 8/1993 | Bruneau |
| 5,272,158 | A | 12/1993 | Hartman et al. |
| 5,294,612 | A | 3/1994 | Bacon et al. |
| 5,310,731 | A | 5/1994 | Olsson et al. |
| 5,364,862 | A | 11/1994 | Spada et al. |
| 5,409,930 | A | 4/1995 | Spada et al. |
| 5,420,419 | A | 5/1995 | Wood |
| 5,428,125 | A | 6/1995 | Hefner, Jr. et al. |
| 5,442,039 | A | 8/1995 | Hefner, Jr. et al. |
| 5,504,103 | A | 4/1996 | Bonjouklian et al. |
| 5,506,347 | A | 4/1996 | Erion et al. |

(Continued)

FOREIGN PATENT DOCUMENTS

| | | |
|---|---|---|
| CA | 1338379 C | 6/1996 |
| CN | 1502608 | 6/2004 |

(Continued)

OTHER PUBLICATIONS

Carlson, R.H. Oncology Times, Jun. 2015, pp. 30-31.*

(Continued)

*Primary Examiner* — Samira J Jean-Louis
(74) *Attorney, Agent, or Firm* — Jones Day

(57) ABSTRACT

Compounds and pharmaceutical compositions that modulate kinase activity, including PI3 kinase activity, and compounds, pharmaceutical compositions, and methods of treatment of diseases and conditions associated with kinase activity, including PI3 kinase activity, are described herein.

11 Claims, 72 Drawing Sheets

(56) References Cited

U.S. PATENT DOCUMENTS

| | | |
|---|---|---|
| 5,527,811 A | 6/1996 | Natsugari et al. |
| 5,561,134 A | 10/1996 | Spada et al. |
| 5,563,257 A | 10/1996 | Zilch et al. |
| 5,593,997 A | 1/1997 | Dow et al. |
| 5,646,128 A | 7/1997 | Firestein et al. |
| 5,652,366 A | 7/1997 | Spada et al. |
| 5,654,307 A | 8/1997 | Bridges et al. |
| 5,665,721 A | 9/1997 | Bhagwat et al. |
| 5,674,998 A | 10/1997 | Boyer et al. |
| 5,679,677 A | 10/1997 | Pill et al. |
| 5,686,455 A | 11/1997 | Adams et al. |
| 5,736,554 A | 4/1998 | Spada et al. |
| 5,747,235 A | 5/1998 | Farid et al. |
| 5,756,502 A | 5/1998 | Padia |
| 5,756,711 A | 5/1998 | Zilch et al. |
| 5,763,596 A | 6/1998 | Boyer et al. |
| 5,763,597 A | 6/1998 | Ugarkar et al. |
| 5,763,608 A | 6/1998 | Bhattacharya et al. |
| 5,763,885 A | 6/1998 | Murphy et al. |
| 5,795,977 A | 8/1998 | Ugarkar et al. |
| 5,811,454 A | 9/1998 | Springer |
| 5,824,492 A | 10/1998 | Hiles et al. |
| 5,858,753 A | 1/1999 | Chantry et al. |
| 5,869,665 A | 2/1999 | Padia |
| 5,872,136 A | 2/1999 | Anthony et al. |
| 5,914,488 A | 6/1999 | Sone |
| 5,919,808 A | 7/1999 | Petrie et al. |
| 5,922,753 A | 7/1999 | Petrie et al. |
| 5,948,776 A | 9/1999 | Petrie et al. |
| 5,965,573 A | 10/1999 | Petrie et al. |
| 5,977,061 A | 11/1999 | Holy et al. |
| 5,977,134 A | 11/1999 | Ciccarone et al. |
| 5,981,533 A | 11/1999 | Traxler et al. |
| 5,985,589 A | 11/1999 | Chantry et al. |
| 5,990,169 A | 11/1999 | Petrie et al. |
| 5,994,358 A | 11/1999 | Petrie et al. |
| 6,001,839 A | 12/1999 | Calderwood et al. |
| 6,037,474 A | 3/2000 | Drauz et al. |
| 6,057,305 A | 5/2000 | Holy et al. |
| 6,084,095 A | 7/2000 | Bridges et al. |
| 6,093,737 A | 7/2000 | Anthony et al. |
| 6,127,121 A | 10/2000 | Meyer, Jr. et al. |
| 6,153,631 A | 11/2000 | Petrie et al. |
| 6,184,377 B1 | 2/2001 | Gao |
| 6,191,170 B1 | 2/2001 | Medina |
| 6,207,697 B1 | 3/2001 | Han et al. |
| 6,251,901 B1 | 6/2001 | Petrie et al. |
| 6,265,410 B1 | 7/2001 | Bridges et al. |
| 6,268,370 B1 | 7/2001 | Adams et al. |
| 6,312,894 B1 | 11/2001 | Hedgpeth et al. |
| 6,323,201 B1 | 11/2001 | Carson et al. |
| 6,342,514 B1 | 1/2002 | Petrie et al. |
| 6,350,741 B1 | 2/2002 | Golec et al. |
| 6,383,790 B1 | 5/2002 | Shokat |
| 6,384,039 B1 | 5/2002 | Fossa |
| 6,387,894 B1 | 5/2002 | Fossa |
| 6,390,821 B1 | 5/2002 | Shokat |
| 6,429,311 B2 | 8/2002 | Gao |
| 6,455,534 B2 | 9/2002 | Bridges et al. |
| 6,469,026 B2 | 10/2002 | Marlowe et al. |
| 6,472,153 B1 | 10/2002 | Dempcy et al. |
| 6,482,623 B1 | 11/2002 | Vanhaesebroeck et al. |
| 6,485,906 B2 | 11/2002 | Meyer, Jr. et al. |
| 6,492,346 B1 | 12/2002 | Hedgpeth et al. |
| 6,506,769 B2 | 1/2003 | Snow et al. |
| 6,518,277 B1 | 2/2003 | Sadhu et al. |
| 6,521,417 B1 | 2/2003 | Shokat |
| 6,521,620 B1 | 2/2003 | Bridges et al. |
| 6,531,491 B1 | 3/2003 | Kania et al. |
| 6,534,524 B1 | 3/2003 | Kania et al. |
| 6,545,004 B1 | 4/2003 | Finer et al. |
| 6,545,005 B1 | 4/2003 | Baxter et al. |
| 6,552,192 B1 | 4/2003 | Hanus et al. |
| 6,562,819 B2 | 5/2003 | Carson et al. |
| 6,562,831 B1 | 5/2003 | Finer et al. |
| 6,583,161 B1 | 6/2003 | Medina |
| 6,596,497 B1 | 7/2003 | Jiang et al. |
| 6,596,718 B1 | 7/2003 | Flohr et al. |
| 6,596,723 B1 | 7/2003 | Watkins et al. |
| 6,613,798 B1 | 9/2003 | Porter et al. |
| 6,630,479 B1 | 10/2003 | Finer et al. |
| 6,630,495 B1 | 10/2003 | Cooke et al. |
| 6,632,789 B1 | 10/2003 | June |
| 6,645,989 B2 | 11/2003 | Adams et al. |
| 6,649,565 B1 | 11/2003 | Feucht et al. |
| 6,649,631 B1 | 11/2003 | Orme et al. |
| 6,653,296 B1 | 11/2003 | Holy et al. |
| 6,653,306 B1 | 11/2003 | Alexander et al. |
| 6,660,744 B1 | 12/2003 | Hirst et al. |
| 6,660,845 B1 | 12/2003 | Gall et al. |
| 6,664,269 B2 | 12/2003 | Martin et al. |
| 6,667,300 B2 | 12/2003 | Sadhu et al. |
| 6,683,108 B1 | 1/2004 | Baxter et al. |
| 6,683,192 B2 | 1/2004 | Baxter et al. |
| 6,689,782 B2 | 2/2004 | Watkins et al. |
| 6,690,583 B1 | 2/2004 | Bergstedt et al. |
| 6,713,484 B2 | 3/2004 | Bridges et al. |
| 6,720,344 B2 | 4/2004 | Kerwin et al. |
| 6,734,187 B1 | 5/2004 | Tanaka et al. |
| 6,753,428 B2 | 6/2004 | Yao et al. |
| 6,770,639 B2 | 8/2004 | Snow et al. |
| 6,777,425 B2 | 8/2004 | Burli et al. |
| 6,777,439 B2 | 8/2004 | Durden |
| 6,790,844 B2 | 9/2004 | Ueno et al. |
| 6,794,379 B2 | 9/2004 | Medina et al. |
| 6,800,620 B2 | 10/2004 | Sadhu et al. |
| 6,831,085 B1 | 12/2004 | Bergnes et al. |
| 6,849,420 B2 | 2/2005 | Vanhasebroeck et al. |
| 6,849,713 B2 | 2/2005 | Zhang et al. |
| 6,852,727 B2 | 2/2005 | Goulet et al. |
| 6,870,055 B2 | 3/2005 | Claremon et al. |
| 6,900,219 B2 | 5/2005 | Ibrahim et al. |
| 6,906,103 B2 | 6/2005 | Zhang et al. |
| 6,916,949 B2 | 7/2005 | Springer et al. |
| 6,919,332 B2 | 7/2005 | Noe et al. |
| 6,921,763 B2 | 7/2005 | Hirst et al. |
| 6,949,535 B2 | 9/2005 | Sadhu et al. |
| 6,964,967 B2 | 11/2005 | Medina et al. |
| 6,995,144 B2 | 2/2006 | Ozaki et al. |
| 7,009,049 B2 | 3/2006 | Bergnes et al. |
| 7,026,461 B1 | 4/2006 | Shokat |
| 7,038,048 B2 | 5/2006 | Dhanak et al. |
| 7,041,676 B2 | 5/2006 | McDonald et al. |
| 7,049,116 B2 | 5/2006 | Shokat |
| 7,049,312 B1 | 5/2006 | Rafferty et al. |
| 7,053,215 B2 | 5/2006 | Medina et al. |
| 7,053,216 B2 | 5/2006 | Sun et al. |
| 7,064,218 B2 | 6/2006 | Dyatkina et al. |
| 7,067,662 B2 | 6/2006 | Medina et al. |
| 7,071,355 B2 | 7/2006 | Leban et al. |
| 7,105,668 B1 | 9/2006 | Bergnes et al. |
| 7,115,627 B2 | 10/2006 | Pinto et al. |
| 7,115,653 B2 | 10/2006 | Baxter et al. |
| 7,144,903 B2 | 12/2006 | Collins et al. |
| 7,148,214 B1 | 12/2006 | Janssens et al. |
| 7,157,487 B2 | 1/2007 | Nakayama et al. |
| 7,161,002 B2 | 1/2007 | Bergnes et al. |
| 7,166,293 B2 | 1/2007 | Teng et al. |
| 7,166,595 B2 | 1/2007 | Zhou et al. |
| 7,192,949 B2 | 3/2007 | Fraley et al. |
| 7,208,601 B2 | 4/2007 | Mjalli et al. |
| 7,214,800 B2 | 5/2007 | Feng et al. |
| 7,217,794 B2 | 5/2007 | Abdel-Meguid et al. |
| 7,230,000 B1 | 6/2007 | Finer et al. |
| 7,235,585 B2 | 6/2007 | Springer et al. |
| 7,244,741 B2 | 7/2007 | Simon et al. |
| 7,247,736 B2 | 7/2007 | Leban et al. |
| 7,262,187 B2 | 8/2007 | Fraley et al. |
| 7,262,204 B2 | 8/2007 | Collins et al. |
| 7,265,111 B2 | 9/2007 | Bigot et al. |
| 7,265,131 B2 | 9/2007 | Johnson et al. |
| 7,294,634 B2 | 11/2007 | Finer et al. |
| 7,329,765 B2 | 2/2008 | Burli et al. |
| 7,332,497 B2 | 2/2008 | Hirst et al. |

(56) References Cited

U.S. PATENT DOCUMENTS

| | | |
|---|---|---|
| 7,332,498 B2 | 2/2008 | Dhanak et al. |
| 7,345,046 B2 | 3/2008 | Wang et al. |
| 7,348,427 B2 | 3/2008 | Burli et al. |
| 7,365,094 B2 | 4/2008 | Leban et al. |
| 7,384,967 B2 | 6/2008 | Polisetti et al. |
| 7,396,836 B2 | 7/2008 | Harada et al. |
| 7,405,235 B2 | 7/2008 | Levy et al. |
| 7,414,036 B2 | 8/2008 | Sevillano et al. |
| 7,429,596 B2 | 9/2008 | Tanaka et al. |
| 7,439,254 B2 | 10/2008 | Bergnes |
| 7,449,477 B2 | 11/2008 | Barda et al. |
| 7,459,462 B2 | 12/2008 | Simon et al. |
| 7,459,472 B2 | 12/2008 | Mjalli et al. |
| 7,470,721 B2 | 12/2008 | Durden |
| 7,501,538 B2 | 3/2009 | Mjalli et al. |
| 7,514,445 B2 | 4/2009 | Freyne et al. |
| 7,528,137 B2 | 5/2009 | Feng et al. |
| 7,534,797 B2 | 5/2009 | Arnold et al. |
| 7,538,135 B2 | 5/2009 | Vedananda |
| 7,541,373 B2 | 6/2009 | Polisetti et al. |
| 7,550,590 B2 | 6/2009 | Feng et al. |
| 7,569,571 B2 | 8/2009 | Dong et al. |
| 7,572,913 B2 | 8/2009 | McKerracher et al. |
| 7,579,348 B2 | 8/2009 | Wang et al. |
| 7,585,868 B2 | 9/2009 | Knight et al. |
| 7,589,098 B2 | 9/2009 | Finer et al. |
| 7,608,594 B2 | 10/2009 | Blagg et al. |
| 7,615,552 B2 | 11/2009 | Ono et al. |
| 7,615,554 B2 | 11/2009 | Selliah et al. |
| 7,622,451 B2 | 11/2009 | Blagg et al. |
| 7,632,839 B2 | 12/2009 | Coleman et al. |
| 7,650,848 B2 | 1/2010 | Brennan et al. |
| 7,652,061 B2 | 1/2010 | Ksander et al. |
| 7,671,200 B2 | 3/2010 | Finer et al. |
| 7,678,803 B2 | 3/2010 | Huang et al. |
| 7,700,607 B2 | 4/2010 | Hu et al. |
| 7,705,018 B2 | 4/2010 | Chen et al. |
| 7,745,485 B2 | 6/2010 | Durden |
| 7,763,628 B2 | 7/2010 | Finer et al. |
| 7,799,795 B2 | 9/2010 | Bergeron et al. |
| 7,825,126 B2 | 11/2010 | Jacobson et al. |
| 7,893,260 B2 | 2/2011 | Chong et al. |
| 7,932,260 B2 | 4/2011 | Fowler et al. |
| 7,939,538 B2 | 5/2011 | Fu et al. |
| 7,939,539 B2 | 5/2011 | Wang et al. |
| 8,013,003 B2 | 9/2011 | Sreet et al. |
| 8,030,318 B2 | 10/2011 | Simmen et al. |
| 8,106,146 B2 | 1/2012 | Benz et al. |
| 8,133,998 B2 | 3/2012 | Pajouhesh et al. |
| 8,193,182 B2 | 6/2012 | Ren et al. |
| 8,232,285 B2 | 7/2012 | Liu et al. |
| 8,236,808 B2 | 8/2012 | Collingwood et al. |
| 8,247,436 B2 | 8/2012 | Baettig et al. |
| 8,389,544 B2 | 3/2013 | Wong et al. |
| 8,399,483 B2 | 3/2013 | Allen et al. |
| 8,399,493 B2 | 3/2013 | Bolea et al. |
| 8,569,316 B2 | 10/2013 | Ettmayer et al. |
| 8,569,323 B2 | 10/2013 | Ren et al. |
| 8,586,619 B2 | 11/2013 | Wu et al. |
| 8,604,032 B2 | 12/2013 | Ren et al. |
| 8,637,666 B2 | 1/2014 | Charrier et al. |
| 8,642,609 B2 | 2/2014 | Makings et al. |
| 8,648,084 B2 | 2/2014 | Bunnelle et al. |
| 8,703,777 B2 | 4/2014 | Ren et al. |
| 8,716,297 B2 | 5/2014 | Woods et al. |
| 8,748,440 B2 | 6/2014 | Martin et al. |
| 8,785,470 B2 | 7/2014 | Castro et al. |
| 8,809,349 B2 | 8/2014 | Ren et al. |
| 8,809,530 B1 | 8/2014 | Wu et al. |
| 8,822,453 B2 | 9/2014 | Matsumura et al. |
| 8,901,133 B2 | 12/2014 | Ren et al. |
| 8,940,742 B2 | 1/2015 | Castro et al. |
| 8,969,363 B2 | 3/2015 | Castro et al. |
| 9,056,877 B2 | 6/2015 | Castro et al. |
| 9,115,141 B2 | 8/2015 | Castro et al. |
| 9,255,108 B2 | 2/2016 | Castro et al. |
| 9,359,365 B2 | 6/2016 | Castro et al. |
| 9,388,183 B2 | 7/2016 | Ren et al. |
| 2001/0019829 A1 | 9/2001 | Nelson et al. |
| 2001/0027197 A1 | 10/2001 | Bridges et al. |
| 2002/0016460 A1 | 2/2002 | Snow et al. |
| 2002/0016976 A1 | 2/2002 | Shokat |
| 2002/0037856 A1 | 3/2002 | Zhang et al. |
| 2002/0102590 A1 | 8/2002 | Taing et al. |
| 2002/0127625 A1 | 9/2002 | Oxelius |
| 2002/0146690 A1 | 10/2002 | Meyer et al. |
| 2002/0147160 A1 | 10/2002 | Bhat et al. |
| 2002/0156081 A1 | 10/2002 | Hirst et al. |
| 2002/0161014 A1 | 10/2002 | Sadhu et al. |
| 2002/0173524 A1 | 11/2002 | Collins et al. |
| 2002/0198236 A1 | 12/2002 | Baxter et al. |
| 2003/0001141 A1 | 1/2003 | Sun et al. |
| 2003/0008896 A1 | 1/2003 | Martin et al. |
| 2003/0018022 A1 | 1/2003 | Collins et al. |
| 2003/0022344 A1 | 1/2003 | Williams et al. |
| 2003/0064997 A1 | 4/2003 | Adams et al. |
| 2003/0073218 A1 | 4/2003 | Shokat |
| 2003/0083268 A1 | 5/2003 | Burli et al. |
| 2003/0113765 A1 | 6/2003 | Dempcy et al. |
| 2003/0119479 A1 | 6/2003 | Arima et al. |
| 2003/0119791 A1 | 6/2003 | Kerwin et al. |
| 2003/0139427 A1 | 7/2003 | Castelhano et al. |
| 2003/0143602 A1 | 7/2003 | Meyer et al. |
| 2003/0144350 A1 | 7/2003 | Stevenson et al. |
| 2003/0166929 A1 | 9/2003 | Snow et al. |
| 2003/0180924 A1 | 9/2003 | DeSimone |
| 2003/0186987 A1 | 10/2003 | Bridges et al. |
| 2003/0187001 A1 | 10/2003 | Calderwood et al. |
| 2003/0195211 A1 | 10/2003 | Sadhu et al. |
| 2003/0199516 A1 | 10/2003 | Moser et al. |
| 2003/0208800 A1 | 11/2003 | Eby et al. |
| 2003/0212113 A1 | 11/2003 | Dyatkina et al. |
| 2003/0220338 A1 | 11/2003 | Watkins et al. |
| 2003/0229097 A1 | 12/2003 | Watkins et al. |
| 2003/0232832 A1 | 12/2003 | Lombardo et al. |
| 2003/0232849 A1 | 12/2003 | Noe et al. |
| 2003/0235822 A1 | 12/2003 | Lokhov et al. |
| 2004/0023996 A1 | 2/2004 | Finer et al. |
| 2004/0039035 A1 | 2/2004 | Collins et al. |
| 2004/0043959 A1 | 3/2004 | Bloom et al. |
| 2004/0043983 A1 | 3/2004 | Li |
| 2004/0067901 A1 | 4/2004 | Bhat et al. |
| 2004/0067915 A1 | 4/2004 | McMahon et al. |
| 2004/0072766 A1 | 4/2004 | June |
| 2004/0072788 A1 | 4/2004 | Bhat et al. |
| 2004/0082567 A1 | 4/2004 | McDonald et al. |
| 2004/0102423 A1 | 5/2004 | McLaughlan et al. |
| 2004/0102437 A1 | 5/2004 | Takami et al. |
| 2004/0110717 A1 | 6/2004 | Carroll et al. |
| 2004/0110945 A1 | 6/2004 | Nakayama et al. |
| 2004/0116689 A1 | 6/2004 | Gall et al. |
| 2004/0122235 A1 | 6/2004 | Polisetti et al. |
| 2004/0127434 A1 | 7/2004 | Bigot et al. |
| 2004/0132732 A1 | 7/2004 | Han et al. |
| 2004/0176458 A1 | 9/2004 | Leban et al. |
| 2004/0176601 A1 | 9/2004 | Goulet et al. |
| 2004/0192758 A1 | 9/2004 | Leban et al. |
| 2004/0242596 A1 | 12/2004 | Kim et al. |
| 2004/0266780 A1 | 12/2004 | Sadhu et al. |
| 2005/0004149 A1 | 1/2005 | Harada et al. |
| 2005/0043239 A1 | 2/2005 | Douangpanya et al. |
| 2005/0049310 A1 | 3/2005 | Mjalli et al. |
| 2005/0054614 A1 | 3/2005 | Diacovo et al. |
| 2005/0059713 A1 | 3/2005 | Mjalli et al. |
| 2005/0065169 A1 | 3/2005 | Wang et al. |
| 2005/0070578 A1 | 3/2005 | Baxter et al. |
| 2005/0080138 A1 | 4/2005 | Guicherit et al. |
| 2005/0085472 A1 | 4/2005 | Tanaka et al. |
| 2005/0101551 A1 | 5/2005 | Sevillano et al. |
| 2005/0124637 A1 | 6/2005 | Cheng et al. |
| 2005/0143317 A1 | 6/2005 | Abdel-Meguid et al. |
| 2005/0152940 A1 | 7/2005 | Hezi-Yamit et al. |
| 2005/0153997 A1 | 7/2005 | Simon et al. |
| 2005/0171148 A1 | 8/2005 | Mjalli et al. |

(56) References Cited

U.S. PATENT DOCUMENTS

| | | |
|---|---|---|
| 2005/0178286 A1 | 8/2005 | Brennan et al. |
| 2005/0182045 A1 | 8/2005 | Nagase et al. |
| 2005/0187418 A1 | 8/2005 | Small et al. |
| 2005/0197340 A1 | 9/2005 | Arora et al. |
| 2005/0203110 A1 | 9/2005 | Coleman et al. |
| 2005/0209254 A1 | 9/2005 | Wang et al. |
| 2005/0214310 A1 | 9/2005 | Toki et al. |
| 2005/0215579 A1 | 9/2005 | Simon et al. |
| 2005/0239809 A1 | 10/2005 | Watts et al. |
| 2005/0250770 A1 | 11/2005 | Ono et al. |
| 2005/0256066 A1 | 11/2005 | Abel et al. |
| 2005/0261317 A1 | 11/2005 | Sadhu et al. |
| 2005/0272751 A1 | 12/2005 | McKerracher et al. |
| 2005/0282834 A1 | 12/2005 | Malik et al. |
| 2006/0019988 A1 | 1/2006 | McDonald et al. |
| 2006/0036093 A1 | 2/2006 | Lin et al. |
| 2006/0041128 A1 | 2/2006 | Aquila et al. |
| 2006/0063751 A1 | 3/2006 | Aquila et al. |
| 2006/0069034 A1 | 3/2006 | Burli et al. |
| 2006/0069106 A1 | 3/2006 | Fu et al. |
| 2006/0079538 A1 | 4/2006 | Hallahan et al. |
| 2006/0106038 A1 | 5/2006 | Bouscary et al. |
| 2006/0116326 A1 | 6/2006 | Burli et al. |
| 2006/0135790 A1 | 6/2006 | Hyett et al. |
| 2006/0156485 A1 | 7/2006 | Lim |
| 2006/0183783 A1 | 8/2006 | Polisetti et al. |
| 2006/0199776 A1 | 9/2006 | Blagg et al. |
| 2006/0205694 A1 | 9/2006 | Alonso et al. |
| 2006/0235031 A1 | 10/2006 | Arnold et al. |
| 2006/0270849 A1 | 11/2006 | Nishino et al. |
| 2006/0276470 A1 | 12/2006 | Jackson et al. |
| 2006/0287295 A1 | 12/2006 | Barlaam et al. |
| 2006/0293274 A1 | 12/2006 | Wu |
| 2007/0015773 A1 | 1/2007 | Bergeron et al. |
| 2007/0017915 A1 | 1/2007 | Weder et al. |
| 2007/0021493 A1 | 1/2007 | Guicherit et al. |
| 2007/0027193 A1 | 2/2007 | Leban et al. |
| 2007/0032640 A1 | 2/2007 | Varghese et al. |
| 2007/0049593 A1 | 3/2007 | Oka et al. |
| 2007/0054915 A1 | 3/2007 | Arora et al. |
| 2007/0066632 A1 | 3/2007 | Hart et al. |
| 2007/0072897 A1 | 3/2007 | Mahaney et al. |
| 2007/0099871 A1 | 5/2007 | Davis et al. |
| 2007/0135454 A1 | 6/2007 | Hollingworth et al. |
| 2007/0142405 A1 | 6/2007 | Dong et al. |
| 2007/0155730 A1 | 7/2007 | Leit et al. |
| 2007/0161644 A1 | 7/2007 | Stockwell |
| 2007/0179151 A1 | 8/2007 | Chen et al. |
| 2007/0207996 A1 | 9/2007 | Auger et al. |
| 2007/0224672 A1 | 9/2007 | Leban et al. |
| 2007/0244133 A1 | 10/2007 | Bower et al. |
| 2007/0249598 A1 | 10/2007 | Wang et al. |
| 2007/0249680 A1 | 10/2007 | Illig et al. |
| 2007/0265231 A1 | 11/2007 | Hofmann et al. |
| 2007/0270452 A1 | 11/2007 | Blagg et al. |
| 2008/0004253 A1 | 1/2008 | Branstetter et al. |
| 2008/0032960 A1 | 2/2008 | Knight et al. |
| 2008/0058521 A1 | 3/2008 | Krishnan et al. |
| 2008/0070864 A1 | 3/2008 | Martin et al. |
| 2008/0070935 A1 | 3/2008 | Huang et al. |
| 2008/0119454 A1 | 5/2008 | Polisetti et al. |
| 2008/0119455 A1 | 5/2008 | Polisetti et al. |
| 2008/0119461 A1 | 5/2008 | Sin et al. |
| 2008/0194552 A1 | 8/2008 | Jones et al. |
| 2008/0200465 A1 | 8/2008 | Burli et al. |
| 2008/0234299 A1 | 9/2008 | Buchstaller et al. |
| 2008/0249090 A1 | 10/2008 | Hu et al. |
| 2008/0261956 A1 | 10/2008 | Choi et al. |
| 2008/0287469 A1 | 11/2008 | Diacovo et al. |
| 2008/0292626 A1 | 11/2008 | Wang et al. |
| 2008/0293674 A1 | 11/2008 | Schwarz et al. |
| 2008/0306053 A1 | 12/2008 | Tachdjian et al. |
| 2008/0306093 A1 | 12/2008 | Servant et al. |
| 2008/0312180 A1 | 12/2008 | Liang et al. |
| 2008/0318942 A1 | 12/2008 | Simon et al. |
| 2009/0030023 A1 | 1/2009 | Harada et al. |
| 2009/0030036 A1 | 1/2009 | Dalton et al. |
| 2009/0053192 A1 | 2/2009 | Millan et al. |
| 2009/0088452 A1 | 4/2009 | Coleman et al. |
| 2009/0099210 A1 | 4/2009 | Aquila et al. |
| 2009/0099214 A1 | 4/2009 | Fairhurst et al. |
| 2009/0105233 A1 | 4/2009 | Chua et al. |
| 2009/0118261 A1 | 5/2009 | Aquila et al. |
| 2009/0118283 A1 | 5/2009 | Defert et al. |
| 2009/0124638 A1 | 5/2009 | Shokat et al. |
| 2009/0124641 A1 | 5/2009 | Coleman et al. |
| 2009/0124654 A1 | 5/2009 | Mjalli et al. |
| 2009/0130097 A1 | 5/2009 | Liu et al. |
| 2009/0137581 A1 | 5/2009 | Chen et al. |
| 2009/0149484 A1 | 6/2009 | Aquila et al. |
| 2009/0163481 A1 | 6/2009 | Murphy et al. |
| 2009/0163525 A1 | 6/2009 | Aquila et al. |
| 2009/0163545 A1 | 6/2009 | Goldfarb |
| 2009/0163709 A1 | 6/2009 | Blagg |
| 2009/0170834 A1 | 7/2009 | Venkat et al. |
| 2009/0170849 A1 | 7/2009 | Aquila et al. |
| 2009/0170879 A1 | 7/2009 | Szucova et al. |
| 2009/0181920 A1 | 7/2009 | Watkins et al. |
| 2009/0181988 A1 | 7/2009 | Tanaka et al. |
| 2009/0187014 A1 | 7/2009 | Blagg |
| 2009/0203689 A1 | 8/2009 | Dhalla et al. |
| 2009/0214465 A1 | 8/2009 | Becklin et al. |
| 2009/0221488 A1 | 9/2009 | Wood et al. |
| 2009/0232768 A1 | 9/2009 | Birkus et al. |
| 2009/0233907 A1 | 9/2009 | Austin et al. |
| 2009/0233947 A1 | 9/2009 | Bayliss et al. |
| 2009/0247513 A1 | 10/2009 | Burli et al. |
| 2009/0247567 A1 | 10/2009 | Do et al. |
| 2009/0253694 A1 | 10/2009 | Ono et al. |
| 2009/0264409 A1 | 10/2009 | Dong et al. |
| 2009/0264423 A2 | 10/2009 | Chua et al. |
| 2009/0270426 A1 | 10/2009 | Knight et al. |
| 2009/0270567 A1 | 10/2009 | Small et al. |
| 2009/0280153 A1 | 11/2009 | Hunter et al. |
| 2009/0291442 A1 | 11/2009 | Hedge et al. |
| 2009/0298856 A1 | 12/2009 | Brown et al. |
| 2009/0306069 A1 | 12/2009 | Rueckle et al. |
| 2009/0312319 A1 | 12/2009 | Ren et al. |
| 2009/0312406 A1 | 12/2009 | Hsieh et al. |
| 2009/0318411 A1 | 12/2009 | Castanedo et al. |
| 2009/0325967 A1 | 12/2009 | Fairhurst et al. |
| 2010/0009963 A1 | 1/2010 | Knight et al. |
| 2010/0022585 A1 | 1/2010 | deLong et al. |
| 2010/0029658 A1 | 2/2010 | Gavish et al. |
| 2010/0029693 A1 | 2/2010 | Douangpanya et al. |
| 2010/0048540 A1 | 2/2010 | Boyle et al. |
| 2010/0048882 A1 | 2/2010 | Blagg et al. |
| 2010/0056494 A1 | 3/2010 | Winzeler et al. |
| 2010/0099871 A1 | 4/2010 | Miller et al. |
| 2010/0105630 A1 | 4/2010 | Blagg |
| 2010/0168153 A1 | 7/2010 | Stowasser et al. |
| 2010/0179167 A1 | 7/2010 | Xu et al. |
| 2010/0189685 A1 | 7/2010 | Byrd et al. |
| 2010/0190749 A1 | 7/2010 | Ren et al. |
| 2010/0226943 A1 | 9/2010 | Brennan et al. |
| 2010/0249030 A1 | 9/2010 | Basso-Porcaro |
| 2010/0280010 A1 | 11/2010 | Gudmundsson et al. |
| 2010/0292188 A1 | 11/2010 | Denonne et al. |
| 2010/0310503 A1 | 12/2010 | Li et al. |
| 2010/0323973 A1 | 12/2010 | Leamon et al. |
| 2011/0014186 A1 | 1/2011 | Ehrhardt et al. |
| 2011/0046165 A1 | 2/2011 | Ren et al. |
| 2011/0059953 A1 | 3/2011 | Fersht et al. |
| 2011/0071148 A1 | 3/2011 | Ding et al. |
| 2011/0123486 A1 | 5/2011 | Robbins et al. |
| 2011/0124641 A1 | 5/2011 | Ren et al. |
| 2011/0144134 A1 | 6/2011 | Shokat et al. |
| 2011/0152242 A1 | 6/2011 | Bayliss et al. |
| 2011/0172228 A1 | 7/2011 | Ren et al. |
| 2011/0217300 A1 | 9/2011 | Liu et al. |
| 2011/0224223 A1 | 9/2011 | Shokat et al. |
| 2011/0269779 A1 | 11/2011 | Wilson et al. |
| 2011/0281866 A1 | 11/2011 | Ren et al. |
| 2011/0301144 A1 | 12/2011 | Knight et al. |

(56) References Cited

U.S. PATENT DOCUMENTS

| | | |
|---|---|---|
| 2011/0313156 A1 | 12/2011 | Engelhardt et al. |
| 2012/0041683 A1 | 2/2012 | Vaske et al. |
| 2012/0046242 A1 | 2/2012 | Moon et al. |
| 2012/0059000 A1 | 3/2012 | Ren et al. |
| 2012/0065154 A1 | 3/2012 | Tanaka et al. |
| 2012/0065205 A1 | 3/2012 | Mercer et al. |
| 2012/0094997 A1 | 4/2012 | England et al. |
| 2012/0122838 A1 | 5/2012 | Ren et al. |
| 2012/0149701 A1 | 6/2012 | Ren et al. |
| 2012/0157306 A1 | 6/2012 | Frankenpohl et al. |
| 2012/0184568 A1 | 7/2012 | Ren et al. |
| 2012/0202784 A1 | 8/2012 | Aronov et al. |
| 2012/0220575 A1 | 8/2012 | Chang et al. |
| 2012/0225866 A1 | 9/2012 | Oshima et al. |
| 2012/0245136 A1 | 9/2012 | Hadida-Ruah et al. |
| 2012/0245166 A1 | 9/2012 | Grimaldi et al. |
| 2012/0245169 A1 | 9/2012 | Ren et al. |
| 2012/0270863 A1 | 10/2012 | Williams et al. |
| 2012/0289493 A1 | 11/2012 | Corkey et al. |
| 2012/0329776 A1 | 12/2012 | Ren et al. |
| 2013/0005802 A1 | 1/2013 | Chen et al. |
| 2013/0029982 A1 | 1/2013 | Castro et al. |
| 2013/0029984 A1 | 1/2013 | Castro et al. |
| 2013/0053362 A1 | 2/2013 | Castro et al. |
| 2013/0116277 A1 | 5/2013 | Dalton et al. |
| 2013/0190308 A1 | 7/2013 | Jain et al. |
| 2013/0267521 A1 | 10/2013 | Castro et al. |
| 2013/0267542 A1 | 10/2013 | Chem et al. |
| 2013/0289033 A1 | 10/2013 | Griffioen et al. |
| 2013/0344061 A1 | 12/2013 | Palombella et al. |
| 2013/0345216 A1 | 12/2013 | Ren et al. |
| 2014/0045825 A1 | 2/2014 | Leahy |
| 2014/0088099 A1 | 3/2014 | Ren et al. |
| 2014/0100214 A1 | 4/2014 | Castro et al. |
| 2014/0120060 A1 | 5/2014 | Palombella et al. |
| 2014/0120083 A1 | 5/2014 | Stem et al. |
| 2014/0155387 A1 | 6/2014 | No et al. |
| 2014/0194417 A1 | 7/2014 | Greenwood et al. |
| 2014/0227321 A1 | 8/2014 | Iadonato et al. |
| 2014/0249145 A1 | 9/2014 | Marugan et al. |
| 2015/0175605 A1 | 6/2015 | Bremner et al. |
| 2015/0225410 A1 | 8/2015 | Castro et al. |
| 2015/0290207 A1 | 10/2015 | Kutok et al. |
| 2015/0291562 A1 | 10/2015 | Crew et al. |
| 2016/0023991 A1 | 1/2016 | Evans et al. |
| 2016/0122365 A1 | 5/2016 | Castro et al. |
| 2016/0168131 A1 | 6/2016 | Du et al. |
| 2017/0014401 A1 | 1/2017 | Dalton et al. |
| 2017/0022184 A1 | 1/2017 | Li et al. |
| 2017/0088553 A1 | 3/2017 | Grenier et al. |
| 2017/0174699 A1 | 6/2017 | Hadari et al. |
| 2017/0226154 A1 | 8/2017 | Evans et al. |
| 2017/0266191 A1 | 9/2017 | Hamdy et al. |
| 2018/0072740 A1 | 3/2018 | Beck et al. |
| 2018/0072743 A1 | 3/2018 | Beck et al. |
| 2018/0154142 A1 | 6/2018 | Guo et al. |
| 2018/0201583 A1 | 7/2018 | O'Gara et al. |
| 2018/0230378 A1 | 8/2018 | Parham et al. |
| 2018/0318254 A1 | 11/2018 | Chen et al. |
| 2019/0022074 A1 | 1/2019 | Hadari et al. |
| 2019/0070166 A1 | 3/2019 | Postrel |
| 2019/0074458 A1 | 3/2019 | Lee et al. |
| 2019/0083626 A1 | 3/2019 | Goldberg et al. |
| 2019/0135833 A1 | 5/2019 | Evans et al. |
| 2019/0152941 A1 | 5/2019 | Gao et al. |
| 2019/0202835 A1 | 7/2019 | Evans |
| 2020/0085925 A1 | 3/2020 | Burkart et al. |
| 2020/0085960 A1 | 3/2020 | Moreau et al. |
| 2020/0165211 A1 | 5/2020 | Landry et al. |
| 2020/0165257 A1 | 5/2020 | Grewal et al. |
| 2020/0171020 A1 | 6/2020 | Balan et al. |
| 2020/0290978 A1 | 9/2020 | Nathanson et al. |
| 2020/0390889 A1 | 12/2020 | Homer et al. |
| 2020/0392153 A1 | 12/2020 | Aktoudianakis et al. |
| 2021/0000966 A1 | 1/2021 | Cipriani et al. |
| 2021/0017607 A1 | 1/2021 | Patnaik et al. |

FOREIGN PATENT DOCUMENTS

| | | |
|---|---|---|
| CN | 101602768 A | 12/2009 |
| CN | 108310384 A | 7/2018 |
| CN | 108658937 A | 10/2018 |
| CN | 110833546 A | 2/2020 |
| DE | 2139107 A1 | 2/1973 |
| DE | 19940859 | 3/2001 |
| DE | 102010013716 | 10/2011 |
| EP | 773023 A1 | 5/1997 |
| EP | 1020445 B1 | 8/2008 |
| EP | 2070932 | 6/2009 |
| GB | 812366 A | 4/1959 |
| GB | 937725 A | 9/1963 |
| GB | 2373186 | 9/2002 |
| JP | 61-109797 A | 5/1986 |
| JP | H05239036 | 9/1993 |
| JP | 05-256693 A | 10/1993 |
| JP | 08295667 A | 11/1996 |
| JP | 09143163 A | 6/1997 |
| JP | 10206995 A | 8/1998 |
| JP | 2000072773 A | 3/2000 |
| JP | 2001250689 | 9/2001 |
| JP | 2002131859 A | 5/2002 |
| JP | 2003073357 A | 3/2003 |
| JP | 2004161716 A | 6/2004 |
| JP | 2005035933 | 2/2005 |
| JP | 2006265107 | 10/2006 |
| JP | 2012184225 | 9/2012 |
| JP | 5569437 | 10/2012 |
| WO | WO 1983/001446 A1 | 4/1983 |
| WO | WO 1991/017161 A1 | 11/1991 |
| WO | WO 1992/014733 A1 | 9/1992 |
| WO | WO 1993/016091 A1 | 8/1993 |
| WO | WO 1993/016092 A1 | 8/1993 |
| WO | WO 1993/018035 A1 | 9/1993 |
| WO | WO 1993/019767 A1 | 10/1993 |
| WO | WO 1993/022443 A1 | 11/1993 |
| WO | WO 1994/013677 A1 | 6/1994 |
| WO | WO 1994/017803 A1 | 8/1994 |
| WO | WO 1994/029436 A1 | 12/1994 |
| WO | WO 1995/010628 A2 | 4/1995 |
| WO | WO 1995/012588 A1 | 5/1995 |
| WO | WO 1995/029673 A1 | 11/1995 |
| WO | WO 1995/032984 A1 | 12/1995 |
| WO | WO 1995/010628 A3 | 9/1996 |
| WO | WO 1996/040706 A1 | 12/1996 |
| WO | WO 1997/010221 | 3/1997 |
| WO | WO 1997/028133 A1 | 8/1997 |
| WO | WO 1997/028161 A1 | 8/1997 |
| WO | WO 1997/036901 | 10/1997 |
| WO | WO 1998/002162 | 1/1998 |
| WO | WO 1998/041525 A1 | 9/1998 |
| WO | WO 1998/052611 A1 | 11/1998 |
| WO | WO 1998/057952 A1 | 12/1998 |
| WO | WO 1999/024416 | 5/1999 |
| WO | WO 2000/017202 A1 | 3/2000 |
| WO | WO 2001/002369 A2 | 1/2001 |
| WO | WO 2001/016114 A2 | 3/2001 |
| WO | WO 2001/019829 A2 | 3/2001 |
| WO | WO 2001/025238 A2 | 4/2001 |
| WO | WO 2001/031063 A1 | 5/2001 |
| WO | WO 2001/038584 A2 | 5/2001 |
| WO | WO 2001/016114 A3 | 8/2001 |
| WO | WO 2001/055140 A1 | 8/2001 |
| WO | WO 2001/056988 A1 | 8/2001 |
| WO | WO 2001/019829 A3 | 9/2001 |
| WO | WO 2001/025238 A3 | 10/2001 |
| WO | WO 2001/038584 A3 | 10/2001 |
| WO | WO 2001/081346 A2 | 11/2001 |
| WO | WO 2001/098278 | 12/2001 |
| WO | WO 2002/006192 A1 | 1/2002 |
| WO | WO 2001/081346 A3 | 3/2002 |
| WO | WO 2002/024655 A1 | 3/2002 |
| WO | WO 2001/002369 A3 | 4/2002 |

(56) References Cited

FOREIGN PATENT DOCUMENTS

| | | |
|---|---|---|
| WO | WO 2002/030944 A2 | 4/2002 |
| WO | WO 2002/050091 | 6/2002 |
| WO | WO 2002/057425 A2 | 7/2002 |
| WO | WO 2002/076986 A1 | 10/2002 |
| WO | WO 2002/080926 A1 | 10/2002 |
| WO | WO 2002/083143 A1 | 10/2002 |
| WO | WO 2002/083884 | 10/2002 |
| WO | WO 2002/088025 A1 | 11/2002 |
| WO | WO 2002/090334 A1 | 11/2002 |
| WO | WO 2002/030944 A3 | 1/2003 |
| WO | WO 2003/000187 A2 | 1/2003 |
| WO | WO 2003/016275 A1 | 2/2003 |
| WO | WO 2003/020279 | 3/2003 |
| WO | WO 2003/020880 A2 | 3/2003 |
| WO | WO 2003/024969 A1 | 3/2003 |
| WO | WO 2003/028341 A2 | 4/2003 |
| WO | WO 2003/035075 A1 | 5/2003 |
| WO | WO 2003/045385 | 6/2003 |
| WO | WO 2003/059884 A1 | 7/2003 |
| WO | WO 2003/076418 | 9/2003 |
| WO | WO 2003/020880 A3 | 10/2003 |
| WO | WO 2003/082341 A1 | 10/2003 |
| WO | WO 2003/106426 A1 | 12/2003 |
| WO | WO 2004/006906 A2 | 1/2004 |
| WO | WO 2004/006906 A3 | 3/2004 |
| WO | WO 2004/018058 A2 | 3/2004 |
| WO | WO 2004/031177 A1 | 4/2004 |
| WO | WO 2004/039774 A2 | 5/2004 |
| WO | WO 2004/018058 A3 | 7/2004 |
| WO | WO 2004/039774 A3 | 7/2004 |
| WO | WO 2004/058717 A1 | 7/2004 |
| WO | WO 2004/060403 A2 | 7/2004 |
| WO | WO 2003/000187 A3 | 8/2004 |
| WO | WO 2004/069145 | 8/2004 |
| WO | WO 2004/087053 A2 | 10/2004 |
| WO | WO 2004/092123 | 10/2004 |
| WO | WO 2004/111014 A1 | 12/2004 |
| WO | WO 2005/002585 A1 | 1/2005 |
| WO | WO 2005/007085 A2 | 1/2005 |
| WO | WO 2005/012323 A2 | 2/2005 |
| WO | WO 2005/016348 A1 | 2/2005 |
| WO | WO 2005/016349 A1 | 2/2005 |
| WO | WO 2005/016528 A2 | 2/2005 |
| WO | WO 2005/021533 A1 | 3/2005 |
| WO | WO 2002/057425 A3 | 4/2005 |
| WO | WO 2005/012323 A3 | 5/2005 |
| WO | WO 2005/016528 A3 | 5/2005 |
| WO | WO 2005/044181 A2 | 5/2005 |
| WO | WO 2005/047289 A1 | 5/2005 |
| WO | WO 2005/061460 A1 | 7/2005 |
| WO | WO 2005/061707 | 7/2005 |
| WO | WO 2005/063258 A1 | 7/2005 |
| WO | WO 2005/067901 A2 | 7/2005 |
| WO | WO 2005/074603 A2 | 8/2005 |
| WO | WO 2005/007085 A3 | 9/2005 |
| WO | WO 2005/097800 A1 | 10/2005 |
| WO | WO 2005/105760 A1 | 11/2005 |
| WO | WO 2005/067901 A3 | 12/2005 |
| WO | WO 2005/112935 A1 | 12/2005 |
| WO | WO 2005/113556 A1 | 12/2005 |
| WO | WO 2005/117889 A1 | 12/2005 |
| WO | WO 2005/120511 A1 | 12/2005 |
| WO | WO 2005/044181 A3 | 3/2006 |
| WO | WO 2006/030032 A1 | 3/2006 |
| WO | WO 2006/038865 A1 | 4/2006 |
| WO | WO 2006/050501 A2 | 5/2006 |
| WO | WO 2006/050946 A1 | 5/2006 |
| WO | WO 2006/068760 A2 | 6/2006 |
| WO | WO 2004/087053 A3 | 8/2006 |
| WO | WO 2006/089106 A2 | 8/2006 |
| WO | WO 2006/108107 A1 | 10/2006 |
| WO | WO 2006/112666 A1 | 10/2006 |
| WO | WO 2005/074603 A3 | 11/2006 |
| WO | WO 2006/114064 A2 | 11/2006 |
| WO | WO 2006/114065 A2 | 11/2006 |
| WO | WO 2006/121522 | 11/2006 |
| WO | WO 2006/068760 A3 | 12/2006 |
| WO | WO 2006/089106 A3 | 12/2006 |
| WO | WO 2006/135479 | 12/2006 |
| WO | WO 2007/002293 A2 | 1/2007 |
| WO | WO 2007/006547 A1 | 1/2007 |
| WO | WO 2007/008541 | 1/2007 |
| WO | WO 2007/015877 | 2/2007 |
| WO | WO 2007/020046 A1 | 2/2007 |
| WO | WO 2007/002293 A3 | 3/2007 |
| WO | WO 2007/025090 A2 | 3/2007 |
| WO | WO 2006/050501 A3 | 5/2007 |
| WO | WO 2007/056155 | 5/2007 |
| WO | WO 2007/061737 A2 | 5/2007 |
| WO | WO 2006/114064 A3 | 6/2007 |
| WO | WO 2006/114065 A3 | 6/2007 |
| WO | WO 2007/025090 A3 | 6/2007 |
| WO | WO 2007/075554 A2 | 7/2007 |
| WO | WO 2007/076055 | 7/2007 |
| WO | WO 2007/079164 A2 | 7/2007 |
| WO | WO 2007/079164 A3 | 9/2007 |
| WO | WO 2007/103308 A2 | 9/2007 |
| WO | WO 2007/112005 A2 | 10/2007 |
| WO | WO 2007/114926 A2 | 10/2007 |
| WO | WO 2007/121453 A2 | 10/2007 |
| WO | WO 2007/121920 A2 | 11/2007 |
| WO | WO 2007/121924 A2 | 11/2007 |
| WO | WO 2007/124854 A1 | 11/2007 |
| WO | WO 2007/125310 A2 | 11/2007 |
| WO | WO 2007/125315 A2 | 11/2007 |
| WO | WO 2007/126841 A2 | 11/2007 |
| WO | WO 2007/134828 A1 | 11/2007 |
| WO | WO 2007/135380 A2 | 11/2007 |
| WO | WO 2007/135398 A1 | 11/2007 |
| WO | WO 2007/061737 A3 | 12/2007 |
| WO | WO 2007/125315 A3 | 12/2007 |
| WO | WO 2007/121920 A3 | 1/2008 |
| WO | WO 2008/001236 A2 | 1/2008 |
| WO | WO 2008/012326 A1 | 1/2008 |
| WO | WO 2008/013840 | 1/2008 |
| WO | WO 2008/013987 | 1/2008 |
| WO | WO 2007/103308 A3 | 2/2008 |
| WO | WO 2007/112005 A3 | 2/2008 |
| WO | WO 2007/125310 A3 | 3/2008 |
| WO | WO 2008/025755 A1 | 3/2008 |
| WO | WO 2008/047821 A1 | 4/2008 |
| WO | WO 2008/054252 | 5/2008 |
| WO | WO 2008/063625 A2 | 5/2008 |
| WO | WO 2008/064018 A1 | 5/2008 |
| WO | WO 2008/070507 A2 | 6/2008 |
| WO | WO 2007/121453 A3 | 7/2008 |
| WO | WO 2008/079028 A1 | 7/2008 |
| WO | WO 2008/082487 A2 | 7/2008 |
| WO | WO 2008/094737 A2 | 8/2008 |
| WO | WO 2008/094909 | 8/2008 |
| WO | WO 2007/121924 A3 | 9/2008 |
| WO | WO 2008/112715 A2 | 9/2008 |
| WO | WO 2007/114926 A3 | 10/2008 |
| WO | WO 2008/118454 A2 | 10/2008 |
| WO | WO 2008/118455 A1 | 10/2008 |
| WO | WO 2008/118468 A1 | 10/2008 |
| WO | WO 2008/120098 | 10/2008 |
| WO | WO 2008/125014 A1 | 10/2008 |
| WO | WO 2008/125207 A1 | 10/2008 |
| WO | WO 2008/127226 A2 | 10/2008 |
| WO | WO 2007/126841 A3 | 11/2008 |
| WO | WO 2008/112715 A3 | 11/2008 |
| WO | WO 2008/118454 A3 | 11/2008 |
| WO | WO 2008/136457 A1 | 11/2008 |
| WO | WO 2008/082487 A3 | 12/2008 |
| WO | WO 2008/127226 A3 | 12/2008 |
| WO | WO 2008/153701 | 12/2008 |
| WO | WO 2009/000412 A1 | 12/2008 |
| WO | WO 2009/002808 | 12/2008 |
| WO | WO 2009/004621 A1 | 1/2009 |
| WO | WO 2009/010925 A2 | 1/2009 |
| WO | WO 2009/018811 | 2/2009 |
| WO | WO 2009/021163 | 2/2009 |
| WO | WO 2009/023718 A2 | 2/2009 |

(56) References Cited

FOREIGN PATENT DOCUMENTS

| | | |
|---|---|---|
| WO | WO 2008/094737 A3 | 3/2009 |
| WO | WO 2009/029617 A1 | 3/2009 |
| WO | WO 2009/023718 A3 | 4/2009 |
| WO | WO 2009/044707 A1 | 4/2009 |
| WO | WO 2009/050506 A2 | 4/2009 |
| WO | WO 2009/064802 A2 | 5/2009 |
| WO | WO 2009/065919 | 5/2009 |
| WO | WO 2009/010925 A3 | 7/2009 |
| WO | WO 2009/064802 A3 | 7/2009 |
| WO | WO 2009/088986 A1 | 7/2009 |
| WO | WO 2009/088990 A1 | 7/2009 |
| WO | WO 2009/097233 | 8/2009 |
| WO | WO 2009/100406 A2 | 8/2009 |
| WO | WO 2009/114826 A2 | 9/2009 |
| WO | WO 2009/117157 A1 | 9/2009 |
| WO | WO 2009/050506 A3 | 11/2009 |
| WO | WO 2009/100406 A3 | 11/2009 |
| WO | WO 2010/006086 A2 | 1/2010 |
| WO | WO 2010/009207 A1 | 1/2010 |
| WO | WO 2010/118207 | 1/2010 |
| WO | WO 2010/014739 A2 | 2/2010 |
| WO | WO 2010/019210 A2 | 2/2010 |
| WO | WO 2010/036380 A1 | 4/2010 |
| WO | WO 2010/039534 A2 | 4/2010 |
| WO | WO 2010/046780 | 4/2010 |
| WO | WO 2010/019210 A3 | 5/2010 |
| WO | WO 2010/051391 | 5/2010 |
| WO | WO 2010/056758 | 5/2010 |
| WO | WO 2010/059969 A2 | 5/2010 |
| WO | WO 2010/065923 A2 | 6/2010 |
| WO | WO 2010/070032 A1 | 6/2010 |
| WO | WO 2010/039534 A3 | 8/2010 |
| WO | WO 2010/092340 A1 | 8/2010 |
| WO | WO 2010/096680 | 8/2010 |
| WO | WO 2010/127208 | 11/2010 |
| WO | WO 2010/133836 A1 | 11/2010 |
| WO | WO 2011/003065 | 1/2011 |
| WO | WO 2011/008302 A1 | 1/2011 |
| WO | WO 2011/020849 | 2/2011 |
| WO | WO 2011/025774 A1 | 3/2011 |
| WO | WO 2011/048111 | 4/2011 |
| WO | WO 2011/058108 A1 | 5/2011 |
| WO | WO 2011/058109 A1 | 5/2011 |
| WO | WO 2011/058110 A1 | 5/2011 |
| WO | WO 2011/075628 A1 | 6/2011 |
| WO | WO 2011/146882 A1 | 11/2011 |
| WO | WO 2011/150201 | 12/2011 |
| WO | WO 2012/009097 A1 | 1/2012 |
| WO | WO 2012/032334 A1 | 3/2012 |
| WO | WO 2012/037204 | 3/2012 |
| WO | WO 2012/040634 | 3/2012 |
| WO | WO 2012/052753 | 4/2012 |
| WO | WO 2012/061696 A1 | 5/2012 |
| WO | WO 2012/064973 A2 | 5/2012 |
| WO | WO 2012/065019 A2 | 5/2012 |
| WO | WO 2012/065057 A2 | 5/2012 |
| WO | WO 2012/165606 | 6/2012 |
| WO | WO 2012/097000 A1 | 7/2012 |
| WO | WO 2012/177997 | 12/2012 |
| WO | WO 2013/012915 | 1/2013 |
| WO | WO 2013/012918 A1 | 1/2013 |
| WO | WO 2013/032591 | 3/2013 |
| WO | WO 2013/038381 | 3/2013 |
| WO | WO 2013/065725 | 5/2013 |
| WO | WO 2013/136076 | 9/2013 |
| WO | WO 2013/154878 A1 | 10/2013 |
| WO | WO 2013/188432 | 12/2013 |
| WO | WO 2013/190555 | 12/2013 |
| WO | WO 2014/034750 | 3/2014 |
| WO | WO 2014/158528 | 10/2014 |
| WO | WO 2015/010641 | 1/2015 |
| WO | WO 2015/048318 | 4/2015 |
| WO | WO 2015/051241 | 4/2015 |
| WO | WO 2015/051244 | 4/2015 |
| WO | WO 2015/091685 | 6/2015 |
| WO | WO 2015/143012 | 9/2015 |
| WO | WO 2016/054491 | 4/2016 |
| WO | WO 2019/200224 A1 | 10/2019 |
| WO | WO 2019/228404 A1 | 12/2019 |
| WO | WO 2019/246315 A1 | 12/2019 |
| WO | WO 2020/037069 A1 | 2/2020 |
| WO | WO 2020/069433 A1 | 4/2020 |
| WO | WO 2020/072445 A1 | 4/2020 |
| WO | WO 2020/081549 A1 | 4/2020 |
| WO | WO 2020/092621 A1 | 5/2020 |
| WO | WO 2020/130125 A1 | 6/2020 |
| WO | WO 2020/168110 A1 | 8/2020 |
| WO | WO 2020/176501 A1 | 9/2020 |
| WO | WO 2020/210379 A1 | 10/2020 |
| WO | WO 2020/251974 A1 | 12/2020 |
| WO | WO 2020/257412 A1 | 12/2020 |
| WO | WO 2021/004421 A1 | 1/2021 |

OTHER PUBLICATIONS

Ashizawa, "Iyakuhin no takeigensho to shoseki no kagaku" (Polymorphism and crystallization of the pharmaceutical drugs), Maruzen Planet Co. Ltd. 2002, pp. 56-102, 304-317 (partial English translation of lines 18 to 24 on p. 307, lines 9 to 16 on p. 312, and Tale 9 on p. 317 attached).

Takata, "Form Screening and Selection of Drug Substance at Drug Discovery Stages", Pharm Stage, vol. 6, No. 10, pp. 20-25, 2007, published by Technical Information Institute Co. Ltd. (partial English translation of line 25 of right column on p. 23 to line 8 of left column on p. 25 attached).

Joule et al., "Structures and spectroscopic properties of aromatic heterocycles", Heterocyclic Chemistry Fourth edition, published 2000, pp. 1-7.

Patent Trial and Appeal Board Standard Operating Procedures 2 (Revision 10), retrieved from the Internet: https://www.uspto.gov/sites/default/files/documents/SOP2%20R10%20FINAL.pdf [accessed Dec. 20, 2020].

Gutekunst, "Haloselectivity of Heterocycles", Baran Group Meeting 2010, retrieved from the Internet: URL: https://www.scripps.edu/baran/images/grpmtgpdf/Gutekunst_Apr_10.pdf [Online dated Feb. 11, 2015].

Littke et al., "Palladium-catalyzed coupling reactions of aryl chlorides." *Angewandte Chemie International Edition* 41.22 (2002): 4176-4211.

Ohsawa et al., "One-step Synthesis of 3-(Dialkylamino)indolizines by the Palladium-catalyzed Reaction of α-Bromopyridine, Propargyl Alcohol, and Secondary Amine", Bull. Chem. Soc. Jpn., 1980, 53, 3273-3275.

Sakamoto et al., "Condensed Heteroaromatic Ring Systems. IX. Total Synthesis of Aaptamine", Chem. Phann. Bull., 1986, 34, 2760-2765.

Anderson et al., "General Catalysts for the Suzuki-Miyaura and Sonogashira Coupling Reactions of Aryl Chlorides and for the Coupling of Challenging Substrate Combinations in Water", Angew. Chem., Int. Ed., 2005, 44, 6173-6177.

Kodama et al., "Site-Specific Functionalization of Proteins by Organopalladium Reactions", ChemBioChem, 2007, 8, 232-238.

Dibowski et al., "Bioconjugation of Peptides by Palladium-Catalyzed C-C Cross-Coupling in Water", Angew. Chem., Int. Ed., 1998, 37, 476-478.

Caira, Mino R. "Crystalline polymorphism of organic compounds." Design of Organic Solids (1998): 163-208.

Hilfker et al., "Relevance of Solid-State Properties for Pharmaceutical Products", Polymorphism in the Pharmaceutical Industiy, 2006, pp. 1-19.

The Chemical Society of Japan, vol. 4, Jikken Kagaku Koza 1 (Encyclopedia of Experimental Chemistry), Basic Operation I, Maruzen Co., Ltd., 1991, pp. 201-202 (partial English translation of p. 201, line 4 to p. 202, line 7 attached).

Yamamoto, "Pharmaceutical Particulate Design by Spray-Drying Technique", Earozoru Kenkyu, 2010, vol. 25, No. 2, pp. 149-154 (partial English translation of p. 149, line 1 of the left column to line 2 of the right column attached).

(56) References Cited

OTHER PUBLICATIONS

Carretero et al., "Dichloro Bis(acetonitrile) Palladium", Encyclopedia of Reagents for Organic Synthesis, John Wiley & Sons, Ltd. Sep. 15, 2008.
Abdel-Mohsen, "Synthesis, Reactions and Antimicrobial Activity of 2-Amino-4-(8-quinolinol-5-yI)-l-(p-tolyl)-pyrrole-3-carbonitrile," *Bull. Korean Chem. Soc.* 26(5):719-728 (2005).
Abe et al., "T cell receptor-mediated recognition of self-ligand induces signaling in immature thymocytes before negative selection," *J. Exp. Med.* 176(2):459-468 (1992).
Abrahamian et al., "Immunological and Clinical Profile of Adult Patients with Selective Immunoglobulin Subclass deficiency: response to intravenous immunoglobulin therapy," *Clin. Exp. Immunol.* 159(3):344-350 (2010).
Abraham, T., "Thermally induced intramolecular cycloaddition reaction of N-phenyl-2-phenylethynlbenzamide potential cure reaction for thermosetting polymers," *J. Polym. Sci. Polym. Chem. Ed.* 20(7):1953-1957 (1982).
Ames et al., "Heterocyclic Syntheses from o-Halogeno-acids. Part II. Thienopyridinones and Thienopyranones from 3-Bromothiophen-2- and 4-Bromothiophen-3-carboxylic Acids," *J.C.S. Perkin I* 1390-1395 (1975).
Anderson et al., "Paradoxical inhibition of T-cell function in response to CTLA-4 blockade; heterogeneity within the human T-cell population," *Nat. Med.* 6(2):211-214 (2000).
Andrews et al., "Effects of the 11β-hydroxysteroid dehydrogenase inhibitor carbenoxolone on insulin sensitive in men with type 2 diabetes," *J. Clin. Endocrinol. Metab.* 88(1):285-291 (2003).
Arcaro et al., "Wortmannin is a potent phosphatidylinositol 3-kinase inhibitor: the role of phosphatidylinositol 3,4,5-triphosphate in neutrophil responses," *Biochem. J.*, 296(Pt 2):297-301 (1993).
Arnold et al., "Pyrrolo[2,3-d]pyrimidines containing an extended 5-substituent as potent and selective inhibitors of Ick I," *Bioorg. Med. Chem. Lett.* 10(19):2167-2170 (2000).
Augustine et al., "Interleukin 2- and polyomavirus middle T antigen-induced modification of phosphatidylinositol 3-kinase activity in activated T lymphocytes," *Mol. Cell. Biol.* 11(9):4431-4440 (1991).
Baggiolini et al., "Inhibition of the phagocytosis-induced respiratory burst by the fungal metabolite wortmannin and some analogues," *Exp. Cell. Res.* 169(2): 408-418 (1987).
Ballell et al. "New Thiopyrazolo[3,4-d] pyrimidine derivatives as anti-mycobacterial agents," *Bioorg. Med. Chem. Lett.* 17(6):1736-1740 (2007).
Banker et al., Modem Pharmaceutics, pp. 451, 596, 3$^{rd}$ ed, Marcel Dekker, New York (1996).
Bansal et al., "The Molecular Biology of Endometrial Cancers and the Implications for Pathogenesis, Classification, and Targeted Therapies," *Cancer Control* 16(1):8-13 (2009).
Barber et al., "PI3Kgamma inhibition blocks glomerulonephritis and extends lifespan in a mouse model of systemic lupus," *Nat. Med.* 11(9):933-935 (2005). (Epub Aug. 28, 2005).
Barf et al., "Arylsulfonamidothiazoles as a new class of potential antidiabetic drags. Discovery of potent and selective inhibitors of the 11β-hydroxysteroid dehydrogenase Type 1," *J. Med. Chem.* 45(18):3813-3815 (2002).
Barnes et al., "Efficacy and Safety of Inhaled Corticosteroids in Asthma—Report of A Workshop Held in Eze, France Oct. 1992," *Am. Rev. Respir. Dis.* 148:S1-S26 (1993).
Bartholomeusz et al., "Targeting the PI3K Signaling Pathway in Cancer Therapy," *Expert Opin. Ther. Targets* 16(1):121-130 (2012).
Basotest®, Test Kit for the Quantitative Determination of the Degranulation of Basophilic Granulocytes in Heparinized Human Whole Blood, version 04/02, pp. 1-10, [www.biocarta.com/TDS/10-0500.pdf], Retrieved from the Internet Nov. 29, 2011.
Beeram et al., "Akt-induced endocrine therapy resistance is reversed by inhibition of mTOR signaling," *Ann Oncol.* 18(8):1323-1328 (2007).
Bell et al., "Glucokinase mutations insulin secretion, and diabetes mellitus", *Annu. Rev. Physiol.* 58:171-186 (1996).

Berndt et al., "The p110δ crystal structure uncovers mechanisms for selectivity and potency of novel PI3K inhibitors," *Nat. Chem. Biol.* 6(2):117-124 (2010).
Bhat et al., "Pyrazolopyrimidine nucleosides. 12. Synthesis and biological activity of certain pyrazolo[3,4-d]pyrimidine nucleosides related to adenosine," *J. Med. Chem.* 24(10):1165-1172 (1981).
Bhatt et al., "Dual inhibition of PI3K and mTOR inhibits autocrine and paracrine proliferative loops in PI3K/Akt/mTOR-addicted lymphomas," *Blood* 115(22):4455-4463 (2010).
Bi et al., "Proliferative defect and embryonic lethality in mice homozygous for a deletion in the p110α subunit of phosphoinositide 3-kinase," *J. Biol. Chem.* 274:10963-10968 (1999).
Billottet et al., "A selective inhibitor of the p110δ isoform of PI 3-kinase inhibits AML cell proliferation and survival and increases the cytotoxic effects of VP16," *Oncogene* 25:6648-6659 (2006).
Billottet et al., "Inhibition of Class 1 Phosphoinositide 3-Kinase Activity Impairs Proliferation and Triggers Apoptosis in Acute Promyelocytic Leukemia without Affecting Atra-Induced Differentiation," *Cancer Res.* 69(3):1027-1036 (2009).
Bishop et al., "Generation of monospecific nanomolar tyrosine kinase inhibitors via a chemical genetic approach," *J. Am. Chem. Soc.* 121(4):627-631 (1999).
Blunden et al., "Mycotoxins in food," *Med. Lab. Sci.* 48(4):271-282 (1991).
Bochner et al., "Immunological aspects of allergic asthma," *Annu. Rev. Immunol.* 12:295-335 (1994).
Bohren et al., "Expression, crystallization and preliminary crystallographic analysis of human carbonyl reductase," *J. Mol. Biol.* 224:659-664 (1994).
Bone et al., "Phosphoinositide 3-kinase signalling regulates early development and developmental haemopoiesis," *J. Cell. Sci.* 120(Pt 10):1752-1762 (2007).
Bowers et al., "A platelet biomarker for assessing phosphoinositide 3-kinase inhibition during cancer chemotherapy," *Mol. Cancer Ther.* 6(9):2600-2607 (2007).
Brzezianska et al., "A Minireview: The Role of MAPK/ERK and PI3K/Akt Pathways in Thyroid Follicular Cell-Derived Neoplasm," *Front. Biosci.* 16:422-439 (2011).
Buitenhuis et al., "The role of the PI3k-PKB signaling module in regulation of hematopoiesis," *Cell Cycle* 8(4):560-566 (2009).
Burger et al., "High-level expression of the T-cell chemokines CCL3 and CCL4 by chronic lymphocytic leukemia B cells in nurselike cell cocultures and after BCR stimulation," *Blood* 113(13):3050-3058 (2009).
Burger et al., "Phosphoinositide 3'-kinase delta: turning off BCR signaling in Chronic Lymphocytic Leukemia," *Oncotarget* 2(10):737-738 (2011).
Burger, "Inhibiting B-Cell Receptor Signaling Pathways in Chronic Lymphocytic Leukemia," *Curr. Mematol. Malig. Rep.* 7:26-33 (2012).
Byrd et al., "Translating PI3K-Delta Inhibitors to the Clinic in Chronic Lymphocytic Leukemia: The Story of CAL-101 (GS1101)," *ASCO Program Proceedings*, pp. 691-694 (2012).
Campora et al., "Binuclear complexes of nickel bridged by hydrocarbon ligands. Isocyanide insertion chemistry and amide formation by intramolecular coupling of acyl and imidoyl functionalities," *Organometallics* 11(1):11-13 (1992).
Campora et al., "Isocyanide insertion chemistry. Synthesis and structural characterization of bridging imidoyl complexes of nickel and amide formation by intramolecular coupling of acyl and imidoyl functionalities," *Organometallics* 12(10):4025-4031 (1993).
Camps et al., "Blockade of PI3Kγ suppresses joint inflammation and damage in mouse models of rheumatoid arthritis," *Nat. Med.* 11(9):936-943 (2005).
Chaisuparat et al., "Dual inhibition of P13Kα and mTOR as an alternative treatment for Kaposi's Sarcoma," *Cancer Res.* 68:8361-8368 (2008).
Chang et al., "The Bruton tyrosine kinase inhibitor PCI-32765 ameliorates autoimmune arthritis by inhibition of multiple effector cells." *Arthritis Research & Therapy* 13:R115 (2011).
Chappelow et al., "Neovascular age-related macular degeneration: potential therapies," *Drugs* 68(8):1029-1036 (2008).

(56) References Cited

OTHER PUBLICATIONS

Chapuis et al., "Dual Inhibition of PI3K and mTORC1/2 Signaling by NVP-BEZ235 as a New Therapeutic Strategy for Acute Myeloid Leukemia," Clin. Cancer Res. 16(22):5424-5435 (2010).
Chawla et al., "Challenges in Polymorphism of Pharmaceuticals," Current Research & Information on Pharmaceutical Science 5(1):9-12 (2004).
Chen et al., "Characterization of Structurally Distinct, Isoform-Selective Phosphoinositide 3'-Kinase Inhibitors in Combination with Radiation in the Treatment of Glioblastoma," Mol. Cancer Ther. 7(4):841-850 (2008).
Cheson et al., "Bendamustine: Rebirth of an Old Drug," J. Clin. Oncol. 27(9):1492-1501 (2009).
Chiarini et al., "Activity of the Novel Dual Phosphatidylinositol 3-Kinase/Mammalian Target of Rapamycin Inhibitor NVP-BEZ235 against T-Cell Acute Lymphoblastic Leukemia," Cancer Res. 70(20):8097-8107 (2010).
Chiarini et al., "Dual Inhibition of Class IA Phosphatidylinositol 3-Kinase and Mammalian Target of Rapamycin as a New Therapeutic Option for T-Cell Acute Lymphoblastic Leukemia," Cancer Res. 69(8): 3520-3528 (2009).
Cho et al., "A novel synthesis of benzo[c]phenanthridine skeleton and biological evaluation of isoquinoline derivatives," Chem. Pharm, Bull.(Tokyo) 47(6):900-902 (1999).
Clayton et al., "A crucial role for the p110delta subunit of phosphatidylinositol 3-kinase in B cell development and activation," J. Exp. Med. 196:753-763 (2002).
Closse et al., "2,3-dihydrobenzofuran-2-ones: a new class of highly potent antiinflammatory agents," J. Med. Chem. 24:1465-1471 (1981).
Courtney et al., "The PI3K Pathway As Drug Target in Human Cancer," J. Clin. Oncol. 28(6):1075-1083 (2010).
Cox et al., "Human colorectal cancer cells efficiently conjugate the cyclopentenone prostaglandin, prostaglandin $J_2$, to glutathione," Biochem. Biophys. Acta. 1584:37-45 (2002).
Cushing et al., "PI3Kδ and PI3Kδ as Targets for Autoimmune and Inflammatory Diseases," J. Med. Chem. 55:8559-8581 (2012).
Dai et al., "Distinct Roles of Phosphoinositide-3 Kinase and Phospholipase Cγ2 in B-Cell Receptor-Mediated Signal Transduction," Mol. Cell. Biol. 26(1):88-99 (2006).
Davids et al., "Decreased mitochondrial apoptotic priming underlies stroma-mediated treatment resistance in chronic lymphocytic leukemia," Blood 120(17):3501-3509 (2012).
Davies et al., "The Human T3 γ Chain is Phosphorylated at Serine 126 in Response to T Lymphocyte Activation," J. Biol. Chem. 262(23):10918-10921 (1987).
Davis et al., "The preparation of substituted 1(2H)-isoquinolinones from dilithiated 2-methyl-N-arylbenzamides, 2-methyl-N-(arylmethyl)-benzamides, or 2-methylbenzoic acid, 2, 2-dimethylhydrazide," Synthetic Commun. 27(17):2961-2969 (1997).
Davis et al., "Chronic active B-cell-receptor signaling in diffuse large B-cell lymphoma," Nature 463:88-92 (2010).
De Whhrs et al., "The Bruton's tyrosine kinase gene is expressed throughout B cell differentiation, from early precursor B cell stages preceding immunoglobulin gene rearrangement up to mature B cell stages," Eur. J. Immunol. 23:3109-3114 (1993).
Diederich et al., "In search for specific inhibitors of human 11β-hydroxysteroid-dehydrogenases (11βHSDs): chenodeoxycholic acid selectively inhibits 11β-HSD-I," Eur. J. Endocrinol. 142(2):200-207 (2000).
Diiksman et al., "271.1 : 2-dihydro-2-thianaphthalene derivatives. Part I. Preparation and reactions of 1 : 2-dihydro-1-keto-2-thianaphthalenes," J. Chem. Soc. 1213-1218 (1951).
Ding et al., "A combinatorial scaffold approach toward kinase-directed heterocycle libraries," J. Am. Chem. Soc. 124(8): 1594-1596 (2002).
Ding et al., "A concise and traceless linker strategy toward combinatorial libraries of 2,6,9-substituted purines," J. Org. Chem. 66(24):8273-8276 (2001).
Ding et al., "Resin-capture and release strategy toward combinatorial libraries of 2,6,9-substituted purines," J. Comb. Chem. 4(2):183-186 (2002).
Donati, G., "Emerging therapies for neovascular age-related macular degeneration: state of the art," Ophthalmologica 221(6):366-377 (2007).
European Examination Report for EP Application No. 07873406.8 dated Sep. 14, 2011.
European Search Report for EP Application No. 05857011.0 dated Feb. 4, 2011.
European Search Report for EP Application No. 09700784.3 dated Oct. 28, 2011.
European Search Report and Search Opinion for EP Application No. 09700424.6 dated Oct. 26, 2011.
European Search Report for EP Application No. 07873406.8 dated Mar. 1, 2010.
European Search Report for EP Application No. 07754845.1 dated Sep. 20, 2011.
Examination Report for GB Application No. GB 0819947.3 dated Oct. 27, 2010.
Extended European Search Report for EP Application No. 09816603.6 dated Mar. 19, 2012.
Extended European Search Report from European Application No. 09700784.3 dated Oct. 28, 2011.
Fajans et al., "Maturity onset diabetes of the young (MODY)," Diabet. Med. 13(9 Suppl 6):S90-S95 (1996).
Feinstein et al., "Regulation of the action of hydrocotisone in airway epithelial cells by 11b-hydroxysterold dehydrogenase," Am. J. Respir. Cell. Mol. Biol. 21(3):403-408 (1999).
Feldman et al., "Active-Site Inhibitors of mTOR Target Rapamycin-Resistant Outputs of mTORC1 and mTORC2," PLoS Biol. 7(2):371-383 (2009).
Fingl et al., "Chapter 1—General Principles," The Pharmacological Basis of Therapeutics, 5th edition, Goodman and Gilman editors, MacMillan Publishings Co., Inc., New York, pp. 1-46, (1975).
Flinn et al., "Preliminary Evidence of Clinical Activity in a Phase I Study of CAL-101, a Selective Inhibitor of the p110δ Isoform of Phosphatidylinositol 3-Kinase (PI3K), in Patients with Select Hematologic Malignancies," J. Clin. Oncol. 27(15s) (Suppl: Abstr 3543) (2009).
Forrest et al., "Caibonyl Reductase," Chem. Biol. Interact. 129(1-2): 21-40 (2000).
Forrest et al., "Induction of a human carbonyl reductase gene located on chromosome 21," Biochem. Biophys. Acta. 1048(2-3):149-155 (1990).
Franzen, "The Suzuki, the Heck, and the Stille reaction—three versatile methods for the introduction of new C-C bonds on solid support," Can. J. Chem. 78:957-962 (2000).
Funder et al., "Mineralocorticoid action: target tissue specificity is enzyme, not receptor, mediated," Science 242:583-585 (1988).
Fung-Leung, W. P., "Phosphoinositide 3-kinase delta (PI3Kδ) in leukocyte signaling and function," Cell Signal 23:603-608 (2011).
Furukawa, T., "Molecular Targeting Therapy for Pancreatic Cancer: Current Knowledge and Perspectives from Bench to Bedside," J. Gastroenterol. 43(12):905-911 (2008).
Garber et al., "Diversity of gene expression in adenocarcinoma of the lung," Proc. Natl. Acad. Sci. U.S.A. 98(24):13784-13789 (2001).
Gillespie et al., "Antagonists of the human adenosine $A_{2A}$ receptor. Part 3: Design and synthesis of pyrazolo[3,4-d]pyrimidines, pyrrolo[2,3-d]pyrimidines and 6-arylpurines," Bioorg. Med. Chem. Lett. 18(9):2924-2929 (2008).
Gonzalez et al., "Protection against daunorubicin cytotoxicity by expression of a cloned human carbonyl reductase cDNA in K562 leukemia cells," Cancer Res. 55(20):4646-4650 (1995).
Graber et al., "The protein tyrosine kinase inhibitor herbimycin A, but not genistein, specifically inhibits signal transduction by the T cell antigen receptor," Int. Immunol. 4(1):1201-1210 (1992).
Graupera et al., "Angiogenesis selectively requires the p110α isoform of PI3K to control endothelial cell migration," Nature 453(7195):662-666 (2008).

(56) References Cited

OTHER PUBLICATIONS

Gunther et al., "Acute pathological effects on rats of orally administered wortmannin-containing preparations and purified wortmannin from Fusarium oxysporum," *Food Chem. Toxicol.* 27(3): 173-179 (1989).
Gunther et al., "Immunosuppressive effects of dietary wortmannin on rats and mice," *Immunopharmacol. Immunotoxicol.* 11(4):559-570 (1989).
Haase et al., "Detection of viral nucleic acids by in situ hybridization," *Methods in Virology* 7:189-226 (1984).
Haluska et al., "The RTK/RAS/BRAF/PI3K Pathways in Melanoma: Biology, Small Molecule Inhibitors, and Potential Applications," *Semin. Oncol.* 34(6):546-554 (2007).
Hanefeld et al., "One-pot synthesis of tetrasubstituted pyrazoles proof of regiochemistry," *J. Chem. Soc. Perkin 1* 1545-1552 (1996).
Harada et al., "Novel role of phosphatidylinositol 3-kinase in CD28-mediated costimulation," *J. Biol. Chem.* 276(12):9003-9008 (2001).
Harding et al., "CD28-mediated signalling co-stimulates murine T cells and prevents induction of anergy in T-cell clones," *Nature* 356(6370):607-609 (1992).
Hasselblom et al., "High immunohistochemical expression of p-AKT predicts inferior survival in patients with diffuse large B-cell lymphoma treated with immunochemotherapy," *Brit. J. Haematol.* 149:560-568 (2010).
Haylock-Jacobs et al., "PI3Kδ drives the pathogenesis of experimental autoimmune encephalomyelitis by inhibiting effector T cell apoptosis and promoting Th17 differentiation," *J. Autoimmun.* 36:278-287 (2011).
Hellwinkel et al., "Heterocyclensynthesen mit MF/A1203-basensystemen; 2-arylbenzofurane and 2,3-diarylisochinolin-1(2H)-one," *Synthesis* 1995( 9):1135-1141 (1995).
Herishanu et al., "The lymph node microenvironment promotes B-cell receptor signaling, NF-κB activation, and tumor proliferation in chronic lymphocytic leukemia," *Blood* 117(2):563-574 (2011).
Herman et al., "Phosphatidylinositol 3-kinase-δ inhibitor CAL-101 shows promising preclinical activity in chronic lymphocytic leukemia by antagonizing intrinsic and extrinsic cellular survival signals," *Blood* 116(12):2078-2088 (2010).
Herman et al., "The role of phosphatidylinositol 3-kinase-δ in the immunomodulatory effects of lenalidomide in chronic lymphocytic leukemia," *Blood* 117(16):4323-4327 (2011).
Herrera et al., "The dual PI3K/mTOR inhibitor BEZ235 is effective in lung cancer cell lines," *Anticancer Res.* 31:849-854 (2011).
Hickey et al., "BCR-ABL Regulates Phosphatidylinositol 3-Kinase-p110γ Transcription and Activation and Is Required for Proliferation and Drug Resistance," *J. Biol. Chem.* 281(5):2441-2450 (2006).
Hirsch et al., "CALming Down T Cell Acute Leukemia," *Cancer Cell* 21:449-450 (2012).
Hirsch et al., "Central Role for G Protein-Coupled Phosphoinositide 3-Kinase γ in Inflammation," *Science* 287:1049-1053 (2000).
Hoellenriegel and Burger, "Phosphoinositide 3'-kinase delta: turning off BCR signaling in Chronic Lymphocytic Leukemia," *Oncotarget* 2(10):737-738 (2011).
Hoellenriegel et al., "The phosphoinositide 3'-kinase delta inhibitor, CAL-101, inhibits B-cell receptor signaling and chemokine networks in chronic lymphocytic leukemia," *Blood* 118(13):3603-3612 (2011).
Hoellenriegel et al., "Phosphoinositide 3'-kinase (PI3K) Delta Inhibition with CAL-101 Blocks B-cell Receptor (BCR) Signaling and the Prosurvival Actions of Nurse-Like Cells (NLC) in Chronic Lymphocytic Leukemia (CLL)," (ASH Annual Meeting 2010).
Honigberg et al., "The Bruton tyrosine kinase inhibitor PCI-32765 blocks B-Cell activation and is efficacious in models of autoimmune disease and B-cell malignancy," *PNAS* 107(29):13075-13080 (2010).
Ikeda et al., "PI3K/p110δ is a novel therapeutic target in multiple myeloma," *Blood* 116(9):1460-1468 (2010).
International Preliminary Report on Patentability and Written Opinion for PCT/US2005/042524 dated May 22, 2007.
International Preliminary Report on Patentability and Written Opinion for PCT/US2007/008355 dated Nov. 4, 2008.
International Preliminary Report on Patentability and Written Opinion for PCT/US2007/008395 dated Oct. 8, 2008.
International Preliminary Report on Patentability and Written Opinion for PCT/US2009/049969 dated Jan. 11, 2011.
International Preliminary Report on Patentability and Written Opinion for PCT/US2009/060985 dated Apr. 19, 2011.
International Preliminary Report on Patentability for PCT/US2009/000038 dated Jul. 6, 2010.
International Preliminary Report on Patentability for PCT/US2009/005380 dated Apr. 7, 2011.
International Preliminary Report on Patentability for PCT/US2010/002020 dated Jan. 26, 2012.
International Preliminary Report on Patentability for PCT/US2009/000042 dated Jul. 6, 2010.
International Search Report & Written Opinion for PCT/US2011/060212 dated Jun. 1, 2012.
International Search Report & Written Opinion issued after Submission of Request for Additional Search for PCT/US2011/060212 dated Jul. 6, 2012.
International Search Report and Written Opinion for PCT/US2009/005380 dated Nov. 20, 2009.
International Search Report and Written Opinion for PCT/US2009/049969 dated Mar. 15, 2010.
International Search Report and Written Opinion for PCT/US2010/033939, dated Nov. 5, 2010.
International Search Report and Written Opinion for PCT/US2012/047190 dated Oct. 2, 2012.
International Search Report and Written Opinion for PCT/US2012/020831 dated May 2, 2012.
International Search Report for PCT/US2011/037412 dated Aug. 22, 2011.
International Search Report for PCT/US1995/005213 dated Aug. 21, 1995.
International Search Report for PCT/US2007/008395 (4 pages) dated Aug. 27, 2008.
International Search Report for PCT/US2009/000038 dated Mar. 11, 2009.
International Search Report for PCT/US2009/000042 dated Mar. 23, 2009.
International Search Report for PCT/US2005/042524 (7 pages) dated Oct. 2, 2006.
International Search Report for PCT/US2007/008355 dated Sep. 25, 2008.
International Search Report for PCT/US2009/060985 dated Jun. 28, 2010.
International Search Report for PCT/US2010/002020 dated Nov. 2, 2010.
Ishiyama et al., "A stoichiometric aromatic C-H borylation catalyzed by iridium(I)/2,2'-bipyridine complexes at room temperature," *Angew. Chem. Int. Ed. Engl.* 41(16):3056-3058 (2002).
Ishiyama et al., "Mild iridium-catalyzed borylation of arenes. High turnover numbers, room temperature reactions, and isolation of a potential intermediate," *J. Am. Chem. Soc.* 124(3):390-391 (2002).
Jackson et al., "PI 3-kinase p110β: a new target for antithrombotic therapy," *Nat. Med.* 11:507-514 (2005).
Jimeno et al., "Phase I Trial of PX-866, a Novel Phosphoinositide-3-Kinase (PI-3K) Inhibitor," *J. Clin. Oncol.* 27:15s (Suppl; Abstract 3542) (2009).
Johnson et al., "Accessory cell-derived signals required for T cell activation," *Immunol. Res.* 48-64 (1993).
Jou et al., "Essential, nomedundant role for the phosphoinositide 3-kinase p110delta in signaling by the B-cell receptor complex," *Mol. Cell. Biol.* 22:8580-8591 (2002).
June et al., "Evidence for the involvement of three distinct signals in the induction of IL-2 gene expression in human T lymphocytes," *J. Immunol.* 143(1):153-161 (1989).
June et al., "Inhibition of tyrosine phosphorylation prevents T-cell receptor mediated signal transduction," *Proc. Natl. Acad. Sci. U.S.A.* 87:7722-7726 (1990).
June et al., "Role of CD28 receptor in T-cell activation." *Immunol. Today* 11(6):211-216 (1990).

(56) References Cited

OTHER PUBLICATIONS

June, C.H., "Signaling transduction in T cells," *Curr. Opin. Immunol.* 3(3):287-293 (1991).
Kajit A et al., "Nickel-catalyzed decarbonylative addition of phthalimides to alkynes," *J. Am. Chem. Soc.* 130(19):6058-6059 (2008).
Kallberg et al., "Short-chain dehydrogenase/reductase (SDR) relationships: a large family with eight clusters common to human, animal, and plant genomes," *Protein Sci.* 11(3):636-641 (2002).
Kallberg et al., "Short-Chain Dehydrogenases/Reductases (SDRs)—Coenzyme-Based Functional Assignments in Completed Genomes," *Eur. J. Biochem.* 269(18):4409-4417 (2002).
Kang et al., "Oncogenic transformation induced by the p110β, -γ, and -δ isoforms of class I phosphoinositide 3-kinase," *PNAS* 103(5):1289-1294 (2006).
Karpeiskii et al., "Pyridoxal-5'-Derivatives of Nucleobases," *Bioorganicheskaya Khimiva* 11(8): 1097-1104 (1985).
Khwaja, A., "PI3K as a Target for Therapy in Haematological Malignancies," *Curr. Top. Microbiol. Immunol.* 347:169-188 (2010).
Kim et al., "Activation and Function of the mTORC1 Pathway in Mast Cells," *J. Immunol.* 180(7):4586-4595 (2008).
Knight et al., "A Pharmacological Map of the PI3-K Family Defines a Role for p110α in Insulin Signaling," *Cell* 125(4):733-747 (2006).
Kong, D. and Yamori, T., "Advances in Development of Phosphatidylinositol 3-Kinase Inhibitors," *Curr. Med. Chem.* 16:2839-2854 (2009).
Kost et al., "Recyclization of 3-Alkyl- and 1,3-Dialkylisoquinolinium Salts to Naphthylamines," *Chemistry of Heterocyclic Compounds* 16(9): 965-970 (1981).
Kraybill et al., "Inhibitor scaffolds as new allele specific kinase substrates," *J. Am. Chem. Soc.* 124(41):12118-12128 (2002).
Kreutzberger et al. "5-Substituierte 4-Aminopyrimidine durch Aminomethynlierung von Acetonitrilen," *Liebigs Ann. Chem.* 537-544 (1977).
Kulkarni et al., "PI3Kbeta plays a critical role in neutrophil activation by immune complexes," *Sci. Signal* 2011, vol. 4, ra23.
Kumar et al., "Keten Dithioacetals. Part 11. Reaction of 3-Cyano-4-Methylthio-2(1H)-pyridones with Hydrazine and Guanidine: Synthesis of Novel Substituted and Fused Pyrazolo[4,3-c]pyridone and Pyrido[4,3-d]pyrimidine derivatives," *J. Chem. Soc. Perkin 1* 8:857-862 (1978).
Kundu et al., "Palladium-catalysed heteroannualation with terminal alkynes; a highly regio- and stereoselective synthesis of (Z)-3-aryl(alykl)idene isoindolin-1-ones," *Tetrahedron* 56(27):4777-4792 (2000).
Kurtova et al., "Diverse marrow stromal cells protect CLL cells from spontaneous and drug-induced apoptosis: development of a reliable and reproducible system to assess stromal cell adhesion-mediated drug resistance," *Blood* 114(20): 4441-4450 (2009).
Kwok et al., "The anti-inflammatory natural product parthenolide from the medicinal herb Feverfew directly binds to and inhibits IκB kinase," *Chem. Biol.* 8(8):759-766 (2001).
Lannutti et al., "CAL-101 a p110δ selective phosphatidylinositol-3-kinase inhibitor for the treatment of B-cell malignancies, inhibits PI3K signaling and cellular viability," *Blood* 117(2):591-594 (2011).
Larabi et al., "Crystal Structure and Mechanism of Activation of TANK-Binding Kinase 1," *Cell Reports* 3:734-746 (2013).
Ledbetter et al., "CD28 ligation in T-cell activation: evidence for two signal transduction pathways," *Blood* 75(7):1531-1539 (1990).
Ledbetter et al., "Crosslinking of surface antigens causes mobilization of intracellular ionized calcium in T lymphocytes," *Proc. Natl. Acad. Sci. U. S. A.* 84(5):1384-1388 (1987).
Lee et al., "All roads lead to mTOR: integrating inflammation and tumor angiogenesis," *Cell Cycle* 6(24):3011-3014 (2007).
Lee et al., "The CD28 signal transduction pathway in T cell activation", Advances in Cell Regulation of Cell Growth, vol. 2, pp. 141-160, New York: Raven Press, Ltd. (1991).
Ley et al., "The T cell receptor/CD3 complex and CD2 stimulate the tyrosine phosphorylation of indistinguishable patterns of polypeptides in the human T leukemic cell line Jurkat," *Eur. J. Immunol.* 21(9):2203-2209 (1991).
Li et al., "Roles of PLC-beta2 and -beta3 and PI3Kgamma in chemoattractant-mediated signal transduction," *Science* 287(5455):1046-1049 (2000).
Liu et al., "Costimulation of T-cell growth," *Curr. Opin. Immunol.* 4(3):265-270 (1992).
Lu et al., "CD28-induced T cell activation. Evidence for a protein-tyrosine kinase signal transduction pathway," *J. Immunol.* 149(1):24-29 (1992).
Majumder et al., "mTOR inhibition reverses Akt-dependent prostate intraepithelial neoplasia through regulation of apoptotic and HIF-1-dependent pathways," *Nat. Med.* 10(6):594-601 (2004).
Markman et al., "Status of PI3K inhibition and biomarker development in cancer therapeutics," *Ann. Oncol.* 21(4):683-691 (2010).
Martelli et al., "The emerging role of the phosphatidylinositol 3-kinase/Akt/mammalian target of rapamycin signaling network in normal myelopoiesis and leukemogenesis," *Biochim. Biophys. Acta.* 803:991-1002 (2010).
Martinez et al., "The Molecular Signature of Mantle Cell Lymphoma Reveals Multiple Signals Favoring Cell Survival," *Cancer Res.* 63:8226-8232 (2003).
Martin-Sanchez et al., "PI3K Inhibition As a Potential Therapeutic Strategy in Peripheral T-Cell Lymphomas," *Blood (ASH Annual Meeting Abstracts)* 118: Abstract 3493 (2011).
Mattes et al., "DNA sequence selectivity of guanine-N7 alkylation by nitrogen mustards," *Nucleic Acids Res.* 14(7):2971-2987 (1986).
Maxwell et al., "Attenuation of phosphoinositide 3-kinase 5 signaling restrains autoimmune disease," *J. Autoimmun.* 38:381-391 (2012).
Mayer et al., "Small molecule inhibitor of mitotic spindle bipolarity identified in a phenotype-based screen," *Science* 286(5441):971-974 (1999).
Mazzoletti and Broggini, "PI3K/AKT/mTOR inhibitors in ovarian cancer," Curr. Med. Chem. 17(36):4433-4447 (2010).
Meadows, S.A., et al., "CAL-101, a Potent Selective Inhibitor of the p110δ Isoform of Phosphatidylinositol 3-Kinase, Attenuates Pathway Signaling, Induces Apoptosis, and Overcomes Signals From the Microenvironment in Cellular Models of Hodgkin Lymphoma," Blood (ASH Annual Meeting Abstracts), 116:Abstract 3926 (2010).
Mellinghoff et al., "TORward AKTually useful mouse models," *Nat. Med.* 10(6):579-580 (2004).
Merida et al., "IL-2 binding activates a tyrosine-phosphorylated phosphatidylinositol-3-kinase," *J. Immunol.* 147(7): 2202-2207 (1991).
Miyaura et al., "Palladium-catalyzed cross-coupling reactions of organoboron compounds," *Chem. Rev.* 95(7):2457-2483 (1995).
Modi et al., "Isoquinolones; part IV-synthesis of methyl, 3-formyl & other 3-substituted N-arylisoquinolones." *Indian J. Chem.* 18B:304-306 (1979).
Moon et al., "A novel microtubule destabilizing entity from orthogonal synthesis of triazine library and zebrafish embryo screening," *J. Am. Chem. Soc.* 124(39):11608-11609 (2002).
Mosmann et al., "The expanding universe of T-cell subsets: Th1, Th2 and more," *Immunology Today* 17(3):138-146 (1996).
Nakanishi et al., "Cloning and sequence analysis of a cDNA encoding tetrameric carbonyl reductase of pig lung," *Biochem. Biophys. Res. Commun.* (3):1311-1316 (1993).
Nemazanyi et al., "3-Amino-4-aryl-1(2H)-isoquinolones," *Chemistry of Heterocyclic Compounds* 27(3):307-308 (1991).
Newman et al., "Solid state analysis of the active pharmaceutical ingredient in drug products," *Drug Discov. Today* 8(19):898-905 (2003).
Nisitani et al., "Posttranscriptional regulation of Bruton's tyrosine kinase expression in antigen receptor-stimulated splenic B cells," *PNAS* 97(6):2737-2742 (2000).
Niswender et al., "Protein engineering of protein kinase a catalytic subunits results in the acquisition of novel inhibitor sensitivity," *J. Biol. Chem.* 277(32):28916-28922 (2002).
Nobel et al., "Purification of full-length recombinant human and rat type 1 11β-hydroxysteroid dehydrogenases with retained oxidoreductase activities," *Protein Expr. Purif.* 26(3):349-356 (2002).
Norman, "Selective PI3K-delta Inhibitors, A Review of the Patent Literature," Expert Opinion on Therapeutic Patents, 21(11): 1773-1790 (2011).

(56) References Cited

OTHER PUBLICATIONS

Nunes et al., "Signalling through CD28 T-cell activation pathway involves an inositol phospholipid-specific phospholipase C activity," *Biochem. J.* 293(Pt 3):835-842 (1993).
Oda et al., "PIK3CA cooperates with other phosphatidylinositol 3'-kinase pathway mutations to effect oncogenic transformation," *Cancer Res.* 68(19):8127-8136 (2008).
Office Action dated Dec. 13, 2012 for U.S. Appl. No. 13/112,611.
Okada et al., "Essential role of phosphatidylinositol 3-kinase in insulin-induced glucose transport and antilipolysis in rat adipocytes. Studies with a selective inhibitor wortmannin," *J. Biol. Chem.* 269(5):3568-3573 (1994).
Okada et al., "Blockage of chemotactic peptide-induced stimulation of neutrophils by wortmannin as a result of selective inhibition of phosphatidylinositol 3-kinase," *J. Biol. Chem.* 269(5):3563-3567 (1994).
Oppermann et al., "Forms and functions of human SDR enzymes," *Chem. Biol. Interact.* 130-132(1-3):699-705 (2001).
O'Shea et al., "Activation of human peripheral blood T lymphocytes by pharmacological induction of protein-tyrosine phosphorylation," *Proc. Natl. Acad. Sci. U. S. A.* 89(21):10306-10310 (1992).
Ozaki et al., "Studies on 4(1H)-quinazolinones. IV. Convenient synthesis of 12-methyl-6H-isoquino [2,1-a] quinazolin-6-one and 6-methyl-13H-quinazolino [3,4-a] quinazolin-13-one," *Chem. Pharm. Bull.* 32(6):2160-2164 (1984).
Ozol et al., "Autoxidative transformations of 2-substituted 3-alkyl-4-hydroxy-1-oxo-1, 2-dihydroisoquinolines," *Chemistry of Heterocyclic Compounds* 14(6):644-648 (1978).
Patel et al., "Immunopathological aspects of age-related macular degeneration," *Semin. Immunopathol.* 30(2):97-110 (2008).
Pérez-Blas et al., "Impaired T cell signal transduction through CD28 in a patient with idiopathic thrombocytopenia," *Clin. Exp. Immunol.* 85(3):424-428 (1991).
Persson, "Glucocorticoids for asthma—early contributions," *Pulm. Pharmacol.* 2(3): 163-166 (1989).
Petrie et al., "Novel biotinylated adenylate analogue derived from pyrazolo[3,4-d]pyrimidine for labeling DNA probes," *Bioconiug. Chem.* 2(6):441-446 (1991).
Pighi et al., "Phospho-proteomic analysis of mantle cell lymphoma cells suggests a pro-survival role of B-cell receptor signaling," *Cell Oncol. (Dordr)* 34(2): 141-153 (2011).
Polak et al., "The PI3K/PKB signaling module as key regulator of hematopoiesis: implications for therapeutic strategies in leukemia," *Blood* 119(4):911-923 (2012).
Porta and Figlin, "Phosphatidylinositol-3-kinase/Akt signaling pathway and kidney cancer, and the therapeutic potential of phosphatidylinositol-3-kinase/Akt inhibitors," *J. Urol.* 182(6):2569-2577 (2009).
Prasad et al., "Phosphatidylinositol (PI) 3-kinase and PI 4-kinase binding to the CD4-p56$^{lck}$ complex: the p56$^{lck}$ SH3 domain binds to PI 3-kinase but not PI 4-kinase," *Mol. Cell. Biol.* 13(12): 7708-7717 (1993).
Prasad et al., "Src-homology 3 domain of protein kinase p59$^{fyn}$ mediates binding to phosphatidylinositol 3-kinase inT cells," *Proc. Natl. Acad. Sci. U. S. A.* 90(15): 7366-7370 (1993).
Prasad et al., "T-cell antigen CD28 interacts with the lipid kinase phosphatidylinositol 3-kinase by a cytoplasmic Tyr(P)-Met-Xaa-Met motif," *Proc. Natl. Acad. Sci. U. S. A.* 91(7): 2834-2838 (1994).
Pudlo et al., "Synthesis, antiproliferative, and antiviral activity of certain 4-substituted and 4,5 disubstituted 7-[1,3-dihydroxy-2-propoxy)methyl]pyrrolo[2,3-d]pyrimidines," *J. Med. Chem.* 33(7):1984-1992 (1990).
Puri and Gold, "Selective inhibitors of phosphoinositide 3-kinase delta: modulators of B-cell function with potential for treating autoimmune inflammatory disease and B-cell malignancies," *Front. Immunol.* 3:256 (2012).
Quiroga et al., "B-cell antigen receptor signaling enhances chronic lymphocytic leukemia cell migration and survival: specific targeting with a novel spleen tyrosine kinase inhibitor, R406," *Blood* 114(5):1029-1037 (2009).

Reif et al., "Divergent regulation of phosphatidylinositol 3-kinase P85α and P85β isoforms upon T cell activation," *J. Biol. Chem.* 268(15):10780-10788 (1993).
Report of the Expert Committee on the Diagnosis and Classification of Diabetes Mellitus, *Diabetes Care* 2( Suppl. 1):S5-S19 (1992).
Rizzatti et al., "Gene expression profiling of mantle cell lymphoma cells reveals aberrant expression of genes from the PI3K-AKT, WNT and TGFβ signaling pathways," *Brit. J. Haematol.* 130:516-526 (2005).
Robertson, "Eicosanoids and human disease", Harrison's Principles of Internal Medicine, Isselbacher K.J. et al. (eds.), vol. 1, pp. 431-435, McGraw-Hill, New York City (1994).
Roller et al., "Blockade of Phosphatidylinositol 3-Kinase (PI3K)δ or PI3Kγ Reduces IL-17 and Ameliorates Imiquimod-Induced Psoriasis-like Dermatitis," *J. Immunol.* 189:4612-4620 (2012).
Romero et al., "Cloning and expression of the bovine 11b-hydroxysteroid dehydrogenase type-2," *J. Steroid Biochem. Mol. Biol.* 72(5):231-237 (2000).
Rommel et al., "PI3Kδ and PI3Kγ: partners in crime in inflammation in rheumatoid arthritis and beyond?" *Nat. Rev. Immunol.* 7:191-201 (2007).
Rott et al., "Recent developments in the use of biologies in psoriasis and autoimmune disorders. The role of autoantibodies," *BMJ* 330(7493):716-720 (2005).
Rudelius et al., "Constitutive activation of Akt contributes to the pathogenesis and survival of mantle cell lymphoma," *Blood* 108(5):1668-1676 (2006).
Saif and Chu, "Biology of colorectal cancer," *Cancer J.* 16(3):196-201 (2010).
Salmena et al., "Tenets of PTEN Tumor Suppression," *Cell* 133(3):403-414 (2008).
Sarker et al., "Targeting the PI3K/AKT pathway for the treatment of prostate cancer," *Clin. Cancer Res.* 15(15):4799-4805 (2009).
Sasaki et al., "Function of PI3Kγ in Thymocyte Development, T Cell Activation, and Neutrophil Migration," *Science* 287:1040-1046 (2000).
Schwartz et al., "Quercetin inhibition of the induction and function of cytotoxic T lymphocytes," *Immunopharmacology* 4(2):125-138 (1982).
Schwartz, "A cell culture model for T lymphocyte clonal anergy," *Science* 248(4961):1349-1356 (1990).
Shapiro et al., "Phase I Dose-Escalation Study of XL147, A PI3K Inhibitor Administered Orally to Patients with Solid Tumors," *J. Clin. Oncol.* 27:146x (Suppl Abstr 3500) (2009).
Shibasaki et al., "Different properties of monomer and heterodimer forms of phosphatidylinositol 3-kinases," *Biochem. J.* 289 (Pt 1):227-231 (1993).
Sinclair et al., "Phosphatidylinositol-3 Kinase Delta (PI3Kδ) Inhibitor AMG 319 Is a Potent, Selective and Orally Bioavailable Small Molecule Inhibitor That Suppresses PI3K-Mediated Signaling and Viability in Neoplastic B Cells," *Blood (ASH Annual Meeting Abstracts)*. 118:Abstract 4964 (2011).
Singer et al., "Optimization of in situ hybridization using isotopic and non-isotopic detection methods," *Biotechniques* 4(3):230-250 (1986).
Smith et al., "Expression of Bruton's Agammaglobulinemia Tyrosine Kinase Gene, BTK, Is Selectively Down-Regulated in T Lymphocytes and Plasma Cells," *J. Immunol.* 152:557-565 (1994).
Soldan et al., "Induction of daunorubicin carbonyl reducing enzymes by daunombicin in sensitive and resistant pancreas carcinoma cells," *Biochem. Pharmacol.* 51(2):117-123 (1996).
Soond et al., "PI3K p110δ regulates T-cell cytokine production during primary and secondary immune responses in mice and humans," *Blood* 115(11):2203-2213 (2010).
Srinivasan et al., "PI3 Kinase Signals BCR-Dependent Mature B Cell Survival," *Cell* 139:573-586 (2009).
Stanoeva et al., "Homophthalic anhydrides and their application to the synthesis of heterocyclic compounds (review)," *Chemistry of Heterocyclic Compounds* 20(12):1305-1315 (1984).
Subramaniam et al., "Targeting Nonclassical Oncogenes for Therapy in T-ALL," *Cancer Cell* 21:459-472 (2012).

(56) References Cited

OTHER PUBLICATIONS

Sujobert et al., "Essential role for the p110δ isoform in phosphoinositide 3-kinase activation and cell proliferation in acute myeloid leukemia," *Blood* 106(3):1063-1066 (2005).
Supplementary European Examination Report EP Application No. 07754845.1 dated Sep. 20, 2011.
Supplementary European Search Report for EP Application No. 07754845 (4 pages) dated Feb. 24, 2010.
Supplementary European Search Report for EP Application No. 10800175.1 dated Nov. 7, 2012.
Sykes et al., "Treatment of severe autoimmune disease by stem-cell transplantation," *Nature* 35(7042):620-627 (2005).
Takeuchi et al., "Synergistic Augmentation of Rapamycin-Induced Autophagy in Malignant Glioma Cells by Phosphatidylinositol 3-Kinase/Protein Kinase B Inhibitors," *Cancer Res.* 65(8):3336-3346 (2005).
Tanaka et al., "An unbiased cell morphology-based screen for new, biologically active small molecules," *PLoS Biol.* 3(5):0764-0776 (2005).
Thompson et al., "Identification of distinct populations of PI-3 kinase activity following T-cell activation," *Oncogene* 7(4):719-725 (1992).
Torbett et al., "A chemical screen in diverse breast cancer cell lines reveals genetic enhancers and suppressors of sensitivity to PI3K isoform-selective inhibition," *Biochem. J.* 415(1):97-110(2008).
Truitt et al., "Stimulation of CD28 triggers an association between CD28 and phosphatidylinositol 3-kinase in Jurkat T cells," *J. Exp. Med.* 179(3):1071-1076 (1994).
Tyukavkina et al., Bioorganicheskaya Khimiya, Moskva, DROFA, pp. 83-85 (2004).
Uddin et al., "Role of phosphatidylinositol 3'-kinase/AKT pathway in diffuse large B-cell lymphoma survival," *Blood* 108(13):4178-4186 (2006).
Ugarkar et al., "Adenosine kinase inhibitors. 2. Synthesis, enzyme inhibition, and antiseizure activity of diaryltubercidin analogues," *J. Med. Chem.* 43(15):2894-2905 (2000).
Vandenberghe et al., "Antibody and B7/BB1-mediated ligation of the CD28 receptor induces tyrosine phosphorylation in human T cells," *J. Exp. Med.* 175(4):951-960 (1992).
Vanhaesebroeck et al., "PI3K: from the bench to the clinic and back," *Curr. Top. Microbiol. Immunol.* 347:1-19 (2010).
Vara et al., "PI3K/Akt Signalling Pathway and Cancer," *Cancer Treat. Rev.* 30(2):193-204 (2004).
Vasilevsky et al., "Study of the Heterocyclization of vic-Substituted Hydrazides of Acetylenylpyrazolecarboxylic Acids into N-Amino Pyrazolopyridinones," *Journal of Heterocyclic Chemistry* 39(6): 1229-1233 (2002).
Vasilevsky et al., "Unexpected results in the heterocyclization of 5-acetylenylpyrazole-4-carboxylic acid hydrazides under the influence of CuCl: formation of a diazepinone and dehydrodimerization into the corresponding bis(pyrazolo [4,3-d] [1,2] diazepinone)," *Tetrahedron Lett.* 46(26):4457-4459 (2005).
Vippagunta et al., "Crystalline Solids," *Adv. Drug Deliv. Rev.* 48(1):3-26 (2001).
Vitali et al., "Immunotherapy in rheumatoid arthritis: a review," *Int. J. Artif. Organs* 16 Suppl. 5:196-200 (1993).
Vlahos et al., "A specific inhibitor of phosphatidylinositol 3-kinase, 2-(4-morpholinyl)-8-phenyl-4H-1-benzopyran-4-one (LY294002)," *J. Biol. Chem.* 269(7):5241-5248 (1994).
Vogt et al., "Phosphatidylinositol 3-kinase: the oncoprotein," *Curr. Top. Microbiol. Immunol.* 347:79-104 (2010).
Vogt et al., "Phosphoinositide 3-kinase: from viral oncoprotein to drug target," *Virology* 344(1):131-138 (2006).
Wagner et al., "A First-in-Human Phase I Study to Evaluate the Pan-PI3K Inhibitor GDC-0941 Administered QD or BID in Patients with Advanced Solid Tumors," *J. Clin. Oncol.* 27:146s (Suppl, Abstr 3501) (2009).
Wahlstrom et al., "Aberrant MAPK and PI3K Signaling Contribute to Chemotherapy Resistance in T Cell Acute Lymphoblastic Leukemia by Altering the Balance of Apoptosis Mediators," *Blood (ASH Annual Meeting Abstracts)* 118: Abstract 3490 (2011).
Ward et al., "Inhibition of CD28-mediated T cell costimulation by the phosphoinositide 3-kinase inhibitor wortmannin," *Eur. J. Immunol.* 25(2):526-532 (1995).
Ward et al., "Ligation of CD28 receptor by B7 induces formation of D-3 phosphoinositides in T lymphocytes independently of T cell receptor/CD3 activation," *Eur. J. Immunol.* 23(10):2572-2577 (1993).
Ward et al., "Regulation of D-3 phosphoinositides during T cell activation via the T cell antigen receptor/CD3 complex and CD2 antigens," *Eur. J. Immunol.* 22(1):45-49 (1992).
Ward et al., "Regulation of phosphoinositide kinases in T cells. Evidence that phosphatidylinositol 3-kinase is not a substrate for T cell antigen receptor-regulated tyrosine kinases," *J. Biol. Chem.* 267(33):23862-23869 (1992).
Ward et al., "Therapeutic potential of phosphoinositide 3-kinase inhibitors," *Chem. Biol.* 10(3):207-213 (2003).
White et al., " 11β-Hydroxysteroid Dehyrdogenase and the Syndrome of Apparent Mineralocorticoid Excess," *Endocr. Rev.* 18(1):135-156 (1997).
Widler et al., "7-alkyl- and 7-Cycloalkyl-5-aryl-pyrrolo[2,3-d]pyrimidines- potent inhibitors of the tyrosine kinase c-Src," *Bioorg. Med. Chem. Lett.* 11(6):849-852 (2001).
Wiesinger et al., "Antiinflammatory activity of the new mould metabolite 11-desacetoxy-wortmannin and of some of its derivatives," *Experientia* 30(2):135-136 (1974).
Wolff, Burger's Medicinal Chemistry, $5^{th}$ ed, Part 1, pp. 975-977, John Wiley & Sons (1995).
Woscholski et al., "A comparison of demethoxyviridin and wortmannin as inhibitors of phosphatidylinositol 3-kinase," *FEBS Lett.* 342(2):109-114 (1994).
Wu et al., "Decreased immunological responses by wortmannin-containing rice culture of Fusarium oxysporum and by purified wortmannin in avian species," *Immunopharmacol. Immunotoxicol.* 14(4):913-923 (1992).
Wu et al., "Wortmannin (a mycotoxin) inhibited immune responses in chickens," *Poultry Sci.* Vo. 71, Suppl 1, pp. 13 (1992).
Yaguchi et al., "Antitumor activity of ZSTK474, a new phosphatidylinositol 3-kinase inhibitor," *J. Natl. Cancer Inst.* 98(8):545-556 (2006).
Yang et al., "A novel activation pathway for mature thymocytes. Costimulation of CD2 (T,p50) and CD28 (T,p44) induces autocrine interleukin 2/interleukin 2 receptor-mediated cell proliferation," *J. Exp. Med.* 168(4):1457-1468 (1988).
Yano et al., "Inhibition of histamine secretion by wortmannin through the blockade of phosphatidylinositol 3-kinase in RBL-2H3 cells," *J. Biol. Chem.* 268(34):25846-25856 (1993).
Yoshida et al., "Quercetin arrests human leukemic T-cells in late G1 phase of the cell cycle," *Cancer Res.* 52(23):6676-6681 (1992).
Zhao and Vogt, "Class I PI3K in oncogenic cellular transformation," *Oncogene* 27(41):5486-5496 (2008).
Abdel-Rahman et al., "Synthesis of heterobicyclic quinazolinones derived from N-[2-(2-chloro-phenyl)-l-(6,8-dibromo-4-oxo-4H-benzo[d][1,3]oxazin-2-yl)-vinyl]-benzamide as antimicrobial agents," Egyptian Journal of Chemistry (2006), 49(4), 461-474.
Abdel-Rahman et al., "Synthesis, reactions and antifungal agents of 2-[benzoylamino-2-(naphthyl- and/or 2'-furyl)]vinyl-4-H-3,1-benzoxazin-4-ones derivatives," Egyptian Journal of Chemistiy (2006), 49(2), 169-184.
Abdel-Rahman, T., "Reactivity of 3-amino-3H-quinazolin-4-one derivatives towards some electrophilic and nucleophilic reagents and using of the products in the building of some interesting heterocycles as anticancer agent," Journal of Heterocyclic Chemistry (2006), 43(3), 527-534.
Abdel-Rahman, T., "Reactivity of 3-amino-3H-quinazolin-4-one derivatives towards some electrophilic and nucleophilic reagents and using of the products in the building of some interesting heterocycles as anticancer agent," Bollettino Chimico Farmaceutico (2005), 144(3), 124-138.
Afantitis et al., "A combined LS-SVM & MLR QSAR workflow for predicting the inhibition of CXCR3 receptor by quinazolinone analogs," Molecular Diversity (2010), 14(2), 225-235.

(56) References Cited

OTHER PUBLICATIONS

Afify, A.A. et al., "Synthesis and reactions of substituted benzoxazinones bearing a bulky group at position-2," Indian Journal of Chemistry, Section B: Organic Chemistry Including Medicinal Chemistiy (1988), 27B(10), 920-25.

Afify, A.A. et al., Synthesis and reactions of substituted benzoxazinones bearing a bulky group at position-2. Part I, Revue Roumaine de Chimie (1990), 35(4), 567-75.

Ahmad, S. et al., "Monoamine oxidase inhibitory activity of 4(3H)-quinazolinones of dopamine," Indian Journal of Pharmaceutical Sciences (1979), 41(3), 126-7.

Aksoy et al., "The p110d isoform of the kinase PI(3)K controls the subcellular compartmentalization of TLR4 signaling and protects from endotoxic shock", Nature Immunology, 2012, vol. 13(11), pp. 1045-1054.

Ali et al., "Leukocyte Extravasation: An Immunoregulatory Role for L-Fucosidase?", J Immunol 2008, vol. 181, pp. 2407-2413.

Avila, M.A. et al., "New therapies for hepatocellular carcinoma," Oncogene (2006), 25(27), 3866-3884.

Balla et al. (Eds.), Phosphoinositides I: Enzymes of Synthesis and Degradation, Chapter 5: PI3Ks—Drug Targets in Inflammation and Cancer Series: Subcellular Biochemistry, vol. 58, 2012, XVI, 356 p.

Bariei, P.L. et al., "A facile one pot synthesis of 2,9-disubstituted 8-azapurin-6-ones (3,5-disubstituted 7-hydroxy-3H-1,2,3-triazolo[4,5-d]pyrimidines)," Journal of Heterocyclic Chemistry (1985), 22(6), 1607-9.

Basso et al., "SCH 1473759, a novel Aurora inhibitor, demonstrates enhanced anti-tumor activity in combination with taxanes and KSP inhibitors", Cancer Chemotherapy and Pharmacology (2011), 68(4), 923-933.

Beer, T. et al., "Southwest oncology group phase II study of ispinesib in androgen-independent prostate cancer previously treated with taxanes," Clinical Genitourinary Cancer (2008), 6(2), 103-109.

Birk et al., "Cell cycle-dependent cytotoxicity and mitotic spindle checkpoint dependency of investigational and approved antimitotic agents", International Journal of Cancer (2012), 130(4), 798-807.

Blagden, S.P. et al., "A phase I trial of ispinesib, a kinesin spindle protein inhibitor, with docetaxel in patients with advanced solid tumours," British Journal of Cancer (2008), 98(5), 894-899.

Bol'But, A.V. et al., "Condensed pyrimidine systems. 5.6-methyl-functionalized in pyrazolo[3,4-d]pyrimidin-4(5H)-ones," Zhurnal Organiclmoi ta Farmatsevticlmoi Khimii (2006), 4(3), 57-61.

Brunton, S. et al., "Potent Inhibitors of the Hedgehog Signaling Pathway," Journal of Medicinal Chemistiy (2008), 51(5), 1108-1110.

Burger et al., "CXCR4: a key receptor in the crosstalk between tumor cells and their microenvironment", Blood, Mar. 1, 2006;107(5), pp. 1761-1767.

Burger et al., "The microenvironment in chronic lymphocytic leukemia (CLL) and other B cell malignancies: insight into disease biology and new targeted therapies", Semin Cancer Biol., Feb. 2014; vol. 24:pp. 71-81.

Burris et al., "A phase I study of ispinesib, a kinesin spindle protein inhibitor, administered weekly for three consecutive weeks of a 28-day cycle in patients with solid tumors", Investigational New Drugs (2011), 29(3), 467-472.

Chau et al., "The association between EGFR variant III, HPV, p16, c-MET, EGFR gene copy numer and response to EGFR inhibitors in patients with recurrent or metastatic squamous cell carcinoma of The head and neck", Head & Neck Oncology (2011), 3(11), 1-11.

Curran et al., "PD-1 and CTLA-4 combination blockade expands infiltrating T cells and reduces regulatory T and myeloid cells within B16 melanoma tumors", PNAS, Mar. 2, 2010, vol. 107(9), pp. 4275-4280.

Davis et al., "Increased therapeutic potential of an experimental anti-mitotic inhibitor SB715992 by genistein in PC-3 human prostate cancer cell line," BMC Cancer (2006), 6, 22.

De Palma and Lewis, "Macrophage Regulation of Tumor Responses to Anticancer Therapies", Cancer Cell, vol. 23, Issue 3, Mar. 18, 2013, pp. 277-286.

Debnath, A et al., "Structure-Based Identification of Small Molecule Antiviral Compounds Targeted to the gp41 Core Structure of the Human Immunodeficiency Virus Type 1," Journal of Medicinal Chemistry (1999), 42(17), 3203-3209.

Denardo et al., "Leukocyte Complexity Predicts Breast Cancer Survival and Functionally Regulates Response to Chemotherapy", Cancer Discovery, Jun. 2011, vol. 1, pp. 54-56.

Duraiswamy et al., "Dual Blockade of PD-1 and CTLA-4 Combined with Tumor Vaccine Effectively Restores T-Cell Rejection Function in Tumors," Cancer Research, Jun. 5, 2013;73(12):3591-603.

El-Bassiouny et al., "Synthesis and some reactions of 2-[a-benzoylamino-b-2-furylvinyl]-6,8-dibromobenzoxazin-4(3H)-one and 3-aminoquinazolin-4(3H)-one derivatives," Asian Journal of Chemistiy (1990), 2(1), 67-72.

El-Farargy et al., "Study on the reactivity of 2-[benzamido-(a-naphthylidene)]-4H-3,1-benzoxazin-4 one towards different carbon and nitrogen nucleophiles," Egyptian Journal of Chemistiy (1993), vol. Date 1992, 35(5), 603-9.

El-Farargy, A.F., "Study on the stability and behavior of 2-[benzamido(naphthylidene)methyl]-4(3H)-quinazolinone," Egyptian Journal of Pharmaceutical Sciences (1991), 32(3-4), 565-74.

Elkafrawy, et al., "Steric and polar factors involving heteroring opening of 2-(a-benzoylamino-p-methoxystyryl)-6,8-dibromo-3,1-benzoxazin-4(H)-one," Indian Journal of Chemistry, Section B: Organic Chemistiy Including Medicinal Chemistiy (1992), 31B(1), 19-23.

El-Khamry et al., "Synthesis and reactions of 2-(a-benzoylamino-p-chlorostyryl)-3,1(4H)-benzoxazin-4-one with some nucleophilic reagents: synthesis of quinazolinone, tetrazole and benzimidazole derivatives," Egyptian Journal of Chemistry (1990), Volume Date 1988, 31(2), 261-9.

El-Nagdy, S. et al., "Behavior of benzoxazinone derivatives bearing a bulky group at position 2 toward some nitrogen and carbon nucleophiles. Part 2," Revue Roumaine de Chimie (1990), 35(1), 55-62.

El-Nagdy, S. et al., "Behavior of benzoxazinone derivatives bearing a bulky group at position-2 towards some nitrogen and carbon nucleophiles," Indian Journal of Chemistry, Section B: Organic Chemistiy Including Medicinal Chemistiy (1989), 28B(2), 126-30.

El-Nagdy, S. et al., "Synthesis and some reactions of 2-(a-benzoylaminostyryl)-3,1(4H)-benzoxazin-4-one and 3-amino-2-(a-benzoylaminostyryl)quinazolin-4(3H)-one," Revue Roumaine de Chimie (1988), 33(8), 827-32.

El-Nagdy, S. et al., "Synthesis and some reactions of 2-(a-benzoylaminostyryl)-3,1(4H)-benzoxazin-4-one and 3-amino-2-(a-benzoylaminostyryl)quinazolin-4(3H)-one," Egyptian Journal of Chemistry (1990), Volume Date 1988, 31(5), 599-606.

El-Nagdy, S., "Synthesis and some reactions of 2-[a-(benzoylamino)styryl]-6,8-dibromo-3,1-benzoxazin-4(H)-one, quinazolin-4(3H)-one, and chloroquinazoline derivatives with some nucleophilic reagents," Asian Journal of Chemistry (1990), 2(4), 368-78.

El-Sharief et al., "Oxidation of 3-aminoquinazolinones with lead tetraacetate. A novel synthesis of naphtho-fused azirino-pyrazolo- and 1,4,5-oxadiazepinoquinazolinones,"Journal of Chemical Research, Synopses (2002), (5), 205-208.

Essawy et al., "Behavior of 2-(a-phenylimido-b-p-nitrophenyl) vinyl-(4H)-3,1-benzoxazin-4-one towards some nucleophiles," Journal of Pure and Applied Sciences (1990), 9(2), 29-35 (abstract only).

Feig et al., "Targeting CXCL12 from FAP-expressing carcinoma associated fibroblasts synergizes with anti-PD-L1 immunotherapy in pancreatic cancer," PNAS, Dec. 10, 2013, vol. 110, No. 50, pp. 20212-20217.

Ferrandi et al., "Phosphoinositide 3-Kinase Inhibition Plays a Crucial Role in Early Steps of Inflammation by Blocking Neutrophil Recruitment", J Pharmacol Exp Ther, Sep. 2007, vol. 322, pp. 923-930.

Fruman, D., "Phosphoinositide 3-kinase and its targets in B-cell and T-cell signaling", Current Opinion in Immunology, vol. 16, Issue 3, Jun. 2004, pp. 314-320.

(56) References Cited

OTHER PUBLICATIONS

Gao, H. et al., "A Dramatic Substituent Effect in Silver(I)-Catalyzed Regioselective Cyclization of ortho-Aikynylaryl Aldehyde Oxime Derivatives," Advanced Synthesis & Catalysis (2009), 351 (1-2), 85-88.
Garg, P. et al., "Synthesis and anti-implantation activity of 2-[2-[2-aryl-4(3H)-oxoquinazolin-3-yl]ethyl]-5-benzylidenecyclohexanone thiosemicarbazones," Biological Memoirs (1988), 14(2), 180-6.
Ghia et al., "Chronic lymphocytic leukemia B cells are endowed with the capacity to attract CD4+, CD40L+ T cells by producing CCL22", Eur J Immunol., May 2002; vol. 32(5): pp. 1403-1413.
Ghosh, T., "Quinazolines. I," Journal of the Indian Chemical Society (1937), 14, 411-13.
Guirguis, D., "The behaviour of some nucleophiles towards 2-[a-(benzoylamino)-b-(2-thienyl)vinyl]benzoxazin-4(3H)-one," Indian Journal of Chemistry, Section B: Organic Chemistiy Including Medicinal Chemistiy (2000), 39B(4), 264-269.
Hardamon et al., "Inhibition of myeloid cell PI3K is a potential therapeutic approach to treat pancreatic cancer", Cancer Research, Apr. 15, 2012; vol. 72, Issue 8, Supplement 1, Abstract 5228.
Hassanein et al., "Synthesis of 2-substituted-10H-[1,2,4]triazino[6,1-b]quinazoline-10-ones and 8,13,14,16-tetrahydronaphtho[2',3':3,4][1,2,5]triazepino[7,1-b]quinazoline-8,13,16-triones with biological interest," Al-Azhar Bulletin of Science (1997), 8(2), 417-434.
Heiser et al., "Subtype and pathway specific responses to anticancer compounds in breast cancer", Proceedings of the National Academy of Sciences of the United States of America (2012), 109(8), 2724-2729.
Herman et al., "Molecular pathways: targeting phosphoinositide 3-kinase p110-delta in chronic lymphocytic leukemia", Clin Cancer Res., Aug. 1, 2012; vol. 18(15): pp. 4013-4018.
Hirsch et al., "Phosphoinositide 3-kinases as a common platform for multi-hormone signaling", J Endocrinol, 2007, vol. 194 (2), pp. 243-256.
Huang, W. et al., "Synthesis and evaluation of quinazolin-4-ones as hypoxia-inducible factor-1 inhibitors," Bioorganic & Medicinal Chemistry Letters (2011), 21(18), 5239-5243.
Jackson, J et al., "Targeted anti-mitotic therapies: can we improve on tubulin agents?" Nature Reviews Cancer (2007), 7(2), 107-117.
Jankowski, F. et al., "Efficient microwave-assisted two-step procedure for the synthesis of 1,3-disubstituted-imidazo[1,5-a]quinazolin-5(4H)-ones," Tetrahedron (2010), 66(1), 128-133.
Jiang, C. et al., "De novo design, synthesis and biological evaluation of 1,4-dihydroquinolin-4-ones and 1,2,3,4-tetrahydroquinazolin-4-ones as potent kinesin spindle protein (KSP) inhibitors", Bioorganic & Medicinal Chemistry (2011), 19(18), 5612-5627.
Jiang, C. et al., "Docking studies on kinesin spindle protein inhibitors: an important cooperative 'minor binding pocket' which increases the binding affinity significantly," Journal of Molecular Modeling (2007), 13(9), 987-992.
Johnson, M. et al., "Discovery and optimization of a series of quinazolinone-derived antagonists of CXCR3," Bioorganic & Medicinal Chemistry Letters (2007), 17(12), 3339-3343.
Kaneda et al., "PI3-kinase gamma controls the macrophage M1-M2 switch, thereby promoting tumor immunosuppression and progression", AACR; Cancer Res 2014, vol. 74 (19 Suppl), Abstract 3650.
Karanov et al., "Cytokinin and anticytokinin activity of some 4-substituted 1H-pyrazoles and 8-aza analogs of adenine," Plant Growth Regulation (1993), 13(1), 7-11.
Kathman, S. et al., "A Bayesian population PK-PD model for ispinesib/docetaxel combination-induced myelosuppression," Cancer Chemotherapy and Pharmacology (2009), 63(3), 469-476.
Kathman, S. et al., "A bayesian population PK-PD model of ispinesib-induced myelosuppression," Clinical Pharmacology & Therapeutics (New York, NY, United States) (2007), 81(1), 88-94.
Kirmani et al., "Studies on the reactivity of 2-methyl-3-phenyl-4(3H)-quinazolinone," Indian Journal of Chemistry, Section B: Organic Chemistry Including Medicinal Chemistry (1979), 17B(5), 445-9.

Knox, J. et al., "A phase II and pharmacokinetic study of SB-715992, in patients with metastatic hepatocellular carcinoma: a study of the National Cancer Institute of Canada Clinical Trials Group (NCIC CTG IND.168)," Investigational New Drugs (2008), 26(3), 265-272.
Lad, L. et al., "Mechanism of Inhibition of Human KSP by Ispinesib," Biochemistry (2008), 47(11), 3576-3585.
Lee, C. et al., "A phase II study of ispinesib (SB-715992) in patients with metastatic or recurrent malignant melanoma: a National Cancer Institute of Canada Clinical Trials Group trial," Investigational New Dmgs (2008), 26(3), 249-255.
Lee, R. et al.,"A University of Chicago consortium phase II trial of SB-715992 in advanced renal cell cancer," Clinical Genitourinary Cancer (2008), 6(1), 21-24.
Lewis and Pollard, "Distinct Role of Macrophages in Different Tumor Microenvironments", Cancer Res 2006, vol. 66 (2), pp. 605-612.
Liu F. et al., "Discovery of tetrahydro-b-carbolines as inhibitors of the mitotic kinesin KSP," Bioorganic & Medicinal Chemistiy (2010), 18(12), 4167-4177.
Liu F. et al., "Pharmacophore identification of KSP inhibitors," Bioorganic & Medicinal Chemistry Letters (2007), 17(3), 722-726.
Liu, D. et al., "Impurity identification in process chemistry by mass spectrometry", Characterization of Impurities and Degradants Using Mass Spectrometry, First Edition, John Wiley & Sons, Inc., Hoboken, NJ, (2011), pp. 251-277.
Mahmoud et al., "Heteroannulated quinazoline and quinazolinone derivatives from (Z)-2-[1-benzamido-2-(3,4,5-trimethoxyphenyl)vinyl]-3,1 -benzoxazin-4(3H)- one," Synthetic Communications (2010), 40(10), 1516-1529.
Mahmoud et al., "Synthesis of new thiadiazoles, 1,2,4-triazolo[3,4-b]-1,3,4-thiadiazoles, and 1,2,4-triazolo[2,3-c]quinazoline derivatives from 4H-3,1-benzoxazin-4-one derivative," Phosphorus, Sulfur and Silicon and the Related Elements (2007), 182(6), 1275-1289.
Mahmoud et al., "Synthesis of novel quinazolinone and fused quinazolinones", European Journal of Chemistiy (2011), 2(3), 404-409.
Marone et al., "Targeting phosphoinositide 3-kinase—Moving towards therapy," Biochimica et Biophysica Acta 1784 (2008) 159-185.
Mealy, et al., "Drugs under development for the treatment of head and neck cancer," Drugs of the Future (2006), 31(7), 627-639.
Monjazeb et al., "Immunoediting and antigen loss: overcoming the Achilles heel of immunotherapy with antigen non-specific therapies", Front. Oncol., 2013, vol. 3, Article 197, pp. 1-10.
Morsy, J.M., "Use of 2-(substituted vinyl)-4(3H)-quinazolinone and -4H-3,1-benzoxazinone in synthesis of heterocycles," Bulgarian Chemical Communications (2007), 39(2), 146-151.
Mossetti et al., "Imides: forgotten players in the Ugi reaction. One-pot multicomponent synthesis of quinazolinones", Chemical Communications, (2011), 47(24), 6966-6968.
Mraz et al., "miR-34a, miR-29c and miR-17-5p are downregulated in CLL patients with TP53 abnormalities", Leukemia (2009), vol. 23(6), pp. 1159-1163.
Natsugari, H. et al., "Novel, Potent, and Orally Active Substance P Antagonists: Synthesis and Antagonist Activity of N-Benzylcarboxamide Derivatives of Pyrido[3,4-b]pyridine," Journal of Medicinal Chemistiy (1995), 38(16), 3106-20.
Ni et al., "Functional Characterization of an Isoform-Selective Inhibitor of PI3K-p110b as a Potential Anticancer Agent", Cancer Discovery, May 2012, vol. 2, pp. 425-433.
Okkenhaug, K., "Signaling by the Phosphoinositide 3-Kinase Family in Immune Cells", Annu. Rev. Immunol., 2013, vol. 31, pp. 675-704.
Pandey, V.K. et al., "Quinazolylthiazoles as CNS acting agents," Acta Pharmaceutica (Zagreb) (1996), 46(1), 51-9.
Pandey, V.K. et al., "Synthesis and antiviral activity of quinazolinyl sydnones," Indian Journal of Heterocyclic Chemistiy (2006), 15(4), 399-400.
Pandey, V.K. et al., "Synthesis of 1-(2'-aryl-4'-oxo(3H)quinazolyl)-3-aryl-5-phenyl-formazans as potential anti-viral agents," Indian Drugs (1999), 36(1), 37-40.

(56) References Cited

OTHER PUBLICATIONS

Pandey, V.K., "Antiparkinsonism and CNS activities of (±)-2-aryl/alkyl-3-{b-(3',4'-dihydroxyphenyl)ethyl}quinazolin-4(3H)-ones," Biological Memoirs (1985), 11(2), 213-15.
Pandey, V.K., "Possible antiparkinsonian compounds. Part XI. Synthesis of 2-aryl/alkyl-3-[b-(3':4'-dihydroxyphenyl)ethyl]-quinazoline(3H)-4-one and2-aryl/alkyl-3-[(7'-(phenothiazinyl)-ethyl]-quinazoline(3H)-4-one," Acta Ciencia Indica (1978), 4(3), 230-5.
Parrish, C et al., "Novel ATP-Competitive Kinesin Spindle Protein Inhibitors," Journal of Medicinal Chemistry (2007), 50(20), 4939-4952.
Pattan, S. et al., "Synthesis and microbiological evaluation of N'-3-(4-(4-chlorophenyl)thiazol-2-yl)quinazolin-4(3H)-ones," Indian Journal of Heterocyclic Chemistry (2005), 15(1), 79-80.
Pattan, S. et al., "Synthesis of N-3(4-(4-chlorophenyl thiazole-2-yl)-(2-(amino)methyl)-quinazoline-4(3H)-one and their derivatives for antitubercular activity," Indian Journal of Chemistry, Section B: Organic Chemistry Including Medicinal Chemistry (2006), 45B(7), 1778-1781.
Pinkerton, A. et al., "Synthesis and SAR of thiophene containing kinesin spindle protein (KSP) inhibitors," Bioorganic & Medicinal Chemistry Letters (2007), 17(13), 3562-3569.
Poupert, J.H., "Drug Design: Basic Principles and Applications", 2 Encyclopedia of Pharmaceutical Technology, 1362-1369, (James Swarbrick ed., 3rd ed., 2007).
Purcell, J. et al., "Activity of the kinesin spindle protein inhibitor ispinesib (SB-715992) in models of breast cancer," Clinical Cancer Research (2010), 16(2), 566-576.
Ries, et al., "Targeting Tumor-Associated Macrophages with Anti-CSF-IR Antibody Reveals a Strategy for Cancer Therapy", Cancer Cell, vol. 25, Issue 6, Jun. 16, 2014, pp. 846-859.
Rodriguez et al., "Synthesis and characterization of tritylthioethanamine derivatives with potent KSP inhibitory activity", Bioorganic & Medicinal Chemistry (2011), 19(18), 5446-5453.
Rommel et al., Taking PI3Kδ and PI3Kγ One Step Ahead: Dual Active PI3Kδ/γ Inhibitors for the Treatment of Immune-Mediated Inflammatory Diseases, Phosphoinositide 3-Kinase in Health and Disease, 2011, vol. 1, pp. 279-299.
Roy et al., "DDB2 Suppresses Epithelial-to-Mesenchymal Transition in Colon Cancer", Cancer Res Jun. 15, 2013, 73(12), pp. 3771-3782.
Sakowicz, R. et al., "Antitumor Activity of a Kinesin Inhibitor," Cancer Research (2004), 64(9), 3276-3280.
Saleh, R.M. et al., "Synthesis and reactions of 2-[1-benzamido-2-(o-chlorophenyl)vinyl]-4H-3,1-benzoxazin-4-one," Revue Roumaine de Chimie (1994), 39(5), 567-76.
Saleh, R.M. et al., "Synthesis and some reactions of 2-(a-benzamido-p-chlorostyryl)-3,1-benzoxazin-4-one," Pakistan Journal of Scientific and Industrial Research (1991), 34(11), 417-21.
Schmid et al., "PI3 Kinase gamma control of Arginase-1 expression promotes tumor immunosuppression", Cancer Research, Apr. 15, 2012, vol. 72, Issue 8, Supplement 1, Abstract 411.
Schmid et al., "ReceptorTyrosineKinasesandTLR/IL1Rs Unexpectedly Activate Myeloid Cell PI3Kg, A Single Convergent Point Promoting Tumor Inflammation and Progression", Cancer Cell, vol. 19, Issue 6, Jun. 14, 2011, pp. 715-727.
Sheth, P. et al., "Novel Benzimidazole Inhibitors Bind to a Unique Site in the Kinesin Spindle Protein Motor Domain," Biochemistry (2010), 49(38), 8350-8358.
Sheth, P. et al., "Thermodynamics of Nucleotide and Inhibitor Binding to Wild-Type and Ispinesib-Resistant Forms of Human Kinesin Spindle Protein," Biochemistry (2009), 48(46), 11045-11055.
Singh, B. et al., "4-Quinazolones. II. Synthesis of some imidazo[1,5-a]quinazolin-5(4H)ones," Journal of the Indian Chemical Society (1969), 46(1), 21-5.
Singh, R. et al., "Synthesis and pharmacological screening of some 2-aryl-3-(phenyl-aryl-hydrazonyl)quinazolin-(3H)4-ones," Indian Drugs (1990), 28(2), 70-4.

Soliman et al., "Synthesis and reactions of substituted benzoxazinones bearing a bulky group at position 2," Revue Roumaine de Chimie (1992), 37(10), 1153-8.
Soliman et al., "Synthesis and reactions of substituted benzoxazinones bearing a bulky group at position 2," Delta Journal of Science (1990), 14(1), 166-80.
Sorbera, L.A. et al., "Ispinesib mesilate," Drugs of the Future (2006), 31(9), 778-787.
Storelli, S. et al., "Synthesis and structure-activity relationship of 3-phenyl-3H-quinazolin-4-one derivatives as CXCR3 chemokine receptor antagonists," Bioorganic & Medicinal Chemistry Letters (2005), 15(11), 2910-2913.
Storelli, S. et al., "Synthesis and structure-activity relationships of 3H-quinazolin-4-ones and 3H-pyrido[2,3-d]pyrimidin-4-ones as CXCR3 receptor antagonists," Archiv der Pharmazie (Weinheim, Germany) (2007), 340(6), 281-291.
Tang, P. et al., "Phase II study of ispinesib in recurrent or metastatic squamous cell carcinoma of the head and neck," Investigational New Drugs (2008), 26(3), 257-264.
Theoclitou et al., "Discovery of(+)-N-(3-Aminopropyl)-N-[1-(5-benzyl-3-methyl-4-oxo-[1,2]thiazolo[5,4-d ]pyrimidin-6-yl)-2-methylpropyl]-4-methylbenzamide (AZD4877), a Kinesin Spindle Protein Inhibitor and Potential Anticancer Agent," Journal of Medicinal Chemistry (2011), 54(19), 6734-6750.
Tiwari, A. et al., "Synthesis and biological properties of 4-(3H)-quinazolone derivatives," European Journal of Medicinal Chemistry (2007), 42(9), 1234-1238.
Tiwari, S. et al., "Possible antifertility compounds—Part III: Synthesis of 2-hippuryl-3-arylquinazolinones," Journal of the Chemical Society of Pakistan (1981), 3(4), 215-17.
Tiwari, S. et al., "Synthesis and central nervous systems activity of 2-aryl-3(3',4'-dihydroxyphenylethyl)-6,8-substituted 4(3H)-quinazolinones," Indian Journal of Pharmaceutical Sciences (1978), 40(2), 40-3.
Tiwari, S. et al., "Synthesis of possible antiparkinsonian compounds. X. Synthesis of 2,6,8-trisubstituted benzoxazinones and their corresponding 3-hydroxyquinazolinones," Journal of the Indian Chemical Society (1975), 52(8), 736-7.
Topalian et al., "Safety, Activity, and Immune Correlates of Anti-PD-1 Antibody in Cancer", N Engl J Med 2012, 366(26), pp. 2443-2454.
Valensin S., et al., "KIF11 inhibition for glioblastoma treatment: reason to hope or a struggle with the brain?" BMC Cancer (2009), 9.
Voultsiadou et al., "Recent advances of kinesin motor inhibitors and their clinical progress", Reviews on Recent Clinical Trials (2011), 6(3), 271-277.
Wang, F. et al., "Triphenylbutanamines: Kinesin Spindle Protein Inhibitors with in Vivo Antitumor Activity," Journal of Medicinal Chemistry (2012), 55 (4), 1511-1525.
Watkins, W. et al., "Quinazolinone fungal efflux pump inhibitors. Part 2: In vitro structure-activity relationships of (N-methylpiperazinyl)-containing derivatives," Bioorganic & Medicinal Chemistry Letters (2004), 14(20), 5133-5137.
White, M., "Targeting mitotic fragility in cancer," Future Oncology (2009), 5(5), 613-615.
Wolchok et al., "Antitumor response and new lesions in advanced melanoma patients on ipilimumab treatment", Wolchok et al., J. Clin. Oncology, 2008 ASCO (Post-Meeting Edition), vol. 26, No. 15S (May 20 Suppl), Abstract 3020.
Wolchok et al., "Nivolumab plus Ipilimumab in Advanced Melanoma", NEJM, 2013, vol. 369, pp. 122-133.
Wurth et al., "CXCL12 modulation of CXCR4 and CXCR7 activity in human glioblastoma stem-like cells and regulation of the tumor microenvironment," Frontiers in Cellular Neuroscience, May 2014, vol. 8, Article 144, pp. 1-19.
Zhang, B. et al., "Crystal structure of HsEg5 in complex with clinical candidate CK0238273 provides insight into inhibitory mechanism, potency, and specificity," Biochemical and Biophysical Research Communications (2008), 72(4), 565-570.
Zhang, B. et al., "Development of a high-throughput robotic fluorescence-based assay for HsEg5 inhibitor screening," Analytical Biochemistry (2005), 345(2), 326-335.

(56) References Cited

OTHER PUBLICATIONS

Banham-Hall et al., "The therapeutic potential for PI3K inhibitors in autoimmune and rheumatic diseases", Open Rheumatol. J. 2012, 6, 245-258.
Bell et al., "SAR studies around a series of triazolopyridines as potent and selective PI3Kc inhibitors", Bioorg. Med. Chem, Lett. 2012, 22, 5257-5263.
Bergamini et al., "A selective inhibitor reveals PI3Kγ dependence of TH17 cell differentiation", Nat. Chem. Biol. 2012, 8, 576-582.
Brachman et al., "PI3K and mTOR inhibitors—a new generation of targeted anticancer agents", Current Opinion in Cell Biology (2009), vol. 21, pp. 194-198.
Bruce et al., "Development of isoform selective PI3K-kinase inhibitors as pharmacological tools for elucidating the PI3K pathway", Bioorg. Med. Chem. Lett. 2012, 22, 5445-5450.
Cantley, L.C., "The phosphoinositide 3-kinase pathway", Science, 2002, 296, 1655-1657.
Collier et al., "Discovery of highly isoform selective thiazolopiperidine inhibitors of phosphoinositide 3-kinase γ", J. Med. Chem. 2015, 58, 5684-5688.
Collier et al., "Structural basis for isoform selectivity in a class of benzothiazole inhibitors of phosphoinositide 3-kinase γ", J. Med Chem. 2015, 58, 517-521.
Dagia et al., "A preferential p110α/γ PI3K inhibitor attenuates experimental inflammation by suppressing the production of proinflammatory mediators in a NF-κB-dependent manner", American Journal of Physiology—Cell Physiology (2010), vol. 298, pp. 929-941.
DeHenau et al., "Checkpoint Blockade Therapy is Improved by Altering the Immune-Suppressive Microenvironment with IPI-549, a Potent and Selective Inhibitor of PI3K-γ, in Preclinical Models," AACR Annual Meeeting 2016, Apr. 17, 2016, New Orleans, Poster 554.
Dushianthan et al., "Acute respiratory distress syndrome and acute lung injury", Post Graduate Medical Journal (2011), vol. 87, pp. 612-622.
Engelman, J. "Targeting PI3K signalling in cancer: opportunities, challenges and limitations", Nature Reviews: Cancer. vol. 9 (2009), pp. 550-562.
Evans, "Principles of Radiopharmacology", Colombett, L.G editor, CRC Press, 1979, pp. 11-13 and 24.
Ghigo et al., "PI3K Inhibition in Inflammation: Toward tailored therapies for specific diseases," BioEssays 32 (2010), pp. 185-196.
Gunderson et al., "Bruton tryrosine kinase-dependent immune cell cross-talk drives pancreas cancer", Cancer Discovery 2016, 6, 270-285.
Hawkins et al., PI3K signalling in inflammation. Biochim. Biophys. Acta, Mol. Cell Biol. Lipids 2015, 1851, 882-897.
Hirsch, E. et al., "Taming the PI3K team to hold inflammation and cancer at bay", Pharmacology & Therapeutics (2008), vol. 118, pp. 192-205.
Joshi et al., "A macrophage-dominant PI3K isoform controls hypoxia-induced HIF1alpha nad HIF2alpha stability and tumor growth, angiogenesis, and metastasis", Mol. Cancer. Res. 2014, 12, 1520-1531.
Kolliputi, N. et al., "IL-6 cytoprotection in hyperoxic acute lung injury occurs via PI3K/Akt-mediated Bax phosphorylation", American Journal of Physiology, Lung Cellular and Molecular Physiology (2009), vol. 297, pp. L6-L16.
Kong, D. et al., "Phosphatidylinositol 3-kinase inhibitors: promising drug candidates for cancer therapy", Cancer Science (2008), vol. 9, pp. 1734-1740.
Kutok et al., "The Potent and Selective Phosphoinositide-3-Kinase (PI3K)-γ Inhibitor, IPI-549, Inhibits Tumor Growth in Murine Syngeneic Solid Tumor Models through Alterations in the Immune Suppressive Microenvironment", CRI-CIMT-EATI-AACR—The Inaugural International Cancer Immunotherapy Conference, Sep. 18, 2015, New York, NY, Poster.
Leahy et al., "Discovery of a novel series of potent and orally bioavailable phosphoinositide 3-kinase γ inhibitiors", J. Med. Chem. 2012, 55, 5467-5482.

Liu, Q. et al. "mTOR mediated anti-cancer drug discovery", Drug Discovery Today: Therapeutic Strategies, (2009), vol. 6, p. 47-55.
NCT02637531: A dose-escalation study to evaluate the safety, tolerability, pharmacokinetics, and pharmacodynamics of IPI-549, www.clinicaltrials.gov, May 19, 2016.
Oka et al., "Discovery of N-{5-[3-(3-hydroxypiperdin-1-yl)-1,2,4-oxadiazol-5-yl]-4-methyl-1,3-thiazol-2-yl}acetamide (TASP0415914) as an orally potent phosphoinosititide 3-kinase γ inhibitor for the treatment of inflammatory diseases", Bioorg. Med. Chem. 2013, 21, 7578-7583.
Reif et al., "Cutting Edge: Differential Roles for Phosphoinositide 3-Kinases, p110γ and p110δ, in Lymphocyte Chemotaxis and Homing," J. Immunol. 173:2236-2240 (2004).
Rivera et al., "Intratumoral myeloid cells regulate repsoniveness and resistance to antiangiogenic therapy", Cell Rep. 2015, 11, 577-591.
Shuttleworth et al., "Progress in the Preclinical Discovery and Clinical Development of Class I and Dual Class I/IV Phosphoinositide 3-Kinase (PI3K) Inhibitors", Current Medicinal Chemistry (2011), vol. 18, pp. 2686-2714.
Sunose et al., "Discovery of 5-(2-amino-[1,2,4]triazolo[1,5-a]pyridin-7-yl)-N-(tert-butyl)pyridine-3-sulfonamide (CZC24758), as a potent, orally bioavailable and selective inhibitor of PI3K forthe treatment of inflammatory disease", Bioorg. Med. Chem. Lett. 2012, 22, 4613-4618.
Thorpe et al.,"PI3K in cancer: divergent rols of isoforms, modes of activation and therapeutic targeting", Nat. Rev. Cancer 2015, 15, 7-24.
Tolcher et al., "A Phase 1/1b First-In-Human Study of IPI-549, a PI3K-g Inhibitor, as Monotherapy and in Combination with an Anti-PD1 Antibody in Subjects with Advanced Solid Tumors", ASCO Annual Meeting 2016, Jun. 3-7, Chicago, IL, Poster.
Vanhaesebroeck et al., "Molecules in medicine mini-review: isoforms of PI3K in biology and disease", J. Mol. Med. 2016, 94, 5-11.
Winkler et al., "PI3K-d and PI3K-g Inhibition by IPI-145 Abrogates Immune Responses and Suppresses Activity in Autoimmune and Inflammatory Disease Models," Chem. Biol. 2013, 20, 1364-1374.
Brunk et al., "Anti-PD-L1 therapy yielded durable responses in early NSCLC trials, Oncology Practice Digital Network", Feb. 2014, pp. 1-3.
Tomasini et al., "Ipilimumab: its potential in non-small cell lung cancer", Ther Ad Med Oncol, 2012, Issue 4, No. 2, pp. 43-50.
Evans et al., "Discovery of a Selective Phosphoinositide-3-Kinase {PI3K}-γ Inhibitor (IPI-549) as an Immuno-Oncology Clinical Candidate," ACS Med. Chem. Lett., 2016, 7, 862-867.
Golub, T.R., et al., "Molecular classification of Cancer: Class Discover and Class Predication by Expression Monitoring," Science, 286:531-537, 1999.
Pomel et al., "Furan-2-ylmethylene Thiazolidinediones as Novel, Potent, and Selective Inhibitors of Phosphoinositide 3-Kinase γ," J. Med. Chem. 49:3857-3871, 2006.
Braga et al., "Crystal polymorphism and multiple crystal forms," Struct. Bond. 132:25-50 (2009).
Zell et al., "Investigation of polymorphism in aspartame and neotame using solid-state NMR spectroscopy," Tetrahedron, 56:6603-6616 (2000).
Pirrung, "Handbook of Synthetic Organic Chemistry," 2nd Ed., 2017, p. 178.
Bernstein, "Polymorphism in Molecular Crystals," Oxford, 2002, p. 46.
Guillory, "Generation of Polymorphs, Hydrates, Solvates, and Amorphous Solids". Chapter 5 in Polymorphism in Pharmaceutical Solids, Ed. By Hany G. Brittain, Dekker: New York, 1999, pp. 183-226.
Brittain, "Effects of Pharmaceutical Processing on Drug Polymorphs and Solvates", Chapter 8 in Polymorphism is Pharmaceutical Solids, Ed. By Hany G. Brittain, Dekker: New York, 1999, pp. 331-360.
Sapey et al., "Abnormal Neutrophil Migration Is a Feature of Early COPO, Present Across Disease Phenotypes and Causally Related to Increased PhosphoINOSitide-3-Kinase Signalling", American Journal of Respiratoly and Critical Care Medicine, 2013, vol. 187, Supp., A3492.

(56) References Cited

OTHER PUBLICATIONS

Pitt et al., "Resistance Mechanisms to Immune-Checkpoint Blockade in Cancer: Tumor-Intrinsic and -Extrinsic Factors", Immunity, 2016, 44, 1255-1269.
Kushner et al., "Pharmacological uses and perspectives of heavy water and deuterated compounds", Can. J. Physiol. Pharmacol. 77: 79-88 ( 1999).
Tung, "The Development of Deuterium-Containing Drugs", 2010.
Anderson et al., "The Use of Esters of N-Hydroxy succinimide in Peptide Synthesis," Journal of the American Chemical Society, 1964, 86:1839-1842.
El-Faham et al., "Peptide Coupling Reagents, More than a Letter Soup," Chem. Rev. 2011, 111:6557-6602.
"Top 10 experimental cancer drugs—2013", May 30, 2013, retrieved from the Internet: https://www.fiercebiotech.com/rd/top-10-experimental-cancer-drugs-2013 [accessed Aug. 2, 2022].
Brahmer et al., "Safety and Activity of Anti-PD-L1 Antibody in Patients with Advanced Cancer", N. Engl, J. Med., 2012, 366(26), 2455-2465.
Makino et al., "Anti-proliferative and anti-migratory properties of coffee diterpenes kahweol acetate and cafestol in human renal cancer cells", Sci. Rep., 2021, 11, 675, 10 pages.
Fruman et al., "PI3K and cancer: lessons, challenges and opportunities", *Nature Reviews Drug Discovery*, 2014, 13(2): 140-156.
McDermott et al., "PD-1 as a potential target in cancer therapy", *Cancer Medicine*, 2013, 2(5):662-673.

\* cited by examiner

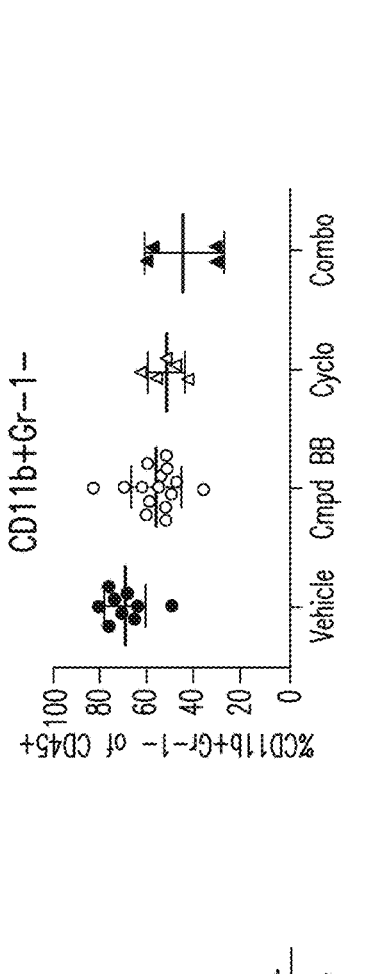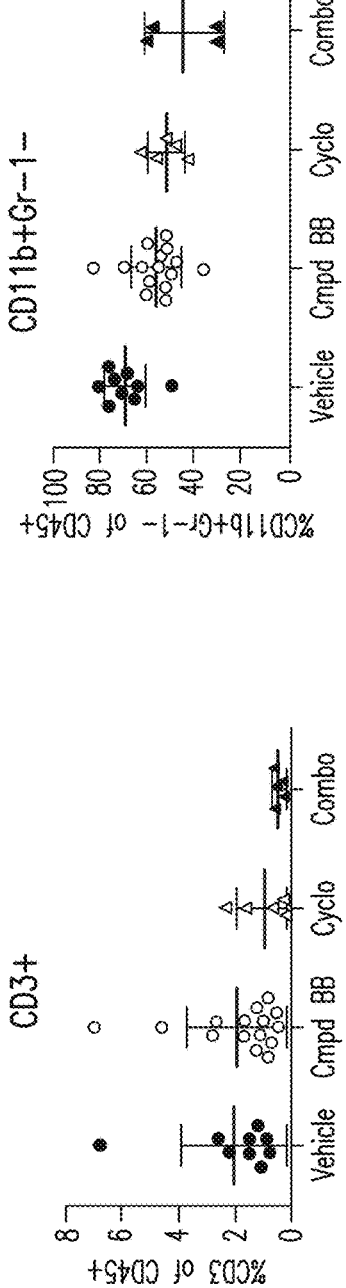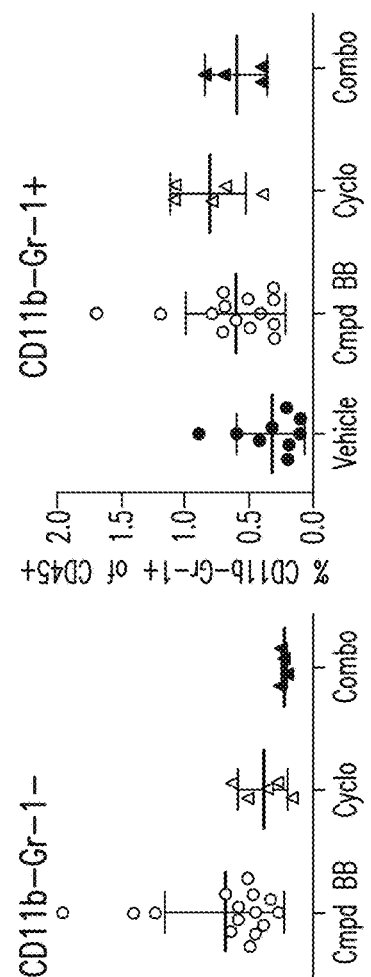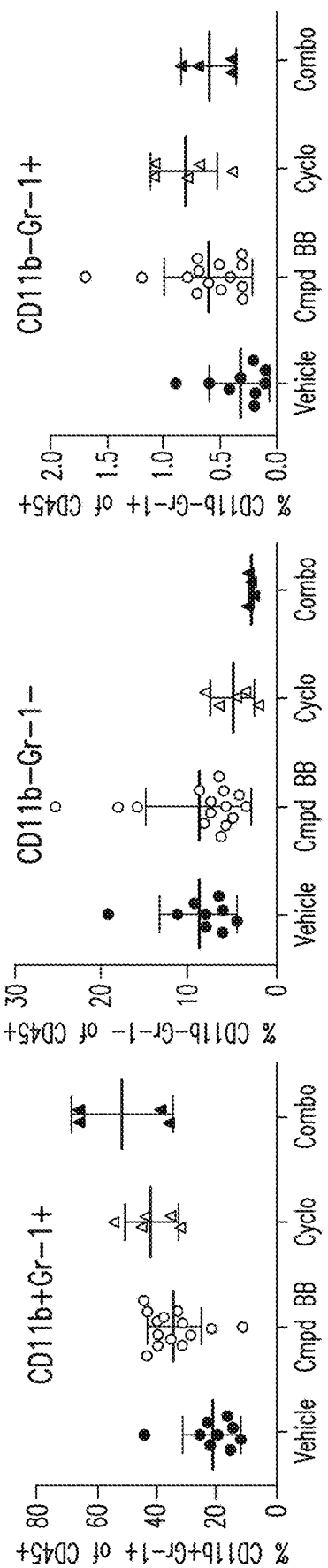
FIG. 49A  FIG. 49B  FIG. 49C  FIG. 49D  FIG. 49E

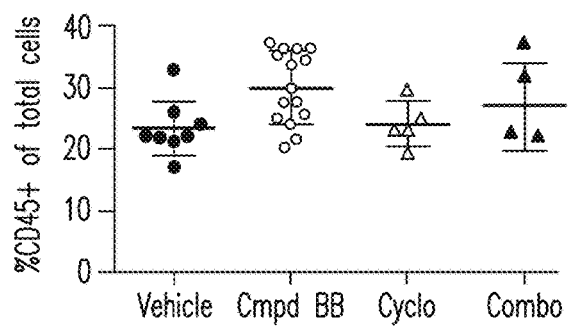 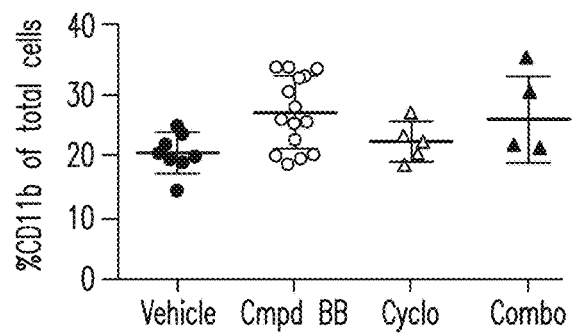
FIG. 52A  FIG. 52B
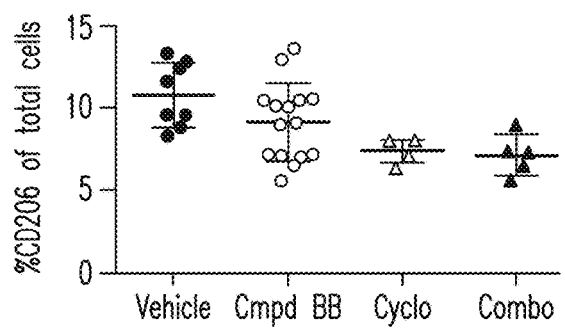
FIG. 52C
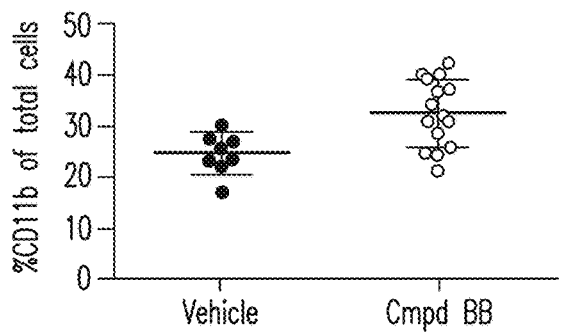 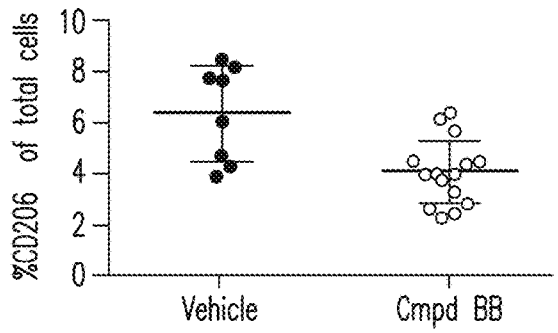
FIG. 52D  FIG. 52E

* Denotes significance vs vehicle by T test, Compound BB p=0.08

HETEROCYCLIC COMPOUNDS AND USES THEREOF

CROSS REFERENCES TO RELATED APPLICATIONS

This application is a continuation application of U.S. application Ser. No. 15/672,964, filed Aug. 9, 2017, which is a continuation application of U.S. application Ser. No. 14/661,656, filed Mar. 18, 2015, now U.S. Pat. No. 9,775,844, which claims priority to U.S. Provisional Application Nos. 61/955,717, filed Mar. 19, 2014, 61/980,484, filed Apr. 16, 2014, 62/000,923, filed May 20, 2014, 62/033,008, filed Aug. 4, 2014, 62/059,766, filed Oct. 3, 2014, 62/075,173, filed Nov. 4, 2014, and 62/101,980, filed Jan. 9, 2015, the entireties of which are incorporated herein by reference.

BACKGROUND

The activity of cells can be regulated by external signals that stimulate or inhibit intracellular events. The process by which stimulatory or inhibitory signals are transmitted into and within a cell to elicit an intracellular response is referred to as signal transduction. Over the past decades, cascades of signal transduction events have been elucidated and found to play a central role in a variety of biological responses. Defects in various components of signal transduction pathways have been found to account for a vast number of diseases, including numerous forms of cancer, inflammatory disorders, metabolic disorders, vascular and neuronal diseases (Gaestel et al. *Current Medicinal Chemistry* (2007) 14:2214-2234).

Kinases represent a class of important signaling molecules. Kinases can generally be classified into protein kinases and lipid kinases, and certain kinases exhibit dual specificities. Protein kinases are enzymes that phosphorylate other proteins and/or themselves (i.e., autophosphorylation). Protein kinases can be generally classified into three major groups based upon their substrate utilization: tyrosine kinases which predominantly phosphorylate substrates on tyrosine residues (e.g., erb2, PDGF receptor, EGF receptor, VEGF receptor, src, abl), serine/threonine kinases which predominantly phosphorylate substrates on serine and/or threonine residues (e.g., mTorC1, mTorC2, ATM, ATR, DNA-PK, Akt), and dual-specificity kinases which phosphorylate substrates on tyrosine, serine and/or threonine residues.

Lipid kinases are enzymes that catalyze the phosphorylation of lipids. These enzymes, and the resulting phosphorylated lipids and lipid-derived biologically active organic molecules play a role in many different physiological processes, including cell proliferation, migration, adhesion, and differentiation. Certain lipid kinases are membrane associated and they catalyze the phosphorylation of lipids contained in or associated with cell membranes. Examples of such enzymes include phosphoinositide(s) kinases (e.g., PI3-kinases, PI4-kinases), diacylglycerol kinases, and sphingosine kinases.

The phosphoinositide 3-kinases (PI3Ks) signaling pathway is one of the most highly mutated systems in human cancers. PI3K signaling is also a key factor in many other diseases in humans. PI3K signaling is involved in many disease states including allergic contact dermatitis, rheumatoid arthritis, osteoarthritis, inflammatory bowel diseases, chronic obstructive pulmonary disorder, psoriasis, multiple sclerosis, asthma, disorders related to diabetic complications, and inflammatory complications of the cardiovascular system such as acute coronary syndrome.

PI3Ks are members of a unique and conserved family of intracellular lipid kinases that phosphorylate the 3'-OH group on phosphatidylinositols or phosphoinositides. The PI3K family comprises 15 kinases with distinct substrate specificities, expression patterns, and modes of regulation. The class I PI3Ks (p110α, p110β, p110δ, and p110γ) are typically activated by tyrosine kinases or G-protein coupled receptors to generate PIP3, which engages downstream effectors such as those in the Akt/PDK1 pathway, mTOR, the Tec family kinases, and the Rho family GTPases. The class II and III PI3Ks play a key role in intracellular trafficking through the synthesis of PI(3)P and PI(3,4)P2. The PI3Ks are protein kinases that control cell growth (mTORC1) or monitor genomic integrity (ATM, ATR, DNA-PK, and hSmg-1).

The delta (δ) isoform of class I PI3K has been implicated, in particular, in a number of diseases and biological processes. PI3K-δ is expressed primarily in hematopoietic cells including leukocytes such as T-cells, dendritic cells, neutrophils, mast cells, B-cells, and macrophages. PI3K-δ is integrally involved in mammalian immune system functions such as T-cell function, B-cell activation, mast cell activation, dendritic cell function, and neutrophil activity. Due to its integral role in immune system function, PI3K-δ is also involved in a number of diseases related to undesirable immune response such as allergic reactions, inflammatory diseases, inflammation mediated angiogenesis, rheumatoid arthritis, and auto-immune diseases such as lupus, asthma, emphysema and other respiratory diseases. Other class I PI3K involved in immune system function includes PI3K-γ, which plays a role in leukocyte signaling and has been implicated in inflammation, rheumatoid arthritis, and autoimmune diseases such as lupus. For example, PI3K-γ and PI3K-δ are highly expressed in leukocytes and have been associated with adaptive and innate immunity; thus, these PI3K isoforms can be important mediators in inflammatory disorders and hematologic malignancies.

The gamma (γ) isoform of class I PI3K consists of a catalytic subunit p110γ, which is associated with a p101 regulatory subunit. PI3K-γ is regulated by G protein-coupled receptors (GPCRs) via association with the β/γ subunits of heterotrimeric G proteins. PI3K-γ is expressed primarily in hematopoietic cells and cardiomyocytes and is involved in inflammation, the innate immune response, myeloid cell differentiation, immune cell trafficking, and mast cell function. Inhibitors of PI3K-γ are useful for treating a variety of inflammatory diseases, allergies, and cardiovascular diseases, among others.

Unlike PI3K-δ, the beta (β) isoform of class I PI3K appears to be ubiquitously expressed. PI3K-β has been implicated primarily in various types of cancer including PTEN-negative cancer (Edgar et al. *Cancer Research* (2010) 70(3):1164-1172), and HER2-overexpressing cancer such as breast cancer and ovarian cancer.

SUMMARY

Described herein are compounds capable of selectively inhibiting one or more isoform(s) of class I PI3K without substantially affecting the activity of the remaining isoforms of the same class. For example, in some embodiments, non-limiting examples of inhibitors capable of selectively inhibiting PI3K-δ and/or PI3K-γ, but without substantially affecting the activity of PI3K-α and/or PI3K-β are disclosed. In one embodiment, the inhibitors provided herein can be effective in ameliorating disease conditions associated with PI3K-δ and/or PI3K-γ activity. In one embodiment, the compounds are capable of selectively inhibiting PI3K-γ over PI3K-δ.

In one aspect, provided herein are compounds of Formula (I″) or (A″):

Formula (I″)

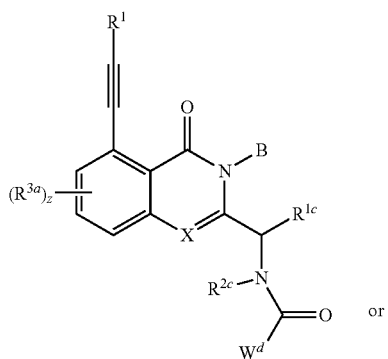

or

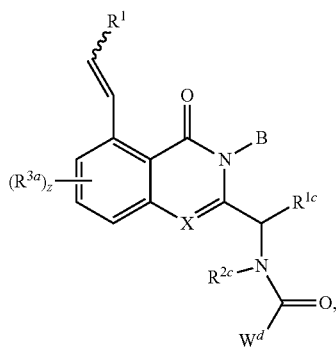

Formula (A″)

or an enantiomer, a mixture of enantiomers, or a mixture of two or more diastereomers thereof, or a pharmaceutically acceptable form thereof, wherein $R^{3a}$, z, $R^{1c}$, $R^{2c}$, $R^1$, X, B, and $W^d$ are defined herein.

In one aspect, provided herein are compounds of Formula (I′) or (A′):

Formula (I′)

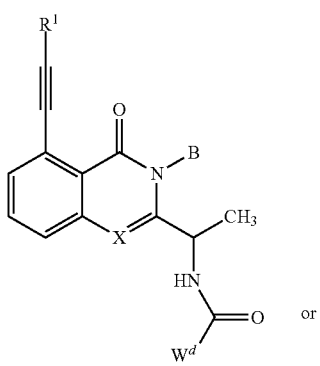

or

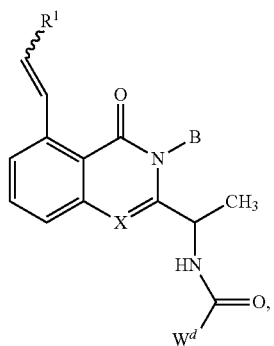

Formula (A′)

or an enantiomer, a mixture of enantiomers, or a mixture of two or more diastereomers thereof, or a pharmaceutically acceptable form thereof, wherein $R^1$, X, B, and $W^d$ are defined herein.

In one aspect, provided herein are compounds of Formula (I) or (A):

Formula (I)

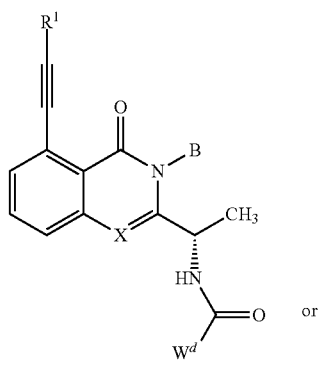

or

Formula (A)

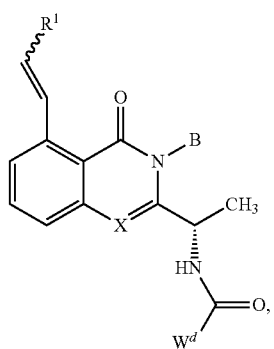

or an enantiomer, a mixture of enantiomers, or a mixture of two or more diastereomers thereof, or a pharmaceutically acceptable form thereof, wherein $R^1$, X, B, and $W^d$ are defined herein.

In one embodiment, the compound of Formula (I″), (I′), (I), (A″), (A′), or (A) is predominately in an (S)-stereochemical configuration. In one embodiment, the compound of Formula (I″), (I′), (I), (A″), (A′), or (A) is the S enantiomer having an enantiomeric excess selected from greater than about 25%, greater than about 55%, greater than about 80%, greater than about 90%, and greater than about 95%. In one embodiment, the compound is present in a pharmaceutical composition comprising the compound, or a pharmaceutically acceptable salt thereof, and one or more pharmaceutically acceptable excipients.

In certain embodiments, a compound disclosed herein selectively modulates PI3K gamma isoform. In certain embodiments, the compound selectively inhibits the gamma isoform over the alpha or beta isoform. By way of non-limiting example, the ratio of selectivity can be greater than a factor of about 10, greater than a factor of about 50, greater than a factor of about 100, greater than a factor of about 200, greater than a factor of about 400, greater than a factor of about 600, greater than a factor of about 800, greater than a factor of about 1000, greater than a factor of about 1500, greater than a factor of about 2000, greater than a factor of about 5000, greater than a factor of about 10,000, or greater than a factor of about 20,000, where selectivity can be measured by ratio of $IC_{50}$ values, among other means. In one embodiment, the selectivity of PI3K gamma isoform over PI3K alpha or beta isoform is measured by the ratio of the $IC_{50}$ value against PI3K alpha or beta isoform to the $IC_{50}$ value against PI3K gamma isoform.

In certain embodiments, a compound disclosed herein selectively modulates PI3K gamma isoform over the delta isoform. By way of non-limiting example, the ratio of selectivity can be greater than a factor of about 10, greater than a factor of about 50, greater than a factor of about 100, greater than a factor of about 200, greater than a factor of about 400, greater than a factor of about 600, greater than a factor of about 800, greater than a factor of about 1000, greater than a factor of about 1500, greater than a factor of about 2000, greater than a factor of about 5000, greater than a factor of about 10,000, or greater than a factor of about 20,000, where selectivity can be measured by ratio of $IC_{50}$ values, among other means. In one embodiment, the selectivity of PI3K gamma isoform over PI3K delta isoform is measured by the ratio of the $IC_{50}$ value against PI3K delta isoform to the $IC_{50}$ value against PI3K gamma isoform.

In certain embodiments, a compound as disclosed herein selectively modulates PI3K delta isoform. In certain embodiments, the compound selectively inhibits the delta isoform over the alpha or beta isoform. By way of non-limiting example, the ratio of selectivity can be greater than a factor of about 10, greater than a factor of about 50, greater than a factor of about 100, greater than a factor of about 200, greater than a factor of about 400, greater than a factor of about 600, greater than a factor of about 800, greater than a factor of about 1000, greater than a factor of about 1500, greater than a factor of about 2000, greater than a factor of about 5000, greater than a factor of about 10,000, or greater than a factor of about 20,000, where selectivity can be measured by ratio of $IC_{50}$ values, among other means. In one embodiment, the selectivity of PI3K delta isoform over PI3K alpha or beta isoform is measured by the ratio of the $IC_{50}$ value against PI3K alpha or beta isoform to the $IC_{50}$ value against PI3K delta isoform.

In certain embodiments, provided herein is a composition (e.g., a pharmaceutical composition) comprising a compound described herein and a pharmaceutically acceptable excipient. In some embodiments, provided herein is a method of inhibiting a PI3 kinase, comprising contacting the PI3 kinase with an effective amount of a compound or a pharmaceutical composition described herein. In certain embodiments, a method is provided for inhibiting a PI3 kinase wherein said PI3 kinase is present in a cell. The inhibition can take place in a subject suffering from a disorder selected from cancer, bone disorder, inflammatory disease, immune disease, nervous system disease (e.g., a neuropsychiatric disorder), metabolic disease, respiratory disease, thrombosis, and cardiac disease, among others. In certain embodiments, a second therapeutic agent is administered to the subject.

In certain embodiments, a method is provided for selectively inhibiting a PI3 kinase gamma isoform over PI3 kinase alpha or beta isoform wherein the inhibition takes place in a cell. Non-limiting examples of the methods disclosed herein can comprise contacting PI3 kinase gamma isoform with an effective amount of a compound or a pharmaceutical composition disclosed herein. In an embodiment, such contact can occur in a cell.

In certain embodiments, a method is provided for selectively inhibiting a PI3 kinase gamma isoform over PI3 kinase alpha or beta isoform wherein the inhibition takes place in a subject suffering from a disorder selected from cancer, bone disorder, inflammatory disease, immune disease, nervous system disease (e.g., a neuropsychiatric disorder), metabolic disease, respiratory disease, thrombosis, and cardiac disease, said method comprising administering an effective amount of a compound or a pharmaceutical composition provided herein to said subject. In certain embodiments, provided herein is a method of treating a subject suffering from a disorder associated with PI3 kinase, said method comprising selectively modulating the PI3 kinase gamma isoform over PI3 kinase alpha or beta isoform by administering an amount of a compound or a pharmaceutical composition provided herein to said subject, wherein said amount is sufficient for selective modulation of PI3 kinase gamma isoform over PI3 kinase alpha or beta isoform.

In certain embodiments, a method is provided for selectively inhibiting a PI3 kinase delta isoform over PI3 kinase alpha or beta isoform wherein the inhibition takes place in a cell. Non-limiting examples of the methods disclosed herein can comprise contacting PI3 kinase delta isoform with an effective amount of a compound or a pharmaceutical composition disclosed herein. In an embodiment, such contact can occur in a cell.

In certain embodiments, a method is provided for selectively inhibiting a PI3 kinase delta isoform over PI3 kinase alpha or beta isoform wherein the inhibition takes place in a subject suffering from a disorder selected from cancer, bone disorder, inflammatory disease, immune disease, nervous system disease (e.g., a neuropsychiatric disorder), metabolic disease, respiratory disease, thrombosis, and cardiac disease, said method comprising administering an effective amount of a compound or a pharmaceutical composition provided herein to said subject. In certain embodiments, provided herein is a method of treating a subject suffering from a disorder associated with PI3 kinase, said method comprising selectively modulating the PI3 kinase delta isoform over PI3 kinase alpha or beta isoform by administering an amount of a compound or a pharmaceutical composition provided herein to said subject, wherein said amount is sufficient for selective modulation of PI3 kinase delta isoform over PI3 kinase alpha or beta isoform.

In certain embodiments, a method is provided for selectively inhibiting a PI3 kinase gamma isoform over PI3 kinase delta isoform wherein the inhibition takes place in a cell. Non-limiting examples of the methods disclosed herein can comprise contacting PI3 kinase gamma isoform with an effective amount of a compound or a pharmaceutical composition disclosed herein. In an embodiment, such contact can occur in a cell.

In certain embodiments, a method is provided for selectively inhibiting a PI3 kinase gamma isoform over PI3 kinase delta isoform wherein the inhibition takes place in a subject suffering from a disorder selected from cancer, bone disorder, inflammatory disease, immune disease, nervous system disease (e.g., a neuropsychiatric disorder), metabolic disease, respiratory disease, thrombosis, and cardiac disease, said method comprising administering an effective amount of a compound or a pharmaceutical composition provided herein to said subject. In certain embodiments, provided herein is a method of treating a subject suffering from a disorder associated with PI3 kinase, said method comprising selectively modulating the PI3 kinase gamma isoform over PI3 kinase delta isoform by administering an amount of a compound or a pharmaceutical composition provided herein to said subject, wherein said amount is sufficient for selective modulation of PI3 kinase gamma isoform over PI3 kinase delta isoform.

In certain embodiments, provided herein is a method of inhibiting a PI3 kinase in a subject suffering from an inflammatory disease, an immune disease, or a respiratory disease, comprising administering to the subject an effective amount of a compound provided herein (e.g., a compound of any of Formulae (I"), (I'), (A'), (I), (A), (II), (III), (IV), (V), (VI), (VII), (IX), (X), (XI), (XII), (XIII), (XIV), (XV), (XVI), and (XVII), e.g., as described herein). In one embodiment, the compound is a selective PI3K-γ inhibitor, e.g., Compound 4. In one embodiment, the subject is a mammal. In one embodiment, the mammal is a human. In one embodiment, the subject is a human.

In some embodiments, the disorder treated by the methods or compounds disclosed herein is a cancer. In some embodiments, the cancer is a solid or soft tissue tumor (e.g., a carcinoid, carcinoma or sarcoma), a hematopoietic tissue tumor (e.g., a heme malignancy), or a metastatic lesion, e.g., a metastatic lesion of any of the cancers or tumors disclosed herein. In one embodiment, the cancer is metastatic cancer to the bone.

In one embodiment, the cancer treated by the methods or compounds disclosed herein is a a soft tissue tumor, a heme malignancy, or a hematological cancer. In one embodiment, the cancer is acute myeloid leukemia (AML), chronic myeloid leukemia (CML), myelodysplastic syndrome (MDS), myeloproliferative disorders, mast cell cancer, Hodgkin disease, non-Hodgkin lymphomas, diffuse large B-cell lymphoma, human lymphotrophic virus type 1 (HTLV-1) leukemia/lymphoma, AIDS-related lymphoma, adult T-cell lymphoma, acute lymphoblastic leukemia (ALL), T-cell acute lymphoblastic leukemia, B-cell acute lymphoblastic leukemia, chronic lymphocytic leukemia, or multiple myeloma (MM). In one embodiment, the cancer is leukemia or lymphoma. In one embodiment, the leukemia is B-cell acute lymphoblastic leukemia (B-ALL), acute myeloid leukemia (AML), acute lymphoblastic leukemia, chronic myeloid leukemia, hairy cell leukemia, myeloproliferative disorders, acute myelogenous leukemia (AML), chronic myelogenous leukemia (CML), chronic lymphocytic leukemia (CLL), multiple myeloma (MM), myelodysplastic syndrome (MDS), or mast cell cancer. In one embodiment, the lymphoma is diffuse large B-cell lymphoma, B-cell immunoblastic lymphoma, small non-cleaved cell or Burkitt lymphoma, human lymphotropic virus-type 1 (HTLV-1) leukemia/lymphoma, adult T-cell lymphoma, Hodgkin disease, or non-Hodgkin lymphomas, or a metastatic lesion thereof.

In one embodiment, the cancer treated by the methods or compounds disclosed herein is a solid tumor (e.g., a carcinoid, carcinoma or sarcoma), or a metastatic lesion thereof. In one embodiment, the cancer is a lung cancer (e.g., non-small cell lung cancer or small cell lung cancer); a skin cancer; a melanoma; a prostate cancer; a glioblastoma; an endometrial cancer; a pancreatic cancer (e.g., pancreatic adenocarcinoma (e.g., pancreatic ductal adenocarcinoma (PDA)); a renal cell carcinoma; a colorectal cancer; a breast cancer (e.g., triple negative breast cancer); a thyroid cancer; a sarcoma, a liver or hepatocellular cancer (HCC), a head and neck cancer, a cervical or vulvar cancer, an esophageal cancer, a gastric cancer, an adrenal cancer, or an ovarian cancer, or a metastatic lesion thereof. In one embodiment, the solid tumor is prostate cancer, breast cancer, or a glioblastoma, or a metastatic lesion thereof.

In some embodiments, the cancer or tumor treated is a solid, fibrotic tumor chosen from one or more of pancreatic (e.g., pancreatic adenocarcinoma or pancreatic ductal adenocarcinoma), breast, colorectal, colon, lung (e.g., a small or non-small cell lung cancer), skin, ovarian, prostate, cervix, gastrointestinal (e.g., carcinoid or stromal), stomach, head and neck, kidney, brain cancer, or a metastatic lesion thereof.

In some embodiments, the cancer or tumor treated using the methods or compounds disclosed herein is a cancer or tumor chosen from one or more of the head, neck, nasal cavity, paranasal sinuses, nasopharynx, oral cavity, oropharynx, larynx, hypopharynx, salivary glands, paragangliomas, pancreas, stomach, skin, esophagus, endometrium, liver and biliary tree, bone, intestine, colon, rectum, ovaries, prostate, lung, breast, lymphatic system, blood, bone marrow central nervous system, brain, or a metastatic lesion thereof.

In some embodiments, the disorder treated by the methods or compounds disclosed herein is an inflammatory disease or an immune disease. In one embodiment, the inflammatory disease or the immune disease is asthma, emphysema, allergy, dermatitis, arthritis (e.g., rheumatoid arthritis), psoriasis, lupus erythematosus, graft versus host disease, inflammatory bowel disease, eczema, scleroderma, Crohn's disease, or multiple sclerosis. In one embodiment, the disorder is rheumatoid arthritis. In one embodiment, the disorder is rheumatoid arthritis, and the amount of the compound is effective to ameliorate one or more symptoms associated with rheumatoid arthritis, wherein the symptom associated with rheumatoid arthritis is independently a reduction in the swelling of the joints, a reduction in serum anti collagen levels, a reduction in bone resorption, a reduction in cartilage damage, a reduction in pannus, or a reduction in inflammation.

In some embodiments, the disorder treated by the methods or compounds disclosed herein is a respiratory disease. In one embodiment, the respiratory disease is asthma, chronic obstructive pulmonary disease (COPD), chronic bronchitis, emphysema, or bronchiectasis. In one embodiment, the disorder is asthma.

In certain embodiments, a method is provided for selectively inhibiting a PI3 kinase gamma isoform over PI3 kinase alpha or beta isoform wherein the inhibition takes place in a subject suffering from a respiratory disease. In one embodiment, the respiratory disease is asthma, chronic obstructive pulmonary disease (COPD), chronic bronchitis, emphysema, or bronchiectasis. In one embodiment, the respiratory disease is asthma. In one embodiment, the respiratory disease is COPD. In one embodiment, the method further comprises administration of one or more therapeutic agents selected from chemotherapeutic agents, cytotoxic agents, and radiation. In one embodiment, the compound is administered in combination with an mTOR inhibitor. In one embodiment, the compound is administered in combination with one or more of: an agent that inhibits IgE production or activity, 2-(4-(6-cyclohexyloxy-2-naphtyloxy)phenylacetamide)benzoic acid, an mTOR inhibitor, rapamycin, a TORC1 inhibitor, a TORC2 inhibitor, an anti-IgE antibody, prednisone, corticosteroid, a leukotriene inhibitor, XOLAIR, ADVAIR, SINGULAIR, or SPIRIVA. In one embodiment, the compound is administered in combination with one or more of: a mitotic inhibitor, an alkylating agent, an anti-metabolite, an intercalating antibiotic, a growth factor inhibitor, a cell cycle inhibitor, an enzyme, a topoisomerase inhibitor, an anti-hormone, an angiogenesis inhibitor, an anti-androgen, or an anti-receptor kinase antibody. In one embodiment, the compound is administered in combination with one or more of: Imatinib Mesylate, bortezomib, bicalutamide, gefitinib, ADRIAMYCIN, alkylating agents, alkyl sulfonates, ethylenimines, altretamine, triethylenemelamine, trietylenephosphoramide, triethylenethiophosphaoramide, trimethylolomelamine, nitrogen mustards, chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard, nitrosureas, antibiotics, anti-metabolites, denopterin, methotrexate, pteropterin, trimetrexate, 5-fluorouracil (5-FU), fludarabine, 6-mercaptopurine, thiamiprine, thioguanine, ancitabine, azacitidine, 6-azauridine, carmofur, cytarabine, dideoxyuridine, doxifluridine, enocitabine, floxuridine, androgens, anti-adrenals, folic acid replenisher, arabinoside, cyclophosphamide, thiotepa, taxanes, anti-hormonal agents, anti-estrogens, tamoxifen, raloxifene, aromatase inhibiting 4(5)-imidazoles, 4-hydroxytamoxifen, trioxifene, keoxifene, onapristone, toremifene, anti-androgens, chlorambucil, gemcitabine, 6-thioguanine; mercaptopurine; cisplatin, carboplatin, vincristine; vinorelbine, vinblastin, ifosfamide, mitomycin C, daunorubicin, doxorubicin, mitoxantrone, HERCEPTIN, AVASTIN, ERBITUX, RITUXAN, TAXOL, ARIMIDEX, TAXOTERE, or an anti-receptor tyrosine kinase antibody selected from cetuximab, panitumumab, trastuzumab, anti CD20 antibody, rituximab, tositumomab, alemtuzumab, bevacizumab, obinutuzumab (GAZYVA), and gemtuzumab. In one embodiment, the compound is administered in combination with one or more of: bortezomib, ADRIAMYCIN, alkylating agents, anti-metabolites, denopterin, pteropterin, trimetrexate, a nitrogen mustard, chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard, methotrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, androgens, cyclophosphamide, taxanes, anti-hormonal agents, gemcitabine; cisplatin, carboplatin, vincristine, vinorelbine, vinblastin, ifosfamide, mitomycin C, daunorubicin, doxorubicin, mitoxantrone, HERCEPTIN, AVASTIN, ERBITUX, RITUXAN, TAXOL, ARIMIDEX, or TAXOTERE. In one embodiment, the compound is administered in combination with one or more of: non-steroidal anti-inflammatory drugs (NSAIDs), corticosteroids, prednisone, chloroquine, hydroxychloroquine, azathioprine, cyclophosphamide, methotrexate, cyclosporine, anti-CD20 antibodies, ENBREL, REMICADE, HUMIRA, AVONEX, or REBIF.

In one embodiment, provided herein is a method of inhibiting a PI3 kinase in a subject suffering from a cancer, comprising administering to the subject an effective amount of a compound provided herein (e.g., a compound of any of Formulae (I"), (I'), (A'), (I), (A), (II), (III), (IV), (V), (VI), (VII), (IX), (X), (XI), (XII), (XIII), (XIV), (XV), (XVI), and (XVII), e.g., as described herein). In one embodiment, the compound is a selective PI3K-γ inhibitor, e.g., Compound 4. In one embodiment, the cancer is selected from acute myeloid leukemia (AML), chronic myeloid leukemia (CML), myelodysplastic syndrome (MDS), myeloproliferative disorders, mast cell cancer, Hodgkin disease, non-Hodgkin lymphomas, diffuse large B-cell lymphoma, human lymphotrophic virus-type 1 (HTLV-1) leukemia/lymphoma, AIDS-related lymphoma, adult T-cell lymphoma, acute lymphoblastic leukemia (ALL), B-cell acute lymphoblastic leukemia, T-cell acute lymphoblastic leukemia, chronic lymphocytic leukemia, or multiple myeloma (MM). In one embodiment, the cancer is leukemia or lymphoma. In one embodiment, the leukemia is selected from B-cell acute lymphoblastic leukemia (B-ALL), acute lymphocytic leukemia, hairy cell leukemia, myelodysplasia, myeloproliferative disorders, acute myelogenous leukemia (AML), chronic myelogenous leukemia (CML), chronic lymphocytic leukemia (CLL), multiple myeloma (MM), myelodysplastic syndrome (MDS), or mast cell cancer. In one embodiment, the lymphoma is selected from diffuse large B-cell lymphoma, B-cell immunoblastic lymphoma, small non-cleaved cell or Burkitt lymphoma, human lymphotropic virus-type 1 (HTLV-1) leukemia/lymphoma, AIDS-related lymphoma, adult T-cell lymphoma, Hodgkin disease, or non-Hodgkin lymphomas. In one embodiment, the compound is administered in combination with one or more therapeutic agents provided herein.

In one embodiment, provided herein is a method of inhibiting a PI3 kinase in a subject suffering from an inflammatory disease or an immune disease, comprising administering to the subject an effective amount of a compound provided herein (e.g., a compound of any of Formulae (I"), (I'), (A'), (I), (A), (II), (III), (IV), (V), (VI), (VII), (IX), (X), (XI), (XII), (XIII), (XIV), (XV), (XVI), and (XVII), e.g., as described herein). In one embodiment, the compound is a selective PI3K-γ inhibitor, e.g., Compound 4. In one embodiment, the inflammatory disease or immune disease is asthma, emphysema, allergy, dermatitis, rheumatoid arthritis, psoriasis, lupus erythematosus, graft versus host disease, inflammatory bowel disease, eczema, scleroderma, Crohn's disease, or multiple sclerosis. In one embodiment, the inflammatory disease or immune disease is rheumatoid arthritis. In one embodiment, the compound is administered in combination with one or more therapeutic agents provided herein.

In one embodiment, provided herein is a method of inhibiting a PI3 kinase in a subject suffering from a respiratory disease, comprising administering to the subject an effective amount of a compound provided herein (e.g., a compound of Formula I). In one embodiment, the respiratory disease is asthma, chronic obstructive pulmonary disease (COPD), chronic bronchitis, emphysema, or bronchiectasis. In one embodiment, the respiratory disease is asthma. In one embodiment, the compound is administered in combination with one or more therapeutic agents provided herein.

In certain embodiments, provided herein is a method of inhibiting PI3K-γ in a subject, comprising administering to the subject an effective amount of a compound provided herein (e.g., a compound of any of Formulae (I"), (I'), (A'), (I), (A), (II), (III), (IV), (V), (VI), (VII), (IX), (X), (XI), (XII), (XIII), (XIV), (XV), (XVI), and (XVII), e.g., as described herein). In one embodiment, the compound is a selective PI3K-γ inhibitor, e.g., Compound 4.

In certain embodiments, provided herein is a method of making a compound described herein.

In certain embodiments, provided herein is a reaction mixture comprising a compound described herein.

In certain embodiments, provided herein is a kit comprising a compound described herein.

In some embodiments, a method is provided for treating a disease or disorder described herein, the method comprising administering a therapeutically effective amount of a compound or a pharmaceutical composition described herein to a subject.

In some embodiments, a method is provided for treating a PI3K mediated disorder in a subject, the method comprising administering a therapeutically effective amount of a compound or a pharmaceutical composition described herein to a subject.

In some embodiments, provided herein is a use of a compound or a pharmaceutical composition described herein for the treatment of a disease or disorder described herein in a subject.

In some embodiments, provided herein is a use of a compound or a pharmaceutical composition described herein for the treatment of a PI3K mediated disorder in a subject.

In some embodiments, provided herein is a use of a compound or a pharmaceutical composition described herein in the manufacture of a medicament for the treatment of a disease or disorder described herein in a subject.

In some embodiments, provided herein is use of a compound or a pharmaceutical composition described herein in the manufacture of a medicament for the treatment of a PI3K mediated disorder in a subject.

Additional features or embodiments of the compounds, compositions or methods described herein include one or more of the following:

In some embodiments, the compound is a PI3K-gamma inhibitor, e.g., a selective PI3K-gamma inhibitor, or a pharmaceutically acceptable form thereof.

In some embodiments, the compound is a compound of any of Formulae (I″), (I′), (A′), (I), (A), (II), (III), (IV), (V), (VI), (VII), (IX), (X), (XI), (XII), (XIII), (XIV), (XV), (XVI), and (XVII), or a pharmaceutically acceptable form thereof. In one embodiment, the compound is a compound of Formula (XVII). In one embodiment, the one or more compounds are PI3K gamma inhibitors, e.g., selective PI3K-gamma inhibitors.

In some embodiments, the compound is chosen from one or more of compounds 2, 4, 7, 9, 17, 19, 21, 26, 27, 30, 32, 35, 37, 38, 40, 41, 52, 60, 61, 63, 73, 75, 77, 79, 80, 81, or 88, or a pharmaceutically acceptable form thereof. In one embodiment, the one or more compounds are PI3K gamma inhibitors, e.g., selective PI3K-gamma inhibitors.

In one embodiment, the compound is a compound of Formula (I″), (I′), or (I), or a pharmaceutically acceptable form thereof. In one embodiment, the compound is a compound of Formula I, or a pharmaceutically acceptable form thereof.

In one embodiment, the compound is Compound 4 (also referred to herein as "Compound BB")

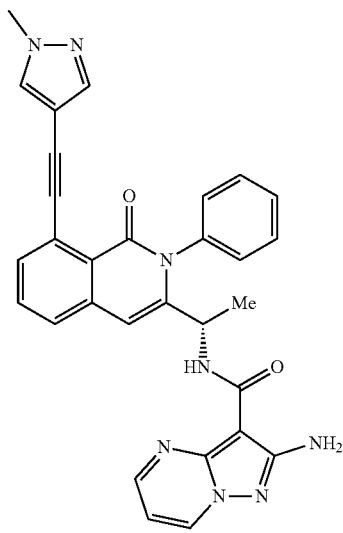 [SMILES: C[C@H](NC(=O)c1c(N)nn2cccnc12)c1cc2cccc(C#Cc3cnn(C)c3)c2c(=O)n1-c1ccccc1]

or a pharmaceutically acceptable form thereof. In some embodiments, Compound 4 is a PI3K gamma inhibitor, e.g., a selective PI3K-gamma inhibitor.

In some embodiments of the methods or uses disclosed herein, the PI3K gamma inhibitor, e.g., the selective PI3K-gamma inhibitor, or a compound as described herein (e.g., compound of any of Formulae (I″), (I′), (A′), (I), (A), (II), (III), (IV), (V), (VI), (VII), (IX), (X), (XI), (XII), (XIII), (XIV), (XV), (XVI), and (XVII), e.g., Compound 4), is administered to a subject at a dose (e.g., a therapeutically effective dose) of about 2 mg, 1-3 mg, 1-5 mg, 1-10 mg, 0.5-20 mg, or 0.1-50 mg. In some embodiments, the dose (e.g., a therapeutically effective dose) is about 2 mg, 1-3 mg, 1-5 mg, 1-10 mg, 0.5-20 mg, 0.1-50 mg, 0.1-75 mg, 0.5-75 mg, 1-75 mg, 0.1-100 mg, 0.5-100 mg, or 1-100 mg. In some embodiments, the dose is about 1-10 mg. In some embodiments, the dose is about 1-50 mg. In some embodiments, the dose is about 1-100 mg.

In some embodiments of the methods or uses disclosed herein, the PI3K gamma inhibitor, e.g., the selective PI3K-gamma inhibitor, or a compound as described herein (e.g., a compound of any of Formulae (I″), (I′), (A′), (I), (A), (II), (III), (IV), (V), (VI), (VII), (IX), (X), (XI), (XII), (XIII), (XIV), (XV), (XVI), and (XVII), e.g., Compound 4), is administered to a subject at a dose (e.g., a therapeutically effective dose) of about 0.029 mg/kg, 0.014-0.14 mg/kg, 0.02-0.04 mg/kg, 0.01-0.05 mg/kg, 0.01-0.1, or 0.01-0.5 mg/kg. In one embodiment, the administration is intratracheally.

In some embodiments of the methods or uses disclosed herein, the PI3K gamma inhibitor, e.g., the selective PI3K-gamma inhibitor, or a compound as described herein (e.g., a compound of any of Formulae (I″), (I′), (A′), (I), (A), (II), (III), (IV), (V), (VI), (VII), (IX), (X), (XI), (XII), (XIII), (XIV), (XV), (XVI), and (XVII), e.g., Compound 4), is administered to a subject at a treatment schedule chosen from, e.g., once every two days, once per day, or twice per day.

In some embodiments of the methods or uses disclosed herein, the PI3K gamma inhibitor, e.g., the selective PI3K-gamma inhibitor, or a compound as described herein (e.g., a compound of any of Formulae (I″), (I′), (A′), (I), (A), (II), (III), (IV), (V), (VI), (VII), (IX), (X), (XI), (XII), (XIII), (XIV), (XV), (XVI), and (XVII), e.g., Compound 4) is administered at a dose such that it selectively inhibits PI3K-gamma but achieves less than 10% or 20% inhibition of PI3K-delta.

In some embodiments of the methods or uses disclosed herein, the PI3K gamma inhibitor, e.g., the selective PI3K-gamma inhibitor, or a compound as described herein (e.g., a compound of any of Formulae (I"), (I'), (A'), (I), (A), (II), (III), (IV), (V), (VI), (VII), (IX), (X), (XI), (XII), (XIII), (XIV), (XV), (XVI), and (XVII), e.g., Compound 4) is administered at a dose such that the compound's level in the subject's blood does not rise higher than a predetermined level, e.g., the IC50 of PI3K-delta, within a selected time period, e.g., 24 hours. In some embodiments of the methods or uses disclosed herein, the PI3K gamma inhibitor or compound is administered at a dose such that the compound's level in the subject's blood does not rise higher than a predetermined level, e.g., the IC20 of PI3K-delta, within a selected time period, e.g., 24 hours.

In some embodiments of the methods or uses disclosed herein, the PI3K gamma inhibitor, e.g., the selective PI3K-gamma inhibitor, or a compound as described herein (e.g., a compound of any of Formulae (I"), (I'), (A'), (I), (A), (II), (III), (IV), (V), (VI), (VII), (IX), (X), (XI), (XII), (XIII), (XIV), (XV), (XVI), and (XVII), e.g., Compound 4), is administered to a subject in an amount such that the level of the compound in the subject's body is above the IC50 of PI3K-gamma during at least 70%, 80%, 90%, 95%, 97%, 98%, 99%, or 99% of selected time period, e.g., 24 hours, immediately following the administration.

In some embodiments of the methods or uses disclosed herein, the PI3K gamma inhibitor, e.g., the selective PI3K-gamma inhibitor, or a compound as described herein (e.g., a compound of any of Formulae (I"), (I'), (A'), (I), (A), (II), (III), (IV), (V), (VI), (VII), (IX), (X), (XI), (XII), (XIII), (XIV), (XV), (XVI), and (XVII), e.g., Compound 4), is administered to a subject in an amount such that the level of the compound in the subject's body is above the IC90 of PI3K-gamma during at least 50%, 60%, 70%, 80%, 90%, 95%, 97%, 98%, 99%, or 99% of a selected time period, e.g., 24 hours, immediately following the administration.

In some embodiments of the methods or uses disclosed herein, the subject is a human and the PI3K gamma inhibitor, e.g., the selective PI3K-gamma inhibitor, or a compound as described herein (e.g., a compound of any of Formulae (I"), (I'), (A'), (I), (A), (II), (III), (IV), (V), (VI), (VII), (IX), (X), (XI), (XII), (XIII), (XIV), (XV), (XVI), and (XVII), e.g., Compound 4) has a half life of about 8-15 hours, or about 10-13 hours.

In some embodiments of the methods or uses disclosed herein, treatment with a PI3K gamma inhibitor, e.g., the selective PI3K-gamma inhibitor, or a compound as described herein (e.g., a compound of any of Formulae (I"), (I'), (A'), (I), (A), (II), (III), (IV), (V), (VI), (VII), (IX), (X), (XI), (XII), (XIII), (XIV), (XV), (XVI), and (XVII), e.g., Compound 4) is more effective than treatment with a PI3K delta selective inhibitor, e.g., when both inhibitors are administered at the same dose and/or through the same route of administration.

In some embodiments of the methods or uses disclosed herein, treatment with a PI3K gamma inhibitor, e.g., the selective PI3K-gamma inhibitor, or a compound as described herein (e.g., a compound of any of Formulae (I"), (I'), (A'), (I), (A), (II), (III), (IV), (V), (VI), (VII), (IX), (X), (XI), (XII), (XIII), (XIV), (XV), (XVI), and (XVII), e.g., Compound 4) is more effective (e.g., at least 10%, 20%, 40%, 60%, or 80% more effective) than treatment with a PI3K delta selective inhibitor, e.g., when both inhibitors are administered at the same dose and/or through the same route of administration.

In some embodiments of the methods or uses disclosed herein, the subject is refractory or has failed to respond to a PI3K-δ inhibitor.

Inflammatory Diseases

Methods of treating or preventing an inflammatory disease in a subject using the PI3K gamma inhibitor, e.g., the selective PI3K-gamma inhibitor, or a compound as described herein (e.g., a compound of any of Formulae (I"), (I'), (A'), (I), (A), (II), (III), (IV), (V), (VI), (VII), (IX), (X), (XI), (XII), (XIII), (XIV), (XV), (XVI), and (XVII), e.g., Compound 4, as described herein) are disclosed. In certain embodiments, the inflammatory disease is chosen from COPD, arthritis, asthma, psoriasis, scleroderma, myositis, sarcoidosis, dermatomyositis, CREST syndrome, systemic lupus erythematosus, Sjorgren syndrome, encephalomyelitis, or inflammatory bowel disease (IBD). In some embodiments, inflammatory disease is COPD or arthritis.

In certain embodiments, the PI3K gamma inhibitor, e.g., the selective PI3K-gamma inhibitor, or a compound as described herein (e.g., a compound of any of Formulae (I"), (I'), (A'), (I), (A), (II), (III), (IV), (V), (VI), (VII), (IX), (X), (XI), (XII), (XIII), (XIV), (XV), (XVI), and (XVII), e.g., Compound 4, as described herein) is administered at a dose such that it selectively inhibits PI3K-gamma but achieves less than 10% or 20% inhibition of PI3K-delta.

In certain embodiments, the PI3K gamma inhibitor, e.g., the selective PI3K-gamma inhibitor, or a compound as described herein (e.g., a compound of any of Formulae (I"), (I'), (A'), (I), (A), (II), (III), (IV), (V), (VI), (VII), (IX), (X), (XI), (XII), (XIII), (XIV), (XV), (XVI), and (XVII), e.g., Compound 4, as described herein) is administered at a dose such that the compound's level in the subject's blood does not rise higher than a predetermined level, e.g., the IC50 of PI3K-delta, within a selected time period, e.g., 24 hours. In certain embodiments, the PI3K gamma inhibitor or a compound, e.g., Compound 4, as described herein) is administered at a dose such that the compound's level in the subject's blood does not rise higher than a predetermined level, e.g., the IC20 of PI3K-delta, within a selected time period, e.g., 24 hours.

In some embodiments of the methods or uses disclosed herein, the subject is refractory or has failed to respond to a PI3K-δ inhibitor.

In certain embodiments, a method of treating or preventing arthritis, or periosteal bone formation, in a subject is disclosed. The method includes administering to the subject a PI3K gamma inhibitor, e.g., the selective PI3K-gamma inhibitor, or a compound as described herein (e.g., a compound of any of Formulae (I"), (I'), (A'), (I), (A), (II), (III), (IV), (V), (VI), (VII), (IX), (X), (XI), (XII), (XIII), (XIV), (XV), (XVI), and (XVII), e.g., Compound 4, as described herein), in a therapeutically effective amount, e.g., an amount sufficient to treat or prevent the arthritis. In certain embodiments, the subject has or is at risk of having, or is identified as having or being at risk of having, periosteal bone formation.

In certain embodiments, the subject has or is identified as having reduced periosteal bone formation after administration of the PI3K gamma inhibitor or a compound as described herein, e.g., the subject shows a reduction in periosteal bone formation or periosteal bone width that is reduced by at least 10%, 20%, 40%, 47%, 50%, 52%, 60%, 80%, or 82% compared to a reference value (e.g., an untreated control), after administration of the PI3K gamma inhibitor or a compound as described herein.

In certain embodiments, the therapeutically effective amount is an amount sufficient to reduce a periosteal bone formation or periosteal bone width by at least 10%, 20%, 40%, 47%, 50%, 52%, 60%, 80%, or 82% compared to a reference value, after administration of the PI3K gamma inhibitor or a compound as described herein.

In certain embodiments, the subject has, or is identified as having, a histopathology score for periosteal bone formation or periosteal bone width that is reduced by at least 1, 2, or 3 points compared to a reference value, after administration of the PI3K gamma inhibitor or a compound as described herein.

In certain embodiments, the therapeutically effective amount is an amount sufficient to reduce a histopathology score for periosteal bone formation or periosteal bone width by at least 1, 2, or 3 points compared to a reference value, after administration of the PI3K gamma inhibitor or a compound as described herein.

In certain embodiments, the subject has, or is identified as having, an inflammation that is reduced by at least 10%, 20%, 27%, 30%, 36%, 40%, 45%, 50%, or 57% compared to a reference value, after administration of the PI3K gamma inhibitor or a compound as described herein.

In certain embodiments, the therapeutically effective amount is an amount that is sufficient to reduce an inflammation by at least 10%, 20%, 27%, 30%, 36%, 40%, 45%, 50%, or 57% compared to a reference value, after administration of the PI3K gamma inhibitor or a compound as described herein.

In certain embodiments, the subject has, or is identified as having, a histopathology score for inflammation that is reduced by at least 1, 2, or 3 points compared to a reference value, after administration of the PI3K gamma inhibitor or a compound as described herein.

In certain embodiments, the therapeutically effective amount is an amount that is sufficient to reduce a histopathology score for inflammation by at least 1, 2, or 3 points compared to a reference value, after administration of the PI3K gamma inhibitor or a compound as described herein.

In certain embodiments, the subject has, or is identified as having, pannus that is reduced by at least 10%, 20%, 28%, 30%, 40%, 44%, 50%, or 60%, 70%, or 71% compared to a reference value, after administration of the PI3K gamma inhibitor or a compound as described herein.

In certain embodiments, the therapeutically effective amount is an amount that is sufficient to reduce pannus by at least 10%, 20%, 28%, 30%, 40%, 44%, 50%, or 60%, 70%, or 71% compared to a reference value, after administration of the PI3K gamma inhibitor or a compound as described herein.

In certain embodiments, the subject has, or is identified as having, a histopathology score for pannus that is reduced by at least 1, 2, or 3 points compared to a reference value, after administration of the PI3K gamma inhibitor or a compound as described herein.

In certain embodiments, the therapeutically effective amount is an amount that is sufficient to reduce a histopathology score for pannus by at least 1, 2, or 3 points compared to a reference value, after administration of the PI3K gamma inhibitor or a compound as described herein.

In certain embodiments, the subject has, or is identified as having, cartilage damage that is reduced by at least 10%, 20%, 28%, 30%, 40%, 45%, 50%, or 59% compared to a reference value, after administration of the PI3K gamma inhibitor or a compound as described herein.

In certain embodiments, the therapeutically effective amount is an amount that is sufficient to reduce cartilage damage by at least 10%, 20%, 28%, 30%, 40%, 45%, 50%, or 59% compared to a reference value, after administration of the PI3K gamma inhibitor or a compound as described herein.

In certain embodiments, the subject has, or is identified as having, a histopathology score for cartilage damage that is reduced by at least 1, 2, or 3 points compared to a reference value, after administration of the PI3K gamma inhibitor or a compound as described herein.

In certain embodiments, the therapeutically effective amount is an amount that is sufficient to reduce a histopathology score for cartilage damage by at least 1, 2, or 3 points compared to a reference value, after administration of the PI3K gamma inhibitor or a compound as described herein.

In certain embodiments, the subject has, or is identified as having, bone resorption that is reduced by at least 10%, 20%, 25%, 30%, 40%, 44%, 50%, 60%, or 65% compared to a reference value, after administration of the PI3K gamma inhibitor or a compound as described herein.

In certain embodiments, the therapeutically effective amount is an amount that is sufficient to reduce bone resorption by at least 10%, 20%, 25%, 30%, 40%, 44%, 50%, 60%, or 65% compared to a reference value, after administration of the PI3K gamma inhibitor.

In certain embodiments, the subject has, or is identified as having, a histopathology score for bone resorption that is reduced by at least 1, 2, or 3 points compared to a reference value, after administration of the PI3K gamma inhibitor or a compound as described herein.

In certain embodiments, the therapeutically effective amount is an amount that is sufficient to reduce a histopathology score for bone resorption by at least 1, 2, or 3 points compared to a reference value, after administration of the PI3K gamma inhibitor or a compound as described herein.

In certain embodiments, the subject has, or is identified as having, joint swelling that is reduced compared to a reference value, after administration of the PI3K gamma inhibitor or a compound as described herein.

In certain embodiments, the therapeutically effective amount is an amount that is sufficient to reduce joint swelling compared to a reference value, after administration of the PI3K gamma inhibitor or a compound as described herein.

In certain embodiments, the subject has, or is identified as having, a histopathology score for joint swelling that is reduced compared to a reference value, after administration of the PI3K gamma inhibitor or a compound as described herein.

In certain embodiments, the subject has, or is identified as having, a histopathology score for joint swelling that is reduced compared to a reference value, after administration of the PI3K gamma inhibitor or a compound as described herein.

In certain embodiments, the subject has, or is identified as having, an anti-collagen level that is reduced compared to a reference value, after administration of the PI3K gamma inhibitor.

In certain embodiments, the therapeutically effective amount is an amount that is sufficient to reduce an anti-collagen level compared to a reference value, after administration of the PI3K gamma inhibitor or a compound as described herein.

In certain embodiments, the subject has, or is identified as having, a histopathology score for an anti-collagen level that is reduced compared to a reference value, after administration of the PI3K gamma inhibitor.

In certain embodiments, the therapeutically effective amount is an amount sufficient to reduce an anti-collagen level compared to a reference value, after administration of the PI3K gamma inhibitor or a compound as described herein.

In certain embodiments, the PI3K gamma inhibitor or a compound as described herein (e.g., a compound of any of Formulae (I"), (I'), (A'), (I), (A), (II), (III), (IV), (V), (VI), (VII), (IX), (X), (XI), (XII), (XIII), (XIV), (XV), (XVI), and (XVII), e.g., Compound 4) is administered at a dose such that it selectively inhibits PI3K-gamma but achieves less than 10% or 20% inhibition of PI3K-delta.

In certain embodiments, the PI3K gamma inhibitor or a compound as described herein (e.g., a compound of any of Formulae (I"), (I'), (A'), (I), (A), (II), (III), (IV), (V), (VI), (VII), (IX), (X), (XI), (XII), (XIII), (XIV), (XV), (XVI), and (XVII), e.g., Compound 4) is administered at a dose such that the compound's level in the subject's blood does not rise higher than a predetermined level, e.g., the IC50 of PI3K-delta, within a selected time period, e.g., 24 hours. In certain embodiments, the PI3K gamma inhibitor or a compound as described herein (e.g., a compound of any of Formulae (I"), (I'), (A'), (I), (A), (II), (III), (IV), (V), (VI), (VII), (IX), (X), (XI), (XII), (XIII), (XIV), (XV), (XVI), and (XVII), e.g., Compound 4) is administered at a dose such that the compound's level in the subject's blood does not rise higher than a predetermined level, e.g., the IC20 of PI3K-delta, within a selected time period, e.g., 24 hours.

In other embodiments, a method of reducing neutrophil migration or infiltration in a subject suffering from an inflammatory disease is provided. The method includes administering to the subject a PI3K gamma inhibitor or a compound as described herein (e.g., a compound of any of Formulae (I"), (I'), (A'), (I), (A), (II), (III), (IV), (V), (VI), (VII), (IX), (X), (XI), (XII), (XIII), (XIV), (XV), (XVI), and (XVII), e.g., Compound 4, as described herein), in an amount sufficient to reduce or inhibit the neutrophil migration or infiltration in the subject.

In certain embodiments, the subject has, or is identified as having, neutrophil migration that is reduced by at least about 10%, 20%, 40%, 60%, 80%, or 90% compared to a reference value, after administration of the PI3K gamma inhibitor or a compound as described herein.

In certain embodiments, the therapeutically effective amount is an amount that is sufficient to reduce neutrophil migration by at least about 10%, 20%, 40%, 60%, 80%, or 90% compared to a reference value, after administration of the PI3K gamma inhibitor or a compound as described herein.

Cancer

Methods of treating or preventing a cancer in a subject using the PI3K gamma inhibitor or a compound as described herein (e.g., a compound of any of Formulae (I"), (I'), (A'), (I), (A), (II), (III), (IV), (V), (VI), (VII), (IX), (X), (XI), (XII), (XIII), (XIV), (XV), (XVI), and (XVII), e.g., Compound 4, as described herein) are disclosed. In certain embodiments, the cancer is, or is identified as being, a solid tumor (e.g., lung cancer, melanoma, breast cancer, sarcoma, hepatocellular cancer, head and neck cancer, cervical or vulvar cancer, esophageal cancer, gastric cancer, adrenal cancer, colon cancer, or glioblastoma) or a hematologic cancer (e.g., a chronic lymphocytic leukemia (CLL)), e.g., as described herein. In one embodiment, the cancer is melanoma, bladder cancer, head and neck cancer, lung cancer (e.g., non-small cell lung cancer), renal cell carcinoma, ovarian cancer, breast cancer (e.g., triple-negative breast cancer), colon cancer, or glioblastoma.

In certain embodiments, the PI3K gamma inhibitor or a compound as described herein (e.g., a compound of any of Formulae (I"), (I'), (A'), (I), (A), (II), (III), (IV), (V), (VI), (VII), (IX), (X), (XI), (XII), (XIII), (XIV), (XV), (XVI), and (XVII), e.g., Compound 4, as described herein) is administered at a dose such that it selectively inhibits PI3K-gamma but achieves less than 10% or 20% inhibition of PI3K-delta.

In certain embodiments, the PI3K gamma inhibitor or a compound as described herein (e.g., a compound of any of Formulae (I"), (I'), (A'), (I), (A), (II), (III), (IV), (V), (VI), (VII), (IX), (X), (XI), (XII), (XIII), (XIV), (XV), (XVI), and (XVII), e.g., Compound 4, as described herein) is administered at a dose such that the compound's level in the subject's blood does not rise higher than a predetermined level, e.g., the IC50 of PI3K-delta, within a selected time period, e.g., 24 hours. In certain embodiments, the PI3K gamma inhibitor or a compound as described herein (e.g., a compound of any of Formulae (I"), (I'), (A'), (I), (A), (II), (III), (IV), (V), (VI), (VII), (IX), (X), (XI), (XII), (XIII), (XIV), (XV), (XVI), and (XVII), e.g., Compound 4, as described herein) is administered at a dose such that the compound's level in the subject's blood does not rise higher than a predetermined level, e.g., the IC20 of PI3K-delta, within a selected time period, e.g., 24 hours.

In some embodiments of the methods or uses disclosed herein, the subject is refractory or has failed to respond to a PI3K-δ inhibitor. In some embodiments, the subject is naive to immunotherapy treatment. In some embodiments, the subject is or has been responsive to an immunotherapy treatment. In one embodiment, the immunotherapy treatment is a treatment with a PD-1 or PD-L1 inhibitor.

In other embodiments, a method of reducing CXCL12-induced CD3+ T cell migration, or CXCL12-induced differentiated macrophage migration into a tumor microenvironment, in a subject is provided. The method includes administering to the subject a PI3K gamma inhibitor or a compound as described herein (e.g., a compound of any of Formulae (I"), (I'), (A'), (I), (A), (II), (III), (IV), (V), (VI), (VII), (IX), (X), (XI), (XII), (XIII), (XIV), (XV), (XVI), and (XVII), e.g., Compound 4, as described herein), in an amount sufficient to reduce or inhibit the CXCL12-induced CD3+ T cell migration, or CXCL12-induced differentiated macrophage migration into a tumor microenvironment in the subject.

In some embodiments of the methods or uses disclosed herein, the subject has, or is identified as having, a reduction in p-AKT levels after administration of the PI3K gamma inhibitor or a compound as described herein.

In some embodiments of the methods or uses disclosed herein, the PI3K gamma inhibitor is administered at a dose such that it selectively inhibits PI3K-gamma but achieves less than 10% or 20% inhibition of PI3K-delta.

In some embodiments of the methods or uses disclosed herein, the PI3K gamma inhibitor or a compound as described herein is administered at a dose such that the compound's level in the subject's blood does not rise higher than a predetermined level, e.g., the IC50 of PI3K-delta, within a selected time period, e.g., 24 hours. In some embodiments of the methods or uses disclosed herein, the PI3K gamma inhibitor or a compound as described herein is administered at a dose such that the compound's level in the subject's blood does not rise higher than a predetermined level, e.g., the IC20 of PI3K-delta, within a selected time period, e.g., 24 hours.

In some embodiments, a method of reducing one or more activities of a pro-tumor immune cell in a subject having a cancer is provided. The method includes administering to the subject a PI3K gamma inhibitor or a compound as described herein (e.g., a compound of any of Formulae (I"), (I'), (A'), (I), (A), (II), (III), (IV), (V), (VI), (VII), (IX), (X), (XI), (XII), (XIII), (XIV), (XV), (XVI), and (XVII), e.g., Compound 4, as described herein), in an amount sufficient to reduce or inhibit the one or more activities of the pro-tumor immune cell.

In some embodiments, the pro-tumor immune cell is a T-cell, an M2 macrophage, a stromal cell, a dendritic cell, an endothelial cell, or a myeloid cell. In one embodiment, the myeloid cell is a tumor associated suppressive myeloid cell. In one embodiment, the tumor associated suppressive myeloid cell is a tumor associated macrophage (TAM), a myeloid derived suppressor cell (MDSC), a monocytic immature myeloid cell (iMc), or a granulocytic iMc/neutrophil.

In certain embodiments, the subject has, or is identified as having, a decrease in numbers of pro-tumor immune cells in a tumor microenvironment, compared to a reference value, after administration of the PI3K gamma inhibitor or a compound as described herein.

In certain embodiments, the amount of the administered is sufficient to produce a decrease in numbers of pro-tumor immune cells in a tumor microenvironment, compared to a reference value, after administration of the PI3K gamma inhibitor or a compound as described herein.

In certain embodiments, the subject has, or is identified as having, increased activity of anti-tumor immune cells, compared to a reference value, after administration of the PI3K gamma inhibitor or a compound as described herein.

In certain embodiments, the amount of the PI3K gamma inhibitor or a compound as described herein is sufficient to produce increased activity of anti-tumor immune cells, compared to a reference value, after administration of the PI3K gamma inhibitor or the compound as described herein.

In certain embodiments, the subject has, or is identified as having, increased infiltration of anti-tumor immune cells into a tumor microenvironment, compared to a reference value, after administration of the PI3K gamma inhibitor or a compound as described herein.

In certain embodiments, the amount of PI3K-gamma inhibitor is sufficient to produce increased infiltration of anti-tumor immune cells into a tumor microenvironment, compared to a reference value, after administration of the PI3K gamma inhibitor or a compound as described herein.

In certain embodiments, the subject has, or is identified as having, an increase in number of anti-tumor immune cells in a tumor microenvironment, compared to a reference value, after administration of the PI3K gamma inhibitor or a compound as described herein.

In certain embodiments, the amount of PI3K-gamma inhibitor is sufficient to produce an increase in number of anti-tumor immune cells in a tumor microenvironment, compared to a reference value, after administration of the PI3K gamma inhibitor or a compound as described herein.

In certain embodiments, the cancer is a CLL. In some embodiments, the tumor microenvironment is a CLL proliferation center.

In certain embodiments, the subject has, or is identified as having, reduced tumor volume, compared to a reference value, after administration of the PI3K gamma inhibitor or a compound as described herein.

In certain embodiments, the amount of the PI3K gamma inhibitor or a compound as described herein is sufficient to produce reduced tumor volume, compared to a reference value, after administration of the PI3K gamma inhibitor or the compound as described herein.

In certain embodiments, the amount of the PI3K gamma inhibitor or a compound as described herein is sufficient to produce a reduction of at least 10%, 20%, 30%, 50%, 60%, or 60% in tumor volume, compared to a reference value, after administration of the PI3K gamma inhibitor or the compound as described herein.

In certain embodiments, the subject has, or is identified as having, an increased level of apoptosis in the cancer cells, compared to a reference value, after administration of the PI3K gamma inhibitor or a compound as described herein.

In certain embodiments, the amount of PI3K gamma inhibitor is sufficient to produce an increased level of apoptosis in the cancer cells, compared to a reference value, after administration of the PI3K gamma inhibitor or a compound as described herein.

In certain embodiments, the subject has, or is identified as having, a 10%, 20%, 30%, 40%, or 50% increase in apoptosis in the cancer cells, compared to a reference value, after administration of the PI3K gamma inhibitor or a compound as described herein.

In certain embodiments, the amount of the PI3K gamma inhibitor or a compound as described herein is sufficient to produce a 10%, 20%, 30%, 40%, or 50% increase in apoptosis in the cancer cells, compared to a reference value, after administration of the PI3K gamma inhibitor or the compound as described herein.

In certain embodiments, the anti-tumor immune cell is an M1 macrophage.

In certain embodiments, the one activity is chosen from one or more of migration of the cell, or signaling to an anti-tumor immune cell.

In certain embodiments, the subject has, or is determined to have reduced levels of p-AKT in the pro-tumor immune cell, compared to a reference value, after administration of the PI3K gamma inhibitor or the compound.

In certain embodiments, the amount is sufficient to reduce p-AKT in the pro-tumor immune cell, compared to a reference value, after administration of the PI3K gamma inhibitor or the compound.

In certain embodiments, the subject has, or is determined to have a reduction of p-AKT levels by about 10%, 20%, 30%, 40%, 50%, or 60%, compared to a reference value, after administration of the PI3K gamma inhibitor or the compound.

In certain embodiments, the subject has, or is determined to have a reduction of p-AKT levels by about 10%, 20%, 30%, 40%, 50%, or 60%, compared to a reference value, after administration of the PI3K gamma inhibitor or the compound.

In certain embodiments, the subject has, or is determined to have lung cancer, breast cancer, colon cancer, or glioblastoma. In certain embodiments, the breast cancer is triple negative breast cancer.

In some embodiments, a method of reducing the level of M2 macrophages in a tumor microenvironment in a subject having a cancer is provided. The method includes administering to the subject a PI3K gamma inhibitor or a compound as described herein (e.g., a compound of any of Formulae (I"), (I'), (A'), (I), (A), (II), (III), (IV), (V), (VI), (VII), (IX), (X), (XI), (XII), (XIII), (XIV), (XV), (XVI), and (XVII), e.g., Compound 4, as described herein), in an amount sufficient to reduce the level of M2 macrophages in a tumor microenvironment.

In certain embodiments, reducing the level of M2 macrophages comprises reducing or inhibiting the differentiation of a tumor associated myeloid cell into an M2 macrophage. Differentiation into an M2 macrophage can be measured by decreased ARG1 levels compared to a reference value, after administration of the compound.

In certain embodiments, the ARG1 level is reduced by at least 10%, 20%, 30%, 40%, 50%, 60%, 70%, 80%, or 90% compared to a reference value, after administration of the compound.

In certain embodiments, differentiation into an M2 macrophage is measured by decreased VEGF levels compared to a reference value, after administration of the compound.

In certain embodiments, the VEGF level is reduced by at least 10%, 20%, 30%, 40%, 50%, 60%, 70%, 80%, or 90% compared to a reference value, after administration of the compound.

In certain embodiments, the subject has, or is determined to have, a normal level of differentiation of myeloid cells into M1 macrophages.

In certain embodiments, the amount is such that the compound does not reduce differentiation of myeloid cells into M1 macrophages.

In certain embodiments, the subject has, or is determined to have, increased anti-tumor immune attack by effector T cells, reduced vascularization of a tumor, reduced ECM breakdown, decreased tumor growth, or any combination thereof, compared to a reference value, after administration of the compound.

In certain embodiments, the cancer is, or is determined to be, a solid tumor (e.g., a cancer chosen from lung cancer, breast cancer, colon cancer, or glioblastoma).

In certain embodiments, the cancer is, or is determined to be, a hematological cancer.

Additional Combinations Therapies:

In other embodiments, provided herein is a method of treating a PI3K-mediated disorder in a subject, comprising administering to a subject a PI3K gamma inhibitor or a compound as described herein (e.g., a compound of any of Formulae (I"), (I'), (A'), (I), (A), (II), (III), (IV), (V), (VI), (VII), (IX), (X), (XI), (XII), (XIII), (XIV), (XV), (XVI), and (XVII), e.g., Compound 4, as described herein) and an immunomodulator.

In certain embodiments, the PI3K-mediated disorder is a cancer, autoimmune disease, or inflammatory disease.

In one embodiment, the cancer is of hematopoietic origin, e.g., a cancer chosen from a leukemia or lymphoma, e.g., B-cell lymphoma, T-cell lymphoma, non-Hodgkin's lymphoma, Hodgkin lymphoma, or anaplastic large cell lymphoma. In one embodiment, the lymphoma is follicular B cell lymphoma.

In other embodiments, the cancer is a solid tumor, e.g., a cancer chosen from a breast cancer, a lung cancer, a colon cancer, melanoma, or a glioblastoma. In one embodiment, the cancer is melanoma, bladder cancer, head and neck cancer, lung cancer (e.g., non-small cell lung cancer), renal cell carcinoma, ovarian cancer, breast cancer (e.g., triple-negative breast cancer), colon cancer, or glioblastoma.

In some embodiments, the subject is naive to immunotherapy treatment. In some embodiments, the subject is or has been responsive to an immunotherapy treatment. In one embodiment, the immunotherapy treatment is a treatment with a PD-1 or PD-L1 inhibitor.

In one embodiment, the immunomodulator is an immune checkpoint therapy, e.g., an immune checkpoint therapy chosen from is an inhibitor of PD-1, PD-L1, PD-L2, CTLA4, TIM3, LAG3, VISTA, BTLA, TIGIT, LAIR1, CD160, 2B4, TGFR-beta, or IDO/TDO, or any combination thereof. In one embodiment, the immune checkpoint therapy is an inhibitor of CTLA-4, PD-1, or PD-L1. The immune checkpoint therapy can be chosen from an antibody or fragment thereof, an inhibitory nucleic acid, a soluble ligand, or a fusion of an immune checkpoint therapy (e.g., CTLA-4, PD-1, or PD-1 ligand) with a Fc region of an immunoglobulin.

In certain embodiments, the immunomodulator is an activator of a costimulatory molecule. In one embodiment, the agonist of the costimulatory molecule is chosen from an agonist (e.g., an agonistic antibody or antigen-binding fragment thereof, or a soluble fusion) of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand.

The certain embodiments, the immunomodulator is chosen from a costimulatory ligand, a MCSF/CSF-1R inhibitor, an immunostimulant, a CXCR4/CXCL12 inhibitor, a CCL2 inhibitor, or a CCR2 inhibitor.

In certain embodiments, the PI3K gamma inhibitor or a compound as described herein and the immunomodulator are in a single dosage form.

In certain embodiments, the PI3K gamma inhibitor or a compound as described herein and the immunomodulator are in separate dosage forms.

In certain embodiments, the PI3K gamma inhibitor or a compound as described herein and the immunomodulator are administered concurrently.

In certain embodiments, the PI3K gamma inhibitor or a compound as described herein is administered subsequent to the immunomodulator.

In certain embodiments, the PI3K gamma inhibitor or a compound as described herein is administered prior to the immunomodulator.

In certain embodiments, the effective amount of the PI3K gamma inhibitor or a compound as described herein, the immunomodulator, or both that is an amount sufficient to cause a decrease in tumor growth of at least 10%, 20%, 30%, 40%, or 50% compared to a reference value, is reduced.

In certain embodiments, the subject has, or is determined to have, a decrease in tumor growth of at least 10%, 20%, 30%, 40%, or 50% compared to a reference value, after administration of the PI3K gamma inhibitor or the compound.

In certain embodiments, the method comprises administration an immune checkpoint therapy, e.g., a PD-1 or PD-L1 inhibitor (e.g., an anti-PD-1 antibody or an anti-PD-L1 antibody).

In certain embodiments, the method further comprises administering an effective amount of a PI3K-δ inhibitor or the compound to the subject.

In certain embodiments, the level of the PI3K gamma inhibitor in the subject's blood is above a predetermined value, e.g., the IC50 of PI3K-gamma, during at least 70%, 80%, 90%, 95%, 97%, 98%, 99%, or 99% of a selected time period, e.g., 24 hours, immediately following the treatment.

In certain embodiments, the level of the PI3K gamma inhibitor in the subject's blood is below a predetermined value, e.g., the IC50 of PI3K-delta, during at least 70%, 80%, 90%, 95%, 97%, 98%, 99%, or 99% of a selected time period, e.g., 24 hours, immediately following the treatment. In certain embodiments, the level of the PI3K gamma inhibitor or the compound in the subject's blood is below a predetermined value, e.g., the IC20 of PI3K-delta, during at least 70%, 80%, 90%, 95%, 97%, 98%, 99%, or 99% of a selected time period, e.g., 24 hours, immediately following the treatment.

Compositions comprising the aforesaid combinations of PI3K gamma inhibitor and the immunomodulator are also provided. The compositions can be provided in the same or in separate dosage forms. The compositions can further include a pharmaceutically acceptable excipient.

In other embodiments, the invention features a method of treating a PI3K-mediated disorder in a subject, comprising administering to the subject a synergistic combination of a PI3K gamma inhibitor (e.g., a compound of any of Formulae (I″), (I′), (A′), (I), (A), (II), (III), (IV), (V), (VI), (VII), (IX), (X), (XI), (XII), (XIII), (XIV), (XV), (XVI), and (XVII), e.g., Compound 4, as described herein) and a PI3K-δ inhibitor.

In certain embodiments, the PI3K-mediated disorder is a cancer, autoimmune disease, or inflammatory disease.

In one embodiment, the cancer is of hematopoietic origin, e.g., a cancer chosen from a leukemia or lymphoma, e.g., B-cell lymphoma, T-cell lymphoma, non-Hodgkin's lymphoma, Hodgkin lymphoma, or anaplastic large cell lymphoma.

In other embodiments, the cancer is a solid tumor, e.g., a cancer chosen from a breast cancer, a lung cancer, a colon cancer, or a glioblastoma.

In certain embodiments, the PI3K gamma inhibitor and the PI3K-δ inhibitor are in a single dosage form.

In certain embodiments, the PI3K gamma inhibitor and the PI3K-δ inhibitor are in separate dosage forms.

In certain embodiments, the PI3K gamma inhibitor and the PI3K-δ inhibitor are administered concurrently.

In certain embodiments, the PI3K gamma inhibitor is administered subsequent to the PI3K-δ inhibitor.

In certain embodiments, the PI3K gamma inhibitor is administered prior to the PI3K-δ inhibitor.

In certain embodiments, the PI3K gamma inhibitor is a selective PI3K-δ inhibitor, e.g., has a delta/gamma selectivity ratio of greater than about 1 to <10, greater than about 10 to <50, or greater than about 50 to <350.

In certain embodiments, the concentration of the PI3K gamma inhibitor, e.g., Compound 4, that is required to achieve inhibition, e.g., 50% inhibition, is lower (e.g., at least 20%, 30%, 40%, or 50% lower) when the PI3K gamma inhibitor is administered in combination with the PI3K-δ inhibitor than when the PI3K gamma inhibitor is administered individually.

In certain embodiments, the concentration of the PI3K-δ inhibitor that is required to achieve inhibition, e.g., 50% inhibition, is lower (e.g., at least 20%, 30%, 40%, or 50% lower) when the second therapeutic agent is administered in combination with the PI3K gamma inhibitor than when the PI3K-δ inhibitor is administered individually.

In certain embodiments, the dose of the PI3K gamma inhibitor that is required to achieve inhibition, e.g., 50% inhibition, is lower (e.g., at least 20%, 30%, 40%, or 50% lower) when the PI3K gamma inhibitor is administered in combination with the PI3K-δ inhibitor than when the PI3K gamma inhibitor is administered individually.

In certain embodiments, the dose of the second therapeutic agent that is required to achieve inhibition, e.g., 50% inhibition, is lower (e.g., at least 20%, 30%, 40%, or 50% lower) when the second therapeutic agent is administered in combination with the PI3K gamma inhibitor than when the PI3K-δ inhibitor is administered individually.

In certain embodiments, the combination is synergistic as indicated by a combination index value that is less than 0.7, 0.5, or 0.1 for the combination of the PI3K gamma inhibitor and the PI3K-δ inhibitor.

In certain embodiments, the combination index value is assessed at 50% inhibition.

In certain embodiments, the combination index value is assessed at 50% growth inhibition.

In certain embodiments, the combination is synergistic as indicated by a Synergy Score that is greater than 1, 2, or 3, for the combination of the PI3K gamma inhibitor and the second therapeutic agent.

In certain embodiments, the combination is synergistic as indicated by a Synergy Score that is greater than 1, 2, or 3, for the combination of the PI3K gamma inhibitor and the PI3K-δ inhibitor for inhibition or growth inhibition.

In certain embodiments, the anti-cancer effect provided by the composition greater than the anti-cancer effect provided by the monotherapy with the PI3K gamma inhibitor or pharmaceutically acceptable form thereof, e.g., is at least 2 fold greater, at least 3 fold greater, at least 5 fold greater, or at least 10 fold greater.

In certain embodiments, the anti-cancer effect provided by the composition is greater than the anti-cancer effect provided by the monotherapy with the PI3K-δ inhibitor or pharmaceutically acceptable form thereof, e.g., is at least 2 fold greater, at least 3 fold greater, at least 5 fold greater, or at least 10 fold greater.

In certain embodiments, one or more side effects of the composition is reduced compared with the side effects of administering a monotherapy comprising the PI3K gamma inhibitor or pharmaceutically acceptable form thereof, without PI3K-δ inhibitor or pharmaceutically acceptable form thereof, at a dose that achieves the same therapeutic effect.

In certain embodiments, one or more side effects of the composition is reduced compared with the side effects of administering a monotherapy comprising the PI3K-δ inhibitor or pharmaceutically acceptable form thereof, without the PI3K gamma inhibitor or pharmaceutically acceptable form thereof, at a dose that achieves the same therapeutic effect.

In another aspect, the invention features a composition comprising a synergistic combination of a PI3K gamma inhibitor (e.g., a compound of any of Formulae (I″), (I′), (A′), (I), (A), (II), (III), (IV), (V), (VI), (VII), (IX), (X), (XI), (XII), (XIII), (XIV), (XV), (XVI), and (XVII), e.g., Compound 4, as described herein) and a PI3K-δ inhibitor. The compositions can be provided in the same or in separate dosage forms.

In certain embodiments, the PI3K-δ inhibitor is a selective PI3K-δ inhibitor, e.g., has a delta/gamma selectivity ratio of greater than about 1 to <10, greater than about 10 to <50, or greater than about 50 to <350.

In certain embodiments, the molar ratio of the PI3K gamma inhibitor to the PI3K-δ inhibitor is in the range of from about 10000:1 to about 1:10000.

In certain embodiments, the molar ratio of the PI3K gamma inhibitor to the PI3K-δ inhibitor is in the range of from about 10:1 to about 1:10.

In certain embodiments, the composition comprises the PI3K gamma inhibitor, or pharmaceutically acceptable form thereof, at an amount of in the range of from about 0.01 mg to about 75 mg and the PI3K-δ inhibitor, or pharmaceutically acceptable form thereof, at an amount of in the range of from about 0.01 mg to about 1100 mg.

In certain embodiments, the PI3K gamma inhibitor or pharmaceutically acceptable form thereof, and the PI3K-δ inhibitor or pharmaceutically acceptable form thereof, are the only therapeutically active ingredients.

In certain embodiments, the PI3K gamma inhibitor or pharmaceutically acceptable form thereof, and the PI3K-δ inhibitor or pharmaceutically acceptable form thereof, are in a single dosage form.

In certain embodiments, the PI3K gamma inhibitor or pharmaceutically acceptable form thereof, and the PI3K-δ inhibitor or pharmaceutically acceptable form thereof, are in separate dosage forms.

In certain embodiments, the combination of the PI3K gamma inhibitor and the PI3K-δ inhibitor are synergistic in treating a cancer, inflammatory disease, or autoimmune disease.

In certain embodiments, the concentration of the PI3K gamma inhibitor that is required to achieve inhibition, e.g., 50% inhibition, is lower (e.g., at least 20%, 30%, 40%, or 50% lower) when the Compound 4 is administered in combination with the PI3K-δ inhibitor than when the Compound 4 is administered individually.

In certain embodiments, the concentration of the second therapeutic agent that is required to achieve inhibition, e.g., 50% inhibition, is lower (e.g., at least 20%, 30%, 40%, or 50% lower) when the second therapeutic agent is administered in combination with the PI3K gamma inhibitor than when the second therapeutic agent is administered individually.

In certain embodiments, the dose of the PI3K gamma inhibitor that is required to achieve inhibition, e.g., 50% inhibition, is lower (e.g., at least 20%, 30%, 40%, or 50% lower) when the PI3K gamma inhibitor is administered in combination with the PI3K-δ inhibitor than when the PI3K gamma inhibitor is administered individually.

In certain embodiments, the dose of the second therapeutic agent that is required to achieve inhibition, e.g., 50% inhibition, is lower (e.g., at least 20%, 30%, 40%, or 50% lower) when the second PI3K-δ inhibitor is administered in combination with the PI3K gamma inhibitor than when the PI3K-δ inhibitor is administered individually.

In certain embodiments, wherein the combination is synergistic as indicated by a combination index value that is less than 0.7, 0.5, or 0.1 for the combination of the PI3K gamma inhibitor and the PI3K-δ inhibitor.

In certain embodiments, the combination index value is assessed at 50% inhibition.

In certain embodiments, the combination index value is assessed at 50% growth inhibition.

In certain embodiments, the combination is synergistic as indicated by a Synergy Score that is greater than 1, 2, or 3, for the combination of the PI3K gamma inhibitor and the PI3K-δ inhibitor.

In certain embodiments, the combination is synergistic as indicated by a Synergy Score that is greater than 1, 2, or 3, for the combination of the PI3K gamma inhibitor and the PI3K-δ inhibitor for inhibition or growth inhibition.

In certain embodiments, the anti-cancer effect provided by the composition greater than the anti-cancer effect provided by the monotherapy with the PI3K gamma inhibitor or pharmaceutically acceptable form thereof, e.g., is at least 2 fold greater, at least 3 fold greater, at least 5 fold greater, or at least 10 fold greater.

In certain embodiments, the anti-cancer effect provided by the composition is greater than the anti-cancer effect provided by the monotherapy with the PI3K-δ inhibitor or pharmaceutically acceptable form thereof, e.g., is at least 2 fold greater, at least 3 fold greater, at least 5 fold greater, or at least 10 fold greater.

In certain embodiments, one or more side effects of the composition is reduced compared with the side effects of administering a monotherapy comprising the PI3K gamma inhibitor or the compound, or pharmaceutically acceptable form thereof, without the PI3K-δ inhibitor or the compound, pharmaceutically acceptable form thereof, at a dose that achieves the same therapeutic effect.

In certain embodiments, one or more side effects of the composition is reduced compared with the side effects of administering a monotherapy comprising the PI3K-δ inhibitor or pharmaceutically acceptable form thereof, without the PI3K gamma inhibitor or pharmaceutically acceptable form thereof, at a dose that achieves the same therapeutic effect.

In certain embodiments, the compositions further comprise a pharmaceutically acceptable excipient.

Bone Disorders

In another aspect, the invention features a method of treating or preventing a bone disorder, e.g., a method of reducing osteoclast activity in a subject having a bone formation disorder. The method includes administering a PI3K gamma inhibitor or a compound as described herein (e.g., a compound of any of Formulae (I″), (I′), (A′), (I), (A), (II), (III), (IV), (V), (VI), (VII), (IX), (X), (XI), (XII), (XIII), (XIV), (XV), (XVI), and (XVII), e.g., Compound 4, as described herein) in an amount sufficient to treat or prevent the bone disorder.

In certain embodiments, the effective amount of the PI3K gamma inhibitor is an amount sufficient to reduce the number of osteoclasts in the subject compared to a reference value, after administration of the compound.

In certain embodiments, the effective amount of the PI3K gamma inhibitor is an amount sufficient to reduce the number of osteoclasts in the subject by about 10%, 20%, 30%, 40%, 50%, 60%, 70%, 80%, or 90% compared to a reference value, after administration of the compound.

In certain embodiments, the subject has, or is determined to have, a reduction in the number of osteoclasts compared to a reference value, after administration of the compound.

In certain embodiments, the subject has, or is determined to have, a reduction in the number of osteoclasts by about 10%, 20%, 30%, 40%, 50%, 60%, 70%, 80%, or 90% compared to a reference value, after administration of the compound.

In certain embodiments, the effective amount is an amount sufficient to result in decreased differentiation of a macrophage into an osteoclast.

In certain embodiments, the effective amount is an amount sufficient to result in differentiation of macrophages into osteoclasts being reduced by about 10%, 20%, 30%, 40%, 50%, 60%, 70%, 80%, or 90%.

In certain embodiments, the subject has, or is determined to have, decreased differentiation of a macrophage into an osteoclast.

In certain embodiments, the subject has, or is determined to have, differentiation of macrophages into osteoclasts being reduced by about 10%, 20%, 30%, 40%, 50%, 60%, 70%, 80%, or 90%.

In certain embodiments, differentiation is measured by identifying TRAP positive cells.

In certain embodiments, which does not result in disruption of the function of a differentiated osteoclast.

In certain embodiments, the bone formation disorder is osteoporosis, osteoporosis pseudoglioma, hyperparathyroidism, hyperthyroidism, Paget's disease, hyperphosphatasemia, fibrous dysplasia, osteogenesis imperfecta, primary and secondary hyperparathyroidism and associated syndromes, hypercalciuria, metastatic osteolytic carcinomas (including medullary carcinoma of the thyroid gland, prostate, renal, breast, and lung cancer), or osteomalacia. In certain embodiments, the compounds provide herein is used in the treatment of osteolytic cancer metastases, fracture repair, rheumatoid arthritis, or other autoimmune diseases to damage of bone and joints.

In certain embodiments, provided herein are methods of treating or preventing a bone formation disorder in a subject, comprising administering to the subject a therapeutically effective amount of a compound provided herein (e.g., a compound of any of Formulae (I"), (I'), (A'), (I), (A), (II), (III), (IV), (V), (VI), (VII), (IX), (X), (XI), (XII), (XIII), (XIV), (XV), (XVI), and (XVII), e.g., a selective PI3K-γ inhibitor, e.g., Compound 4), or a pharmaceutically acceptable form thereof.

In one embodiment, the number of osteoclasts in the subject is reduced by about 10%, 20%, 30%, 40%, 50%, 60%, 70%, 80%, or 90% compared to a reference value, after administration of the compound. In one embodiment, the differentiation of macrophage cells into osteoclasts is reduced by about 10%, 20%, 30%, 40%, 50%, 60%, 70%, 80%, or 90% compared to a reference value, after administration of the compound. In one embodiment, the differentiation of macrophage cells into osteoclasts is measured by identifying TRAP positive cells.

In one embodiment, the method does not result in disruption of the function of differentiated osteoclasts.

In one embodiment, the bone formation disorder is osteoporosis, osteoporosis pseudoglioma, hyperparathyroidism, hyperthyroidism, Paget's disease, hyperphosphatasemia, fibrous dysplasia, osteogenesis imperfecta, primary and secondary hyperparathyroidism and associated syndromes, hypercalciuria, metastatic osteolytic carcinomas (including medullary carcinoma of the thyroid gland, prostate, renal, breast, and lung cancer), or osteomalacia.

Combination with Radiation Therapy:

In another aspect, the invention features a method of treating a solid tumor, comprising administering to a subject in need thereof an effective amount of a PI3K gamma inhibitor or a compound as described herein (e.g., a compound of any of Formulae (I"), (I'), (A'), (I), (A), (II), (III), (IV), (V), (VI), (VII), (IX), (X), (XI), (XII), (XIII), (XIV), (XV), (XVI), and (XVII), e.g., Compound 4, as described herein):

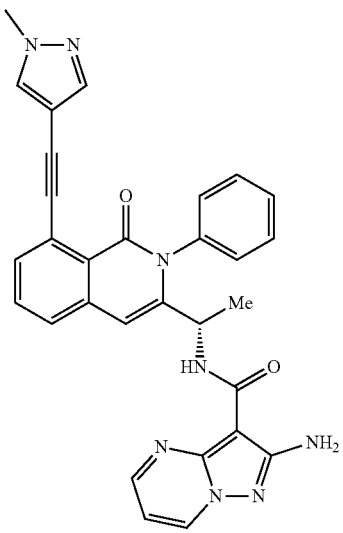

or a pharmaceutically acceptable form thereof.

In embodiment, the treatment can be, e.g., either prior to administering the radiation therapy, after administering radiation therapy, or at the same time as administering radiation therapy. In another embodiment, the treatment can be, e.g., either after administering radiation therapy, or at the same time as administering radiation therapy. In another embodiment, the treatment can be after administering radiation therapy.

In certain embodiments, the cancer is selected from one or more of: a cancer of the pulmonary system, a brain cancer, a cancer of the gastrointestinal tract, a skin cancer, a genitourinary cancer, a pancreatic cancer, a lung cancer, a medullobastoma, a basal cell carcinoma, a glioma, a breast cancer, a prostate cancer, a testicular cancer, an esophageal cancer, a hepatocellular cancer, a gastric cancer, a gastrointestinal stromal tumor (GIST), a colon cancer, a colorectal cancer, an ovarian cancer, a melanoma, a neuroectodermal tumor, head and neck cancer, a sarcoma, a soft-tissue sarcoma, fibrosarcoma, myxosarcoma, liposarcoma, a chondrosarcoma, an osteogenic sarcoma, a chordoma, an angiosarcoma, an endotheliosarcoma, a lymphangiosarcoma, a lymphangioendotheliosarcoma, a synovioma, a mesothelioma, a leiomyosarcoma, a cervical cancer, a uterine cancer, an endometrial cancer, a carcinoma, a bladder carcinoma, an epithelial carcinoma, a squamous cell carcinoma, an adenocarcinoma, a bronchogenic carcinoma, a renal cell carcinoma, a hepatoma, a bile duct carcinoma, a neuroendocrine cancer, a carcinoid tumor, diffuse type giant cell tumor, and glioblastoma. In certain embodiments, the solid tumor is a lung tumor, breast tumor, colon tumor, brain tumor, bone tumor, glioblastoma, or a metastatic lesion thereof. In one embodiment, the combination of radiation and/or PI3K-gamma inhibition is such that accumulation of tumor supporting-myeloid cells into the radiated tumor is reduced or prevented, thus impairing tumor regrowth following radiation therapy.

Intratracheal Administration

In some aspects, the present disclosure provides a method of treating (e.g., ameliorating, preventing, and/or managing) a pulmonary or respiratory disease in a subject, comprising administering to a subject in need thereof by inhalation a therapeutically or prophylactically effective amount of a PI3K gamma inhibitor or a compound as described herein (e.g., a compound of any of Formulae (I"), (I'), (A'), (I), (A), (II), (III), (IV), (V), (VI), (VII), (IX), (X), (XI), (XII), (XIII), (XIV), (XV), (XVI), and (XVII), e.g., Compound 4, as described herein):

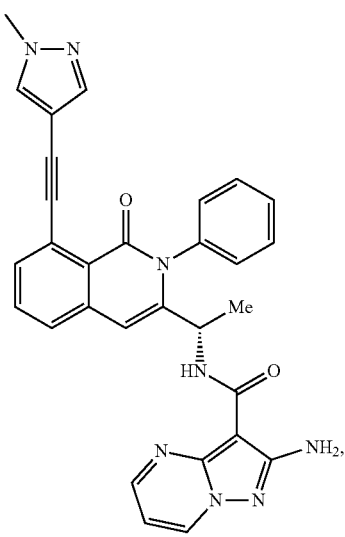

or an enantiomer, a mixture of enantiomers, or a mixture of two or more diastereomers thereof, or a pharmaceutically acceptable form thereof.

In some aspects, this disclosure provides a method of eliciting a prolonged anti-inflammatory effect in a lung in a subject suffering from a pulmonary or respiratory disease, comprising administering to the subject by inhalation a therapeutically or prophylactically effective amount of the PI3K gamma inhibitor or a compound as described herein (e.g., Compound 4) or an enantiomer, a mixture of enantiomers, or a mixture of two or more diastereomers thereof, or a pharmaceutically acceptable form thereof, wherein the compound is retained in lung for a period longer than what is provided by oral administration.

In some embodiments, the compound is retained in the lung for a period that is sufficient to administer the compound once a day, twice a day, three times a day, four times a day, five times a day, or once every two day.

In some embodiments, the compound is retained in lung for about 1 hour, about 3 hours, about 6 hours, about 12 hours, about 24 hours, about 48 hours, or about 72 hours longer than what is provided by oral administration.

In some embodiments, the compound is administered at a dose of less than 0.01 µg/kg/day, less than 0.02 µg/kg/day, less than 0.05 µg/kg/day, less than 0.1 µg/kg/day, less than 0.2 µg/kg/day, less than 0.5 µg/kg/day, less than 1 µg/kg/day, less than 2 µg/kg/day, less than 5 µg/kg/day, less than 10 µg/kg/day, less than 20 µg/kg/day, less than 50 µg/kg/day, or less than 100 µg/kg/day. In some embodiments, the compound is administered at a dose of about 0.01 µg/kg/day, about 0.02 µg/kg/day, about 0.05 µg/kg/day, about 0.1 µg/kg/day, about 0.2 µg/kg/day, about 0.5 µg/kg/day, about 1 µg/kg/day, about 2 µg/kg/day, about 5 µg/kg/day, about 10 µg/kg/day, about 20 µg/kg/day, about 50 µg/kg/day, or about 100 µg/kg/day. In some embodiments, the compound is administered at a dose of from about 0.01 µg/kg/day to about 100 µg/kg/day, from about 0.01 µg/kg/day to about 50 µg/kg/day, from about 0.01 µg/kg/day to about 20 µg/kg/day, from about 0.01 µg/kg/day to about 10 µg/kg/day, from about 0.01 µg/kg/day to about 5 µg/kg/day, from about 0.01 µg/kg/day to about 1 µg/kg/day, from about 0.05 µg/kg/day to about 1 µg/kg/day, or from about 0.1 µg/kg/day to about 1 µg/kg/day.

In some embodiments, the compound is administered once daily (QD), twice daily (BID), three times daily (TID), or four times daily (QID).

In some embodiments, administering an effective amount of the compound does not result in, or results in reduced, one or more common side effects associated with treatment of pulmonary or respiratory diseases. In some embodiments, the common side effect associated with treatment of pulmonary or respiratory diseases is oral candidiasis, thrush, dysphonia, reflex cough, bronchospasm, poor growth, decreased bone density, disseminated varicella infection, easy bruising, cataracts, glaucoma, adrenal gland suppression, stomach upset, headache, liver test abnormalities, skin rashes, Churg Strauss syndrome, bad taste in month, cough, itching, sore throat, sneezing, stuffy nose, shortness of breath, wheezing, viral illness, upper respiratory tract infections, sinusitis, feeling dizzy or faint, hives, changes in voice, swelling of the tongue, or difficulty in swallowing.

In some embodiments, administering an effective amount of the compound reduces one of more of symptoms associated with pulmonary or respiratory diseases. In some embodiments, the symptom associated with pulmonary or respiratory diseases is wheezing, coughing, chest tightness, shortness of breath, difficulty in breathing, or use of accessory muscle.

In some embodiments, administering an effective amount of the compound by inhalation results in higher than about 20%, higher than about 30%, higher than about 40%, or higher than about 50% of the administered dose of the compound remaining in lung of the subject at about 24 hours after the administration.

In some embodiments, administering an effective amount of the compound by inhalation results in that the lung concentration of the compound is about 100, about 200, about 500, about 1000, about 2000, about 3000, about 4000, about 5000, about 6000, about 7000, about 8000, about 9000, or about 10000 times higher than the plasma concentration of the compound at about 5 hours after the administration. In some embodiments, administering an effective amount of the compound by inhalation results in that the lung concentration of the compound is about 100, about 200, about 500, about 1000, about 2000, about 3000, about 4000, about 5000, about 6000, about 7000, about 8000, about 9000, or about 10000 times higher than the plasma concentration of the compound at about 12 hours after the administration. In some embodiments, administering an effective amount of the compound by inhalation results in that the lung concentration of the compound is about 100, about 200, about 500, about 1000, about 2000, about 3000, about 4000, about 5000, about 6000, about 7000, about 8000, about 9000, or about 10000 times higher than the plasma concentration of the compound at about 24 hours after the administration.

In some embodiments, the pulmonary or respiratory disease is selected from the group consisting of pulmonary inflammation, asthma, cystic fibrosis, emphysema, chronic obstructive pulmonary disorder (COPD), chronic bronchitis, bronchiectasis, acute respiratory distress syndrome, restrictive lung diseases, respiratory tract infections, pleural cavity diseases, pulmonary vascular disease, pulmonary embolism, pulmonary arterial hypertension, pulmonary edema, pulmonary hemorrhage, and pulmonary hyperplasia.

In some embodiments, the pulmonary or respiratory disease is chronic obstructive pulmonary disorder. In some embodiments, the pulmonary or respiratory disease is asthma. In some embodiments, the asthma is selected from the group consisting of severe or refractory asthma, atopic asthma, non-atopic asthma, type 1 brittle asthma, type 2 brittle asthma, asthma attack, status asthmaticus, exercise-induced asthma, and occupational asthma.

In some embodiments, the subject is a mammal. In some embodiments, the subject is a human.

In some embodiments, the method further comprises administration of an additional therapeutic agent, e.g., an agent selected from one or more of Arcapta (indacaterol maleate inhalation powder), Daliresp (roflumilast), Dulera (mometasone furoate+formoterol fumarate dihydrate), Alvesco (ciclesonide), Brovana (arformoterol tartrate), Spiriva HandiHaler (tiotropium bromide), Xolair (omalizumab), Qvar (beclomethasone dipropionate), Xopenex (levalbuterol), DuoNeb (albuterol sulfate and ipratropium bromide), Foradil Aerolizer (formoterol fumarate inhalation powder), Accolate (zafirlukast), Singulair (montelukast sodium), Flovent Rotadisk (Rotadisk (fluticasone propionate inhalation powder), Tilade (nedocromil sodium), Vanceril (beclomethasone dipropionate, 84 mcg), Zyflo (Zileuton), and Azmacort (triamcinolone acetonide) Inhalation Aerosol.

Abbreviations for PI3K isoforms are provided interchangeably throughout as either the Greek letter or corresponding name. For example, the terms PI3K-γ and PI3K-gamma, or PI3K-δ and PI3K-delta are used interchangeably throughout.

INCORPORATION BY REFERENCE

All publications, patents, and patent applications mentioned in this specification are herein incorporated by reference to the same extent as if each individual publication, patent, or patent application was specifically and individually indicated to be incorporated by reference. In case of conflict, the present application, including any definitions herein, will control.

BRIEF DESCRIPTION OF THE DRAWINGS

FIG. 27A shows the effect on tumor volume over time. FIG. 27B shows the percent survival over time.

FIG. 32B is a repeat study.

FIG. 38A shows that TAMs are decreased in Compound BB-treated LLC tumor brei model. FIG. 38B shows that Monocytic iMCs are decreased in Compound BB-treated CT26 subcutaneous tumors.

FIGS. 49A, 49B, 49C, 49D, and 49E show CD11b/Gr-1 plots after treatment with Compound BB+/– cyclophosphamide in the LLC tumor brei model. FIG. 49A shows the percentage of cells that are CD3 relative to CD45+. FIG. 49B shows the percentage of cells that are CD11b+Gr-1– relative to CD45+. FIG. 49C shows the percentage of cells that are CD11b+Gr-1+ relative to CD45+.

FIG. 49D shows the percentage of cells that are CD11b-Gr-1– relative to CD45+. FIG. 49E shows the percentage of cells that are CD11b-Gr-1+ relative to CD45+.

FIG. 50A shows the percentage of cells that are CD11b+ relative to CD45. FIG. 50B shows the percentage of cells that are CD11b+Ly6C+ relative to CD45+. FIG. 50C shows the percentage of cells that are CD11b+Ly6C+Ly6G+ relative to CD45+. FIG. 50D shows the percentage of cells that are CD11b+Ly6C-Ly6G– relative to CD45+.

FIG. 51A shows the percentage of cells that are CD3+ relative to CD45+. FIG. 51B shows the percentage of cells that are CD4+CD8– relative to CD45+. FIG. 51C shows the percentage of cells that are CD4+CD8+ relative to CD45+. FIG. 51D shows the percentage of cells that are CD4-CD8+ relative to CD45+. FIG. 51E shows the percentage of cells that are CD4-CD8– relative to CD45+.

FIGS. 52A, 52B, 52C, 52D, and 52E show the percentage of cells that are CD45+, CD11b+, or CD206+, expressed as a percent of total cells, in LLC tumor brei model treated with Compound BB+/– cyclophosphamide. FIG. 52A shows the percentage of cells that are CD45+ expressed as a percent of total cells. FIG. 52B shows the percentage of cells that are CD11b expressed as a percent of total cells. FIG. 52C shows the percentage of cells that are CD206 expressed as a percent of total cells.

FIG. 52D shows the percentage of cells that are CD11b expressed as a percent of total cells. FIG. 52E shows the percentage of cells that are CD206 expressed as a percent of total cells.

FIG. 55A shows the effect of vehicle treated tumor-derived cell mediated T cell proliferation. FIG. 55B shows the effect of Compound BB treated tumor-derived cell mediated T cell proliferation. FIG. 55C shows the effect of anti PDL-1 treated tumor-derived cell mediated T cell proliferation.

DETAILED DESCRIPTION

Figure 1:
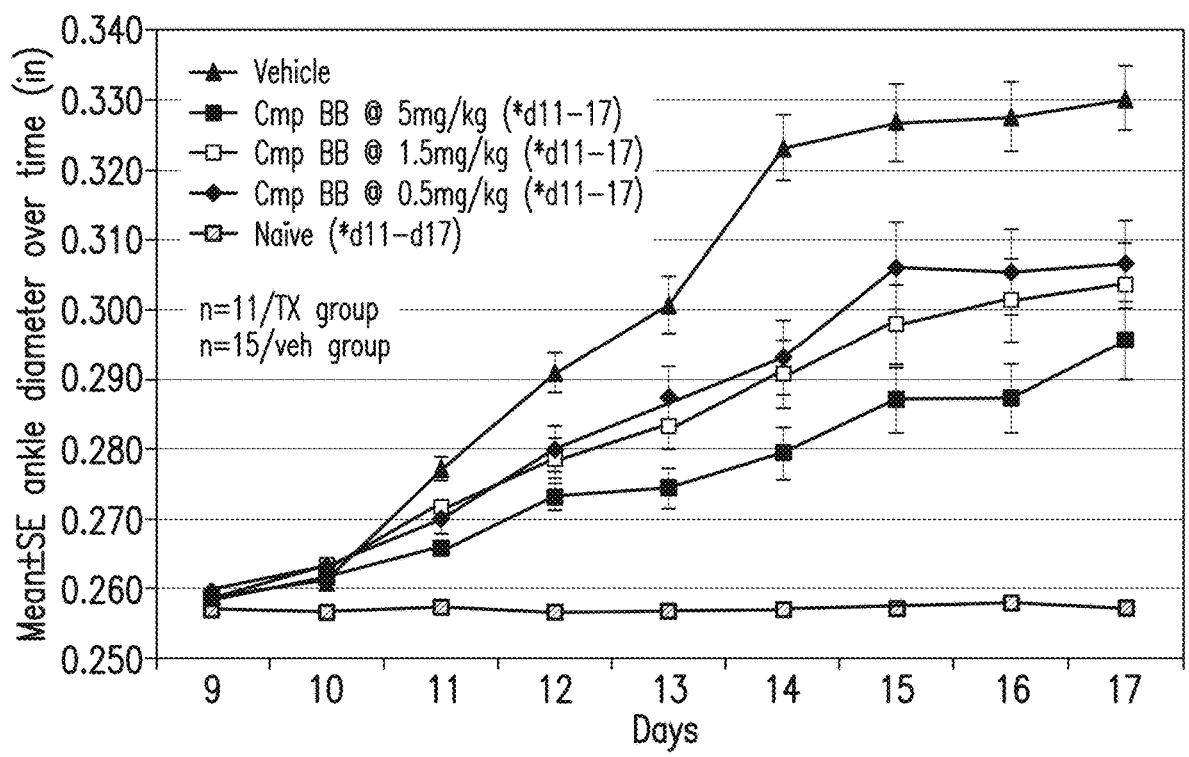
FIG. 1 shows the effect of Compound BB in the collagen induced arthritis rat model as measured by the mean ankle diameter over time.

In one embodiment, provided are heterocyclyl compounds, and pharmaceutically acceptable forms thereof, including, but not limited to, salts, hydrates, solvates, isomers, prodrugs, and isotopically labeled derivatives thereof.

In another embodiment, provided are methods of treating and/or managing various diseases and disorders, which comprises administering to a patient a therapeutically effective amount of a compound provided herein, or a pharmaceutically acceptable form (e.g., salts, hydrates, solvates, isomers, prodrugs, and isotopically labeled derivatives) thereof. Examples of diseases and disorders are described herein.

In another embodiment, provided are methods of preventing various diseases and disorders, which comprises administering to a patient in need of such prevention a prophylactically effective amount of a compound provided herein, or a pharmaceutically acceptable form (e.g., salts, hydrates, solvates, isomers, prodrugs, and isotopically labeled derivatives) thereof. Examples of diseases and disorders are described herein.

In other embodiments, a compound provided herein, or a pharmaceutically acceptable form (e.g., salts, hydrates, solvates, isomers, prodrugs, and isotopically labeled derivatives) thereof, is administered in combination with another drug ("second active agent") or treatment. Second active agents include small molecules and large molecules (e.g., proteins and antibodies), examples of which are provided herein, as well as stem cells. Other methods or therapies that can be used in combination with the administration of compounds provided herein include, but are not limited to, surgery, blood transfusions, immunotherapy, biological therapy, radiation therapy, and other non-drug based therapies presently used to treat, prevent or manage various disorders described herein.

Also provided are pharmaceutical compositions (e.g., single unit dosage forms) that can be used in the methods provided herein. In one embodiment, pharmaceutical compositions comprise a compound provided herein, or a pharmaceutically acceptable form (e.g., salts, hydrates, solvates, isomers, prodrugs, and isotopically labeled derivatives) thereof, and optionally one or more second active agents.

While specific embodiments have been discussed, the specification is illustrative only and not restrictive. Many variations of this disclosure will become apparent to those skilled in the art upon review of this specification.

Unless defined otherwise, all technical and scientific terms used herein have the same meaning as is commonly understood by one of skill in the art to which this specification pertains.

As used in the specification and claims, the singular form "a", "an" and "the" includes plural references unless the context clearly dictates otherwise.

As used herein, and unless otherwise indicated, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

As used herein, "agent" or "biologically active agent" or "second active agent" refers to a biological, pharmaceutical, or chemical compound or other moiety. Non-limiting examples include simple or complex organic or inorganic molecules, a peptide, a protein, an oligonucleotide, an antibody, an antibody derivative, an antibody fragment, a vitamin, a vitamin derivative, a carbohydrate, a toxin, or a chemotherapeutic compound, and metabolites thereof. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. A skilled artisan can readily recognize that there is no limit as to the structural nature of the agents of this disclosure.

The term "agonist" as used herein refers to a compound or agent having the ability to initiate or enhance a biological function of a target protein or polypeptide, such as increasing the activity or expression of the target protein or polypeptide. Accordingly, the term "agonist" is defined in the context of the biological role of the target protein or polypeptide. While some agonists herein specifically interact with (e.g., bind to) the target, compounds and/or agents that initiate or enhance a biological activity of the target protein or polypeptide by interacting with other members of the signal transduction pathway of which the target polypeptide is a member are also specifically included within this definition.

The terms "antagonist" and "inhibitor" are used interchangeably, and they refer to a compound or agent having the ability to inhibit a biological function of a target protein or polypeptide, such as by inhibiting the activity or expression of the target protein or polypeptide. Accordingly, the terms "antagonist" and "inhibitor" are defined in the context of the biological role of the target protein or polypeptide. While some antagonists herein specifically interact with (e.g., bind to) the target, compounds that inhibit a biological activity of the target protein or polypeptide by interacting with other members of the signal transduction pathway of which the target protein or polypeptide are also specifically included within this definition. Non-limiting examples of biological activity inhibited by an antagonist include those associated with the development, growth, or spread of a tumor, or an undesired immune response as manifested in autoimmune disease. The term "inhibition" or "inhibitor" as used in this context includes a reduction in a certain parameter, e.g., an activity, of a given molecule, e.g., a PI3K isoform. For example, inhibition of an activity, e.g., a PI3K activity, of at least 5%, 10%, 20%, 30%, 40% or more is included by this term. Thus, inhibition need not be 100%.

An "anti-cancer agent", "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, or buccal administration, or inhalation, or in the form of a suppository.

The term "cell proliferation" refers to a phenomenon by which the cell number has changed as a result of division.

This term also encompasses cell growth by which the cell morphology has changed (e.g., increased in size) consistent with a proliferative signal.

The term "tumor" refers to any neoplastic cell growth and proliferation, whether malignant or benign, and any pre-cancerous and cancerous cells and tissues. As used herein, the term "neoplastic" refers to any form of dysregulated or unregulated cell growth, whether malignant or benign, resulting in abnormal tissue growth. Thus, "neoplastic cells" include malignant and benign cells having dysregulated or unregulated cell growth.

The term "cancer" includes, but is not limited to, solid tumors and blood born tumors. The term "cancer" refers to disease of skin tissues, organs, blood, and vessels, including, but not limited to, cancers of the bladder, bone or blood, brain, breast, cervix, chest, colon, endometrium, esophagus, eye, head, kidney, liver, lymph nodes, lung, mouth, neck, ovaries, pancreas, prostate, rectum, stomach, testis, throat, and uterus.

Hematopoietic origin refers to involving cells generated during hematopoiesis, a process by which cellular elements of blood, such as lymphocytes, leukocytes, platelets, erythrocytes and natural killer cells are generated. Cancers of hematopoietic origin includes lymphoma and leukemia.

"Resistant" or "refractory" or "refractive" refers to when a cancer that has a reduced responsiveness to a treatment, e.g., up to the point where the cancer does not respond to treatment. The cancer can be resistant at the beginning of treatment, or it may become resistant during treatment. The cancer subject can have one or more mutations that cause it to become resistant to the treatment, or the subject may have developed such mutations during treatment. In one embodiment, the cancer or subject has failed to respond to a given therapeutic treatment (e.g., has failed to respond by at least 10%, 20%, 30%, 40%, 50%, 60%, 70%, 80%, 90%, or 100% to a given treatment). Failed treatment can be measured by, e.g., tumor volume or the length of time before tumor regrowth occurs.

By "hyperproliferative cancerous disease or disorder" is meant all neoplastic cell growth and proliferation, whether malignant or benign, including all transformed cells and tissues and all cancerous cells and tissues. Hyperproliferative diseases or disorders include, but are not limited to, precancerous lesions, abnormal cell growth, benign tumors, malignant tumors, and "cancer."

Combination therapy or "in combination with" refer to the use of more than one compound or agent to treat a particular disorder or condition. For example, Compound 4 may be administered in combination with at least one additional therapeutic agent. By "in combination with," it is not intended to imply that the other therapy and Compound 4 must be administered at the same time and/or formulated for delivery together, although these methods of delivery are within the scope of this disclosure. Compound 4 can be administered concurrently with, prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks before), or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks after), one or more other additional agents. In general, each therapeutic agent will be administered at a dose and/or on a time schedule determined for that particular agent. The other therapeutic agent can be administered with Compound 4 herein in a single composition or separately in a different composition. Higher combinations, e.g., triple therapy, are also contemplated herein.

As used herein, a "monotherapy" refers to the use of an agent individually (e.g., as a single compound or agent), e.g., without a second active ingredient to treat the same indication, e.g., cancer. For example, in this context, the term monotherapy includes the use of either the PI3K inhibitor or the second agent individually to treat the cancer.

The term "synergy" or "synergistic" encompasses a more than additive effect of a combination of two or more agents compared to their individual effects. In certain embodiments, synergy or synergistic effect refers to an advantageous effect of using two or more agents in combination, e.g., in a pharmaceutical composition, or in a method of treatment. In certain embodiments, one or more advantageous effects is achieved by using a PI3K inhibitor in combination with a second therapeutic agent (e.g., one or more second therapeutic agents) as described herein.

In embodiments, the synergistic effect is that a lower dosage of one or both of the agents is needed to achieve an effect. For example, the combination can provide a selected effect, e.g., a therapeutic effect, when at least one of the agents is administered at a lower dosage than the dose of that agent that would be required to achieve the same therapeutic effect when the agent is administered as a monotherapy. In certain embodiments, the combination of a PI3K inhibitor (e.g., Compound 4) and a second agent (as described herein) allows the PI3K inhibitor to be administered at a lower dosage than would be required to achieve the same therapeutic effect if the PI3K inhibitor were administered as a monotherapy.

In embodiments, a synergistic effect refers to the combination of a PI3K inhibitor (e.g., Compound 4, or a pharmaceutically acceptable form thereof), and a second therapeutic agent (e.g., one or more additional therapeutic agent(s), or a pharmaceutically acceptable form thereof, as described herein), results in a therapeutic effect greater than the additive effect of the PI3K inhibitor and the second agent.

In embodiments, a synergistic effect means that combination index value is less than a selected value, e.g., for a given effect, e.g., at a selected percentage (e.g., 50%) inhibition or growth inhibition, e.g., as described herein in the Examples. In embodiments, a synergistic effect means that the synergy score is 1 or more. In certain embodiments, the synergy score is greater than 1. In certain embodiments, the synergy score is greater than 3.

Combination index (CI) is a measure of potency shifting. The combination index is known in the art and is described, e.g., in Chou et al., Adv Enzyme Regul 1984; 22: 27-55 and in U.S. Patent Publication No. 2013/0295102, the contents of which are incorporated herein by reference. A CI value of greater than 1 indicates antagonistic effect; a CI value of 1.0 is indicative of an additive effect; and a CI value of less than 1 is indicative of a synergistic effect resulting from the combination. The CI value can be determined at various percentages of inhibition or growth inhibition.

The CI provides an estimate of the fraction of the original (monotherapy) doses of each of two drugs would be needed in combination relative to the single agent doses required to achieve a chosen effect level. For example, when the combination index has a value of 0.1, only about one tenth of the total fractional amounts of the individual agents (expressed as a fraction of the amount of that agent when administered as a monotherapy to achieve a chosen effect) are needed for the combination to reach the same chosen effect level. For example, if a dose of 100 mg/kg of drug A individually or a dose of 200 mg/kg of drug B individually is needed to achieve the chosen effect, and the combination index is 0.1, then approximately 5 mg/kg of drug A and 10 mg/kg of drug B would achieve the chosen effect (one twentieth of the original doses of each of the single agents adds up to a total of one tenth). The doses of the single agents need not be reduced by the same fractional value so long as the sum of their fractional values adds up to the combination index; thus, in this example, a dose of approximately 8 mg/kg of drug A and 4 mg/kg of drug B would also achieve the chosen effect (this is 0.08 times the original dose of drug A and 0.02 times the original dose of drug B; the sum of the fractional amounts (0.08+0.02) is equal to the combination index of 0.1.)

According to one embodiment, synergy score is a measure of the combination effects in excess of Loewe additivity. In one example, synergy score is a scalar measure to characterize the strength of synergistic interaction. The Synergy score can be calculated as:

$$\text{Synergy Score} = \log f_X \log f_Y \Sigma \max(0, I_{data})(I_{data} - I_{Loewe})$$

In this example, the fractional inhibition for each component agent and combination point in the matrix is calculated relative to the median of all vehicle-treated control wells. The example Synergy Score equation integrates the experimentally-observed activity volume at each point in the matrix in excess of a model surface numerically derived from the activity of the component agents using the Loewe model for additivity. Additional terms in the Synergy Score equation (above) are used to normalize for various dilution factors used for individual agents and to allow for comparison of synergy scores across an entire experiment. The inclusion of positive inhibition gating or an $I_{data}$ multiplier removes noise near the zero effect level, and biases results for synergistic interactions at that occur at high activity levels. According to other embodiments, a synergy score can be calculated based on a curve fitting approach where the curvature of the synergy score is extrapolated by introducing a median value and origin value (e.g., a dose zero value).

The synergy score measure can be used for the self-cross analysis. Synergy scores of self-crosses are expected to be additive by definition and, therefore, maintain a synergy score of zero. However, while some self-cross synergy scores are near zero, many are greater suggesting that experimental noise or non-optimal curve fitting of the single agent dose responses are contributing to the slight perturbations in the score. This strategy is cell line-centric, focusing on self-cross behavior in each cell line versus a global review of cell line panel activity. Combinations where the synergy score is greater than the mean self-cross plus two standard deviations or three standard deviations can be considered candidate synergies at 95% and 99% confidence levels, respectively. Additivity should maintain a synergy score of zero, and synergy score of two or three standard deviations indicate synergism at statistically significant levels of 95% and 99%.

Loewe Volume (Loewe Vol) can be used to assess the overall magnitude of the combination interaction in excess of the Loewe additivity model. Loewe Volume is particularly useful when distinguishing synergistic increases in a phenotypic activity (positive Loewe Volume) versus synergistic antagonisms (negative Loewe Volume). When antagonisms are observed, the Loewe Volume should be assessed to examine if there is any correlation between antagonism and a particular drug target-activity or cellular genotype. This model defines additivity as a non-synergistic combination interaction where the combination dose matrix surface should be indistinguishable from either drug crossed with itself. The calculation for Loewe additivity is:

$$I_{Loewe} \text{ that satisfies } (X/X_1)+(Y/Y_1)=1$$

where $X_1$ and $Y_1$ are the single agent effective concentrations for the observed combination effect I. For example, if 50% inhibition is achieved separately by 1 μM of drug A or 1 μM of drug B, a combination of 0.5 μM of A and 0.5 μM of B should also inhibit by 50%.

The term "co-administration," "administered in combination with," and their grammatical equivalents, as used herein, encompass administration of two or more agents to subject so that both agents and/or their metabolites are present in the subject at the same time. Co-administration includes simultaneous administration in separate compositions, administration at different times in separate compositions, or administration in a composition in which both agents are present.

The term "effective amount" or "therapeutically effective amount" refers to that amount of a compound or pharmaceutical composition described herein that is sufficient to effect the intended application including, but not limited to, disease treatment, as illustrated below. The therapeutically effective amount can vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of platelet adhesion and/or cell migration. The specific dose will vary depending on, for example, the particular compounds chosen, the dosing regimen to be followed, whether it is administered in combination with other agents, timing of administration, the tissue to which it is administered, and the physical delivery system in which it is carried.

As used herein, the terms "treatment", "treating", "palliating" and "ameliorating" are used interchangeably herein. These terms refer to an approach for obtaining beneficial or desired results including, but not limited to, therapeutic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient can still be afflicted with the underlying disorder.

As used herein, the terms "prevention" and "preventing" are used herein to refer to an approach for obtaining beneficial or desired results including, but not limited, to prophylactic benefit. For prophylactic benefit, the pharmaceutical compositions can be administered to a patient at risk of developing a particular disease, or to a patient reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

"Signal transduction" or "signaling pathway" is a process during which stimulatory or inhibitory signals are transmitted into and within a cell to elicit an intracellular response. A "modulator" of a signal transduction pathway refers to a compound which modulates the activity of one or more cellular proteins mapped to the same specific signal transduction pathway. A modulator can augment (agonist) or suppress or inhibit (antagonist) the activity of a signaling molecule.

In certain embodiments, the signal transduction is mediated by one or more phosphoinositide 3-kinases (PI3Ks). PI3Ks are members of a conserved family of lipid kinases that regulate numerous cell functions, including proliferation, differentiation, cell survival and metabolism. Several classes of PI3Ks exist in mammalian cells, including Class IA subgroup (e.g., PI3K-$\alpha$, $\beta$, $\delta$), which are generally activated by receptor tyrosine kinases (RTKs); Class IB (e.g., PI3K-$\gamma$), which is activated by G-protein coupled receptors (GPCRs), among others. PI3Ks exert their biological activities via a "PI3K-mediated signaling pathway" that includes several components that directly and/or indirectly transduce a signal triggered by a PI3K, including the generation of second messenger phophotidylinositol, 3,4,5-triphosphate (PIP3) at the plasma membrane, activation of heterotrimeric G protein signaling, and generation of further second messengers such as cAMP, DAG, and IP3, all of which leads to an extensive cascade of protein kinase activation (reviewed in Vanhaesebroeck, B. et al. (2001) Annu Rev Biochem. 70:535-602). In certain embodiments, the compounds disclosed herein inhibit a PI3 kinase or PI3K) isoform, e.g., one, two, three or more of PI3K-$\alpha$, $\beta$, $\delta$ or -$\gamma$.

In the context of biological molecules, to "decrease", "suppress," "ameliorate," "reduce," "inhibit," or the like, includes decreasing a level or an activity (e.g., one or more functions) of a given molecule. The level of a given molecule, e.g., mRNA or protein level, or the activity can be measured in a sample, or using the assays described in the Examples herein.

To "decrease," "ameliorate," "reduce," "inhibit," (or the like) a disorder or condition, or a symptom associated with a disorder or condition includes reducing the severity and/or frequency of one or more symptoms of the disorder or condition, or reducing or delaying the onset of the disorder or condition and/or one or more symptoms of the disorder or condition. In some embodiments, the symptom is reduced by at least about 2%, at least about 5%, at least about 10%, at least about 15%, at least about 20%, at least about 25%, at least about 30%, at least about 40%, at least about 50%, at least about 60%, at least about 70%, at least about 80%, at least about 90%, or at least about 95% relative to a control level.

The term "inhibition" or "inhibit" as used in this context includes a reduction in a certain parameter, e.g., an activity, of a given molecule, e.g., a PI3K isoform. For example, inhibition of an activity, e.g., a PI3K activity, of at least 5%, 10%, 20%, 30%, 40% or more is included by this term. Thus, inhibition need not be 100%. In certain embodiments, a PI3K inhibitor as disclosed herein inhibits a PI3 kinase of the gamma isoform (a "PI3K-$\gamma$ isoform).

The term "selective inhibition" or "selectively inhibit" as applied to a biologically active agent refers to the agent's ability to selectively reduce the target signaling activity as compared to off-target signaling activity, via direct or indirect interaction with the target. For example, a compound that selectively inhibits one isoform of PI3K over another isoform of PI3K has an activity of at least greater than about 1× against a first isoform relative to the compound's activity against the second isoform (e.g., at least about 2×, 3×, 5×, 10×, 20×, 50×, 100×, 200×, 50×, or 1000×). In certain embodiments, these terms refer to (1) a compound of described herein that selectively inhibits the gamma isoform over the alpha, beta, or delta isoform; or (2) a compound described herein that selectively inhibits the delta isoform over the alpha or beta isoform. By way of non-limiting example, the ratio of selectivity can be greater than a factor of about 1, greater than a factor of about 2, greater than a factor of about 3, greater than a factor of about 5, greater than a factor of about 10, greater than a factor of about 50, greater than a factor of about 100, greater than a factor of about 200, greater than a factor of about 400, greater than a factor of about 600, greater than a factor of about 800, greater than a factor of about 1000, greater than a factor of about 1500, greater than a factor of about 2000, greater than a factor of about 5000, greater than a factor of about 10,000, or greater than a factor of about 20,000, where selectivity can be measured by ratio of IC50 values, which in turn can be measured by, e.g., in vitro or in vivo assays such as those described in Examples described herein. In one embodiment, the selectivity of a first PI3K isoform over a second PI3K isoform is measured by the ratio of the IC50 value against the second PI3K isoform to the IC50 value against the first PI3K gamma isoform. For example, a delta/gamma selectivity ratio of a compound can be measured by the ratio of the compound's inhibitory activity against the delta isoform in terms of IC50 or the like to the compound's inhibitory activity against the gamma isoform in terms of IC50 or the like. If the delta/gamma selectivity ratio is larger than 1, the compound selectively inhibits the gamma isoform over the delta isoform. In certain embodiments, the PI3K gamma isoform IC50 activity of a compound of provided herein can be less than about 1000 nM, less than about 500 nM, less than about 400 nM, less than about 300 nM, less than about 200 nM, less than about 100 nM, less than about 75 nM, less than about 50 nM, less than about 25 nM, less than about 20 nM, less than about 15 nM, less than about 10 nM, less than about 5 nM, or less than about 1 nM. In certain embodiments, the PI3K delta isoform IC50 activity of a compound provided herein can be less than about 1000 nM, less than about 500 nM, less than about 400 nM, less than about 300 nM, less than about 200 nM, less than about 100 nM, less than about 75 nM, less than about 50 nM, less than about 25 nM, less than about 20 nM, less than about 15 nM, less than about 10 nM, less than about 5 nM, or less than about 1 nM.

In certain embodiments, a PI3K-$\gamma$ inhibitor selectively inhibits the gamma isoform over the alpha, beta, or delta isoform (also referred to herein as a "PI3K-$\gamma$-selective inhibitor." In one embodiment, the PI3K-$\gamma$ inhibitor selectively inhibits the gamma isoform over the alpha or beta isoform. In one embodiment, the PI3K-$\gamma$ inhibitor selectively inhibits the gamma isoform over the alpha, beta, and delta isoforms. In one embodiment, the PI3K-$\gamma$ inhibitor selectively inhibits the gamma isoform over the alpha and beta isoforms. In one embodiment, the PI3K-$\gamma$ inhibitor selectively inhibits the gamma isoform over the alpha and beta isoforms, but not the delta isoform. By way of non-limiting example, the ratio of selectivity can be greater than a factor of about 10, greater than a factor of about 50, greater than a factor of about 100, greater than a factor of about 200, greater than a factor of about 400, greater than a factor of about 600, greater than a factor of about 800, greater than a factor of about 1000, greater than a factor of about 1500, greater than a factor of about 2000, greater than a factor of about 5000, greater than a factor of about 10,000, or greater than a factor of about 20,000, where selectivity can be measured by ratio of IC50 values, among other means. In one embodiment, the selectivity of PI3K gamma isoform over another PI3K isoform is measured by the ratio of the IC50 value against the other PI3K isoform to the IC50 value against PI3K gamma isoform. In certain embodiments, the PI3 kinase gamma isoform IC50 activity of a compound as disclosed herein can be less than about 1000 nM, less than about 100 nM, less than about 10 nM, or less than about 1 nM. For example, a compound that selectively inhibits one isoform of PI3K over another isoform of PI3K has an activity of at least 2× against a first isoform relative to the compound's activity against the second isoform (e.g., at least about 3×, 5×, OX, 20×, 50×, 100×, 200×, 50×, or 1000×).

In certain embodiments, a PI3K-γ selective inhibitor is used or administered to a subject at a lower dose (e.g., by about 10%, by about 20%, by about 30%, by about 40%, by about 50%, by about 60%, by about 70%, or by about 80%) as compared to treatment with a PI3K-γ non-selective or less selective PI3K-γ inhibitor (e.g., a PI3Kpan inhibitors, e.g., inhibiting PI3K-α, β, δ, and γ).

"Radiation therapy" means exposing a patient to radiation emitters such as, but not limited to, alpha-particle emitting radionuclides (e.g., actinium and thorium radionuclides), low linear energy transfer (LET) radiation emitters (e.g., beta emitters), conversion electron emitters (e.g., strontium-89 and samarium-153-EDTMP), or high-energy radiation, including without limitation x-rays, gamma rays, and neutrons. Radiation therapy can be performed using routine methods and compositions known to the practitioner.

As used herein, a "reference value" refers to a value to which a given value can be compared. In some embodiments, the reference value refers to a control (e.g., an untreated control, e.g., an untreated or placebo-treated subject or an untreated sample); the course of disease without treatment; a healthy subject or an average of healthy subjects; a subject at a different time interval, e.g., prior to, during, or after the treatment).

"Subject" to which administration is contemplated includes, but is not limited to, humans (e.g., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys.

The term "in vivo" refers to an event that takes place in a subject's body.

The term "in vitro" refers to an event that takes places outside of a subject's body. For example, an in vitro assay encompasses any assay conducted outside of a subject. In vitro assays encompass cell-based assays in which cells, alive or dead, are employed. In vitro assays also encompass a cell-free assay in which no intact cells are employed.

Chemical Definitions

As used herein, "pharmaceutically acceptable esters" include, but are not limited to, alkyl, alkenyl, alkynyl, aryl, aralkyl, and cycloalkyl esters of acidic groups, including, but not limited to, carboxylic acids, phosphoric acids, phosphinic acids, sulfonic acids, sulfinic acids, and boronic acids.

As used herein, "pharmaceutically acceptable enol ethers" include, but are not limited to, derivatives of formula —C═C(OR) where R can be selected from alkyl, alkenyl, alkynyl, aryl, aralkyl, and cycloalkyl. Pharmaceutically acceptable enol esters include, but are not limited to, derivatives of formula —C═C(OC(O)R) where R can be selected from hydrogen, alkyl, alkenyl, alkynyl, aryl, aralkyl, and cycloalkyl.

As used herein, a "pharmaceutically acceptable form" of a disclosed compound includes, but is not limited to, pharmaceutically acceptable salts, hydrates, solvates, isomers, prodrugs, and isotopically labeled derivatives of disclosed compounds. In one embodiment, a "pharmaceutically acceptable form" includes, but is not limited to, pharmaceutically acceptable salts, isomers, prodrugs and isotopically labeled derivatives of disclosed compounds.

In certain embodiments, the pharmaceutically acceptable form is a pharmaceutically acceptable salt. As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in *J. Pharmaceutical Sciences* (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, naphthalene-m,n-bis-sulfonates, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, naphthalene-m,n-bis-sulfonic acids and the like.

Pharmaceutically acceptable salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, iron, zinc, copper, manganese, aluminum, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate. Organic bases from which salts can be derived include, for example, primary, secondary, and tertiary amines, substituted amines including naturally occurring substituted amines, cyclic amines, basic ion exchange resins, and the like, such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

In certain embodiments, the pharmaceutically acceptable form is a solvate (e.g., a hydrate). As used herein, the term "solvate" refers to compounds that further include a stoichiometric or non-stoichiometric amount of solvent bound by non-covalent intermolecular forces. The solvate can be of a disclosed compound or a pharmaceutically acceptable salt thereof. Where the solvent is water, the solvate is a "hydrate". Pharmaceutically acceptable solvates and hydrates are complexes that, for example, can include 1 to about 100, or 1 to about 10, or one to about 2, about 3 or about 4, solvent or water molecules. It will be understood that the term "compound" as used herein encompasses the compound and solvates of the compound, as well as mixtures thereof.

In certain embodiments, the pharmaceutically acceptable form is a prodrug. As used herein, the term "prodrug" refers to compounds that are transformed in vivo to yield a disclosed compound or a pharmaceutically acceptable form of the compound. A prodrug can be inactive when administered to a subject, but is converted in vivo to an active compound, for example, by hydrolysis (e.g., hydrolysis in blood). In certain cases, a prodrug has improved physical and/or delivery properties over the parent compound. Prodrugs are typically designed to enhance pharmaceutically and/or pharmacokinetically based properties associated with the parent compound. The prodrug compound often offers advantages of solubility, tissue compatibility or delayed release in a mammalian organism (see, e.g., Bundgard, H., *Design of Prodrugs* (1985), pp. 7-9, 21-24 (Elsevier, Amsterdam). A discussion of prodrugs is provided in Higuchi, T., et al., "Pro-drugs as Novel Delivery Systems," *A.C.S. Symposium Series*, Vol. 14, and in *Bioreversible Carriers in Drug Design*, ed. Edward B. Roche, American Pharmaceutical Association and Pergamon Press, 1987, both of which are incorporated in full by reference herein. Exemplary advantages of a prodrug can include, but are not limited to, its physical properties, such as enhanced water solubility for parenteral administration at physiological pH compared to the parent compound, or it enhances absorption from the digestive tract, or it can enhance drug stability for long-term storage.

The term "prodrug" is also meant to include any covalently bonded carriers, which release the active compound in vivo when such prodrug is administered to a subject. Prodrugs of an active compound, as described herein, can be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. Other examples of prodrugs include compounds that comprise —NO, —NO$_2$, —ONO, or —ONO$_2$ moieties. Prodrugs can typically be prepared using well-known methods, such as those described in *Burger's Medicinal Chemistry and Drug Discovery*, 172-178, 949-982 (Manfred E. Wolff ed., 5th ed., 1995), and *Design of Prodrugs* (H. Bundgaard ed., Elsevier, New York, 1985).

For example, if a disclosed compound or a pharmaceutically acceptable form of the compound contains a carboxylic acid functional group, a prodrug can comprise a pharmaceutically acceptable ester formed by the replacement of the hydrogen atom of the acid group with a group such as $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as 0-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl.

Similarly, if a disclosed compound or a pharmaceutically acceptable form of the compound contains an alcohol functional group, a prodrug can be formed by the replacement of the hydrogen atom of the alcohol group with a group such as $(C_1-C_6)$alkanoyloxymethyl, 1-(($C_1-C_6$)alkanoyloxy)ethyl, 1-methyl-1-(($C_1-C_6$)alkanoyloxy)ethyl $(C_1-C_6)$ alkoxycarbonyloxymethyl, N—$(C_1-C_6)$alkoxycarbonylaminomethyl, succinoyl, $(C_1-C_6)$alkanoyl, α-amino$(C_1-C_4)$alkanoyl, arylacyl and α-aminoacyl, or α-aminoacyl-α-aminoacyl, where each α-aminoacyl group is independently selected from naturally occurring L-amino acids, P(O)(OH)$_2$, —P(O)(O($C_1-C_6$)alkyl)$_2$, and glycosyl (the radical resulting from the removal of a hydroxyl group of the hemiacetal form of a carbohydrate).

If a disclosed compound or a pharmaceutically acceptable form of the compound incorporates an amine functional group, a prodrug can be formed by the replacement of a hydrogen atom in the amine group with a group such as R-carbonyl, RO-carbonyl, NRR'-carbonyl where R and R' are each independently $(C_1-C_{10})$alkyl, $(C_3-C_7)$cycloalkyl, benzyl, a natural α-aminoacyl or natural α-aminoacyl-natural α-aminoacyl, —C(OH)C(O)OY$^1$ wherein Y$^1$ is H, $(C_1-C_6)$alkyl or benzyl, —C(Y$^2$)Y$^3$ wherein Y$^2$ is $(C_1-C_4)$ alkyl and Y$^3$ is $(C_1-C_6)$alkyl, carboxy$(C_1-C_6)$alkyl, amino$(C_1-C_4)$ alkyl or mono-N— or di-N,N—$(C_1-C_6)$alkylaminoalkyl, —C(Y$^4$)Y$^5$ wherein Y$^4$ is H or methyl and Y$^5$ is mono-N— or di-N,N—$(C_1-C_6)$alkylamino, morpholino, piperidin-1-yl or pyrrolidin-1-yl.

In certain embodiments, the pharmaceutically acceptable form is an isomer. "Isomers" are different compounds that have the same molecular formula. "Atropisomers" are stereoisomers from hindered rotation about single bonds and can be resolved or isolated by methods known to those skilled in the art. For example, certain B substituents of a compound of Formula (I) provided herein with ortho or meta substituted phenyl may form atropisomers, where they may be separated and isolated.

"Stereoisomers" are isomers that differ only in the way the atoms are arranged in space. As used herein, the term "isomer" includes any and all geometric isomers and stereoisomers. For example, "isomers" include geometric double bond cis- and trans-isomers, also termed E- and Z-isomers; R- and S-enantiomers; diastereomers, (d)-isomers and (l)-isomers, racemic mixtures thereof, and other mixtures thereof, as falling within the scope of this disclosure.

In certain embodiments, the symbol ===== denotes a bond that can be a single or double as described herein.

In certain embodiments, provided herein are various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring, and the term "trans" represents substituents on opposite sides of the plane of the ring. Mixtures of compounds wherein the substituents are disposed on both the same and opposite sides of the plane of the ring are designated "cis/trans."

"Enantiomers" are a pair of stereoisomers that are non-superimposable mirror images of each other. A mixture of a pair of enantiomers in any proportion can be known as a "racemic" mixture. The term "(±)" is used to designate a racemic mixture where appropriate. "Diastereoisomers" are stereoisomers that have at least two asymmetric atoms, but which are not mirror-images of each other. The absolute stereochemistry can be specified according to the Cahn-Ingold-Prelog R-S system. When a compound is an enantiomer, the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry at each asymmetric atom, as (R)— or (S)—. The present chemical entities, pharmaceutical compositions and methods are meant to include all such possible isomers, including racemic mixtures, optically substantially pure forms and intermediate mixtures. Optically active (R)- and (S)-isomers can be prepared, for example, using chiral synthons or chiral reagents, or resolved using conventional techniques.

The "enantiomeric excess" or "% enantiomeric excess" of a composition can be calculated using the equation shown below. In the example shown below, a composition contains 90% of one enantiomer, e.g., an S enantiomer, and 10% of the other enantiomer, e.g., an R enantiomer.

ee=(90−10)/100=80%.

Thus, a composition containing 90% of one enantiomer and 10% of the other enantiomer is said to have an enantiomeric excess of 80%. Some compositions described herein contain an enantiomeric excess of at least about 1%, about 5%, about 10%, about 20%, about 30%, about 40%, about 50%, about 75%, about 90%, about 95%, or about 99% of the S enantiomer. In other words, the compositions contain an enantiomeric excess of the S enantiomer over the R enantiomer. In other embodiments, some compositions described herein contain an enantiomeric excess of at least about 1%, about 5%, about 10%, about 20%, about 30%, about 40%, about 50%, about 75%, about 90%, about 95%, or about 99% of the R enantiomer. In other words, the compositions contain an enantiomeric excess of the R enantiomer over the S enantiomer.

For instance, an isomer/enantiomer can, in some embodiments, be provided substantially free of the corresponding enantiomer, and can also be referred to as "optically enriched," "enantiomerically enriched," "enantiomerically pure" and "non-racemic," as used interchangeably herein. These terms refer to compositions in which the amount of one enantiomer is greater than the amount of that one enantiomer in a control mixture of the racemic composition (e.g., greater than 1:1 by weight). For example, an enantiomerically enriched preparation of the S enantiomer, means a preparation of the compound having greater than about 50% by weight of the S enantiomer relative to the total weight of the preparation (e.g., total weight of S and R isomers). such as at least about 75% by weight, further such as at least about 80% by weight. In some embodiments, the enrichment can be much greater than about 80% by weight, providing a "substantially enantiomerically enriched," "substantially enantiomerically pure" or a "substantially non-racemic" preparation, which refers to preparations of compositions which have at least about 85% by weight of one enantiomer relative to the total weight of the preparation, such as at least about 90% by weight, and further such as at least about 95% by weight. In certain embodiments, the compound provided herein is made up of at least about 90% by weight of one enantiomer. In other embodiments, the compound is made up of at least about 95%, about 98%, or about 99% by weight of one enantiomer.

In some embodiments, the compound is a racemic mixture of (S)- and (R)-isomers. In other embodiments, provided herein is a mixture of compounds wherein individual compounds of the mixture exist predominately in an (S)- or (R)-isomeric configuration. For example, in some embodiments, the compound mixture has an (S)-enantiomeric excess of greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, greater than about 96%, greater than about 97%, greater than about 98%, or greater than about 99%. In some embodiments, the compound mixture has an (S)-enantiomeric excess of about 55%, about 60%, about 65%, about 70%, about 75%, about 80%, about 85%, about 90%, about 95%, about 96%, about 97%, about 98%, about 99%, or about 99.5%, or more. In some embodiments, the compound mixture has an (S)-enantiomeric excess of about 55% to about 99.5%, about 60% to about 99.5%, about 65% to about 99.5%, about 70% to about 99.5%, about 75% to about 99.5%, about 80% to about 99.5%, about 85% to about 99.5%, about 90% to about 99.5%, about 95% to about 99.5%, about 96% to about 99.5%, about 97% to about 99.5%, about 98% to about 99.5%, or about 99% to about 99.5%, or more than about 99.5%.

In other embodiments, the compound mixture has an (R)-enantiomeric excess of greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, greater than about 96%, greater than about 97%, greater than about 98%, or greater than about 99%. In some embodiments, the compound mixture has an (R)-enantiomeric excess of about 55%, about 60%, about 65%, about 70%, about 75%, about 80%, about 85%, about 90%, about 95%, about 96%, about 97%, about 98%, about 99%, or about 99.5%, or more. In some embodiments, the compound mixture has an (R)-enantiomeric excess of about 55% to about 99.5%, about 60% to about 99.5%, about 65% to about 99.5%, about 70% to about 99.5%, about 75% to about 99.5%, about 80% to about 99.5%, about 85% to about 99.5%, about 90% to about 99.5%, about 95% to about 99.5%, about 96% to about 99.5%, about 97% to about 99.5%, about 98% to about 99.5%, or about 99% to about 99.5%, or more than about 99.5%.

In other embodiments, the compound mixture contains identical chemical entities except for their stereochemical orientations, namely (S)- or (R)-isomers. For example, if a compound disclosed herein has —CH(R)— unit, and R is not hydrogen, then the —CH(R)— is in an (S)- or (R)-stereochemical orientation for each of the identical chemical entities (i.e., (S)- or (R)-stereoisomers). In some embodiments, the mixture of identical chemical entities (i.e., mixture of stereoisomers) is a racemic mixture of (S)- and (R)-isomers. In another embodiment, the mixture of the identical chemical entities (i.e., mixture of stereoisomers) contains predominately (S)-isomer or predominately (R)-isomer. For example, in some embodiments, the (S)-isomer in the mixture of identical chemical entities (i.e., mixture of stereoisomers) is present at about 55%, about 60%, about 65%, about 70%, about 75%, about 80%, about 85%, about 90%, about 95%, about 96%, about 97%, about 98%, about 99%, or about 99.5% by weight, or more, relative to the total weight of the mixture of (S)- and (R)-isomers. In some embodiments, the (S)-isomer in the mixture of identical chemical entities (i.e., mixture of stereoisomers) is present at an (S)-enantiomeric excess of about 10% to about 99.5%, about 20% to about 99.5%, about 30% to about 99.5%, about 40% to about 99.5%, about 50% to about 99.5%, about 55% to about 99.5%, about 60% to about 99.5%, about 65% to about 99.5%, about 70% to about 99.5%, about 75% to about 99.5%, about 80% to about 99.5%, about 85% to about 99.5%, about 90% to about 99.5%, about 95% to about 99.5%, about 96% to about 99.5%, about 97% to about 99.5%, about 98% to about 99.5%, or about 99% to about 99.5%, or more than about 99.5%.

In other embodiments, the (R)-isomer in the mixture of identical chemical entities (i.e., mixture of stereoisomers) is present at about 55%, about 60%, about 65%, about 70%, about 75%, about 80%, about 85%, about 90%, about 95%, about 96%, about 97%, about 98%, about 99%, or about 99.5% by weight, or more, relative to the total weight of the mixture of (S)- and (R)-isomers. In some embodiments, the (R)-isomers in the mixture of identical chemical entities (i.e., mixture of stereoisomers) is present at an (R)-enantiomeric excess of about 10% to about 99.5%, about 20% to about 99.5%, about 30% to about 99.5%, about 40% to about 99.5%, about 50% to about 99.5%, about 55% to about 99.5%, about 60% to about 99.5%, about 65% to about 99.5%, about 70% to about 99.5%, about 75% to about 99.5%, about 80% to about 99.5%, about 85% to about 99.5%, about 90% to about 99.5%, about 95% to about 99.5%, about 96% to about 99.5%, about 97% to about 99.5%, about 98% to about 99.5%, or about 99% to about 99.5%, or more than about 99.5%.

Enantiomers can be isolated from racemic mixtures by any method known to those skilled in the art, including chiral high pressure liquid chromatography (HPLC), the formation and crystallization of chiral salts, or prepared by asymmetric syntheses. See, for example, *Enantiomers, Racemates and Resolutions* (Jacques, Ed., Wiley Interscience, New York, 1981); Wilen et al., *Tetrahedron* 33:2725 (1977); *Stereochemistry of Carbon Compounds* (E. L. Eliel, Ed., McGraw-Hill, N Y, 1962); and *Tables of Resolving Agents and Optical Resolutions* p. 268 (E. L. Eliel, Ed., Univ. of Notre Dame Press, Notre Dame, Ind. 1972).

In certain embodiments, the pharmaceutically acceptable form is a tautomer. As used herein, the term "tautomer" is a type of isomer that includes two or more interconvertible compounds resulting from at least one formal migration of a hydrogen atom and at least one change in valency (e.g., a single bond to a double bond, a triple bond to a double bond, or a triple bond to a single bond, or vice versa). "Tautomerization" includes prototropic or proton-shift tautomerization, which is considered a subset of acid-base chemistry. "Prototropic tautomerization" or "proton-shift tautomerization" involves the migration of a proton accompanied by changes in bond order. The exact ratio of the tautomers depends on several factors, including temperature, solvent, and pH. Where tautomerization is possible (e.g., in solution), a chemical equilibrium of tautomers can be reached. Tautomerizations (i.e., the reaction providing a tautomeric pair) can be catalyzed by acid or base, or can occur without the action or presence of an external agent. Exemplary tautomerizations include, but are not limited to, keto-enol; amide-imide; lactam-lactim; enamine-imine; and enamine-(a different) enamine tautomerizations. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

Unless otherwise stated, structures depicted herein are also meant to include compounds which differ only in the presence of one or more isotopically enriched atoms. For example, compounds having the present structures except for the replacement or enrichment of a hydrogen by deuterium or tritium at one or more atoms in the molecule, or the replacement or enrichment of a carbon by $^{13}C$ or $^{14}C$ at one or more atoms in the molecule, are within the scope of this disclosure. In one embodiment, provided herein are isotopically labeled compounds having one or more hydrogen atoms replaced by or enriched by deuterium. In one embodiment, provided herein are isotopically labeled compounds having one or more hydrogen atoms replaced by or enriched by tritium. In one embodiment, provided herein are isotopically labeled compounds having one or more carbon atoms replaced or enriched by $^{13}C$. In one embodiment, provided herein are isotopically labeled compounds having one or more carbon atoms replaced or enriched by $^{14}C$.

The disclosure also embraces isotopically labeled compounds which are identical to those recited herein, except that one or more atoms are replaced by an atom having an atomic mass or mass number different from the atomic mass or mass number usually found in nature. Examples of isotopes that can be incorporated into disclosed compounds include isotopes of hydrogen, carbon, nitrogen, oxygen, phosphorus, sulfur, fluorine, and chlorine, such as, e.g., $^{2}H$, $^{3}H$, $^{13}C$, $^{14}C$, $^{5}N$, $^{18}O$, $^{17}O$, $^{31}P$, $^{32}P$, $^{35}S$, $^{18}F$, and $^{36}Cl$, respectively. Certain isotopically-labeled disclosed compounds (e.g., those labeled with $^{3}H$ and/or $^{14}C$) are useful in compound and/or substrate tissue distribution assays. Tritiated (i.e., $^3$H) and carbon-14 (i.e., $^{14}$C) isotopes can allow for ease of preparation and detectability. Further, substitution with heavier isotopes such as deuterium (i.e., $^2$H) can afford certain therapeutic advantages resulting from greater metabolic stability (e.g., increased in vivo half-life or reduced dosage requirements). Isotopically labeled disclosed compounds can generally be prepared by substituting an isotopically labeled reagent for a non-isotopically labeled reagent. In some embodiments, provided herein are compounds that can also contain unnatural proportions of atomic isotopes at one or more of atoms that constitute such compounds. All isotopic variations of the compounds as disclosed herein, whether radioactive or not, are encompassed within the scope of the present disclosure.

"Pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions as disclosed herein is contemplated. Supplementary active ingredients can also be incorporated into the pharmaceutical compositions.

Definitions of specific functional groups and chemical terms are described in more detail below. The chemical elements are identified in accordance with the Periodic Table of the Elements, CAS version, Handbook of Chemistry and Physics, 75th ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th ed., John Wiley & Sons, Inc., New York, 2001; Larock, *Comprehensive Organic Transformations*, VCH Publishers, Inc., New York, 1989; and Carruthers, Some *Modern Methods of Organic Synthesis*, 3rd ed., Cambridge University Press, Cambridge, 1987.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Alkyl" refers to a straight or branched hydrocarbon chain radical consisting solely of carbon and hydrogen atoms, containing no unsaturation, having, in some embodiments, from one to ten carbon atoms (e.g., $C_1$-$C_{10}$ alkyl). Linear or straight alkyl refers to an alkyl with no branching, e.g., methyl, ethyl, n-propyl. Whenever it appears herein, a numerical range such as "1 to 10" refers to each integer in the given range; e.g., "1 to 10 carbon atoms" means that the alkyl group can consist of 1 carbon atom, 2 carbon atoms, 3 carbon atoms, 4 carbon atoms, etc., up to and including 10 carbon atoms, although the present definition also covers the occurrence of the term "alkyl" where no numerical range is designated. In some embodiments, an alkyl is a $C_1$-$C_6$ alkyl group. In some embodiments, alkyl groups have 1 to 10, 1 to 6, 1 to 4, or 1 to 3 carbon atoms. Representative saturated straight chain alkyls include, but are not limited to, -methyl, -ethyl, -n-propyl, -n-butyl, -n-pentyl, and -n-hexyl; while saturated branched alkyls include, but are not limited to, -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, and the like. The alkyl is attached to the parent molecule by a single bond. Unless stated otherwise in the specification, an alkyl group is optionally substituted by one or more of substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or —O—P(=O)(OR$^a$)$_2$, where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

"Perhaloalkyl" refers to an alkyl group in which all of the hydrogen atoms have been replaced with a halogen selected from fluoro, chloro, bromo, and iodo. In some embodiments, all of the hydrogen atoms are each replaced with fluoro. In some embodiments, all of the hydrogen atoms are each replaced with chloro. Examples of perhaloalkyl groups include —CF$_3$, —CF$_2$CF$_3$, —CF$_2$CF$_2$CF$_3$, —CCl$_3$, —CFCl$_2$, —CF$_2$Cl and the like. "Haloalkyl" refers to an alkyl group in which one or more of the hydrogen atoms have been replaced with a halogen independently selected from fluoro, chloro, bromo, and iodo.

"Alkyl-cycloalkyl" refers to an -(alkyl)cycloalkyl radical where alkyl and cycloalkyl are as disclosed herein and which are optionally substituted by one or more of the substituents described as suitable substituents for alkyl and cycloalkyl respectively. The "alkyl-cycloalkyl" is bonded to the parent molecular structure through the alkyl group. The terms "alkenyl-cycloalkyl" and "alkynyl-cycloalkyl" mirror the above description of "alkyl-cycloalkyl" wherein the term "alkyl" is replaced with "alkenyl" or "alkynyl" respectively, and "alkenyl" or "alkynyl" are as described herein.

"Alkylaryl" refers to an -(alkyl)aryl radical where aryl and alkyl are as disclosed herein and which are optionally substituted by one or more of the substituents described as suitable substituents for aryl and alkyl respectively. The "alkylaryl" is bonded to the parent molecular structure through the alkyl group. The terms "-(alkenyl)aryl" and "-(alkynyl)aryl" mirror the above description of "-(alkyl)aryl" wherein the term "alkyl" is replaced with "alkenyl" or "alkynyl" respectively, and "alkenyl" or "alkynyl" are as described herein.

"Alkyl-heteroaryl" refers to an -(alkyl)heteroaryl radical where heteroaryl and alkyl are as disclosed herein and which are optionally substituted by one or more of the substituents described as suitable substituents for heteroaryl and alkyl respectively. The "alkyl-heteroaryl" is bonded to the parent molecular structure through the alkyl group. The terms "-(alkenyl)heteroaryl" and "-(alkynyl)heteroaryl" mirror the above description of "-(alkyl)heteroaryl" wherein the term "alkyl" is replaced with "alkenyl" or "alkynyl" respectively, and "alkenyl" or "alkynyl" are as described herein.

"Alkyl-heterocyclyl" refers to an -(alkyl)heterocyclyl radical where alkyl and heterocyclyl are as disclosed herein and which are optionally substituted by one or more of the substituents described as suitable substituents for heterocyclyl and alkyl respectively. The "alkyl-heterocyclyl" is bonded to the parent molecular structure through the alkyl group. The terms "-(alkenyl)heterocyclyl" and "-(alkynyl) heterocyclyl" mirror the above description of "-(alkyl)heterocyclyl" wherein the term "alkyl" is replaced with "alkenyl" or "alkynyl" respectively, and "alkenyl" or "alkynyl" are as described herein.

"Alkenyl" refers to a straight or branched hydrocarbon chain radical group consisting solely of carbon and hydrogen atoms, containing at least one double bond, and in some embodiments, having from two to ten carbon atoms (i.e., $C_2$-$C_{10}$ alkenyl). Whenever it appears herein, a numerical range such as "2 to 10" refers to each integer in the given range; e.g., "2 to 10 carbon atoms" means that the alkenyl group can consist of 2 carbon atoms, 3 carbon atoms, 4 carbon atoms, etc., up to and including 10 carbon atoms. In certain embodiments, an alkenyl comprises two to eight carbon atoms. In other embodiments, an alkenyl comprises two to five carbon atoms (e.g., $C_2$-$C_5$ alkenyl). The alkenyl is attached to the parent molecular structure by a single bond, for example, ethenyl (i.e., vinyl), prop-1-enyl (i.e., allyl), but-1-enyl, pent-1-enyl, penta-1,4-dienyl, and the like. The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$) and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless stated otherwise in the specification, an alkenyl group is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t R^a$ (where t is 1 or 2), —S(O)$_t$O$R^a$ (where t is 1 or 2), —S(O)$_t$N($R^a$)$_2$ (where t is 1 or 2), or —O—P(═O)(O$R^a$)$_2$, where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

"Alkynyl" refers to a straight or branched hydrocarbon chain radical group consisting solely of carbon and hydrogen atoms, containing at least one triple bond, having, in some embodiments, from two to ten carbon atoms (i.e., $C_2$-$C_{10}$ alkynyl). Whenever it appears herein, a numerical range such as "2 to 10" refers to each integer in the given range; e.g., "2 to 10 carbon atoms" means that the alkynyl group can consist of 2 carbon atoms, 3 carbon atoms, 4 carbon atoms, etc., up to and including 10 carbon atoms. In certain embodiments, an alkynyl comprises two to eight carbon atoms. In other embodiments, an alkynyl has two to five carbon atoms (e.g., $C_2$-$C_5$ alkynyl). The alkynyl is attached to the parent molecular structure by a single bond, for example, ethynyl, propynyl, butynyl, pentynyl, hexynyl, and the like. Unless stated otherwise in the specification, an alkynyl group is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t R^a$ (where t is 1 or 2), —S(O)$_t$O$R^a$ (where t is 1 or 2), —S(O)$_t$N($R^a$)$_2$ (where t is 1 or 2), or —O—P(═O)(O$R^a$)$_2$, where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

The term "alkoxy" refers to the group —O-alkyl (in some embodiments, including from 1 to 10 carbon atoms), of a straight, branched, cyclic configuration and combinations thereof, attached to the parent molecular structure through an oxygen. Examples include methoxy, ethoxy, propoxy, isopropoxy, cyclopropyloxy, cyclohexyloxy, and the like. "Lower alkoxy" refers to alkoxy groups containing one to six carbons. In some embodiments, $C_1$-$C_4$ alkoxy is an alkoxy group which encompasses both straight and branched chain alkyls of from 1 to 4 carbon atoms. Unless stated otherwise in the specification, an alkoxy group is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t R^a$ (where t is 1 or 2), —S(O)$_t$O$R^a$ (where t is 1 or 2), —S(O)$_t$N($R^a$)$_2$ (where t is 1 or 2), or —O—P(═O)(O$R^a$)$_2$, where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein. The terms "alkenoxy" and "alkynoxy" mirror the above description of "alkoxy" wherein the prefix "alk" is replaced with "alken" or "alkyn" respectively, and the parent "alkenyl" or "alkynyl" terms are as described herein.

The term "alkoxycarbonyl" refers to a group of the formula (alkoxy)(C═O)— attached to the parent molecular structure through the carbonyl carbon (in some embodiments, having from 1 to 10 carbon atoms). Thus a $C_1$-$C_6$ alkoxycarbonyl group comprises an alkoxy group having from 1 to 6 carbon atoms attached through its oxygen to a carbonyl linker. The $C_1$-$C_6$ designation does not include the carbonyl carbon in the atom count. "Lower alkoxycarbonyl" refers to an alkoxycarbonyl group wherein the alkyl portion of the alkoxy group is a lower alkyl group. In some embodiments, $C_1$-$C_4$ alkoxycarbonyl comprises an alkoxy group which encompasses both straight and branched chain alkoxy groups of from 1 to 4 carbon atoms. Unless stated otherwise in the specification, an alkoxycarbonyl group is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t R^a$ (where t is 1 or 2), —S(O)$_t$O$R^a$ (where t is 1 or 2), —S(O)$_t$N($R^a$)$_2$ (where t is 1 or 2), or —O—P(=O)(O$R^a$)$_2$, where each $R^a$ is independently hydrogen, alkyl, haloalkyl, carbocyclyl, carbocyclylalkyl, aryl, aralkyl, heterocycloalkyl, heterocycloalkylalkyl, heteroaryl, or heteroarylalkyl, and each of these moieties can be optionally substituted as defined herein. The terms "alkenoxycarbonyl" and "alkynoxycarbonyl" mirror the above description of "alkoxycarbonyl" wherein the prefix "alk" is replaced with "alken" or "alkyn" respectively, and the parent "alkenyl" or "alkynyl" terms are as described herein.

"Acyl" refers to R—C(O)— groups such as, but not limited to, H, (alkyl)-C(O)—, (alkenyl)-C(O)—, (alkynyl)-C(O)—, (aryl)-C(O)—, (cycloalkyl)-C(O)—, (heteroaryl)-C(O)—, (heteroalkyl)-C(O)—, and (heterocycloalkyl)-C(O)—, wherein the group is attached to the parent molecular structure through the carbonyl functionality. In some embodiments, provided herein is a $C_1$-$C_{10}$ acyl radical which refers to the total number of chain or ring atoms of the, for example, alkyl, alkenyl, alkynyl, aryl, cyclohexyl, heteroaryl or heterocycloalkyl portion plus the carbonyl carbon of acyl. For example, a $C_4$-acyl has three other ring or chain atoms plus carbonyl. If the R radical is heteroaryl or heterocycloalkyl, the hetero ring or chain atoms contribute to the total number of chain or ring atoms. Unless stated otherwise in the specification, the "R" of an acyloxy group can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)S(O)$R^a$ (where t is 1 or 2), —S(O)$_t$O$R^a$ (where t is 1 or 2), —S(O)N($R^a$)$_2$ (where t is 1 or 2), or —O—P(=O)(O$R^a$)$_2$, where each $R^a$ is independently hydrogen, alkyl, haloalkyl, carbocyclyl, carbocyclylalkyl, aryl, aralkyl, heterocycloalkyl, heterocycloalkylalkyl, heteroaryl, or heteroarylalkyl, and each of these moieties can be optionally substituted as defined herein.

"Acyloxy" refers to a R(C=O)O— radical wherein "R" can be H, alkyl, alkenyl, alkynyl, heteroalkyl, heteroalkenyl, heteroalkynyl, aryl, cyclohexyl, heteroaryl, or heterocycloalkyl, which are as described herein. The acyloxy group is attached to the parent molecular structure through the oxygen functionality. In some embodiments, an acyloxy group is a $C_1$-$C_4$ acyloxy radical which refers to the total number of chain or ring atoms of the alkyl, alkenyl, alkynyl, aryl, cyclohexyl, heteroaryl or heterocycloalkyl portion of the acyloxy group plus the carbonyl carbon of acyl, e.g., a $C_4$-acyloxy has three other ring or chain atoms plus carbonyl. If the R radical is heteroaryl or heterocycloalkyl, the hetero ring or chain atoms contribute to the total number of chain or ring atoms. Unless stated otherwise in the specification, the "R" of an acyloxy group is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t R^a$ (where t is 1 or 2), —S(O)$_t$O$R^a$ (where t is 1 or 2), —S(O)N($R^a$)$_2$ (where t is 1 or 2), or —O—P(=O)(O$R^a$)$_2$, where each $R^a$ is independently hydrogen, alkyl, haloalkyl, carbocyclyl, carbocyclylalkyl, aryl, aralkyl, heterocycloalkyl, heterocycloalkylalkyl, heteroaryl, or heteroarylalkyl and each of these moieties can be optionally substituted as defined herein.

"Amino" or "amine" refers to a —N($R^b$)$_2$, —N($R^b$)$R^b$—, or —$R^b$N($R^b$)$R^b$— radical group, where each $R^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon), and heteroarylalkyl, unless stated otherwise in the specification, each of which moiety can itself be optionally substituted as described herein. When a —N($R^b$)$_2$ group has two $R^b$ other than hydrogen, they can be combined with the nitrogen atom to form a 3-, 4-, 5-, 6-, 7-, or 8-membered ring. For example, —N($R^b$)$_2$ is meant to include, but not be limited to, 1-pyrrolidinyl and 4-morpholinyl. Unless stated otherwise in the specification, an amino group is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t R^a$(where t is 1 or 2), —S(O)$_t$O$R^a$ (where t is 1 or 2), —S(O)$_t$N($R^a$)$_2$ (where t is 1 or 2), or —O—P(=O)(O$R^a$)$_2$, where each $R^a$ is independently hydrogen, alkyl, haloalkyl, carbocyclyl, carbocyclylalkyl, aryl, aralkyl, heterocycloalkyl, heterocycloalkylalkyl, heteroaryl, or heteroarylalkyl, and each of these moieties can be optionally substituted as defined herein.

The terms "amine" and "amino" can also refer to N-oxides of the groups —$N^+$(H)($R^a$)$O^-$, and —$N^+$($R^a$)($R^a$)$O^-$, where $R^a$ is as described above, where the N-oxide is bonded to the parent molecular structure through the N atom. N-oxides can be prepared by treatment of the corresponding amino group with, for example, hydrogen peroxide or m-chloroperoxybenzoic acid. The person skilled in the art is familiar with reaction conditions for carrying out the N-oxidation.

"Amide" or "amido" refers to a chemical moiety with formula —C(O)N($R^b$)$_2$ or —N$R^b$C(O)$R^b$, where $R^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon), and heteroarylalkyl, unless stated otherwise in the specification, each of which moiety can itself be optionally substituted as described herein. In some embodiments, an amido or amide radical is a $C_1$-$C_4$ amido or amide radical, which includes the amide carbonyl in the total number of carbons in the radical. When a —C(O)N($R^b$)$_2$ has two $R^b$ other than hydrogen, they can be combined with the nitrogen atom to form a 3-, 4-, 5-, 6-, 7-, or 8-membered ring. For example, N($R^b$)$_2$ portion of a —C(O)N($R^b$)$_2$ radical is meant to include, but not be limited to, 1-pyrrolidinyl and 4-morpholinyl. Unless stated otherwise in the specification, an amido $R^b$ group is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or —O—P(=O)(O$R^a$)$_2$, where each $R^a$ is independently hydrogen, alkyl, haloalkyl, carbocyclyl, carbocyclylalkyl, aryl, aralkyl, heterocycloalkyl, heterocycloalkylalkyl, heteroaryl, or heteroarylalkyl, and each of these moieties can be optionally substituted as defined herein.

The term "amide" or "amido" is inclusive of an amino acid or a peptide molecule. Any amine, hydroxy, or carboxyl side chain on the compounds described herein can be transformed into an amide group. The procedures and specific groups to make such amides are known to those of skill in the art and can readily be found in reference sources such as Greene and Wuts, *Protective Groups in Organic Synthesis*, 4th Ed., John Wiley & Sons, New York, N.Y., 2006, which is incorporated herein by reference in its entirety.

"Amidino" refers to the —C(=N$R^b$)N($R^b$)$_2$, —N($R^b$)—C(=N$R^b$)—$R^b$, and —N($R^b$)—C(=N$R^b$)-radicals, where each $R^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon), and heteroarylalkyl, unless stated otherwise in the specification, each of which moiety can itself be optionally substituted as described herein.

"Aryl" refers to a radical with six to fourteen ring atoms (e.g., $C_6$-$C_4$ or $C_6$-$C_{10}$ aryl) which has at least one carbocyclic ring having a conjugated pi electron system which is aromatic (e.g., having 6, 10, or 14π electrons shared in a cyclic array) (e.g., phenyl, fluorenyl, and naphthyl). In one embodiment, bivalent radicals formed from substituted benzene derivatives and having the free valences at ring atoms are named as substituted phenylene radicals. In other embodiments, bivalent radicals derived from univalent monocyclic or polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 10 aryl" refers to each integer in the given range; e.g., "6 to 10 ring atoms" means that the aryl group can consist of 6 ring atoms, 7 ring atoms, etc., up to and including 10 ring atoms. The term includes monocyclic or fused-ring polycyclic (i.e., rings which share adjacent pairs of ring atoms) groups. Unless stated otherwise in the specification, an aryl moiety can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or —O—P(=O)(O$R^a$)$_2$, where each $R^a$ is independently hydrogen, alkyl, haloalkyl, carbocyclyl, carbocyclylalkyl, aryl, aralkyl, heterocycloalkyl, heterocycloalkylalkyl, heteroaryl, or heteroarylalkyl, and each of these moieties can be optionally substituted as defined herein. In one embodiment, unless stated otherwise, "aryl" also includes ring systems wherein the aryl ring, as defined above, is fused with one or more cycloalkyl or heterocyclyl groups wherein the point of attachment to the parent molecular structure is on the aryl ring.

"Aralkyl" or "arylalkyl" refers to an (aryl)alkyl-radical where aryl and alkyl are as disclosed herein and which are optionally substituted by one or more of the substituents described as suitable substituents for aryl and alkyl respectively. The "aralkyl" or "arylalkyl" is bonded to the parent molecular structure through the alkyl group. The terms "aralkenyl/arylalkenyl" and "aralkynyl/arylalkynyl" mirror the above description of "aralkyl/arylalkyl" wherein the "alkyl" is replaced with "alkenyl" or "alkynyl" respectively, and the "alkenyl" or "alkynyl" terms are as described herein.

"Azide" refers to a —$N_3$ radical.

"Carbamate" refers to any of the following radicals: —O—(C=O)—N($R^b$)—, —O—(C=O)—N($R^b$)$_2$, —N($R^b$)—(C=O)—O—, and —N($R^b$)—(C=O)—O$R^b$, wherein each $R^b$ is independently selected from H, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon), and heteroarylalkyl, unless stated otherwise in the specification, each of which moiety can itself be optionally substituted as described herein.

"Carbonate" refers to a —O—(C=O)—O— or —O—(C=O)—OR radical, where R can be hydrogen, alkyl, alkenyl, alkynyl, heteroalkyl, heteroalkenyl, heteroalkynyl, aryl, cyclohexyl, heteroaryl, or heterocycloalkyl, which are as described herein.

"Carbonyl" refers to a —(C=O)— radical.

"Carboxaldehyde" refers to a —(C=O)H radical.

"Carboxyl" refers to a —(C=O)OH radical.

"Cyano" refers to a —CN radical.

"Cycloalkyl," or alternatively, "carbocyclyl," refers to a monocyclic or polycyclic radical that contains only carbon and hydrogen, and can be saturated or partially unsaturated. Partially unsaturated cycloalkyl groups can be termed "cycloalkenyl" if the carbocycle contains at least one double bond, or "cycloalkynyl" if the carbocycle contains at least one triple bond. Cycloalkyl groups include groups having from 3 to 10 ring atoms (e.g., $C_3$-$C_{10}$ cycloalkyl). Whenever it appears herein, a numerical range such as "3 to 10" refers to each integer in the given range; e.g., "3 to 10 carbon atoms" means that the cycloalkyl group can consist of 3 carbon atoms, 4 carbon atoms, 5 carbon atoms, etc., up to and including 10 carbon atoms. The term "cycloalkyl" also includes bridged and spiro-fused cyclic structures containing no heteroatoms. The term also includes monocyclic or fused-ring polycyclic (i.e., rings which share adjacent pairs of ring atoms) groups. In some embodiments, it is a $C_3$-$C_8$ cycloalkyl radical. In some embodiments, it is a $C_3$-$C_5$ cycloalkyl radical. Illustrative examples of cycloalkyl groups include, but are not limited to the following moieties: $C_{3-6}$ carbocyclyl groups include, without limitation, cyclopropyl ($C_3$), cyclobutyl ($C_4$), cyclopentyl ($C_5$), cyclopentenyl ($C_5$), cyclohexyl ($C_6$), cyclohexenyl ($C_6$), cyclohexadienyl ($C_6$), and the like. Examples of $C_{3-8}$ carbocyclyl groups include the aforementioned $C_{3-6}$ carbocyclyl groups as well as cycloheptyl ($C_7$), cycloheptadienyl ($C_7$), cycloheptatrienyl ($C_7$), cyclooctyl ($C_8$), bicyclo[2.2.1]heptanyl, bicyclo[2.2.2]octanyl, and the like. Examples of $C_{3-10}$ carbocyclyl groups include the aforementioned $C_{3-8}$ carbocyclyl groups as well as octahydro-1H-indenyl, decahydronaphthalenyl, spiro[4.5]decanyl, and the like. Unless stated otherwise in the specification, a cycloalkyl group is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or —O—P(=O)(OR$^a$)$_2$, where each R$^a$ is independently hydrogen, alkyl, haloalkyl, carbocyclyl, carbocyclylalkyl, aryl, aralkyl, heterocycloalkyl, heterocycloalkylalkyl, heteroaryl, or heteroarylalkyl, and each of these moieties can be optionally substituted as defined herein. In one embodiment, unless stated otherwise, "cycloalkyl" or "carbocyclyl" also includes ring systems wherein the cycloalkyl or carbocyclyl ring, as defined above, is fused with one or more aryl or heteroaryl groups wherein the point of attachment to the parent molecular structure is on the cycloalkyl or carbocyclyl ring.

"Cycloalkyl-alkyl" refers to a -(cycloalkyl)alkyl radical where cycloalkyl and alkyl are as disclosed herein and which are optionally substituted by one or more of the substituents described as suitable substituents for cycloalkyl and alkyl respectively. The "cycloalkyl-alkyl" is bonded to the parent molecular structure through the cycloalkyl group. The terms "cycloalkyl-alkenyl" and "cycloalkyl-alkynyl" mirror the above description of "cycloalkyl-alkyl" wherein the term "alkyl" is replaced with "alkenyl" or "alkynyl" respectively, and "alkenyl" or "alkynyl" are as described herein.

"Cycloalkyl-heterocycloalkyl" refers to a -(cycloalkyl)heterocyclylalkyl radical where cycloalkyl and heterocycloalkyl are as disclosed herein and which are optionally substituted by one or more of the substituents described as suitable substituents for heterocycloalkyl and cycloalkyl respectively. The "cycloalkyl-heterocycloalkyl" is bonded to the parent molecular structure through the cycloalkyl group.

"Cycloalkyl-heteroaryl" refers to a -(cycloalkyl)heteroaryl radical where cycloalkyl and heteroaryl are as disclosed herein and which are optionally substituted by one or more of the substituents described as suitable substituents for heteroaryl and cycloalkyl respectively. The "cycloalkyl-heteroaryl" is bonded to the parent molecular structure through the cycloalkyl group.

As used herein, a "covalent bond" or "direct bond" refers to a single bond joining two groups.

"Ester" refers to a radical of formula —COOR, where R is selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon), and heteroarylalkyl. Any amine, hydroxy, or carboxyl side chain on the compounds described herein can be esterified. The procedures and specific groups to make such esters are known to those of skill in the art and can readily be found in reference sources such as Greene and Wuts, *Protective Groups in Organic Synthesis,* 4th Ed., John Wiley & Sons, New York, N.Y., 2006, which is incorporated herein by reference in its entirety. Unless stated otherwise in the specification, an ester group can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or —O—P(=O)(OR$^a$)$_2$, where each R$^a$ is independently hydrogen, alkyl, haloalkyl, carbocyclyl, carbocyclylalkyl, aryl, aralkyl, heterocycloalkyl, heterocycloalkylalkyl, heteroaryl, or heteroarylalkyl, and each of these moieties can be optionally substituted as defined herein.

"Ether" refers to a —R$^b$—O—R$^b$ radical where each R$^b$ is independently selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon), and heteroarylalkyl, unless stated otherwise in the specification, each of which moiety can itself be optionally substituted as described herein.

"Halo", "halide", or, alternatively, "halogen" means fluoro, chloro, bromo, or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine, such as, but not limited to, trifluoromethyl, difluoromethyl, 2,2,2-trifluoroethyl, 1-fluoromethyl-2-fluoroethyl, and the like. Each of the alkyl, alkenyl, alkynyl and alkoxy groups are as defined herein and can be optionally further substituted as defined herein.

"Heteroalkyl", "heteroalkenyl" and "heteroalkynyl" include alkyl, alkenyl and alkynyl radicals, respectively, which have one or more skeletal chain atoms selected from an atom other than carbon, e.g., oxygen, nitrogen, sulfur, and phosphorus, or combinations thereof. A numerical range can be given, e.g., $C_1$-$C_4$ heteroalkyl which refers to the chain length in total, which in this example can be up to 4 atoms long. For example, a —$CH_2OCH_2CH_3$ radical is referred to as a "$C_4$" heteroalkyl, which includes the heteroatom center in the atom chain length description. Connection to the parent molecular structure can be through either a heteroatom or a carbon in the heteroalkyl chain. For example, an N-containing heteroalkyl moiety refers to a group in which at least one of the skeletal atoms is a nitrogen atom. One or more heteroatom(s) in the heteroalkyl radical can be optionally oxidized. One or more nitrogen atoms, if present, can also be optionally quaternized. For example, heteroalkyl also includes skeletal chains substituted with one or more nitrogen oxide (—O—) substituents. Exemplary heteroalkyl groups include, without limitation, ethers such as methoxyethanyl (—$CH_2CH_2OCH_3$), ethoxymethanyl (—$CH_2OCH_2CH_3$), (methoxymethoxy)ethanyl (—$CH_2CH_2$—$OCH_2OCH_3$), (methoxymethoxy)methanyl (—$CH_2OCH_2OCH_3$), and (methoxyethoxy)methanyl (—$CH_2OCH_2CH_2OCH_3$), and the like; amines such as —$CH_2CH_2NHCH_3$, —$CH_2CH_2N(CH_3)_2$, —$CH_2NHCH_2CH_3$, —$CH_2N(CH_2CH_3)(CH_3)$, and the like. Heteroalkyl, heteroalkenyl, and heteroalkynyl groups can each be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —$Si(R^a)_3$, —$OR^a$, —$SR^a$, —$OC(O)$—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, —$N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or —O—$P(=O)(OR^a)_2$, where each $R^a$ is independently hydrogen, alkyl, haloalkyl, carbocyclyl, carbocyclylalkyl, aryl, aralkyl, heterocycloalkyl, heterocycloalkylalkyl, heteroaryl, or heteroarylalkyl, and each of these moieties can be optionally substituted as defined herein.

"Heteroalkyl-aryl" refers to a -(heteroalkyl)aryl radical where heteroalkyl and aryl are as disclosed herein and which are optionally substituted by one or more of the substituents described as suitable substituents for heteroalkyl and aryl respectively. The "heteroalkyl-aryl" is bonded to the parent molecular structure through an atom of the heteroalkyl group.

"Heteroalkyl-heteroaryl" refers to a -(heteroalkyl)heteroaryl radical where heteroalkyl and heteroaryl are as disclosed herein and which are optionally substituted by one or more of the substituents described as suitable substituents for heteroalkyl and heteroaryl respectively. The "heteroalkyl-heteroaryl" is bonded to the parent molecular structure through an atom of the heteroalkyl group.

"Heteroalkyl-heterocycloalkyl" refers to a -(heteroalkyl) heterocycloalkyl radical where heteroalkyl and heterocycloalkyl are as disclosed herein and which are optionally substituted by one or more of the substituents described as suitable substituents for heteroalkyl and heterocycloalkyl respectively. The "heteroalkyl-heterocycloalkyl" is bonded to the parent molecular structure through an atom of the heteroalkyl group.

"Heteroalkyl-cycloalkyl" refers to a -(heteroalkyl)cycloalkyl radical where heteroalkyl and cycloalkyl are as disclosed herein and which are optionally substituted by one or more of the substituents described as suitable substituents for heteroalkyl and cycloalkyl respectively. The "heteroalkyl-cycloalkyl" is bonded to the parent molecular structure through an atom of the heteroalkyl group.

"Heteroaryl", or alternatively, "heteroaromatic", refers to a radical of a 5- to 18-membered monocyclic or polycyclic (e.g., bicyclic or tricyclic) aromatic ring system (e.g., having 6, 10 or 14π electrons shared in a cyclic array) having ring carbon atoms and 1 to 6 ring heteroatoms provided in the aromatic ring system, wherein each heteroatom is independently selected from nitrogen, oxygen, phosphorous, and sulfur ("5- to 18-membered heteroaryl"). Heteroaryl polycyclic ring systems can include one or more heteroatoms in one or more rings. Whenever it appears herein, a numerical range such as "5 to 18" refers to each integer in the given range; e.g., "5 to 18 ring atoms" means that the heteroaryl group can consist of 5 ring atoms, 6 ring atoms, 7 ring atoms, 8 ring atoms, 9 ring atoms, 10 ring atoms, etc., up to and including 18 ring atoms. In one embodiment, bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene.

For example, an N-containing "heteroaromatic" or "heteroaryl" moiety refers to an aromatic group in which at least one of the skeletal atoms of the ring is a nitrogen atom. One or more heteroatom(s) in the heteroaryl radical can be optionally oxidized. One or more nitrogen atoms, if present, can also be optionally quaternized. Heteroaryl also includes ring systems substituted with one or more nitrogen oxide (—O—) substituents, such as pyridinyl N-oxides. The heteroaryl is attached to the parent molecular structure through any atom of the ring(s).

"Heteroaryl" also includes ring systems wherein the heteroaryl ring, as defined above, is fused with one or more aryl groups wherein the point of attachment to the parent molecular structure is either on the aryl or on the heteroaryl ring, or wherein the heteroaryl ring, as defined above, is fused with one or more cycloalkyl or heterocyclyl groups wherein the point of attachment to the parent molecular structure is on the heteroaryl ring. For polycyclic heteroaryl groups wherein one ring does not contain a heteroatom (e.g., indolyl, quinolinyl, carbazolyl and the like), the point of attachment to the parent molecular structure can be on either the ring bearing a heteroatom (e.g., 2-indolyl) or the ring that does not contain a heteroatom (e.g., 5-indolyl). In some embodiments, a heteroaryl group is a 5 to 10 membered aromatic ring system having ring carbon atoms and 1 to 4 ring heteroatoms provided in the aromatic ring system, wherein each heteroatom is independently selected from nitrogen, oxygen, phosphorous, and sulfur ("5- to 10-membered heteroaryl"). In some embodiments, a heteroaryl group is a 5- to 8-membered aromatic ring system having ring carbon atoms and 1 to 4 ring heteroatoms provided in the aromatic ring system, wherein each heteroatom is independently selected from nitrogen, oxygen, phosphorous, and sulfur ("5- to 8-membered heteroaryl"). In some embodiments, a heteroaryl group is a 5- to 6-membered aromatic ring system having ring carbon atoms and 1 to 4 ring heteroatoms provided in the aromatic ring system, wherein each heteroatom is independently selected from nitrogen, oxygen, phosphorous, and sulfur ("5- to 6-membered heteroaryl"). In some embodiments, the 5- to 6-membered heteroaryl has 1 to 3 ring heteroatoms independently selected from nitrogen, oxygen, phosphorous, and sulfur. In some embodiments, the 5- to 6-membered heteroaryl has 1 to 2 ring heteroatoms independently selected from nitrogen, oxygen, phosphorous, and sulfur. In some embodiments, the 5- to 6-membered heteroaryl has 1 ring heteroatom selected from nitrogen, oxygen, phosphorous, and sulfur.

Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d] pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pridinyl, and thiophenyl (i.e., thienyl).

Unless stated otherwise in the specification, a heteroaryl moiety is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or —O—P(=O)(OR$^a$)$_2$, where each R$^a$ is independently hydrogen, alkyl, haloalkyl, carbocyclyl, carbocyclylalkyl, aryl, aralkyl, heterocycloalkyl, heterocycloalkylalkyl, heteroaryl, or heteroarylalkyl, and each of these moieties can be optionally substituted as defined herein.

"Heteroaryl-alkyl" refers to a -(heteroaryl)alkyl radical where heteroaryl and alkyl are as disclosed herein and which are optionally substituted by one or more of the substituents described as suitable substituents for heteroaryl and alkyl respectively. The "heteroaryl-alkyl" is bonded to the parent molecular structure through any atom of the heteroaryl group.

"Heteroaryl-heterocycloalkyl" refers to an -(heteroaryl)heterocycloalkyl radical where heteroaryl and heterocycloalkyl are as disclosed herein and which are optionally substituted by one or more of the substituents described as suitable substituents for heteroaryl and heterocycloalkyl respectively. The "heteroaryl-heterocycloalkyl" is bonded to the parent molecular structure through an atom of the heteroaryl group.

"Heteroaryl-cycloalkyl" refers to an -(heteroaryl)cycloalkyl radical where heteroaryl and cycloalkyl are as disclosed herein and which are optionally substituted by one or more of the substituents described as suitable substituents for heteroaryl and cycloalkyl respectively. The "heteroarylcycloalkyl" is bonded to the parent molecular structure through a carbon atom of the heteroaryl group.

"Heterocyclyl", "heterocycloalkyl" or 'heterocarbocyclyl" each refer to any 3- to 18-membered non-aromatic radical monocyclic or polycyclic moiety comprising at least one ring heteroatom selected from nitrogen, oxygen, phosphorous, and sulfur. A heterocyclyl group can be a monocyclic, bicyclic, tricyclic or tetracyclic ring system, wherein the polycyclic ring systems can be a fused, bridged or spiro ring system. Heterocyclyl polycyclic ring systems can include one or more heteroatoms in one or more rings. A heterocyclyl group can be saturated or partially unsaturated. Partially unsaturated heterocycloalkyl groups can be termed "heterocycloalkenyl" if the heterocyclyl contains at least one double bond, or "heterocycloalkynyl" if the heterocyclyl contains at least one triple bond. Whenever it appears herein, a numerical range such as "5 to 18" refers to each integer in the given range; e.g., "5 to 18 ring atoms" means that the heterocyclyl group can consist of 5 ring atoms, 6 ring atoms, 7 ring atoms, 8 ring atoms, 9 ring atoms, 10 ring atoms, etc., up to and including 18 ring atoms. In one embodiment, bivalent radicals derived from univalent heterocyclyl radicals whose names end in "-yl" by removal of one hydrogen atom from the atom with the free valence are named by adding "-idene" to the name of the corresponding univalent radical, e.g., a piperidyl group with two points of attachment is a piperidylidene.

An N-containing heterocyclyl moiety refers to an nonaromatic group in which at least one of the ring atoms is a nitrogen atom. The heteroatom(s) in the heterocyclyl radical can be optionally oxidized. One or more nitrogen atoms, if present, can be optionally quaternized. Heterocyclyl also includes ring systems substituted with one or more nitrogen oxide (—O—) substituents, such as piperidinyl N-oxides. The heterocyclyl is attached to the parent molecular structure through any atom of any of the ring(s).

"Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment to the parent molecular structure is on the heterocyclyl ring. In some embodiments, a heterocyclyl group is a 3- to 10-membered non-aromatic ring system having ring carbon atoms and 1 to 4 ring heteroatoms, wherein each heteroatom is independently selected from nitrogen, oxygen, phosphorous, and sulfur ("3- to 10-membered heterocyclyl"). In some embodiments, a heterocyclyl group is a 5- to 8-membered non-aromatic ring system having ring carbon atoms and 1 to 4 ring heteroatoms, wherein each heteroatom is independently selected from nitrogen, oxygen, phosphorous, and sulfur ("5- to 8-membered heterocyclyl"). In some embodiments, a heterocyclyl group is a 5- to 6-membered non-aromatic ring system having ring carbon atoms and 1 to 4 ring heteroatoms, wherein each heteroatom is independently selected from nitrogen, oxygen, phosphorous, and sulfur ("5- to 6-membered heterocyclyl"). In some embodiments, the 5- to 6-membered heterocyclyl has 1 to 3 ring heteroatoms independently selected from nitrogen, oxygen, phosphorous, and sulfur. In some embodiments, the 5- to 6-membered heterocyclyl has 1 to 2 ring heteroatoms independently selected from nitrogen, oxygen, phosphorous, and sulfur. In some embodiments, the 5- to 6-membered heterocyclyl has 1 ring heteroatom selected from nitrogen, oxygen, phosphorous, and sulfur.

Exemplary 3-membered heterocyclyls containing 1 heteroatom include, without limitation, azirdinyl, oxiranyl, thiorenyl. Exemplary 4-membered heterocyclyls containing 1 heteroatom include, without limitation, azetidinyl, oxetanyl and thietanyl. Exemplary 5-membered heterocyclyls containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2, 5-dione. Exemplary 5-membered heterocyclyls containing 2 heteroatoms include, without limitation, dioxolanyl, oxathiolanyl and dithiolanyl. Exemplary 5-membered heterocyclyls containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl, and triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydro-pyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

Unless stated otherwise, heterocyclyl moieties are optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or —O—P(=O)(OR$^a$)$_2$, where each R$^a$ is independently hydrogen, alkyl, haloalkyl, carbocyclyl, carbocyclylalkyl, aryl, aralkyl, heterocycloalkyl, heterocycloalkylalkyl, heteroaryl, or heteroarylalkyl, and each of these moieties can be optionally substituted as defined herein.

"Heterocyclyl-alkyl" refers to a -(heterocyclyl)alkyl radical where heterocyclyl and alkyl are as disclosed herein and which are optionally substituted by one or more of the substituents described as suitable substituents for heterocyclyl and alkyl respectively. The "heterocyclyl-alkyl" is bonded to the parent molecular structure through any atom of the heterocyclyl group. The terms "heterocyclyl-alkenyl" and "heterocyclyl-alkynyl" mirror the above description of "heterocyclyl-alkyl" wherein the term "alkyl" is replaced with "alkenyl" or "alkynyl" respectively, and "alkenyl" or "alkynyl" are as described herein.

"Imino" refers to the "—C(=N—R$^b$)—R$^b$" radical where each R$^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon), and heteroarylalkyl, unless stated otherwise in the specification, each of which moiety can itself be optionally substituted as described herein.

"Moiety" refers to a specific segment or functional group of a molecule. Chemical moieties are often recognized chemical entities embedded in or appended to a molecule.

"Nitro" refers to the —NO$_2$ radical.

"Oxa" refers to the —O— radical.

"Oxo" refers to the =O radical.

"Phosphate" refers to a —O—P(=O)(OR$^b$)$_2$ radical, where each R$^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon), and heteroarylalkyl, unless stated otherwise in the specification, each of which moiety can itself be optionally substituted as described herein. In some embodiments, when R$^a$ is hydrogen and depending on the pH, the hydrogen can be replaced by an appropriately charged counter ion.

"Phosphonate" refers to a —O—P(=O)(R$^b$)(OR$^b$) radical, where each R$^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) and heteroarylalkyl, unless stated otherwise in the specification, each of which moiety can itself be optionally substituted as described herein. In some embodiments, when R$^a$ is hydrogen and depending on the pH, the hydrogen can be replaced by an appropriately charged counter ion.

"Phosphinate" refers to a —P(=O)(R$^b$)(OR$^b$) radical, where each R$^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon), and heteroarylalkyl, unless stated otherwise in the specification, each of which moiety can itself be optionally substituted as described herein. In some embodiments, when $R^a$ is hydrogen and depending on the pH, the hydrogen can be replaced by an appropriately charged counter ion.

A "leaving group or atom" is any group or atom that will, under the reaction conditions, cleave from the starting material, thus promoting reaction at a specified site. Suitable non-limiting examples of such groups, unless otherwise specified, include halogen atoms, mesyloxy, p-nitrobenzensulphonyloxy, trifluoromethyloxy, and tosyloxy groups.

"Protecting group" has the meaning conventionally associated with it in organic synthesis, e.g., a group that selectively blocks one or more reactive sites in a multifunctional compound such that a chemical reaction can be carried out selectively on another unprotected reactive site and such that the group can readily be removed after the selective reaction is complete. A variety of protecting groups are disclosed, for example, in T. H. Greene and P. G. M. Wuts, *Protective Groups in Organic Synthesis*, Fourth Edition, John Wiley & Sons, New York (2006), incorporated herein by reference in its entirety. For example, a hydroxy protected form is where at least one of the hydroxy groups present in a compound is protected with a hydroxy protecting group. Likewise, amines and other reactive groups can similarly be protected.

As used herein, the terms "substituted" or "substitution" mean that at least one hydrogen present on a group atom (e.g., a carbon or nitrogen atom) is replaced with a permissible substituent, e.g., a substituent which upon substitution for the hydrogen results in a stable compound, e.g., a compound which does not spontaneously undergo transformation such as by rearrangement, cyclization, elimination, or other reaction. Unless otherwise indicated, a "substituted" group can have a substituent at one or more substitutable positions of the group, and when more than one position in any given structure is substituted, the substituent is either the same or different at each position. Substituents can include one or more group(s) individually and independently selected from acyl, alkyl, alkenyl, alkynyl, alkoxy, alkylaryl, cycloalkyl, aralkyl, aryl, aryloxy, amino, amido, azide, carbonate, carbonyl, heteroalkyl, heteroaryl, heteroarylalkyl, heterocycloalkyl, hydroxy, cyano, halo, haloalkoxy, haloalkyl, ester, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si$(R^a)_3$, —OR$^a$, —SR$^a$, —OC(O)—R$^a$, —N$(R^a)_2$, —C(O)R$^a$, —C(O)OR$^a$, —OC(O)N$(R^a)_2$, —C(O)N$(R^a)_2$, —N$(R^a)$C(O)OR$^a$, —N$(R^a)$C(O)R$^a$, —N$(R^a)$C(O)N$(R^a)_2$, —N$(R^a)$C(NR$^a$)N$(R^a)_2$, —N$(R^a)$S(O)$_t$R$^a$ (where t is 1 or 2), —S(O)$_t$OR$^a$ (where t is 1 or 2), —S(O)$_t$N$(R^a)_2$ (where t is 1 or 2), and —O—P(=O)(OR$^a)_2$, where each R$^a$ is independently hydrogen, alkyl, haloalkyl, carbocyclyl, carbocyclylalkyl, aryl, aralkyl, heterocycloalkyl, heterocycloalkylalkyl, heteroaryl, or heteroarylalkyl, and each of these moieties can be optionally substituted as defined herein. For example, a cycloalkyl substituent can have a halide substituted at one or more ring carbons, and the like. The protecting groups that can form the protective derivatives of the above substituents are known to those of skill in the art and can be found in references such as Greene and Wuts, above.

"Silyl" refers to a —Si$(R^b)_3$ radical where each R$^b$ is independently selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon), and heteroarylalkyl, unless stated otherwise in the specification, each of which moiety can itself be optionally substituted as described herein.

"Sulfanyl", "sulfide", and "thio" each refer to the radical —S—R$^b$, wherein R$^b$ is selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon), and heteroarylalkyl, unless stated otherwise in the specification, each of which moiety can itself be optionally substituted as described herein. For instance, an "alkylthio" refers to the "alkyl-S—" radical, and "arylthio" refers to the "aryl-S—" radical, each of which are bound to the parent molecular group through the S atom. The terms "sulfide", "thiol", "mercapto", and "mercaptan" can also each refer to the group —R$^b$SH.

"Sulfinyl" or "sulfoxide" refers to the —S(O)—R$^b$ radical, wherein for "sulfinyl", R$^b$ is H, and for "sulfoxide", R$^b$ is selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon), and heteroarylalkyl, unless stated otherwise in the specification, each of which moiety can itself be optionally substituted as described herein.

"Sulfonyl" or "sulfone" refers to the —S(O$_2$)—R$^b$ radical, wherein R$^b$ is selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon), and heteroarylalkyl, unless stated otherwise in the specification, each of which moiety can itself be optionally substituted as described herein.

"Sulfonamidyl" or "sulfonamido" refers to the following radicals: —S(=O)$_2$—N$(R^b)_2$, —N$(R^b)$—S(=O)$_2$R$^b$, —S(=O)$_2$—N$(R^b)$—, or —N$(R^b)$—S(=O)$_2$—, where each R$^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon), and heteroarylalkyl, unless stated otherwise in the specification, each of which moiety can itself be optionally substituted as described herein. The R$^b$ groups in —S(=O)$_2$—N$(R^b)_2$ or —N$(R^b)$—S(=O)$_2$—R$^b$ can be taken together with the nitrogen to which they are attached to form a 4-, 5-, 6-, 7-, or 8-membered heterocyclyl ring. In some embodiments, the term designates a $C_1$-$C_4$ sulfonamido, wherein each R$^b$ in the sulfonamido contains 1 carbon, 2 carbons, 3 carbons, or 4 carbons total.

"Sulfoxyl" refers to a —S(=O)$_2$OH radical.

"Sulfonate" refers to a —S(=O)$_2$—OR radical, wherein R$^b$ is selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon), and heteroarylalkyl, unless stated otherwise in the specification, each of which moiety can itself be optionally substituted as described herein.

"Thiocarbonyl" refers to a —(C=S)— radical.

"Urea" refers to a —N$(R^b)$—(C=O)—N$(R^b)_2$ or —N$(R^b)$—(C=O)—N$(R^b)$— radical, where each R$^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon), and heteroarylalkyl, unless stated otherwise in the specification, each of which moiety can itself be optionally substituted as described herein.

Where substituent groups are specified by their conventional chemical formulae, written from left to right, they equally encompass the chemically identical substituents that would result from writing the structure from right to left, e.g., —CH$_2$O— is equivalent to —OCH$_2$—.

Compounds

In certain embodiments, provided herein are compounds of Formula (I″) or Formula (A″):

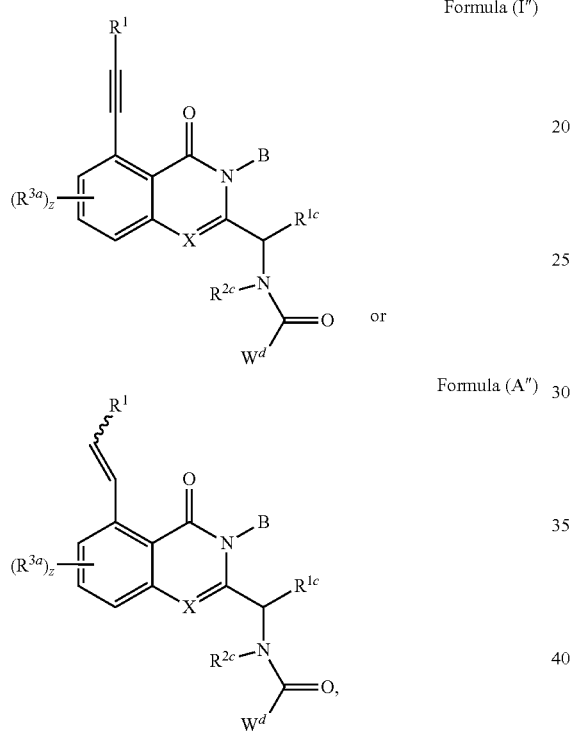

wherein:
R$^1$ is hydrogen, alkyl, alkenyl, alkynyl, cycloalkyl, heterocycloalkyl, aryl, heteroaryl, —COR$^2$, —COOR$^3$, or —CONR$^4$R$^5$;
z is 0, 1, 2, or 3;
each instance of R$^{3a}$ is independently hydrogen, alkyl, alkenyl, alkynyl, alkoxyl, halogen, cyano, amino, cycloalkyl, heterocycloalkyl, aryl, or heteroaryl;
B is hydrogen, alkyl, alkenyl, alkynyl, cycloalkyl, heterocycloalkyl, aryl, heteroaryl, —COR$^2$, —COOR$^3$, —CONR$^4$R$^5$, or —Si(R$^6$)$_3$;
  wherein R$^2$, R$^3$, R$^4$, R$^5$, and R$^6$ are each, independently, hydrogen, alkyl, alkenyl, alkynyl, cycloalkyl, heterocycloalkyl, aryl, or heteroaryl;
R$^{1c}$ is hydrogen, alkyl, alkenyl, or alkynyl;
R$^{2c}$ is hydrogen, alkyl, alkenyl, or alkynyl;
W$^d$ is heteroaryl, cycloalkyl, heterocycloalkyl, or aryl; and
X is CR$^{1a}$ or N;
  wherein R$^{1a}$ is hydrogen, halo, alkyl, alkenyl, alkynyl, or CN;
  wherein each alkyl, alkenyl, or alkynyl is optionally substituted with one or more halo, OH, alkoxy, NH$_2$, NH(alkyl), N(alkyl)$_2$, COH, CO(alkyl), COOH, COO (alkyl), CONH$_2$, CONH(alkyl), CON(alkyl)$_2$, S(O)(alkyl), S(O)$_2$(alkyl), cycloalkyl, heterocycloalkyl, aryl or heteroaryl;
  wherein each cycloalkyl, heterocycloalkyl, aryl or heteroaryl is optionally substituted with one or more halo, alkyl, alkenyl, alkynyl, OH, alkoxy, oxo, NH$_2$, NH(alkyl), N(alkyl)$_2$, COH, CO(alkyl), COOH, COO(alkyl), CONH$_2$, CONH(alkyl), CON(alkyl)$_2$, S(O)(alkyl), or S(O)$_2$(alkyl);
wherein in Formula (I″), when X is CH, B is unsubstituted phenyl, and W$^d$ is

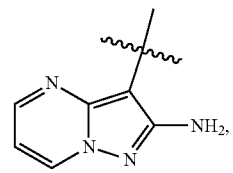 [SMILES: *c1c(N)nn2cccnc12]

then R$^1$ is not hydrogen, Si(CH$_3$)$_3$, CH$_2$Si(CH$_3$)$_3$, methyl, (CH$_2$)NH$_2$, (CH$_2$)$_2$NH$_2$, (CH$_2$)NHSO$_2$CH$_3$, or (CH$_2$)$_n$NHC(O)R$^{1x}$; n is 1 or 2; R$^{1x}$ is methyl, C$_2$ alkene, cyclohexyl, cyclopentyl, tetrahydrofuranyl, furanyl, or pyrrolidinyl, where the alkene, cyclohexyl, cyclopentyl, tetrahydrofuranyl, furanyl, or pyrrolidinyl is optionally substituted with one or two groups independently selected from oxo and cyano;
wherein in Formula (A″), when X is CH, B is unsubstituted phenyl, and W$^d$ is

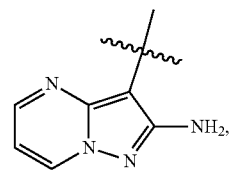 [SMILES: *c1c(N)nn2cccnc12]

then R$^1$ is not phenyl;
or a pharmaceutically acceptable form thereof.

In one embodiment, B is alkyl, alkenyl, alkynyl, cycloalkyl, heterocycloalkyl, aryl, heteroaryl, —COR$^2$, —COOR$^3$, or —CONR$^4$R$^5$. In one embodiment, B is alkyl, alkenyl, alkynyl, cycloalkyl, heterocycloalkyl, aryl, heteroaryl, —COR$^2$, —COOR$^3$, or —CONR$^4$R$^5$, wherein the point of attachment for the heterocycloalkyl and heteroaryl is a carbon atom.

In one embodiment, R$^{1c}$ is alkyl, alkenyl, or alkynyl.

In one embodiment, R1c is hydrogen. In one embodiment, R$^{1c}$ is alkyl. In one embodiment, R$^{1c}$ is methyl or ethyl. In one embodiment, R$^{1c}$ is methyl. In one embodiment, R$^{1c}$ is ethyl.

In one embodiment, R$^{2c}$ is hydrogen.

In one embodiment, in Formula (I″), X is N and R$^2$ is hydrogen.

In one embodiment, z is 0. In another embodiment, z is 1. In another embodiment, z is 2. In another embodiment, z is 3.

In one embodiment, each instance of R$^{3a}$ is independently hydrogen, alkyl, or halogen. In one embodiment, each instance of R$^{3a}$ is independently hydrogen, methyl, fluoro, chloro, or bromo.

In certain embodiments, provided herein are compounds of Formula (I″) or Formula (A″):

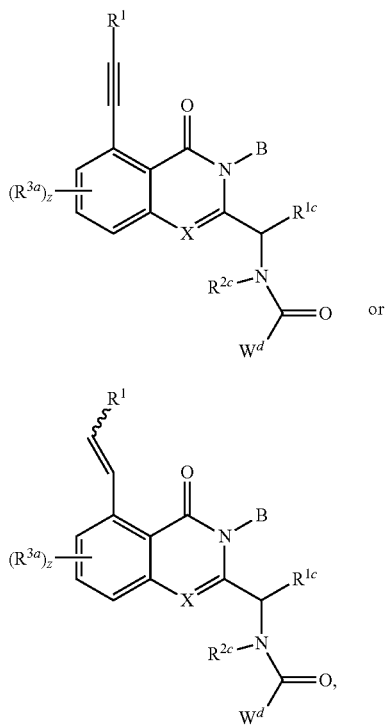

Formula (I″)

Formula (A″)

wherein:
R¹ is hydrogen, alkyl, alkenyl, alkynyl, cycloalkyl, heterocycloalkyl, aryl, heteroaryl, —COR², —COOR³, or —CONR⁴R⁵;
z is 0, 1, 2, or 3;
each instance of $R^{3a}$ is independently hydrogen, alkyl, alkenyl, alkynyl, alkoxyl, halogen, cyano, amino, cycloalkyl, heterocycloalkyl, aryl, or heteroaryl;
B is alkyl, alkenyl, alkynyl, cycloalkyl, heterocycloalkyl, aryl, heteroaryl, —COR², —COOR³, or —CONR⁴R⁵, wherein the point of attachment for the heterocycloalkyl and heteroaryl is a carbon atom;
wherein R², R³, R⁴, and R⁵ are each, independently, hydrogen, alkyl, alkenyl, alkynyl, cycloalkyl, heterocycloalkyl, aryl, or heteroaryl;
$R^{1c}$ is alkyl, alkenyl, or alkynyl;
$R^{2c}$ is hydrogen;
$W^d$ is heteroaryl, cycloalkyl, heterocycloalkyl, or aryl; and
X is $CR^{1c}$ or N;
wherein $R^{1a}$ is hydrogen, halo, alkyl, alkenyl, alkynyl, or CN;
wherein each alkyl, alkenyl, or alkynyl is optionally substituted with one or more halo, OH, alkoxy, NH₂, NH(alkyl), N(alkyl)₂, COH, CO(alkyl), COOH, COO(alkyl), CONH₂, CONH(alkyl), CON(alkyl)₂, S(O)(alkyl), S(O)₂(alkyl), cycloalkyl, heterocycloalkyl, aryl or heteroaryl;
wherein each cycloalkyl, heterocycloalkyl, aryl or heteroaryl is optionally substituted with one or more halo, alkyl, alkenyl, alkynyl, OH, alkoxy, oxo, NH₂, NH(alkyl), N(alkyl)₂, COH, CO(alkyl), COOH, COO(alkyl), CONH₂, CONH(alkyl), CON(alkyl)₂, S(O)(alkyl), or S(O)₂(alkyl);
wherein in Formula (I″), when X is CH, B is unsubstituted phenyl, and $W^d$ is

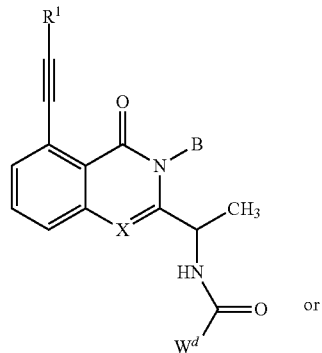

then R¹ is not hydrogen, Si(CH₃)₃, CH₂Si(CH₃)₃, methyl, (CH₂)NH₂, (CH₂)₂NH₂, (CH₂)NHSO₂CH₃, or (CH₂)ₙNHC(O)$R^{1x}$; n is 1 or 2; $R^{1x}$ is methyl, C₂ alkene, cyclohexyl, cyclopentyl, tetrahydrofuranyl, furanyl, or pyrrolidinyl, where the alkene, cyclohexyl, cyclopentyl, tetrahydrofuranyl, furanyl, or pyrrolidinyl is optionally substituted with one or two groups independently selected from oxo and cyano;
wherein in Formula (A″), when X is CH, B is unsubstituted phenyl, and $W^d$ is

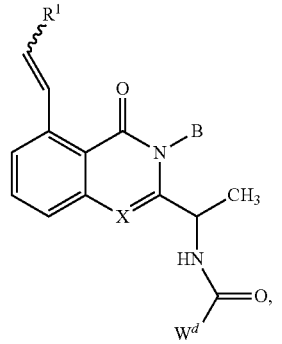

then R¹ is not phenyl;
or a pharmaceutically acceptable form thereof.
In certain embodiments, provided herein are compounds of Formula (I') or Formula (A'):

Formula (I')

Formula (A')

wherein:
R¹ is hydrogen, alkyl, alkenyl, alkynyl, cycloalkyl, heterocycloalkyl, aryl, heteroaryl, —COR², —COOR³, or —CONR⁴R⁵;

B is hydrogen, alkyl, alkenyl, alkynyl, cycloalkyl, heterocycloalkyl, aryl, heteroaryl, —COR², —COOR³, —CONR⁴R⁵, or —Si(R⁶)₃;
  wherein R², R³, R⁴, R⁵, and R⁶ are each, independently, hydrogen, alkyl, alkenyl, alkynyl, cycloalkyl, heterocycloalkyl, aryl, or heteroaryl;
$W^d$ is heteroaryl, cycloalkyl, heterocycloalkyl, or aryl; and
X is $CR^{1a}$ or N;
  wherein $R^{1a}$ is hydrogen, halo, alkyl, alkenyl, alkynyl, or CN;
  wherein each alkyl, alkenyl, or alkynyl is optionally substituted with one or more halo, haloalkyl, OH, alkoxy, NH₂, NH(alkyl), N(alkyl)₂, COH, CO(alkyl), COOH, COO(alkyl), CONH₂, CONH(alkyl), CON(alkyl)₂, S(O)(alkyl), S(O)₂(alkyl), cycloalkyl, heterocycloalkyl, aryl or heteroaryl;
  wherein each cycloalkyl, heterocycloalkyl, aryl or heteroaryl is optionally substituted with one or more halo, haloalkyl, alkyl, alkenyl, alkynyl, OH, alkoxy, oxo, NH₂, NH(alkyl), N(alkyl)₂, COH, CO(alkyl), COOH, COO(alkyl), CONH₂, CONH(alkyl), CON(alkyl)₂, S(O)(alkyl), or S(O)₂(alkyl);
  wherein in Formula (I"), when X is CH, B is unsubstituted phenyl, and $W^d$ is

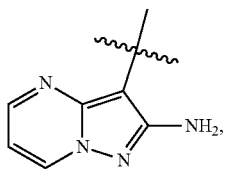 [SMILES: *c1c(N)nn2cccnc12]

then R¹ is not hydrogen, Si(CH₃)₃, CH₂Si(CH₃)₃, methyl, (CH₂)NH₂, (CH₂)₂NH₂, (CH₂)NHSO₂CH₃, or (CH₂)ₙNHC(O)R¹ˣ; n is 1 or 2; $R^{1x}$ is methyl, C₂ alkene, cyclohexyl, cyclopentyl, tetrahydrofuranyl, furanyl, or pyrrolidinyl, where the alkene, cyclohexyl, cyclopentyl, tetrahydrofuranyl, furanyl, or pyrrolidinyl is optionally substituted with one or two groups independently selected from oxo and cyano;
  wherein in Formula (A"), when X is CH, B is unsubstituted phenyl, and $W^d$ is

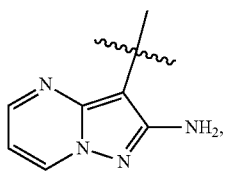 [SMILES: *c1c(N)nn2cccnc12]

then R¹ is not phenyl;
or a pharmaceutically acceptable form thereof.
In certain embodiments, provided herein are compounds of Formula (I) or Formula (A):

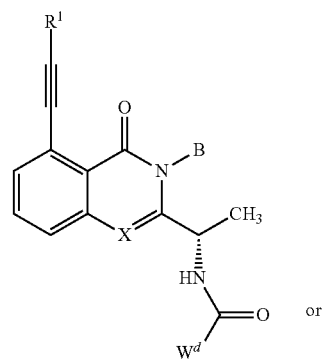

Formula (I)

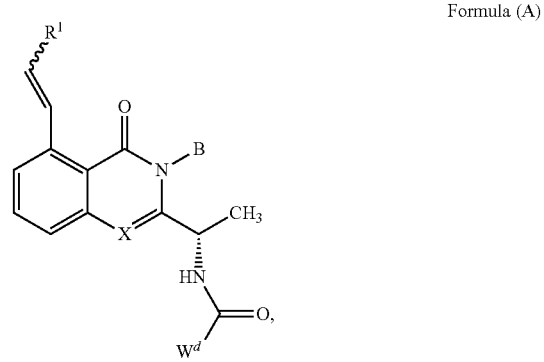

Formula (A)

wherein:
R¹ is hydrogen, alkyl, alkenyl, alkynyl, cycloalkyl, heterocycloalkyl, aryl, heteroaryl, —COR², —COOR³, or —CONR⁴R⁵;
B is hydrogen, alkyl, alkenyl, alkynyl, cycloalkyl, heterocycloalkyl, aryl, heteroaryl, —COR², —COOR³, —CONR⁴R⁵, or —Si(R⁶)₃;
  wherein R², R³, R⁴, R⁵, and R⁶ are each, independently, hydrogen, alkyl, alkenyl, alkynyl, cycloalkyl, heterocycloalkyl, aryl, or heteroaryl;
$W^d$ is heteroaryl, cycloalkyl, heterocycloalkyl, or aryl; and
X is $CR^{1a}$ or N;
  wherein $R^{1a}$ is hydrogen, halo, alkyl, alkenyl, alkynyl, or CN;
  wherein each alkyl, alkenyl, or alkynyl is optionally substituted with one or more halo, OH, alkoxy, NH₂, NH(alkyl), N(alkyl)₂, COH, CO(alkyl), COOH, COO(alkyl), CONH₂, CONH(alkyl), CON(alkyl)₂, S(O)(alkyl), S(O)₂(alkyl), cycloalkyl, heterocycloalkyl, aryl or heteroaryl;
  wherein each cycloalkyl, heterocycloalkyl, aryl or heteroaryl is optionally substituted with one or more halo, alkyl, alkenyl, alkynyl, OH, alkoxy, oxo, NH₂, NH(alkyl), N(alkyl)₂, COH, CO(alkyl), COOH, COO(alkyl), CONH₂, CONH(alkyl), CON(alkyl)₂, S(O)(alkyl), or S(O)₂(alkyl);
  wherein in Formula (I"), when X is CH, B is unsubstituted phenyl, and $W^d$ is

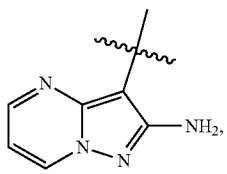 [SMILES: *c1c(N)nn2cccnc12]

then R$^1$ is not hydrogen, Si(CH$_3$)$_3$, CH$_2$Si(CH$_3$)$_3$, methyl, (CH$_2$)NH$_2$, (CH$_2$)$_2$NH$_2$, (CH$_2$)NHSO$_2$CH$_3$, or (CH$_2$)$_n$NHC(O)R$^{1x}$; n is 1 or 2; R$^{1x}$ is methyl, C$_2$ alkene, cyclohexyl, cyclopentyl, tetrahydrofuranyl, furanyl, or pyrrolidinyl, where the alkene, cyclohexyl, cyclopentyl, tetrahydrofuranyl, furanyl, or pyrrolidinyl is optionally substituted with one or two groups independently selected from oxo and cyano;

wherein in Formula (A"), when X is CH, B is unsubstituted phenyl, and W$^d$ is

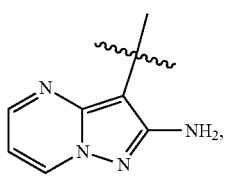 [SMILES: *c1c(N)nn2cccnc12]

then R$^1$ is not phenyl;
or a pharmaceutically acceptable form thereof.

In certain embodiments, provided herein is a mixture of compounds of Formula (I"), (I'), (I), (A"), (A'), or (A) wherein individual compounds of the mixture exist predominately in an (S)- or (R)-isomeric configuration. For example, the compound mixture has an (S)-enantiomeric purity of greater than about 55%, about 60%, about 65%, about 70%, about 75%, about 80%, about 85%, about 90%, about 95%, about 96%, about 97%, about 98%, about 99%, about 99.5%, or more. In other embodiments, the compound mixture has an (S)-enantiomeric purity of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more.

In other embodiments, the compound mixture has an (R)-enantiomeric purity of greater than about 55%, about 60%, about 65%, about 70%, about 75%, about 80%, about 85%, about 90%, about 95%, about 96%, about 97%, about 98%, about 99%, about 99.5%, or more. In some other embodiments, the compound mixture has an (R)-enantiomeric purity of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to about 99.5%, greater than about 99% to about 99.5%, or more.

In certain embodiments, provided herein are compounds of Formula (I'):

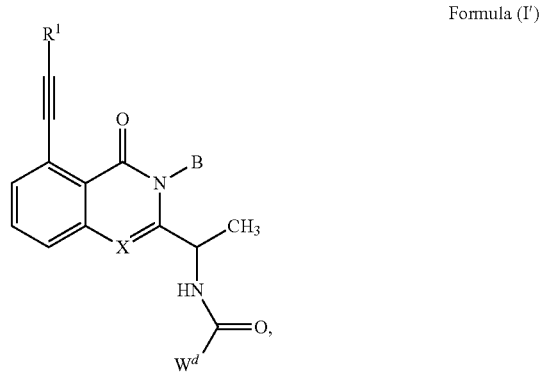

Formula (I')

or a pharmaceutically acceptable form thereof, wherein R$^1$, B, W$^d$ and X are as defined herein.

In certain embodiments, provided herein are compounds of Formula (I):

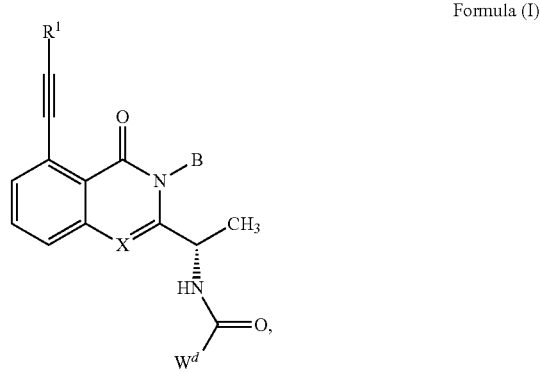

Formula (I)

or a pharmaceutically acceptable form thereof, wherein R$^1$, B, W$^d$ and X are as defined herein.

In certain embodiments, R$^1$ is branched alkyl, 5- or 6-membered aryl, 5- or 6-membered heteroaryl, 5- or 6-membered cycloalkyl, or 5- or 6-membered heterocycloalkyl,

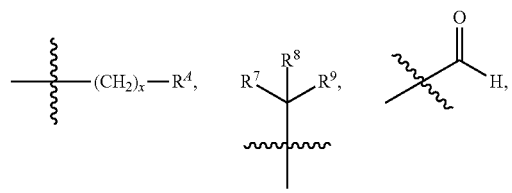

cyclopropyl, or methyl, wherein R$^4$ is OH, alkoxy, cycloalkyl, heterocycloalkyl, aryl, or heteroaryl;

x is 1, 2, 3, 4, 5, or 6;

R$^7$, R$^8$, and R$^9$ are each, independently, hydrogen, OH, alkoxy, NH$_2$, NH(alkyl), N(alkyl)$_2$, alkyl, alkenyl, alkynyl, cycloalkyl, heterocycloalkyl, aryl, or heteroaryl.

In some embodiments, $R^4$ is hydroxyl, alkoxy or heterocycloalkyl. In some embodiments, $R^7$, $R^8$, and $R^9$ are, independently, alkyl of 1-4 carbons, amino, hydroxyl, or alkoxy of 1-4 carbons.

In certain embodiments, $R^1$ is a 5- to 10-membered heteroaryl. In certain embodiments, $R^1$ is a 5- or 6-membered heteroaryl. In certain embodiments, $R^1$ is a 6-membered heteroaryl. In certain embodiments, $R^1$ is a pyridinyl. In certain embodiments, $R^1$ is a pyrimidinyl. In certain embodiments, $R^1$ is a 5-membered heteroaryl. In certain embodiments, $R^1$ is a thiazolyl. In certain embodiments, $R^1$ is a pyrazolyl. In certain embodiments, $R^1$ is an imidazolyl. In certain embodiments, the heteroaryl is substituted with one or more alkyl.

In some embodiments, $R^1$ is: methyl,

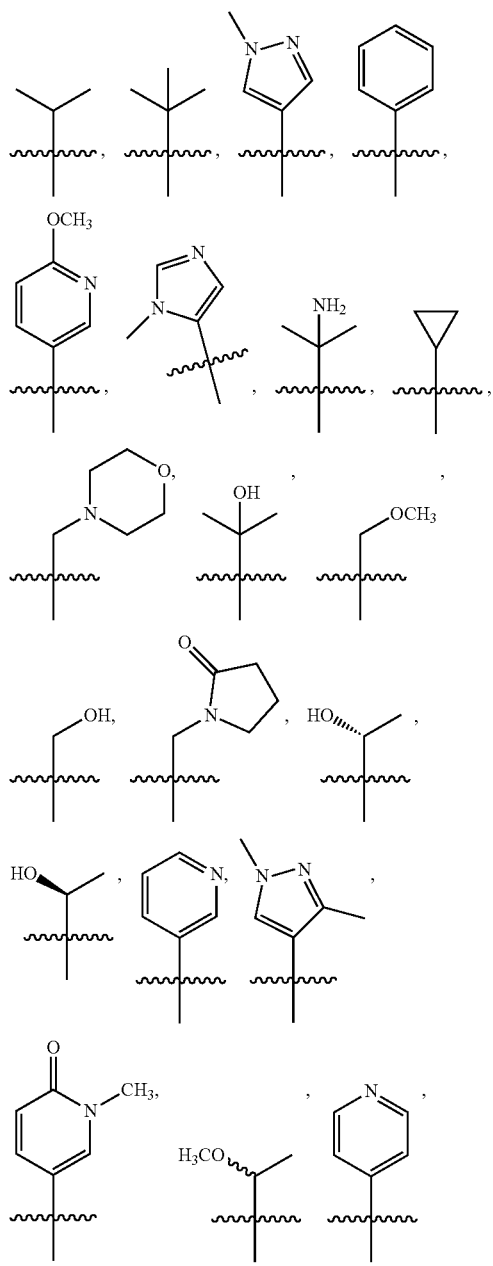

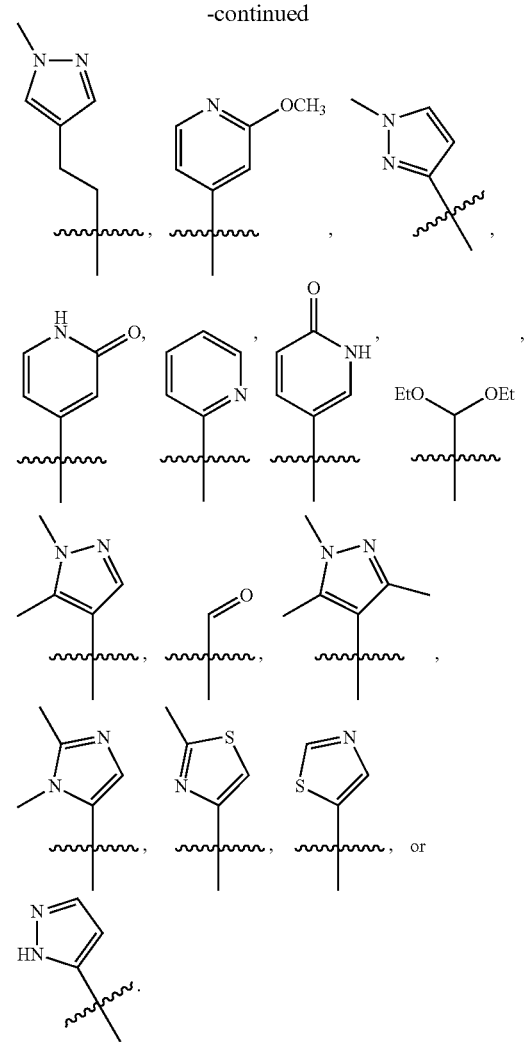

In some embodiments, B is phenyl substituted with 0, 1, 2, or 3 occurrence(s) of $R^z$. In some embodiments, B is unsubstituted phenyl. In some embodiments, B is phenyl substituted with 1 or 2 occurrence(s) of $R^z$. In some embodiments, B is phenyl optionally substituted at the para position with $R^z$. In some embodiments, B is phenyl optionally mono-substituted at the meta position with $R^z$. In some embodiments, B is phenyl optionally mono-substituted at the ortho position with $R^z$. In some embodiments, B is phenyl optionally di-substituted at the meta positions with $R^z$. In some embodiments, B is phenyl optionally di-substituted at the ortho positions with $R^z$. In some embodiments, B is phenyl optionally di-substituted at the meta and ortho positions with $R^z$. In some embodiments, B is phenyl optionally di-substituted at the meta and para positions with $R^z$. In some embodiments, B is phenyl optionally di-substituted at the ortho and para positions with $R^z$. In some embodiments, B is phenyl not substituted at the ortho positions. In some embodiments, $R^z$ is halo or alkyl. In some embodiments, B is methyl, isopropyl, or cyclopropyl. In some embodiments, B is cyclohexyl or optionally substituted alkyl. In some embodiments, B is aryl, heteroaryl, cycloalkyl, or heterocycloalkyl. In some embodiments B is 5- or 6-membered aryl or 3- to 6-membered cycloalkyl. In some embodiments, B is

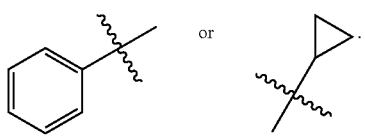
In some embodiments, B is one of the following moieties:
—CH₃, —CH₂CH₃, —CH(CH₃)₂,
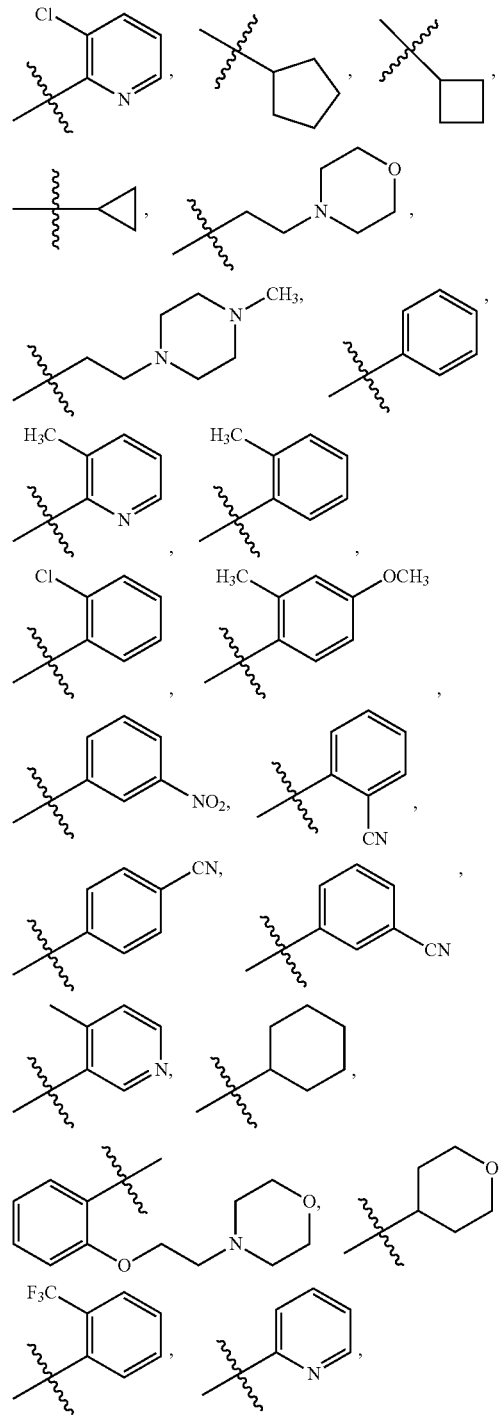
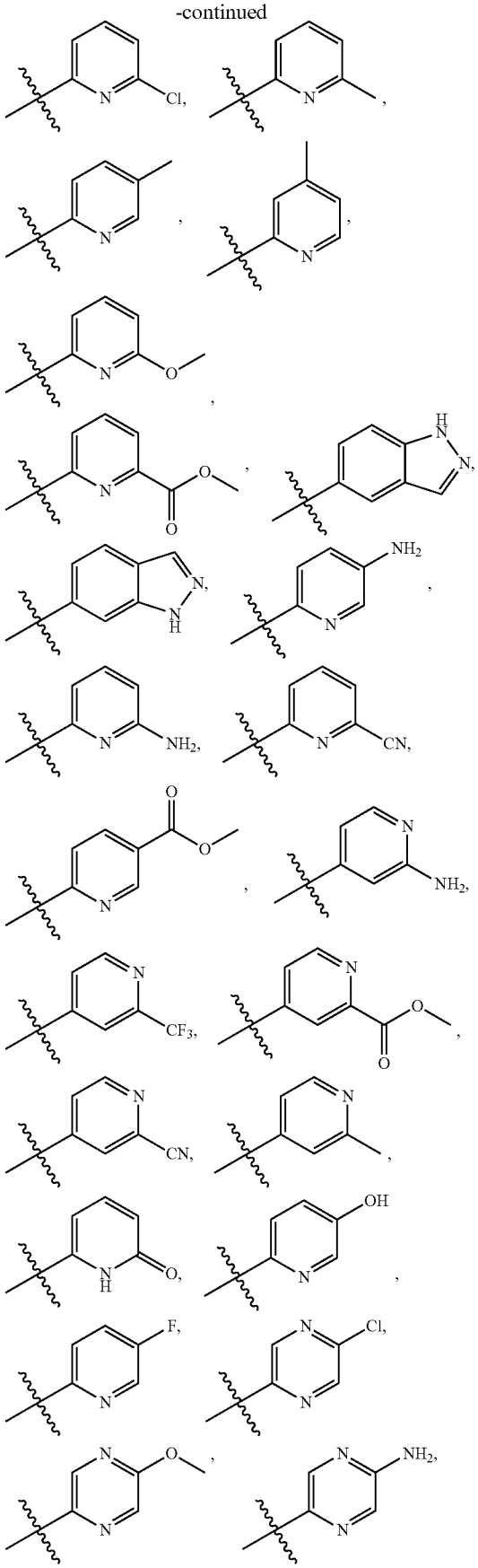

-continued
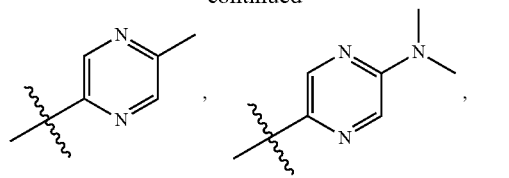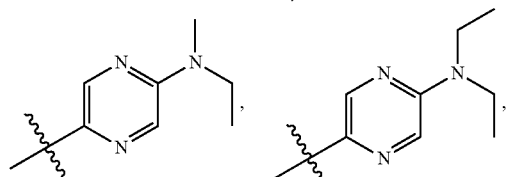
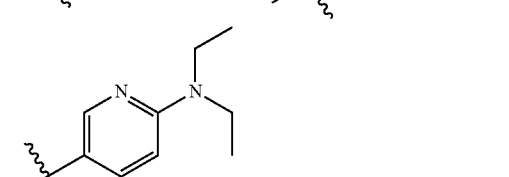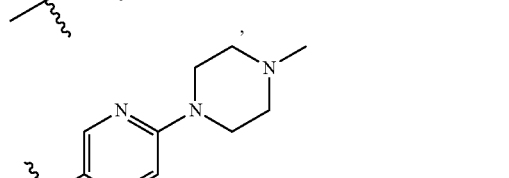
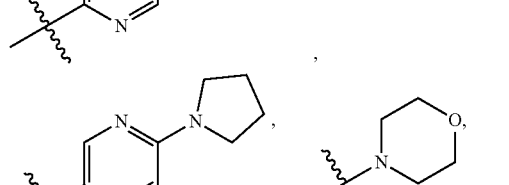
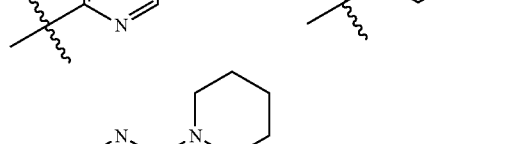
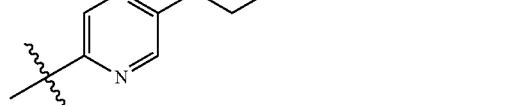
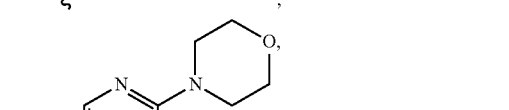
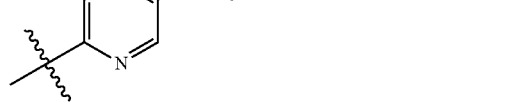
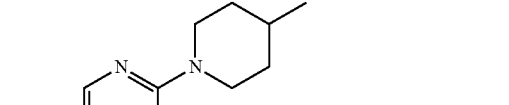
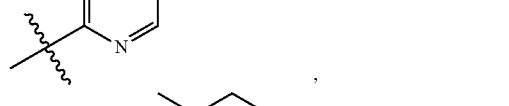
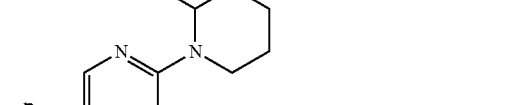
-continued
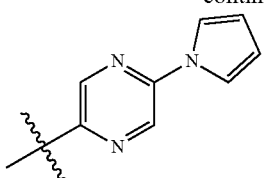
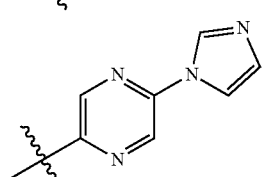
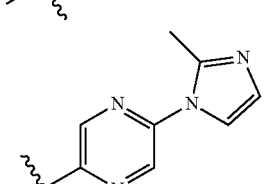
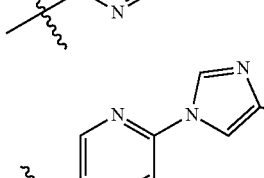
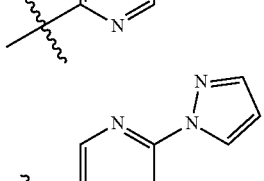
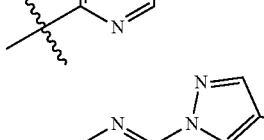
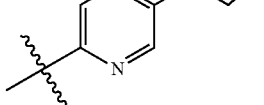
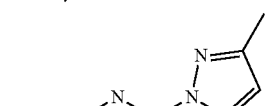
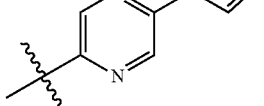
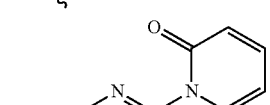
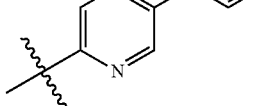
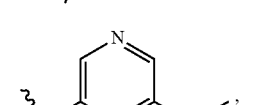
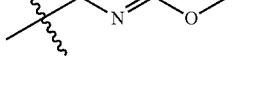

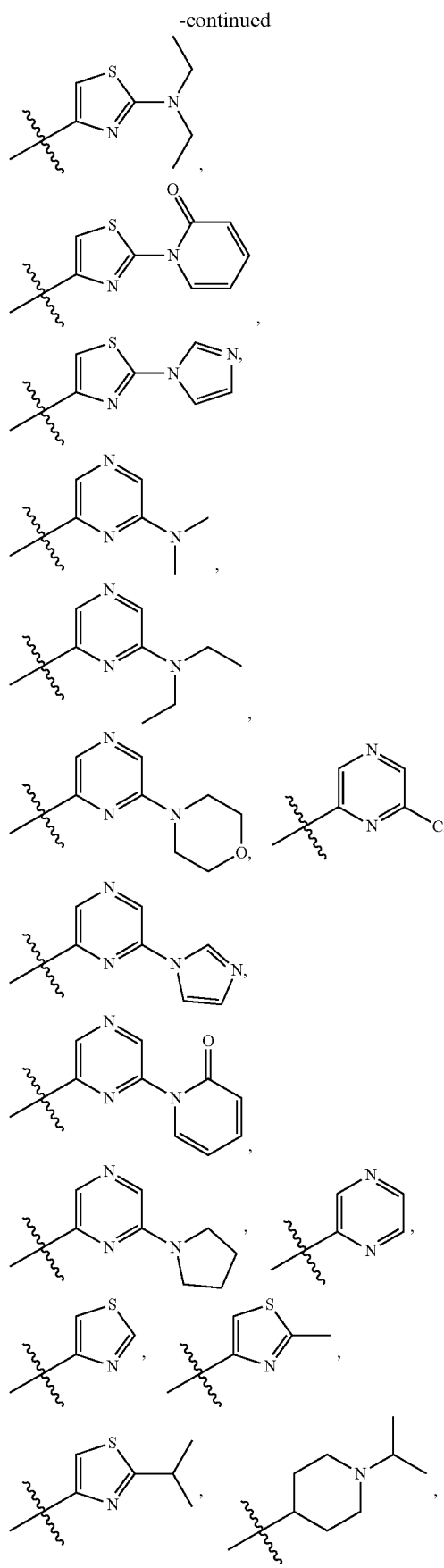
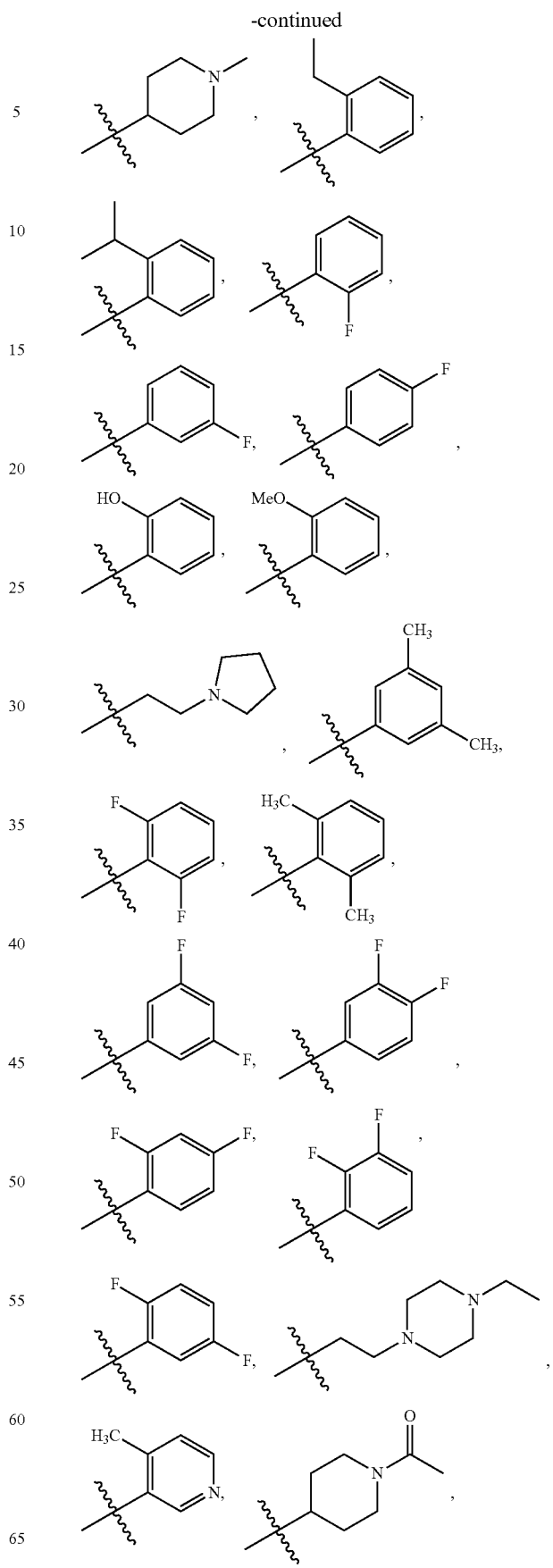

In some embodiments, B is selected from the moieties presented in Table 1.

TABLE 1

Illustrative B moieties of the compounds described herein.

| Sub-class # | B |
|---|---|
| B-1 | cyclopentyl |
| B-2 | 4-(N-isopropyl)piperidinyl |
| B-3 | —CH(CH₃)₂ |
| B-4 | 2-(trifluoromethyl)phenyl |
| B-5 | cyclopropylmethyl |
| B-6 | 2-chlorophenyl |
| B-7 | 2-methylphenyl |
| B-8 | 3-methylpyridin-2-yl |
| B-9 | 2-ethylphenyl |
| B-10 | 2-fluorophenyl |
| B-11 | 4-(N-methyl)piperidinyl |
| B-12 | 2-isopropylphenyl |
| B-13 | 2-methoxyphenyl |
| B-14 | 3-fluorophenyl |
| B-15 | 2-hydroxyphenyl |
| B-16 | 2-cyanophenyl |

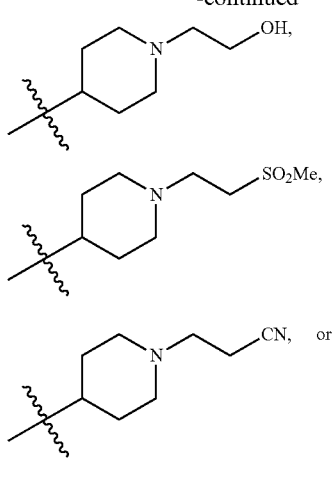

TABLE 1-continued

Illustrative B moieties of the compounds described herein.

| Sub-class # | B |
|---|---|
| B-17 | 3-cyanophenyl |
| B-18 | 4-cyanophenyl |
| B-19 | 3-(morpholin-4-yl)propyl |
| B-20 | phenyl |
| B-21 | 2-methyl-4-methoxyphenyl |
| B-22 | 4-methylpyridin-3-yl |
| B-23 | 3-nitrophenyl |
| B-24 | 2-(2-(morpholin-4-yl)ethoxy)phenyl |
| B-25 | tetrahydro-2H-pyran-4-yl |
| B-26 | 3-(4-methylpiperazin-1-yl)propyl |
| B-27 | pyridin-2-yl |
| B-28 | 6-chloropyridin-2-yl |
| B-29 | 6-methylpyridin-2-yl |
| B-30 | 5-methylpyridin-2-yl |
| B-31 | 4-methylpyridin-2-yl |
| B-32 | 6-methoxypyridin-2-yl |
| B-33 | 2-(trifluoromethyl)pyridin-4-yl |
| B-34 | 1H-indazol-5-yl |
| B-35 | 1H-indazol-6-yl |
| B-36 | 5-aminopyridin-2-yl |

TABLE 1-continued
Illustrative B moieties of the compounds described herein.
| Sub-class # | B |
|---|---|
| B-37 | 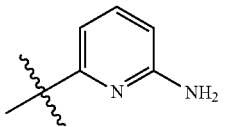 [SMILES: *c1cccc(N)n1] |
| B-38 | 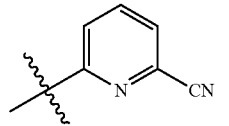 [SMILES: *c1cccc(C#N)n1] |
| B-39 | 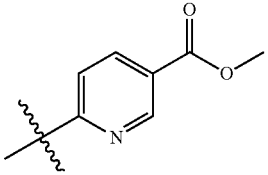 [SMILES: *c1ccc(C(=O)OC)cn1] |
| B-40 | 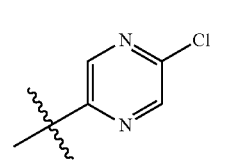 [SMILES: *c1cnc(Cl)cn1] |
| B-41 | 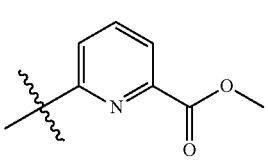 [SMILES: *c1cccc(C(=O)OC)n1] |
| B-42 | 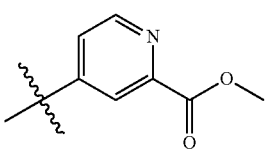 [SMILES: *c1ccnc(C(=O)OC)c1] |
| B-43 | 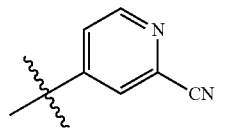 [SMILES: *c1ccnc(C#N)c1] |
| B-44 | 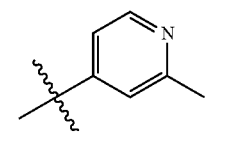 [SMILES: *c1ccnc(C)c1] |
| B-45 | 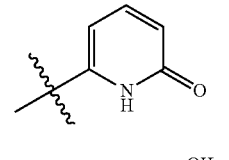 |
| B-46 | 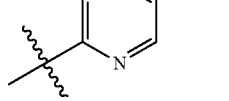 |
| B-47 | 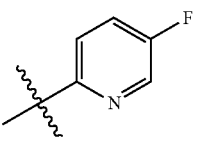 [SMILES: *c1ccc(F)cn1] |
| B-48 | 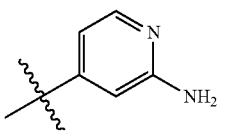 [SMILES: *c1ccnc(N)c1] |
| B-49 | 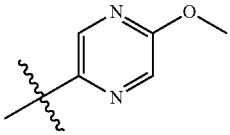 [SMILES: *c1cnc(OC)cn1] |
| B-50 | 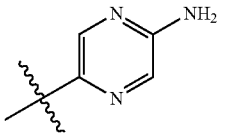 [SMILES: *c1cnc(N)cn1] |
| B-51 | 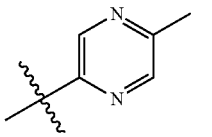 [SMILES: *c1cnc(C)cn1] |
| B-52 | 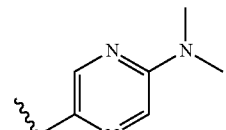 |
| B-53 | 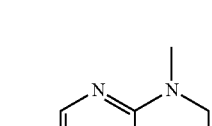 |
| B-54 | 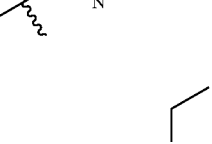 |

TABLE 1-continued
Illustrative B moieties of the compounds described herein.
| Sub-class # | B |
|---|---|
| B-55 | 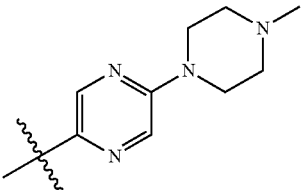 [SMILES: *c1cnc(N2CCN(C)CC2)cn1] |
| B-56 | 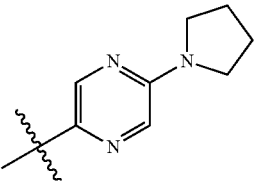 [SMILES: *c1cnc(N2CCCC2)cn1] |
| B-57 | 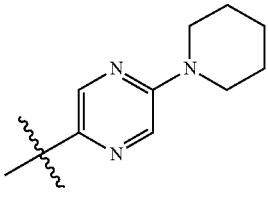 [SMILES: *c1cnc(N2CCCCC2)cn1] |
| B-58 | 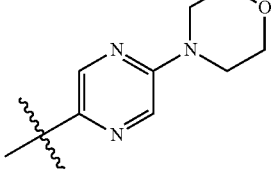 |
| B-59 | 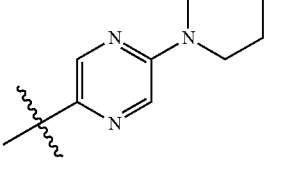 |
| B-60 | 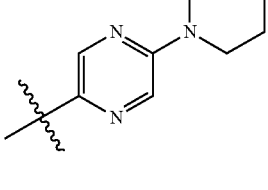 |
| B-61 | 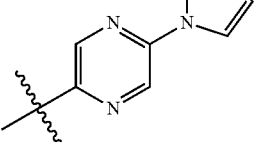 |
| B-62 | 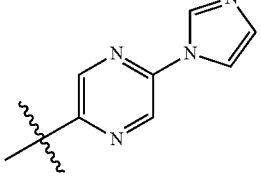 |
| B-63 | 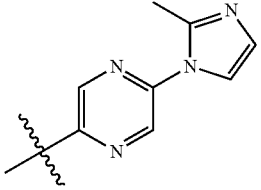 [SMILES: *c1cnc(-n2ccnc2C)cn1] |
| B-64 | 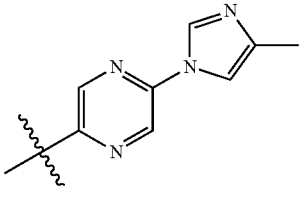 [SMILES: *c1cnc(-n2cnc(C)c2)cn1] |
| B-65 | 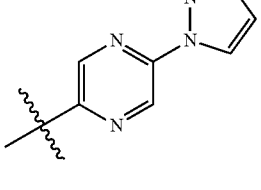 |
| B-66 | 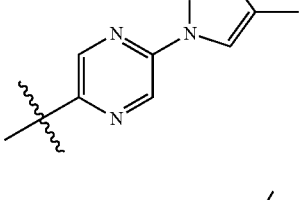 |
| B-67 | 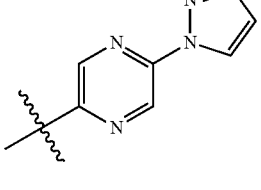 |
| B-68 | 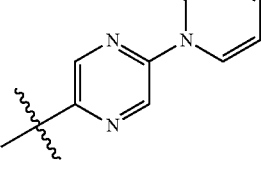 |

TABLE 1-continued

Illustrative B moieties of the compounds described herein.

| Subclass # | B |
|---|---|
| B-69 | pyrazine with CN substituent |
| B-70 | pyrazine with OMe substituent |
| B-71 | pyrazine with N(CH3)2 substituent |
| B-72 | pyrazine with N(Et)2 substituent |
| B-73 | pyrazine with morpholinyl substituent |
| B-74 | pyrazine with Cl substituent |
| B-75 | pyrazine with imidazol-1-yl substituent |
| B-76 | pyrazine with 2-oxopyridin-1-yl substituent |
| B-77 | pyrazine with pyrrolidin-1-yl substituent |
| B-78 | pyrazine (unsubstituted) |
| B-79 | thiazole |
| B-80 | 2-methylthiazole |
| B-81 | 2-isopropylthiazole |
| B-82 | thiazole with N(Me)(Et) substituent |
| B-83 | thiazole with N(Et)2 substituent |
| B-84 | thiazole with 2-oxopyridin-1-yl substituent |
| B-85 | thiazole with imidazol-1-yl substituent |
| B-86 | cyclohexyl |
| B-87 | —CH$_3$ |
| B-88 | —CH$_2$CH$_3$ |

US 11,541,059 B2
95
TABLE 1-continued
Illustrative B moieties of the compounds described herein.
| Sub-class # | B |
|---|---|
| B-89 | 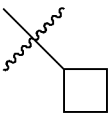 [SMILES: *C1CCC1] |
| B-90 | 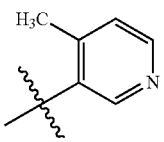 [SMILES: *c1cnccc1C] |
| B-91 | 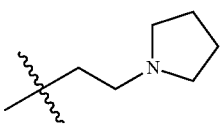 [SMILES: *CCN1CCCC1] |
| B-92 | 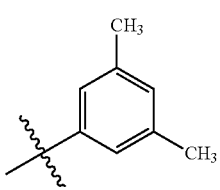 [SMILES: *c1cc(C)cc(C)c1] |
| B-93 | 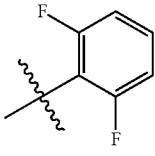 |
| B-94 | 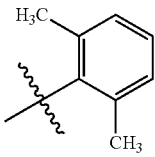 |
| B-95 | 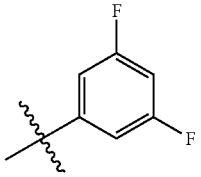 [SMILES: *c1cc(F)cc(F)c1] |
| B-96 | 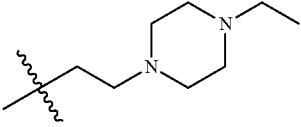 [SMILES: *CCN1CCN(CC)CC1] |
| B-97 | 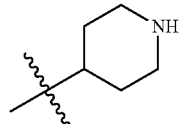 [SMILES: *C1CCNCC1] |
96
TABLE 1-continued
Illustrative B moieties of the compounds described herein.
| Sub-class # | B |
|---|---|
| B-98 | 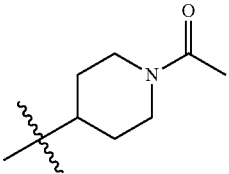 [SMILES: *C1CCN(C(C)=O)CC1] |
| B-99 | 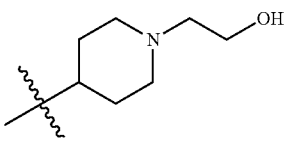 |
| B-100 | 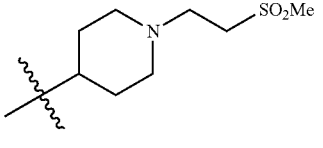 [SMILES: *C1CCN(CCS(C)(=O)=O)CC1] |
| B-101 | 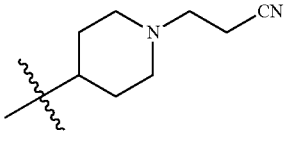 [SMILES: *C1CCN(CCC#N)CC1] |
| B-102 | 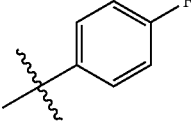 |
| B-103 | 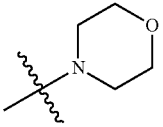 [SMILES: *N1CCOCC1] |
| B-104 | 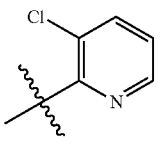 [SMILES: *c1ncccc1Cl] |
| B-105 | 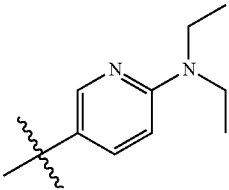 [SMILES: *c1ccc(N(CC)CC)nc1] |
| B-106 | 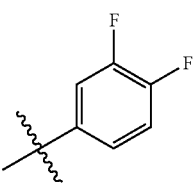 [SMILES: *c1ccc(F)c(F)c1] |

TABLE 1-continued

Illustrative B moieties of the compounds described herein.

| Sub-class # | B |
|---|---|
| B-107 | (2,4-difluorophenyl) |
| B-108 | (2,3-difluorophenyl) |
| B-109 | (2,5-difluorophenyl) |

In some embodiments, $W^d$ is aryl (e.g., a monocyclic aryl or a bicyclic aryl). In some embodiments, $W^d$ is substituted or unsubstituted phenyl. In some embodiments, $W^d$ is bicyclic aryl (e.g., substituted or unsubstituted naphthyl). In some embodiments, $W^d$ is

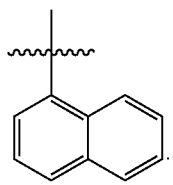 [SMILES: *c1cccc2ccccc12]

In certain embodiments, $W^d$ is heteroaryl (e.g., monocyclic heteroaryl, e.g., a monocyclic 5- or 6-membered heteroaryl; or bicyclic heteroaryl, e.g., a 5/6-bicyclic heteroaryl or a 6/6-bicyclic heteroaryl).

In some embodiments, $W^d$ is

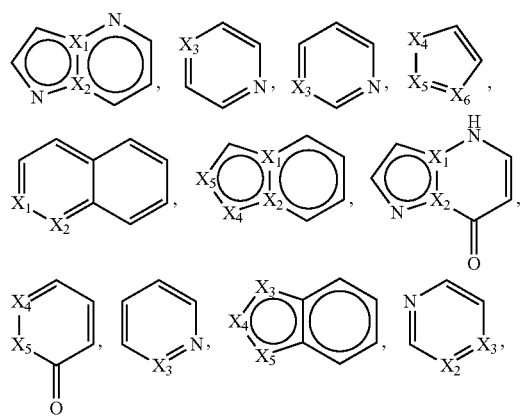

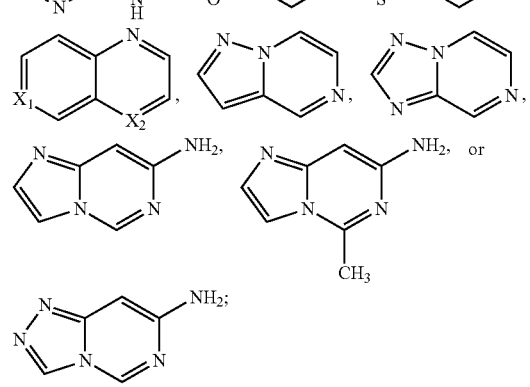

wherein $X_1$, $X_2$ and $X_3$ are each independently C, $CR^{13}$, or N;

$X_4$, $X_5$ and $X_6$ are each independently N, $NR^{12}$, $CR^{13}$, S, or O; and wherein each of the $W^d$ group is optionally substituted with one or more of $R^{10}$, $R^{11}$, $R^{12}$, and $R^{13}$, where $R^{10}$, $R^{11}$, $R^{12}$ and $R^{13}$ are each independently hydrogen, alkyl, heteroalkyl, alkenyl, alkynyl, cycloalkyl, heterocyclyl, aryl, arylalkyl, heteroaryl, heteroarylalkyl, alkoxy, heterocyclyloxy, amido, amino, acyl, acyloxy, alkoxycarbonyl, sulfonamido, halo, cyano, hydroxyl, nitro, phosphate, urea, carbonate, or NR'R" wherein R' and R" together with the nitrogen to which they are attached form a cyclic moiety; and the point of attachment is at any open position on the $W_d$ group.

In some embodiments, $W^d$ is

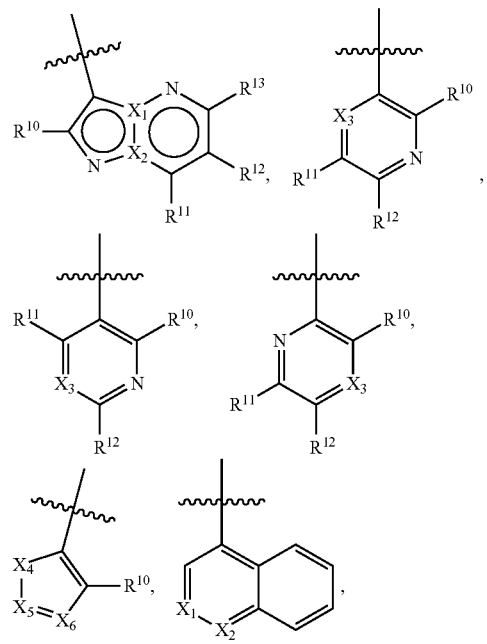

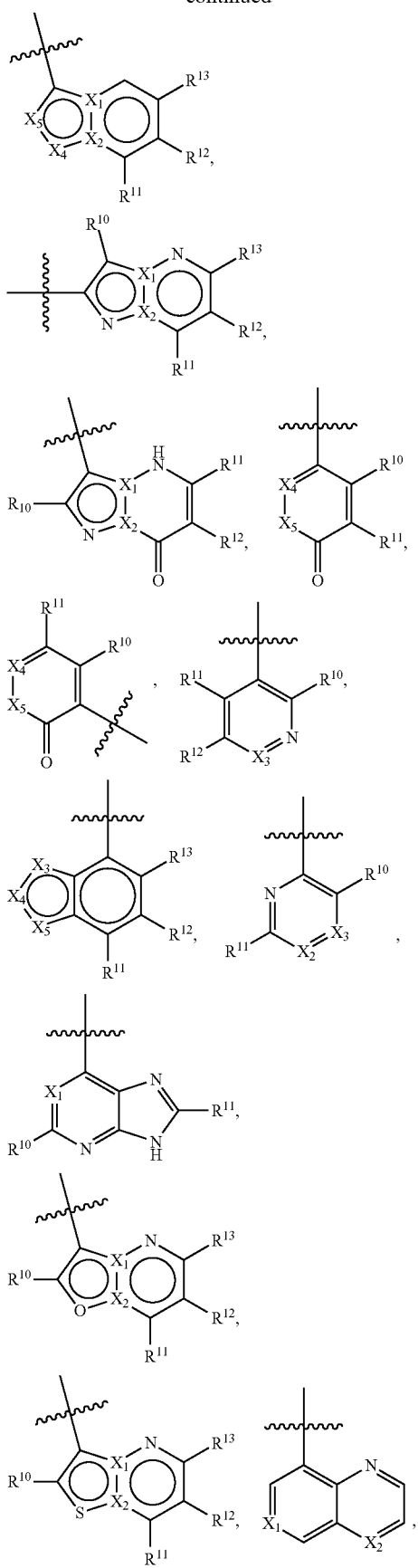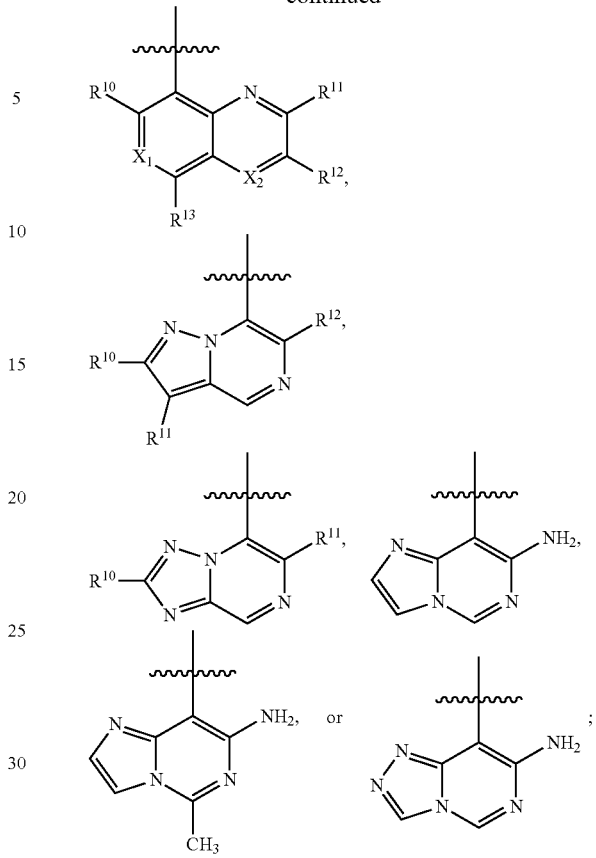

wherein
- $X_1$, $X_2$ and $X_3$ are each independently C, $CR^3$, or N;
- $X_4$, $X_5$ and $X_6$ are each independently N, $NR^{12}$, $CR^{13}$ S, or O; and
- $R^{10}$, $R^{11}$, $R^{12}$, and $R^{13}$ are each independently hydrogen, alkyl, heteroalkyl, alkenyl, alkynyl, cycloalkyl, heterocyclyl, aryl, arylalkyl, heteroaryl, heteroarylalkyl, alkoxy, heterocyclyloxy, amido, amino, acyl, acyloxy, alkoxycarbonyl, sulfonamido, halo, cyano, hydroxyl, nitro, phosphate, urea, carbonate, or NR'R" wherein R' and R" together with the nitrogen to which they are attached form a cyclic moiety.

In certain embodiments, $X_1$ is N. In some embodiments, $X_1$ is $CR^{13}$. In some embodiments, $X_1$ is C.

In certain embodiments, $X_2$ is N. In some embodiments, $X_2$ is $CR^{13}$. In some embodiments, $X_2$ is C.

In certain embodiments, $X_3$ is N. In some embodiments, $X_3$ is $CR^{13}$.

In certain embodiments, $X_4$ is N. In some embodiments, $X_4$ is $CR^{13}$. In some embodiments, $X_4$ is S.

In certain embodiments, $X_5$ is $NR^2$. In some embodiments, $X_5$ is $CR^{13}$. In some embodiments, $X_5$ is O. In some embodiments, $X_5$ is S.

In certain embodiments, $X_6$ is N. In some embodiments, $X_6$ is NH. In some embodiments, $X_6$ is $CR^{13}$. In some embodiments, $X_6$ is NH. In some embodiments, $X_6$ is O.

In some embodiments, each $R^{10}$ is independently hydrogen, halo (e.g., fluoro, chloro, or bromo), cyano, hydroxyl, alkyl (e.g., methyl or $CF_3$), alkoxyl, amino (e.g., cycloalkylamino (e.g., cyclopropylamino), alkylamino (e.g., methylamino or dimethylamino), or $NH_2$), aryl (e.g., substituted or unsubstituted phenyl), heteroaryl (e.g., a 5- or 6-membered heteroaryl, e.g., pyrazolyl, pyridinyl, among others), heterocyclyl (e.g., N-morpholinyl), or amido. In some embodiments, each $R^{10}$ is independently hydrogen, alkyl (e.g., methyl), amino (e.g., cyclopropylamino, methylamino or $NH_2$), heterocyclyl (e.g., N-morpholinyl), heteroaryl (e.g., 4-pyrazolyl), amido or halo (e.g., chloro). In one embodiment, $R^{10}$ is $NH_2$. In one embodiment, $R^{10}$ is H.

In certain embodiments, each $R^{11}$ is independently hydrogen, halo (e.g., fluoro, chloro, or bromo), cyano, hydroxyl, alkyl (e.g., methyl or $CF_3$), alkoxyl, amino (e.g., cycloalkylamino (e.g., cyclopropylamino), alkylamino (e.g., methylamino or dimethylamino), or $NH_2$), aryl (e.g., substituted or unsubstituted phenyl), heteroaryl (e.g., a 5- or 6-membered heteroaryl, e.g., pyrazolyl, pyridinyl, among others), heterocyclyl (e.g., N-morpholinyl), or amido. In some embodiments, each $R^{11}$ is independently hydrogen, amino, halo (e.g., bromo), aryl (e.g., phenyl) or alkyl (e.g., methyl). In one embodiment, $R^{11}$ is H.

In certain embodiments, each $R^{12}$ is independently hydrogen, halo (e.g., fluoro, chloro, or bromo), cyano, hydroxyl, alkyl (e.g., methyl or $CF_3$), alkoxyl, amino (e.g., cycloalkylamino (e.g., cyclopropylamino), alkylamino (e.g., methylamino or dimethylamino), or $NH_2$), aryl (e.g., substituted or unsubstituted phenyl), heteroaryl (e.g., a 5- or 6-membered heteroaryl, e.g., pyrazolyl, pyridinyl, among others), heterocyclyl (e.g., N-morpholinyl), or amido. In some embodiments, each $R^{12}$ is independently hydrogen, amino, or alkyl (e.g., methyl). In one embodiment, $R^{12}$ is H.

In certain embodiments, each $R^{13}$ is independently hydrogen, halo (e.g., fluoro, chloro, or bromo), cyano, hydroxyl, alkyl (e.g., methyl or $CF_3$), alkoxyl, amino (e.g., cycloalkylamino (e.g., cyclopropylamino), alkylamino (e.g., methylamino or dimethylamino), or $NH_2$), aryl (e.g., substituted or unsubstituted phenyl), heteroaryl (e.g., a 5- or 6-membered heteroaryl, e.g., pyrazolyl, pyridinyl, among others), heterocyclyl (e.g., N-morpholinyl), or amido. In some embodiments, each $R^{13}$ is independently hydrogen, amino (e.g., $NH_2$), amido (e.g., NH—C(=O)Me), or alkyl (e.g., methyl). In one embodiment, $R^{13}$ is H.

In some embodiments, $W^d$ is

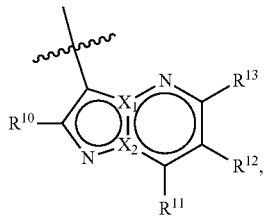

wherein one of $X_1$ and $X_2$ is C and the other is N; and $R^{10}$, $R^{11}$, $R^{12}$, and $R^{13}$ areas defined herein. In some embodiments, $R^{10}$ is hydrogen, halo (e.g., fluoro, chloro, or bromo), cyano, hydroxyl, alkyl (e.g., methyl or $CF_3$), alkoxyl, amino (e.g., cycloalkylamino (e.g., cyclopropylamino), alkylamino (e.g., methylamino or dimethylamino), or $NH_2$), aryl (e.g., substituted or unsubstituted phenyl), heteroaryl (e.g., a 5- or 6-membered heteroaryl, e.g., pyrazolyl, pyridinyl, among others), heterocyclyl (e.g., N-morpholinyl), or amido. In some embodiments, $R^{10}$ is hydrogen, alkyl (e.g., methyl), amino (e.g., cyclopropylamino, methylamino or $NH_2$), heterocyclyl (e.g., N-morpholinyl), heteroaryl (e.g., 4-pyrazolyl), amido or halo (e.g., chloro). In one embodiment, $R^{10}$ is $NH_2$. In one embodiment, $R^{10}$ is H. In specific embodiment, one of $X_1$ and $X_2$ is C and the other is N; $R^{10}$ is H or $NH_2$; and $R^{11}$, $R^{12}$, and $R^{13}$ are as defined herein. In specific embodiments, all of $R^{11}$, $R^{12}$, and $R^{13}$ are H. In specific embodiments, two of $R^{11}$, $R^{12}$, and $R^{13}$ are H, and one of $R^{11}$, $R^{12}$, and $R^{13}$ is alkyl (e.g., methyl or $CF_3$), halo, cyano, aryl (e.g., phenyl), or heteroaryl (e.g., a 5- or 6-membered heteroaryl, such as, pyridinyl, pyrimidinyl, pyrazolyl, thiazolyl, imidazolyl, among others); and in some embodiments, the aryl and heteroaryl is optionally substituted with one or more substituents, such as, for example, halo (e.g., F or Cl), cyano, hydroxyl, alkyl (e.g., methyl or $CF_3$), alkoxyl (e.g., methoxy, $OCF_3$, ethoxy, or isopropyloxy), sulfonyl (e.g., $S(O)_2Me$), sulfonamidyl (e.g., $S(O)_2NH_2$, $S(O)_2NHMe$, $S(O)_2N(Me)_2$, $S(O)_2NH$-i-Pr, $S(O)_2NH$-t-Bu, $S(O)_2NH$-c-Pr, $S(O)_2NHPh$, $S(O)_2$—N-pyrrolidinyl, $S(O)_2$—N-morpholinyl, $S(O)_2$—N-piperazinyl, $S(O)_2$-4-methyl-N-piperazinyl, $NHS(O)_2Me$, $NHS(O)_2Et$, $NHS(O)_2$-c-Pr), or sulfonylurea (e.g., $NHS(O)_2N(Me)_2$).

In some embodiments, $W^d$ is.

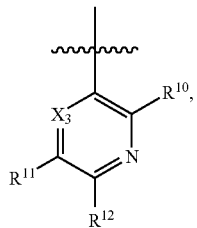

wherein $X_3$ is N or $CR^{13}$; and $R^{10}$, $R^{11}$, $R^{12}$, and $R^{13}$ are as defined herein. In specific embodiments, $X_3$ is N or $CR^{13}$; $R^{10}$ is H or $NH_2$; and $R^{11}$, $R^2$, and $R^{13}$ areas defined herein. In specific embodiments, $R^{10}$ is $NH_2$. In specific embodiments, $X_3$ is N. In specific embodiments, one of $R^{11}$ and $R^{12}$ is H, and the other is alkyl (e.g., methyl or $CF_3$), halo, cyano, aryl (e.g., phenyl), or heteroaryl (e.g., a 5- or 6-membered heteroaryl, such as, pyridinyl, pyrimidinyl, pyrazolyl, thiazolyl, imidazolyl, among others); and in some embodiments, the aryl and heteroaryl is optionally substituted with one or more substituents, such as, for example, halo (e.g., F or Cl), cyano, hydroxyl, alkyl (e.g., methyl or $CF_3$), alkoxyl (e.g., methoxy, $OCF_3$, ethoxy, or isopropyloxy), sulfonyl (e.g., $S(O)_2Me$), sulfonamidyl (e.g., $S(O)_2NH_2$, $S(O)_2NHMe$, $S(O)_2N(Me)_2$, $S(O)_2NH$-i-Pr, $S(O)_2NH$-t-Bu, $S(O)_2NH$-c-Pr, $S(O)_2NHPh$, $S(O)_2$—N-pyrrolidinyl, $S(O)_2$—N— morpholinyl, $S(O)_2$—N-piperazinyl, $S(O)_2$-4-methyl-N-piperazinyl, $NHS(O)_2Me$, $NHS(O)_2$-c-Pr), or sulfonylurea (e.g., $NHS(O)_2N(Me)_2$).

In some embodiments, $W^d$ is:

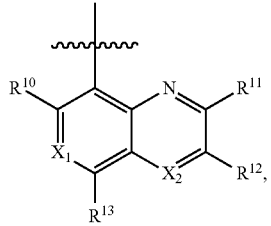

wherein one of $X_1$ and $X_2$ is N and the other is $CR^1$; and $R^{10}$, $R^{11}$, $R^{12}$, and $R^{13}$ are as defined herein. In specific embodiment, one of $X_1$ and $X_2$ is N and the other is $CR^{13}$; $R^{10}$ is H or $NH_2$; and $R^{11}$, $R^2$, and $R^{13}$ are as defined herein. In specific embodiments, $X_1$ is N and $X_2$ is $CR^{13}$. In specific embodiments, $X_1$ is N and $X_2$ is CH. In specific embodiments, $R^{10}$ is $NH_2$. In specific embodiments, $R^{11}$, $R^{12}$ and $R^{13}$ are H. In specific embodiments, at least one of $R^{11}$, $R^{12}$ and $R^{13}$ is not H. In specific embodiments, one occurrence of $R^{11}$, $R^{12}$ and $R^{13}$ is not H and the other occurrences of $R^{11}$, $R^{12}$ and $R^{13}$ are H, and the one occurrence of $R^{11}$, $R^{12}$ and $R^{13}$ (which is not hydrogen) is alkyl (e.g., methyl or $CF_3$), halo, cyano, aryl (e.g., phenyl), or heteroaryl (e.g., a 5- or 6-membered heteroaryl, such as, pyridinyl, pyrimidinyl, pyrazolyl, thiazolyl, imidazolyl, among others); and in some embodiments, the aryl and heteroaryl is optionally substituted with one or more substituents, such as, for example, halo (e.g., F or Cl), cyano, hydroxyl, alkyl (e.g., methyl or $CF_3$), alkoxyl (e.g., methoxy, $OCF_3$, ethoxy, or isopropyloxy), sulfonyl (e.g., $S(O)_2Me$), sulfonamidyl (e.g., $S(O)_2NH_2$, $S(O)_2NHMe$, $S(O)_2N(Me)_2$, $S(O)_2NH-i-Pr$, $S(O)_2NH-t-Bu$, $S(O)_2NH-c-Pr$, $S(O)_2NHPh$, $S(O)_2$—N-pyrrolidinyl, $S(O)_2$—N-morpholinyl, $S(O)_2$—N-piperazinyl, $S(O)_2$-4-methyl-N-piperazinyl, $NHS(O)_2Me$, $NHS(O)_2$-c-Pr), or sulfonylurea (e.g., $NHS(O)_2N(Me)_2$).

In exemplary embodiments, $W^d$ is one of the following moieties:

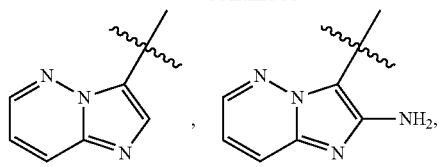

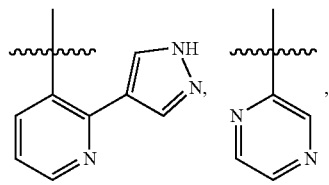

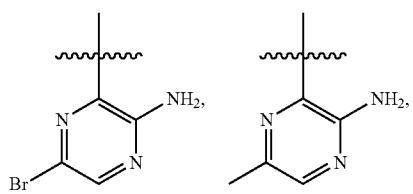

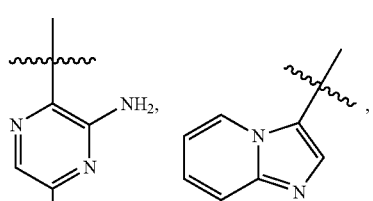

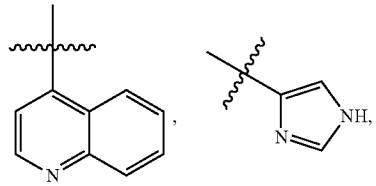

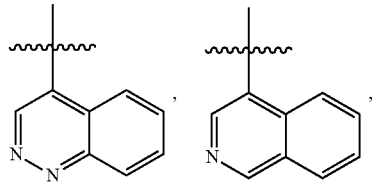

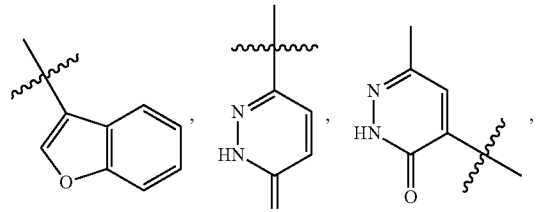

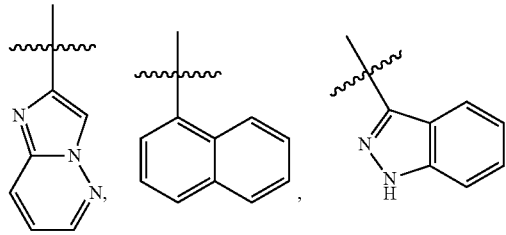

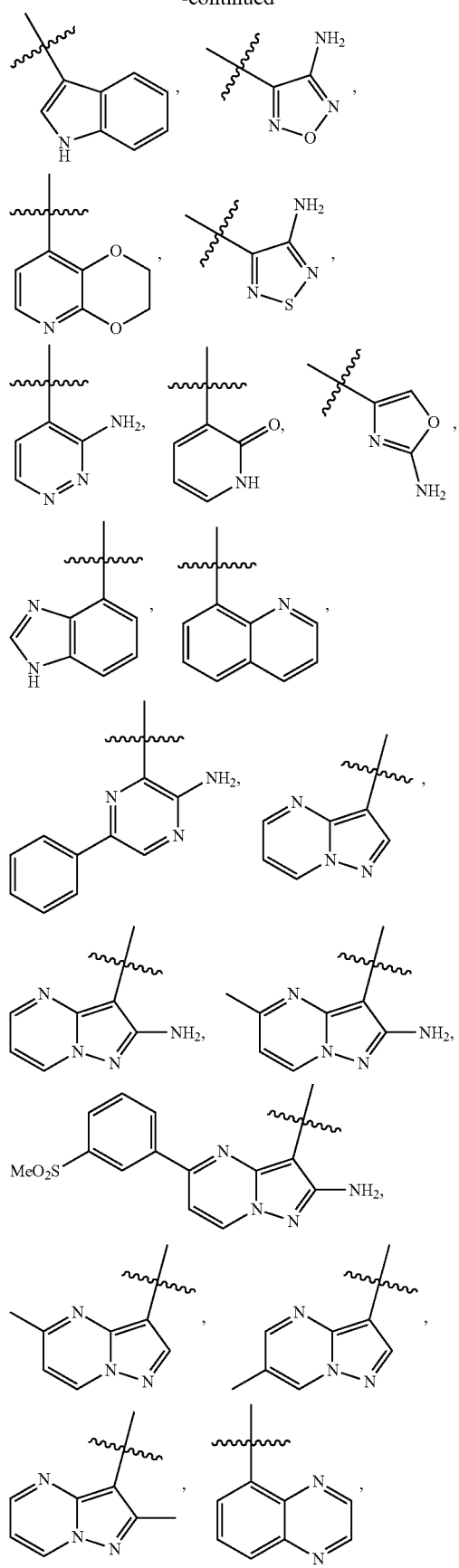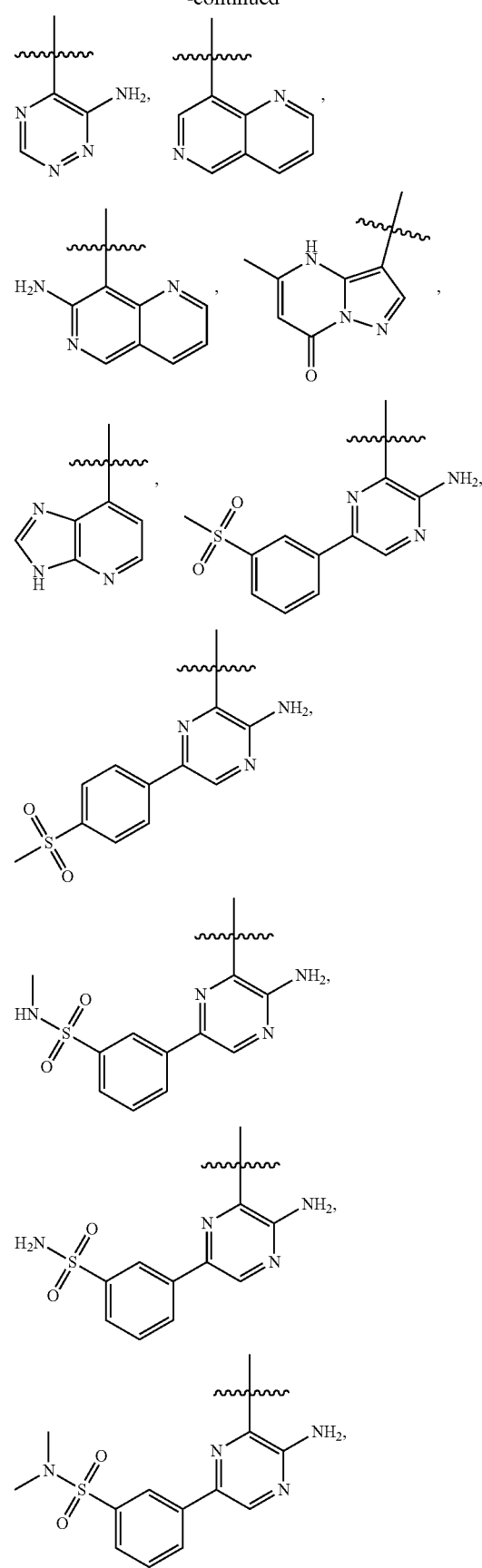

107
-continued
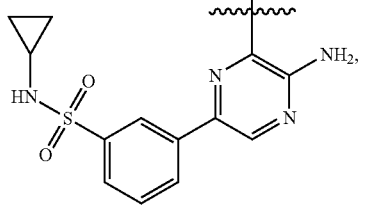
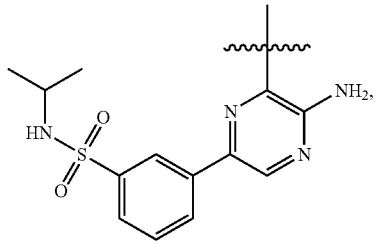
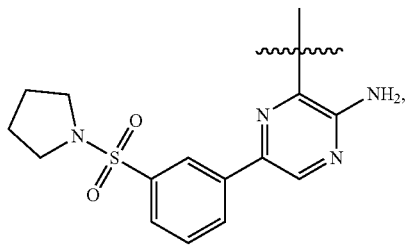
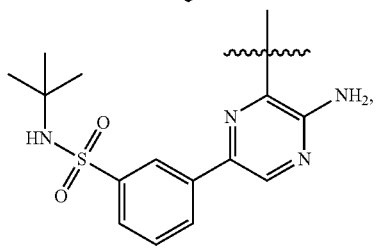
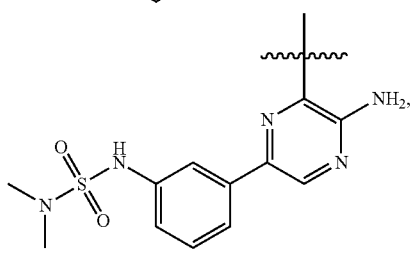
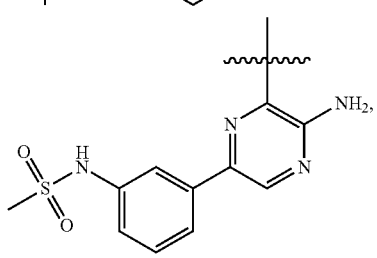
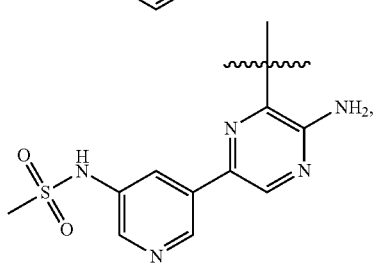
108
-continued
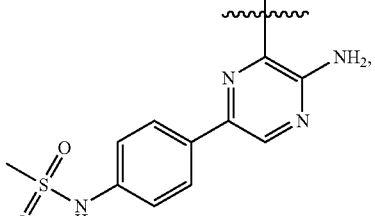
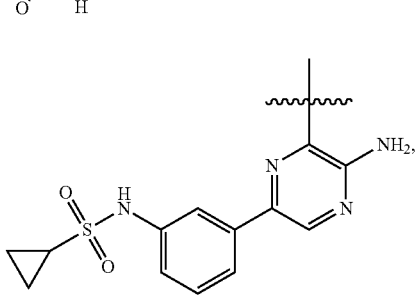
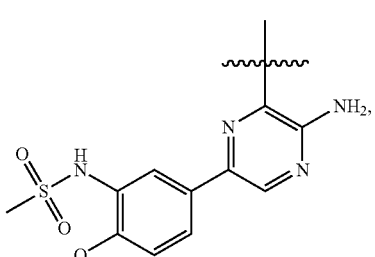
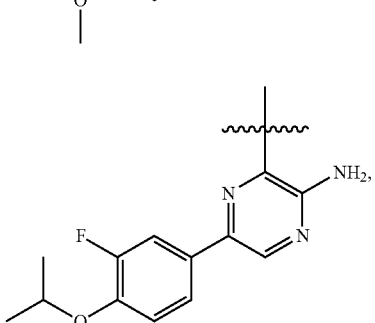
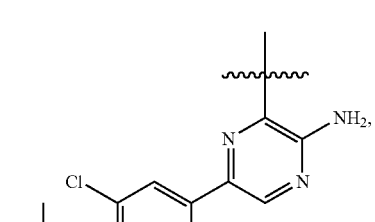
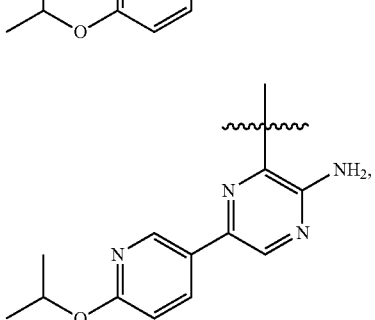

-continued
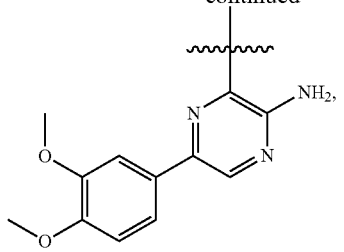
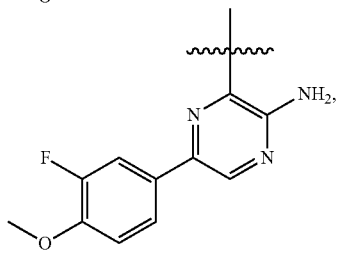
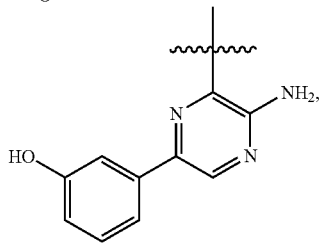
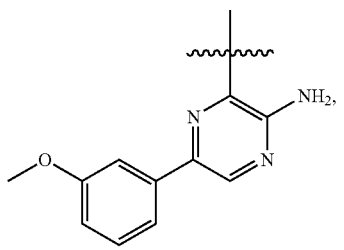
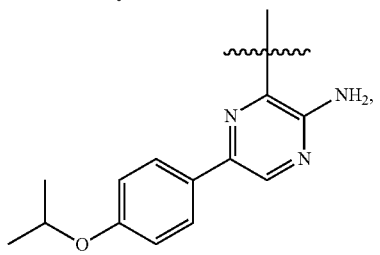
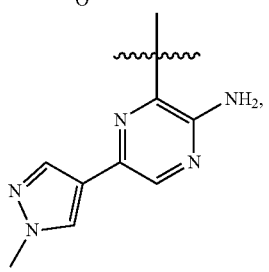
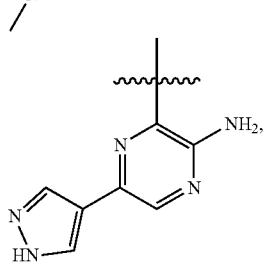
-continued
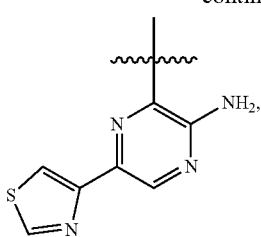
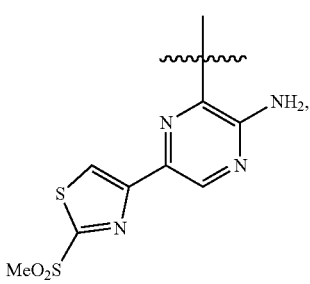
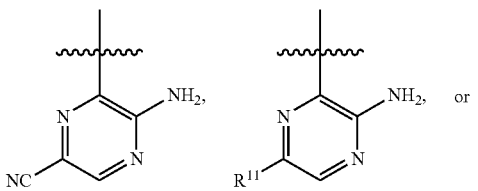
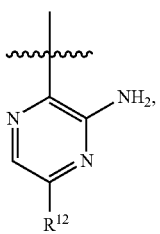
wherein $R^{11}$ and $R^{12}$ are as defined herein.
In some embodiments, $W^d$ is
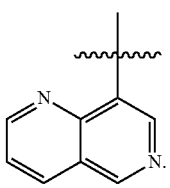 [SMILES: *c1cncc2cccnc12]
In some embodiments, $W^d$ is
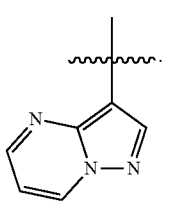 [SMILES: *c1cnn2cccnc12]

In some embodiments, $W^d$ is

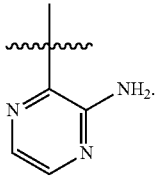 [SMILES: *c1nccnc1N]

In some embodiments, $W^d$ is

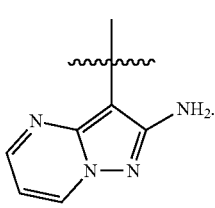 [SMILES: *c1c(N)nn2cccnc12]

In some embodiments, X is CH. In some embodiments, X is N.

In some embodiments, in Formula (I"), (I'), or (I), when X is CH, B is unsubstituted phenyl, and $W^d$ is

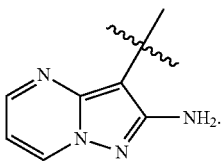 [SMILES: *c1c(N)nn2cccnc12]

then $R^1$ is not hydrogen, Si(CH$_3$)$_3$, CH$_2$Si(CH$_3$)$_3$, methyl, (CH$_2$)NH$_2$, (CH$_2$)$_2$NH$_2$, (CH$_2$)NHSO$_2$CH$_3$, or (CH$_2$)$_n$NHC(O)R$^{1x}$; n is 1 or 2; R$^{1x}$ is methyl, C$_2$ alkene, cyclohexyl, cyclopentyl, tetrahydrofuranyl, furanyl, or pyrrolidinyl, where the alkene, cyclohexyl, cyclopentyl, tetrahydrofuranyl, furanyl, or pyrrolidinyl is optionally substituted with one or two groups independently selected from oxo and cyano.

In some embodiments, in Formula (I"), (I'), or (I), when X is CH, B is unsubstituted phenyl, and $W^d$ is

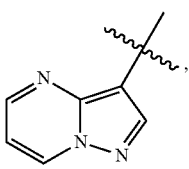 [SMILES: *c1cnn2cccnc12]

then $R^1$ is not (CH$_2$)$_n$NHC(O)R$^{1x}$; n is 1; R$^{1x}$ is tetrahydrofuranyl or pyrrolidinyl, where the tetrahydrofuranyl or pyrrolidinyl is optionally substituted with oxo.

In some embodiments, in Formula (A"), (A'), or (A), when X is CH, B is unsubstituted phenyl, and $W^d$ is

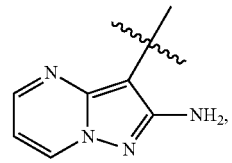

then $R^1$ is not phenyl.

In some embodiments, the compound is a compound of formula II:

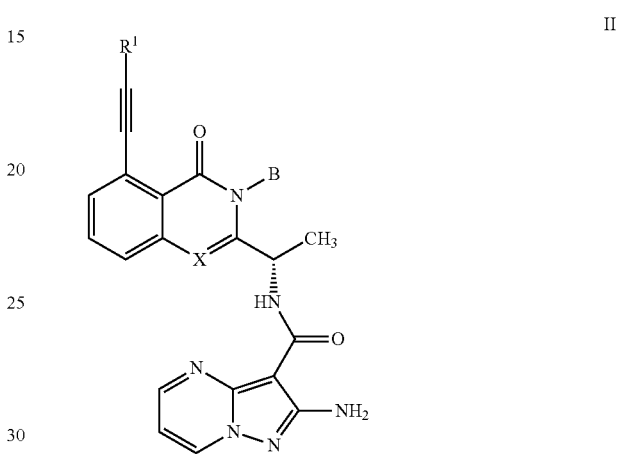

II wherein $R^1$, B, and X are as defined herein. In some embodiments, $R^1$ is hydrogen, alkyl, alkenyl, alkynyl, cycloalkyl, heterocycloalkyl, aryl, heteroaryl, —COR$^2$, —COOR$^3$, or —CONR$^4$R$^5$;

B is hydrogen, alkyl, alkenyl, alkynyl, cycloalkyl, heterocycloalkyl, aryl, heteroaryl, —COR$^2$, —COOR$^3$, —CONR$^4$R$^5$, or —Si(R$^6$)$_3$;

wherein $R^2$, $R^3$, $R^4$, $R^5$, and $R^6$ are each, independently, hydrogen, alkyl, alkenyl, alkynyl, cycloalkyl, heterocycloalkyl, aryl, or heteroaryl;

X is CR$^{1a}$ or N;

wherein R$^{1a}$ is hydrogen, halo, alkyl, alkenyl, alkynyl, or CN;

wherein each alkyl, alkenyl, or alkynyl is optionally substituted with one or more halo, OH, alkoxy, NH$_2$, NH(alkyl), N(alkyl)$_2$, COH, CO(alkyl), COOH, COO(alkyl), CONH$_2$, CONH(alkyl), CON(alkyl)$_2$, S(O)(alkyl), S(O)$_2$(alkyl), cycloalkyl, heterocycloalkyl, aryl or heteroaryl;

wherein each cycloalkyl, heterocycloalkyl, aryl or heteroaryl is optionally substituted with one or more halo, alkyl, alkenyl, alkynyl, OH, alkoxy, oxo, NH$_2$, NH(alkyl), N(alkyl)$_2$, COH, CO(alkyl), COOH, COO(alkyl), CONH$_2$, CONH(alkyl), CON(alkyl)$_2$, S(O)(alkyl), or S(O)$_2$(alkyl); and wherein when X is CH, and B is unsubstituted phenyl, then $R^1$ is not hydrogen, Si(CH$_3$)$_3$, CH$_2$Si(CH$_3$)$_3$, methyl, (CH$_2$)NH$_2$, (CH$_2$)$_2$NH$_2$, (CH$_2$)NHSO$_2$CH$_3$, or (CH$_2$)$_n$NHC(O)R$^{1x}$; n is 1 or 2; R$^{1x}$ is methyl, C$_2$ alkene, cyclohexyl, cyclopentyl, tetrahydrofuranyl, furanyl, or pyrrolidinyl, where the alkene, cyclohexyl, cyclopentyl, tetrahydrofuranyl, furanyl, or pyrrolidinyl is optionally substituted with one or two groups independently selected from oxo and cyano.

In some embodiments, the compound is a compound of formula III:

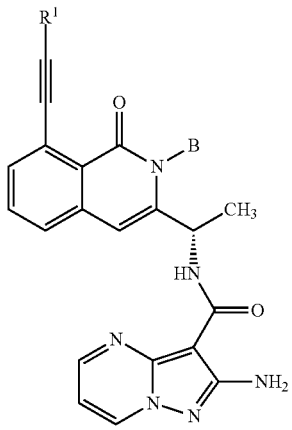

III wherein $R^1$ and B are defined herein. In some embodiments, $R^1$ is hydrogen, alkyl, alkenyl, alkynyl, cycloalkyl, heterocycloalkyl, aryl, heteroaryl, —$COR^2$, —$COOR^3$, or —$CONR^4R^5$;

B is hydrogen, alkyl, alkenyl, alkynyl, cycloalkyl, heterocycloalkyl, aryl, heteroaryl, —$COR^2$, —$COOR^3$, —$CONR^4R^5$, or —$Si(R^6)_3$;

wherein $R^2$, $R^3$, $R^4$, $R^5$, and $R^6$ are each, independently, hydrogen, alkyl, alkenyl, alkynyl, cycloalkyl, heterocycloalkyl, aryl, or heteroaryl;

wherein each alkyl, alkenyl, or alkynyl is optionally substituted with one or more halo, OH, alkoxy, $NH_2$, NH(alkyl), N(alkyl)$_2$, COH, CO(alkyl), COOH, COO(alkyl), CONH$_2$, CONH(alkyl), CON(alkyl)$_2$, S(O)(alkyl), S(O)$_2$(alkyl), cycloalkyl, heterocycloalkyl, aryl or heteroaryl;

wherein each cycloalkyl, heterocycloalkyl, aryl or heteroaryl is optionally substituted with one or more halo, alkyl, alkenyl, alkynyl, OH, alkoxy, oxo, $NH_2$, NH(alkyl), N(alkyl)$_2$, COH, CO(alkyl), COOH, COO(alkyl), CONH$_2$, CONH(alkyl), CON(alkyl)$_2$, S(O)(alkyl), or S(O)$_2$(alkyl); and wherein when B is unsubstituted phenyl, then $R^1$ is not hydrogen, Si(CH$_3$)$_3$, CH$_2$Si(CH$_3$)$_3$, methyl, (CH$_2$)NH$_2$, (CH$_2$)$_2$NH$_2$, (CH$_2$)NHSO$_2$CH$_3$, or (CH$_2$)$_n$NHC(O)R$^{1x}$; n is 1 or 2; R$^{1x}$ is methyl, C$_2$ alkene, cyclohexyl, cyclopentyl, tetrahydrofuranyl, furanyl, or pyrrolidinyl, where the alkene, cyclohexyl, cyclopentyl, tetrahydrofuranyl, furanyl, or pyrrolidinyl is optionally substituted with one or two groups independently selected from oxo and cyano.

In some embodiments, the compound is a compound of formula IV:

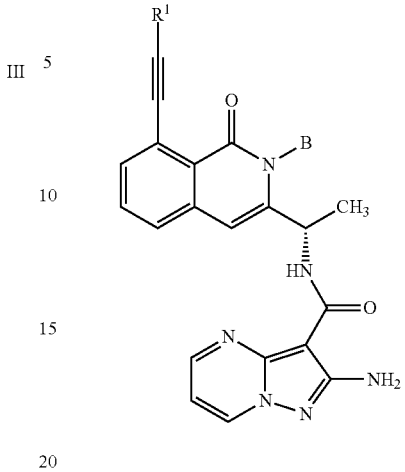

IV wherein $R^1$ and B are as defined herein. In some embodiments, $R^1$ is hydrogen, alkyl, alkenyl, alkynyl, cycloalkyl, heterocycloalkyl, aryl, heteroaryl, —$COR^2$, —$COOR^3$, or —$CONR^4R^5$;

B is hydrogen, alkyl, alkenyl, alkynyl, cycloalkyl, heterocycloalkyl, aryl, heteroaryl, —$COR^2$, —$COOR^3$, —$CONR^4R^5$, or —$Si(R^6)_3$;

wherein $R^2$, $R^3$, $R^4$, $R^5$, and $R^6$ are each, independently, hydrogen, alkyl, alkenyl, alkynyl, cycloalkyl, heterocycloalkyl, aryl, or heteroaryl;

wherein each alkyl, alkenyl, or alkynyl is optionally substituted with one or more halo, OH, alkoxy, $NH_2$, NH(alkyl), N(alkyl)$_2$, COH, CO(alkyl), COOH, COO(alkyl), CONH$_2$, CONH(alkyl), CON(alkyl)$_2$, S(O)(alkyl), S(O)$_2$(alkyl), cycloalkyl, heterocycloalkyl, aryl or heteroaryl; and wherein each cycloalkyl, heterocycloalkyl, aryl or heteroaryl is optionally substituted with one or more halo, alkyl, alkenyl, alkynyl, OH, alkoxy, oxo, $NH_2$, NH(alkyl), N(alkyl)$_2$, COH, CO(alkyl), COOH, COO(alkyl), CONH$_2$, CONH(alkyl), CON(alkyl)$_2$, S(O)(alkyl), or S(O)$_2$(alkyl).

In some embodiments of formula II, III, and IV, B is phenyl substituted with 0, 1, 2, or 3 occurrence(s) of $R^Z$. In some embodiments, B is unsubstituted phenyl. In some embodiments, B is phenyl substituted with 1 or 2 occurrence(s) of $R^Z$. In some embodiments, $R^Z$ is halo or alkyl. In some embodiments, B is methyl, isopropyl, or cyclopropyl. In some embodiments, B is cyclohexyl or optionally substituted alkyl. In some embodiments, B is aryl, heteroaryl, cycloalkyl, or heterocycloalkyl. In some embodiments, B is 5- or 6-membered aryl or 3- to 6-membered cycloalkyl. In some embodiments, B is

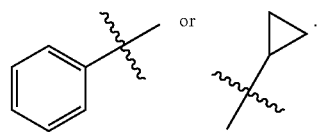

In some embodiments, the compound is a compound of formula V:

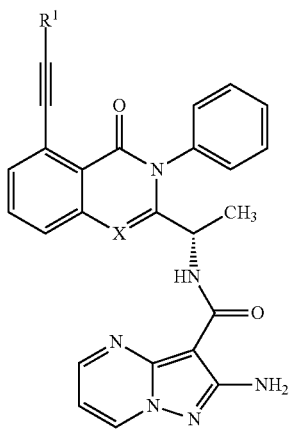

V

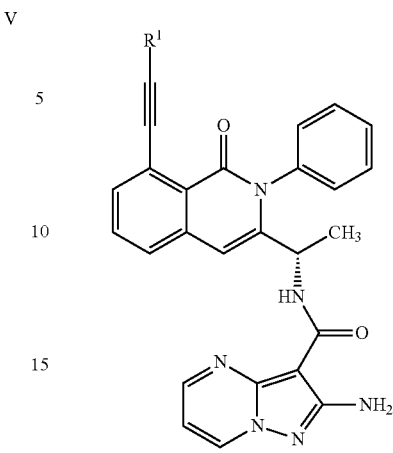

VI wherein $R^1$ and X are as defined herein. In some embodiments, $R^1$ is hydrogen, alkyl, alkenyl, alkynyl, cycloalkyl, heterocycloalkyl, aryl, heteroaryl, —COR$^2$, —COOR$^3$, or —CONR$^4$R$^5$;

wherein $R^2$, $R^3$, $R^4$, and $R^5$ are each, independently, hydrogen, alkyl, alkenyl, alkynyl, cycloalkyl, heterocycloalkyl, aryl, or heteroaryl;

X is CR$^{1a}$ or N;

wherein $R^{1a}$ is hydrogen, halo, alkyl, alkenyl, alkynyl, or CN;

wherein each alkyl, alkenyl, or alkynyl is optionally substituted with one or more halo, OH, alkoxy, NH$_2$, NH(alkyl), N(alkyl)$_2$, COH, CO(alkyl), COOH, COO(alkyl), CONH$_2$, CONH(alkyl), CON(alkyl)$_2$, S(O)(alkyl), S(O)$_2$(alkyl), cycloalkyl, heterocycloalkyl, aryl or heteroaryl;

wherein each cycloalkyl, heterocycloalkyl, aryl or heteroaryl is optionally substituted with one or more halo, alkyl, alkenyl, alkynyl, OH, alkoxy, oxo, NH$_2$, NH(alkyl), N(alkyl)$_2$, COH, CO(alkyl), COOH, COO(alkyl), CONH$_2$, CONH(alkyl), CON(alkyl)$_2$, S(O)(alkyl), or S(O)$_2$(alkyl); and wherein when X is CH, then $R^1$ is not hydrogen, Si(CH$_3$)$_3$, CH$_2$Si(CH$_3$)$_3$, methyl, (CH$_2$)NH$_2$, (CH$_2$)$_2$NH$_2$, (CH$_2$)NHSO$_2$CH$_3$, or (CH$_2$)$_n$NHC(O)R$^{1x}$; n is 1 or 2; R$^{1x}$ is methyl, C$_2$ alkene, cyclohexyl, cyclopentyl, tetrahydrofuranyl, furanyl, or pyrrolidinyl, where the alkene, cyclohexyl, cyclopentyl, tetrahydrofuranyl, furanyl, or pyrrolidinyl is optionally substituted with one or two groups independently selected from oxo and cyano.

In some embodiments, the compound is a compound of formula VI:

wherein $R^1$ is as defined herein. In some embodiments, $R^1$ is hydrogen, alkyl, alkenyl, alkynyl, cycloalkyl, heterocycloalkyl, aryl, heteroaryl, —COR$^2$, —COOR$^3$, or —CONR$^4$R$^5$;

wherein $R^2$, $R^3$, $R^4$, and $R^5$ are each, independently, hydrogen, alkyl, alkenyl, alkynyl, cycloalkyl, heterocycloalkyl, aryl, or heteroaryl;

wherein each alkyl, alkenyl, or alkynyl is optionally substituted with one or more halo, OH, alkoxy, NH$_2$, NH(alkyl), N(alkyl)$_2$, COH, CO(alkyl), COOH, COO(alkyl), CONH$_2$, CONH(alkyl), CON(alkyl)$_2$, S(O)(alkyl), S(O)$_2$(alkyl), cycloalkyl, heterocycloalkyl, aryl or heteroaryl;

wherein each cycloalkyl, heterocycloalkyl, aryl or heteroaryl is optionally substituted with one or more halo, alkyl, alkenyl, alkynyl, OH, alkoxy, oxo, NH$_2$, NH(alkyl), N(alkyl)$_2$, COH, CO(alkyl), COOH, COO(alkyl), CONH$_2$, CONH(alkyl), CON(alkyl)$_2$, S(O)(alkyl), or S(O)$_2$(alkyl); and wherein $R^1$ is not hydrogen, Si(CH$_3$)$_3$, CH$_2$Si(CH$_3$)$_3$, methyl, (CH$_2$)NH$_2$, (CH$_2$)$_2$NH$_2$, (CH$_2$)NHSO$_2$CH$_3$, or (CH$_2$)$_n$NHC(O)R$^{1x}$; n is 1 or 2; R$^{1x}$ is methyl, C$_2$ alkene, cyclohexyl, cyclopentyl, tetrahydrofuranyl, furanyl, or pyrrolidinyl, where the alkene, cyclohexyl, cyclopentyl, tetrahydrofuranyl, furanyl, or pyrrolidinyl is optionally substituted with one or two groups independently selected from oxo and cyano;

In some embodiments, the compound is a compound of formula VII:

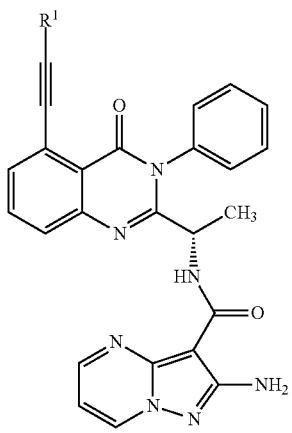

VII wherein $R^1$ is as defined herein. In some embodiments, $R^1$ is hydrogen, alkyl, alkenyl, alkynyl, cycloalkyl, heterocycloalkyl, aryl, heteroaryl, —$COR^2$, —$COOR^3$, or —$CONR^4R^5$;
  wherein $R^2$, $R^3$, $R^4$, and $R^5$ are each, independently, hydrogen, alkyl, alkenyl, alkynyl, cycloalkyl, heterocycloalkyl, aryl, or heteroaryl;
  wherein each alkyl, alkenyl, or alkynyl is optionally substituted with one or more halo, OH, alkoxy, $NH_2$, NH(alkyl), $N(alkyl)_2$, COH, CO(alkyl), COOH, COO(alkyl), $CONH_2$, CONH(alkyl), $CON(alkyl)_2$, S(O)(alkyl), $S(O)_2$(alkyl), cycloalkyl, heterocycloalkyl, aryl or heteroaryl; and
  wherein each cycloalkyl, heterocycloalkyl, aryl or heteroaryl is optionally substituted with one or more halo, alkyl, alkenyl, alkynyl, OH, alkoxy, oxo, $NH_2$, NH(alkyl), $N(alkyl)_2$, COH, CO(alkyl), COOH, COO(alkyl), $CONH_2$, CONH(alkyl), $CON(alkyl)_2$, S(O)(alkyl), or $S(O)_2$(alkyl).

In some embodiments, the compound is a compound of formula VIII:

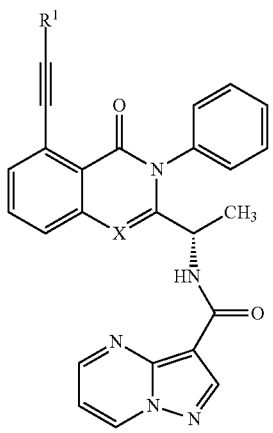

VIII wherein X and $R^1$ are as defined herein. In some embodiments, $R^1$ is hydrogen, alkyl, alkenyl, alkynyl, cycloalkyl, heterocycloalkyl, aryl, heteroaryl, —$COR^2$, —$COOR^3$, or —$CONR^4R^5$;
  wherein $R^2$, $R^3$, $R^4$, and $R^5$ are each, independently, hydrogen, alkyl, alkenyl, alkynyl, cycloalkyl, heterocycloalkyl, aryl, or heteroaryl;

X is $CR^{1a}$ or N;
  wherein $R^{1a}$ is hydrogen, halo, alkyl, alkenyl, alkynyl, or CN;
  wherein each alkyl, alkenyl, or alkynyl is optionally substituted with one or more halo, OH, alkoxy, $NH_2$, NH(alkyl), $N(alkyl)_2$, COH, CO(alkyl), COOH, COO(alkyl), $CONH_2$, CONH(alkyl), $CON(alkyl)_2$, S(O)(alkyl), $S(O)_2$(alkyl), cycloalkyl, heterocycloalkyl, aryl or heteroaryl;
  wherein each cycloalkyl, heterocycloalkyl, aryl or heteroaryl is optionally substituted with one or more halo, alkyl, alkenyl, alkynyl, OH, alkoxy, oxo, $NH_2$, NH(alkyl), $N(alkyl)_2$, COH, CO(alkyl), COOH, COO(alkyl), $CONH_2$, CONH(alkyl), $CON(alkyl)_2$, S(O)(alkyl), or $S(O)_2$(alkyl); and
  wherein when X is CH and $W^d$ is

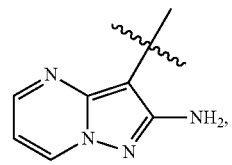 [SMILES: *c1c(N)nn2cccnc12]

then $R^1$ is not hydrogen, $Si(CH_3)_3$, $CH_2Si(CH_3)_3$, methyl, $(CH_2)NH_2$, $(CH_2)_2NH_2$, $(CH_2)NHSO_2CH_3$, or $(CH_2)_nNHC(O)R^{1x}$; n is 1 or 2; $R^{1x}$ is methyl, $C_2$ alkene, cyclohexyl, cyclopentyl, tetrahydrofuranyl, furanyl, or pyrrolidinyl, where the alkene, cyclohexyl, cyclopentyl, tetrahydrofuranyl, furanyl, or pyrrolidinyl is optionally substituted with one or two groups independently selected from oxo and cyano.

In some embodiments of formulas II-VIII, $R^1$ is branched alkyl, 5- or 6-membered aryl, 5- or 6-membered heteroaryl, 5- or 6-membered cycloalkyl, or 5- or 6-membered heterocycloalkyl,

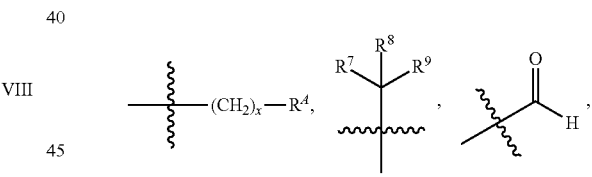

cyclopropyl, or methyl, wherein $R^A$ is OH, alkoxy, cycloalkyl, heterocycloalkyl, aryl, or heteroaryl;
x is 1, 2, 3, 4, 5, or 6;
$R^7$, $R^8$, and $R^9$ are each, independently, hydrogen, OH, alkoxy, $NH_2$, NH(alkyl), $N(alkyl)_2$, alkyl, alkenyl, alkynyl, cycloalkyl, heterocycloalkyl, aryl, or heteroaryl.

In some embodiments, $R^A$ is hydroxyl, alkoxy or heterocycloalkyl. In some embodiments, $R^7$, $R^8$, and $R^9$ are, independently, alkyl of 1-4 carbons, amino, hydroxyl, or alkoxy of 1-4 carbons.

In certain embodiments, $R^1$ is a 5- to 10-membered heteroaryl. In certain embodiments, $R^1$ is a 5- to 6-membered heteroaryl. In certain embodiments, $R^1$ is a 6-membered heteroaryl. In certain embodiments, $R^1$ is a pyridinyl. In certain embodiments, $R^1$ is a pyrimidinyl. In certain embodiments, $R^1$ is a 5-membered heteroaryl. In certain embodiments, $R^1$ is a thiazolyl. In certain embodiments, $R^1$ is a pyrazolyl. In certain embodiments, $R^1$ is an imidazolyl. In certain embodiments, the heteroaryl is substituted with one or more alkyl.

In some embodiments of formulas II-VIII, R¹ is: methyl,

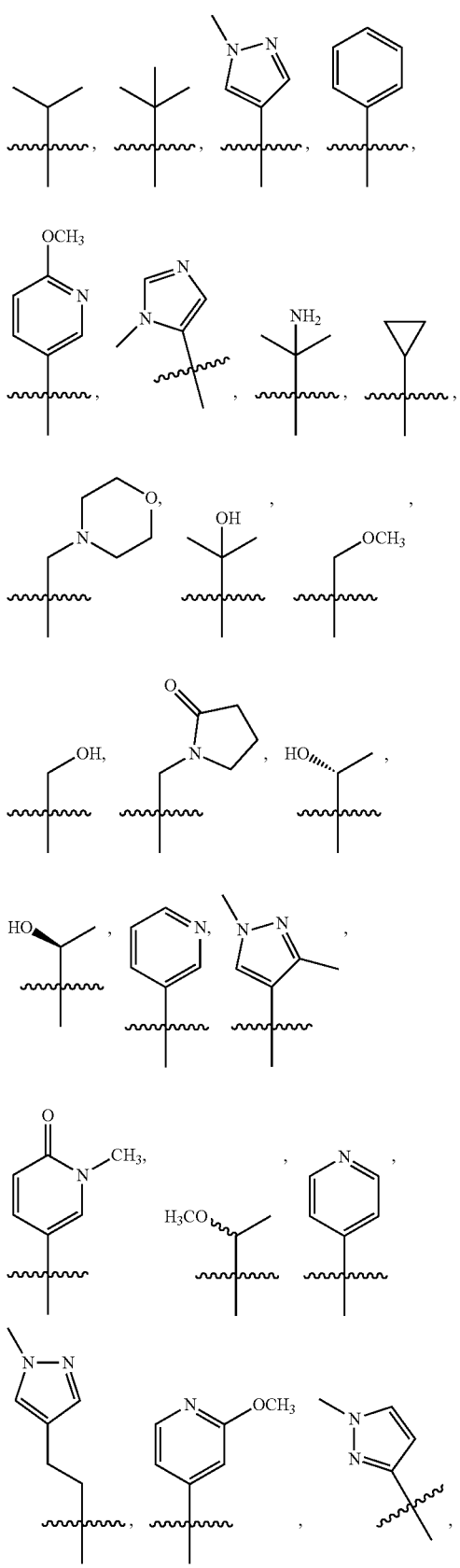

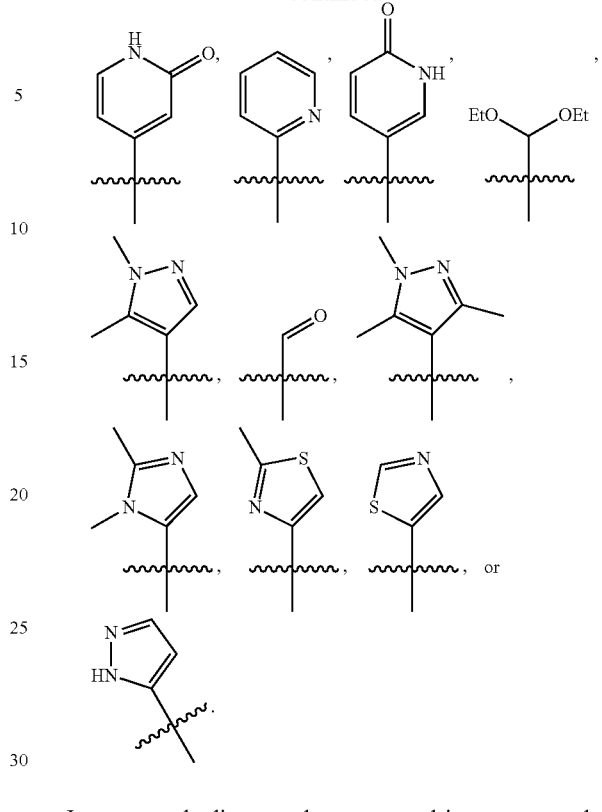

In some embodiments, the compound is a compound of formula IX:

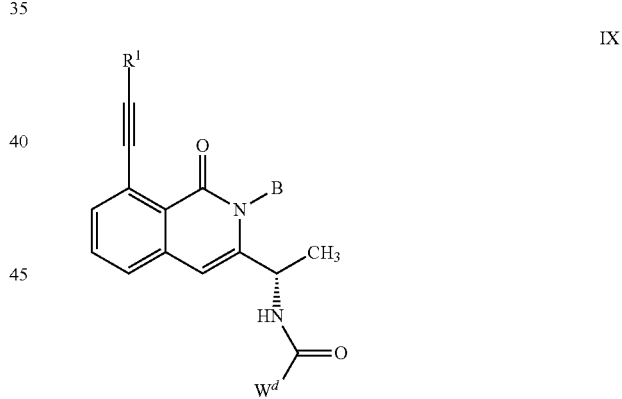

IX wherein R¹, B, and $W^d$ are as defined herein. In some embodiments, R¹ is hydrogen, alkyl, alkenyl, alkynyl, cycloalkyl, heterocycloalkyl, aryl, heteroaryl, —COR², —COOR³, or —CONR⁴R⁵;

B is hydrogen, alkyl, alkenyl, alkynyl, cycloalkyl, heterocycloalkyl, aryl, heteroaryl, —COR², —COOR³, —CONR⁴R⁵, or —Si(R⁶)₃;

wherein R², R³, R⁴, R⁵, and R⁶ are each, independently, hydrogen, alkyl, alkenyl, alkynyl, cycloalkyl, heterocycloalkyl, aryl, or heteroaryl;

$W^d$ is heteroaryl, cycloalkyl, heterocycloalkyl, or aryl; and wherein each alkyl, alkenyl, or alkynyl is optionally substituted with one or more halo, OH, alkoxy, NH₂, NH(alkyl), N(alkyl)₂, COH, CO(alkyl), COOH, COO(alkyl), CONH₂, CONH(alkyl), CON(alkyl)₂, S(O)(alkyl), S(O)₂(alkyl), cycloalkyl, heterocycloalkyl, aryl or heteroaryl;

wherein each cycloalkyl, heterocycloalkyl, aryl or heteroaryl is optionally substituted with one or more halo, alkyl, alkenyl, alkynyl, OH, alkoxy, oxo, $NH_2$, NH(alkyl), N(alkyl)$_2$, COH, CO(alkyl), COOH, COO(alkyl), $CONH_2$, CONH(alkyl), CON(alkyl)$_2$, S(O)(alkyl), S(O)$_2$(alkyl); and wherein when B is unsubstituted phenyl and $W^d$ is

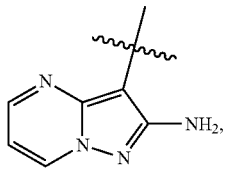 [SMILES: *c1c(N)nn2cccnc12]

then $R^1$ is not hydrogen, Si(CH$_3$)$_3$, CH$_2$Si(CH$_3$)$_3$, methyl, (CH$_2$)NH$_2$, (CH$_2$)$_2$NH$_2$, (CH$_2$)NHSO$_2$CH$_3$, or (CH$_2$)$_n$NHC(O)R$^{1x}$; n is 1 or 2; R$^{1x}$ is methyl, C$_2$ alkene, cyclohexyl, cyclopentyl, tetrahydrofuranyl, furanyl, or pyrrolidinyl, where the alkene, cyclohexyl, cyclopentyl, tetrahydrofuranyl, furanyl, or pyrrolidinyl is optionally substituted with one or two groups independently selected from oxo and cyano.

In some embodiments, the compound is a compound of formula X:

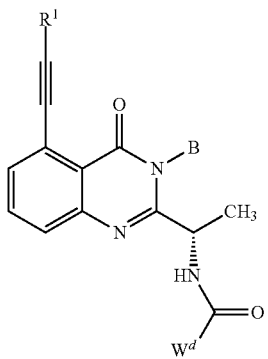

X wherein $R^1$, B, and $W^d$ are as defined herein. In some embodiments, $R^1$ is hydrogen, alkyl, alkenyl, alkynyl, cycloalkyl, heterocycloalkyl, aryl, heteroaryl, —COR$^2$, —COOR$^3$, or —CONR$^4$R$^5$;

B is hydrogen, alkyl, alkenyl, alkynyl, cycloalkyl, heterocycloalkyl, aryl, heteroaryl, —COR$^2$, —COOR$^3$, —CONR$^4$R$^5$, or —Si(R$^6$)$_3$;

wherein R$^2$, R$^3$, R$^4$, R$^5$, and R$^6$ are each, independently, hydrogen, alkyl, alkenyl, alkynyl, cycloalkyl, heterocycloalkyl, aryl, or heteroaryl;

$W^d$ is heteroaryl, cycloalkyl, heterocycloalkyl, or aryl; and
wherein each alkyl, alkenyl, or alkynyl is optionally substituted with one or more halo, OH, alkoxy, NH$_2$, NH(alkyl), N(alkyl)$_2$, COH, CO(alkyl), COOH, COO(alkyl), CONH$_2$, CONH(alkyl), CON(alkyl)$_2$, S(O)(alkyl), S(O)$_2$(alkyl), cycloalkyl, heterocycloalkyl, aryl or heteroaryl; and wherein each cycloalkyl, heterocycloalkyl, aryl or heteroaryl is optionally substituted with one or more halo, alkyl, alkenyl, alkynyl, OH, alkoxy, oxo, NH$_2$, NH(alkyl), N(alkyl)$_2$, COH, CO(alkyl), COOH, COO(alkyl), CONH$_2$, CONH(alkyl), CON(alkyl)$_2$, S(O)(alkyl), or S(O)$_2$(alkyl).

In some embodiments of formulas I-X, $R^1$ is

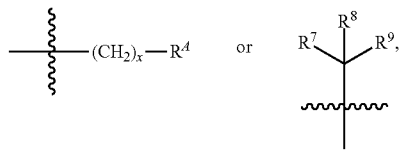

wherein $R^A$ and $R^7$-$R^9$ are as defined herein.

In certain embodiments, $R^1$ is a 5- to 10-membered heteroaryl. In certain embodiments, $R^1$ is a 5- to 6-membered heteroaryl. In certain embodiments, $R^1$ is a 6-membered heteroaryl. In certain embodiments, $R^1$ is a pyridinyl. In certain embodiments, $R^1$ is a pyrimidinyl. In certain embodiments, $R^1$ is a 5-membered heteroaryl. In certain embodiments, $R^1$ is a thiazolyl. In certain embodiments, $R^1$ is a pyrazolyl. In certain embodiments, $R^1$ is an imidazolyl. In certain embodiments, the heteroaryl is substituted with one or more alkyl.

In some embodiments, the compound is a compound of formula XI:

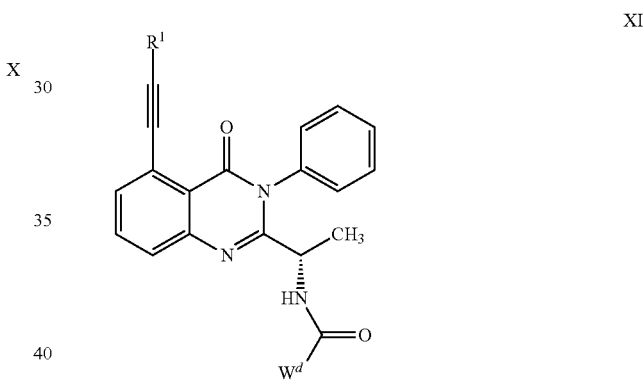

XI wherein $R^1$ and $W^d$ are as defined herein. In some embodiments, $R^1$ is hydrogen, alkyl, alkenyl, alkynyl, cycloalkyl, heterocycloalkyl, aryl, heteroaryl, —COR$^2$, —COOR$^3$, or —CONR$^4$R$^5$;

wherein R$^2$, R$^3$, R$^4$, and R$^5$ are each, independently, hydrogen, alkyl, alkenyl, alkynyl, cycloalkyl, heterocycloalkyl, aryl, or heteroaryl;

$W^d$ is heteroaryl, cycloalkyl, heterocycloalkyl, or aryl; and
wherein each alkyl, alkenyl, or alkynyl is optionally substituted with one or more halo, OH, alkoxy, NH$_2$, NH(alkyl), N(alkyl)$_2$, COH, CO(alkyl), COOH, COO(alkyl), CONH$_2$, CONH(alkyl), CON(alkyl)$_2$, S(O)(alkyl), S(O)$_2$(alkyl), cycloalkyl, heterocycloalkyl, aryl or heteroaryl; and wherein each cycloalkyl, heterocycloalkyl, aryl or heteroaryl is optionally substituted with one or more halo, alkyl, alkenyl, alkynyl, OH, alkoxy, oxo, NH$_2$, NH(alkyl), N(alkyl)$_2$, COH, CO(alkyl), COOH, COO(alkyl), CONH$_2$, CONH(alkyl), CON(alkyl)$_2$, S(O)(alkyl), or S(O)$_2$(alkyl).

In some embodiments, the compound is a compound of formula XII:

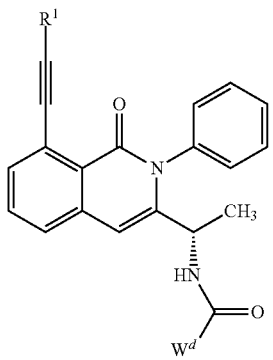

XII wherein $R^1$ and $W^d$ are as defined herein. In some embodiments, $R^1$ is hydrogen, alkyl, alkenyl, alkynyl, cycloalkyl, heterocycloalkyl, aryl, heteroaryl, —$COR^2$, —$COOR^3$, or —$CONR^4R^5$;

wherein $R^2$, $R^3$, $R^4$, and $R^5$ are each, independently, hydrogen, alkyl, alkenyl, alkynyl, cycloalkyl, heterocycloalkyl, aryl, or heteroaryl;

$W^d$ is heteroaryl, cycloalkyl, heterocycloalkyl, or aryl; and wherein each alkyl, alkenyl, or alkynyl is optionally substituted with one or more halo, OH, alkoxy, $NH_2$, NH(alkyl), N(alkyl)$_2$, COH, CO(alkyl), COOH, COO(alkyl), $CONH_2$, CONH(alkyl), CON(alkyl)$_2$, S(O)(alkyl), S(O)$_2$(alkyl), cycloalkyl, heterocycloalkyl, aryl or heteroaryl;

wherein each cycloalkyl, heterocycloalkyl, aryl or heteroaryl is optionally substituted with one or more halo, alkyl, alkenyl, alkynyl, OH, alkoxy, oxo, $NH_2$, NH(alkyl), N(alkyl)$_2$, COH, CO(alkyl), COOH, COO(alkyl), $CONH_2$, CONH(alkyl), CON(alkyl)$_2$, S(O)(alkyl), or S(O)$_2$(alkyl); and wherein when $W^d$ is

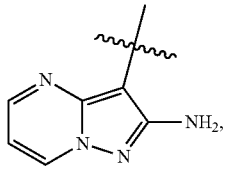 [SMILES: *c1c(N)nn2cccnc12]

then $R^1$ is not hydrogen, Si(CH$_3$)$_3$, CH$_2$Si(CH$_3$)$_3$, methyl, (CH$_2$)NH$_2$, (CH$_2$)$_2$NH$_2$, (CH$_2$)NHSO$_2$CH$_3$, or (CH$_2$)$_n$NHC(O)R$^{1x}$; n is 1 or 2; R$^{1x}$ is methyl, C$_2$ alkene, cyclohexyl, cyclopentyl, tetrahydrofuranyl, furanyl, or pyrrolidinyl, where the alkene, cyclohexyl, cyclopentyl, tetrahydrofuranyl, furanyl, or pyrrolidinyl is optionally substituted with one or two groups independently selected from oxo and cyano In some embodiments, the compound is a compound of formula XIII,

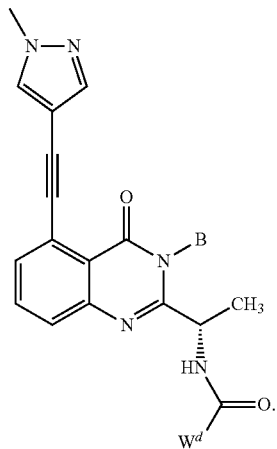

XIII wherein B and $W^d$ are as defined herein. In some embodiments, B is hydrogen, alkyl, alkenyl, alkynyl, cycloalkyl, heterocycloalkyl, aryl, heteroaryl, —$COR^2$, —$COOR^3$, —$CONR^4R^5$, or —Si(R$^6$)$_3$;

wherein $R^2$, $R^3$, $R^4$, $R^5$, and $R^6$ are each, independently, hydrogen, alkyl, alkenyl, alkynyl, cycloalkyl, heterocycloalkyl, aryl, or heteroaryl;

$W^d$ is heteroaryl, cycloalkyl, heterocycloalkyl, or aryl; and wherein each alkyl, alkenyl, or alkynyl is optionally substituted with one or more halo, OH, alkoxy, $NH_2$, NH(alkyl), N(alkyl)$_2$, COH, CO(alkyl), COOH, COO(alkyl), $CONH_2$, CONH(alkyl), CON(alkyl)$_2$, S(O)(alkyl), S(O)$_2$(alkyl), cycloalkyl, heterocycloalkyl, aryl or heteroaryl; and wherein each cycloalkyl, heterocycloalkyl, aryl or heteroaryl is optionally substituted with one or more halo, alkyl, alkenyl, alkynyl, OH, alkoxy, oxo, $NH_2$, NH(alkyl), N(alkyl)$_2$, COH, CO(alkyl), COOH, COO(alkyl), $CONH_2$, CONH(alkyl), CON(alkyl)$_2$, S(O)(alkyl), or S(O)$_2$(alkyl).

In some embodiments, the compound is a compound of formula XIV:

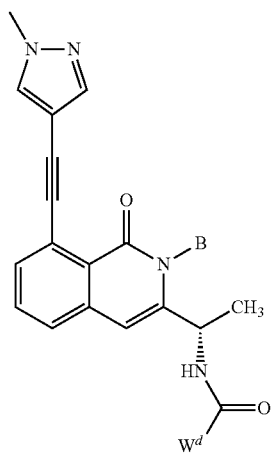

XIV wherein B and $W^d$ are as defined herein. In some embodiments, B is hydrogen, alkyl, alkenyl, alkynyl, cycloalkyl, heterocycloalkyl, aryl, heteroaryl, —$COR^2$, —$COOR^3$, —$CONR^4R^5$, or —Si(R$^6$)$_3$;

wherein $R^2$, $R^3$, $R^4$, $R^5$, and $R^6$ are each, independently, hydrogen, alkyl, alkenyl, alkynyl, cycloalkyl, heterocycloalkyl, aryl, or heteroaryl;

$W^d$ is heteroaryl, cycloalkyl, heterocycloalkyl, or aryl; and wherein each alkyl, alkenyl, or alkynyl is optionally substituted with one or more halo, OH, alkoxy, $NH_2$, NH(alkyl), N(alkyl)$_2$, COH, CO(alkyl), COOH, COO(alkyl), $CONH_2$, CONH(alkyl), CON(alkyl)$_2$, S(O)(alkyl), S(O)$_2$(alkyl), cycloalkyl, heterocycloalkyl, aryl or heteroaryl; and wherein each cycloalkyl, heterocycloalkyl, aryl or heteroaryl is optionally substituted with one or more halo, alkyl, alkenyl, alkynyl, OH, alkoxy, oxo, $NH_2$, NH(alkyl), N(alkyl)$_2$, COH, CO(alkyl), COOH, COO(alkyl), $CONH_2$, CONH(alkyl), CON(alkyl)$_2$, S(O)(alkyl), or S(O)$_2$(alkyl).

In some embodiments, the compound is a compound of formula XV:

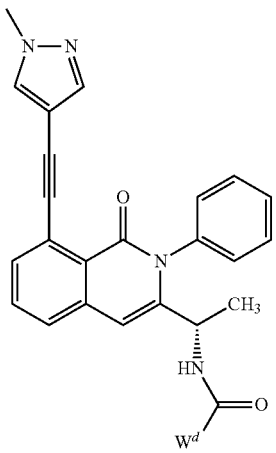

XV wherein $W^d$ is as defined herein. In some embodiments, $W^d$ is cycloalkyl, heterocycloalkyl, aryl, or heteroaryl; and wherein each cycloalkyl, heterocycloalkyl, aryl or heteroaryl is optionally substituted with one or more halo, alkyl, alkenyl, alkynyl, OH, alkoxy, oxo, $NH_2$, NH(alkyl), N(alkyl)$_2$, COH, CO(alkyl), COOH, COO(alkyl), $CONH_2$, CONH(alkyl), or CON(alkyl)$_2$.

In some embodiments, the compound is a compound of formula XVI:

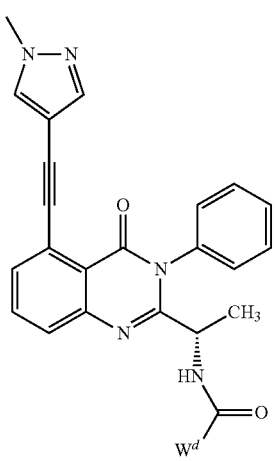

XVI wherein $W^d$ is defined herein. In some embodiments, $W^d$ is cycloalkyl, heterocycloalkyl, aryl, or heteroaryl; and wherein each cycloalkyl, heterocycloalkyl, aryl or heteroaryl is optionally substituted with one or more halo, alkyl, alkenyl, alkynyl, OH, alkoxy, oxo, $NH_2$, NH(alkyl), N(alkyl)$_2$, COH, CO(alkyl), COOH, COO(alkyl), $CONH_2$, CONH(alkyl), or CON(alkyl)$_2$.

In some embodiments of formulas IX-XVI, $W^d$ is

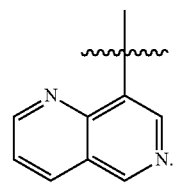 [SMILES: *c1cncc2cccnc12]

In some embodiments of formulas IX-XVI, $W^d$ is

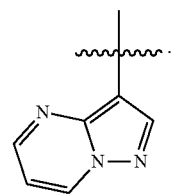

In some embodiments of formulas IX-XVI, $W^d$ is

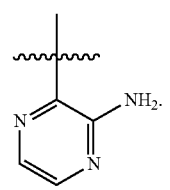 [SMILES: *c1nccnc1N]

In some embodiments of formulas IX-XVI, $W^d$ is

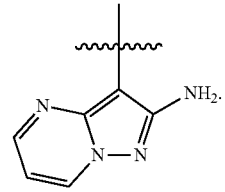 [SMILES: *c1c(N)nn2cccnc12]

In some embodiments of formulas I-XII, $R^1$ is not hydrogen. In some embodiments of formulas I-XII, $R^1$ is not linear alkyl or hydrogen. In some embodiments of formulas I-XII, $R^1$ is not linear $C_1$-$C_3$ alkyl or hydrogen. In some embodiments of formulas I-XII, $R^1$ is not methyl or hydrogen.

In certain embodiments, provided herein are compounds of Formula (A):

Formula (A)

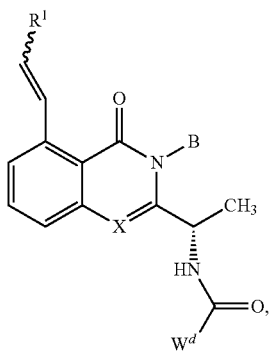

or a pharmaceutically acceptable form thereof, wherein $R^1$, B, $W^d$ and X are as defined herein. In certain embodiments, $R^1$ is alkyl or heteroaryl. In certain embodiments, $R^1$ is heteroaryl. In certain embodiments, $R^1$ is alkyl. In certain embodiments, B is phenyl. In certain embodiments, X is CH or N. In certain embodiments, X is CH.
In certain embodiments, X is N. In certain embodiments, $W^d$ is

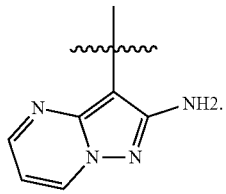 [SMILES: *c1c(N)nn2cccnc12]

In certain embodiments, the compound of formula (A"), (A'), or (A) is a mixture of trans and cis (e.g., where $R^1$ is trans or cis). In certain embodiments, $R^1$ is trans. In certain embodiments, $R^1$ is cis. In certain embodiments, the percentage of trans to cis is about 50%, greater than about 50%, greater than about 55%, greater than about 60%, greater than about 65%, greater than about 70%, greater than about 75%, greater than about 80%, greater than about 85%, greater than about 90%, greater than about 95%, greater than about 96%, greater than about 97%, greater than about 98%, or greater than about 99%.

In one embodiment, provided herein is a compound of Formula XVII:

Formula XVII

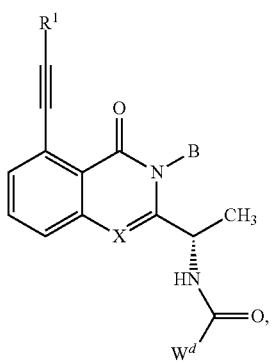

wherein:
$R^1$ and B are each, independently, linear or branched alkyl, alkenyl, alkynyl, cycloalkyl, heterocycloalkyl, aryl, heteroaryl, —$COR^2$, —$COOR^3$, —$CONR^4R^5$, or —$Si(R^6)_3$;
  wherein $R^2$, $R^3$, $R^4$, $R^5$, and $R^6$ are each, independently, hydrogen, alkyl, alkenyl, alkynyl, cycloalkyl, heterocycloalkyl, aryl, or heteroaryl;
$W^d$ is heteroaryl, cycloalkyl, heterocycloalkyl, or aryl; and
X is CH or N;
  wherein when X is CH, B is unsubstituted phenyl, $W^d$ is

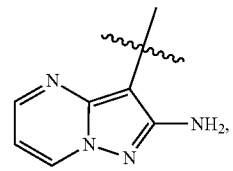 [SMILES: *c1c(N)nn2cccnc12]

and $R^1$ is a linear alkyl, then the linear alkyl contains at least three consecutively bonded carbons;
wherein when X is CH, B is unsubstituted phenyl, and $W^d$ is

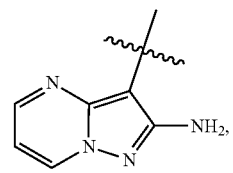 [SMILES: *c1c(N)nn2cccnc12]

then $R^1$ is not $Si(CH_3)_3$;
or a pharmaceutically acceptable form thereof.

In some embodiments of Formula XVII, $R^1$ is branched alkyl, 5- or 6-membered aryl, 5- or 6-membered heteroaryl, 5- or 6-membered cycloalkyl, or 5- to 6-membered heterocycloalkyl,

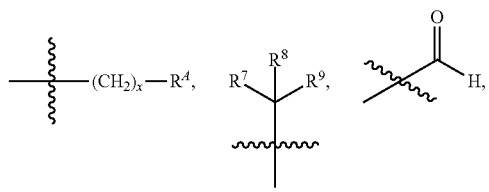

cyclopropyl, or methyl,
wherein $R^A$ is hydroxyl, alkoxy, cycloalkyl, heterocycloalkyl, aryl, or heteroaryl;
x is 1, 2, 3, 4, 5 or 6;
$R^7$, $R^8$, and $R^9$ are each, independently, hydrogen, hydroxyl, alkoxy, amino, alkyl, alkenyl, alkynyl, cycloalkyl, heterocycloalkyl, aryl, or heteroaryl, wherein at least two of $R^7$, $R^8$, and $R^9$ are not hydrogen.

In some embodiments of Formula XVII, $R^A$ is hydroxyl, alkoxy or heterocycloalkyl.

In some embodiments of Formula XVII, $R^7$, $R^8$, and $R^9$ are, independently, alkyl of 1-4 carbons, amino, hydroxyl, or alkoxy of 1-4 carbons.

In some embodiments of Formula XVII, $R_1$ is: methyl,

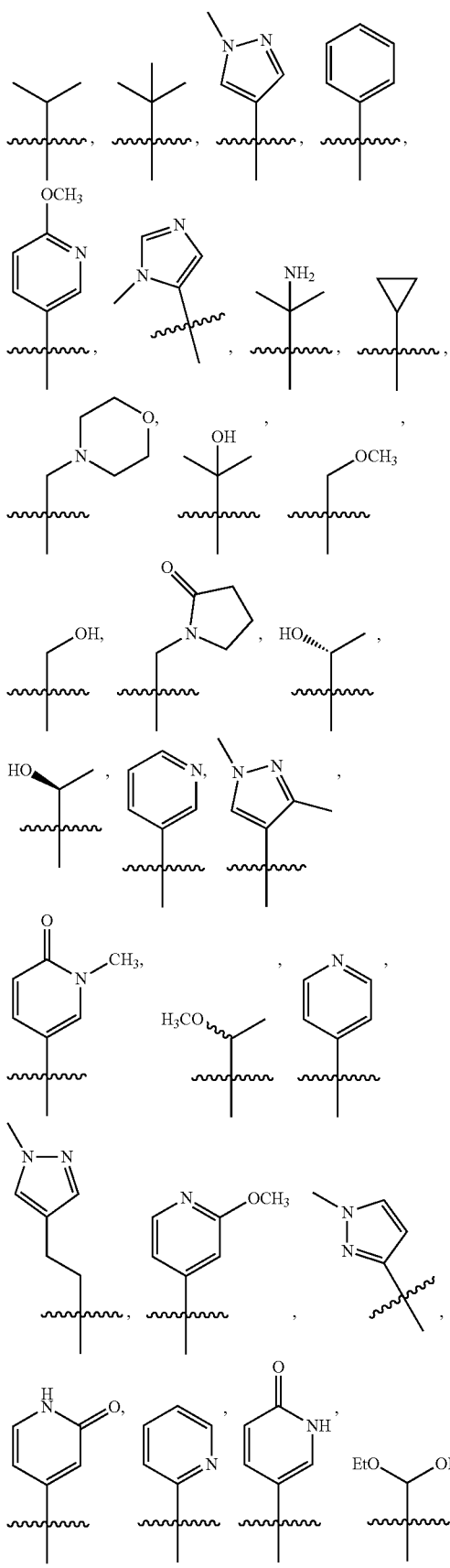

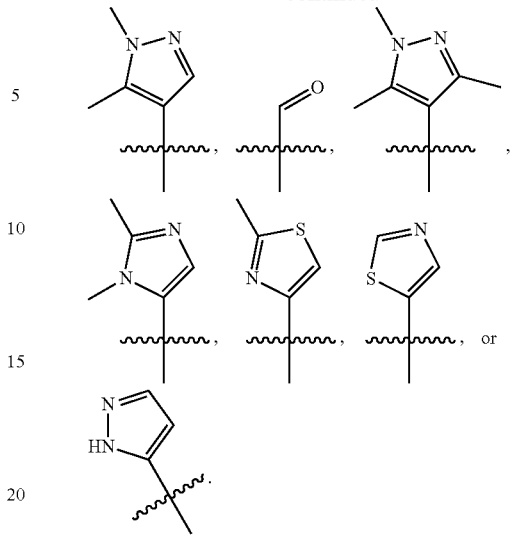

In some embodiments of Formula XVII, B is phenyl substituted with 0, 1, 2, or 3 occurrence(s) of $R^Z$. In some embodiments, B is unsubstituted phenyl. In some embodiments, B is phenyl substituted with 1 or 2 occurrence(s) of $R^Z$. In some embodiments, $R^Z$ is halo or alkyl. In some embodiments, B is methyl, isopropyl, or cyclopropyl. In some embodiments, B is cyclohexyl or optionally substituted alkyl.

In some embodiments of Formula XVII, B is aryl, heteroaryl, cycloalkyl, or heterocycloalkyl.

In some embodiments of Formula XVII, B is 5- or 6-membered aryl or 3-6-membered cycloalkyl.

In some embodiments of Formula XVII, B is

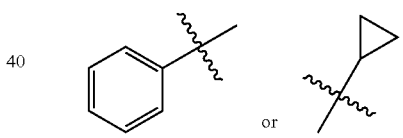

In some embodiments of Formula XVII, $W^d$ is

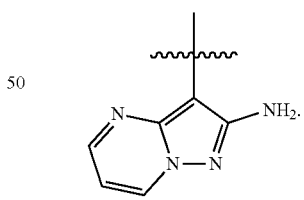

In some embodiments of Formula XVII, $W^d$ is

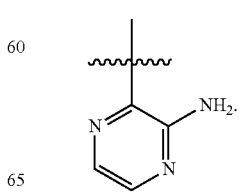

In some embodiments of Formula XVII, $W^d$ is

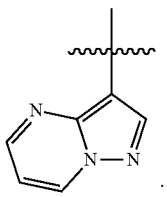 [SMILES: *c1cnn2cccnc12]

In some embodiments of Formula XVII, $W^d$ is

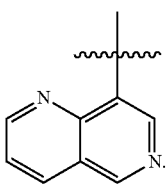

In some embodiments of Formula XVII, X is CH. In some embodiments, X is N.

In some embodiments of Formula XVII, when X is CH, B is unsubstituted phenyl; $W^d$ is

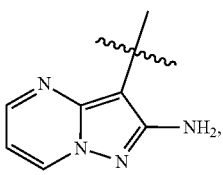 [SMILES: *c1c(N)nn2cccnc12]

and $R^1$ is a linear alkyl, the linear alkyl contains at least four consecutively bonded carbons.

In some embodiments of Formula XVII, the compounds have the following formula:

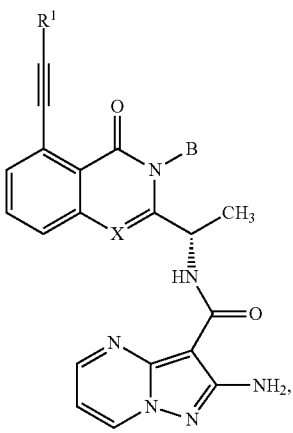

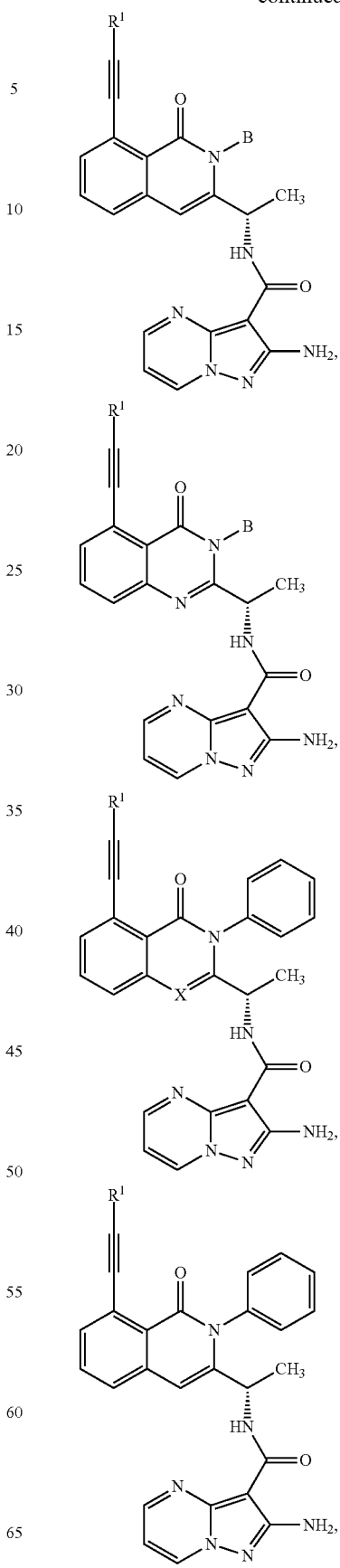

133
-continued
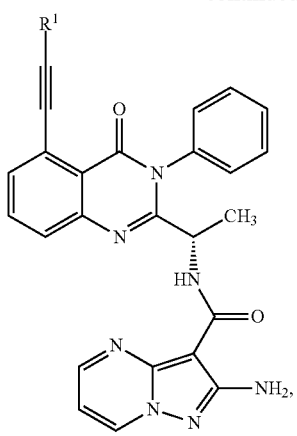
,
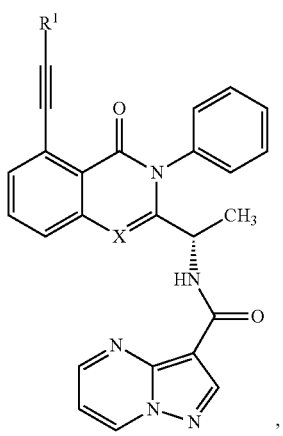
,
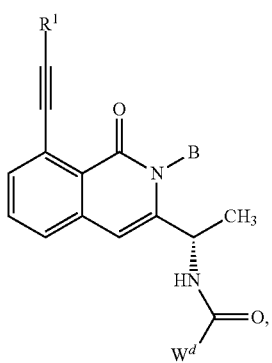
,
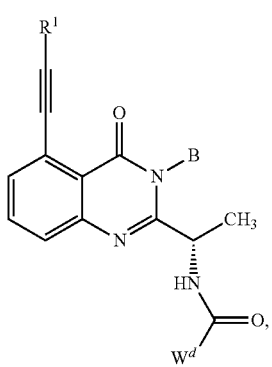
,
134
-continued
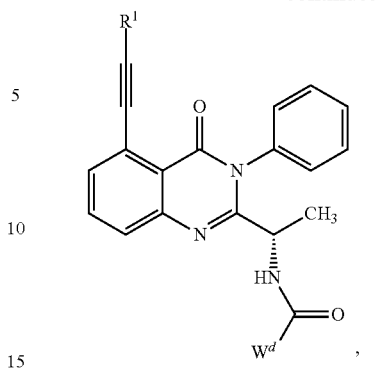
,
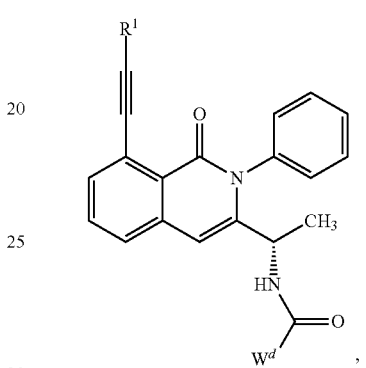
,
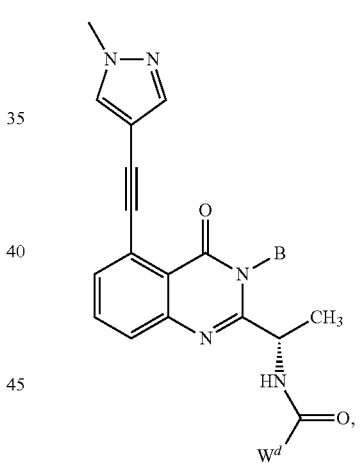
,
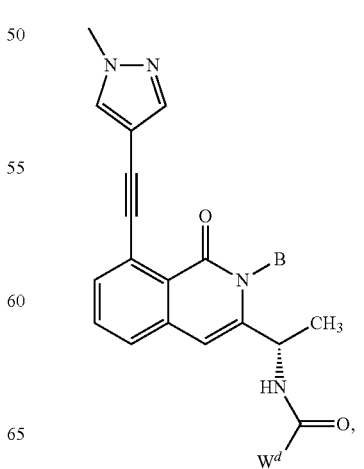
,

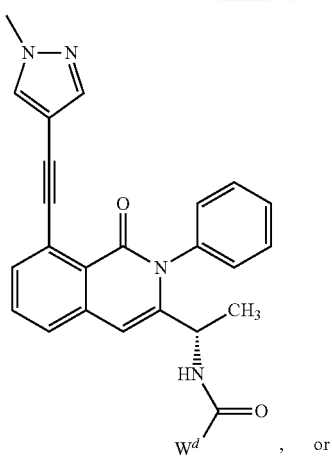
, or
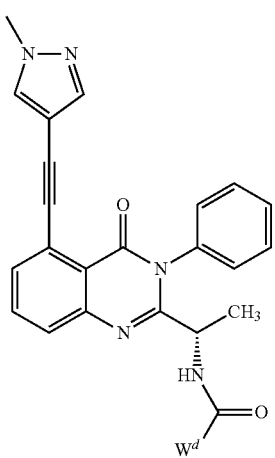
.
In some embodiments of Formula XVII, the compound has the following formula:
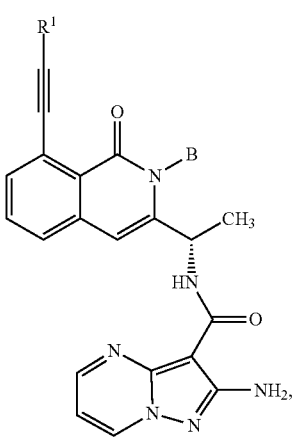
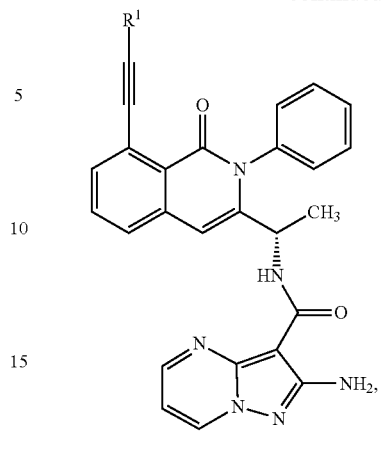
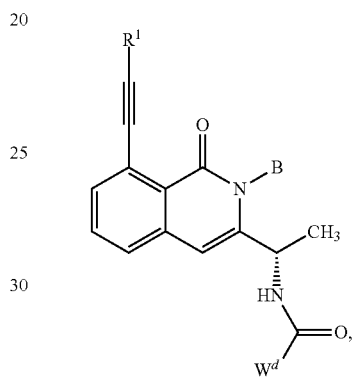
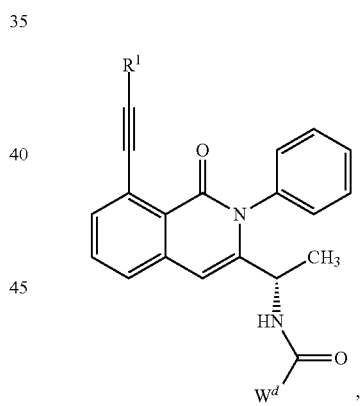
,
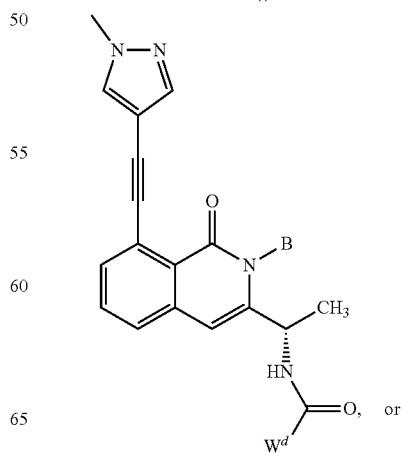
, or

137

-continued

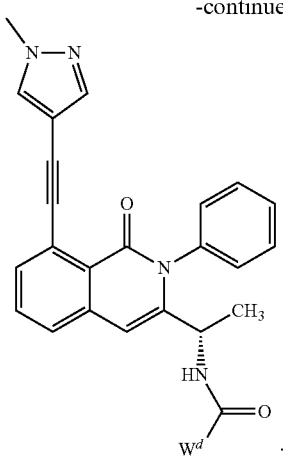

In some embodiments, R¹ is a heteroaryl, aryl, cycloalkyl, heterocycloalkyl. In certain embodiments, R¹ is a heteroaryl. In certain embodiments, R¹ is a heteroaryl substituted with a ionic or polar group. In some embodiments, an ionic or polar group is a the part of a compound increases the solubility, stability, or metabolism or reduce the off-target effect of the compound. In some embodiments, provided herein is a compound of the following formulae

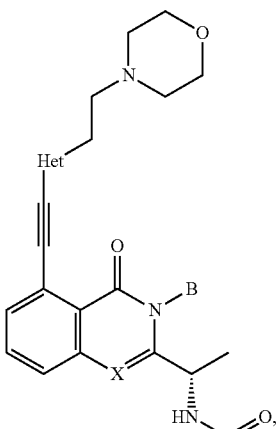

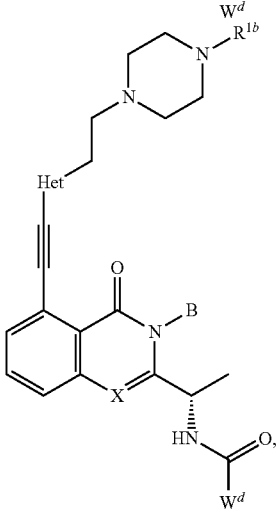

138

-continued

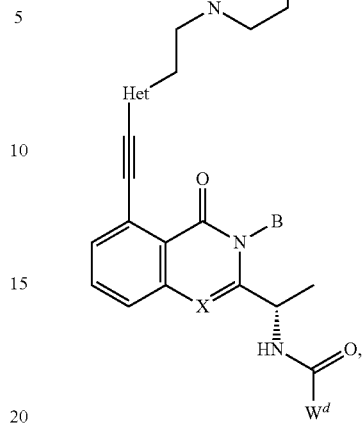

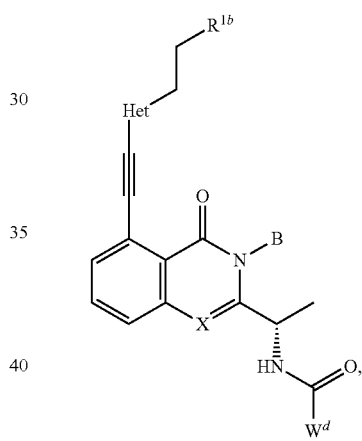

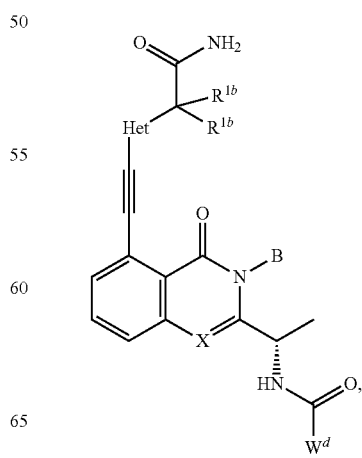

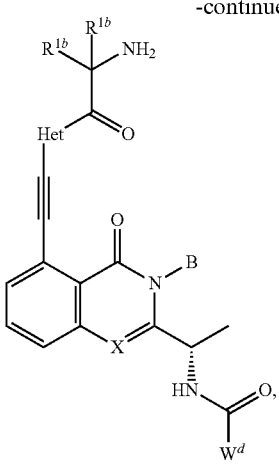

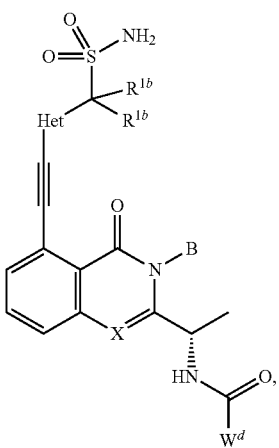

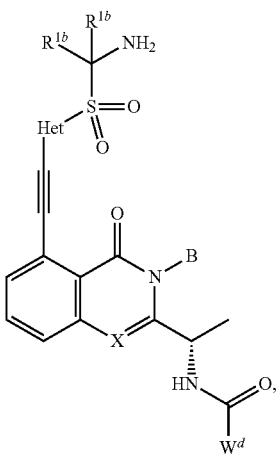

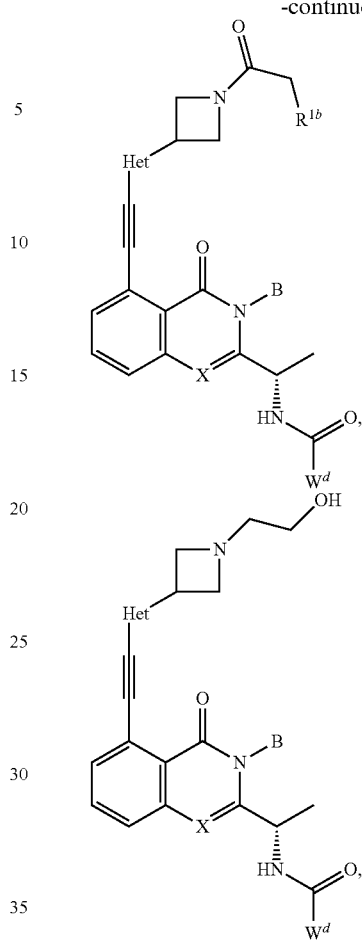

wherein X, B, and $W^d$ are as defined herein;
Het is heteroaryl; and
$R^{1b}$ is halo, haloalkyl, alkyl, alkenyl, alkynyl, OH, alkoxy, oxo, $NH_2$, NH(alkyl), N(alkyl)$_2$, COH, CO(alkyl), COOH, COO(alkyl), $CONH_2$, CONH(alkyl), CON(alkyl)$_2$, S(O)(alkyl), S(O)$_2$(alkyl), S(O)$_2NH_2$, S(O)$_2$NH(alkyl), or S(O)$_2$N(alkyl)$_2$.

In certain embodiments, alkyl is $C_1$-$C_8$ alkyl. In certain embodiments, alkyl is $C_1$-$C_6$ alkyl. In another embodiment, alkyl is $C_1$-$C_3$ alkyl. In certain embodiments, alkenyl is $C_2$-$C_8$ alkenyl. In certain embodiments, alkenyl is $C_2$-$C_6$ alkenyl. In another embodiment, alkenyl is $C_2$-$C_3$ alkenyl. In certain embodiments, alkynyl is $C_2$-$C_8$ alkynyl. In certain embodiments, alkynyl is $C_2$-$C_6$ alkynyl. In another embodiment, alkynyl is $C_2$-$C_3$ alkynyl.

In certain embodiments, cycloalkyl is $C_3$-$C_8$ cycloalkyl. In certain embodiments, cycloalkyl is $C_3$-$C_6$ cycloalkyl. In certain embodiments, cycloalkyl is $C_3$-$C_4$ cycloalkyl. In certain embodiments, heterocycloalkyl is a 3 to 14 membered saturated or partially saturated cycle containing one or more heteroatoms selected from a group consisting of N, O, and S. In certain embodiments, heterocycloalkyl is 3 to 10 membered. In another embodiment, heterocycloalkyl is 3 to 6 membered. In another embodiment, heterocycloalkyl is 6 membered. In certain embodiments, aryl is a $C_6$-$C_{14}$ aromatic cycle. In certain embodiments, aryl is $C_6$-$C_{10}$. In another embodiment, aryl is $C_6$. In certain embodiments, heteroaryl is a 5 to 14 membered aromatic cycle containing one or more heteroatoms selected from a group consisting of N, O, and S. In certain embodiments, heteroaryl is 5 to 10 membered. In another embodiment, heteroaryl is 5 to 6 membered. In another embodiment, heteroaryl is 6 membered.
In certain embodiments, the compound provided herein is not a compound selected from:
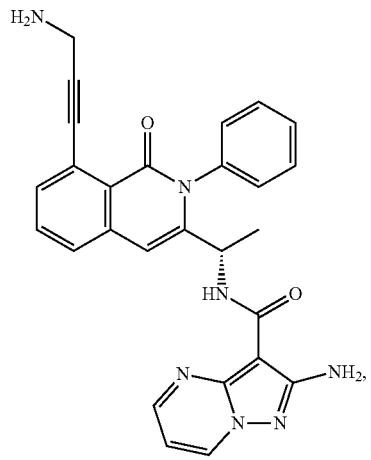
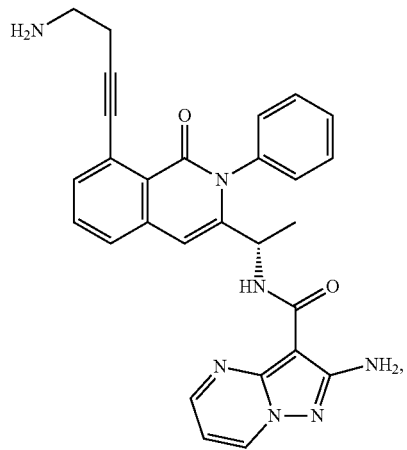
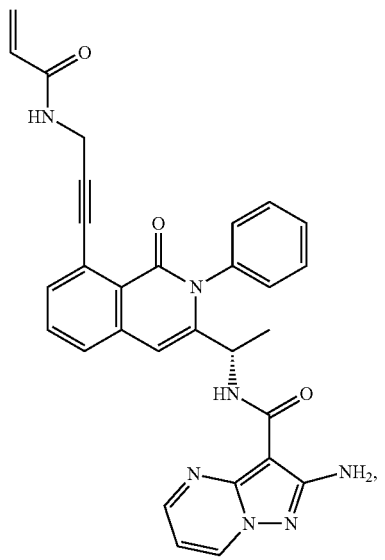
-continued
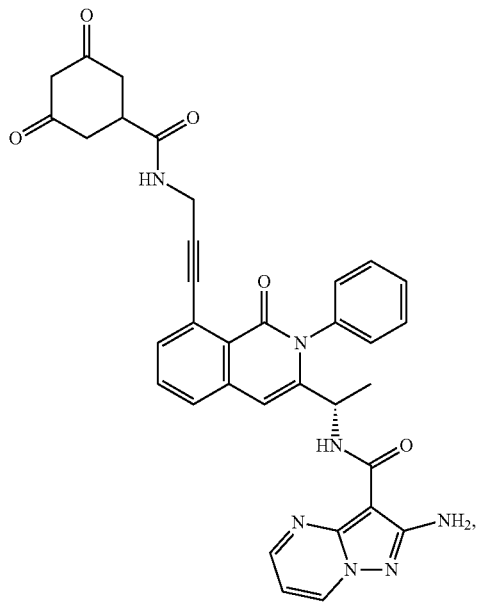
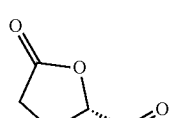

143
-continued
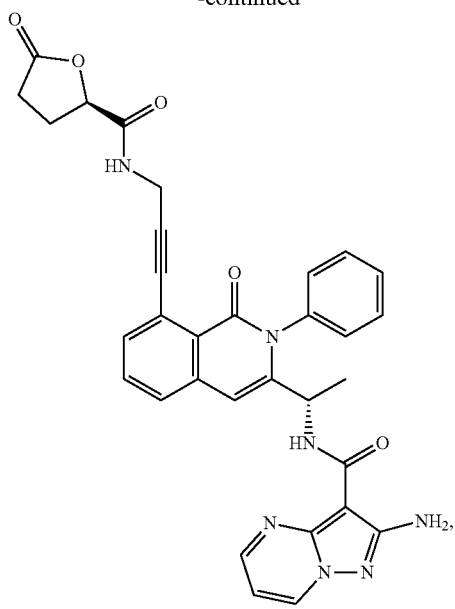
144
-continued
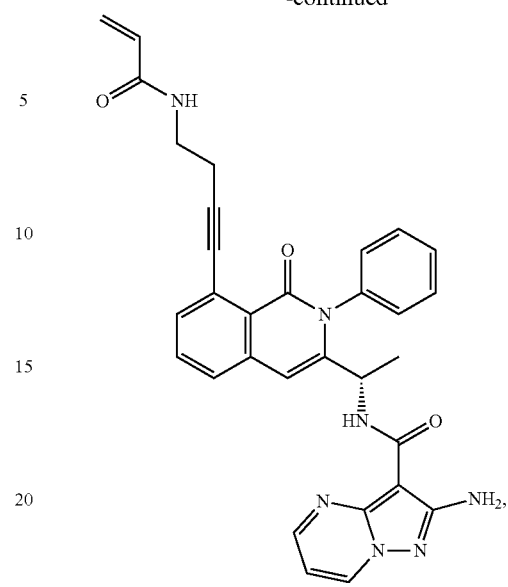
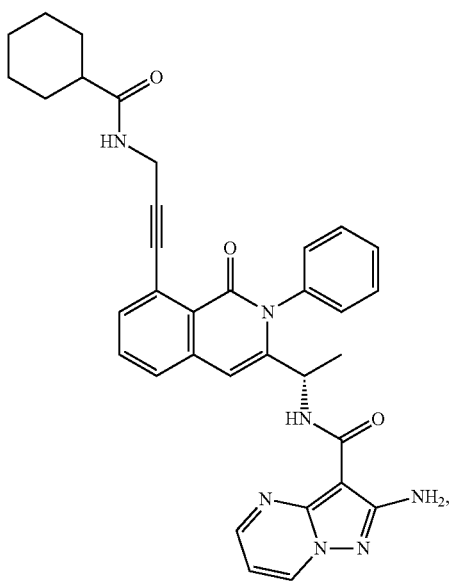
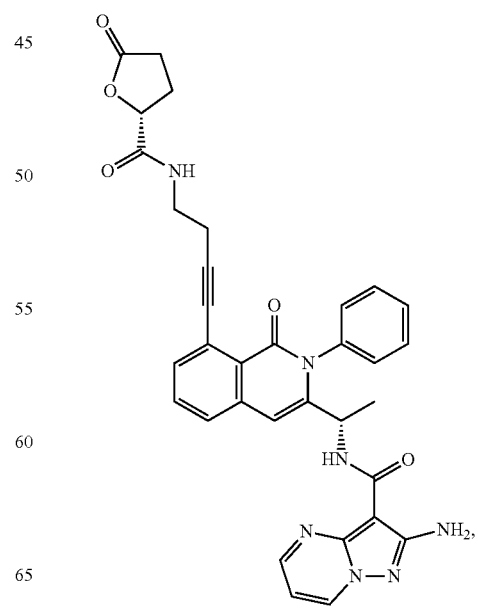

145
-continued
146
-continued
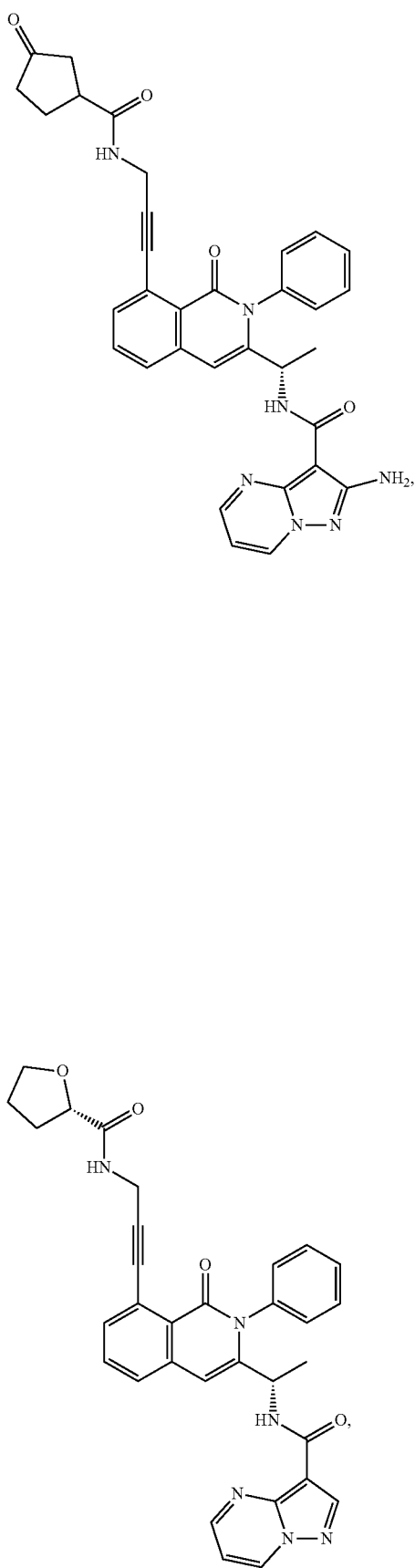
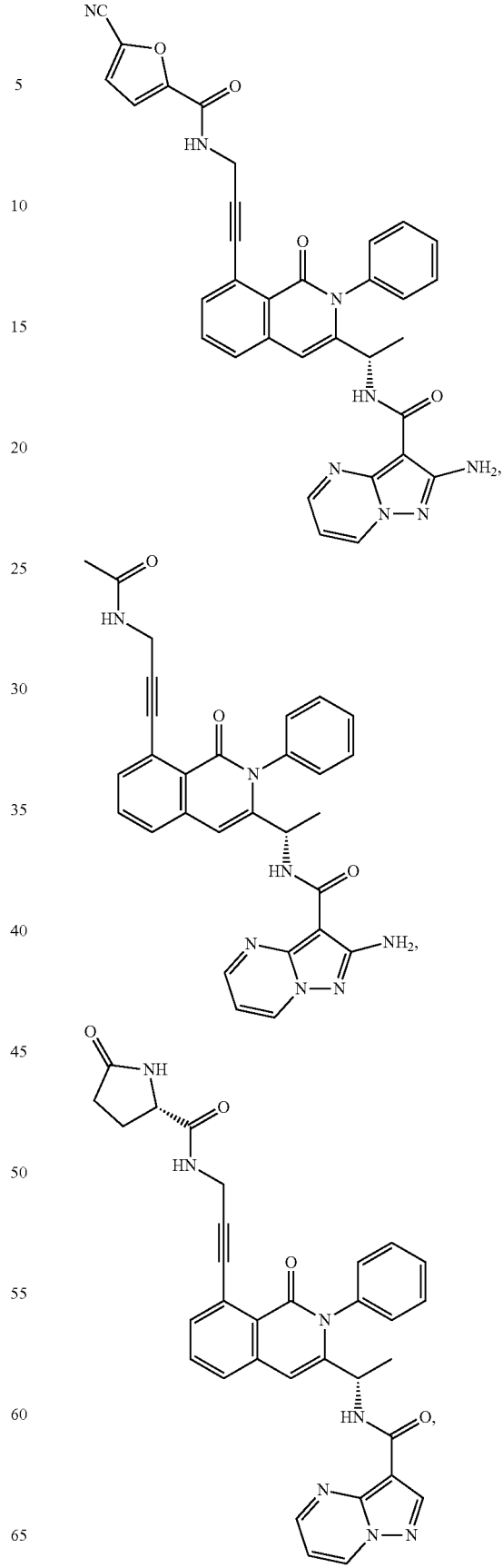

147
-continued
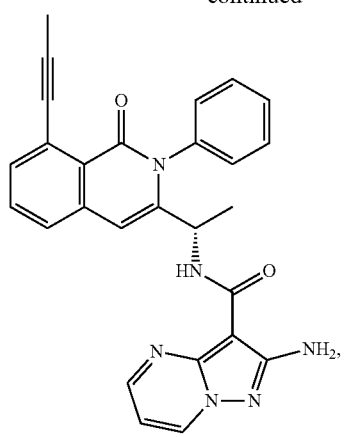
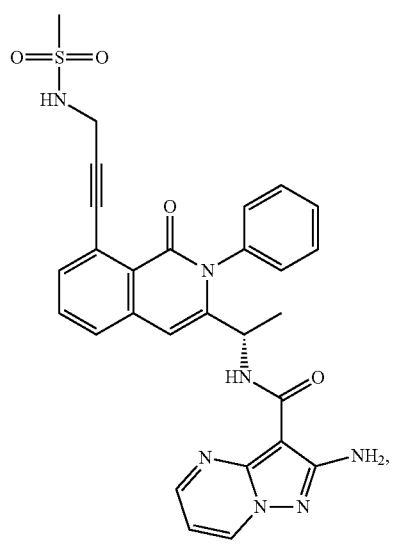
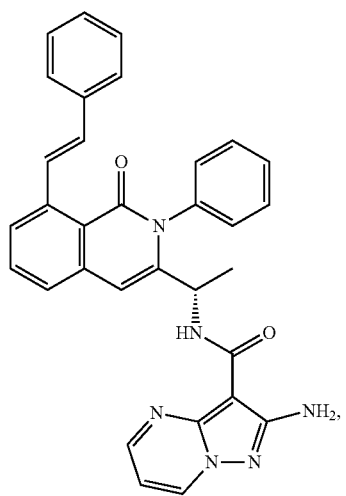
148
-continued
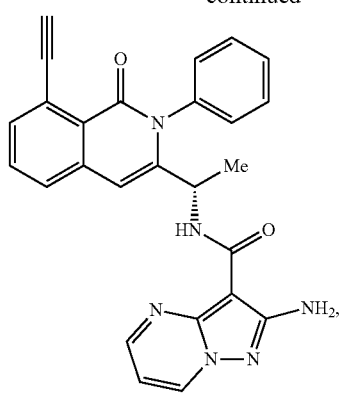
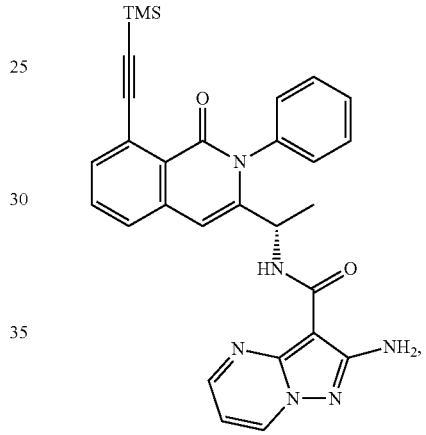
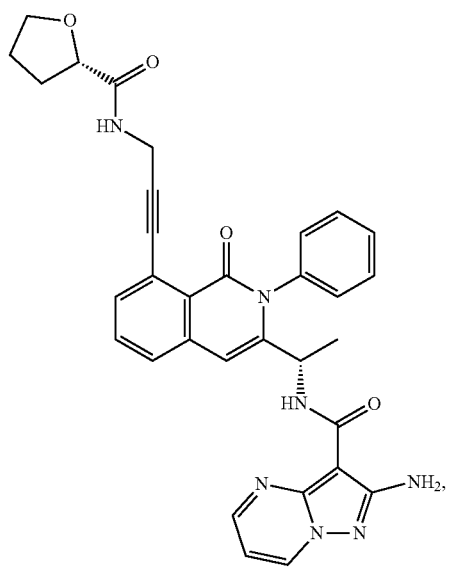

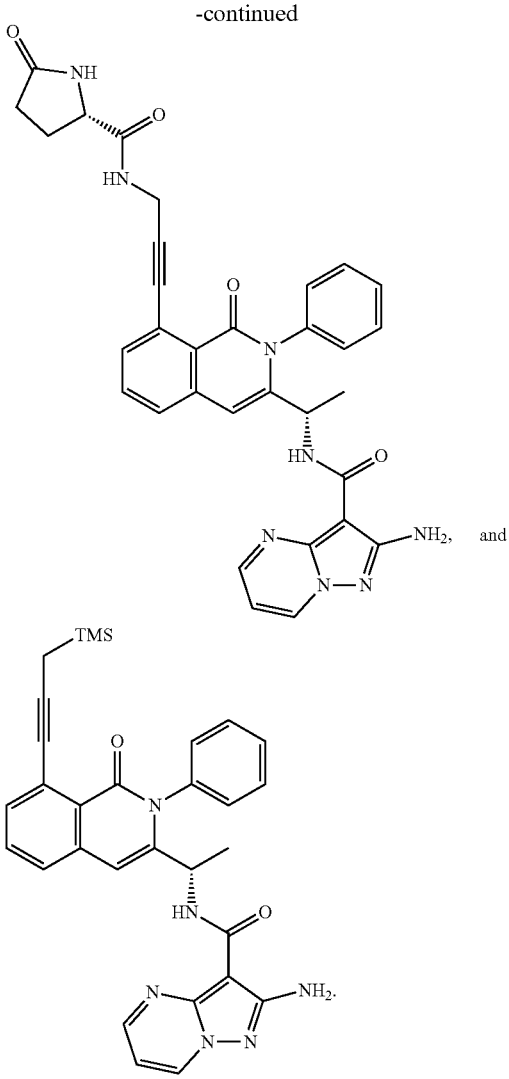

and

In certain embodiments, the compound of Formula (I″), (I′), (I), (A″), (A′), or (A) is in an (S)-stereochemical configuration.

In certain embodiments, the compound of Formula (I″), (I′), (I), (A″), (A′), or (A) is the S-enantiomer having an enantiomeric purity greater than 75%.

In certain embodiments, the compound of Formula (I′) or (A′) is a compound in Table 3, Table 4, Table 5, Table 6, Table 7, Table 8, Table 9, Table 10, Table 11, Table 12, Table 13, or Table 14, or a pharmaceutically acceptable form thereof.

In certain embodiments, the compound of Formula (I′) or (A′) is a compound in Table 3, Table 4, Table 5, or Table 6 or a pharmaceutically acceptable form thereof.

In certain embodiments, the compound of Formula (I′) or (A′) is a compound in Table 3 or Table 4 or a pharmaceutically acceptable form thereof. In certain embodiments, the compound of Formula (I′) or (A′) is a compound in Table 3 or a pharmaceutically acceptable form thereof. In certain embodiments, the compound of Formula (I′) or (A′) is a compound in Table 5 or a pharmaceutically acceptable form thereof. In certain embodiments, the compound of Formula (I′) or (A′) is a compound in Table 7 or a pharmaceutically acceptable form thereof. In certain embodiments, the compound of Formula (I′) or (A′) is a compound in Table 9 or a pharmaceutically acceptable form thereof. In certain embodiments, the compound of Formula (I′) or (A′) is a compound in Table 11 or a pharmaceutically acceptable form thereof. In certain embodiments, the compound of Formula (I′) or (A′) is a compound in Table 13 or a pharmaceutically acceptable form thereof. In certain embodiments, the compound of Formula (I′) or (A′) is a compound in Table 4 or a pharmaceutically acceptable form thereof. In certain embodiments, the compound of Formula (I′) or (A′) is a compound in Table 6 or a pharmaceutically acceptable form thereof. In certain embodiments, the compound of Formula (I′) or (A′) is a compound in Table 8 or a pharmaceutically acceptable form thereof. In certain embodiments, the compound of Formula (I′) or (A′) is a compound in Table 10 or a pharmaceutically acceptable form thereof. In certain embodiments, the compound of Formula (I′) or (A′) is a compound in Table 12 or a pharmaceutically acceptable form thereof. In certain embodiments, the compound of Formula (I′) or (A′) is a compound in Table 14 or a pharmaceutically acceptable form thereof.

TABLE 3

Compound 1

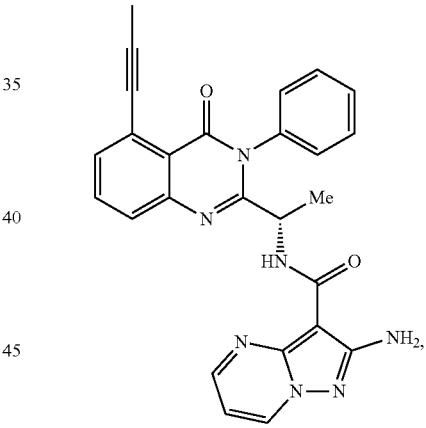

Compound 2

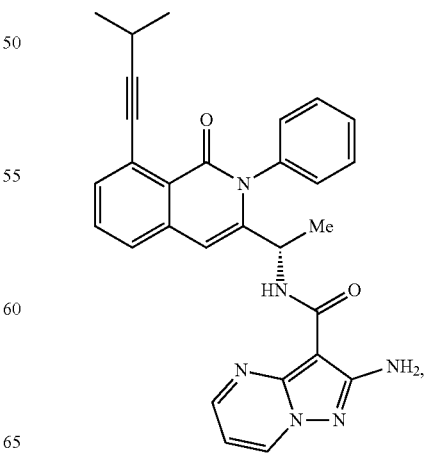

TABLE 3-continued
Compound 3
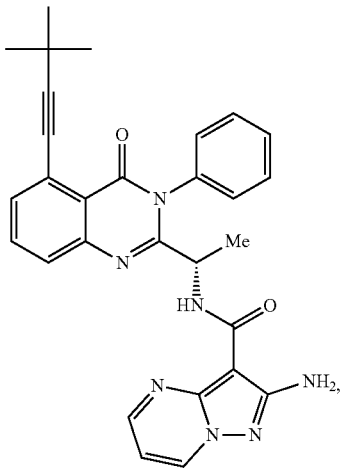 [SMILES: C[C@H](NC(=O)c1c(N)nn2cccnc12)c1nc2cccc(C#CC(C)(C)C)c2c(=O)n1-c1ccccc1]
Compound 4
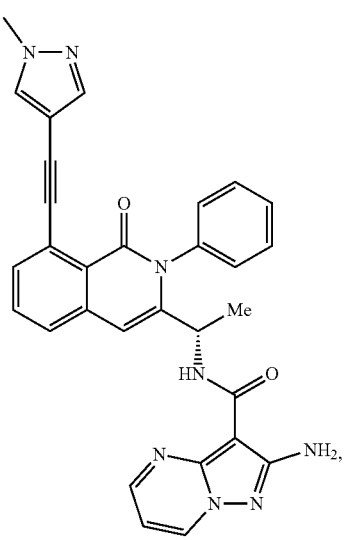 [SMILES: C[C@H](NC(=O)c1c(N)nn2cccnc12)c1cc2cccc(C#Cc3cnn(C)c3)c2c(=O)n1-c1ccccc1]
Compound 5
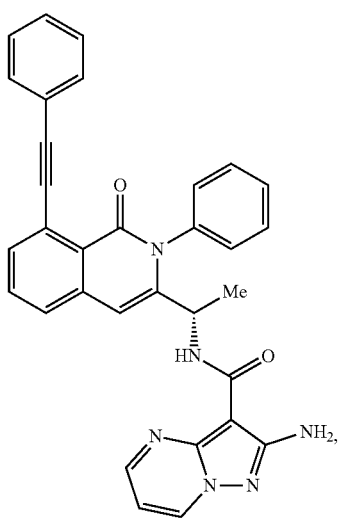 [SMILES: C[C@H](NC(=O)c1c(N)nn2cccnc12)c1cc2cccc(C#Cc3ccccc3)c2c(=O)n1-c1ccccc1]
TABLE 3-continued
Compound 6
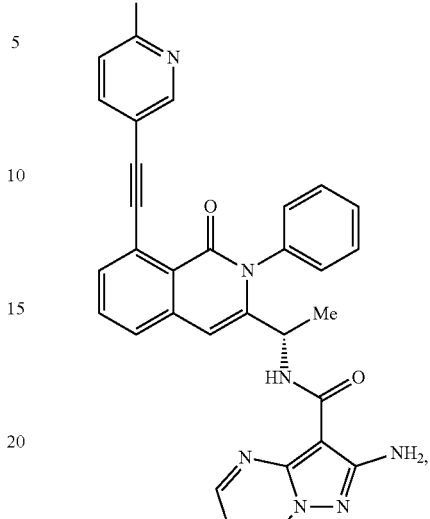
Compound 7
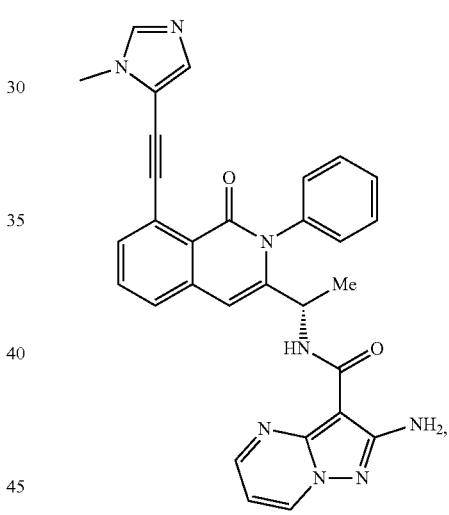
Compound 8
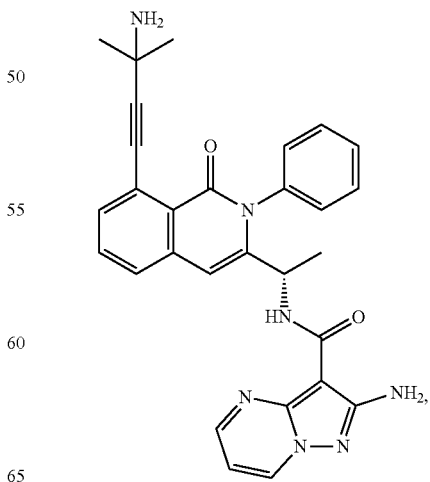

TABLE 3-continued
Compound 9
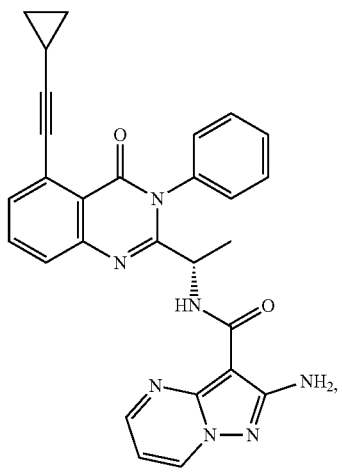 [SMILES: C[C@H](NC(=O)c1c(N)nn2cccnc12)c1nc2cccc(C#CC3CC3)c2c(=O)n1-c1ccccc1]
Compound 10
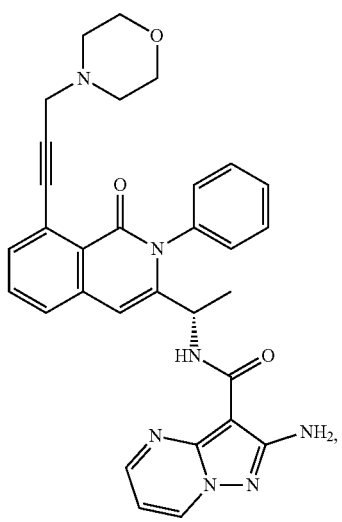 [SMILES: C[C@H](NC(=O)c1c(N)nn2cccnc12)c1cc2cccc(C#CCN3CCOCC3)c2c(=O)n1-c1ccccc1]
Compound 11
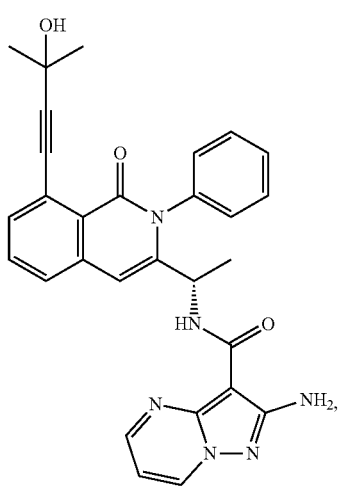 [SMILES: C[C@H](NC(=O)c1c(N)nn2cccnc12)c1cc2cccc(C#CC(C)(C)O)c2c(=O)n1-c1ccccc1]
TABLE 3-continued
Compound 12
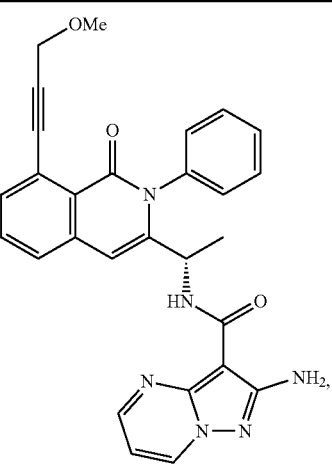
Compound 13
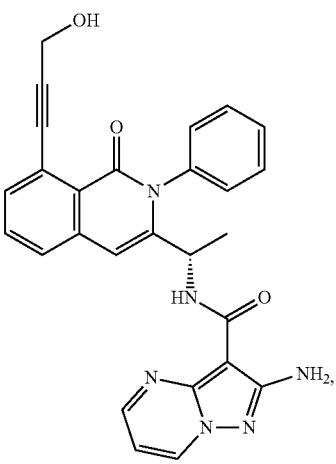 [SMILES: C[C@H](NC(=O)c1c(N)nn2cccnc12)c1cc2cccc(C#CCO)c2c(=O)n1-c1ccccc1]
Compound 14
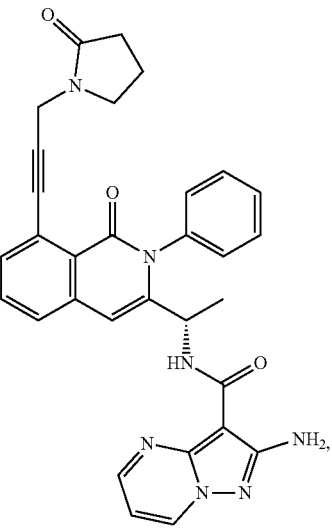 [SMILES: C[C@H](NC(=O)c1c(N)nn2cccnc12)c1cc2cccc(C#CCN3CCCC3=O)c2c(=O)n1-c1ccccc1]

TABLE 3-continued
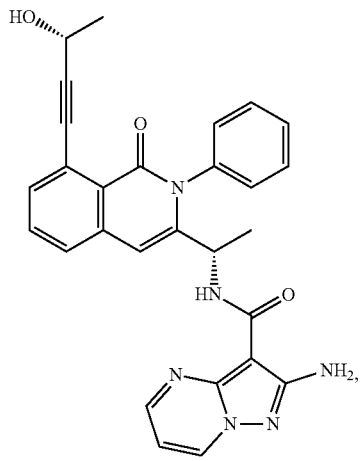 [SMILES: C[C@H](NC(=O)c1c(N)nn2cccnc12)c1cc2cccc(C#C[C@@H](C)O)c2c(=O)n1-c1ccccc1]
Compound 15
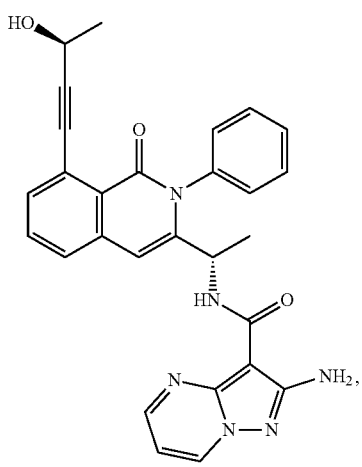 [SMILES: C[C@H](O)C#Cc1cccc2cc([C@H](C)NC(=O)c3c(N)nn4cccnc34)n(-c3ccccc3)c(=O)c12]
Compound 16
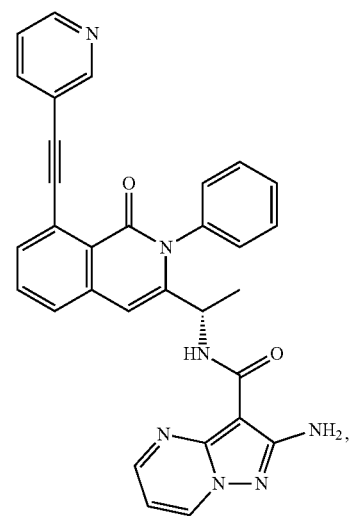 [SMILES: C[C@H](NC(=O)c1c(N)nn2cccnc12)c1cc2cccc(C#Cc3cccnc3)c2c(=O)n1-c1ccccc1]
Compound 17
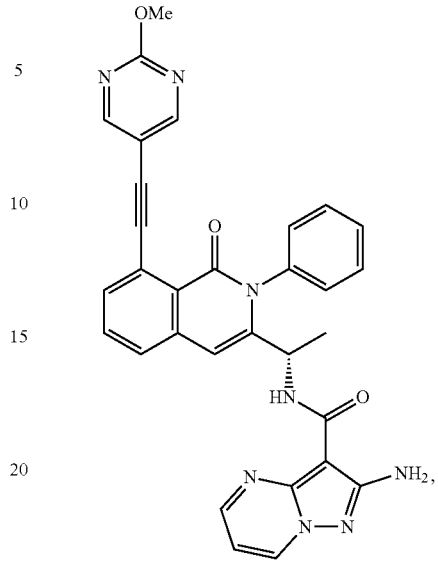
Compound 18
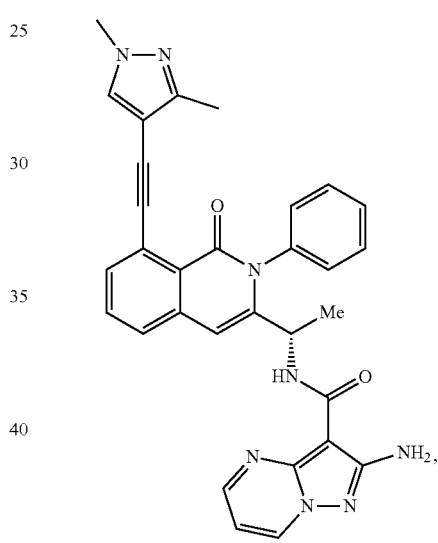
Compound 19
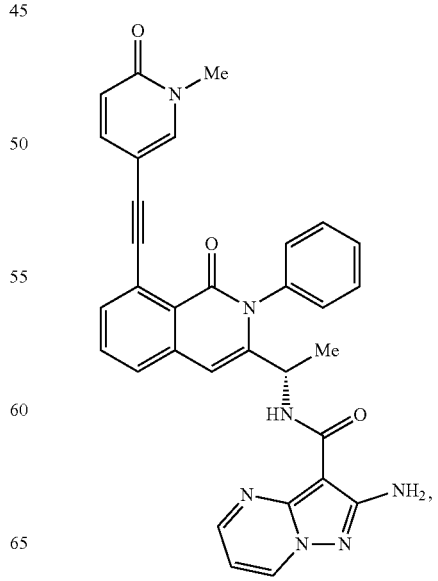
Compound 20

TABLE 3-continued
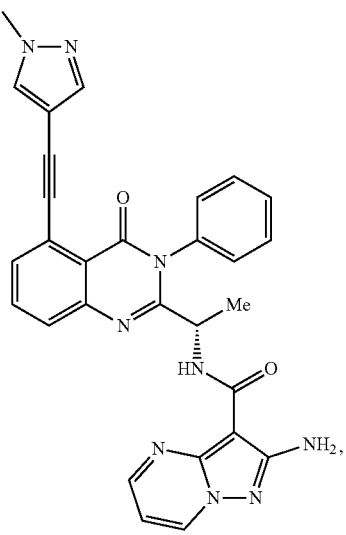 [SMILES: C[C@H](NC(=O)c1c(N)nn2cccnc12)c1nc2cccc(C#Cc3cnn(C)c3)c2c(=O)n1-c1ccccc1]
Compound 21
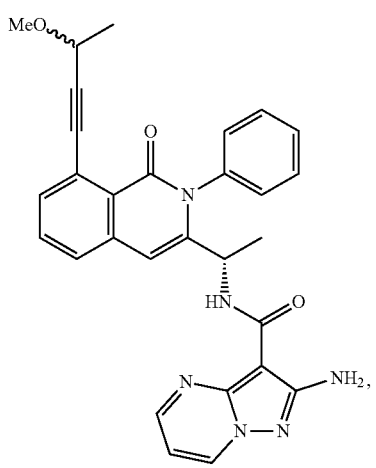 [SMILES: COC(C)C#Cc1cccc2cc([C@H](C)NC(=O)c3c(N)nn4cccnc34)n(-c3ccccc3)c(=O)c12]
Compound 22
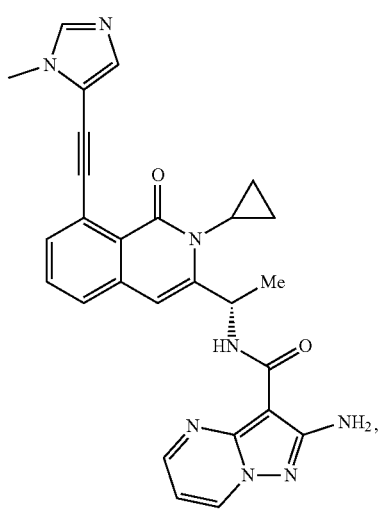 [SMILES: C[C@H](NC(=O)c1c(N)nn2cccnc12)c1cc2cccc(C#Cc3cncn3C)c2c(=O)n1C1CC1]
Compound 23
TABLE 3-continued
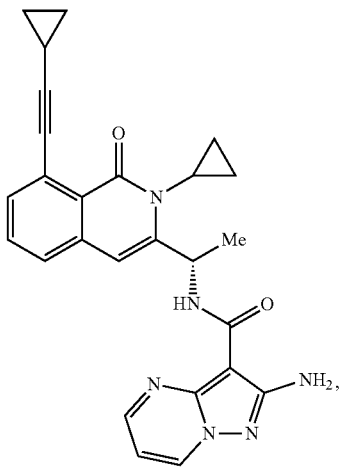 [SMILES: C[C@H](NC(=O)c1c(N)nn2cccnc12)c1cc2cccc(C#CC3CC3)c2c(=O)n1C1CC1]
Compound 24
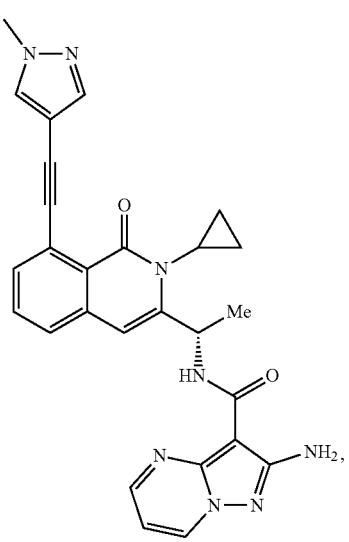 [SMILES: C[C@H](NC(=O)c1c(N)nn2cccnc12)c1cc2cccc(C#Cc3cnn(C)c3)c2c(=O)n1C1CC1]
Compound 25
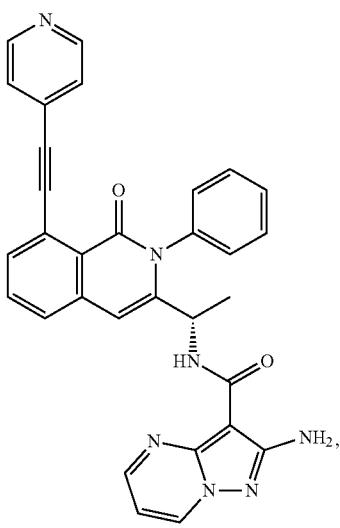 [SMILES: C[C@H](NC(=O)c1c(N)nn2cccnc12)c1cc2cccc(C#Cc3ccncc3)c2c(=O)n1-c1ccccc1]
Compound 26

TABLE 3-continued
Compound 27
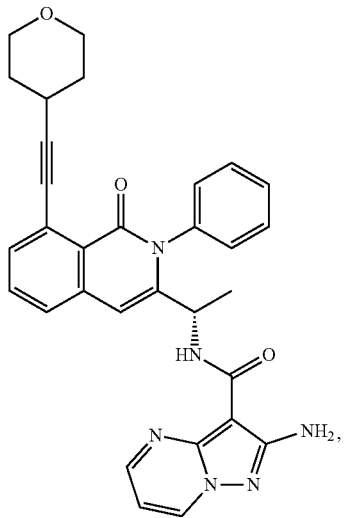 [SMILES: C[C@H](NC(=O)c1c(N)nn2cccnc12)c1cc2cccc(C#CC3CCOCC3)c2c(=O)n1-c1ccccc1]
Compound 28
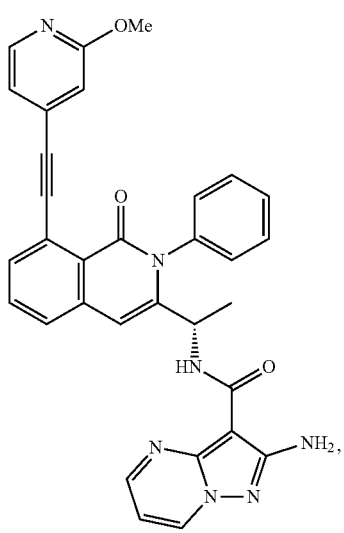 [SMILES: COc1cc(C#Cc2cccc3cc([C@H](C)NC(=O)c4c(N)nn5cccnc45)n(-c4ccccc4)c(=O)c23)ccn1]
Compound 29
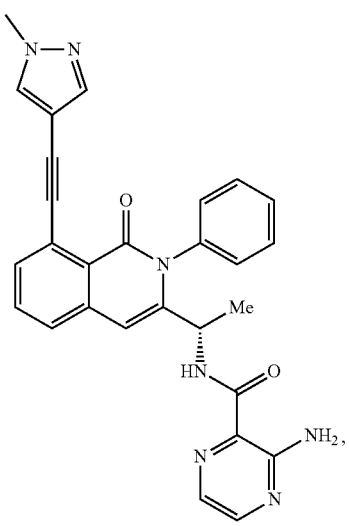 [SMILES: C[C@H](NC(=O)c1nccnc1N)c1cc2cccc(C#Cc3cnn(C)c3)c2c(=O)n1-c1ccccc1]
TABLE 3-continued
Compound 30
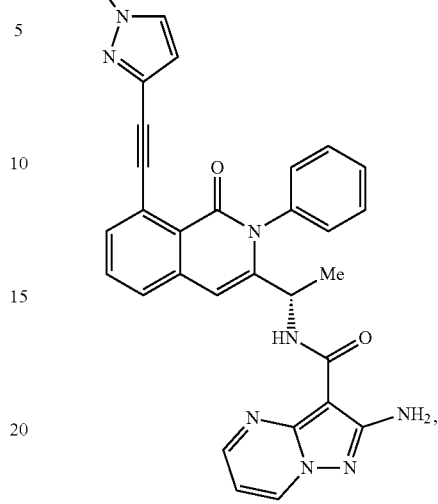
Compound 31
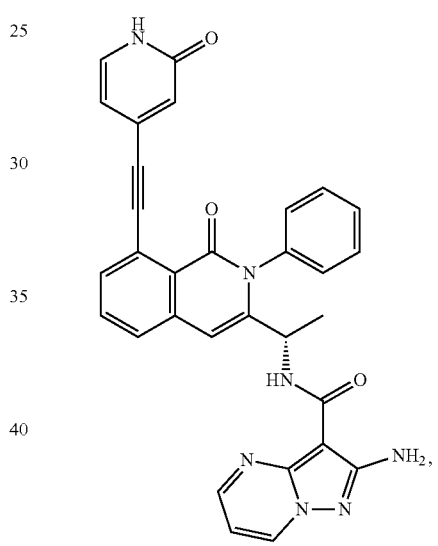
Compound 32
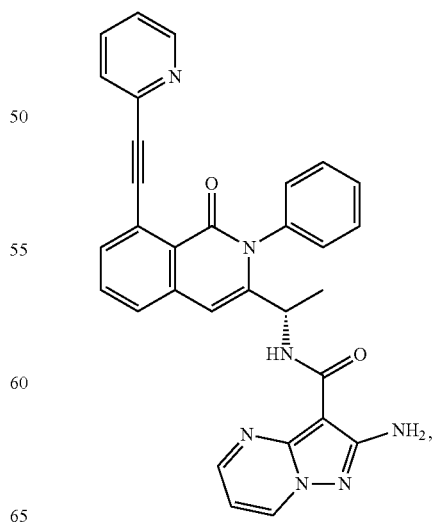

TABLE 3-continued
Compound 33
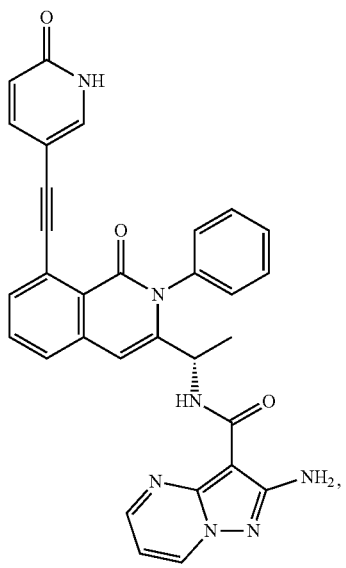 [SMILES: C[C@H](NC(=O)c1c(N)nn2cccnc12)c1cc2cccc(C#Cc3ccc(=O)[nH]c3)c2c(=O)n1-c1ccccc1]
Compound 34
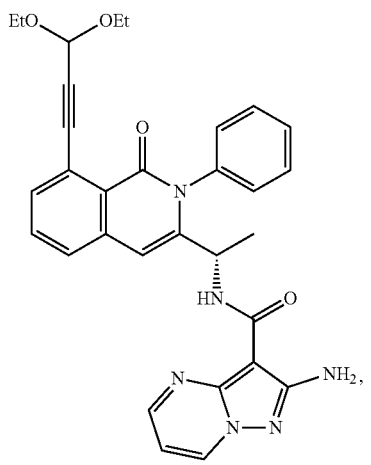 [SMILES: CCOC(C#Cc1cccc2cc([C@H](C)NC(=O)c3c(N)nn4cccnc34)n(-c3ccccc3)c(=O)c12)OCC]
Compound 35
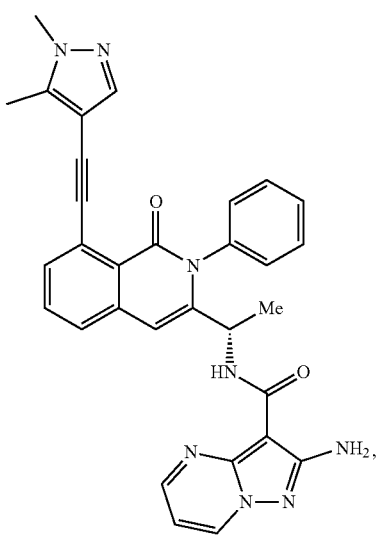 [SMILES: Cc1c(C#Cc2cccc3cc([C@H](C)NC(=O)c4c(N)nn5cccnc45)n(-c4ccccc4)c(=O)c23)cnn1C]
TABLE 3-continued
Compound 36
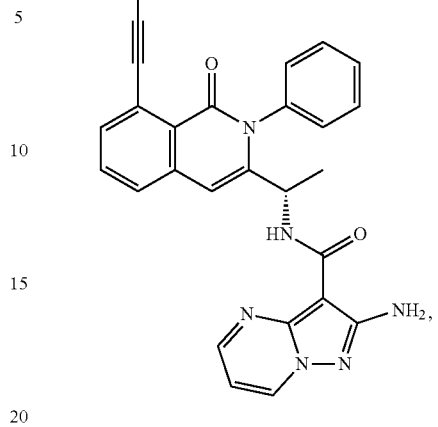
Compound 37
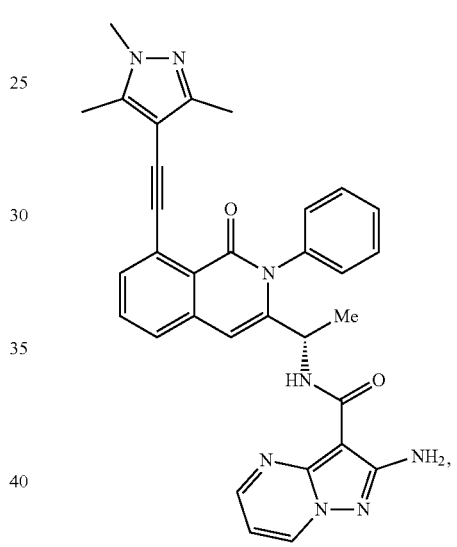
Compound 38
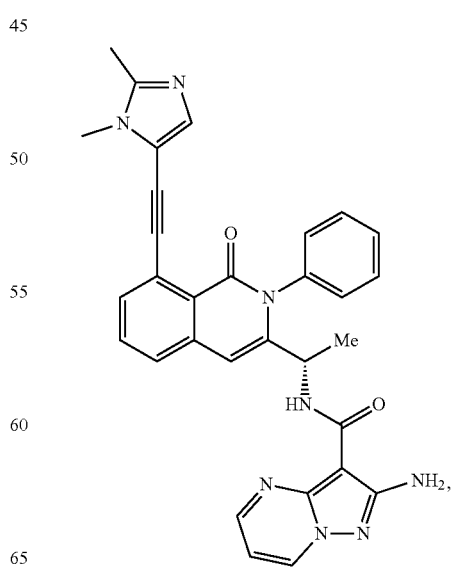

TABLE 3-continued
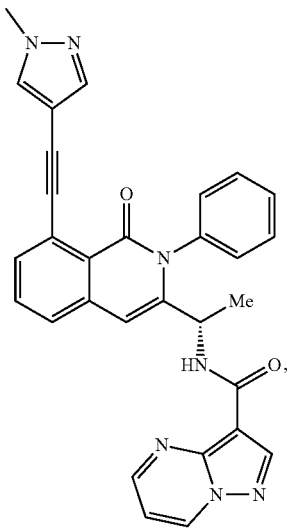
Compound 39
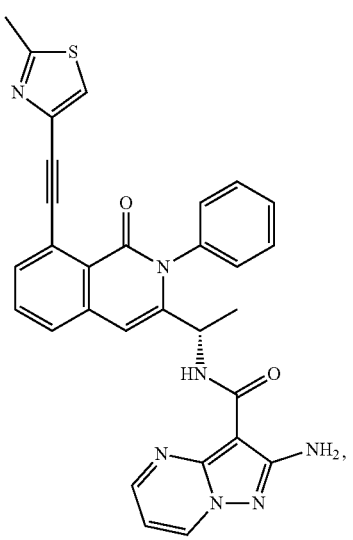
Compound 40
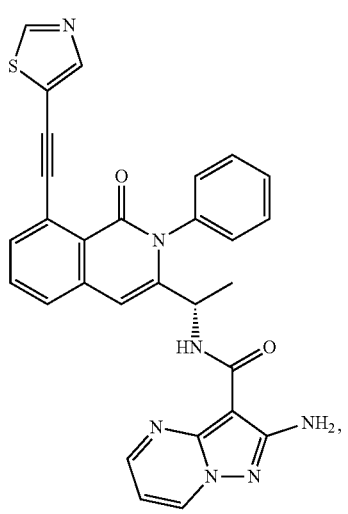
Compound 41
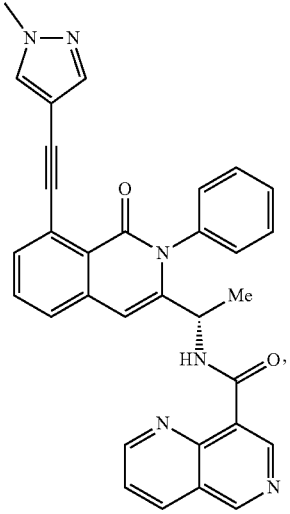 [SMILES: C[C@H](NC(=O)c1cncc2cccnc12)c1cc2cccc(C#Cc3cnn(C)c3)c2c(=O)n1-c1ccccc1]
Compound 42
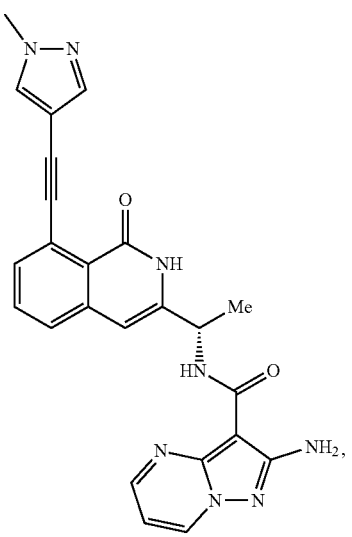
Compound 43
Compound 44

TABLE 3-continued
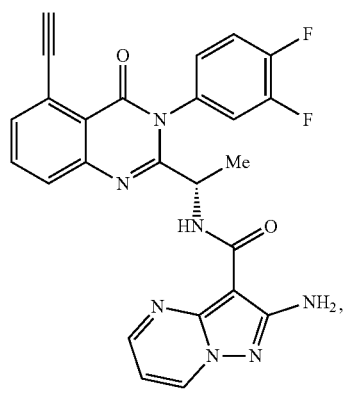 [SMILES: C#Cc1cccc2nc([C@H](C)NC(=O)c3c(N)nn4cccnc34)n(-c3ccc(F)c(F)c3)c(=O)c12]
Compound 45
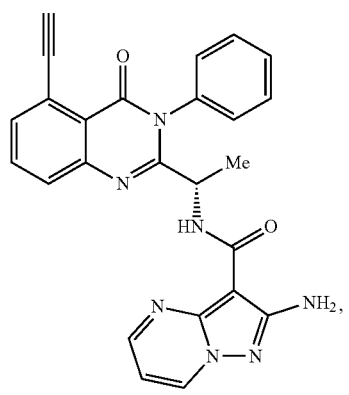 [SMILES: C#Cc1cccc2nc([C@H](C)NC(=O)c3c(N)nn4cccnc34)n(-c3ccccc3)c(=O)c12]
Compound 46
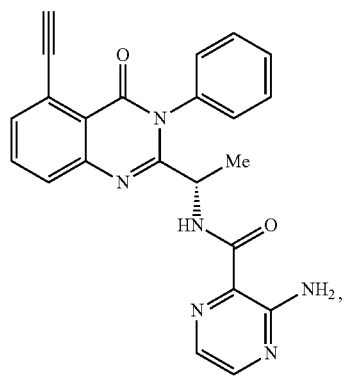 [SMILES: C#Cc1cccc2nc([C@H](C)NC(=O)c3nccnc3N)n(-c3ccccc3)c(=O)c12]
Compound 47
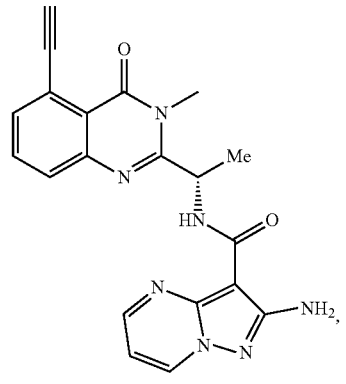 [SMILES: C#Cc1cccc2nc([C@H](C)NC(=O)c3c(N)nn4cccnc34)n(C)c(=O)c12]
Compound 48
TABLE 3-continued
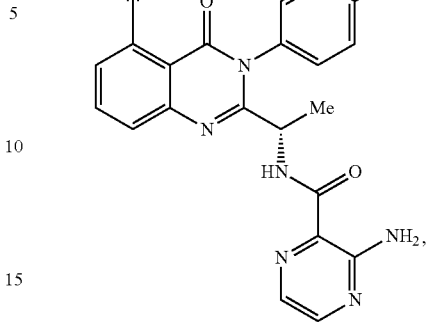
Compound 49
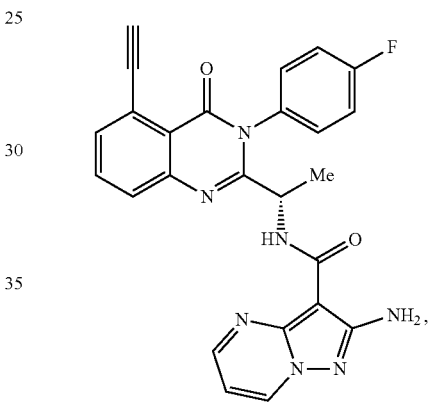
Compound 50
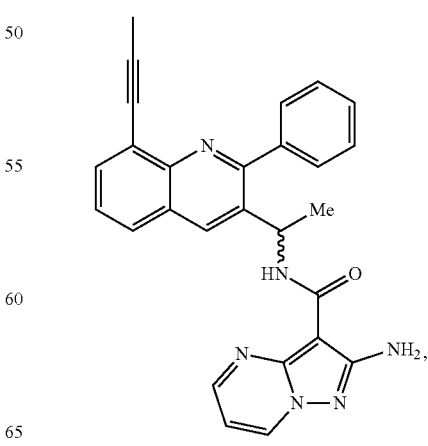
Compound 51

TABLE 3-continued
Compound 52
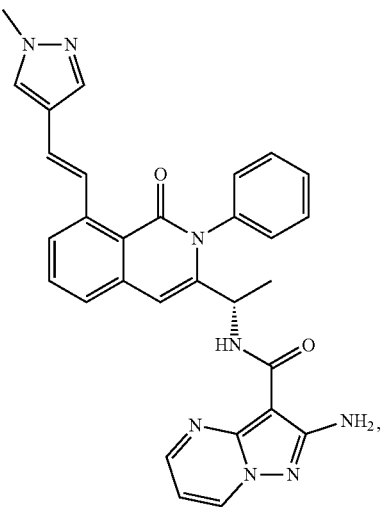 [SMILES: C[C@H](NC(=O)c1c(N)nn2cccnc12)c1cc2cccc(/C=C/c3cnn(C)c3)c2c(=O)n1-c1ccccc1]
Compound 53
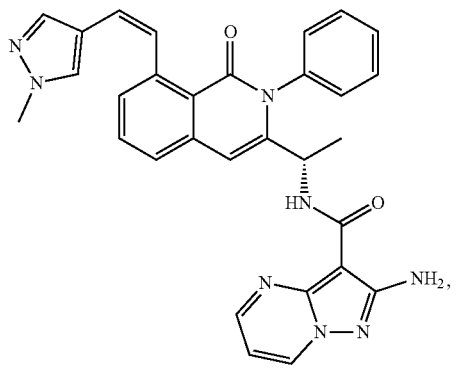 [SMILES: C[C@H](NC(=O)c1c(N)nn2cccnc12)c1cc2cccc(/C=C\c3cnn(C)c3)c2c(=O)n1-c1ccccc1]
Compound 54
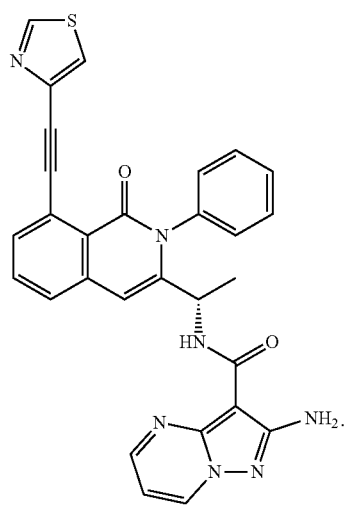
TABLE 3-continued
Compound 55
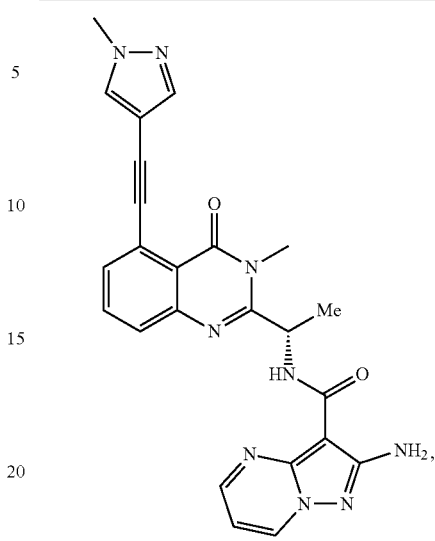
Compound 56
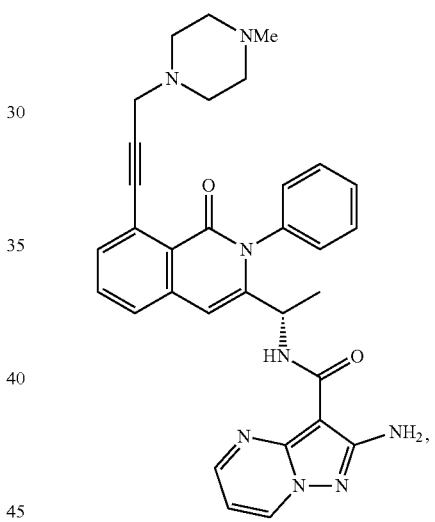
Compound 57
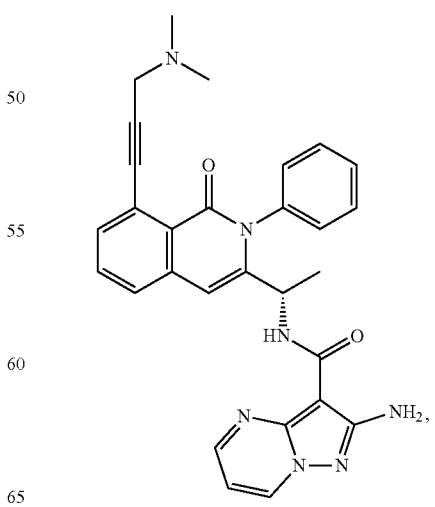

TABLE 3-continued
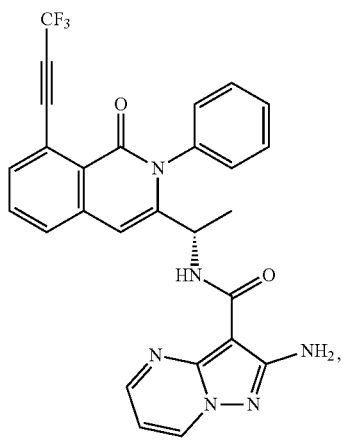 [SMILES: C[C@H](NC(=O)c1c(N)nn2cccnc12)c1cc2cccc(C#CC(F)(F)F)c2c(=O)n1-c1ccccc1]
Compound 58
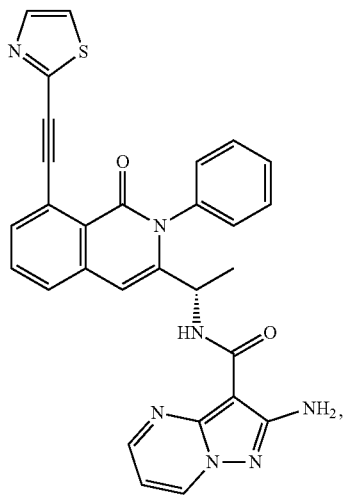
Compound 59
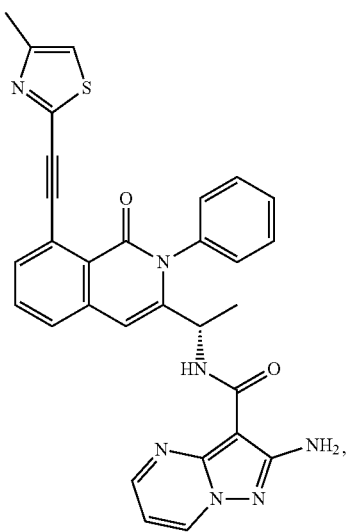
Compound 60
TABLE 3-continued
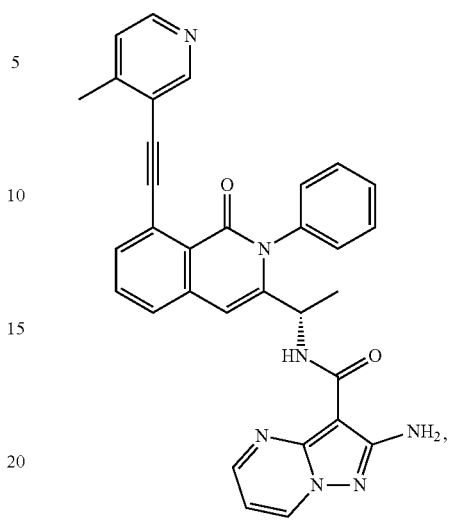
Compound 61
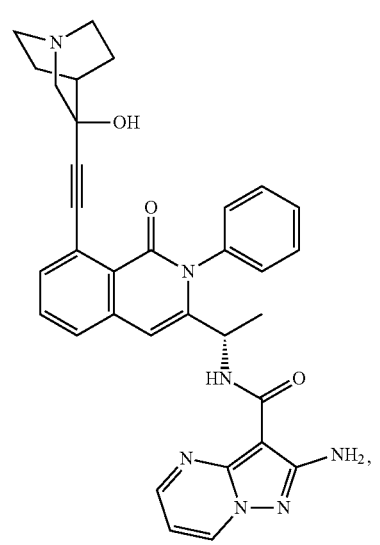 [SMILES: C[C@H](NC(=O)c1c(N)nn2cccnc12)c1cc2cccc(C#CC3(O)CN4CCC3CC4)c2c(=O)n1-c1ccccc1]
Compound 62
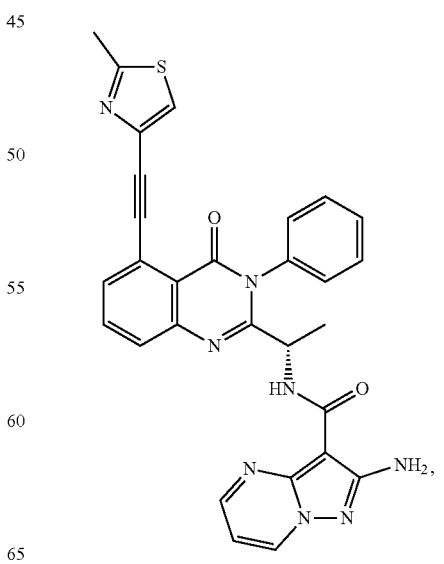
Compound 63

TABLE 3-continued
Compound 64
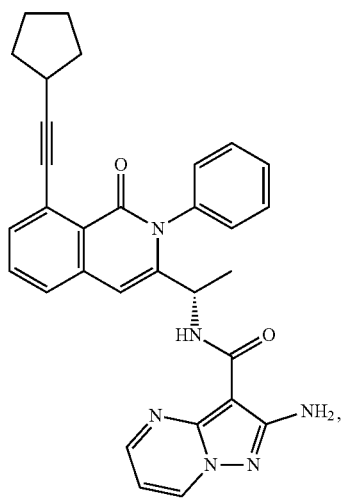 [SMILES: C[C@H](NC(=O)c1c(N)nn2cccnc12)c1cc2cccc(C#CC3CCCC3)c2c(=O)n1-c1ccccc1]
Compound 65
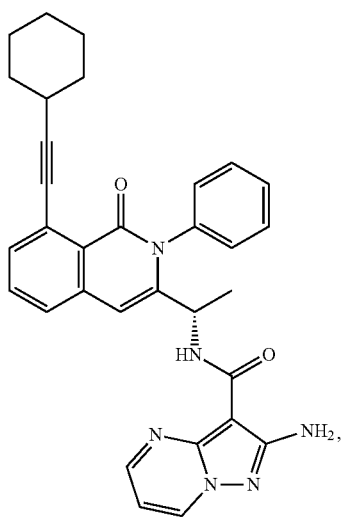 [SMILES: C[C@H](NC(=O)c1c(N)nn2cccnc12)c1cc2cccc(C#CC3CCCCC3)c2c(=O)n1-c1ccccc1]
Compound 66
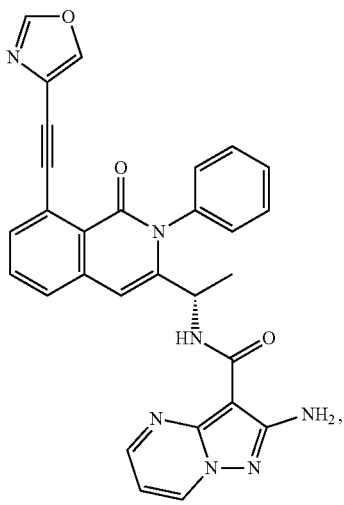
TABLE 3-continued
Compound 67
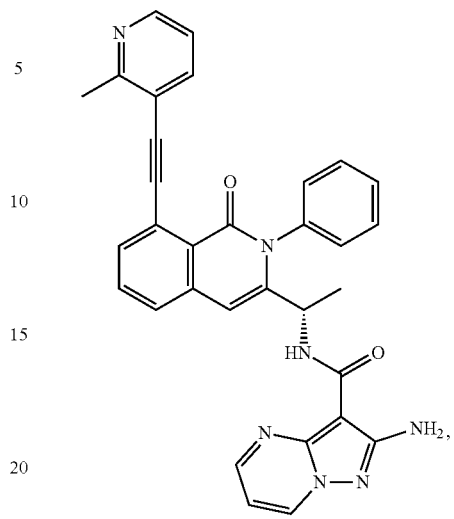
Compound 68
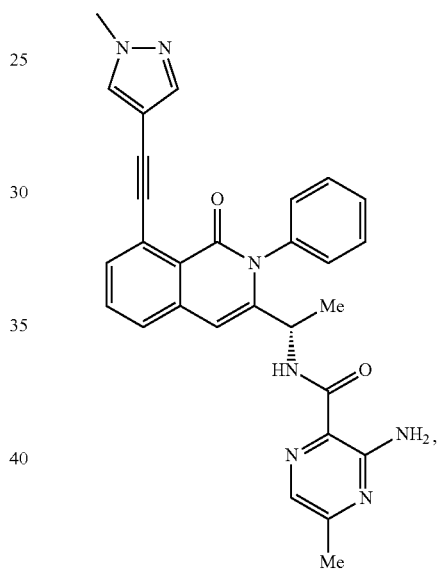
Compound 69
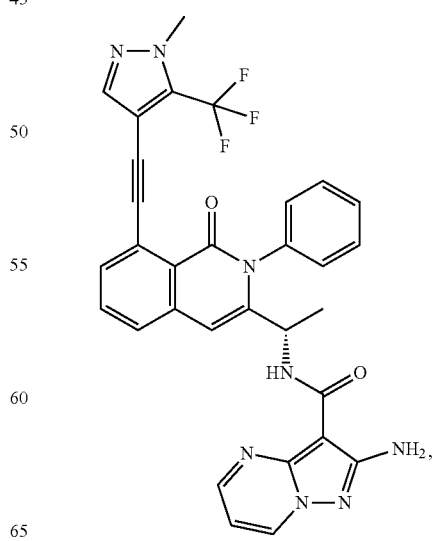

TABLE 3-continued
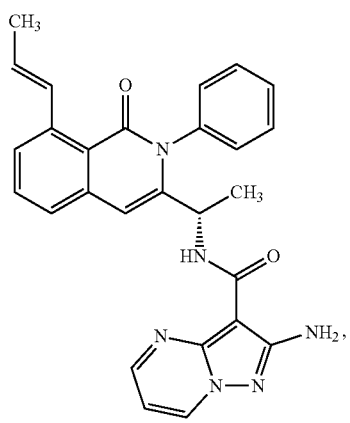
Compound 70
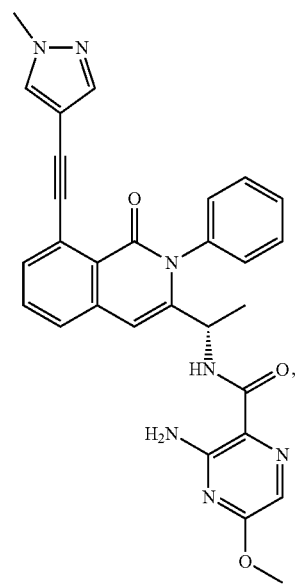
Compound 71
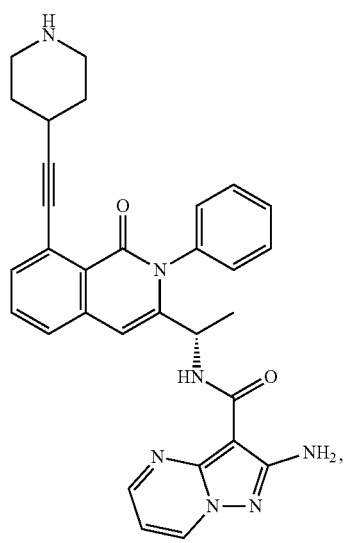 [SMILES: C[C@H](NC(=O)c1c(N)nn2cccnc12)c1cc2cccc(C#CC3CCNCC3)c2c(=O)n1-c1ccccc1]
Compound 72
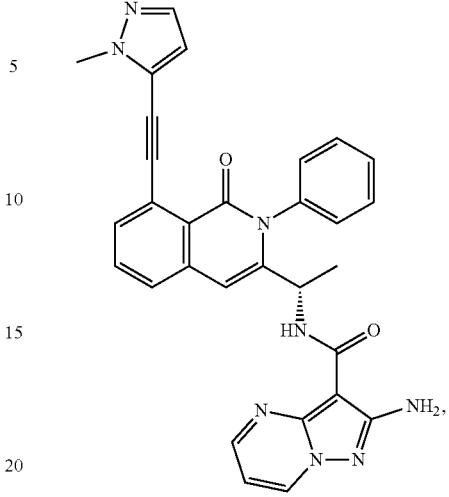
Compound 73
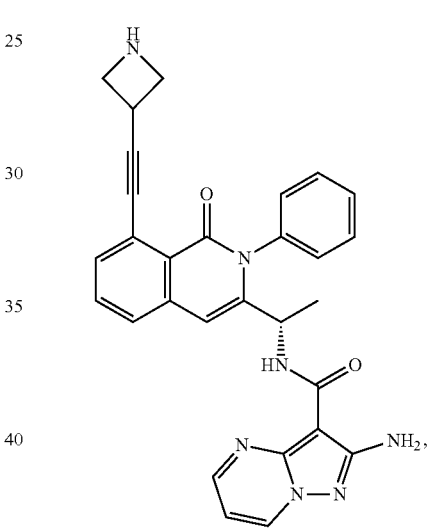
Compound 74
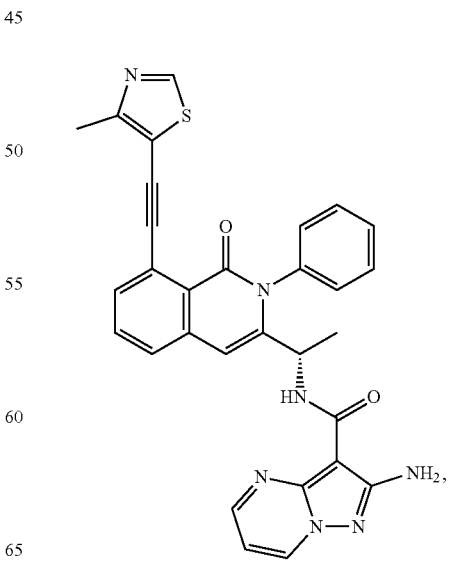
Compound 75

TABLE 3-continued
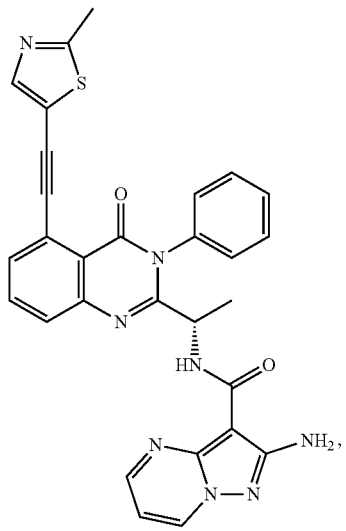 [SMILES: Cc1ncc(C#Cc2cccc3nc([C@H](C)NC(=O)c4c(N)nn5cccnc45)n(-c4ccccc4)c(=O)c23)s1]
Compound 76
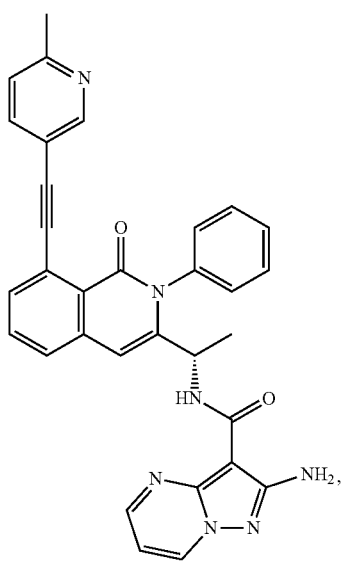 [SMILES: Cc1ccc(C#Cc2cccc3cc([C@H](C)NC(=O)c4c(N)nn5cccnc45)n(-c4ccccc4)c(=O)c23)cn1]
Compound 77
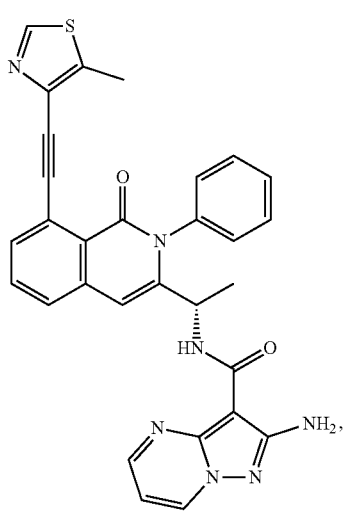
Compound 78
TABLE 3-continued
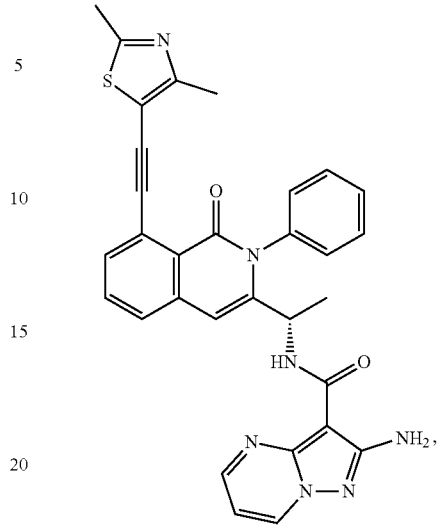
Compound 79
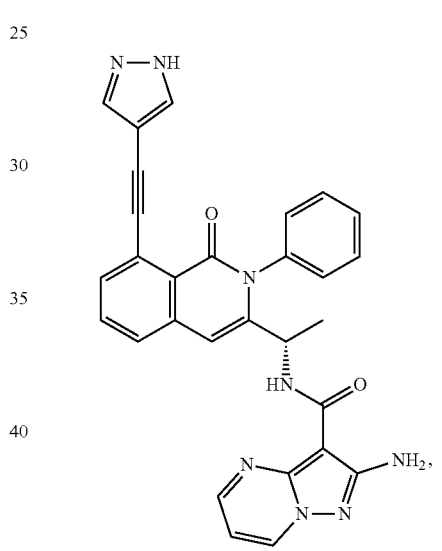
Compound 80
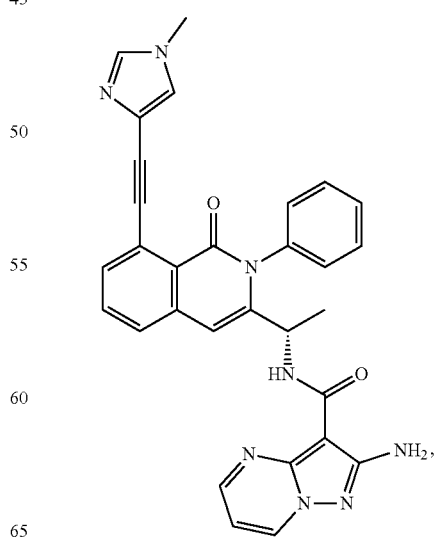
Compound 81

TABLE 3-continued
Compound 82
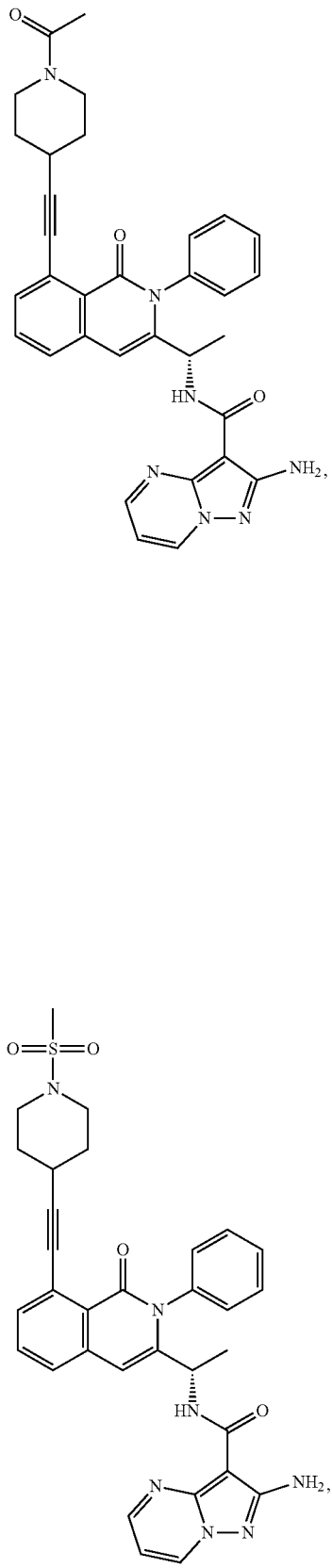
Compound 83
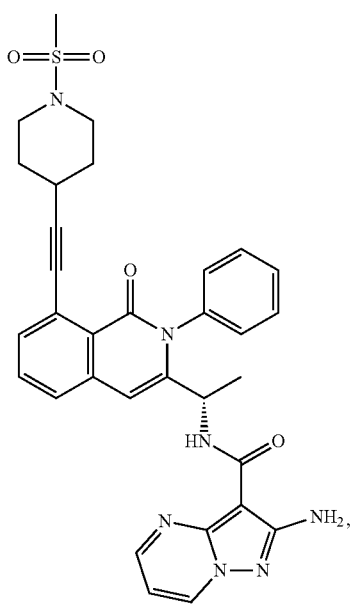
Compound 84
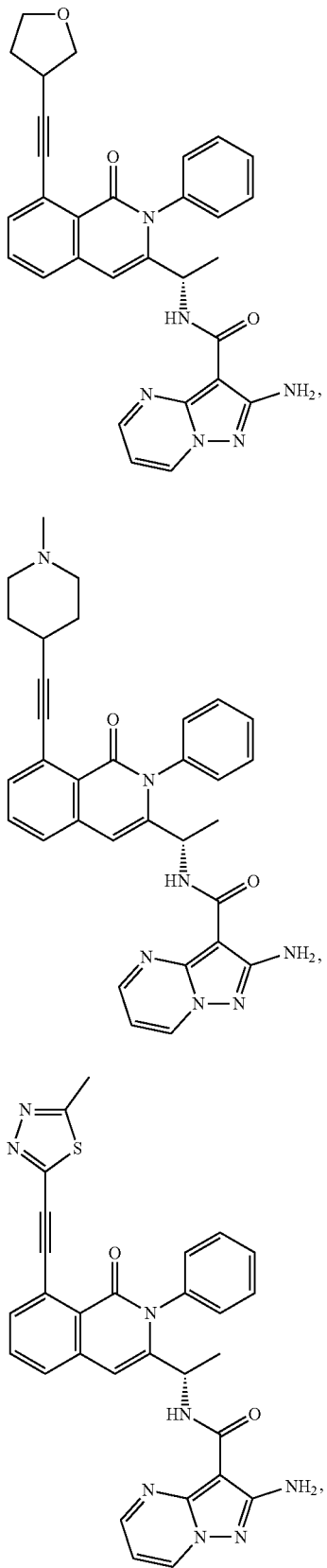
Compound 85
Compound 86
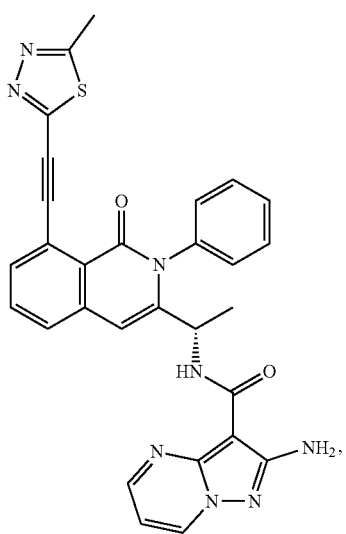 [SMILES: Cc1nnc(C#Cc2cccc3cc([C@H](C)NC(=O)c4c(N)nn5cccnc45)n(-c4ccccc4)c(=O)c23)s1]

TABLE 3-continued
Compound 87
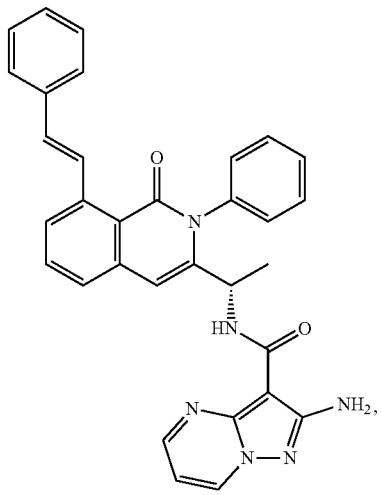
Compound 88
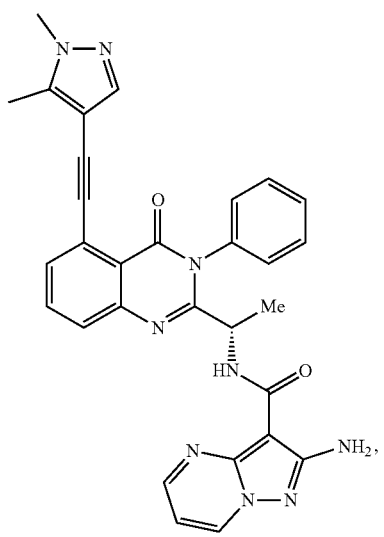 [SMILES: Cc1c(C#Cc2cccc3nc([C@H](C)NC(=O)c4c(N)nn5cccnc45)n(-c4ccccc4)c(=O)c23)cnn1C]
Compound 89
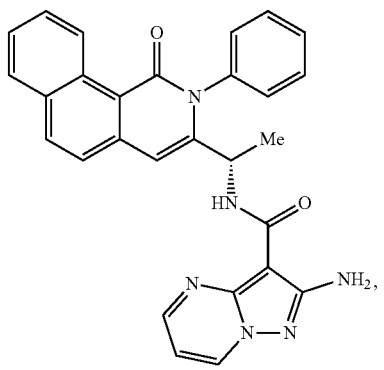 [SMILES: C[C@H](NC(=O)c1c(N)nn2cccnc12)c1cc2ccc3ccccc3c2c(=O)n1-c1ccccc1]
TABLE 3-continued
Compound 90
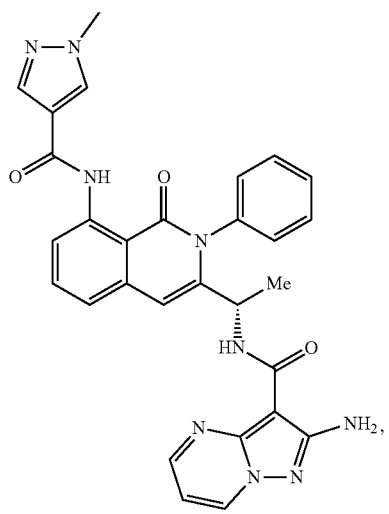 [SMILES: C[C@H](NC(=O)c1c(N)nn2cccnc12)c1cc2cccc(NC(=O)c3cnn(C)c3)c2c(=O)n1-c1ccccc1]
Compound 91
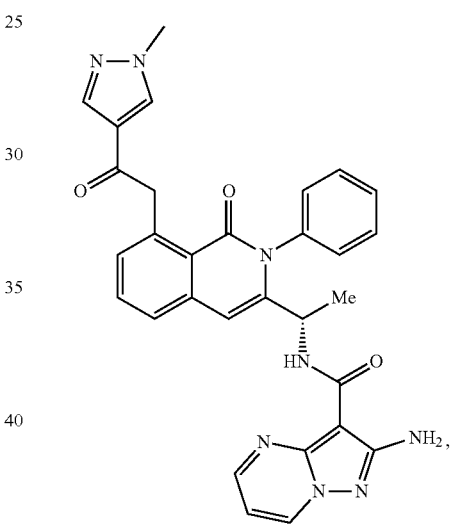
Compound 92
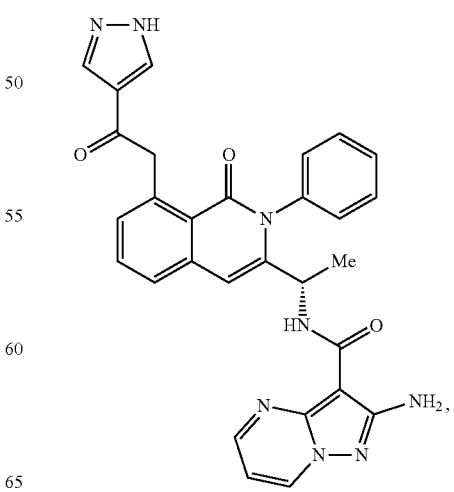

TABLE 3-continued
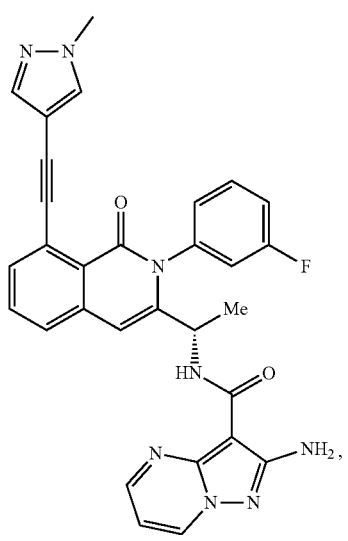 [SMILES: C[C@H](NC(=O)c1c(N)nn2cccnc12)c1cc2cccc(C#Cc3cnn(C)c3)c2c(=O)n1-c1cccc(F)c1]
Compound 93
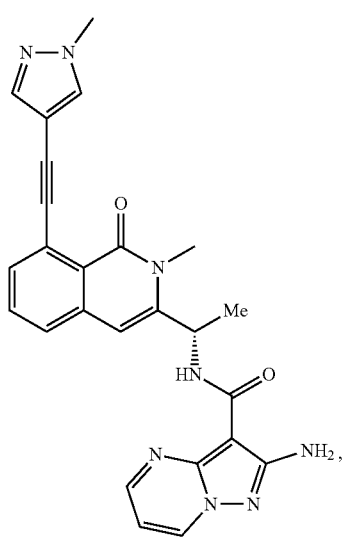 [SMILES: C[C@H](NC(=O)c1c(N)nn2cccnc12)c1cc2cccc(C#Cc3cnn(C)c3)c2c(=O)n1C]
Compound 94
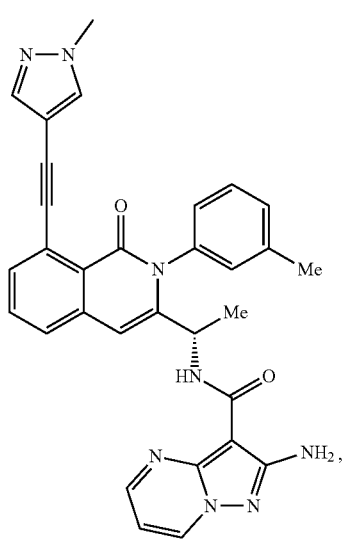 [SMILES: Cc1cccc(-n2c([C@H](C)NC(=O)c3c(N)nn4cccnc34)cc3cccc(C#Cc4cnn(C)c4)c3c2=O)c1]
Compound 95
TABLE 3-continued
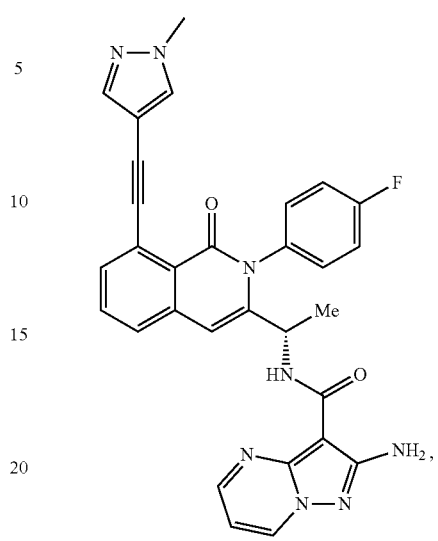
Compound 96
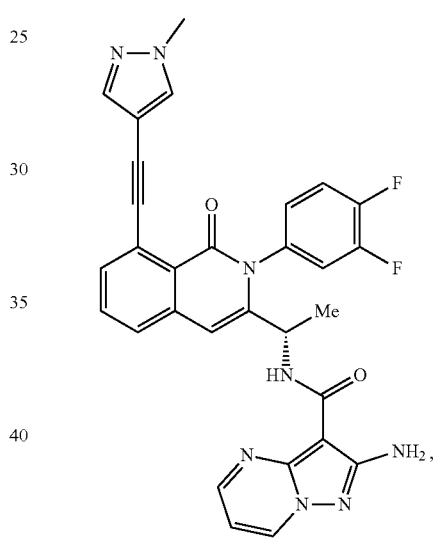
Compound 97
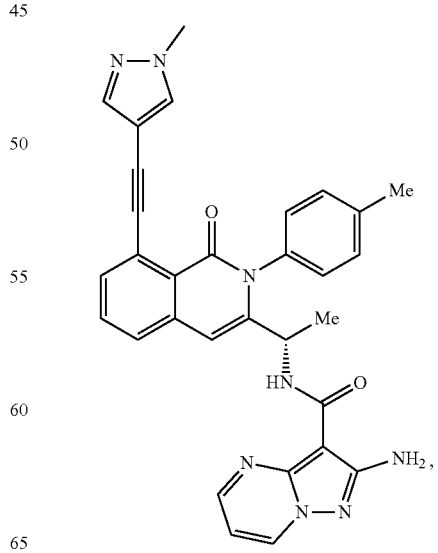
Compound 98

TABLE 3-continued
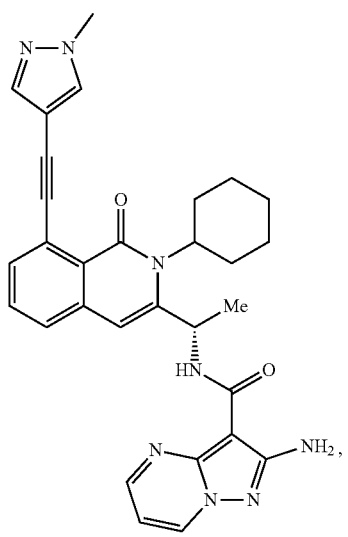 [SMILES: C[C@H](NC(=O)c1c(N)nn2cccnc12)c1cc2cccc(C#Cc3cnn(C)c3)c2c(=O)n1C1CCCCC1]
Compound 99
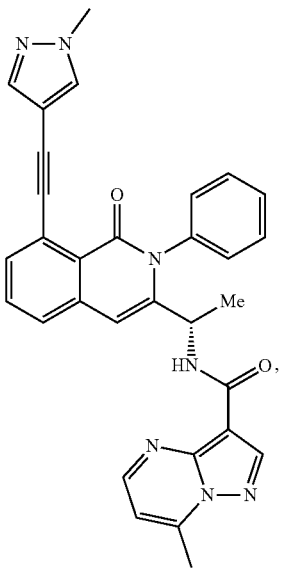
Compound 102
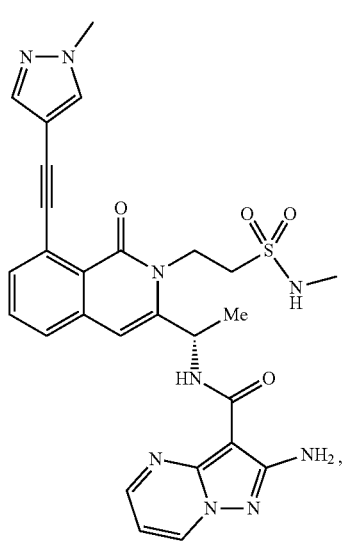 [SMILES: CNS(=O)(=O)CCn1c([C@H](C)NC(=O)c2c(N)nn3cccnc23)cc2cccc(C#Cc3cnn(C)c3)c2c1=O]
Compound 100
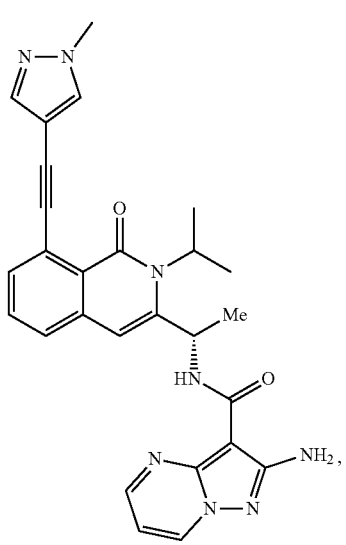
Compound 103
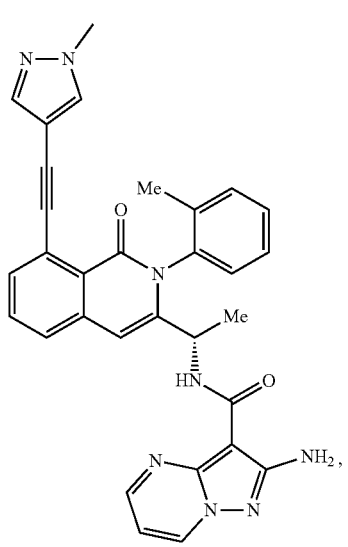 [SMILES: Cc1ccccc1-n1c([C@H](C)NC(=O)c2c(N)nn3cccnc23)cc2cccc(C#Cc3cnn(C)c3)c2c1=O]
Compound 101
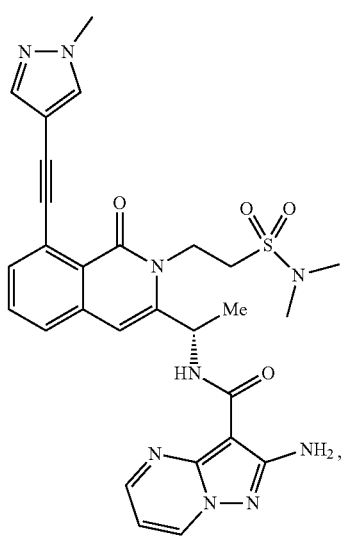 [SMILES: C[C@H](NC(=O)c1c(N)nn2cccnc12)c1cc2cccc(C#Cc3cnn(C)c3)c2c(=O)n1CCS(=O)(=O)N(C)C]
Compound 104

TABLE 3-continued
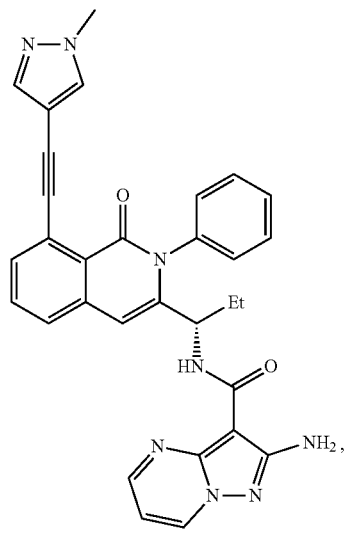 [SMILES: CC[C@H](NC(=O)c1c(N)nn2cccnc12)c1cc2cccc(C#Cc3cnn(C)c3)c2c(=O)n1-c1ccccc1]
Compound 105
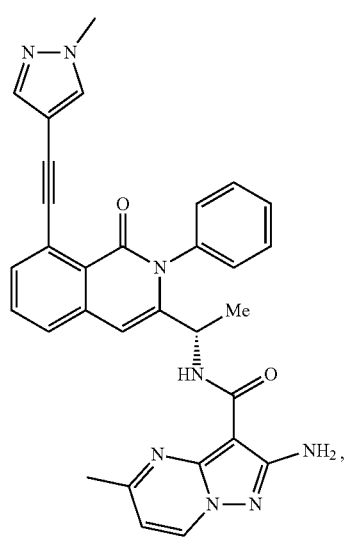 [SMILES: Cc1ccn2nc(N)c(C(=O)N[C@@H](C)c3cc4cccc(C#Cc5cnn(C)c5)c4c(=O)n3-c3ccccc3)c2n1]
Compound 106
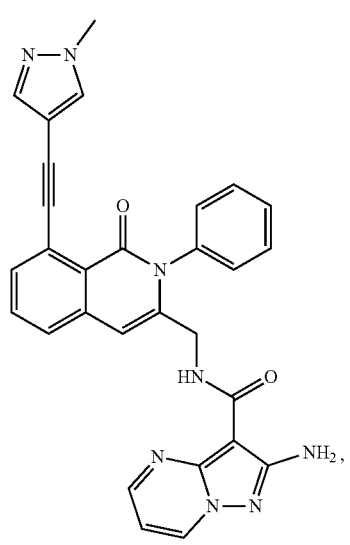 [SMILES: Cn1cc(C#Cc2cccc3cc(CNC(=O)c4c(N)nn5cccnc45)n(-c4ccccc4)c(=O)c23)cn1]
Compound 107
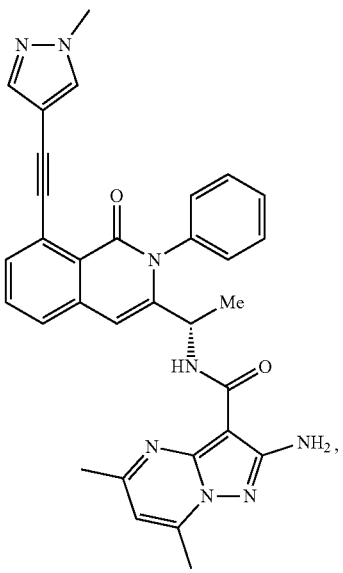 [SMILES: Cc1cc(C)n2nc(N)c(C(=O)N[C@@H](C)c3cc4cccc(C#Cc5cnn(C)c5)c4c(=O)n3-c3ccccc3)c2n1]
Compound 108
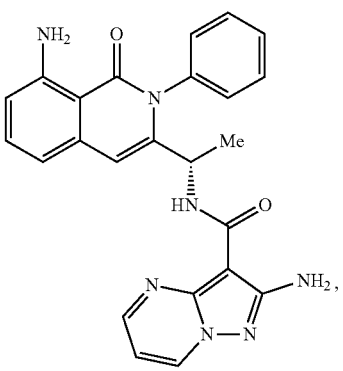 [SMILES: C[C@H](NC(=O)c1c(N)nn2cccnc12)c1cc2cccc(N)c2c(=O)n1-c1ccccc1]
Compound 109
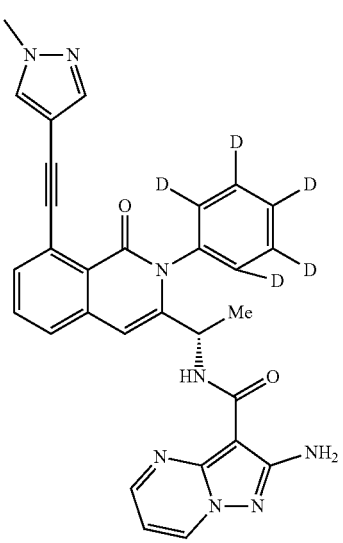 [SMILES: [2H]c1c([2H])c([2H])c(-n2c([C@H](C)NC(=O)c3c(N)nn4cccnc34)cc3cccc(C#Cc4cnn(C)c4)c3c2=O)c([2H])c1[2H]]
Compound 110

TABLE 4
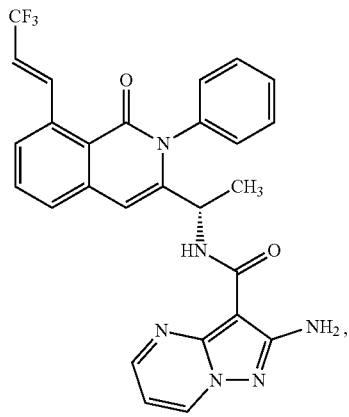 [SMILES: C[C@H](NC(=O)c1c(N)nn2cccnc12)c1cc2cccc(/C=C/C(F)(F)F)c2c(=O)n1-c1ccccc1]
Compound 1001
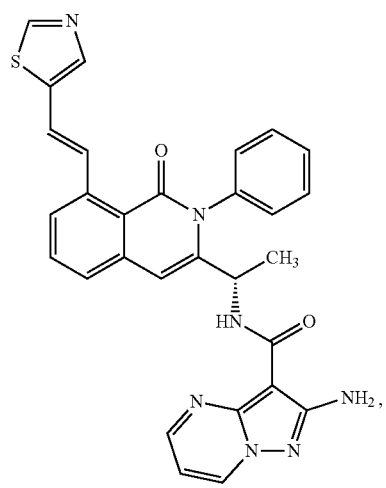 [SMILES: C[C@H](NC(=O)c1c(N)nn2cccnc12)c1cc2cccc(/C=C/c3cncs3)c2c(=O)n1-c1ccccc1]
Compound 1002
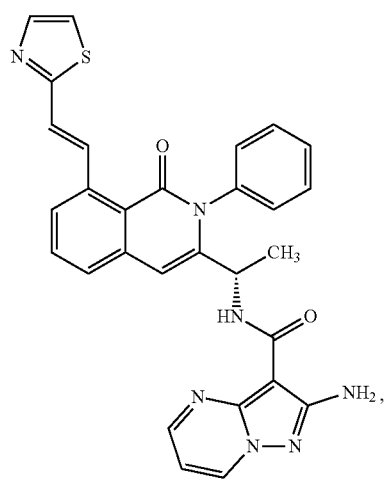 [SMILES: C[C@H](NC(=O)c1c(N)nn2cccnc12)c1cc2cccc(/C=C/c3nccs3)c2c(=O)n1-c1ccccc1]
Compound 1003

TABLE 4-continued
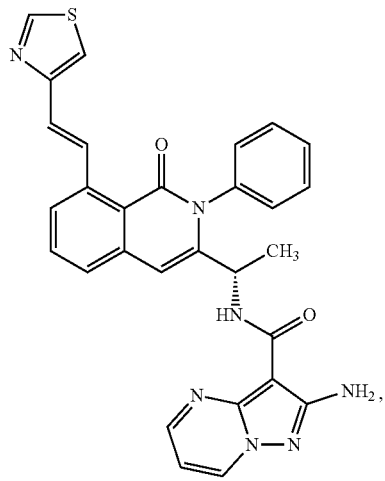 [SMILES: C[C@H](NC(=O)c1c(N)nn2cccnc12)c1cc2cccc(/C=C/c3cscn3)c2c(=O)n1-c1ccccc1]
Compound 1004
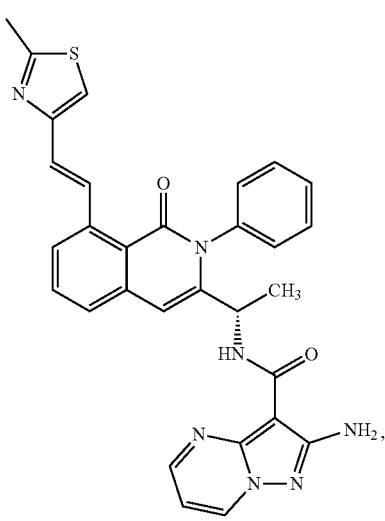 [SMILES: Cc1nc(/C=C/c2cccc3cc([C@H](C)NC(=O)c4c(N)nn5cccnc45)n(-c4ccccc4)c(=O)c23)cs1]
Compound 1005
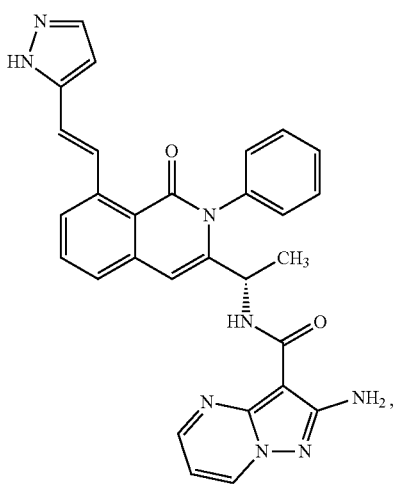 [SMILES: C[C@H](NC(=O)c1c(N)nn2cccnc12)c1cc2cccc(/C=C/c3ccn[nH]3)c2c(=O)n1-c1ccccc1]
Compound 1006

TABLE 4-continued
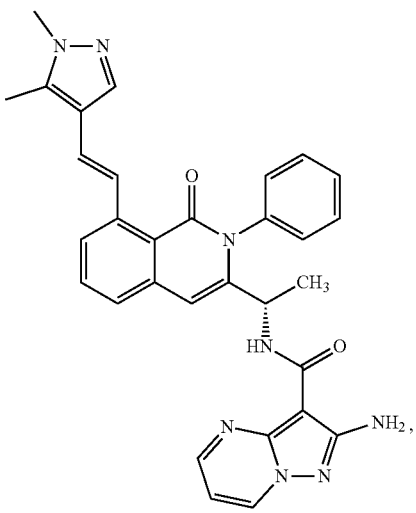 [SMILES: Cc1c(/C=C/c2cccc3cc([C@H](C)NC(=O)c4c(N)nn5cccnc45)n(-c4ccccc4)c(=O)c23)cnn1C]
Compound 1007
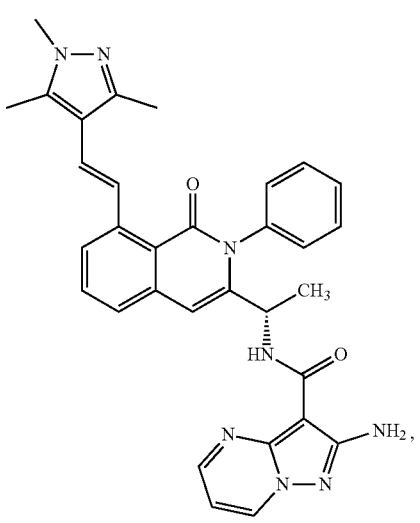 [SMILES: Cc1nn(C)c(C)c1/C=C/c1cccc2cc([C@H](C)NC(=O)c3c(N)nn4cccnc34)n(-c3ccccc3)c(=O)c12]
Compound 1008
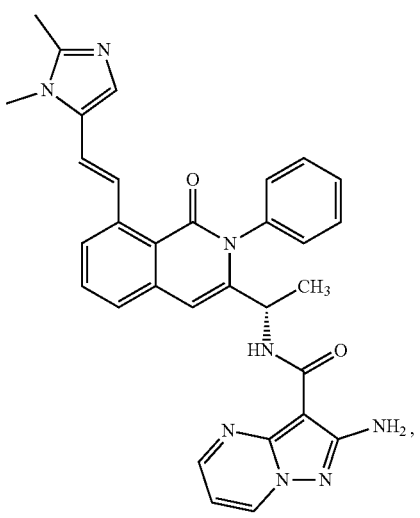 [SMILES: Cc1ncc(/C=C/c2cccc3cc([C@H](C)NC(=O)c4c(N)nn5cccnc45)n(-c4ccccc4)c(=O)c23)n1C]
Compound 1009

TABLE 4-continued
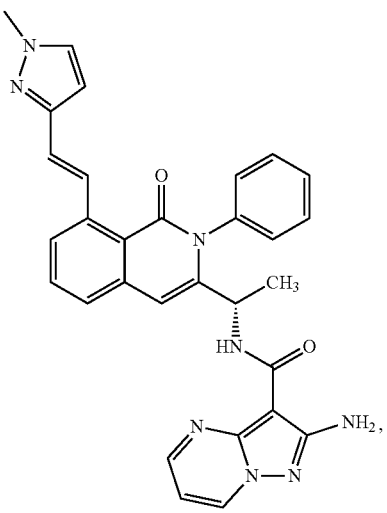
Compound 1010
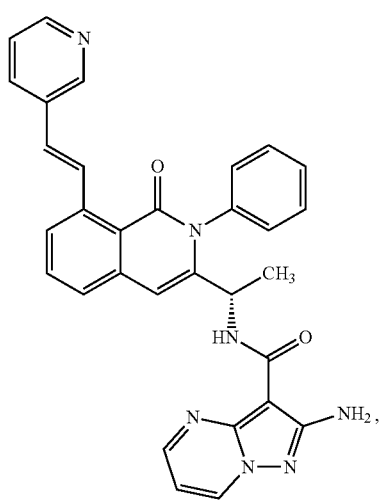 [SMILES: C[C@H](NC(=O)c1c(N)nn2cccnc12)c1cc2cccc(/C=C/c3cccnc3)c2c(=O)n1-c1ccccc1]
Compound 1011
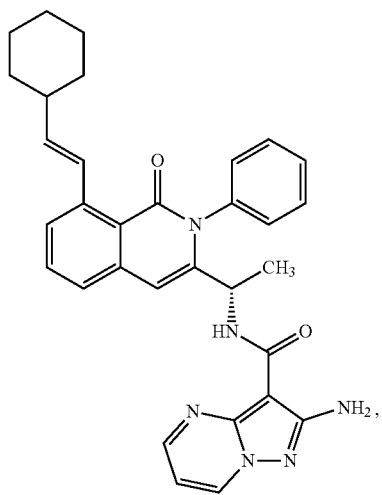 [SMILES: C[C@H](NC(=O)c1c(N)nn2cccnc12)c1cc2cccc(/C=C/C3CCCCC3)c2c(=O)n1-c1ccccc1]
Compound 1012

TABLE 4-continued
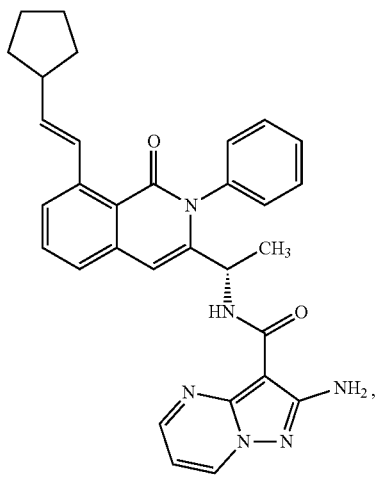 [SMILES: C[C@H](NC(=O)c1c(N)nn2cccnc12)c1cc2cccc(/C=C/C3CCCC3)c2c(=O)n1-c1ccccc1]
Compound 1013
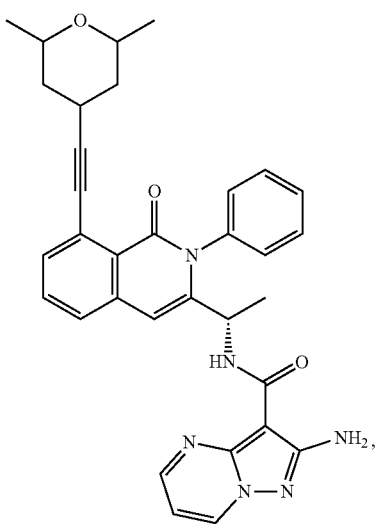 [SMILES: CC1CC(C#Cc2cccc3cc([C@H](C)NC(=O)c4c(N)nn5cccnc45)n(-c4ccccc4)c(=O)c23)CC(C)O1]
Compound 1014
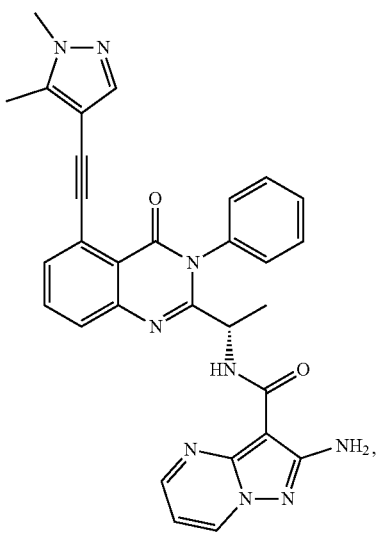 [SMILES: Cc1c(C#Cc2cccc3nc([C@H](C)NC(=O)c4c(N)nn5cccnc45)n(-c4ccccc4)c(=O)c23)cnn1C]
Compound 1015

TABLE 4-continued
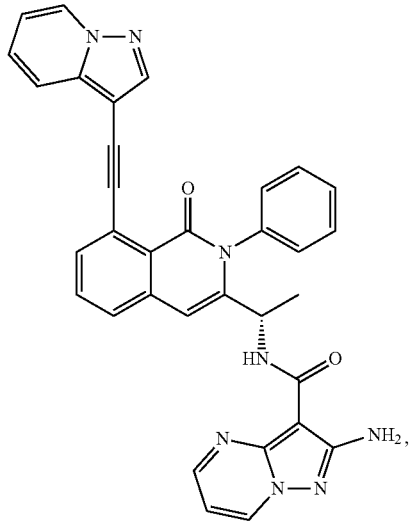 [SMILES: C[C@H](NC(=O)c1c(N)nn2cccnc12)c1cc2cccc(C#Cc3cnn4ccccc34)c2c(=O)n1-c1ccccc1]
Compound 1016
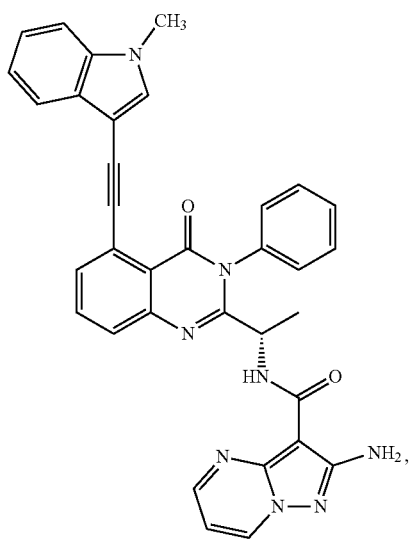 [SMILES: C[C@H](NC(=O)c1c(N)nn2cccnc12)c1nc2cccc(C#Cc3cn(C)c4ccccc34)c2c(=O)n1-c1ccccc1]
Compound 1017
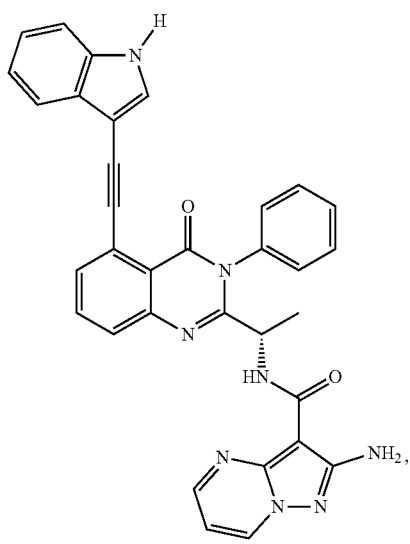 [SMILES: C[C@H](NC(=O)c1c(N)nn2cccnc12)c1nc2cccc(C#Cc3c[nH]c4ccccc34)c2c(=O)n1-c1ccccc1]
Compound 1018

TABLE 4-continued
| | |
|---|---|
| 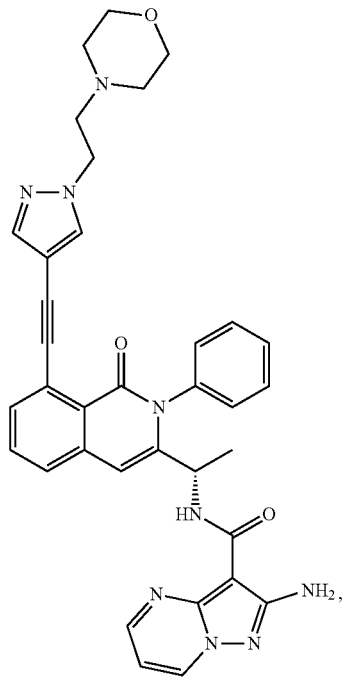 [SMILES: C[C@H](NC(=O)c1c(N)nn2cccnc12)c1cc2cccc(C#Cc3cnn(CCN4CCOCC4)c3)c2c(=O)n1-c1ccccc1] | Compound 1019 |
| 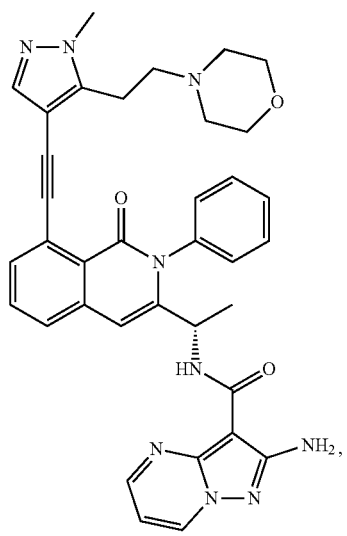 [SMILES: C[C@H](NC(=O)c1c(N)nn2cccnc12)c1cc2cccc(C#Cc3cnn(C)c3CCN3CCOCC3)c2c(=O)n1-c1ccccc1] | Compound 1020 |

TABLE 4-continued
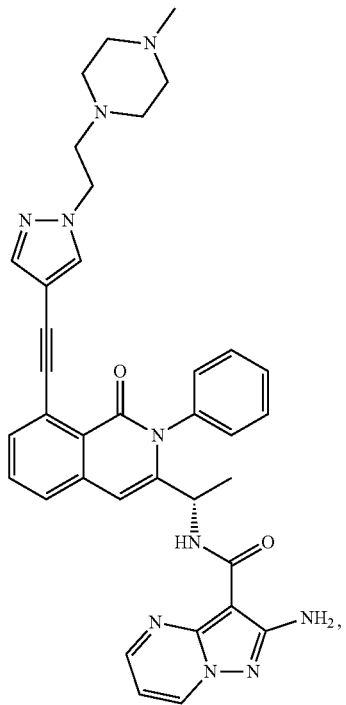 [SMILES: C[C@H](NC(=O)c1c(N)nn2cccnc12)c1cc2cccc(C#Cc3cnn(CCN4CCN(C)CC4)c3)c2c(=O)n1-c1ccccc1]
Compound 1021
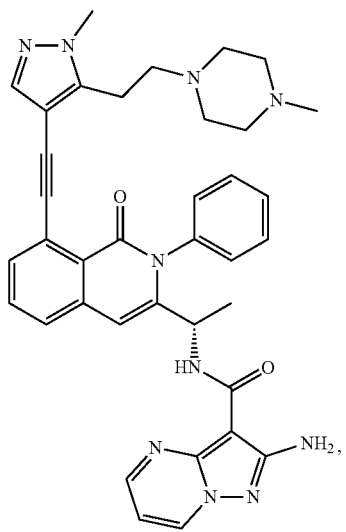 [SMILES: C[C@H](NC(=O)c1c(N)nn2cccnc12)c1cc2cccc(C#Cc3cnn(C)c3CCN3CCN(C)CC3)c2c(=O)n1-c1ccccc1]
Compound 1022

TABLE 4-continued
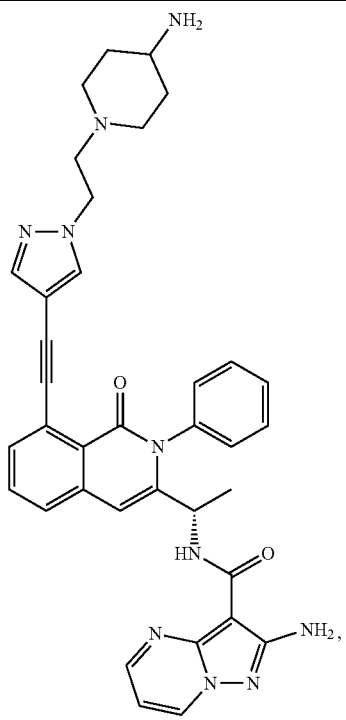
Compound 1023
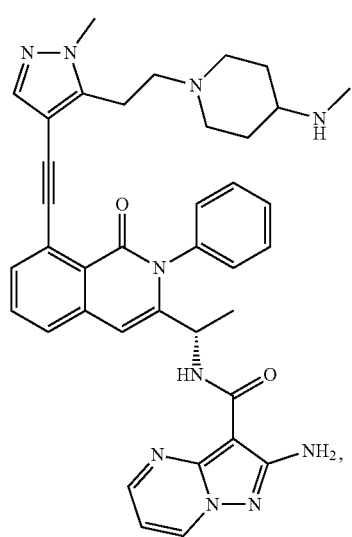 [SMILES: CNC1CCN(CCc2c(C#Cc3cccc4cc([C@H](C)NC(=O)c5c(N)nn6cccnc56)n(-c5ccccc5)c(=O)c34)cnn2C)CC1]
Compound 1024

TABLE 4-continued
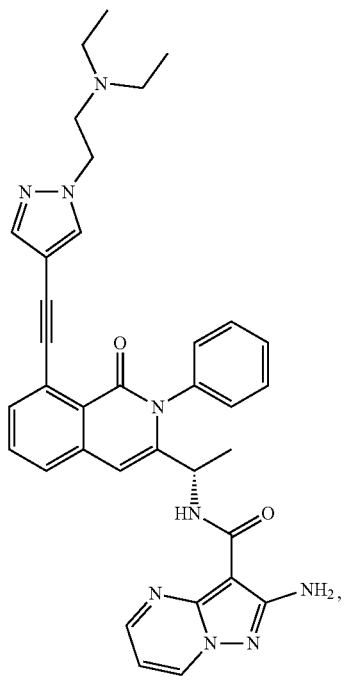 [SMILES: CCN(CC)CCn1cc(C#Cc2cccc3cc([C@H](C)NC(=O)c4c(N)nn5cccnc45)n(-c4ccccc4)c(=O)c23)cn1]
Compound 1025
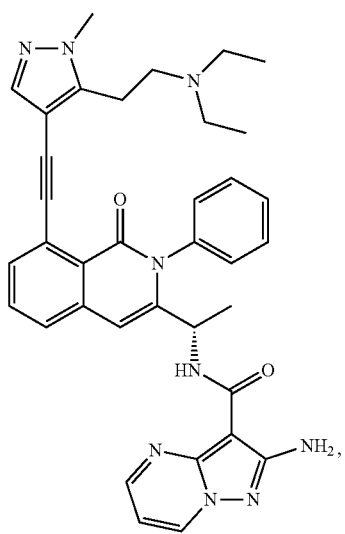 [SMILES: CCN(CC)CCc1c(C#Cc2cccc3cc([C@H](C)NC(=O)c4c(N)nn5cccnc45)n(-c4ccccc4)c(=O)c23)cnn1C]
Compound 1026

TABLE 4-continued
Compound 1027
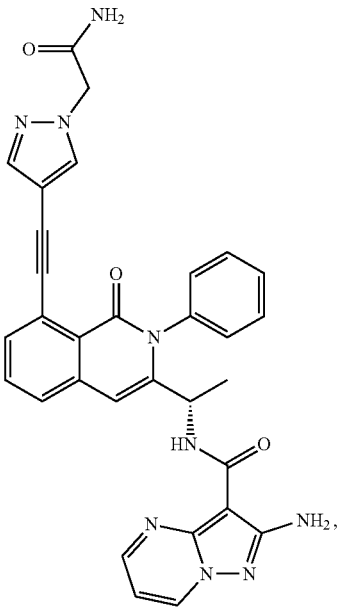 [SMILES: C[C@H](NC(=O)c1c(N)nn2cccnc12)c1cc2cccc(C#Cc3cnn(CC(N)=O)c3)c2c(=O)n1-c1ccccc1]
Compound 1028
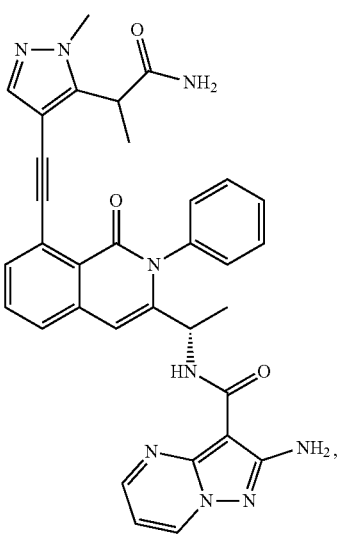 [SMILES: CC(C(N)=O)c1c(C#Cc2cccc3cc([C@H](C)NC(=O)c4c(N)nn5cccnc45)n(-c4ccccc4)c(=O)c23)cnn1C]

TABLE 4-continued
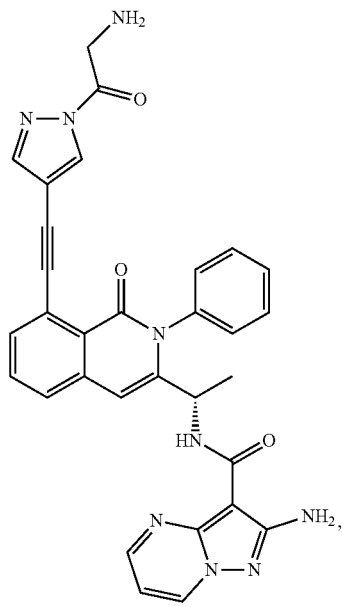 [SMILES: C[C@H](NC(=O)c1c(N)nn2cccnc12)c1cc2cccc(C#Cc3cnn(C(=O)CN)c3)c2c(=O)n1-c1ccccc1]
Compound 1029
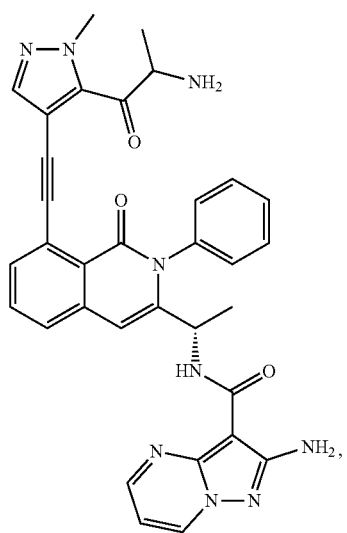 [SMILES: CC(N)C(=O)c1c(C#Cc2cccc3cc([C@H](C)NC(=O)c4c(N)nn5cccnc45)n(-c4ccccc4)c(=O)c23)cnn1C]
Compound 1030

TABLE 4-continued
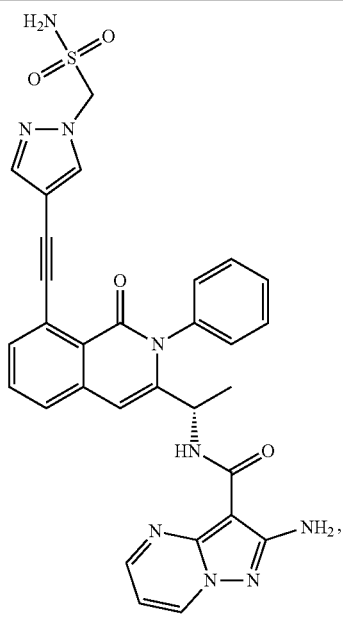 [SMILES: C[C@H](NC(=O)c1c(N)nn2cccnc12)c1cc2cccc(C#Cc3cnn(CS(N)(=O)=O)c3)c2c(=O)n1-c1ccccc1]
Compound 1031
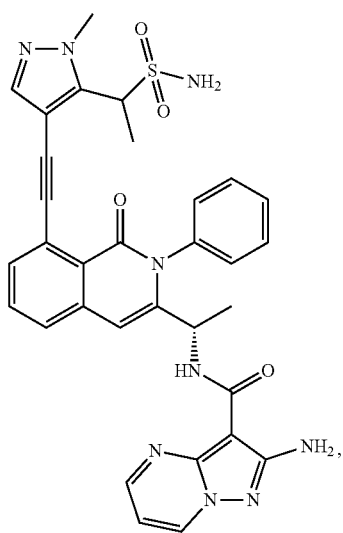 [SMILES: CC(c1c(C#Cc2cccc3cc([C@H](C)NC(=O)c4c(N)nn5cccnc45)n(-c4ccccc4)c(=O)c23)cnn1C)S(N)(=O)=O]
Compound 1032

TABLE 4-continued
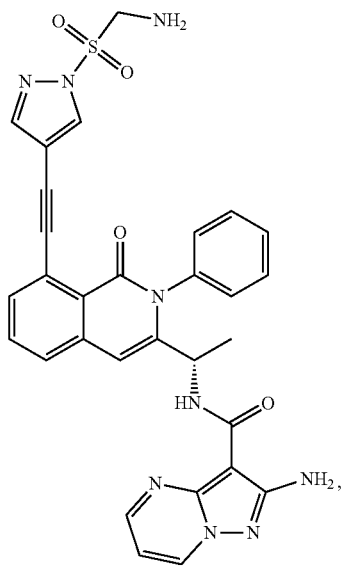 [SMILES: C[C@H](NC(=O)c1c(N)nn2cccnc12)c1cc2cccc(C#Cc3cnn(S(=O)(=O)CN)c3)c2c(=O)n1-c1ccccc1]
Compound 1033
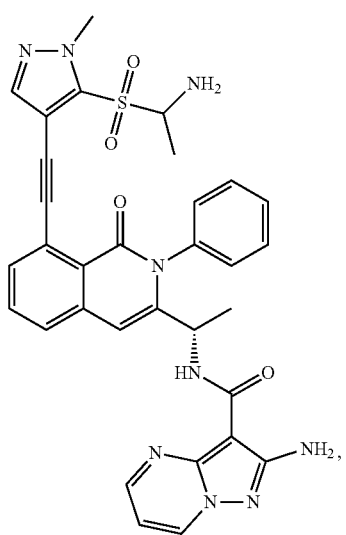 [SMILES: CC(N)S(=O)(=O)c1c(C#Cc2cccc3cc([C@H](C)NC(=O)c4c(N)nn5cccnc45)n(-c4ccccc4)c(=O)c23)cnn1C]
Compound 1034

TABLE 4-continued
Compound 1035
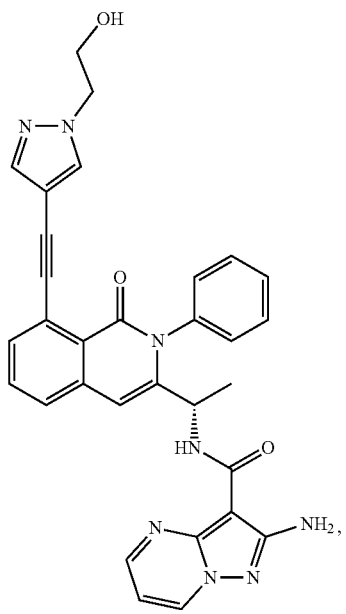 [SMILES: C[C@H](NC(=O)c1c(N)nn2cccnc12)c1cc2cccc(C#Cc3cnn(CCO)c3)c2c(=O)n1-c1ccccc1]
Compound 1036
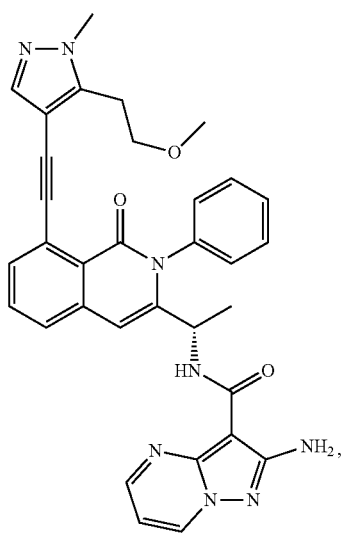 [SMILES: COCCc1c(C#Cc2cccc3cc([C@H](C)NC(=O)c4c(N)nn5cccnc45)n(-c4ccccc4)c(=O)c23)cnn1C]

TABLE 4-continued
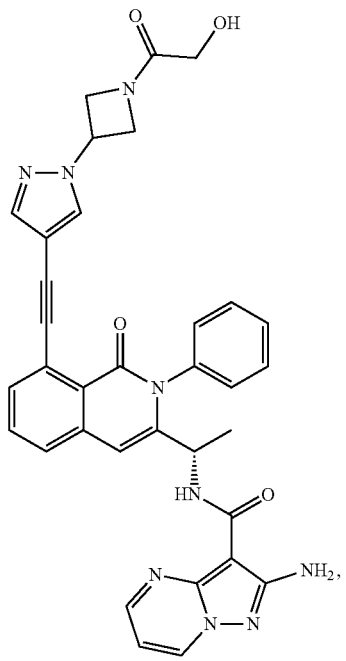 [SMILES: C[C@H](NC(=O)c1c(N)nn2cccnc12)c1cc2cccc(C#Cc3cnn(C4CN(C(=O)CO)C4)c3)c2c(=O)n1-c1ccccc1]
Compound 1037
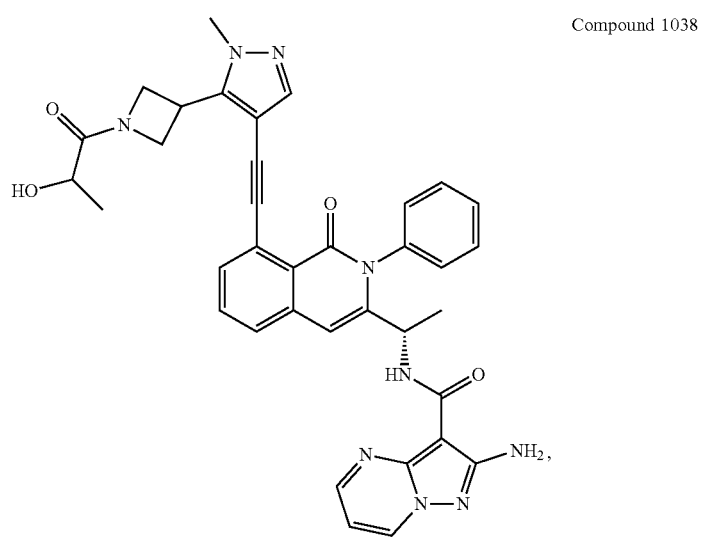
Compound 1038

TABLE 4-continued
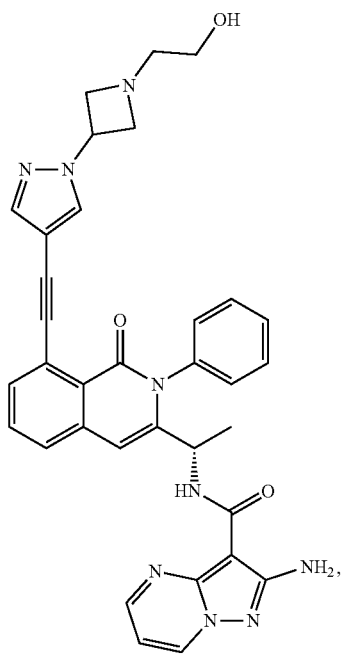 [SMILES: C[C@H](NC(=O)c1c(N)nn2cccnc12)c1cc2cccc(C#Cc3cnn(C4CN(CCO)C4)c3)c2c(=O)n1-c1ccccc1]
Compound 1039
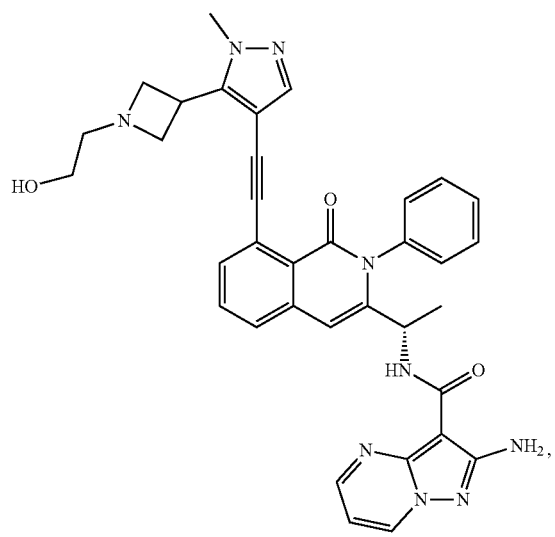 [SMILES: C[C@H](NC(=O)c1c(N)nn2cccnc12)c1cc2cccc(C#Cc3cnn(C)c3C3CN(CCO)C3)c2c(=O)n1-c1ccccc1]
Compound 1040

TABLE 4-continued
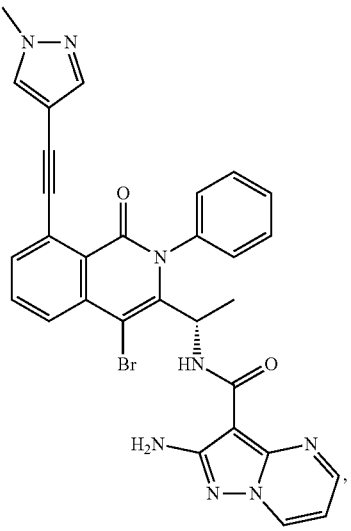 [SMILES: C[C@H](NC(=O)c1c(N)nn2cccnc12)c1c(Br)c2cccc(C#Cc3cnn(C)c3)c2c(=O)n1-c1ccccc1]
Compound 1041
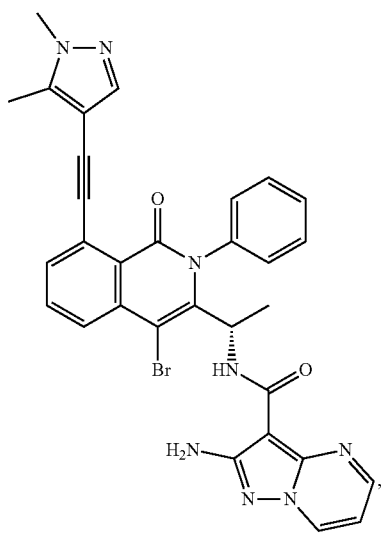 [SMILES: Cc1c(C#Cc2cccc3c(Br)c([C@H](C)NC(=O)c4c(N)nn5cccnc45)n(-c4ccccc4)c(=O)c23)cnn1C]
Compound 1042
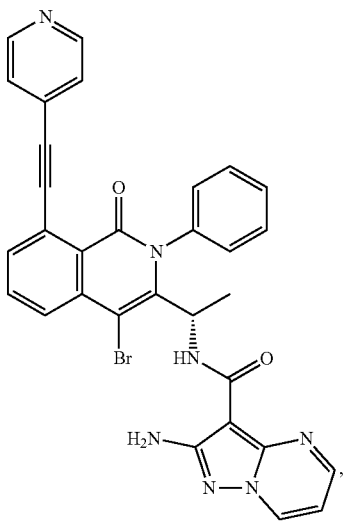 [SMILES: C[C@H](NC(=O)c1c(N)nn2cccnc12)c1c(Br)c2cccc(C#Cc3ccncc3)c2c(=O)n1-c1ccccc1]
Compound 1043

TABLE 4-continued
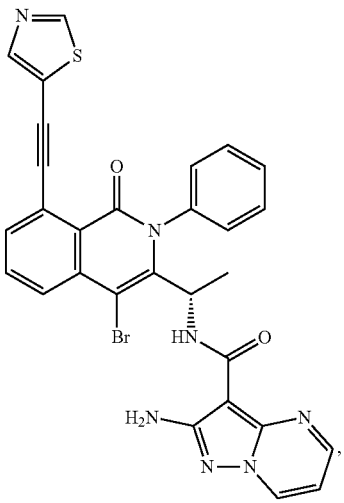 [SMILES: C[C@H](NC(=O)c1c(N)nn2cccnc12)c1c(Br)c2cccc(C#Cc3cncs3)c2c(=O)n1-c1ccccc1]
Compound 1044
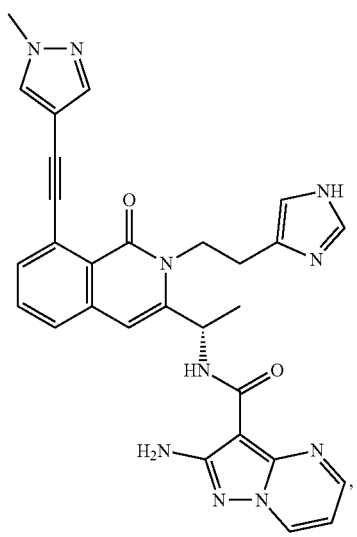
Compound 1045
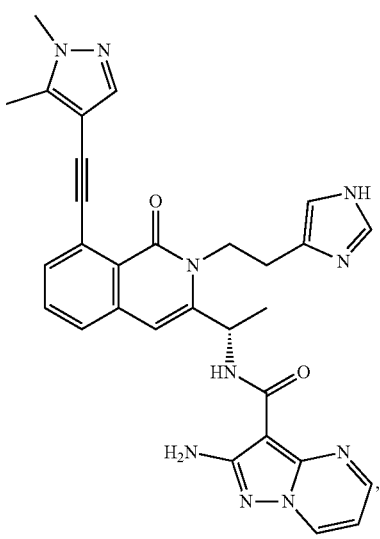 [SMILES: Cc1c(C#Cc2cccc3cc([C@H](C)NC(=O)c4c(N)nn5cccnc45)n(CCc4c[nH]cn4)c(=O)c23)cnn1C]
Compound 1046

TABLE 4-continued
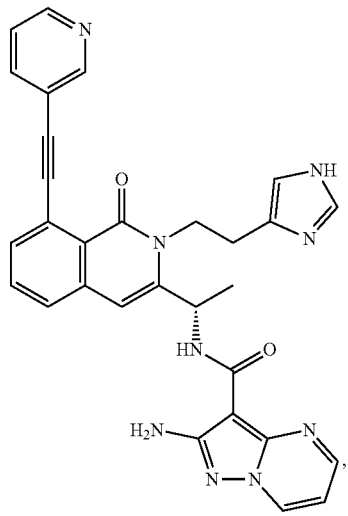
Compound 1047
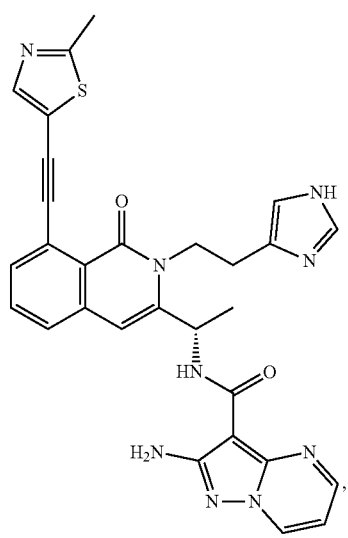
Compound 1048
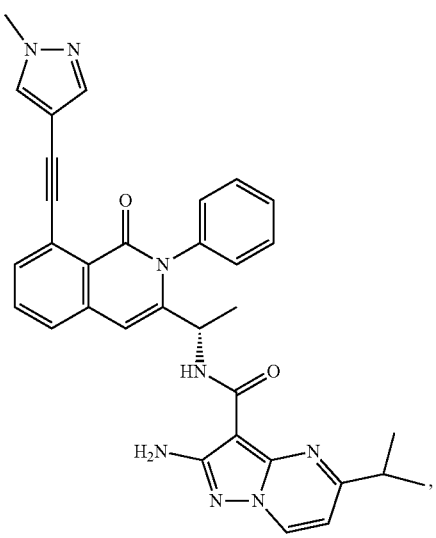 [SMILES: CC(C)c1ccn2nc(N)c(C(=O)N[C@@H](C)c3cc4cccc(C#Cc5cnn(C)c5)c4c(=O)n3-c3ccccc3)c2n1]
Compound 1049

TABLE 4-continued
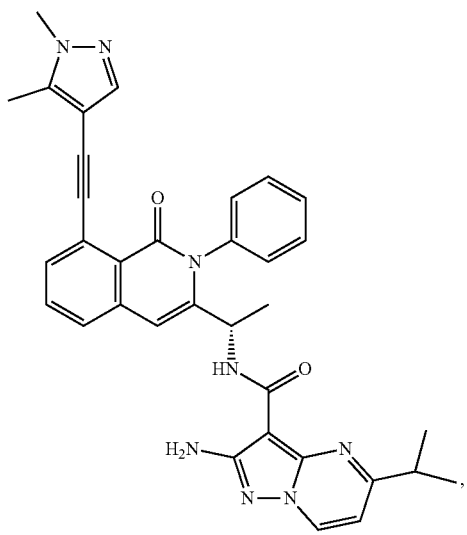 [SMILES: Cc1c(C#Cc2cccc3cc([C@H](C)NC(=O)c4c(N)nn5ccc(C(C)C)nc45)n(-c4ccccc4)c(=O)c23)cnn1C]
Compound 1050
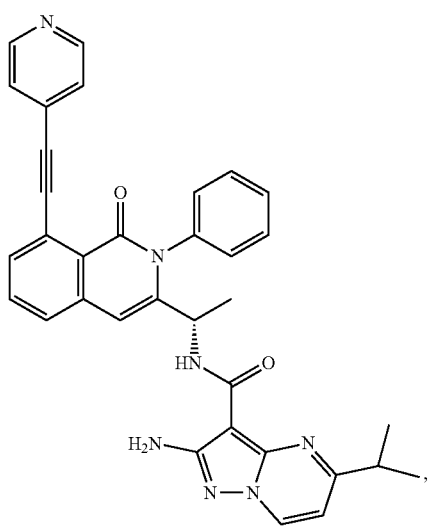
Compound 1051
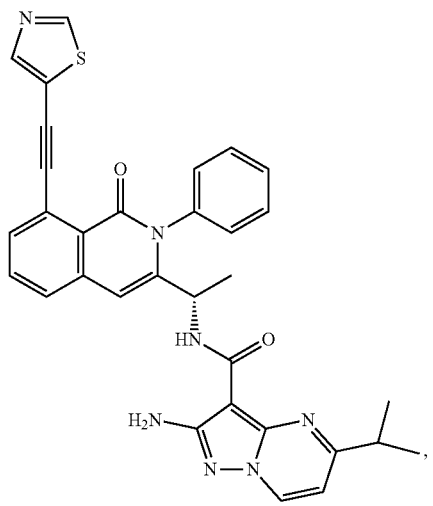
Compound 1052

TABLE 4-continued
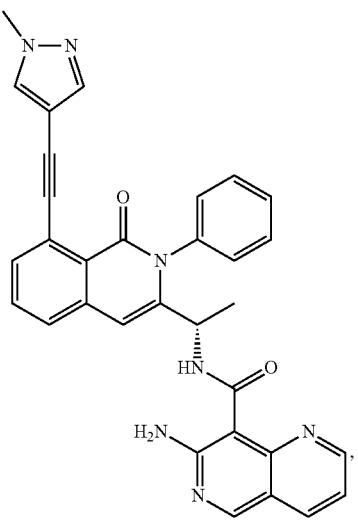
Compound 1053
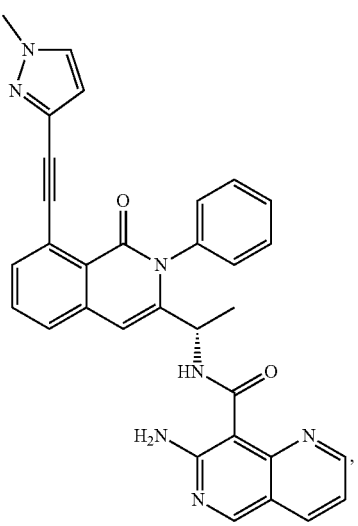 [SMILES: C[C@H](NC(=O)c1c(N)ncc2cccnc12)c1cc2cccc(C#Cc3ccn(C)n3)c2c(=O)n1-c1ccccc1]
Compound 1054
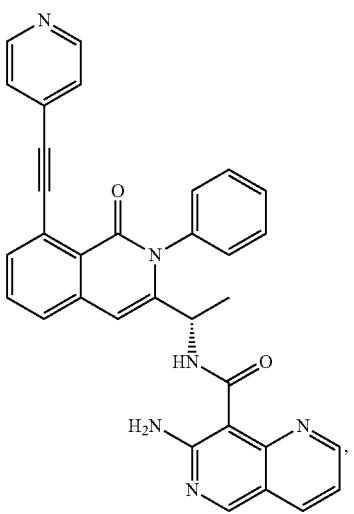 [SMILES: C[C@H](NC(=O)c1c(N)ncc2cccnc12)c1cc2cccc(C#Cc3ccncc3)c2c(=O)n1-c1ccccc1]
Compound 1055

TABLE 4-continued
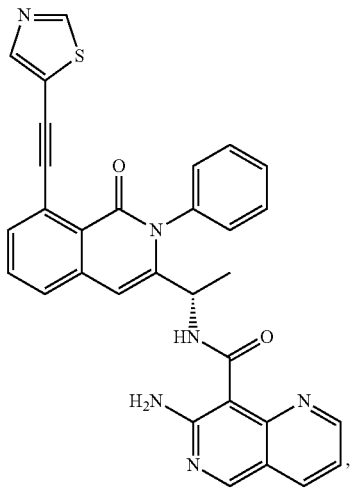 [SMILES: C[C@H](NC(=O)c1c(N)ncc2cccnc12)c1cc2cccc(C#Cc3cncs3)c2c(=O)n1-c1ccccc1]
Compound 1056
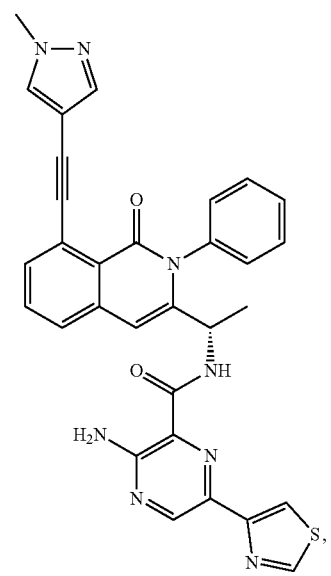 [SMILES: C[C@H](NC(=O)c1nc(-c2cscn2)cnc1N)c1cc2cccc(C#Cc3cnn(C)c3)c2c(=O)n1-c1ccccc1]
Compound 1057
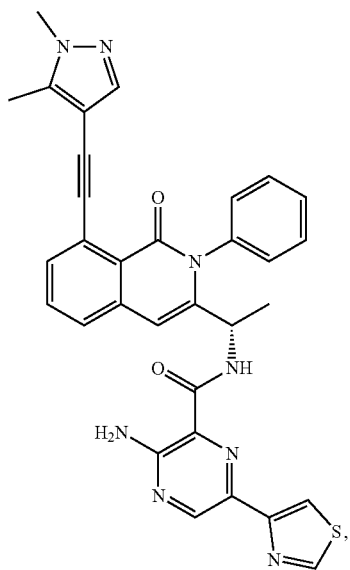 [SMILES: Cc1c(C#Cc2cccc3cc([C@H](C)NC(=O)c4nc(-c5cscn5)cnc4N)n(-c4ccccc4)c(=O)c23)cnn1C]
Compound 1058

TABLE 4-continued
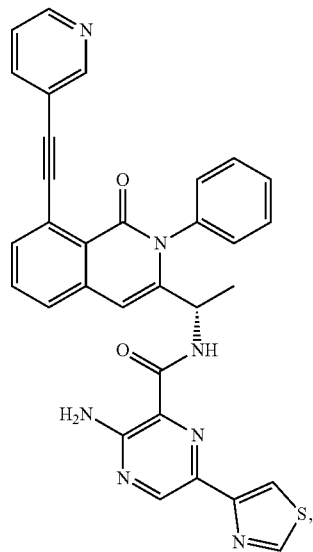 [SMILES: C[C@H](NC(=O)c1nc(-c2cscn2)cnc1N)c1cc2cccc(C#Cc3cccnc3)c2c(=O)n1-c1ccccc1]
Compound 1059
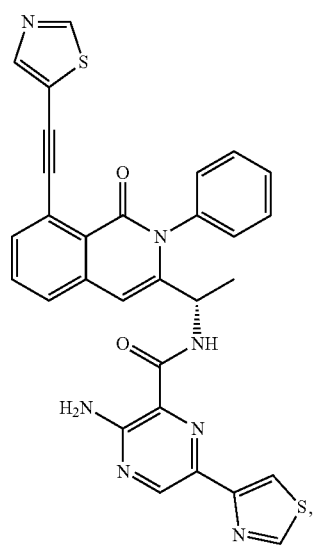 [SMILES: C[C@H](NC(=O)c1nc(-c2cscn2)cnc1N)c1cc2cccc(C#Cc3cncs3)c2c(=O)n1-c1ccccc1]
Compound 1060

TABLE 4-continued
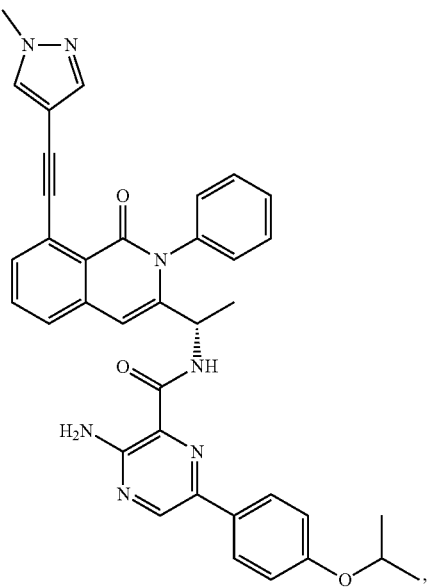 [SMILES: CC(C)Oc1ccc(-c2cnc(N)c(C(=O)N[C@@H](C)c3cc4cccc(C#Cc5cnn(C)c5)c4c(=O)n3-c3ccccc3)n2)cc1]
Compound 1061
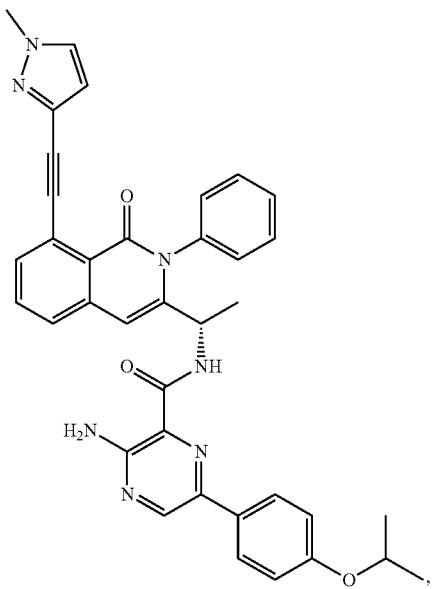 [SMILES: CC(C)Oc1ccc(-c2cnc(N)c(C(=O)N[C@@H](C)c3cc4cccc(C#Cc5ccn(C)n5)c4c(=O)n3-c3ccccc3)n2)cc1]
Compound 1062

TABLE 4-continued
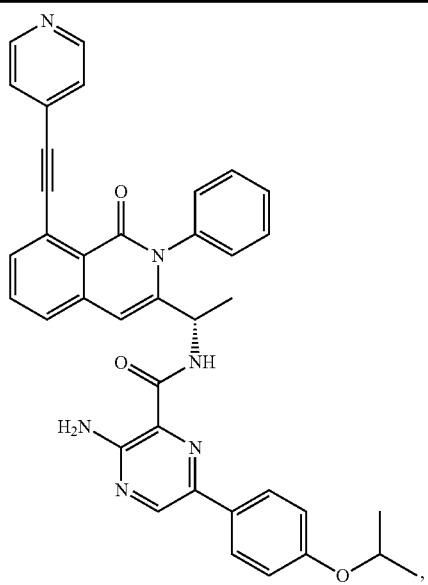
Compound 1063
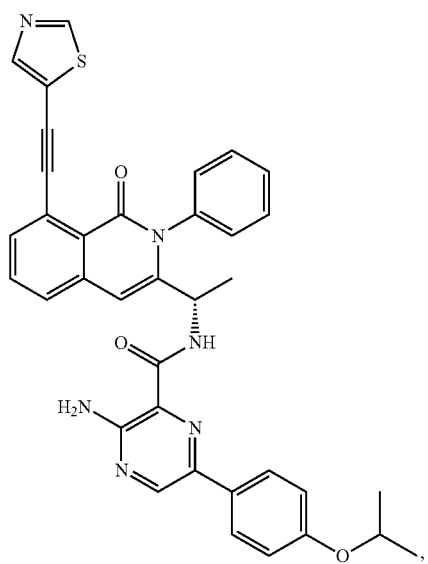 [SMILES: CC(C)Oc1ccc(-c2cnc(N)c(C(=O)N[C@@H](C)c3cc4cccc(C#Cc5cncs5)c4c(=O)n3-c3ccccc3)n2)cc1]
Compound 1064

TABLE 4-continued
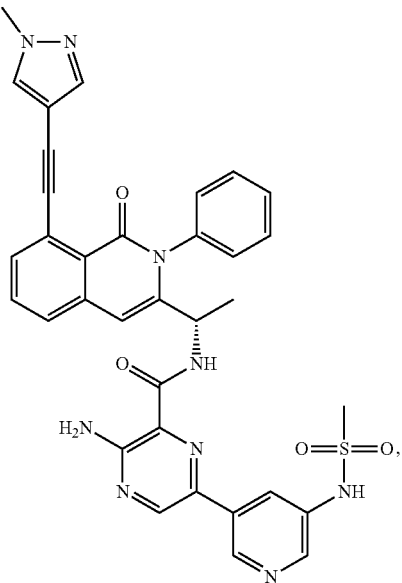 [SMILES: C[C@H](NC(=O)c1nc(-c2cncc(NS(C)(=O)=O)c2)cnc1N)c1cc2cccc(C#Cc3cnn(C)c3)c2c(=O)n1-c1ccccc1]
Compound 1065
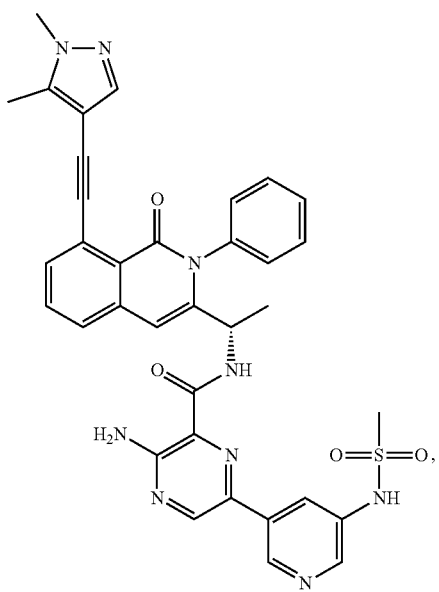 [SMILES: Cc1c(C#Cc2cccc3cc([C@H](C)NC(=O)c4nc(-c5cncc(NS(C)(=O)=O)c5)cnc4N)n(-c4ccccc4)c(=O)c23)cnn1C]
Compound 1066

TABLE 4-continued
Compound 1067
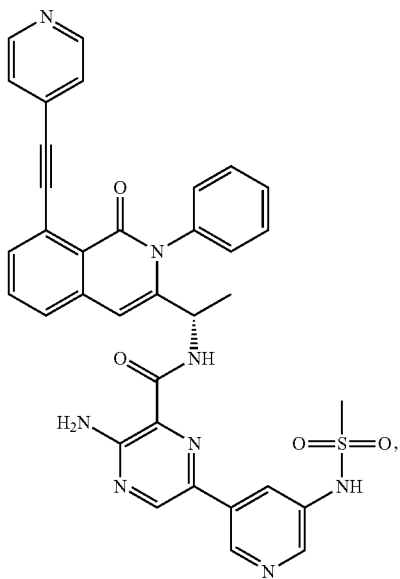 [SMILES: C[C@H](NC(=O)c1nc(-c2cncc(NS(C)(=O)=O)c2)cnc1N)c1cc2cccc(C#Cc3ccncc3)c2c(=O)n1-c1ccccc1]
Compound 1068
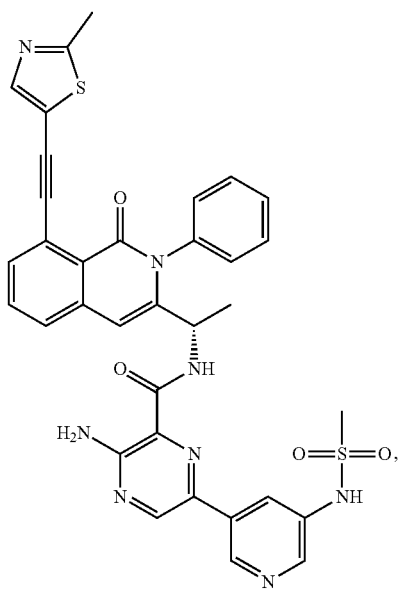 [SMILES: Cc1ncc(C#Cc2cccc3cc([C@H](C)NC(=O)c4nc(-c5cncc(NS(C)(=O)=O)c5)cnc4N)n(-c4ccccc4)c(=O)c23)s1]

TABLE 4-continued
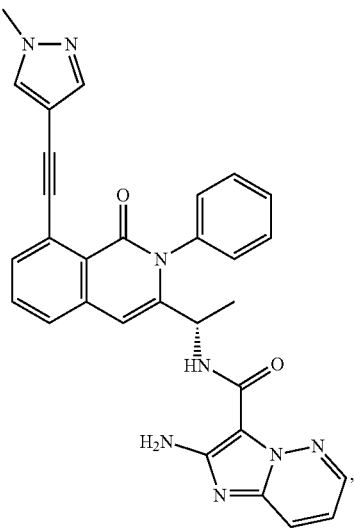 [SMILES: C[C@H](NC(=O)c1c(N)nc2cccnn12)c1cc2cccc(C#Cc3cnn(C)c3)c2c(=O)n1-c1ccccc1]
Compound 1069
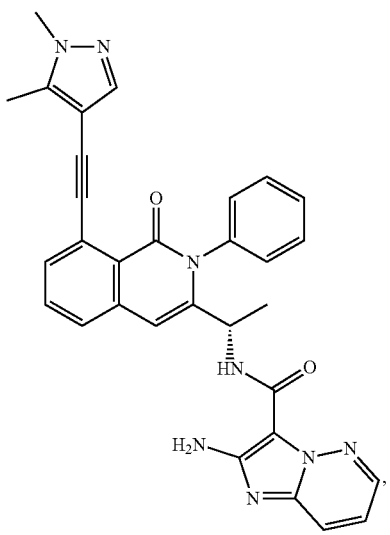 [SMILES: Cc1c(C#Cc2cccc3cc([C@H](C)NC(=O)c4c(N)nc5cccnn45)n(-c4ccccc4)c(=O)c23)cnn1C]
Compound 1070
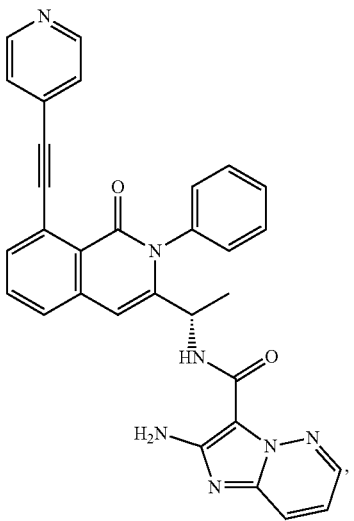 [SMILES: C[C@H](NC(=O)c1c(N)nc2cccnn12)c1cc2cccc(C#Cc3ccncc3)c2c(=O)n1-c1ccccc1]
Compound 1071

TABLE 4-continued
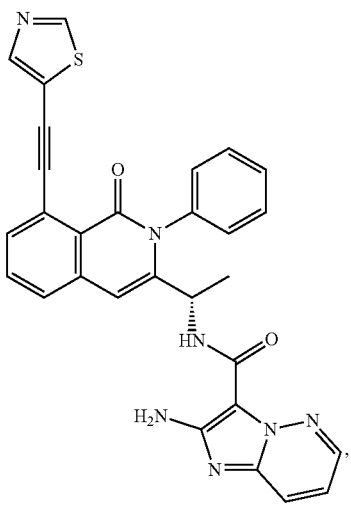 [SMILES: C[C@H](NC(=O)c1c(N)nc2cccnn12)c1cc2cccc(C#Cc3cncs3)c2c(=O)n1-c1ccccc1]
Compound 1072
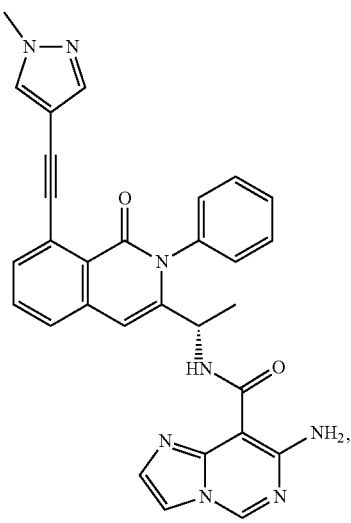 [SMILES: C[C@H](NC(=O)c1c(N)ncn2ccnc12)c1cc2cccc(C#Cc3cnn(C)c3)c2c(=O)n1-c1ccccc1]
Compound 1073
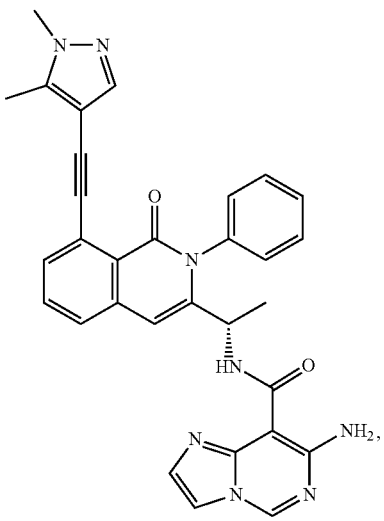 [SMILES: Cc1c(C#Cc2cccc3cc([C@H](C)NC(=O)c4c(N)ncn5ccnc45)n(-c4ccccc4)c(=O)c23)cnn1C]
Compound 1074

TABLE 4-continued
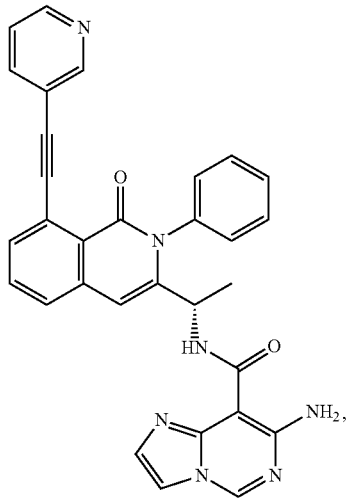 [SMILES: C[C@H](NC(=O)c1c(N)ncn2ccnc12)c1cc2cccc(C#Cc3cccnc3)c2c(=O)n1-c1ccccc1]
Compound 1075
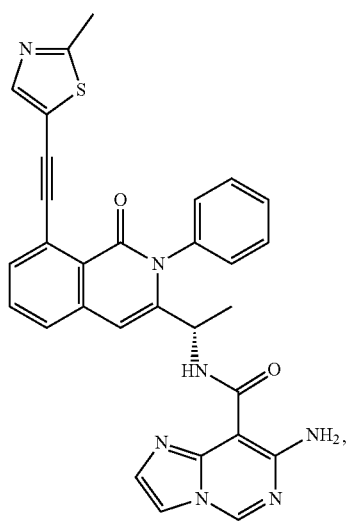 [SMILES: Cc1ncc(C#Cc2cccc3cc([C@H](C)NC(=O)c4c(N)ncn5ccnc45)n(-c4ccccc4)c(=O)c23)s1]
Compound 1076
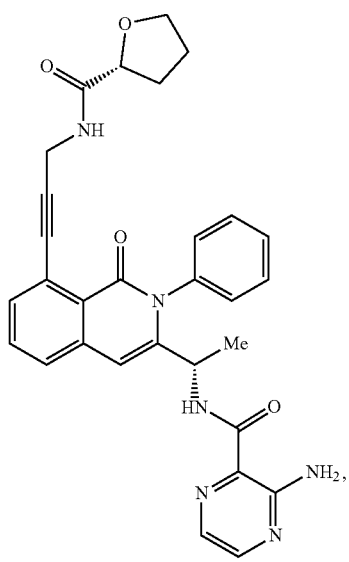 [SMILES: C[C@H](NC(=O)c1nccnc1N)c1cc2cccc(C#CCNC(=O)[C@H]3CCCO3)c2c(=O)n1-c1ccccc1]
Compound 1077

TABLE 4-continued
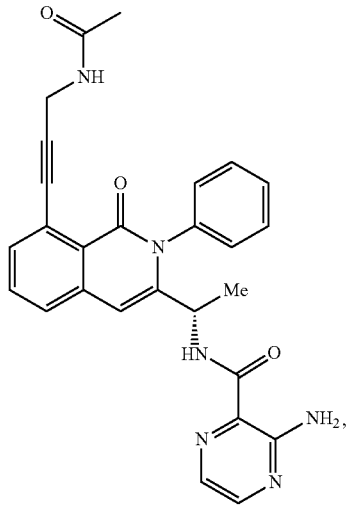 [SMILES: CC(=O)NCC#Cc1cccc2cc([C@H](C)NC(=O)c3nccnc3N)n(-c3ccccc3)c(=O)c12]
Compound 1078
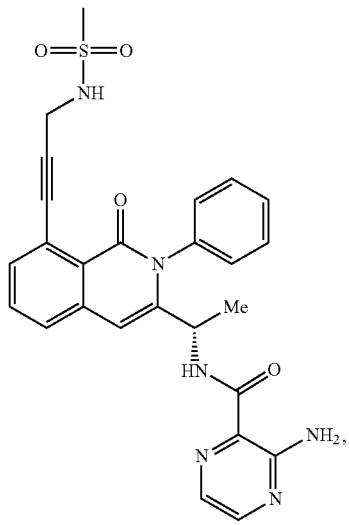 [SMILES: C[C@H](NC(=O)c1nccnc1N)c1cc2cccc(C#CCNS(C)(=O)=O)c2c(=O)n1-c1ccccc1]
Compound 1079
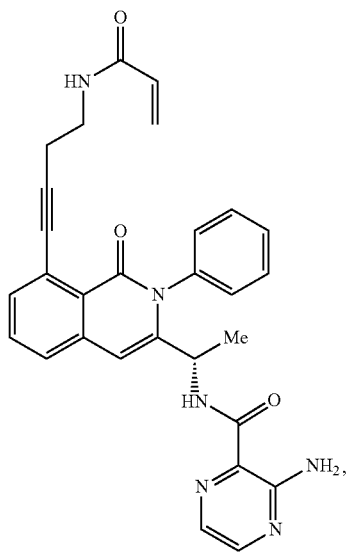 [SMILES: C=CC(=O)NCCC#Cc1cccc2cc([C@H](C)NC(=O)c3nccnc3N)n(-c3ccccc3)c(=O)c12]
Compound 1080

TABLE 4-continued
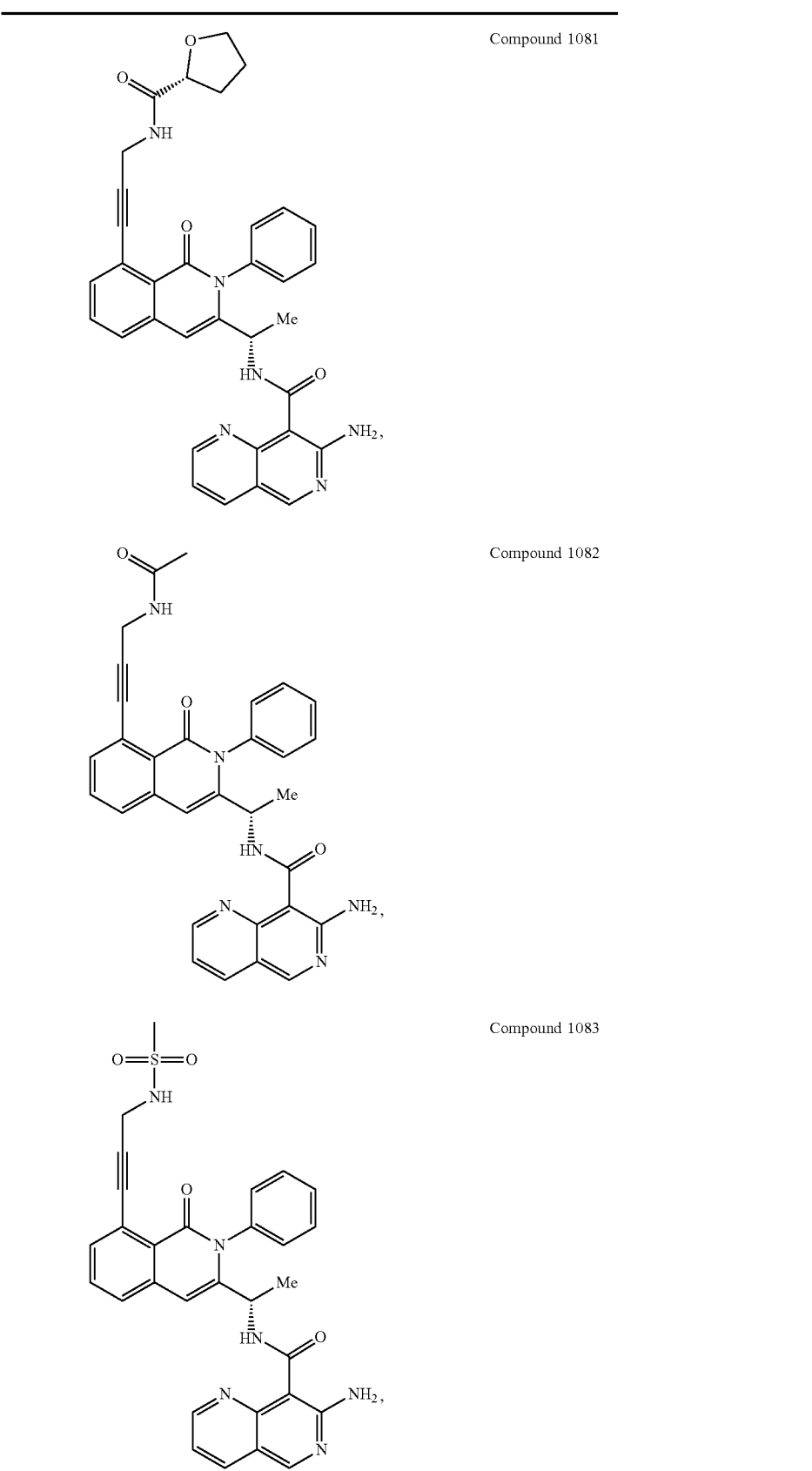
Compound 1081
Compound 1082
Compound 1083

TABLE 4-continued
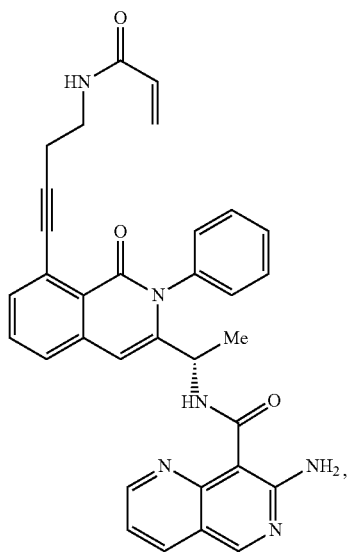 [SMILES: C=CC(=O)NCCC#Cc1cccc2cc([C@H](C)NC(=O)c3c(N)ncc4cccnc34)n(-c3ccccc3)c(=O)c12]
Compound 1084
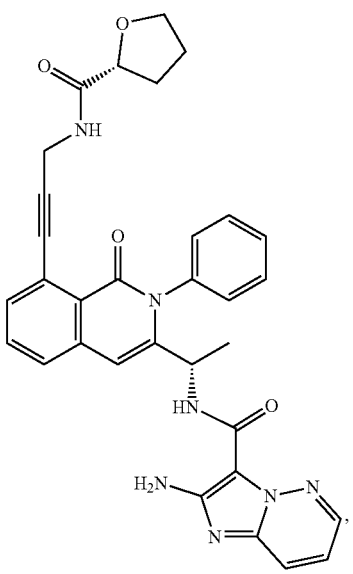 [SMILES: C[C@H](NC(=O)c1c(N)nc2cccnn12)c1cc2cccc(C#CCNC(=O)[C@H]3CCCO3)c2c(=O)n1-c1ccccc1]
Compound 1085
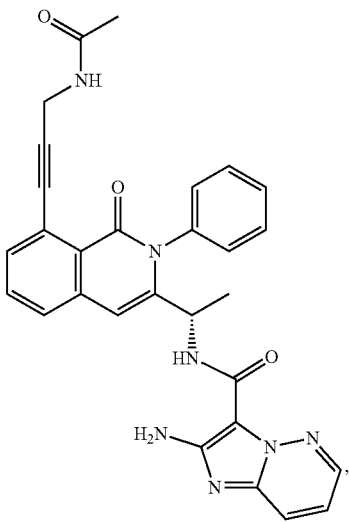 [SMILES: CC(=O)NCC#Cc1cccc2cc([C@H](C)NC(=O)c3c(N)nc4cccnn34)n(-c3ccccc3)c(=O)c12]
Compound 1086

TABLE 4-continued
Compound 1087
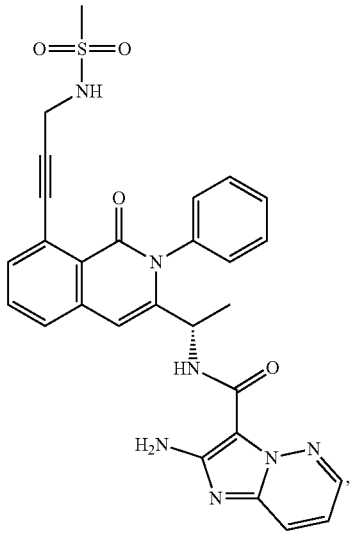 [SMILES: C[C@H](NC(=O)c1c(N)nc2cccnn12)c1cc2cccc(C#CCNS(C)(=O)=O)c2c(=O)n1-c1ccccc1]
Compound 1088
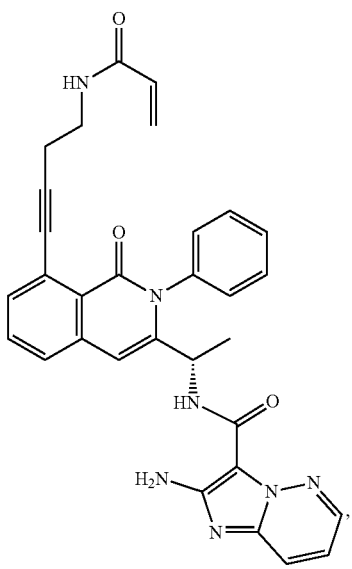 [SMILES: C=CC(=O)NCCC#Cc1cccc2cc([C@H](C)NC(=O)c3c(N)nc4cccnn34)n(-c3ccccc3)c(=O)c12]
Compound 1089
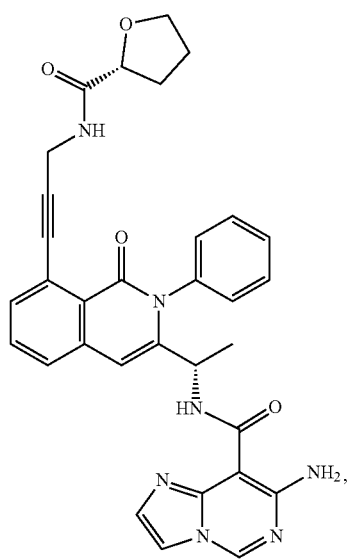 [SMILES: C[C@H](NC(=O)c1c(N)ncn2ccnc12)c1cc2cccc(C#CCNC(=O)[C@H]3CCCO3)c2c(=O)n1-c1ccccc1]

TABLE 4-continued
Compound 1090
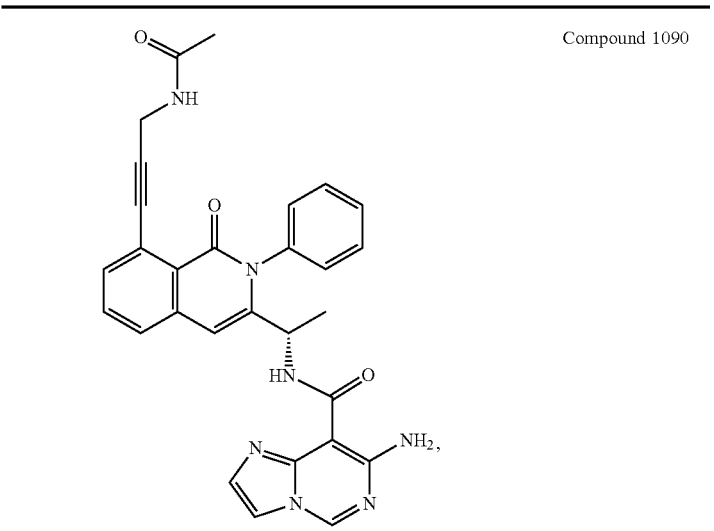
Compound 1091
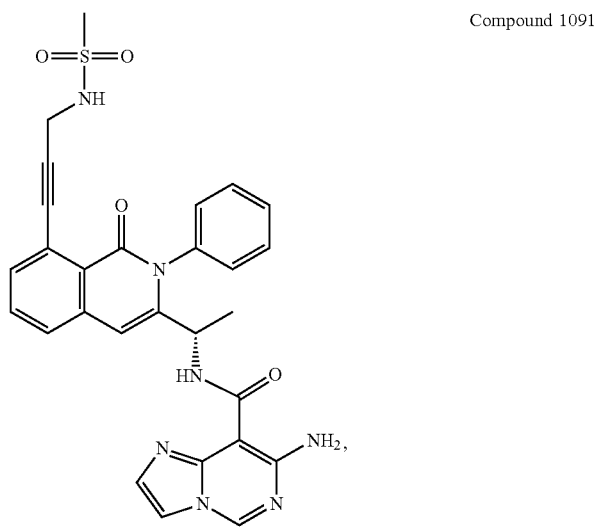
Compound 1092
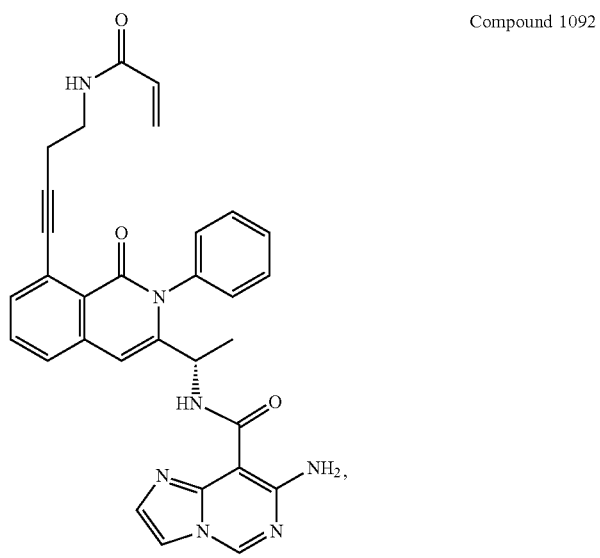

TABLE 4-continued
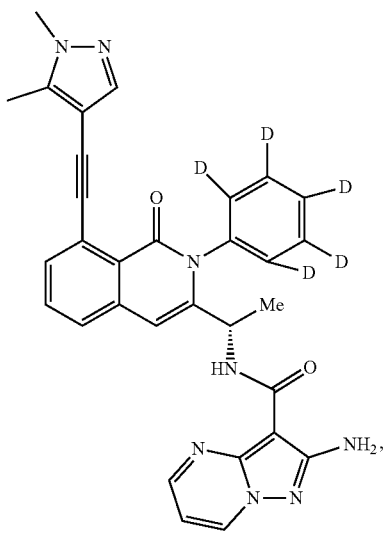 [SMILES: [2H]c1c([2H])c([2H])c(-n2c([C@H](C)NC(=O)c3c(N)nn4cccnc34)cc3cccc(C#Cc4cnn(C)c4C)c3c2=O)c([2H])c1[2H]]
Compound 1093
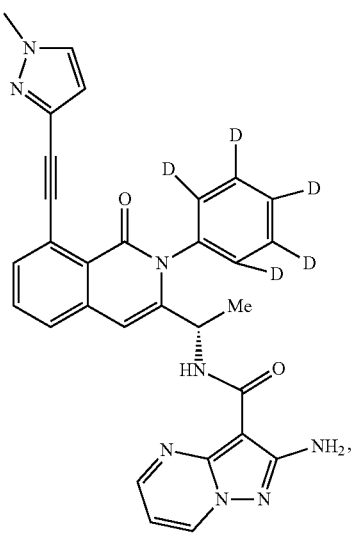 [SMILES: [2H]c1c([2H])c([2H])c(-n2c([C@H](C)NC(=O)c3c(N)nn4cccnc34)cc3cccc(C#Cc4ccn(C)n4)c3c2=O)c([2H])c1[2H]]
Compound 1094
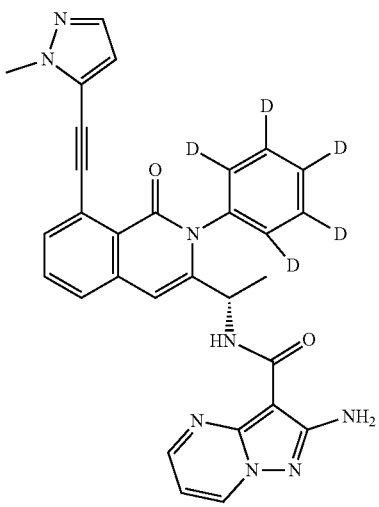 [SMILES: [2H]c1c([2H])c([2H])c(-n2c([C@H](C)NC(=O)c3c(N)nn4cccnc34)cc3cccc(C#Cc4ccnn4C)c3c2=O)c([2H])c1[2H]]
Compound 1095

TABLE 5
Compound 2001
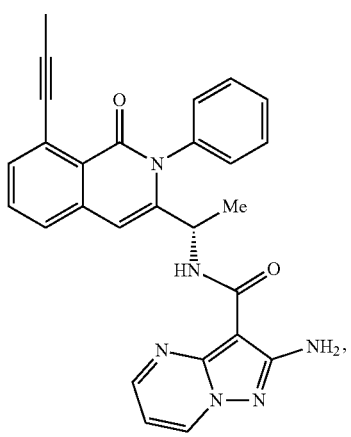 [SMILES: CC#Cc1cccc2cc([C@H](C)NC(=O)c3c(N)nn4cccnc34)n(-c3ccccc3)c(=O)c12]
Compound 2002
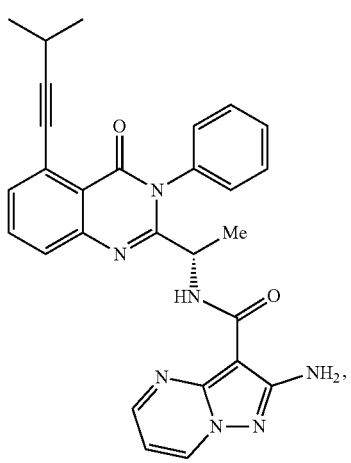 [SMILES: CC(C)C#Cc1cccc2nc([C@H](C)NC(=O)c3c(N)nn4cccnc34)n(-c3ccccc3)c(=O)c12]
Compound 2003
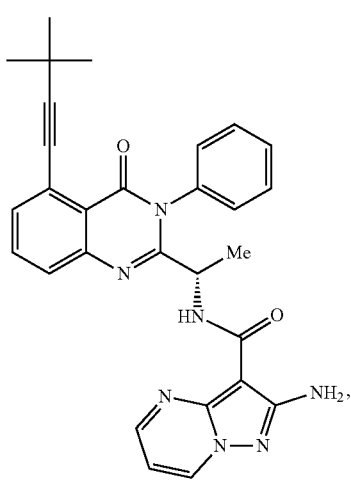 [SMILES: C[C@H](NC(=O)c1c(N)nn2cccnc12)c1nc2cccc(C#CC(C)(C)C)c2c(=O)n1-c1ccccc1]
TABLE 5-continued
Compound 2004
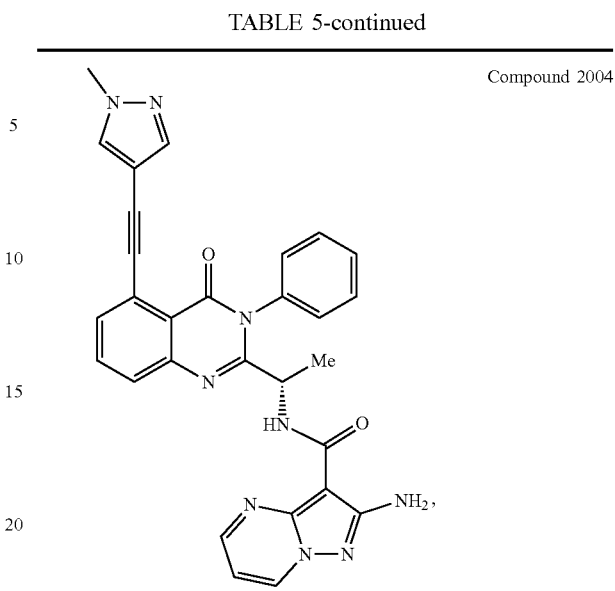
Compound 2005
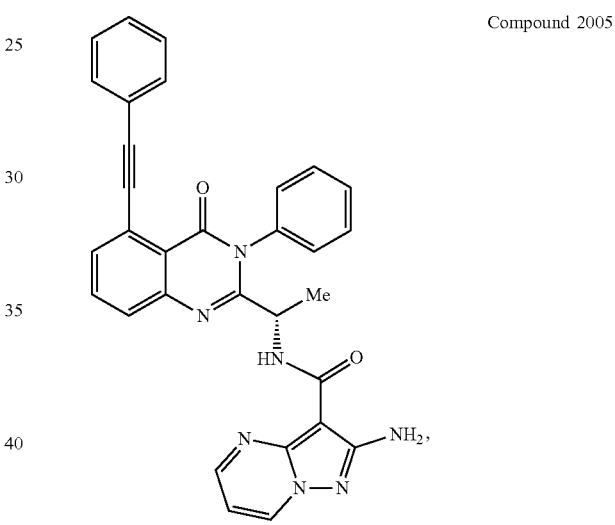
Compound 2006
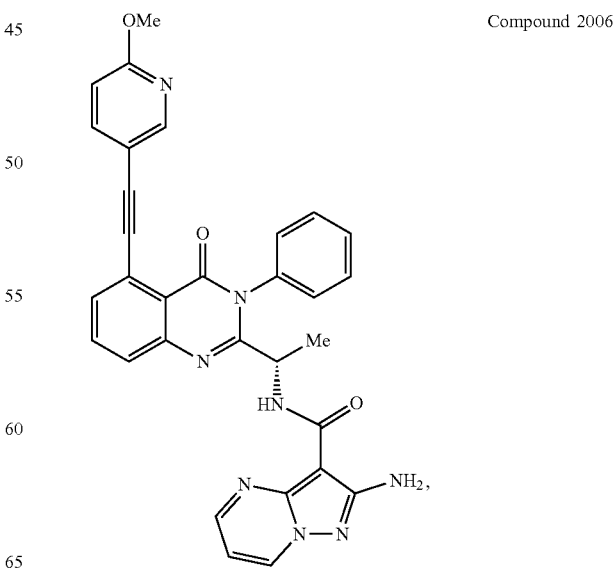

TABLE 5-continued
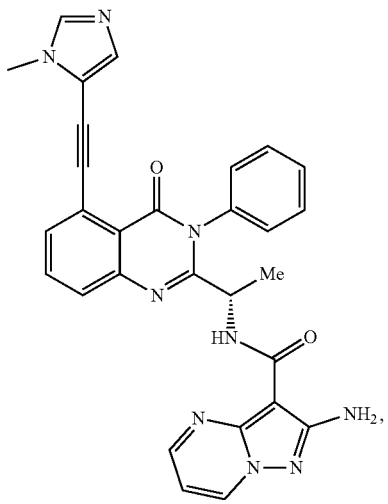 [SMILES: C[C@H](NC(=O)c1c(N)nn2cccnc12)c1nc2cccc(C#Cc3cncn3C)c2c(=O)n1-c1ccccc1]
Compound 2007
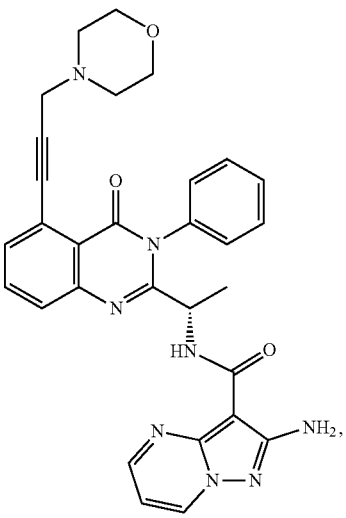
Compound 2010
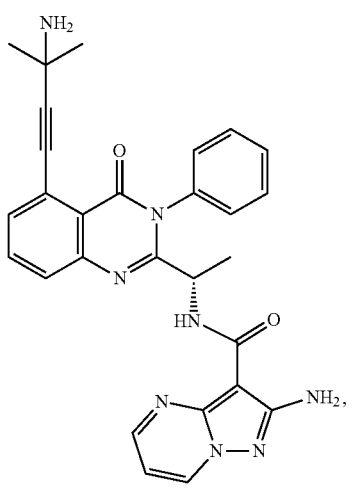 [SMILES: C[C@H](NC(=O)c1c(N)nn2cccnc12)c1nc2cccc(C#CC(C)(C)N)c2c(=O)n1-c1ccccc1]
Compound 2008
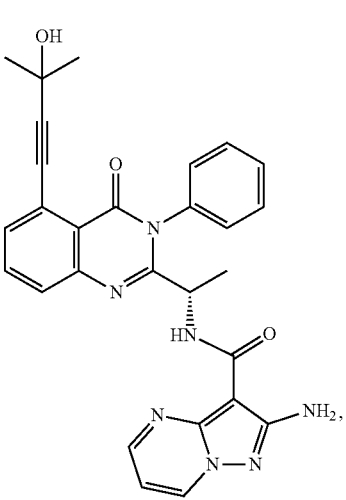
Compound 2011
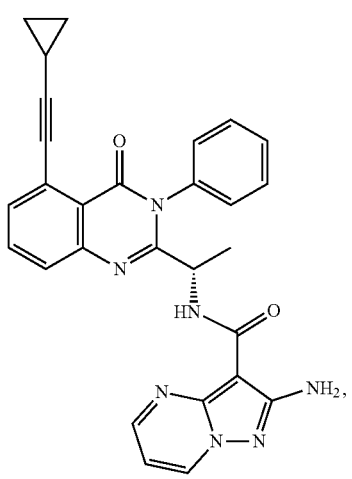 [SMILES: C[C@H](NC(=O)c1c(N)nn2cccnc12)c1nc2cccc(C#CC3CC3)c2c(=O)n1-c1ccccc1]
Compound 2009
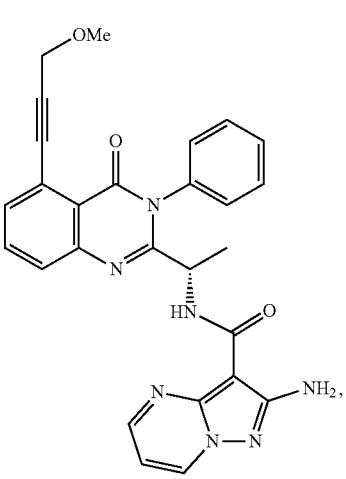 [SMILES: COCC#Cc1cccc2nc([C@H](C)NC(=O)c3c(N)nn4cccnc34)n(-c3ccccc3)c(=O)c12]
Compound 2012

TABLE 5-continued
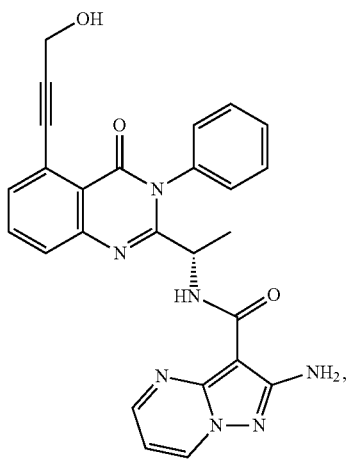 [SMILES: C[C@H](NC(=O)c1c(N)nn2cccnc12)c1nc2cccc(C#CCO)c2c(=O)n1-c1ccccc1]
Compound 2013
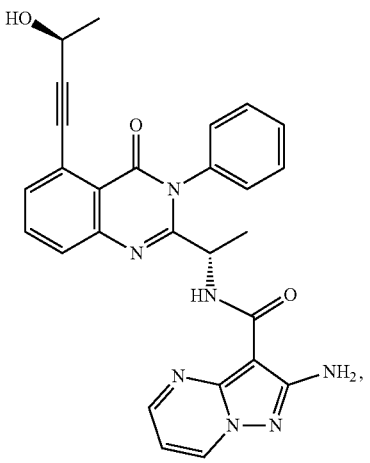
Compound 2016
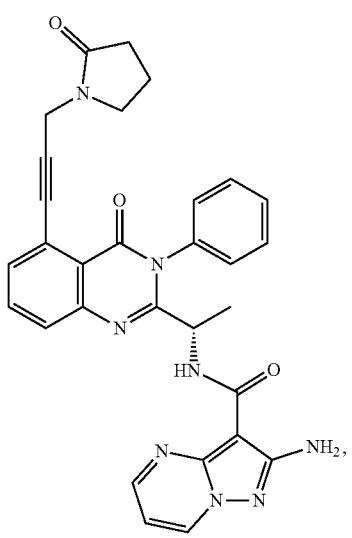 [SMILES: C[C@H](NC(=O)c1c(N)nn2cccnc12)c1nc2cccc(C#CCN3CCCC3=O)c2c(=O)n1-c1ccccc1]
Compound 2014
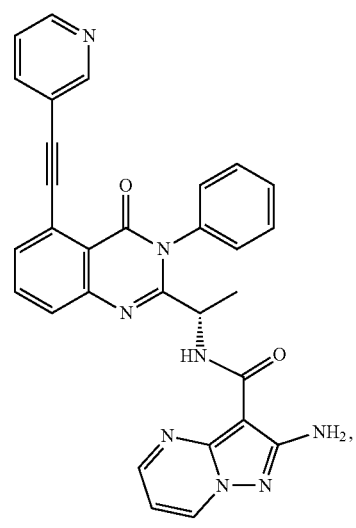
Compound 2017
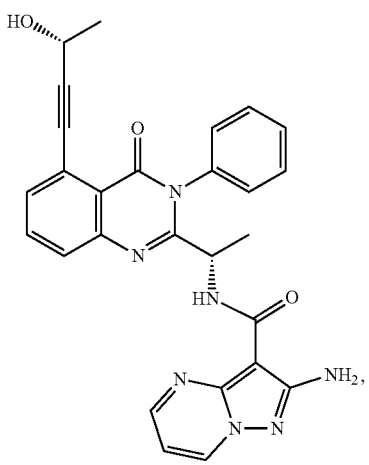 [SMILES: C[C@H](NC(=O)c1c(N)nn2cccnc12)c1nc2cccc(C#C[C@@H](C)O)c2c(=O)n1-c1ccccc1]
Compound 2015
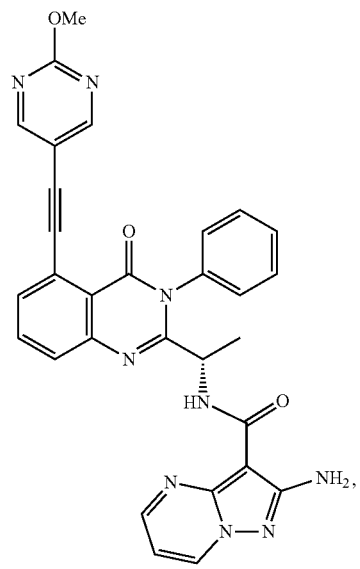 [SMILES: COc1ncc(C#Cc2cccc3nc([C@H](C)NC(=O)c4c(N)nn5cccnc45)n(-c4ccccc4)c(=O)c23)cn1]
Compound 2018

TABLE 5-continued
Compound 2019
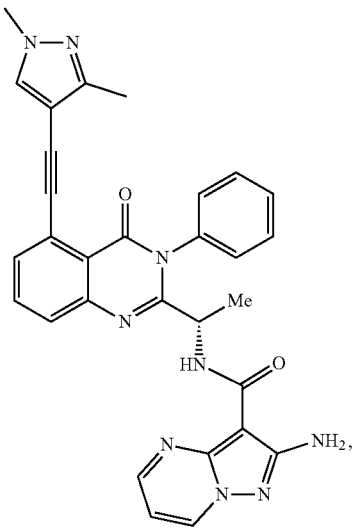
Compound 2020
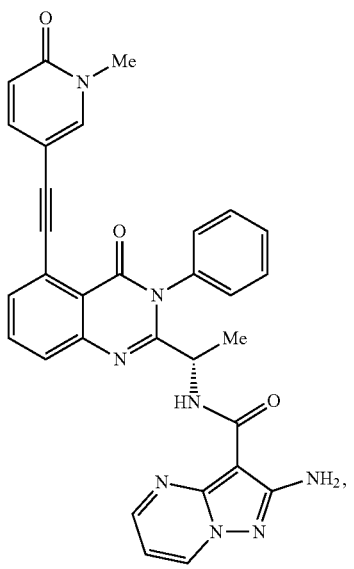 [SMILES: C[C@H](NC(=O)c1c(N)nn2cccnc12)c1nc2cccc(C#Cc3ccc(=O)n(C)c3)c2c(=O)n1-c1ccccc1]
Compound 2021
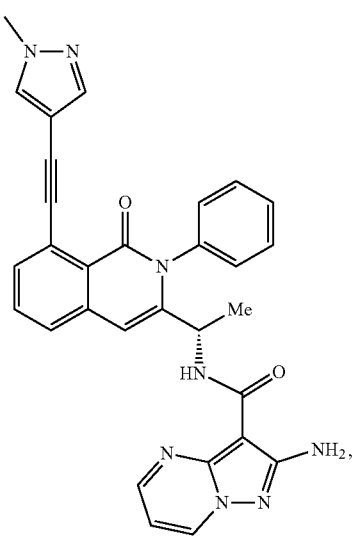 [SMILES: C[C@H](NC(=O)c1c(N)nn2cccnc12)c1cc2cccc(C#Cc3cnn(C)c3)c2c(=O)n1-c1ccccc1]
TABLE 5-continued
Compound 2022
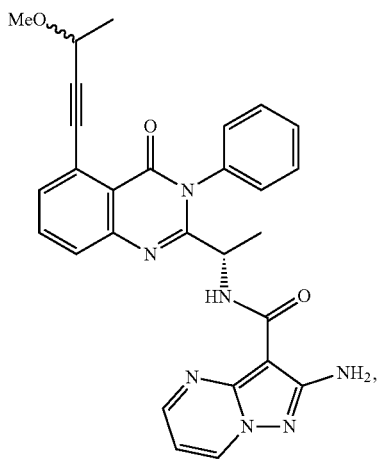 [SMILES: COC(C)C#Cc1cccc2nc([C@H](C)NC(=O)c3c(N)nn4cccnc34)n(-c3ccccc3)c(=O)c12]
Compound 2023
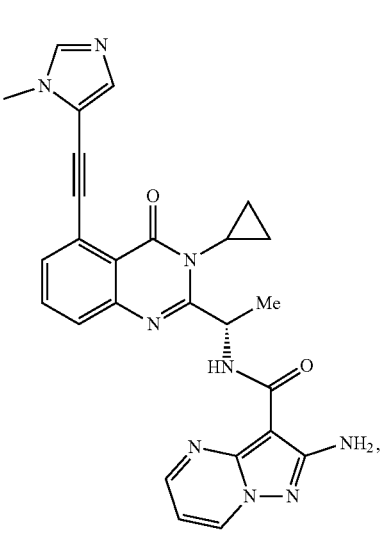 [SMILES: C[C@H](NC(=O)c1c(N)nn2cccnc12)c1nc2cccc(C#Cc3cncn3C)c2c(=O)n1C1CC1]
Compound 2024
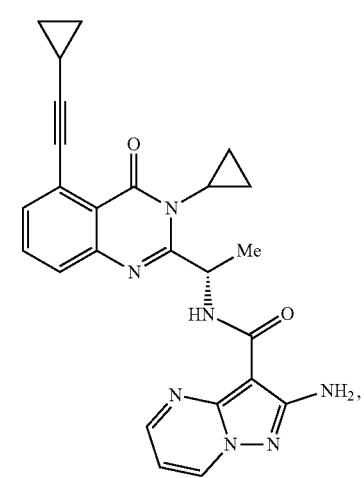 [SMILES: C[C@H](NC(=O)c1c(N)nn2cccnc12)c1nc2cccc(C#CC3CC3)c2c(=O)n1C1CC1]

TABLE 5-continued
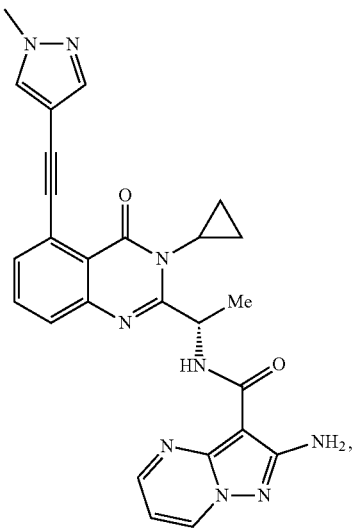 [SMILES: C[C@H](NC(=O)c1c(N)nn2cccnc12)c1nc2cccc(C#Cc3cnn(C)c3)c2c(=O)n1C1CC1]
Compound 2025
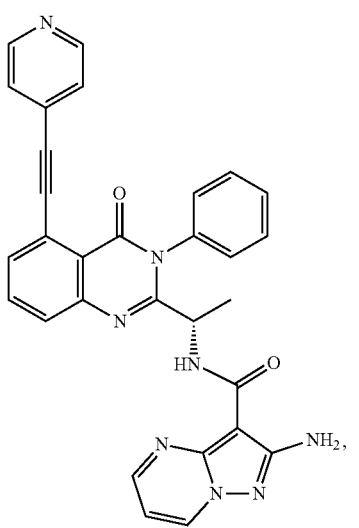 [SMILES: C[C@H](NC(=O)c1c(N)nn2cccnc12)c1nc2cccc(C#Cc3ccncc3)c2c(=O)n1-c1ccccc1]
Compound 2026
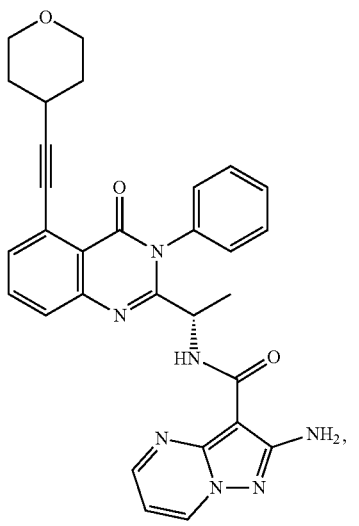 [SMILES: C[C@H](NC(=O)c1c(N)nn2cccnc12)c1nc2cccc(C#CC3CCOCC3)c2c(=O)n1-c1ccccc1]
Compound 2027
TABLE 5-continued
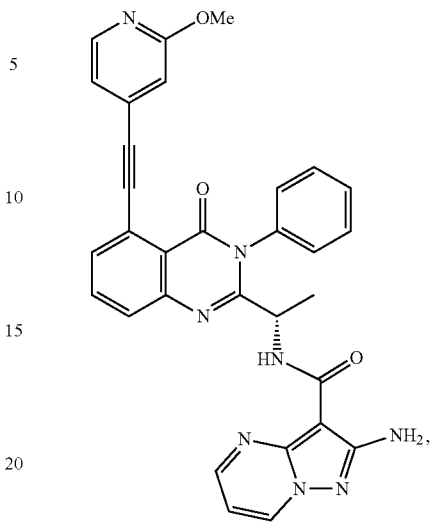
Compound 2028
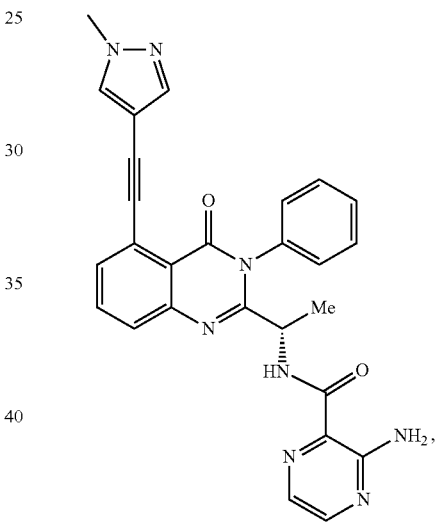
Compound 2029
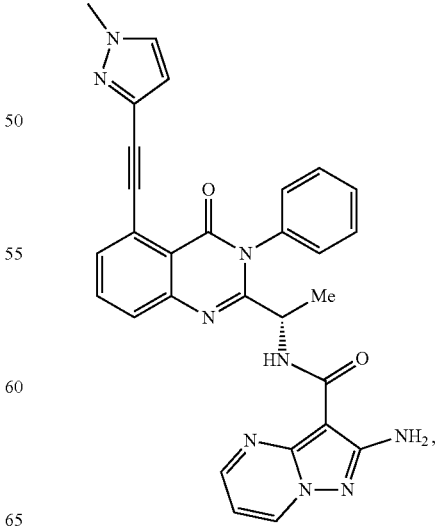
Compound 2030

TABLE 5-continued
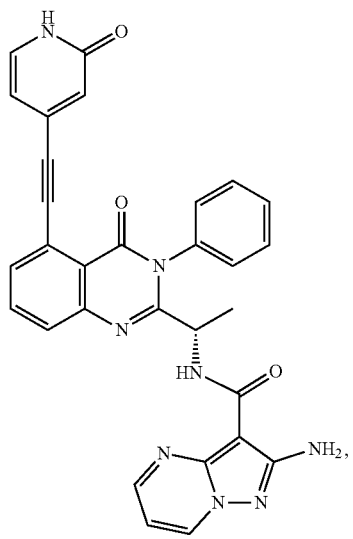 [SMILES: C[C@H](NC(=O)c1c(N)nn2cccnc12)c1nc2cccc(C#Cc3cc[nH]c(=O)c3)c2c(=O)n1-c1ccccc1]
Compound 2031
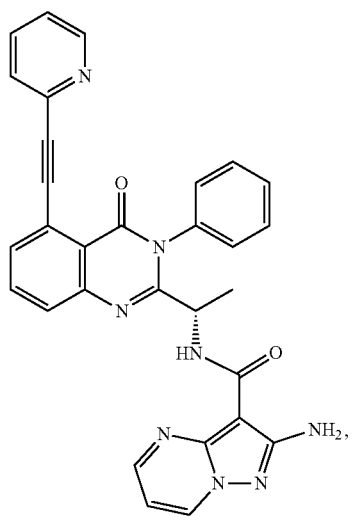 [SMILES: C[C@H](NC(=O)c1c(N)nn2cccnc12)c1nc2cccc(C#Cc3ccccn3)c2c(=O)n1-c1ccccc1]
Compound 2032
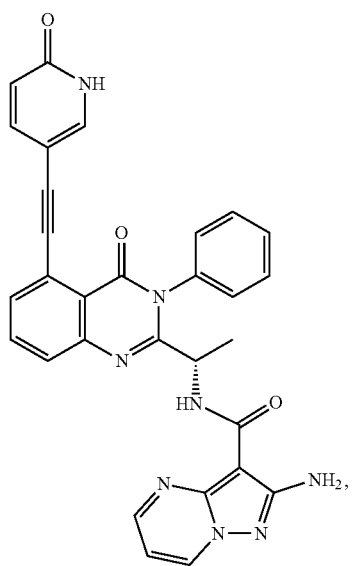 [SMILES: C[C@H](NC(=O)c1c(N)nn2cccnc12)c1nc2cccc(C#Cc3ccc(=O)[nH]c3)c2c(=O)n1-c1ccccc1]
Compound 2033
TABLE 5-continued
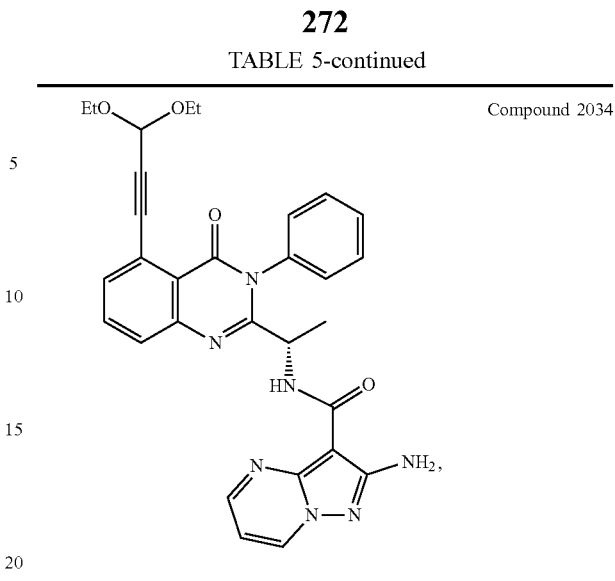
Compound 2034
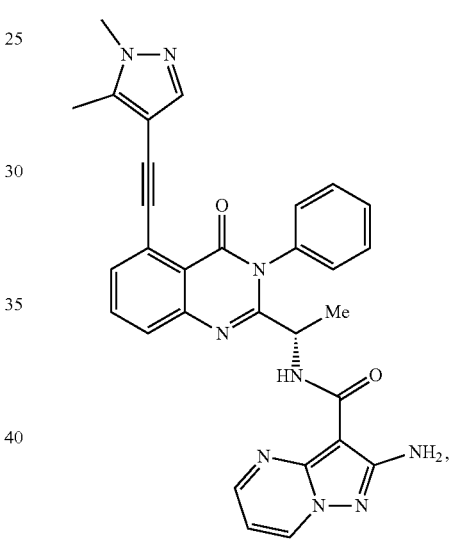
Compound 2035
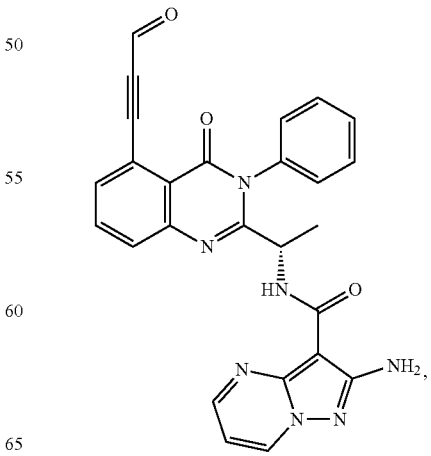
Compound 2036

TABLE 5-continued
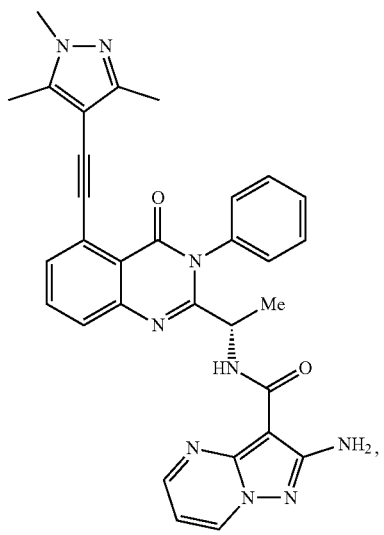
Compound 2037
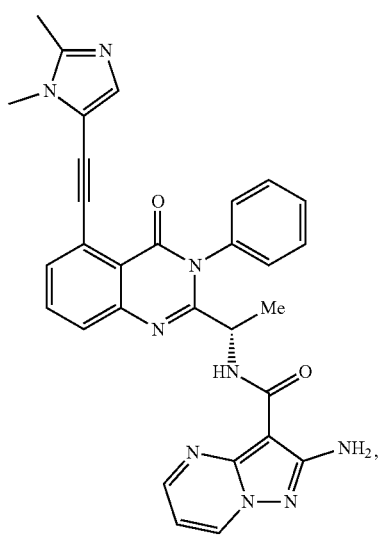 [SMILES: Cc1ncc(C#Cc2cccc3nc([C@H](C)NC(=O)c4c(N)nn5cccnc45)n(-c4ccccc4)c(=O)c23)n1C]
Compound 2038
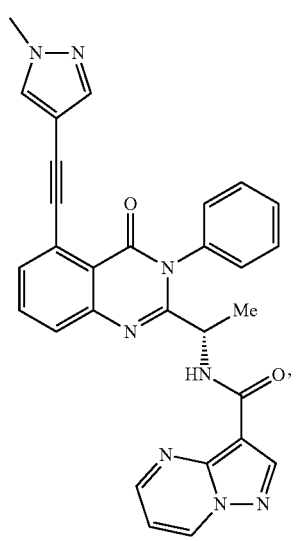 [SMILES: C[C@H](NC(=O)c1cnn2cccnc12)c1nc2cccc(C#Cc3cnn(C)c3)c2c(=O)n1-c1ccccc1]
Compound 2039
TABLE 5-continued
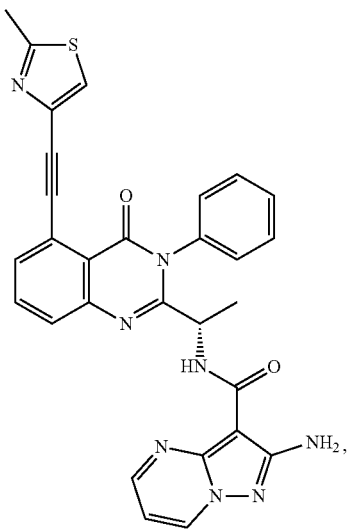 [SMILES: Cc1nc(C#Cc2cccc3nc([C@H](C)NC(=O)c4c(N)nn5cccnc45)n(-c4ccccc4)c(=O)c23)cs1]
Compound 2040
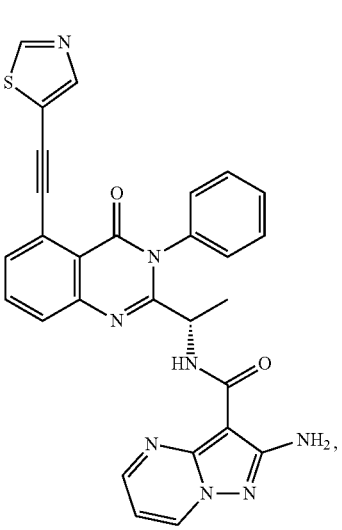 [SMILES: C[C@H](NC(=O)c1c(N)nn2cccnc12)c1nc2cccc(C#Cc3cncs3)c2c(=O)n1-c1ccccc1]
Compound 2041
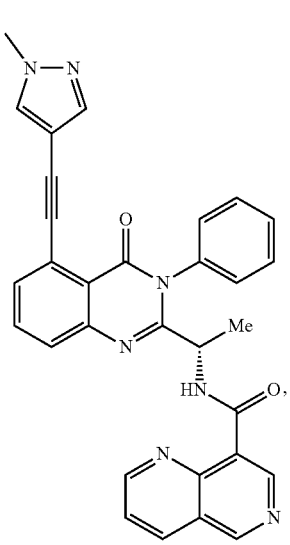
Compound 2042

TABLE 5-continued
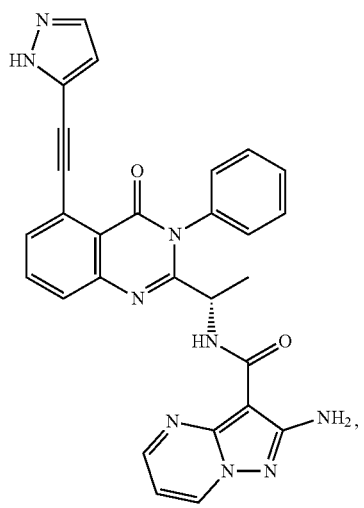 [SMILES: C[C@H](NC(=O)c1c(N)nn2cccnc12)c1nc2cccc(C#Cc3ccn[nH]3)c2c(=O)n1-c1ccccc1]
Compound 2043
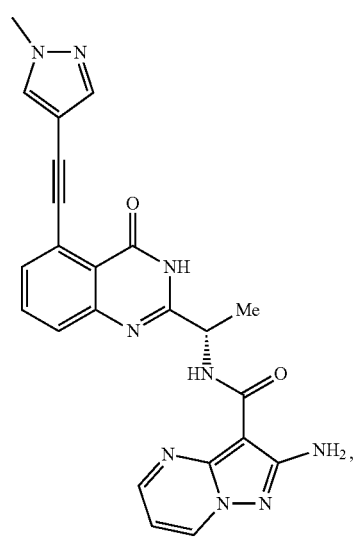 [SMILES: C[C@H](NC(=O)c1c(N)nn2cccnc12)c1nc2cccc(C#Cc3cnn(C)c3)c2c(=O)[nH]1]
Compound 2044
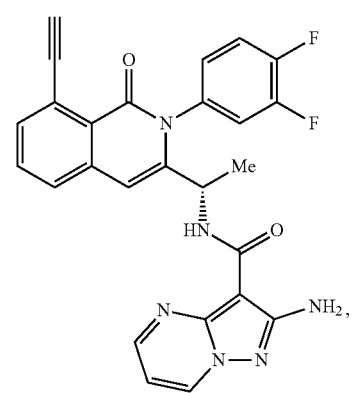 [SMILES: C#Cc1cccc2cc([C@H](C)NC(=O)c3c(N)nn4cccnc34)n(-c3ccc(F)c(F)c3)c(=O)c12]
Compound 2045
TABLE 5-continued
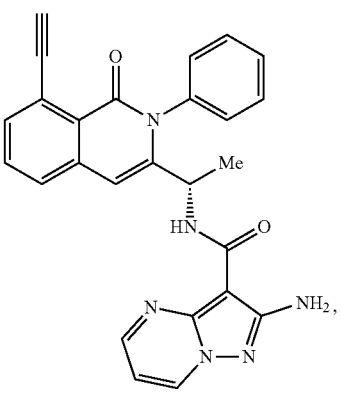 [SMILES: C#Cc1cccc2cc([C@H](C)NC(=O)c3c(N)nn4cccnc34)n(-c3ccccc3)c(=O)c12]
Compound 2046
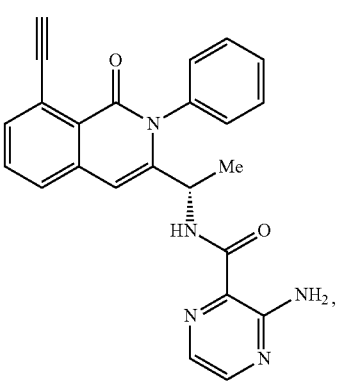 [SMILES: C#Cc1cccc2cc([C@H](C)NC(=O)c3nccnc3N)n(-c3ccccc3)c(=O)c12]
Compound 2047
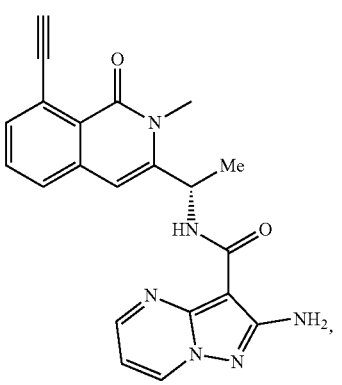 [SMILES: C#Cc1cccc2cc([C@H](C)NC(=O)c3c(N)nn4cccnc34)n(C)c(=O)c12]
Compound 2048
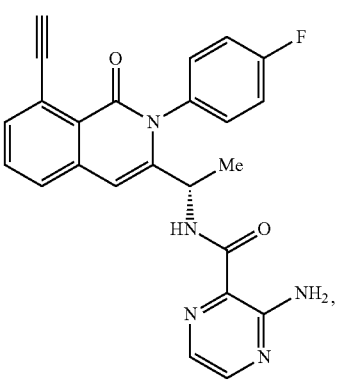 [SMILES: C#Cc1cccc2cc([C@H](C)NC(=O)c3nccnc3N)n(-c3ccc(F)cc3)c(=O)c12]
Compound 2049

TABLE 5-continued
Compound 2050
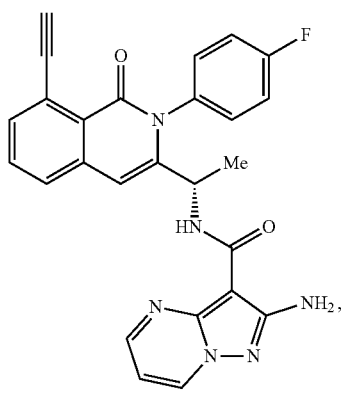 [SMILES: C#Cc1cccc2cc([C@H](C)NC(=O)c3c(N)nn4cccnc34)n(-c3ccc(F)cc3)c(=O)c12]
Compound 2051
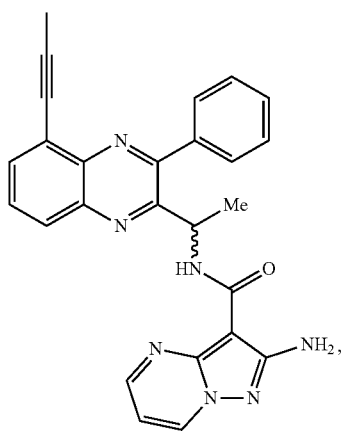 [SMILES: CC#Cc1cccc2nc(C(C)NC(=O)c3c(N)nn4cccnc34)c(-c3ccccc3)nc12]
Compound 2052
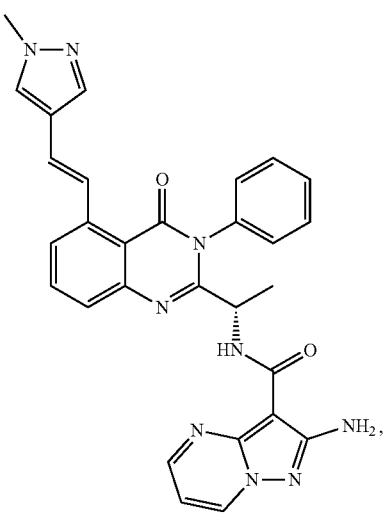 [SMILES: C[C@H](NC(=O)c1c(N)nn2cccnc12)c1nc2cccc(/C=C/c3cnn(C)c3)c2c(=O)n1-c1ccccc1]
TABLE 5-continued
Compound 2053
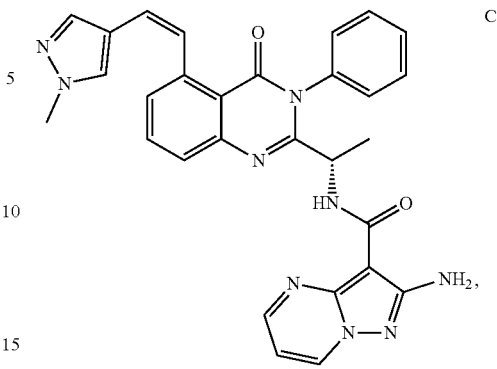
Compound 2054
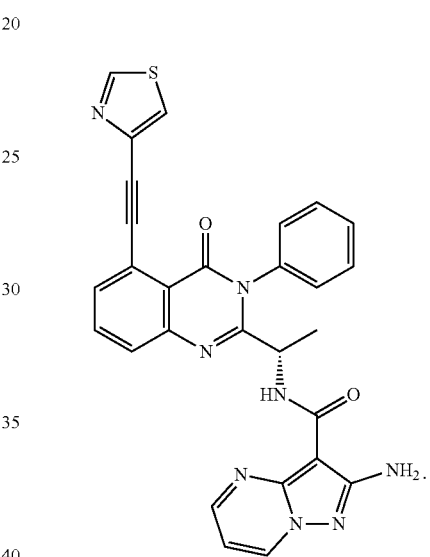
Compound 2055
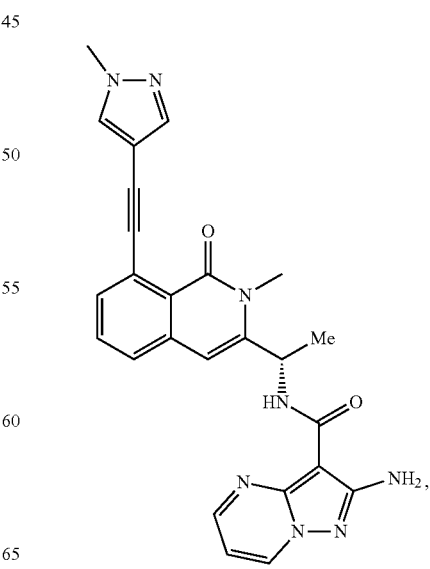

TABLE 5-continued
Compound 2056
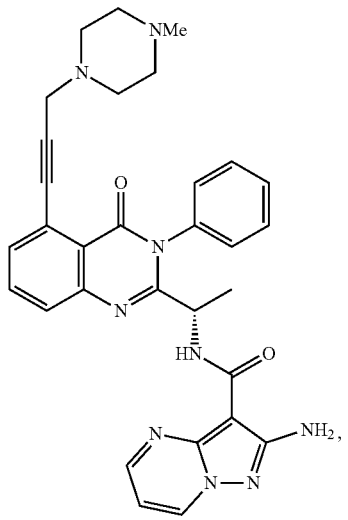 [SMILES: C[C@H](NC(=O)c1c(N)nn2cccnc12)c1nc2cccc(C#CCN3CCN(C)CC3)c2c(=O)n1-c1ccccc1]
Compound 2057
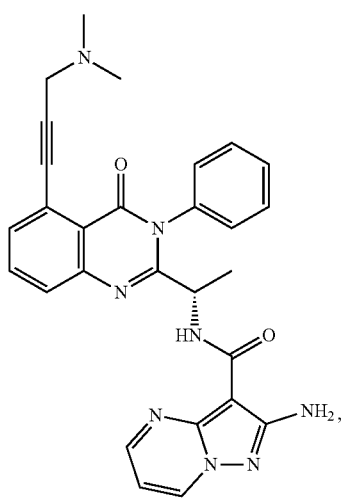
Compound 2058
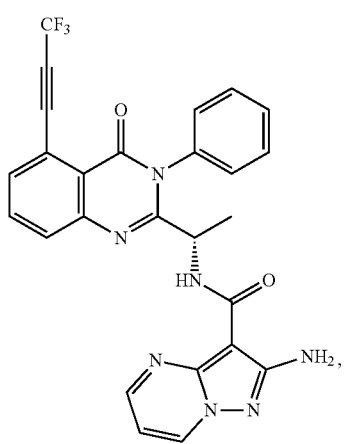
TABLE 5-continued
Compound 2059
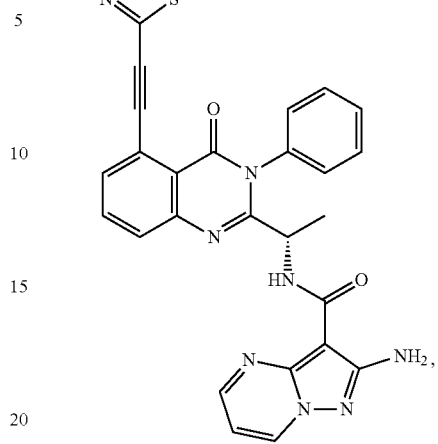
Compound 2060
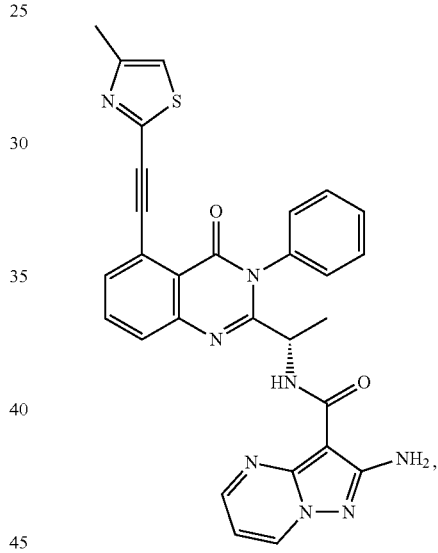
Compound 2061
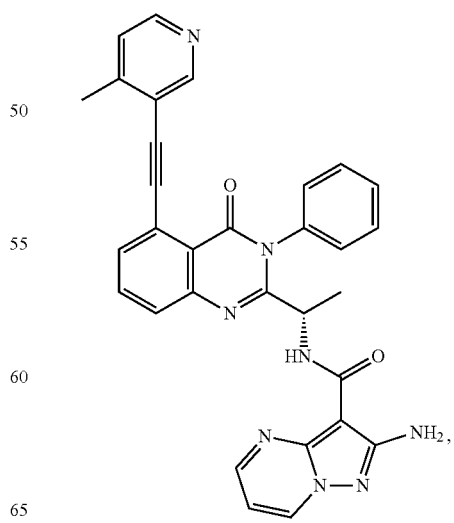

TABLE 5-continued
Compound 2062
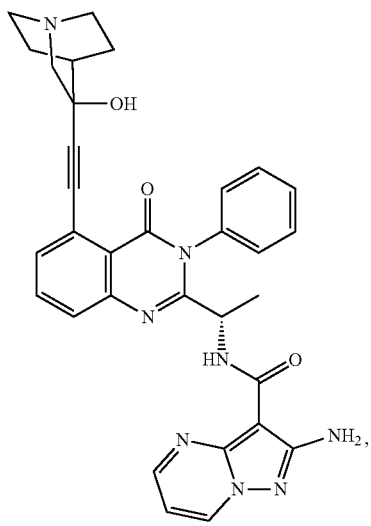 [SMILES: C[C@H](NC(=O)c1c(N)nn2cccnc12)c1nc2cccc(C#CC3(O)CN4CCC3CC4)c2c(=O)n1-c1ccccc1]
Compound 2063
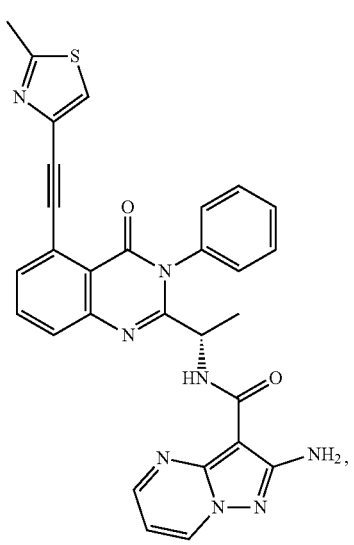 [SMILES: Cc1nc(C#Cc2cccc3nc([C@H](C)NC(=O)c4c(N)nn5cccnc45)n(-c4ccccc4)c(=O)c23)cs1]
Compound 2064
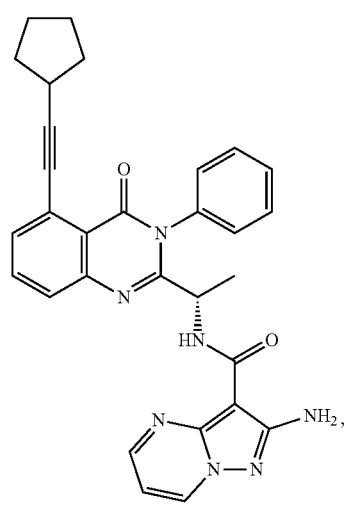
TABLE 5-continued
Compound 2065
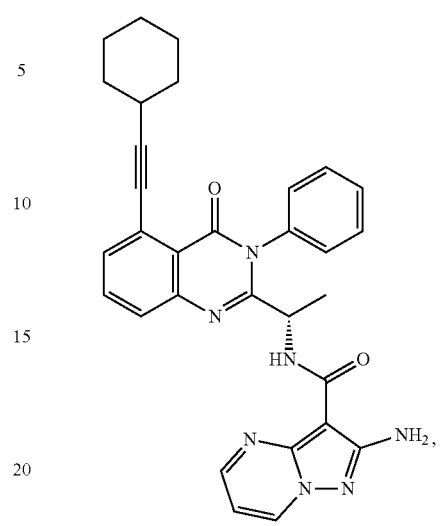
Compound 2066
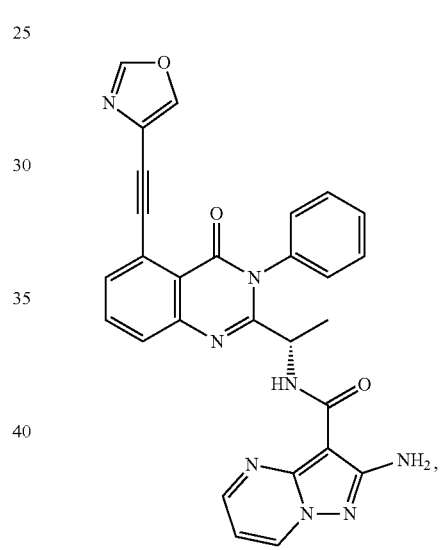
Compound 2067
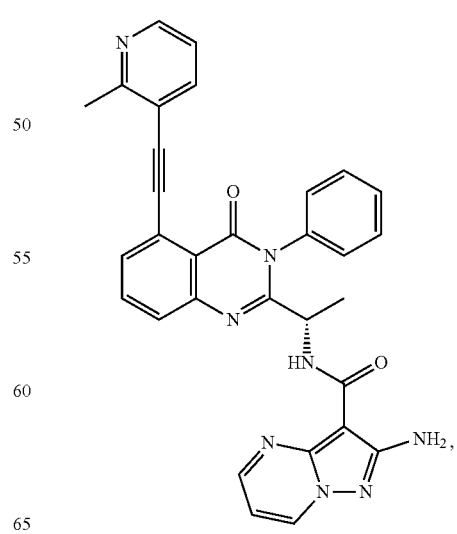

TABLE 5-continued
Compound 2068
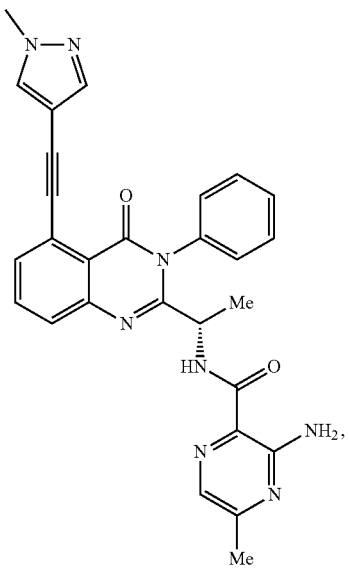 [SMILES: Cc1cnc(C(=O)N[C@@H](C)c2nc3cccc(C#Cc4cnn(C)c4)c3c(=O)n2-c2ccccc2)c(N)n1]
Compound 2069
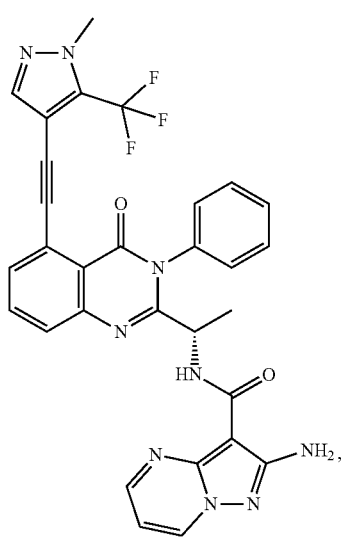 [SMILES: C[C@H](NC(=O)c1c(N)nn2cccnc12)c1nc2cccc(C#Cc3cnn(C)c3C(F)(F)F)c2c(=O)n1-c1ccccc1]
Compound 2070
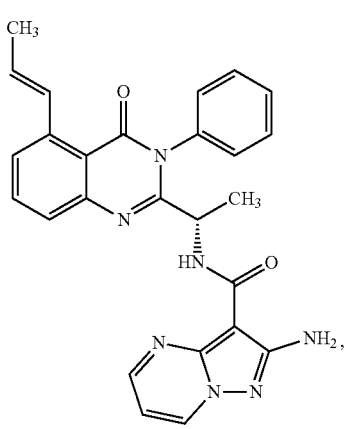
TABLE 5-continued
Compound 2071
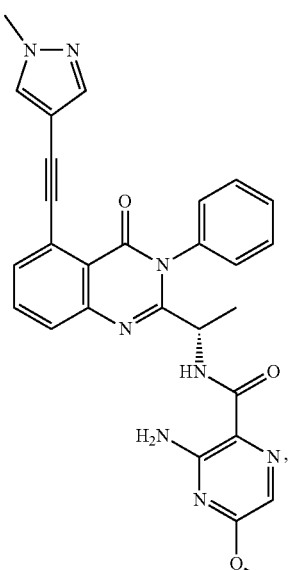
Compound 2072
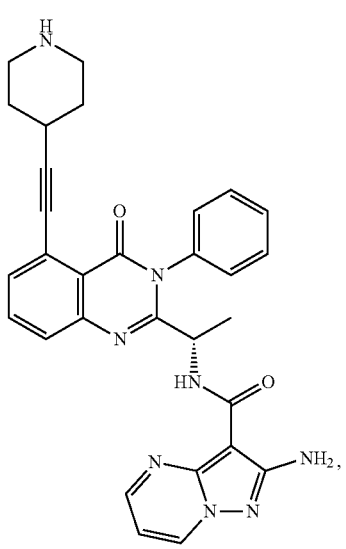 [SMILES: C[C@H](NC(=O)c1c(N)nn2cccnc12)c1nc2cccc(C#CC3CCNCC3)c2c(=O)n1-c1ccccc1]
Compound 2073
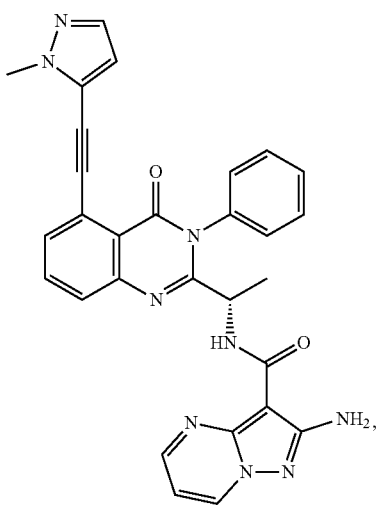 [SMILES: C[C@H](NC(=O)c1c(N)nn2cccnc12)c1nc2cccc(C#Cc3ccnn3C)c2c(=O)n1-c1ccccc1]

TABLE 5-continued
Compound 2074
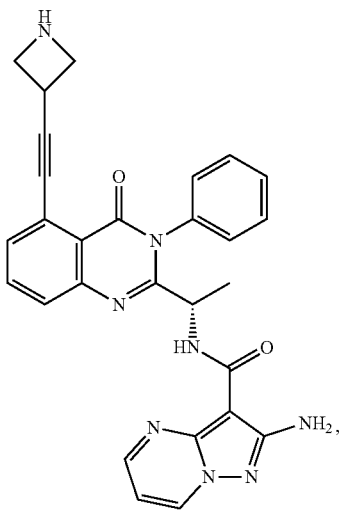 [SMILES: C[C@H](NC(=O)c1c(N)nn2cccnc12)c1nc2cccc(C#CC3CNC3)c2c(=O)n1-c1ccccc1]
Compound 2075
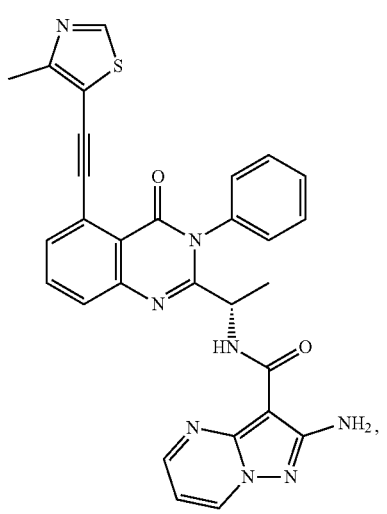 [SMILES: Cc1ncsc1C#Cc1cccc2nc([C@H](C)NC(=O)c3c(N)nn4cccnc34)n(-c3ccccc3)c(=O)c12]
Compound 2076
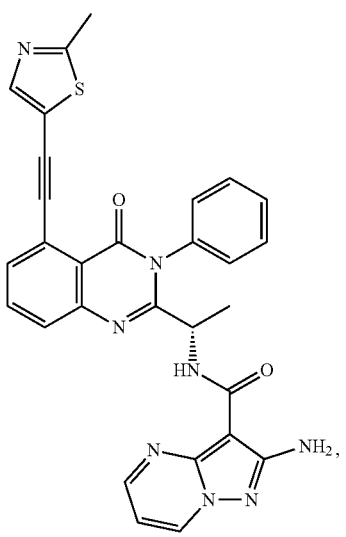 [SMILES: Cc1ncc(C#Cc2cccc3nc([C@H](C)NC(=O)c4c(N)nn5cccnc45)n(-c4ccccc4)c(=O)c23)s1]
TABLE 5-continued
Compound 2077
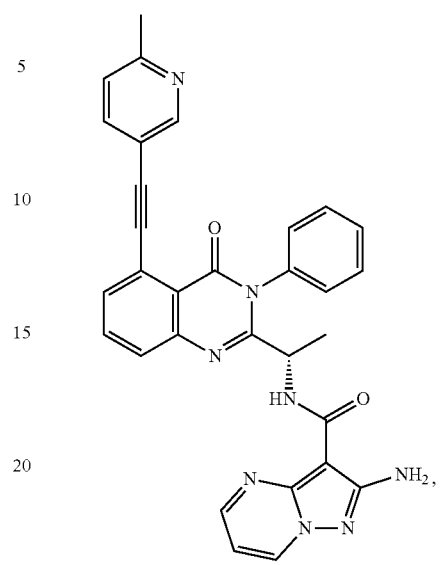
Compound 2078
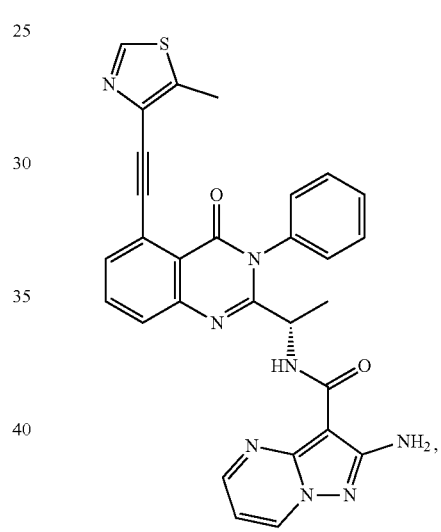
Compound 2079
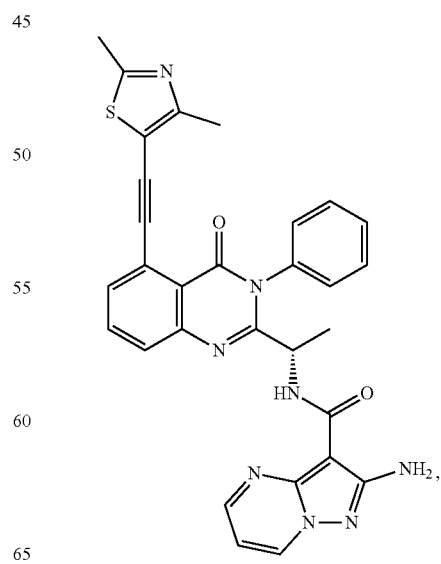

TABLE 5-continued
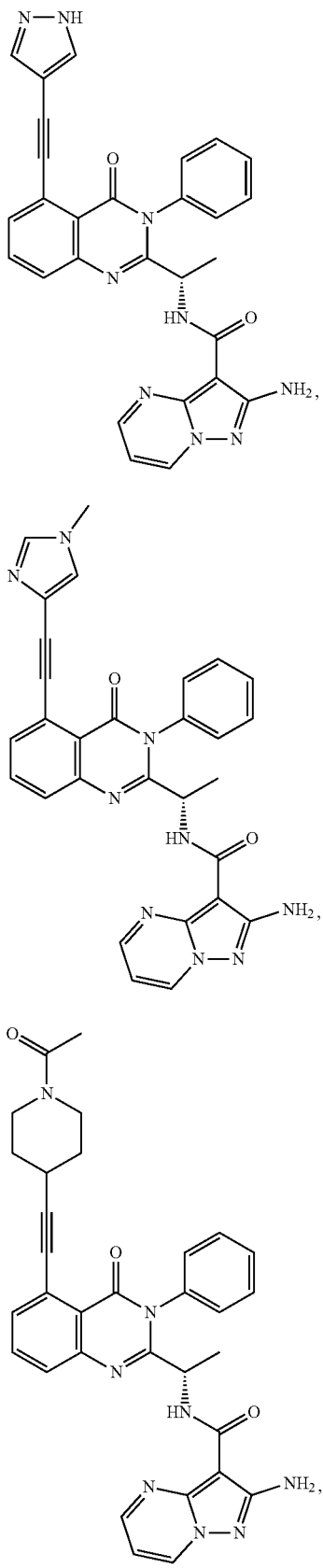
Compound 2080
Compound 2081
Compound 2082
TABLE 5-continued
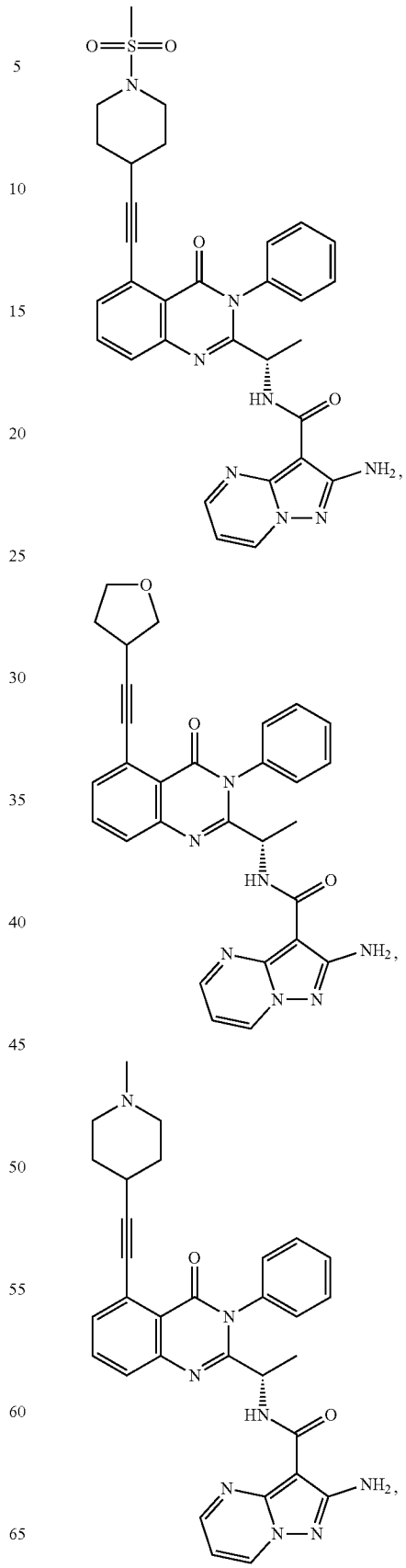
Compound 2083
Compound 2084
Compound 2085

TABLE 5-continued
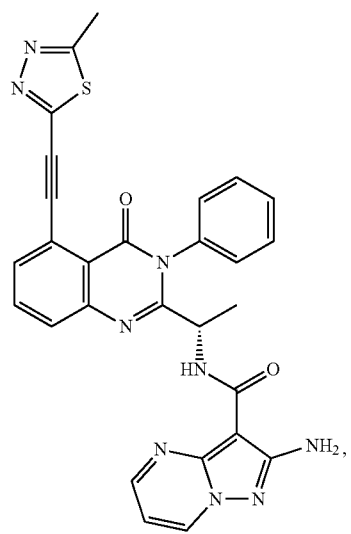
Compound 2086
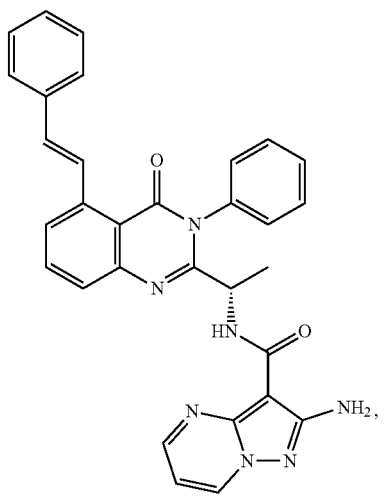 [SMILES: C[C@H](NC(=O)c1c(N)nn2cccnc12)c1nc2cccc(/C=C/c3ccccc3)c2c(=O)n1-c1ccccc1]
Compound 2087
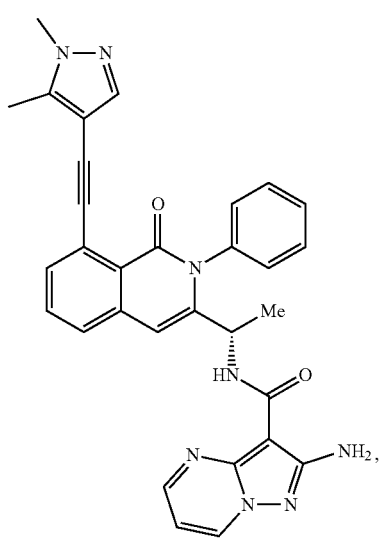 [SMILES: Cc1c(C#Cc2cccc3cc([C@H](C)NC(=O)c4c(N)nn5cccnc45)n(-c4ccccc4)c(=O)c23)cnn1C]
Compound 2088
TABLE 5-continued
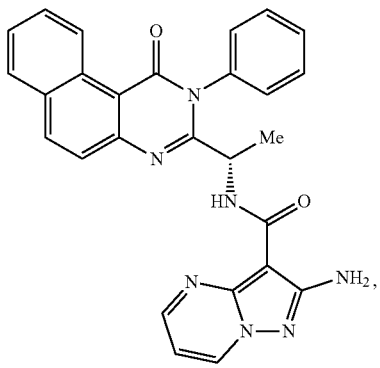 [SMILES: C[C@H](NC(=O)c1c(N)nn2cccnc12)c1nc2ccc3ccccc3c2c(=O)n1-c1ccccc1]
Compound 2089
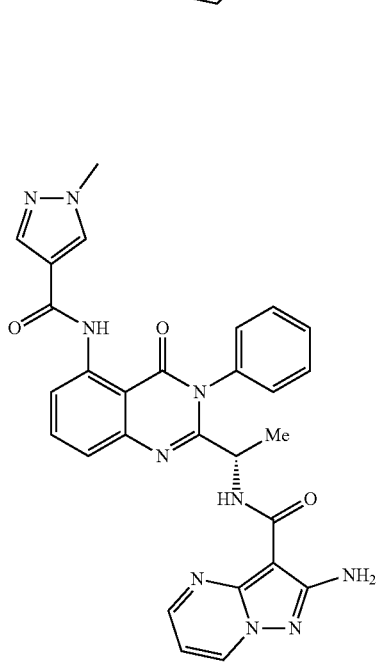
Compound 2090
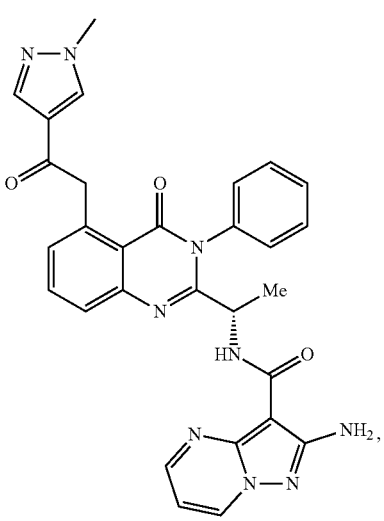 [SMILES: C[C@H](NC(=O)c1c(N)nn2cccnc12)c1nc2cccc(CC(=O)c3cnn(C)c3)c2c(=O)n1-c1ccccc1]
Compound 2091

TABLE 5-continued
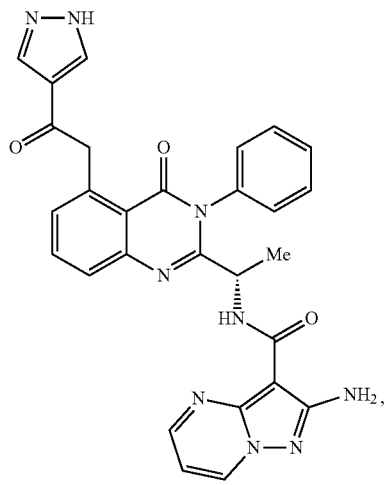 [SMILES: C[C@H](NC(=O)c1c(N)nn2cccnc12)c1nc2cccc(CC(=O)c3cn[nH]c3)c2c(=O)n1-c1ccccc1]
Compound 2092
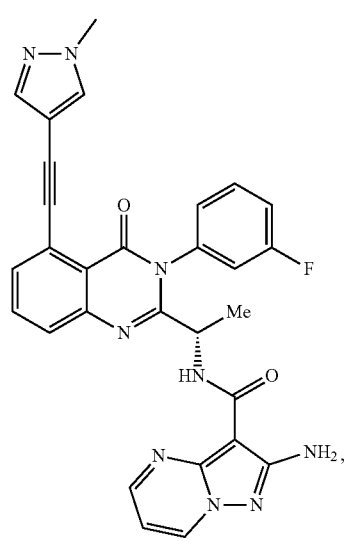 [SMILES: C[C@H](NC(=O)c1c(N)nn2cccnc12)c1nc2cccc(C#Cc3cnn(C)c3)c2c(=O)n1-c1cccc(F)c1]
Compound 2093
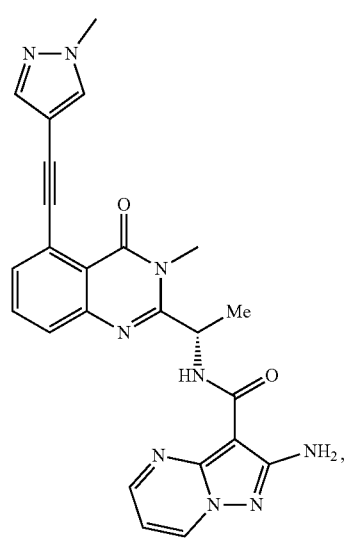 [SMILES: C[C@H](NC(=O)c1c(N)nn2cccnc12)c1nc2cccc(C#Cc3cnn(C)c3)c2c(=O)n1C]
Compound 2094
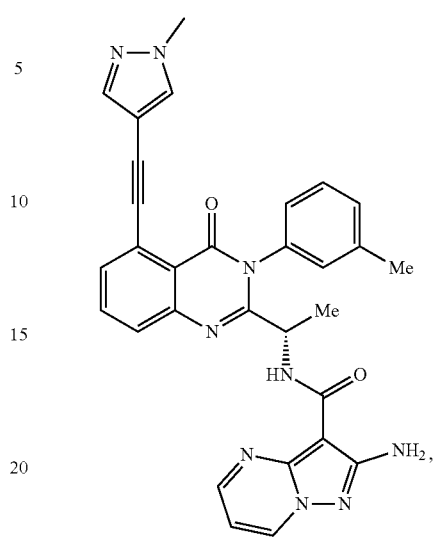
Compound 2095
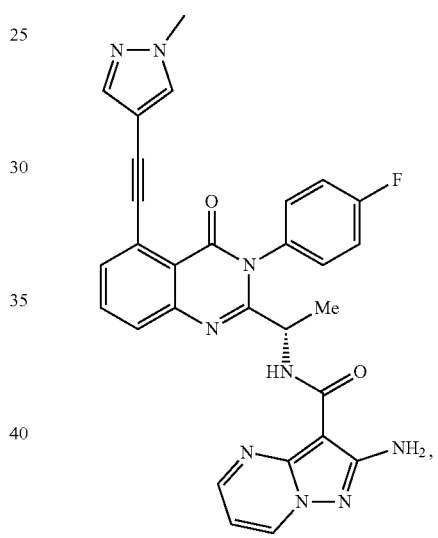
Compound 2096
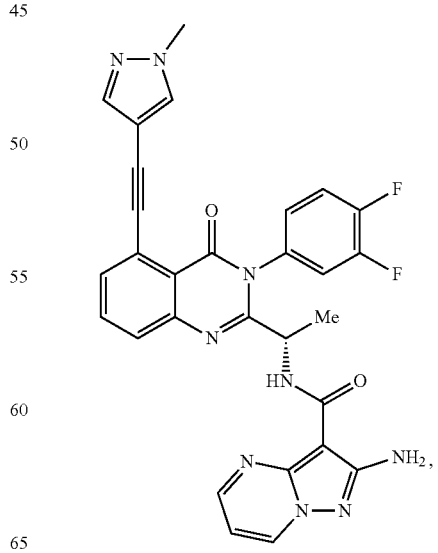
Compound 2097

TABLE 5-continued
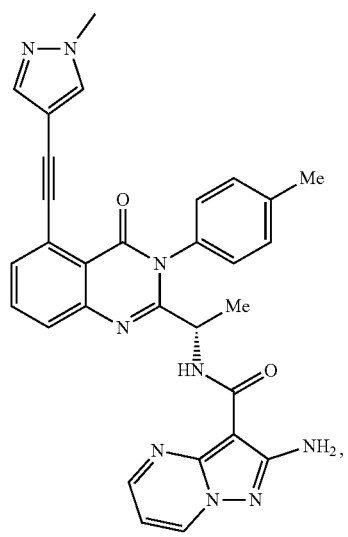
Compound 2098
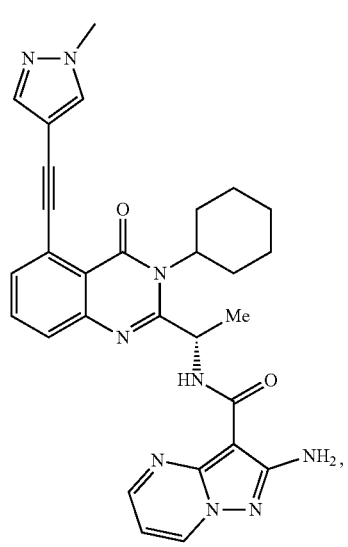 [SMILES: C[C@H](NC(=O)c1c(N)nn2cccnc12)c1nc2cccc(C#Cc3cnn(C)c3)c2c(=O)n1C1CCCCC1]
Compound 2099
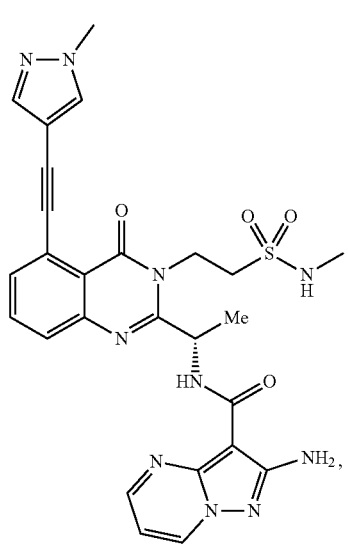 [SMILES: CNS(=O)(=O)CCn1c([C@H](C)NC(=O)c2c(N)nn3cccnc23)nc2cccc(C#Cc3cnn(C)c3)c2c1=O]
Compound 2100
TABLE 5-continued
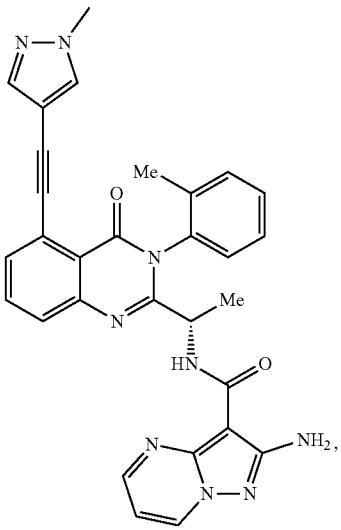
Compound 2101
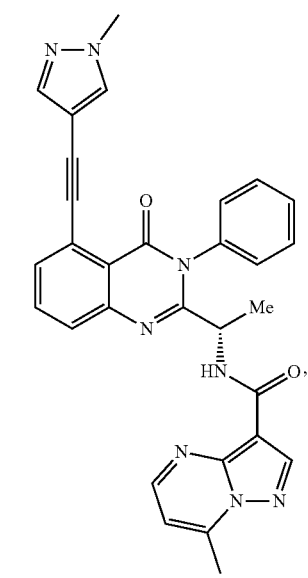 [SMILES: Cc1ccnc2c(C(=O)N[C@@H](C)c3nc4cccc(C#Cc5cnn(C)c5)c4c(=O)n3-c3ccccc3)cnn12]
Compound 2102
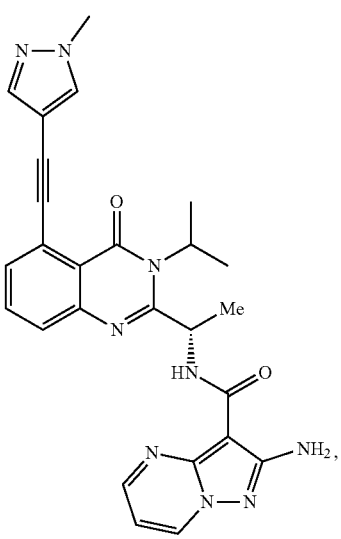 [SMILES: CC(C)n1c([C@H](C)NC(=O)c2c(N)nn3cccnc23)nc2cccc(C#Cc3cnn(C)c3)c2c1=O]
Compound 2103

TABLE 5-continued
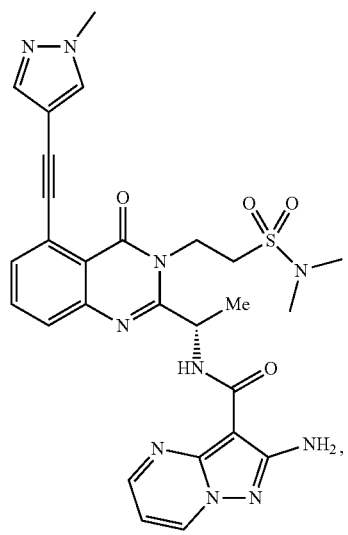 [SMILES: C[C@H](NC(=O)c1c(N)nn2cccnc12)c1nc2cccc(C#Cc3cnn(C)c3)c2c(=O)n1CCS(=O)(=O)N(C)C]
Compound 2104
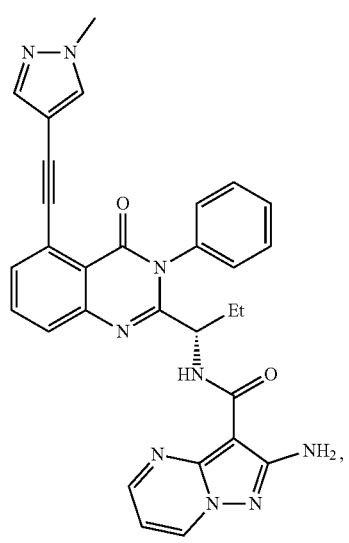 [SMILES: CC[C@H](NC(=O)c1c(N)nn2cccnc12)c1nc2cccc(C#Cc3cnn(C)c3)c2c(=O)n1-c1ccccc1]
Compound 2105
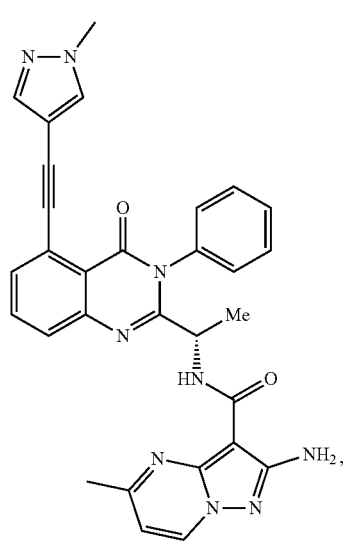
Compound 2106
TABLE 5-continued
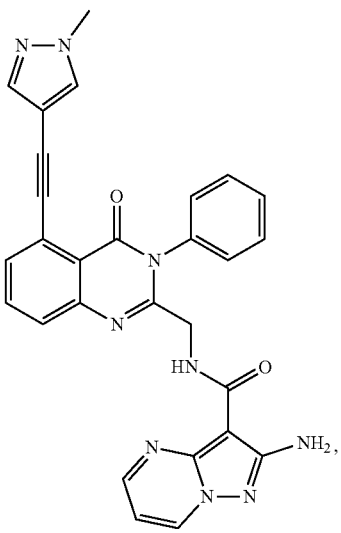 [SMILES: Cn1cc(C#Cc2cccc3nc(CNC(=O)c4c(N)nn5cccnc45)n(-c4ccccc4)c(=O)c23)cn1]
Compound 2107
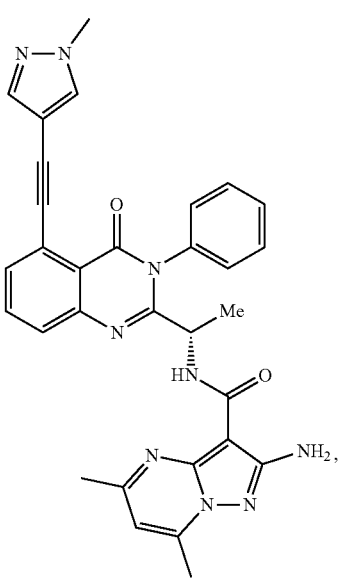
Compound 2108
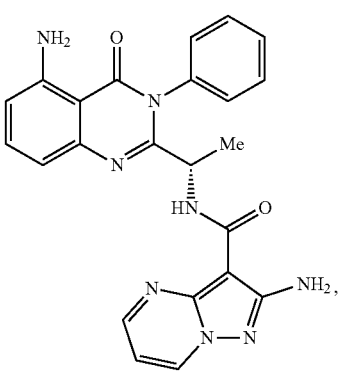
Compound 2109

TABLE 5-continued
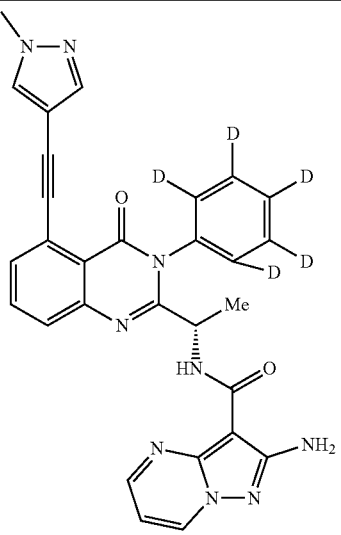
Compound 2110
TABLE 6
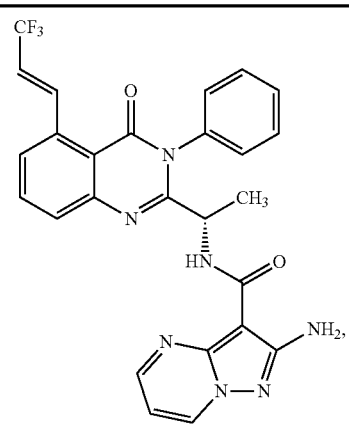
Compound 3001
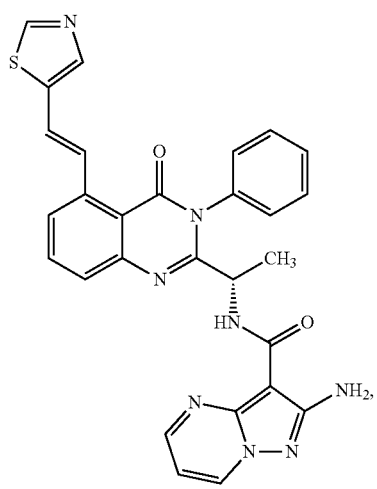 [SMILES: C[C@H](NC(=O)c1c(N)nn2cccnc12)c1nc2cccc(/C=C/c3cncs3)c2c(=O)n1-c1ccccc1]
Compound 3002

TABLE 6-continued
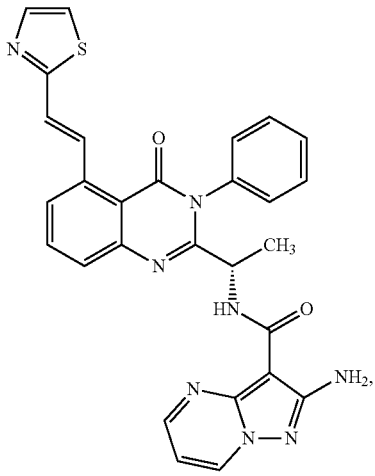 [SMILES: C[C@H](NC(=O)c1c(N)nn2cccnc12)c1nc2cccc(/C=C/c3nccs3)c2c(=O)n1-c1ccccc1]
Compound 3003
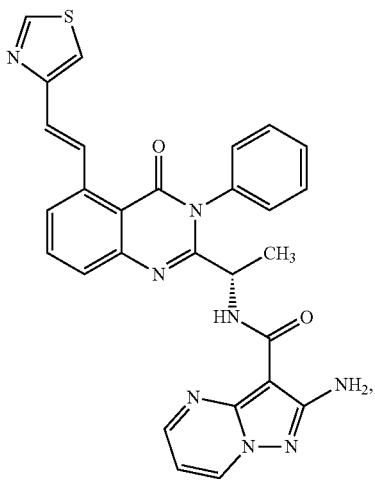 [SMILES: C[C@H](NC(=O)c1c(N)nn2cccnc12)c1nc2cccc(/C=C/c3cscn3)c2c(=O)n1-c1ccccc1]
Compound 3004
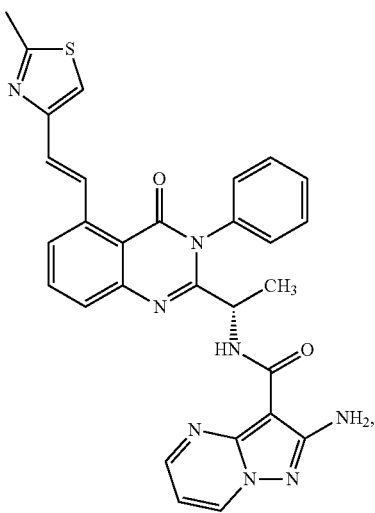 [SMILES: Cc1nc(/C=C/c2cccc3nc([C@H](C)NC(=O)c4c(N)nn5cccnc45)n(-c4ccccc4)c(=O)c23)cs1]
Compound 3005

TABLE 6-continued
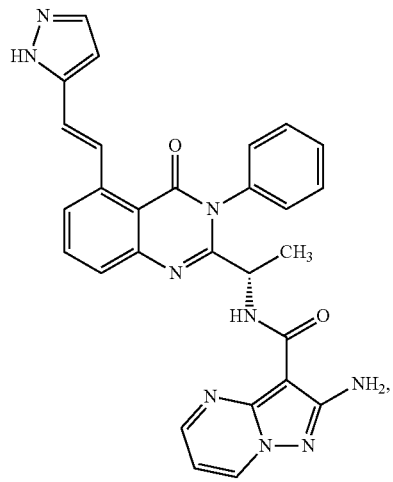
Compound 3006
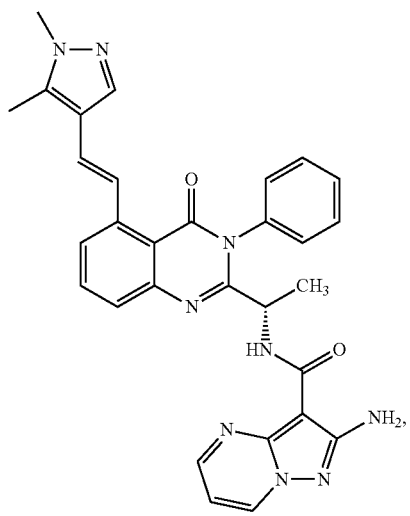 [SMILES: Cc1c(/C=C/c2cccc3nc([C@H](C)NC(=O)c4c(N)nn5cccnc45)n(-c4ccccc4)c(=O)c23)cnn1C]
Compound 3007
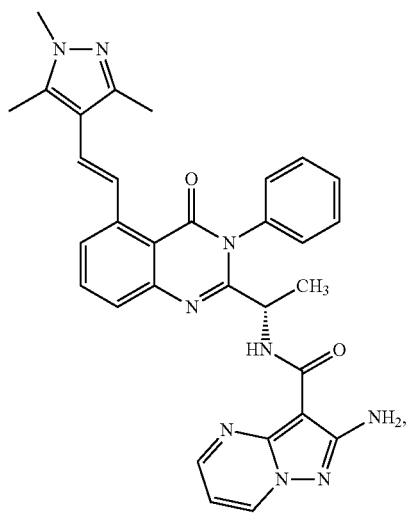 [SMILES: Cc1nn(C)c(C)c1/C=C/c1cccc2nc([C@H](C)NC(=O)c3c(N)nn4cccnc34)n(-c3ccccc3)c(=O)c12]
Compound 3008

TABLE 6-continued
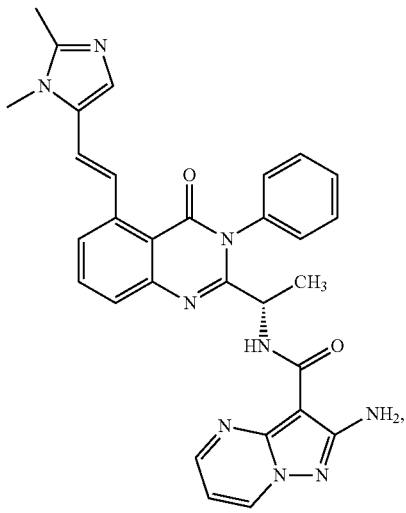 [SMILES: Cc1ncc(/C=C/c2cccc3nc([C@H](C)NC(=O)c4c(N)nn5cccnc45)n(-c4ccccc4)c(=O)c23)n1C]
Compound 3009
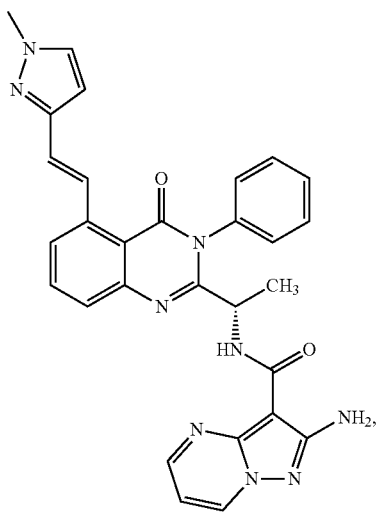 [SMILES: C[C@H](NC(=O)c1c(N)nn2cccnc12)c1nc2cccc(/C=C/c3ccn(C)n3)c2c(=O)n1-c1ccccc1]
Compound 3010
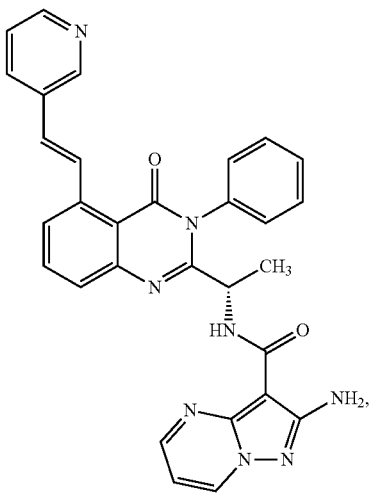 [SMILES: C[C@H](NC(=O)c1c(N)nn2cccnc12)c1nc2cccc(/C=C/c3cccnc3)c2c(=O)n1-c1ccccc1]
Compound 3011

TABLE 6-continued
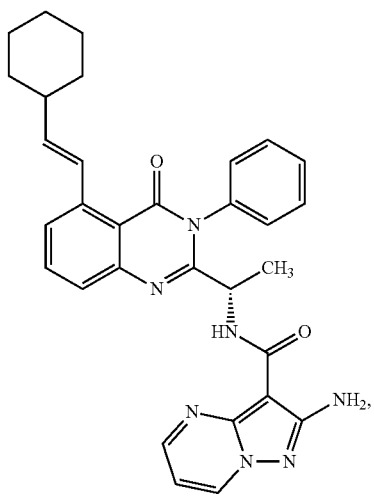 [SMILES: C[C@H](NC(=O)c1c(N)nn2cccnc12)c1nc2cccc(/C=C/C3CCCCC3)c2c(=O)n1-c1ccccc1]
Compound 3012
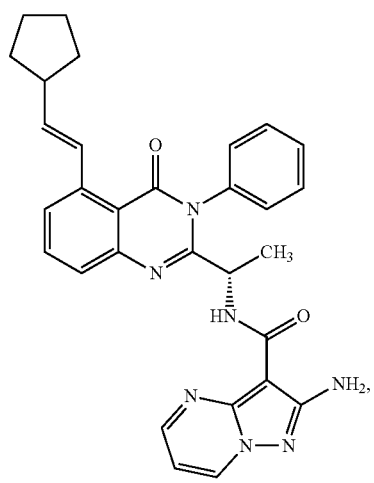 [SMILES: C[C@H](NC(=O)c1c(N)nn2cccnc12)c1nc2cccc(/C=C/C3CCCC3)c2c(=O)n1-c1ccccc1]
Compound 3013
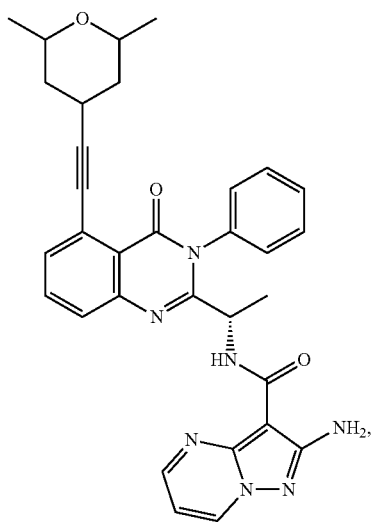 [SMILES: CC1CC(C#Cc2cccc3nc([C@H](C)NC(=O)c4c(N)nn5cccnc45)n(-c4ccccc4)c(=O)c23)CC(C)O1]
Compound 3014

TABLE 6-continued
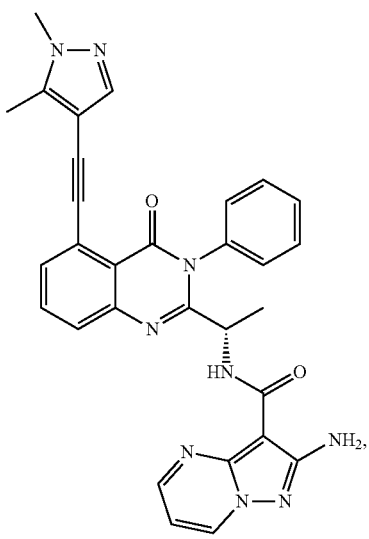 [SMILES: Cc1c(C#Cc2cccc3nc([C@H](C)NC(=O)c4c(N)nn5cccnc45)n(-c4ccccc4)c(=O)c23)cnn1C]
Compound 3015
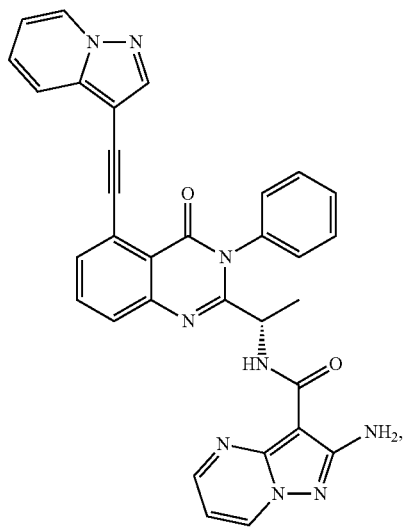 [SMILES: C[C@H](NC(=O)c1c(N)nn2cccnc12)c1nc2cccc(C#Cc3cnn4ccccc34)c2c(=O)n1-c1ccccc1]
Compound 3016
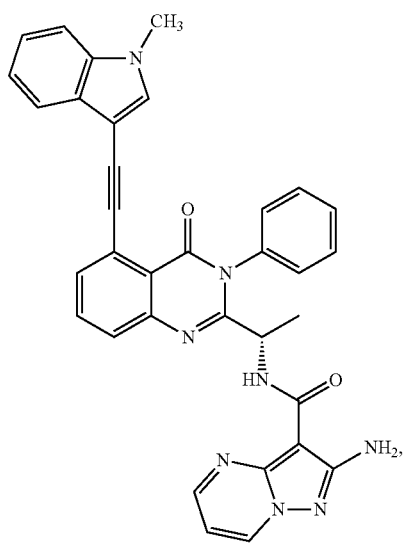 [SMILES: C[C@H](NC(=O)c1c(N)nn2cccnc12)c1nc2cccc(C#Cc3cn(C)c4ccccc34)c2c(=O)n1-c1ccccc1]
Compound 3017

TABLE 6-continued
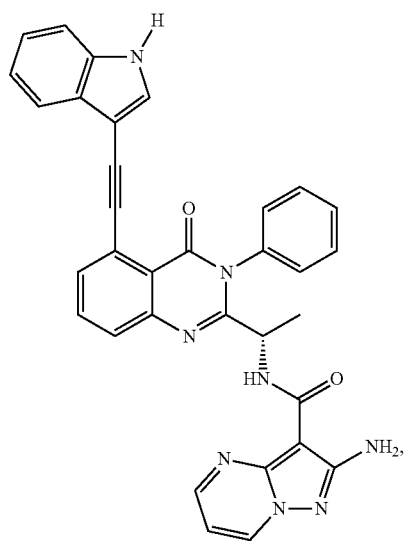 [SMILES: C[C@H](NC(=O)c1c(N)nn2cccnc12)c1nc2cccc(C#Cc3c[nH]c4ccccc34)c2c(=O)n1-c1ccccc1]
Compound 3018
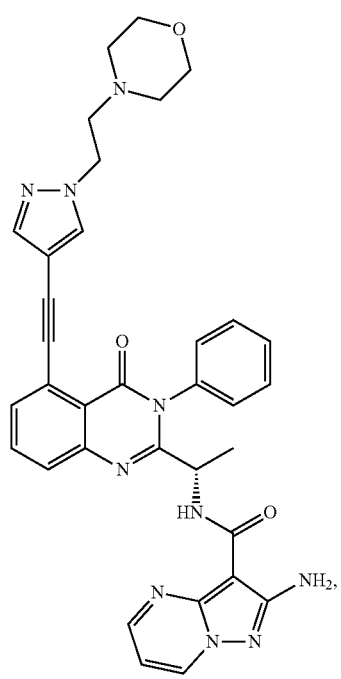 [SMILES: C[C@H](NC(=O)c1c(N)nn2cccnc12)c1nc2cccc(C#Cc3cnn(CCN4CCOCC4)c3)c2c(=O)n1-c1ccccc1]
Compound 3019

TABLE 6-continued
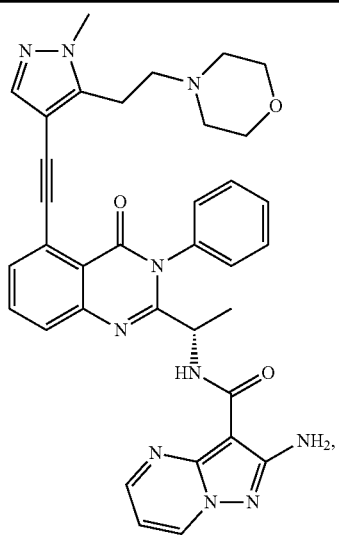
Compound 3020
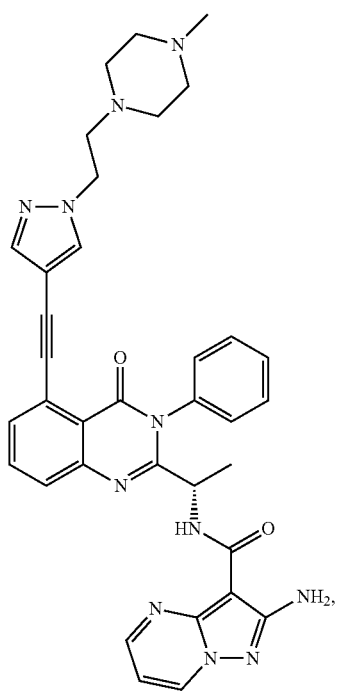 [SMILES: C[C@H](NC(=O)c1c(N)nn2cccnc12)c1nc2cccc(C#Cc3cnn(CCN4CCN(C)CC4)c3)c2c(=O)n1-c1ccccc1]
Compound 3021

TABLE 6-continued
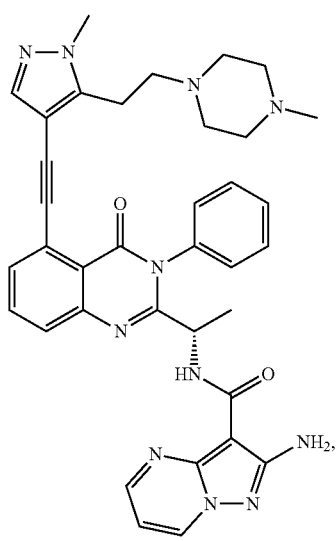 [SMILES: C[C@H](NC(=O)c1c(N)nn2cccnc12)c1nc2cccc(C#Cc3cnn(C)c3CCN3CCN(C)CC3)c2c(=O)n1-c1ccccc1]
Compound 3022
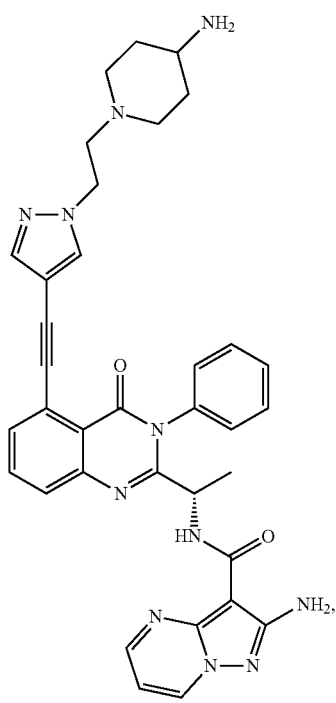 [SMILES: C[C@H](NC(=O)c1c(N)nn2cccnc12)c1nc2cccc(C#Cc3cnn(CCN4CCC(N)CC4)c3)c2c(=O)n1-c1ccccc1]
Compound 3023

TABLE 6-continued
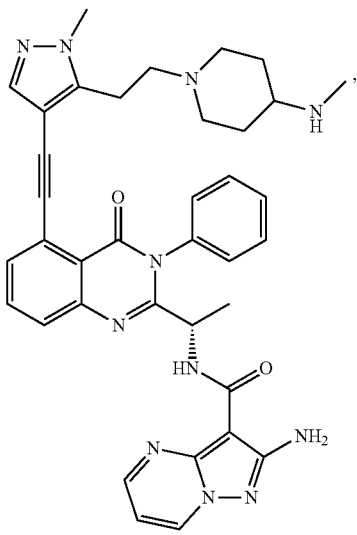 [SMILES: CNC1CCN(CCc2c(C#Cc3cccc4nc([C@H](C)NC(=O)c5c(N)nn6cccnc56)n(-c5ccccc5)c(=O)c34)cnn2C)CC1]
Compound 3024
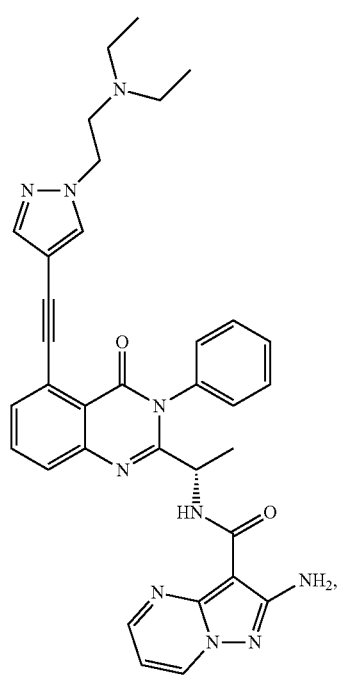 [SMILES: CCN(CC)CCn1cc(C#Cc2cccc3nc([C@H](C)NC(=O)c4c(N)nn5cccnc45)n(-c4ccccc4)c(=O)c23)cn1]
Compound 3025

TABLE 6-continued
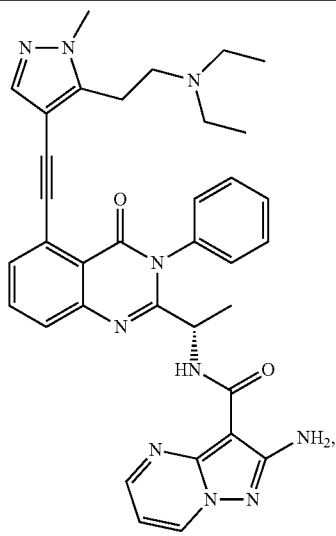
Compound 3026
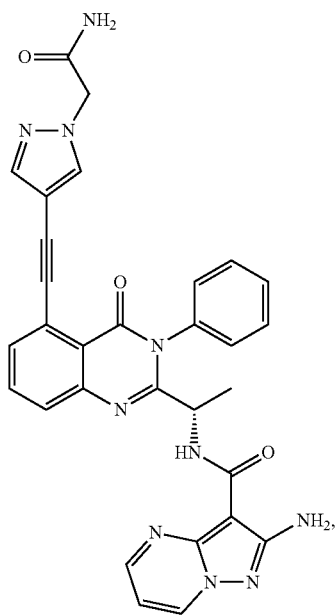 [SMILES: C[C@H](NC(=O)c1c(N)nn2cccnc12)c1nc2cccc(C#Cc3cnn(CC(N)=O)c3)c2c(=O)n1-c1ccccc1]
Compound 3027
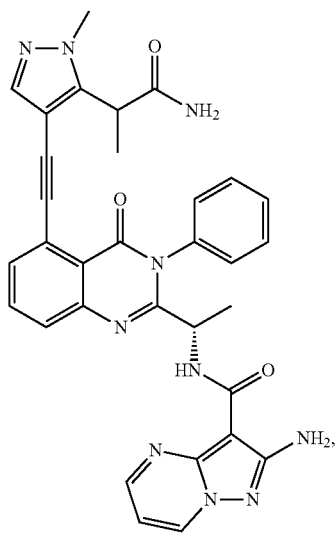 [SMILES: CC(C(N)=O)c1c(C#Cc2cccc3nc([C@H](C)NC(=O)c4c(N)nn5cccnc45)n(-c4ccccc4)c(=O)c23)cnn1C]
Compound 3028

TABLE 6-continued
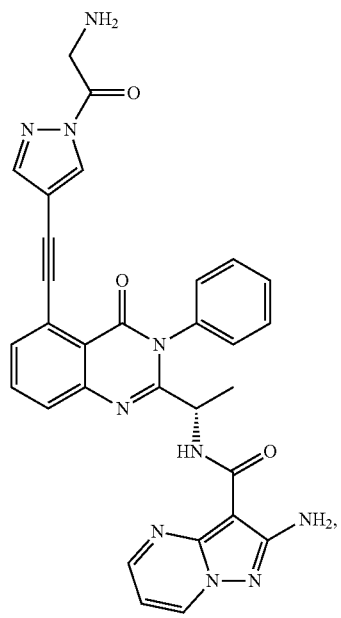 [SMILES: C[C@H](NC(=O)c1c(N)nn2cccnc12)c1nc2cccc(C#Cc3cnn(C(=O)CN)c3)c2c(=O)n1-c1ccccc1]
Compound 3029
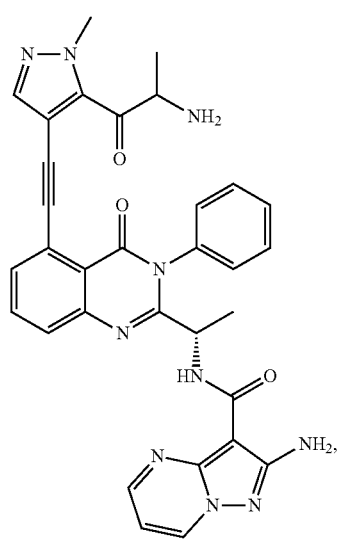 [SMILES: CC(N)C(=O)c1c(C#Cc2cccc3nc([C@H](C)NC(=O)c4c(N)nn5cccnc45)n(-c4ccccc4)c(=O)c23)cnn1C]
Compound 3030

TABLE 6-continued
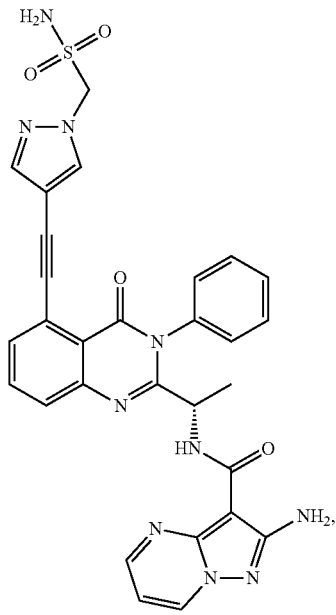 [SMILES: C[C@H](NC(=O)c1c(N)nn2cccnc12)c1nc2cccc(C#Cc3cnn(CS(N)(=O)=O)c3)c2c(=O)n1-c1ccccc1]
Compound 3031
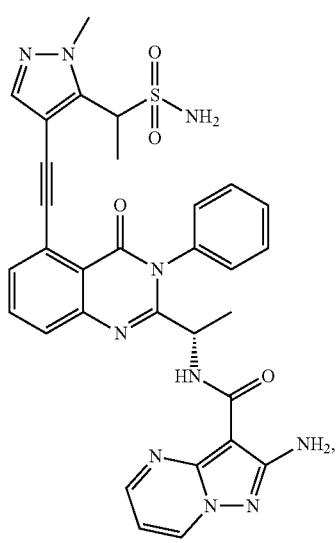 [SMILES: CC(c1c(C#Cc2cccc3nc([C@H](C)NC(=O)c4c(N)nn5cccnc45)n(-c4ccccc4)c(=O)c23)cnn1C)S(N)(=O)=O]
Compound 3032

TABLE 6-continued
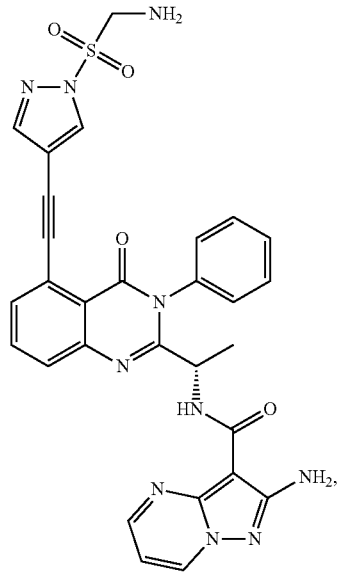 [SMILES: C[C@H](NC(=O)c1c(N)nn2cccnc12)c1nc2cccc(C#Cc3cnn(S(=O)(=O)CN)c3)c2c(=O)n1-c1ccccc1]
Compound 3033
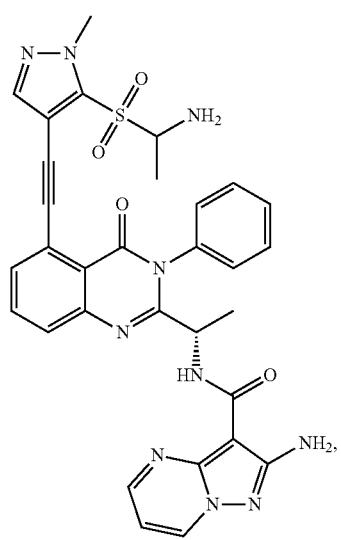 [SMILES: CC(N)S(=O)(=O)c1c(C#Cc2cccc3nc([C@H](C)NC(=O)c4c(N)nn5cccnc45)n(-c4ccccc4)c(=O)c23)cnn1C]
Compound 3034

TABLE 6-continued
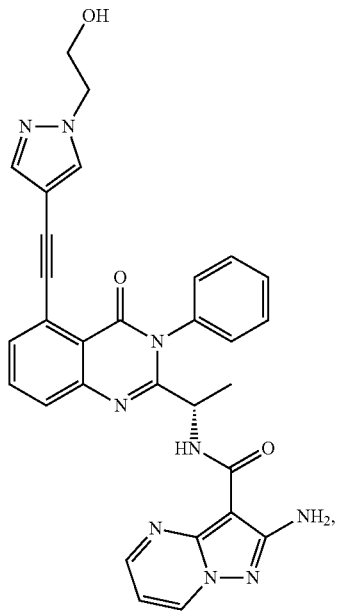 [SMILES: C[C@H](NC(=O)c1c(N)nn2cccnc12)c1nc2cccc(C#Cc3cnn(CCO)c3)c2c(=O)n1-c1ccccc1]
Compound 3035
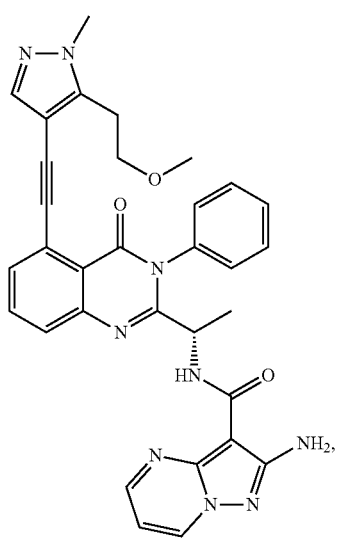 [SMILES: COCCc1c(C#Cc2cccc3nc([C@H](C)NC(=O)c4c(N)nn5cccnc45)n(-c4ccccc4)c(=O)c23)cnn1C]
Compound 3036

TABLE 6-continued
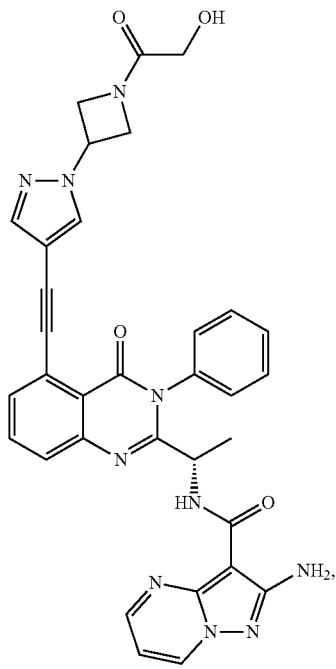 [SMILES: C[C@H](NC(=O)c1c(N)nn2cccnc12)c1nc2cccc(C#Cc3cnn(C4CN(C(=O)CO)C4)c3)c2c(=O)n1-c1ccccc1]
Compound 3037
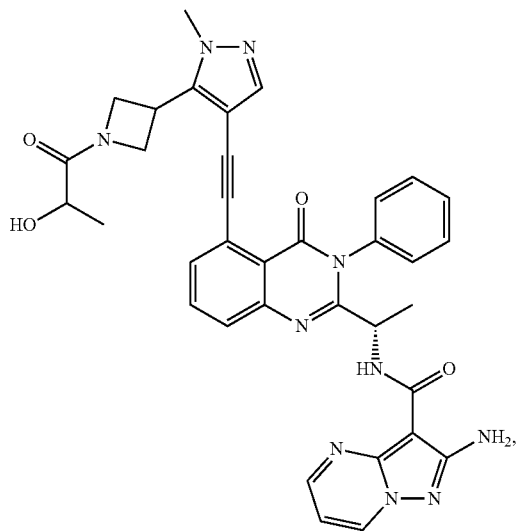 [SMILES: CC(O)C(=O)N1CC(c2c(C#Cc3cccc4nc([C@H](C)NC(=O)c5c(N)nn6cccnc56)n(-c5ccccc5)c(=O)c34)cnn2C)C1]
Compound 3038

TABLE 6-continued
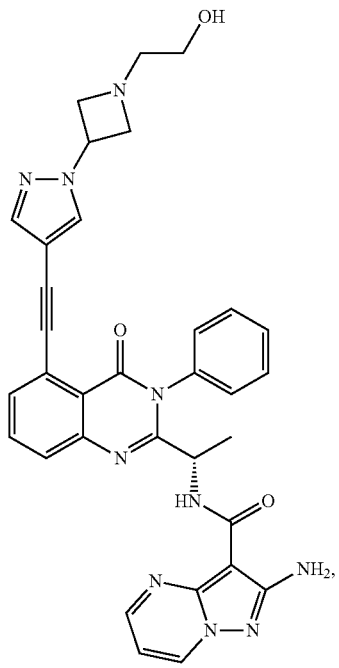 [SMILES: C[C@H](NC(=O)c1c(N)nn2cccnc12)c1nc2cccc(C#Cc3cnn(C4CN(CCO)C4)c3)c2c(=O)n1-c1ccccc1]
Compound 3039
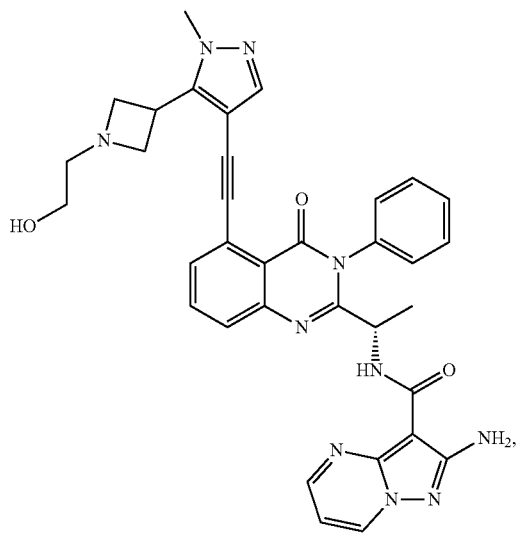 [SMILES: C[C@H](NC(=O)c1c(N)nn2cccnc12)c1nc2cccc(C#Cc3cnn(C)c3C3CN(CCO)C3)c2c(=O)n1-c1ccccc1]
Compound 3040

TABLE 6-continued
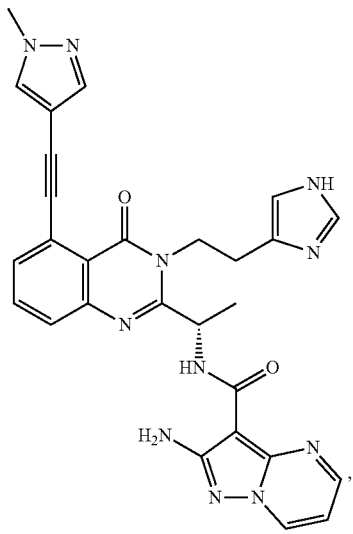 [SMILES: C[C@H](NC(=O)c1c(N)nn2cccnc12)c1nc2cccc(C#Cc3cnn(C)c3)c2c(=O)n1CCc1c[nH]cn1]
Compound 3045
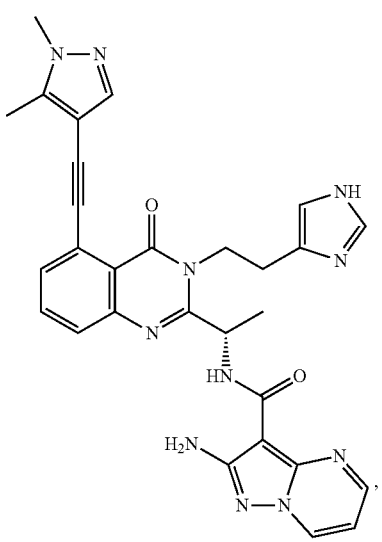 [SMILES: Cc1c(C#Cc2cccc3nc([C@H](C)NC(=O)c4c(N)nn5cccnc45)n(CCc4c[nH]cn4)c(=O)c23)cnn1C]
Compound 3046
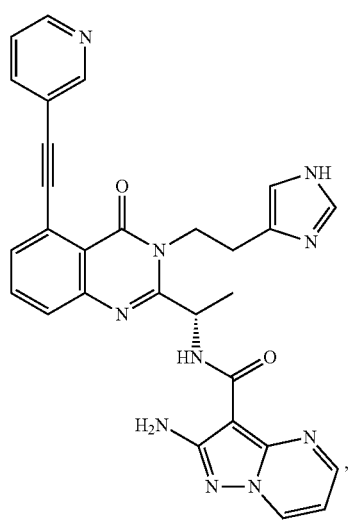 [SMILES: C[C@H](NC(=O)c1c(N)nn2cccnc12)c1nc2cccc(C#Cc3cccnc3)c2c(=O)n1CCc1c[nH]cn1]
Compound 3047

TABLE 6-continued
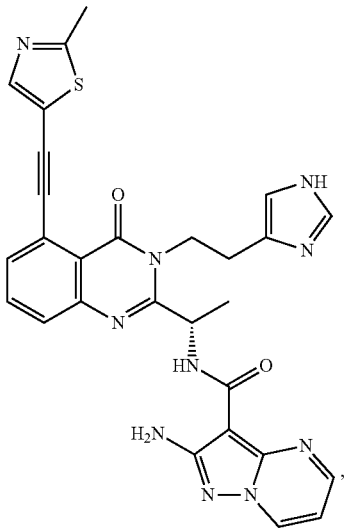 [SMILES: Cc1ncc(C#Cc2cccc3nc([C@H](C)NC(=O)c4c(N)nn5cccnc45)n(CCc4c[nH]cn4)c(=O)c23)s1]
Compound 3048
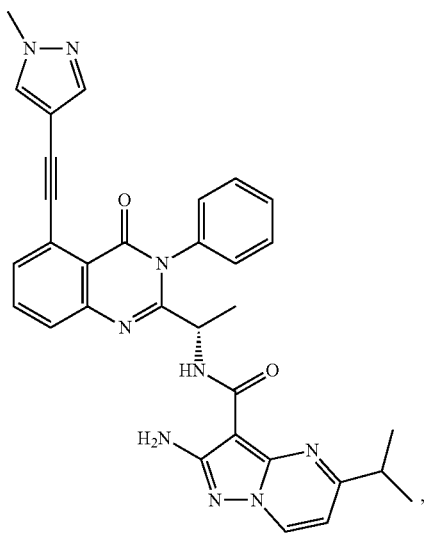 [SMILES: CC(C)c1ccn2nc(N)c(C(=O)N[C@@H](C)c3nc4cccc(C#Cc5cnn(C)c5)c4c(=O)n3-c3ccccc3)c2n1]
Compound 3049
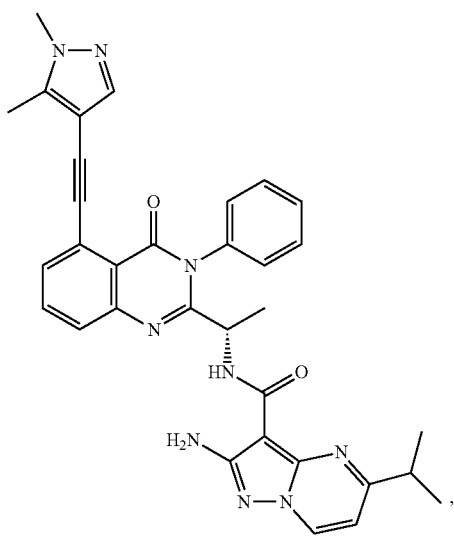 [SMILES: Cc1c(C#Cc2cccc3nc([C@H](C)NC(=O)c4c(N)nn5ccc(C(C)C)nc45)n(-c4ccccc4)c(=O)c23)cnn1C]
Compound 3050

TABLE 6-continued
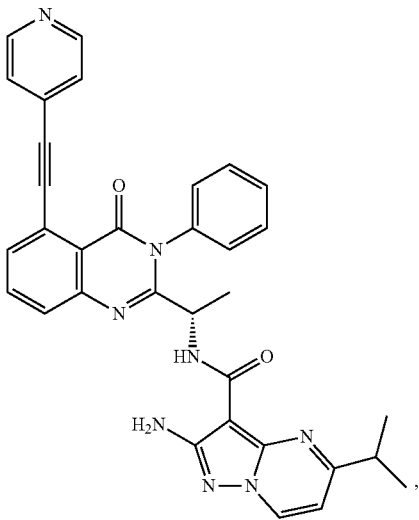 [SMILES: CC(C)c1ccn2nc(N)c(C(=O)N[C@@H](C)c3nc4cccc(C#Cc5ccncc5)c4c(=O)n3-c3ccccc3)c2n1]
Compound 3051
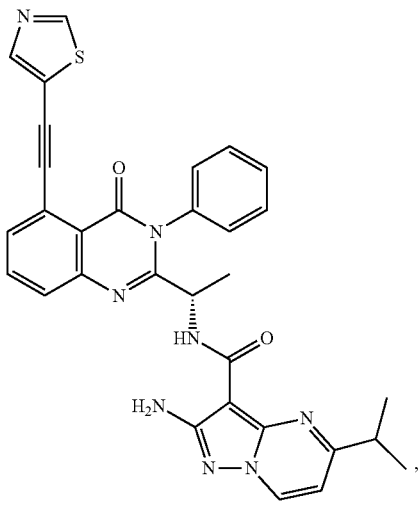 [SMILES: CC(C)c1ccn2nc(N)c(C(=O)N[C@@H](C)c3nc4cccc(C#Cc5cncs5)c4c(=O)n3-c3ccccc3)c2n1]
Compound 3052
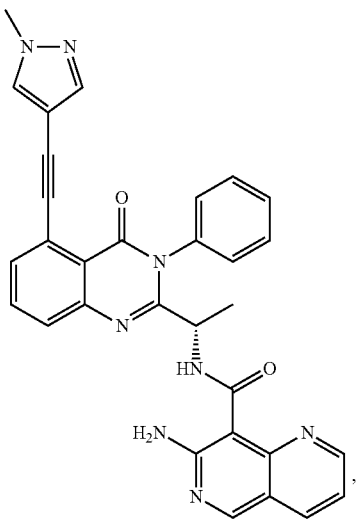 [SMILES: C[C@H](NC(=O)c1c(N)ncc2cccnc12)c1nc2cccc(C#Cc3cnn(C)c3)c2c(=O)n1-c1ccccc1]
Compound 3053

TABLE 6-continued
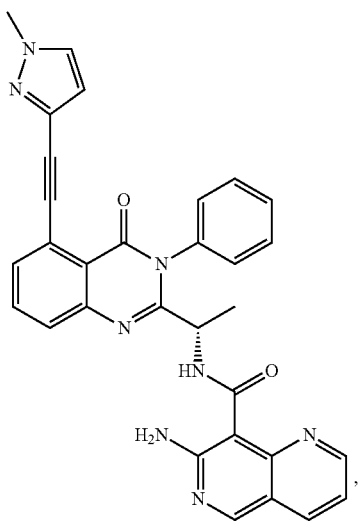 [SMILES: C[C@H](NC(=O)c1c(N)ncc2cccnc12)c1nc2cccc(C#Cc3ccn(C)n3)c2c(=O)n1-c1ccccc1]
Compound 3054
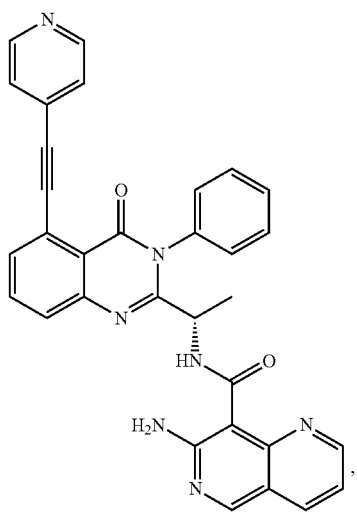 [SMILES: C[C@H](NC(=O)c1c(N)ncc2cccnc12)c1nc2cccc(C#Cc3ccncc3)c2c(=O)n1-c1ccccc1]
Compound 3055
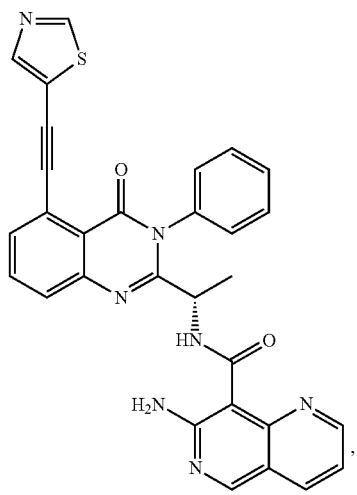 [SMILES: C[C@H](NC(=O)c1c(N)ncc2cccnc12)c1nc2cccc(C#Cc3cncs3)c2c(=O)n1-c1ccccc1]
Compound 3056

TABLE 6-continued
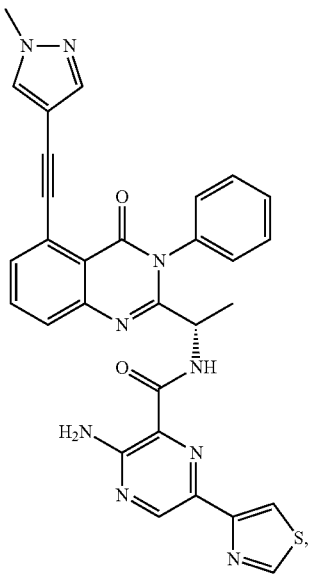 [SMILES: C[C@H](NC(=O)c1nc(-c2cscn2)cnc1N)c1nc2cccc(C#Cc3cnn(C)c3)c2c(=O)n1-c1ccccc1]
Compound 3057
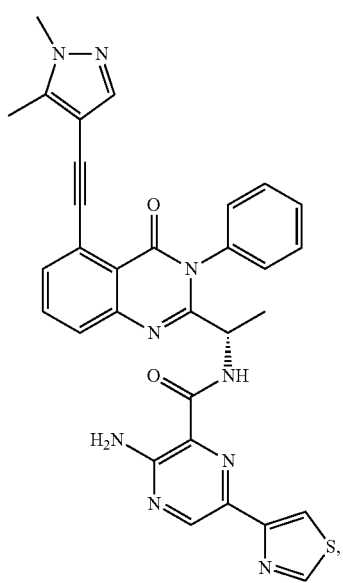 [SMILES: Cc1c(C#Cc2cccc3nc([C@H](C)NC(=O)c4nc(-c5cscn5)cnc4N)n(-c4ccccc4)c(=O)c23)cnn1C]
Compound 3058

TABLE 6-continued
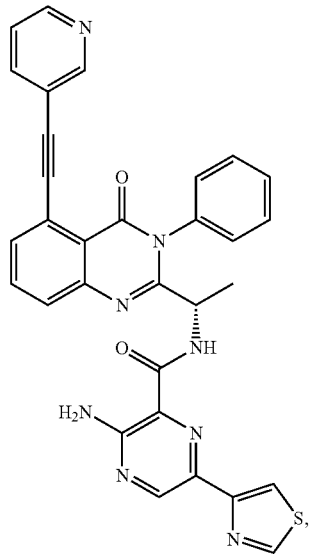 [SMILES: C[C@H](NC(=O)c1nc(-c2cscn2)cnc1N)c1nc2cccc(C#Cc3cccnc3)c2c(=O)n1-c1ccccc1]
Compound 3059
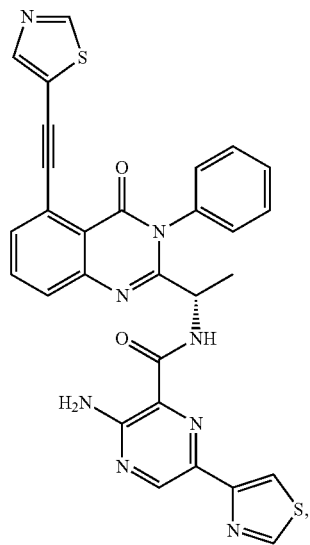
Compound 3060

TABLE 6-continued
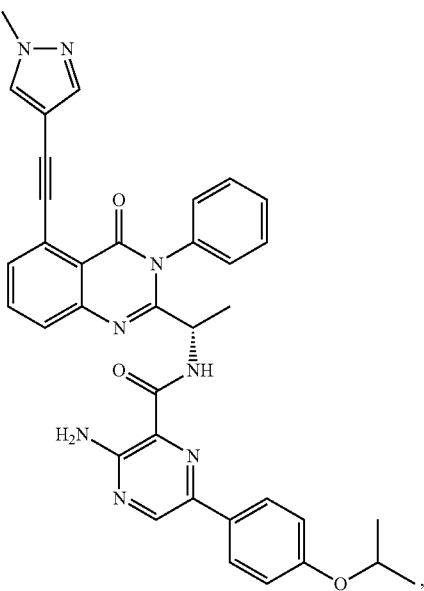 [SMILES: CC(C)Oc1ccc(-c2cnc(N)c(C(=O)N[C@@H](C)c3nc4cccc(C#Cc5cnn(C)c5)c4c(=O)n3-c3ccccc3)n2)cc1]
Compound 3061
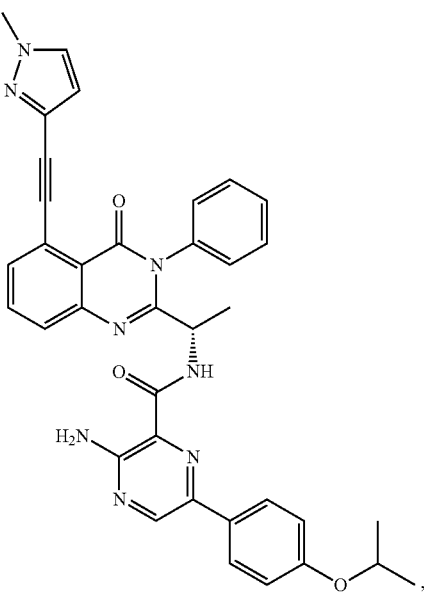 [SMILES: CC(C)Oc1ccc(-c2cnc(N)c(C(=O)N[C@@H](C)c3nc4cccc(C#Cc5ccn(C)n5)c4c(=O)n3-c3ccccc3)n2)cc1]
Compound 3062

TABLE 6-continued
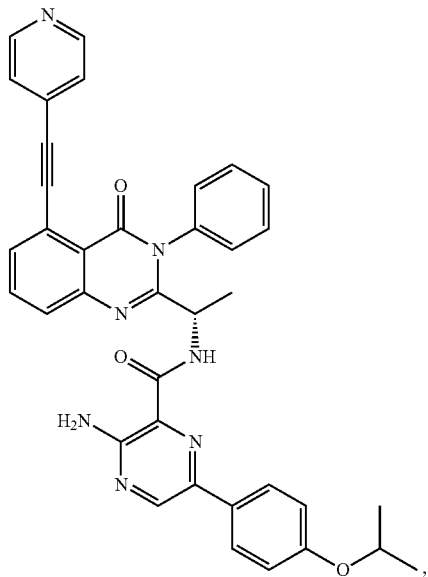
Compound 3063
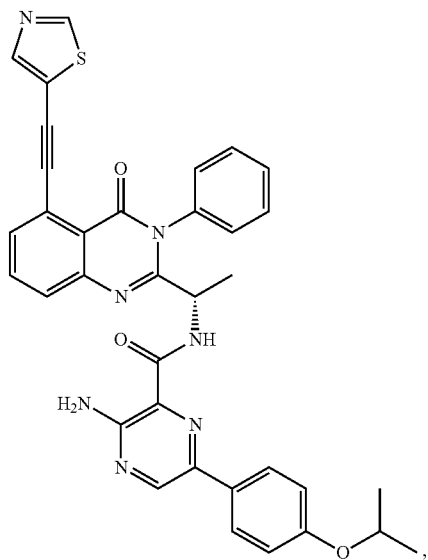 [SMILES: CC(C)Oc1ccc(-c2cnc(N)c(C(=O)N[C@@H](C)c3nc4cccc(C#Cc5cncs5)c4c(=O)n3-c3ccccc3)n2)cc1]
Compound 3064

TABLE 6-continued
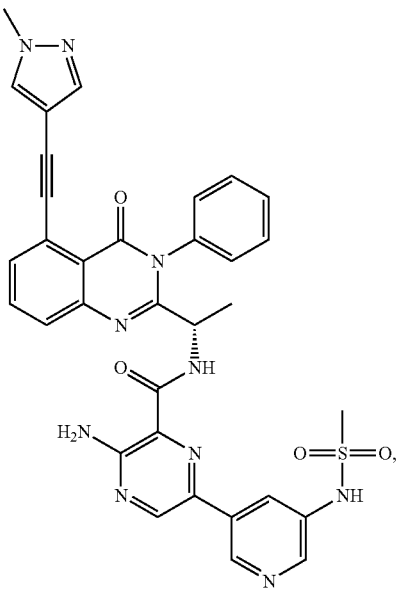 [SMILES: C[C@H](NC(=O)c1nc(-c2cncc(NS(C)(=O)=O)c2)cnc1N)c1nc2cccc(C#Cc3cnn(C)c3)c2c(=O)n1-c1ccccc1]
Compound 3065
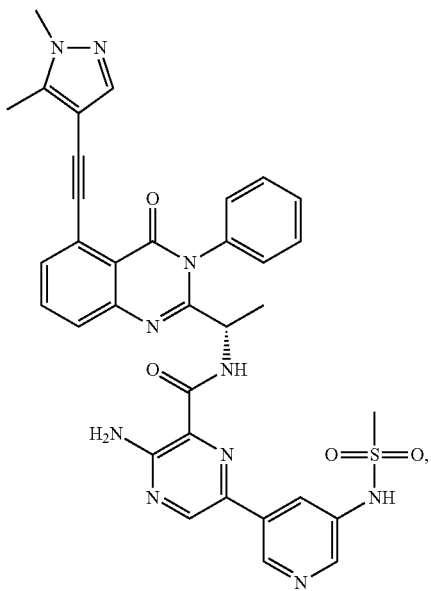 [SMILES: Cc1c(C#Cc2cccc3nc([C@H](C)NC(=O)c4nc(-c5cncc(NS(C)(=O)=O)c5)cnc4N)n(-c4ccccc4)c(=O)c23)cnn1C]
Compound 3066

TABLE 6-continued
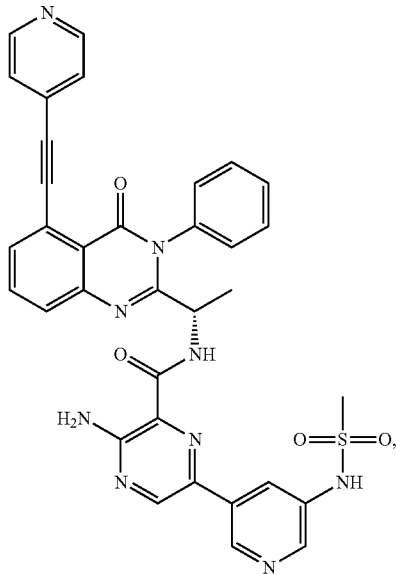
Compound 3067
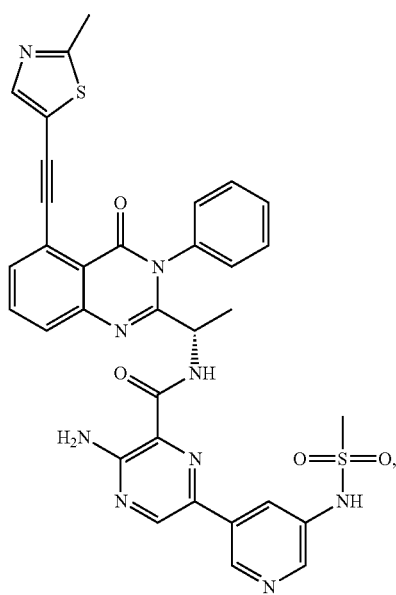 [SMILES: Cc1ncc(C#Cc2cccc3nc([C@H](C)NC(=O)c4nc(-c5cncc(NS(C)(=O)=O)c5)cnc4N)n(-c4ccccc4)c(=O)c23)s1]
Compound 3068

TABLE 6-continued
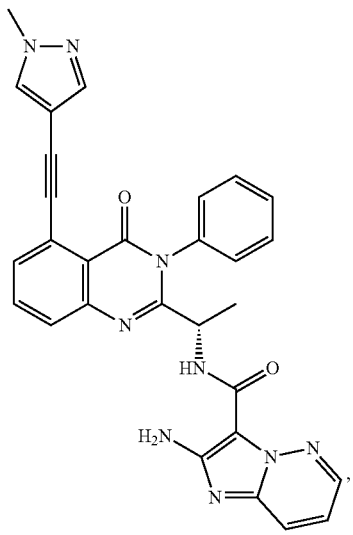 [SMILES: C[C@H](NC(=O)c1c(N)nc2cccnn12)c1nc2cccc(C#Cc3cnn(C)c3)c2c(=O)n1-c1ccccc1]
Compound 3069
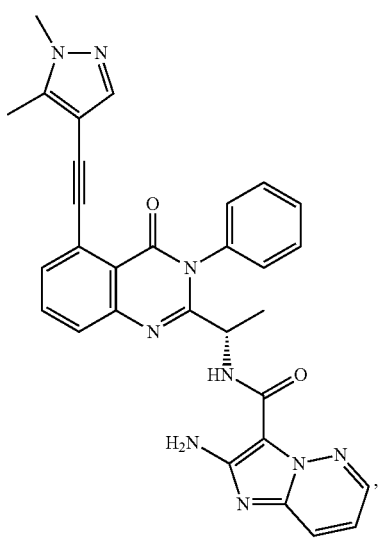 [SMILES: Cc1c(C#Cc2cccc3nc([C@H](C)NC(=O)c4c(N)nc5cccnn45)n(-c4ccccc4)c(=O)c23)cnn1C]
Compound 3070
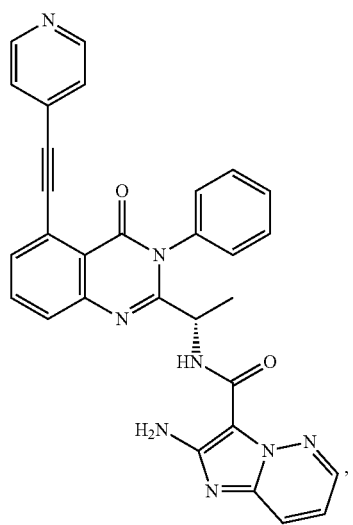 [SMILES: C[C@H](NC(=O)c1c(N)nc2cccnn12)c1nc2cccc(C#Cc3ccncc3)c2c(=O)n1-c1ccccc1]
Compound 3071

TABLE 6-continued
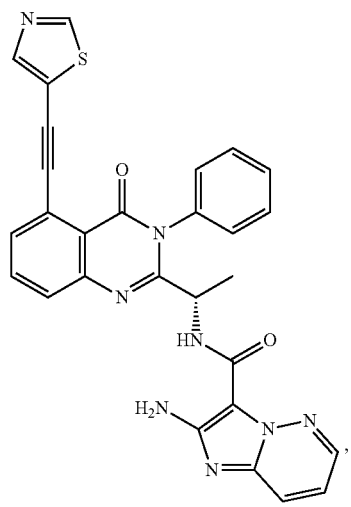 [SMILES: C[C@H](NC(=O)c1c(N)nc2cccnn12)c1nc2cccc(C#Cc3cncs3)c2c(=O)n1-c1ccccc1]
Compound 3072
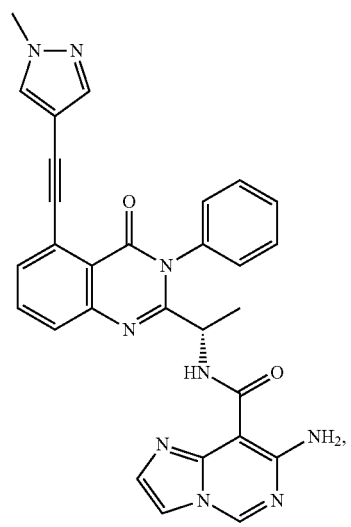 [SMILES: C[C@H](NC(=O)c1c(N)ncn2ccnc12)c1nc2cccc(C#Cc3cnn(C)c3)c2c(=O)n1-c1ccccc1]
Compound 3073
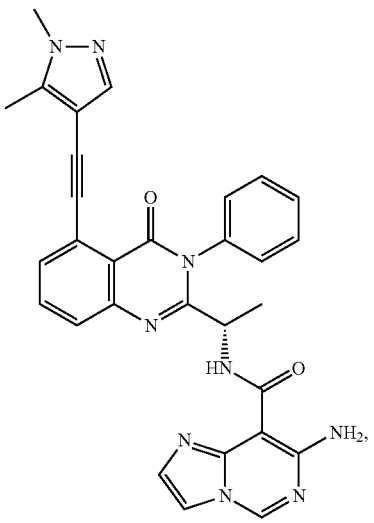 [SMILES: Cc1c(C#Cc2cccc3nc([C@H](C)NC(=O)c4c(N)ncn5ccnc45)n(-c4ccccc4)c(=O)c23)cnn1C]
Compound 3074

TABLE 6-continued
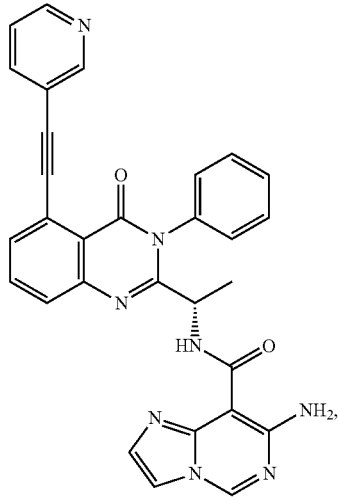 [SMILES: C[C@H](NC(=O)c1c(N)ncn2ccnc12)c1nc2cccc(C#Cc3cccnc3)c2c(=O)n1-c1ccccc1]
Compound 3075
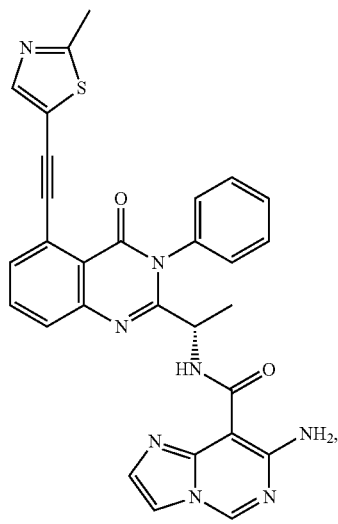
Compound 3076
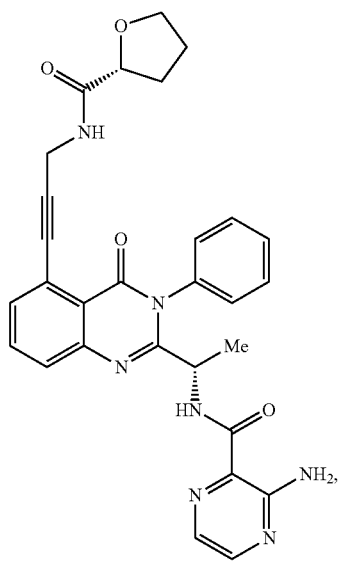 [SMILES: C[C@H](NC(=O)c1nccnc1N)c1nc2cccc(C#CCNC(=O)[C@H]3CCCO3)c2c(=O)n1-c1ccccc1]
Compound 3077

TABLE 6-continued
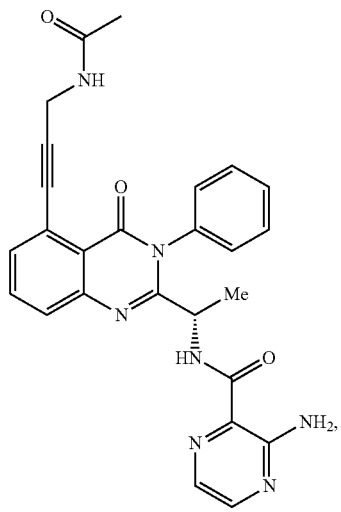 [SMILES: CC(=O)NCC#Cc1cccc2nc([C@H](C)NC(=O)c3nccnc3N)n(-c3ccccc3)c(=O)c12]
Compound 3078
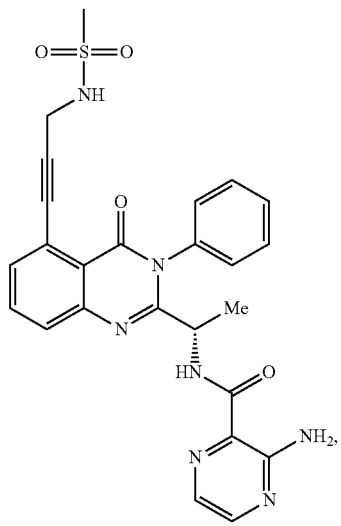 [SMILES: C[C@H](NC(=O)c1nccnc1N)c1nc2cccc(C#CCNS(C)(=O)=O)c2c(=O)n1-c1ccccc1]
Compound 3079
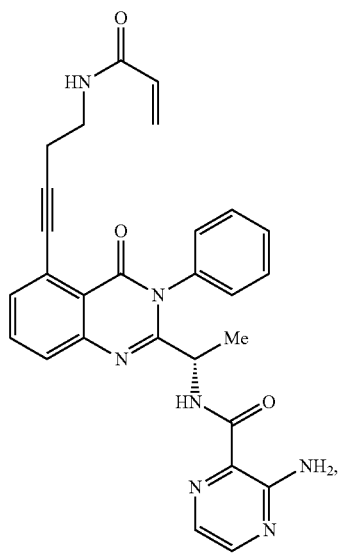 [SMILES: C=CC(=O)NCCC#Cc1cccc2nc([C@H](C)NC(=O)c3nccnc3N)n(-c3ccccc3)c(=O)c12]
Compound 3080

TABLE 6-continued
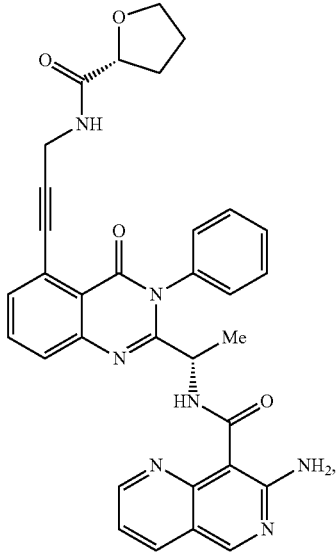 [SMILES: C[C@H](NC(=O)c1c(N)ncc2cccnc12)c1nc2cccc(C#CCNC(=O)[C@H]3CCCO3)c2c(=O)n1-c1ccccc1]
Compound 3081
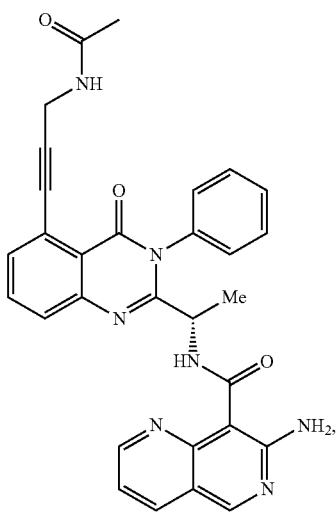 [SMILES: CC(=O)NCC#Cc1cccc2nc([C@H](C)NC(=O)c3c(N)ncc4cccnc34)n(-c3ccccc3)c(=O)c12]
Compound 3082
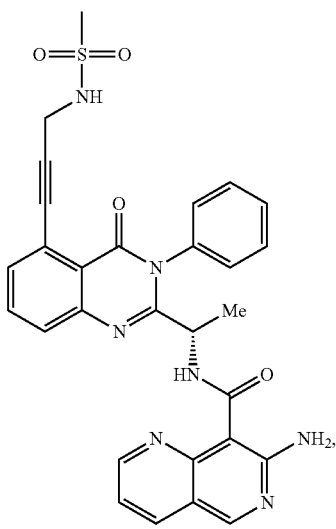 [SMILES: C[C@H](NC(=O)c1c(N)ncc2cccnc12)c1nc2cccc(C#CCNS(C)(=O)=O)c2c(=O)n1-c1ccccc1]
Compound 3083

TABLE 6-continued
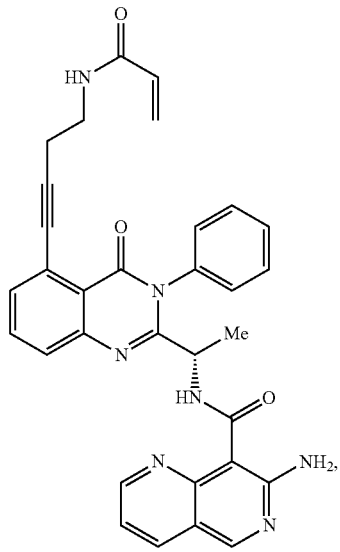 [SMILES: C=CC(=O)NCCC#Cc1cccc2nc([C@H](C)NC(=O)c3c(N)ncc4cccnc34)n(-c3ccccc3)c(=O)c12]
Compound 3084
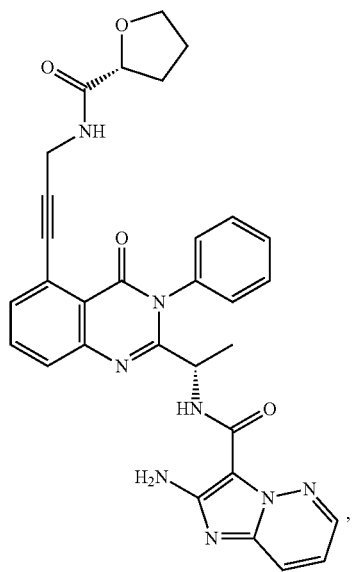 [SMILES: C[C@H](NC(=O)c1c(N)nc2cccnn12)c1nc2cccc(C#CCNC(=O)[C@H]3CCCO3)c2c(=O)n1-c1ccccc1]
Compound 3085
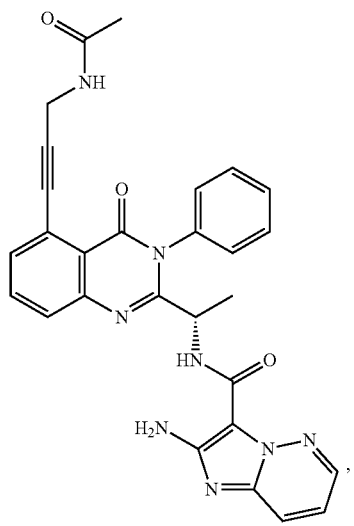
Compound 3086

TABLE 6-continued
Compound 3087
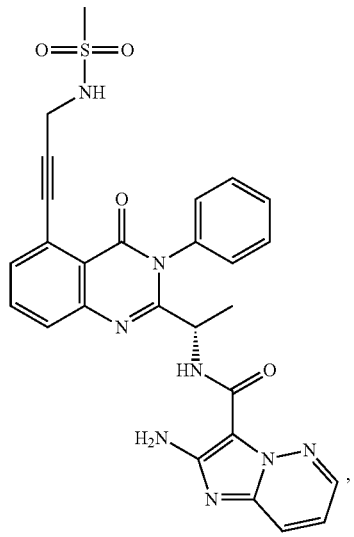 [SMILES: C[C@H](NC(=O)c1c(N)nc2cccnn12)c1nc2cccc(C#CCNS(C)(=O)=O)c2c(=O)n1-c1ccccc1]
Compound 3088
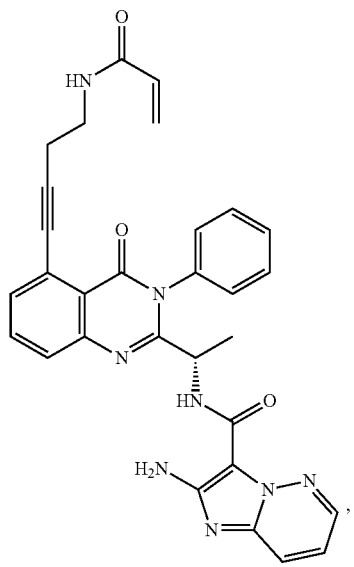 [SMILES: C=CC(=O)NCCC#Cc1cccc2nc([C@H](C)NC(=O)c3c(N)nc4cccnn34)n(-c3ccccc3)c(=O)c12]
Compound 3089
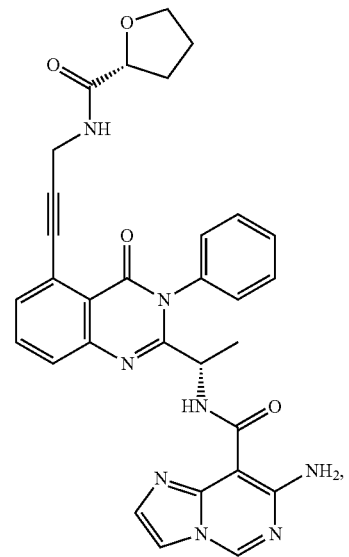 [SMILES: C[C@H](NC(=O)c1c(N)ncn2ccnc12)c1nc2cccc(C#CCNC(=O)[C@H]3CCCO3)c2c(=O)n1-c1ccccc1]

TABLE 6-continued
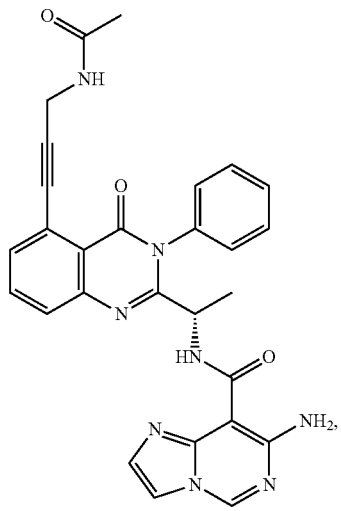 [SMILES: CC(=O)NCC#Cc1cccc2nc([C@H](C)NC(=O)c3c(N)ncn4ccnc34)n(-c3ccccc3)c(=O)c12]
Compound 3090
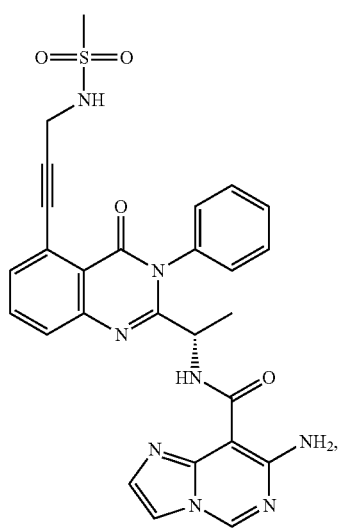 [SMILES: C[C@H](NC(=O)c1c(N)ncn2ccnc12)c1nc2cccc(C#CCNS(C)(=O)=O)c2c(=O)n1-c1ccccc1]
Compound 3091
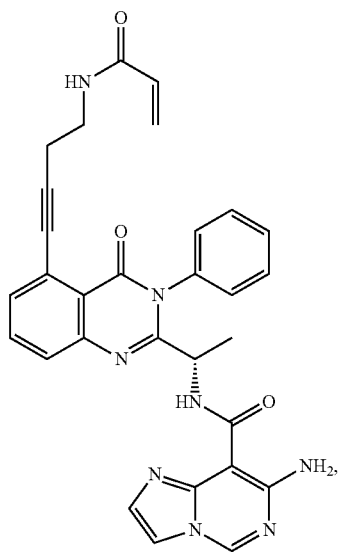 [SMILES: C=CC(=O)NCCC#Cc1cccc2nc([C@H](C)NC(=O)c3c(N)ncn4ccnc34)n(-c3ccccc3)c(=O)c12]
Compound 3092

TABLE 6-continued
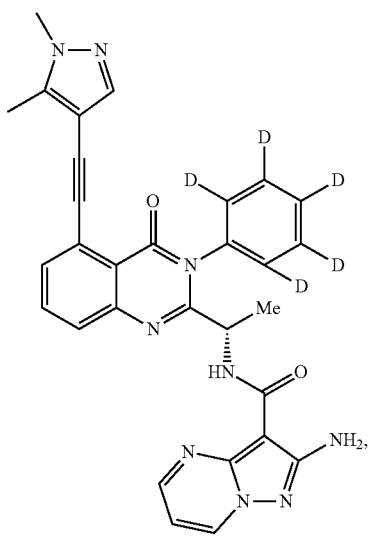
Compound 3093
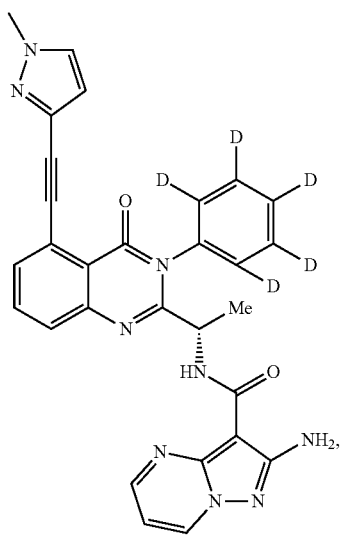
Compound 3094
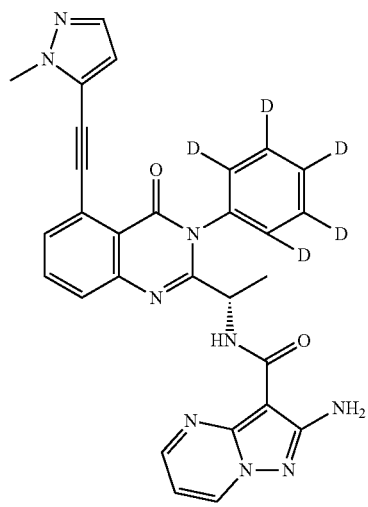 [SMILES: [2H]c1c([2H])c([2H])c(-n2c([C@H](C)NC(=O)c3c(N)nn4cccnc34)nc3cccc(C#Cc4ccnn4C)c3c2=O)c([2H])c1[2H]]
Compound 3095

TABLE 7
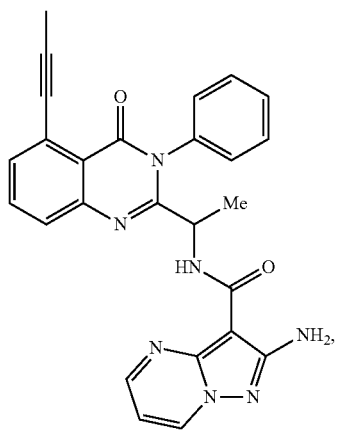 [SMILES: CC#Cc1cccc2nc(C(C)NC(=O)c3c(N)nn4cccnc34)n(-c3ccccc3)c(=O)c12]
Compound 1'
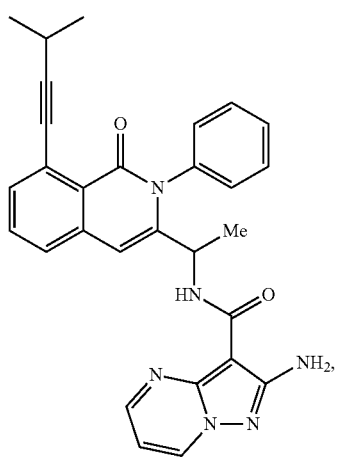 [SMILES: CC(C)C#Cc1cccc2cc(C(C)NC(=O)c3c(N)nn4cccnc34)n(-c3ccccc3)c(=O)c12]
Compound 2'
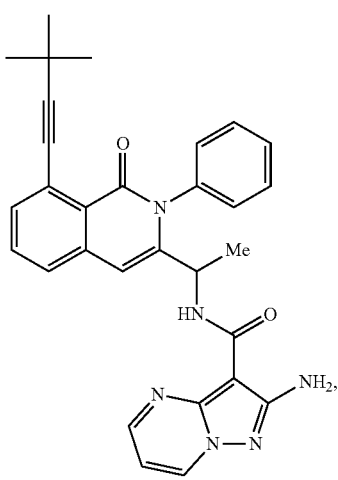 [SMILES: CC(NC(=O)c1c(N)nn2cccnc12)c1cc2cccc(C#CC(C)(C)C)c2c(=O)n1-c1ccccc1]
Compound 3'
TABLE 7-continued
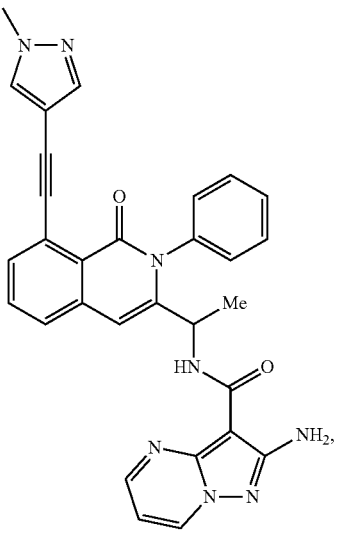 [SMILES: CC(NC(=O)c1c(N)nn2cccnc12)c1cc2cccc(C#Cc3cnn(C)c3)c2c(=O)n1-c1ccccc1]
Compound 4'
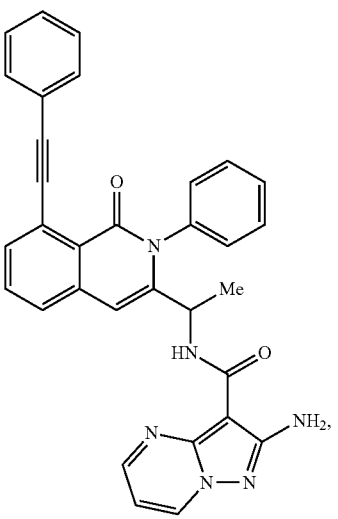 [SMILES: CC(NC(=O)c1c(N)nn2cccnc12)c1cc2cccc(C#Cc3ccccc3)c2c(=O)n1-c1ccccc1]
Compound 5'
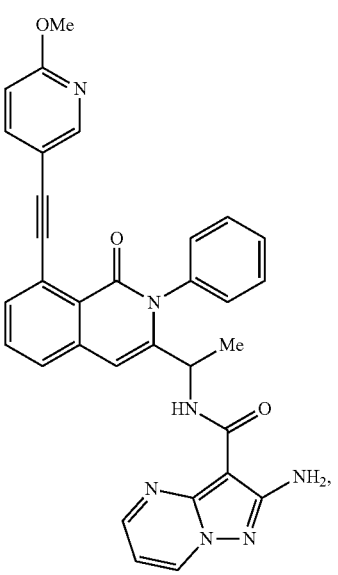 [SMILES: COc1ccc(C#Cc2cccc3cc(C(C)NC(=O)c4c(N)nn5cccnc45)n(-c4ccccc4)c(=O)c23)cn1]
Compound 6'

TABLE 7-continued
Compound 7'
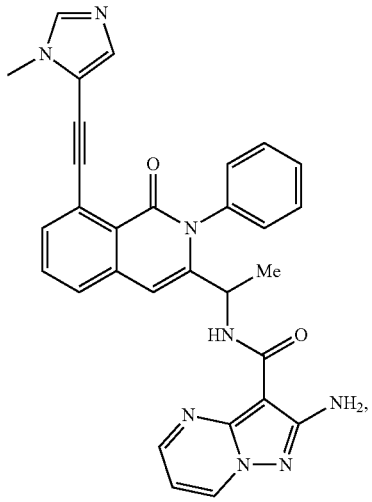 [SMILES: CC(NC(=O)c1c(N)nn2cccnc12)c1cc2cccc(C#Cc3cncn3C)c2c(=O)n1-c1ccccc1]
Compound 8'
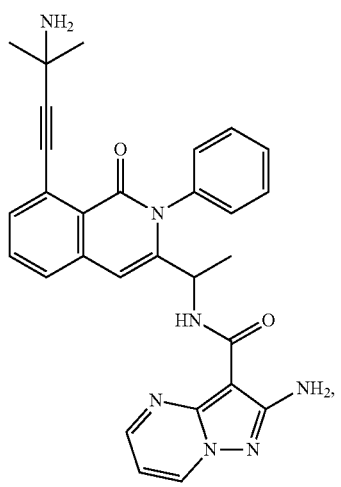 [SMILES: CC(NC(=O)c1c(N)nn2cccnc12)c1cc2cccc(C#CC(C)(C)N)c2c(=O)n1-c1ccccc1]
Compound 9'
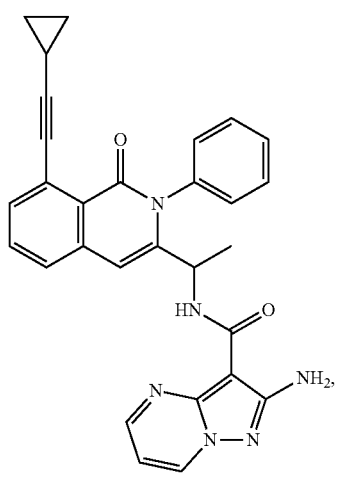 [SMILES: CC(NC(=O)c1c(N)nn2cccnc12)c1cc2cccc(C#CC3CC3)c2c(=O)n1-c1ccccc1]
TABLE 7-continued
Compound 10'
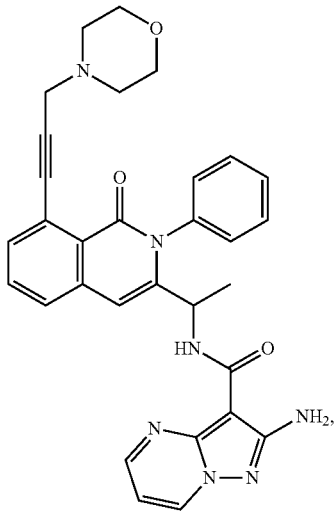 [SMILES: CC(NC(=O)c1c(N)nn2cccnc12)c1cc2cccc(C#CCN3CCOCC3)c2c(=O)n1-c1ccccc1]
Compound 11'
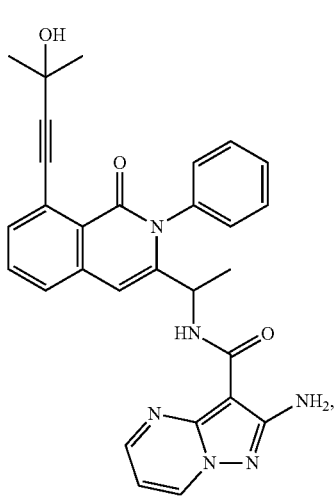 [SMILES: CC(NC(=O)c1c(N)nn2cccnc12)c1cc2cccc(C#CC(C)(C)O)c2c(=O)n1-c1ccccc1]
Compound 12'
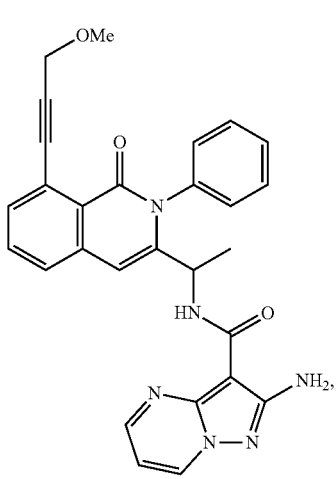 [SMILES: COCC#Cc1cccc2cc(C(C)NC(=O)c3c(N)nn4cccnc34)n(-c3ccccc3)c(=O)c12]

TABLE 7-continued
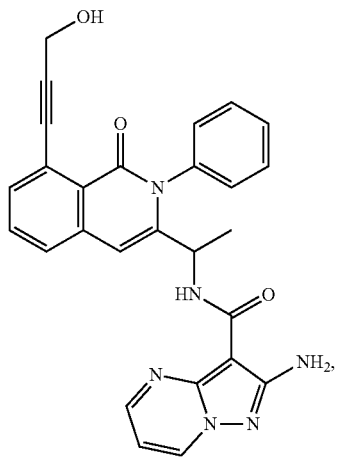
Compound 13'
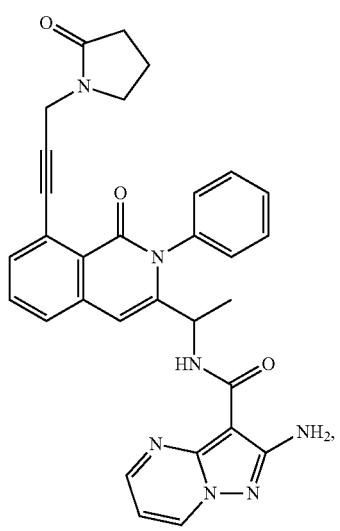 [SMILES: CC(NC(=O)c1c(N)nn2cccnc12)c1cc2cccc(C#CCN3CCCC3=O)c2c(=O)n1-c1ccccc1]
Compound 14'
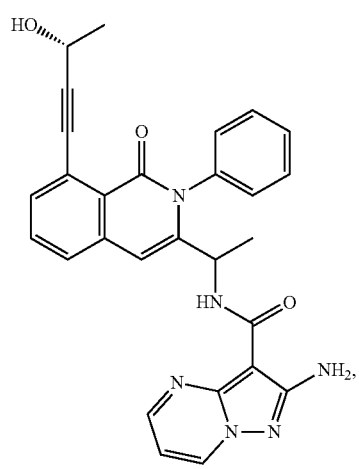
Compound 15'
TABLE 7-continued
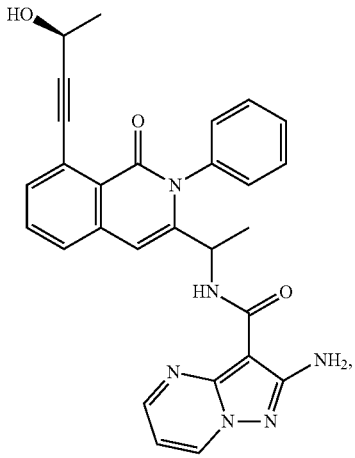 [SMILES: CC(NC(=O)c1c(N)nn2cccnc12)c1cc2cccc(C#C[C@H](C)O)c2c(=O)n1-c1ccccc1]
Compound 16'
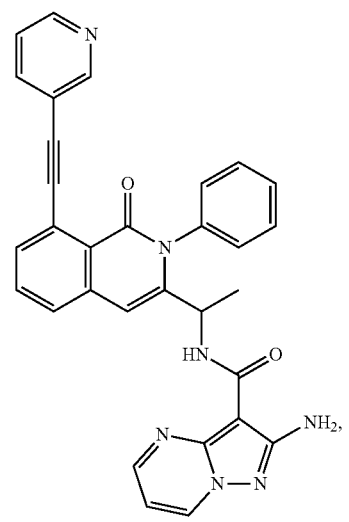 [SMILES: CC(NC(=O)c1c(N)nn2cccnc12)c1cc2cccc(C#Cc3cccnc3)c2c(=O)n1-c1ccccc1]
Compound 17'
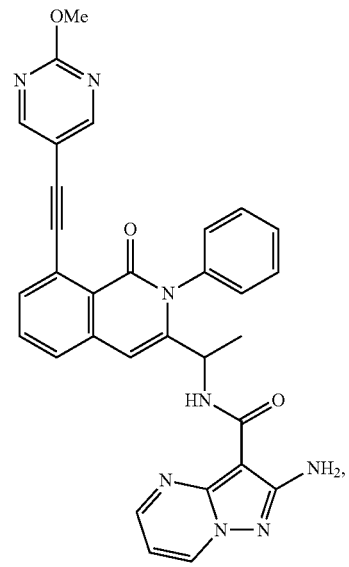 [SMILES: COc1ncc(C#Cc2cccc3cc(C(C)NC(=O)c4c(N)nn5cccnc45)n(-c4ccccc4)c(=O)c23)cn1]
Compound 18'

TABLE 7-continued
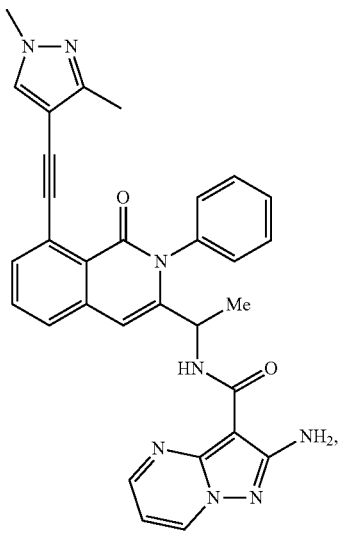 [SMILES: Cc1nn(C)cc1C#Cc1cccc2cc(C(C)NC(=O)c3c(N)nn4cccnc34)n(-c3ccccc3)c(=O)c12]
Compound 19'
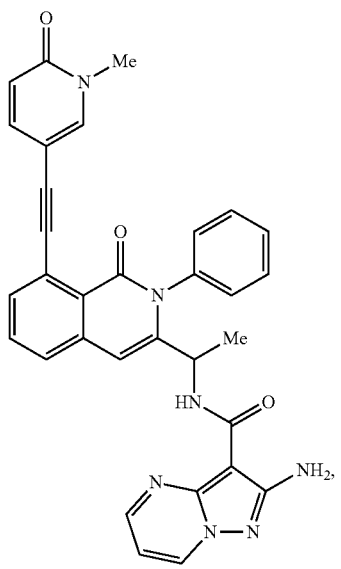 [SMILES: CC(NC(=O)c1c(N)nn2cccnc12)c1cc2cccc(C#Cc3ccc(=O)n(C)c3)c2c(=O)n1-c1ccccc1]
Compound 20'
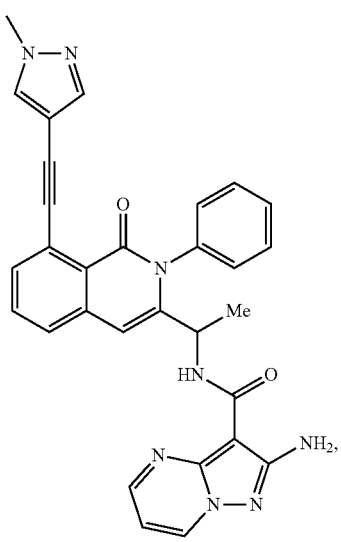 [SMILES: CC(NC(=O)c1c(N)nn2cccnc12)c1cc2cccc(C#Cc3cnn(C)c3)c2c(=O)n1-c1ccccc1]
Compound 21'
TABLE 7-continued
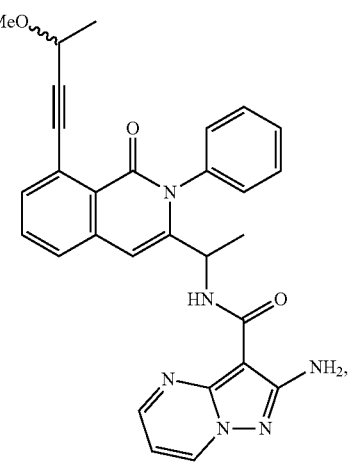
Compound 22'
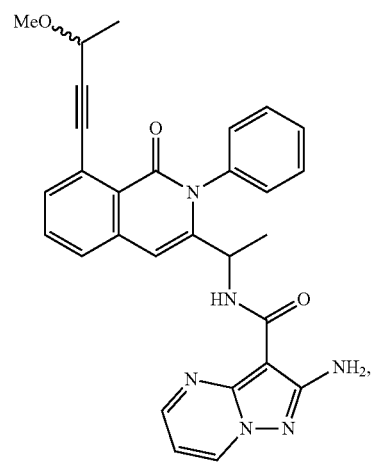 [SMILES: COC(C)C#Cc1cccc2cc(C(C)NC(=O)c3c(N)nn4cccnc34)n(-c3ccccc3)c(=O)c12]
Compound 23'
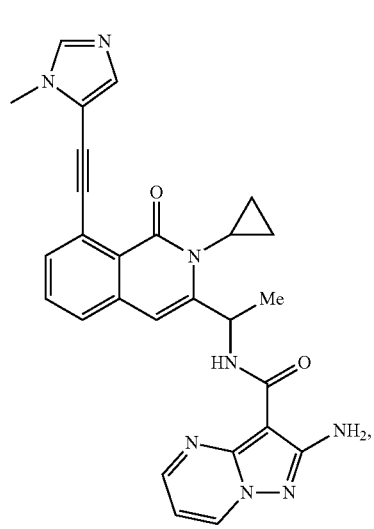 [SMILES: CC(NC(=O)c1c(N)nn2cccnc12)c1cc2cccc(C#Cc3cncn3C)c2c(=O)n1C1CC1]
Compound 24'

TABLE 7-continued
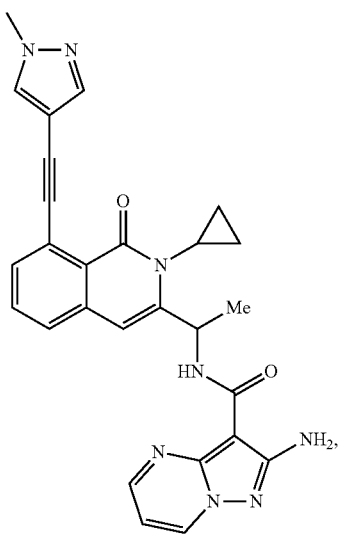 [SMILES: CC(NC(=O)c1c(N)nn2cccnc12)c1cc2cccc(C#Cc3cnn(C)c3)c2c(=O)n1C1CC1]
Compound 25'
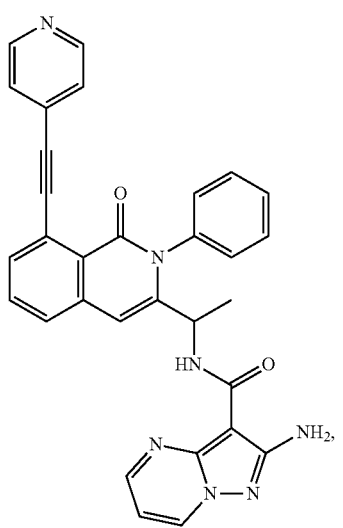 [SMILES: CC(NC(=O)c1c(N)nn2cccnc12)c1cc2cccc(C#Cc3ccncc3)c2c(=O)n1-c1ccccc1]
Compound 26'
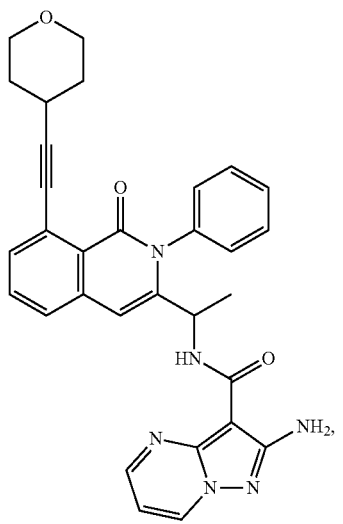
Compound 27'
TABLE 7-continued
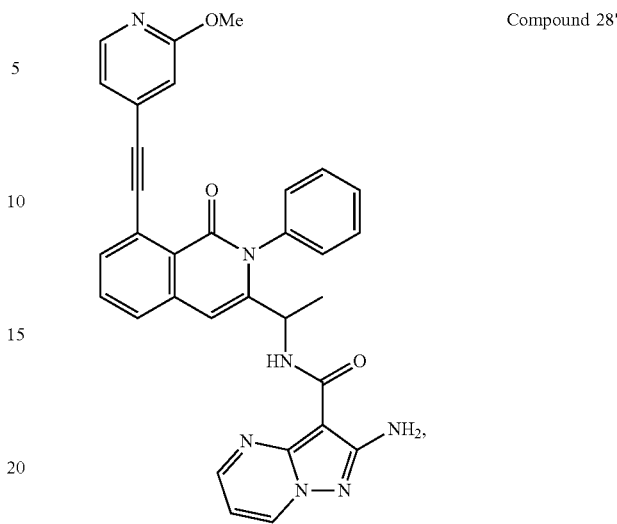
Compound 28'
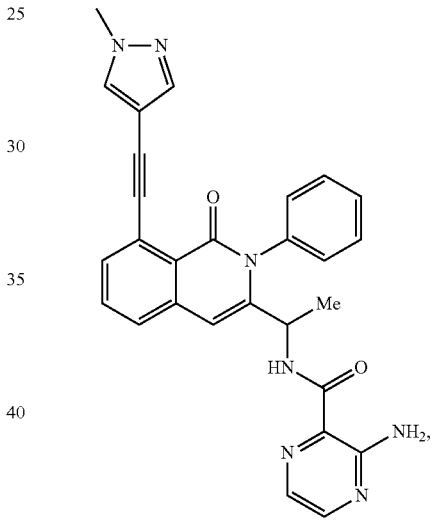
Compound 29'
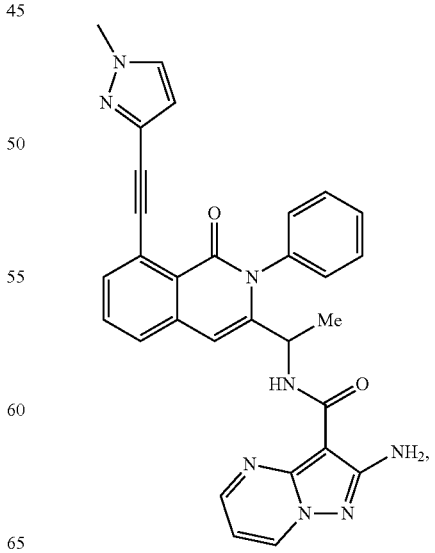
Compound 30'

TABLE 7-continued
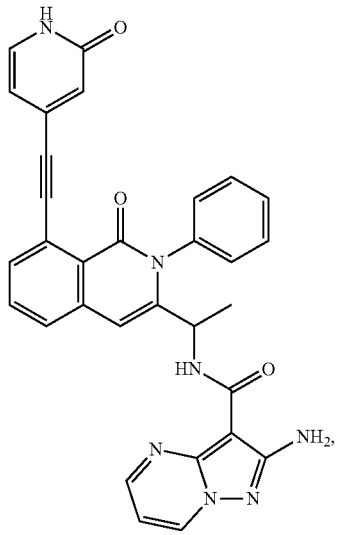 [SMILES: CC(NC(=O)c1c(N)nn2cccnc12)c1cc2cccc(C#Cc3cc[nH]c(=O)c3)c2c(=O)n1-c1ccccc1]
Compound 31'
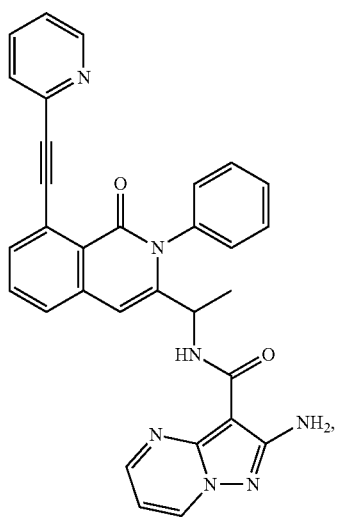 [SMILES: CC(NC(=O)c1c(N)nn2cccnc12)c1cc2cccc(C#Cc3ccccn3)c2c(=O)n1-c1ccccc1]
Compound 32'
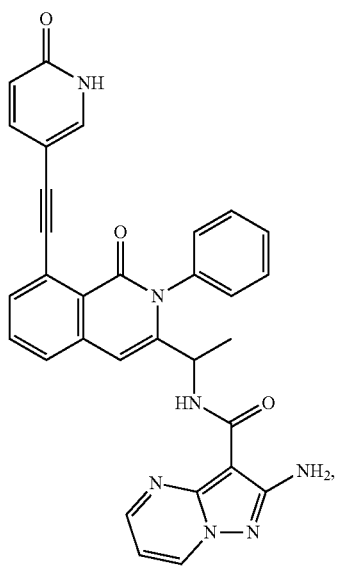 [SMILES: CC(NC(=O)c1c(N)nn2cccnc12)c1cc2cccc(C#Cc3ccc(=O)[nH]c3)c2c(=O)n1-c1ccccc1]
Compound 33'
TABLE 7-continued
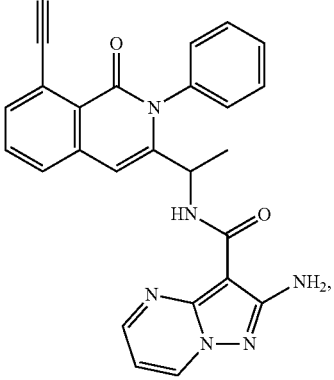
Compound 34'
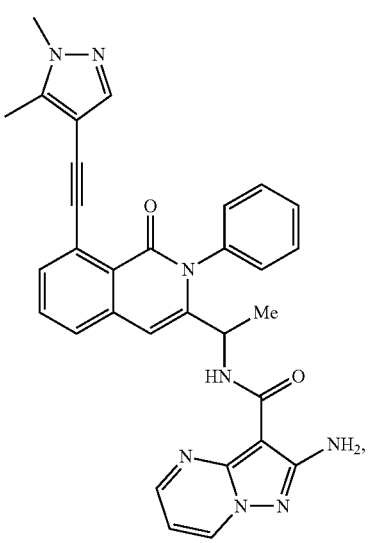 [SMILES: Cc1c(C#Cc2cccc3cc(C(C)NC(=O)c4c(N)nn5cccnc45)n(-c4ccccc4)c(=O)c23)cnn1C]
Compound 35'
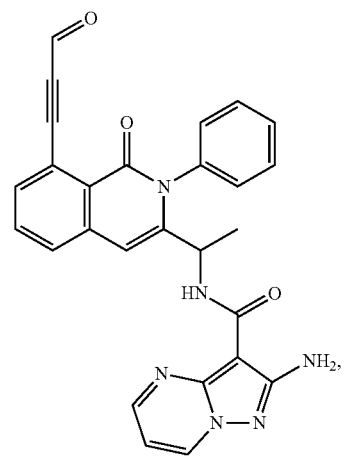 [SMILES: CC(NC(=O)c1c(N)nn2cccnc12)c1cc2cccc(C#CC=O)c2c(=O)n1-c1ccccc1]
Compound 36A'

TABLE 7-continued
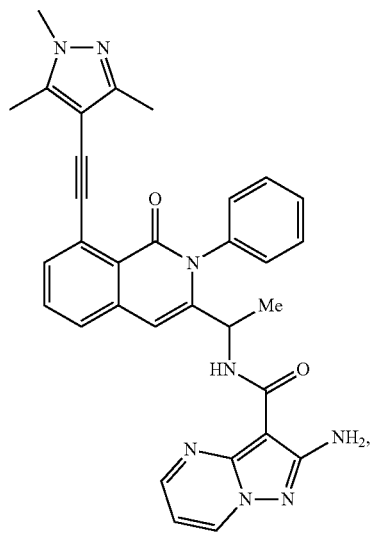 [SMILES: Cc1nn(C)c(C)c1C#Cc1cccc2cc(C(C)NC(=O)c3c(N)nn4cccnc34)n(-c3ccccc3)c(=O)c12]
Compound 37'
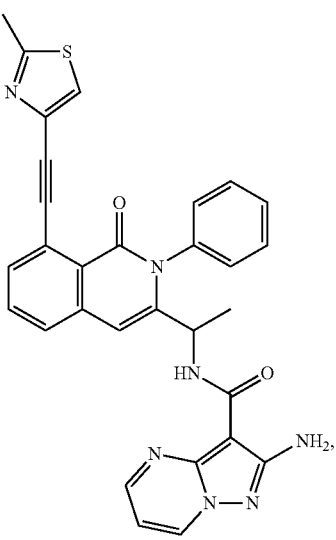
Compound 40'
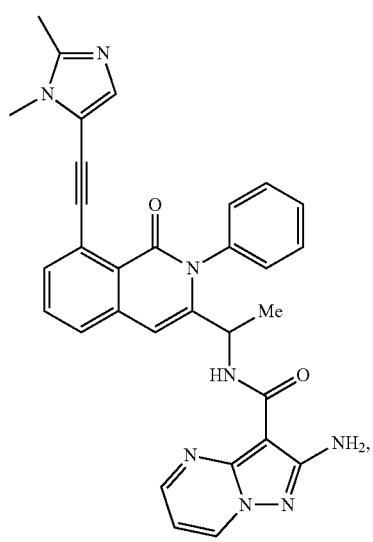 [SMILES: Cc1ncc(C#Cc2cccc3cc(C(C)NC(=O)c4c(N)nn5cccnc45)n(-c4ccccc4)c(=O)c23)n1C]
Compound 38'
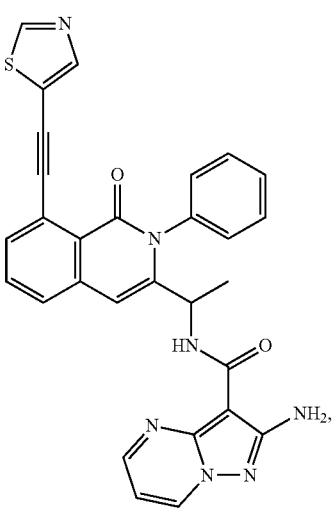
Compound 41'
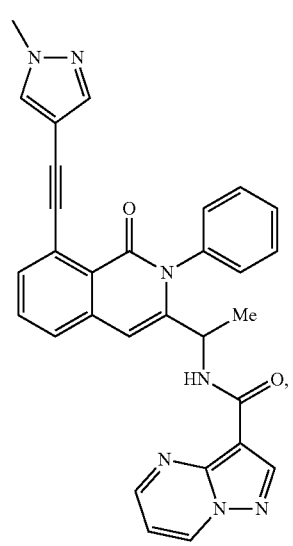 [SMILES: CC(NC(=O)c1cnn2cccnc12)c1cc2cccc(C#Cc3cnn(C)c3)c2c(=O)n1-c1ccccc1]
Compound 39'
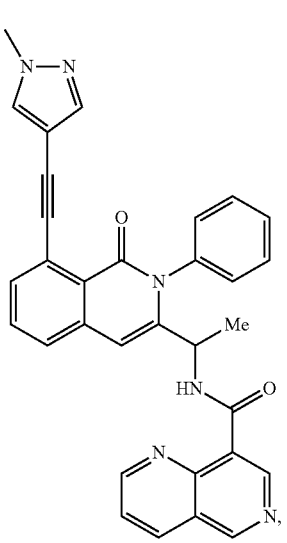 [SMILES: CC(NC(=O)c1cncc2cccnc12)c1cc2cccc(C#Cc3cnn(C)c3)c2c(=O)n1-c1ccccc1]
Compound 42'

TABLE 7-continued
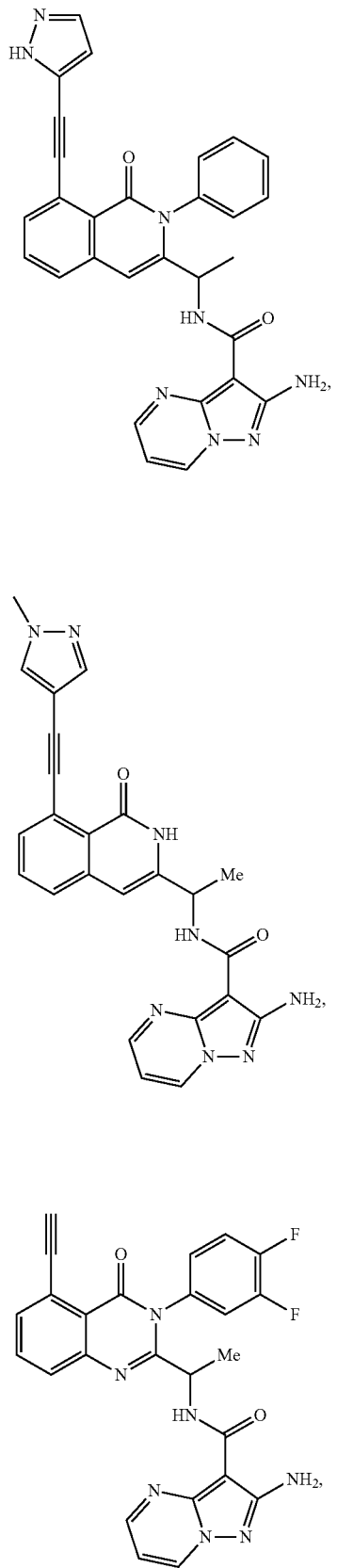
Compound 43'
Compound 44'
Compound 45'
TABLE 7-continued
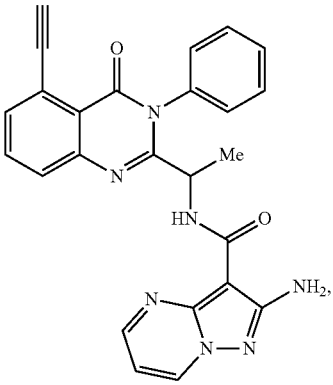 [SMILES: C#Cc1cccc2nc(C(C)NC(=O)c3c(N)nn4cccnc34)n(-c3ccccc3)c(=O)c12]
Compound 46'
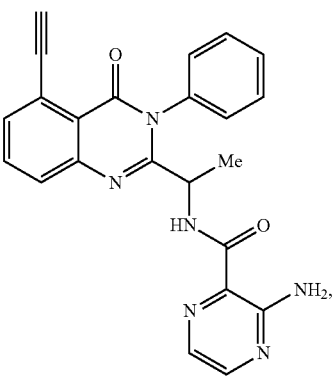 [SMILES: C#Cc1cccc2nc(C(C)NC(=O)c3nccnc3N)n(-c3ccccc3)c(=O)c12]
Compound 47'
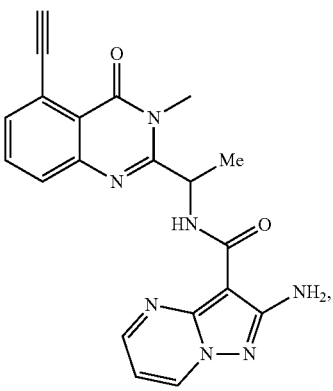 [SMILES: C#Cc1cccc2nc(C(C)NC(=O)c3c(N)nn4cccnc34)n(C)c(=O)c12]
Compound 48'
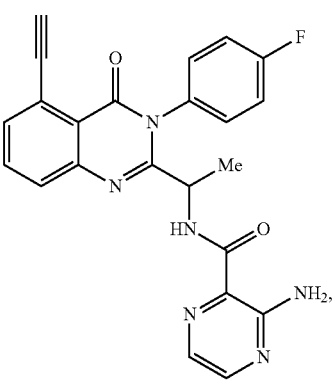 [SMILES: C#Cc1cccc2nc(C(C)NC(=O)c3nccnc3N)n(-c3ccc(F)cc3)c(=O)c12]
Compound 49'

TABLE 7-continued
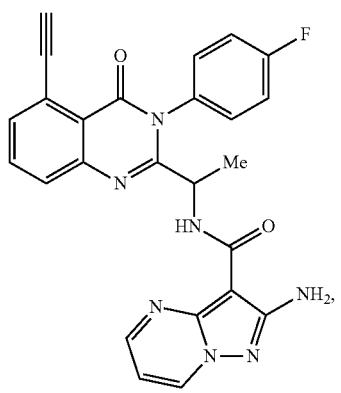 [SMILES: C#Cc1cccc2nc(C(C)NC(=O)c3c(N)nn4cccnc34)n(-c3ccc(F)cc3)c(=O)c12]
Compound 50'
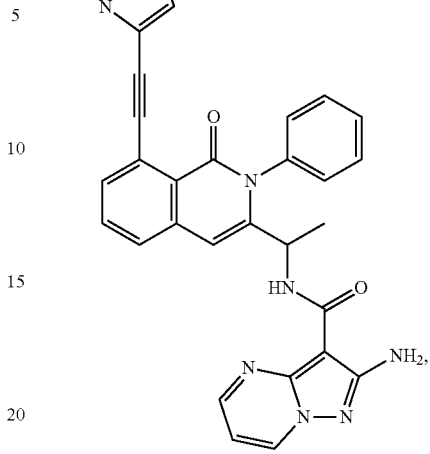
Compound 54'
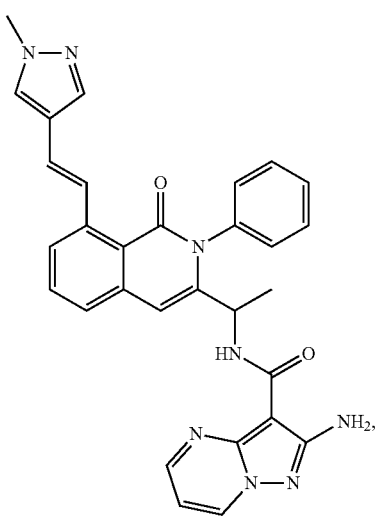 [SMILES: CC(NC(=O)c1c(N)nn2cccnc12)c1cc2cccc(/C=C/c3cnn(C)c3)c2c(=O)n1-c1ccccc1]
Compound 52'
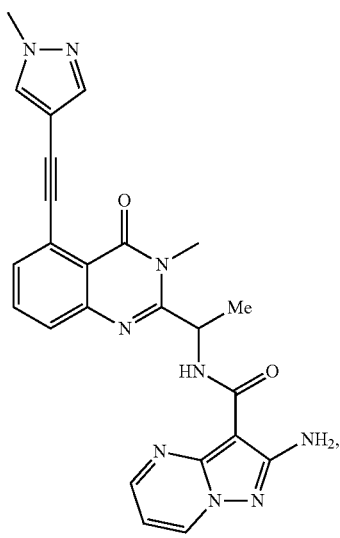 [SMILES: CC(NC(=O)c1c(N)nn2cccnc12)c1nc2cccc(C#Cc3cnn(C)c3)c2c(=O)n1C]
Compound 55'
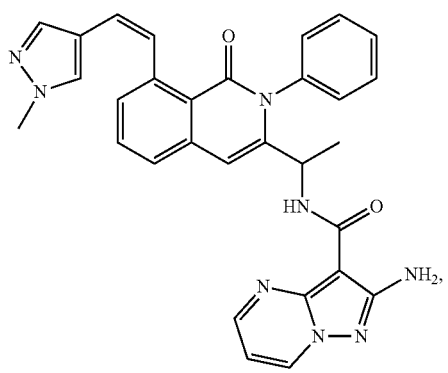
Compound 53'
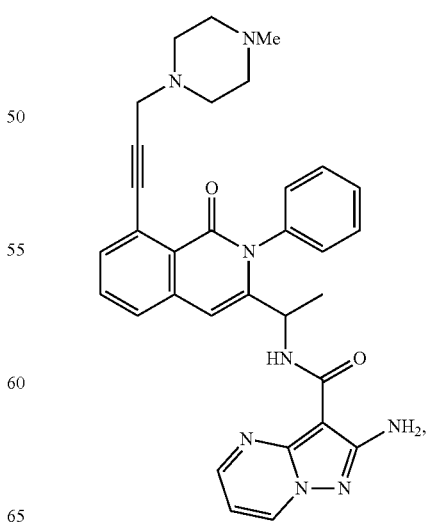
Compound 56'

TABLE 7-continued
Compound 57'
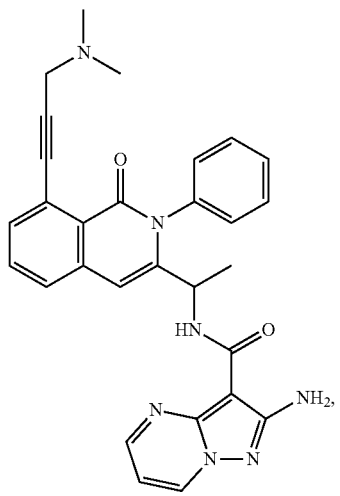 [SMILES: CC(NC(=O)c1c(N)nn2cccnc12)c1cc2cccc(C#CCN(C)C)c2c(=O)n1-c1ccccc1]
Compound 58'
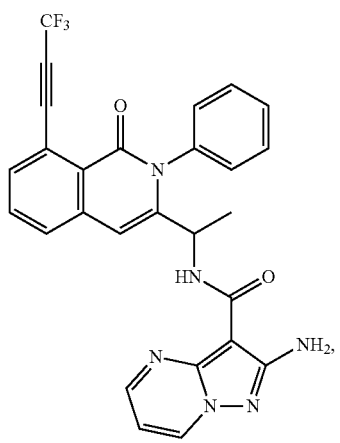 [SMILES: CC(NC(=O)c1c(N)nn2cccnc12)c1cc2cccc(C#CC(F)(F)F)c2c(=O)n1-c1ccccc1]
Compound 59'
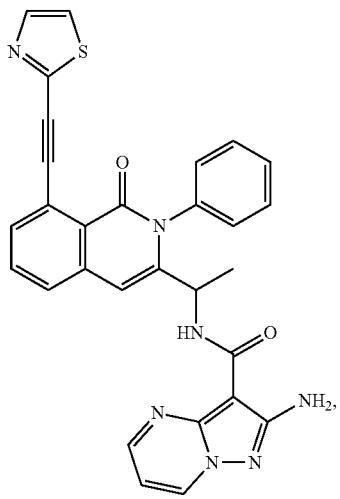 [SMILES: CC(NC(=O)c1c(N)nn2cccnc12)c1cc2cccc(C#Cc3nccs3)c2c(=O)n1-c1ccccc1]
TABLE 7-continued
Compound 60'
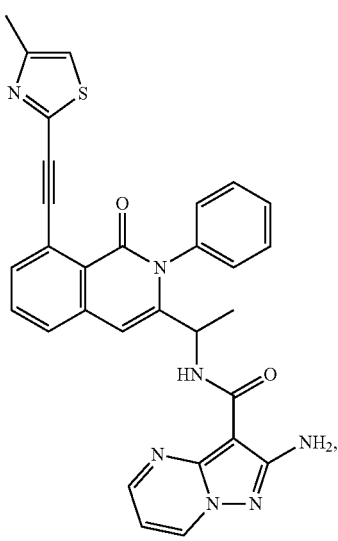 [SMILES: Cc1csc(C#Cc2cccc3cc(C(C)NC(=O)c4c(N)nn5cccnc45)n(-c4ccccc4)c(=O)c23)n1]
Compound 61'
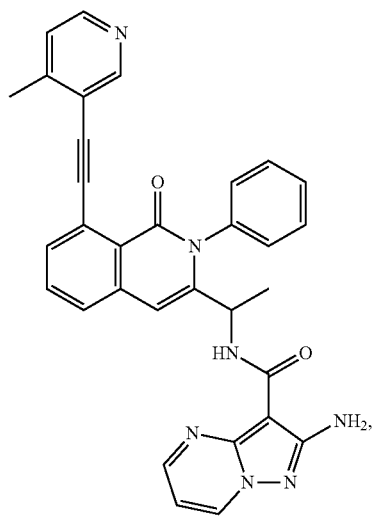 [SMILES: Cc1ccncc1C#Cc1cccc2cc(C(C)NC(=O)c3c(N)nn4cccnc34)n(-c3ccccc3)c(=O)c12]
Compound 62'
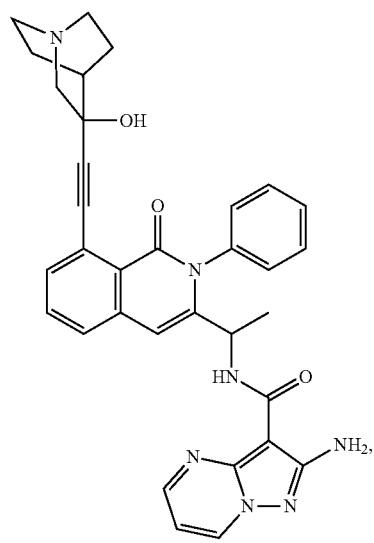 [SMILES: CC(NC(=O)c1c(N)nn2cccnc12)c1cc2cccc(C#CC3(O)CN4CCC3CC4)c2c(=O)n1-c1ccccc1]

TABLE 7-continued
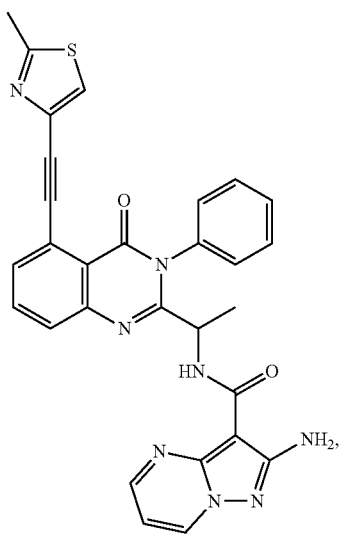 [SMILES: Cc1nc(C#Cc2cccc3nc(C(C)NC(=O)c4c(N)nn5cccnc45)n(-c4ccccc4)c(=O)c23)cs1]
Compound 63'
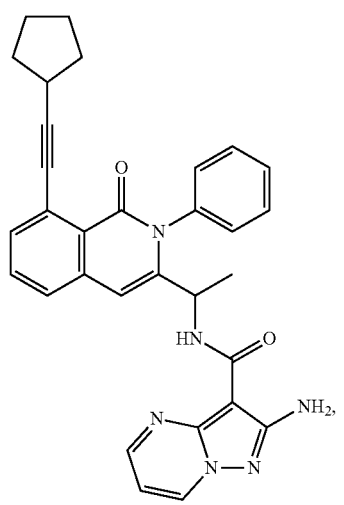 [SMILES: CC(NC(=O)c1c(N)nn2cccnc12)c1cc2cccc(C#CC3CCCC3)c2c(=O)n1-c1ccccc1]
Compound 64'
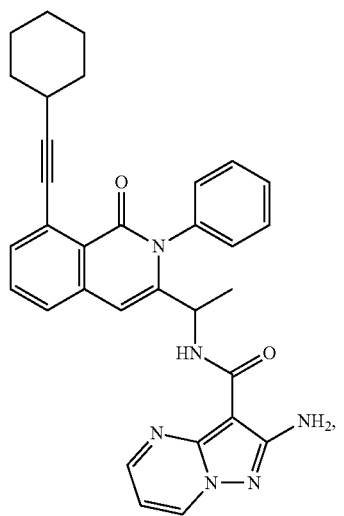 [SMILES: CC(NC(=O)c1c(N)nn2cccnc12)c1cc2cccc(C#CC3CCCCC3)c2c(=O)n1-c1ccccc1]
Compound 65'
TABLE 7-continued
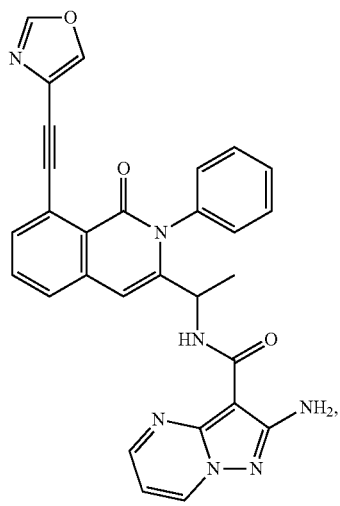
Compound 66'
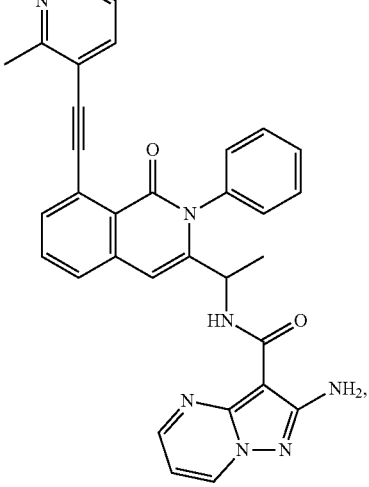
Compound 67'
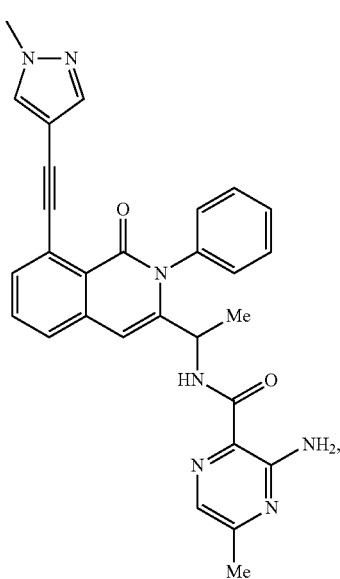 [SMILES: Cc1cnc(C(=O)NC(C)c2cc3cccc(C#Cc4cnn(C)c4)c3c(=O)n2-c2ccccc2)c(N)n1]
Compound 68'

TABLE 7-continued
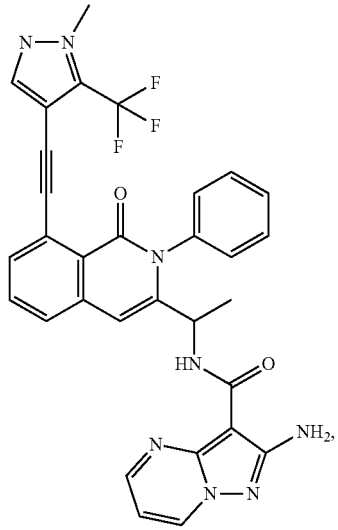
Compound 69'
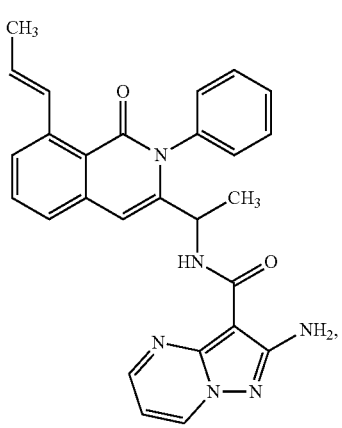 [SMILES: C/C=C/c1cccc2cc(C(C)NC(=O)c3c(N)nn4cccnc34)n(-c3ccccc3)c(=O)c12]
Compound 70'
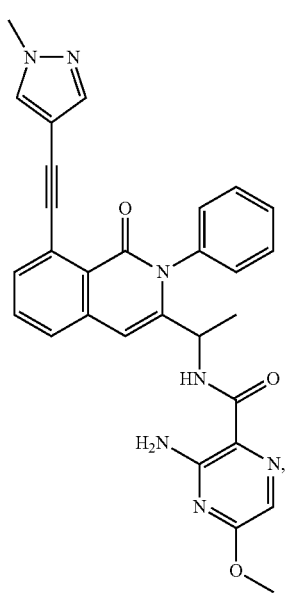
Compound 71'
TABLE 7-continued
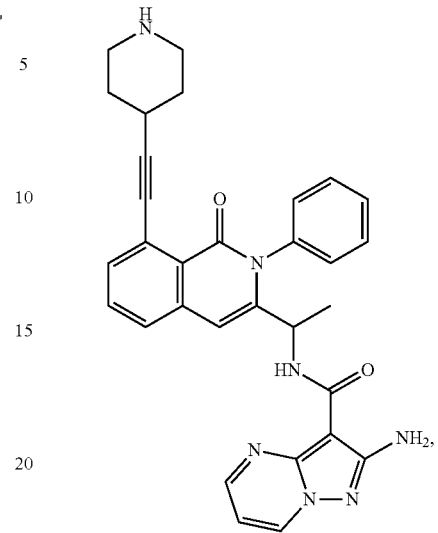
Compound 72'
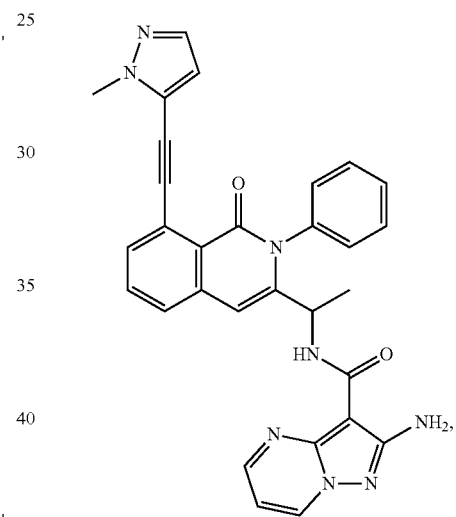
Compound 73'
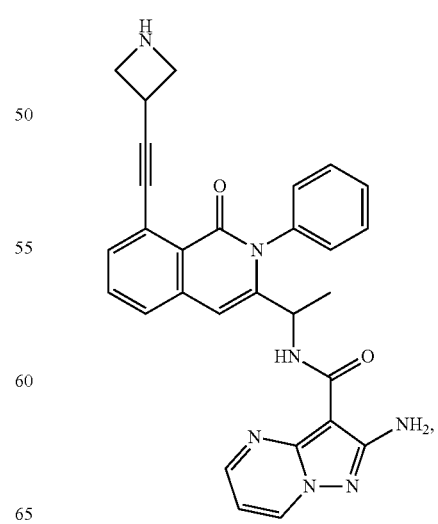
Compound 74'

TABLE 7-continued
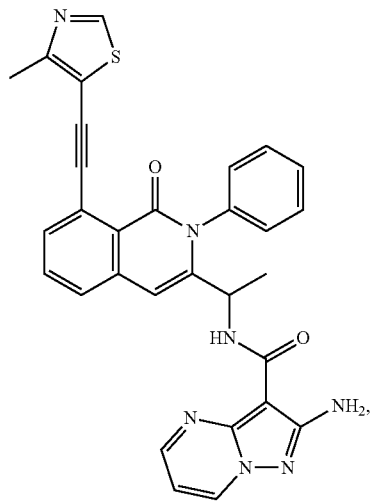 [SMILES: Cc1ncsc1C#Cc1cccc2cc(C(C)NC(=O)c3c(N)nn4cccnc34)n(-c3ccccc3)c(=O)c12]
Compound 75'
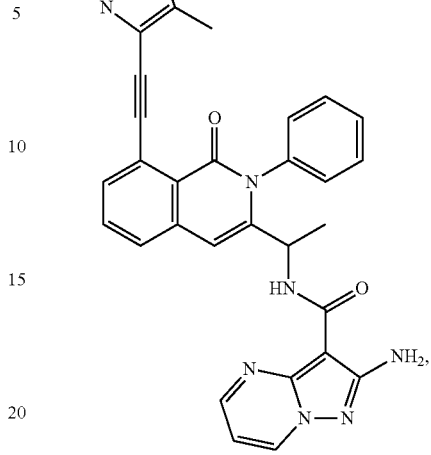
Compound 78'
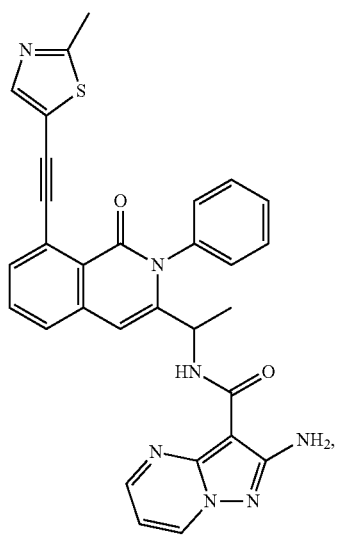 [SMILES: Cc1ncc(C#Cc2cccc3cc(C(C)NC(=O)c4c(N)nn5cccnc45)n(-c4ccccc4)c(=O)c23)s1]
Compound 76'
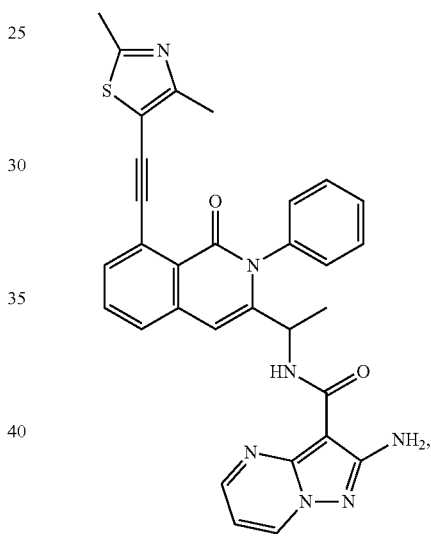
Compound 79'
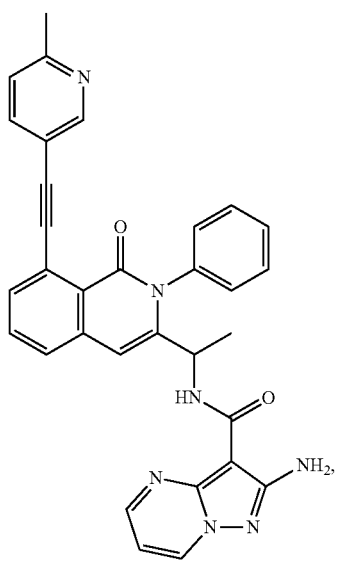 [SMILES: Cc1ccc(C#Cc2cccc3cc(C(C)NC(=O)c4c(N)nn5cccnc45)n(-c4ccccc4)c(=O)c23)cn1]
Compound 77'
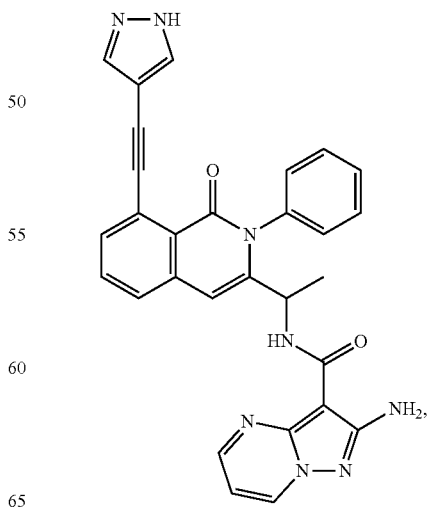
Compound 80'

TABLE 7-continued
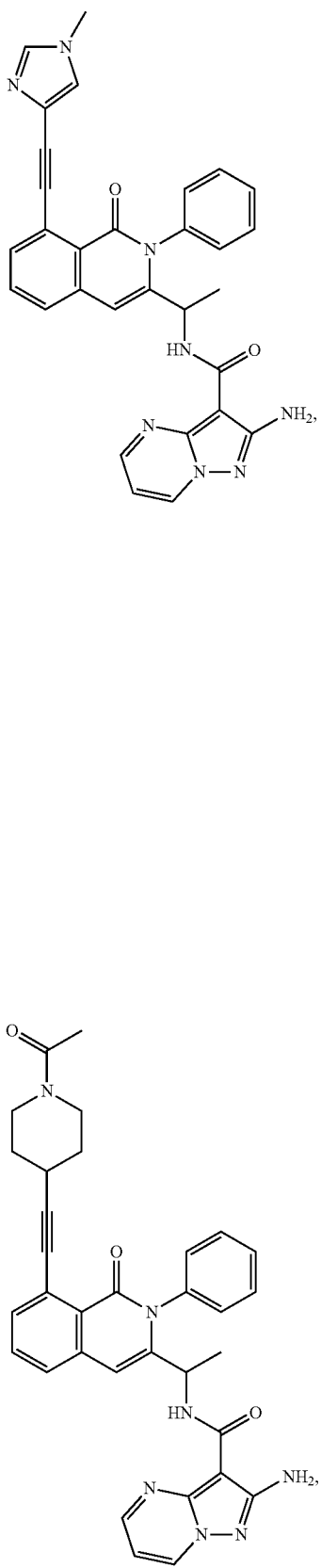
Compound 81'
Compound 82'
TABLE 7-continued
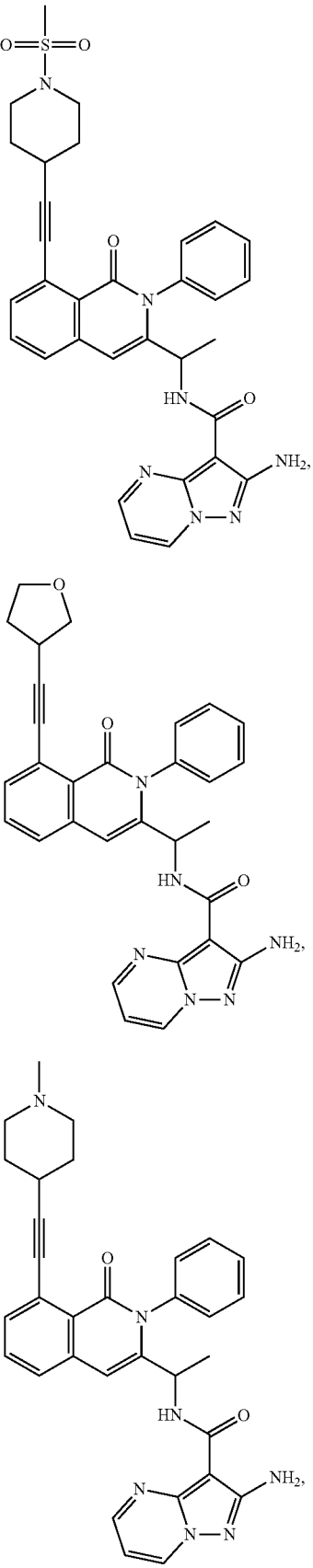
Compound 83'
Compound 84'
Compound 85'

TABLE 7-continued
Compound 86'
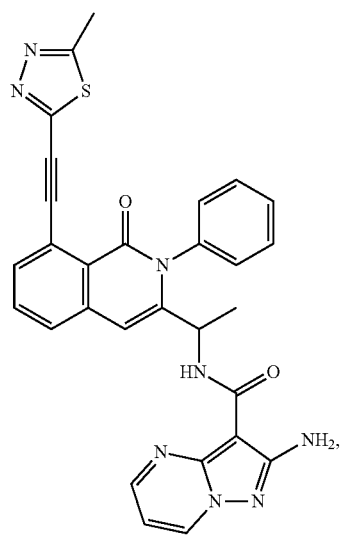 [SMILES: Cc1nnc(C#Cc2cccc3cc(C(C)NC(=O)c4c(N)nn5cccnc45)n(-c4ccccc4)c(=O)c23)s1]
Compound 87'
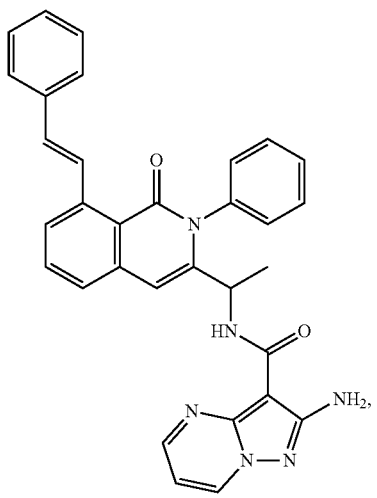 [SMILES: CC(NC(=O)c1c(N)nn2cccnc12)c1cc2cccc(/C=C/c3ccccc3)c2c(=O)n1-c1ccccc1]
Compound 88'
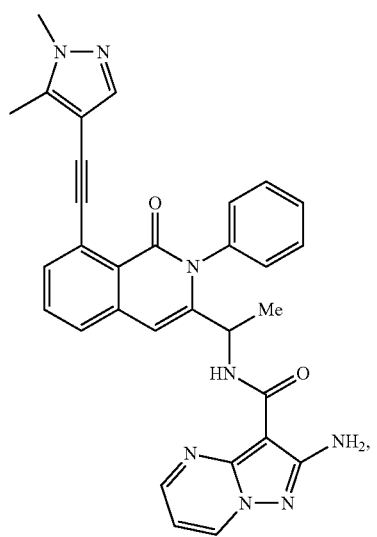 [SMILES: Cc1c(C#Cc2cccc3cc(C(C)NC(=O)c4c(N)nn5cccnc45)n(-c4ccccc4)c(=O)c23)cnn1C]
TABLE 7-continued
Compound 89'
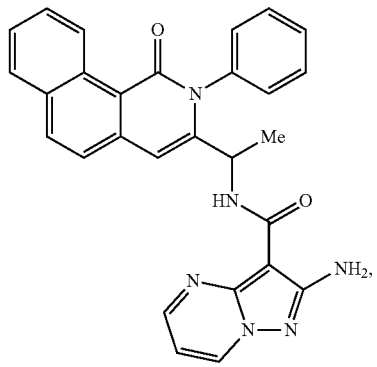 [SMILES: CC(NC(=O)c1c(N)nn2cccnc12)c1cc2ccc3ccccc3c2c(=O)n1-c1ccccc1]
Compound 90'
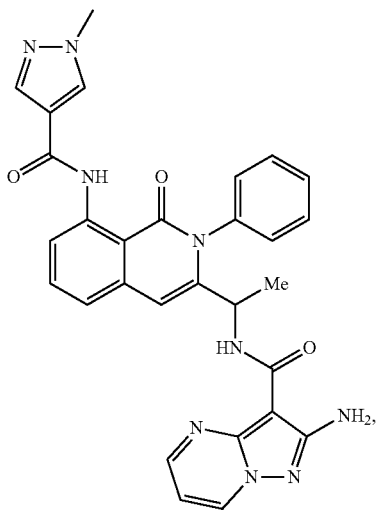 [SMILES: CC(NC(=O)c1c(N)nn2cccnc12)c1cc2cccc(NC(=O)c3cnn(C)c3)c2c(=O)n1-c1ccccc1]
Compound 91'
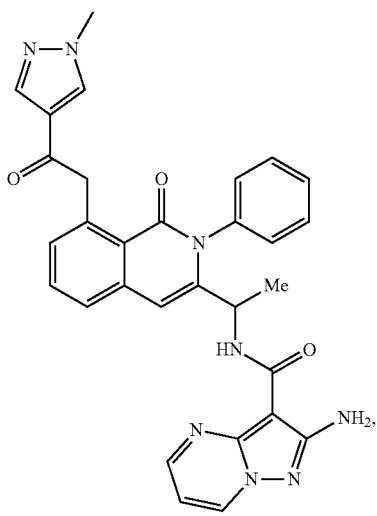

TABLE 7-continued
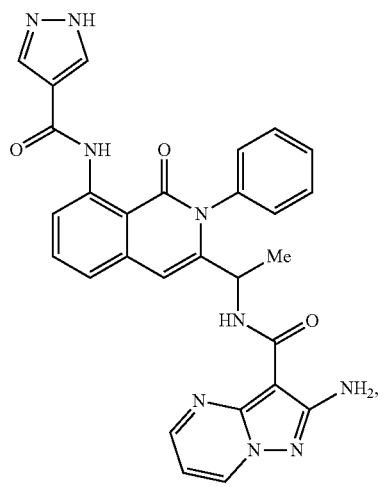 [SMILES: CC(NC(=O)c1c(N)nn2cccnc12)c1cc2cccc(NC(=O)c3cn[nH]c3)c2c(=O)n1-c1ccccc1]
Compound 92'
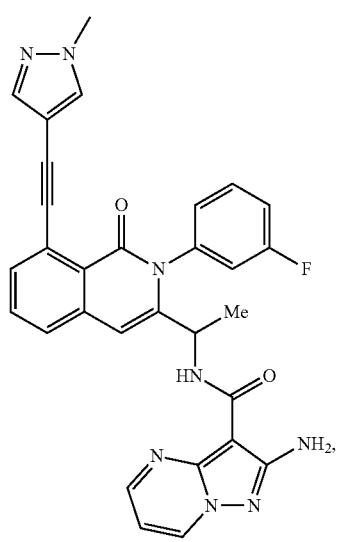 [SMILES: CC(NC(=O)c1c(N)nn2cccnc12)c1cc2cccc(C#Cc3cnn(C)c3)c2c(=O)n1-c1cccc(F)c1]
Compound 93'
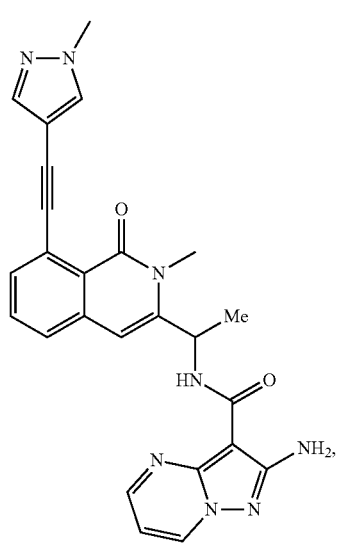 [SMILES: CC(NC(=O)c1c(N)nn2cccnc12)c1cc2cccc(C#Cc3cnn(C)c3)c2c(=O)n1C]
Compound 94'
TABLE 7-continued
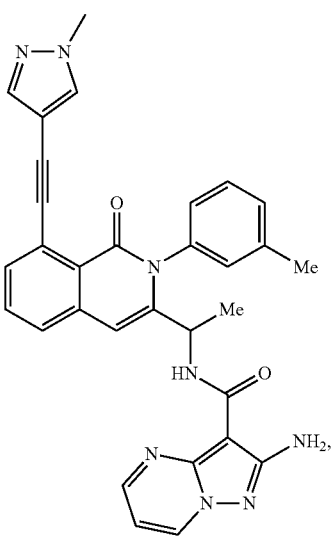 [SMILES: Cc1cccc(-n2c(C(C)NC(=O)c3c(N)nn4cccnc34)cc3cccc(C#Cc4cnn(C)c4)c3c2=O)c1]
Compound 95'
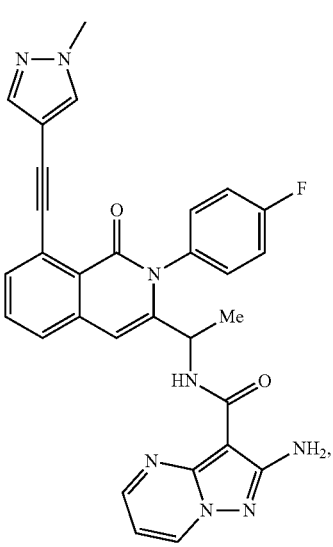 [SMILES: CC(NC(=O)c1c(N)nn2cccnc12)c1cc2cccc(C#Cc3cnn(C)c3)c2c(=O)n1-c1ccc(F)cc1]
Compound 96'
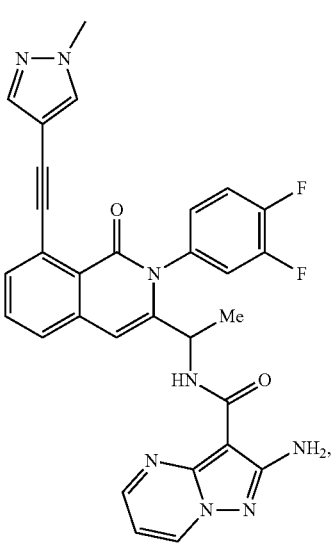 [SMILES: CC(NC(=O)c1c(N)nn2cccnc12)c1cc2cccc(C#Cc3cnn(C)c3)c2c(=O)n1-c1ccc(F)c(F)c1]
Compound 97'

TABLE 7-continued
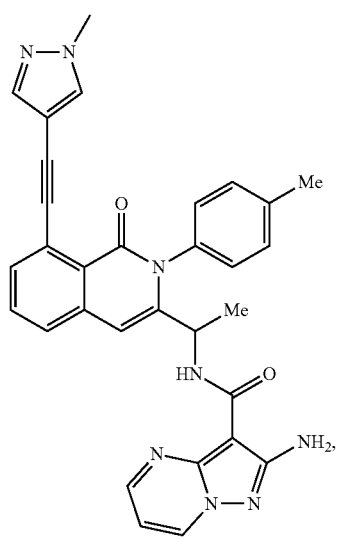 [SMILES: Cc1ccc(-n2c(C(C)NC(=O)c3c(N)nn4cccnc34)cc3cccc(C#Cc4cnn(C)c4)c3c2=O)cc1]
Compound 98'
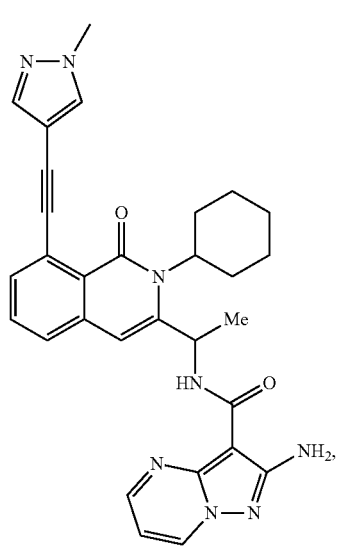 [SMILES: CC(NC(=O)c1c(N)nn2cccnc12)c1cc2cccc(C#Cc3cnn(C)c3)c2c(=O)n1C1CCCCC1]
Compound 99'
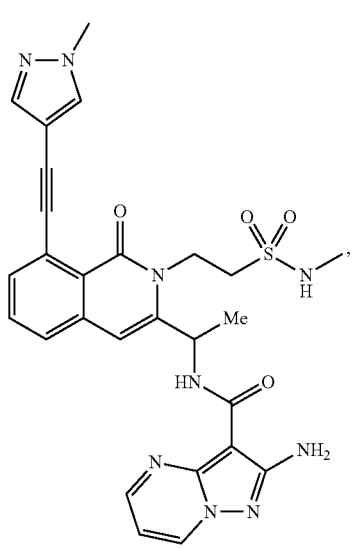 [SMILES: CNS(=O)(=O)CCn1c(C(C)NC(=O)c2c(N)nn3cccnc23)cc2cccc(C#Cc3cnn(C)c3)c2c1=O]
Compound 100'
TABLE 7-continued
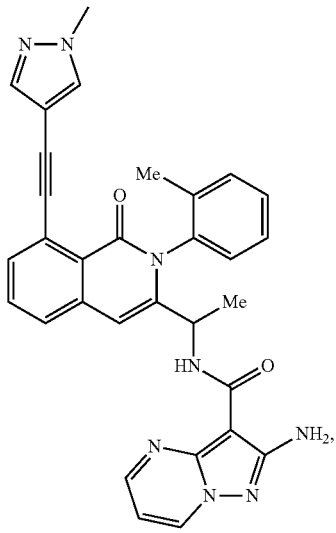 [SMILES: Cc1ccccc1-n1c(C(C)NC(=O)c2c(N)nn3cccnc23)cc2cccc(C#Cc3cnn(C)c3)c2c1=O]
Compound 101'
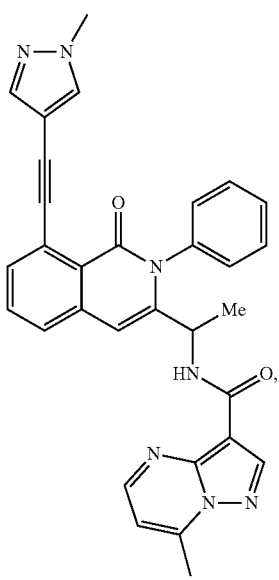 [SMILES: Cc1ccnc2c(C(=O)NC(C)c3cc4cccc(C#Cc5cnn(C)c5)c4c(=O)n3-c3ccccc3)cnn12]
Compound 102'
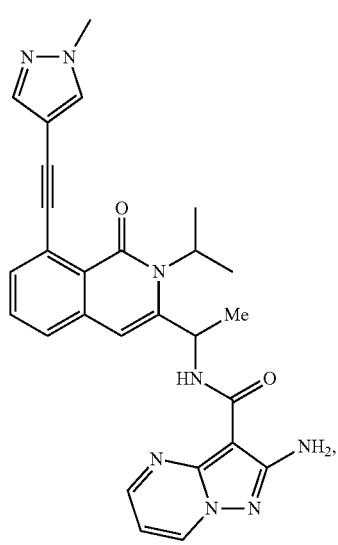 [SMILES: CC(NC(=O)c1c(N)nn2cccnc12)c1cc2cccc(C#Cc3cnn(C)c3)c2c(=O)n1C(C)C]
Compound 103'

TABLE 7-continued
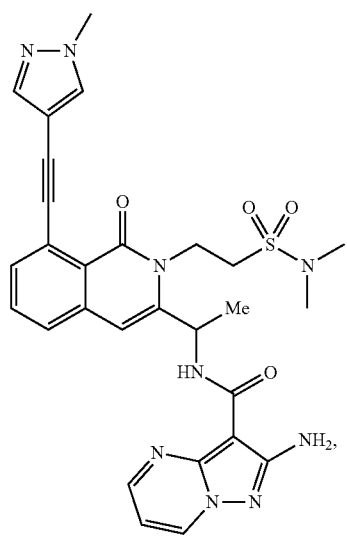 [SMILES: CC(NC(=O)c1c(N)nn2cccnc12)c1cc2cccc(C#Cc3cnn(C)c3)c2c(=O)n1CCS(=O)(=O)N(C)C]
Compound 104'
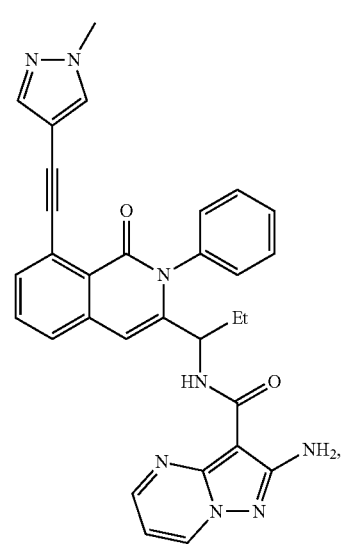 [SMILES: CCC(NC(=O)c1c(N)nn2cccnc12)c1cc2cccc(C#Cc3cnn(C)c3)c2c(=O)n1-c1ccccc1]
Compound 105'
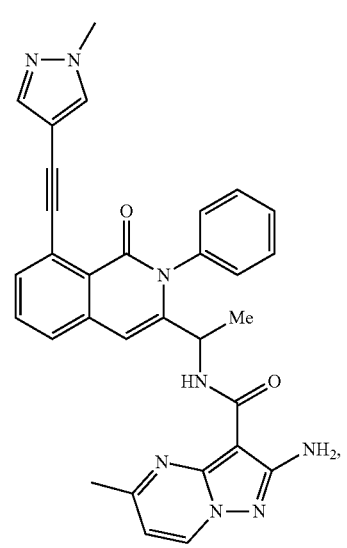 [SMILES: Cc1ccn2nc(N)c(C(=O)NC(C)c3cc4cccc(C#Cc5cnn(C)c5)c4c(=O)n3-c3ccccc3)c2n1]
Compound 106'
TABLE 7-continued
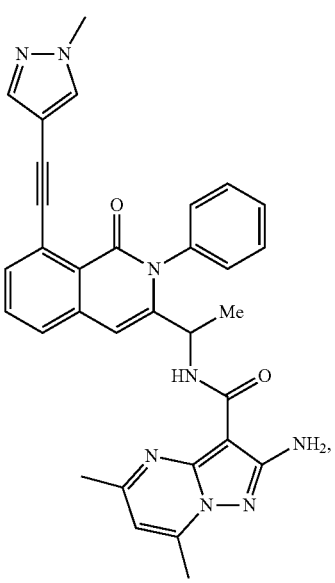 [SMILES: Cc1cc(C)n2nc(N)c(C(=O)NC(C)c3cc4cccc(C#Cc5cnn(C)c5)c4c(=O)n3-c3ccccc3)c2n1]
Compound 108'
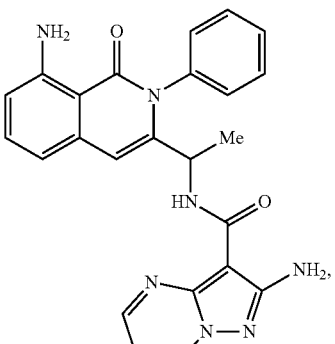
Compound 109'
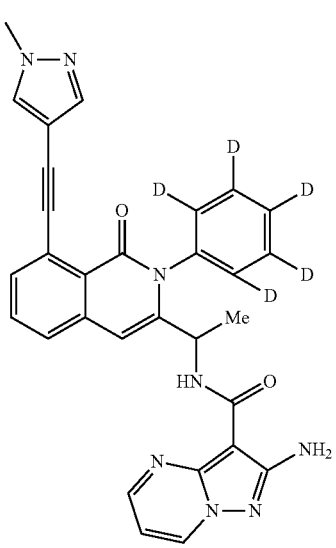 [SMILES: [2H]c1c([2H])c([2H])c(-n2c(C(C)NC(=O)c3c(N)nn4cccnc34)cc3cccc(C#Cc4cnn(C)c4)c3c2=O)c([2H])c1[2H]]
Compound 110'

TABLE 8
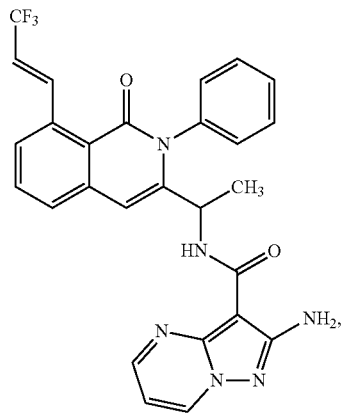 [SMILES: CC(NC(=O)c1c(N)nn2cccnc12)c1cc2cccc(/C=C/C(F)(F)F)c2c(=O)n1-c1ccccc1]
Compound 1001'
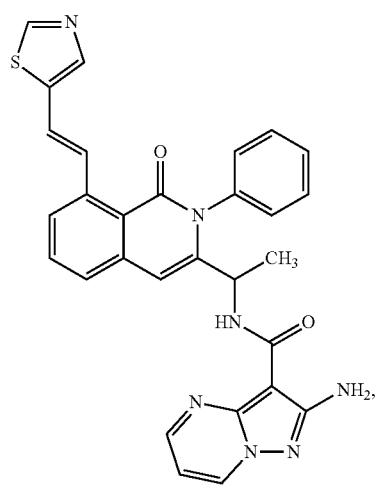 [SMILES: CC(NC(=O)c1c(N)nn2cccnc12)c1cc2cccc(/C=C/c3cncs3)c2c(=O)n1-c1ccccc1]
Compound 1002'
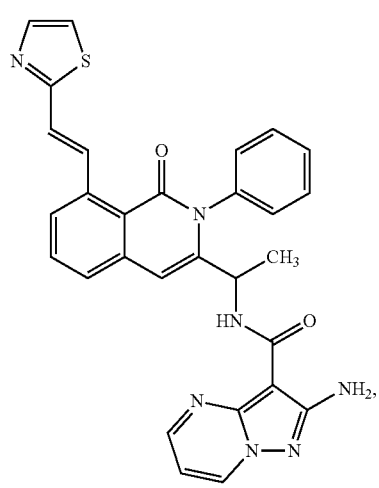 [SMILES: CC(NC(=O)c1c(N)nn2cccnc12)c1cc2cccc(/C=C/c3nccs3)c2c(=O)n1-c1ccccc1]
Compound 1003'

TABLE 8-continued
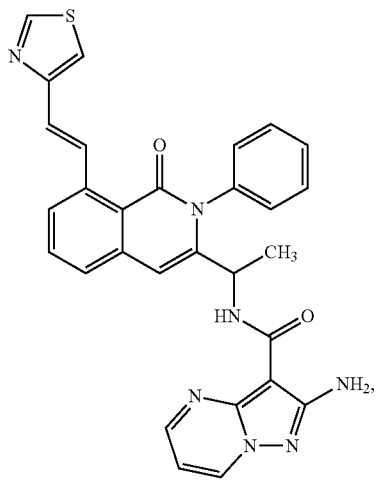
Compound 1004'
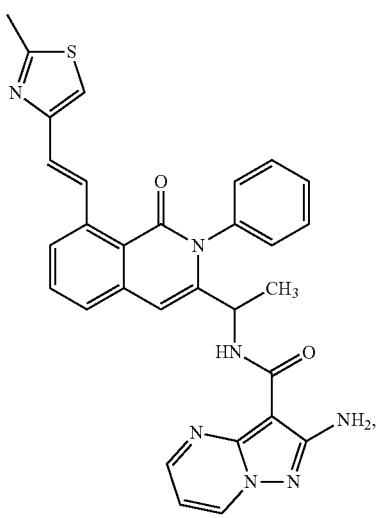 [SMILES: Cc1nc(/C=C/c2cccc3cc(C(C)NC(=O)c4c(N)nn5cccnc45)n(-c4ccccc4)c(=O)c23)cs1]
Compound 1005'
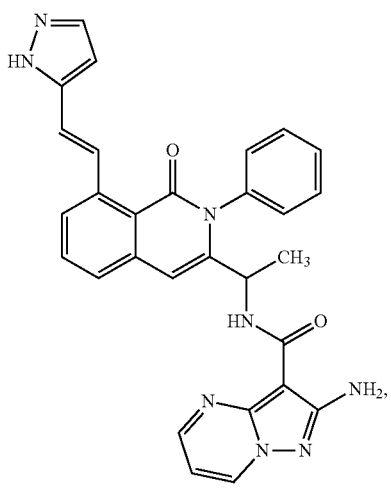 [SMILES: CC(NC(=O)c1c(N)nn2cccnc12)c1cc2cccc(/C=C/c3ccn[nH]3)c2c(=O)n1-c1ccccc1]
Compound 1006'

TABLE 8-continued
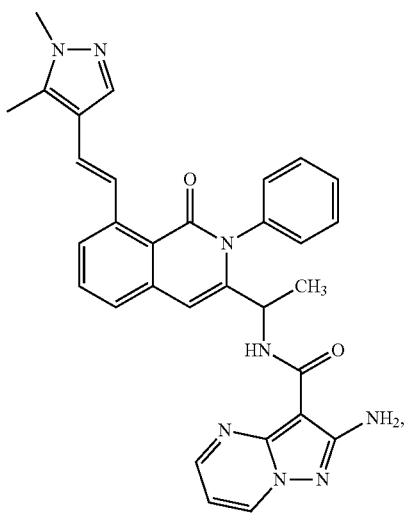 [SMILES: Cc1c(/C=C/c2cccc3cc(C(C)NC(=O)c4c(N)nn5cccnc45)n(-c4ccccc4)c(=O)c23)cnn1C]
Compound 1007'
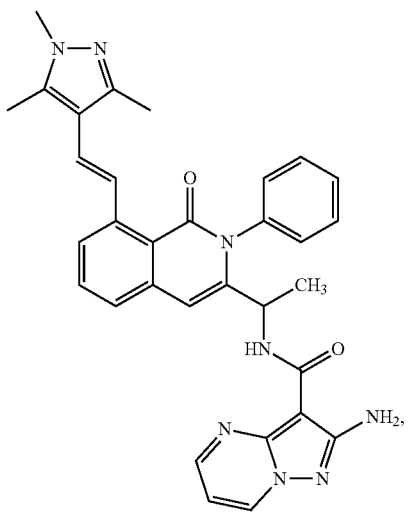 [SMILES: Cc1nn(C)c(C)c1/C=C/c1cccc2cc(C(C)NC(=O)c3c(N)nn4cccnc34)n(-c3ccccc3)c(=O)c12]
Compound 1008'
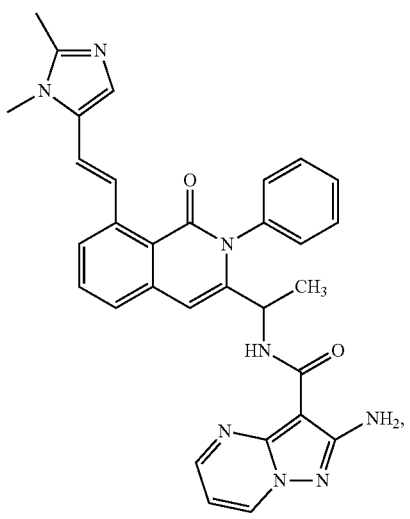 [SMILES: Cc1ncc(/C=C/c2cccc3cc(C(C)NC(=O)c4c(N)nn5cccnc45)n(-c4ccccc4)c(=O)c23)n1C]
Compound 1009'

TABLE 8-continued
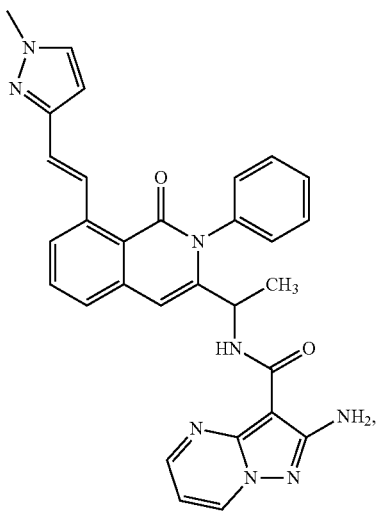 [SMILES: CC(NC(=O)c1c(N)nn2cccnc12)c1cc2cccc(/C=C/c3ccn(C)n3)c2c(=O)n1-c1ccccc1]
Compound 1010'
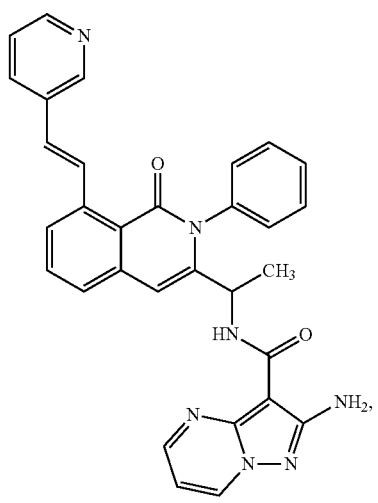
Compound 1011'
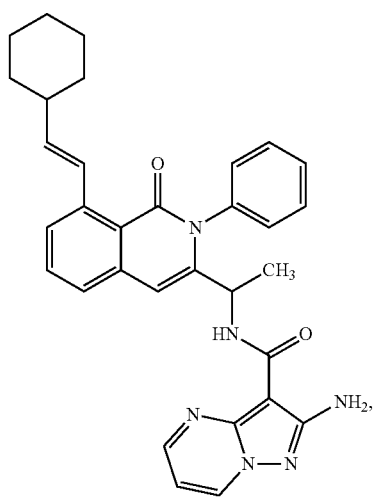 [SMILES: CC(NC(=O)c1c(N)nn2cccnc12)c1cc2cccc(/C=C/C3CCCCC3)c2c(=O)n1-c1ccccc1]
Compound 1012'

TABLE 8-continued
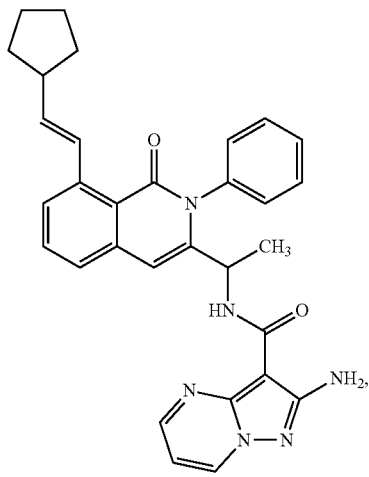 [SMILES: CC(NC(=O)c1c(N)nn2cccnc12)c1cc2cccc(/C=C/C3CCCC3)c2c(=O)n1-c1ccccc1]
Compound 1013'
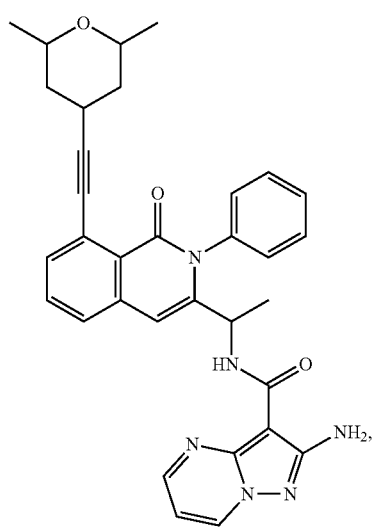 [SMILES: CC1CC(C#Cc2cccc3cc(C(C)NC(=O)c4c(N)nn5cccnc45)n(-c4ccccc4)c(=O)c23)CC(C)O1]
Compound 1014'
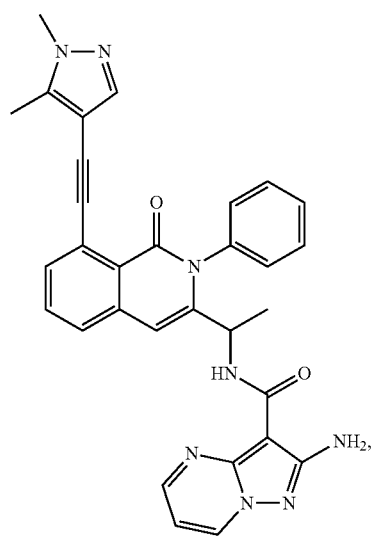 [SMILES: Cc1c(C#Cc2cccc3cc(C(C)NC(=O)c4c(N)nn5cccnc45)n(-c4ccccc4)c(=O)c23)cnn1C]
Compound 1015'

TABLE 8-continued
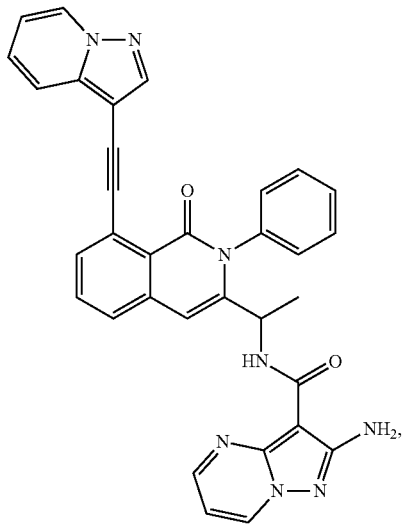 [SMILES: CC(NC(=O)c1c(N)nn2cccnc12)c1cc2cccc(C#Cc3cnn4ccccc34)c2c(=O)n1-c1ccccc1]
Compound 1016'
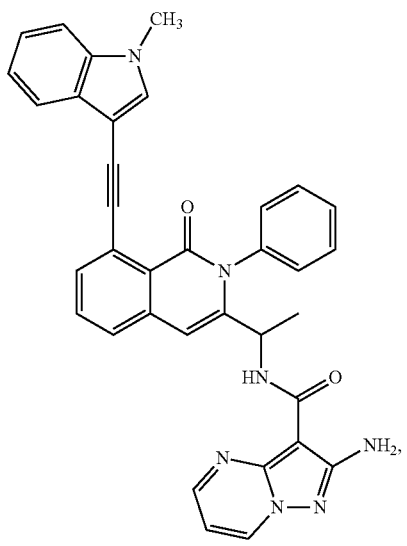 [SMILES: CC(NC(=O)c1c(N)nn2cccnc12)c1cc2cccc(C#Cc3cn(C)c4ccccc34)c2c(=O)n1-c1ccccc1]
Compound 1017'
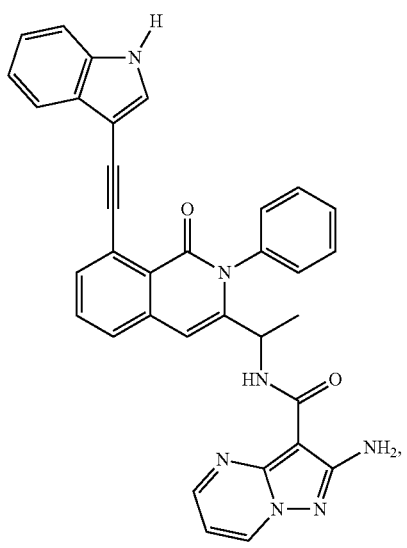
Compound 1018'

TABLE 8-continued
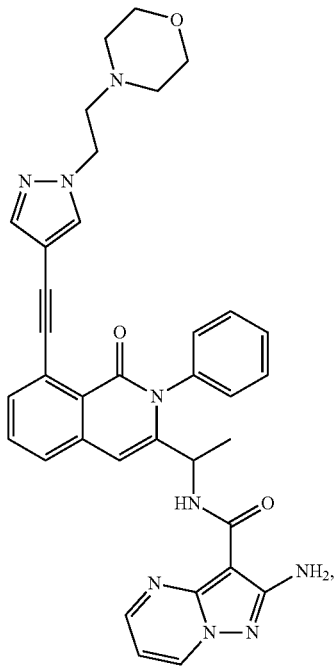
Compound 1019'
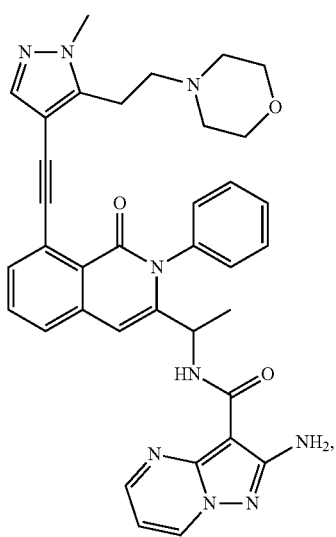 [SMILES: CC(NC(=O)c1c(N)nn2cccnc12)c1cc2cccc(C#Cc3cnn(C)c3CCN3CCOCC3)c2c(=O)n1-c1ccccc1]
Compound 1020'

TABLE 8-continued
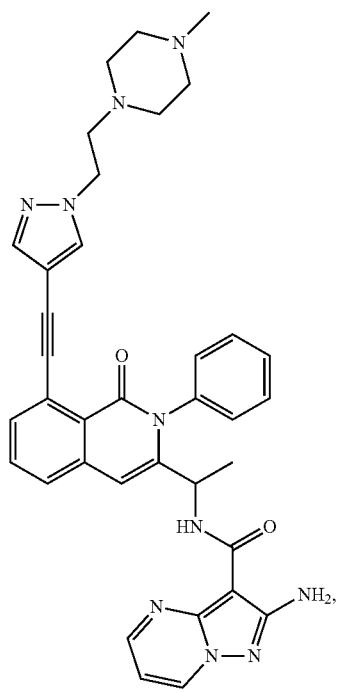 [SMILES: CC(NC(=O)c1c(N)nn2cccnc12)c1cc2cccc(C#Cc3cnn(CCN4CCN(C)CC4)c3)c2c(=O)n1-c1ccccc1]
Compound 1021'
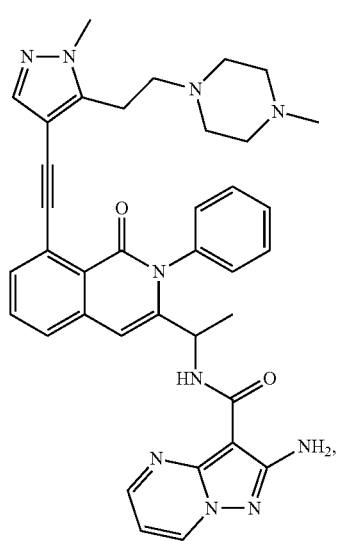 [SMILES: CC(NC(=O)c1c(N)nn2cccnc12)c1cc2cccc(C#Cc3cnn(C)c3CCN3CCN(C)CC3)c2c(=O)n1-c1ccccc1]
Compound 1022'

TABLE 8-continued
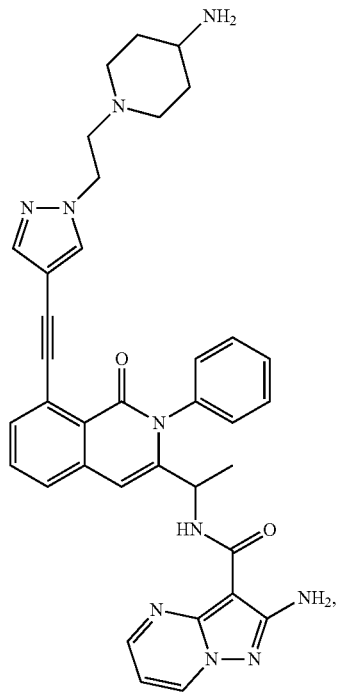 [SMILES: CC(NC(=O)c1c(N)nn2cccnc12)c1cc2cccc(C#Cc3cnn(CCN4CCC(N)CC4)c3)c2c(=O)n1-c1ccccc1]
Compound 1023'
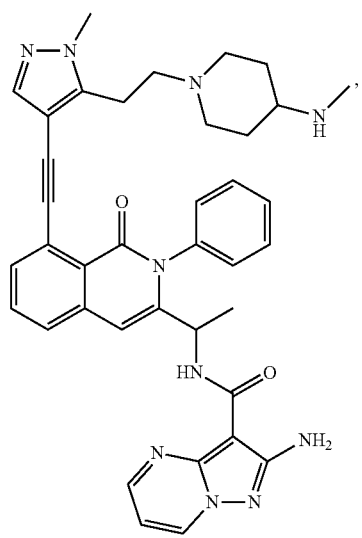 [SMILES: CNC1CCN(CCc2c(C#Cc3cccc4cc(C(C)NC(=O)c5c(N)nn6cccnc56)n(-c5ccccc5)c(=O)c34)cnn2C)CC1]
Compound 1024'

TABLE 8-continued
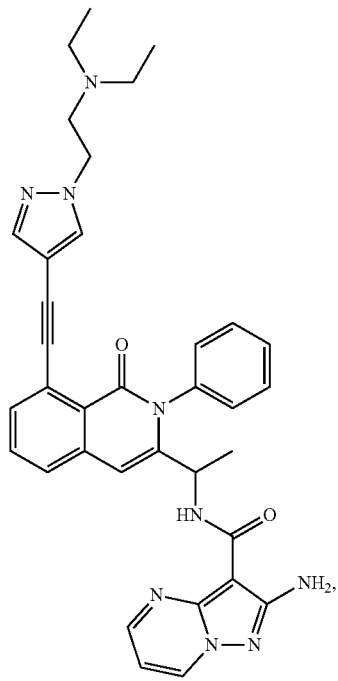 [SMILES: CCN(CC)CCn1cc(C#Cc2cccc3cc(C(C)NC(=O)c4c(N)nn5cccnc45)n(-c4ccccc4)c(=O)c23)cn1]
Compound 1025'
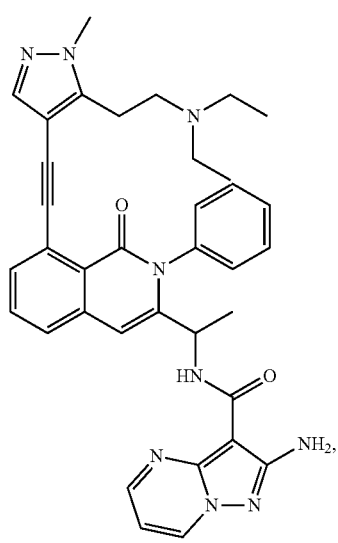 [SMILES: CCN(CC)CCc1c(C#Cc2cccc3cc(C(C)NC(=O)c4c(N)nn5cccnc45)n(-c4ccccc4)c(=O)c23)cnn1C]
Compound 1026'

TABLE 8-continued
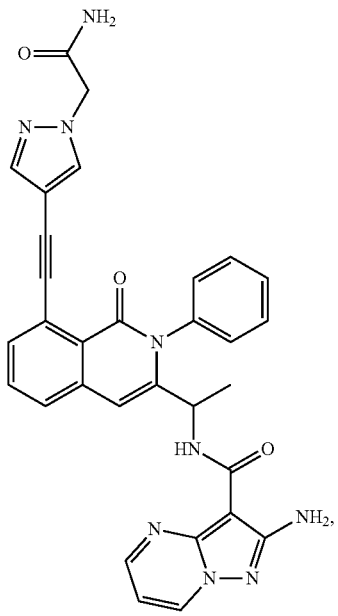 [SMILES: CC(NC(=O)c1c(N)nn2cccnc12)c1cc2cccc(C#Cc3cnn(CC(N)=O)c3)c2c(=O)n1-c1ccccc1]
Compound 1027'
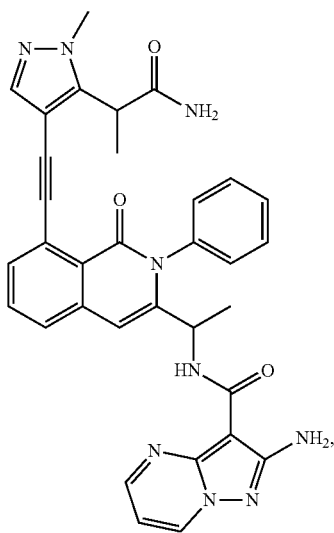 [SMILES: CC(NC(=O)c1c(N)nn2cccnc12)c1cc2cccc(C#Cc3cnn(C)c3C(C)C(N)=O)c2c(=O)n1-c1ccccc1]
Compound 1028'

TABLE 8-continued
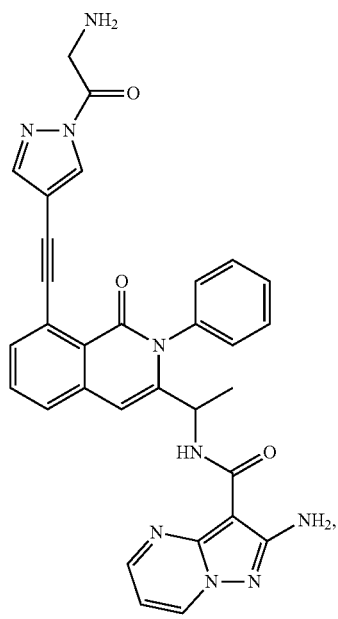 [SMILES: CC(NC(=O)c1c(N)nn2cccnc12)c1cc2cccc(C#Cc3cnn(C(=O)CN)c3)c2c(=O)n1-c1ccccc1]
Compound 1029'
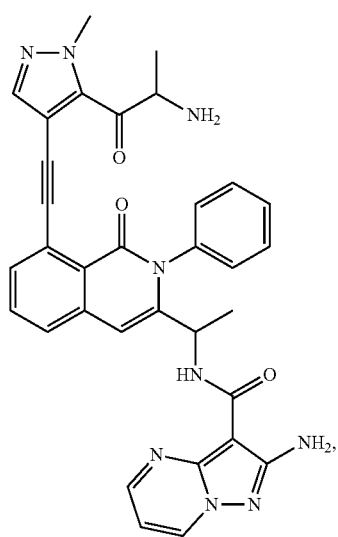 [SMILES: CC(N)C(=O)c1c(C#Cc2cccc3cc(C(C)NC(=O)c4c(N)nn5cccnc45)n(-c4ccccc4)c(=O)c23)cnn1C]
Compound 1030'

TABLE 8-continued
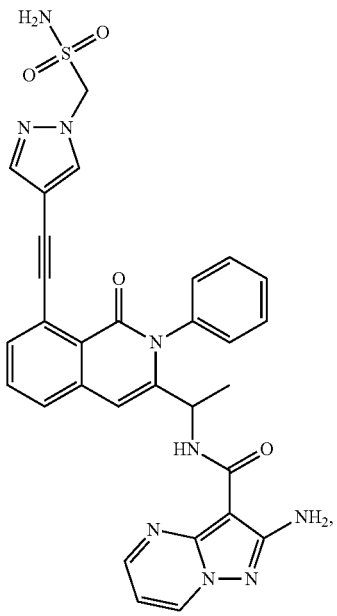 [SMILES: CC(NC(=O)c1c(N)nn2cccnc12)c1cc2cccc(C#Cc3cnn(CS(N)(=O)=O)c3)c2c(=O)n1-c1ccccc1]
Compound 1031'
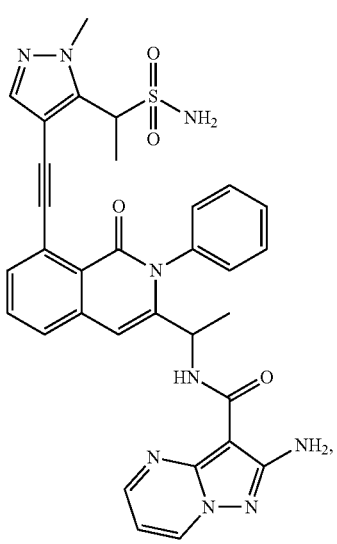 [SMILES: CC(NC(=O)c1c(N)nn2cccnc12)c1cc2cccc(C#Cc3cnn(C)c3C(C)S(N)(=O)=O)c2c(=O)n1-c1ccccc1]
Compound 1032'

TABLE 8-continued
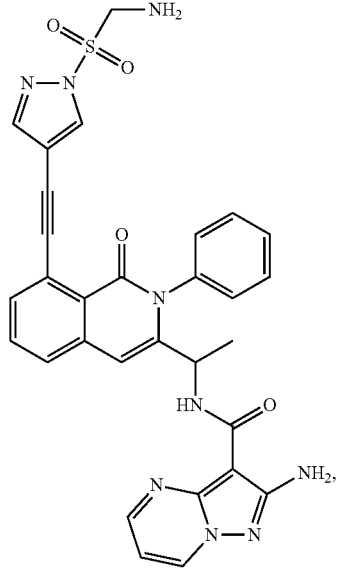 [SMILES: CC(NC(=O)c1c(N)nn2cccnc12)c1cc2cccc(C#Cc3cnn(S(=O)(=O)CN)c3)c2c(=O)n1-c1ccccc1]
Compound 1033'
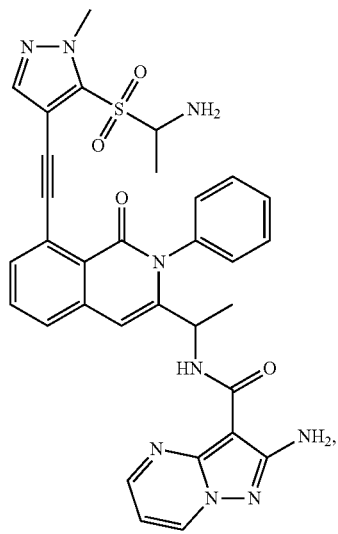 [SMILES: CC(NC(=O)c1c(N)nn2cccnc12)c1cc2cccc(C#Cc3cnn(C)c3S(=O)(=O)C(C)N)c2c(=O)n1-c1ccccc1]
Compound 1034'

TABLE 8-continued
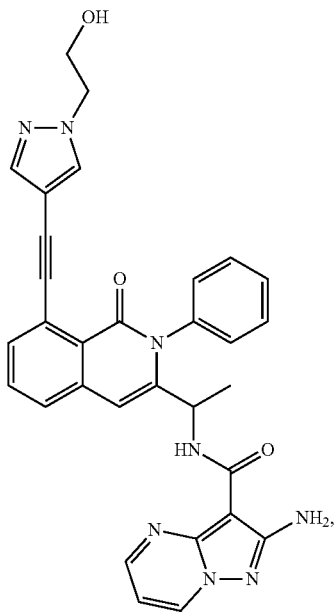 [SMILES: CC(NC(=O)c1c(N)nn2cccnc12)c1cc2cccc(C#Cc3cnn(CCO)c3)c2c(=O)n1-c1ccccc1]
Compound 1035'
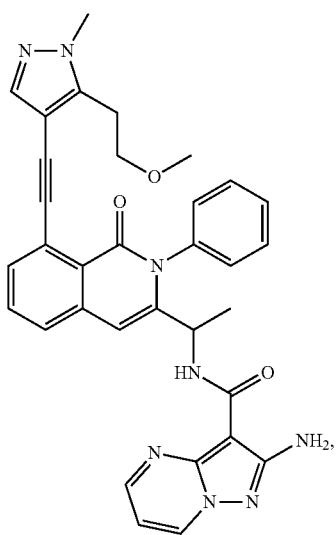 [SMILES: COCCc1c(C#Cc2cccc3cc(C(C)NC(=O)c4c(N)nn5cccnc45)n(-c4ccccc4)c(=O)c23)cnn1C]
Compound 1036'

TABLE 8-continued
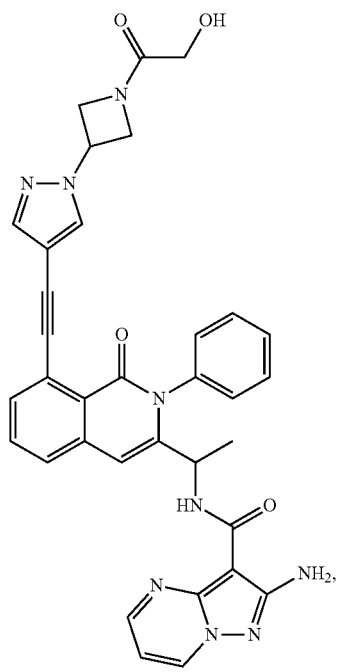 [SMILES: CC(NC(=O)c1c(N)nn2cccnc12)c1cc2cccc(C#Cc3cnn(C4CN(C(=O)CO)C4)c3)c2c(=O)n1-c1ccccc1]
Compound 1037'
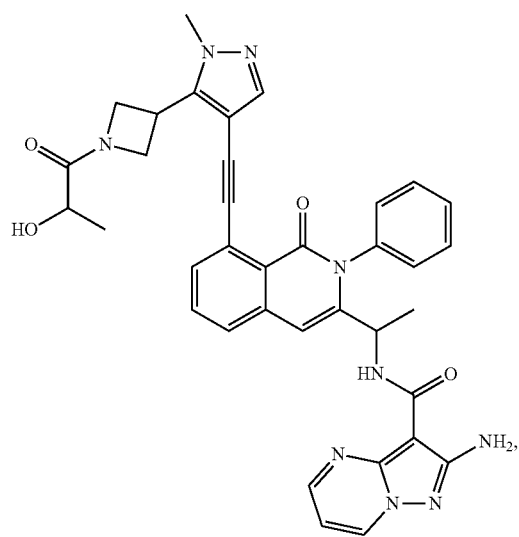 [SMILES: CC(O)C(=O)N1CC(c2c(C#Cc3cccc4cc(C(C)NC(=O)c5c(N)nn6cccnc56)n(-c5ccccc5)c(=O)c34)cnn2C)C1]
Compound 1038'

TABLE 8-continued
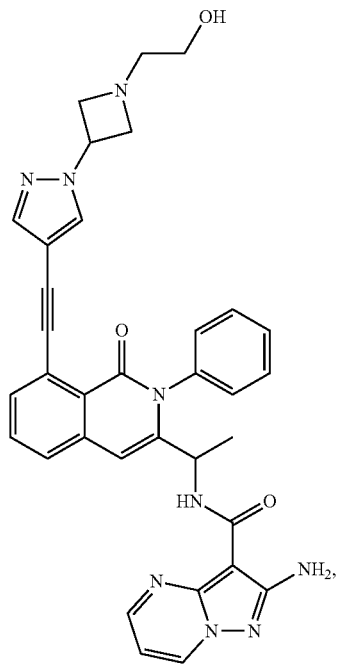 [SMILES: CC(NC(=O)c1c(N)nn2cccnc12)c1cc2cccc(C#Cc3cnn(C4CN(CCO)C4)c3)c2c(=O)n1-c1ccccc1]
Compound 1039'
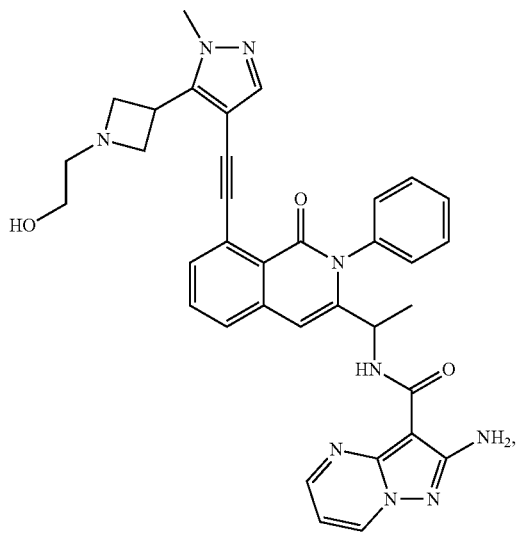 [SMILES: CC(NC(=O)c1c(N)nn2cccnc12)c1cc2cccc(C#Cc3cnn(C)c3C3CN(CCO)C3)c2c(=O)n1-c1ccccc1]
Compound 1040'

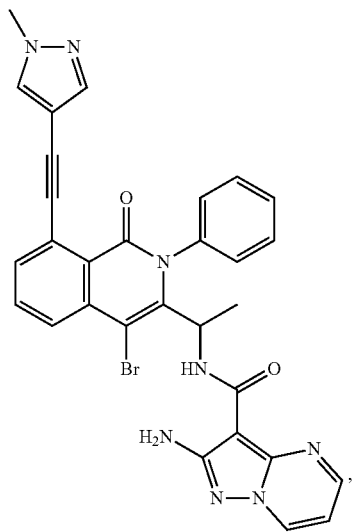 [SMILES: CC(NC(=O)c1c(N)nn2cccnc12)c1c(Br)c2cccc(C#Cc3cnn(C)c3)c2c(=O)n1-c1ccccc1]
Compound 1041'
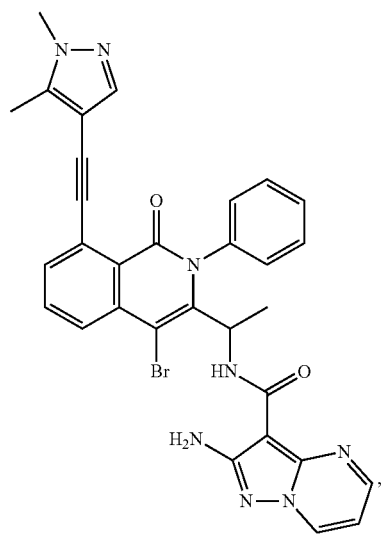 [SMILES: Cc1c(C#Cc2cccc3c(Br)c(C(C)NC(=O)c4c(N)nn5cccnc45)n(-c4ccccc4)c(=O)c23)cnn1C]
Compound 1042'
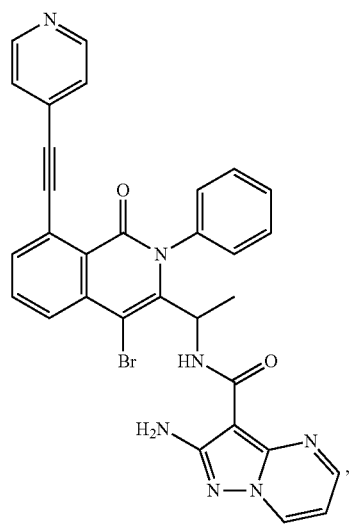 [SMILES: CC(NC(=O)c1c(N)nn2cccnc12)c1c(Br)c2cccc(C#Cc3ccncc3)c2c(=O)n1-c1ccccc1]
Compound 1043'

TABLE 8-continued
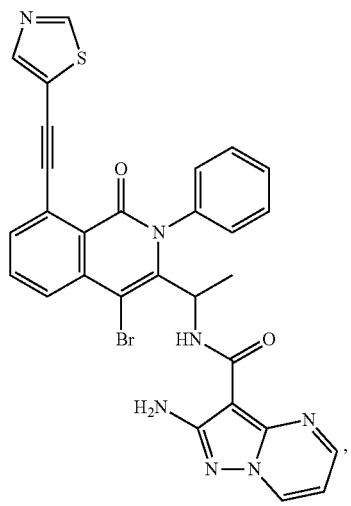 [SMILES: CC(NC(=O)c1c(N)nn2cccnc12)c1c(Br)c2cccc(C#Cc3cncs3)c2c(=O)n1-c1ccccc1]
Compound 1044'
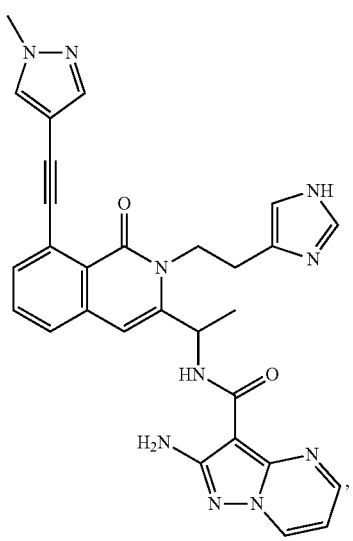
Compound 1045'
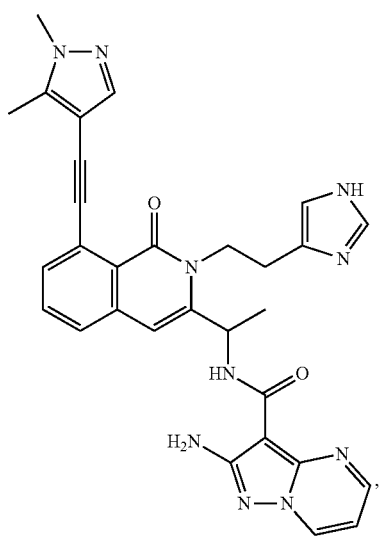 [SMILES: Cc1c(C#Cc2cccc3cc(C(C)NC(=O)c4c(N)nn5cccnc45)n(CCc4c[nH]cn4)c(=O)c23)cnn1C]
Compound 1046'

TABLE 8-continued
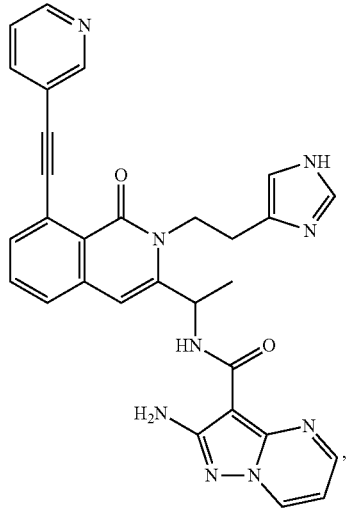 [SMILES: CC(NC(=O)c1c(N)nn2cccnc12)c1cc2cccc(C#Cc3cccnc3)c2c(=O)n1CCc1c[nH]cn1]
Compound 1047'
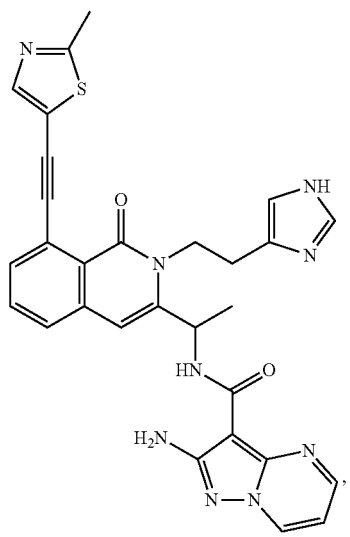 [SMILES: Cc1ncc(C#Cc2cccc3cc(C(C)NC(=O)c4c(N)nn5cccnc45)n(CCc4c[nH]cn4)c(=O)c23)s1]
Compound 1048'
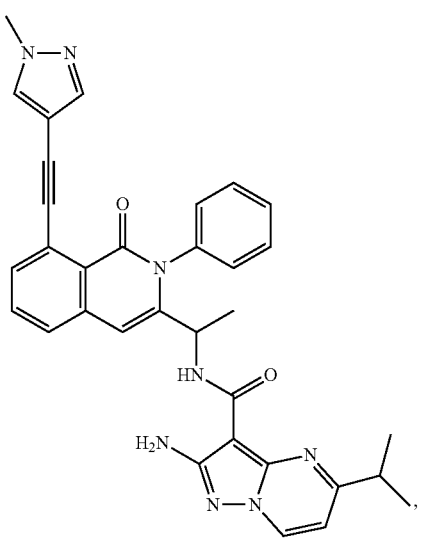 [SMILES: CC(C)c1ccn2nc(N)c(C(=O)NC(C)c3cc4cccc(C#Cc5cnn(C)c5)c4c(=O)n3-c3ccccc3)c2n1]
Compound 1049'

TABLE 8-continued
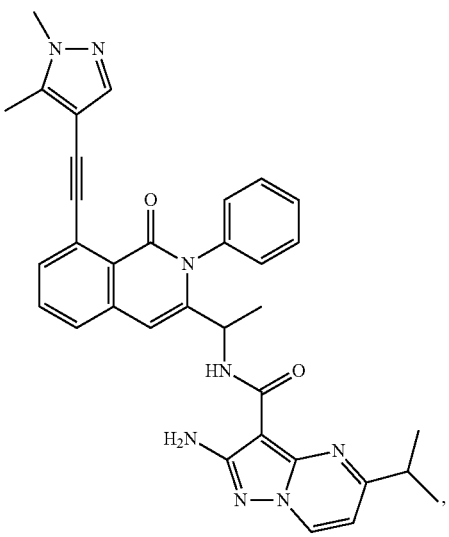 [SMILES: Cc1c(C#Cc2cccc3cc(C(C)NC(=O)c4c(N)nn5ccc(C(C)C)nc45)n(-c4ccccc4)c(=O)c23)cnn1C]
Compound 1050'
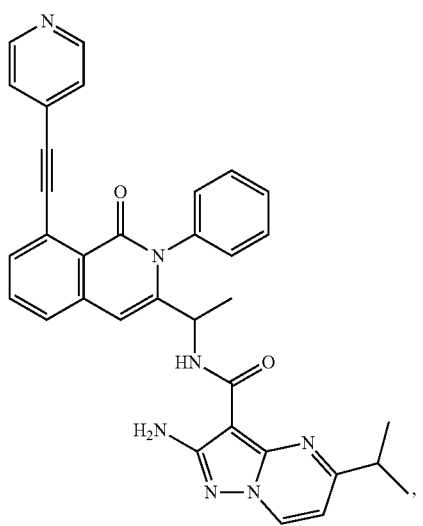 [SMILES: CC(C)c1ccn2nc(N)c(C(=O)NC(C)c3cc4cccc(C#Cc5ccncc5)c4c(=O)n3-c3ccccc3)c2n1]
Compound 1051'
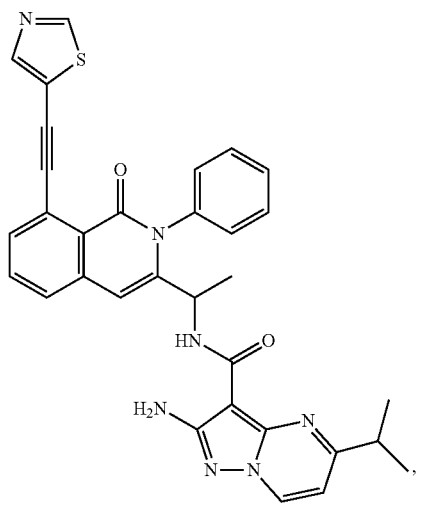 [SMILES: CC(C)c1ccn2nc(N)c(C(=O)NC(C)c3cc4cccc(C#Cc5cncs5)c4c(=O)n3-c3ccccc3)c2n1]
Compound 1052'

TABLE 8-continued
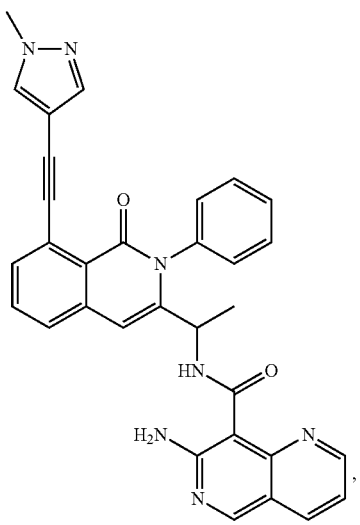
Compound 1053'
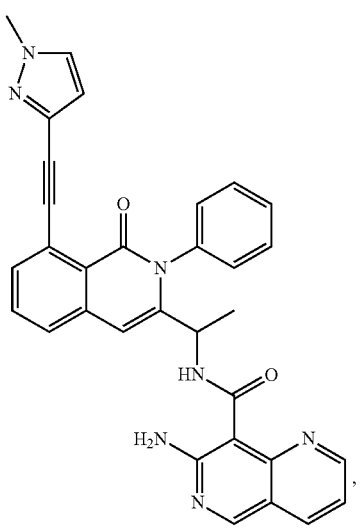
Compound 1054'
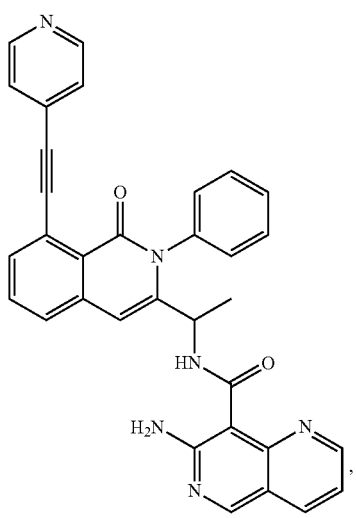 [SMILES: CC(NC(=O)c1c(N)ncc2cccnc12)c1cc2cccc(C#Cc3ccncc3)c2c(=O)n1-c1ccccc1]
Compound 1055'

TABLE 8-continued
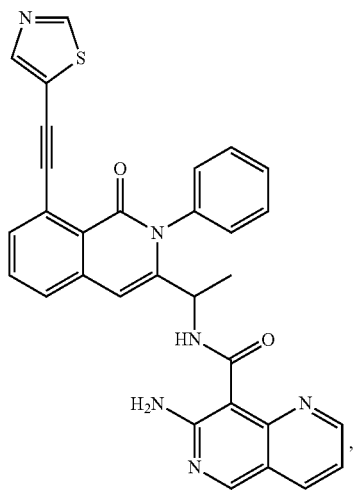 [SMILES: CC(NC(=O)c1c(N)ncc2cccnc12)c1cc2cccc(C#Cc3cncs3)c2c(=O)n1-c1ccccc1]
Compound 1056'
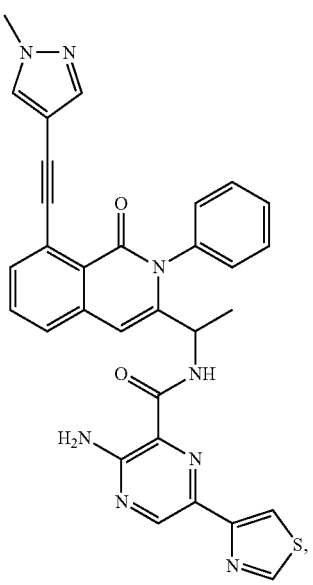 [SMILES: CC(NC(=O)c1nc(-c2cscn2)cnc1N)c1cc2cccc(C#Cc3cnn(C)c3)c2c(=O)n1-c1ccccc1]
Compound 1057'
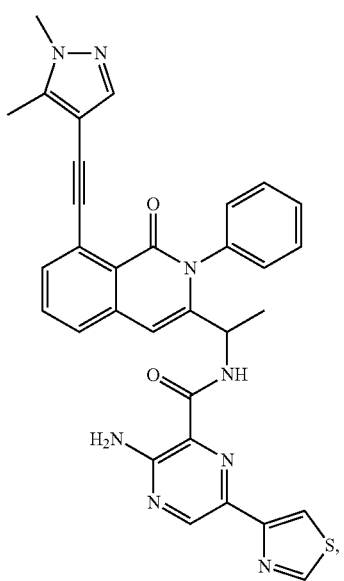 [SMILES: Cc1c(C#Cc2cccc3cc(C(C)NC(=O)c4nc(-c5cscn5)cnc4N)n(-c4ccccc4)c(=O)c23)cnn1C]
Compound 1058'

TABLE 8-continued
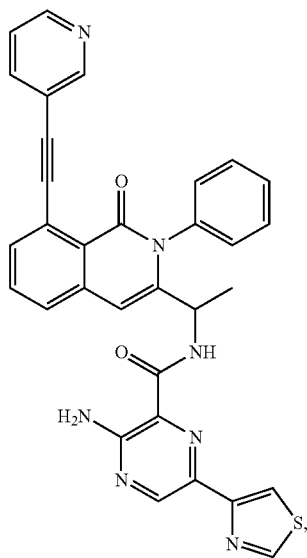 [SMILES: CC(NC(=O)c1nc(-c2cscn2)cnc1N)c1cc2cccc(C#Cc3cccnc3)c2c(=O)n1-c1ccccc1]
Compound 1059'
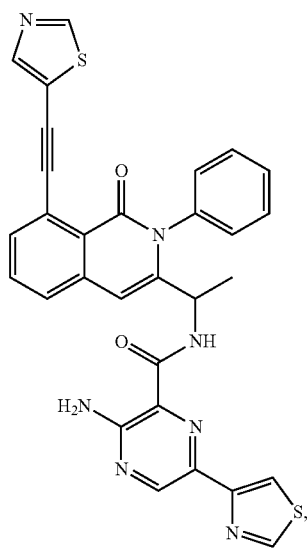 [SMILES: CC(NC(=O)c1nc(-c2cscn2)cnc1N)c1cc2cccc(C#Cc3cncs3)c2c(=O)n1-c1ccccc1]
Compound 1060'

TABLE 8-continued
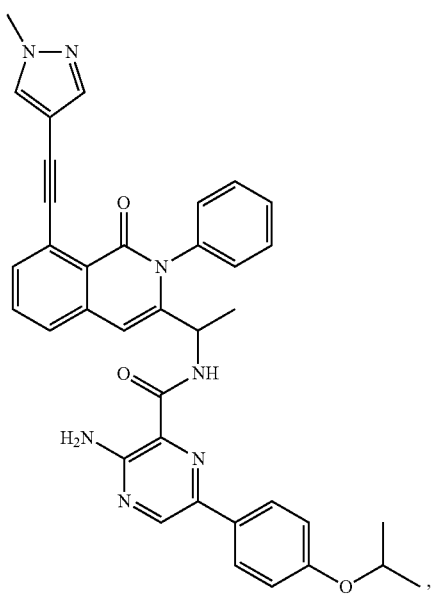 [SMILES: CC(C)Oc1ccc(-c2cnc(N)c(C(=O)NC(C)c3cc4cccc(C#Cc5cnn(C)c5)c4c(=O)n3-c3ccccc3)n2)cc1]
Compound 1061'
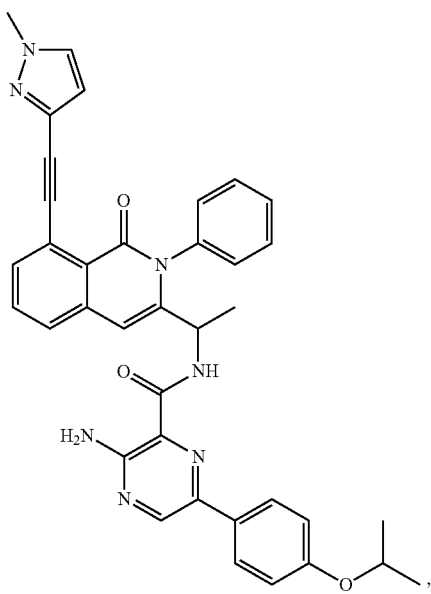 [SMILES: CC(C)Oc1ccc(-c2cnc(N)c(C(=O)NC(C)c3cc4cccc(C#Cc5ccn(C)n5)c4c(=O)n3-c3ccccc3)n2)cc1]
Compound 1062'

TABLE 8-continued
Compound 1063'
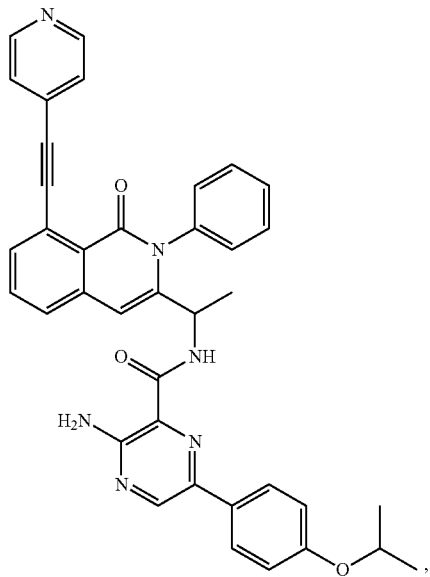 [SMILES: CC(C)Oc1ccc(-c2cnc(N)c(C(=O)NC(C)c3cc4cccc(C#Cc5ccncc5)c4c(=O)n3-c3ccccc3)n2)cc1]
Compound 1064'
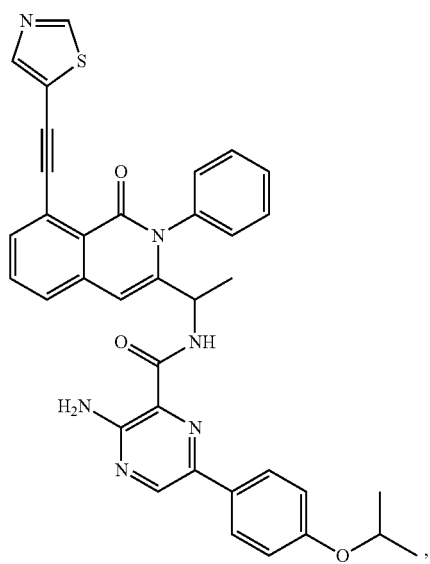 [SMILES: CC(C)Oc1ccc(-c2cnc(N)c(C(=O)NC(C)c3cc4cccc(C#Cc5cncs5)c4c(=O)n3-c3ccccc3)n2)cc1]

TABLE 8-continued
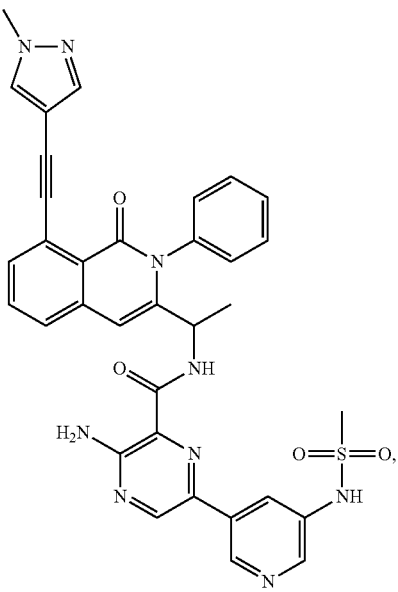 [SMILES: CC(NC(=O)c1nc(-c2cncc(NS(C)(=O)=O)c2)cnc1N)c1cc2cccc(C#Cc3cnn(C)c3)c2c(=O)n1-c1ccccc1]
Compound 1065'
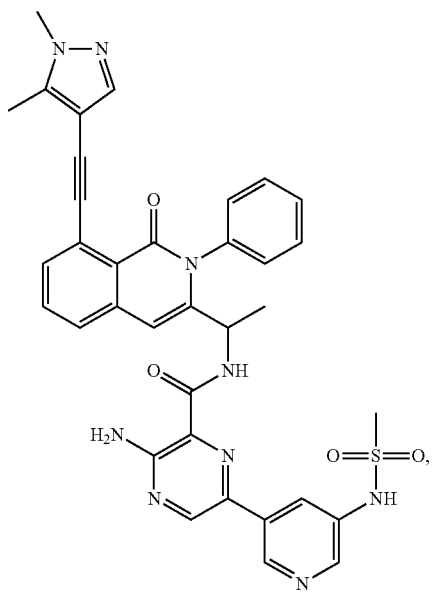 [SMILES: Cc1c(C#Cc2cccc3cc(C(C)NC(=O)c4nc(-c5cncc(NS(C)(=O)=O)c5)cnc4N)n(-c4ccccc4)c(=O)c23)cnn1C]
Compound 1066'

TABLE 8-continued
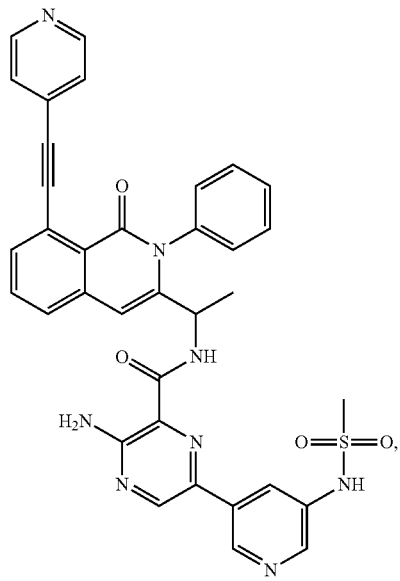
Compound 1067'
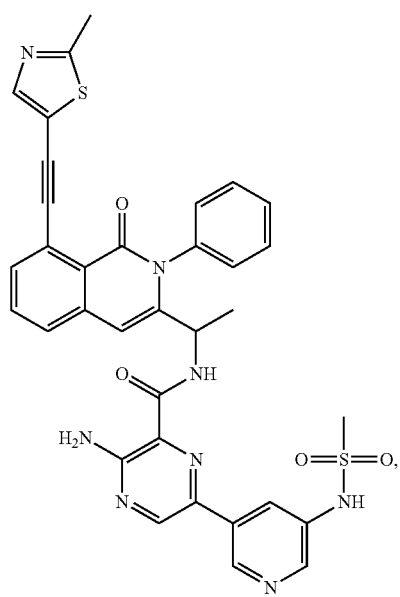
Compound 1068'

TABLE 8-continued
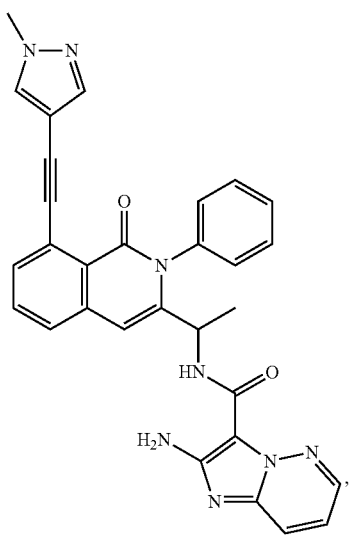
Compound 1069'
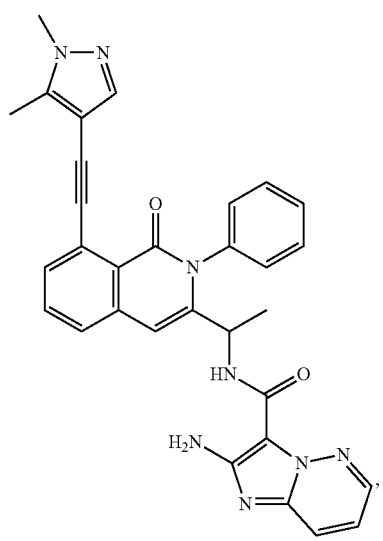 [SMILES: Cc1c(C#Cc2cccc3cc(C(C)NC(=O)c4c(N)nc5cccnn45)n(-c4ccccc4)c(=O)c23)cnn1C]
Compound 1070'
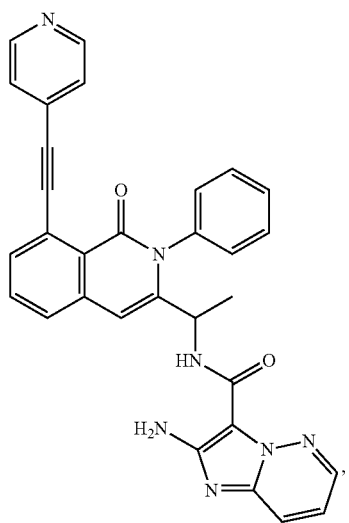 [SMILES: CC(NC(=O)c1c(N)nc2cccnn12)c1cc2cccc(C#Cc3ccncc3)c2c(=O)n1-c1ccccc1]
Compound 1071'

TABLE 8-continued
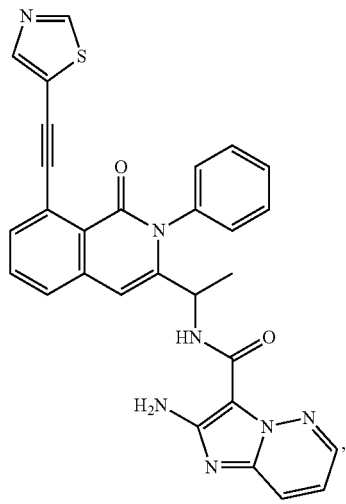 [SMILES: CC(NC(=O)c1c(N)nc2cccnn12)c1cc2cccc(C#Cc3cncs3)c2c(=O)n1-c1ccccc1]
Compound 1072'
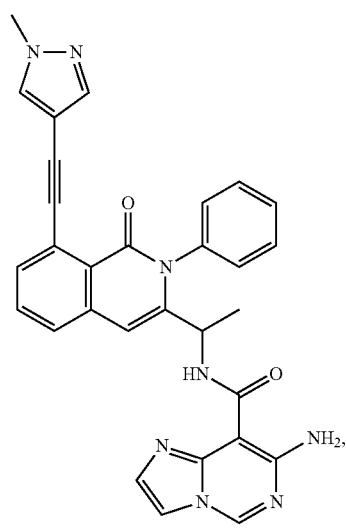 [SMILES: CC(NC(=O)c1c(N)ncn2ccnc12)c1cc2cccc(C#Cc3cnn(C)c3)c2c(=O)n1-c1ccccc1]
Compound 1073'
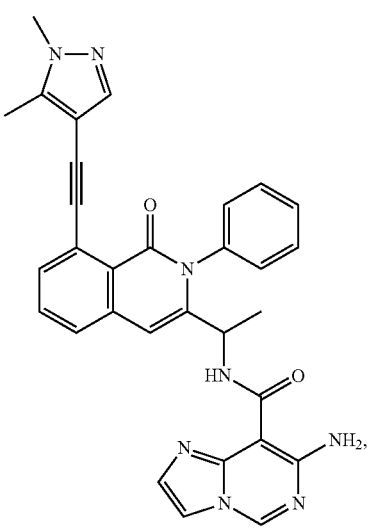 [SMILES: Cc1c(C#Cc2cccc3cc(C(C)NC(=O)c4c(N)ncn5ccnc45)n(-c4ccccc4)c(=O)c23)cnn1C]
Compound 1074'

TABLE 8-continued
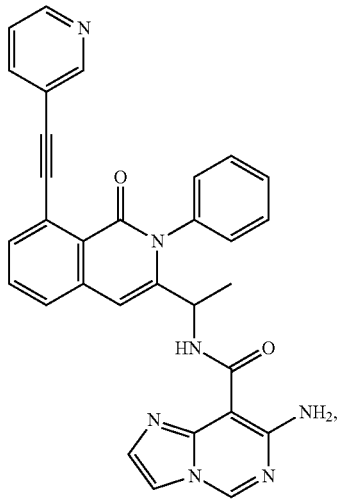 [SMILES: CC(NC(=O)c1c(N)ncn2ccnc12)c1cc2cccc(C#Cc3cccnc3)c2c(=O)n1-c1ccccc1]
Compound 1075'
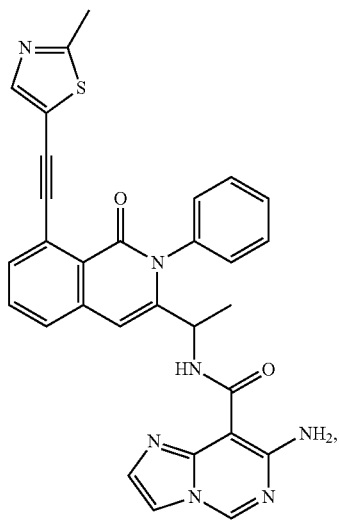 [SMILES: Cc1ncc(C#Cc2cccc3cc(C(C)NC(=O)c4c(N)ncn5ccnc45)n(-c4ccccc4)c(=O)c23)s1]
Compound 1076'
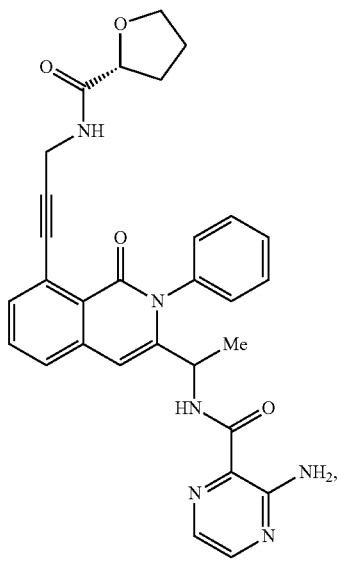 [SMILES: CC(NC(=O)c1nccnc1N)c1cc2cccc(C#CCNC(=O)[C@H]3CCCO3)c2c(=O)n1-c1ccccc1]
Compound 1077'

TABLE 8-continued
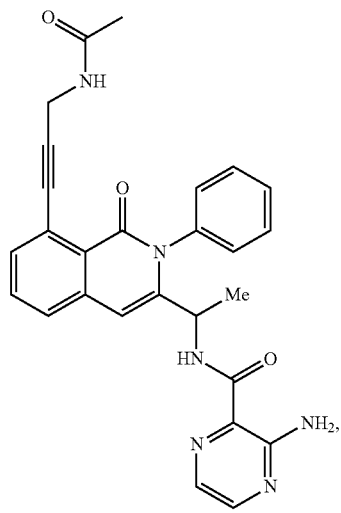 [SMILES: CC(=O)NCC#Cc1cccc2cc(C(C)NC(=O)c3nccnc3N)n(-c3ccccc3)c(=O)c12]
Compound 1078'
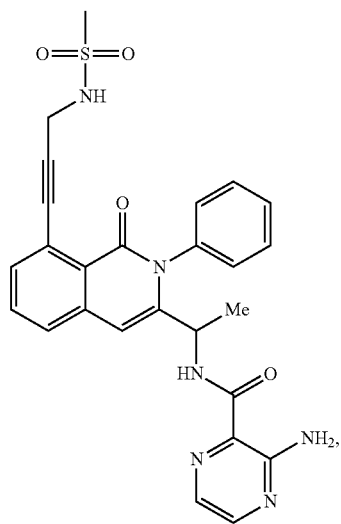 [SMILES: CC(NC(=O)c1nccnc1N)c1cc2cccc(C#CCNS(C)(=O)=O)c2c(=O)n1-c1ccccc1]
Compound 1079'
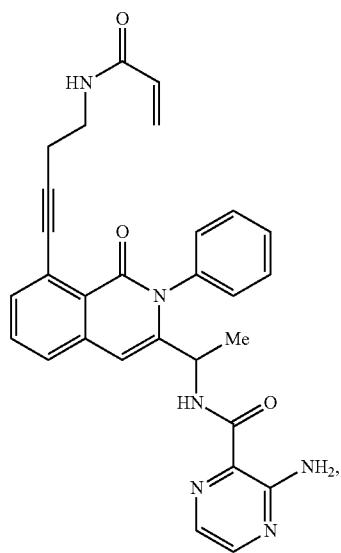 [SMILES: C=CC(=O)NCCC#Cc1cccc2cc(C(C)NC(=O)c3nccnc3N)n(-c3ccccc3)c(=O)c12]
Compound 1080'

TABLE 8-continued
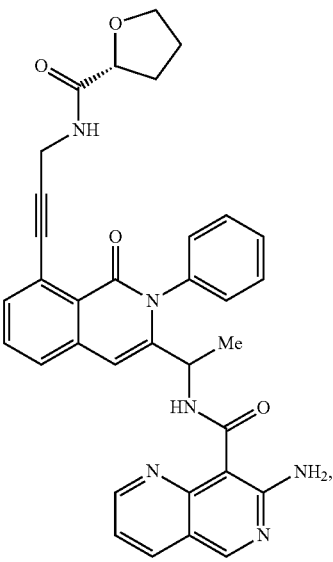 [SMILES: CC(NC(=O)c1c(N)ncc2cccnc12)c1cc2cccc(C#CCNC(=O)[C@H]3CCCO3)c2c(=O)n1-c1ccccc1]
Compound 1081'
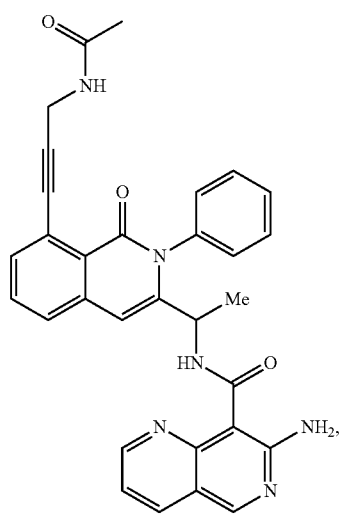 [SMILES: CC(=O)NCC#Cc1cccc2cc(C(C)NC(=O)c3c(N)ncc4cccnc34)n(-c3ccccc3)c(=O)c12]
Compound 1082'
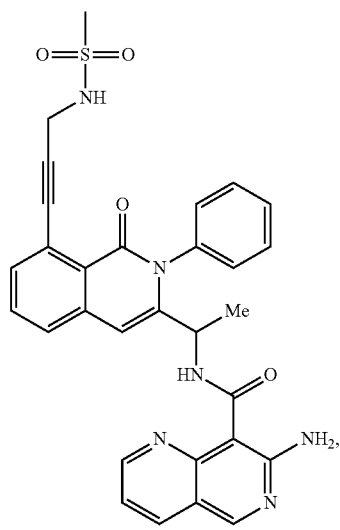 [SMILES: CC(NC(=O)c1c(N)ncc2cccnc12)c1cc2cccc(C#CCNS(C)(=O)=O)c2c(=O)n1-c1ccccc1]
Compound 1083'

TABLE 8-continued
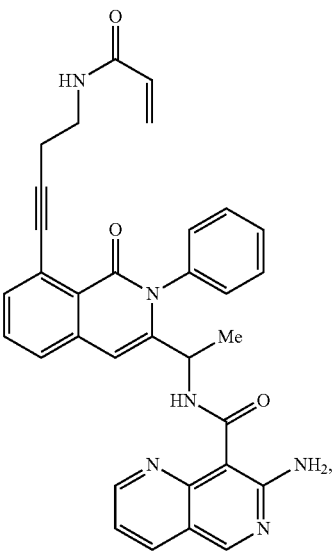 [SMILES: C=CC(=O)NCCC#Cc1cccc2cc(C(C)NC(=O)c3c(N)ncc4cccnc34)n(-c3ccccc3)c(=O)c12]
Compound 1084'
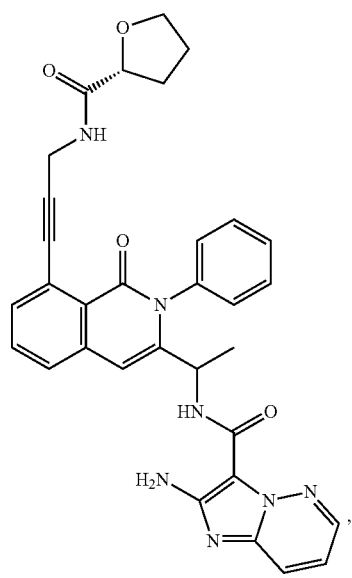 [SMILES: CC(NC(=O)c1c(N)nc2cccnn12)c1cc2cccc(C#CCNC(=O)[C@H]3CCCO3)c2c(=O)n1-c1ccccc1]
Compound 1085'
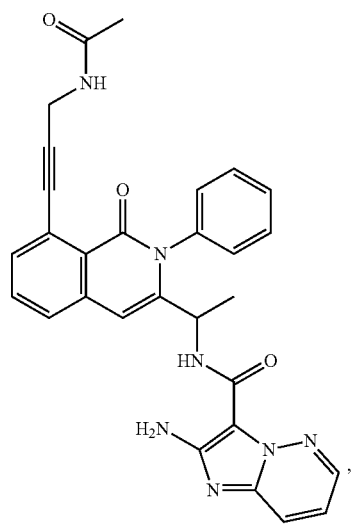 [SMILES: CC(=O)NCC#Cc1cccc2cc(C(C)NC(=O)c3c(N)nc4cccnn34)n(-c3ccccc3)c(=O)c12]
Compound 1086'

TABLE 8-continued
Compound 1087'
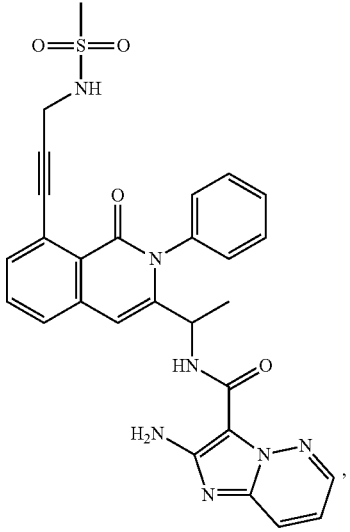 [SMILES: CC(NC(=O)c1c(N)nc2cccnn12)c1cc2cccc(C#CCNS(C)(=O)=O)c2c(=O)n1-c1ccccc1]
Compound 1088'
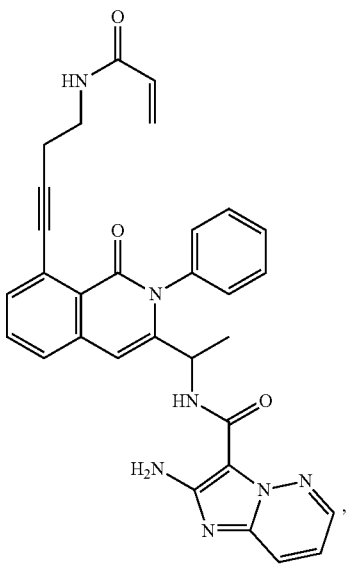 [SMILES: C=CC(=O)NCCC#Cc1cccc2cc(C(C)NC(=O)c3c(N)nc4cccnn34)n(-c3ccccc3)c(=O)c12]
Compound 1089'
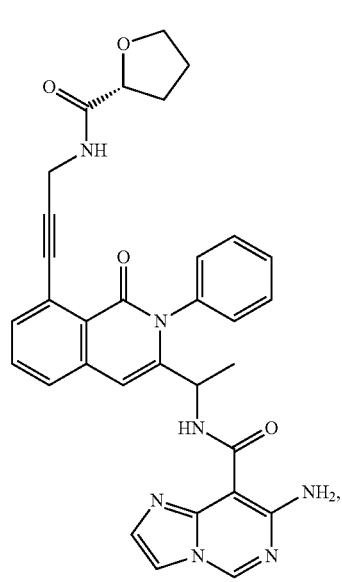 [SMILES: CC(NC(=O)c1c(N)ncn2ccnc12)c1cc2cccc(C#CCNC(=O)[C@H]3CCCO3)c2c(=O)n1-c1ccccc1]

TABLE 8-continued
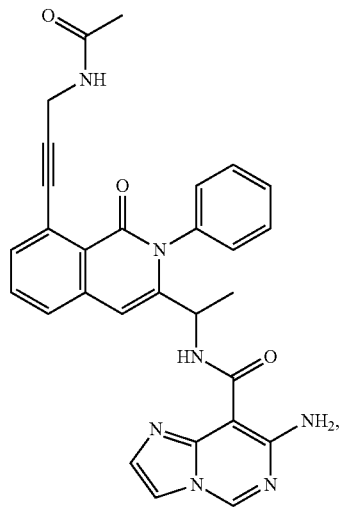 [SMILES: CC(=O)NCC#Cc1cccc2cc(C(C)NC(=O)c3c(N)ncn4ccnc34)n(-c3ccccc3)c(=O)c12]
Compound 1090'
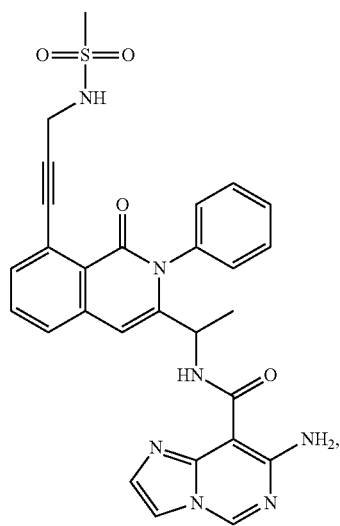 [SMILES: CC(NC(=O)c1c(N)ncn2ccnc12)c1cc2cccc(C#CCNS(C)(=O)=O)c2c(=O)n1-c1ccccc1]
Compound 1091'
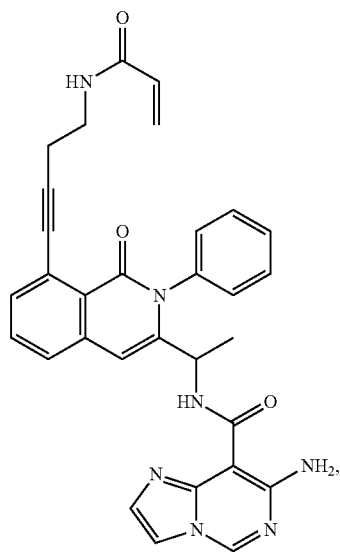 [SMILES: C=CC(=O)NCCC#Cc1cccc2cc(C(C)NC(=O)c3c(N)ncn4ccnc34)n(-c3ccccc3)c(=O)c12]
Compound 1092'

TABLE 8-continued
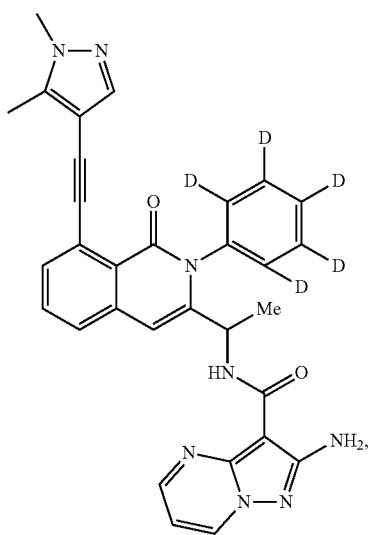 [SMILES: [2H]c1c([2H])c([2H])c(-n2c(C(C)NC(=O)c3c(N)nn4cccnc34)cc3cccc(C#Cc4cnn(C)c4C)c3c2=O)c([2H])c1[2H]]
Compound 1093'
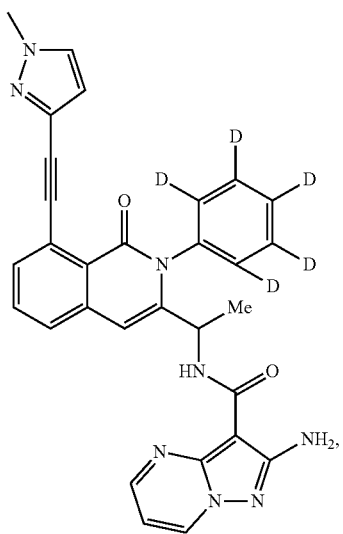 [SMILES: [2H]c1c([2H])c([2H])c(-n2c(C(C)NC(=O)c3c(N)nn4cccnc34)cc3cccc(C#Cc4ccn(C)n4)c3c2=O)c([2H])c1[2H]]
Compound 1094'
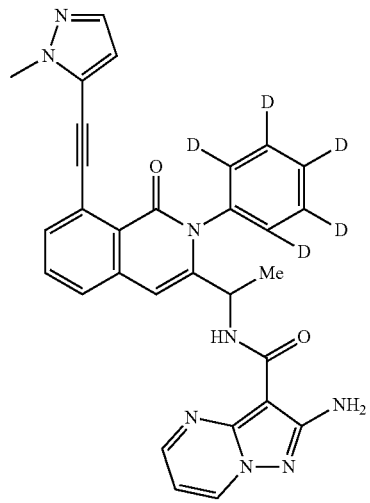 [SMILES: [2H]c1c([2H])c([2H])c(-n2c(C(C)NC(=O)c3c(N)nn4cccnc34)cc3cccc(C#Cc4ccnn4C)c3c2=O)c([2H])c1[2H]]
Compound 1095'

TABLE 9
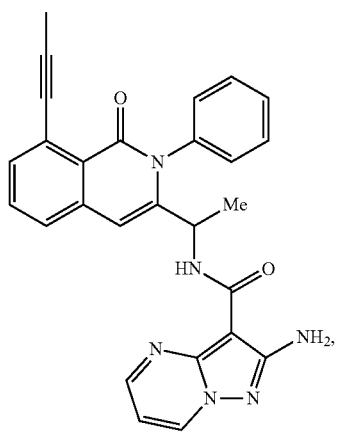 [SMILES: CC#Cc1cccc2cc(C(C)NC(=O)c3c(N)nn4cccnc34)n(-c3ccccc3)c(=O)c12]
Compound 2001'
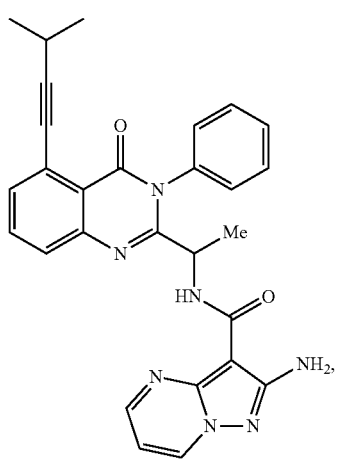 [SMILES: CC(C)C#Cc1cccc2nc(C(C)NC(=O)c3c(N)nn4cccnc34)n(-c3ccccc3)c(=O)c12]
Compound 2002'
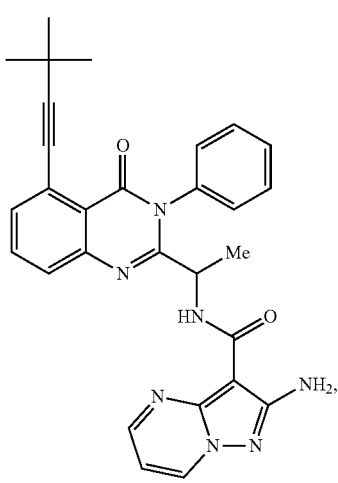 [SMILES: CC(NC(=O)c1c(N)nn2cccnc12)c1nc2cccc(C#CC(C)(C)C)c2c(=O)n1-c1ccccc1]
Compound 2003'
TABLE 9-continued
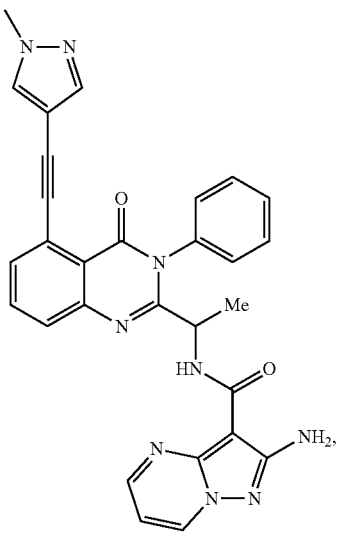 [SMILES: CC(NC(=O)c1c(N)nn2cccnc12)c1nc2cccc(C#Cc3cnn(C)c3)c2c(=O)n1-c1ccccc1]
Compound 2004'
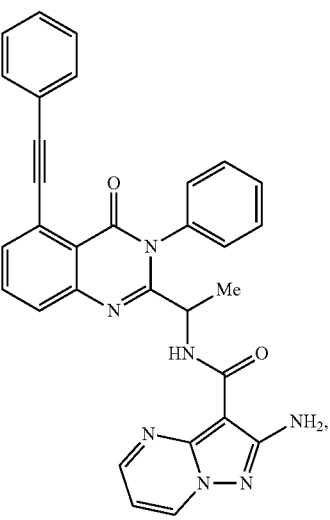 [SMILES: CC(NC(=O)c1c(N)nn2cccnc12)c1nc2cccc(C#Cc3ccccc3)c2c(=O)n1-c1ccccc1]
Compound 2005'
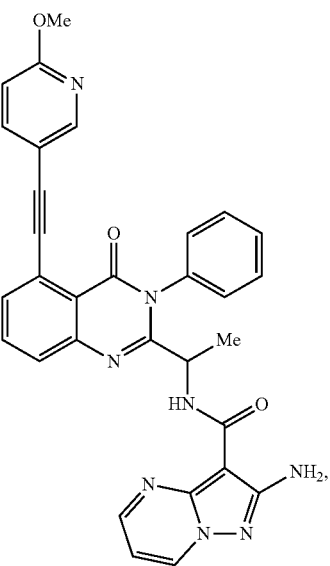
Compound 2006'

TABLE 9-continued
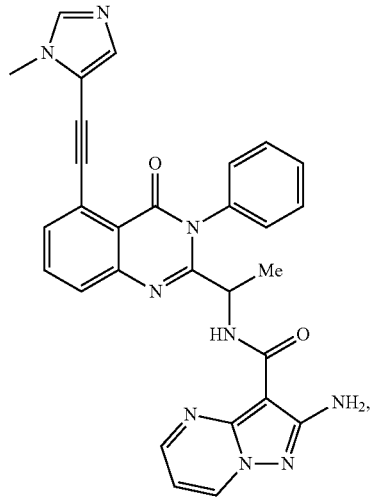 [SMILES: CC(NC(=O)c1c(N)nn2cccnc12)c1nc2cccc(C#Cc3cncn3C)c2c(=O)n1-c1ccccc1]
Compound 2007'
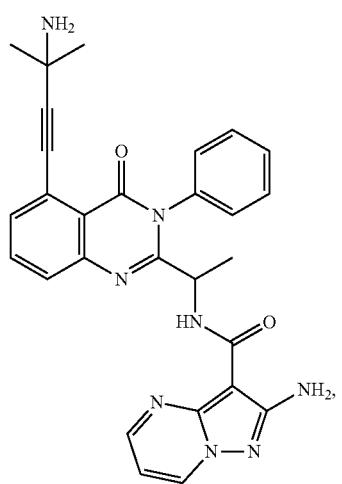 [SMILES: CC(NC(=O)c1c(N)nn2cccnc12)c1nc2cccc(C#CC(C)(C)N)c2c(=O)n1-c1ccccc1]
Compound 2008'
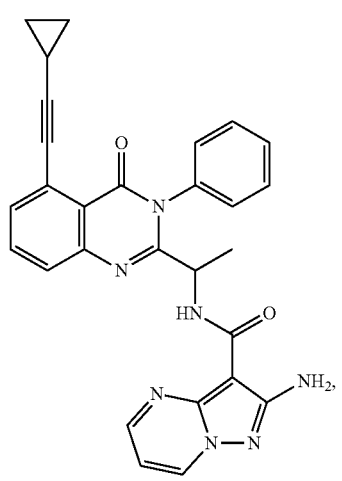
Compound 2009'
TABLE 9-continued
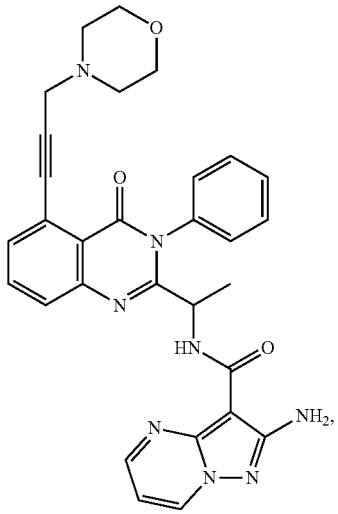 [SMILES: CC(NC(=O)c1c(N)nn2cccnc12)c1nc2cccc(C#CCN3CCOCC3)c2c(=O)n1-c1ccccc1]
Compound 2010'
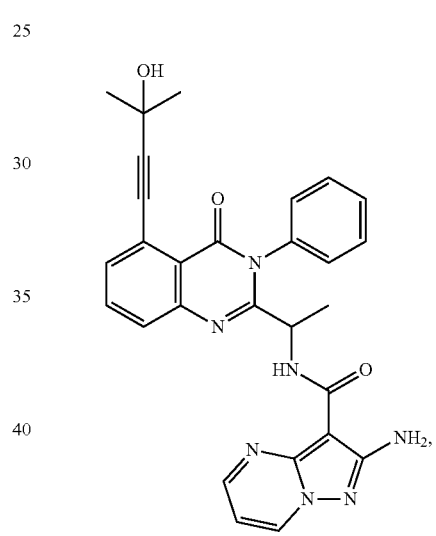
Compound 2011'
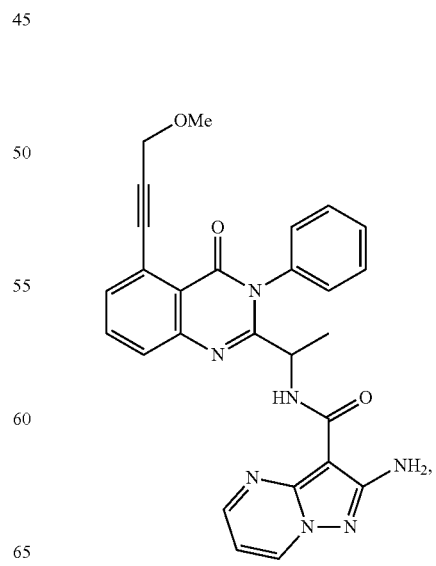
Compound 2012'

TABLE 9-continued
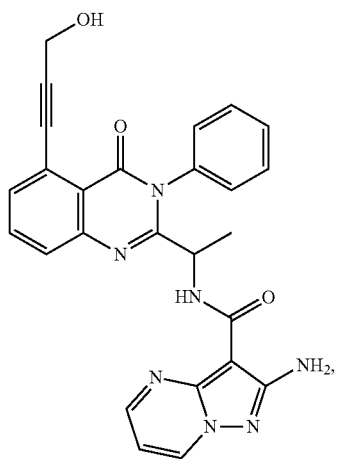 [SMILES: CC(NC(=O)c1c(N)nn2cccnc12)c1nc2cccc(C#CCO)c2c(=O)n1-c1ccccc1]
Compound 2013'
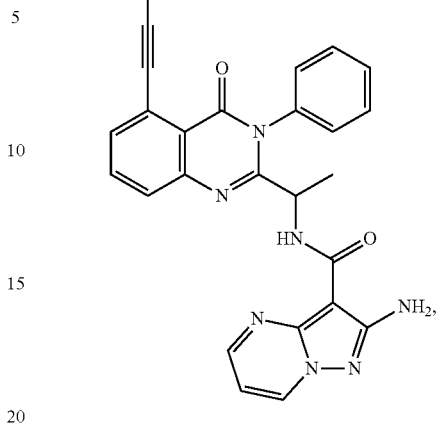
Compound 2016'
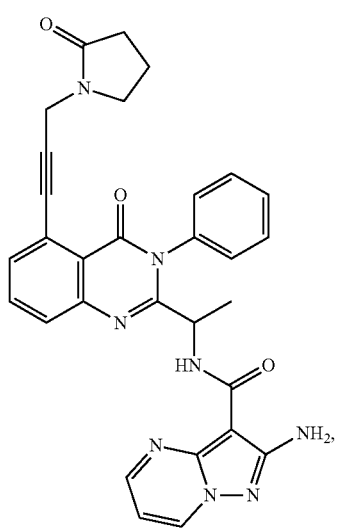 [SMILES: CC(NC(=O)c1c(N)nn2cccnc12)c1nc2cccc(C#CCN3CCCC3=O)c2c(=O)n1-c1ccccc1]
Compound 2014'
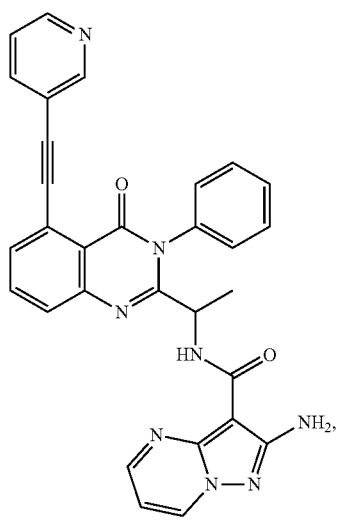
Compound 2017'
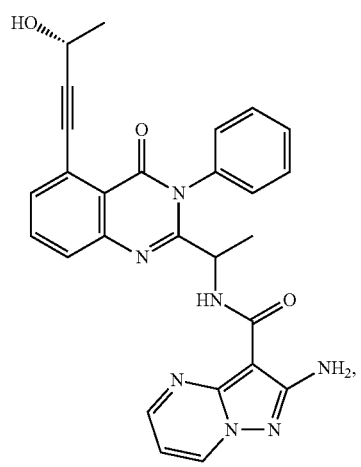 [SMILES: CC(NC(=O)c1c(N)nn2cccnc12)c1nc2cccc(C#C[C@@H](C)O)c2c(=O)n1-c1ccccc1]
Compound 2015'
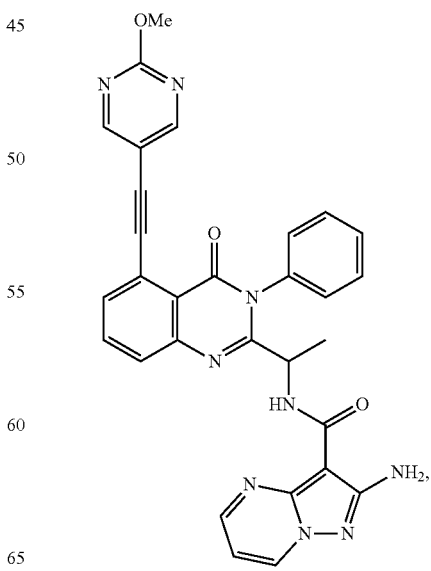
Compound 2018'

TABLE 9-continued
Compound 2019'
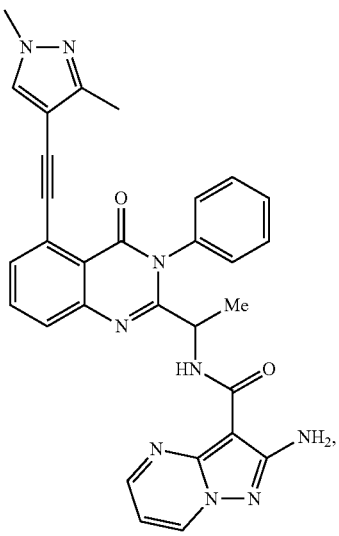 [SMILES: Cc1nn(C)cc1C#Cc1cccc2nc(C(C)NC(=O)c3c(N)nn4cccnc34)n(-c3ccccc3)c(=O)c12]
Compound 2020'
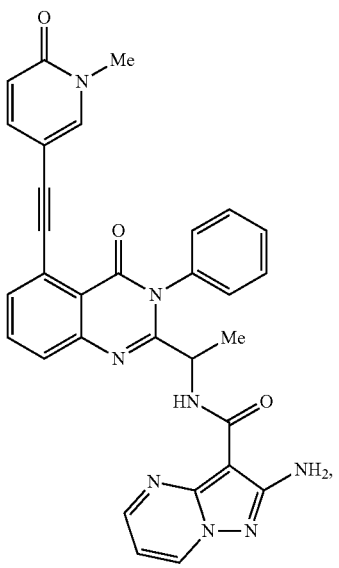
Compound 2021'
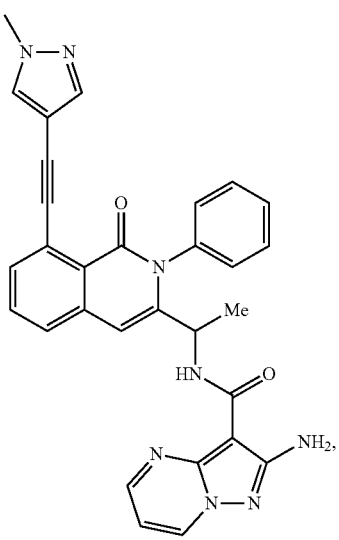 [SMILES: CC(NC(=O)c1c(N)nn2cccnc12)c1cc2cccc(C#Cc3cnn(C)c3)c2c(=O)n1-c1ccccc1]
TABLE 9-continued
Compound 2022'
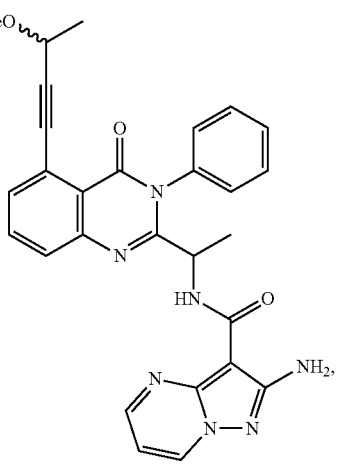
Compound 2023'
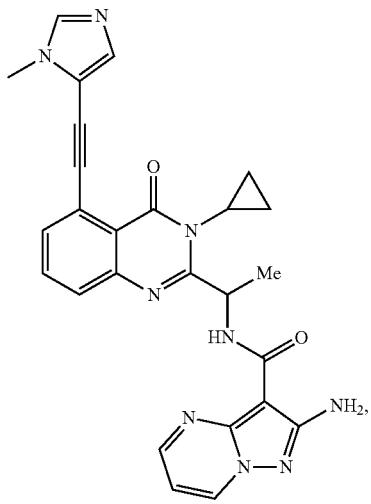
Compound 2024'
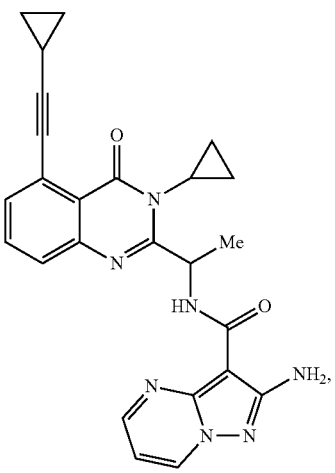 [SMILES: CC(NC(=O)c1c(N)nn2cccnc12)c1nc2cccc(C#CC3CC3)c2c(=O)n1C1CC1]

TABLE 9-continued
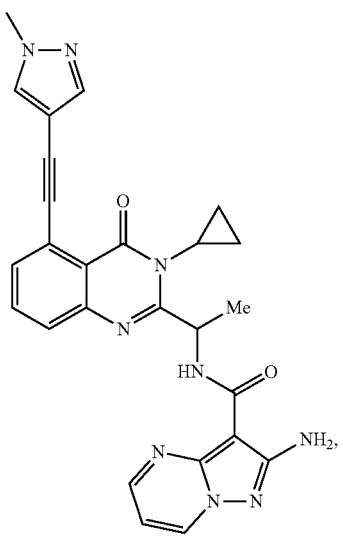 [SMILES: CC(NC(=O)c1c(N)nn2cccnc12)c1nc2cccc(C#Cc3cnn(C)c3)c2c(=O)n1C1CC1]
Compound 2025'
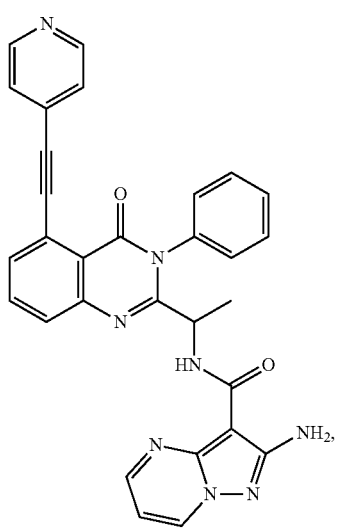 [SMILES: CC(NC(=O)c1c(N)nn2cccnc12)c1nc2cccc(C#Cc3ccncc3)c2c(=O)n1-c1ccccc1]
Compound 2026'
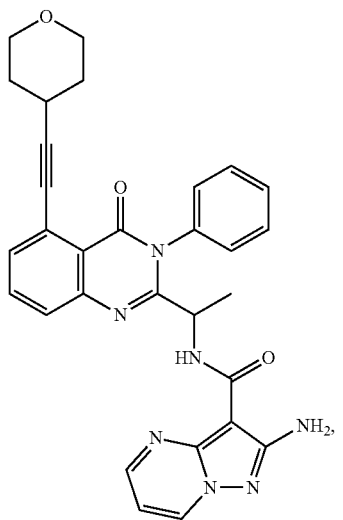 [SMILES: CC(NC(=O)c1c(N)nn2cccnc12)c1nc2cccc(C#CC3CCOCC3)c2c(=O)n1-c1ccccc1]
Compound 2027'
TABLE 9-continued
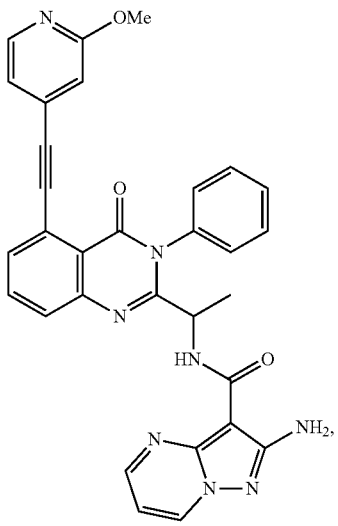 [SMILES: COc1cc(C#Cc2cccc3nc(C(C)NC(=O)c4c(N)nn5cccnc45)n(-c4ccccc4)c(=O)c23)ccn1]
Compound 2028'
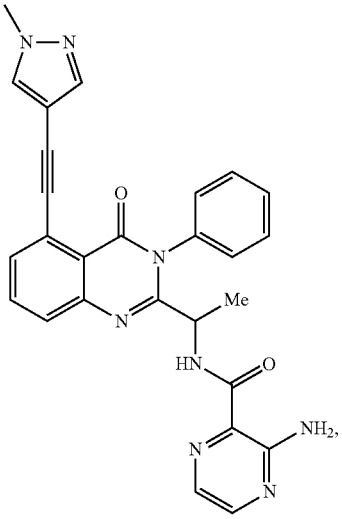 [SMILES: CC(NC(=O)c1nccnc1N)c1nc2cccc(C#Cc3cnn(C)c3)c2c(=O)n1-c1ccccc1]
Compound 2029'
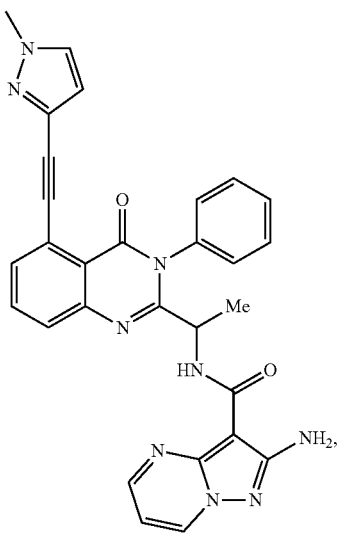 [SMILES: CC(NC(=O)c1c(N)nn2cccnc12)c1nc2cccc(C#Cc3ccn(C)n3)c2c(=O)n1-c1ccccc1]
Compound 2030'

TABLE 9-continued
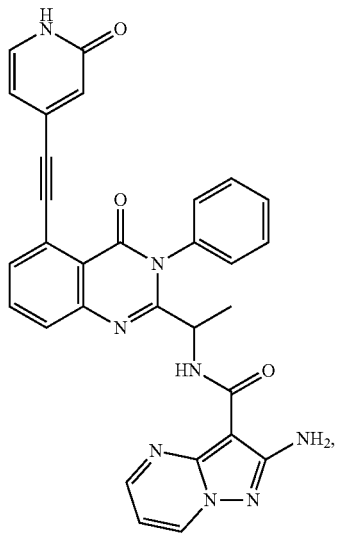 [SMILES: CC(NC(=O)c1c(N)nn2cccnc12)c1nc2cccc(C#Cc3cc[nH]c(=O)c3)c2c(=O)n1-c1ccccc1]
Compound 2031'
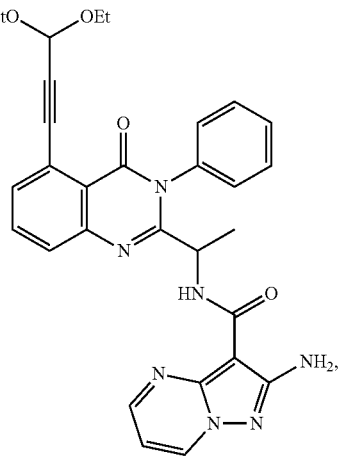
Compound 2034'
Compound 2032'
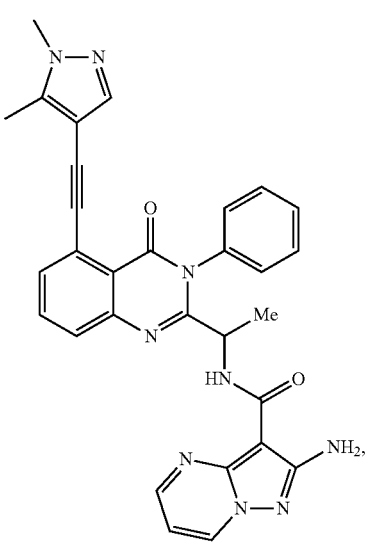 [SMILES: Cc1c(C#Cc2cccc3nc(C(C)NC(=O)c4c(N)nn5cccnc45)n(-c4ccccc4)c(=O)c23)cnn1C]
Compound 2035'
Compound 2033'
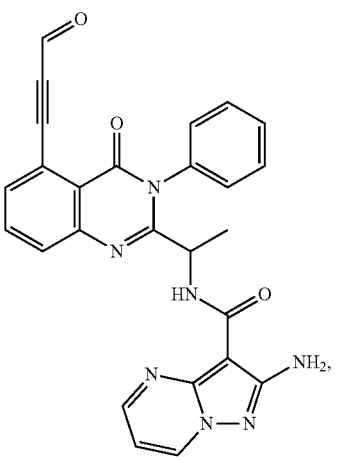 [SMILES: CC(NC(=O)c1c(N)nn2cccnc12)c1nc2cccc(C#CC=O)c2c(=O)n1-c1ccccc1]
Compound 2036'

TABLE 9-continued
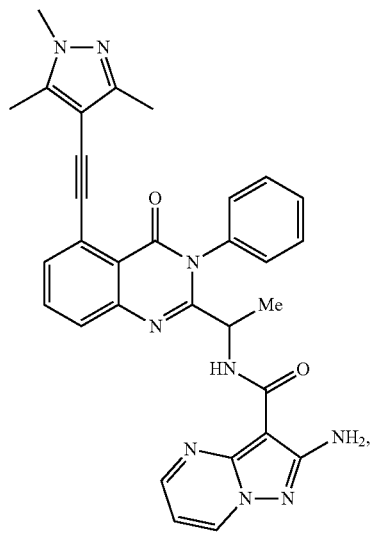 [SMILES: Cc1nn(C)c(C)c1C#Cc1cccc2nc(C(C)NC(=O)c3c(N)nn4cccnc34)n(-c3ccccc3)c(=O)c12]
Compound 2037'
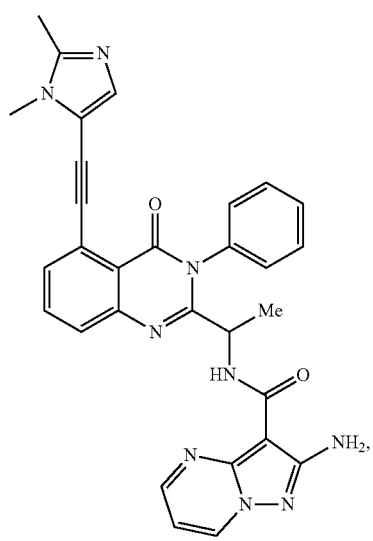
Compound 2038'
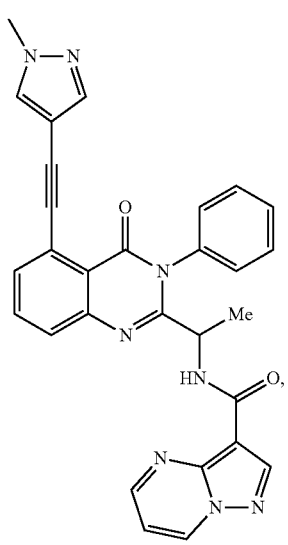
Compound 2039'
TABLE 9-continued
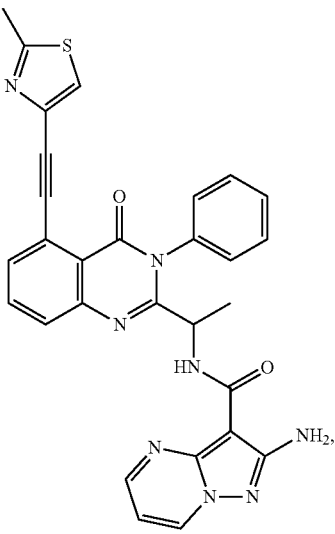
Compound 2040'
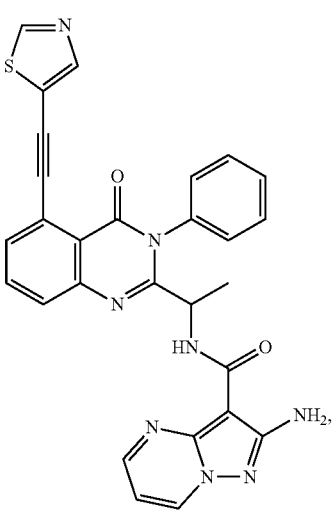
Compound 2041'
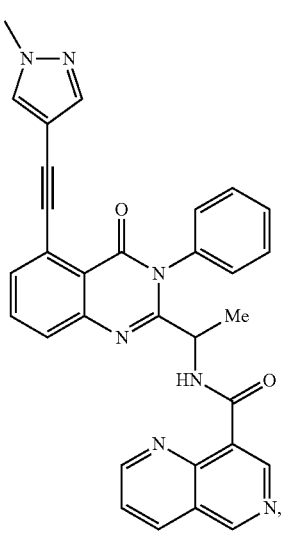 [SMILES: CC(NC(=O)c1cncc2cccnc12)c1nc2cccc(C#Cc3cnn(C)c3)c2c(=O)n1-c1ccccc1]
Compound 2042'

TABLE 9-continued
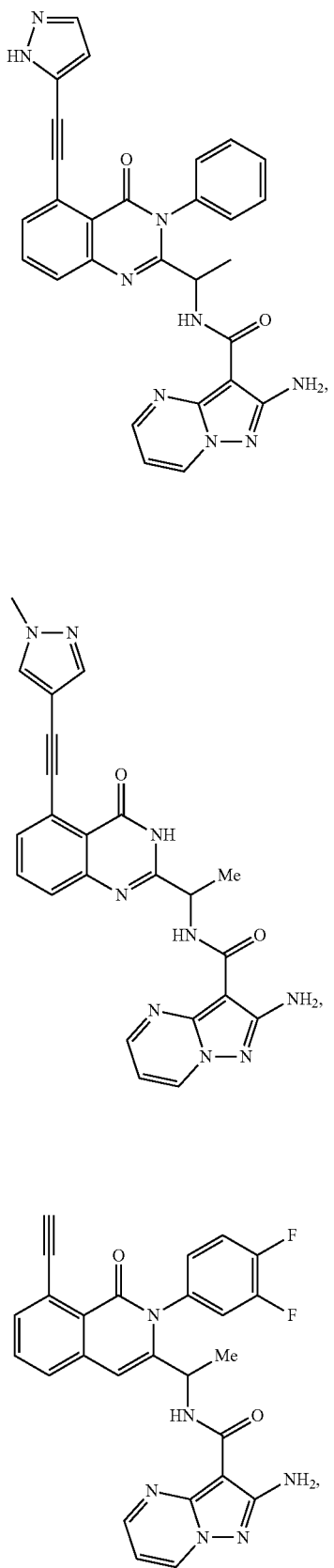
Compound 2043'
Compound 2044'
Compound 2045'
TABLE 9-continued
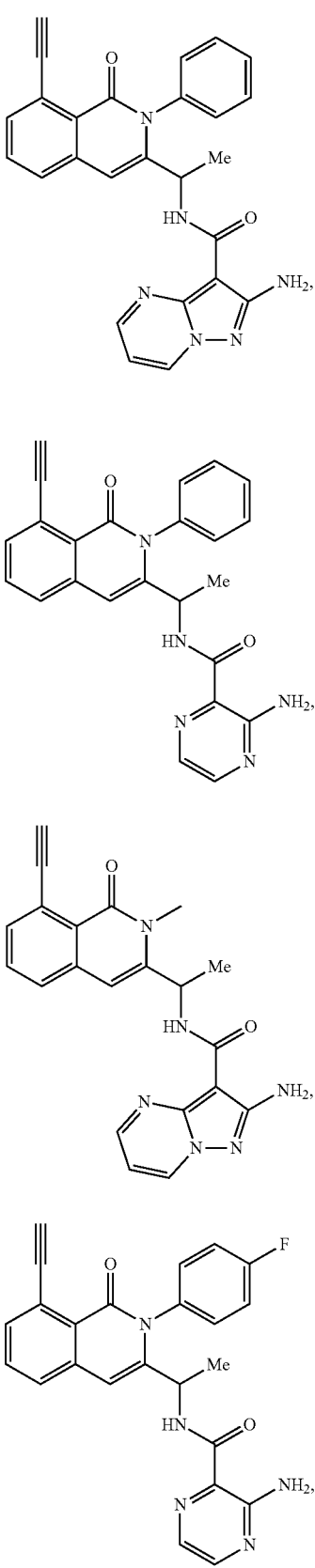
Compound 2046'
Compound 2047'
Compound 2048'
Compound 2049'

TABLE 9-continued
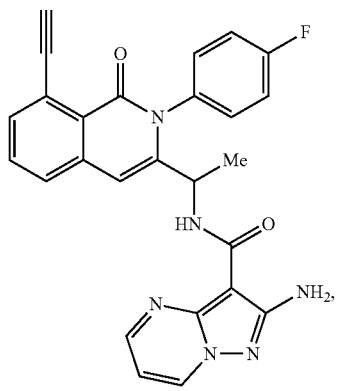 [SMILES: C#Cc1cccc2cc(C(C)NC(=O)c3c(N)nn4cccnc34)n(-c3ccc(F)cc3)c(=O)c12]
Compound 2050'
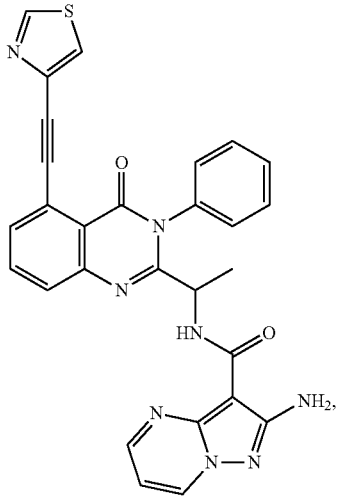
Compound 2054'
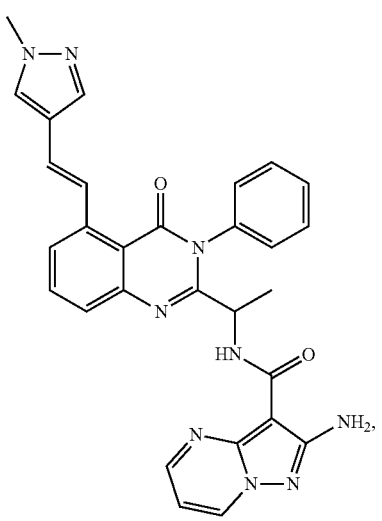 [SMILES: CC(NC(=O)c1c(N)nn2cccnc12)c1nc2cccc(/C=C/c3cnn(C)c3)c2c(=O)n1-c1ccccc1]
Compound 2052'
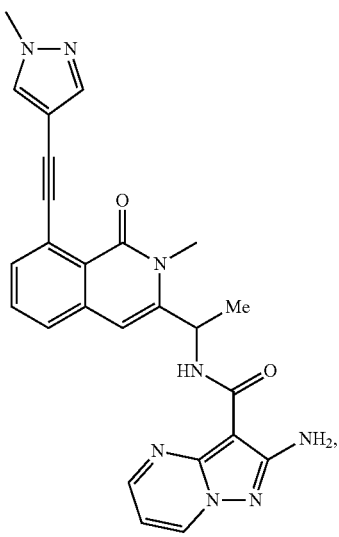 [SMILES: CC(NC(=O)c1c(N)nn2cccnc12)c1cc2cccc(C#Cc3cnn(C)c3)c2c(=O)n1C]
Compound 2055'
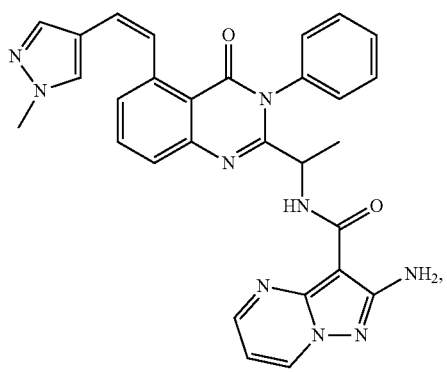
Compound 2053'
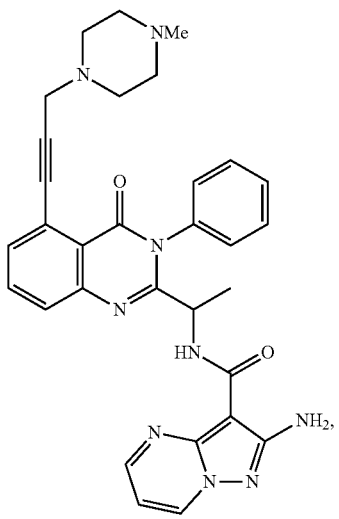 [SMILES: CC(NC(=O)c1c(N)nn2cccnc12)c1nc2cccc(C#CCN3CCN(C)CC3)c2c(=O)n1-c1ccccc1]
Compound 2056'

TABLE 9-continued
Compound 2057'
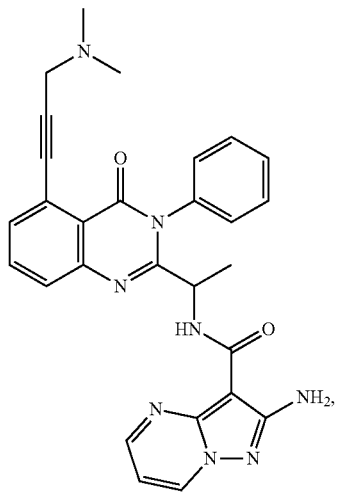 [SMILES: CC(NC(=O)c1c(N)nn2cccnc12)c1nc2cccc(C#CCN(C)C)c2c(=O)n1-c1ccccc1]
Compound 2058'
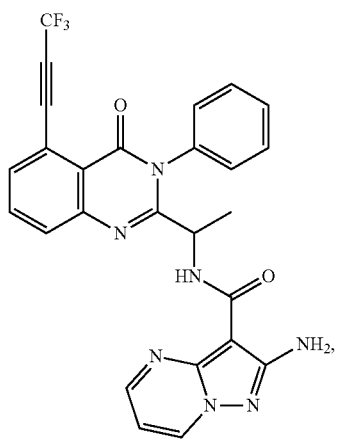 [SMILES: CC(NC(=O)c1c(N)nn2cccnc12)c1nc2cccc(C#CC(F)(F)F)c2c(=O)n1-c1ccccc1]
Compound 2059'
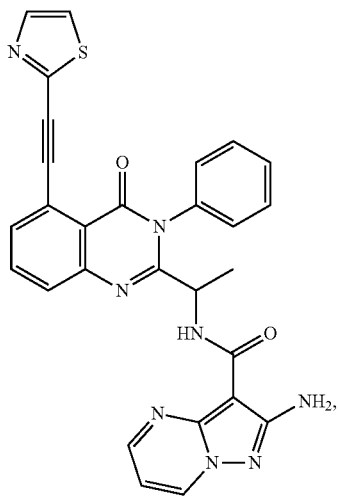 [SMILES: CC(NC(=O)c1c(N)nn2cccnc12)c1nc2cccc(C#Cc3nccs3)c2c(=O)n1-c1ccccc1]
TABLE 9-continued
Compound 2060'
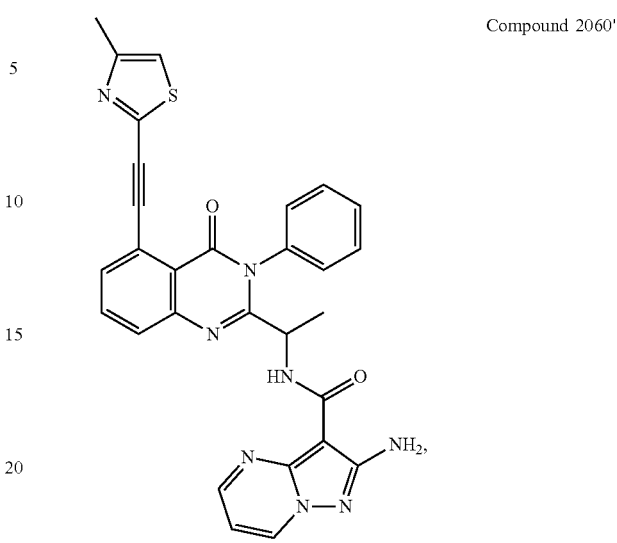
Compound 2061'
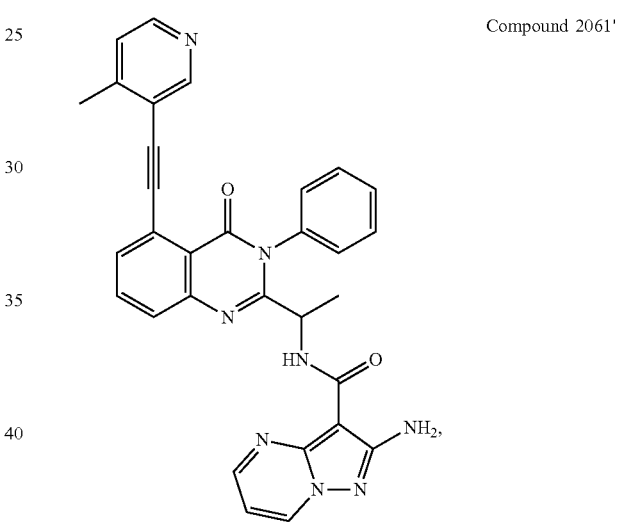
Compound 2062'
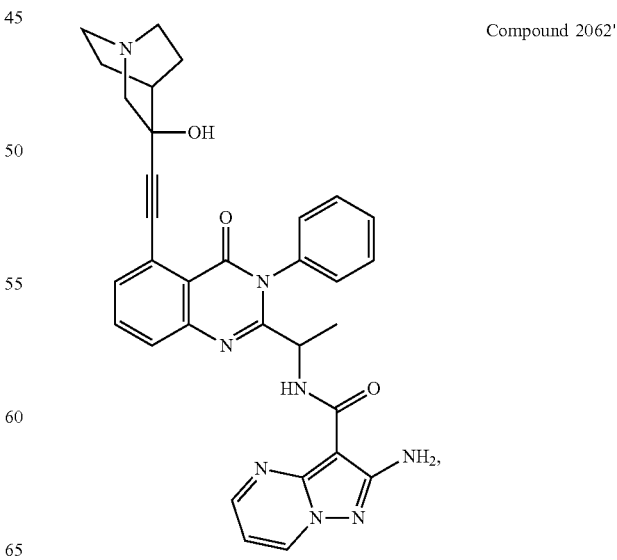

TABLE 9-continued
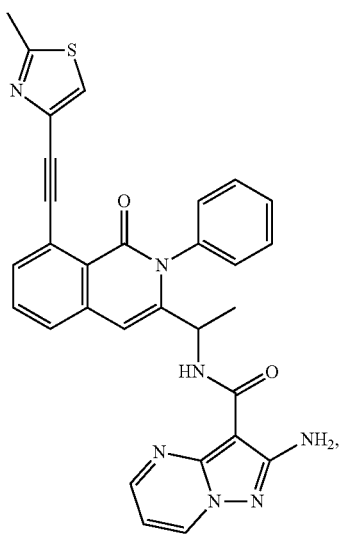 [SMILES: Cc1nc(C#Cc2cccc3cc(C(C)NC(=O)c4c(N)nn5cccnc45)n(-c4ccccc4)c(=O)c23)cs1]
Compound 2063'
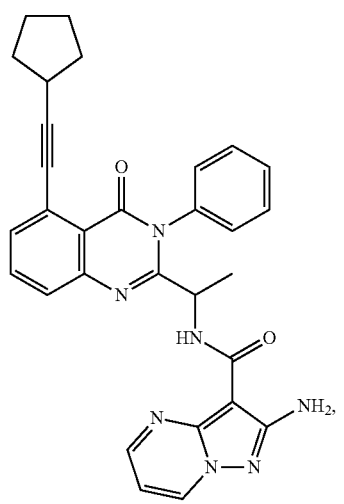 [SMILES: CC(NC(=O)c1c(N)nn2cccnc12)c1nc2cccc(C#CC3CCCC3)c2c(=O)n1-c1ccccc1]
Compound 2064'
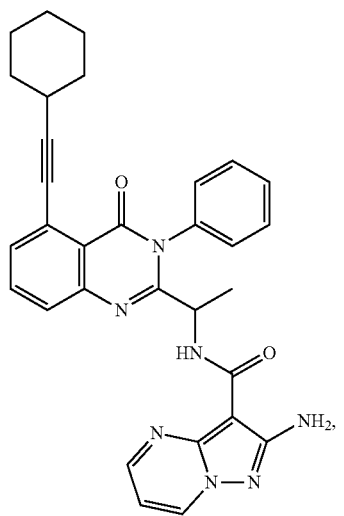 [SMILES: CC(NC(=O)c1c(N)nn2cccnc12)c1nc2cccc(C#CC3CCCCC3)c2c(=O)n1-c1ccccc1]
Compound 2065'
TABLE 9-continued
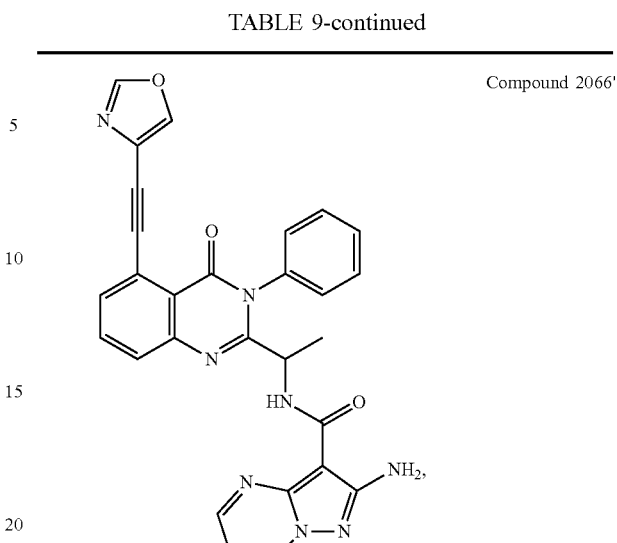
Compound 2066'
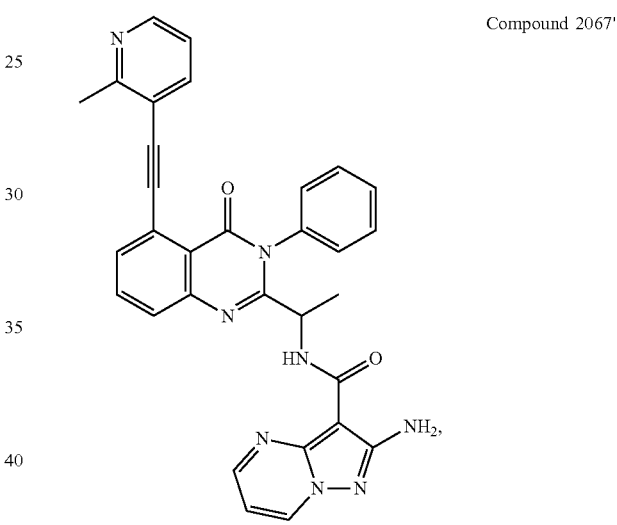
Compound 2067'
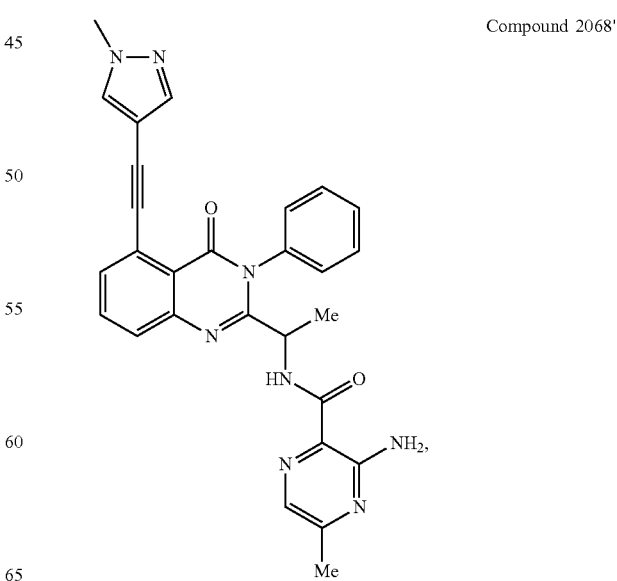
Compound 2068'

TABLE 9-continued
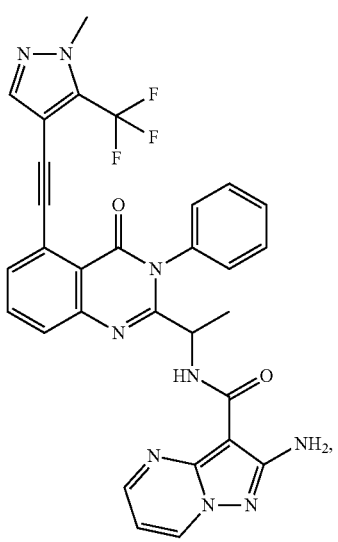 [SMILES: CC(NC(=O)c1c(N)nn2cccnc12)c1nc2cccc(C#Cc3cnn(C)c3C(F)(F)F)c2c(=O)n1-c1ccccc1]
Compound 2069'
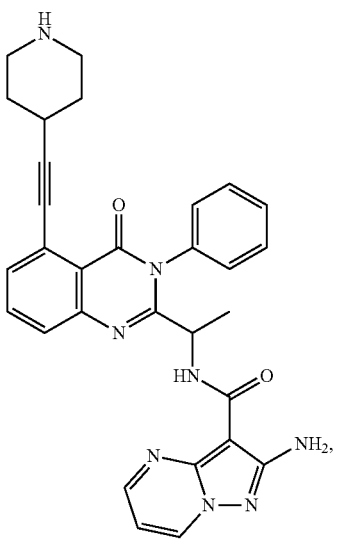
Compound 2072'
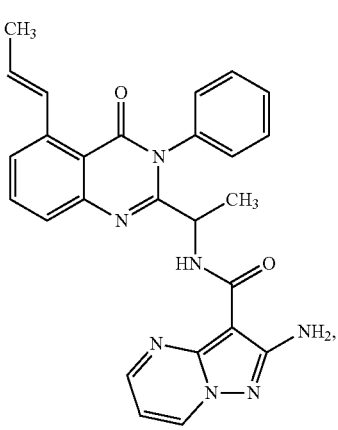 [SMILES: C/C=C/c1cccc2nc(C(C)NC(=O)c3c(N)nn4cccnc34)n(-c3ccccc3)c(=O)c12]
Compound 2070'
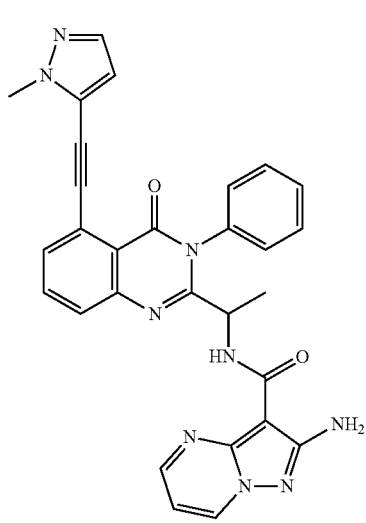
Compound 2073'
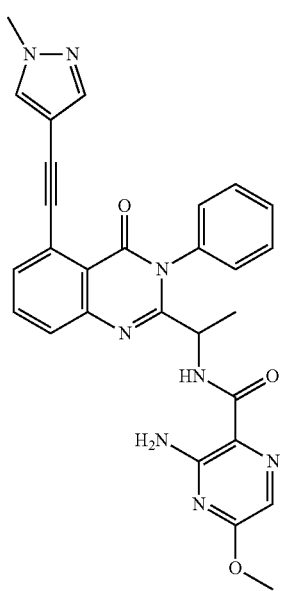
Compound 2071'
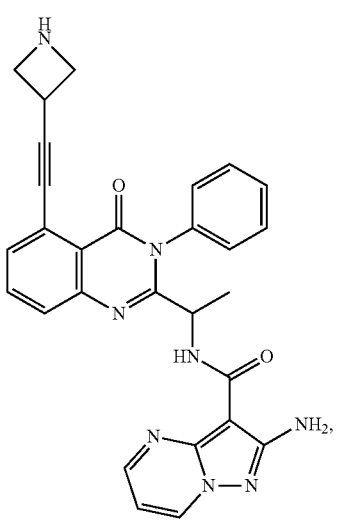 [SMILES: CC(NC(=O)c1c(N)nn2cccnc12)c1nc2cccc(C#CC3CNC3)c2c(=O)n1-c1ccccc1]
Compound 2074'

TABLE 9-continued
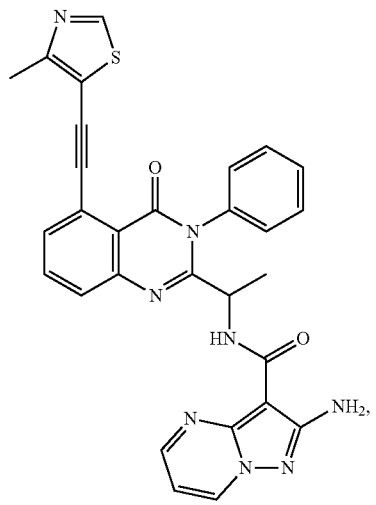 [SMILES: Cc1ncsc1C#Cc1cccc2nc(C(C)NC(=O)c3c(N)nn4cccnc34)n(-c3ccccc3)c(=O)c12]
Compound 2075'
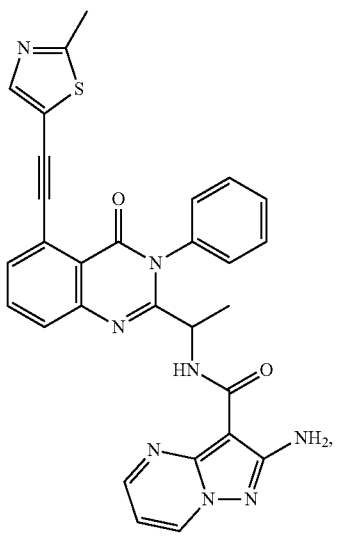 [SMILES: Cc1ncc(C#Cc2cccc3nc(C(C)NC(=O)c4c(N)nn5cccnc45)n(-c4ccccc4)c(=O)c23)s1]
Compound 2076'
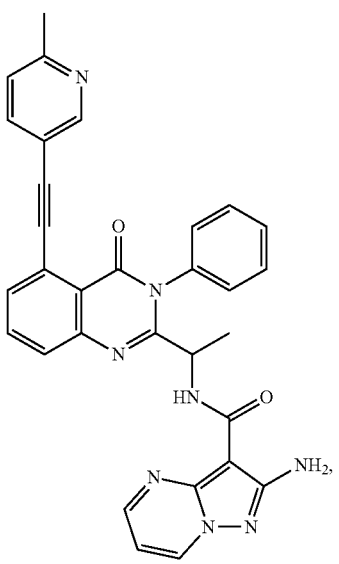 [SMILES: Cc1ccc(C#Cc2cccc3nc(C(C)NC(=O)c4c(N)nn5cccnc45)n(-c4ccccc4)c(=O)c23)cn1]
Compound 2077'
TABLE 9-continued
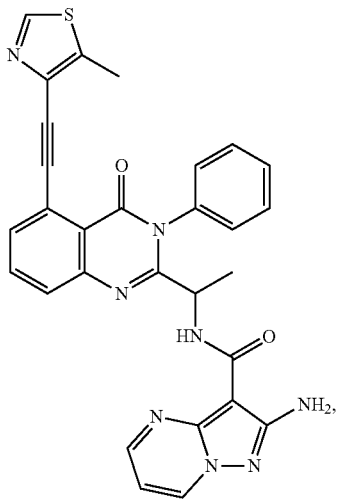 [SMILES: Cc1scnc1C#Cc1cccc2nc(C(C)NC(=O)c3c(N)nn4cccnc34)n(-c3ccccc3)c(=O)c12]
Compound 2078'
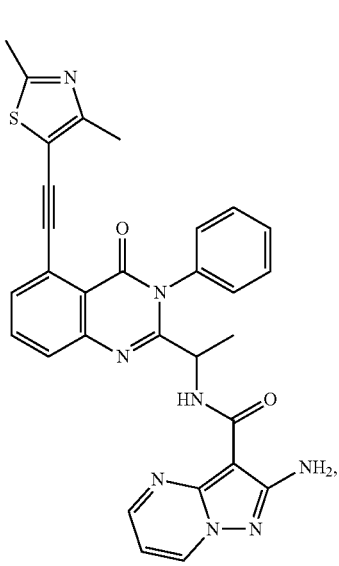
Compound 2079'
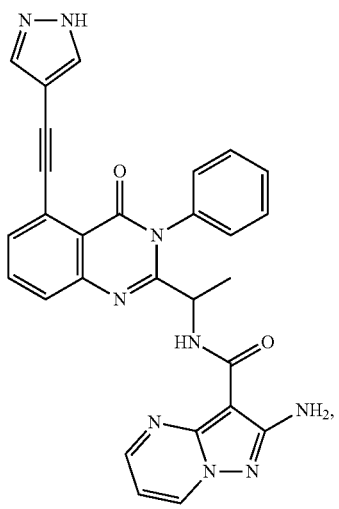 [SMILES: CC(NC(=O)c1c(N)nn2cccnc12)c1nc2cccc(C#Cc3cn[nH]c3)c2c(=O)n1-c1ccccc1]
Compound 2080'

TABLE 9-continued
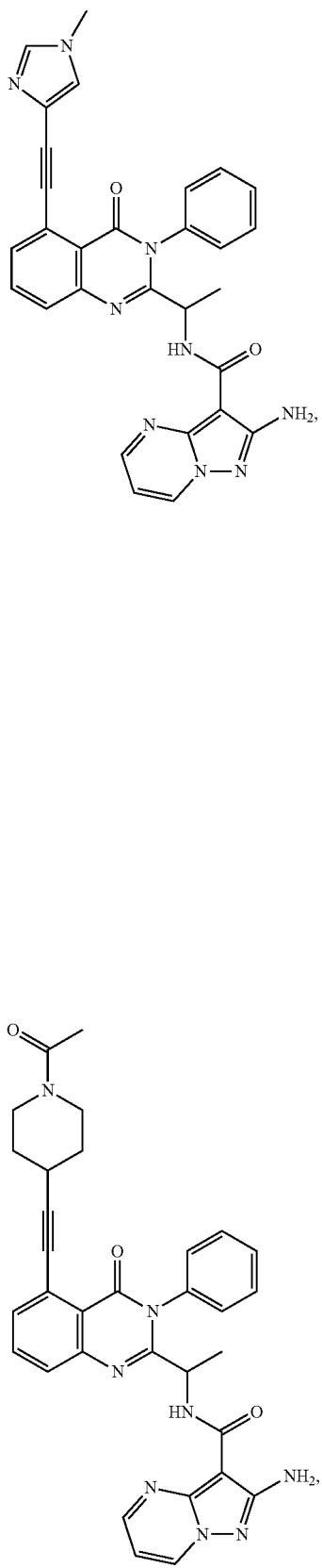
Compound 2081'
Compound 2082'
TABLE 9-continued
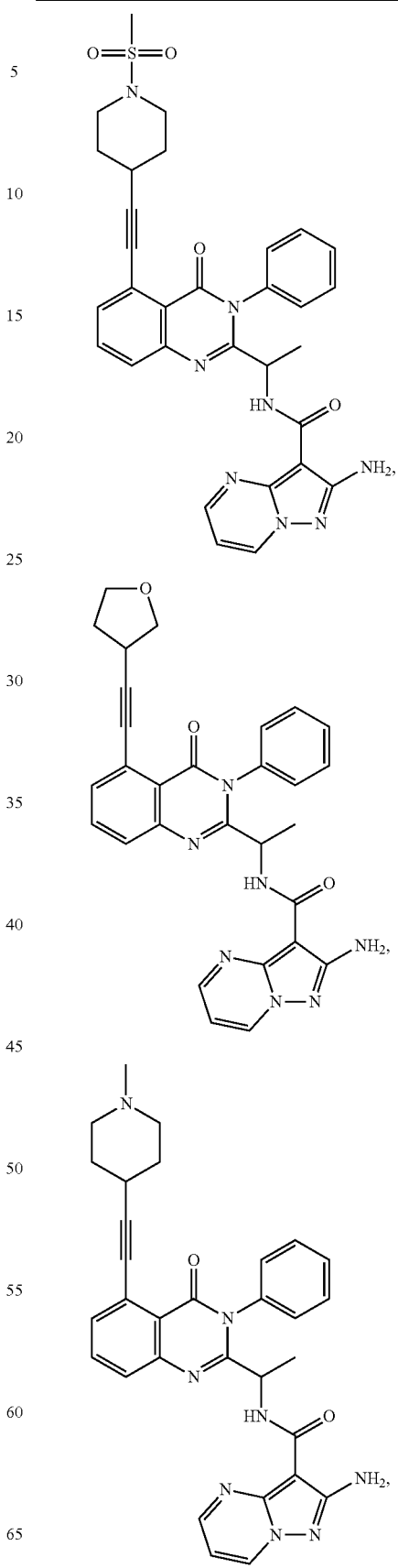
Compound 2083'
Compound 2084'
Compound 2085'

TABLE 9-continued
Compound 2086'
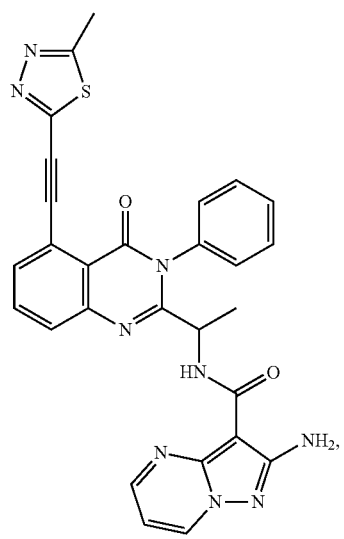 [SMILES: Cc1nnc(C#Cc2cccc3nc(C(C)NC(=O)c4c(N)nn5cccnc45)n(-c4ccccc4)c(=O)c23)s1]
Compound 2087'
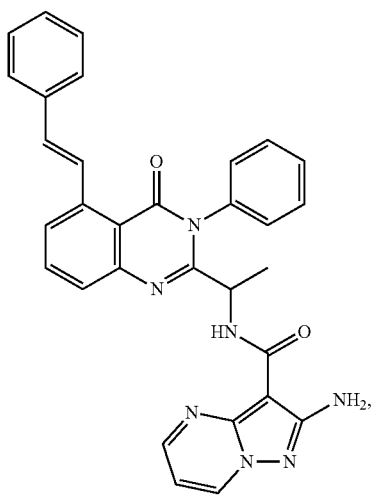 [SMILES: CC(NC(=O)c1c(N)nn2cccnc12)c1nc2cccc(/C=C/c3ccccc3)c2c(=O)n1-c1ccccc1]
Compound 2088'
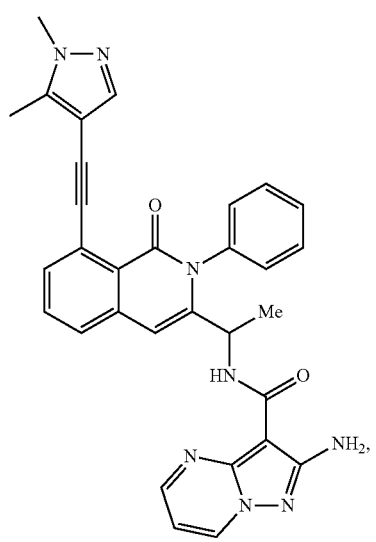 [SMILES: Cc1c(C#Cc2cccc3cc(C(C)NC(=O)c4c(N)nn5cccnc45)n(-c4ccccc4)c(=O)c23)cnn1C]
TABLE 9-continued
Compound 2089'
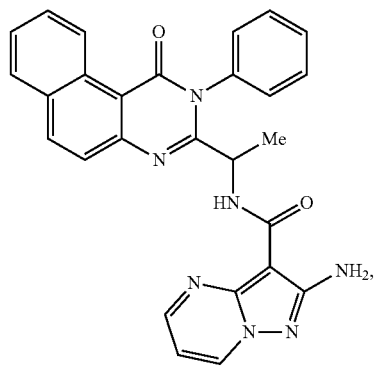 [SMILES: CC(NC(=O)c1c(N)nn2cccnc12)c1nc2ccc3ccccc3c2c(=O)n1-c1ccccc1]
Compound 2090'
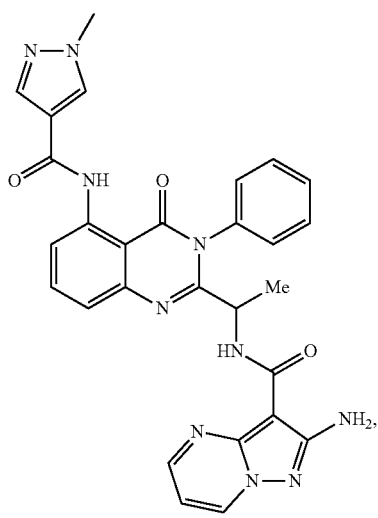 [SMILES: CC(NC(=O)c1c(N)nn2cccnc12)c1nc2cccc(NC(=O)c3cnn(C)c3)c2c(=O)n1-c1ccccc1]
Compound 2091'
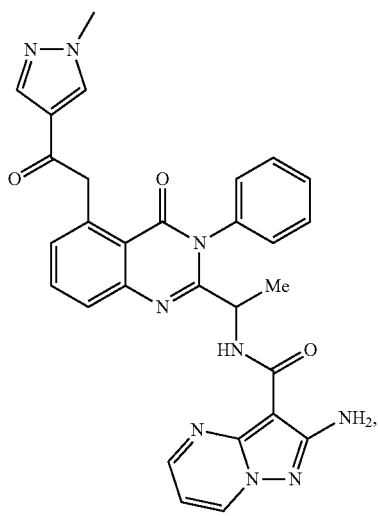 [SMILES: CC(NC(=O)c1c(N)nn2cccnc12)c1nc2cccc(CC(=O)c3cnn(C)c3)c2c(=O)n1-c1ccccc1]

TABLE 9-continued
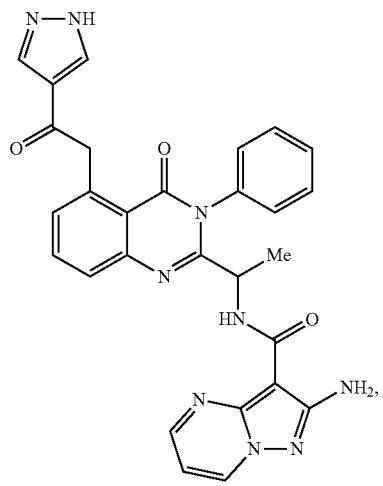 [SMILES: CC(NC(=O)c1c(N)nn2cccnc12)c1nc2cccc(CC(=O)c3cn[nH]c3)c2c(=O)n1-c1ccccc1]
Compound 2092'
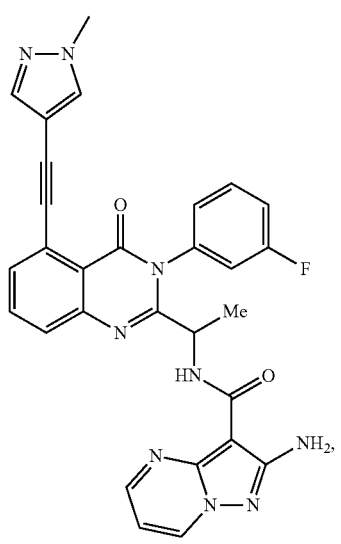 [SMILES: CC(NC(=O)c1c(N)nn2cccnc12)c1nc2cccc(C#Cc3cnn(C)c3)c2c(=O)n1-c1cccc(F)c1]
Compound 2093'
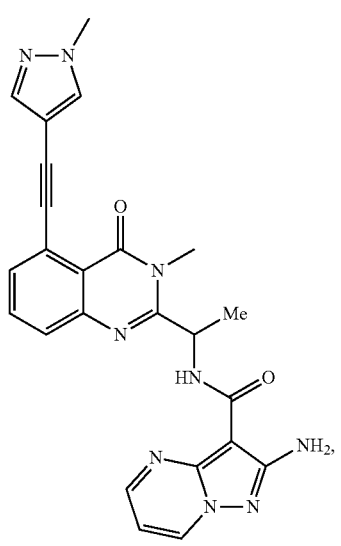
Compound 2094'
TABLE 9-continued
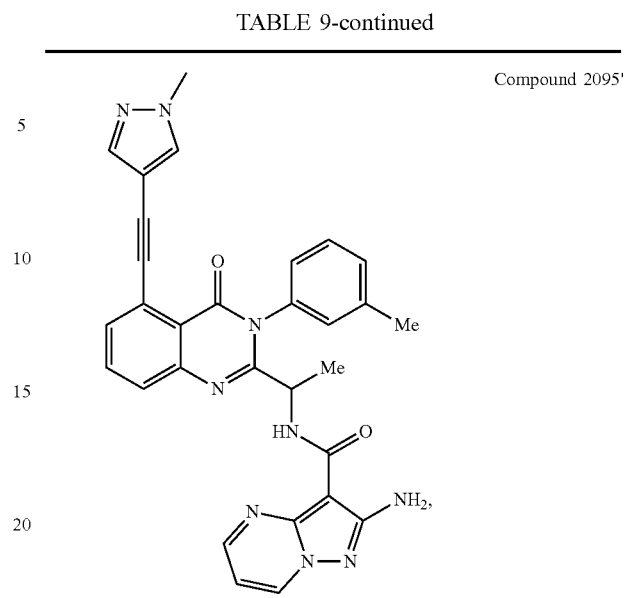
Compound 2095'
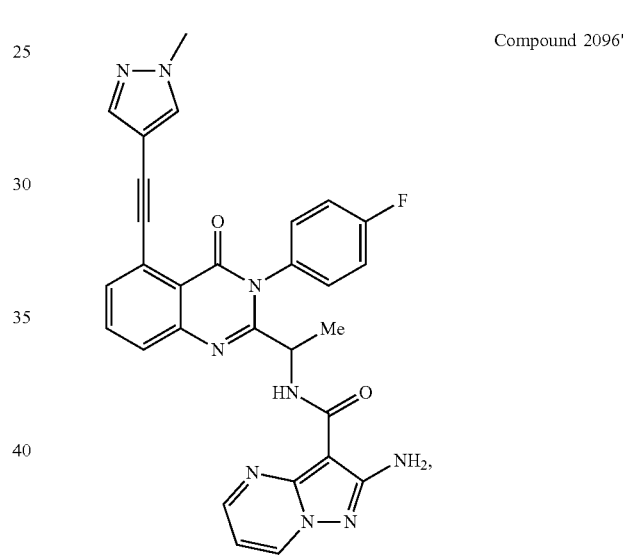
Compound 2096'
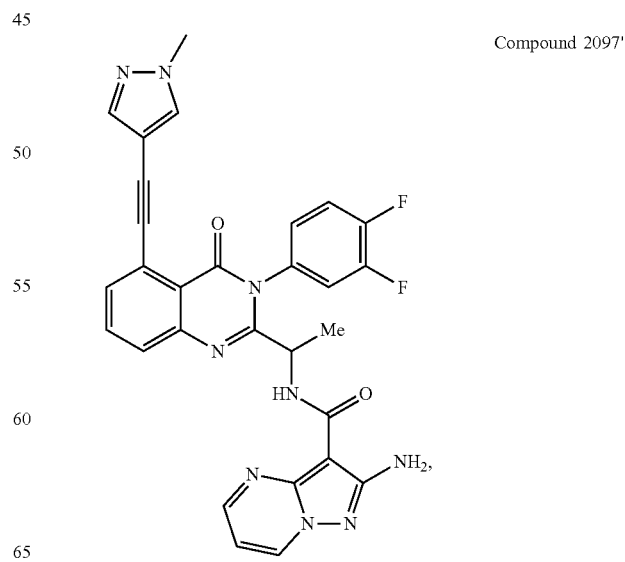
Compound 2097'

TABLE 9-continued
Compound 2098'
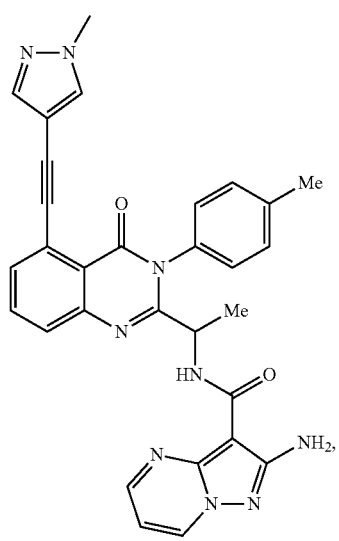 [SMILES: Cc1ccc(-n2c(C(C)NC(=O)c3c(N)nn4cccnc34)nc3cccc(C#Cc4cnn(C)c4)c3c2=O)cc1]
Compound 2099'
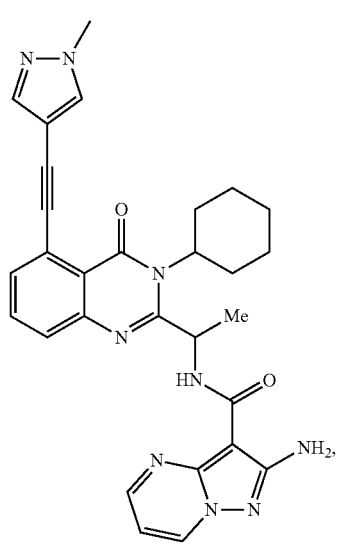 [SMILES: CC(NC(=O)c1c(N)nn2cccnc12)c1nc2cccc(C#Cc3cnn(C)c3)c2c(=O)n1C1CCCCC1]
Compound 2100'
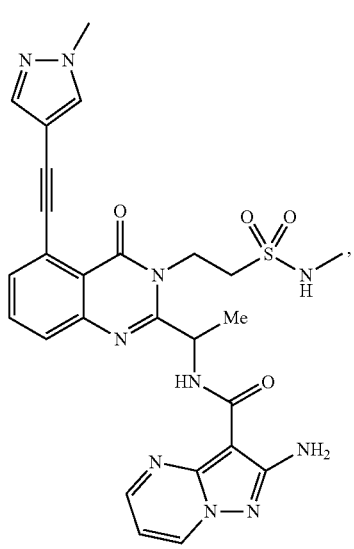 [SMILES: CNS(=O)(=O)CCn1c(C(C)NC(=O)c2c(N)nn3cccnc23)nc2cccc(C#Cc3cnn(C)c3)c2c1=O]
TABLE 9-continued
Compound 2101'
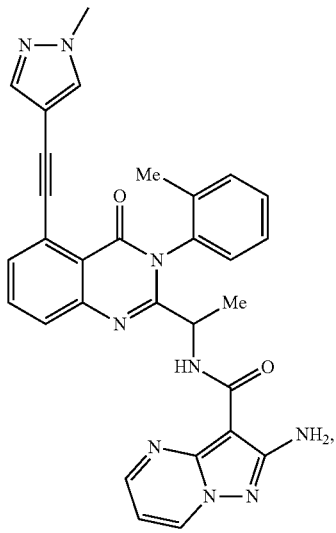 [SMILES: Cc1ccccc1-n1c(C(C)NC(=O)c2c(N)nn3cccnc23)nc2cccc(C#Cc3cnn(C)c3)c2c1=O]
Compound 2102'
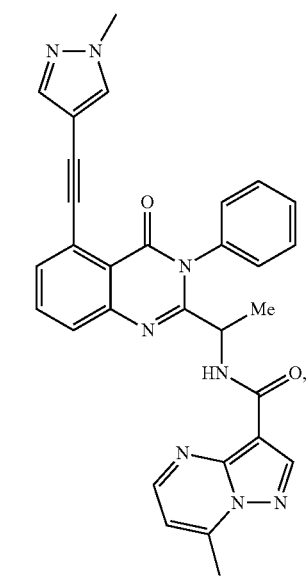
Compound 2103'
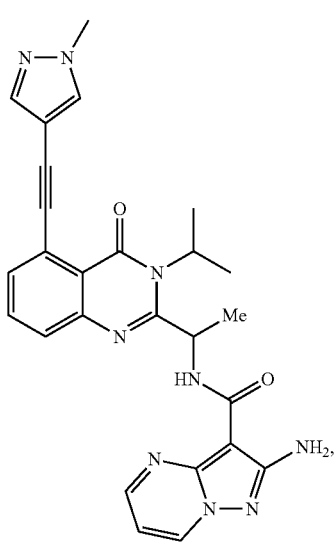 [SMILES: CC(NC(=O)c1c(N)nn2cccnc12)c1nc2cccc(C#Cc3cnn(C)c3)c2c(=O)n1C(C)C]

TABLE 9-continued
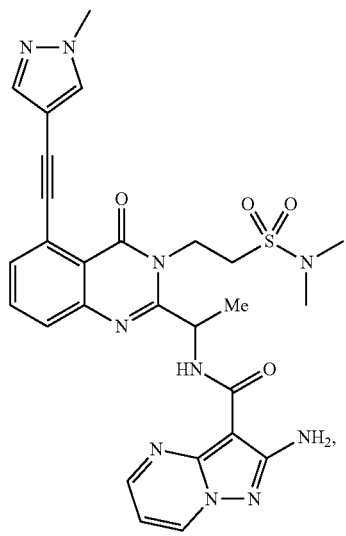 [SMILES: CC(NC(=O)c1c(N)nn2cccnc12)c1nc2cccc(C#Cc3cnn(C)c3)c2c(=O)n1CCS(=O)(=O)N(C)C]
Compound 2104'
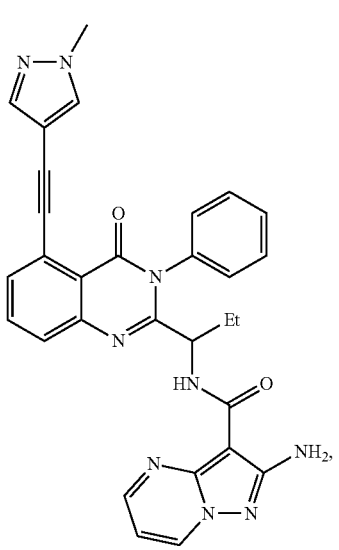 [SMILES: CCC(NC(=O)c1c(N)nn2cccnc12)c1nc2cccc(C#Cc3cnn(C)c3)c2c(=O)n1-c1ccccc1]
Compound 2105'
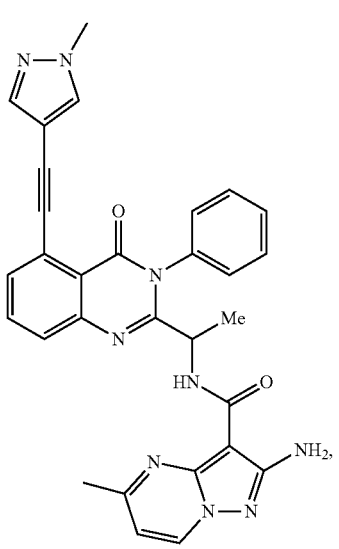 [SMILES: Cc1ccn2nc(N)c(C(=O)NC(C)c3nc4cccc(C#Cc5cnn(C)c5)c4c(=O)n3-c3ccccc3)c2n1]
Compound 2106'
TABLE 9-continued
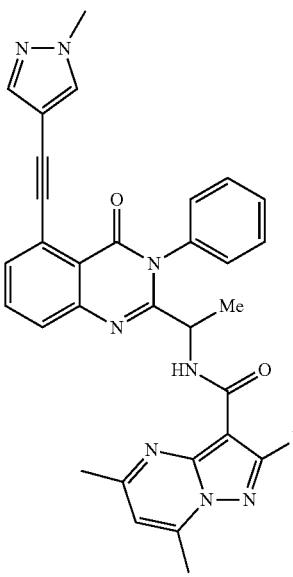
Compound 2108'
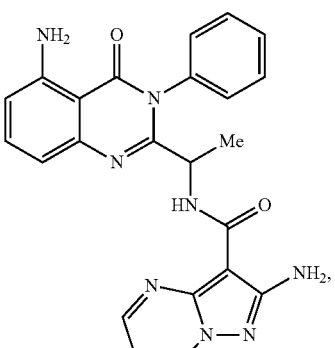
Compound 2109'
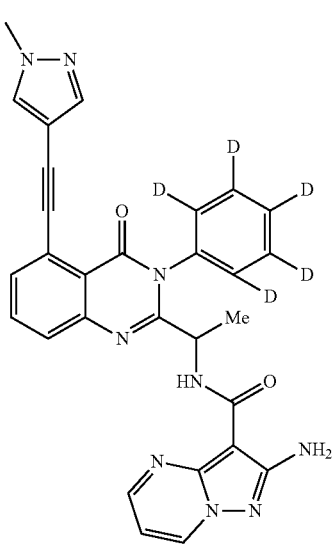 [SMILES: [2H]c1c([2H])c([2H])c(-n2c(C(C)NC(=O)c3c(N)nn4cccnc34)nc3cccc(C#Cc4cnn(C)c4)c3c2=O)c([2H])c1[2H]]
Compound 2110'

TABLE 10
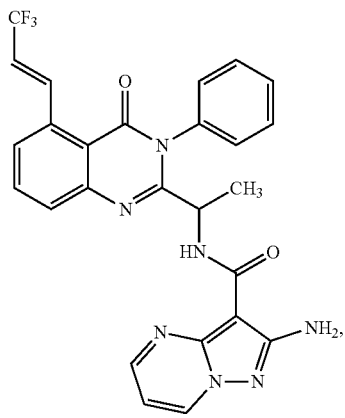
Compound 3001'
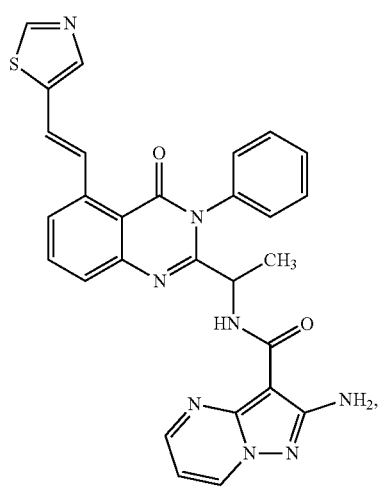 [SMILES: CC(NC(=O)c1c(N)nn2cccnc12)c1nc2cccc(/C=C/c3cncs3)c2c(=O)n1-c1ccccc1]
Compound 3002'
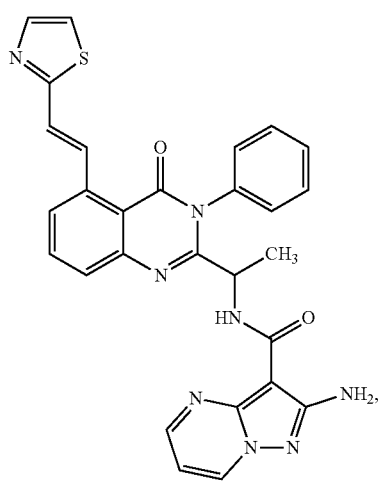 [SMILES: CC(NC(=O)c1c(N)nn2cccnc12)c1nc2cccc(/C=C/c3nccs3)c2c(=O)n1-c1ccccc1]
Compound 3003'

TABLE 10-continued
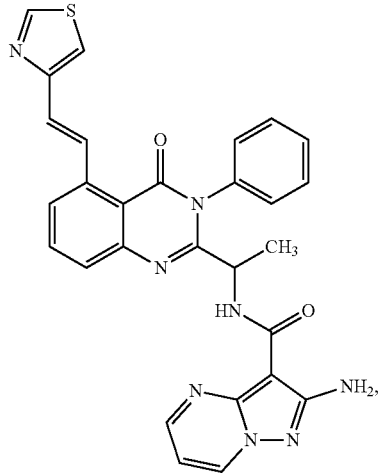 [SMILES: CC(NC(=O)c1c(N)nn2cccnc12)c1nc2cccc(/C=C/c3cscn3)c2c(=O)n1-c1ccccc1]
Compound 3004'
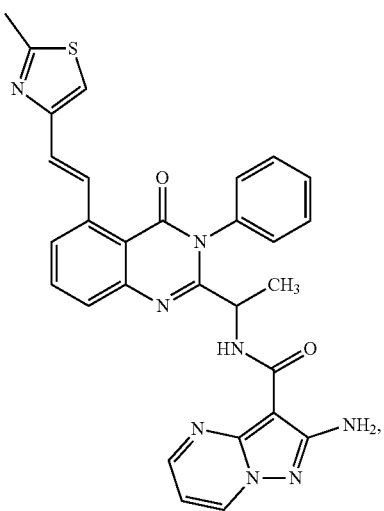 [SMILES: Cc1nc(/C=C/c2cccc3nc(C(C)NC(=O)c4c(N)nn5cccnc45)n(-c4ccccc4)c(=O)c23)cs1]
Compound 3005'
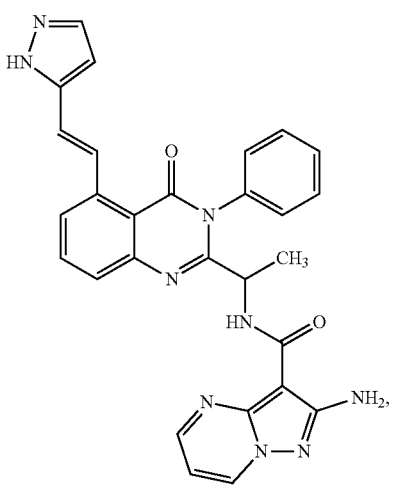
Compound 3006'

TABLE 10-continued
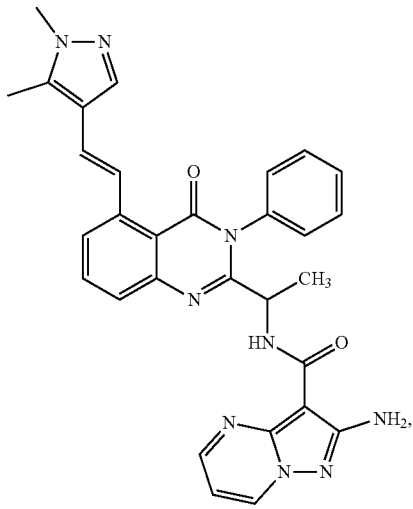 [SMILES: Cc1c(/C=C/c2cccc3nc(C(C)NC(=O)c4c(N)nn5cccnc45)n(-c4ccccc4)c(=O)c23)cnn1C]
Compound 3007'
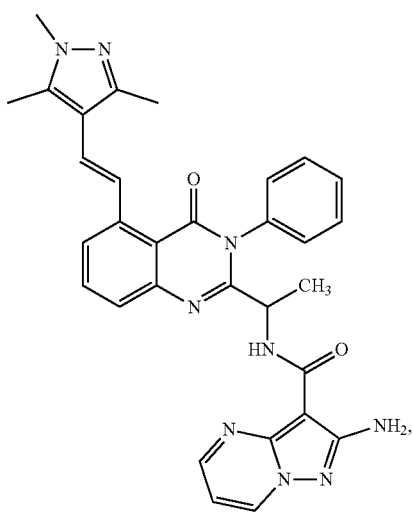 [SMILES: Cc1nn(C)c(C)c1/C=C/c1cccc2nc(C(C)NC(=O)c3c(N)nn4cccnc34)n(-c3ccccc3)c(=O)c12]
Compound 3008'
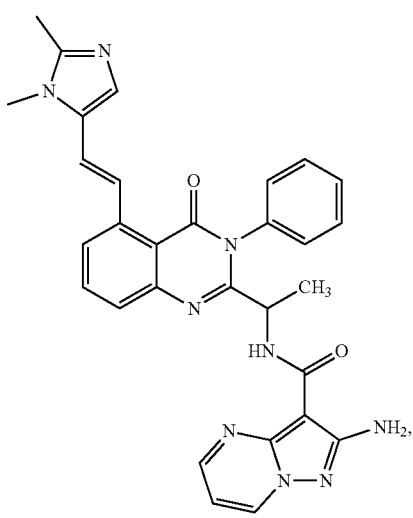 [SMILES: Cc1ncc(/C=C/c2cccc3nc(C(C)NC(=O)c4c(N)nn5cccnc45)n(-c4ccccc4)c(=O)c23)n1C]
Compound 3009'

TABLE 10-continued
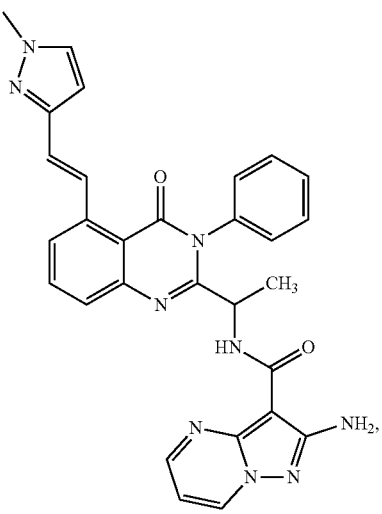 [SMILES: CC(NC(=O)c1c(N)nn2cccnc12)c1nc2cccc(/C=C/c3ccn(C)n3)c2c(=O)n1-c1ccccc1]
Compound 3010'
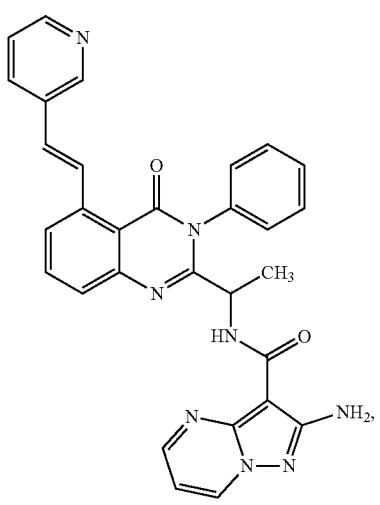 [SMILES: CC(NC(=O)c1c(N)nn2cccnc12)c1nc2cccc(/C=C/c3cccnc3)c2c(=O)n1-c1ccccc1]
Compound 3011'
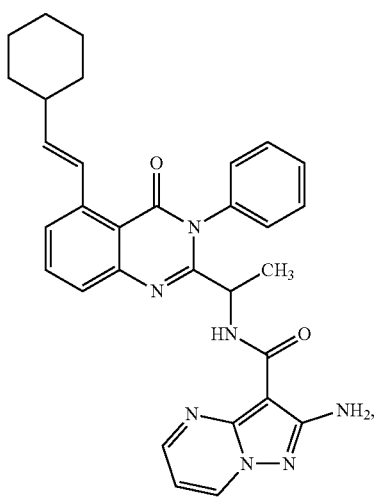 [SMILES: CC(NC(=O)c1c(N)nn2cccnc12)c1nc2cccc(/C=C/C3CCCCC3)c2c(=O)n1-c1ccccc1]
Compound 3012'

TABLE 10-continued
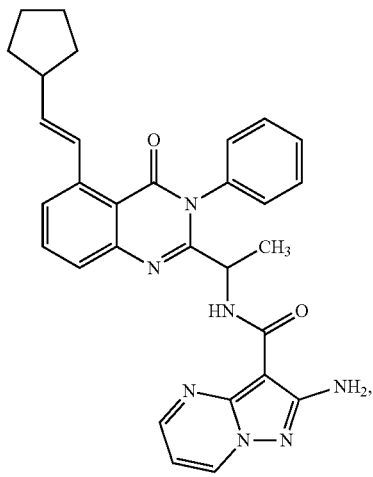 [SMILES: CC(NC(=O)c1c(N)nn2cccnc12)c1nc2cccc(/C=C/C3CCCC3)c2c(=O)n1-c1ccccc1]
Compound 3013'
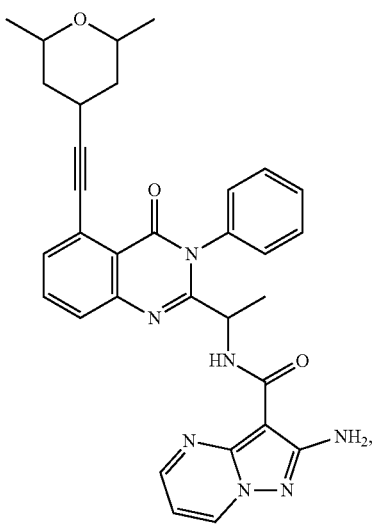 [SMILES: CC1CC(C#Cc2cccc3nc(C(C)NC(=O)c4c(N)nn5cccnc45)n(-c4ccccc4)c(=O)c23)CC(C)O1]
Compound 3014'
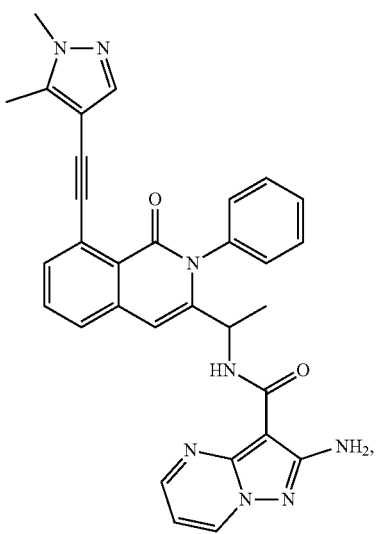 [SMILES: Cc1c(C#Cc2cccc3cc(C(C)NC(=O)c4c(N)nn5cccnc45)n(-c4ccccc4)c(=O)c23)cnn1C]
Compound 3015'

TABLE 10-continued
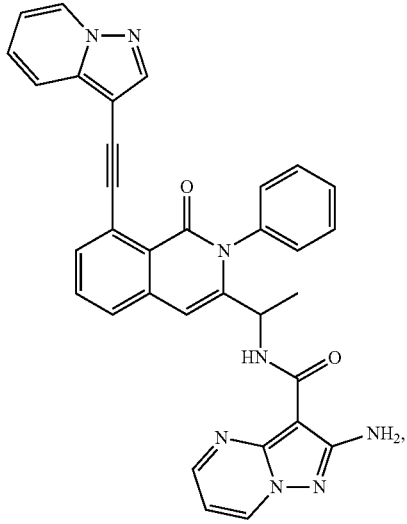 [SMILES: CC(NC(=O)c1c(N)nn2cccnc12)c1cc2cccc(C#Cc3cnn4ccccc34)c2c(=O)n1-c1ccccc1]
Compound 3016'
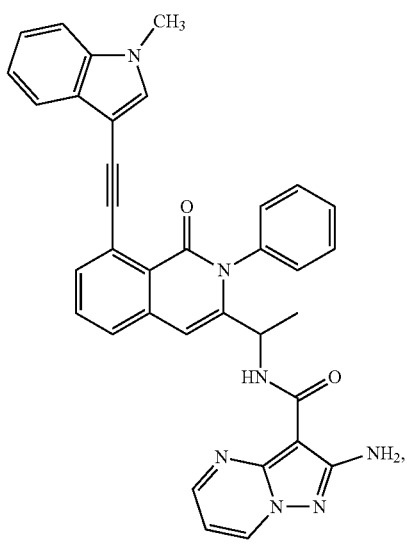 [SMILES: CC(NC(=O)c1c(N)nn2cccnc12)c1cc2cccc(C#Cc3cn(C)c4ccccc34)c2c(=O)n1-c1ccccc1]
Compound 3017'
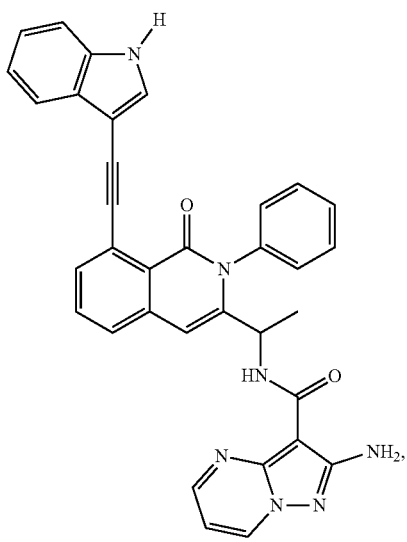 [SMILES: CC(NC(=O)c1c(N)nn2cccnc12)c1cc2cccc(C#Cc3c[nH]c4ccccc34)c2c(=O)n1-c1ccccc1]
Compound 3018'

TABLE 10-continued
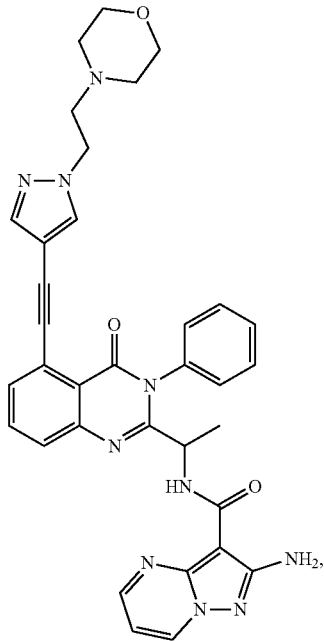 [SMILES: CC(NC(=O)c1c(N)nn2cccnc12)c1nc2cccc(C#Cc3cnn(CCN4CCOCC4)c3)c2c(=O)n1-c1ccccc1]
Compound 3019'
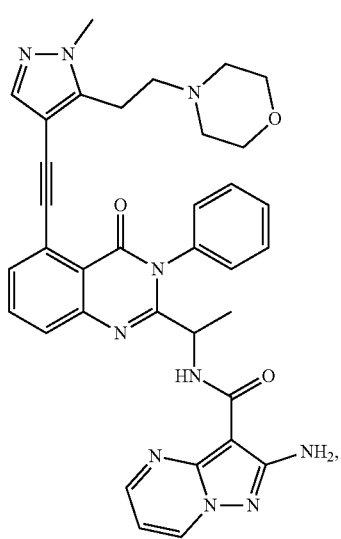 [SMILES: CC(NC(=O)c1c(N)nn2cccnc12)c1nc2cccc(C#Cc3cnn(C)c3CCN3CCOCC3)c2c(=O)n1-c1ccccc1]
Compound 3020'

TABLE 10-continued
Compound 3021'
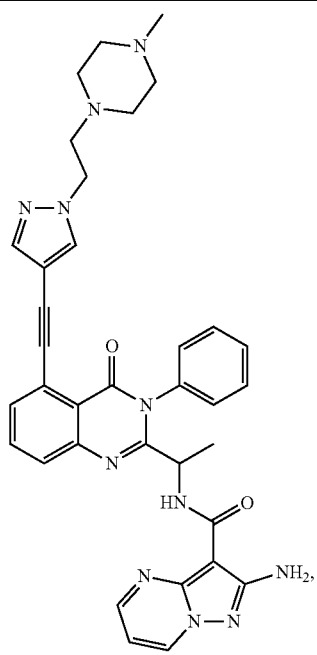
Compound 3022'
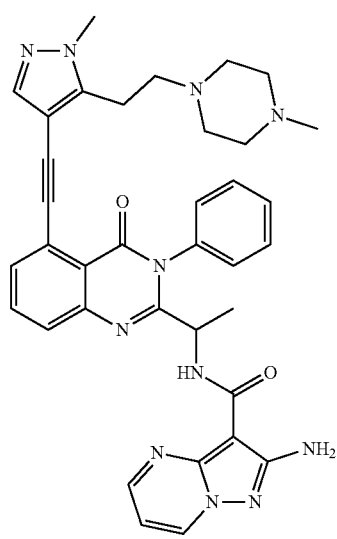

TABLE 10-continued
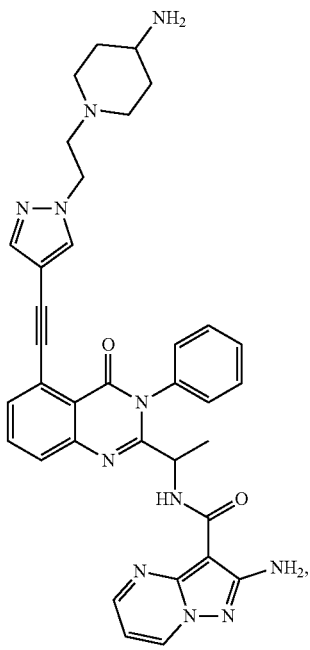 [SMILES: CC(NC(=O)c1c(N)nn2cccnc12)c1nc2cccc(C#Cc3cnn(CCN4CCC(N)CC4)c3)c2c(=O)n1-c1ccccc1]
Compound 3023'
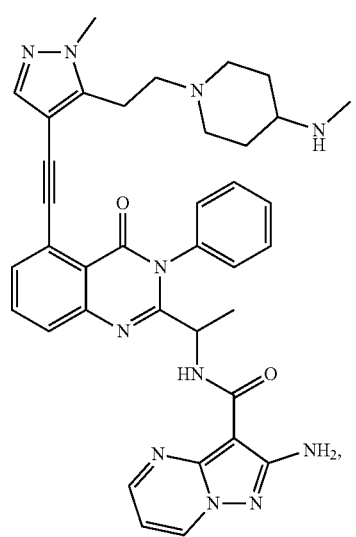 [SMILES: CNC1CCN(CCc2c(C#Cc3cccc4nc(C(C)NC(=O)c5c(N)nn6cccnc56)n(-c5ccccc5)c(=O)c34)cnn2C)CC1]
Compound 3024'

TABLE 10-continued
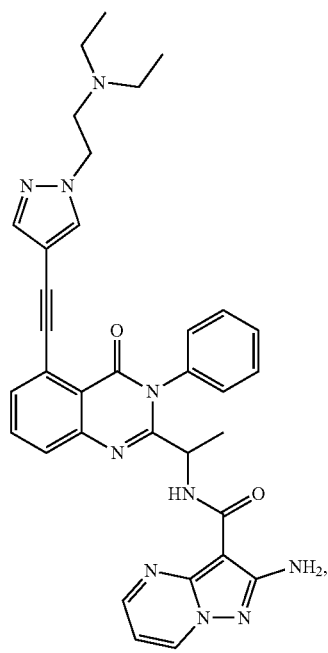 [SMILES: CCN(CC)CCn1cc(C#Cc2cccc3nc(C(C)NC(=O)c4c(N)nn5cccnc45)n(-c4ccccc4)c(=O)c23)cn1]
Compound 3025'
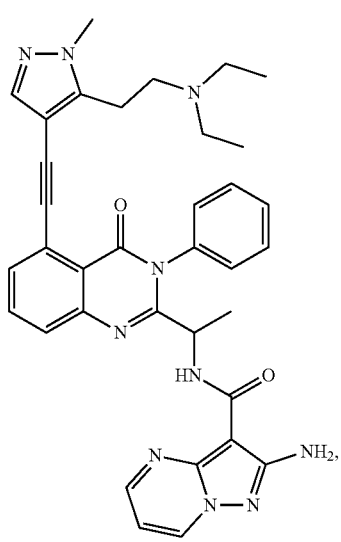 [SMILES: CCN(CC)CCc1c(C#Cc2cccc3nc(C(C)NC(=O)c4c(N)nn5cccnc45)n(-c4ccccc4)c(=O)c23)cnn1C]
Compound 3026'

TABLE 10-continued
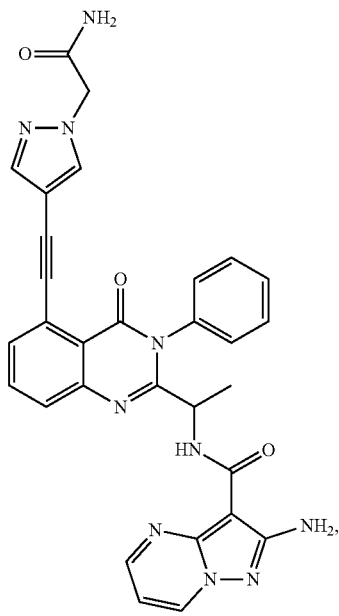 [SMILES: CC(NC(=O)c1c(N)nn2cccnc12)c1nc2cccc(C#Cc3cnn(CC(N)=O)c3)c2c(=O)n1-c1ccccc1]
Compound 3027'
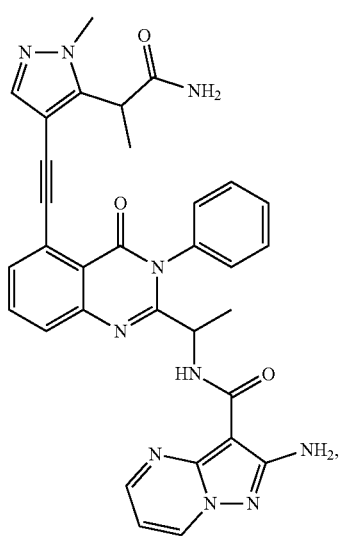 [SMILES: CC(NC(=O)c1c(N)nn2cccnc12)c1nc2cccc(C#Cc3cnn(C)c3C(C)C(N)=O)c2c(=O)n1-c1ccccc1]
Compound 3028'

TABLE 10-continued
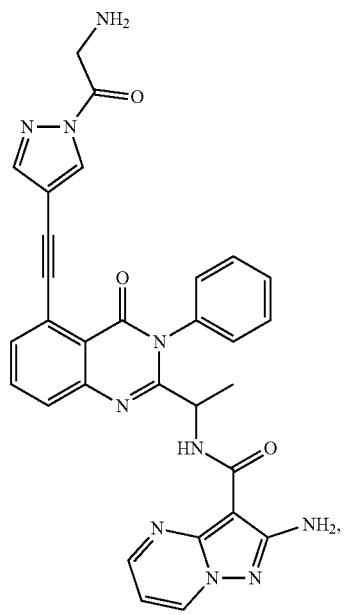 [SMILES: CC(NC(=O)c1c(N)nn2cccnc12)c1nc2cccc(C#Cc3cnn(C(=O)CN)c3)c2c(=O)n1-c1ccccc1]
Compound 3029'
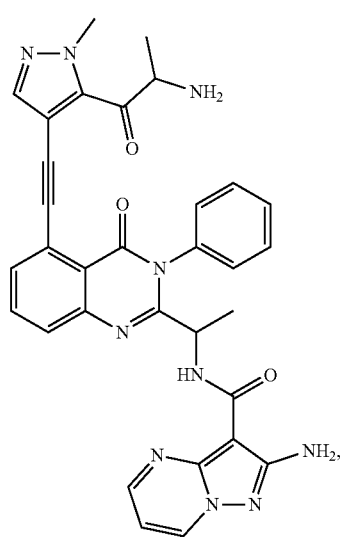 [SMILES: CC(N)C(=O)c1c(C#Cc2cccc3nc(C(C)NC(=O)c4c(N)nn5cccnc45)n(-c4ccccc4)c(=O)c23)cnn1C]
Compound 3030'

TABLE 10-continued
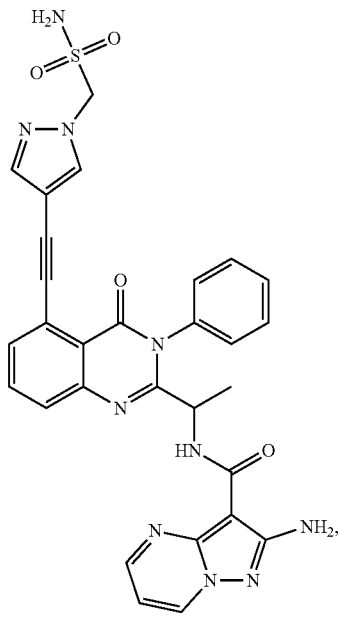 [SMILES: CC(NC(=O)c1c(N)nn2cccnc12)c1nc2cccc(C#Cc3cnn(CS(N)(=O)=O)c3)c2c(=O)n1-c1ccccc1]
Compound 3031'
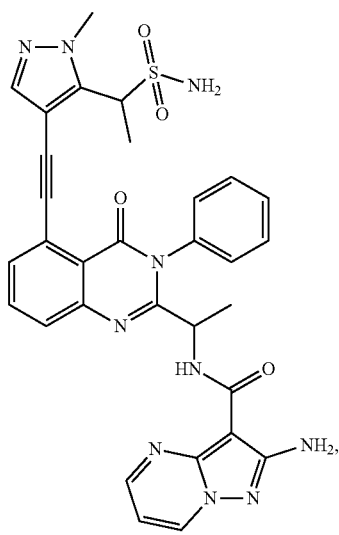 [SMILES: CC(NC(=O)c1c(N)nn2cccnc12)c1nc2cccc(C#Cc3cnn(C)c3C(C)S(N)(=O)=O)c2c(=O)n1-c1ccccc1]
Compound 3032'

TABLE 10-continued
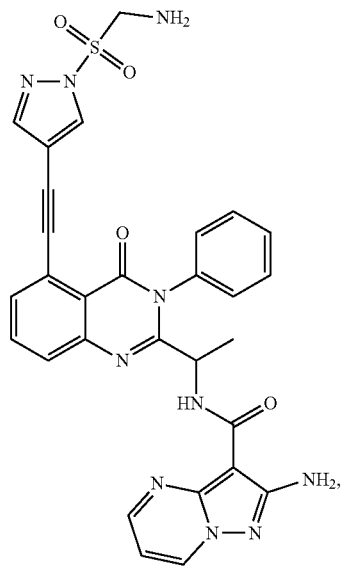 [SMILES: CC(NC(=O)c1c(N)nn2cccnc12)c1nc2cccc(C#Cc3cnn(S(=O)(=O)CN)c3)c2c(=O)n1-c1ccccc1]
Compound 3033'
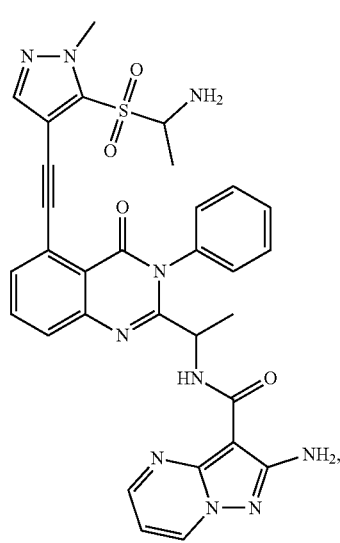 [SMILES: CC(NC(=O)c1c(N)nn2cccnc12)c1nc2cccc(C#Cc3cnn(C)c3S(=O)(=O)C(C)N)c2c(=O)n1-c1ccccc1]
Compound 3034'

TABLE 10-continued
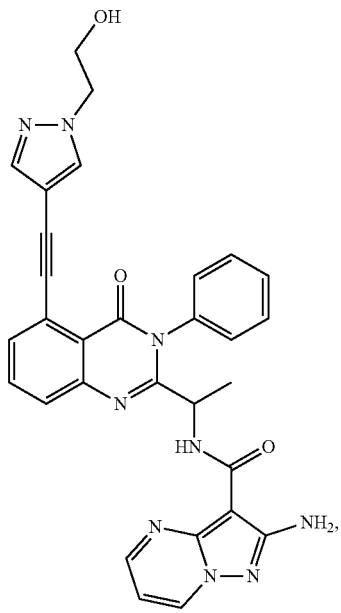 [SMILES: CC(NC(=O)c1c(N)nn2cccnc12)c1nc2cccc(C#Cc3cnn(CCO)c3)c2c(=O)n1-c1ccccc1]
Compound 3035'
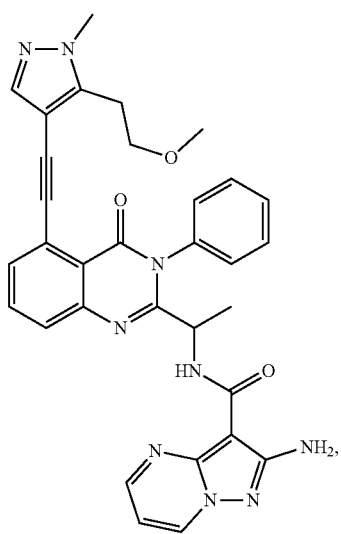 [SMILES: COCCc1c(C#Cc2cccc3nc(C(C)NC(=O)c4c(N)nn5cccnc45)n(-c4ccccc4)c(=O)c23)cnn1C]
Compound 3036'

TABLE 10-continued
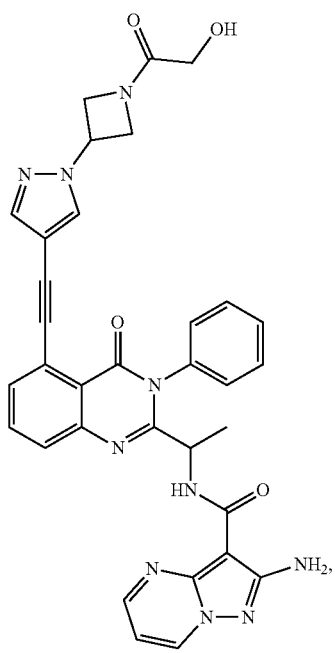
Compound 3037'
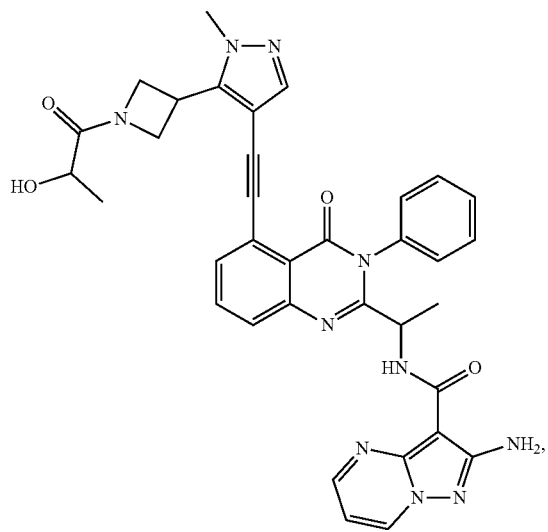 [SMILES: CC(O)C(=O)N1CC(c2c(C#Cc3cccc4nc(C(C)NC(=O)c5c(N)nn6cccnc56)n(-c5ccccc5)c(=O)c34)cnn2C)C1]
Compound 3038'

TABLE 10-continued
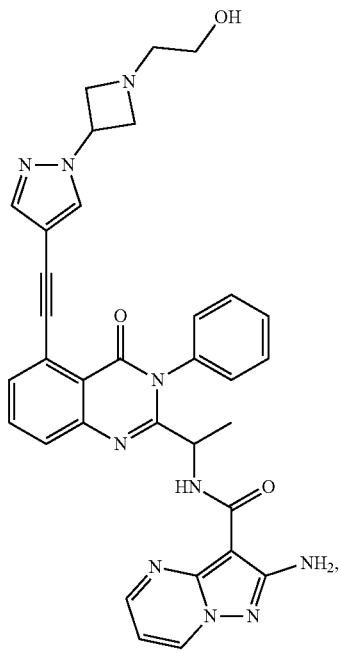 [SMILES: CC(NC(=O)c1c(N)nn2cccnc12)c1nc2cccc(C#Cc3cnn(C4CN(CCO)C4)c3)c2c(=O)n1-c1ccccc1]
Compound 3039'
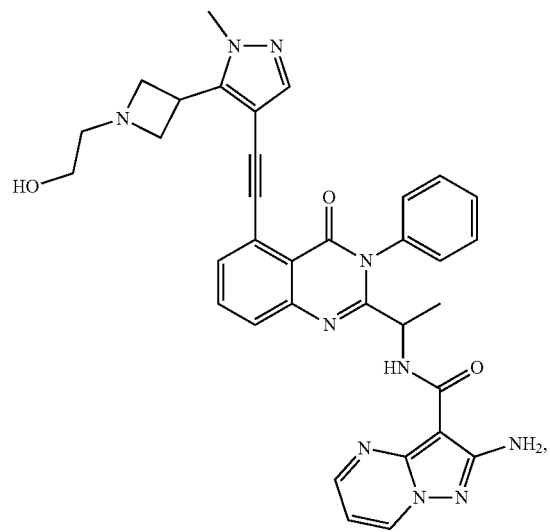 [SMILES: CC(NC(=O)c1c(N)nn2cccnc12)c1nc2cccc(C#Cc3cnn(C)c3C3CN(CCO)C3)c2c(=O)n1-c1ccccc1]
Compound 3040'

TABLE 10-continued
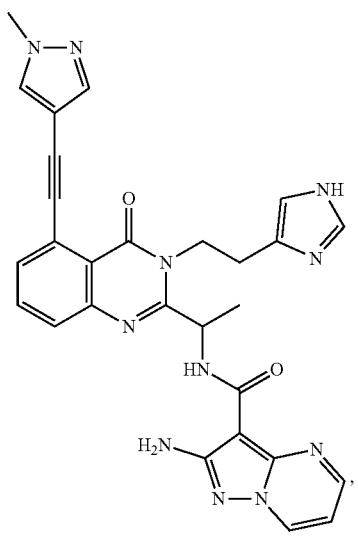 [SMILES: CC(NC(=O)c1c(N)nn2cccnc12)c1nc2cccc(C#Cc3cnn(C)c3)c2c(=O)n1CCc1c[nH]cn1]
Compound 3045'
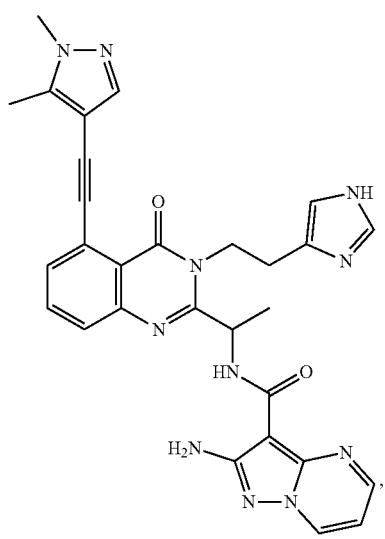 [SMILES: Cc1c(C#Cc2cccc3nc(C(C)NC(=O)c4c(N)nn5cccnc45)n(CCc4c[nH]cn4)c(=O)c23)cnn1C]
Compound 3046'
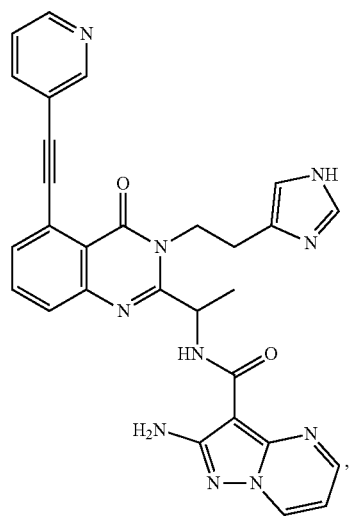 [SMILES: CC(NC(=O)c1c(N)nn2cccnc12)c1nc2cccc(C#Cc3cccnc3)c2c(=O)n1CCc1c[nH]cn1]
Compound 3047'

TABLE 10-continued
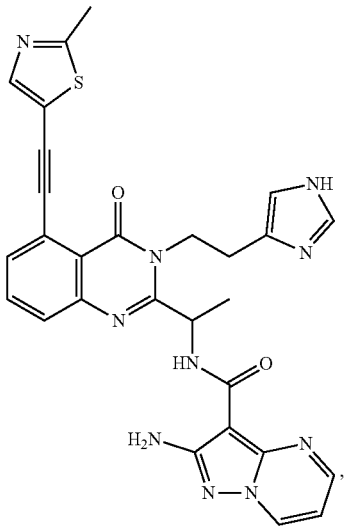 [SMILES: Cc1ncc(C#Cc2cccc3nc(C(C)NC(=O)c4c(N)nn5cccnc45)n(CCc4c[nH]cn4)c(=O)c23)s1]
Compound 3048'
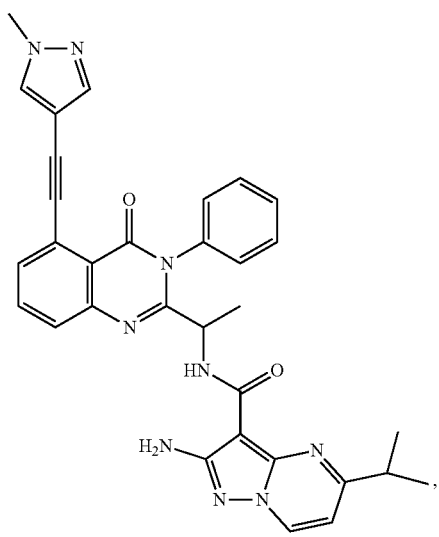 [SMILES: CC(C)c1ccn2nc(N)c(C(=O)NC(C)c3nc4cccc(C#Cc5cnn(C)c5)c4c(=O)n3-c3ccccc3)c2n1]
Compound 3049'
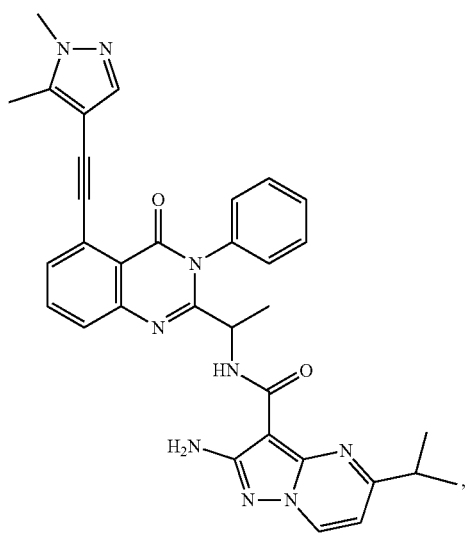 [SMILES: Cc1c(C#Cc2cccc3nc(C(C)NC(=O)c4c(N)nn5ccc(C(C)C)nc45)n(-c4ccccc4)c(=O)c23)cnn1C]
Compound 3050'

TABLE 10-continued
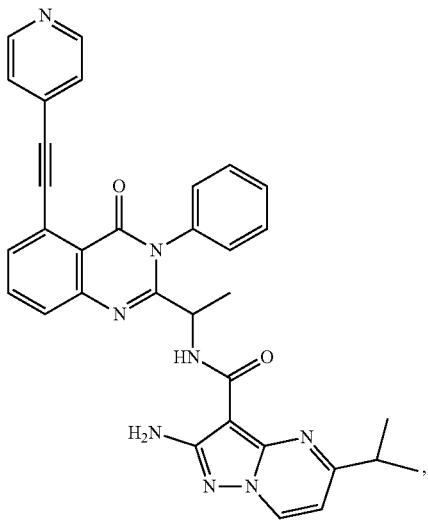 [SMILES: CC(C)c1ccn2nc(N)c(C(=O)NC(C)c3nc4cccc(C#Cc5ccncc5)c4c(=O)n3-c3ccccc3)c2n1]
Compound 3051'
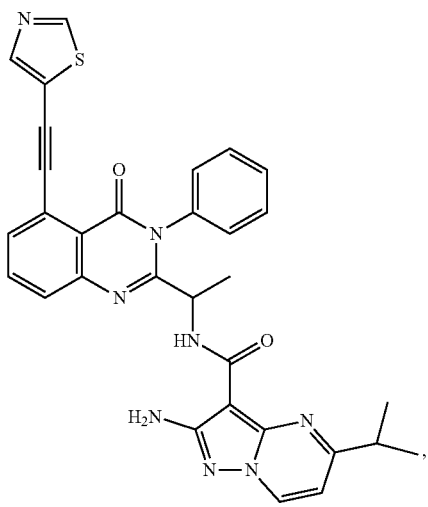 [SMILES: CC(C)c1ccn2nc(N)c(C(=O)NC(C)c3nc4cccc(C#Cc5cncs5)c4c(=O)n3-c3ccccc3)c2n1]
Compound 3052'
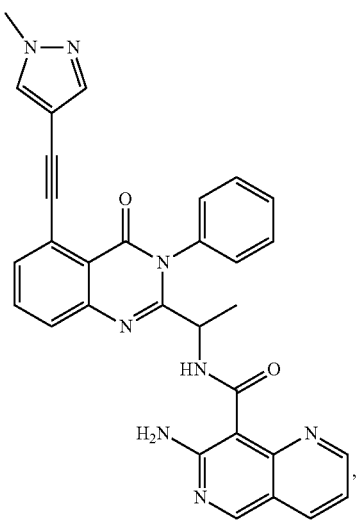 [SMILES: CC(NC(=O)c1c(N)ncc2cccnc12)c1nc2cccc(C#Cc3cnn(C)c3)c2c(=O)n1-c1ccccc1]
Compound 3053'

TABLE 10-continued
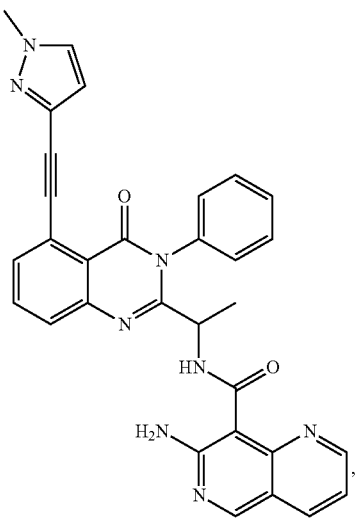 [SMILES: CC(NC(=O)c1c(N)ncc2cccnc12)c1nc2cccc(C#Cc3ccn(C)n3)c2c(=O)n1-c1ccccc1]
Compound 3054'
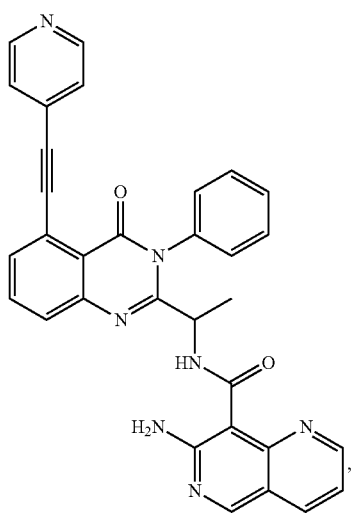 [SMILES: CC(NC(=O)c1c(N)ncc2cccnc12)c1nc2cccc(C#Cc3ccncc3)c2c(=O)n1-c1ccccc1]
Compound 3055'
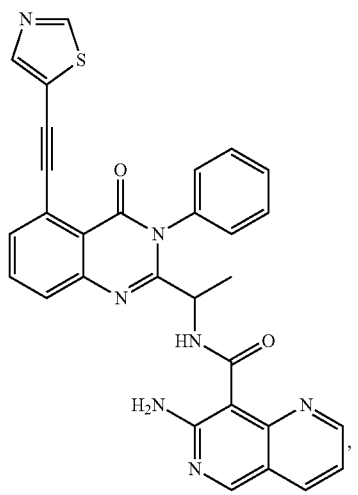 [SMILES: CC(NC(=O)c1c(N)ncc2cccnc12)c1nc2cccc(C#Cc3cncs3)c2c(=O)n1-c1ccccc1]
Compound 3056'

TABLE 10-continued
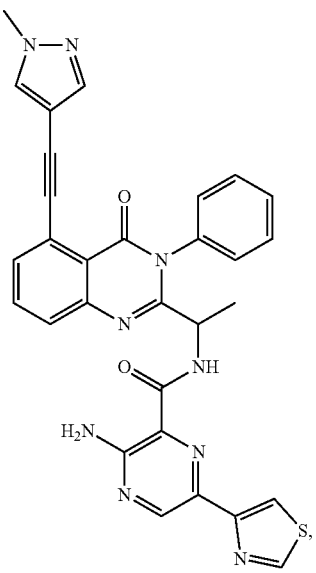 [SMILES: CC(NC(=O)c1nc(-c2cscn2)cnc1N)c1nc2cccc(C#Cc3cnn(C)c3)c2c(=O)n1-c1ccccc1]
Compound 3057'
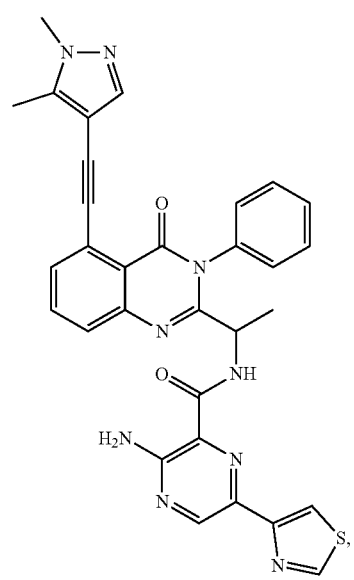
Compound 3058'

TABLE 10-continued
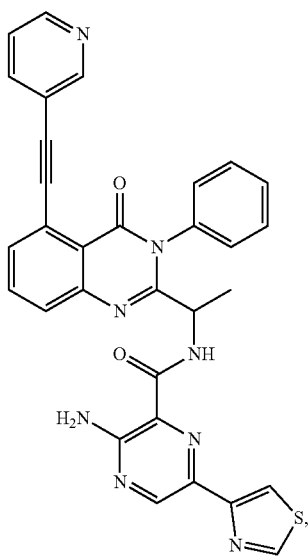 [SMILES: CC(NC(=O)c1nc(-c2cscn2)cnc1N)c1nc2cccc(C#Cc3cccnc3)c2c(=O)n1-c1ccccc1]
Compound 3059'
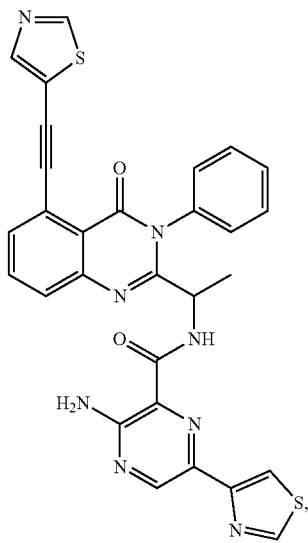 [SMILES: CC(NC(=O)c1nc(-c2cscn2)cnc1N)c1nc2cccc(C#Cc3cncs3)c2c(=O)n1-c1ccccc1]
Compound 3060'

TABLE 10-continued
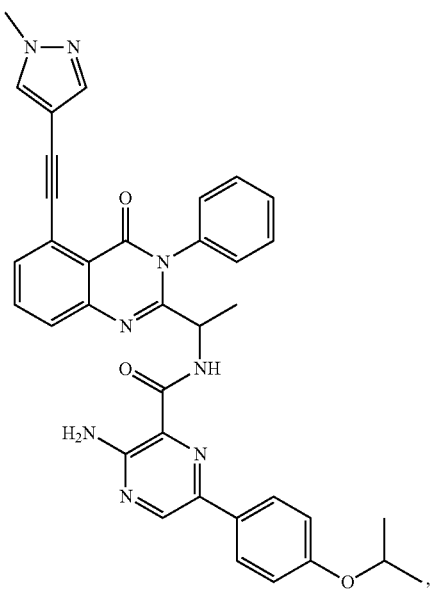 [SMILES: CC(C)Oc1ccc(-c2cnc(N)c(C(=O)NC(C)c3nc4cccc(C#Cc5cnn(C)c5)c4c(=O)n3-c3ccccc3)n2)cc1]
Compound 3061'
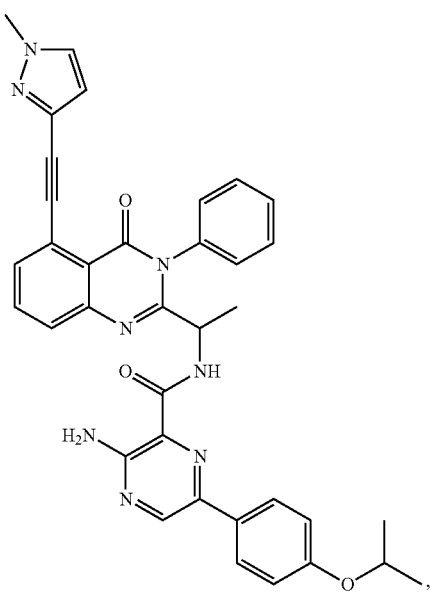 [SMILES: CC(C)Oc1ccc(-c2cnc(N)c(C(=O)NC(C)c3nc4cccc(C#Cc5ccn(C)n5)c4c(=O)n3-c3ccccc3)n2)cc1]
Compound 3062'

TABLE 10-continued
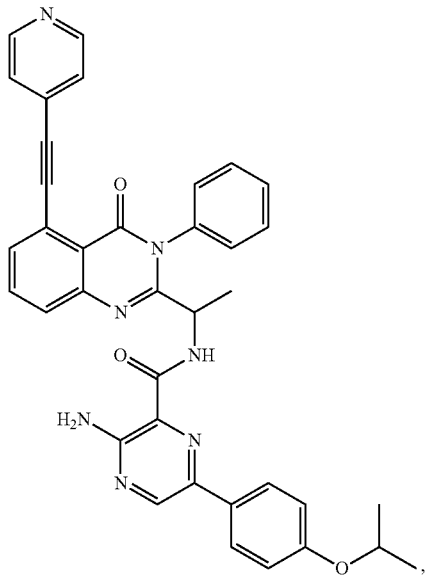
Compound 3063'
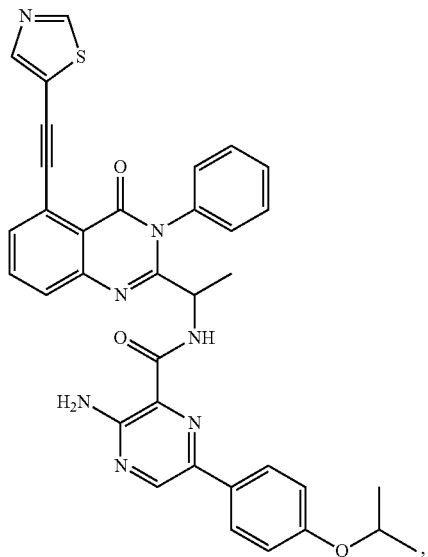
Compound 3064'

TABLE 10-continued
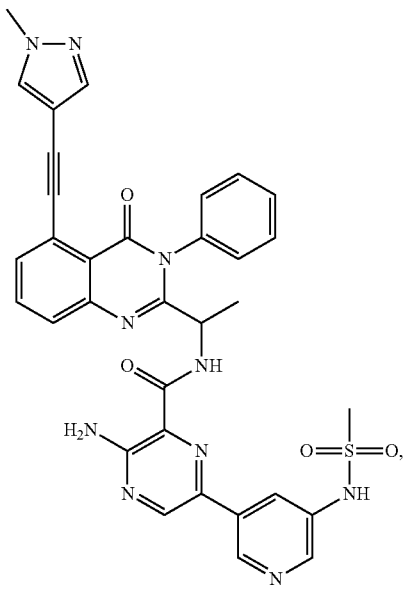 [SMILES: CC(NC(=O)c1nc(-c2cncc(NS(C)(=O)=O)c2)cnc1N)c1nc2cccc(C#Cc3cnn(C)c3)c2c(=O)n1-c1ccccc1]
Compound 3065'
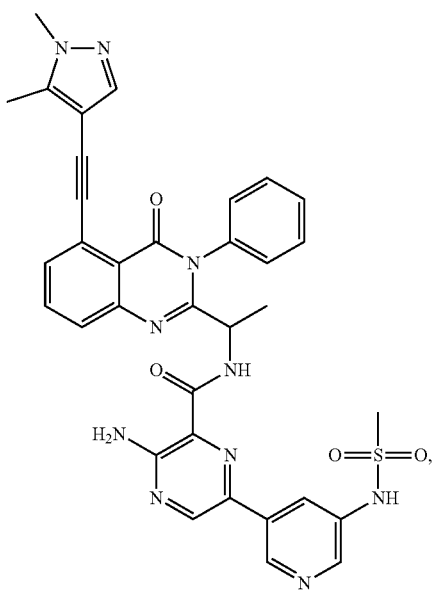
Compound 3066'

TABLE 10-continued
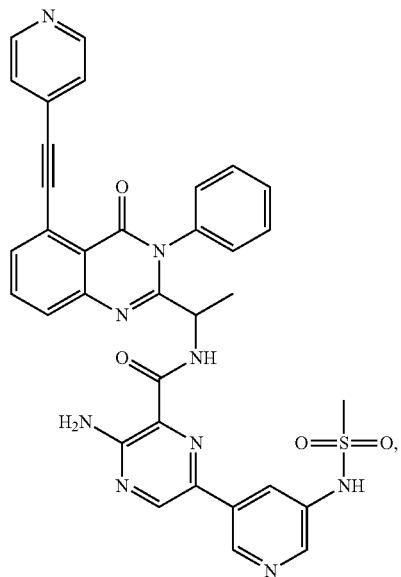 [SMILES: CC(NC(=O)c1nc(-c2cncc(NS(C)(=O)=O)c2)cnc1N)c1nc2cccc(C#Cc3ccncc3)c2c(=O)n1-c1ccccc1]
Compound 3067'
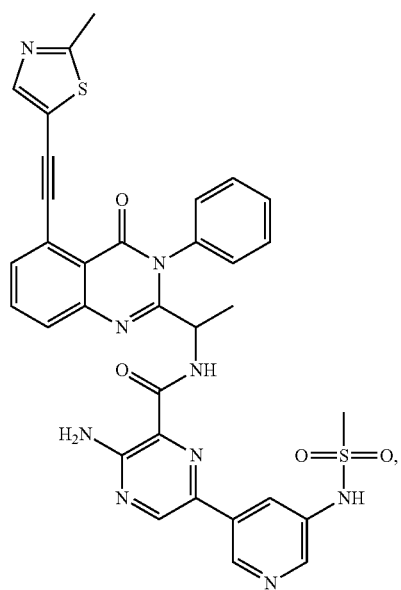 [SMILES: Cc1ncc(C#Cc2cccc3nc(C(C)NC(=O)c4nc(-c5cncc(NS(C)(=O)=O)c5)cnc4N)n(-c4ccccc4)c(=O)c23)s1]
Compound 3068'

TABLE 10-continued
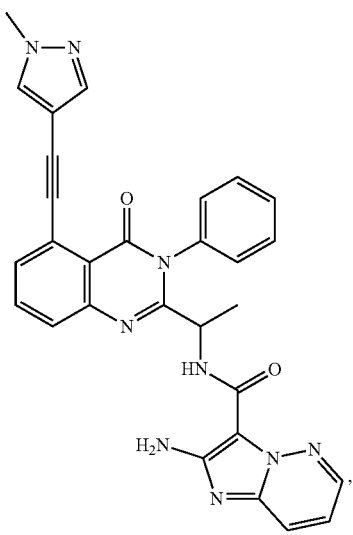 [SMILES: CC(NC(=O)c1c(N)nc2cccnn12)c1nc2cccc(C#Cc3cnn(C)c3)c2c(=O)n1-c1ccccc1]
Compound 3069'
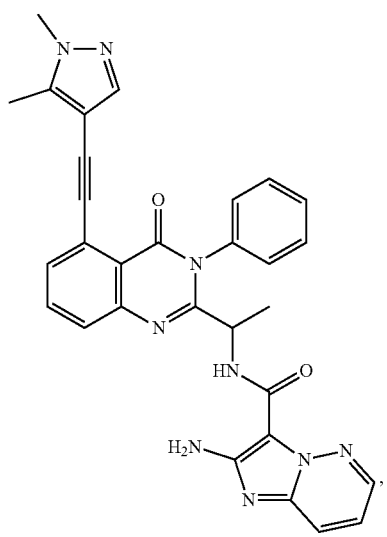 [SMILES: Cc1c(C#Cc2cccc3nc(C(C)NC(=O)c4c(N)nc5cccnn45)n(-c4ccccc4)c(=O)c23)cnn1C]
Compound 3070'
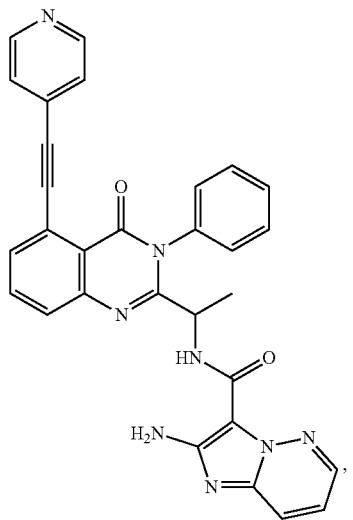 [SMILES: CC(NC(=O)c1c(N)nc2cccnn12)c1nc2cccc(C#Cc3ccncc3)c2c(=O)n1-c1ccccc1]
Compound 3071'

TABLE 10-continued
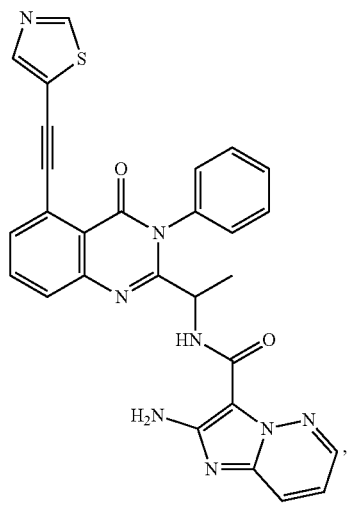 [SMILES: CC(NC(=O)c1c(N)nc2cccnn12)c1nc2cccc(C#Cc3cncs3)c2c(=O)n1-c1ccccc1]
Compound 3072'
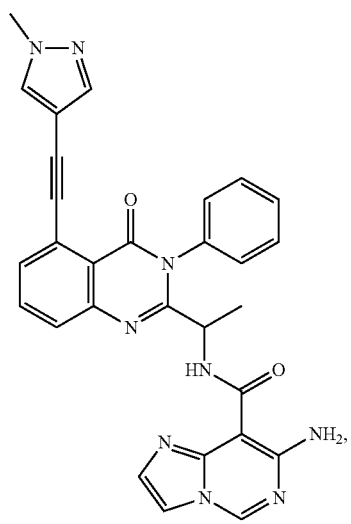 [SMILES: CC(NC(=O)c1c(N)ncn2ccnc12)c1nc2cccc(C#Cc3cnn(C)c3)c2c(=O)n1-c1ccccc1]
Compound 3073'
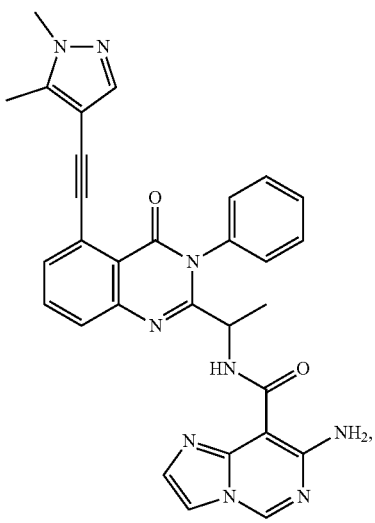
Compound 3074'

TABLE 10-continued
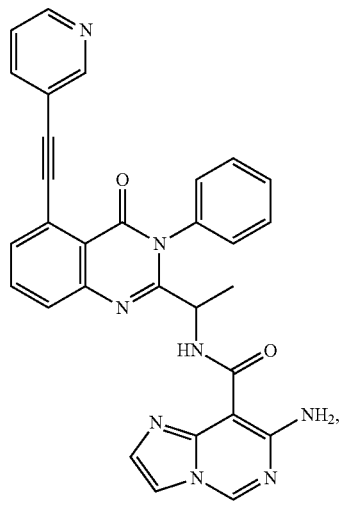 [SMILES: CC(NC(=O)c1c(N)ncn2ccnc12)c1nc2cccc(C#Cc3cccnc3)c2c(=O)n1-c1ccccc1]
Compound 3075'
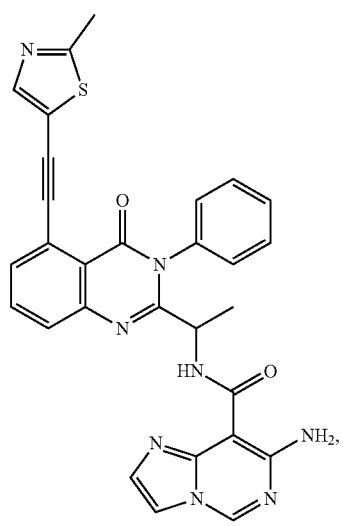 [SMILES: Cc1ncc(C#Cc2cccc3nc(C(C)NC(=O)c4c(N)ncn5ccnc45)n(-c4ccccc4)c(=O)c23)s1]
Compound 3076'
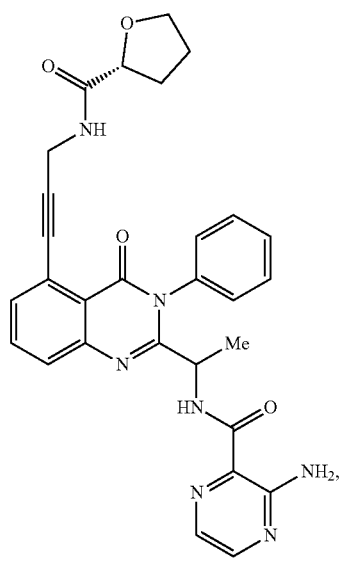 [SMILES: CC(NC(=O)c1nccnc1N)c1nc2cccc(C#CCNC(=O)[C@H]3CCCO3)c2c(=O)n1-c1ccccc1]
Compound 3077'

TABLE 10-continued
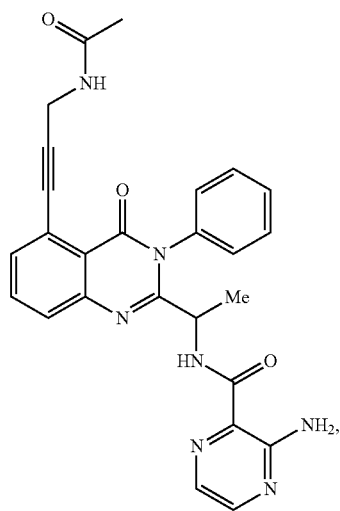 [SMILES: CC(=O)NCC#Cc1cccc2nc(C(C)NC(=O)c3nccnc3N)n(-c3ccccc3)c(=O)c12]
Compound 3078'
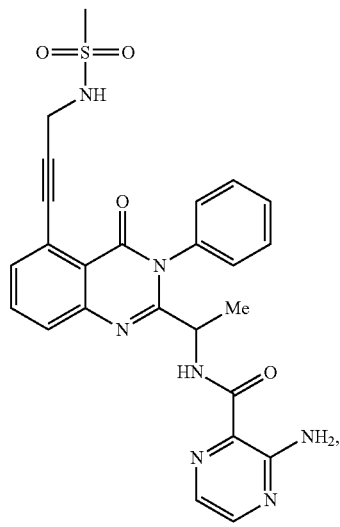 [SMILES: CC(NC(=O)c1nccnc1N)c1nc2cccc(C#CCNS(C)(=O)=O)c2c(=O)n1-c1ccccc1]
Compound 3079'
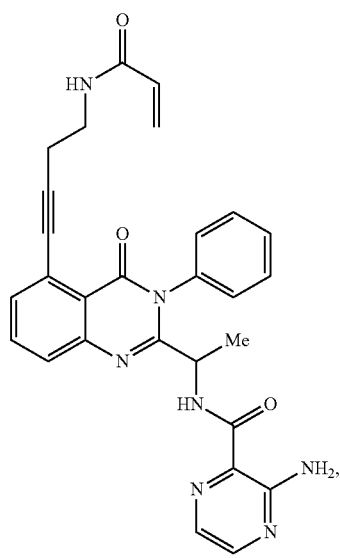 [SMILES: C=CC(=O)NCCC#Cc1cccc2nc(C(C)NC(=O)c3nccnc3N)n(-c3ccccc3)c(=O)c12]
Compound 3080'

TABLE 10-continued
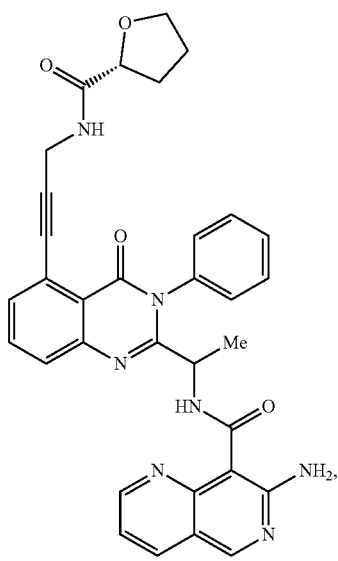 [SMILES: CC(NC(=O)c1c(N)ncc2cccnc12)c1nc2cccc(C#CCNC(=O)[C@H]3CCCO3)c2c(=O)n1-c1ccccc1]
Compound 3081'
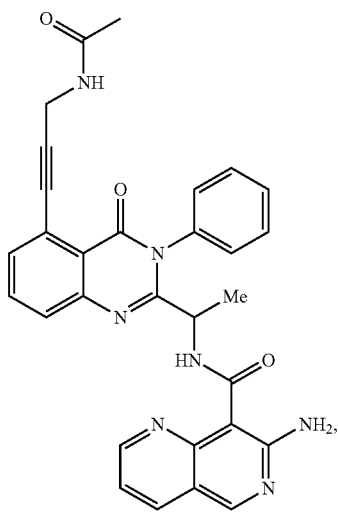 [SMILES: CC(=O)NCC#Cc1cccc2nc(C(C)NC(=O)c3c(N)ncc4cccnc34)n(-c3ccccc3)c(=O)c12]
Compound 3082'
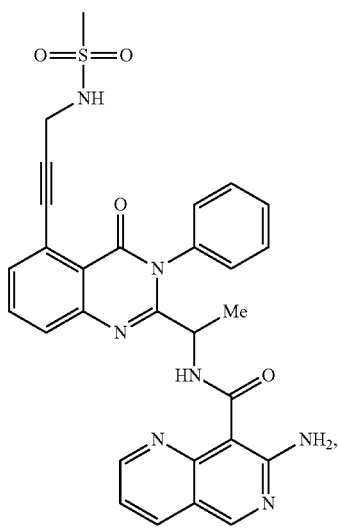
Compound 3083'

TABLE 10-continued
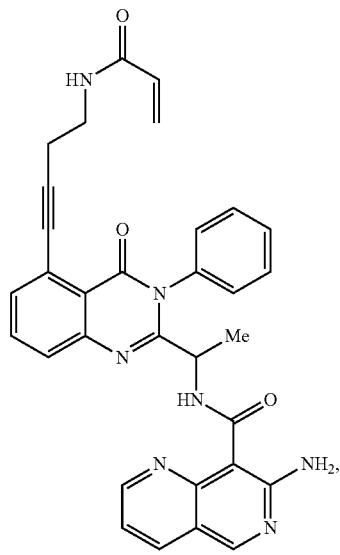 [SMILES: C=CC(=O)NCCC#Cc1cccc2nc(C(C)NC(=O)c3c(N)ncc4cccnc34)n(-c3ccccc3)c(=O)c12]
Compound 3084'
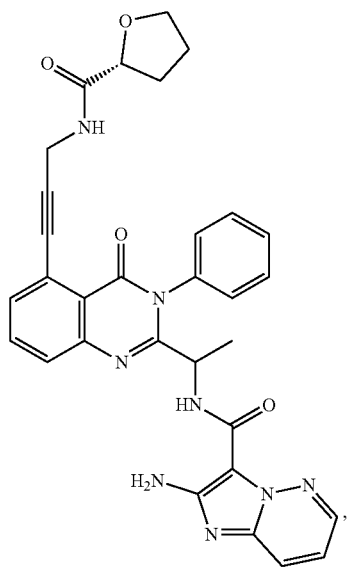 [SMILES: CC(NC(=O)c1c(N)nc2cccnn12)c1nc2cccc(C#CCNC(=O)[C@H]3CCCO3)c2c(=O)n1-c1ccccc1]
Compound 3085'
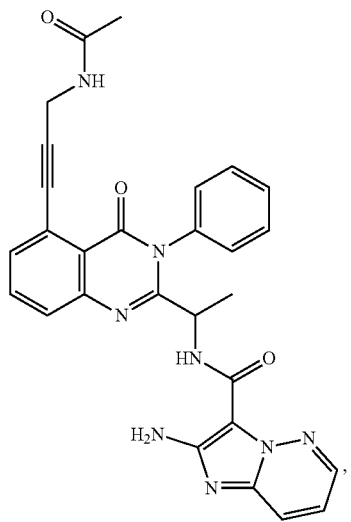 [SMILES: CC(=O)NCC#Cc1cccc2nc(C(C)NC(=O)c3c(N)nc4cccnn34)n(-c3ccccc3)c(=O)c12]
Compound 3086'

TABLE 10-continued
Compound 3087'
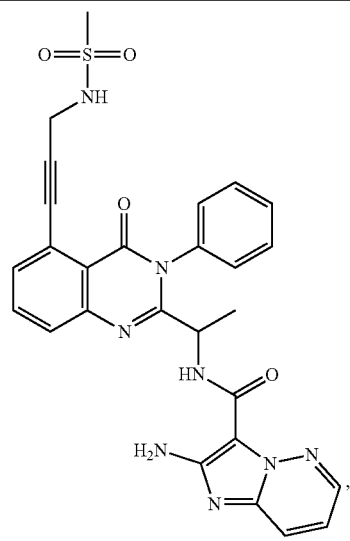
Compound 3088'
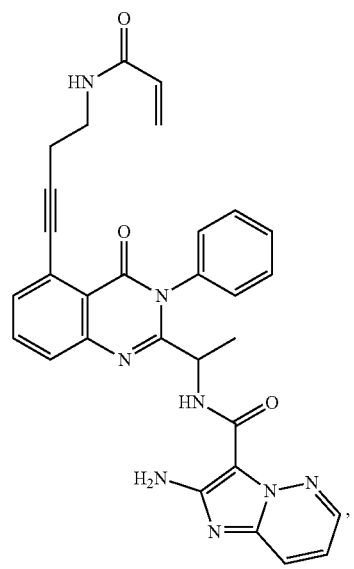 [SMILES: C=CC(=O)NCCC#Cc1cccc2nc(C(C)NC(=O)c3c(N)nc4cccnn34)n(-c3ccccc3)c(=O)c12]
Compound 3089'
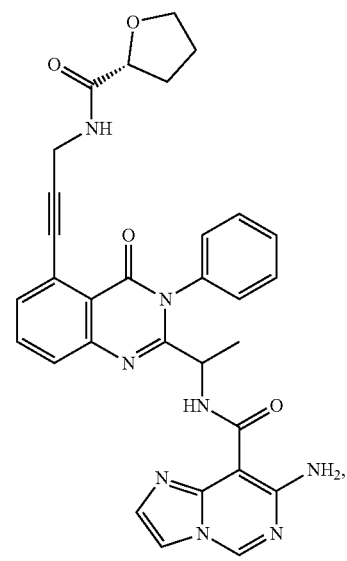 [SMILES: CC(NC(=O)c1c(N)ncn2ccnc12)c1nc2cccc(C#CCNC(=O)[C@H]3CCCO3)c2c(=O)n1-c1ccccc1]

TABLE 10-continued
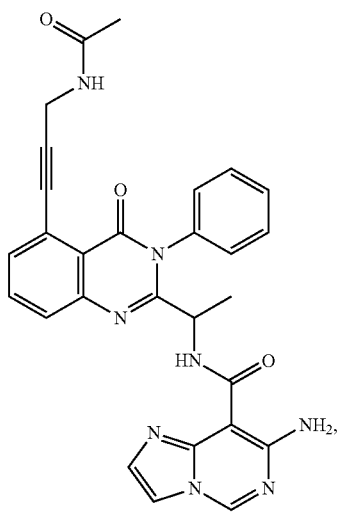 [SMILES: CC(=O)NCC#Cc1cccc2nc(C(C)NC(=O)c3c(N)ncn4ccnc34)n(-c3ccccc3)c(=O)c12]
Compound 3090'
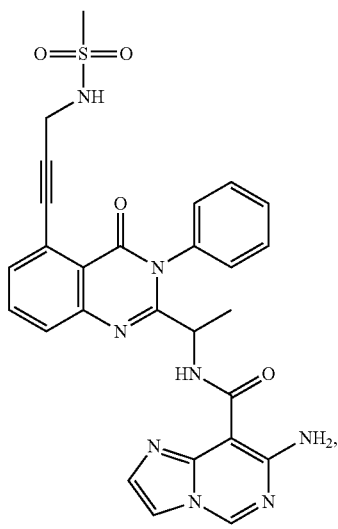 [SMILES: CC(NC(=O)c1c(N)ncn2ccnc12)c1nc2cccc(C#CCNS(C)(=O)=O)c2c(=O)n1-c1ccccc1]
Compound 3091'
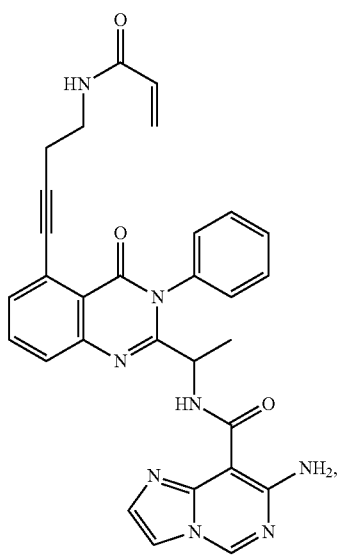 [SMILES: C=CC(=O)NCCC#Cc1cccc2nc(C(C)NC(=O)c3c(N)ncn4ccnc34)n(-c3ccccc3)c(=O)c12]
Compound 3092'

TABLE 10-continued
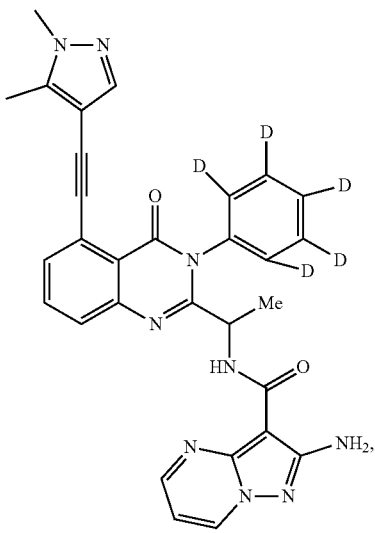 [SMILES: [2H]c1c([2H])c([2H])c(-n2c(C(C)NC(=O)c3c(N)nn4cccnc34)nc3cccc(C#Cc4cnn(C)c4C)c3c2=O)c([2H])c1[2H]]
Compound 3093'
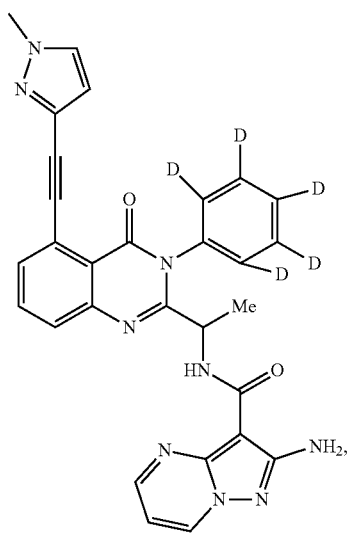 [SMILES: [2H]c1c([2H])c([2H])c(-n2c(C(C)NC(=O)c3c(N)nn4cccnc34)nc3cccc(C#Cc4ccn(C)n4)c3c2=O)c([2H])c1[2H]]
Compound 3094'
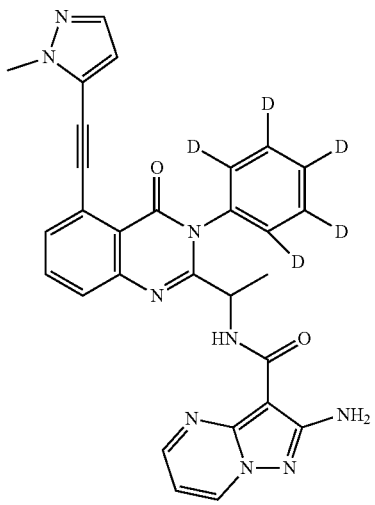 [SMILES: [2H]c1c([2H])c([2H])c(-n2c(C(C)NC(=O)c3c(N)nn4cccnc34)nc3cccc(C#Cc4ccnn4C)c3c2=O)c([2H])c1[2H]]
Compound 3095'

TABLE 11
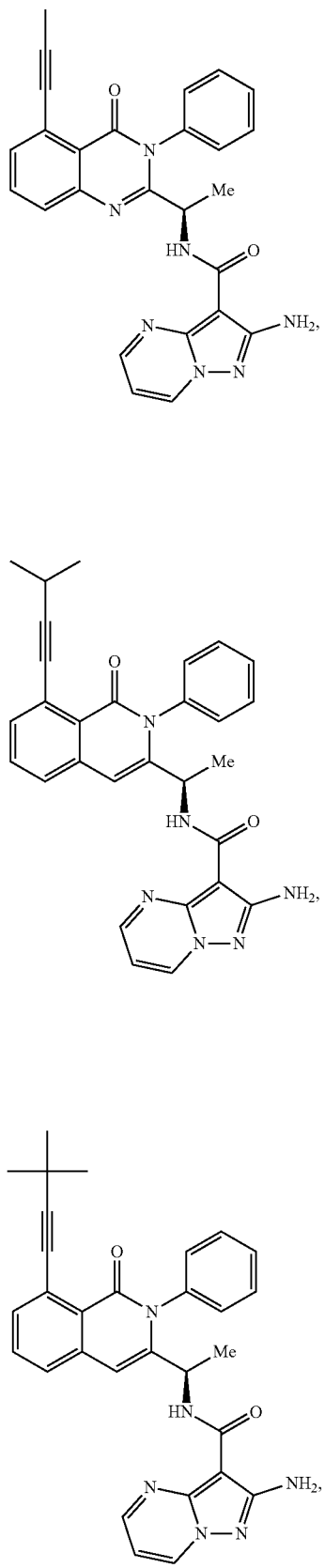
Compound 1r
Compound 2r
Compound 3r
TABLE 11-continued
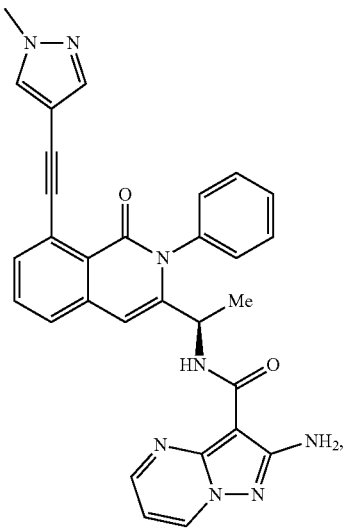
Compound 4r
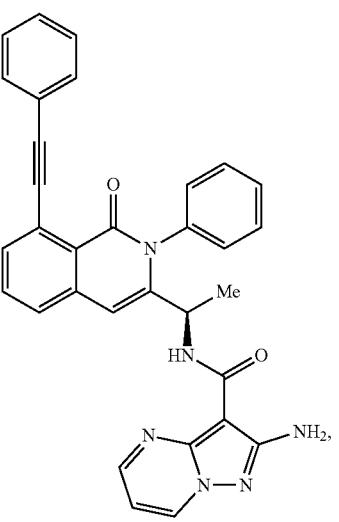 [SMILES: C[C@@H](NC(=O)c1c(N)nn2cccnc12)c1cc2cccc(C#Cc3ccccc3)c2c(=O)n1-c1ccccc1]
Compound 5r
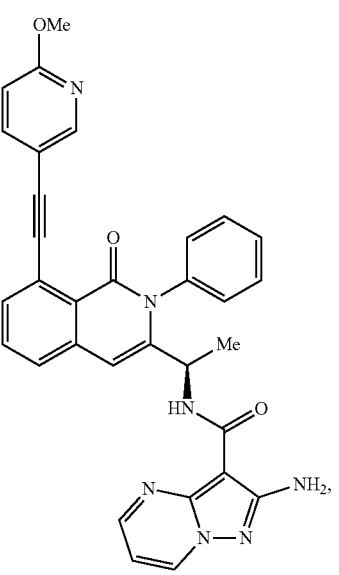 [SMILES: COc1ccc(C#Cc2cccc3cc([C@@H](C)NC(=O)c4c(N)nn5cccnc45)n(-c4ccccc4)c(=O)c23)cn1]
Compound 6r TABLE 11-continued
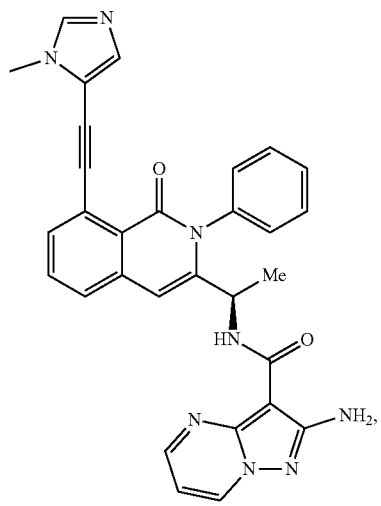 [SMILES: C[C@@H](NC(=O)c1c(N)nn2cccnc12)c1cc2cccc(C#Cc3cncn3C)c2c(=O)n1-c1ccccc1]
Compound 7r
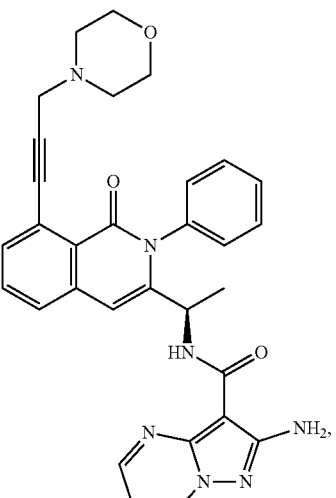
Compound 10r
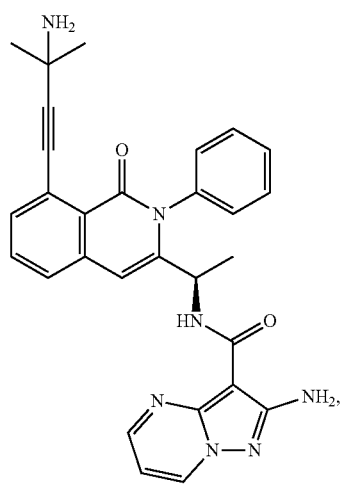 [SMILES: C[C@@H](NC(=O)c1c(N)nn2cccnc12)c1cc2cccc(C#CC(C)(C)N)c2c(=O)n1-c1ccccc1]
Compound 8r
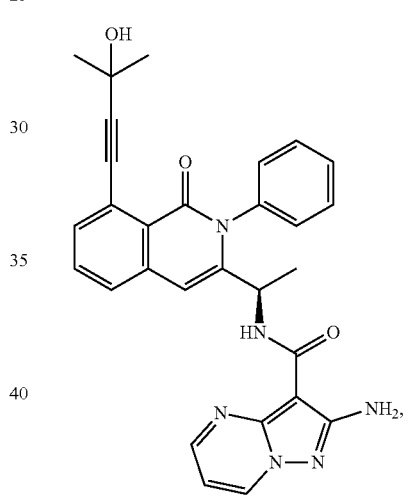
Compound 11r
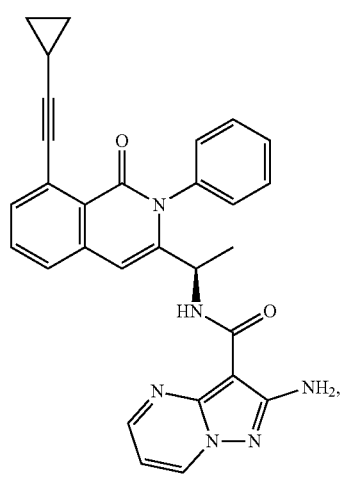
Compound 9r
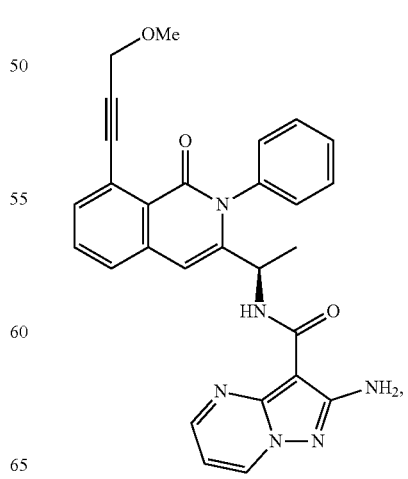
Compound 12r TABLE 11-continued
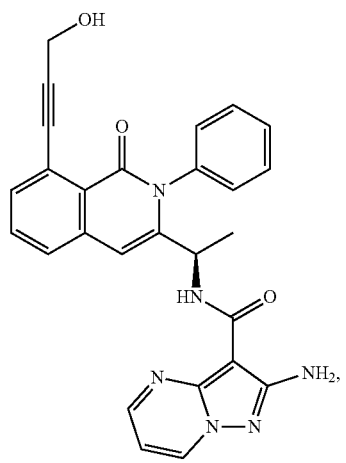 [SMILES: C[C@@H](NC(=O)c1c(N)nn2cccnc12)c1cc2cccc(C#CCO)c2c(=O)n1-c1ccccc1]
Compound 13r
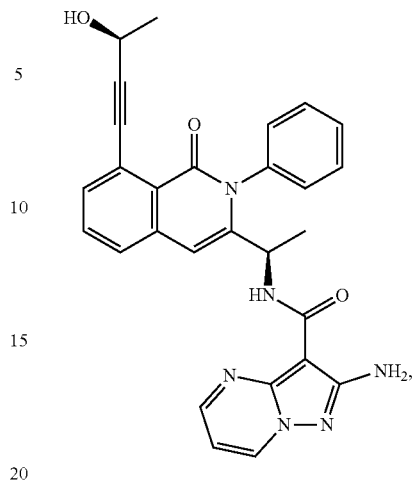
Compound 16r
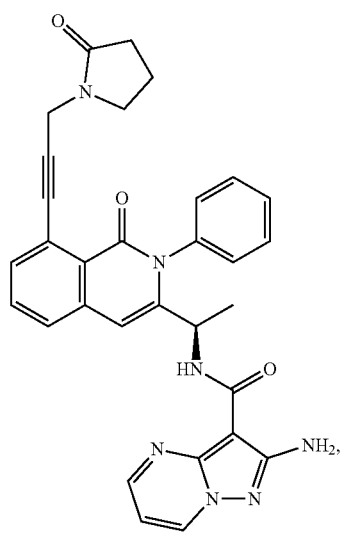
Compound 14r
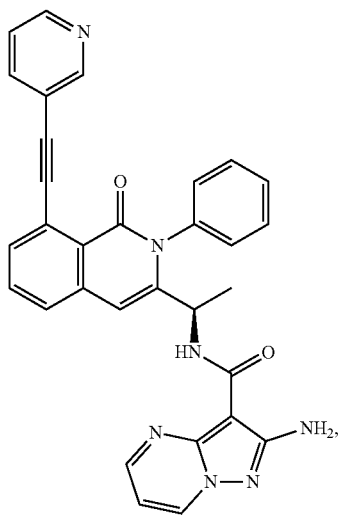 [SMILES: C[C@@H](NC(=O)c1c(N)nn2cccnc12)c1cc2cccc(C#Cc3cccnc3)c2c(=O)n1-c1ccccc1]
Compound 17r
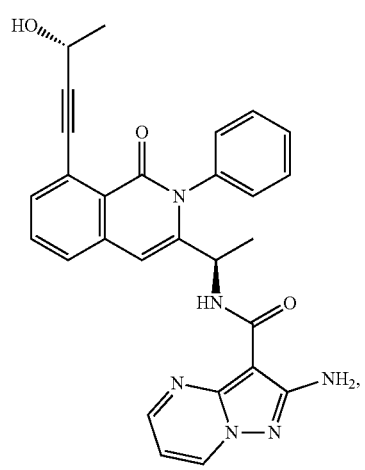
Compound 15r
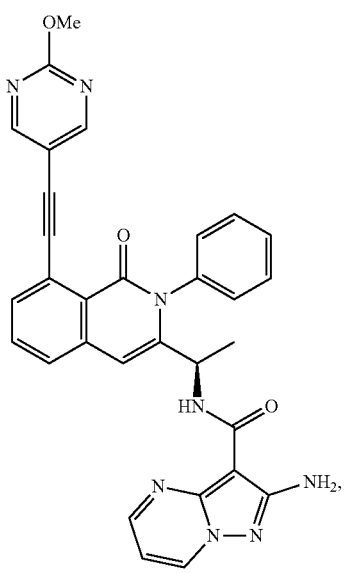
Compound 18r TABLE 11-continued
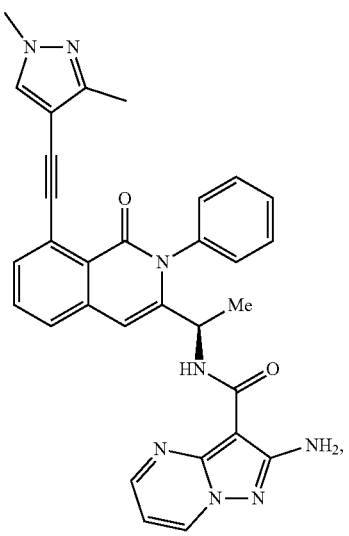 [SMILES: Cc1nn(C)cc1C#Cc1cccc2cc([C@@H](C)NC(=O)c3c(N)nn4cccnc34)n(-c3ccccc3)c(=O)c12]
Compound 19r
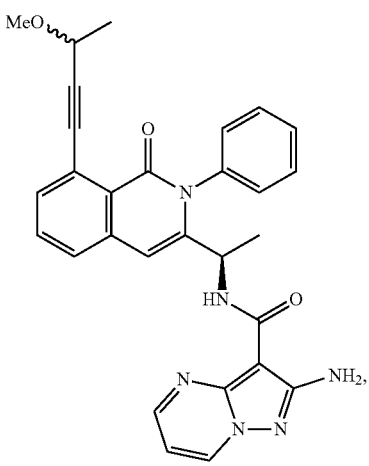
Compound 22r
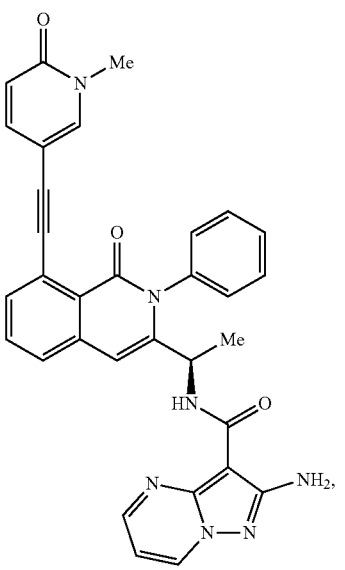
Compound 20r
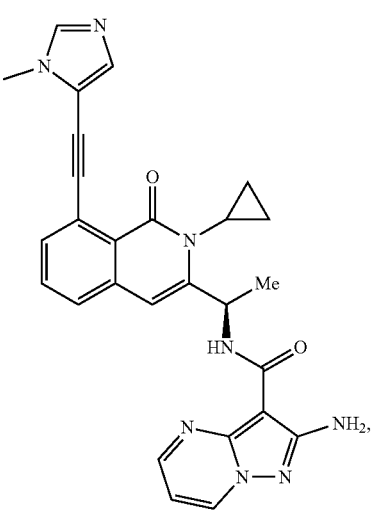
Compound 23r
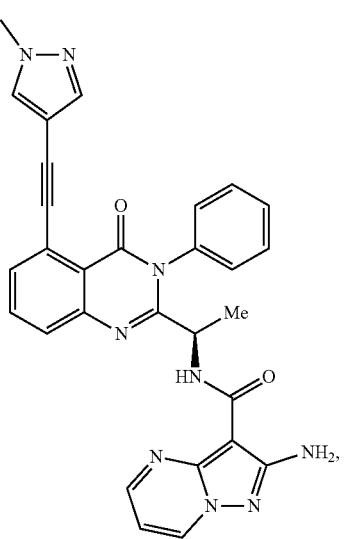 [SMILES: C[C@@H](NC(=O)c1c(N)nn2cccnc12)c1nc2cccc(C#Cc3cnn(C)c3)c2c(=O)n1-c1ccccc1]
Compound 21r
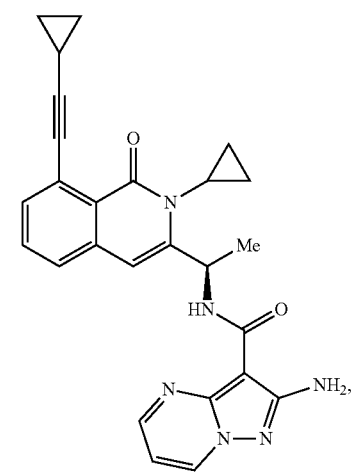 [SMILES: C[C@@H](NC(=O)c1c(N)nn2cccnc12)c1cc2cccc(C#CC3CC3)c2c(=O)n1C1CC1]
Compound 24r TABLE 11-continued
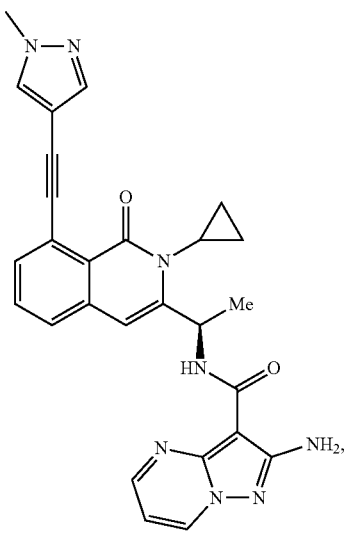 [SMILES: C[C@@H](NC(=O)c1c(N)nn2cccnc12)c1cc2cccc(C#Cc3cnn(C)c3)c2c(=O)n1C1CC1]
Compound 25r
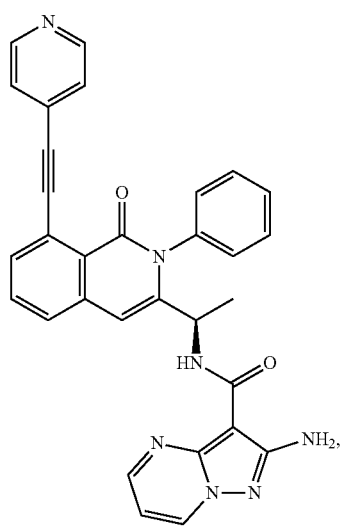
Compound 26r
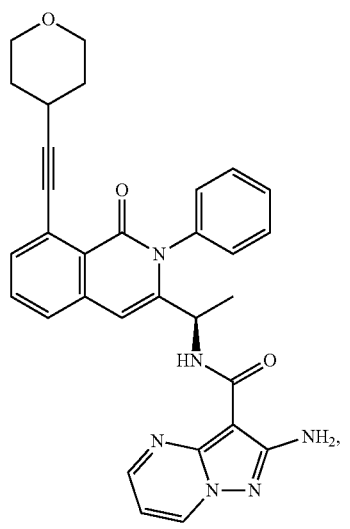
Compound 27r
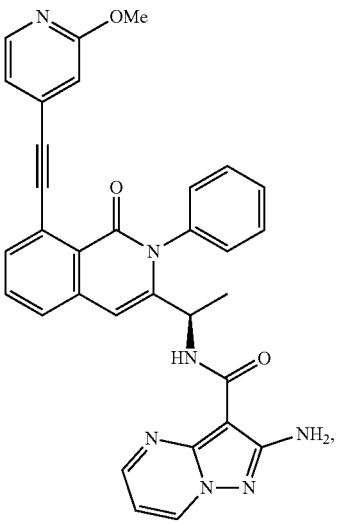 [SMILES: COc1cc(C#Cc2cccc3cc([C@@H](C)NC(=O)c4c(N)nn5cccnc45)n(-c4ccccc4)c(=O)c23)ccn1]
Compound 28r
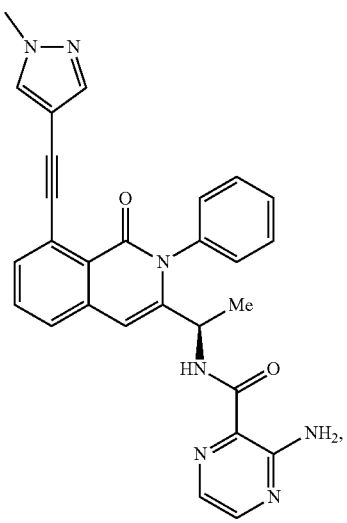 [SMILES: C[C@@H](NC(=O)c1nccnc1N)c1cc2cccc(C#Cc3cnn(C)c3)c2c(=O)n1-c1ccccc1]
Compound 29r
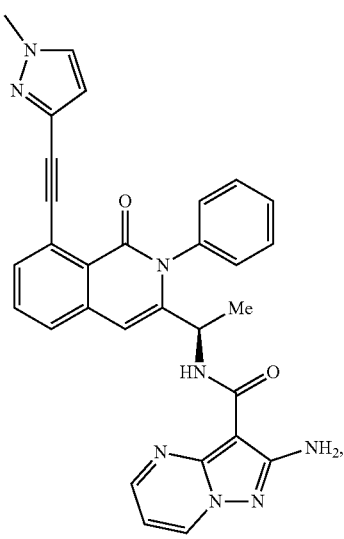 [SMILES: C[C@@H](NC(=O)c1c(N)nn2cccnc12)c1cc2cccc(C#Cc3ccn(C)n3)c2c(=O)n1-c1ccccc1]
Compound 30r TABLE 11-continued
Compound 31r
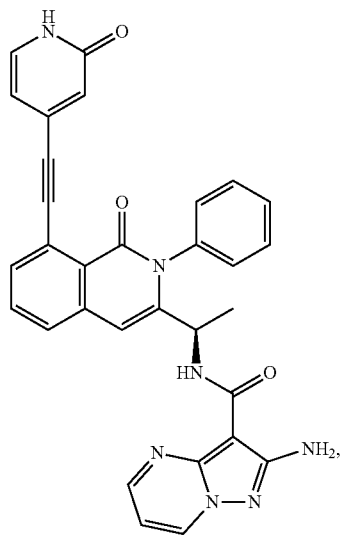
Compound 32r
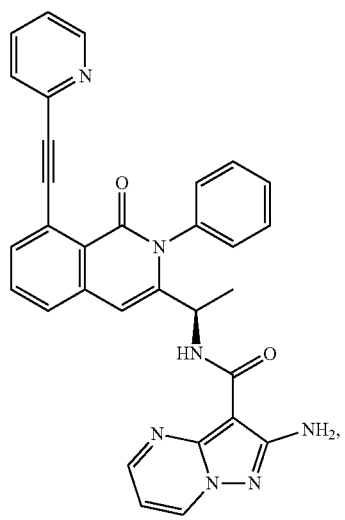 [SMILES: C[C@@H](NC(=O)c1c(N)nn2cccnc12)c1cc2cccc(C#Cc3ccccn3)c2c(=O)n1-c1ccccc1]
Compound 33r
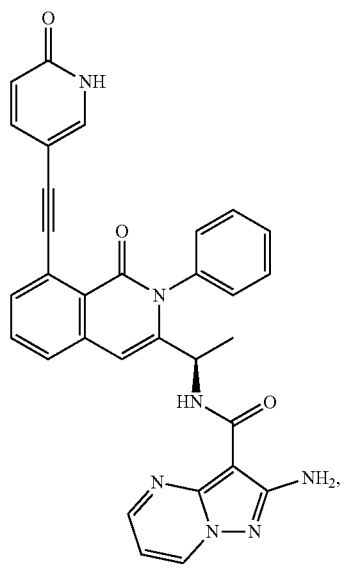
TABLE 11-continued
Compound 34r
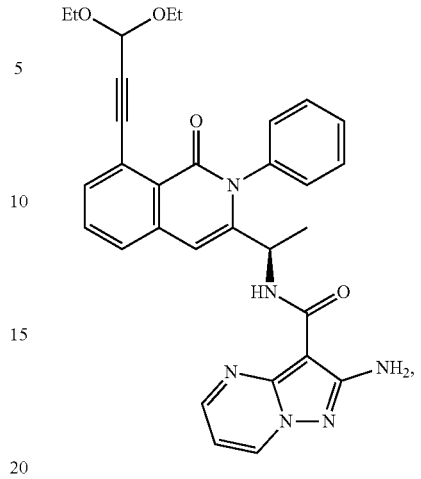
Compound 35r
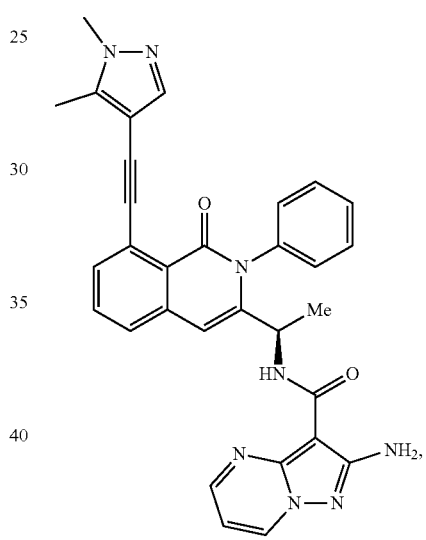
Compound 36r
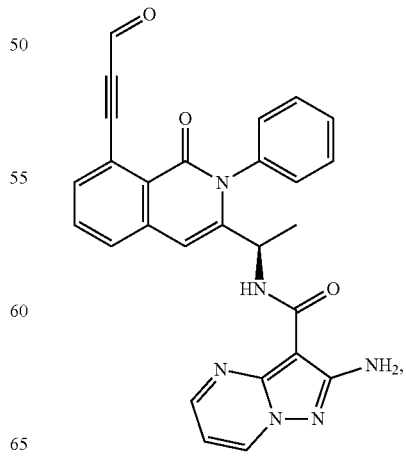

TABLE 11-continued
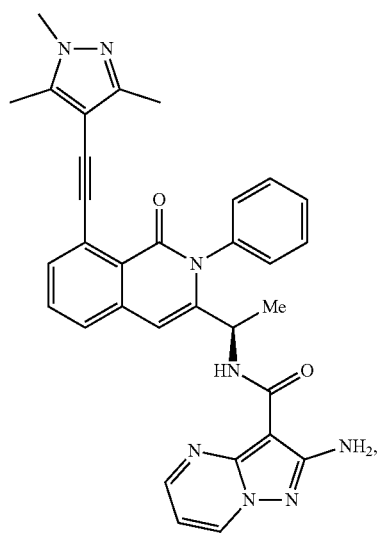
Compound 37r
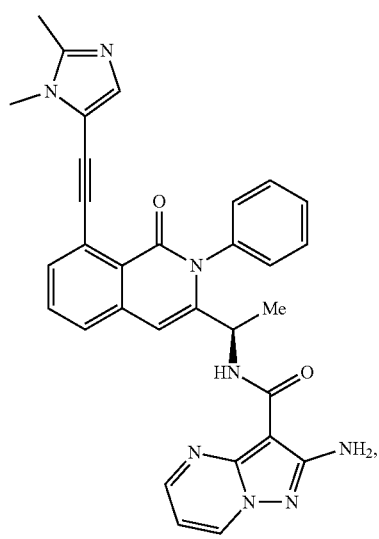
Compound 38r
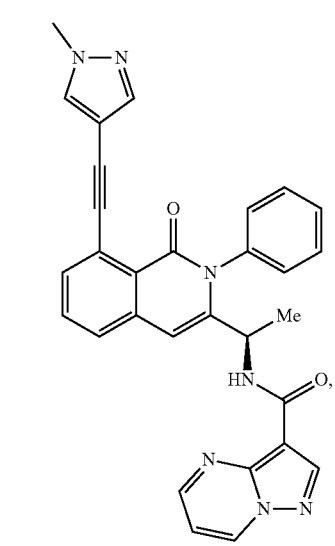 [SMILES: C[C@@H](NC(=O)c1cnn2cccnc12)c1cc2cccc(C#Cc3cnn(C)c3)c2c(=O)n1-c1ccccc1]
Compound 39r
TABLE 11-continued

Compound 40r
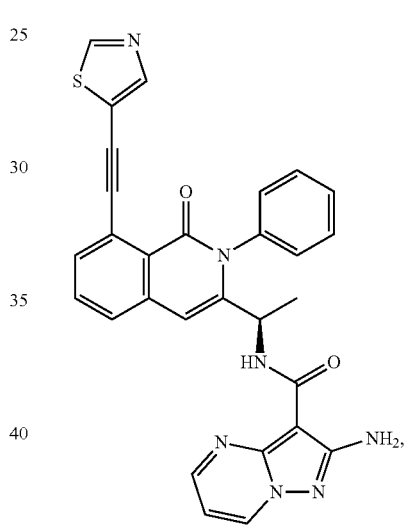
Compound 41r
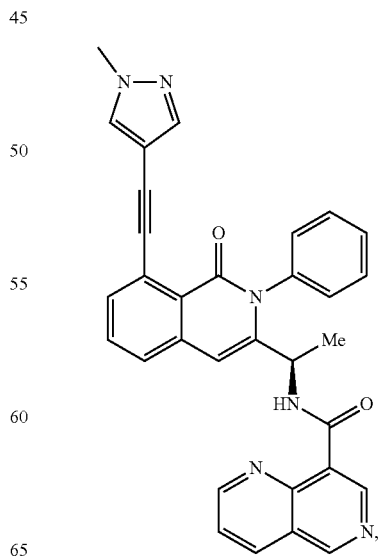
Compound 42r TABLE 11-continued
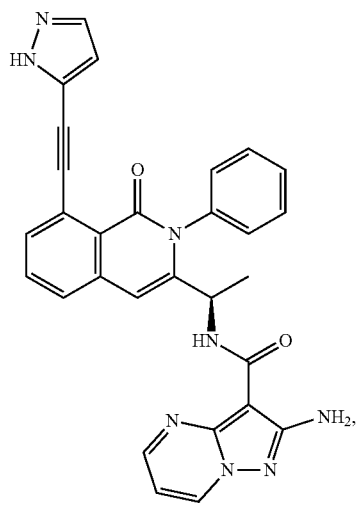
Compound 43r
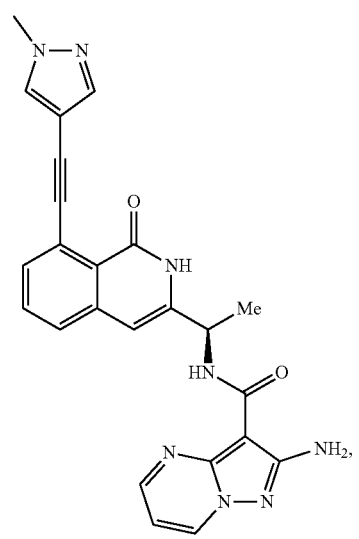
Compound 44r
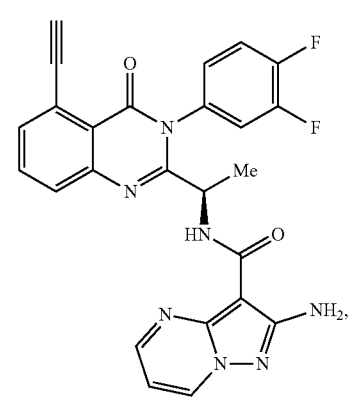 [SMILES: C#Cc1cccc2nc([C@@H](C)NC(=O)c3c(N)nn4cccnc34)n(-c3ccc(F)c(F)c3)c(=O)c12]
Compound 45r
TABLE 11-continued
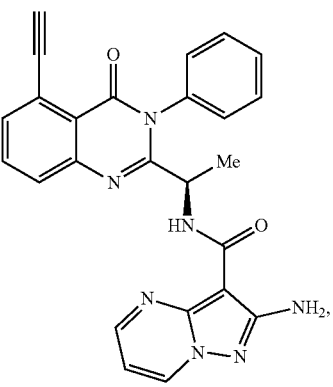 [SMILES: C#Cc1cccc2nc([C@@H](C)NC(=O)c3c(N)nn4cccnc34)n(-c3ccccc3)c(=O)c12]
Compound 46r
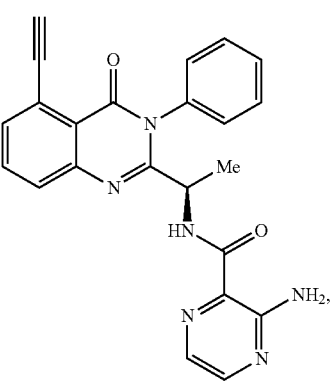 [SMILES: C#Cc1cccc2nc([C@@H](C)NC(=O)c3nccnc3N)n(-c3ccccc3)c(=O)c12]
Compound 47r
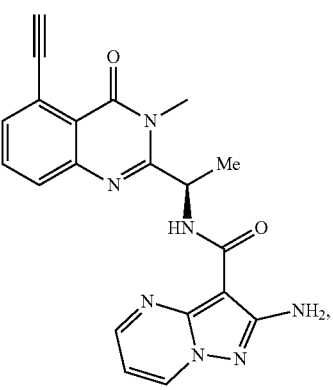 [SMILES: C#Cc1cccc2nc([C@@H](C)NC(=O)c3c(N)nn4cccnc34)n(C)c(=O)c12]
Compound 48r
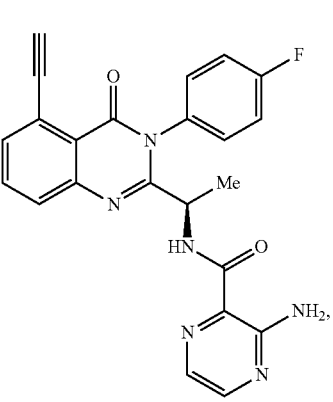 [SMILES: C#Cc1cccc2nc([C@@H](C)NC(=O)c3nccnc3N)n(-c3ccc(F)cc3)c(=O)c12]
Compound 49r TABLE 11-continued
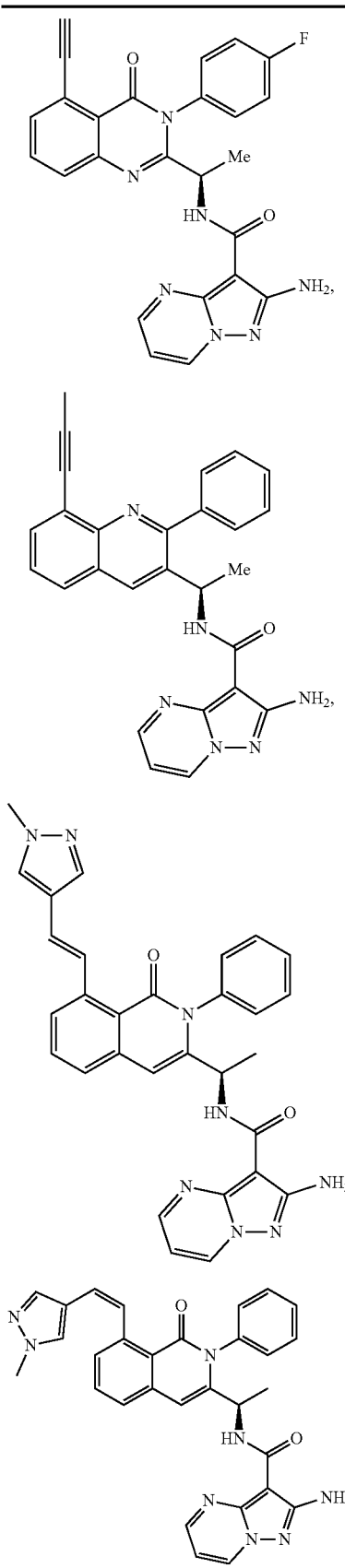
Compound 50r
Compound 51r
Compound 52r
Compound 53r
TABLE 11-continued
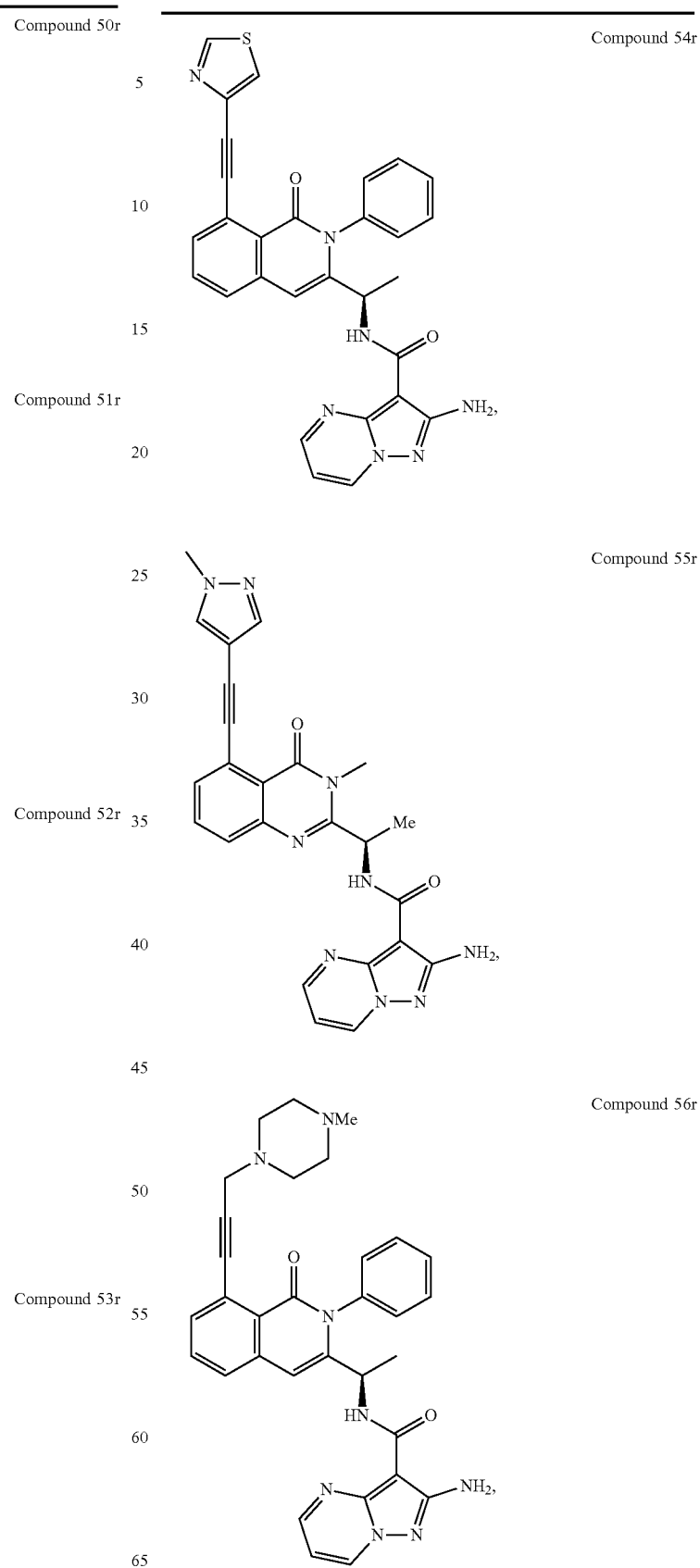
Compound 54r
Compound 55r
Compound 56r TABLE 11-continued
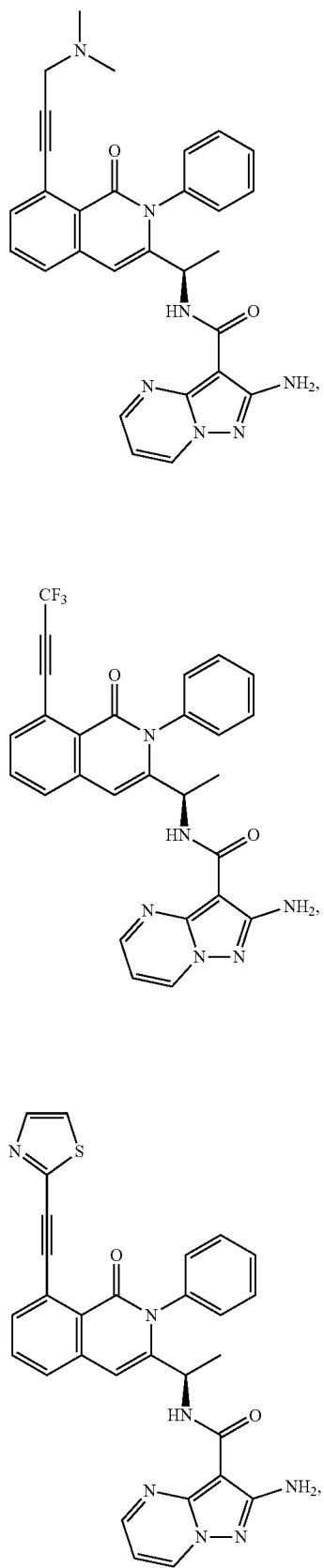
Compound 57r
Compound 58r
Compound 59r
TABLE 11-continued
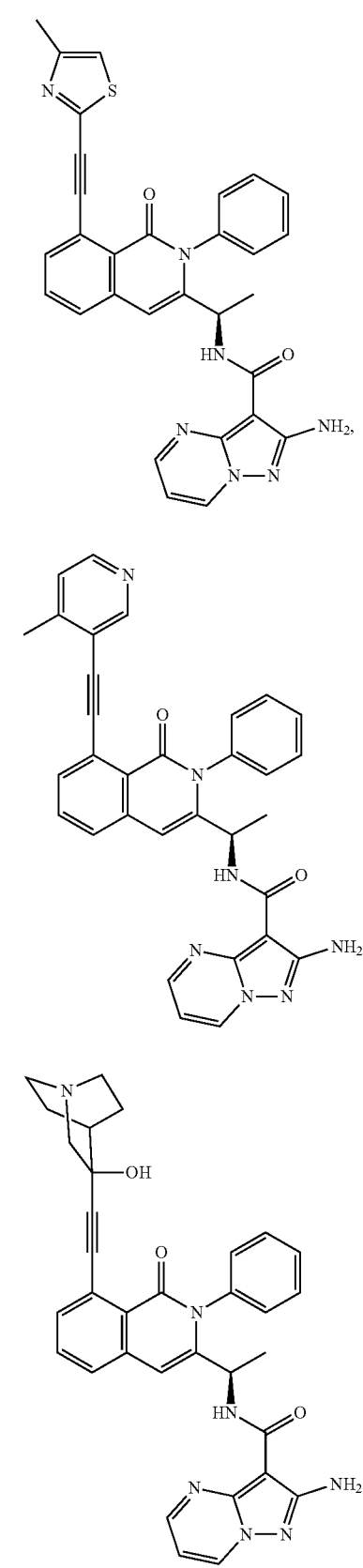
Compound 60r
Compound 61r
Compound 62r TABLE 11-continued
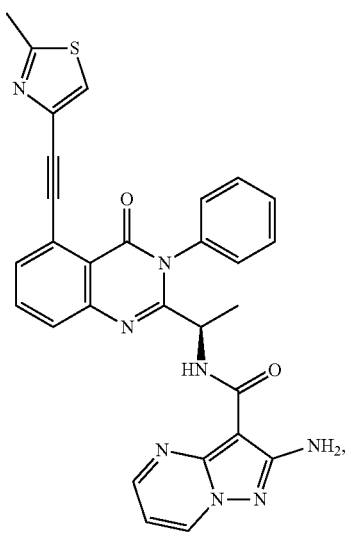
Compound 63r
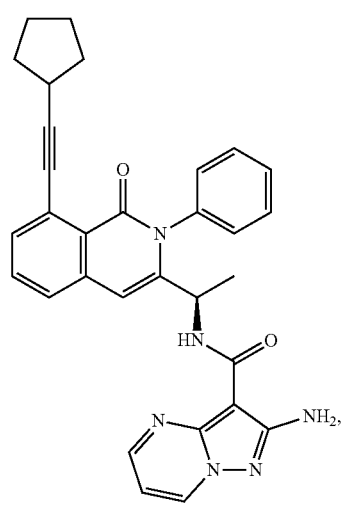
Compound 64r
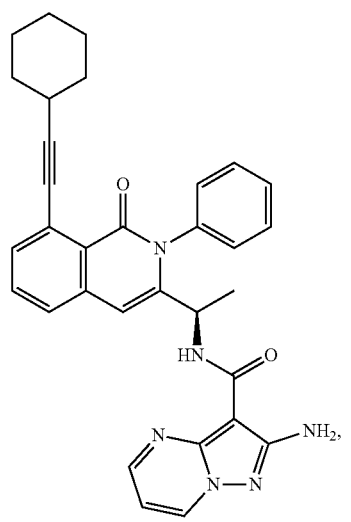 [SMILES: C[C@@H](NC(=O)c1c(N)nn2cccnc12)c1cc2cccc(C#CC3CCCCC3)c2c(=O)n1-c1ccccc1]
Compound 65r
TABLE 11-continued
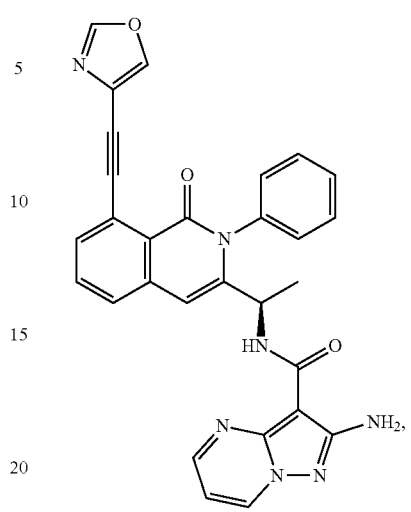
Compound 66r
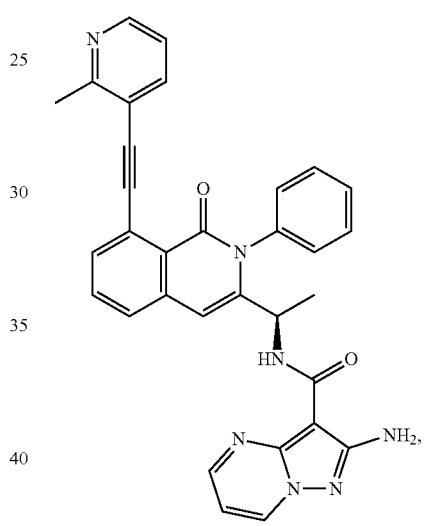
Compound 67r
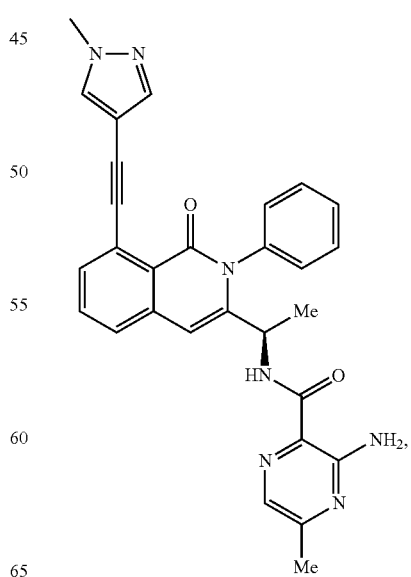
Compound 68r TABLE 11-continued
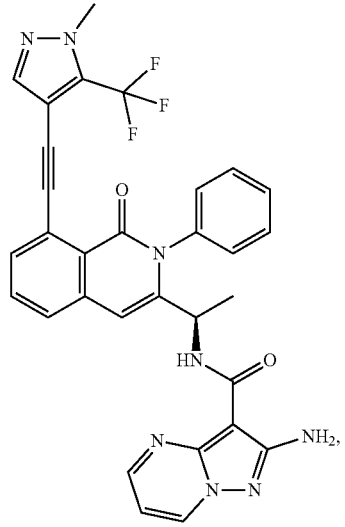
Compound 69r
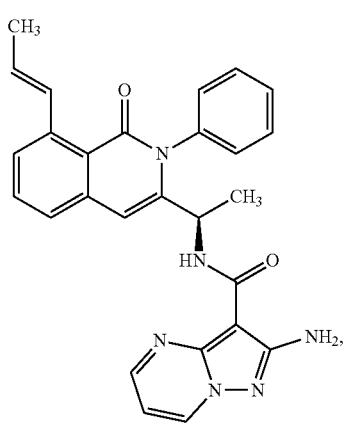 [SMILES: C/C=C/c1cccc2cc([C@@H](C)NC(=O)c3c(N)nn4cccnc34)n(-c3ccccc3)c(=O)c12]
Compound 70r
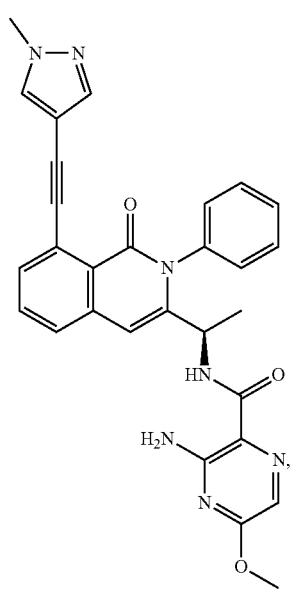
Compound 71r
TABLE 11-continued
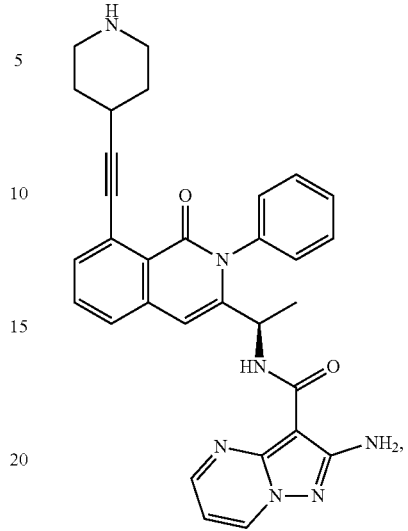
Compound 72r
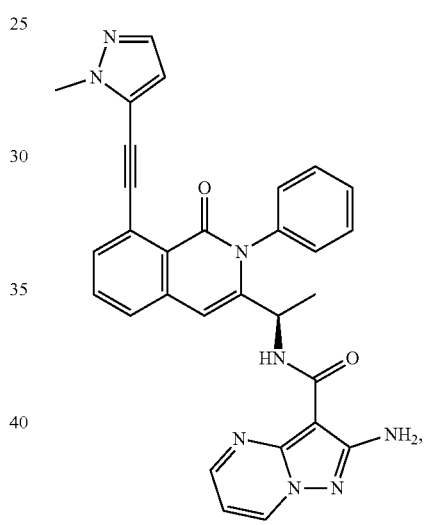
Compound 73r
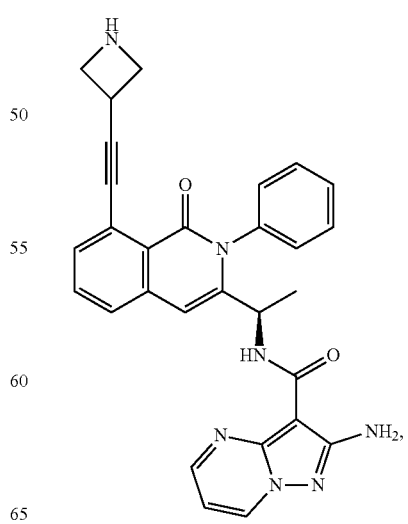
Compound 74r TABLE 11-continued
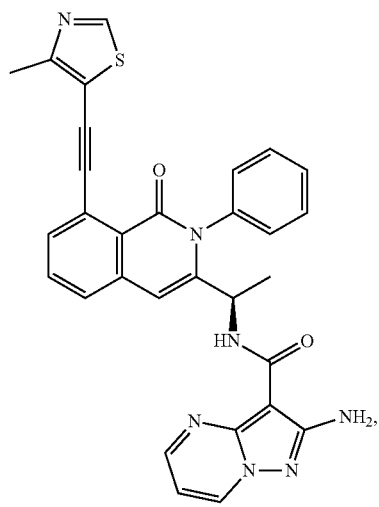
Compound 75r
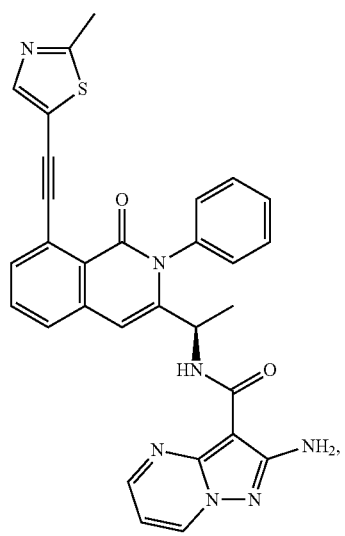
Compound 76r
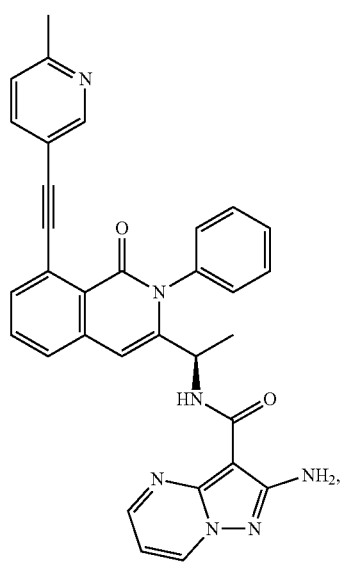 [SMILES: Cc1ccc(C#Cc2cccc3cc([C@@H](C)NC(=O)c4c(N)nn5cccnc45)n(-c4ccccc4)c(=O)c23)cn1]
Compound 77r
TABLE 11-continued
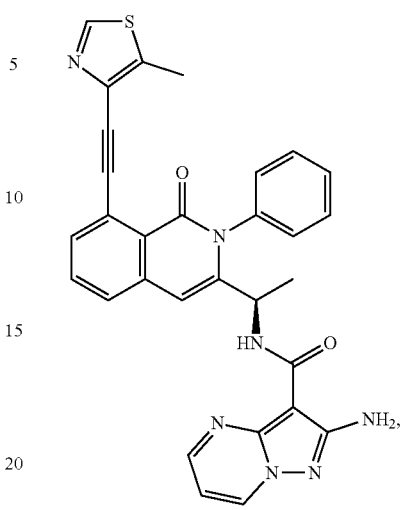
Compound 78r
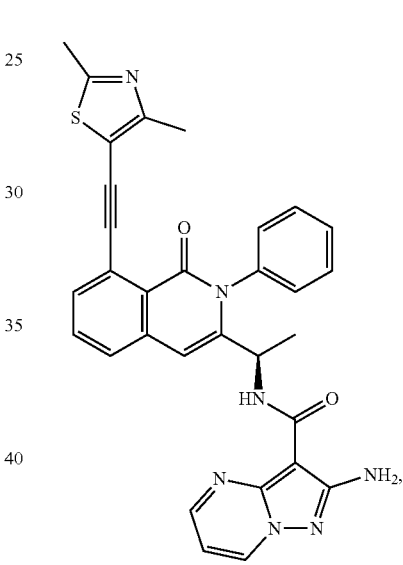
Compound 79r
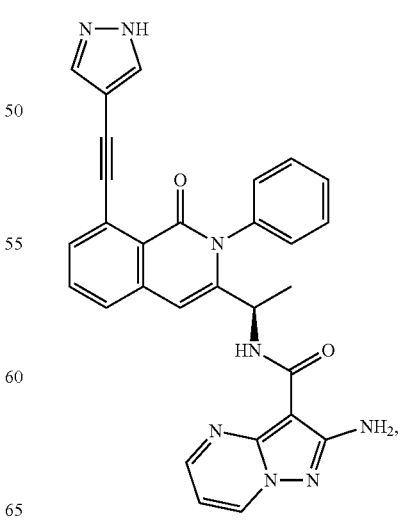
Compound 80r TABLE 11-continued
Compound 81r
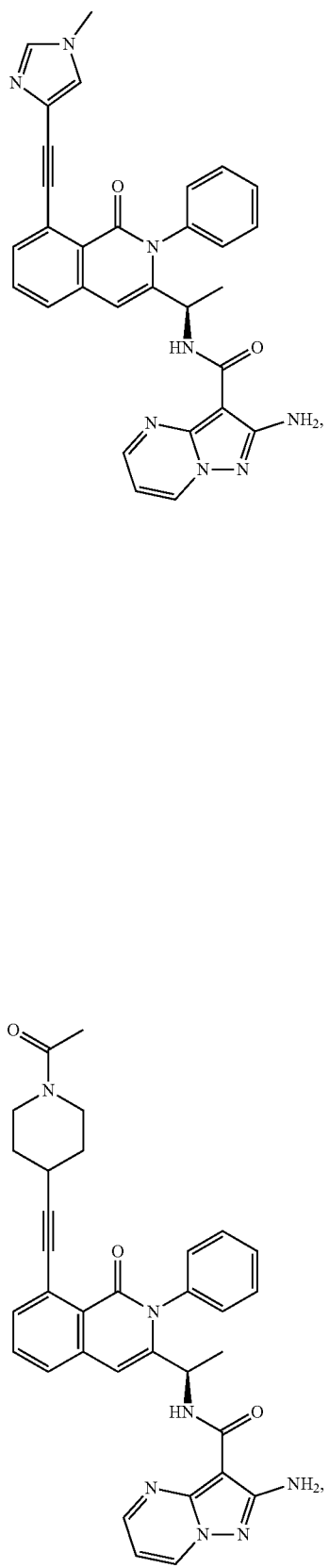
Compound 82r
Compound 83r
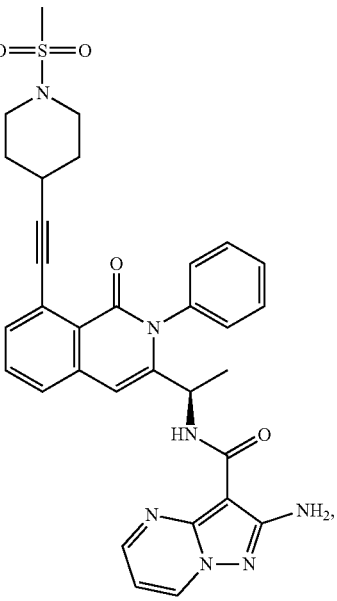
Compound 84r
Compound 85r TABLE 11-continued
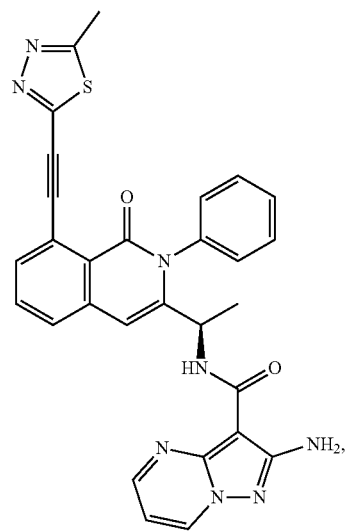
Compound 86r
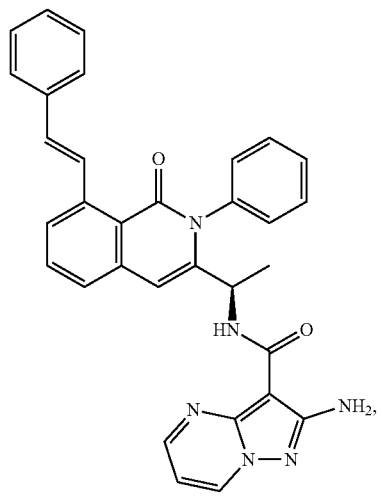 [SMILES: C[C@@H](NC(=O)c1c(N)nn2cccnc12)c1cc2cccc(/C=C/c3ccccc3)c2c(=O)n1-c1ccccc1]
Compound 87r
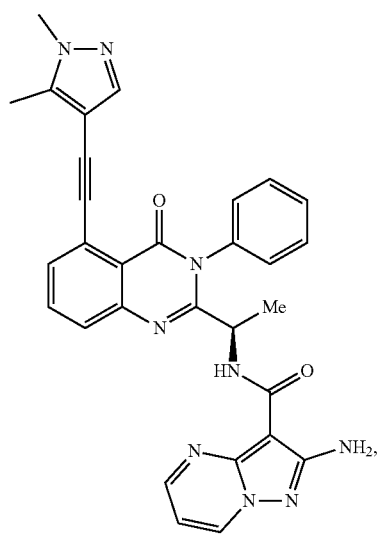 [SMILES: Cc1c(C#Cc2cccc3nc([C@@H](C)NC(=O)c4c(N)nn5cccnc45)n(-c4ccccc4)c(=O)c23)cnn1C]
Compound 88r
TABLE 11-continued
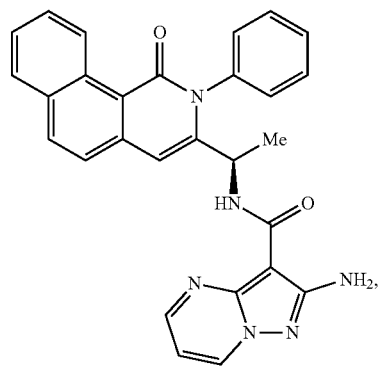
Compound 89r
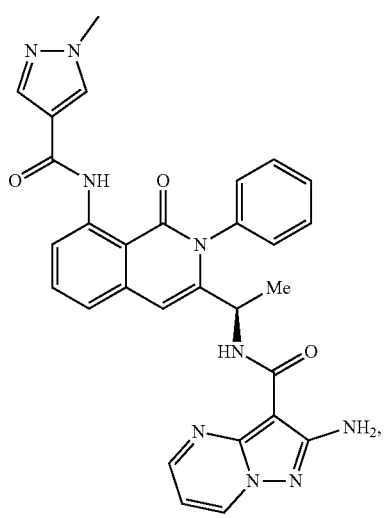
Compound 90r
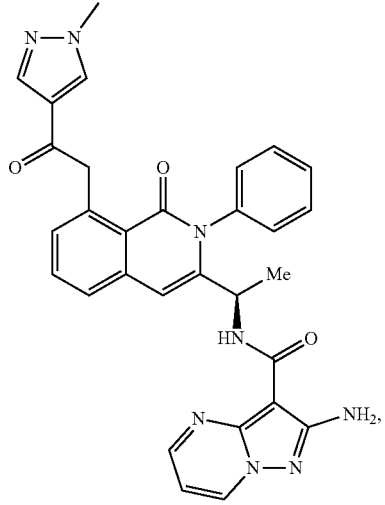
Compound 91r TABLE 11-continued
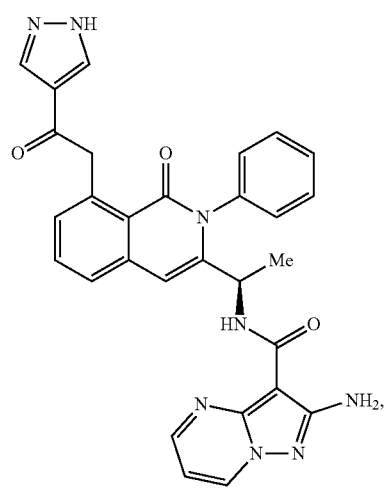 [SMILES: C[C@@H](NC(=O)c1c(N)nn2cccnc12)c1cc2cccc(CC(=O)c3cn[nH]c3)c2c(=O)n1-c1ccccc1]
Compound 92r
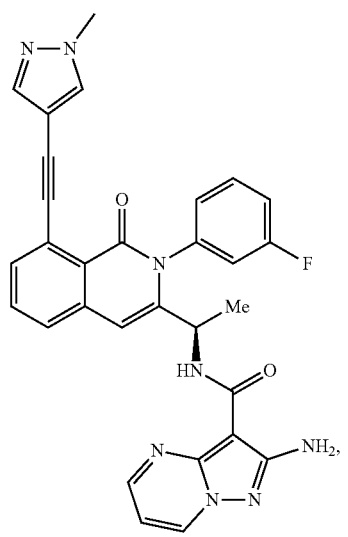
Compound 93r
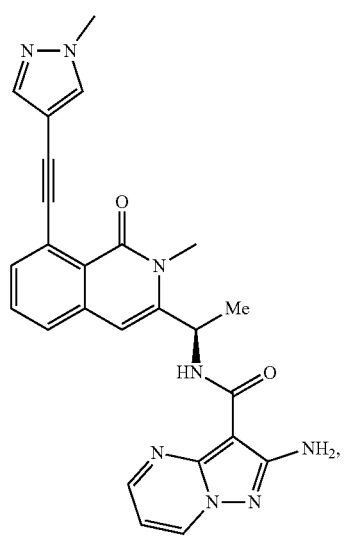
Compound 94r
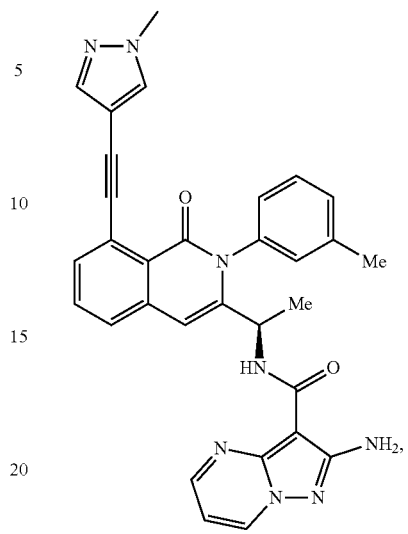
Compound 95r
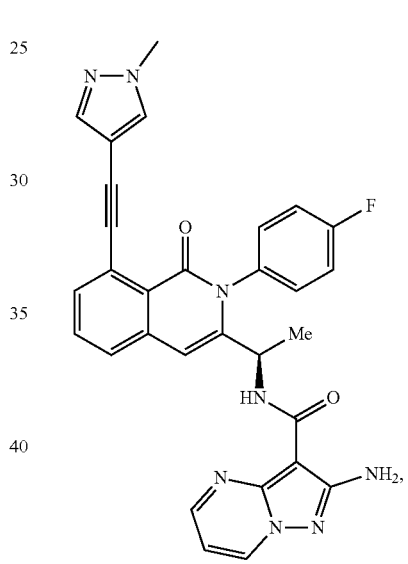
Compound 96r
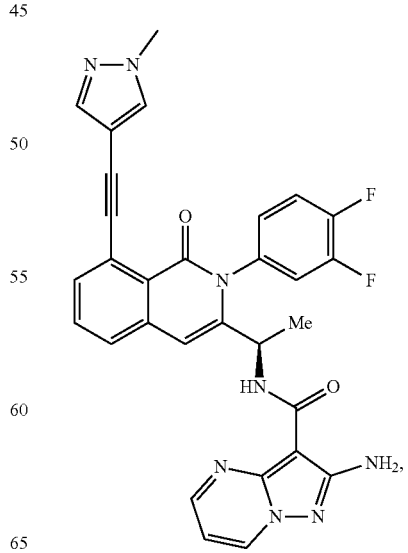
Compound 97r TABLE 11-continued
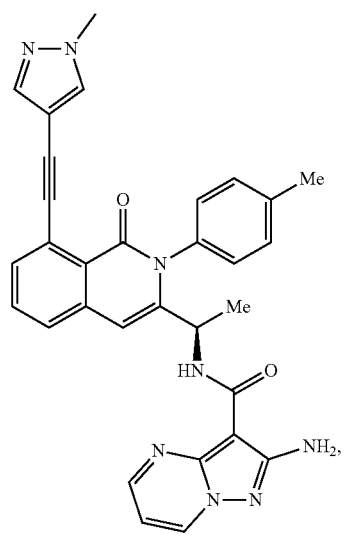
Compound 98r
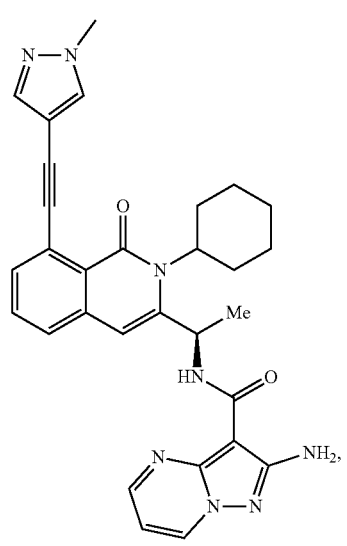
Compound 99r
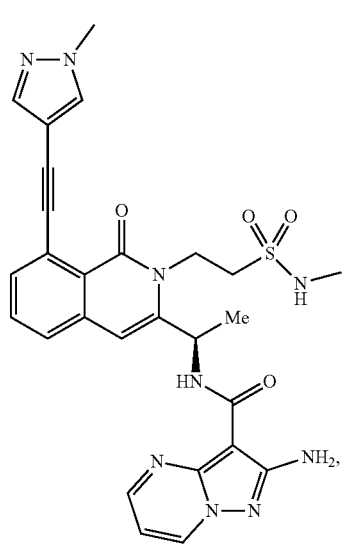 [SMILES: CNS(=O)(=O)CCn1c([C@@H](C)NC(=O)c2c(N)nn3cccnc23)cc2cccc(C#Cc3cnn(C)c3)c2c1=O]
Compound 100r
TABLE 11-continued
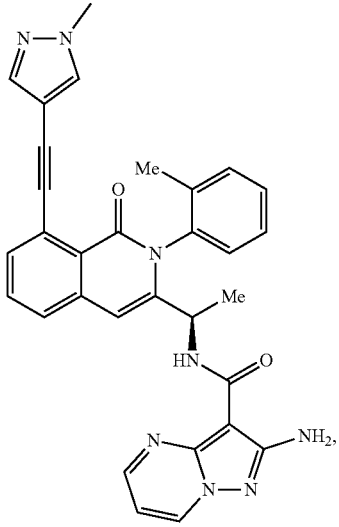
Compound 101r
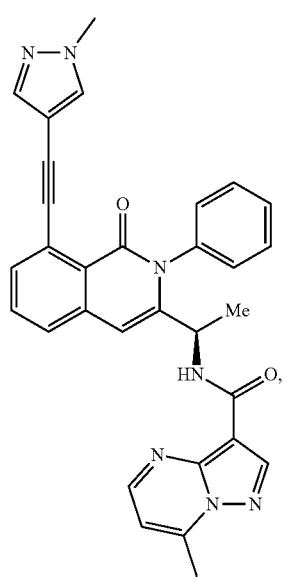 [SMILES: Cc1ccnc2c(C(=O)N[C@H](C)c3cc4cccc(C#Cc5cnn(C)c5)c4c(=O)n3-c3ccccc3)cnn12]
Compound 102r
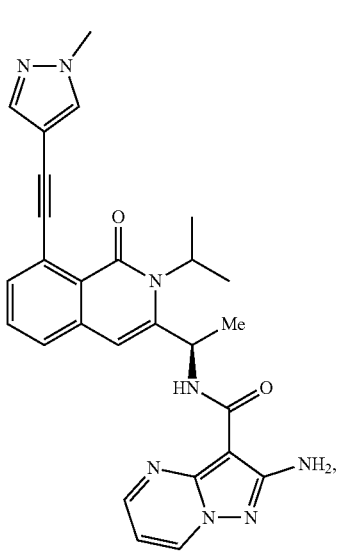
Compound 103r TABLE 11-continued
Compound 104r
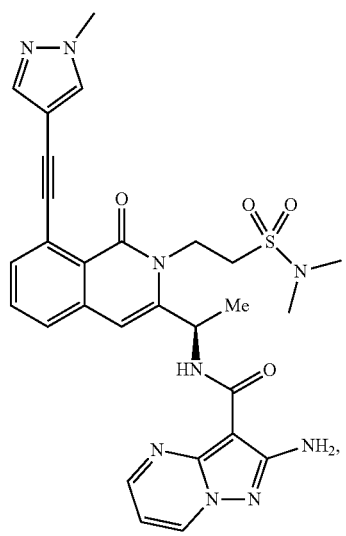 [SMILES: C[C@@H](NC(=O)c1c(N)nn2cccnc12)c1cc2cccc(C#Cc3cnn(C)c3)c2c(=O)n1CCS(=O)(=O)N(C)C]
Compound 105r
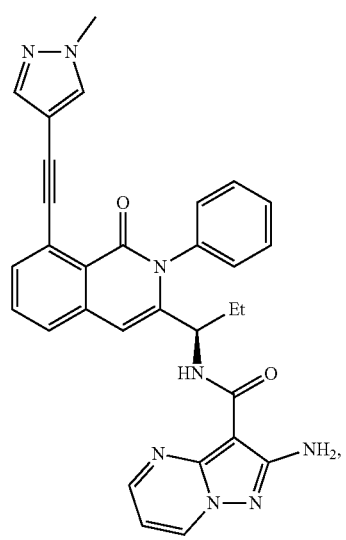
Compound 106r
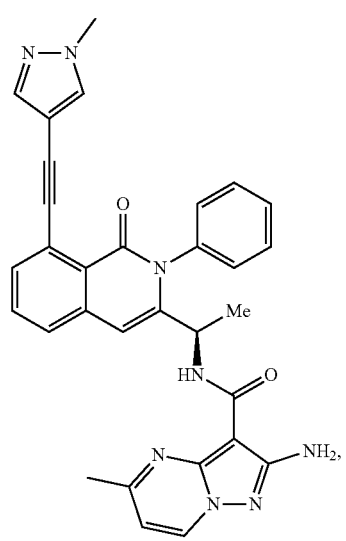 [SMILES: Cc1ccn2nc(N)c(C(=O)N[C@H](C)c3cc4cccc(C#Cc5cnn(C)c5)c4c(=O)n3-c3ccccc3)c2n1]
TABLE 11-continued
Compound 108r
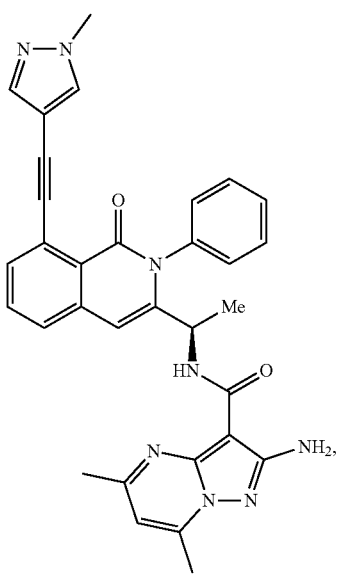 [SMILES: Cc1cc(C)n2nc(N)c(C(=O)N[C@H](C)c3cc4cccc(C#Cc5cnn(C)c5)c4c(=O)n3-c3ccccc3)c2n1]
Compound 109r
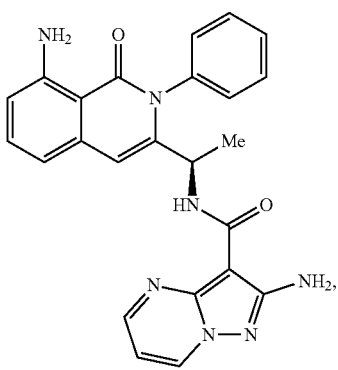 [SMILES: C[C@@H](NC(=O)c1c(N)nn2cccnc12)c1cc2cccc(N)c2c(=O)n1-c1ccccc1]
Compound 110r
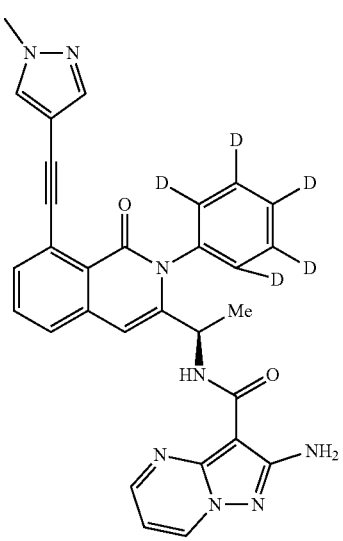 [SMILES: [2H]c1c([2H])c([2H])c(-n2c([C@@H](C)NC(=O)c3c(N)nn4cccnc34)cc3cccc(C#Cc4cnn(C)c4)c3c2=O)c([2H])c1[2H]]

TABLE 12
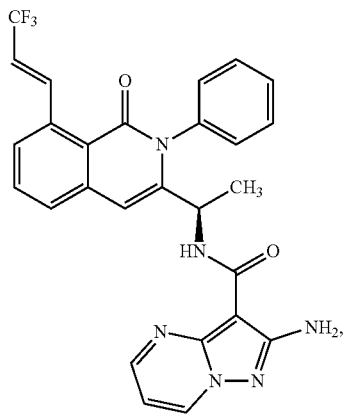
Compound 1001r
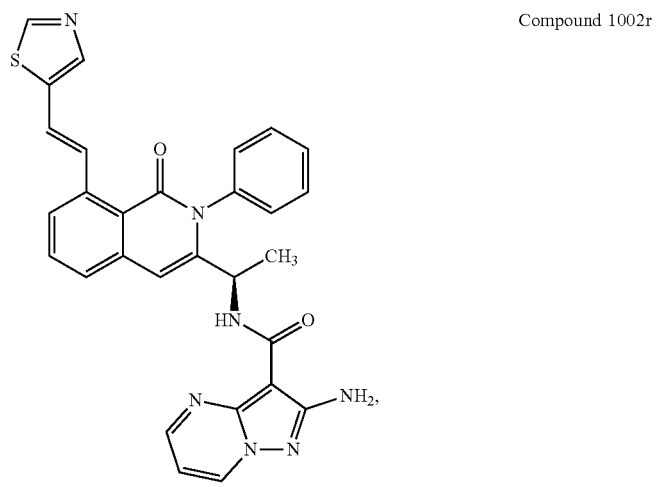
Compound 1002r
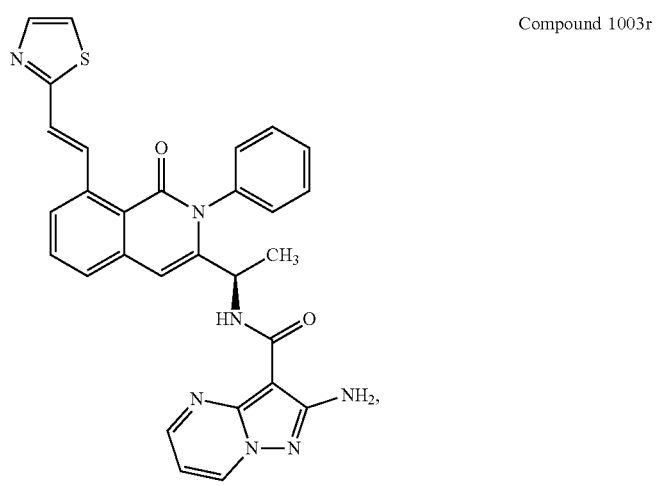
Compound 1003r TABLE 12-continued
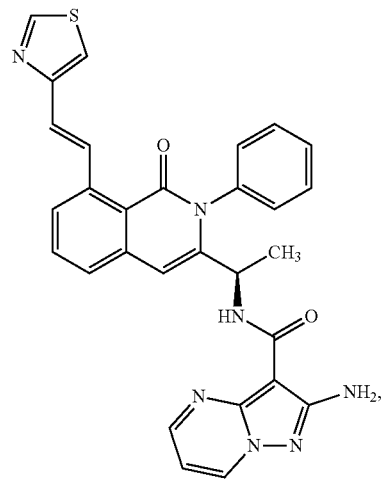
Compound 1004r
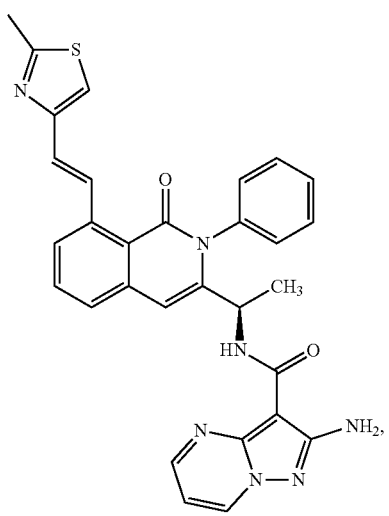 [SMILES: Cc1nc(/C=C/c2cccc3cc([C@@H](C)NC(=O)c4c(N)nn5cccnc45)n(-c4ccccc4)c(=O)c23)cs1]
Compound 1005r
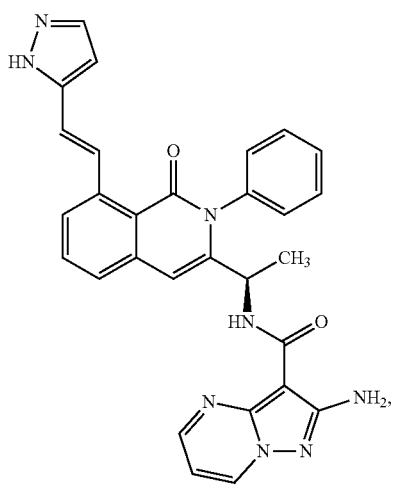
Compound 1006r TABLE 12-continued
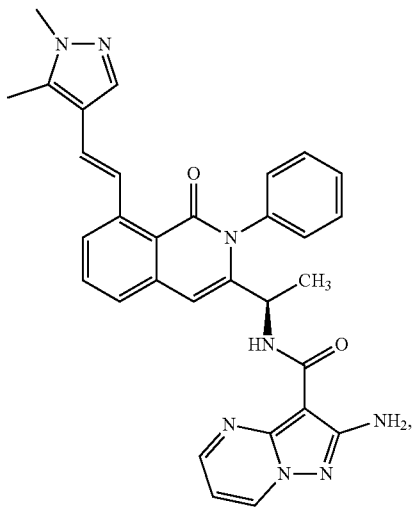
Compound 1007r
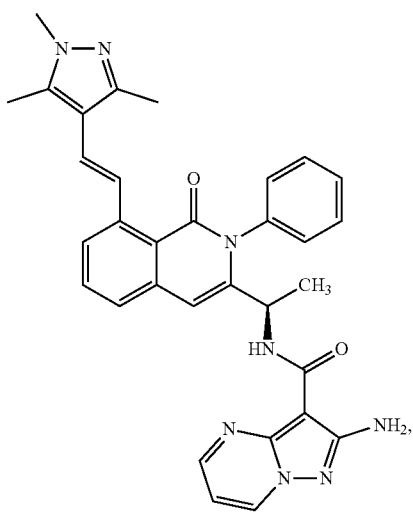
Compound 1008r
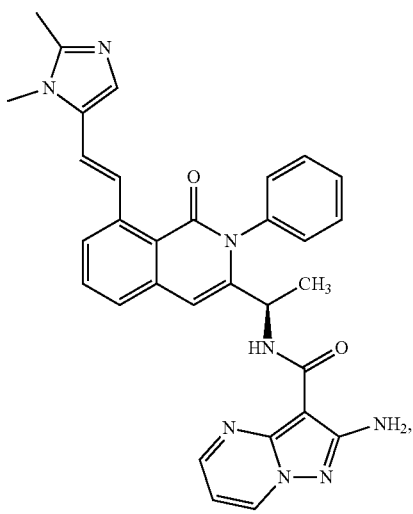
Compound 1009r TABLE 12-continued
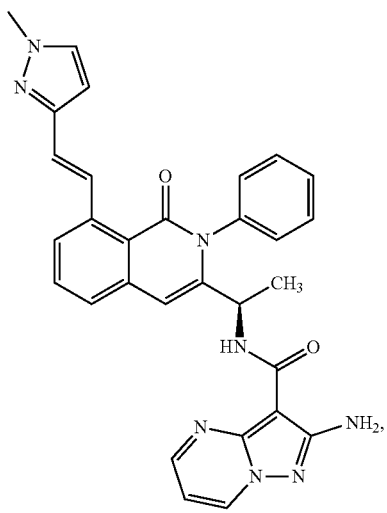 [SMILES: C[C@@H](NC(=O)c1c(N)nn2cccnc12)c1cc2cccc(/C=C/c3ccn(C)n3)c2c(=O)n1-c1ccccc1]
Compound 1010r
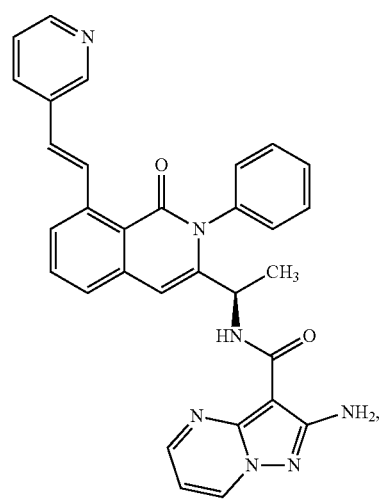
Compound 1011r
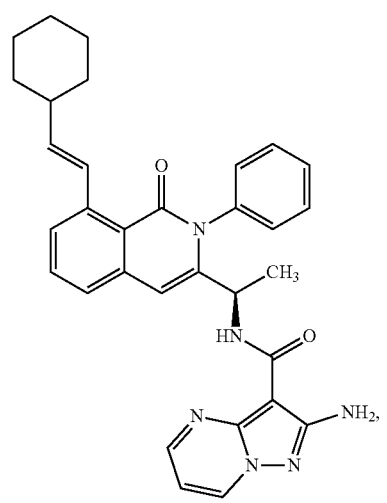
Compound 1012r TABLE 12-continued
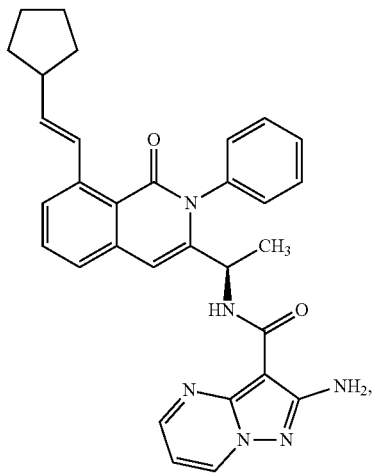 [SMILES: C[C@@H](NC(=O)c1c(N)nn2cccnc12)c1cc2cccc(/C=C/C3CCCC3)c2c(=O)n1-c1ccccc1]
Compound 1013r
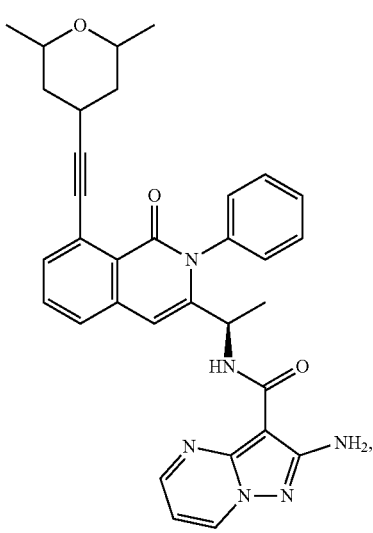
Compound 1014r
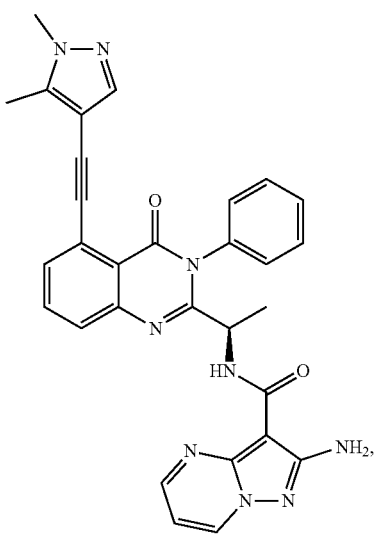 [SMILES: Cc1c(C#Cc2cccc3nc([C@@H](C)NC(=O)c4c(N)nn5cccnc45)n(-c4ccccc4)c(=O)c23)cnn1C]
Compound 1015r TABLE 12-continued
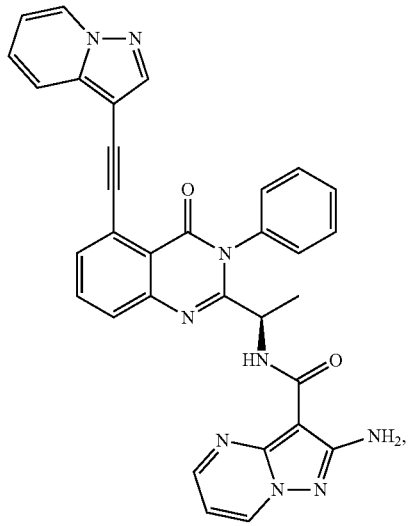 [SMILES: C[C@@H](NC(=O)c1c(N)nn2cccnc12)c1nc2cccc(C#Cc3cnn4ccccc34)c2c(=O)n1-c1ccccc1]
Compound 1016r
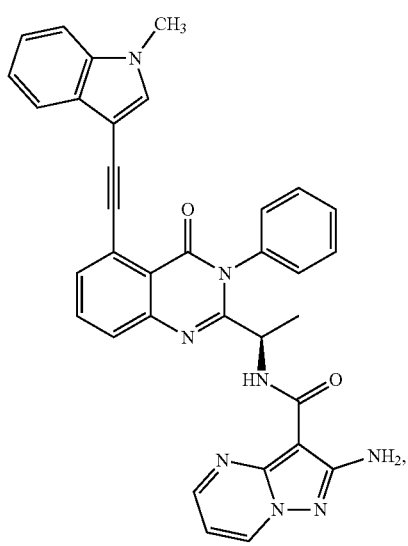 [SMILES: C[C@@H](NC(=O)c1c(N)nn2cccnc12)c1nc2cccc(C#Cc3cn(C)c4ccccc34)c2c(=O)n1-c1ccccc1]
Compound 1017r
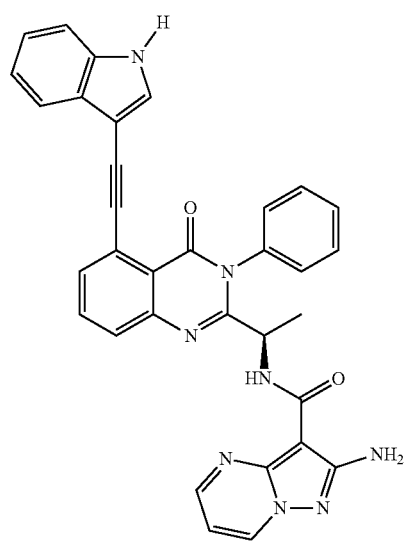 [SMILES: C[C@@H](NC(=O)c1c(N)nn2cccnc12)c1nc2cccc(C#Cc3c[nH]c4ccccc34)c2c(=O)n1-c1ccccc1]
Compound 1018r TABLE 12-continued
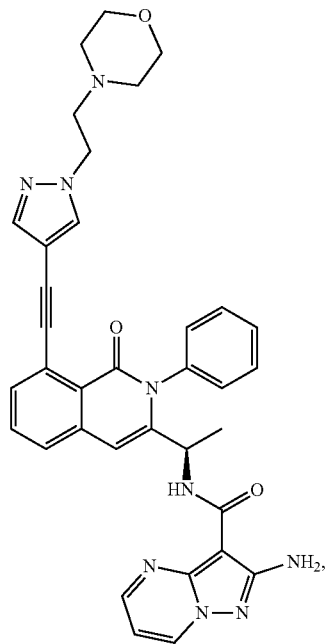 [SMILES: C[C@@H](NC(=O)c1c(N)nn2cccnc12)c1cc2cccc(C#Cc3cnn(CCN4CCOCC4)c3)c2c(=O)n1-c1ccccc1]
Compound 1019r
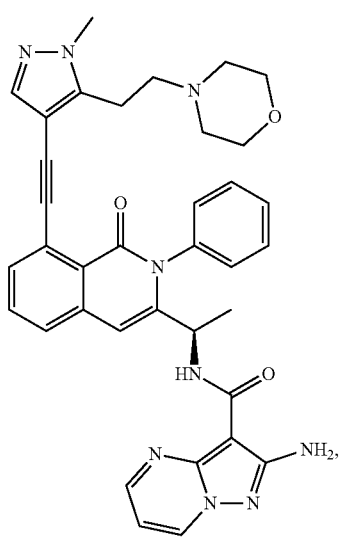
Compound 1020r TABLE 12-continued
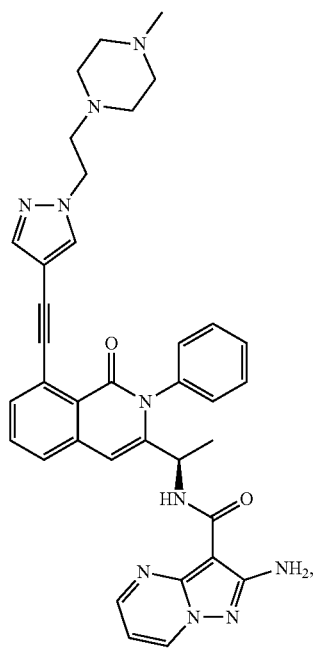 [SMILES: C[C@@H](NC(=O)c1c(N)nn2cccnc12)c1cc2cccc(C#Cc3cnn(CCN4CCN(C)CC4)c3)c2c(=O)n1-c1ccccc1]
Compound 1021r
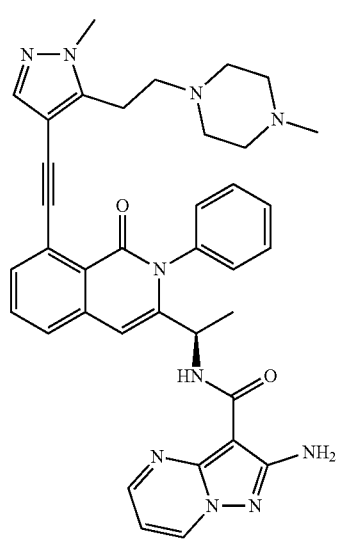
Compound 1022r TABLE 12-continued
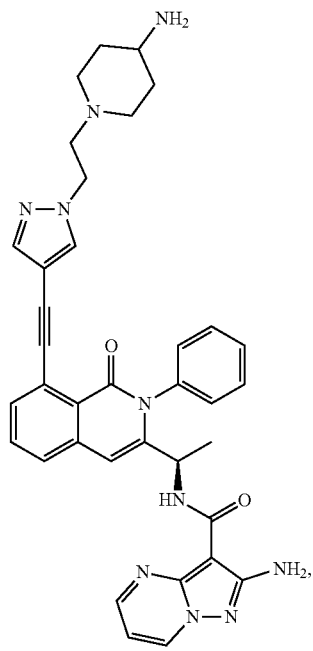 [SMILES: C[C@@H](NC(=O)c1c(N)nn2cccnc12)c1cc2cccc(C#Cc3cnn(CCN4CCC(N)CC4)c3)c2c(=O)n1-c1ccccc1]
Compound 1023r
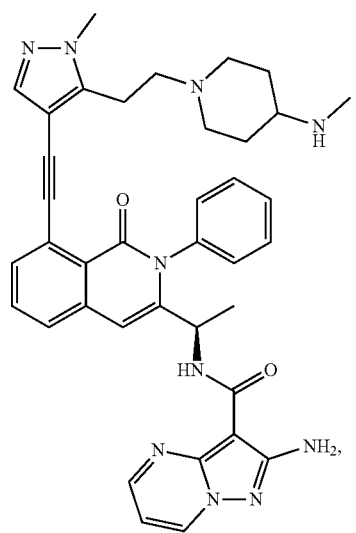 [SMILES: CNC1CCN(CCc2c(C#Cc3cccc4cc([C@@H](C)NC(=O)c5c(N)nn6cccnc56)n(-c5ccccc5)c(=O)c34)cnn2C)CC1]
Compound 1024r TABLE 12-continued
Compound 1025r
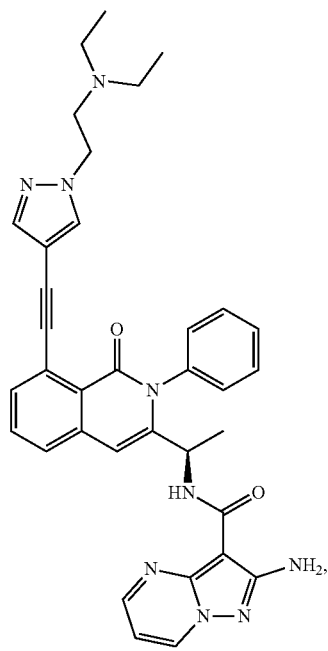 [SMILES: CCN(CC)CCn1cc(C#Cc2cccc3cc([C@@H](C)NC(=O)c4c(N)nn5cccnc45)n(-c4ccccc4)c(=O)c23)cn1]
Compound 1026r
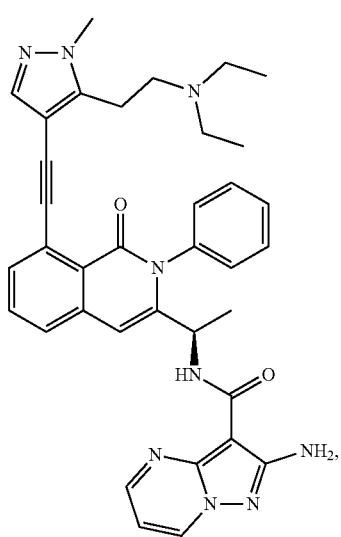

TABLE 12-continued
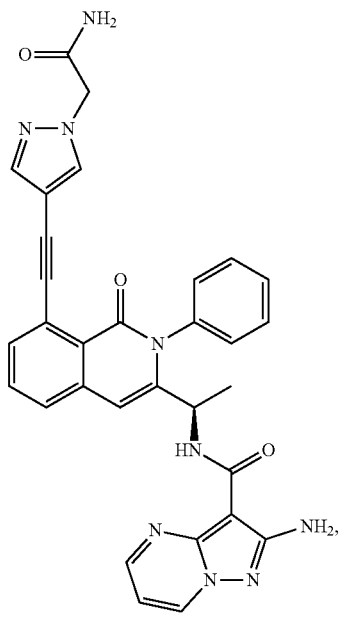
Compound 1027r
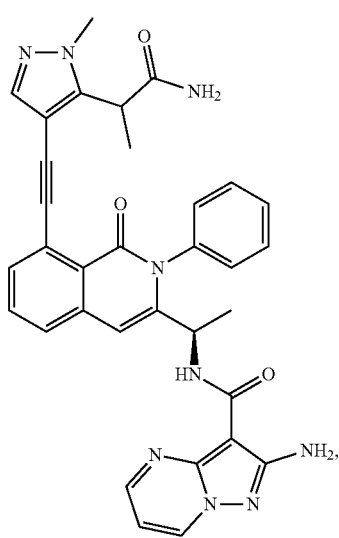
Compound 1028r

TABLE 12-continued
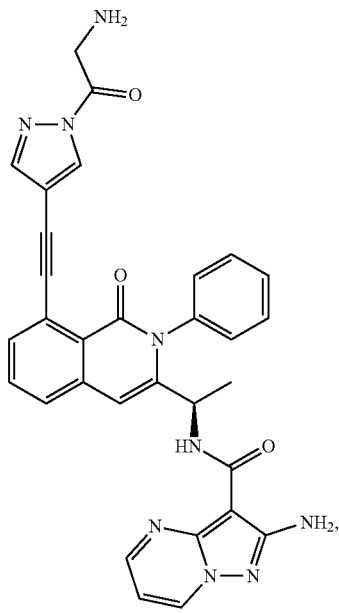
Compound 1029r
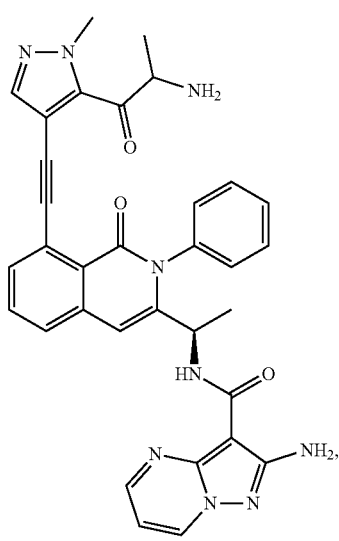
Compound 1030r

TABLE 12-continued
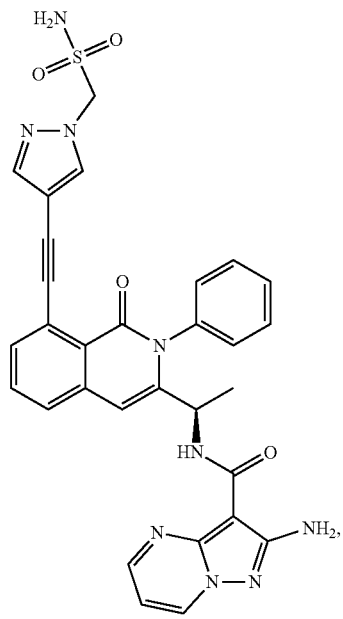 [SMILES: C[C@@H](NC(=O)c1c(N)nn2cccnc12)c1cc2cccc(C#Cc3cnn(CS(N)(=O)=O)c3)c2c(=O)n1-c1ccccc1]
Compound 1031r
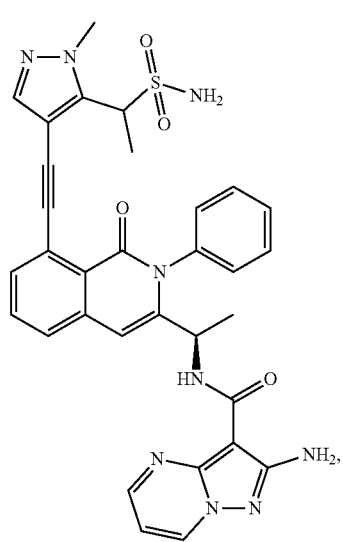
Compound 1032r

TABLE 12-continued
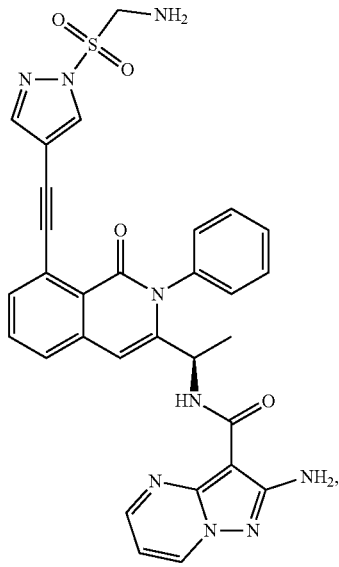
Compound 1033r
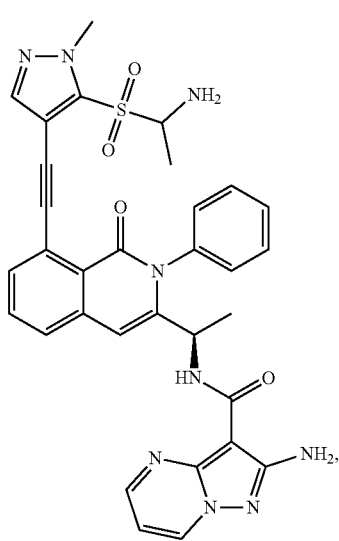 [SMILES: CC(N)S(=O)(=O)c1c(C#Cc2cccc3cc([C@@H](C)NC(=O)c4c(N)nn5cccnc45)n(-c4ccccc4)c(=O)c23)cnn1C]
Compound 1034r

TABLE 12-continued
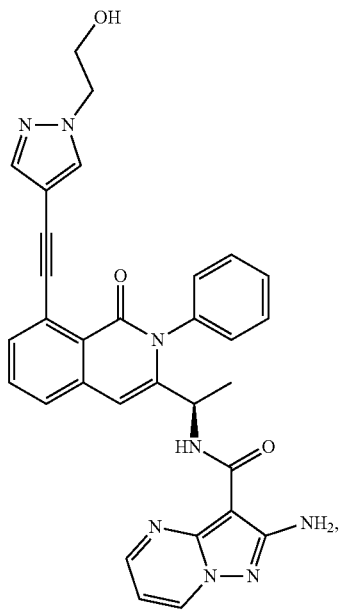
Compound 1035r
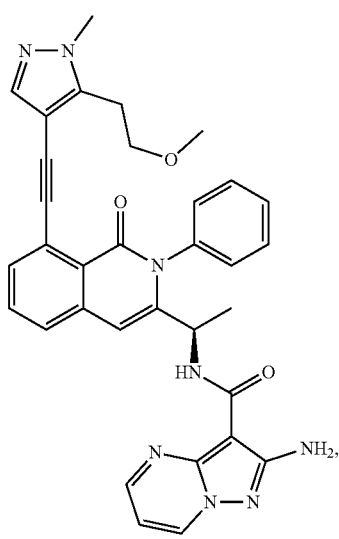
Compound 1036r

TABLE 12-continued
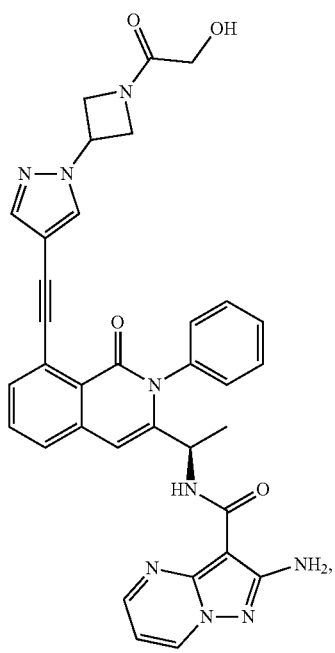
Compound 1037r
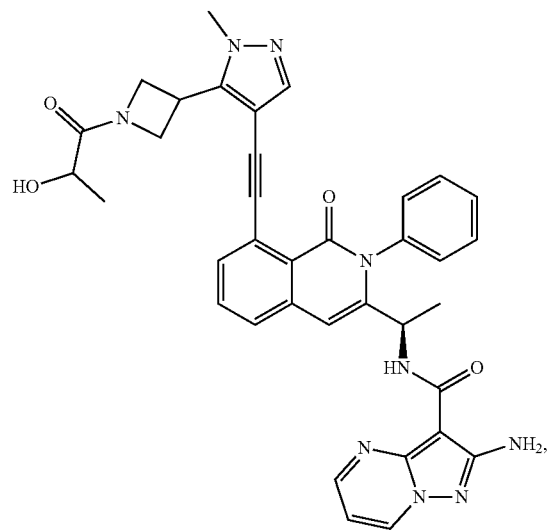 [SMILES: CC(O)C(=O)N1CC(c2c(C#Cc3cccc4cc([C@@H](C)NC(=O)c5c(N)nn6cccnc56)n(-c5ccccc5)c(=O)c34)cnn2C)C1]
Compound 1038r

TABLE 12-continued
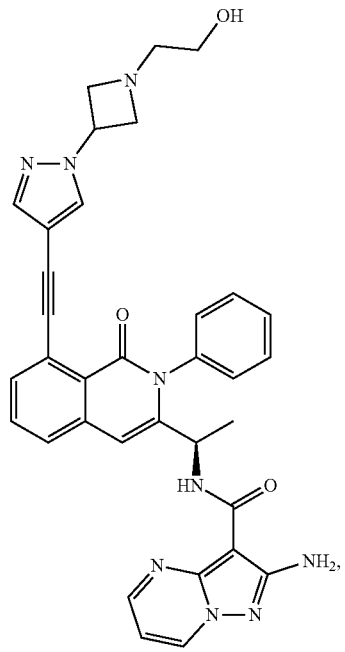
Compound 1039r
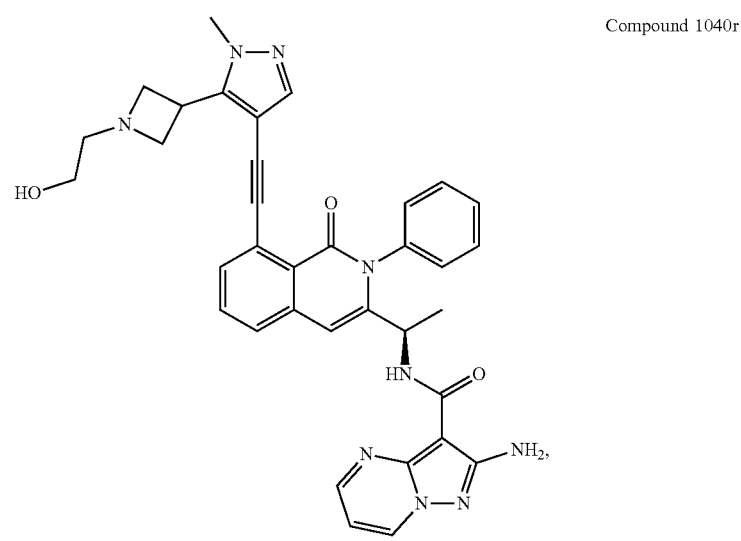
Compound 1040r

TABLE 12-continued
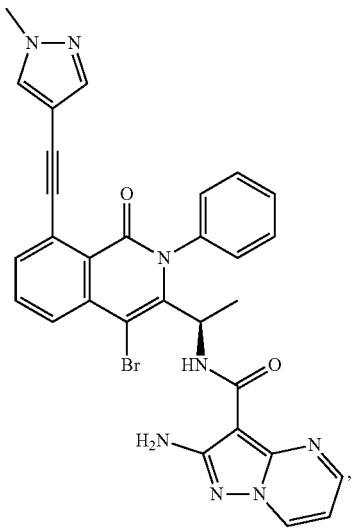 [SMILES: C[C@@H](NC(=O)c1c(N)nn2cccnc12)c1c(Br)c2cccc(C#Cc3cnn(C)c3)c2c(=O)n1-c1ccccc1]
Compound 1041r
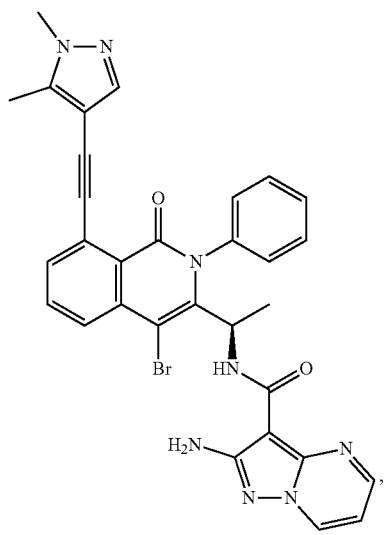 [SMILES: Cc1c(C#Cc2cccc3c(Br)c([C@@H](C)NC(=O)c4c(N)nn5cccnc45)n(-c4ccccc4)c(=O)c23)cnn1C]
Compound 1042r
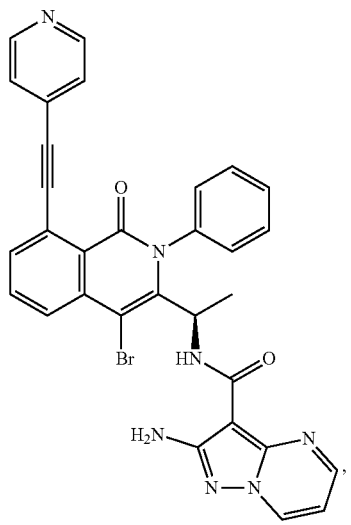 [SMILES: C[C@@H](NC(=O)c1c(N)nn2cccnc12)c1c(Br)c2cccc(C#Cc3ccncc3)c2c(=O)n1-c1ccccc1]
Compound 1043r TABLE 12-continued
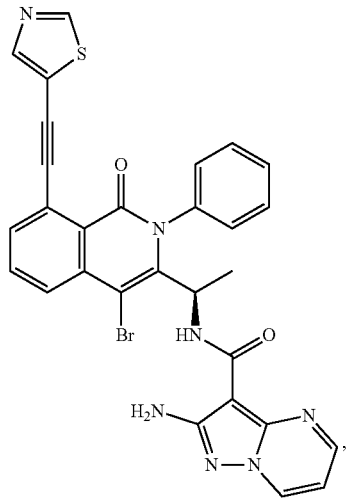 [SMILES: C[C@@H](NC(=O)c1c(N)nn2cccnc12)c1c(Br)c2cccc(C#Cc3cncs3)c2c(=O)n1-c1ccccc1]
Compound 1044r
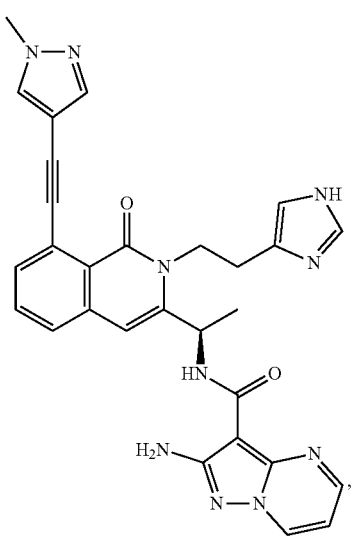 [SMILES: C[C@@H](NC(=O)c1c(N)nn2cccnc12)c1cc2cccc(C#Cc3cnn(C)c3)c2c(=O)n1CCc1c[nH]cn1]
Compound 1045r
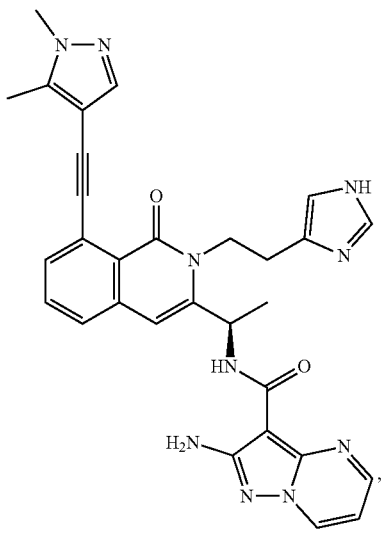 [SMILES: Cc1c(C#Cc2cccc3cc([C@@H](C)NC(=O)c4c(N)nn5cccnc45)n(CCc4c[nH]cn4)c(=O)c23)cnn1C]
Compound 1046r TABLE 12-continued
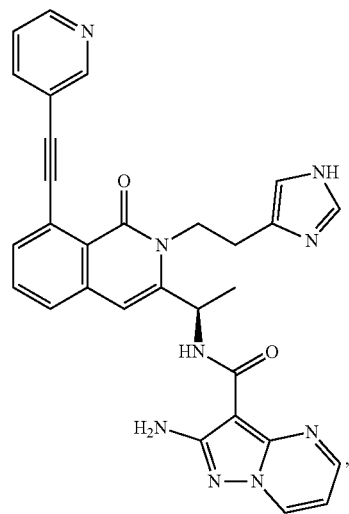 [SMILES: C[C@@H](NC(=O)c1c(N)nn2cccnc12)c1cc2cccc(C#Cc3cccnc3)c2c(=O)n1CCc1c[nH]cn1]
Compound 1047r
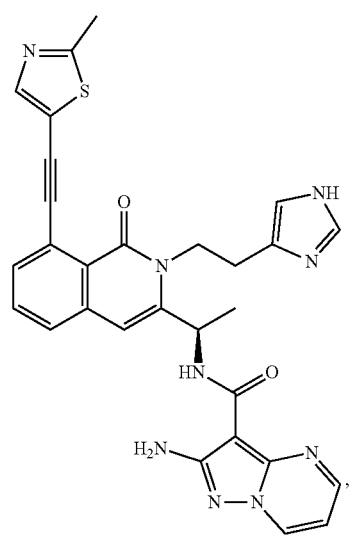 [SMILES: Cc1ncc(C#Cc2cccc3cc([C@@H](C)NC(=O)c4c(N)nn5cccnc45)n(CCc4c[nH]cn4)c(=O)c23)s1]
Compound 1048r
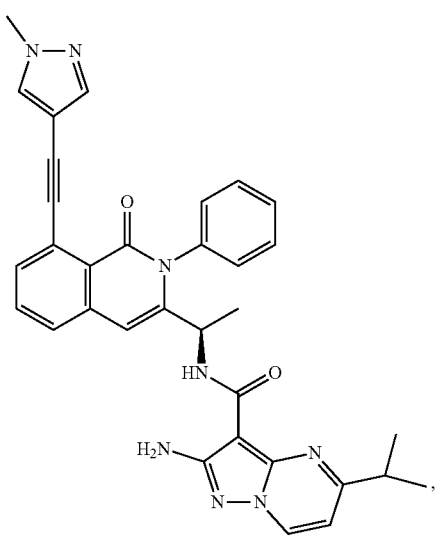 [SMILES: CC(C)c1ccn2nc(N)c(C(=O)N[C@H](C)c3cc4cccc(C#Cc5cnn(C)c5)c4c(=O)n3-c3ccccc3)c2n1]
Compound 1049r TABLE 12-continued
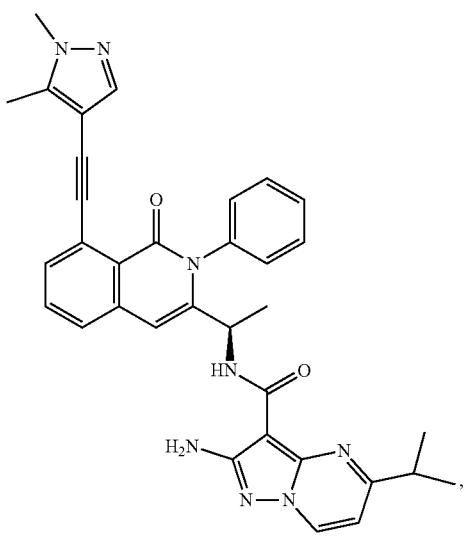 [SMILES: Cc1c(C#Cc2cccc3cc([C@@H](C)NC(=O)c4c(N)nn5ccc(C(C)C)nc45)n(-c4ccccc4)c(=O)c23)cnn1C]
Compound 1050r
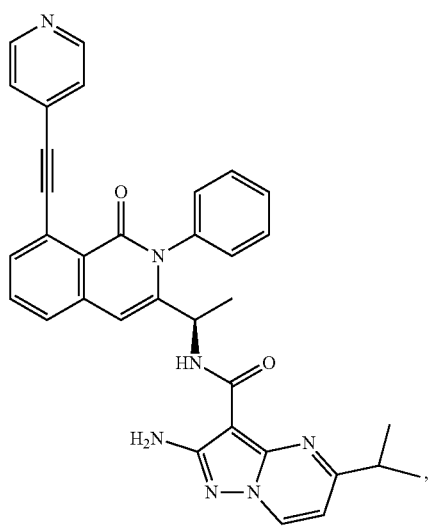 [SMILES: CC(C)c1ccn2nc(N)c(C(=O)N[C@H](C)c3cc4cccc(C#Cc5ccncc5)c4c(=O)n3-c3ccccc3)c2n1]
Compound 1051r
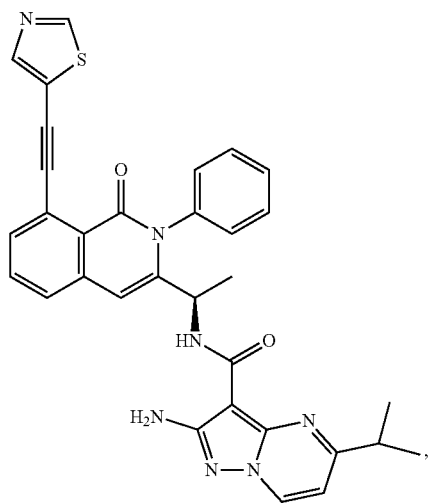 [SMILES: CC(C)c1ccn2nc(N)c(C(=O)N[C@H](C)c3cc4cccc(C#Cc5cncs5)c4c(=O)n3-c3ccccc3)c2n1]
Compound 1052r TABLE 12-continued
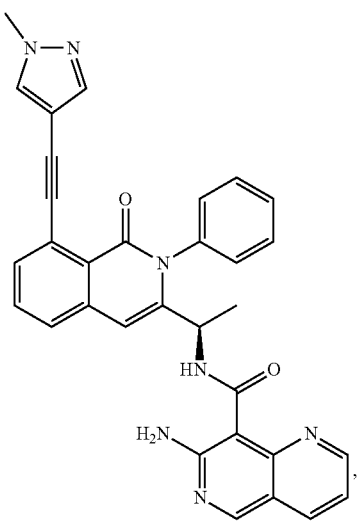 [SMILES: C[C@@H](NC(=O)c1c(N)ncc2cccnc12)c1cc2cccc(C#Cc3cnn(C)c3)c2c(=O)n1-c1ccccc1]
Compound 1053r
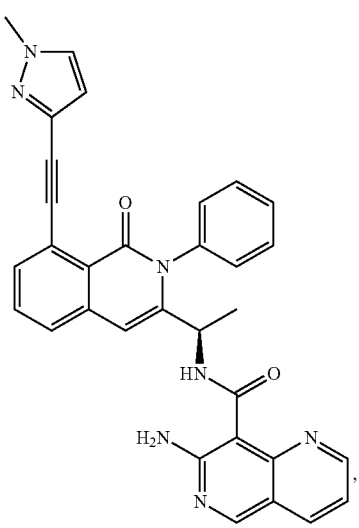 [SMILES: C[C@@H](NC(=O)c1c(N)ncc2cccnc12)c1cc2cccc(C#Cc3ccn(C)n3)c2c(=O)n1-c1ccccc1]
Compound 1054r
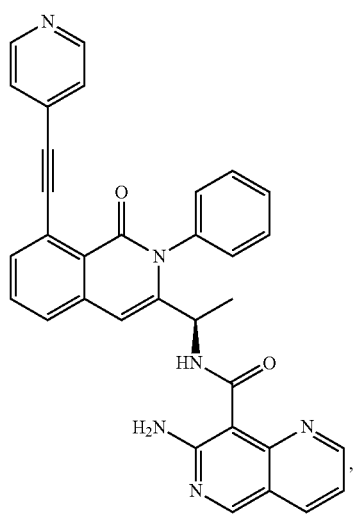 [SMILES: C[C@@H](NC(=O)c1c(N)ncc2cccnc12)c1cc2cccc(C#Cc3ccncc3)c2c(=O)n1-c1ccccc1]
Compound 1055r TABLE 12-continued
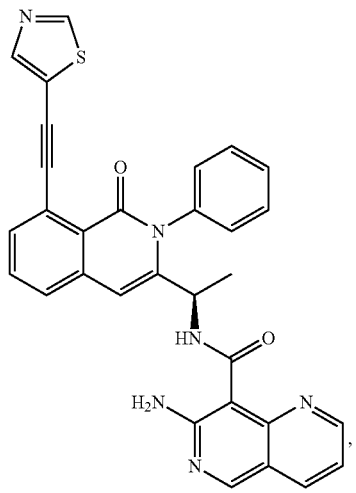 [SMILES: C[C@@H](NC(=O)c1c(N)ncc2cccnc12)c1cc2cccc(C#Cc3cncs3)c2c(=O)n1-c1ccccc1]
Compound 1056r
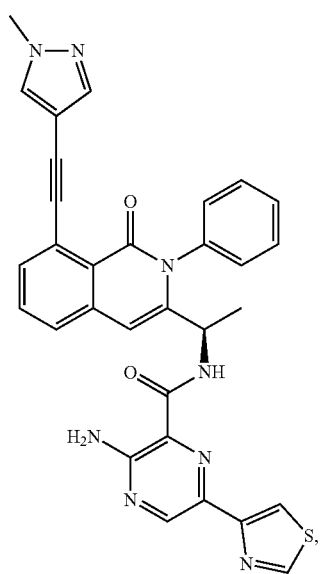 [SMILES: C[C@@H](NC(=O)c1nc(-c2cscn2)cnc1N)c1cc2cccc(C#Cc3cnn(C)c3)c2c(=O)n1-c1ccccc1]
Compound 1057r
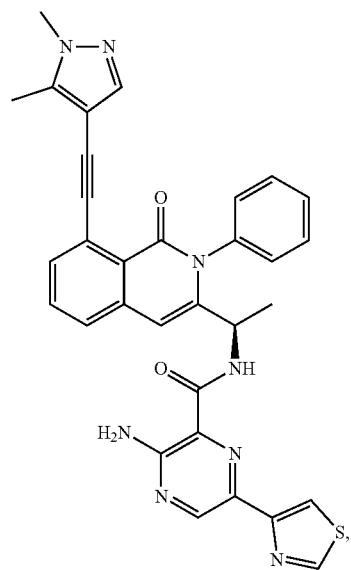
Compound 1058r TABLE 12-continued
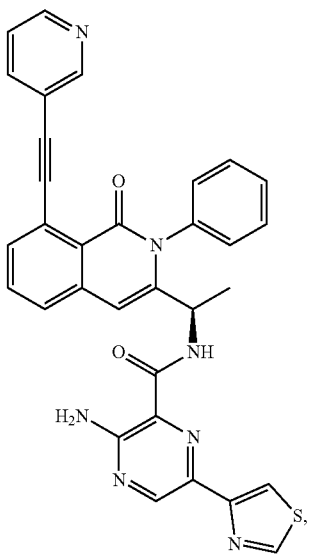 [SMILES: C[C@@H](NC(=O)c1nc(-c2cscn2)cnc1N)c1cc2cccc(C#Cc3cccnc3)c2c(=O)n1-c1ccccc1]
Compound 1059r
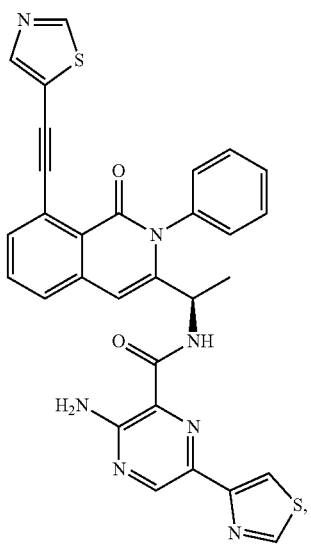
Compound 1060r TABLE 12-continued
Compound 1061r
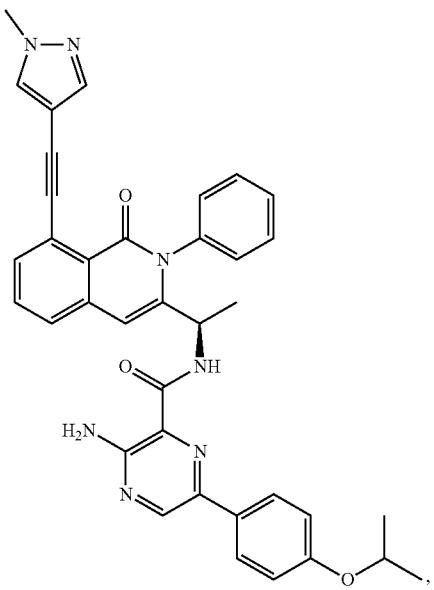 [SMILES: CC(C)Oc1ccc(-c2cnc(N)c(C(=O)N[C@H](C)c3cc4cccc(C#Cc5cnn(C)c5)c4c(=O)n3-c3ccccc3)n2)cc1]
Compound 1062r
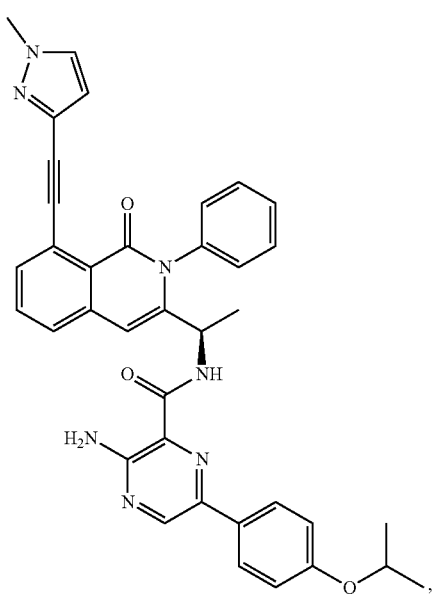 [SMILES: CC(C)Oc1ccc(-c2cnc(N)c(C(=O)N[C@H](C)c3cc4cccc(C#Cc5ccn(C)n5)c4c(=O)n3-c3ccccc3)n2)cc1]

TABLE 12-continued
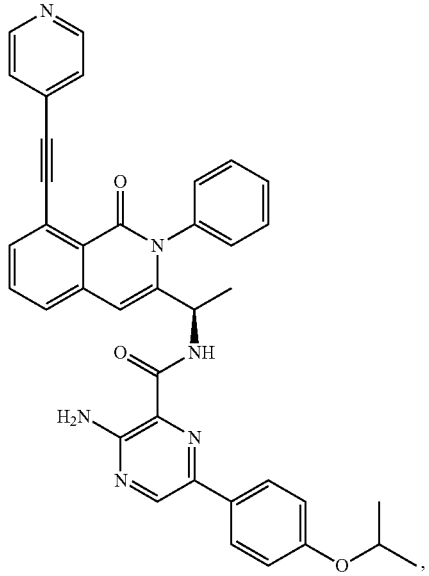 [SMILES: CC(C)Oc1ccc(-c2cnc(N)c(C(=O)N[C@H](C)c3cc4cccc(C#Cc5ccncc5)c4c(=O)n3-c3ccccc3)n2)cc1]
Compound 1063r
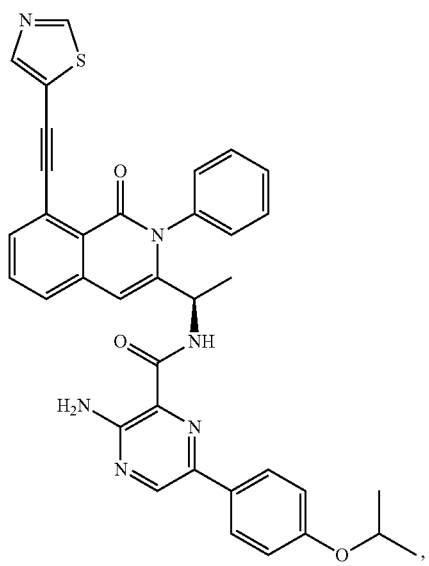 [SMILES: CC(C)Oc1ccc(-c2cnc(N)c(C(=O)N[C@H](C)c3cc4cccc(C#Cc5cncs5)c4c(=O)n3-c3ccccc3)n2)cc1]
Compound 1064r

TABLE 12-continued
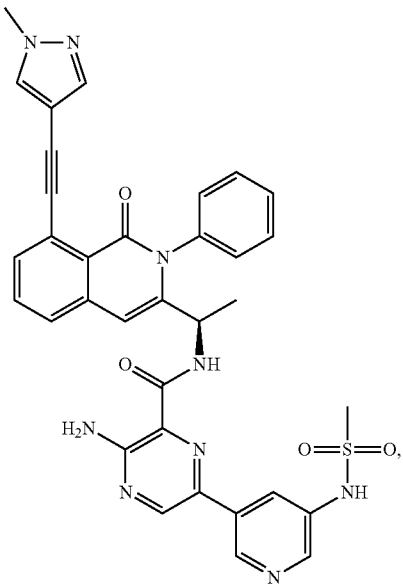 [SMILES: C[C@@H](NC(=O)c1nc(-c2cncc(NS(C)(=O)=O)c2)cnc1N)c1cc2cccc(C#Cc3cnn(C)c3)c2c(=O)n1-c1ccccc1]
Compound 1065r
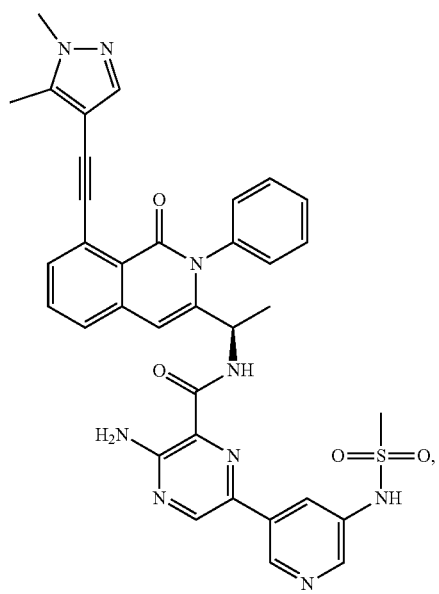
Compound 1066r

TABLE 12-continued
Compound 1067r
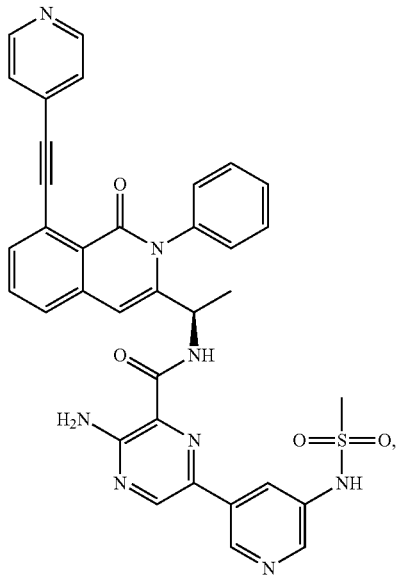 [SMILES: C[C@@H](NC(=O)c1nc(-c2cncc(NS(C)(=O)=O)c2)cnc1N)c1cc2cccc(C#Cc3ccncc3)c2c(=O)n1-c1ccccc1]
Compound 1068r
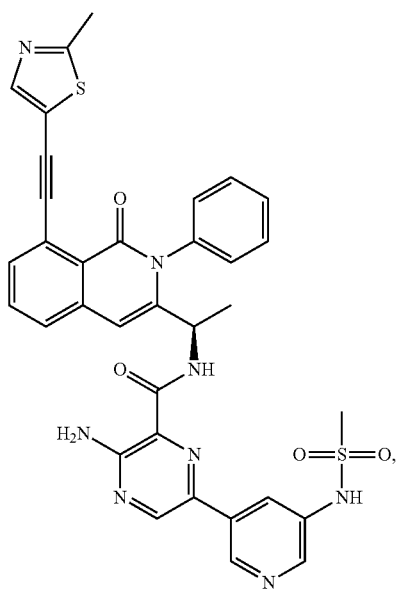 [SMILES: Cc1ncc(C#Cc2cccc3cc([C@@H](C)NC(=O)c4nc(-c5cncc(NS(C)(=O)=O)c5)cnc4N)n(-c4ccccc4)c(=O)c23)s1]

TABLE 12-continued
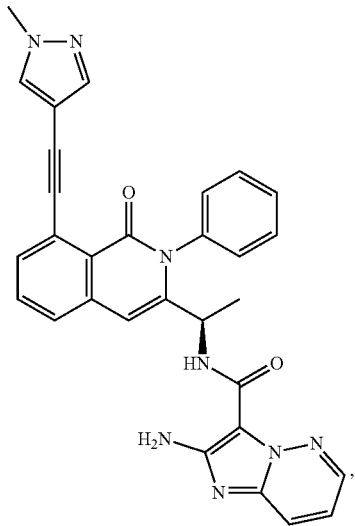 [SMILES: C[C@@H](NC(=O)c1c(N)nc2cccnn12)c1cc2cccc(C#Cc3cnn(C)c3)c2c(=O)n1-c1ccccc1]
Compound 1069r
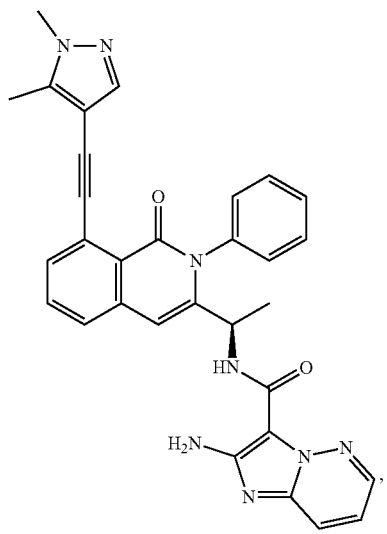 [SMILES: Cc1c(C#Cc2cccc3cc([C@@H](C)NC(=O)c4c(N)nc5cccnn45)n(-c4ccccc4)c(=O)c23)cnn1C]
Compound 1070r
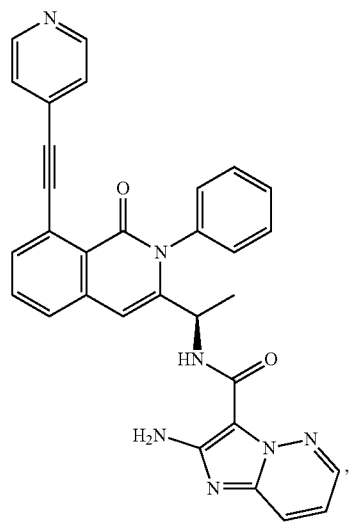 [SMILES: C[C@@H](NC(=O)c1c(N)nc2cccnn12)c1cc2cccc(C#Cc3ccncc3)c2c(=O)n1-c1ccccc1]
Compound 1071r TABLE 12-continued
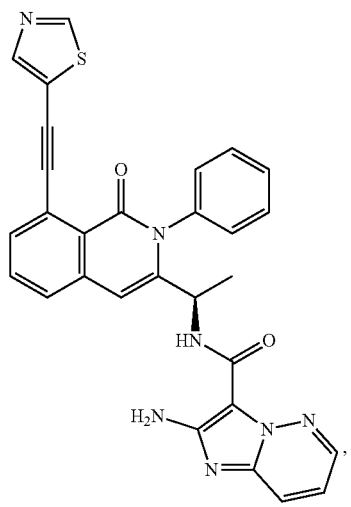 [SMILES: C[C@@H](NC(=O)c1c(N)nc2cccnn12)c1cc2cccc(C#Cc3cncs3)c2c(=O)n1-c1ccccc1]
Compound 1072r
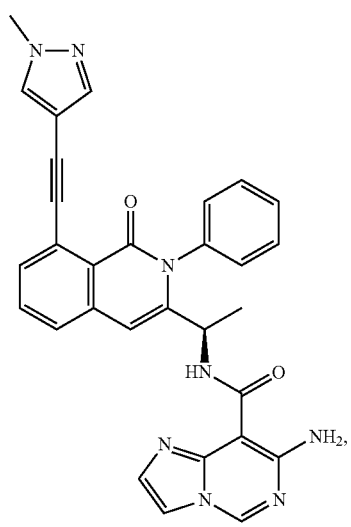 [SMILES: C[C@@H](NC(=O)c1c(N)ncn2ccnc12)c1cc2cccc(C#Cc3cnn(C)c3)c2c(=O)n1-c1ccccc1]
Compound 1073r
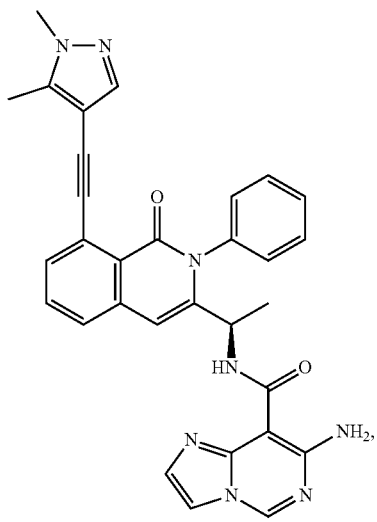 [SMILES: Cc1c(C#Cc2cccc3cc([C@@H](C)NC(=O)c4c(N)ncn5ccnc45)n(-c4ccccc4)c(=O)c23)cnn1C]
Compound 1074r TABLE 12-continued
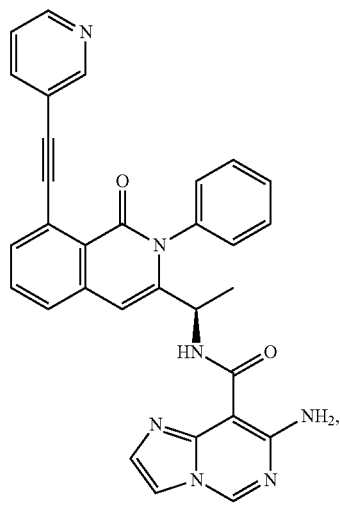 [SMILES: C[C@@H](NC(=O)c1c(N)ncn2ccnc12)c1cc2cccc(C#Cc3cccnc3)c2c(=O)n1-c1ccccc1]
Compound 1075r
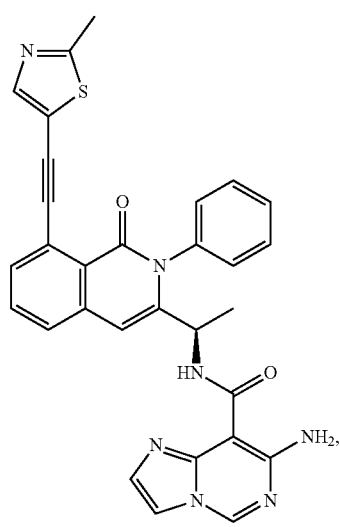 [SMILES: Cc1ncc(C#Cc2cccc3cc([C@@H](C)NC(=O)c4c(N)ncn5ccnc45)n(-c4ccccc4)c(=O)c23)s1]
Compound 1076r
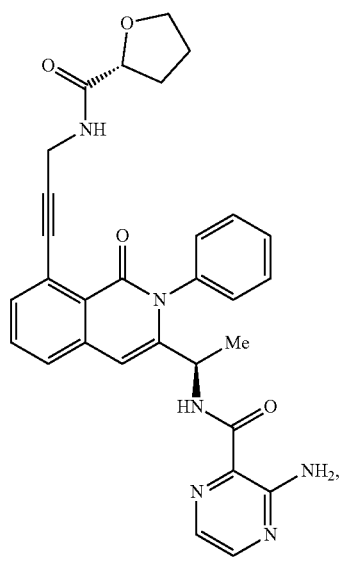 [SMILES: C[C@@H](NC(=O)c1nccnc1N)c1cc2cccc(C#CCNC(=O)[C@H]3CCCO3)c2c(=O)n1-c1ccccc1]
Compound 1077r TABLE 12-continued
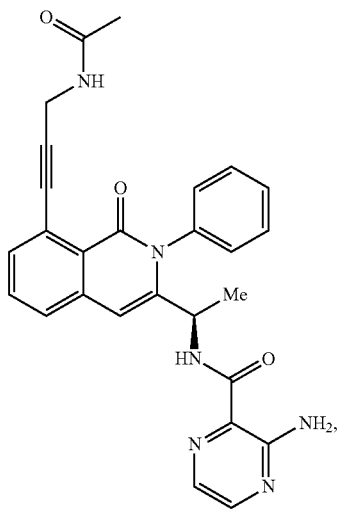 [SMILES: CC(=O)NCC#Cc1cccc2cc([C@@H](C)NC(=O)c3nccnc3N)n(-c3ccccc3)c(=O)c12]
Compound 1078r
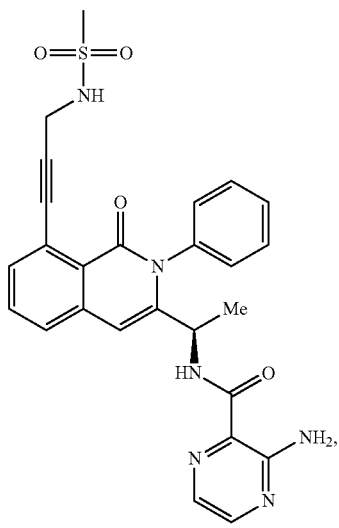 [SMILES: C[C@@H](NC(=O)c1nccnc1N)c1cc2cccc(C#CCNS(C)(=O)=O)c2c(=O)n1-c1ccccc1]
Compound 1079r
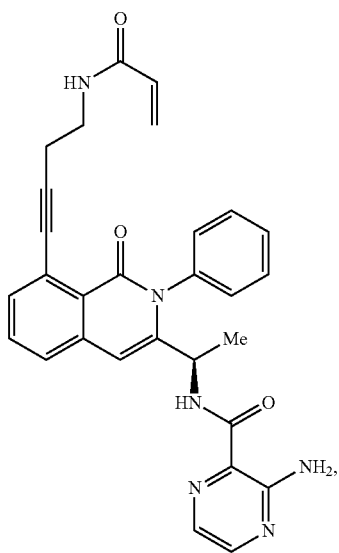 [SMILES: C=CC(=O)NCCC#Cc1cccc2cc([C@@H](C)NC(=O)c3nccnc3N)n(-c3ccccc3)c(=O)c12]
Compound 1080r TABLE 12-continued
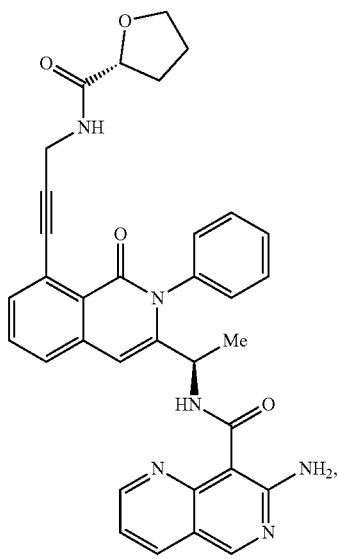 [SMILES: C[C@@H](NC(=O)c1c(N)ncc2cccnc12)c1cc2cccc(C#CCNC(=O)[C@H]3CCCO3)c2c(=O)n1-c1ccccc1]
Compound 1081r
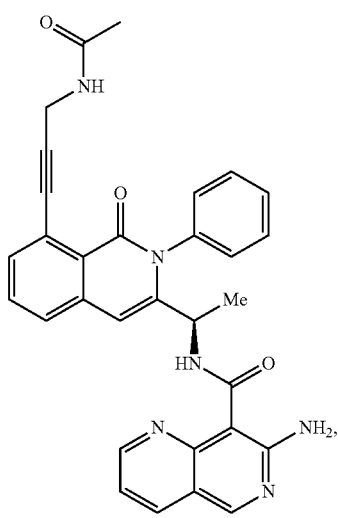 [SMILES: CC(=O)NCC#Cc1cccc2cc([C@@H](C)NC(=O)c3c(N)ncc4cccnc34)n(-c3ccccc3)c(=O)c12]
Compound 1082r
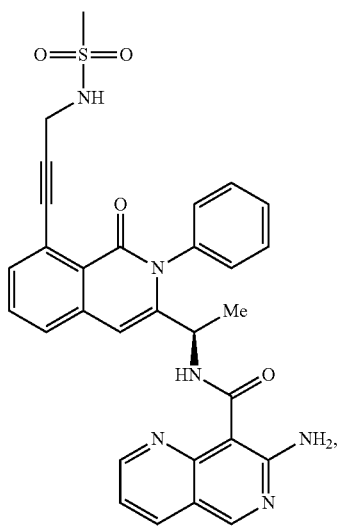 [SMILES: C[C@@H](NC(=O)c1c(N)ncc2cccnc12)c1cc2cccc(C#CCNS(C)(=O)=O)c2c(=O)n1-c1ccccc1]
Compound 1083r TABLE 12-continued
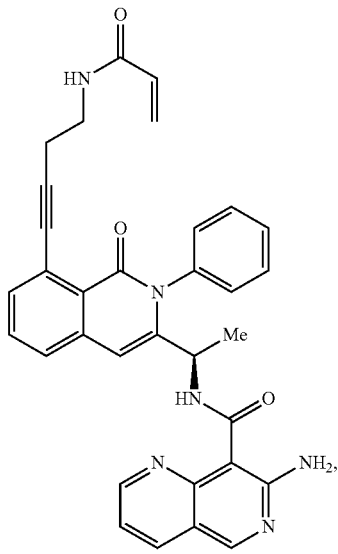 [SMILES: C=CC(=O)NCCC#Cc1cccc2cc([C@@H](C)NC(=O)c3c(N)ncc4cccnc34)n(-c3ccccc3)c(=O)c12]
Compound 1084r
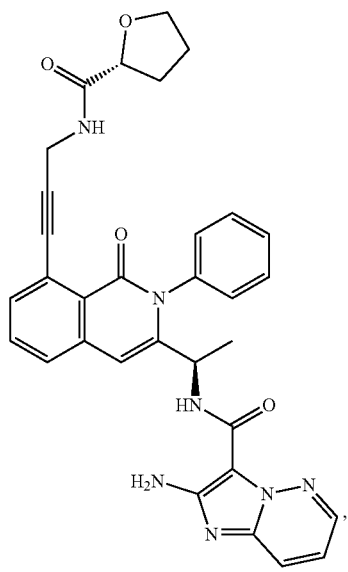 [SMILES: C[C@@H](NC(=O)c1c(N)nc2cccnn12)c1cc2cccc(C#CCNC(=O)[C@H]3CCCO3)c2c(=O)n1-c1ccccc1]
Compound 1085r
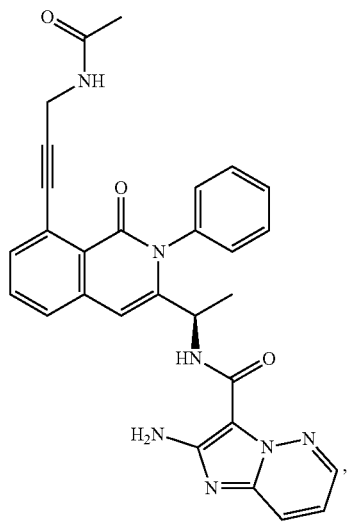 [SMILES: CC(=O)NCC#Cc1cccc2cc([C@@H](C)NC(=O)c3c(N)nc4cccnn34)n(-c3ccccc3)c(=O)c12]
Compound 1086r TABLE 12-continued
Compound 1087r
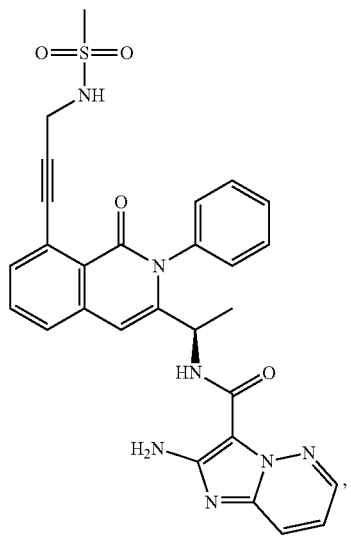 [SMILES: C[C@@H](NC(=O)c1c(N)nc2cccnn12)c1cc2cccc(C#CCNS(C)(=O)=O)c2c(=O)n1-c1ccccc1]
Compound 1088r
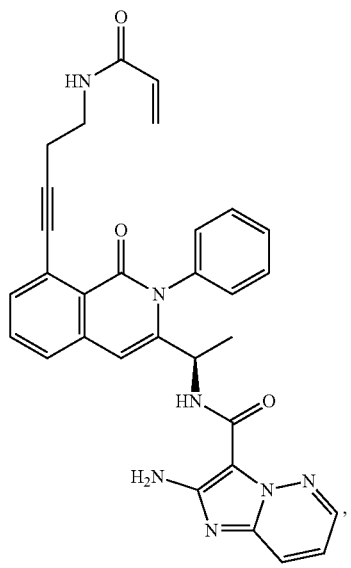 [SMILES: C=CC(=O)NCCC#Cc1cccc2cc([C@@H](C)NC(=O)c3c(N)nc4cccnn34)n(-c3ccccc3)c(=O)c12]
Compound 1089r
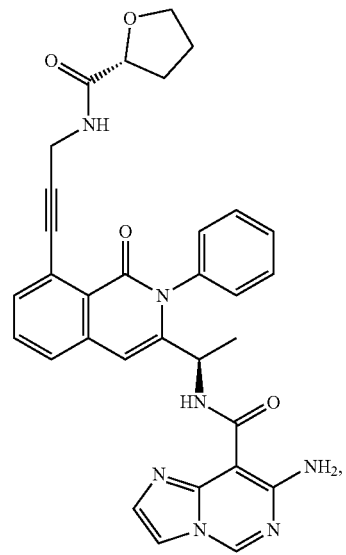 [SMILES: C[C@@H](NC(=O)c1c(N)ncn2ccnc12)c1cc2cccc(C#CCNC(=O)[C@H]3CCCO3)c2c(=O)n1-c1ccccc1]

TABLE 12-continued
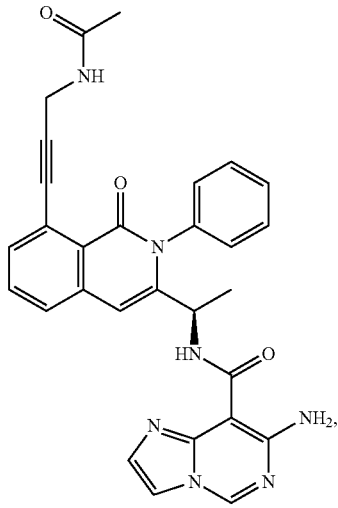 [SMILES: CC(=O)NCC#Cc1cccc2cc([C@@H](C)NC(=O)c3c(N)ncn4ccnc34)n(-c3ccccc3)c(=O)c12]
Compound 1090r
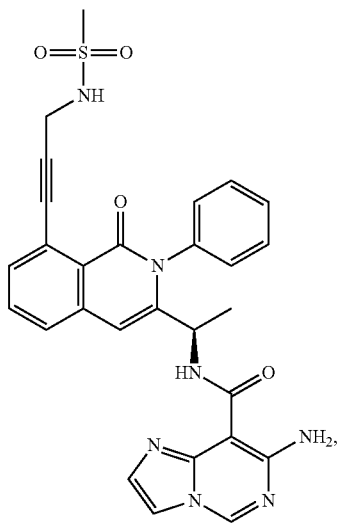 [SMILES: C[C@@H](NC(=O)c1c(N)ncn2ccnc12)c1cc2cccc(C#CCNS(C)(=O)=O)c2c(=O)n1-c1ccccc1]
Compound 1091r
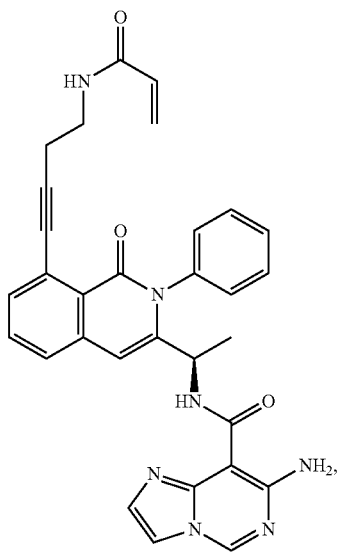 [SMILES: C=CC(=O)NCCC#Cc1cccc2cc([C@@H](C)NC(=O)c3c(N)ncn4ccnc34)n(-c3ccccc3)c(=O)c12]
Compound 1092r TABLE 12-continued
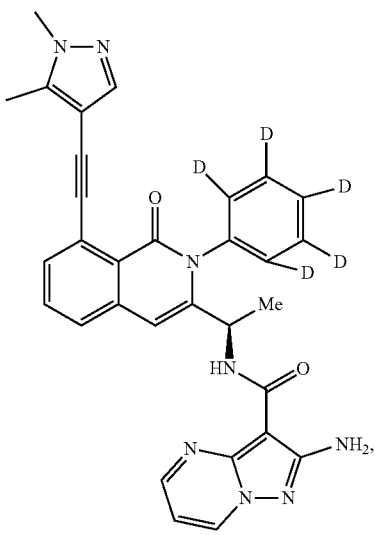 [SMILES: [2H]c1c([2H])c([2H])c(-n2c([C@@H](C)NC(=O)c3c(N)nn4cccnc34)cc3cccc(C#Cc4cnn(C)c4C)c3c2=O)c([2H])c1[2H]]
Compound 1093r
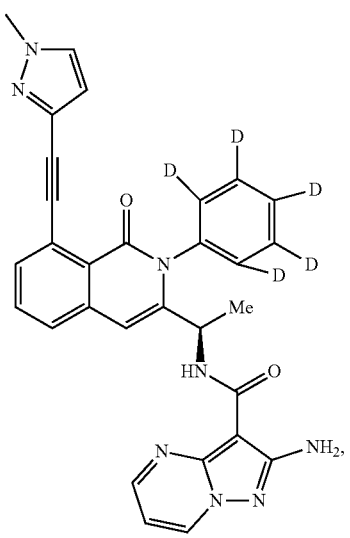 [SMILES: [2H]c1c([2H])c([2H])c(-n2c([C@@H](C)NC(=O)c3c(N)nn4cccnc34)cc3cccc(C#Cc4ccn(C)n4)c3c2=O)c([2H])c1[2H]]
Compound 1094r
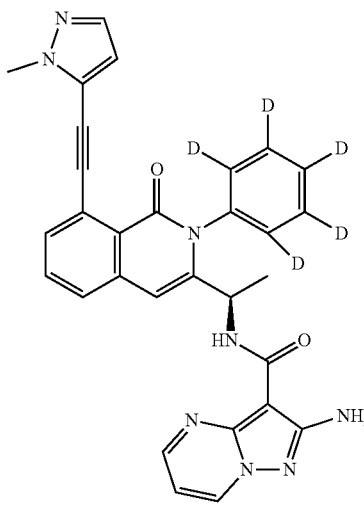
Compound 1095r TABLE 13
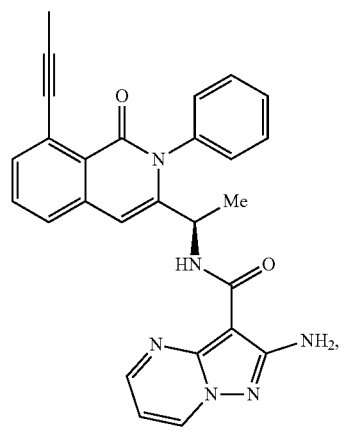 [SMILES: CC#Cc1cccc2cc([C@@H](C)NC(=O)c3c(N)nn4cccnc34)n(-c3ccccc3)c(=O)c12]
Compound 2001r
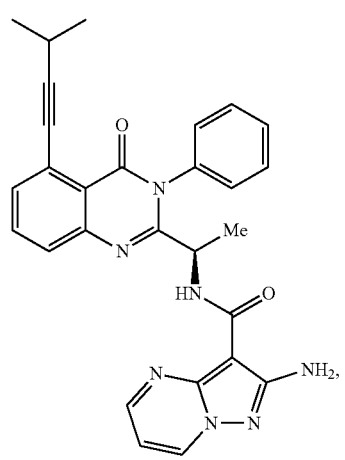 [SMILES: CC(C)C#Cc1cccc2nc([C@@H](C)NC(=O)c3c(N)nn4cccnc34)n(-c3ccccc3)c(=O)c12]
Compound 2002r
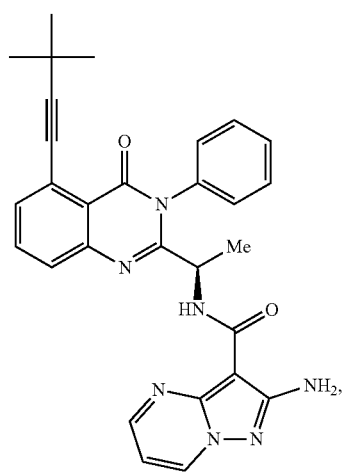 [SMILES: C[C@@H](NC(=O)c1c(N)nn2cccnc12)c1nc2cccc(C#CC(C)(C)C)c2c(=O)n1-c1ccccc1]
Compound 2003r
TABLE 13-continued
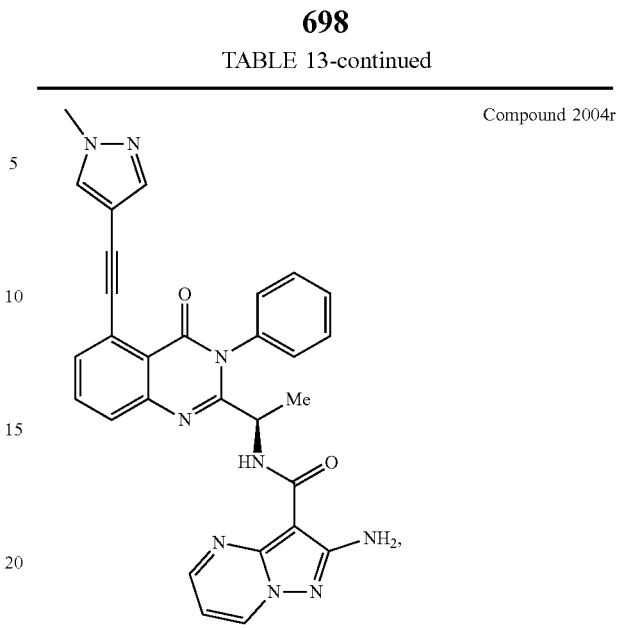
Compound 2004r
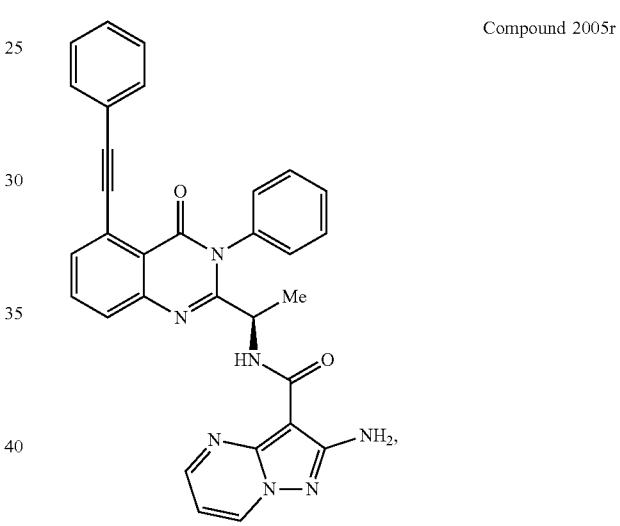
Compound 2005r
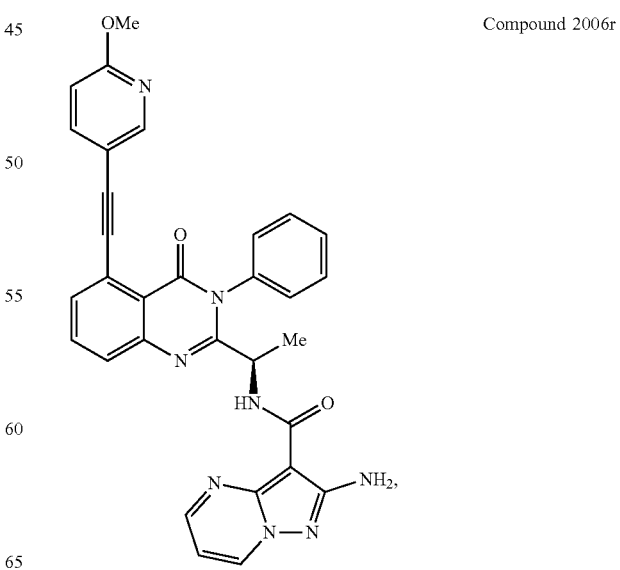
Compound 2006r TABLE 13-continued
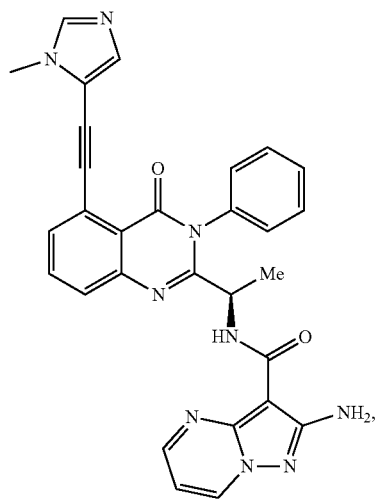 [SMILES: C[C@@H](NC(=O)c1c(N)nn2cccnc12)c1nc2cccc(C#Cc3cncn3C)c2c(=O)n1-c1ccccc1]
Compound 2007r
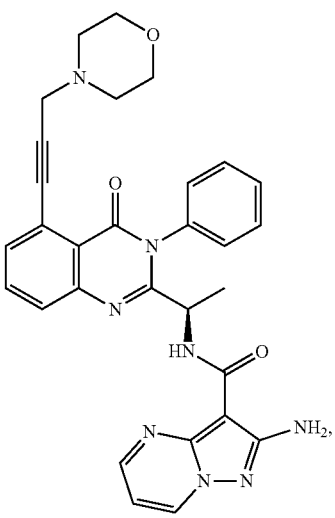
Compound 2010r
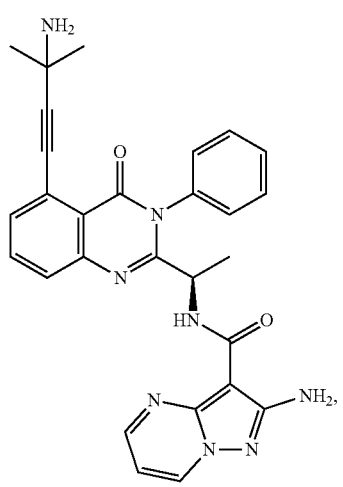 [SMILES: C[C@@H](NC(=O)c1c(N)nn2cccnc12)c1nc2cccc(C#CC(C)(C)N)c2c(=O)n1-c1ccccc1]
Compound 2008r
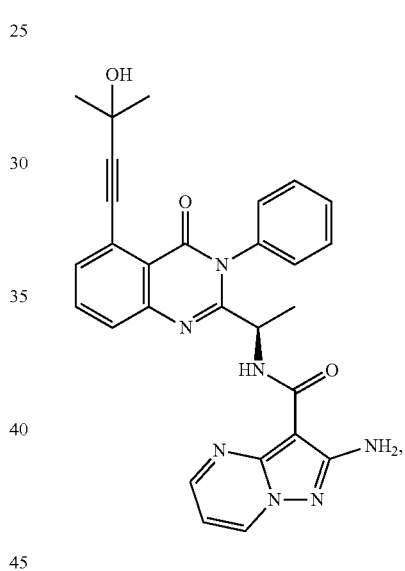
Compound 2011r
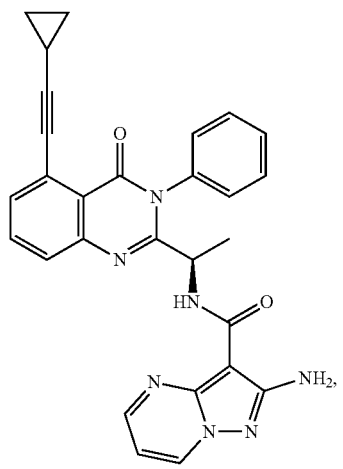 [SMILES: C[C@@H](NC(=O)c1c(N)nn2cccnc12)c1nc2cccc(C#CC3CC3)c2c(=O)n1-c1ccccc1]
Compound 2009r
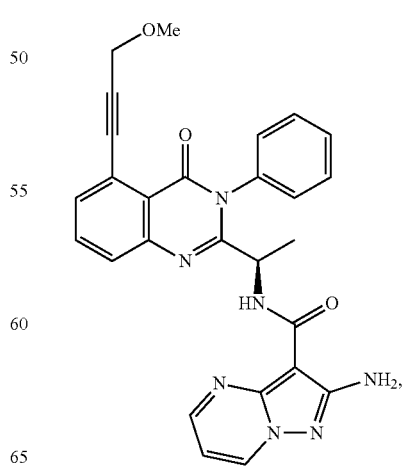
Compound 2012r TABLE 13-continued
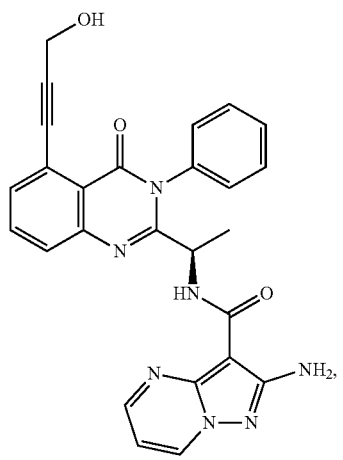 [SMILES: C[C@@H](NC(=O)c1c(N)nn2cccnc12)c1nc2cccc(C#CCO)c2c(=O)n1-c1ccccc1]
Compound 2013r
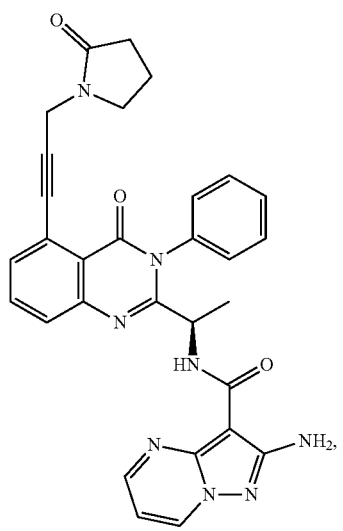 [SMILES: C[C@@H](NC(=O)c1c(N)nn2cccnc12)c1nc2cccc(C#CCN3CCCC3=O)c2c(=O)n1-c1ccccc1]
Compound 2014r
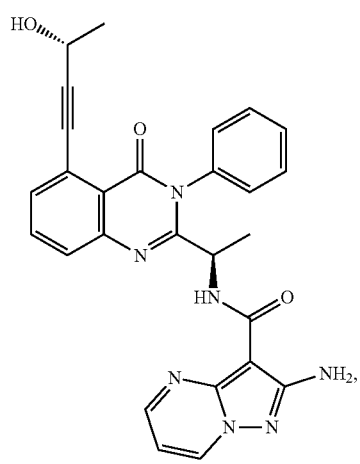 [SMILES: C[C@@H](O)C#Cc1cccc2nc([C@@H](C)NC(=O)c3c(N)nn4cccnc34)n(-c3ccccc3)c(=O)c12]
Compound 2015r
TABLE 13-continued
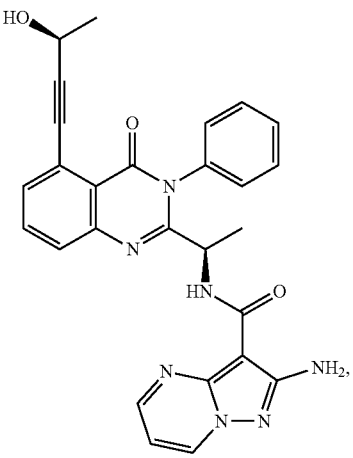 [SMILES: C[C@H](O)C#Cc1cccc2nc([C@@H](C)NC(=O)c3c(N)nn4cccnc34)n(-c3ccccc3)c(=O)c12]
Compound 2016r
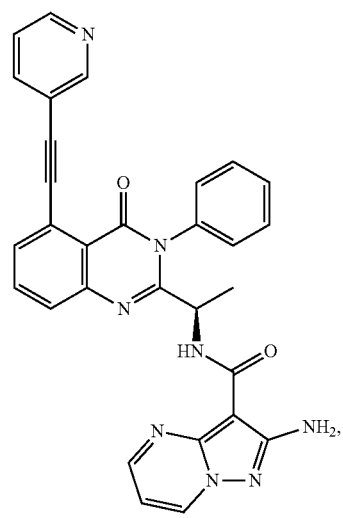 [SMILES: C[C@@H](NC(=O)c1c(N)nn2cccnc12)c1nc2cccc(C#Cc3cccnc3)c2c(=O)n1-c1ccccc1]
Compound 2017r
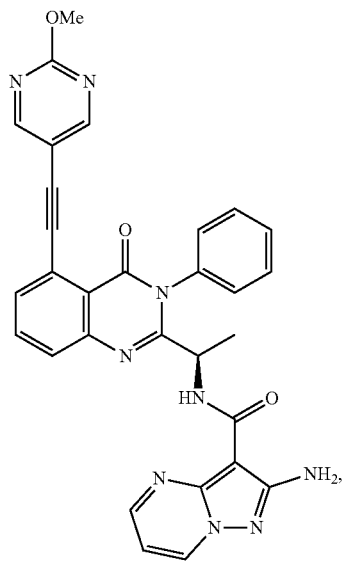 [SMILES: COc1ncc(C#Cc2cccc3nc([C@@H](C)NC(=O)c4c(N)nn5cccnc45)n(-c4ccccc4)c(=O)c23)cn1]
Compound 2018r TABLE 13-continued
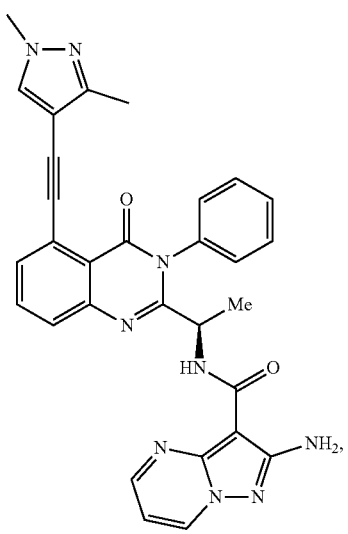 [SMILES: Cc1nn(C)cc1C#Cc1cccc2nc([C@@H](C)NC(=O)c3c(N)nn4cccnc34)n(-c3ccccc3)c(=O)c12]
Compound 2019r
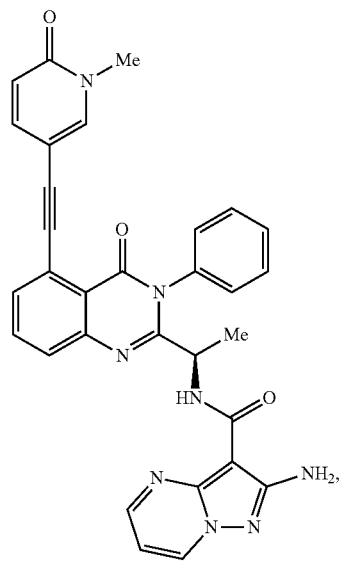 [SMILES: C[C@@H](NC(=O)c1c(N)nn2cccnc12)c1nc2cccc(C#Cc3ccc(=O)n(C)c3)c2c(=O)n1-c1ccccc1]
Compound 2020r
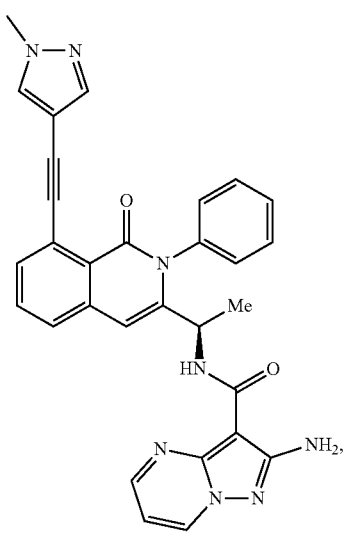 [SMILES: C[C@@H](NC(=O)c1c(N)nn2cccnc12)c1cc2cccc(C#Cc3cnn(C)c3)c2c(=O)n1-c1ccccc1]
Compound 2021r
TABLE 13-continued
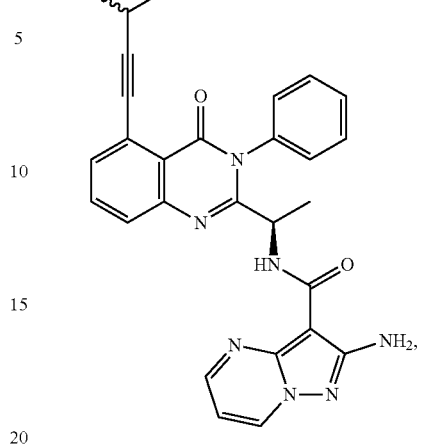
Compound 2022r
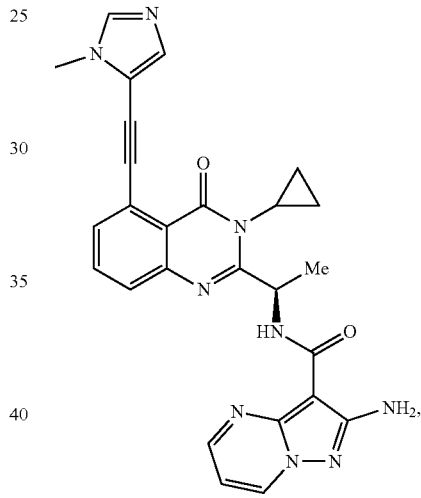
Compound 2023r
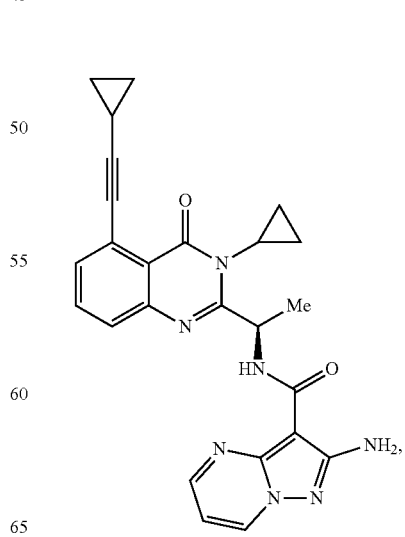
Compound 2024r TABLE 13-continued
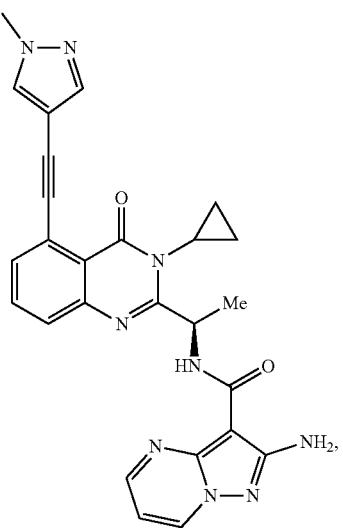 [SMILES: C[C@@H](NC(=O)c1c(N)nn2cccnc12)c1nc2cccc(C#Cc3cnn(C)c3)c2c(=O)n1C1CC1]
Compound 2025r
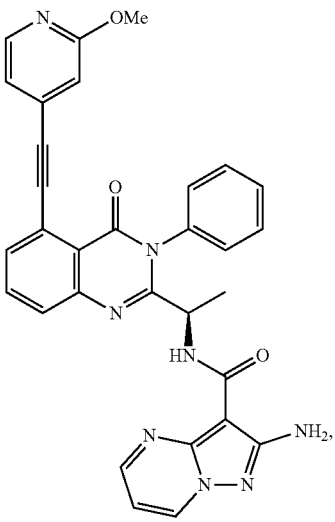
Compound 2028r
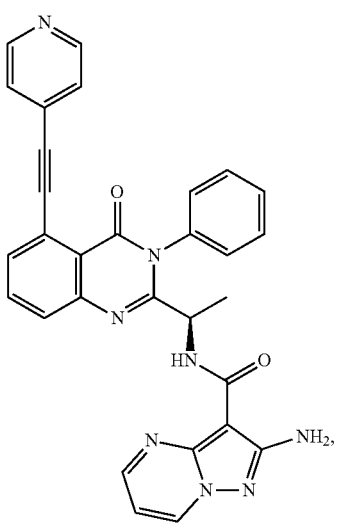 [SMILES: C[C@@H](NC(=O)c1c(N)nn2cccnc12)c1nc2cccc(C#Cc3ccncc3)c2c(=O)n1-c1ccccc1]
Compound 2026r
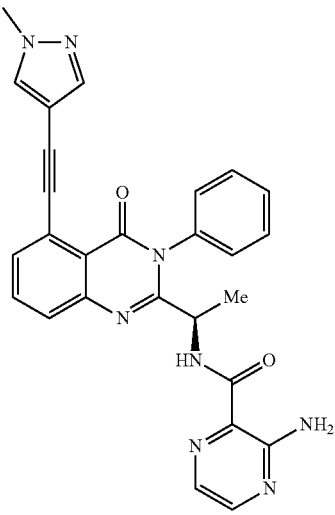
Compound 2029r
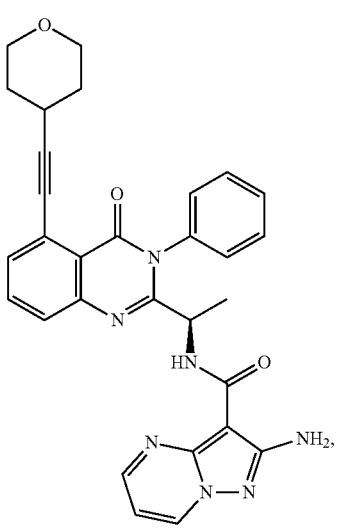 [SMILES: C[C@@H](NC(=O)c1c(N)nn2cccnc12)c1nc2cccc(C#CC3CCOCC3)c2c(=O)n1-c1ccccc1]
Compound 2027r
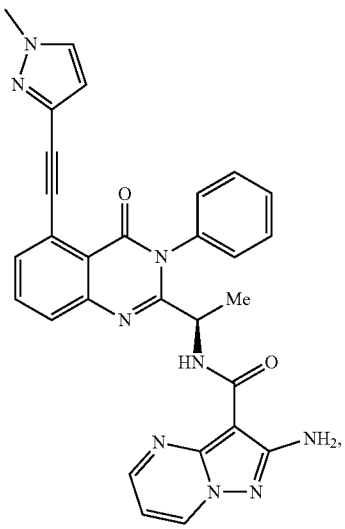
Compound 2030r TABLE 13-continued
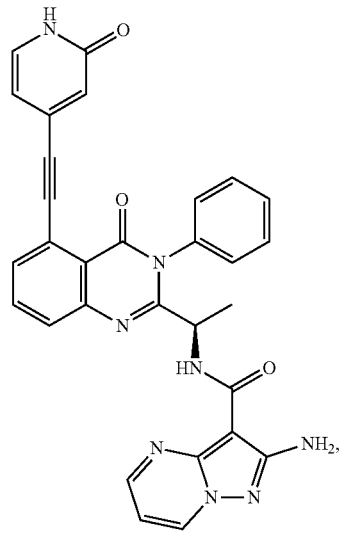 [SMILES: C[C@@H](NC(=O)c1c(N)nn2cccnc12)c1nc2cccc(C#Cc3cc[nH]c(=O)c3)c2c(=O)n1-c1ccccc1]
Compound 2031r
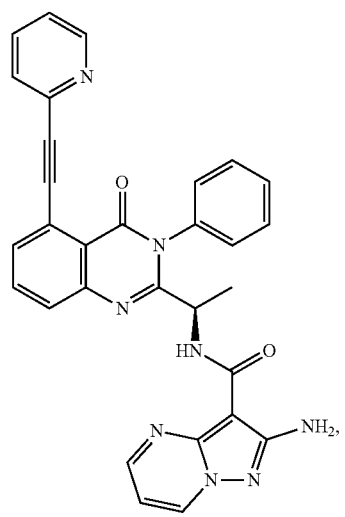 [SMILES: C[C@@H](NC(=O)c1c(N)nn2cccnc12)c1nc2cccc(C#Cc3ccccn3)c2c(=O)n1-c1ccccc1]
Compound 2032r
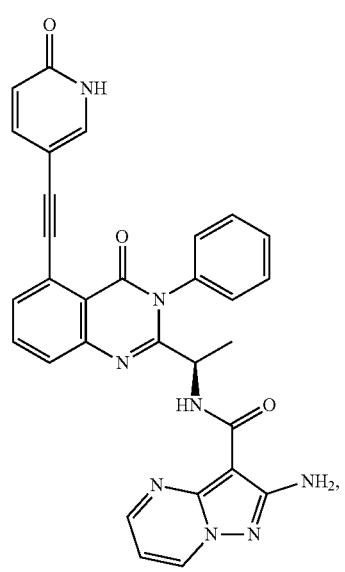 [SMILES: C[C@@H](NC(=O)c1c(N)nn2cccnc12)c1nc2cccc(C#Cc3ccc(=O)[nH]c3)c2c(=O)n1-c1ccccc1]
Compound 2033r
TABLE 13-continued
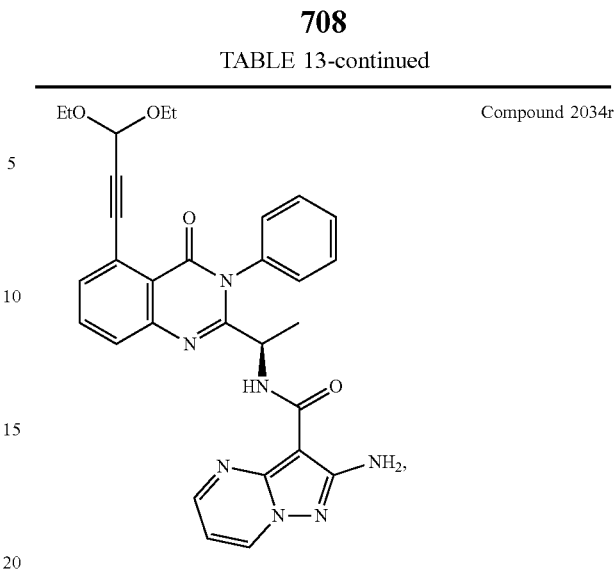
Compound 2034r
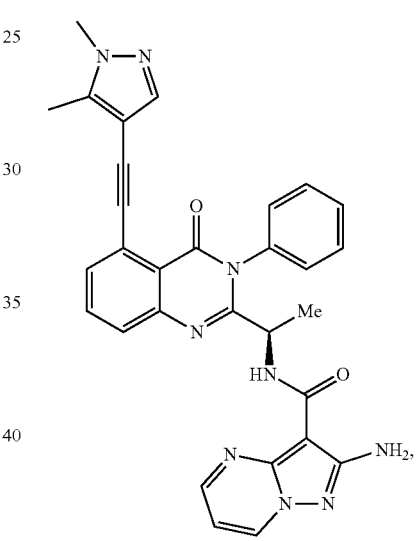
Compound 2035r
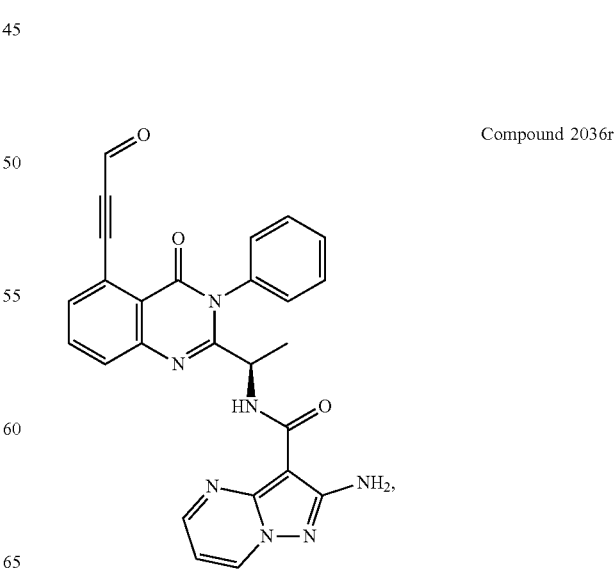
Compound 2036r TABLE 13-continued
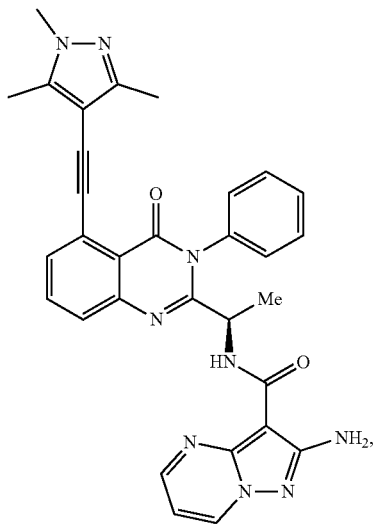 [SMILES: Cc1nn(C)c(C)c1C#Cc1cccc2nc([C@@H](C)NC(=O)c3c(N)nn4cccnc34)n(-c3ccccc3)c(=O)c12]
Compound 2037r
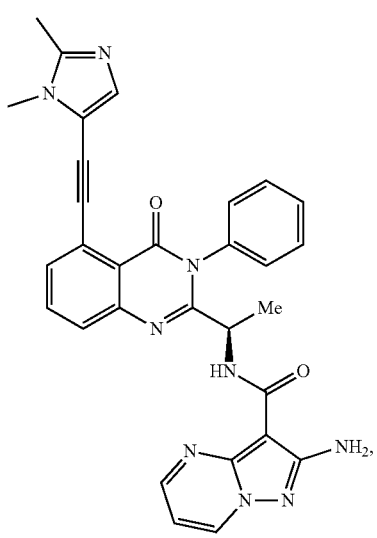 [SMILES: Cc1ncc(C#Cc2cccc3nc([C@@H](C)NC(=O)c4c(N)nn5cccnc45)n(-c4ccccc4)c(=O)c23)n1C]
Compound 2038r
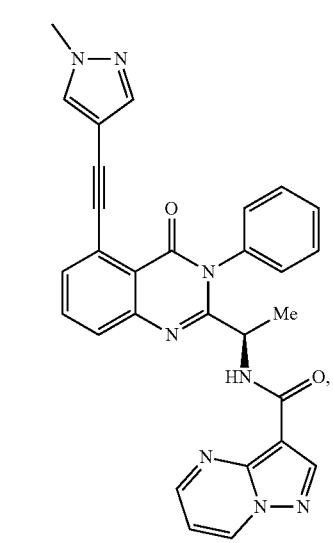 [SMILES: C[C@@H](NC(=O)c1cnn2cccnc12)c1nc2cccc(C#Cc3cnn(C)c3)c2c(=O)n1-c1ccccc1]
Compound 2039r
TABLE 13-continued
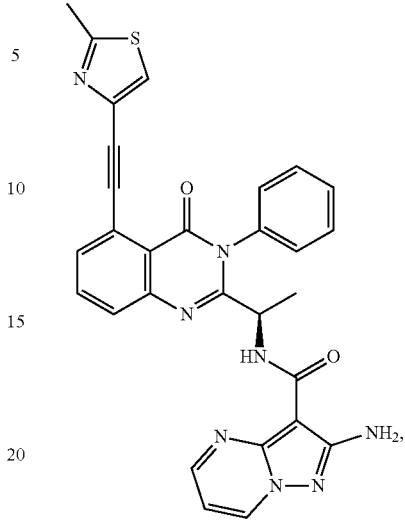
Compound 2040r
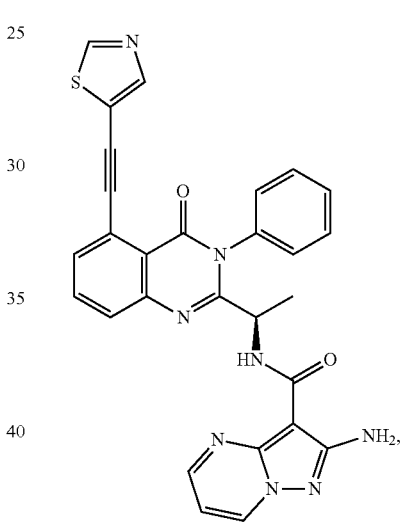
Compound 2041r
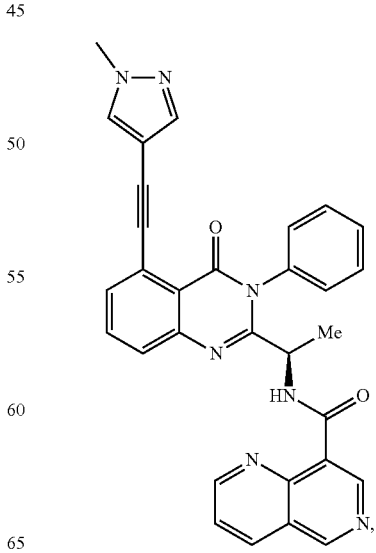
Compound 2042r TABLE 13-continued
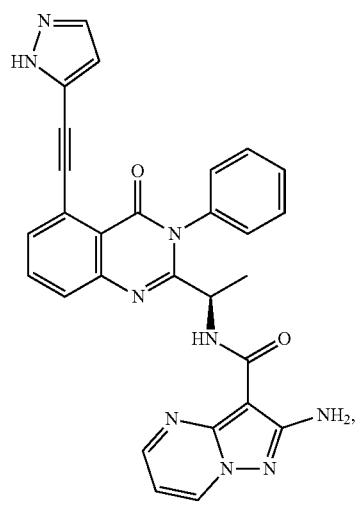
Compound 2043r
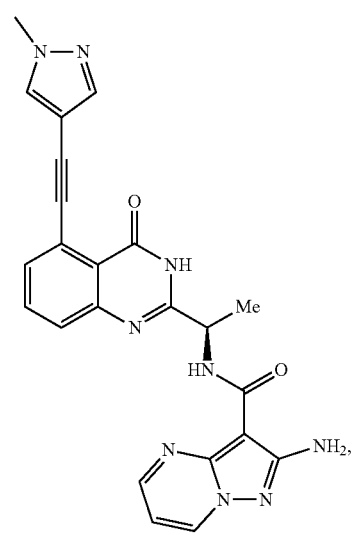 [SMILES: C[C@@H](NC(=O)c1c(N)nn2cccnc12)c1nc2cccc(C#Cc3cnn(C)c3)c2c(=O)[nH]1]
Compound 2044r
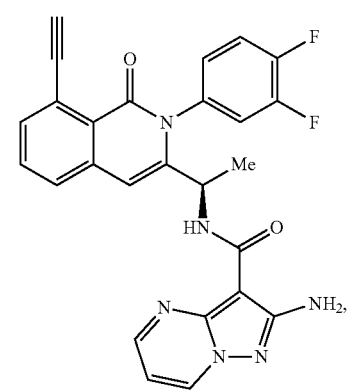 [SMILES: C#Cc1cccc2cc([C@@H](C)NC(=O)c3c(N)nn4cccnc34)n(-c3ccc(F)c(F)c3)c(=O)c12]
Compound 2045r
TABLE 13-continued
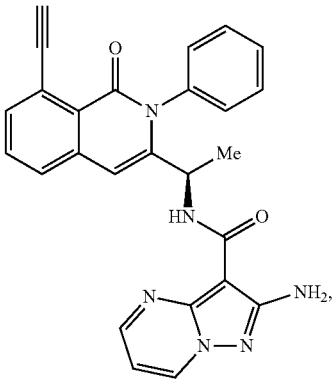 [SMILES: C#Cc1cccc2cc([C@@H](C)NC(=O)c3c(N)nn4cccnc34)n(-c3ccccc3)c(=O)c12]
Compound 2046r
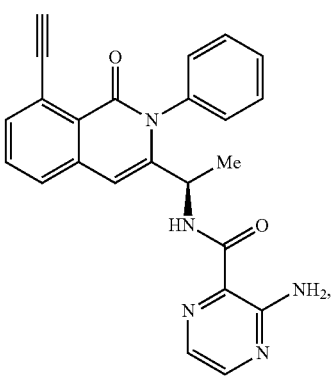 [SMILES: C#Cc1cccc2cc([C@@H](C)NC(=O)c3nccnc3N)n(-c3ccccc3)c(=O)c12]
Compound 2047r
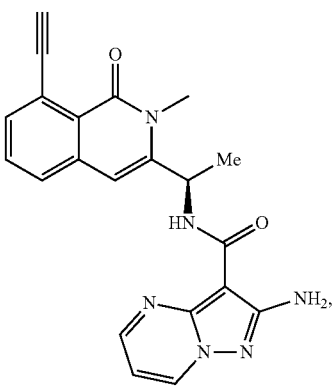 [SMILES: C#Cc1cccc2cc([C@@H](C)NC(=O)c3c(N)nn4cccnc34)n(C)c(=O)c12]
Compound 2048r
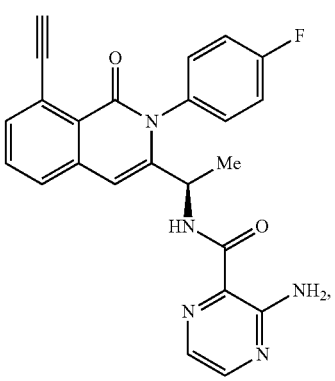 [SMILES: C#Cc1cccc2cc([C@@H](C)NC(=O)c3nccnc3N)n(-c3ccc(F)cc3)c(=O)c12]
Compound 2049r TABLE 13-continued
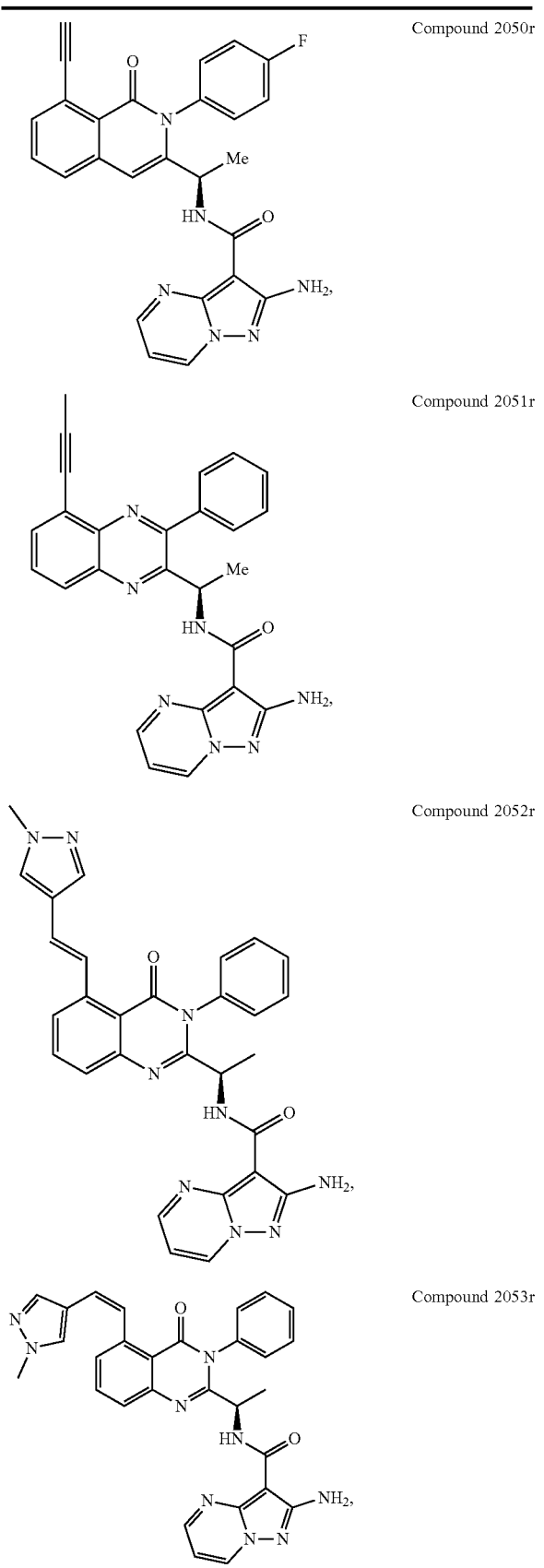
Compound 2050r
Compound 2051r
Compound 2052r
Compound 2053r
TABLE 13-continued
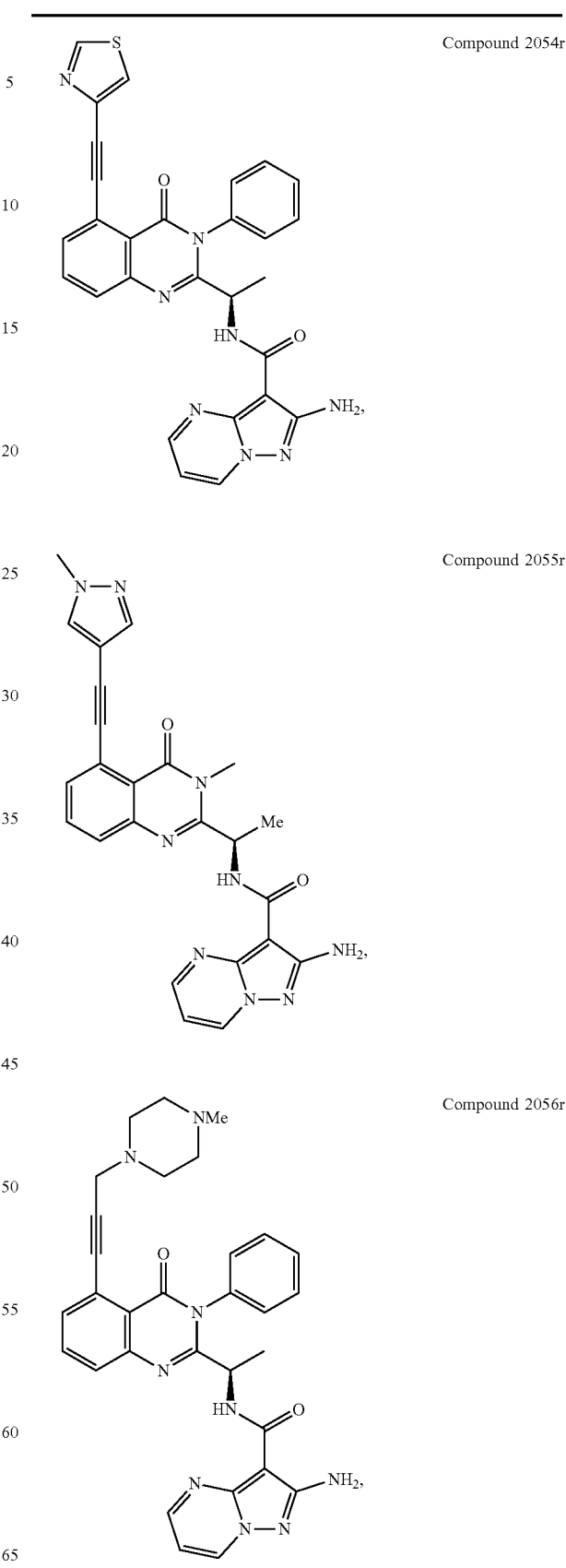
Compound 2054r
Compound 2055r
Compound 2056r TABLE 13-continued
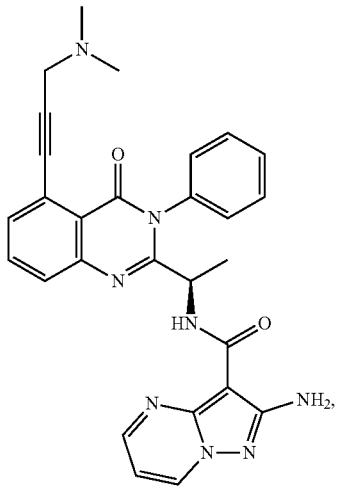 [SMILES: C[C@@H](NC(=O)c1c(N)nn2cccnc12)c1nc2cccc(C#CCN(C)C)c2c(=O)n1-c1ccccc1]
Compound 2057r
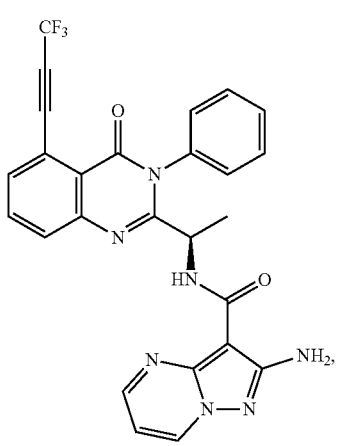 [SMILES: C[C@@H](NC(=O)c1c(N)nn2cccnc12)c1nc2cccc(C#CC(F)(F)F)c2c(=O)n1-c1ccccc1]
Compound 2058r
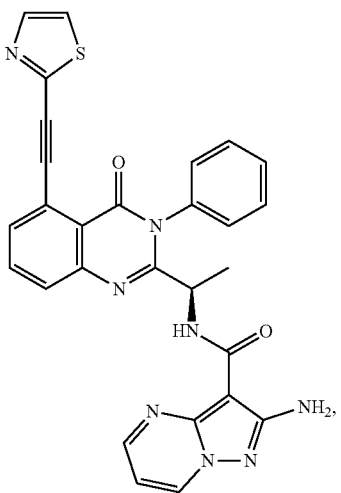 [SMILES: C[C@@H](NC(=O)c1c(N)nn2cccnc12)c1nc2cccc(C#Cc3nccs3)c2c(=O)n1-c1ccccc1]
Compound 2059r
TABLE 13-continued
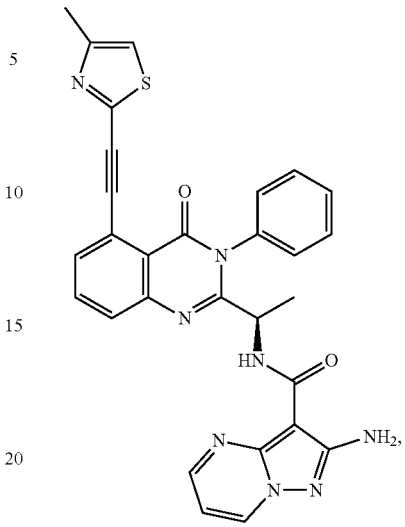
Compound 2060r
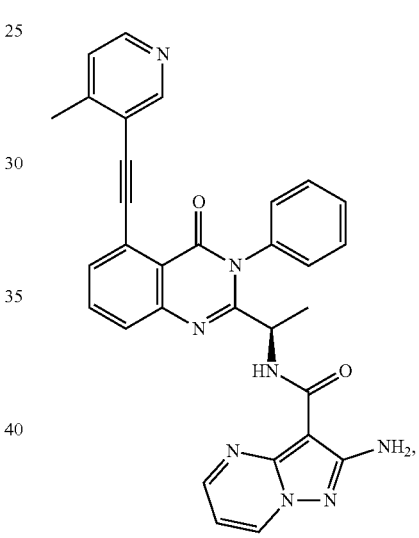
Compound 2061r
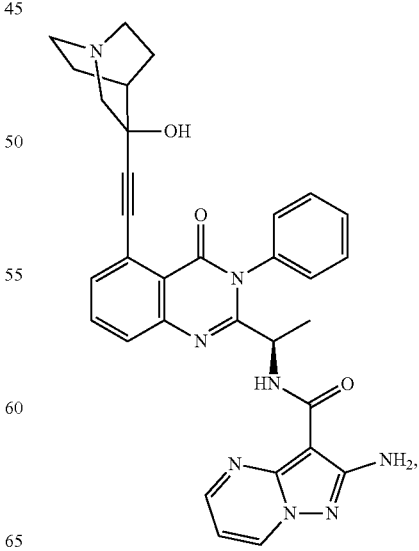
Compound 2062r TABLE 13-continued
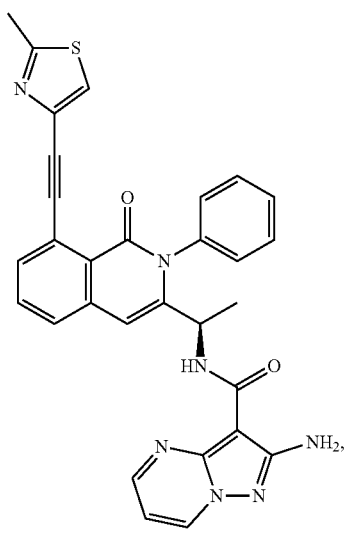 [SMILES: Cc1nc(C#Cc2cccc3cc([C@@H](C)NC(=O)c4c(N)nn5cccnc45)n(-c4ccccc4)c(=O)c23)cs1]
Compound 2063r
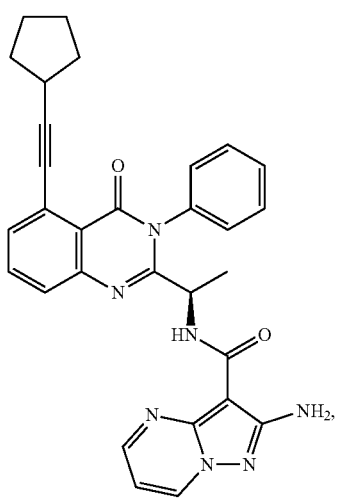 [SMILES: C[C@@H](NC(=O)c1c(N)nn2cccnc12)c1nc2cccc(C#CC3CCCC3)c2c(=O)n1-c1ccccc1]
Compound 2064r
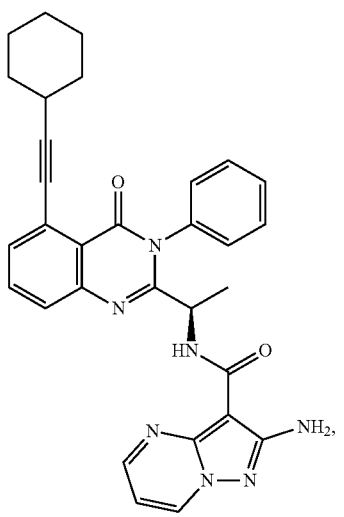 [SMILES: C[C@@H](NC(=O)c1c(N)nn2cccnc12)c1nc2cccc(C#CC3CCCCC3)c2c(=O)n1-c1ccccc1]
Compound 2065r
TABLE 13-continued
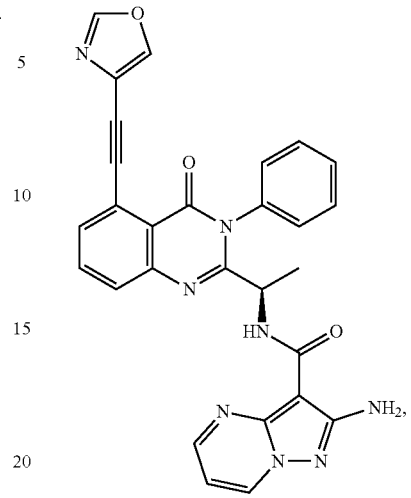
Compound 2066r
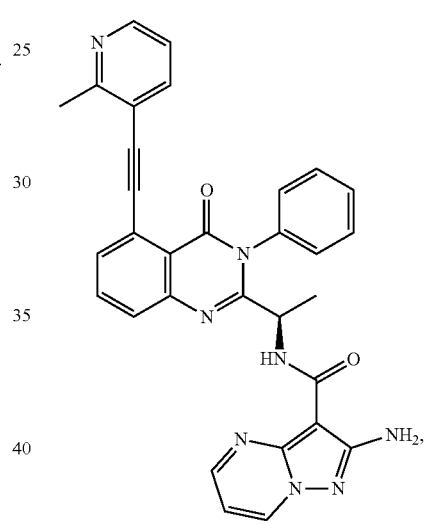
Compound 2067r
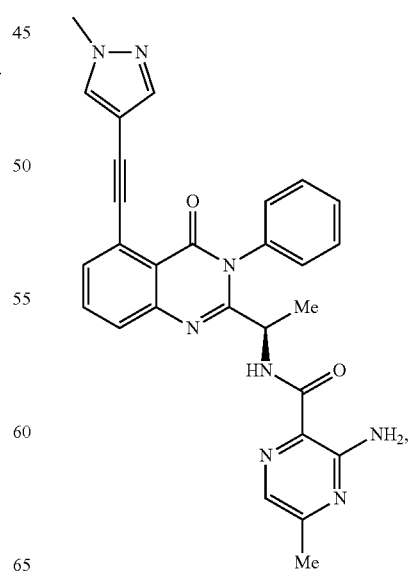
Compound 2068r TABLE 13-continued
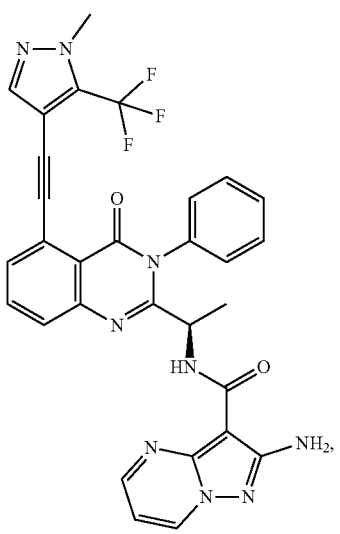 [SMILES: C[C@@H](NC(=O)c1c(N)nn2cccnc12)c1nc2cccc(C#Cc3cnn(C)c3C(F)(F)F)c2c(=O)n1-c1ccccc1]
Compound 2069r
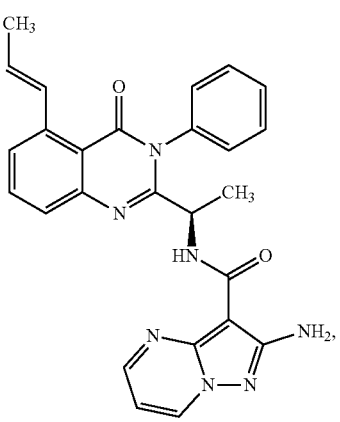
Compound 2070r
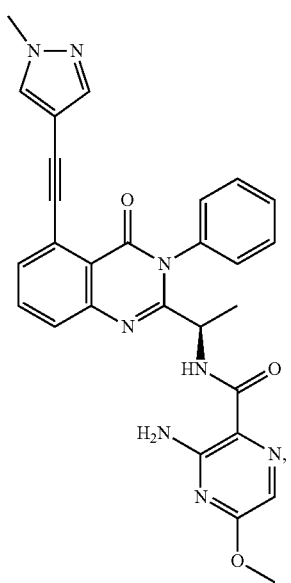
Compound 2071r
TABLE 13-continued
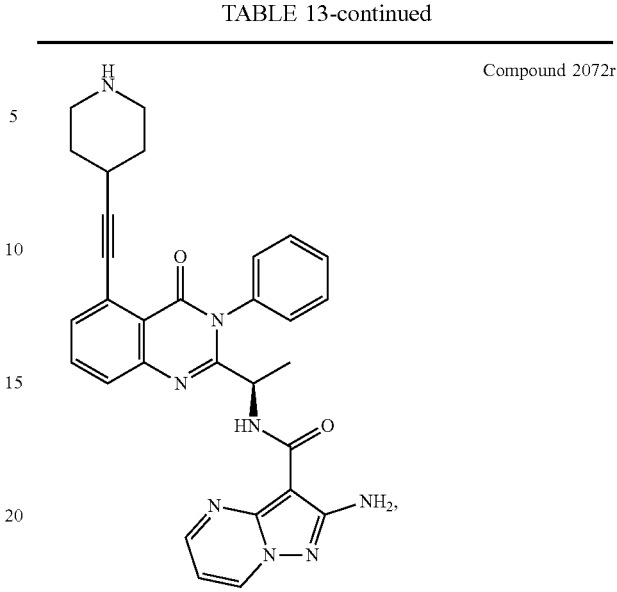
Compound 2072r
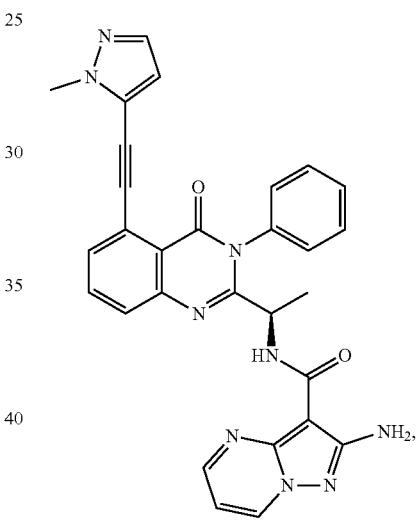
Compound 2073r
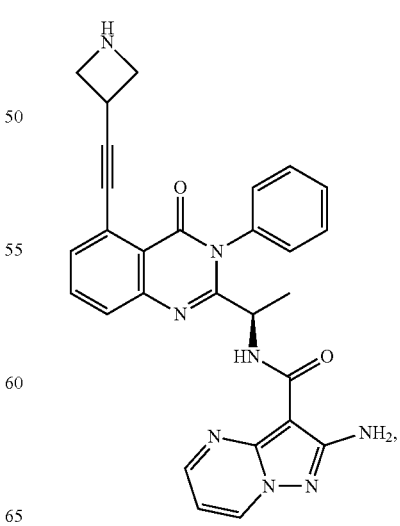
Compound 2074r TABLE 13-continued
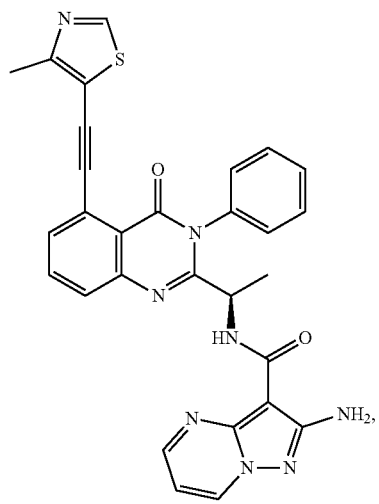 [SMILES: Cc1ncsc1C#Cc1cccc2nc([C@@H](C)NC(=O)c3c(N)nn4cccnc34)n(-c3ccccc3)c(=O)c12]
Compound 2075r
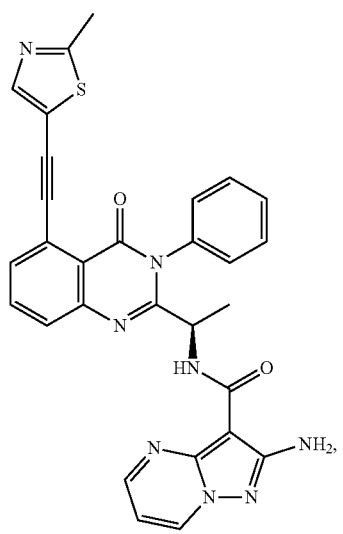 [SMILES: Cc1ncc(C#Cc2cccc3nc([C@@H](C)NC(=O)c4c(N)nn5cccnc45)n(-c4ccccc4)c(=O)c23)s1]
Compound 2076r
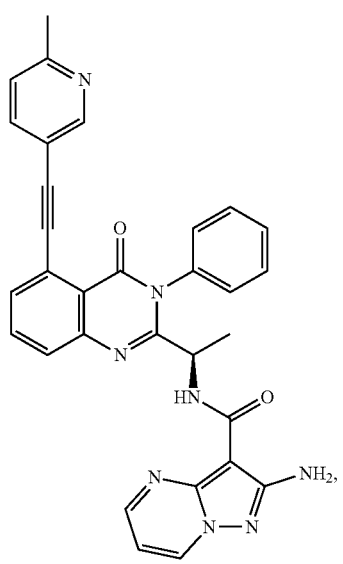 [SMILES: Cc1ccc(C#Cc2cccc3nc([C@@H](C)NC(=O)c4c(N)nn5cccnc45)n(-c4ccccc4)c(=O)c23)cn1]
Compound 2077r
TABLE 13-continued
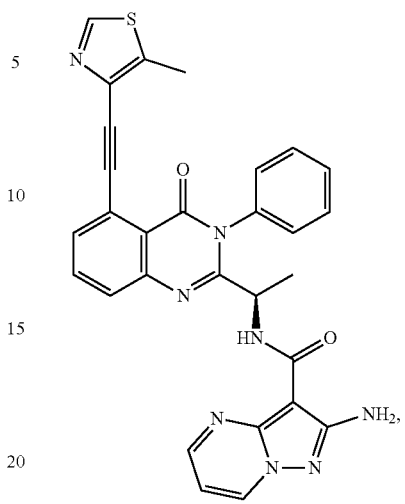
Compound 2078r
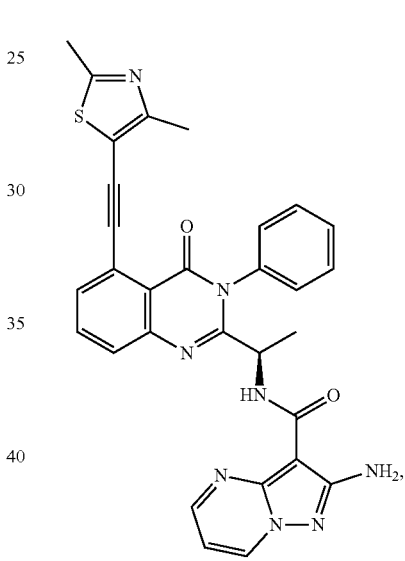
Compound 2079r
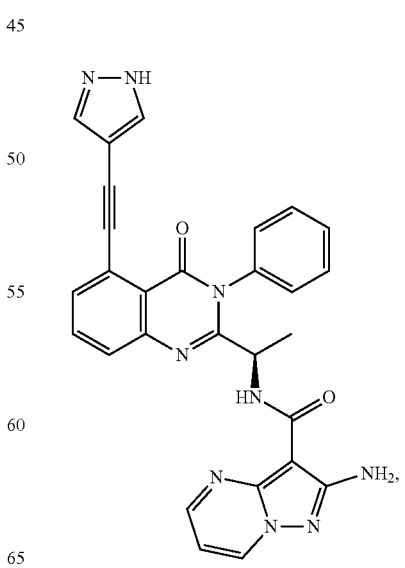
Compound 2080r TABLE 13-continued
Compound 2081r
Compound 2082r
Compound 2083r
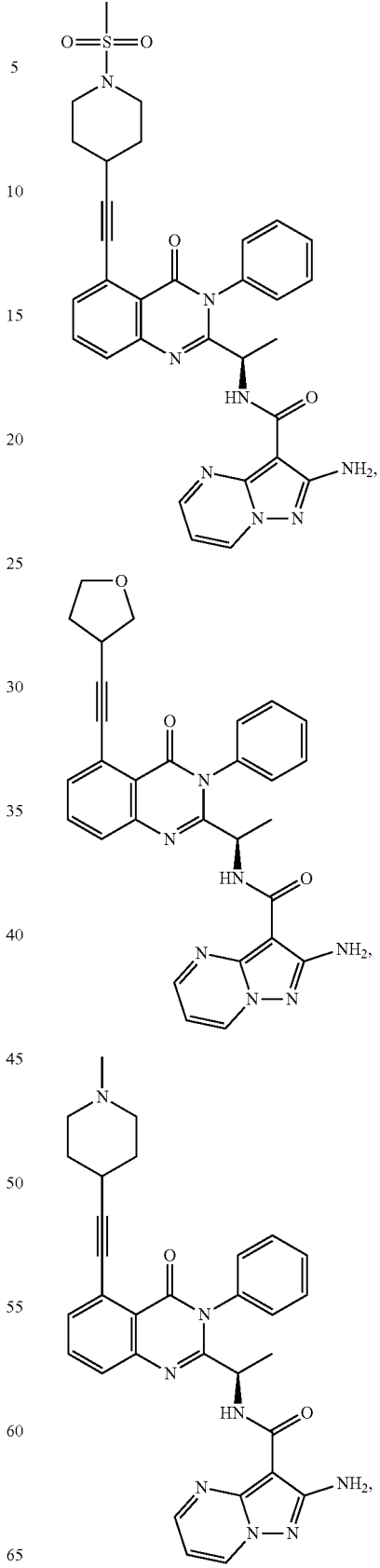
Compound 2084r
Compound 2085r TABLE 13-continued
Compound 2086r
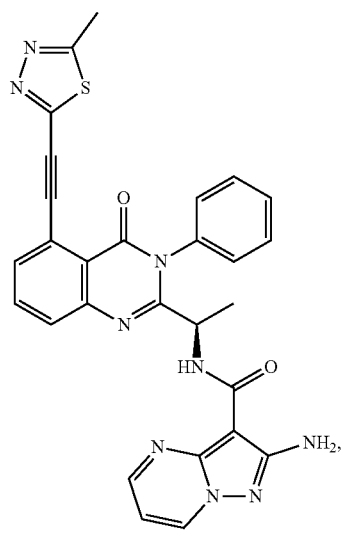 [SMILES: Cc1nnc(C#Cc2cccc3nc([C@@H](C)NC(=O)c4c(N)nn5cccnc45)n(-c4ccccc4)c(=O)c23)s1]
Compound 2087r
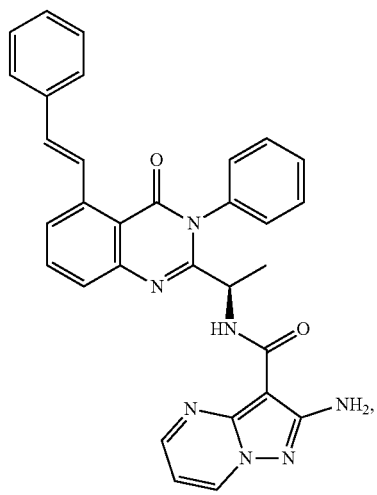 [SMILES: C[C@@H](NC(=O)c1c(N)nn2cccnc12)c1nc2cccc(/C=C/c3ccccc3)c2c(=O)n1-c1ccccc1]
Compound 2088r
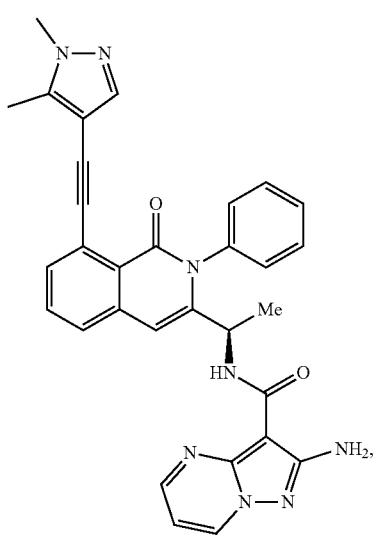 [SMILES: Cc1c(C#Cc2cccc3cc([C@@H](C)NC(=O)c4c(N)nn5cccnc45)n(-c4ccccc4)c(=O)c23)cnn1C]
TABLE 13-continued
Compound 2089r
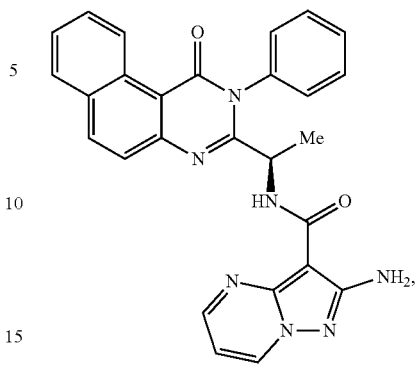
Compound 2090r
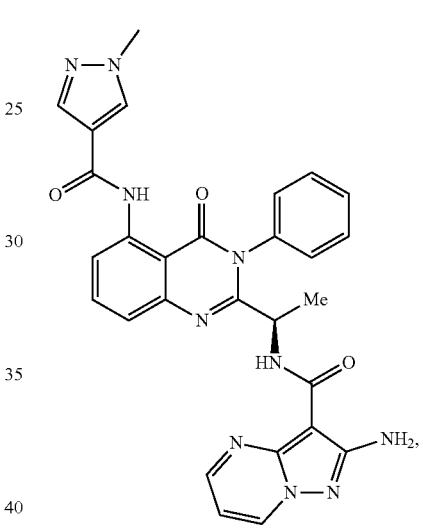
Compound 2091r
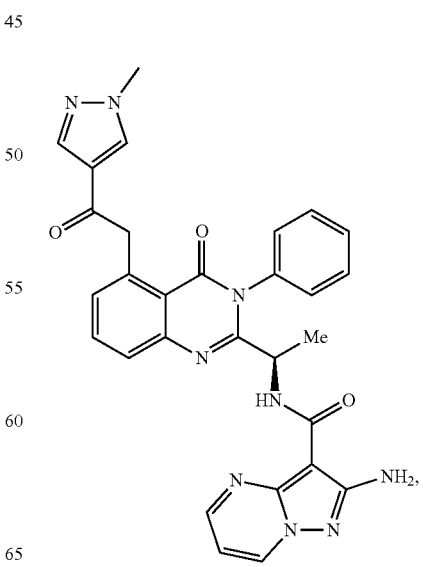

TABLE 13-continued
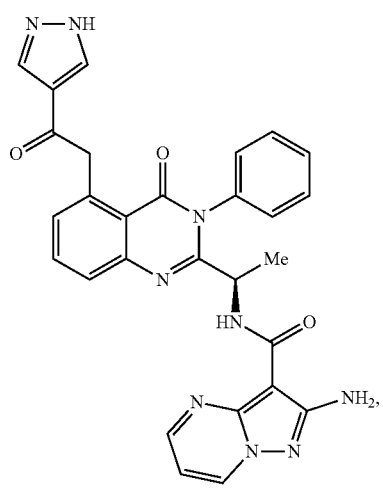 [SMILES: C[C@@H](NC(=O)c1c(N)nn2cccnc12)c1nc2cccc(CC(=O)c3cn[nH]c3)c2c(=O)n1-c1ccccc1]
Compound 2092r
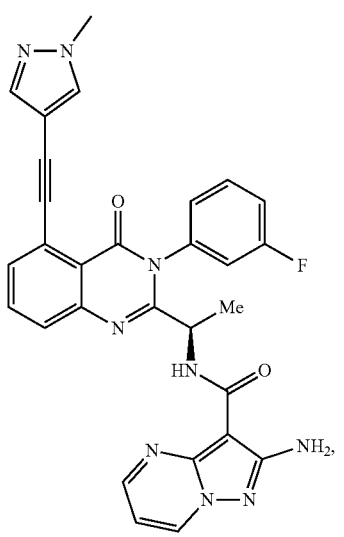 [SMILES: C[C@@H](NC(=O)c1c(N)nn2cccnc12)c1nc2cccc(C#Cc3cnn(C)c3)c2c(=O)n1-c1cccc(F)c1]
Compound 2093r
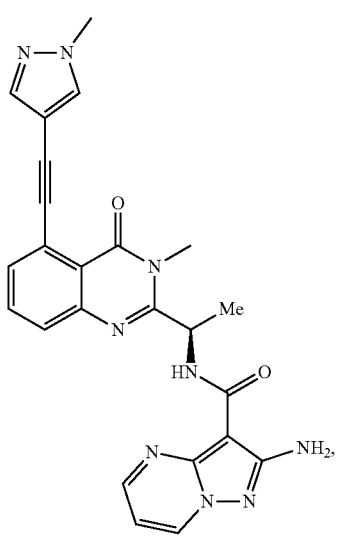 [SMILES: C[C@@H](NC(=O)c1c(N)nn2cccnc12)c1nc2cccc(C#Cc3cnn(C)c3)c2c(=O)n1C]
Compound 2094r
TABLE 13-continued
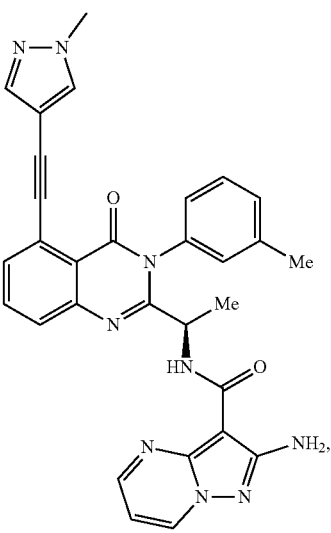 [SMILES: Cc1cccc(-n2c([C@@H](C)NC(=O)c3c(N)nn4cccnc34)nc3cccc(C#Cc4cnn(C)c4)c3c2=O)c1]
Compound 2095r
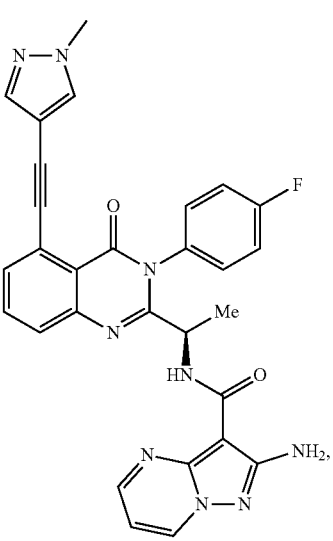 [SMILES: C[C@@H](NC(=O)c1c(N)nn2cccnc12)c1nc2cccc(C#Cc3cnn(C)c3)c2c(=O)n1-c1ccc(F)cc1]
Compound 2096r
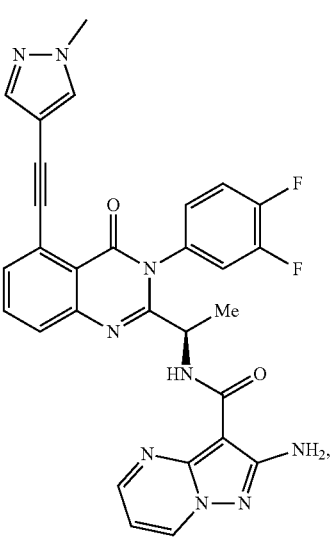 [SMILES: C[C@@H](NC(=O)c1c(N)nn2cccnc12)c1nc2cccc(C#Cc3cnn(C)c3)c2c(=O)n1-c1ccc(F)c(F)c1]
Compound 2097r TABLE 13-continued
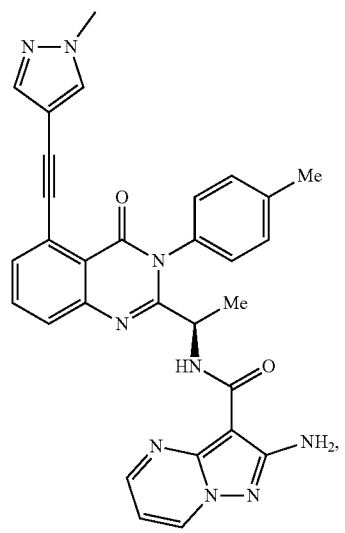 [SMILES: Cc1ccc(-n2c([C@@H](C)NC(=O)c3c(N)nn4cccnc34)nc3cccc(C#Cc4cnn(C)c4)c3c2=O)cc1]
Compound 2098r
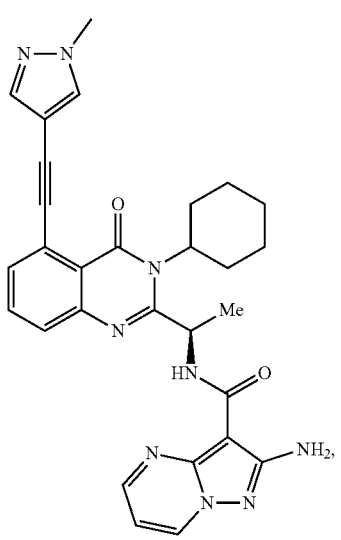 [SMILES: C[C@@H](NC(=O)c1c(N)nn2cccnc12)c1nc2cccc(C#Cc3cnn(C)c3)c2c(=O)n1C1CCCCC1]
Compound 2099r
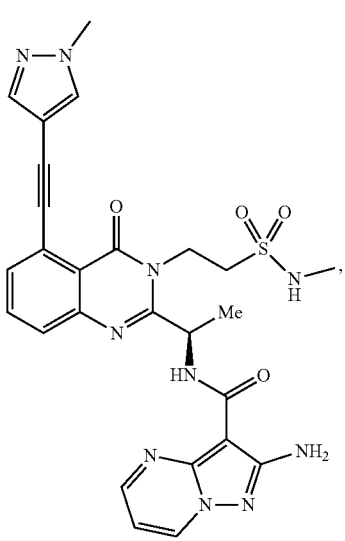 [SMILES: CNS(=O)(=O)CCn1c([C@@H](C)NC(=O)c2c(N)nn3cccnc23)nc2cccc(C#Cc3cnn(C)c3)c2c1=O]
Compound 2100r
TABLE 13-continued
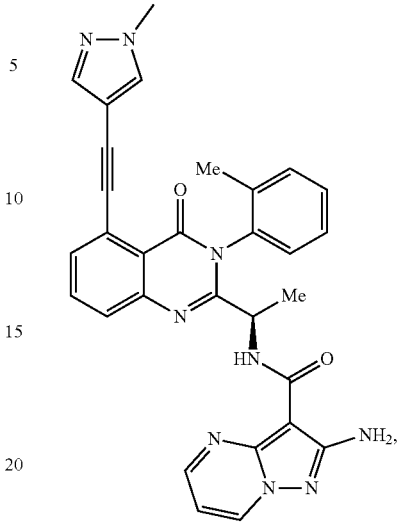
Compound 2101r
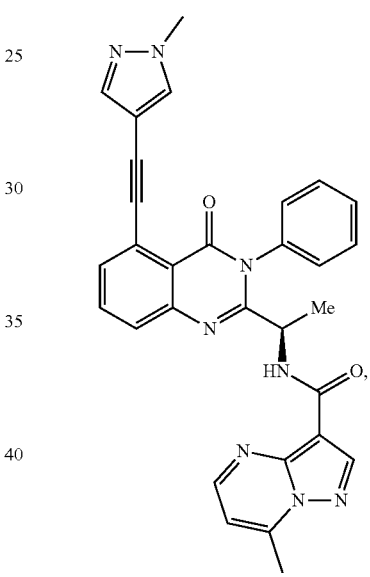
Compound 2102r
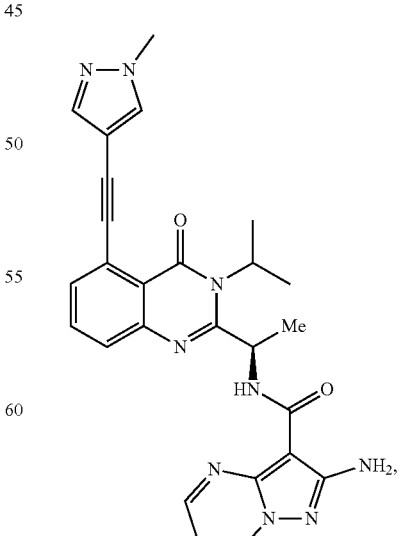
Compound 2103r TABLE 13-continued
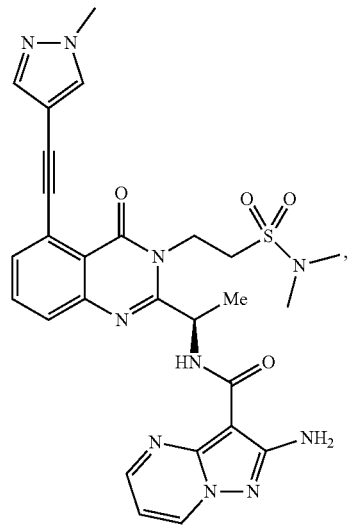 [SMILES: C[C@@H](NC(=O)c1c(N)nn2cccnc12)c1nc2cccc(C#Cc3cnn(C)c3)c2c(=O)n1CCS(=O)(=O)N(C)C]
Compound 2104r
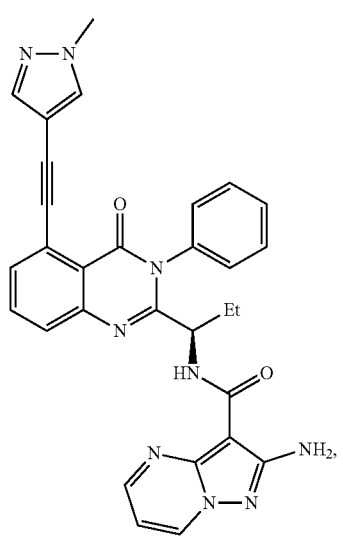 [SMILES: CC[C@@H](NC(=O)c1c(N)nn2cccnc12)c1nc2cccc(C#Cc3cnn(C)c3)c2c(=O)n1-c1ccccc1]
Compound 2105r
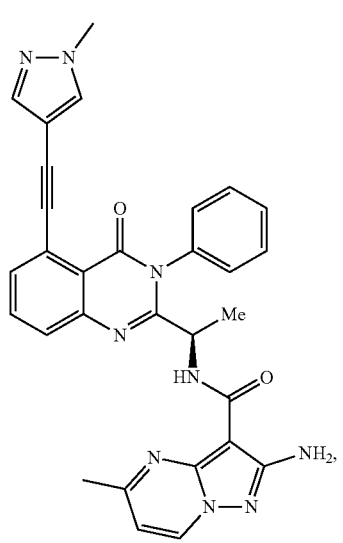 [SMILES: Cc1ccn2nc(N)c(C(=O)N[C@H](C)c3nc4cccc(C#Cc5cnn(C)c5)c4c(=O)n3-c3ccccc3)c2n1]
Compound 2106r
TABLE 13-continued
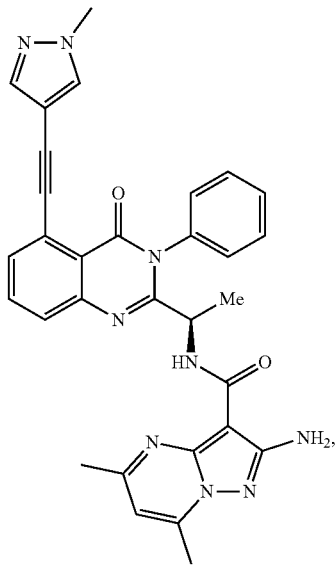 [SMILES: Cc1cc(C)n2nc(N)c(C(=O)N[C@H](C)c3nc4cccc(C#Cc5cnn(C)c5)c4c(=O)n3-c3ccccc3)c2n1]
Compound 2108r
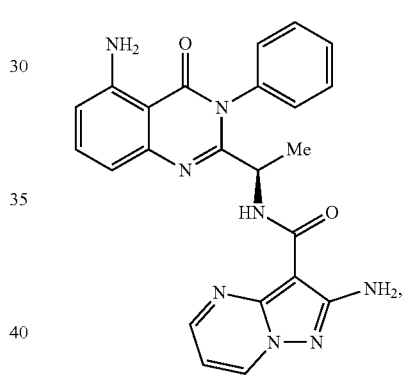
Compound 2109r
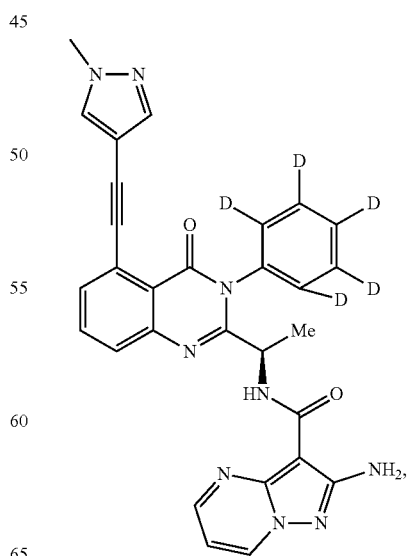
Compound 2110r TABLE 14
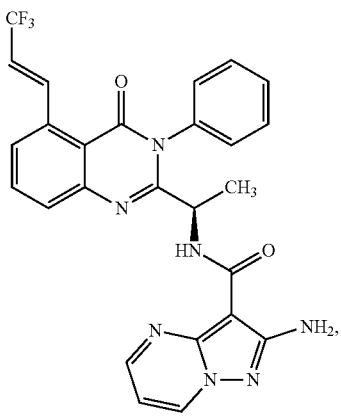
Compound 3001r
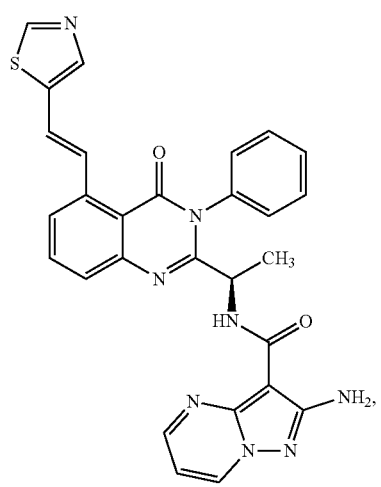 [SMILES: C[C@@H](NC(=O)c1c(N)nn2cccnc12)c1nc2cccc(/C=C/c3cncs3)c2c(=O)n1-c1ccccc1]
Compound 3002r
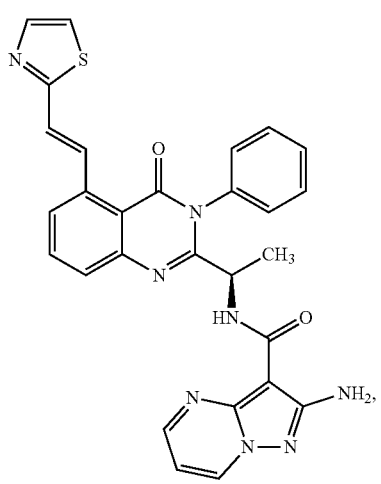 [SMILES: C[C@@H](NC(=O)c1c(N)nn2cccnc12)c1nc2cccc(/C=C/c3nccs3)c2c(=O)n1-c1ccccc1]
Compund 3003r

TABLE 14-continued
Compound 3004r
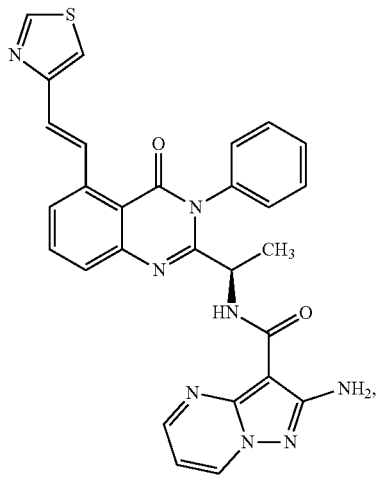 [SMILES: C[C@@H](NC(=O)c1c(N)nn2cccnc12)c1nc2cccc(/C=C/c3cscn3)c2c(=O)n1-c1ccccc1]
Compound 3005r
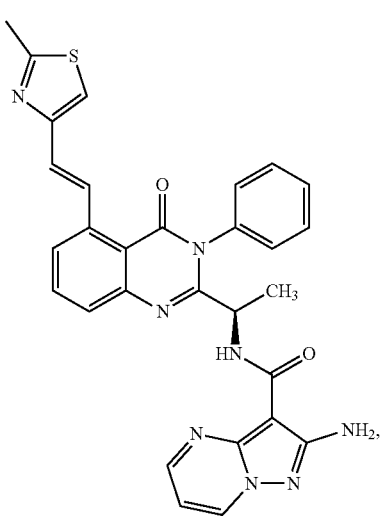 [SMILES: Cc1nc(/C=C/c2cccc3nc([C@@H](C)NC(=O)c4c(N)nn5cccnc45)n(-c4ccccc4)c(=O)c23)cs1]
Compound 3006r
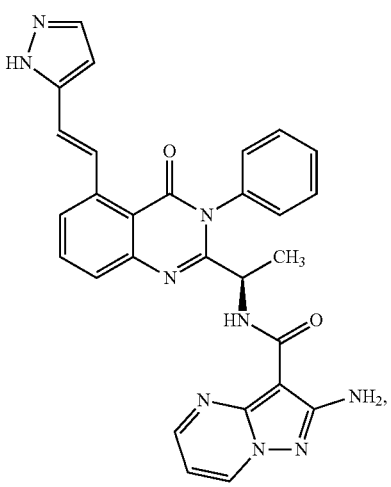

TABLE 14-continued
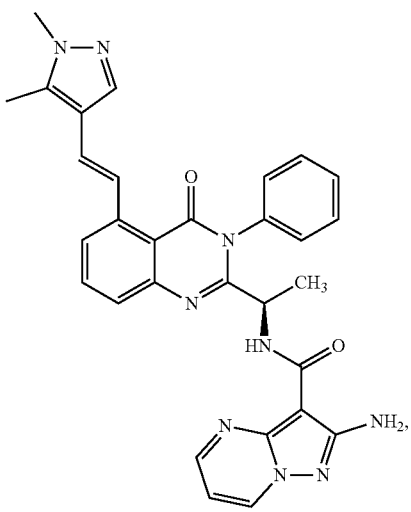 [SMILES: Cc1c(/C=C/c2cccc3nc([C@@H](C)NC(=O)c4c(N)nn5cccnc45)n(-c4ccccc4)c(=O)c23)cnn1C]
Compound 3007r
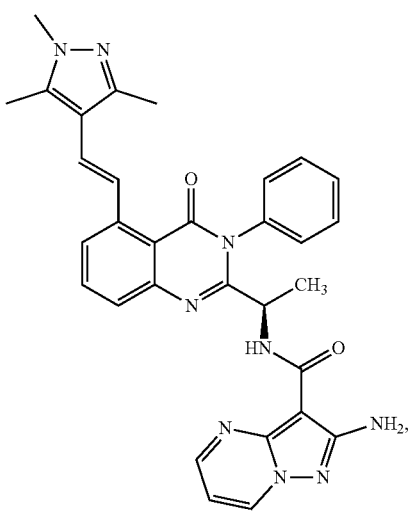 [SMILES: Cc1nn(C)c(C)c1/C=C/c1cccc2nc([C@@H](C)NC(=O)c3c(N)nn4cccnc34)n(-c3ccccc3)c(=O)c12]
Compound 3008r
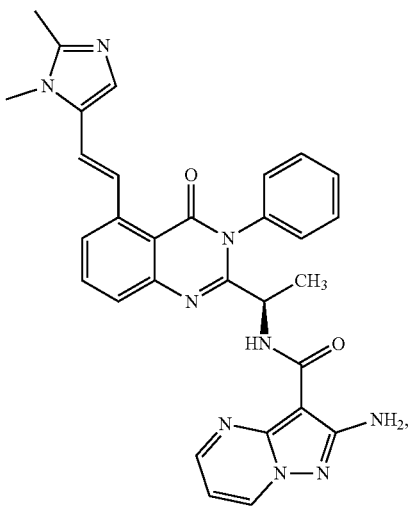 [SMILES: Cc1ncc(/C=C/c2cccc3nc([C@@H](C)NC(=O)c4c(N)nn5cccnc45)n(-c4ccccc4)c(=O)c23)n1C]
Compound 3009r TABLE 14-continued
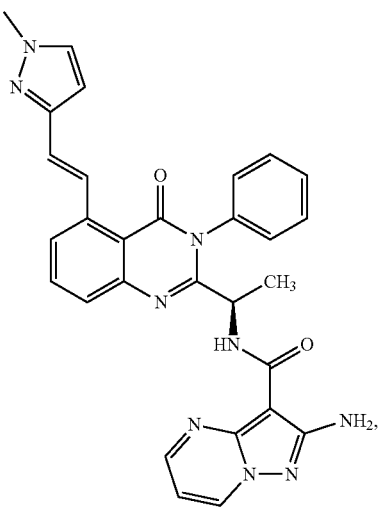 [SMILES: C[C@@H](NC(=O)c1c(N)nn2cccnc12)c1nc2cccc(/C=C/c3ccn(C)n3)c2c(=O)n1-c1ccccc1]
Compound 3010r
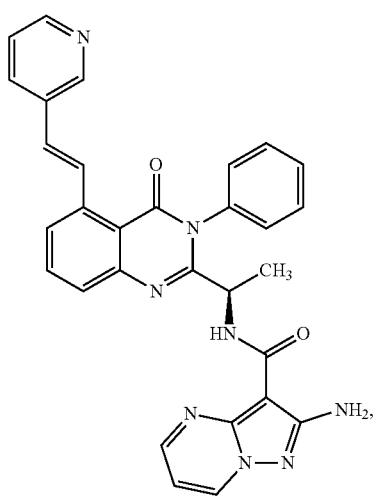 [SMILES: C[C@@H](NC(=O)c1c(N)nn2cccnc12)c1nc2cccc(/C=C/c3cccnc3)c2c(=O)n1-c1ccccc1]
Compound 3011r
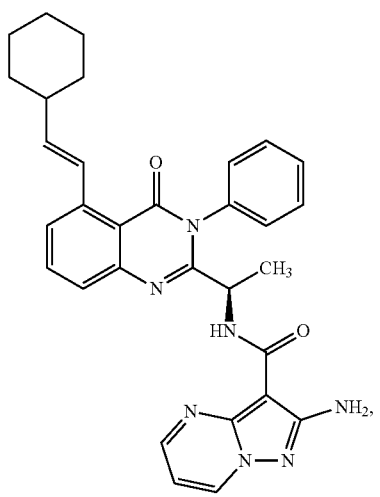 [SMILES: C[C@@H](NC(=O)c1c(N)nn2cccnc12)c1nc2cccc(/C=C/C3CCCCC3)c2c(=O)n1-c1ccccc1]
Compound 3012r TABLE 14-continued
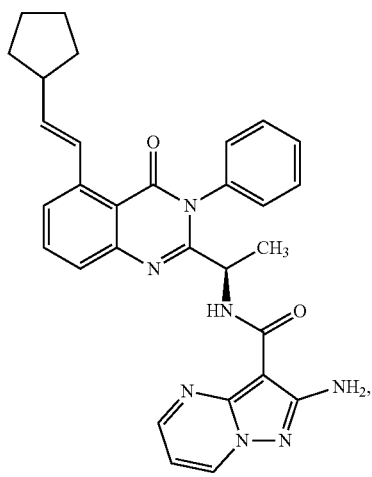 [SMILES: C[C@@H](NC(=O)c1c(N)nn2cccnc12)c1nc2cccc(/C=C/C3CCCC3)c2c(=O)n1-c1ccccc1]
Compound 3013r
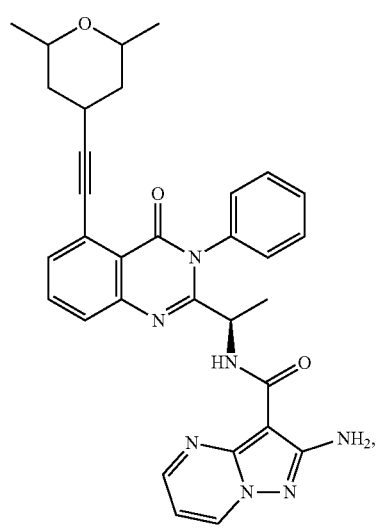 [SMILES: CC1CC(C#Cc2cccc3nc([C@@H](C)NC(=O)c4c(N)nn5cccnc45)n(-c4ccccc4)c(=O)c23)CC(C)O1]
Compound 3014r
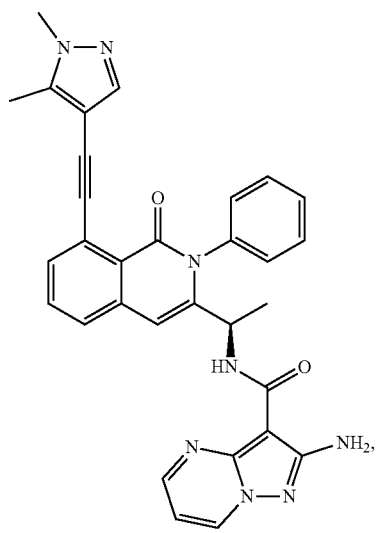 [SMILES: Cc1c(C#Cc2cccc3cc([C@@H](C)NC(=O)c4c(N)nn5cccnc45)n(-c4ccccc4)c(=O)c23)cnn1C]
Compound 3015r TABLE 14-continued
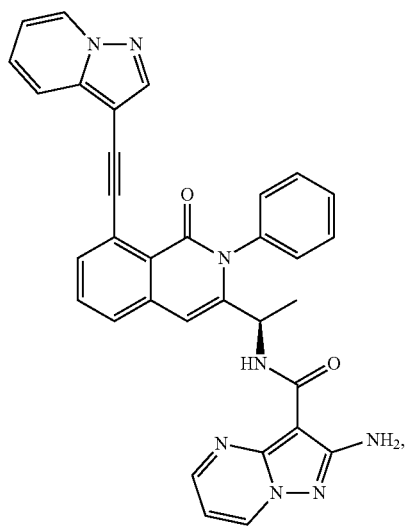 [SMILES: C[C@@H](NC(=O)c1c(N)nn2cccnc12)c1cc2cccc(C#Cc3cnn4ccccc34)c2c(=O)n1-c1ccccc1]
Compound 3016r
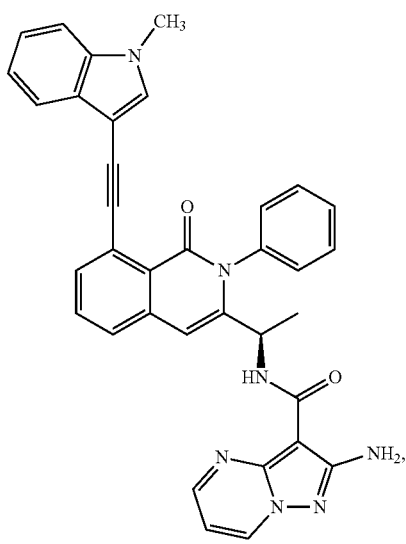 [SMILES: C[C@@H](NC(=O)c1c(N)nn2cccnc12)c1cc2cccc(C#Cc3cn(C)c4ccccc34)c2c(=O)n1-c1ccccc1]
Compound 3017r
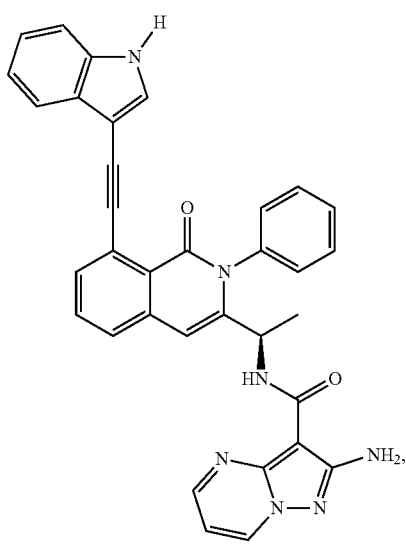 [SMILES: C[C@@H](NC(=O)c1c(N)nn2cccnc12)c1cc2cccc(C#Cc3c[nH]c4ccccc34)c2c(=O)n1-c1ccccc1]
Compound 3018r TABLE 14-continued
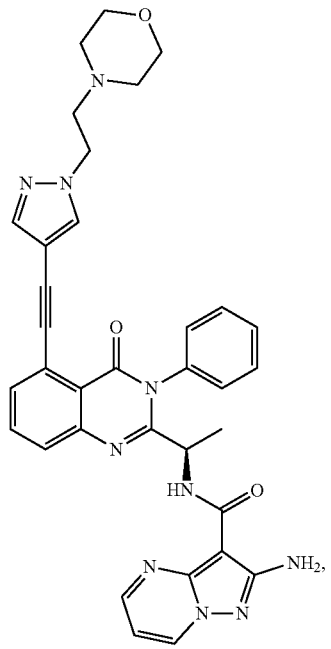
Compound 3019r
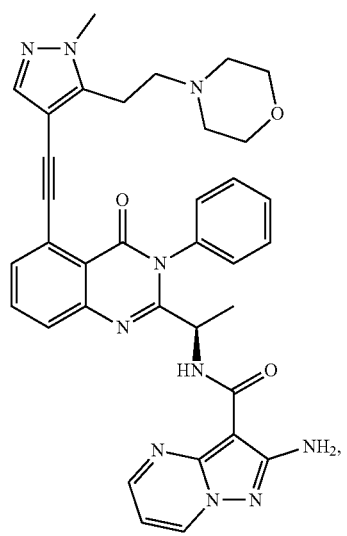 [SMILES: C[C@@H](NC(=O)c1c(N)nn2cccnc12)c1nc2cccc(C#Cc3cnn(C)c3CCN3CCOCC3)c2c(=O)n1-c1ccccc1]
Compound 3020r TABLE 14-continued
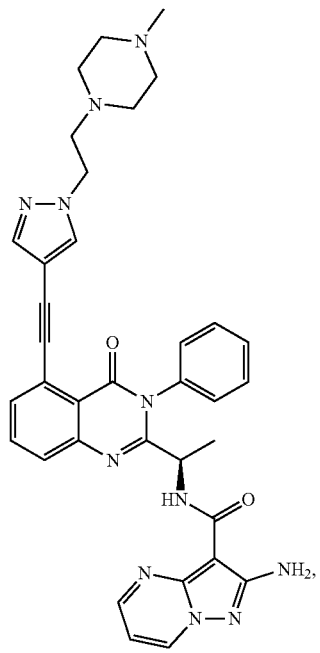
Compound 3021r
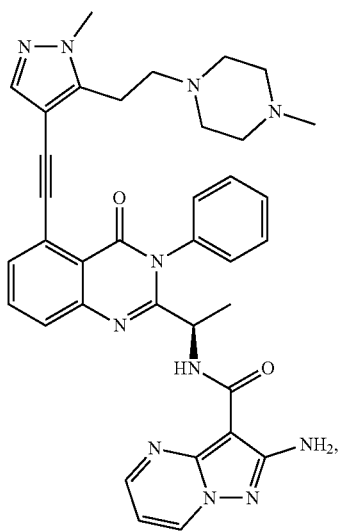 [SMILES: C[C@@H](NC(=O)c1c(N)nn2cccnc12)c1nc2cccc(C#Cc3cnn(C)c3CCN3CCN(C)CC3)c2c(=O)n1-c1ccccc1]
Compound 3022r TABLE 14-continued
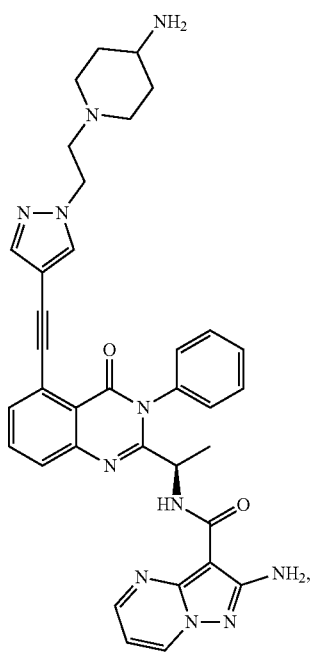
Compound 3023r
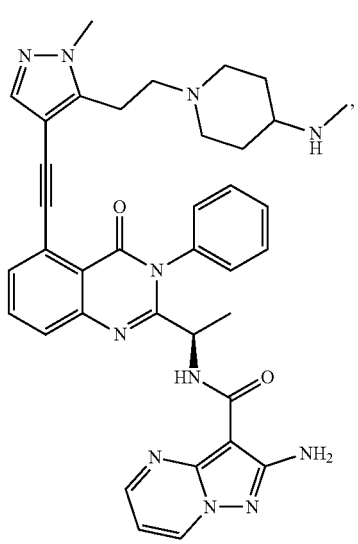 [SMILES: CNC1CCN(CCc2c(C#Cc3cccc4nc([C@@H](C)NC(=O)c5c(N)nn6cccnc56)n(-c5ccccc5)c(=O)c34)cnn2C)CC1]
Compound 3024r TABLE 14-continued
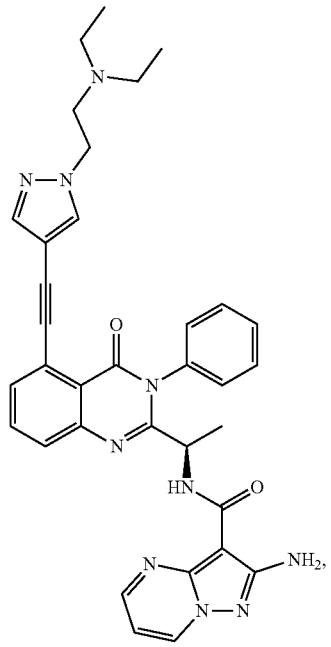
Compound 3025r
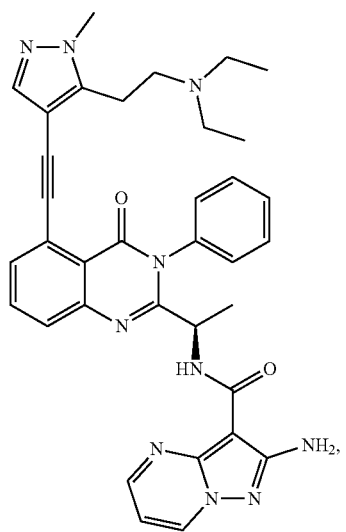 [SMILES: CCN(CC)CCc1c(C#Cc2cccc3nc([C@@H](C)NC(=O)c4c(N)nn5cccnc45)n(-c4ccccc4)c(=O)c23)cnn1C]
Compound 3026r TABLE 14-continued
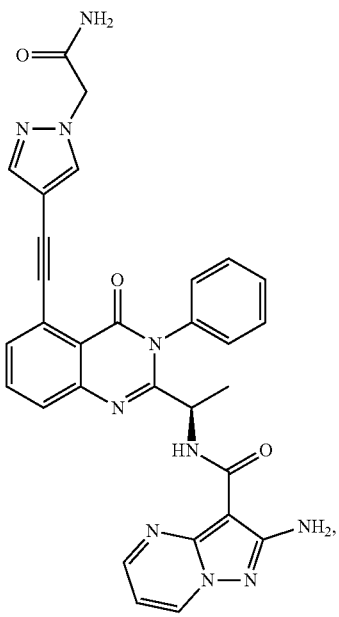 [SMILES: C[C@@H](NC(=O)c1c(N)nn2cccnc12)c1nc2cccc(C#Cc3cnn(CC(N)=O)c3)c2c(=O)n1-c1ccccc1]
Compound 3027r
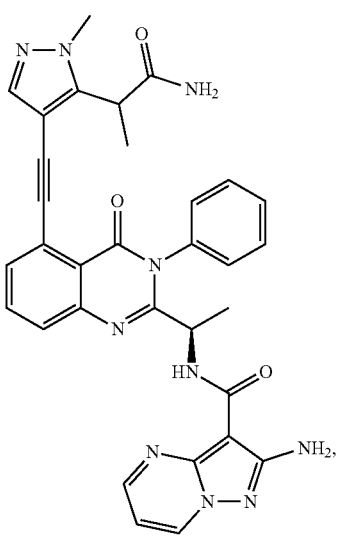 [SMILES: CC(C(N)=O)c1c(C#Cc2cccc3nc([C@@H](C)NC(=O)c4c(N)nn5cccnc45)n(-c4ccccc4)c(=O)c23)cnn1C]
Compound 3028r TABLE 14-continued
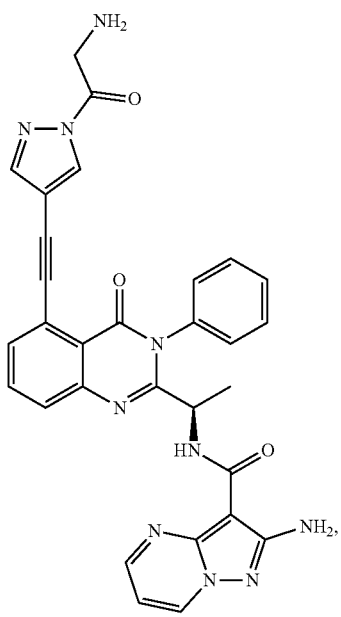 [SMILES: C[C@@H](NC(=O)c1c(N)nn2cccnc12)c1nc2cccc(C#Cc3cnn(C(=O)CN)c3)c2c(=O)n1-c1ccccc1]
Compound 3029r
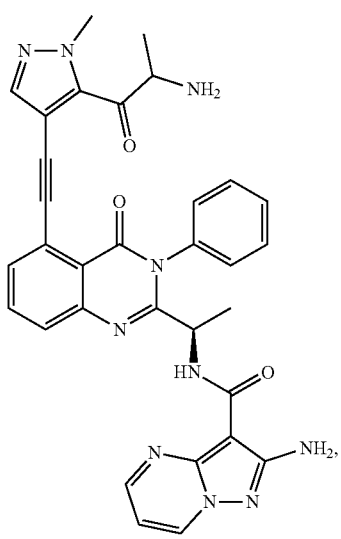 [SMILES: CC(N)C(=O)c1c(C#Cc2cccc3nc([C@@H](C)NC(=O)c4c(N)nn5cccnc45)n(-c4ccccc4)c(=O)c23)cnn1C]
Compound 3030r TABLE 14-continued
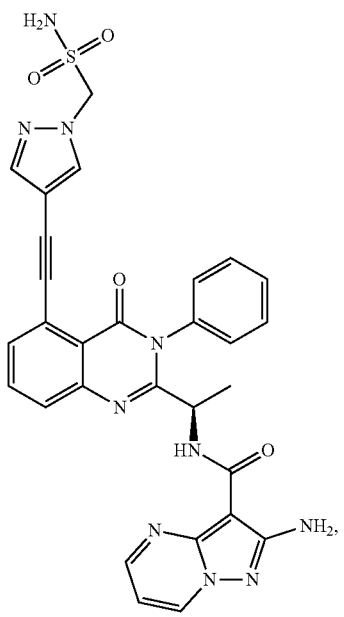 [SMILES: C[C@@H](NC(=O)c1c(N)nn2cccnc12)c1nc2cccc(C#Cc3cnn(CS(N)(=O)=O)c3)c2c(=O)n1-c1ccccc1]
Compound 3031r
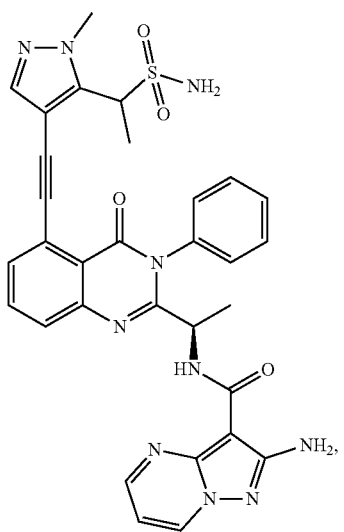 [SMILES: CC(c1c(C#Cc2cccc3nc([C@@H](C)NC(=O)c4c(N)nn5cccnc45)n(-c4ccccc4)c(=O)c23)cnn1C)S(N)(=O)=O]
Compound 3032r TABLE 14-continued
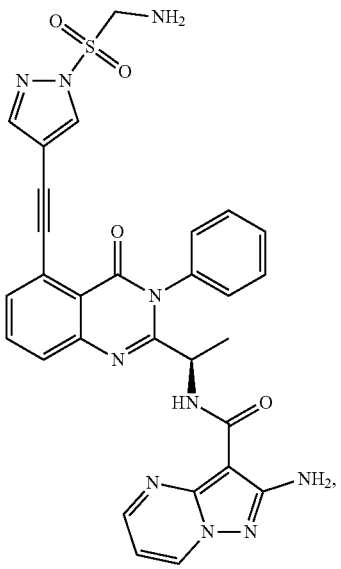 [SMILES: C[C@@H](NC(=O)c1c(N)nn2cccnc12)c1nc2cccc(C#Cc3cnn(S(=O)(=O)CN)c3)c2c(=O)n1-c1ccccc1]
Compound 3033r
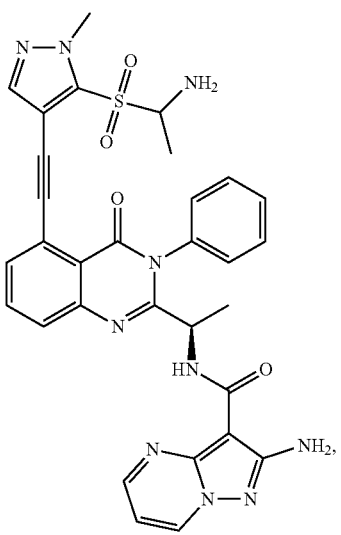 [SMILES: CC(N)S(=O)(=O)c1c(C#Cc2cccc3nc([C@@H](C)NC(=O)c4c(N)nn5cccnc45)n(-c4ccccc4)c(=O)c23)cnn1C]
Compound 3034r TABLE 14-continued
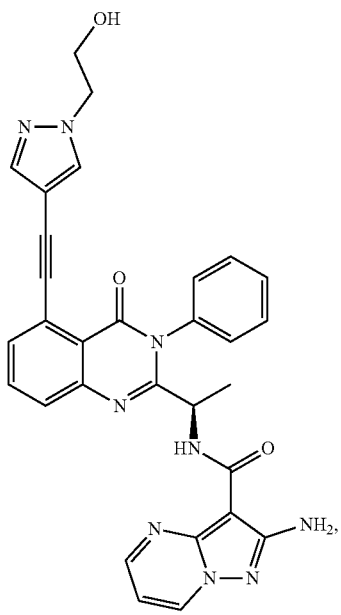 [SMILES: C[C@@H](NC(=O)c1c(N)nn2cccnc12)c1nc2cccc(C#Cc3cnn(CCO)c3)c2c(=O)n1-c1ccccc1]
Compound 3035r
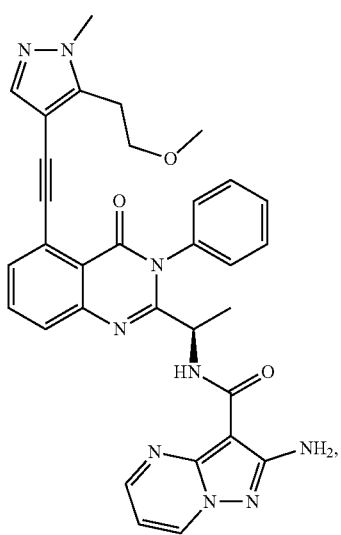 [SMILES: COCCc1c(C#Cc2cccc3nc([C@@H](C)NC(=O)c4c(N)nn5cccnc45)n(-c4ccccc4)c(=O)c23)cnn1C]
Compound 3036r TABLE 14-continued
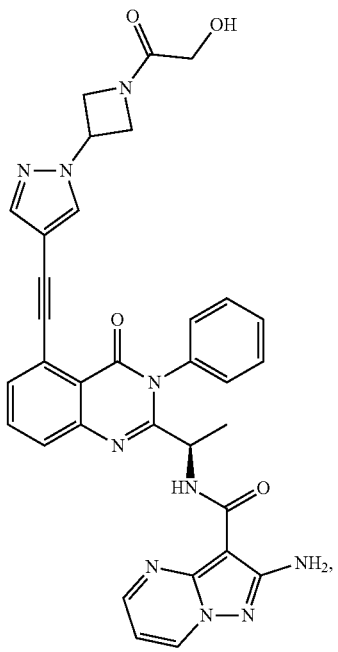 [SMILES: C[C@@H](NC(=O)c1c(N)nn2cccnc12)c1nc2cccc(C#Cc3cnn(C4CN(C(=O)CO)C4)c3)c2c(=O)n1-c1ccccc1]
Compound 3037r
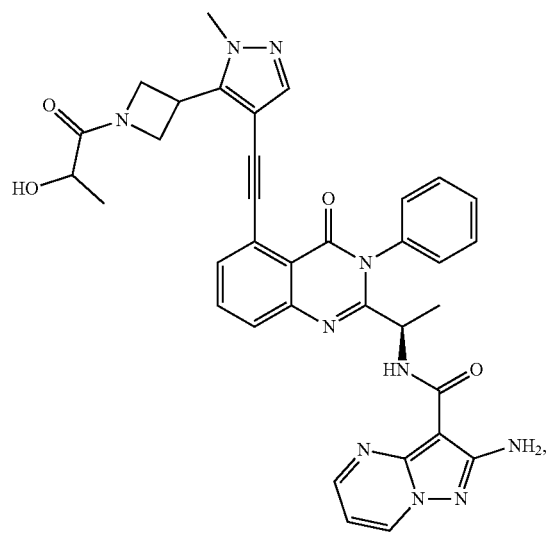
Compound 3038r TABLE 14-continued
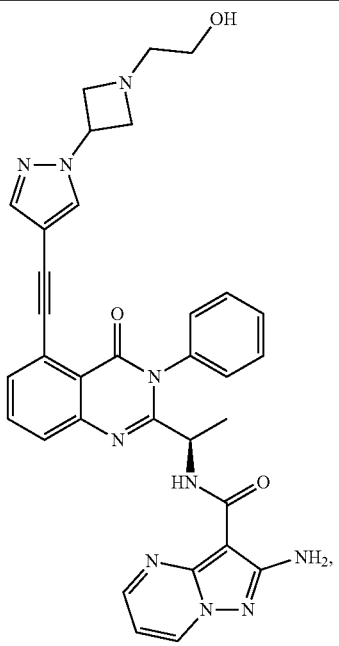
Compound 3039r
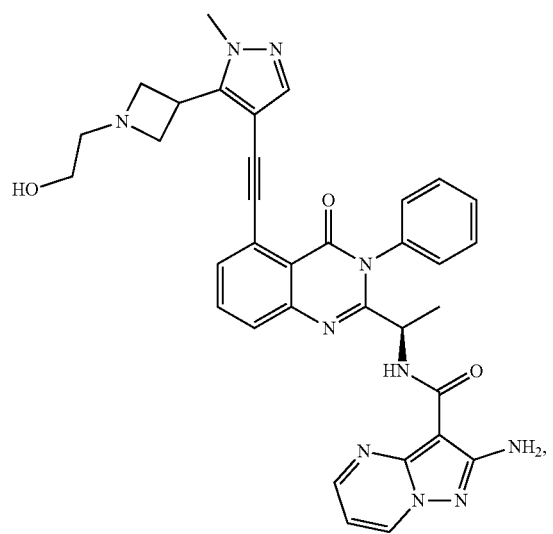
Compound 3040r TABLE 14-continued
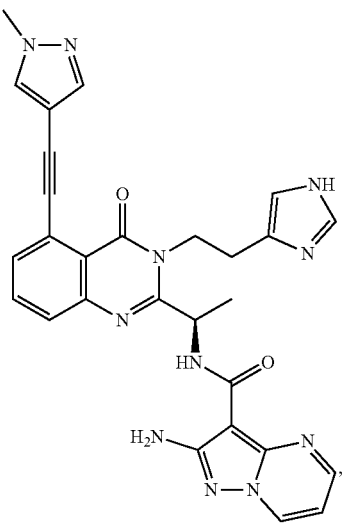 [SMILES: C[C@@H](NC(=O)c1c(N)nn2cccnc12)c1nc2cccc(C#Cc3cnn(C)c3)c2c(=O)n1CCc1c[nH]cn1]
Compound 3045r
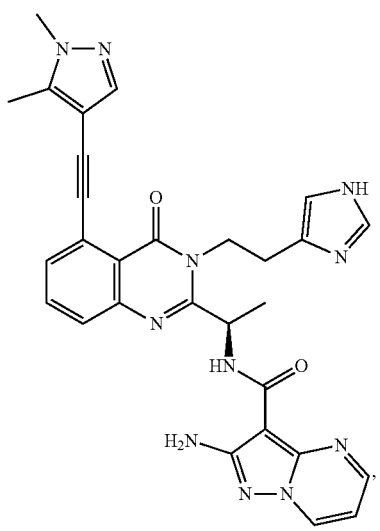 [SMILES: Cc1c(C#Cc2cccc3nc([C@@H](C)NC(=O)c4c(N)nn5cccnc45)n(CCc4c[nH]cn4)c(=O)c23)cnn1C]
Compound 3046r
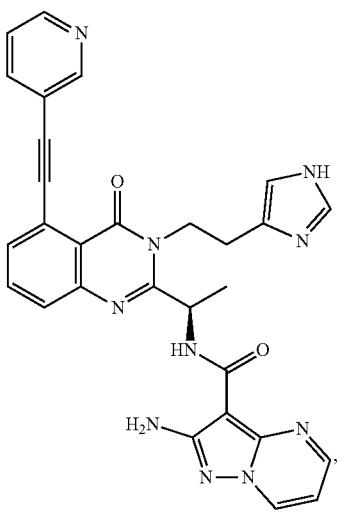 [SMILES: C[C@@H](NC(=O)c1c(N)nn2cccnc12)c1nc2cccc(C#Cc3cccnc3)c2c(=O)n1CCc1c[nH]cn1]
Compound 3047r TABLE 14-continued
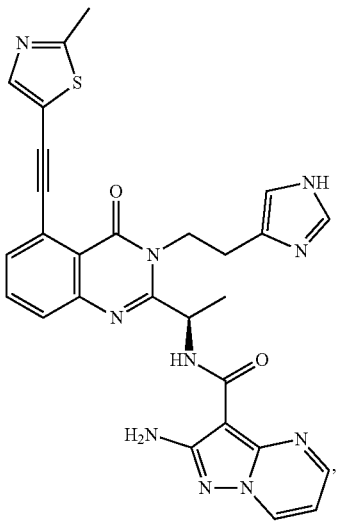 [SMILES: Cc1ncc(C#Cc2cccc3nc([C@@H](C)NC(=O)c4c(N)nn5cccnc45)n(CCc4c[nH]cn4)c(=O)c23)s1]
Compound 3048r
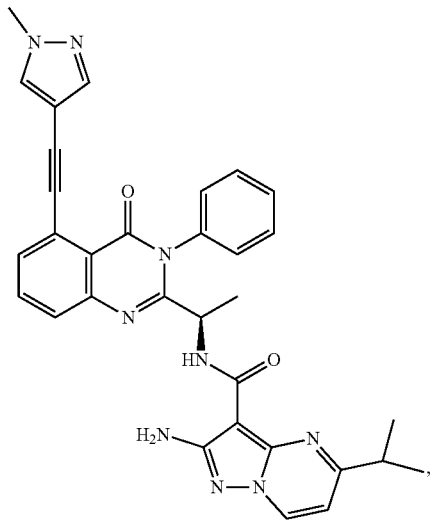 [SMILES: CC(C)c1ccn2nc(N)c(C(=O)N[C@H](C)c3nc4cccc(C#Cc5cnn(C)c5)c4c(=O)n3-c3ccccc3)c2n1]
Compound 3049r
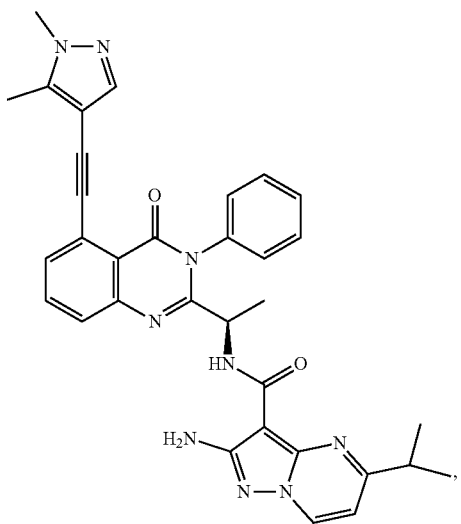 [SMILES: Cc1c(C#Cc2cccc3nc([C@@H](C)NC(=O)c4c(N)nn5ccc(C(C)C)nc45)n(-c4ccccc4)c(=O)c23)cnn1C]
Compound 3050r TABLE 14-continued
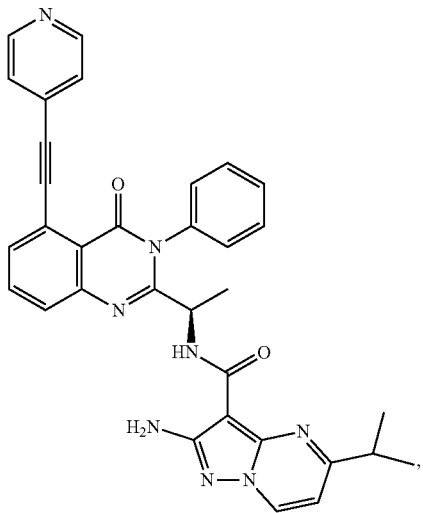 [SMILES: CC(C)c1ccn2nc(N)c(C(=O)N[C@H](C)c3nc4cccc(C#Cc5ccncc5)c4c(=O)n3-c3ccccc3)c2n1]
Compound 3051r
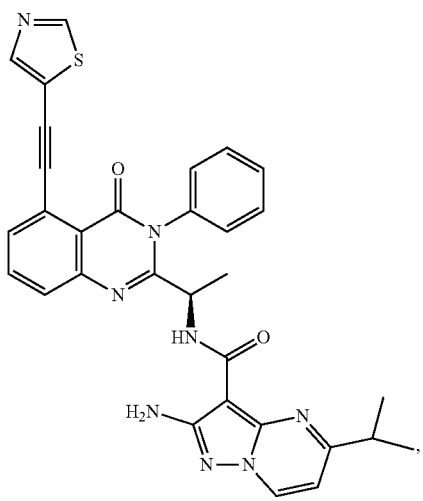 [SMILES: CC(C)c1ccn2nc(N)c(C(=O)N[C@H](C)c3nc4cccc(C#Cc5cncs5)c4c(=O)n3-c3ccccc3)c2n1]
Compound 3052r
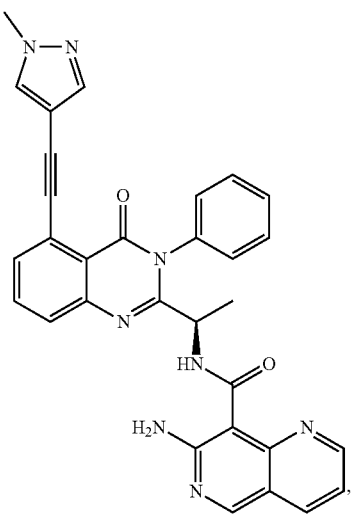 [SMILES: C[C@@H](NC(=O)c1c(N)ncc2cccnc12)c1nc2cccc(C#Cc3cnn(C)c3)c2c(=O)n1-c1ccccc1]
Compound 3053r TABLE 14-continued
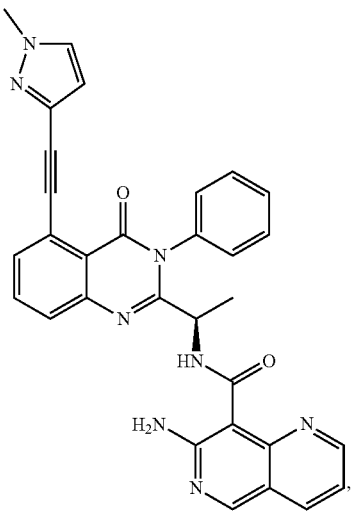 [SMILES: C[C@@H](NC(=O)c1c(N)ncc2cccnc12)c1nc2cccc(C#Cc3ccn(C)n3)c2c(=O)n1-c1ccccc1]
Compound 3054r
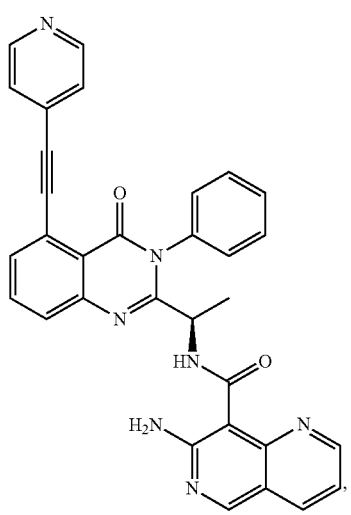 [SMILES: C[C@@H](NC(=O)c1c(N)ncc2cccnc12)c1nc2cccc(C#Cc3ccncc3)c2c(=O)n1-c1ccccc1]
Compound 3055r
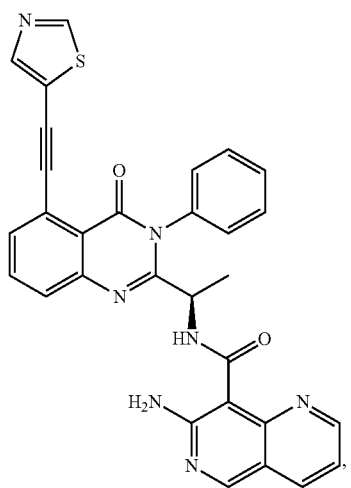 [SMILES: C[C@@H](NC(=O)c1c(N)ncc2cccnc12)c1nc2cccc(C#Cc3cncs3)c2c(=O)n1-c1ccccc1]
Compound 3056r TABLE 14-continued
Compound 3057r
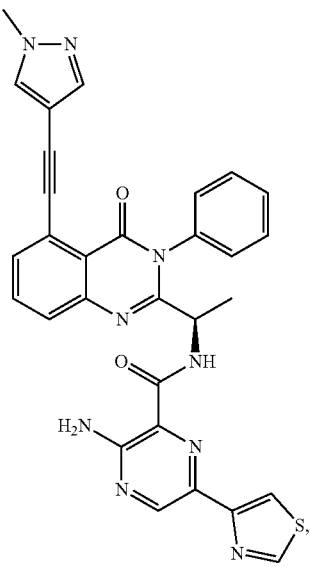 [SMILES: C[C@@H](NC(=O)c1nc(-c2cscn2)cnc1N)c1nc2cccc(C#Cc3cnn(C)c3)c2c(=O)n1-c1ccccc1]
Compound 3058r
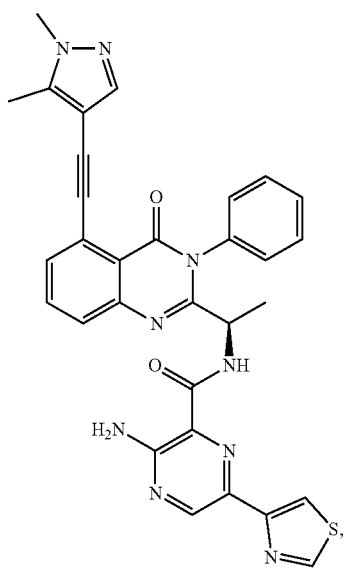 [SMILES: Cc1c(C#Cc2cccc3nc([C@@H](C)NC(=O)c4nc(-c5cscn5)cnc4N)n(-c4ccccc4)c(=O)c23)cnn1C]
Compound 3059r
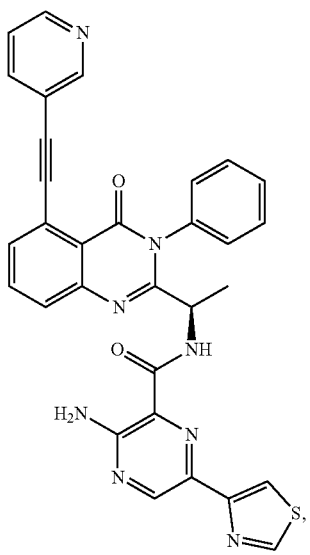 [SMILES: C[C@@H](NC(=O)c1nc(-c2cscn2)cnc1N)c1nc2cccc(C#Cc3cccnc3)c2c(=O)n1-c1ccccc1]

TABLE 14-continued
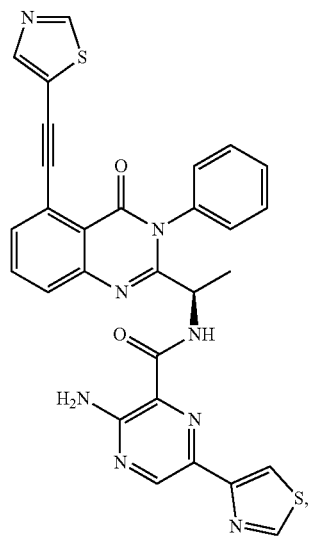 [SMILES: C[C@@H](NC(=O)c1nc(-c2cscn2)cnc1N)c1nc2cccc(C#Cc3cncs3)c2c(=O)n1-c1ccccc1]
Compound 3060r
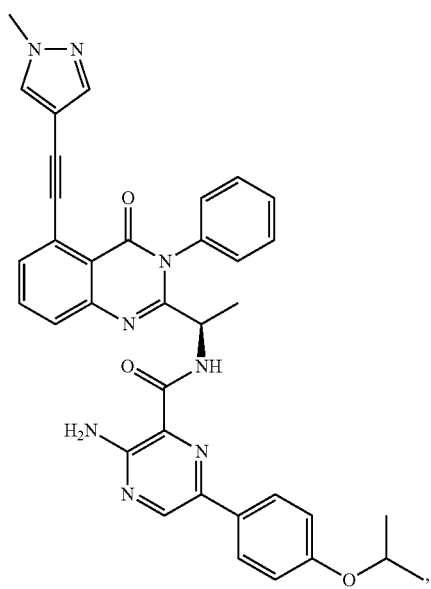 [SMILES: CC(C)Oc1ccc(-c2cnc(N)c(C(=O)N[C@H](C)c3nc4cccc(C#Cc5cnn(C)c5)c4c(=O)n3-c3ccccc3)n2)cc1]
Compound 3061r

TABLE 14-continued
Compound 3062r
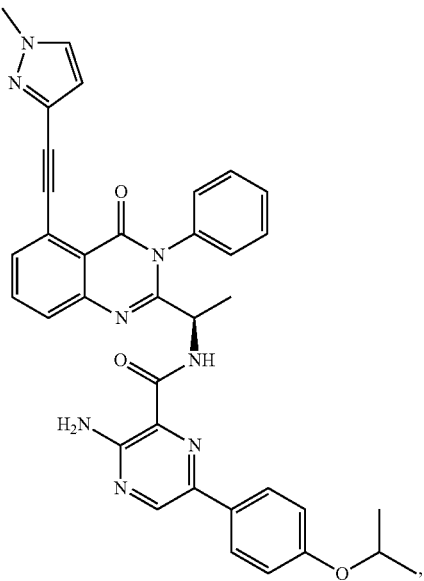 [SMILES: CC(C)Oc1ccc(-c2cnc(N)c(C(=O)N[C@H](C)c3nc4cccc(C#Cc5ccn(C)n5)c4c(=O)n3-c3ccccc3)n2)cc1]
Compound 3063r
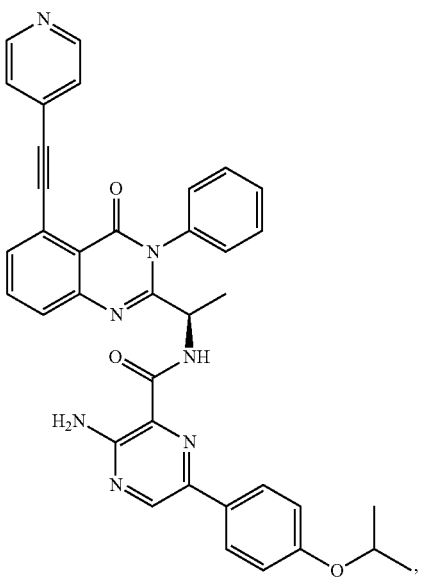 [SMILES: CC(C)Oc1ccc(-c2cnc(N)c(C(=O)N[C@H](C)c3nc4cccc(C#Cc5ccncc5)c4c(=O)n3-c3ccccc3)n2)cc1]

TABLE 14-continued
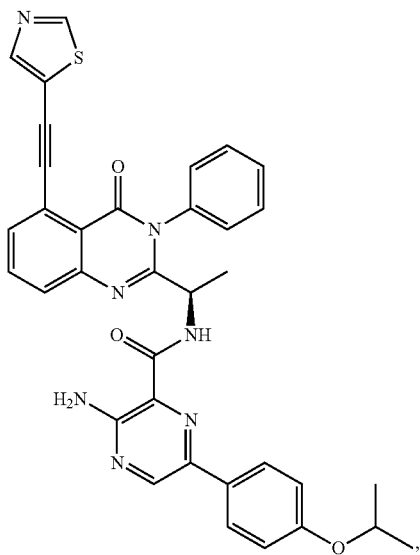 [SMILES: CC(C)Oc1ccc(-c2cnc(N)c(C(=O)N[C@H](C)c3nc4cccc(C#Cc5cncs5)c4c(=O)n3-c3ccccc3)n2)cc1]
Compound 3064r
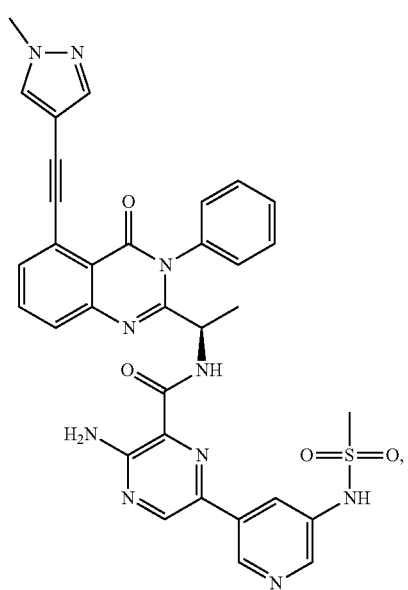 [SMILES: C[C@@H](NC(=O)c1nc(-c2cncc(NS(C)(=O)=O)c2)cnc1N)c1nc2cccc(C#Cc3cnn(C)c3)c2c(=O)n1-c1ccccc1]
Compound 3065r

TABLE 14-continued
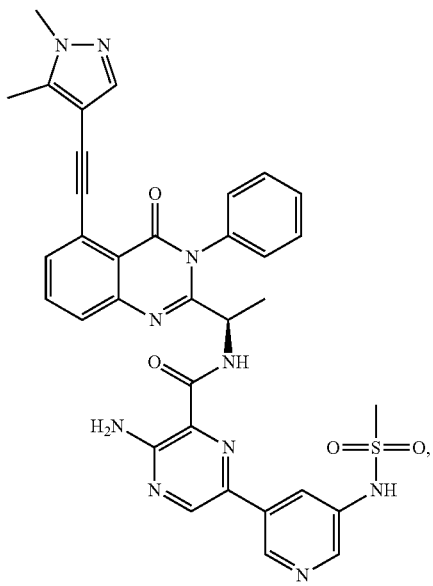 [SMILES: Cc1c(C#Cc2cccc3nc([C@@H](C)NC(=O)c4nc(-c5cncc(NS(C)(=O)=O)c5)cnc4N)n(-c4ccccc4)c(=O)c23)cnn1C]
Compound 3066r
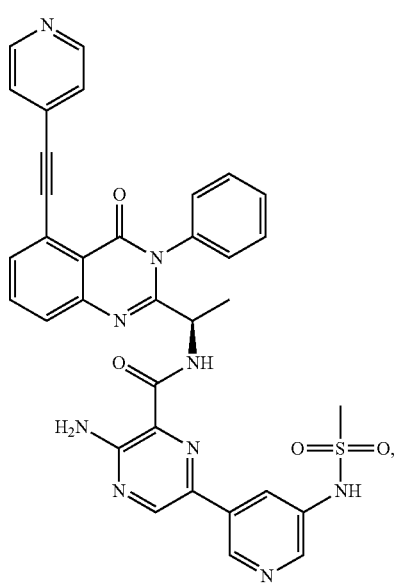 [SMILES: C[C@@H](NC(=O)c1nc(-c2cncc(NS(C)(=O)=O)c2)cnc1N)c1nc2cccc(C#Cc3ccncc3)c2c(=O)n1-c1ccccc1]
Compound 3067r

TABLE 14-continued
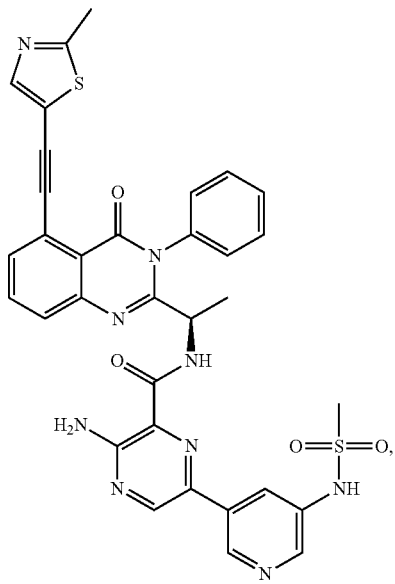 [SMILES: Cc1ncc(C#Cc2cccc3nc([C@@H](C)NC(=O)c4nc(-c5cncc(NS(C)(=O)=O)c5)cnc4N)n(-c4ccccc4)c(=O)c23)s1]
Compound 3068r
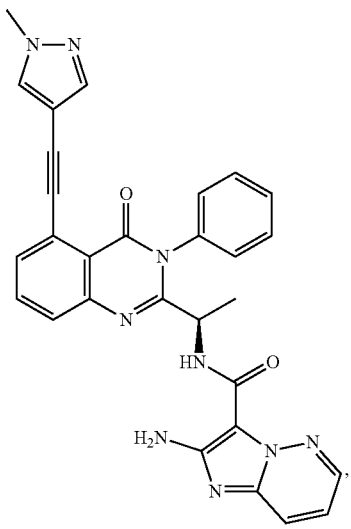 [SMILES: C[C@@H](NC(=O)c1c(N)nc2cccnn12)c1nc2cccc(C#Cc3cnn(C)c3)c2c(=O)n1-c1ccccc1]
Compound 3069r
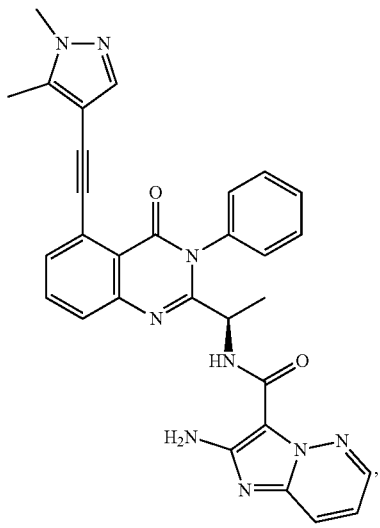 [SMILES: Cc1c(C#Cc2cccc3nc([C@@H](C)NC(=O)c4c(N)nc5cccnn45)n(-c4ccccc4)c(=O)c23)cnn1C]
Compound 3070r TABLE 14-continued
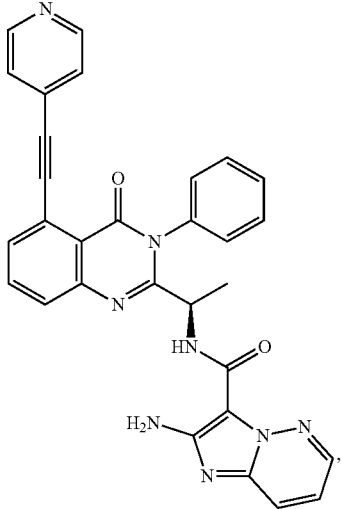 [SMILES: C[C@@H](NC(=O)c1c(N)nc2cccnn12)c1nc2cccc(C#Cc3ccncc3)c2c(=O)n1-c1ccccc1]
Compound 3071r
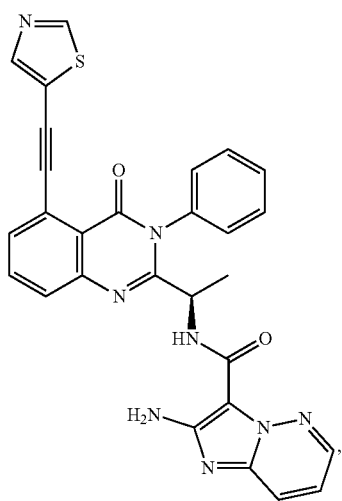 [SMILES: C[C@@H](NC(=O)c1c(N)nc2cccnn12)c1nc2cccc(C#Cc3cncs3)c2c(=O)n1-c1ccccc1]
Compound 3072r
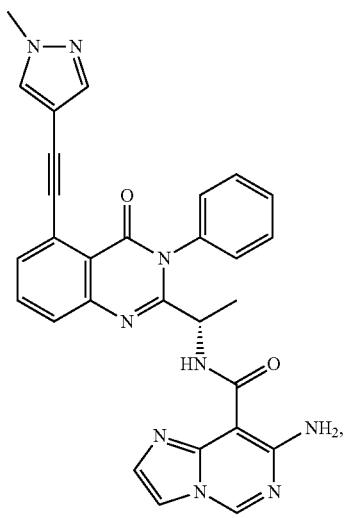 [SMILES: C[C@H](NC(=O)c1c(N)ncn2ccnc12)c1nc2cccc(C#Cc3cnn(C)c3)c2c(=O)n1-c1ccccc1]
Compound 3073r TABLE 14-continued
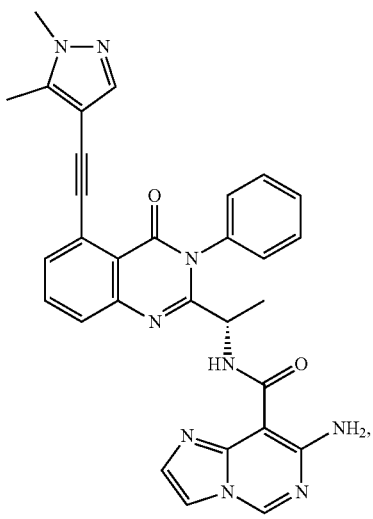 [SMILES: Cc1c(C#Cc2cccc3nc([C@H](C)NC(=O)c4c(N)ncn5ccnc45)n(-c4ccccc4)c(=O)c23)cnn1C]
Compound 3074r
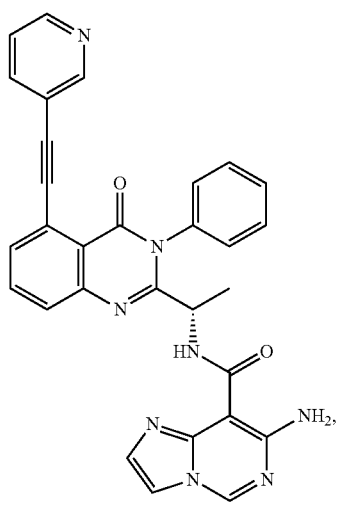 [SMILES: C[C@H](NC(=O)c1c(N)ncn2ccnc12)c1nc2cccc(C#Cc3cccnc3)c2c(=O)n1-c1ccccc1]
Compound 3075r
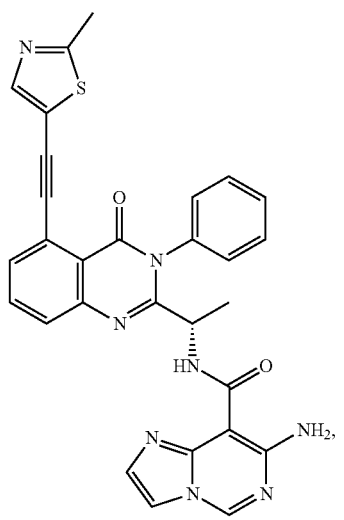 [SMILES: Cc1ncc(C#Cc2cccc3nc([C@H](C)NC(=O)c4c(N)ncn5ccnc45)n(-c4ccccc4)c(=O)c23)s1]
Compound 3076r TABLE 14-continued
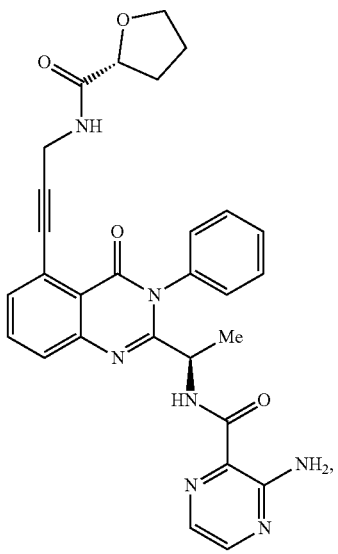 [SMILES: C[C@@H](NC(=O)c1nccnc1N)c1nc2cccc(C#CCNC(=O)[C@H]3CCCO3)c2c(=O)n1-c1ccccc1]
Compound 3077r
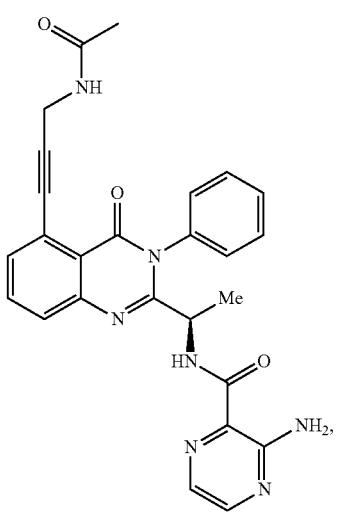 [SMILES: CC(=O)NCC#Cc1cccc2nc([C@@H](C)NC(=O)c3nccnc3N)n(-c3ccccc3)c(=O)c12]
Compound 3078r
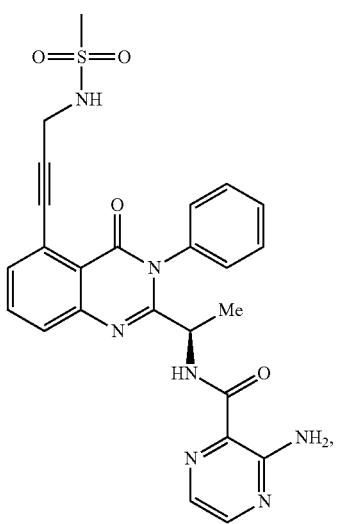 [SMILES: C[C@@H](NC(=O)c1nccnc1N)c1nc2cccc(C#CCNS(C)(=O)=O)c2c(=O)n1-c1ccccc1]
Compound 3079r TABLE 14-continued
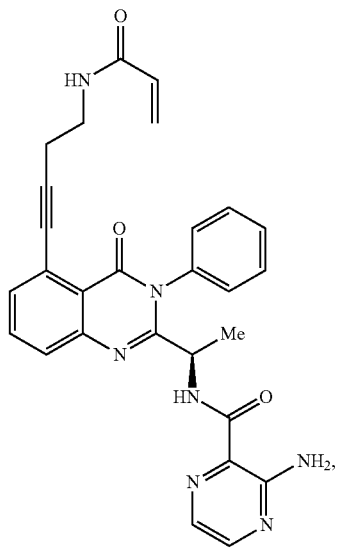 [SMILES: C=CC(=O)NCCC#Cc1cccc2nc([C@@H](C)NC(=O)c3nccnc3N)n(-c3ccccc3)c(=O)c12]
Compound 3080r
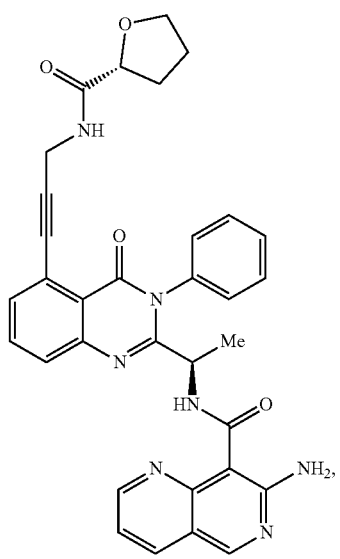 [SMILES: C[C@@H](NC(=O)c1c(N)ncc2cccnc12)c1nc2cccc(C#CCNC(=O)[C@H]3CCCO3)c2c(=O)n1-c1ccccc1]
Compound 3081r
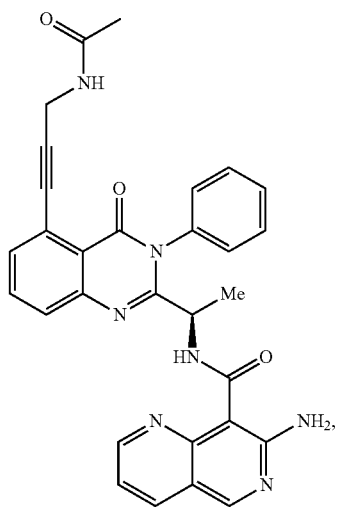 [SMILES: CC(=O)NCC#Cc1cccc2nc([C@@H](C)NC(=O)c3c(N)ncc4cccnc34)n(-c3ccccc3)c(=O)c12]
Compound 3082r TABLE 14-continued
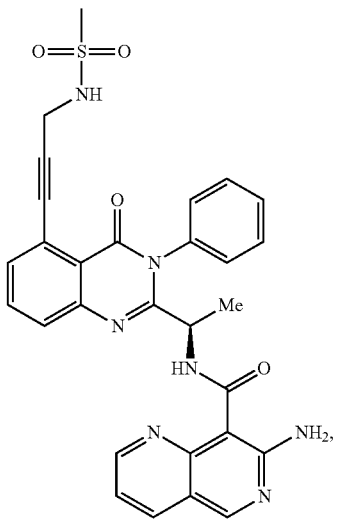 [SMILES: C[C@@H](NC(=O)c1c(N)ncc2cccnc12)c1nc2cccc(C#CCNS(C)(=O)=O)c2c(=O)n1-c1ccccc1]
Compound 3083r
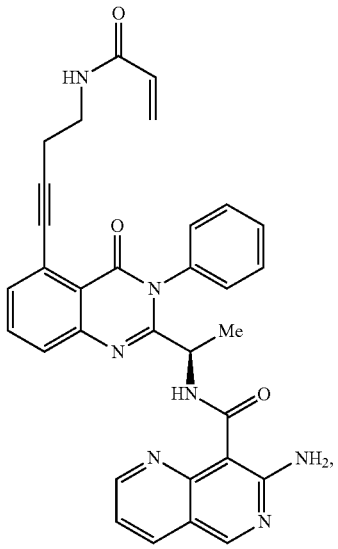 [SMILES: C=CC(=O)NCCC#Cc1cccc2nc([C@@H](C)NC(=O)c3c(N)ncc4cccnc34)n(-c3ccccc3)c(=O)c12]
Compound 3084r
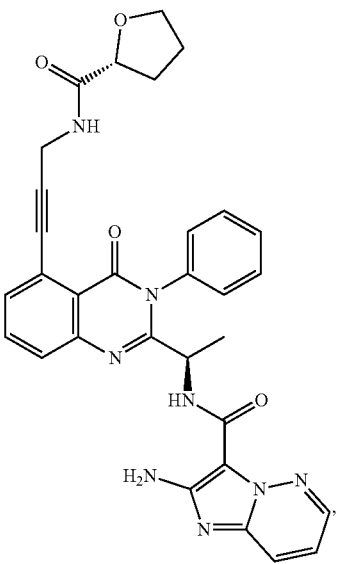 [SMILES: C[C@@H](NC(=O)c1c(N)nc2cccnn12)c1nc2cccc(C#CCNC(=O)[C@H]3CCCO3)c2c(=O)n1-c1ccccc1]
Compound 3085r TABLE 14-continued
Compound 3086r
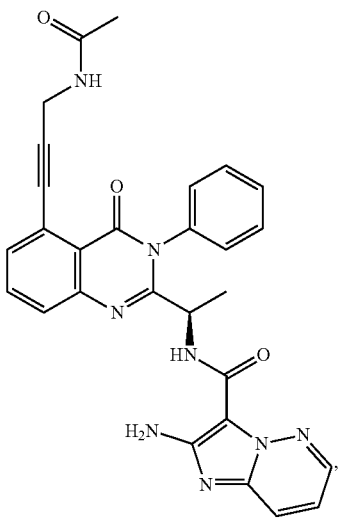 [SMILES: CC(=O)NCC#Cc1cccc2nc([C@@H](C)NC(=O)c3c(N)nc4cccnn34)n(-c3ccccc3)c(=O)c12]
Compound 3087r
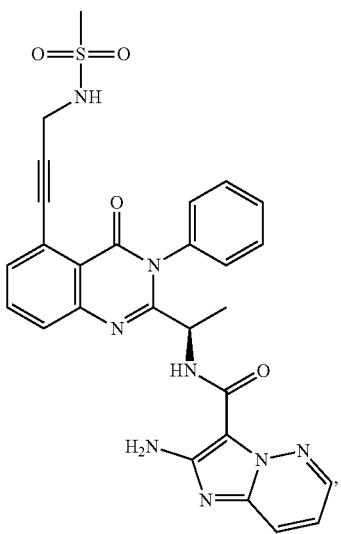 [SMILES: C[C@@H](NC(=O)c1c(N)nc2cccnn12)c1nc2cccc(C#CCNS(C)(=O)=O)c2c(=O)n1-c1ccccc1]
Compound 3088r
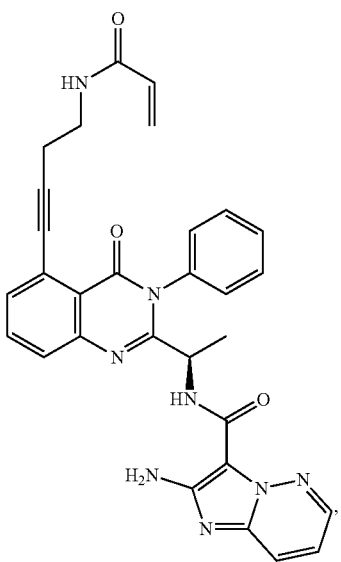 [SMILES: C=CC(=O)NCCC#Cc1cccc2nc([C@@H](C)NC(=O)c3c(N)nc4cccnn34)n(-c3ccccc3)c(=O)c12]

TABLE 14-continued
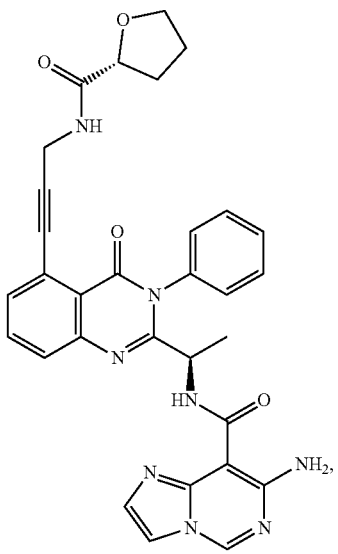 [SMILES: C[C@@H](NC(=O)c1c(N)ncn2ccnc12)c1nc2cccc(C#CCNC(=O)[C@H]3CCCO3)c2c(=O)n1-c1ccccc1]
Compound 3089r
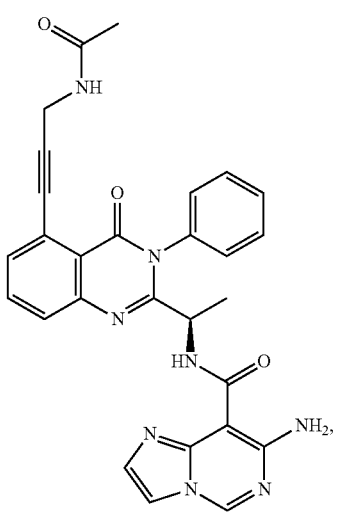 [SMILES: CC(=O)NCC#Cc1cccc2nc([C@@H](C)NC(=O)c3c(N)ncn4ccnc34)n(-c3ccccc3)c(=O)c12]
Compound 3090r
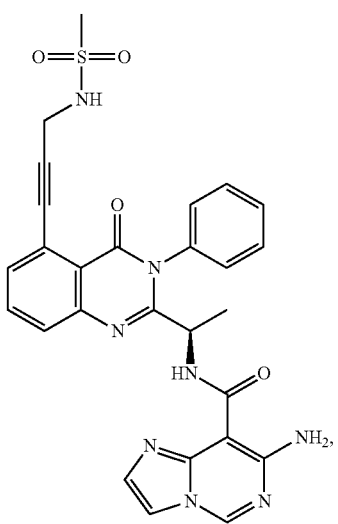 [SMILES: C[C@@H](NC(=O)c1c(N)ncn2ccnc12)c1nc2cccc(C#CCNS(C)(=O)=O)c2c(=O)n1-c1ccccc1]
Compound 3091r TABLE 14-continued
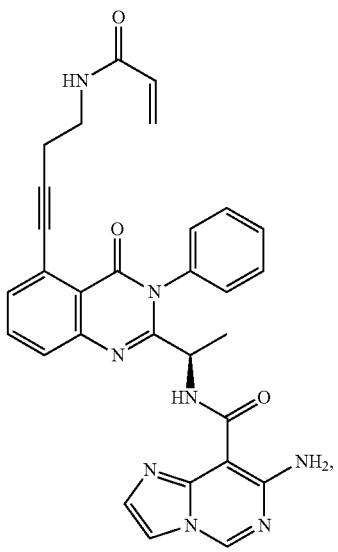 [SMILES: C=CC(=O)NCCC#Cc1cccc2nc([C@@H](C)NC(=O)c3c(N)ncn4ccnc34)n(-c3ccccc3)c(=O)c12]
Compound 3092r
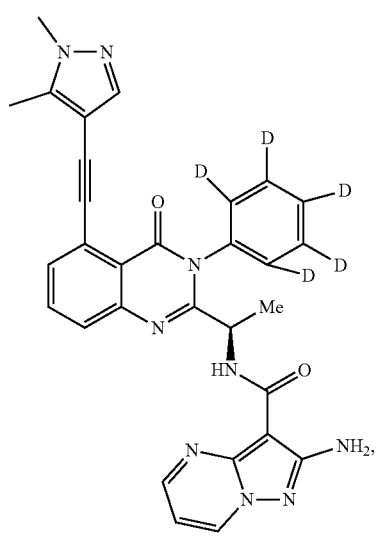 [SMILES: [2H]c1c([2H])c([2H])c(-n2c([C@@H](C)NC(=O)c3c(N)nn4cccnc34)nc3cccc(C#Cc4cnn(C)c4C)c3c2=O)c([2H])c1[2H]]
Compound 3093r
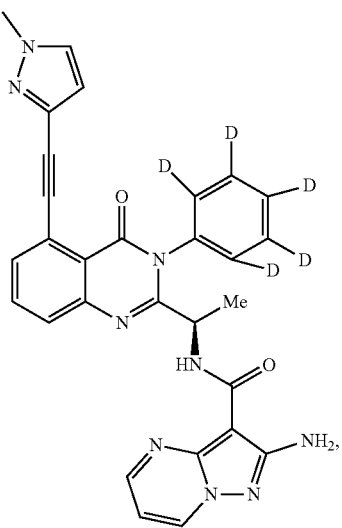 [SMILES: [2H]c1c([2H])c([2H])c(-n2c([C@@H](C)NC(=O)c3c(N)nn4cccnc34)nc3cccc(C#Cc4ccn(C)n4)c3c2=O)c([2H])c1[2H]]
Compound 3094r TABLE 14-continued

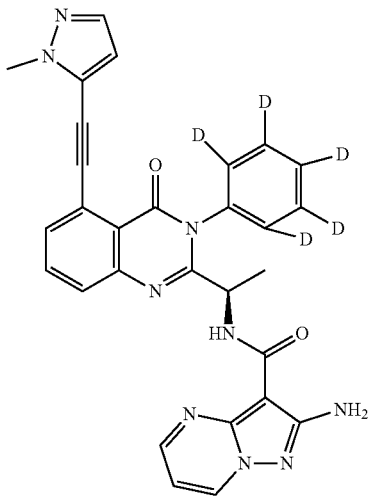 [SMILES: [2H]c1c([2H])c([2H])c(-n2c([C@@H](C)NC(=O)c3c(N)nn4cccnc34)nc3cccc(C#Cc4ccnn4C)c3c2=O)c([2H])c1[2H]]

Compound 3095r

In some embodiments, the compound provided herein is:

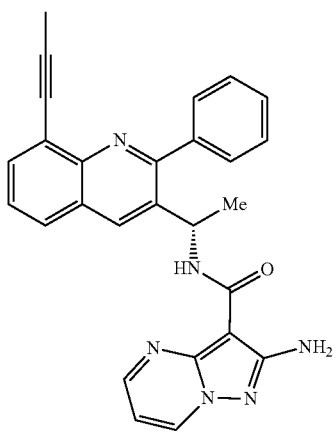 [SMILES: CC#Cc1cccc2cc([C@H](C)NC(=O)c3c(N)nn4cccnc34)c(-c3ccccc3)nc12]

or a pharmaceutically acceptable form thereof.

Provided herein, Compound AA has the structure:

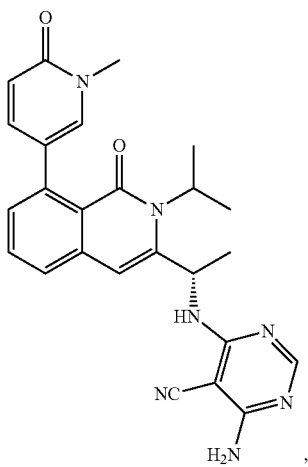 [SMILES: CC(C)n1c([C@H](C)Nc2ncnc(N)c2C#N)cc2cccc(-c3ccc(=O)n(C)c3)c2c1=O]

Compound AA is disclosed as Compound 359 in International Application WO2013/032591. As described in Table 4 of International Application WO2013/032591, Compound AA has a PI3K-delta IC50 of less than 100 nM, a PI3K-gamma IC50 of 1 uM to 100 nM, a PI3K-alpha IC50 of greater than 1 uM to 10 uM, and a PI3K-beta IC50 of greater than 1 uM to 10 uM.

Provided herein, compound BB is Compound 4 of the structure:

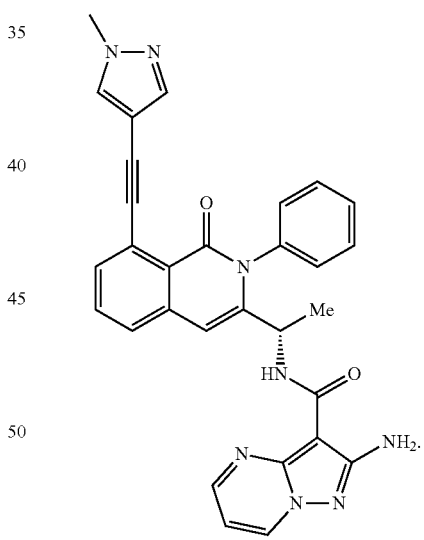

In some embodiments, one or more compounds described herein bind to a PI3 kinase (e.g., bind selectively). In some embodiments, one or more compounds described herein bind selectively to a γ- or δ-subtype of a PI3 kinase. In some embodiments, one or more compounds described herein bind selectively to a γ-subtype of a PI3 kinase. In some embodiments, one or more compounds described herein bind selectively to a δ-subtype of a PI3 kinase. In one embodiment, one or more compounds described herein selectively binds to δ over γ. In one embodiment, one or more compounds described herein selectively binds to γ over δ.

In certain embodiments provided herein are methods of treating or preventing a PI3K mediated disorder in a subject, the method comprising administering a therapeutically effective amount of a compound provided herein or composition provided herein to said subject. In certain embodiments, provided herein is the use of a compound provided herein in the manufacture of a medicament for treating or preventing a PI3K mediated disorder in a subject. In certain embodiments, a compound provided herein is for use in treating or preventing a PI3K mediated disorder in a subject. In certain embodiments, the disorder is cancer, an inflammatory disease, or an auto-immune disease. In certain embodiments, the PI3K mediated disorder is a PI3K-γ mediated disorder. In certain embodiments, the PI3K mediated disorder is a PI3K-δ mediated disorder. In certain embodiments, provided herein are methods for selectively inhibiting PI3K gamma over PI3K delta in a cell or subject comprising contacting the cell or administering to the subject a compound provided herein. In certain embodiments, provided wherein are methods for selectively inhibiting PI3K gamma over PI3K delta in a cell or subject comprising contacting the cell or administering to the subject (i) a compound selected from compound 2, 4, 7, 9, 17, 19, 21, 26, 27, 30, 32, 35, 37, 38, 40, 41, 52, 60, 61, 63, 73, 75, 77, 79, 80, 81, 88, and 89; or (ii) a compound is selected from compound 1, 3, 6, 10, 11, 12, 16, 18, 20, 22, 25, 28, 34, 39, 42, 43, 53, 55, 59, 64, 65, 66, 67, 70, 76, 78, 82, 83, 84, 85, 86, and 90; or (iii) a compound selected from compound 8, 13, 15, 23, 29, 33, 45, 51, 54, 57, and 68; or (iv) a compound selected from compound 5, 14, 24, 31, 36, 46, 50, 69, 72, 74, and 91.

In certain embodiments, the compound is selected from compound 2, 4, 7, 9, 17, 19, 21, 26, 27, 30, 32, 35, 37, 38, 40, 41, 52, 60, 61, 63, 73, 75, 77, 79, 80, 81, 88, and 89. In certain embodiments, the compound is selected from compound 1, 3, 6, 10, 11, 12, 16, 18, 20, 22, 25, 28, 34, 39, 42, 43, 53, 55, 59, 64, 65, 66, 67, 70, 76, 78, 82, 83, 84, 85, 86, and 90. In certain embodiments, the compound is selected from compound 8, 13, 15, 23, 29, 33, 45, 51, 54, 57, and 68. In certain embodiments, the compound is selected from compound 5, 14, 24, 31, 36, 46, 50, 69, 72, 74, and 91.

In certain embodiments, provided herein are methods of synthesizing a compound provided herein. Provided herein are methods of making a PI3K-γ selective compound comprising synthesizing a compound containing both (a) a non-terminal alkyne substituted bicyclic heterocyclic group and (b) an amido group. In some embodiments, the compound selectively binds to PI3K-γ over PI3K-δ.

In some embodiments, the $IC_{50}$ of a compound provided herein for p110α, p110β, p110γ, or p110δ is less than about 1 μM, less than about 100 nM, less than about 50 nM, less than about 10 nM, less than 1 nM, or even less than about 0.5 nM.

In some embodiments, non-limiting exemplary compounds exhibit one or more functional characteristics disclosed herein. For example, one or more compounds provided herein bind specifically to a PI3 kinase. In some embodiments, the $IC_{50}$ of a compound provided herein for p110α, p110β, p110γ, or p110δ is less than about 1 μM, less than about 100 nM, less than about 50 nM, less than about 10 nM, less than about 1 nM, less than about 0.5 nM, less than about 100 μM, or less than about 50 μM.

In some embodiments, one or more of the compounds provided herein can selectively inhibit one or more members of type I or class I phosphatidylinositol 3-kinases (PI3-kinase) with an $IC_{50}$ value of about 100 nM, about 50 nM, about 10 nM, about 5 nM, about 100 μM, about 10 μM, or about 1 μM, or less, as measured in an in vitro kinase assay.

In some embodiments, one or more of the compounds provided herein can selectively inhibit one or two members of type I or class I phosphatidylinositol 3-kinases (PI3-kinase), such as, PI3-kinase α, PI3-kinase β, PI3-kinase γ, and PI3-kinase δ. In some aspects, some of the compounds provided herein selectively inhibit PI3-kinase δ as compared to all other type I PI3-kinases. In other aspects, some of the compounds provided herein selectively inhibit PI3-kinase δ and PI3-kinase γ as compared to the rest of the type I PI3-kinases. In other aspects, some of the compounds provided herein selectively inhibit PI3-kinase γ as compared to all other type I PI3-kinases.

In yet another aspect, an inhibitor that selectively inhibits one or more members of type I PI3-kinases, or an inhibitor that selectively inhibits one or more type I PI3-kinase mediated signaling pathways, alternatively can be understood to refer to a compound that exhibits a 50% inhibitory concentration ($IC_{50}$) with respect to a given type I PI3-kinase, that is at least about 10-fold, at least about 20-fold, at least about 50-fold, at least about 100-fold, at least about 200-fold, at least about 500-fold, at least about 1000-fold, at least about 2000-fold, at least about 5000-fold, or at least about 10,000-fold, lower than the inhibitor's $IC_{50}$ with respect to the rest of the other type I PI3-kinases. In one embodiment, an inhibitor selectively inhibits PI3-kinase δ as compared to PI3-kinase β with at least about 10-fold lower $IC_{50}$ for PI3-kinase δ. In certain embodiments, the $IC_{50}$ for PI3-kinase δ is below about 100 nM, while the $IC_{50}$ for PI3-kinase β is above about 1000 nM. In certain embodiments, the $IC_{50}$ for PI3-kinase δ is below about 50 nM, while the $IC_{50}$ for PI3-kinase β is above about 5000 nM. In certain embodiments, the $IC_{50}$ for PI3-kinase δ is below about 10 nM, while the $IC_{50}$ for PI3-kinase β is above about 1000 nM, above about 5,000 nM, or above about 10,000 nM. In one embodiment, an inhibitor selectively inhibits PI3-kinase γ as compared to PI3-kinase β with at least about 10-fold lower $IC_{50}$ for PI3-kinase γ. In certain embodiments, the $IC_{50}$ for PI3-kinase γ is below about 100 nM, while the $IC_{50}$ for PI3-kinase β is above about 1000 nM. In certain embodiments, the $IC_{50}$ for PI3-kinase γ is below about 50 nM, while the $IC_{50}$ for PI3-kinase β is above about 5000 nM. In certain embodiments, the $IC_{50}$ for PI3-kinase γ is below about 10 nM, while the $IC_{50}$ for PI3-kinase β is above about 1000 nM, above about 5,000 nM, or above about 10,000 nM.

A PI3K gamma compound, e.g., a PI3K gamma inhibitor, can inhibit PI3K gamma and can optionally also inhibit other PI3K isoforms such as PI3K delta. In one embodiment, a PI3K gamma inhibitor is also an inhibitor of PI3K delta, i.e., a dual inhibitor of PI3K gamma and PI3K delta. In one embodiment, the dual inhibitor has an IC50 for PI3K gamma that is within 10-fold of its IC50 for PI3K delta.

A PI3K gamma selective compound, e.g., a PI3K gamma selective inhibitor, can exhibit a 50% inhibitory concentration (IC50) with respect to PI3K gamma, that is at least about 10-fold lower than the compound's IC50 with respect to the rest of the other type I PI3-kinases. In some embodiments, the PI3K gamma selective compound exhibits a 50% inhibitory concentration (IC50) with respect to PI3K gamma, that is at least about at least about 20-fold, at least about 30-fold, at least about 40-fold, at least about 50-fold, at least about 60-fold, at least about 70-fold, at least about 80-fold, at least about 90-fold, at least about 100-fold, at least about 200-fold, at least about 500-fold, at least about 1000-fold, at least about 2000-fold, at least about 5000-fold, or at least about 10,000-fold, lower than the compound's IC50 with respect to the rest of the other type I PI3-kinases. In one embodiment, an inhibitor selectively inhibits PI3-kinase γ as compared to PI3-kinase δ with at least about 10-fold lower IC50 for PI3-kinase γ. In some embodiments, a PI3K gamma selective compound has an IC50 of about 1.8 nM for PI3K gamma, a PI3K beta or PI3K delta IC50 of about 180 nM, an IC90 value for PI3K gamma of about 16 nM, and an IC20 value for PI3K beta or PI3K delta of about 45 nM.

A PI3K delta compound, e.g., a PI3K delta inhibitor, can inhibit PI3K delta and can optionally also inhibit other PI3K isoforms such as PI3K gamma. In one embodiment, a PI3K delta inhibitor is also an inhibitor of PI3K gamma.

A PI3K delta selective compound, e.g., a PI3K delta selective inhibitor, can exhibit a 50% inhibitory concentration (IC50) with respect to PI3K delta, that is at least about 10-fold lower than the compound's IC50 with respect to the rest of the other type I PI3-kinases. In some embodiments, the PI3K delta selective compound exhibits a 50% inhibitory concentration (IC50) with respect to PI3K delta, that is at least about 20-fold, at least about 30-fold, at least about 40-fold, at least about 50-fold, at least about 60-fold, at least about 70-fold, at least about 80-fold, at least about 90-fold, at least about 100-fold, at least about 200-fold, at least about 500-fold, at least about 1000-fold, at least about 2000-fold, at least about 5000-fold, or at least about 10,000-fold, lower than the compound's IC50 with respect to the rest of the other type I PI3-kinases. In one embodiment, an inhibitor selectively inhibits PI3-kinase δ as compared to PI3-kinase γ with at least about 10-fold lower IC50 for PI3-kinase δ.

Pharmaceutical Compositions

In some embodiments, provided herein are pharmaceutical compositions comprising a compound as disclosed herein, or an enantiomer, a mixture of enantiomers, or a mixture of two or more diastereomers thereof, or a pharmaceutically acceptable form thereof (e.g., pharmaceutically acceptable salts, hydrates, solvates, isomers, prodrugs, and isotopically labeled derivatives), and a pharmaceutically acceptable excipient, diluent, or carrier, including inert solid diluents and fillers, sterile aqueous solution and various organic solvents, permeation enhancers, solubilizers and adjuvants. In some embodiments, a pharmaceutical composition described herein includes a second active agent such as an additional therapeutic agent, (e.g., a chemotherapeutic).

Formulations

Pharmaceutical compositions can be specially formulated for administration in solid or liquid form, including those adapted for the following: oral administration, for example, drenches (aqueous or non-aqueous solutions or suspensions), tablets (e.g., those targeted for buccal, sublingual, and systemic absorption), capsules, boluses, powders, granules, pastes for application to the tongue, and intraduodenal routes; parenteral administration, including intravenous, intraarterial, subcutaneous, intramuscular, intravascular, intraperitoneal or infusion as, for example, a sterile solution or suspension, or sustained-release formulation; topical application, for example, as a cream, ointment, or a controlled-release patch or spray applied to the skin; intravaginally or intrarectally, for example, as a pessary, cream, stent or foam; sublingually; ocularly; pulmonarily; local delivery by catheter or stent; intrathecally, or nasally.

Examples of suitable aqueous and nonaqueous carriers which can be employed in pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions can also contain adjuvants such as preservatives, wetting agents, emulsifying agents, dispersing agents, lubricants, and/or antioxidants. Prevention of the action of microorganisms upon the compounds described herein can be ensured by the inclusion of various antibacterial and antifungal agents, for example, paraben, chlorobutanol, phenol sorbic acid, and the like. It can also be desirable to include isotonic agents, such as sugars, sodium chloride, and the like into the compositions. In addition, prolonged absorption of the injectable pharmaceutical form can be brought about by the inclusion of agents which delay absorption such as aluminum monostearate and gelatin.

Methods of preparing these formulations or compositions include the step of bringing into association a compound described herein and/or the chemotherapeutic with the carrier and, optionally, one or more accessory ingredients. In general, the formulations are prepared by uniformly and intimately bringing into association a compound as disclosed herein with liquid carriers, or finely divided solid carriers, or both, and then, if necessary, shaping the product.

Preparations for such pharmaceutical compositions are well-known in the art. See, e.g., Anderson, Philip O.; Knoben, James E.; Troutman, William G, eds., *Handbook of Clinical Drug Data*, Tenth Edition, McGraw-Hill, 2002; Pratt and Taylor, eds., *Principles of Drug Action*, Third Edition, Churchill Livingston, N.Y., 1990; Katzung, ed., *Basic and Clinical Pharmacology*, Twelfth Edition, McGraw Hill, 2011; Goodman and Gilman, eds., *The Pharmacological Basis of Therapeutics*, Tenth Edition, McGraw Hill, 2001; *Remingtons Pharmaceutical Sciences*, 20th Ed., Lippincott Williams & Wilkins., 2000; Martindale, *The Extra Pharmacopoeia*, Thirty-Second Edition (The Pharmaceutical Press, London, 1999); all of which are incorporated by reference herein in their entirety. Except insofar as any conventional excipient medium is incompatible with the compounds provided herein, such as by producing any undesirable biological effect or otherwise interacting in a deleterious manner with any other component(s) of the pharmaceutically acceptable composition, the excipient's use is contemplated to be within the scope of this disclosure.

In some embodiments, pharmaceutical compositions provided herein include CD44 (cluster of differentiation 44) targeted nanoparticle formulations. CD44 is a transmembrane glycoprotein that plays a role in the cell signaling cascades associated with cancer initiation and progression. CD44 is over-expressed on the surface of certain cancers, and hyaluronic acid has an affinity for these over-expressed CD44. Targeted drug delivery system based on hyaluronic acid (e.g., hyaluronic acid modified mesoporous silica nanoparticles) can be an effective means to deliver drugs to cancer cells. See, e.g., S. Arpicco, et al., *Molecules*, 2014, 19, 3193-3230.

In some embodiments, the concentration of one or more of the compounds provided in the disclosed pharmaceutical compositions is less than about 100%, about 90%, about 80%, about 70%, about 60%, about 50%, about 40%, about 30%, about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, about 2%, about 1%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.009%, about 0.008%, about 0.007%, about 0.006%, about 0.005%, about 0.004%, about 0.003%, about 0.002%, about 0.001%, about 0.0009%, about 0.0008%, about 0.0007%, about 0.0006%, about 0.0005%, about 0.0004%, about 0.0003%, about 0.0002%, or about 0.0001%, w/w, w/v or v/v.

In some embodiments, the concentration of one or more of the compounds as disclosed herein is greater than about 90%, about 80%, about 70%, about 60%, about 50%, about 40%, about 30%, about 20%, about 19.75%, about 19.50%, about 19.25%, about 19%, about 18.75%, about 18.50%, about 18.25%, about 18%, about 17.75%, about 17.50%, about 17.25%, about 17%, about 16.75%, about 16.50%, about 16.25%, about 16%, about 15.75%, about 15.50%, about 15.25%, about 15%, about 14.75%, about 14.50%, about 14.25%, about 14%, about 13.75%, about 13.50%, about 13.25%, about 13%, about 12.75%, about 12.50%, about 12.25%, about 12%, about 11.75%, about 11.50%, about 11.25%, about 11%, about 10.75%, about 10.50%, about 10.25%, about 10%, about 9.75%, about 9.50%, about 9.25%, about 9%, about 8.75%, about 8.50%, about 8.25%, about 8%, about 7.75%, about 7.50%, about 7.25%, about 7%, about 6.75%, about 6.50%, about 6.25%, about 6%, about 5.75%, about 5.50%, about 5.25%, about 5%, about 4.75%, about 4.50%, about 4.25%, about 4%, about 3.75%, about 3.50%, about 3.25%, about 3%, about 2.75%, about 2.50%, about 2.25%, about 2%, about 1.75%, about 1.50%, about 1.25%, about 1%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.009%, about 0.008%, about 0.007%, about 0.006%, about 0.005%, about 0.004%, about 0.003%, about 0.002%, about 0.001%, about 0.0009%, about 0.0008%, about 0.0007%, about 0.0006%, about 0.0005%, about 0.0004%, about 0.0003%, about 0.0002%, or about 0.0001%, w/w, w/v, or v/v.

In some embodiments, the concentration of one or more of the compounds as disclosed herein is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, or approximately 1% to approximately 10%, w/w, w/v or v/v.

In some embodiments, the concentration of one or more of the compounds as disclosed herein is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, or approximately 0.1% to approximately 0.9%, w/w, w/v or v/v.

In some embodiments, the amount of one or more of the compounds as disclosed herein is equal to or less than about 10 g, about 9.5 g, about 9.0 g, about 8.5 g, about 8.0 g, about 7.5 g, about 7.0 g, about 6.5 g, about 6.0 g, about 5.5 g, about 5.0 g, about 4.5 g, about 4.0 g, about 3.5 g, about 3.0 g, about 2.5 g, about 2.0 g, about 1.5 g, about 1.0 g, about 0.95 g, about 0.9 g, about 0.85 g, about 0.8 g, about 0.75 g, about 0.7 g, about 0.65 g, about 0.6 g, about 0.55 g, about 0.5 g, about 0.45 g, about 0.4 g, about 0.35 g, about 0.3 g, about 0.25 g, about 0.2 g, about 0.15 g, about 0.1 g, about 0.09 g, about 0.08 g, about 0.07 g, about 0.06 g, about 0.05 g, about 0.04 g, about 0.03 g, about 0.02 g, about 0.01 g, about 0.009 g, about 0.008 g, about 0.007 g, about 0.006 g, about 0.005 g, about 0.004 g, about 0.003 g, about 0.002 g, about 0.001 g, about 0.0009 g, about 0.0008 g, about 0.0007 g, about 0.0006 g, about 0.0005 g, about 0.0004 g, about 0.0003 g, about 0.0002 g, or about 0.0001 g.

In some embodiments, the amount of one or more of the compounds as disclosed herein is more than about 0.0001 g, about 0.0002 g, about 0.0003 g, about 0.0004 g, about 0.0005 g, about 0.0006 g, about 0.0007 g, about 0.0008 g, about 0.0009 g, about 0.001 g, about 0.0015 g, about 0.002 g, about 0.0025 g, about 0.003 g, about 0.0035 g, about 0.004 g, about 0.0045 g, about 0.005 g, about 0.0055 g, about 0.006 g, about 0.0065 g, about 0.007 g, about 0.0075 g, about 0.008 g, about 0.0085 g, about 0.009 g, about 0.0095 g, about 0.01 g, about 0.015 g, about 0.02 g, about 0.025 g, about 0.03 g, about 0.035 g, about 0.04 g, about 0.045 g, about 0.05 g, about 0.055 g, about 0.06 g, about 0.065 g, about 0.07 g, about 0.075 g, about 0.08 g, about 0.085 g, about 0.09 g, about 0.095 g, about 0.1 g, about 0.15 g, about 0.2 g, about 0.25 g, about 0.3 g, about 0.35 g, about 0.4 g, about 0.45 g, about 0.5 g, about 0.55 g, about 0.6 g, about 0.65 g, about 0.7 g, about 0.75 g, about 0.8 g, about 0.85 g, about 0.9 g, about 0.95 g, about 1 g, about 1.5 g, about 2 g, about 2.5 g, about 3 g, about 3.5 g, about 4 g, about 4.5 g, about 5 g, about 5.5 g, about 6 g, about 6.5 g, about 7 g, about 7.5 g, about 8 g, about 8.5 g, about 9 g, about 9.5 g, or about 10 g.

In some embodiments, the amount of one or more of the compounds as disclosed herein is in the range of about 0.0001 to about 10 g, about 0.0005 to about 9 g, about 0.001 to about 8 g, about 0.005 to about 7 g, about 0.01 to about 6 g, about 0.05 to about 5 g, about 0.1 to about 4 g, about 0.5 to about 4 g, or about 1 to about 3 g.

1A. Formulations for Oral Administration

In some embodiments, provided herein are pharmaceutical compositions for oral administration containing a compound as disclosed herein, and a pharmaceutical excipient suitable for oral administration. In some embodiments, provided herein are pharmaceutical compositions for oral administration containing: (i) an effective amount of a disclosed compound; optionally (ii) an effective amount of one or more second agents; and (iii) one or more pharmaceutical excipients suitable for oral administration. In some embodiments, the pharmaceutical composition further contains: (iv) an effective amount of a third agent.

In some embodiments, the pharmaceutical composition can be a liquid pharmaceutical composition suitable for oral consumption. Pharmaceutical compositions suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more ingredients. In general, the pharmaceutical compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

The present disclosure further encompasses anhydrous pharmaceutical compositions and dosage forms comprising an active ingredient, since water can facilitate the degradation of some compounds. For example, water can be added (e.g., about 5%) in the pharmaceutical arts as a means of simulating long-term storage in order to determine characteristics such as shelf-life or the stability of formulations over time. Anhydrous pharmaceutical compositions and dosage forms can be prepared using anhydrous or low moisture containing ingredients and low moisture or low humidity conditions. For example, pharmaceutical compositions and dosage forms which contain lactose can be made anhydrous if substantial contact with moisture and/or humidity during manufacturing, packaging, and/or storage is expected. An anhydrous pharmaceutical composition can be prepared and stored such that its anhydrous nature is maintained. Accordingly, anhydrous pharmaceutical compositions can be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the pharmaceutical compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. In some embodiments, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants can be used in the pharmaceutical compositions as provided herein to provide tablets that disintegrate when exposed to an aqueous environment. Too much of a disintegrant can produce tablets which can disintegrate in the bottle. Too little can be insufficient for disintegration to occur and can thus alter the rate and extent of release of the active ingredient(s) from the dosage form. Thus, a sufficient amount of disintegrant that is neither too little nor too much to detrimentally alter the release of the active ingredient(s) can be used to form the dosage forms of the compounds disclosed herein. The amount of disintegrant used can vary based upon the type of formulation and mode of administration, and can be readily discernible to those of ordinary skill in the art. About 0.5 to about 15 weight percent of disintegrant, or about 1 to about 5 weight percent of disintegrant, can be used in the pharmaceutical composition. Disintegrants that can be used to form pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the active ingredient therein can be combined with various sweetening or flavoring agents, coloring matter or dyes and, for example, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms include, but are not limited to, hydrophilic surfactants, lipophilic surfactants, and mixtures thereof. That is, a mixture of hydrophilic surfactants can be employed, a mixture of lipophilic surfactants can be employed, or a mixture of at least one hydrophilic surfactant and at least one lipophilic surfactant can be employed.

A suitable hydrophilic surfactant can generally have an HLB value of at least about 10, while suitable lipophilic surfactants can generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants can be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof, lysophospholipids and derivatives thereof, carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof, carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants can be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants can include, but are not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of glycerides, vegetable oils, hydrogenated vegetable oils, fatty acids, and sterols; polyoxyethylene sterols, derivatives, and analogues thereof, polyoxyethylated vitamins and derivatives thereof, polyoxyethylene-polyoxypropylene block copolymers; and mixtures thereof, polyethylene glycol sorbitan fatty acid esters and hydrophilic transesterification products of a polyol with at least one member of triglycerides, vegetable oils, and hydrogenated vegetable oils. The polyol can be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of glycerides, vegetable oils, hydrogenated vegetable oils, fatty acids and sterols; oil-soluble vitamins/vitamin derivatives; and mixtures thereof. Within this group, non-limiting examples of lipophilic surfactants include glycerol fatty acid esters, propylene glycol fatty acid esters, and mixtures thereof, or are hydrophobic transesterification products of a polyol with at least one member of vegetable oils, hydrogenated vegetable oils, and triglycerides.

In one embodiment, the pharmaceutical composition can include a solubilizer to ensure good solubilization and/or dissolution of a compound as provided herein and to minimize precipitation of the compound. This can be especially important for pharmaceutical compositions for non-oral use, e.g., pharmaceutical compositions for injection. A solubilizer can also be added to increase the solubility of the hydrophilic drug and/or other components, such as surfactants, or to maintain the pharmaceutical composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, E-caprolactone and isomers thereof, 6-valerolactone and isomers thereof, p-butyrolactone and isomers thereof, and other solubilizers known in the art, such as dimethyl acetamide, dimethyl isosorbide, N-methyl pyrrolidones, monooctanoin, diethylene glycol monoethyl ether, and water.

Mixtures of solubilizers can also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. In some embodiments, solubilizers include sorbitol, glycerol, triacetin, ethyl alcohol, PEG-400, glycofurol and propylene glycol.

The amount of solubilizer that can be included is not particularly limited. The amount of a given solubilizer can be limited to a bioacceptable amount, which can be readily determined by one of skill in the art. In some circumstances, it can be advantageous to include amounts of solubilizers far in excess of bioacceptable amounts, for example to maximize the concentration of the drug, with excess solubilizer removed prior to providing the pharmaceutical composition to a subject using conventional techniques, such as distillation or evaporation. Thus, if present, the solubilizer can be in a weight ratio of about 10%, 25%, 50%, 100%, or up to about 200% by weight, based on the combined weight of the drug, and other excipients. If desired, very small amounts of solubilizer can also be used, such as about 5%, 2%, 1% or even less. Typically, the solubilizer can be present in an amount of about 1% to about 100%, more typically about 5% to about 25% by weight.

The pharmaceutical composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, oils, odorants, opacifiers, suspending agents, binders, fillers, plasticizers, lubricants, and mixtures thereof.

Exemplary preservatives can include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *Litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

In addition, an acid or a base can be incorporated into the pharmaceutical composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl)aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Examples can include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

1B. Formulations for Parenteral Administration

In some embodiments, provided herein are pharmaceutical compositions for parenteral administration containing a compound as disclosed herein, and a pharmaceutical excipient suitable for parenteral administration. In some embodiments, provided herein are pharmaceutical compositions for parenteral administration containing: (i) an effective amount of a disclosed compound; optionally (ii) an effective amount of one or more second agents; and (iii) one or more pharmaceutical excipients suitable for parenteral administration. In some embodiments, the pharmaceutical composition further contains: (iv) an effective amount of a third agent.

The forms in which the disclosed pharmaceutical compositions can be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils can also be employed.

Aqueous solutions in saline are also conventionally used for injection. Ethanol, glycerol, propylene glycol, liquid polyethylene glycol, and the like (and suitable mixtures thereof), cyclodextrin derivatives, and vegetable oils can also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound as disclosed herein in the required amount in the appropriate solvent with various other ingredients as enumerated above, as appropriate, followed by filtered sterilization. Generally, dispersions are prepared by incorporating the various sterilized active ingredients into a sterile vehicle which contains the basic dispersion medium and the appropriate other ingredients from those enumerated above. In the case of sterile powders for the preparation of sterile injectable solutions, certain methods of preparation are vacuum-drying and freeze-drying techniques which yield a powder of the active ingredient plus any additional ingredient from a previously sterile-filtered solution thereof.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. Injectable compositions can contain from about 0.1 to about 5% w/w of a compound as disclosed herein.

1C. Formulations for Topical Administration

In some embodiments, provided herein are pharmaceutical compositions for topical (e.g., transdermal) administration containing a compound as disclosed herein, and a pharmaceutical excipient suitable for topical administration. In some embodiments, provided herein are pharmaceutical compositions for topical administration containing: (i) an effective amount of a disclosed compound; optionally (ii) an effective amount of one or more second agents; and (iii) one or more pharmaceutical excipients suitable for topical administration. In some embodiments, the pharmaceutical composition further contains: (iv) an effective amount of a third agent.

Pharmaceutical compositions provided herein can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation can provide more immediate exposure of the active ingredient to the chosen area.

The pharmaceutical compositions also can comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the disclosed methods employs transdermal delivery devices ("patches"). Such transdermal patches can be used to provide continuous or discontinuous infusion of a compound as provided herein in controlled amounts, either with or without another agent.

The construction and use of transdermal patches for the delivery of pharmaceutical agents is well known in the art. See, e.g., U.S. Pat. Nos. 5,023,252, 4,992,445 and 5,001,139. Such patches can be constructed for continuous, pulsatile, or on demand delivery of pharmaceutical agents.

Suitable devices for use in delivering intradermal pharmaceutically acceptable compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Topically-administrable formulations can, for example, comprise from about 1% to about 10% (w/w) of a compound provided herein relative to the total weight of the formulation, although the concentration of the compound provided herein in the formulation can be as high as the solubility limit of the compound in the solvent. In some embodiments, topically-administrable formulations can, for example, comprise from about 1% to about 9% (w/w) of a compound provided herein, such as from about 1% to about 8% (w/w), further such as from about 1% to about 7% (w/w), further such as from about 1% to about 6% (w/w), further such as from about 1% to about 5% (w/w), further such as from about 1% to about 4% (w/w), further such as from about 1% to about 3% (w/w), and further such as from about 1% to about 2% (w/w) of a compound provided herein. Formulations for topical administration can further comprise one or more of the additional pharmaceutically acceptable excipients described herein.

1D. Formulations for Inhalation Administration

In some embodiments, provided herein are pharmaceutical compositions for inhalation administration containing a compound as disclosed herein, and a pharmaceutical excipient suitable for topical administration. In some embodiments, provided herein are pharmaceutical compositions for inhalation administration containing: (i) an effective amount of a disclosed compound; optionally (ii) an effective amount of one or more second agents; and (iii) one or more pharmaceutical excipients suitable for inhalation administration. In some embodiments, the pharmaceutical composition further contains: (iv) an effective amount of a third agent.

Pharmaceutical compositions for inhalation or insufflation include solutions and suspensions in pharmaceutically acceptable, aqueous or organic solvents, or mixtures thereof, and powders. The liquid or solid pharmaceutical compositions can contain suitable pharmaceutically acceptable excipients as described herein. In some embodiments, the pharmaceutical compositions are administered by the oral or nasal respiratory route for local or systemic effect. Pharmaceutical compositions in pharmaceutically acceptable solvents can be nebulized by use of inert gases. Nebulized solutions can be inhaled directly from the nebulizing device or the nebulizing device can be attached to a face mask tent, or intermittent positive pressure breathing machine. Solution, suspension, or powder pharmaceutical compositions can be administered, e.g., orally or nasally, from devices that deliver the formulation in an appropriate manner.

Also provided herein are formulations to be administered by inhalation. All types of inhalable formulation known in the art can be used in connection with methods provided herein.

In a dry powder inhaler, the dose to be administered is stored in the form of a non-pressurized dry powder and, on actuation of the inhaler, the particles of the powder are inhaled by the patient. Dry powder inhalers can be "passive" devices in which the patient's breath is the only source of gas which provides a motive force in the device, or "active" devices in which a source of compressed gas or alternative energy source is used. Formulations provided herein can be administered with either passive or active inhaler devices.

While it is desirable for as large a proportion as possible of the particles of active material to be delivered to the deep lung, it is usually preferable for as little as possible of the other components to penetrate the deep lung. Therefore, powders generally include particles of an active material, and carrier particles for carrying the particles of active material. The carrier particles can be composed of any pharmacologically inert material or combination of materials which is acceptable for inhalation. In some embodiments, carrier particles are composed of one or more crystalline sugars. In some embodiments, the carrier particles can be composed of one or more sugar alcohols or polyols. In some embodiments, the carrier particles are particles of dextrose or lactose. In some embodiments, the amount of carrier particles is up to 95%, up to 90%, up to 80%, or up to 50% by weight based on the total weight of the composition.

An additive material can also be provided in a dose which indicates to the patient that the dose has been administered. (See, e.g., WO 01/82906). The additive material, also referred to as indicator material, can be present in the powder as formulated for the dry powder inhaler, or be present in a separate form, such as in a separate location within the inhaler such that the additive becomes entrained in the airflow generated on inhalation simultaneously or sequentially with the powder containing the active material. Accordingly, provided herein is a formulation comprising a compound provided herein (e.g., Compound 4), or an enantiomer, a mixture of enantiomers, or a mixture of two or more diastereomers thereof, or a pharmaceutically acceptable form thereof, in combination with a carrier material.

Formulations provided herein, when inhaled, in some embodiments exhibit a time to therapeutic effect of less than 3 hours, 2 hours, 1 hour, 30 minutes, 15 minutes, 10 minutes, or 5 minutes. In some embodiments, formulations provided herein, when inhaled, will have a therapeutic duration of about 1 to 48 hours.

In certain embodiments of the present invention, each dose is stored in a "blister" of a blister pack. In this regard, since an active agent may be susceptible to oxidation, it is sometimes important to prevent (or substantially limit) oxidation of the active agent prior to administration. Thus, in some embodiments, exposure of the formulation to air prior to administration is prevented by storing each dose in a sealed blister. In some embodiments, oxidation is further prevented (or limited) by placing a plurality of blisters into a further sealed container, such as a sealed bag made, for example of a foil such as aluminum foil. In some embodiments, the use of the sealed blisters (and optional sealed bags) can minimize the need to include anti-oxidants in the formulation.

In case of administration by a dry powder inhaler of the particles of active ingredient to the lung where they can be absorbed, the particle size characteristics of the powder are particularly important. In particular, for the effective delivery of active ingredient deep into the lung, the active particles should be small and well dispersed on actuation of the inhaler. In some embodiments, a fine particle fraction of at least 35% is generated on actuation of the inhaler device. In some embodiments, a fine particle fraction of at least 60%, at least 70%, or at least 80% is generated on actuation.

In certain embodiments, the formulation can also contain fine particles of an excipient material, which can be a material such as one of those referred to above as being suitable for use as a carrier material, for example, a crystalline sugar such as dextrose or lactose. The fine excipient material can be of the same or a different material from the carrier particles, where both are present. In certain embodiments, where any carrier particles and/or any fine excipient material present is of a material itself capable of inducing a sensation in the oropharyngeal region, the carrier particles and/or the fine excipient material can also be the indicator material. For example, the carrier particles and/or any fine particle excipient can comprise mannitol. In certain embodiments, the amount of fine excipient material, if present, can be up to 50%, up to 30%, or up to 20%, by weight, based on the total weight of the composition.

Formulations provided herein can also be formulated with additional excipients to aid delivery and release. In certain embodiments, powder can be formulated with relatively large carrier particles which aid the flow properties of the powder. Examples of large carrier particles include, but are not limited to, lactose particles having a mass medium aerodynamic diameter of greater than 90 microns. In some embodiments, hydrophobic microparticles can be dispersed within a carrier material. For example, the hydrophobic microparticles can be dispersed within a polysaccharide matrix, with the overall composition formulated as microparticles for direct delivery to the lung. The polysaccharide acts as a further barrier to the immediate release of the active agent. This can further aid the controlled release process. An example of a suitable polysaccharide is xanthan gum. Examples of hydrophobic materials include, but are not limited to, solid state fatty acids such as oleic acid, lauric acid, palmitic acid, stearic acid, erucic acid, behenic acid, or derivatives (e.g., esters and salts) thereof. Specific examples of such materials include, but are not limited to, phosphatidylcholines, phosphatidylglycerols and other natural and synthetic lung surfactants. In some embodiments, formulations provided herein contain metal stearates, in particular magnesium stearate, which has been approved for delivery via the lung.

Formulations provided herein can also include one or more force control additives (FCAs) in addition to the carrier and the active ingredient. In some embodiments, the FCAs can be provided in an amount from about 0.1% to about 10% by weight, from about 0.15% to 5% by weight, or from about 0.5% to about 2% by weight of the total composition. In some embodiment, FCAs include, but are not limited to, anti-adherent materials. In some embodiments, FCAs include, but are not limited to, magnesium stearate, leucine, lecithin, and sodium stearyl fumarate, and those described in U.S. Pat. No. 6,153,224, which is hereby incorporated by reference.

In certain embodiments, formulations provided herein can be a "carrier free" formulation, which includes only the active ingredient and one or more anti-adherents. Such carrier free formulations are described in WO 97/03649, the entire disclosure of which is hereby incorporated by reference.

As used herein, and unless otherwise specified, the term "anti-adherent material" refers to those additive materials which will decrease the cohesion between the particles of the powder. Those materials will include, but are not limited to, leucine and lecithin. In some embodiments, the anti-adherent material comprises an amino acid. Amino acids have been found to provide, when present as anti-adherent material, high respirable fraction of the active material and also good flow properties of the powder. In some embodiments, the amino acid is leucine, in particular L-leucine. In some embodiments, the D- and DL-forms can also be used. The anti-adherent material can comprise one or more of any of the following amino acids: leucine, isoleucine, lysine, valine, methionine, cysteine, phenylalanine. In some embodiments, the anti-adherent material can include magnesium stearate or colloidal silicon dioxide.

In some embodiments, formulations provided herein are an aerosol formulation. In some embodiments, the aerosol formulation can be contained in a canister. Examples of aerosol formulation include, but are not limited to, an aerosol solution formulation and an aerosol suspension formulation. In certain embodiments, the aerosol formulation can contain a compound provided herein, optionally in combination with other active ingredient(s), in a propellant or in a propellant/solvent system and, optionally, further pharmaceutical acceptable additive or excipient.

The propellant can be any pressure-liquefied propellant and is preferably a hydrofluoroalkane (HFA) or a mixture of different HFAs, including, but not limited to, HFA 134a (1,1,1,2-tetrafluoroethane), HFA 227 (1,1,1,2,3,3,3-heptafluoropropane), and mixtures thereof.

The solvent generally has a higher polarity than that of the propellant and can include one or more substances such as a pharmaceutically acceptable alcohol (e.g., ethanol), a polyol, such as propylene glycol or polyethylene glycol, or mixtures thereof. In some embodiments, the solvent is a lower branched or linear alkyl ($C_1$-$C_4$) alcohols such as ethanol and isopropyl alcohol. In one embodiment, the co-solvent is ethanol.

In some embodiments, the active ingredient of the formulation is substantially completely and homogeneously dissolved in the propellant/solvent system, i.e., the formulation is a solution formulation.

Optionally, the formulation can comprise other pharmaceutically acceptable additives or excipients, which are substantially inert materials that are non-toxic and do not interact in negative manner with other components of the formulation. In some embodiments, the formulation can comprise one or more co-solvents, surfactants, carbohydrate, phospholipid, polymer, wetting agent, stabilizers, lubricants, or low volatility components.

In some embodiments, a suitable amount of an acid (organic or inorganic acid (mineral acids)) can be used as stabilizer. Examples include, but are not limited to, pharmaceutically acceptable monoprotic or polyprotic acid, such as: hydrogen halides (hydrochloric acid, hydrobromic acid, hydroiodic acid, etc.), phosphoric acid, nitric acid, sulphuric acid, and halogen oxoacids.

In some embodiments, low volatility components can be used in order to increase the mass median aerodynamic diameter (MMAD) of the aerosol particles upon actuation of the inhaler and/or to improve the solubility of the active ingredient in the propellant/solvent system. In some embodiments, the low volatility component has a vapor pressure at 25° C. lower than 0.1 kPa, or lower than 0.05 kPa. Examples of low-volatility components include, but are not limited to: esters such as isopropyl myristate, ascorbyl myristate, tocopherol esters; glycols such as propylene glycol, polyethylene glycol, glycerol; and surface active agents such as saturated organic carboxylic acids (e.g., lauric, myristic, stearic acid) and unsaturated carboxylic acids (e.g., oleic or ascorbic acid). The amount of low volatility component can vary from 0.1 to 10% w/w, from 0.5 to 5% (w/w), or from 1 to 2% (w/w).

In some embodiments, water at an amount between 0.005 and 0.3% (w/w) can be added to the formulations in order to favorably affect the solubility of the active ingredient without increasing the MMAD of the aerosol droplets upon actuation.

1E. Formulations for Ocular Administration

In some embodiments, the disclosure provides a pharmaceutical composition for treating ophthalmic disorders. The pharmaceutical composition can contain an effective amount of a compound as disclosed herein and a pharmaceutical excipient suitable for ocular administration. Pharmaceutical compositions suitable for ocular administration can be presented as discrete dosage forms, such as drops or sprays each containing a predetermined amount of an active ingredient a solution, or a suspension in an aqueous or non-aqueous liquid, an oil-in-water emulsion, or a water-in-oil liquid emulsion. Other administration forms include intraocular injection, intravitreal injection, topically, or through the use of a drug eluting device, microcapsule, implant, or microfluidic device. In some cases, the compounds as disclosed herein are administered with a carrier or excipient that increases the intraocular penetrance of the compound such as an oil and water emulsion with colloid particles having an oily core surrounded by an interfacial film. It is contemplated that all local routes to the eye can be used including topical, subconjunctival, periocular, retrobulbar, subtenon, intracameral, intravitreal, intraocular, subretinal, juxtascleral and suprachoroidal administration. Systemic or parenteral administration can be feasible including, but not limited to intravenous, subcutaneous, and oral delivery. An exemplary method of administration will be intravitreal or subtenon injection of solutions or suspensions, or intravitreal or subtenon placement of bioerodible or non-bioerodible devices, or by topical ocular administration of solutions or suspensions, or posterior juxtascleral administration of a gel or cream formulation.

Eye drops can be prepared by dissolving the active ingredient in a sterile aqueous solution such as physiological saline, buffering solution, etc., or by combining powder compositions to be dissolved before use. Other vehicles can be chosen, as is known in the art, including, but not limited to: balance salt solution, saline solution, water soluble polyethers such as polyethyene glycol, polyvinyls, such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate. In some embodiments, additives ordinarily used in the eye drops can be added. Such additives include isotonizing agents (e.g., sodium chloride, etc.), buffer agent (e.g., boric acid, sodium monohydrogen phosphate, sodium dihydrogen phosphate, etc.), preservatives (e.g., benzalkonium chloride, benzethonium chloride, chlorobutanol, etc.), thickeners (e.g., saccharide such as lactose, mannitol, maltose, etc.; e.g., hyaluronic acid or its salt such as sodium hyaluronate, potassium hyaluronate, etc.; e.g., mucopolysaccharide such as chondroitin sulfate, etc.; e.g., sodium polyacrylate, carboxyvinyl polymer, crosslinked polyacrylate, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art).

In some cases, the colloid particles include at least one cationic agent and at least one non-ionic sufactant such as a poloxamer, tyloxapol, a polysorbate, a polyoxyethylene castor oil derivative, a sorbitan ester, or a polyoxyl stearate. In some cases, the cationic agent is an alkylamine, a tertiary alkyl amine, a quartemary ammonium compound, a cationic lipid, an amino alcohol, a biguanidine salt, a cationic compound or a mixture thereof. In some cases, the cationic agent is a biguanidine salt such as chlorhexidine, polyaminopropyl biguanidine, phenformin, alkylbiguanidine, or a mixture thereof. In some cases, the quaternary ammonium compound is a benzalkonium halide, lauralkonium halide, cetrimide, hexadecyltrimethylammonium halide, tetradecyltrimethylammonium halide, dodecyltrimethylammonium halide, cetrimonium halide, benzethonium halide, behenalkonium halide, cetalkonium halide, cetethyldimonium halide, cetylpyridinium halide, benzododecinium halide, chlorallyl methenamine halide, myristylalkonium halide, stearalkonium halide or a mixture of two or more thereof. In some cases, cationic agent is a benzalkonium chloride, lauralkonium chloride, benzododecinium bromide, benzethenium chloride, hexadecyltrimethylammonium bromide, tetradecyltrimethylammonium bromide, dodecyltrimethylammonium bromide or a mixture of two or more thereof. In some cases, the oil phase is mineral oil and light mineral oil, medium chain triglycerides (MCT), coconut oil; hydrogenated oils comprising hydrogenated cottonseed oil, hydrogenated palm oil, hydrogenate castor oil or hydrogenated soybean oil; polyoxyethylene hydrogenated castor oil derivatives comprising poluoxyl-40 hydrogenated castor oil, polyoxyl-60 hydrogenated castor oil or polyoxyl-100 hydrogenated castor oil.

1F. Formulations for Controlled Release Administration

In some embodiments, provided herein are pharmaceutical compositions for controlled release administration containing a compound as disclosed herein, and a pharmaceutical excipient suitable for controlled release administration. In some embodiments, provided herein are pharmaceutical compositions for controlled release administration containing: (i) an effective amount of a disclosed compound; optionally (ii) an effective amount of one or more second agents; and (iii) one or more pharmaceutical excipients suitable for controlled release administration. In some embodiments, the pharmaceutical composition further contains: (iv) an effective amount of a third agent.

Active agents such as the compounds provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598, 123; and 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; 6,699,500 each of which is incorporated herein by reference. Such dosage forms can be used to provide slow or controlled release of one or more active agents using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active agents provided herein. Thus, the pharmaceutical compositions provided encompass single unit dosage forms suitable for oral administration such as, but not limited to, tablets, capsules, gelcaps, and caplets that are adapted for controlled release.

All controlled release pharmaceutical products have a common goal of improving drug therapy over that achieved by their non controlled counterparts. In some embodiments, the use of a controlled release preparation in medical treatment is characterized by a minimum of drug substance being employed to cure or control the disease, disorder, or condition in a minimum amount of time. Advantages of controlled release formulations include extended activity of the drug, reduced dosage frequency, and increased subject compliance. In addition, controlled release formulations can be used to affect the time of onset of action or other characteristics, such as blood levels of the drug, and can thus affect the occurrence of side (e.g., adverse) effects.

In some embodiments, controlled release formulations are designed to initially release an amount of a compound as disclosed herein that promptly produces the desired therapeutic effect, and gradually and continually release other amounts of the compound to maintain this level of therapeutic or prophylactic effect over an extended period of time. In order to maintain this constant level of the compound in the body, the compound should be released from the dosage form at a rate that will replace the amount of drug being metabolized and excreted from the body. Controlled release of an active agent can be stimulated by various conditions including, but not limited to, pH, temperature, enzymes, water, or other physiological conditions or compounds.

In certain embodiments, the pharmaceutical composition can be administered using intravenous infusion, an implantable osmotic pump, a transdermal patch, liposomes, or other modes of administration. In one embodiment, a pump can be used (see, Sefton, *CRC Crit. Ref Biomed. Eng.* 14:201 (1987); Buchwald et al., *Surgery* 88:507 (1980); Saudek et al., *N. Engl. J. Med.* 321:574 (1989)). In another embodiment, polymeric materials can be used. In yet another embodiment, a controlled release system can be placed in a subject at an appropriate site determined by a practitioner of skill, e.g., thus requiring only a fraction of the systemic dose (see, e.g., Goodson, *Medical Applications of Controlled Release,* 115-138 (vol. 2, 1984). Other controlled release systems are discussed in the review by Langer, *Science* 249:1527-1533 (1990). The one or more active agents can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The one or more active agents then diffuse through the outer polymeric membrane in a release rate controlling step. The percentage of active agent in such parenteral compositions is highly dependent on the specific nature thereof, as well as the needs of the subject.

Dosage

A compound described herein (e.g., a PI3K-γ inhibitor such as Compound 4) can be delivered in the form of pharmaceutically acceptable compositions which comprise a therapeutically effective amount of one or more compounds described herein and/or one or more additional therapeutic agents such as a chemotherapeutic, formulated together with one or more pharmaceutically acceptable excipients. In some instances, the compound described herein and the additional therapeutic agent are administered in separate pharmaceutical compositions and can (e.g., because of different physical and/or chemical characteristics) be administered by different routes (e.g., one therapeutic is administered orally, while the other is administered intravenously). In other instances, the compound described herein and the additional therapeutic agent can be administered separately, but via the same route (e.g., both orally or both intravenously). In still other instances, the compound described herein and the additional therapeutic agent can be administered in the same pharmaceutical composition.

The selected dosage level will depend upon a variety of factors including, for example, the activity of the particular compound employed, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

In general, a suitable daily dose of a compound described herein and/or a chemotherapeutic will be that amount of the compound which, in some embodiments, can be the lowest dose effective to produce a therapeutic effect. Such an effective dose will generally depend upon the factors described herein. Generally, doses of the compounds described herein for a patient, when used for the indicated effects, will range from about 0.0001 mg to about 100 mg per day, or about 0.001 mg to about 100 mg per day, or about 0.01 mg to about 100 mg per day, or about 0.1 mg to about 100 mg per day, or about 0.0001 mg to about 500 mg per day, or about 0.001 mg to about 500 mg per day, or about 0.01 mg to 1000 mg, or about 0.01 mg to about 500 mg per day, or about 0.1 mg to about 500 mg per day, or about 1 mg to 50 mg per day, or about 5 mg to 40 mg per day. In some embodiments, range is from about 1 mg to about 100 mg, about 1 mg to about 200 mg, about 1 mg to about 500 mg, about 1 mg to about 1000 mg, about 100 mg to about 200 mg, about 100 mg to about 500 mg, about 100 to about 750 mg, about 100 mg to about 1000 mg. An exemplary dosage is about 10 to 30 mg per day. In some embodiments, for a 70 kg human, a suitable dose would be about 0.05 to about 7 g/day, such as about 0.05 to about 2.5 g/day. Actual dosage levels of the active ingredients in the pharmaceutical compositions described herein can be varied so as to obtain an amount of the active ingredient which is effective to achieve the desired therapeutic response for a particular patient, composition, and mode of administration, without being toxic to the patient. In some instances, dosage levels below the lower limit of the aforesaid range can be more than adequate, while in other cases still larger doses can be employed without causing any harmful side effect, e.g., by dividing such larger doses into several small doses for administration throughout the day.

Pharmacokinetic studies in animals provided herein suggest efficacious dose ranges for Compound 4. Generally speaking, to specifically inhibit PI3K-γ, one can administer a dose of a specific PI3K-γ inhibitor that results in an unbound plasma concentration of the drug that is above a predetermined threshold (e.g., the IC50, IC60, IC70, IC80, or IC90 for PI3K-γ) for a selected time (e.g., 1 hour, 2 h, 3 h, 6 h, 12 h, 24 h, 2 days, 3 d, 5 d, or 7 d). This dose may be selected such that the plasma concentration is below a second predetermined threshold (e.g., the IC20, IC30, IC40, or IC50 for PI3K-δ, -α, or β) the for a selected time (e.g., 1 hour, 2 h, 3 h, 6 h, 12 h, 24 h, 2 days, 3 d, 5 d, or 7 d). In some embodiments, the PI3K-γ inhibitor, e.g., Compound 4, is administered at a dose that results in an unbound plasma concentration of Compound 4 that is above the IC90 of PI3K-γ for at least 1 hour, 2 h, 3 h, 6 h, 12 h, or 24 h. In some embodiments, the PI3K-γ inhibitor, e.g., Compound 4, is administered at a dose that results in an unbound plasma concentration of Compound 4 that is above the IC50 of PI3K-γ for at least 1 hour, 2 h, 3 h, 6 h, 12 h, or 24 h.

Based on non-human animal studies, a predicted human dose to achieve exposure at the IC90 for PI3K-γ is approximately 2 mg. Accordingly, in some embodiments, the methods herein involve administering a selective PI3K-γ inhibitor, e.g., Compound 4, to a human, wherein each dose is about 2 mg, 1-3 mg, 1-5 mg, 1-10 mg, 0.5-20 mg, or 0.1-50 mg. In some embodiments, the dose (e.g., a therapeutically effective dose) is about 2 mg, 1-3 mg, 1-5 mg, 1-10 mg, 0.5-20 mg, 0.1-50 mg, 0.1-75 mg, 0.5-75 mg, 1-75 mg, 0.1-100 mg, 0.5-100 mg, or 1-100 mg. In some embodiments, the dose is about 1-10 mg. In some embodiments, the dose is about 1-50 mg. In some embodiments, the dose is about 1-100 mg. In a 70 kg human, a 2 mg dose corresponds to 0.029 mg/kg. Accordingly, in some embodiments, the methods herein involve administering a selective PI3K-γ inhibitor, e.g., Compound 4, to a human, wherein each dose is about 0.029 mg/kg, 0.014-0.14 mg/kg, 0.02-0.04 mg/kg, 0.01-0.05 mg/kg, 0.01-0.1, or 0.01-0.5 mg/kg.

In some embodiments, the compounds can be administered daily, every other day, three times a week, twice a week, weekly, or bi-weekly. The dosing schedule can include a "drug holiday," e.g., the drug can be administered for two weeks on, one week off, or three weeks on, one week off, or four weeks on, one week off, etc., or continuously, without a drug holiday. The compounds can be administered orally, intravenously, intraperitoneally, topically, transdermally, intramuscularly, subcutaneously, intranasally, sublingually, or by any other route.

In some embodiments, a compound as provided herein is administered in multiple doses. Dosing can be about once, twice, three times, four times, five times, six times, or more than six times per day. Dosing can be about once a month, about once every two weeks, about once a week, or about once every other day. In another embodiment, a compound as disclosed herein and another agent are administered together from about once per day to about 6 times per day. In another embodiment, the administration of a compound as provided herein and an agent continues for less than about 7 days. In yet another embodiment, the administration continues for more than about 6 days, about 10 days, about 14 days, about 28 days, about two months, about six months, or about one year. In some cases, continuous dosing is achieved and maintained as long as necessary.

Based on non-human animal studies provided herein the oral half-life of Compound 4 in humans is expected to be about 10-13 hours. This finding informs the timing of administration of a PI3K-γ inhibitor such as Compound 4. For instance, in some embodiments, the timing is selected such that an unbound plasma concentration of the drug that is above a predetermined threshold (e.g., the IC50, IC60, IC70, IC80, or IC90 for PI3K-γ) for a selected time (e.g., 1 hour, 2 h, 3 h, 6 h, 12 h, 24 h, 2 days, 3 d, 5 d, or 7 d). The timing of administration may also be chosen such that the plasma level is below a second predetermined threshold (e.g., the IC20, IC30, IC40, or IC50 for PI3K-δ, -α, or β) the for a selected time (e.g., 1 hour, 2 h, 3 h, 6 h, 12 h, 24 h, 2 days, 3 d, 5 d, or 7 d). In some embodiments, the PI3K-γ inhibitor, e.g., Compound 4, is administered with timing that results in an unbound plasma concentration of Compound 4 that is above the IC90 of PI3K-γ for at least 1 hour, 2 h, 3 h, 6 h, 12 h, or 24 h. In some embodiments, the PI3K-γ inhibitor, e.g., Compound 4, is administered with timing that results in an unbound plasma concentration of Compound 4 that is above the IC50 of PI3K-γ for at least 1 hour, 2 h, 3 h, 6 h, 12 h, or 24 h.

Accordingly, in some embodiments, the methods herein involve administering a selective PI3K-γ inhibitor, e.g., Compound 4, to a human, about once per day. In embodiments, the selective PI3K-γ inhibitor, e.g., Compound 4, is administered to a human once every two days. In embodiments, the selective PI3K-γ inhibitor, e.g., Compound 4, is administered to a human twice or three times per day.

Administration of the pharmaceutical compositions as disclosed herein can continue as long as necessary. In some embodiments, an agent as disclosed herein is administered for more than about 1, about 2, about 3, about 4, about 5, about 6, about 7, about 14, or about 28 days. In some embodiments, an agent as disclosed herein is administered for less than about 28, about 14, about 7, about 6, about 5, about 4, about 3, about 2, or about 1 day. In some embodiments, an agent as disclosed herein is administered chronically on an ongoing basis, e.g., for the treatment of chronic effects.

Since the compounds described herein can be administered in combination with other treatments (such as additional chemotherapeutics, radiation or surgery), the doses of each agent or therapy can be lower than the corresponding dose for single-agent therapy. The dose for single-agent therapy can range from, for example, about 0.0001 to about 200 mg, or about 0.001 to about 100 mg, or about 0.01 to about 100 mg, or about 0.1 to about 100 mg, or about 1 to about 50 mg per kilogram of body weight per day. In some embodiments, the dose is about 1 mg/kg, about 5 mg/kg, about 7.5 mg/kg, about 10 mg/kg, about 15 mg/kg, about 20 mg/kg, about 25 mg/kg, about 50 mg/kg, about 75 mg/kg, or about 100 mg/kg per day. In some embodiments, the dose is about 1 mg/kg, about 7.5 mg/kg, about 20 mg/kg, or about 50 mg/kg per day.

When a compound provided herein, is administered in a pharmaceutical composition that comprises one or more agents, and the agent has a shorter half-life than the compound provided herein unit dose forms of the agent and the compound provided herein can be adjusted accordingly.

Kits

In some embodiments, provided herein are kits. The kits can include a compound or pharmaceutical composition as described herein, in suitable packaging, and written material that can include instructions for use, discussion of clinical studies, listing of side effects, and the like. Such kits can also include information, such as scientific literature references, package insert materials, clinical trial results, and/or summaries of these and the like, which indicate or establish the activities and/or advantages of the pharmaceutical composition, and/or which describe dosing, administration, side effects, drug interactions, or other information useful to the health care provider. Such information can be based on the results of various studies, for example, studies using experimental animals involving in vivo models and studies based on human clinical trials.

In some embodiments, a memory aid is provided with the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several tablets or capsules to be taken on a given day.

The kit can further contain another agent. In some embodiments, the compound as disclosed herein and the agent are provided as separate pharmaceutical compositions in separate containers within the kit. In some embodiments, the compound as disclosed herein and the agent are provided as a single pharmaceutical composition within a container in the kit. Suitable packaging and additional articles for use (e.g., measuring cup for liquid preparations, foil wrapping to minimize exposure to air, and the like) are known in the art and can be included in the kit. In other embodiments, kits can further comprise devices that are used to administer the active agents. Examples of such devices include, but are not limited to, syringes, drip bags, patches, and inhalers. Kits described herein can be provided, marketed and/or promoted to health providers, including physicians, nurses, pharmacists, formulary officials, and the like. Kits can also, in some embodiments, be marketed directly to the consumer.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. The strength of the sheet is such that the tablets or capsules can be removed from the blister pack by manually applying pressure on the recesses whereby an opening is formed in the sheet at the place of the recess. The tablet or capsule can then be removed via said opening.

Kits can further comprise pharmaceutically acceptable vehicles that can be used to administer one or more active agents. For example, if an active agent is provided in a solid form that must be reconstituted for parenteral administration, the kit can comprise a sealed container of a suitable vehicle in which the active agent can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

The present disclosure further encompasses anhydrous pharmaceutical compositions and dosage forms comprising an active ingredient, since water can facilitate the degradation of some compounds. For example, water can be added (e.g., about 5%) in the pharmaceutical arts as a means of simulating long-term storage in order to determine characteristics such as shelf-life or the stability of formulations over time. Anhydrous pharmaceutical compositions and dosage forms can be prepared using anhydrous or low moisture containing ingredients and low moisture or low humidity conditions. For example, pharmaceutical compositions and dosage forms which contain lactose can be made anhydrous if substantial contact with moisture and/or humidity during manufacturing, packaging, and/or storage is expected. An anhydrous pharmaceutical composition can be prepared and stored such that its anhydrous nature is maintained. Accordingly, anhydrous pharmaceutical compositions can be packaged using materials known to prevent exposure to water such that they can be included in suitable formulary kits. Examples of suitable packaging include, but are not limited to, hermetically sealed foils, plastic or the like, unit dose containers, blister packs, and strip packs.

Therapeutic Methods

Phosphoinositide 3-kinases (PI3Ks) are members of a conserved family of lipid kinases that regulate numerous cell functions, including proliferation, differentiation, cell survival and metabolism. Several classes of PI3Ks exist in mammalian cells, including Class IA subgroup (e.g., PI3K-$\alpha$, $\beta$, $\delta$), which are generally activated by receptor tyrosine kinases (RTKs); Class IB (e.g., PI3K-$\gamma$), which is activated by G-protein coupled receptors (GPCRs), among others. PI3Ks exert their biological activities via a "PI3K-mediated signaling pathway" that includes several components that directly and/or indirectly transduce a signal triggered by a PI3K, including the generation of second messenger phophotidylinositol, 3,4,5-triphosphate (PIP3) at the plasma membrane, activation of heterotrimeric G protein signaling, and generation of further second messengers such as cAMP, DAG, and IP3, all of which leads to an extensive cascade of protein kinase activation (reviewed in Vanhaesebroeck, B. et al. (2001) *Annu Rev Biochem.* 70:535-602). For example, PI3K-$\delta$ is activated by cellular receptors through interaction between the PI3K regulatory subunit (p85) SH2 domains, or through direct interaction with RAS. PIP3 produced by PI3K activates effector pathways downstream through interaction with plextrin homology (PH) domain containing enzymes (e.g., PDK-1 and AKT [PKB]). (Fung-Leung W P. (2011) *Cell Signal.* 23(4):603-8). Unlike PI3K-δ, PI3K-γ is not associated with a regulatory subunit of the p85 family, but rather with a regulatory subunit in the p101 or p84 families. PI3K-γ is associated with GPCRs, and is responsible for the very rapid induction of PIP3. PI3K-γ can be also activated by RAS.

In some embodiments, provided herein are methods of modulating a PI3 kinase activity (e.g., selectively modulating) by contacting the kinase with an effective amount of a compound as provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein. Modulation can be inhibition (e.g., reduction) or activation (e.g., enhancement) of kinase activity. In some embodiments, provided herein are methods of inhibiting kinase activity by contacting the kinase with an effective amount of a compound as provided herein in solution. In some embodiments, provided herein are methods of inhibiting the kinase activity by contacting a cell, tissue, organ that express the kinase of interest, with a compound provided herein. In some embodiments, provided herein are methods of inhibiting kinase activity in a subject by administering into the subject an effective amount of a compound as provided herein, or a pharmaceutically acceptable form thereof. In some embodiments, the kinase activity is inhibited (e.g., reduced) by more than about 25%, 30%, 40%, 50%, 60%, 70%, 80%, or 90%, when contacted with a compound provided herein as compared to the kinase activity without such contact. In some embodiments, provided herein are methods of inhibiting PI3 kinase activity in a subject (including mammals such as humans) by contacting said subject with an amount of a compound as provided herein sufficient to inhibit or reduce the activity of the PI3 kinase in said subject.

In some embodiments, the kinase is a lipid kinase or a protein kinase. In some embodiments, the kinase is selected from a PI3 kinase including different isoforms, such as PI3 kinase α, PI3 kinase β, PI3 kinase γ, PI3 kinase δ; DNA-PK; mTOR; Abl, VEGFR, Ephrin receptor B4 (EphB4); TEK receptor tyrosine kinase (TIE2); FMS-related tyrosine kinase 3 (FLT-3); Platelet derived growth factor receptor (PDGFR); RET; ATM; ATR; hSmg-1; Hck; Src; Epidermal growth factor receptor (EGFR); KIT; Insulin Receptor (IR); and IGFR.

As used herein, a "PI3K-mediated disorder" refers to a disease or condition involving aberrant PI3K-mediated signaling pathway. In one embodiment, provided herein is a method of treating a PI3K mediated disorder in a subject, the method comprising administering a therapeutically effective amount of a compound as provided herein, or a pharmaceutically acceptable form thereof, or a pharmaceutical composition as provided herein. In some embodiments, provided herein is a method of treating a PI3K-δ or PI3K-γ mediated disorder in a subject, the method comprising administering a therapeutically effective amount of a compound as provided herein, or a pharmaceutically acceptable form thereof, or a pharmaceutical composition as provided herein. In some embodiments, provided herein is a method for inhibiting at least one of PI3K-δ and PI3K-γ, the method comprising contacting a cell expressing PI3K in vitro or in vivo with an effective amount of a compound or composition provided herein. PI3Ks have been associated with a wide range of conditions, including immunity, cancer and thrombosis (reviewed in Vanhaesebroeck, B. et al. (2010) *Current Topics in Microbiology and Immunology*, DOI 10.1007/ 82_2010_65). For example, Class I PI3Ks, particularly PI3K-γ and PI3K-δ isoforms, are highly expressed in leukocytes and have been associated with adaptive and innate immunity; thus, these PI3Ks are believed to be important mediators in inflammatory disorders and hematologic malignancies (reviewed in Harris, S J et al. (2009) *Curr Opin Investig Drugs* 10(11):1151-62); Rommel C. et al. (2007) *Nat Rev Immunol* 7(3):191-201; Durand C A et al. (2009) *J Immunol.* 183(9):5673-84; Dil N, Marshall A J. (2009) *Mol Immunol.* 46(10):1970-8; Al-Alwan M M et al. (2007) *J Immunol.* 178(4):2328-35; Zhang T T, et al. (2008) *J Allergy Clin Immunol.* 2008; 122(4):811-819.e2; Srinivasan L, et al. (2009) *Cell* 139(3):573-86)

PI3K-γ Activities

PI3K-γ is a Class 1B PI3K that associates with the p101 and p84 (p87PIKAP) adaptor proteins, and canonically signals through GPCRs. Non-canonical activation through tyrosine kinase receptors and RAS can occur. Activated PI3K-γ leads to production of PIP3, which serves as a docking site for downstream effector proteins including AKT and BTK, bringing these enzymes to the cell membrane where they may be activated. A scaffolding role for PI3K-γ has been proposed and may contribute to the activation of the RAS/MEK/ERK pathway. The interaction with the RAS pathway explains activities attributed to kinase dead PI3K-γ in cells or in animals. PI3K-γ is essential for function of a variety of immune cells and pathways. Chemokine responses (including IL-8, fMLP, and C5a), leading to neutrophil, basophil or monocyte cell migration, is dependent on PI3K-γ (HIRSCH et al., "Central Role for G Protein-Coupled Phosphoinositide 3-Kinase γ in Inflammation," *Science* 287:1049-1053 (2000); SASAKI et al., "Function of PI3Kγ in Thymocyte Development, T Cell Activation, and Neutrophil Migration," *Science* 287:1040-1046 (2000); LI et al., "Roles of PLC-β2 and -β3 and PI3Kγ in Chemoattractant-Mediated Signal Transduction," *Science* 287:1046-1049 (2000)). The requirement for PI3K-γ-dependent neutrophil migration is demonstrated by failure of arthritis development in the K/BXN serum transfer arthritis model in PI3K-γ knockout mice (Randis et al., *Eur. J Immunol.*, 2008, 38(5), 1215-24). Similarly, the mice fail to develop cellular inflammation and airway hyper-responsiveness in the ovalbumin induced asthma model (Takeda et al., *J. Allergy Clin. Immunol.*, 2009; 123, 805-12). PI3K-γ deficient mice also have defects in T-helper cell function. T-cell cytokine production and proliferation in response to activation is reduced, and T helper dependent viral clearance is defective (Sasaki et al., *Science,* 2000, 287, 1040-46). T cell dependent inflammatory disease models including EAE also do not develop in PI3K-γ deficient mice, and both the T-cell activation defect and cellular migration defects may contribute to efficacy in this model (Comerfold, *PLOS One,* 2012, 7, e45095). The imiquimod psoriasis model has also been used to demonstrate the importance of PI3K-γ in the inflammatory response. Using PI3K-γ deficient mice in this model, the accumulation of γδ T cells in the skin is blocked, as well as dendritic cell maturation and migration (ROLLER et al., "Blockade of Phosphatidylinositol 3-Kinase (PI3K)δ or PI3Kγ Reduces IL-17 and Ameliorates Imiquimod-Induced Psoriasis-like Dermatitis," *J. Immunol.* 189:4612-4620 (2012)). The role of PI3K-γ in cellular trafficking can also be demonstrated in oncology models where tumor inflammation is important for growth and metastasis of cancers. In the Lewis Lung Carcinoma model, monocyte activation, migration, and differentiation in tumors are defective. This defect results in a reduction in tumor growth and extended survival in PI3K-γ deficient mice (Schmid et al., *Cancer Cell,* 2011, 19, 715-27) or upon treatment with inhibitors that target PI3K-γ. In pancreatic cancer, PI3K-γ can be inappropriately expressed, and in this solid tumor cancer or others where PI3K-γ plays a functional role, inhibition of PI3K-γ can be beneficial.

For instance, while not wishing to be bound by theory, PI3K-γ is expressed in Gr1+CD11b+ myeloid cells, and directly promotes myeloid cell invasion and consequently, immunosuppression of pancreatic ductal carcinomas. Hardamon et. al., Proceedings: AACR 103rd Annual Meeting 2012, Cancer Research: Apr. 15, 2012; Volume 72, Issue 8, Supplement 1. Inhibition of PI3K-γ also shows promise for the treatment of hematologic malignancies. In a T-ALL model employing a T cell directed knockout of pten, PI3K-δ and PI3K-γ are both essential for the appropriate development of disease, as shown with genetic deletion of both genes (Subramaniam et al. *Cancer Cell* 21, 459-472, 2012). In addition, in this T-ALL model, treatment with a small molecule inhibitor of both kinases leads to extended survival of these mice. In CLL, chemokine networks support a pseudo-follicular microenvironment that includes Nurse like cells, stromal cells and T-helper cells. The roles of PI3K-γ in the normal chemokine signaling and T cell biology suggest the value of inhibiting this target in CLL (BURGER, "Inhibiting B-Cell Receptor Signaling Pathways in Chronic Lymphocytic Leukemia," *Curr. Mematol. Malig. Rep.* 7:26-33 (2012)). Accordingly, PI3K-γ inhibitors are therapeutically interesting for diseases of the immune system where cell trafficking and T cell or myeloid cell function is important. In oncology, solid tumors that are dependent on tumor inflammation, or tumors with high levels of PI3K-γ expression, can be targeted. For hematological cancers, a special role for PI3K-γ and PI3K-δ isoforms in TALL and potentially in CLL suggests targeting these PI3Ks in these diseases.

Without being limited by a particular theory, PI3K-γ has been shown to play roles in inflammation, arthritis, asthma, allergy, multiple sclerosis (MS), and cancer, among others (e.g., Ruckle et al., *Nature Rev., Drug Discovery,* 2006, 5, 903-18; Schmid et al., "Myeloid cells in tumor inflammation," *Vascular Cell,* 2012, doi:10.1186/2045-824X-4-14). For example, PI3K-γ functions in multiple signaling pathways involved in leukocyte activation and migration. PI3K-γ has been shown to drive priming and survival of autoreactive CD4$^+$ T cells during experimental autoimmune encephalomyelitis (EAE), a model for MS. When administered from onset of EAE, a PI3K-γ inhibitor has been shown to cause inhibition and reversal of clinical disease, and reduction of demyelination and cellular pathology in the CNS (Comerford et al., *PLOS One,* 2012, 7, e45095). PI3K-γ also regulates thymocyte development, T cell activation, neutrophil migration, and the oxidative burst (Sasaki et al., *Science,* 2000, 287, 1040-46). In addition, it is shown that allergic airway hyper-responsiveness, inflammation, and remodeling do not develop in PI3K-γ deficient mice (Takeda et al., *J. Allergy Clin. Immunol.,* 2009; 123, 805-12). PI3K-γ is shown to be required for chemoattractant-induced production of phosphatidylinositol 3,4,5-trisphosphate and has an important role in chemoattractant-induced superoxide production and chemotaxis in mouse neutrophils and in production of T cell-independent antigen-specific antibodies composed of the immunoglobulin λ light chain (Li et al., *Science,* 2000, 287, 1046-49). PI3K-γ is reported to be a crucial signaling molecule required for macrophage accumulation in inflammation (Hirsch et al., *Science,* 2000, 287, 1049-53). In cancers, pharmacological or genetic blockade of p110γ suppresses inflammation, growth, and metastasis of implanted and spontaneous tumors, suggesting that PI3K-γ can be an important therapeutic target in oncology (Schmid et al., *Cancer Cell,* 2011, 19, 715-27). For example, it is shown that PI3K-γ has a tumor-specific high accumulation in pancreatic ductal adenocarcinoma (PDAC) in human, signifying a role of PI3K-γ in pancreatic cancer (Edling et al., *Human Cancer Biology,* 2010, 16(2), 4928-37).

In certain embodiments, provided herein are methods of treating or preventing a PI3K-gamma mediated disorder in a subject, comprising administering to the subject a therapeutically effective amount of a compound provided herein (e.g., a compound of any of Formulae (I"), (I'), (A'), (I), (A), (II), (III), (IV), (V), (VI), (VII), (IX), (X), (XI), (XII), (XIII), (XIV), (XV), (XVI), and (XVII), e.g., a selective PI3K-γ inhibitor, e.g., Compound 4), or a pharmaceutically acceptable form thereof.

In one embodiment, the subject has or is at risk of having a PI3K-gamma mediated disorder selected from cancer, an inflammatory disease, or an autoimmune disease. In one embodiment, the cancer is a solid tumor. In one embodiment, the cancer is selected from one or more of a cancer of the pulmonary system, a brain cancer, a cancer of the gastrointestinal tract, a skin cancer, a genitourinary cancer, a pancreatic cancer, a lung cancer, a medullobastoma, a basal cell carcinoma, a glioma, a breast cancer, a prostate cancer, a testicular cancer, an esophageal cancer, a hepatocellular cancer, a gastric cancer, a gastrointestinal stromal tumor (GIST), a colon cancer, a colorectal cancer, an ovarian cancer, a melanoma, a neuroectodermal tumor, head and neck cancer, a sarcoma, a soft-tissue sarcoma, fibrosarcoma, myxosarcoma, liposarcoma, a chondrosarcoma, an osteogenic sarcoma, a chordoma, an angiosarcoma, an endotheliosarcoma, a lymphangiosarcoma, a lymphangioendotheliosarcoma, a synovioma, a mesothelioma, a leiomyosarcoma, a cervical cancer, a uterine cancer, an endometrial cancer, a carcinoma, a bladder carcinoma, an epithelial carcinoma, a squamous cell carcinoma, an adenocarcinoma, a bronchogenic carcinoma, a renal cell carcinoma, a hepatoma, a bile duct carcinoma, a neuroendocrine cancer, a carcinoid tumor, diffuse type giant cell tumor, and glioblastoma.

In one embodiment, the cancer is a hematological cancer.
In one embodiment, the inflammatory disease is arthritis.
In one embodiment, the subject is a human. In one embodiment, the subject is identified as having or being at risk of having a PI3K-gamma mediated disorder via the use of a biomarker.

In one embodiment, the therapeutically effective dose is about 2 mg, about 1-3 mg, about 1-5 mg, about 1-10 mg, about 0.5-20 mg, about 0.1-50 mg per day, about 0.1-75 mg per day, about 0.1-100 mg per day, about 0.1-250 mg per day, about 0.1-500 mg per day, about 0.1-1000 mg per day, about 1-50 mg per day, about 1-75 mg per day, about 1-100 mg per day, about 1-250 mg per day, about 1-500 mg per day, about 1-1000 mg per day, about 10-50 mg per day, about 10-75 mg per day, about 10-100 mg per day, about 10-250 mg per day, about 10-500 mg per day, about 10-1000 mg per day, about 100-500 mg per day, or about 100-1000 mg per day. In one embodiment, the therapeutically effective dose is about 0.029 mg/kg, about 0.014-0.14 mg/kg, about 0.02-0.04 mg/kg, about 0.01-0.05 mg/kg, about 0.01-0.1, or about 0.01-0.5 mg/kg. In one embodiment, the compound is administered once every two days. In one embodiment, wherein the compound is administered once per day. In one embodiment, the compound is administered twice per day.

In one embodiment, the compound is administered at a dose such that the level of the compound in the subject is higher than the compound's IC50 of PI3K-gamma inhibition during at least 70%, 80%, 90%, 95%, 97%, 98%, or 99% of a selected time period, e.g., 6 hours, 12 hours, 24 hours, or 48 hours immediately following the administration. In one embodiment, the compound is administered at a dose such that the level of the compound in the subject is higher than the compound's IC90 of PI3K-gamma inhibition during at least 50%, 60%, 70%, 80%, 90%, 95%, 97%, 98%, or 99% of a selected time period, e.g., 6 hours, 12 hours, 24 hours, or 48 hours, immediately following the administration. In one embodiment, the compound is administered at a dose such that the level of the compound in the subject does not rise higher than the compound's IC20 or IC50 of PI3K-delta inhibition within a selected time period, e.g., 6 hours, 12 hours, 24 hours, or 48 hours, immediately following the administration. In one embodiment, the level of the compound is measured from the subject's plasma. In one embodiment, the level of the compound is measured from the subject's tissue. In one embodiment, the compound is administered at a dose such that it provides at least 50% inhibition of PI3K-gamma in the subject but less than 10% or 20% inhibition of PI3K-delta in the subject.

In one embodiment, the subject is a human and the compound has a half life of about 10-13 hours in the subject. In one embodiment, the method further comprises administering to the subject a second therapeutic agent that is a P-gp substrate. In one embodiment, the second therapeutic agent is Norvir (ritonavir).

PI3K-b and/or PI3K-γ Activities

PI3K-δ has roles in impairments of B-cell signaling and development, antibody production, T-cell function, Th1 and Th2 differentiation, and mast and basophil degranulation. Without being limited by a particular theory, PI3K-γ has roles in T-cell function, neutrophil and macrophage recruitment, macrophage activation, neutrophil oxidative burst, and dendritic cell migration. Inhibition of PI3K-δ and/or PI3K-γ isoforms can result in efficacy against inflammation and cancer, e.g., in arthritis, asthma, multiple sclerosis (MS), and tumor models. For example, deficiency in PI3K-δ and/or PI3K-γ can result in efficacy in K/BxN arthritis model (Kyburz et al., *Springer Semin. Immunopathology,* 2003, 25, 79-90) or K/BxN serum transfer model of arthritis (Randis et al., *Eur. J. Immunol.,* 2008, 38(5), 1215-24), where it is shown that recognition of the immune complexes depends on both PI3K-δ and PI3K-γ, whereas cell migration is dependent on PI3K-γ. Deficiency in PI3K-δ or PI3K-γ can also result in efficacy in murine ovalbumin (OVA) induced allergic asthma model (Lee et al., *FASEB J,* 2006, 20, 455-65; Takeda et al., *J. Allergy Clin. Immunol.,* 2009; 123, 805-12), where it is shown that inhibition of either PI3K-δ or PI3K-γ inhibits ovalbumin induced lung infiltration and improves airway responsiveness. Deficiency in PI3K-δ or PI3K-γ can also result in efficacy in murine experimental autoimmune encephalomyelitis (model for MS), where it is shown that PI3K-γ deletion may provide better efficacy as compared to PI3K-δ deletion (Haylock-Jacob et al., *J. Autoimmunity,* 2011, 36, 278-87; Comerford et al., *PLOS One,* 2012, 7, e45095), including reduction in T-cell receptor induced CD4+ T cell activation, leukocyte infiltration and Th1/Th17 responses, and dendritic cell migration (Comerfold, *PLOS One,* 2012, 7, e45095). Furthermore, inhibition of PI3K-γ can also result in decreased tumor inflammation and growth (e.g., Lewis lung carcinoma model, Schmid et al., *Cancer Cell,* 2011, 19(6), 715-27). PI3K-γ deletion combined with PI3K-δ deletion results in increased survival in T-cell acute lymphoblastic leukemia (T-ALL) (Subramaniam et al., *Cancer Cell,* 2012, 21, 459-72). Inhibitors of both PI3K-δ and PI3K-γ are also shown to be efficacious in PTEN-deleted T-ALL cell line (MOLT-4). In the absence of PTEN phosphatase tumor suppressor function, PI3K-δ or PI3K-γ alone can support the development of leukemia, whereas inactivation of both isoforms suppresses tumor formation. Thus, inhibitors of PI3K-δ and/or PI3K-γ can be useful in treating inflammation, such as arthritis, allergic asthma, and MS; and in treating cancer, for example, due to effects such as reductions in solid tumor associated inflammation, angiogenesis and tumor progression.

The importance of PI3K-δ in the development and function of B-cells is supported from inhibitor studies and genetic models. PI3K-δ is an important mediator of B-cell receptor (BCR) signaling, and is upstream of AKT, calcium flux, PLCγ, MAP kinase, P70S6k, and FOXO3a activation. PI3K-δ is also important in IL4R, SIP, and CXCR5 signaling, and has been shown to modulate responses to toll-like receptors 4 and 9. Inhibitors of PI3K-δ have shown the importance of PI3K-δ in B-cell development (Marginal zone and B1 cells), B-cell activation, chemotaxis, migration and homing to lymphoid tissue, and in the control of immunoglobulin class switching leading to the production of IgE. Clayton E et al. (2002) *J Exp Med.* 196(6):753-63; Bilancio A, et al. (2006) *Blood* 107(2):642-50; Okkenhaug K. et al. (2002) *Science* 297(5583):1031-4; Al-Alwan M M et al. (2007) *J Immunol.* 178(4):2328-35; Zhang T T, et al. (2008) *J Allergy Clin Immunol.* 2008; 122(4):811-819.e2; Srinivasan L, et al. (2009) *Cell* 139(3):573-86).

In T-cells, PI3K-δ has been demonstrated to have a role in T-cell receptor and cytokine signaling, and is upstream of AKT, PLCγ, and GSK3b. In PI3K-δ deletion or kinase-dead knock-in mice, or in inhibitor studies, T-cell defects including proliferation, activation, and differentiation have been observed, leading to reduced T helper cell 2 (TH2) response, memory T-cell specific defects (DTH reduction), defects in antigen dependent cellular trafficking, and defects in chemotaxis/migration to chemokines (e.g., SIP, CCR7, CD62L). (Garçon F. et al. (2008) *Blood* 111(3):1464-71; Okkenhaug K et al. (2006). *J Immunol.* 177(8):5122-8; Soond D R, et al. (2010) *Blood* 115(11):2203-13; Reif K, (2004). *J Immunol.* 2004; 173(4):2236-40; Ji H. et al. (2007) *Blood* 110(8): 2940-7; Webb L M, et al. (2005) *J Immunol.* 175(5):2783-7; Liu D, et al. (2010) *J Immunol.* 184(6):3098-105; Haylock-Jacobs S, et al. (2011) *J Autoimmun.* 2011; 36(3-4):278-87; Jarmin S J, et al. (2008) *J Clin Invest.* 118(3):1154-64).

Numerous publications support roles of PI3K-δ and PI3K-γ in the differentiation, maintenance, and activation of immune and malignant cells, as described in more detail herein.

PI3K-δ and PI3K-γ isoforms are preferentially expressed in leukocytes where they have distinct and non-overlapping roles in immune cell development and function. See, e.g., PURI and GOLD, "Selective inhibitors of phosphoinositide 3-kinase delta: modulators of B-cell function with potential for treating autoimmune inflammatory disease and B-cell malignancies," *Front. Immunol.* 3:256 (2012); BUITEN-HUIS et al., "The role of the PI3K-PKB signaling module in regulation of hematopoiesis," *Cell Cycle* 8(4):560-566 (2009); HOELLENRIEGEL and BURGER, "Phosphoinositide 3-kinase delta: turning off BCR signaling in Chronic Lymphocytic Leukemia," *Oncotarget* 2(10):737-738 (2011); HIRSCH et al., "Central Role for G Protein-Coupled Phosphoinositide 3-Kinase γ in Inflammation," *Science* 287: 1049-1053 (2000); LI et al., "Roles of PLC-β2 and -β3 and PI3Kγ in Chemoattractant-Mediated Signal Transduction," *Science* 287:1046-1049 (2000); SASAKI et al., "Function of PI3Kγ in Thymocyte Development, T Cell Activation, and Neutrophil Migration," *Science* 287:1040-1046 (2000); CUSHING et al., "PI3Kδ and PI3Kγ as Targets for Autoimmune and Inflammatory Diseases," *J Med. Chem.* 55:8559-8581 (2012); MAXWELL et al., "Attenuation of phosphoinositide 3-kinase δ signaling restrains autoimmune disease," *J. Autoimmun.* 38:381-391 (2012); HAYLOCK-JACOBS et al., "PI3Kδ drives the pathogenesis of experimental autoimmune encephalomyelitis by inhibiting effector T cell apoptosis and promoting Th17 differentiation," *J Autoimmun.* 36:278-287 (2011); SOOND et al., "PI3K p110δ regulates T-cell cytokine production during primary and secondary immune responses in mice and humans," *Blood* 115(11):2203-2213 (2010); ROLLER et al., "Blockade of Phosphatidylinositol 3-Kinase (PI3K)δ or PI3Kγ Reduces IL-17 and Ameliorates Imiquimod-Induced Psoriasis-like Dermatitis," *J. Immunol.* 189:4612-4620 (2012); CAMPS et al., "Blockade of PI3Kγ suppresses joint inflammation and damage in mouse models of rheumatoid arthritis," *Nat. Med.* 11(9):936-943 (2005). As key enzymes in leukocyte signaling, PI3K-δ and PI3K-γ facilitate normal B-cell, T-cell and myeloid cell functions including differentiation, activation, and migration. See, e.g., HOELLENR-IEGEL and BURGER, "Phosphoinositide 3-kinase delta: turning off BCR signaling in Chronic Lymphocytic Leukemia," *Oncotarget* 2(10):737-738 (2011); CUSHING et al., "PI3Kδ and PI3Kγ as Targets for Autoimmune and Inflammatory Diseases," *J Med. Chem.* 55:8559-8581 (2012). PI3K-δ or PI3K-γ activity is critical for preclinical models of autoimmune and inflammatory diseases. See, e.g., HIRSCH et al., "Central Role for G Protein-Coupled Phosphoinositide 3-Kinase γ in Inflammation," *Science* 287:1049-1053 (2000); LI et al., "Roles of PLC-β2 and -β3 and PI3Kγ in Chemoattractant-Mediated Signal Transduction," *Science* 287:1046-1049 (2000); SASAKI et al., "Function of PI3Kγ in Thymocyte Development, T Cell Activation, and Neutrophil Migration," *Science* 287:1040-1046 (2000); CUSHING et al., "PI3Kδ and PI3Kγ as Targets for Autoimmune and Inflammatory Diseases," *J Med. Chem.* 55:8559-8581 (2012); MAXWELL et al., "Attenuation of phosphoinositide 3-kinase δ signaling restrains autoimmune disease," *J. Autoimmun.* 38:381-391 (2012); HAYLOCK-JACOBS et al., "PI3Kδ drives the pathogenesis of experimental autoimmune encephalomyelitis by inhibiting effector T cell apoptosis and promoting Th17 differentiation," *J. Autoimmun.* 36:278-287 (2011); SOOND et al., "PI3K p110δ regulates T-cell cytokine production during primary and secondary immune responses in mice and humans," *Blood* 115(11): 2203-2213 (2010); ROLLER et al., "Blockade of Phosphatidylinositol 3-Kinase (PI3K)δ or PI3Kγ Reduces IL-17 and Ameliorates Imiquimod-Induced Psoriasis-like Dermatitis," *J. Immunol.* 189:4612-4620 (2012); CAMPS et al., "Blockade of PI3Kγ suppresses joint inflammation and damage in mouse models of rheumatoid arthritis," *Nat. Med.* 11(9): 936-943 (2005). Given the key role for PI3K-δ and PI3K-γ in immune function, inhibitors of the PI3K-δ and/or γ have therapeutic potential in immune-related inflammatory or neoplastic diseases.

PI3K-δ and PI3K-γ are central to the growth and survival of B- and T-cell malignancies and inhibition of these isoforms may effectively limit these diseases. See, e.g., SUBRAMANIAM et al., "Targeting Nonclassical Oncogenes for Therapy in T-*ALL*," *Cancer Cell* 21:459-472 (2012); LANNUTTI et al., "CAL-101 a p110δ selective phosphatidylinositol-3-kinase inhibitor for the treatment of B-cell malignancies, inhibits PI3K signaling and cellular viability," *Blood* 117(2):591-594 (2011). PI3K-δ and PI3K-γ support the growth and survival of certain B-cell malignancies by mediating intracellular BCR signaling and interactions between the tumor cells and their microenvironment. See, e.g., PURI and GOLD, "Selective inhibitors of phosphoinositide 3-kinase delta: modulators of B-cell function with potential for treating autoimmune inflammatory disease and B-cell malignancies," *Front. Immunol.* 3:256 (2012); HOELLENRIEGEL et al., "The phosphoinositide 3-kinase delta inhibitor, CAL-101, inhibits B-cell receptor signaling and chemokine networks in chronic lymphocytic leuckemia," *Blood* 118(13):3603-3612 (2011); BURGER, "Inhibiting B-Cell Receptor Signaling Pathways in Chronic Lymphocytic Leukemia," *Curr. Mematol. Malig. Rep.* 7:26-33 (2012). Increased BCR signaling is a central pathologic mechanism of B-cell malignancies and PI3K activation is a direct consequence of BCR pathway activation. See, e.g., BURGER, "Inhibiting B-Cell Receptor Signaling Pathways in Chronic Lymphocytic Leukemia," *Curr. Mematol. Malig. Rep.* 7:26-33 (2012); HERISHANU et al., "The lymph node microenvironment promotes B-cell receptor signaling, NF-κB activation, and tumor proliferation in chronic lymphocytic leukemia," *Blood* 117(2):563-574 (2011); DAVIS et al., "Chronic active B-cell-receptor signaling in diffuse large B-cell lymphoma," *Nature* 463:88-92 (2010); PIGHI et al., "Phospho-proteomic analysis of mantle cell lymphoma cells suggests a pro-survival role of B-cell receptor signaling," *Cell Oncol.* (*Dordr*) 34(2):141-153 (2011); RIZZATTI et al., "Gene expression profiling of mantle cell lymphoma cells reveals aberrant expression of genes from the PI3K-AKT, WNT and TGFβ signaling pathways," *Brit. J Haematol.* 130:516-526 (2005); MARTINEZ et al., "The Molecular Signature of Mantle Cell Lymphoma Reveals Multiple Signals Favoring Cell Survival," *Cancer Res.* 63:8226-8232 (2003). Interactions between malignant B-cells and supporting cells (eg, stromal cells, nurse-like cells) in the tumor microenvironment are important for tumor cell survival, proliferation, homing, and tissue retention. See, e.g., BURGER, "Inhibiting B-Cell Receptor Signaling Pathways in Chronic Lymphocytic Leukemia," *Curr. Mematol. Malig. Rep.* 7:26-33 (2012); HERISHANU et al., "The lymph node microenvironment promotes B-cell receptor signaling, NF-κB activation, and tumor proliferation in chronic lymphocytic leukemia," *Blood* 117(2):563-574 (2011); KURTOVA et al., "Diverse marrow stromal cells protect CLL cells from spontaneous and drug-induced apoptosis: development of a reliable and reproducible system to assess stromal cell adhesion-mediated drug resistance," *Blood* 114 (20): 4441-4450 (2009); BURGER et al., "High-level expression of the T-cell chemokines CCL3 and CCL4 by chronic lymphocytic leukemia B cells in nurselike cell cocultures and after BCR stimulation," *Blood* 113(13) 3050-3058 (2009); QUIROGA et al., "B-cell antigen receptor signaling enhances chronic lymphocytic leukemia cell migration and survival: specific targeting with a novel spleen tyrosine kinase inhibitor, R406," *Blood* 114(5):1029-1037 (2009). Inhibiting PI3K-δ,γ with an inhibitor in certain malignant B-cells can block the BCR-mediated intracellular survival signaling as well as key interactions with their microenvironment that are critical for their growth.

PI3K-δ and PI3K-γ also play a direct role in the survival and proliferation of certain T-cell malignancies. See, e.g., SUBRAMANIAM et al., "Targeting Nonclassical Oncogenes for Therapy in T-ALL," *Cancer Cell* 21:459-472 (2012). Aberrant PI3K-δ and PI3K-γ activity provides the signals necessary for the development and growth of certain T-cell malignancies. While BTK is expressed in B-cells, it is not expressed in T-cells, and therefore BTK is not a viable target for the treatment of T-cell malignancies. See, e.g., NISITANI et al., "Posttranscriptional regulation of Bruton's tyrosine kinase expression in antigen receptor-stimulated splenic B cells," *PNAS* 97(6):2737-2742 (2000); DE WEERS et al., "The Bruton's tyrosine kinase gene is expressed throughout B cell differentiation, from early precursor B cell stages preceding immunoglobulin gene rearrangement up to mature B cell stages," *Eur. J. Immunol.* 23:3109-3114 (1993); SMITH et al., "Expression of Bruton's Agammaglobulinemia Tyrosine Kinase Gene, BTK, Is Selectively Down-Regulated in T Lymphocytes and Plasma Cells," *J. Immunol.* 152:557-565 (1994). PI3K-δ and/or γ inhibitors may have unique therapeutic potential in T-cell malignancies.

In neutrophils, PI3K-δ, along with PI3K-γ, contribute to the responses to immune complexes, FCγRII signaling, including migration and neutrophil respiratory burst. Human neutrophils undergo rapid induction of PIP3 in response to formyl peptide receptor (FMLP) or complement component C5a (C5a) in a PI3K-γ dependent manner, followed by a longer PIP3 production period that is PI3K-δ dependent, and is essential for respiratory burst. The response to immune complexes is contributed by PI3K-δ, PI3K-γ, and PI3K-D, and is an important mediator of tissue damage in models of autoimmune disease (Randis™ et al. (2008) *Eur J Immunol.* 38(5):1215-24; Pinho V, (2007) *J Immunol.* 179(11):7891-8; Sadhu C. et al. (2003) *J Immunol.* 170(5):2647-54; Condliffe A M et al. (2005) *Blood* 106(4):1432-40). It has been reported that in certain autoimmune diseases, preferential activation of PI3K-β may be involved (Kulkami et al., *Immunology* (2011) 4(168) ra23: 1-11). It was also reported that PI3K-β-deficient mice were highly protected in an FcγR-dependent model of autoantibody-induced skin blistering and partially protected in an FcγR-dependent model of inflammatory arthritis, whereas combined deficiency of PI3K-β and PI3K-δ resulted in near complete protection in inflammatory arthritis (Id.).

In macrophages collected from patients with chronic obstructive pulmonary disease (COPD), glucocorticoid responsiveness can be restored by treatment of the cells with inhibitors of PI3K-δ. Macrophages also rely on PI3K-δ and PI3K-γ for responses to immune complexes through the arthus reaction (FCγR and C5a signaling) (Randis T M, et al. (2008) *Eur J Immunol.* 38(5):1215-24; Marwick J A et al. (2009) *Am J Respir Crit Care Med.* 179(7):542-8; Konrad S, et al. (2008) *J Biol Chem.* 283(48):33296-303).

Theophylline increases histone deacetylase-2 and corticosteroid sensitivity in vitro and in smoking mice in vivo by inhibiting PI3 kinase (e.g., PI3K-delta). PI3K is activated in COPD lungs and certain PI3K inhibitors have been shown to mimic the effects of theophylline in reversing corticosteroid resistance. Yasuo, T., et al., Am J Respir Crit Care Med 2010; 182:897-904. While not wishing to be bound by theory, a rationale for the use of PI3K inhibitors (e.g., compounds provided herein) to treat COPD is that a PI3K inhibitor can increase the corticosteroid sensitivity in a subject.

In mast cells, stem cell factor—(SCF) and IL3-dependent proliferation, differentiation and function are PI3K-δ dependent, as is chemotaxis. The allergen/IgE crosslinking of FCγR1 resulting in cytokine release and degranulation of the mast cells is severely inhibited by treatment with PI3K-δ inhibitors, suggesting a role for PI3K-δ in allergic disease (Ali K et al. (2004) *Nature* 431(7011):1007-11; Lee K S, et al. (2006) *FASEB J.* 20(3):455-65; Kim M S, et al. (2008) *Trends Immunol.* 29(10):493-501).

Natural killer (NK) cells are dependent on both PI3K-δ and PI3K-γ for efficient migration towards chemokines including CXCL10, CCL3, SP and CXCL12, or in response to LPS in the peritoneum (Guo H, et al. (2008) *J Exp Med.* 205(10):2419-35; Tassi I, et al. (2007) *Immunity* 27(2):214-27; Saudemont A, (2009) *Proc Natl Acad Sci USA.* 106(14): 5795-800; Kim N, et al. (2007) *Blood* 110(9):3202-8).

The roles of PI3K-δ and PI3K-γ in the differentiation, maintenance, and activation of immune cells support a role for these enzymes in inflammatory disorders ranging from autoimmune diseases (e.g., rheumatoid arthritis, multiple sclerosis) to allergic inflammatory disorders, such as asthma, and inflammatory respiratory disease, such as COPD. Extensive evidence is available in experimental animal models, or can be evaluated using art-recognized animal models. In an embodiment, described herein is a method of treating inflammatory disorders ranging from autoimmune diseases (e.g., rheumatoid arthritis, multiple sclerosis) to allergic inflammatory disorders, such as asthma and COPD using a compound described herein.

For example, inhibitors of PI3K-δ and/or -γ have been shown to have anti-inflammatory activity in several autoimmune animal models for rheumatoid arthritis (Williams, O. et al. (2010) Chem Biol, 17(2):123-34; WO 2009/088986; WO2009/088880; WO 2011/008302; each incorporated herein by reference). PI3K-δ is expressed in the RA synovial tissue (especially in the synovial lining which contains fibroblast-like synoviocytes (FLS), and selective PI3K-δ inhibitors have been shown to be effective in inhibiting synoviocyte growth and survival (Bartok et al. (2010) *Arthritis Rheum* 62 Suppl 10:362). Several PI3K-δ and -γ inhibitors have been shown to ameliorate arthritic symptoms (e.g., swelling of joints, reduction of serum-induced collagen levels, reduction of joint pathology and/or inflammation), in art-recognized models for RA, such as collagen-induced arthritis and adjuvant induced arthritis (WO 2009/088986; WO2009/088880; WO 2011/008302; each incorporated herein by reference).

The role of PI3K-δ has also been shown in models of T-cell dependent response, including the DTH model. In the murine experimental autoimmune encephalomyelitis (EAE) model of multiple sclerosis, the PI3K-γ/δ-double mutant mice are resistant. PI3K-δ inhibitors have also been shown to block EAE disease induction and development of TH-17 cells both in vitro and in vivo (Haylock-Jacobs, S. et al. (2011) *J. Autoimmunity* 36(3-4):278-87).

Systemic lupus erythematosus (SLE) is a complex disease that at different stages requires memory T-cells, B-cell polyclonal expansion and differentiation into plasma cells, and the innate immune response to endogenous damage associated molecular pattern molecules (DAMPS), and the inflammatory responses to immune complexes through the complement system as well as the Fc receptors. The role of PI3K-δ and PI3K-γ together in these pathways and cell types suggest that blockade with an inhibitor would be effective in these diseases. A role for PI3K in lupus is also predicted by two genetic models of lupus. The deletion of phosphatase and tensin homolog (PTEN) leads to a lupus-like phenotype, as does a transgenic activation of Class 1A PI3Ks, which includes PI3K-δ. The deletion of PI3K-γ in the transgenically activated class 1A lupus model is protective, and treatment with a PI3K-γ selective inhibitor in the murine MLR/lpr model of lupus improves symptoms (Barber, D F et al. (2006) *J. Immunol.* 176(1): 589-93).

In allergic disease, PI3K-δ has been shown by genetic models and by inhibitor treatment to be essential for mast-cell activation in a passive cutaneous anaphalaxis assay (Ali K et al. (2008) *J Immunol.* 180(4):2538-44; Ali K, (2004) *Nature* 431(7011):1007-11). In a pulmonary measure of response to immune complexes (Arthus reaction) a PI3K-δ knockout is resistant, showing a defect in macrophage activation and C5a production. Knockout studies and studies with inhibitors for both PI3K-δ and PI3K-γ support a role for both of these enzymes in the ovalbumin induced allergic airway inflammation and hyper-responsiveness model (Lee K S et al. (2006) *FASEB J.* 20(3):455-65). Reductions of infiltration of eosinophils, neutrophils, and lymphocytes as well as TH2 cytokines (IL4, IL5, and IL13) were seen with both PI3K-δ specific and dual PI3K-δ and PI3K-γ inhibitors in the Ova induced asthma model (Lee K S et al. (2006) *J Allergy Clin Immunol* 118(2):403-9).

PI3K-δ and PI3K-γ inhibition can be used in treating COPD. In the smoked mouse model of COPD, the PI3K-δ knockout does not develop smoke induced glucocorticoid resistance, while wild-type and PI3K-γ knockout mice do. An inhaled formulation of dual PI3K-δ and PI3K-γ inhibitor blocked inflammation in a LPS or smoke COPD models as measured by neutrophilia and glucocorticoid resistance (Doukas J, et al. (2009) *J Pharmacol Exp Ther.* 328(3):758-65).

PI3K-b and/or PI3K-γ Isoforms in Certain Cancers

Class I PI3Ks, particularly PI3K-δ and PI3K-γ isoforms, are also associated with cancers (reviewed, e.g., in Vogt, P K et al. (2010) *Curr Top Microbiol Immunol.* 347:79-104; Fresno Vara, J A et al. (2004) *Cancer Treat Rev.* 30(2):193-204; Zhao, L and Vogt, P K. (2008) *Oncogene* 27(41):5486-96). Inhibitors of PI3K, e.g., PI3K-δ and/or PI3K-γ, have been shown to have anti-cancer activity (e.g., Courtney, K D et al. (2010) *J Clin Oncol.* 28(6):1075-1083); Markman, B et al. (2010) *Ann Oncol.* 21(4):683-91; Kong, D and Yamori, T (2009) *Curr Med Chem.* 16(22):2839-54; Jimeno, A et al. (2009) *J Clin Oncol.* 27:156s (suppl; abstr 3542); Flinn, I W et al. (2009) *J Clin Oncol.* 27:156s (suppl; abstr 3543); Shapiro, G et al. (2009) *J Clin Oncol.* 27:146s (suppl; abstr 3500); Wagner, A J et al. (2009) *J Clin Oncol.* 27:146s (suppl; abstr 3501); Vogt, P K et al. (2006) *Virology* 344(1):131-8; Ward, S et al. (2003) *Chem Biol.* 10(3):207-13; WO 2011/041399; US 2010/0029693; US 2010/0305096; US 2010/0305084; each incorporated herein by reference).

In one embodiment, described herein is a method of treating cancer. In one embodiment, provided herein is a method of treating a hematological caner comprising administering a pharmaceutically effective amount of a compound provided herein to a subject in need thereof. In one embodiment, provided herein is a method of treating a solid tumor comprising administering a pharmaceutically effective amount of a compound provided herein to a subject in need thereof. Types of cancer that can be treated with an inhibitor of PI3K (particularly, PI3K-δ and/or PI3K-γ) include, e.g., leukemia, chronic lymphocytic leukemia, acute myeloid leukemia, chronic myeloid leukemia (e.g., Salmena, L et al. (2008) *Cell* 133:403-414; Chapuis, N et al. (2010) *Clin Cancer Res.* 16(22):5424-35; Khwaja, A (2010) *Curr Top Microbiol Immunol.* 347:169-88); lymphoma, e.g., non-Hodgkin's lymphoma (e.g., Salmena, L et al. (2008) *Cell* 133:403-414); lung cancer, e.g., non-small cell lung cancer, small cell lung cancer (e.g., Herrera, V A et al. (2011) *Anticancer Res.* 31(3):849-54); melanoma (e.g., Haluska, F et al. (2007) *Semin Oncol.* 34(6):546-54); prostate cancer (e.g., Sarker, D et al. (2009) *Clin Cancer Res.* 15(15):4799-805); glioblastoma (e.g., Chen, J S et al. (2008) *Mol Cancer Ther.* 7:841-850); endometrial cancer (e.g., Bansal, N et al. (2009) *Cancer Control.* 16(1):8-13); pancreatic cancer (e.g., Furukawa, T (2008) *J Gastroenterol.* 43(12):905-11); renal cell carcinoma (e.g., Porta, C and Figlin, R A (2009) *J Urol.* 182(6):2569-77); colorectal cancer (e.g., Saif, M W and Chu, E (2010) *Cancer J.* 16(3):196-201); breast cancer (e.g., Torbett, N E et al. (2008) *Biochem J.* 415:97-100); thyroid cancer (e.g., Brzezianska, E and Pastuszak-Lewandoska, D (2011) *Front Biosci.* 16:422-39); and ovarian cancer (e.g., Mazzoletti, M and Broggini, M (2010) *Curr Med Chem.* 17(36):4433-47).

Numerous publications support a role of PI3K-δ and PI3K-γ in treating hematological cancers. PI3K-δ and PI3K-γ are highly expressed in the heme compartment, and solid tumors, including prostate, breast and glioblastomas (Chen J. S. et al. (2008) *Mol Cancer Ther.* 7(4):841-50; Ikeda H. et al. (2010) *Blood* 116(9):1460-8).

In hematological cancers including acute myeloid leukemia (AML), multiple myeloma (MM), and chronic lymphocytic leukemia (CLL), overexpression and constitutive activation of PI3K-δ supports the model that PI3K-δ inhibition would be therapeutic Billottet C, et al. (2006) *Oncogene* 25(50):6648-59; Billottet C, et al. (2009) *Cancer Res.* 69(3):1027-36; Meadows, SA, 52$^{nd}$ Annual ASH Meeting and Exposition; 2010 Dec. 4-7; Orlando, Fla.; Ikeda H, et al. (2010) *Blood* 116(9):1460-8; Herman S E et al. (2010) *Blood* 116(12):2078-88; Herman S E et al. (2011). *Blood* 117(16): 4323-7.

In one embodiment, described herein is a method of treating hematological cancers including, but not limited to acute myeloid leukemia (AML), multiple myeloma (MM), and chronic lymphocytic leukemia (CLL).

A PI3K-δ inhibitor (CAL-101) has been evaluated in a phase 1 trial in patients with haematological malignancies, and showed activity in CLL in patients with poor prognostic characteristics. In CLL, inhibition of PI3K-δ not only affects tumor cells directly, but it also affects the ability of the tumor cells to interact with their microenvironment. This microenvironment includes contact with and factors from stromal cells, T-cells, nurse like cells, as well as other tumor cells. CAL-101 suppresses the expression of stromal and T-cell derived factors including CCL3, CCL4, and CXCL13, as well as the CLL tumor cells' ability to respond to these factors. CAL-101 treatment in CLL patients induces rapid lymph node reduction and redistribution of lymphocytes into the circulation, and affects tonic survival signals through the BCR, leading to reduced cell viability, and an increase in apoptosis. Single agent CAL-101 treatment was also active in mantle cell lymphoma and refractory non Hodgkin's lymphoma (Furman, R R, et al. 52$^{nd}$ Annual ASH Meeting and Exposition; 2010 Dec. 4-7; Orlando, Fla.; Hoellenriegel, J, et al. 52$^{nd}$ Annual ASH Meeting and Exposition; 2010 Dec. 4-7; Orlando, Fla.; Webb, H K, et al. 52$^{nd}$ Annual ASH Meeting and Exposition; 2010 Dec. 4-7; Orlando, Fla.; Meadows, et al. 52$^{nd}$ Annual ASH Meeting and Exposition; 2010 Dec. 4-7; Orlando, Fla.; Kahl, B, et al. 52$^{nd}$ Annual ASH Meeting and Exposition; 2010 Dec. 4-7; Orlando, Fla.; Lannutti B J, et al. (2011) *Blood* 117(2):591-4).

PI3K-δ inhibitors have shown activity against PI3K-δ positive gliomas in vitro (Kashishian A, et al. Poster presented at: The American Association of Cancer Research 102$^{nd}$ Annual Meeting; 2011 Apr. 2-6; Orlando, Fla.). In this subset of tumors, treatment with the PI3K-δ inhibitor either alone or in combination with a cytotoxic agent can be effective.

Another mechanism for PI3K-δ inhibitors to have an effect in solid tumors involves the tumor cells' interaction with their micro-environment. PI3K-δ, PI3K-γ, and PI3K-β are expressed in the immune cells that infiltrate tumors, including tumor infiltrating lymphocytes, macrophages, and neutrophils. PI3K-δ inhibitors can modify the function of these tumor-associated immune cells and how they respond to signals from the stroma, the tumor, and each other, and in this way affect tumor cells and metastasis (Hoellenriegel, J, et al. 52$^{nd}$ Annual ASH Meeting and Exposition; 2010 Dec. 4-7; Orlando, Fla.).

PI3K-δ is also expressed in endothelial cells. It has been shown that tumors in mice treated with PI3K-δ selective inhibitors are killed more readily by radiation therapy. In this same study, capillary network formation is impaired by the PI3K inhibitor, and it is postulated that this defect contributes to the greater killing with radiation. PI3K-δ inhibitors can affect the way in which tumors interact with their microenvironment, including stromal cells, immune cells, and endothelial cells and be therapeutic either on its own or in conjunction with another therapy (Meadows, S A, et al. Paper presented at: 52$^{nd}$ Annual ASH Meeting and Exposition; 2010 Dec. 4-7; Orlando, Fla.; Geng L, et al. (2004) *Cancer Res.* 64(14):4893-9).

Accordingly, provided herein is a method of treating or preventing a cancer or disease (including but not limited to a hematologic malignancy, or a specific type or sub-type of cancer or disease, such as a specific type or sub-type of hematologic malignancy), with a PI3K-γ selective inhibitor, wherein the adverse effects associated with administration of inhibitors for other isoform(s) of PI3K (e.g., PI3K-α and/or PI3K-β) are reduced. In one embodiment, provided herein is a method of treating or preventing the cancer or disease, with a PI3K-γ selective inhibitor, at a lower (e.g., by about 10%, by about 20%, by about 30%, by about 40%, by about 50%, by about 60%, by about 70%, or by about 80%) dose as compared to treatment with a PI3K-γ non-selective or less selective PI3K-γ inhibitor (e.g., a PI3Kpan inhibitors, e.g., inhibiting PI3K-α, β, δ, and γ).

The role of PI3K-γ pathway in promoting myeloid cell trafficking to tumors and the role of blockade of p100γ in suppression of tumor inflammation and growth in breast cancer, pancreatic cancer, and lung cancer are reported, for example, in Schmid et al. (2011) *Cancer Cell* 19, 715-727, the entirety of which is incorporated herein by reference. In one embodiment, provided herein is a method of treating or preventing pancreatic cancer with a PI3K inhibitor.

In another embodiment, provided herein is a method of treating or preventing breast cancer with a PI3K inhibitor. In yet another embodiment, provided herein is a method of treating or preventing lung cancer with a PI3K inhibitor. In one embodiment, the PI3K inhibitor is a PI3K-γ inhibitor, selective or non-selective over one or more other PI3K isoform(s). In one embodiment, the PI3K inhibitor is a PI3K-γ selective inhibitor.

While not wishing to be bound by theory, it is believed that tumor growth is influenced by two classes of immune cells in the tumor microenvironment: effector cells which include cytotoxic cells and M1 macrophages, and which have anti-tumor activity, and suppressor cells, which include M2 macrophages, MDSC (myeloid derived suppressor cell), Tregs (regulatory T cell), and regulatory dendritic cells, which have pro-tumor activity because they inhibit the effector cells. An abundance of suppressor cells can lead to tumor immune tolerance, and enhancement of tumor growth.

Certain of these cell types are briefly described. M1 denotes a pro-inflammatory (anti-tumor) phenotype of a MDSC or TAM. M2 denotes an anti-inflammatory (pro-tumor) phenotype of a MDSC or TAM.

PI3K-γ is not expressed in at least some cancer cell types. Schmid et al., 2011, Cancer Cell 19. Accordingly, in some embodiments, the PI3K-γ inhibitor reduces cancer cell growth without having a substantial direct effect on the cancer cell itself. For instance, in some embodiments, the PI3K-γ inhibitor inhibits cancer cell growth through changes in the tumor microenvironment, e.g., the immune cells in close proximity to the cancer cells.

Evidence provided in the Examples herein, combined with evidence in the literature, support the idea that a PI3K-γ inhibitor can reduce tumor associated myeloid cells. For instance, in PI3K-y-deficient mice, tumor-associated myeloid cells are reduced. Schmid et al., 2011, Cancer Cell 19. Together, these data indicate that a large class of PI3K-γ inhibitors should reduce tumor associated myeloid cells, thereby increasing the immune response against cancer cells, and treating the cancer. While not wishing to be bound by theory, a PI3K-γ may operate through the following mechanism. PI3K-γ signaling may tilt the balance of immune cells towards pro-tumor M2 cells and away from anti-tumor M1 cells, by inducing expression of immunosuppressive, wound healing genes such as Arginase1, TGFbeta1, PDGFBB, MMP9, and MMPI3, and suppressing pro-inflammatory factors such as IL12, iNos, and interferon gamma. Blocking PI3K-γ signaling with an inhibitor tilts the balance towards anti-tumor M1 cells by stimulating a T cell activating gene expression program. Kaneda et al. PI3-kinase gamma controls the macrophage M1-M2 switch, thereby promoting tumor immunosuppression and progression. [abstract]. In: Proceedings of the 105th Annual Meeting of the American Association for Cancer Research; 2014 Apr. 5-9; San Diego, Calif. Philadelphia (Pa.): AACR; Cancer Res 2014; 74(19 Suppl):Abstract nr 3650. doi: 10.1158/1538-7445.AM2014-3650.

In some embodiments, a PI3K-γ inhibitor provided herein is administered to a patient in order to block a homeostatic down-regulation of T cell response. While not wishing to be bound by theory, this may allow the body to raise an effective immune response against the cancer cell. Exemplary agents of this type include immune checkpoint therapeutics, e.g., agents that act on CTLA-4, PD-1, or PD-L1, e.g., antibodies that bind to CTLA-4, PD-1, or PD-L1. Immune checkpoint therapeutics are described in more detail below.

In some embodiments, a PI3K-γ inhibitor provided herein is administered to a patient in order to eliminate immunosuppressive cells in the tumor microenvironment. The immunosuppressive cell may be, e.g., a T regulatory cell (e.g., a cell that secretes mediators that induce CD8+ cytotoxic T cell death); a Tumor-associated macrophage (TAM; e.g., anM2 (pro-tumor) TAMS that blocks T cell activity and promotes angiogenesis); or a myeloid-derived suppressor cell (MDSC; e.g., a cell that secretes mediators that inhibit T cell differentiation and proliferation).

In some embodiments, a compound provided herein is administered to a patient in order to reduce the migration or differentiation of a tumor associated myeloid cell. In some embodiments, the compound is a compound that shows signle agent activity in a syngeneic model system. In some embodiments, the compound is administered in combination with a second therapeutic, as discussed herein. In some embodiments, the administration results in a reduction in the level of MDSCs in the tumor microenvironment; the level of M2 TAMS in the tumor microenvironment; the level of T-regulatory cells in the tumor microenvironment, or any combination thereof. In some embodiments, the administration results in an unchanged or increased level of T-effector cells in the tumor microenvironment. In embodiments, the administration results in an increase in an immune response to the tumor, e.g., an increase in the levels or tumorattacking activity of cytotoxic T cells, M1 inflammatory TAMs, or a combination thereof.

In some embodiments, an MDSC has one or more of the following properties: suppressing anti-tumor immune attack; inducing vascularization of the tumor; inducing ECM breakdown, e.g., which may contribute to metastasis; and supporting tumor growth. Accordingly, in some embodiments, administration of a PI3K-γ inhibitor described herein inhibits one or more of these functions in an MDSC.

TAMs (tumor-associated macrophages) can also have one or more of the following properties: suppressing anti-tumor immune attack; inducing vascularization of the tumor; inducing ECM breakdown, e.g., which may contribute to metastasis; and supporting tumor growth. Accordingly, in some embodiments, administration of a PI3K-γ inhibitor as described herein inhibits one or more of these functions in a TAM.

In embodiments, a PI3K-γ inhibitor is administered to a patient who has received chemotherapy and/or radiation therapy. While not wishing to be bound by theory, in some embodiments, chemotherapy or radiation therapy results in a wound healing response that leads to repopulation of the cancer site, e.g., tumor, with TAMs and MDSCs. Administering the PI3K-γ inhibitor, in some embodiments, reduces the levels of TAMs and MDSCs in the microenvironment, decreasing their support for tumor cell growth and/or allowing the immune system to attack the cancer cells. See Claire E. Lewis, "Imaging immune cell infiltrating tumors in zebrafish", AACR Annual Meeting (Apr. 5, 2014).

While not wishing to be bound by theory, a rationale for the use of a PI3K gamma inhibitor as adjunct therapy to radiation is to prevent the accumulation of tumor supporting myeloid cells into the radiated tumor, thus impairing tumor regrowth following radiation therapy. This is supported by work of Kioi et al. (2010) *Clin Invest.* 120(3):694-705 showing that an inhibitor of myeloid cell migration into post-irradiated tumors (e.g., AMD3100) blocked tumor vasculogenesis and tumor regrowth.

In certain embodiments, provided herein is a method of treating a disorder or disease provided herein, comprising administering a compound provided herein, e.g., a PI3K γ selective inhibitor, a PI3K δ selective inhibitor, or a PI3K γ/δ dual inhibitor. Without being limited by a particular theory, in some embodiments, selectively inhibiting PI3K-γ isoform can provide a treatment regimen where adverse effects associated with administration of a non-selective PI3K inhibitor are minimized or reduced. Without being limited by a particular theory, in some embodiments, selectively inhibiting PI3K-δ isoform can provide a treatment regimen where adverse effects associated with administration of a non-selective PI3K inhibitor are minimized or reduced. Without being limited by a particular theory, in some embodiments, selectively inhibiting PI3K-δ and γ isoform can provide a treatment regimen where adverse effects associated with administration of a non-selective PI3K inhibitor are minimized or reduced. Without being limited by a particular theory, it is believed that the adverse effects can be reduced by avoiding the inhibition of other isoforms (e.g., α or β) of PI3K.

In one embodiment, the adverse effect is hyperglycemia. In another embodiment, the adverse effect is rash. In another embodiment, the adverse effect is impaired male fertility that may result from inhibition of β isoform of PI3K (see, e.g., Ciraolo et al., *Molecular Biology of the Cell,* 21: 704-711 (2010)). In another embodiment, the adverse effect is testicular toxicity that may result from inhibition of PI3K-β (see, e.g., Wisler et al., Amgen SOT, Abstract ID #2334 (2012)). In another embodiment, the adverse effect is embryonic lethality (see, e.g., Bi et al., *J Biol Chem,* 274: 10963-10968 (1999)). In another embodiment, the adverse effect is defective platelet aggregation (see, e.g., Kulkami et al., *Science,* 287: 1049-1053 (2000)). In another embodiment, the adverse effect is functionally defective neutrophil (id.).

In certain embodiments, provided herein is a method of treating or preventing cancer (e.g., colon cancer, melanoma, bladder cancer, renal cancer, breast, lung cancer, glioblastoma, solid tumors, and a cancer of hematopoietic origin (e.g., DLBCL, CLL, Hodgkin lymphoma, non-Hodgkin lymphomas)) comprising administering to the subject a PI3K inhibitor (e.g., a PI3K-γ inhibitor, e.g., a compound of any of Formulae (I"), (I'), (A'), (I), (A), (II), (III), (IV), (V), (VI), (VII), (IX), (X), (XI), (XII), (XIII), (XIV), (XV), (XVI), and (XVII), e.g., Compound 4, as described herein).

Without being bound by a particular theory, a rationale for the use of a PI3K inhibitor to treat or prevent cancer is that cells derived from tumors (e.g., from CT26 mouse tumors) can suppress anti-tumor immune cell function, including T-cell proliferation, as shown in the examples provide herein, and treatment with a compound provided herein can release the suppression. The tumor microenvironment can inhibit the activation and proliferation of immune effector cells due to the presence of suppressive myeloid cells (e.g., myeloid derived suppressor cells or MDSC and M2 macrophages). Compounds provided herein can affect the number and activity M2 macrophages in a tumor microenvironment, e.g., reduce or inhibit the level of M2, pro-tumor macrophages. The reduction or inhibition of M2 macrophages, which produce anti-inflammatory cytokines and other factors, would lead to increased anti-tumor immunity, including T cell proliferation. Therefore, a compound provided herein can treat or prevent cancer such as colon cancer, melanoma, bladder cancer, renal cancer, breast, lung cancer, glioblastoma, solid tumors, and a cancer of hematopoietic origin (e.g., lymphoma, DLBCL, CLL, Hodgkin disease, non-Hodgkin lymphomas). Further, it has also been shown in the examples provided herein that anti-PDL1 can also release suppression of T cell proliferation by blocking the interaction between PD1 on T cells and PDL1 on tumor cells and regulatory cells. The cytotoxic T cells that are induced to proliferate and survive by both anti PDL-1 and compound BB are hypothesized to slow tumor growth. Compounds provided herein can relieve immunosuppression which can lead to T cells proliferation and activation. Compounds provided herein can treat or prevent cancer by inducing T cell mediated immunity. In one embodiment, the compound provided herein can decrease tumor volume. In one embodiment, a combination of a PI3K inhibitor such as a compound provided herein and anti-PDL1 would be effective in treating or preventing cancer by inducing T cell mediated tumor immunity. In some embodiments, the effect of a compound provided herein on T-cell function can be assessed by analyzing the pro-inflammatory cytokine levels in tumor tissues and serum, e.g., a MSD pro-inflammatory panel. In another embodiment, the pro-inflammatory cytokines are selected from IFN-γ, IL-1β, IL-10, IL-12 p70, IL-2, IL-4, IL-5, IL-6, KC/GRO, and TNF-α. In one embodiment, the effect of a compound provided herein on T cell function can be assessed by analyzing the IFN-γ level. For example, tumor tissues and serum treated with a compound provided herein, e.g., Compound 4, can be assessed by analyzing the IFN-γ level.

Treatment of Neuropsychiatric Disorders

In other embodiments, inhibition of PI3K (such as PI3K-δ and/or PI3K-γ) can be used to treat a neuropsychiatric disorder, e.g., an autoimmune brain disorder. Infectious and immune factors have been implicated in the pathogenesis of several neuropsychiatric disorders, including, but not limited to, Sydenham's chorea (SC) (Garvey, M. A. et al. (2005) *J. Child Neurol.* 20:424-429), Tourette's syndrome (TS), obsessive compulsive disorder (OCD) (Asbahr, F. R. et al. (1998) *Am. J. Psychiatry* 155:1122-1124), attention deficit/hyperactivity disorder (AD/HD) (Hirschtritt, M. E. et al. (2008) *Child Neuropsychol.* 1:1-16; Peterson, B. S. et al. (2000) *Arch. Gen. Psychiatry* 57:364-372), anorexia nervosa (Sokol, M. S. (2000) *J. Child Adolesc. Psychopharmacol.* 10:133-145; Sokol, M. S. et al. (2002) *Am. J. Psychiatry* 159:1430-1432), depression (Leslie, D. L. et al. (2008) *J. Am. Acad. Child Adolesc. Psychiatry* 47:1166-1172), and autism spectrum disorders (ASD) (Hollander, E. et al. (1999) *Am. J. Psychiatry* 156:317-320; Margutti, P. et al. (2006) *Curr. Neurovasc. Res.* 3:149-157). A subset of childhood obsessive compulsive disorders and tic disorders has been grouped as Pediatric Autoimmune Neuropsychiatric Disorders Associated with Streptococci (PANDAS). PANDAS disorders provide an example of disorders where the onset and exacerbation of neuropsychiatric symptoms is preceded by a streptococcal infection (Kurlan, R., Kaplan, E. L. (2004) *Pediatrics* 113:883-886; Garvey, M. A. et al. (1998) *J. Clin. Neurol.* 13:413-423). Many of the PANDAS disorders share a common mechanism of action resulting from antibody responses against streptococcal associated epitopes, such as GlcNAc, which produces neurological effects (Kirvan. C. A. et al. (2006) *J Neuroimmunol.* 179: 173-179). Autoantibodies recognizing central nervous system (CNS) epitopes are also found in sera of most PANDAS subjects (Yaddanapudi, K. et al. (2010) *Mol. Psychiatry* 15:712-726). Thus, several neuropsychiatric disorders have been associated with immune and autoimmune components, making them suitable for therapies that include PI3K-δ and/or PI3K-γ inhibition.

In certain embodiments, a method of treating (e.g., reducing or ameliorating one or more symptoms of) a neuropsychiatric disorder, (e.g., an autoimmune brain disorder), using a PI3K-δ and/or PI3K-γ inhibitor is described, alone or in combination therapy. For example, one or more PI3K-δ and/or PI3K-γ inhibitors described herein can be used alone or in combination with any suitable therapeutic agent and/or modalities, e.g., dietary supplement, for treatment of neuropsychiatric disorders. Exemplary neuropsychiatric disorders that can be treated with the PI3K-δ and/or PI3K-γ inhibitors described herein include, but are not limited to, PANDAS disorders, Sydenham's chorea, Tourette's syndrome, obsessive compulsive disorder, attention deficit/hyperactivity disorder, anorexia nervosa, depression, and autism spectrum disorders. Pervasive Developmental Disorder (PDD) is an exemplary class of autism spectrum disorders that includes Autistic Disorder, Asperger's Disorder, Childhood Disintegrative Disorder (CDD), Rett's Disorder and PDD—Not Otherwise Specified (PDD-NOS). Animal models for evaluating the activity of the PI3K-δ and/or PI3K-γ inhibitor are known in the art. For example, a mouse model of PANDAS disorders is described in, e.g., Yaddanapudi, K. et al. (2010) supra; and Hoffman, K. I. et al. (2004) *J. Neurosci.* 24:1780-1791.

In some embodiments, provided herein is a method for treating rheumatoid arthritis or asthma in a subject, or for reducing a rheumatoid arthritis-associated symptom or an asthma-associated symptom in a subject, comprising administering an effective amount of a PI3K-γ inhibitor to a subject in need thereof, wherein one or more of the adverse effects associated with administration of inhibitors for one or more other isoforms of PI3K are reduced. In one embodiment, the one or more other isoforms of PI3K is PI3K-α, PI3K-β, and/or PI3K-δ. In one embodiment, the one or more other isoforms of PI3K is PI3K-α and/or PI3K-β. In one embodiment, the method is for treating rheumatoid arthritis in a subject, or for reducing a rheumatoid arthritis-associated symptom in a subject. In another embodiment, the method is for treating asthma in a subject, or for reducing an asthma-associated symptom in a subject.

In some embodiments, provided herein are methods of using a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, to treat disease conditions, including, but not limited to, diseases associated with malfunctioning of one or more types of PI3 kinase. In one embodiment, a detailed description of conditions and disorders mediated by p110δ kinase activity is set forth in Sadu et al., WO 01/81346, which is incorporated herein by reference in its entirety for all purposes.

In some embodiments, the disclosure relates to a method of treating a hyperproliferative disorder in a subject that comprises administering to said subject a therapeutically effective amount of a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein. In some embodiments, said method relates to the treatment of cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS-related (e.g., Lymphoma and Kaposi's Sarcoma) or viral-induced cancer. In some embodiments, said method relates to the treatment of a non-cancerous hyperproliferative disorder such as benign hyperplasia of the skin (e.g., psoriasis), restenosis, or prostate (e.g., benign prostatic hypertrophy (BPH)).

Treatment of Cancers

In certain embodiments, provided herein are methods of modulating tumor microenvironment of cancer cells in a subject, comprising administering to the subject a therapeutically effective amount of a compound provided herein (e.g., a compound of any of Formulae (I"), (I'), (A'), (I), (A), (II), (III), (IV), (V), (VI), (VII), (IX), (X), (XI), (XII), (XIII), (XIV), (XV), (XVI), and (XVII), e.g., a selective PI3K-γ inhibitor, e.g., Compound 4), or a pharmaceutically acceptable form thereof.

As used herein and unless otherwise specified, "tumor microenvironment" refers to the cellular and extracellular environment where the tumors are located. This location can include surrounding blood vessels, immune cells, fibroblasts, secreted signaling molecules, and the extracelluar matrix. The tumor microenvironment includes non-neoplastic stromal and immune cells that provide growth and survival support to the neoplastic tumor.

As used herein and unless otherwise specified, "immunotherapy" refers to treatments that stimulate, enhance, or suppress the body's own immune system to fight a disease. Diseases that may be suitable for immunotherapy treatment include, but are not limited to, cancer, inflammatory diseases, and infectious diseases. Immunotherapy includes a variety of treatments that work in different ways. For example, some are intended to boost the immune system defenses in a general way; others help train the immune system to recognize and attack cancer cells specifically. Cancer immunotherapies include, but are not limited to, cell-based therapies (also known as cancer vaccines), antibody therapies, and cytokine therapies (e.g., interleukin-2 and interferon-α).

Many cancers are known to be susceptible to the treatment of one or more immunotherapies, including treatment targeting the effector cells in the tumor microenvironment (e.g., immune checkpoint therapy such as PD-1/PD-L1 inhibitors and CTLA-4 inhibitors), treatment targeting suppressor cells in the tumor microenvironment (e.g., CSF-1R inhibitors (affecting MDSC and TAM) and IDO/TDO inhibitors). Without being limited by a particular theory, a compound provided herein (e.g., a compound of any of Formulae (I"), (I'), (A'), (I), (A), (II), (III), (IV), (V), (VI), (VII), (IX), (X), (XI), (XII), (XIII), (XIV), (XV), (XVI), and (XVII), e.g., a selective PI3K-γ inhibitor, e.g., Compound 4) may affect MDSC, TAM, and other components in the tumor microenvironment. The role of TAM in tumor microenvironment is described, e.g., in Lewis and Pollard, Cancer Res. 2006; 66: (2). Jan. 15, 2006.

In one embodiment, the number of one or more pro-tumor immune cells in the tumor microenvironment is reduced, or the activity of one or more pro-tumor immune cells in the tumor microenvironment is reduced or inhibited, after administration of the compound. In some embodiments, the pro-tumor immune cell is a T-cell, an M2 macrophage, a stromal cell, a dendritic cell, an endothelial cell, or a myeloid cell. In one embodiment, the myeloid cell is a tumor associated suppressive myeloid cell. In one embodiment, the tumor associated suppressive myeloid cell is identified by (i) CD45+, CD11b+, Ly6C+ and Ly6G+, (ii) CD45+, CD11b+, Ly6C− and Ly6G−, (iii) CD45+, CD11b+, Ly6C− and Ly6G+, or (iv) CD45+, CD11b+, Ly6C+ and Ly6G−. In one embodiment, the tumor associated suppressive myeloid cell is a tumor associated macrophage (TAM), a myeloid derived suppressor cell (MDSC), a monocytic immature myeloid cell (iMc), or a granulocytic iMc/neutrophil. In one embodiment, the TAM is identified by CD45+, CD11b+, Ly6C−, and Ly6G−. In one embodiment, the myeloid derived suppressor cell (MDSC) is identified by CD45+, CD11b+, Ly6C− and Ly6G+. In one embodiment, the monocytic immature myeloid cell (iMc) is identified by CD45+, CD11b+, Ly6C+ and Ly6G−. In one embodiment, the granulocytic iMc/neutrophil is identified by CD45+, CD11b+, Ly6C+ and Ly6G+. See e.g., Coussens L M. et al., Cancer Discov. 2011 June; 1(1):54-67.

In one embodiment, the activation of M2 macrophage in the tumor microenvironment is reduced or inhibited after administration of the compound. In one embodiment, the p-AKT level in the M2 macrophage is reduced after administration of the compound. In one embodiment, the number of M2 macrophage cells in the tumor microenvironment is reduced after administration of the compound. In one embodiment, the migration of M2 macrophage cells into the tumor microenvironment is reduced or inhibited after administration of the compound. In one embodiment, the differentiation of myeloid cells into M2 macrophage cells in the tumor microenvironment is reduced or inhibited after administration of the compound. In one embodiment, the differentiation into M2 macrophage cells is measured by Arginase-1 (ARG1) level or VEGF level, and the ARG1 level or VEGF level is reduced by at least 10%, 20%, 30%, 40%, 50%, 60%, 70%, 80%, or 90% compared to a reference value.

In one embodiment, the number of myeloid-derived suppressor cells in the tumor microenvironment is reduced after administration of the compound. In one embodiment, the differentiation of bone marrow cells into myeloid-derived suppressor cells is reduced or inhibited after administration of the compound. In one embodiment, the differentiation into myeloid-derived suppressor cells is measured by Arginase-1 (ARG1) level, VEGF level, or iNOS level, and the ARG1 level, VEGF level, or iNOS level is reduced by at least 10%, 20%, 30%, 40%, 50%, 60%, 70%, 80%, or 90% compared to a reference value.

In one embodiment, the production of proangiogeneic factor is reduced or inhibited after administration of the compound. In one embodiment, the proangiogeneic factor is reduced or inhibited by reduction or inhibition of macrophage or MDSC differentiation. In one embodiment, the proangiogeneic factor is VEGF.

In one embodiment, the effect of the compounds provided herein (e.g., Compound 4) on MDSC (e.g., human MDSC) function is measured by expression of iNOS and arginase and production of ROS and IL-10, measured by the suppression function of the MDSC (e.g., in co-culture assays with CD8+), measured by activation of pAKT in response to a stimulant (e.g., CXCL12, IL-1b, TNF-α, or CSF1), or measured by transwell chemotaxis assays (T cells and MDSC).

In one embodiment, the effect of the compounds provided herein (e.g., Compound 4) on MDSC (e.g., murine MDSC) function and macrophage M2-polarization is measured by isolating myeloid cells from bone marrow, polarizing with IFNg or IL-4 and then testing for secretion of TNF-α, IL-12, ROS production in M1 and IL-10, IL-1b, or VEGF, or measured by methods provided herein or elsewhere.

In one embodiment, the effect of the compounds provided herein (e.g., Compound 4) on myeloid and CD8+ is measured by in vivo models (e.g., MC38 and 4T1). In one embodiment, the effect is measured by TGI, MDSC and macrophage infiltrate, CD8+, and IFN-gamma production in CD8+.

In one embodiment, the effect of the compounds provided herein (e.g., Compound 4) on myeloid and CD8+ is measured by QT-PCR or intracellular FACS of myeloid infiltrate. In one embodiment, the effect is measured by expression of functional markers (e.g., iNOS, arginase, or IL-10).

In one embodiment, the number of one or more anti-tumor immune cells in the tumor microenvironment is increased, or the activity of one or more anti-tumor immune cells in the tumor microenvironment is increased, after administration of the compound.

In one embodiment, the cancer susceptible to the treatment of one or more immunotherapies is a hematological cancer. In one embodiment, the hematological cancer is chronic lymphocytic leukemia (CLL). In one embodiment, the tumor microenvironment is a CLL proliferation center. In one embodiment, the hematological cancer is lymphoma.

In one embodiment, the cancer susceptible to the treatment of one or more immunotherapies is a solid tumor. In one embodiment, the solid tumor is lung cancer, breast cancer, colon cancer, or glioblastoma. In one embodiment, the cancer is selected from one or more of a cancer of the pulmonary system, a brain cancer, a cancer of the gastrointestinal tract, a skin cancer, a genitourinary cancer, a pancreatic cancer, a lung cancer, a medulloblastoma, a basal cell carcinoma, a glioma, a breast cancer, a prostate cancer, a testicular cancer, an esophageal cancer, a hepatocellular cancer, a gastric cancer, a gastrointestinal stromal tumor (GIST), a colon cancer, a colorectal cancer, an ovarian cancer, a melanoma, a neuroectodermal tumor, head and neck cancer, a sarcoma, a soft-tissue sarcoma, fibrosarcoma, myxosarcoma, liposarcoma, a chondrosarcoma, an osteogenic sarcoma, a chordoma, an angiosarcoma, an endotheliosarcoma, a lymphangiosarcoma, a lymphangioendotheliosarcoma, a synovioma, a mesothelioma, a leiomyosarcoma, a cervical cancer, a uterine cancer, an endometrial cancer, a carcinoma, a bladder carcinoma, an epithelial carcinoma, a squamous cell carcinoma, an adenocarcinoma, a bronchogenic carcinoma, a renal cell carcinoma, a hepatoma, a bile duct carcinoma, a neuroendocrine cancer, a carcinoid tumor, diffuse type giant cell tumor, andglioblastoma. In one embodiment, the solid tumor is melanoma, bladder cancer, head and neck cancer, lung cancer (e.g., non-small cell lung cancer), renal cell carcinoma, ovarian cancer, breast cancer (e.g., triple-negative breast cancer), colon cancer, or glioblastoma.

In one embodiment, the solid tumor is melanoma. In one embodiment, the solid tumor is lung cancer. In one embodiment, the solid tumor is non-small cell lung cancer. In one embodiment, the solid tumor is renal cell carcinoma. Melanoma, lung cancer (e.g., non-small cell lung cancer), and renal cell carcinoma are known to be sensitive to immunotherapies. Data linking a poor prognosis to high TAM cell counts have been reported in breast, prostate, endometrial, bladder, kidney, esophageal, superficial, carcinoma, melanoma, and follicular lymphoma cancers. See e.g., Lewis and Pollard, Cancer Res. 2006; 66: (2). Jan. 15, 2006. One anti-PD-1 antibody drug, nivolumab, (Opdivo—Bristol Myers Squibb), produced complete or partial responses in non-small-cell lung cancer, melanoma, and renal-cell cancer, in a clinical trial with a total of 296 patients.

In one embodiment, the solid tumor is head and neck cancer. Head and neck tumors tend to be highly immunogenic and have strong anti-PD-1/PD-L1 efficacy. In one embodiment, the solid tumor is bladder cancer. Bladder cancer also has strong anti-PD-1/PD-L1 efficacy. A high number of TAM cells has been associated with a poor prognosis and increased tumor angiogenesis in bladder cancer.

In one embodiment, the solid tumor is breast cancer. In one embodiment, the breast cancer is triple-negative breast cancer. A high number of TAM cells has been associated with a poor prognosis of breast cancer. See e.g., Lewis and Pollard, Cancer Res. 2006; 66: (2). Jan. 15, 2006. In one embodiment, the solid tumor is ovarian cancer. In one embodiment, the solid tumor is colon cancer. Breast cancer, ovarian cancer, and colon cancer are known to be sensitive to immunotherapies (e.g., bevacizumab and trastuzumab) and can also have anti-PD-1/PD-L1 efficacy.

In one embodiment, the solid tumor is glioblastoma. In one embodiment, the solid tumor is glioblastoma multiforme. It has been reported that PI3K-gamma expression is upregulated in brain microglia. Without being limited by a particular theory, PI3K-γ inhibitors provided herein (e.g., Compound BB) may have P-glycoprotein inhibitory activity and thus can cross the blood brain barrier.

In one embodiment, the anti-tumor immune attack by effector T cells is increased, vascularization of the tumor is reduced, extracellular matrix (ECM) breakdown is reduced, or tumor growth is decreased, compared to a reference value, after administration of the compound.

In one embodiment, the tumor volume of the cancer is reduced after administration of the compound. In one embodiment, the tumor volume of the cancer is reduced by at least 10%, 20%, 30%, 50%, 60%, or 60%, compared to a reference value.

In one embodiment, the level of apoptosis of the cancer cells is increased after administration of the compound. In one embodiment, the level of apoptosis of the cancer cells is increased by at least 10%, 20%, 30%, 40%, or 50%, compared to a reference value.

In some embodiments, the subject is naive to immunotherapy treatment. In some embodiments, the subject is naive to radiation therapy treatment. In some embodiments, the subject is naive to chemotherapy treatment.

In some embodiments, the subject has been pre-treated or previously treated with one or more immunotherapy treatments. In one embodiment, the subject is responsive to the pre-treatment or previous treatment with the immunotherapy. In one embodiment, the immunotherapy treatment is a checkpoint treatment such as a PD-1 or PD-L1 inhibitor. In one embodiment, the subject is a smoker. It has been reported that smoker patients may respond better to immunotherapy (e.g., a PD-L1 inhibitor MPDL3280A) than non-smoker patients in a phase I clinical study for patients with melanoma or cancers of the lung, kidney, colon, GI tract, or head and neck cancers.

In one embodiment, the cancer is melanoma, and the subject has been pre-treated or previously treated with one or more immunotherapy treatments. In one embodiment, the subject has been pre-treated or previously treated with two or more immunotherapy treatments.

In one embodiment, the cancer is head and neck cancer, lung cancer (e.g., non-small cell lung cancer), renal cell carcinoma, or bladder cancer, and the subject has been pre-treated or previously treated with one immunotherapy treatment.

In one embodiment, the cancer is breast cancer (e.g., triple-negative breast cancer), ovarian cancer, glioblastoma, or colon cancer, and the subject is naive to immunotherapy treatment.

In one embodiment, provided herein is a method of treating, preventing, or managing melanoma in a subject, comprising administering to the subject a therapeutically effective amount of a compound provided herein (e.g., Compound 4), or a pharmaceutically acceptable form thereof, wherein the subject has been pre-treated or previously treated with one or more immunotherapy treatments. In one embodiment, the immunotherapy treatment is ipilimumab (Yervoy), interleukin-2, vemurafenib, dabrafenib, or trametinib.

In one embodiment, provided herein is a method of treating, preventing, or managing lung cancer (e.g., non-small cell lung cancer) in a subject, comprising administering to the subject a therapeutically effective amount of a compound provided herein (e.g., Compound 4), or a pharmaceutically acceptable form thereof, wherein the subject has been pre-treated or previously treated with one or more immunotherapy treatments. In one embodiment, the immunotherapy treatment is bevacizumab, erlotinib, gefitinib, afatinib, or denosumab.

In one embodiment, provided herein is a method of treating, preventing, or managing renal cell carcinoma in a subject, comprising administering to the subject a therapeutically effective amount of a compound provided herein (e.g., Compound 4), or a pharmaceutically acceptable form thereof, wherein the subject has been pre-treated or previously treated with one or more immunotherapy treatments. In one embodiment, the immunotherapy treatment is bevacizumab, interleukin-2, axitinib, carfilzomib, everolimus, interferon-α, lenalidomide, pazopanib, sirolimus (rapamycin), sorafenib, sunitinib, temsirolimus, thalidomide, or tivozanib.

In one embodiment, provided herein is a method of treating, preventing, or managing bladder cancer in a subject, comprising administering to the subject a therapeutically effective amount of a compound provided herein (e.g., Compound 4), or a pharmaceutically acceptable form thereof, wherein the subject has been pre-treated or previously treated with one or more immunotherapy treatments. In one embodiment, the immunotherapy treatment is *Bacillus* Calmette-Gudrin (BCG).

In one embodiment, provided herein is a method of treating, preventing, or managing head and neck cancer in a subject, comprising administering to the subject a therapeutically effective amount of a compound provided herein (e.g., Compound 4), or a pharmaceutically acceptable form thereof, wherein the subject has been pre-treated or previously treated with one or more immunotherapy treatments. In one embodiment, the immunotherapy treatment is cetuximab, nimotuzumab, bevacizumab, or erlotinib.

In one embodiment, provided herein is a method of treating, preventing, or managing breast cancer (e.g., triple-negative breast cancer) in a subject, comprising administering to the subject a therapeutically effective amount of a compound provided herein (e.g., Compound 4), or a pharmaceutically acceptable form thereof, wherein the subject has been pre-treated or previously treated with one or more immunotherapy treatments. In one embodiment, the immunotherapy treatment is bevacizumab or trastuzumab.

In one embodiment, provided herein is a method of treating, preventing, or managing ovarian cancer in a subject, comprising administering to the subject a therapeutically effective amount of a compound provided herein (e.g., Compound 4), or a pharmaceutically acceptable form thereof, wherein the subject has been pre-treated or previously treated with one or more immunotherapy treatments. In one embodiment, the immunotherapy treatment is bevacizumab.

In one embodiment, provided herein is a method of treating, preventing, or managing colon cancer in a subject, comprising administering to the subject a therapeutically effective amount of a compound provided herein (e.g., Compound 4), or a pharmaceutically acceptable form thereof, wherein the subject has been pre-treated or previously treated with one or more immunotherapy treatments. In one embodiment, the immunotherapy treatment is bevacizumab, cetuximab, or panitumumab.

In some embodiments, the disclosure relates to a method of treating a cancer of hematopoietic origin. In certain embodiments, the cancer of hematopoietic origin is lymphoma or leukemia. In some embodiments, the cancer of hematopoietic origin is selected from acute lymphocytic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM); peripheral T cell lymphomas (PTCL), adult T cell leukemia/lymphoma (ATLL), cutaneous T-cell lymphoma (CTCL), large granular lymphocytic leukemia (LGL), acute myelocytic leukemia (AML), Hodgkin lymphoma (HL), non-Hodgkin lymphoma (NHL), follicular lymphoma, diffuse large B-cell lymphoma (DLBCL), mantle cell lymphoma (MCL), mastocytosis (e.g., systemic mastocytosis), multiple myeloma (MM), myelodysplastic syndrome (MDS), myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelogenous leukemia (CML), chronic neutrophilic leukemia (CNL), and hypereosinophilic syndrome (HES)).

In some embodiments, the disclosure relates to a method of treating a solid tumor. In some embodiments, the solid tumor is selected from ovarian cancer, colon cancer, fibrosarcoma, pancreatic cancer, lung cancer, breast cancer, lymphoma, melanoma, and glioblastoma. In some embodiment, the solid tumor is a CNS tumor. In one embodiment, the CNS tumor is glioblastoma. The ADME data provide herein indicate that a compound provide herein (e.g., Compound BB) may show good permeability cross blood-brain-barrier and can achieving efficacious concentration in a CNS tumor.

In one embodiment, a PI3K-γ inhibitor such a Compound BB can be an inhibitor of P-gp (P-glycoprotein). P-glycoprotein impedes the entry of various drugs that are used in the treatment, for example, of central nervous system diseases. Without being bound by a particular theory, the P-gp substrate may help maintain normal levels of P-gp activity in a patient being treated with a PI3K-γ inhibitor. In some embodiments, a PI3K-γ inhibitor such a Compound BB may not be effluxed from a tumor and thus can maintain efficacious concentration of the a PI3K-γ inhibitor in a tumor. For example, the concentration can be maintained for about at least 6 hours, at least 10 hours, at least 12 hours, at least 24 hours, or at least 48 hours. In one embodiment, a PI3K-γ inhibitor such a Compound BB can be administered once daily.

In some embodiments, a PI3K-γ inhibitor such a Compound BB is administered to a patient in combination with a second therapeutic that is a P-gp substrate. In another embodiment, a PI3K-γ inhibitor such a Compound BB can inhibit the efflux of the second therapeutic such as a cancer drug that is a P-gp substrate. Therefore, a PI3K-γ inhibitor provided herein such a Compound BB can be efficacious in maintaining the concentration of the co-administered cancer drug in a tumor. For example, the concentration can be maintained for about at least 6 hours, at least 10 hours, at least 12 hours, at least 24 hours, or at least 48 hours. In one embodiment, a PI3K-γ inhibitor such a Compound BB can be administered once daily.

P-glycoprotein is a component of the blood-brain barrier and is present on the surface of the endothelial cells of the barrier. A PI3K-γ inhibitor provided herein such as Compound BB can be a P-glycoprotein inhibitor and thus can cross the blood brain barrier. In some embodiments, a PI3K-γ inhibitor provided herein such as Compound BB can maintain an efficacious concentration in CNS tumor or a brain tumor (e.g., glioblastoma).

As used herein "solid tumor" refers to an abnormal mass of tissue. Solid tumors may be benign or malignant. A solid tumor grows in an anatomical site outside the bloodstream (in contrast, for example, to cancers of hematopoietic origin such as leukemias) and requires the formation of small blood vessels and capillaries to supply nutrients, etc. to the growing tumor mass. Solid tumors are named for the type of cells that form them. Non-limiting examples of solid tumors are sarcomas, carcinomas (epithelial tumors), melanomas, and glioblastomas.

In some embodiments, the disclosure relates to a method of inhibiting growth of a tumor. "Inhibiting growth of a tumor" refers to slowing tumor growth and/or reducing tumor size. "Inhibiting growth of a tumor" thus includes killing tumor cells as well as slowing or arresting tumor cell growth.

Exemplary solid tumors include, but are not limited to, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma;

glioma, e.g., astrocytoma, oligodendroglioma; medulloblastoma), cervical cancer (e.g., cervical adenocarcinoma), colorectal cancer (e.g., colon cancer, rectal cancer, colorectal adenocarcinoma), gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC)), kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), pancreatic cancer (e.g., pancreatic andenocarcinoma, intraductal papillary mucinous neoplasm (IPMN)), prostate cancer (e.g., prostate adenocarcinoma), skin cancer (e.g., squamous cell carcinoma (SCC), keratoacanthoma (A), melanoma, basal cell carcinoma (BCC)) and soft tissue sarcoma (e.g., malignant fibrous histiocytoma (MFH), liposarcoma, malignant peripheral nerve sheath tumor (MPNST), chondrosarcoma, fibrosarcoma, myxosarcoma, osteosarcoma).

In some embodiments, the disclosure relates to a method of treating a cancer of hematopoietic origin comprising administering to a subject a gamma selective compound. In certain embodiments, the cancer of hematopoietic origin is lymphoma or leukemia. In some embodiments, the cancer of hematopoietic origin is selected from acute lymphocytic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM); peripheral T cell lymphomas (PTCL), adult T cell leukemia/lymphoma (ATLL), cutaneous T-cell lymphoma (CTCL), large granular lymphocytic leukemia (LGL), acute myelocytic leukemia (AML), Hodgkin lymphoma (HL), non-Hodgkin lymphoma (NHL), follicular lymphoma, diffuse large B-cell lymphoma (DLBCL), mantle cell lymphoma (MCL), mastocytosis (e.g., systemic mastocytosis), multiple myeloma (MM), myelodysplastic syndrome (MDS), myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelogenous leukemia (CML), chronic neutrophilic leukemia (CNL), and hypereosinophilic syndrome (HES)).

In some embodiments, the disclosure relates to a method of treating a solid tumor comprising administering to a subject a gamma selective compound. In some embodiments, the solid tumor is selected from ovarian cancer, colon cancer, fibrosarcoma, pancreatic cancer, lung cancer, breast cancer, lymphoma, melanoma, and glioblastoma.

In some embodiments, the disclosure relates to a method of treating an inflammatory disease comprising administering to a subject a gamma selective compound.

In some embodiment, the gamma selective compound has a delta/gamma selectivity ratio of >1 to <10, 10 to <50, or 50 to <350 can be combined with a compound that has a gamma/delta selectivity ratio of greater than a factor of about 1, greater than a factor of about 2, greater than a factor of about 3, greater than a factor of about 5, greater than a factor of about 10, greater than a factor of about 50, greater than a factor of about 100, greater than a factor of about 200, greater than a factor of about 400, greater than a factor of about 600, greater than a factor of about 800, greater than a factor of about 1000, greater than a factor of about 1500, greater than a factor of about 2000, greater than a factor of about 5000, greater than a factor of about 10,000, or greater than a factor of about 20,000.

Patients that can be treated with a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, according to the methods as provided herein include, for example, but not limited to, patients that have been diagnosed as having psoriasis; restenosis; atherosclerosis; ischemic stroke, BPH; breast cancer such as a ductal carcinoma, lobular carcinoma, medullary carcinomas, colloid carcinomas, tubular carcinomas, and inflammatory breast cancer; ovarian cancer, including epithelial ovarian tumors such as adenocarcinoma in the ovary and an adenocarcinoma that has migrated from the ovary into the abdominal cavity; uterine cancer; cervical cancer such as adenocarcinoma in the cervix epithelial including squamous cell carcinoma and adenocarcinomas; prostate cancer, such as a prostate cancer selected from the following: an adenocarcinoma or an adenocarcinoma that has migrated to the bone; pancreatic cancer such as epitheliod carcinoma in the pancreatic duct tissue and an adenocarcinoma in a pancreatic duct; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute lymphoblastic leukemia, chronic myelogenous leukemia, hairy cell leukemia, myelodysplasia, myeloproliferative disorders, NK cell leukemia (e.g., blastic plasmacytoid dendritic cell neoplasm), acute myelogenous leukemia (AML), chronic myelogenous leukemia (CML), mastocytosis, chronic lymphocytic leukemia (CLL), multiple myeloma (MM), and myelodysplastic syndrome (MDS); bone cancer; lung cancer such as non-small cell lung cancer (NSCLC), which is divided into squamous cell carcinomas, adenocarcinomas, and large cell undifferentiated carcinomas, and small cell lung cancer; skin cancer such as basal cell carcinoma, melanoma, squamous cell carcinoma and actinic keratosis, which is a skin condition that sometimes develops into squamous cell carcinoma; eye retinoblastoma; cutaneous or intraocular (eye) melanoma; primary liver cancer; kidney cancer; thyroid cancer such as papillary, follicular, medullary and anaplastic; lymphoma such as diffuse large B-cell lymphoma, B-cell immunoblastic lymphoma, NK cell lymphoma (e.g., blastic plasmacytoid dendritic cell neoplasm), and Burkitt lymphoma; Kaposi's Sarcoma; viral-induced cancers including hepatitis B virus (HBV), hepatitis C virus (HCV), and hepatocellular carcinoma; human lymphotropic virus-type 1 (HTLV-1) and adult T-cell leukemia/lymphoma; and human papilloma virus (HPV) and cervical cancer; central nervous system cancers (CNS) such as primary brain tumor, which includes gliomas (astrocytoma, anaplastic astrocytoma, or glioblastoma multiforme), oligodendroglioma, ependymoma, meningioma, lymphoma, schwannoma, and medulloblastoma; peripheral nervous system (PNS) cancers such as acoustic neuromas and malignant peripheral nerve sheath tumor (MPNST) including neurofibromas and schwannomas, malignant fibrocytoma, malignant fibrous histiocytoma, malignant meningioma, malignant mesothelioma, and malignant mixed Müllerian tumor; oral cavity and oropharyngeal cancers such as, hypopharyngeal cancer, laryngeal cancer, nasopharyngeal cancer, and oropharyngeal cancer;

stomach cancers such as lymphomas, gastric stromal tumors, and carcinoid tumors; testicular cancers such as germ cell tumors (GCTs), which include seminomas and nonseminomas, and gonadal stromal tumors, which include Leydig cell tumors and Sertoli cell tumors; thymus cancer such as to thymomas, thymic carcinomas, Hodgkin lymphoma, non-Hodgkin lymphomas, carcinoids or carcinoid tumors; rectal cancer; and colon cancer.

Patients that can be treated with compounds provided herein, or pharmaceutically acceptable salt, ester, prodrug, solvate, hydrate or derivative of said compounds, according to the methods provided herein include, for example, patients that have been diagnosed as having conditions including, but not limited to, acoustic neuroma, adenocarcinoma, adrenal gland cancer, anal cancer, angiosarcoma (e.g., lymphangiosarcoma, lymphangioendotheliosarcoma, hemangiosarcoma), benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer, esophageal cancer (e.g., adenocarcinoma of the esophagus, Barrett's adenocarinoma), Ewing sarcoma, familiar hypereosinophilia, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leukemia (e.g., acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM); peripheral T cell lymphomas (PTCL), adult T cell leukemia/lymphoma (ATLL), cutaneous T-cell lymphoma (CTCL), large granular lymphocytic leukemia (LGL), acute myelocytic leukemia (AML), chronic myelocytic leukemia (CML), chronic lymphocytic leukemia (CLL)), lymphoma (e.g., Hodgkin lymphoma (HL), non-Hodgkin lymphoma (NHL), follicular lymphoma, diffuse large B-cell lymphoma (DLBCL), mantle cell lymphoma (MCL)), leiomyosarcoma (LMS), mastocytosis (e.g., systemic mastocytosis), multiple myeloma (MM), myelodysplastic syndrome (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelogenous leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), Paget's disease of the vulva, Paget's disease of the penis, papillary adenocarcinoma, pancreatic cancer (e.g., pancreatic adenocarcinoma, intraductal papillary mucinous neoplasm (IPMN)), pinealoma, primitive neuroectodermal tumor (PNT), prostate cancer (e.g., prostate adenocarcinoma), rhabdomyosarcoma, retinoblastoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), and Waldenstrm's macroglobulinemia.

Without being limited by a particular theory, in one embodiment, the cancer or disease being treated or prevented, such as a blood disorder or hematologic malignancy, has a high expression level of one or more PI3K isoform(s) (e.g., PI3K-α, PI3K-β, PI3K-δ, or PI3K-γ, or a combination thereof). In one embodiment, the cancer or disease that can be treated or prevented by methods, compositions, or kits provided herein includes a blood disorder or a hematologic malignancy, including, but not limited to, myeloid disorder, lymphoid disorder, leukemia, lymphoma, myelodysplastic syndrome (MDS), myeloproliferative disease (MPD), mast cell disorder, and myeloma (e.g., multiple myeloma), among others. In one embodiment, the blood disorder or the hematologic malignancy includes, but is not limited to, acute lymphoblastic leukemia (ALL), T-cell ALL (T-ALL), B-cell ALL (B-ALL), acute myeloid leukemia (AML), chronic lymphocytic leukemia (CLL), chronic myelogenous leukemia (CML), blast phase CML, small lymphocytic lymphoma (SLL), CLL/SLL, transformed CLL, Richter syndrome Hodgkin lymphoma (HL), non-Hodgkin lymphoma (NHL), B-cell NHL, T-cell NHL, indolent NHL (iNHL), diffuse large B-cell lymphoma (DLBCL), mantle cell lymphoma (MCL), aggressive B-cell NHL, B-cell lymphoma (BCL), Richter's syndrome (RS), T-cell lymphoma (TCL), peripheral T-cell lymphoma (PTCL), cutaneous T-cell lymphoma (CTCL), transformed mycosis fungoides, Sézary syndrome, anaplastic large-cell lymphoma (ALCL), follicular lymphoma (FL), Waldenstrom macroglobulinemia (WM), lymphoplasmacytic lymphoma, Burkitt lymphoma, multiple myeloma (MM), amyloidosis, MPD, essential thrombocytosis (ET), myelofibrosis (MF), polycythemia vera (PV), chronic myelomonocytic leukemia (CMML), myelodysplastic syndrome (MDS), angioimmunoblastic lymphoma, high-risk MDS, and low-risk MDS. In one embodiment, the hematologic malignancy is relapsed. In one embodiment, the hematologic malignancy is refractory. In one embodiment, the cancer or disease is in a pediatric patient (including an infantile patient). In one embodiment, the cancer or disease is in an adult patient. Additional embodiments of a cancer or disease being treated or prevented by methods, compositions, or kits provided herein are described herein elsewhere.

In exemplary embodiments, the cancer or hematologic malignancy is CLL. In exemplary embodiments, the cancer or hematologic malignancy is CLL/SLL. In exemplary embodiments, the cancer or hematologic malignancy is transformed CLL or Richter syndrome. In exemplary embodiments, the cancer or hematologic malignancy is SLL. In one embodiment, without being limited by a particular theory, a compound provided herein (e.g., a PI3K-γ selective compound provided herein) inhibits the migration and/or activation of T-cells and myeloid cells (e.g., macrophages or polarized M2 macrophages), reducing survival and/or proliferative support provided by those cells to malignant CLL cells within the tumor microenvironment (TME). In one embodiment, without being limited by a particular theory, the migration of CD3+ T cells to the CLL-associated chemokine CXCL12 is blocked by a compound provided herein (e.g., a PI3K-γ selective compound provided herein). In another embodiment, without being limited by a particular theory, a compound provided herein (e.g., a PI3K-γ selective compound provided herein) block the myeloid cell mediated re-growth of a cancer following chemotherapy through its effects on inhibiting the post-chemotherapy migration of myeloid cells into a tumor.

In exemplary embodiments, the cancer or hematologic malignancy is iNHL. In exemplary embodiments, the cancer or hematologic malignancy is DLBCL. In exemplary embodiments, the cancer or hematologic malignancy is B-cell NHL (e.g., aggressive B-cell NHL). In exemplary embodiments, the cancer or hematologic malignancy is MCL. In exemplary embodiments, the cancer or hematologic malignancy is RS. In exemplary embodiments, the cancer or hematologic malignancy is AML. In exemplary embodiments, the cancer or hematologic malignancy is MM. In exemplary embodiments, the cancer or hematologic malignancy is ALL. In exemplary embodiments, the cancer or hematologic malignancy is T-ALL. In exemplary embodiments, the cancer or hematologic malignancy is B-ALL. In exemplary embodiments, the cancer or hematologic malignancy is TCL. In exemplary embodiments, the cancer or hematologic malignancy is ALCL. In exemplary embodiments, the cancer or hematologic malignancy is leukemia. In exemplary embodiments, the cancer or hematologic malignancy is lymphoma. In exemplary embodiments, the cancer or hematologic malignancy is T-cell lymphoma. In exemplary embodiments, the cancer or hematologic malignancy is MDS (e.g., low grade MDS). In exemplary embodiments, the cancer or hematologic malignancy is MPD. In exemplary embodiments, the cancer or hematologic malignancy is a mast cell disorder. In exemplary embodiments, the cancer or hematologic malignancy is Hodgkin lymphoma (HL). In exemplary embodiments, the cancer or hematologic malignancy is non-Hodgkin lymphoma. In exemplary embodiments, the cancer or hematologic malignancy is PTCL. In exemplary embodiments, the cancer or hematologic malignancy is CTCL (e.g., mycosis fungoides or Sézary syndrome). In exemplary embodiments, the cancer or hematologic malignancy is WM. In exemplary embodiments, the cancer or hematologic malignancy is CML. In exemplary embodiments, the cancer or hematologic malignancy is FL. In exemplary embodiments, the cancer or hematologic malignancy is transformed mycosis fungoides. In exemplary embodiments, the cancer or hematologic malignancy is Sézary syndrome. In exemplary embodiments, the cancer or hematologic malignancy is acute T-cell leukemia. In exemplary embodiments, the cancer or hematologic malignancy is acute B-cell leukemia. In exemplary embodiments, the cancer or hematologic malignancy is Burkitt lymphoma. In exemplary embodiments, the cancer or hematologic malignancy is myeloproliferative neoplasms. In exemplary embodiments, the cancer or hematologic malignancy is splenic marginal zone. In exemplary embodiments, the cancer or hematologic malignancy is nodal marginal zone. In exemplary embodiments, the cancer or hematologic malignancy is extranodal marginal zone.

In one embodiment, the cancer or hematologic malignancy is a B cell lymphoma. In a specific embodiment, provided herein is a method of treating or managing a B cell lymphoma comprising administering to a patient a therapeutically effective amount of a compound provided herein, or a pharmaceutically acceptable derivative (e.g., salt or solvate) thereof. Also provided herein is a method of treating or lessening one or more of the symptoms associated with a B cell lymphoma comprising administering to a patient a therapeutically effective amount of a compound provided herein, or a pharmaceutically acceptable derivative (e.g., salt or solvate) thereof. In one embodiment, the B cell lymphoma is iNHL. In another embodiment, the B cell lymphoma is follicular lymphoma. In another embodiment, the B cell lymphoma is Waldenstrom macroglobulinemia (lymphoplasmacytic lymphoma). In another embodiment, the B cell lymphoma is marginal zone lymphoma (MZL). In another embodiment, the B cell lymphoma is MCL. In another embodiment, the B cell lymphoma is HL. In another embodiment, the B cell lymphoma is aNHL. In another embodiment, the B cell lymphoma is DLBCL. In another embodiment, the B cell lymphoma is Richters lymphoma.

In one embodiment, the cancer or hematologic malignancy is a T cell lymphoma. In a specific embodiment, provided herein is a method of treating or managing a T cell lymphoma comprising administering to a patient a therapeutically effective amount of a compound provided herein, or a pharmaceutically acceptable derivative (e.g., salt or solvate) thereof. Also provided herein is a method of treating or lessening one or more of the symptoms associated with a T cell lymphoma comprising administering to a patient a therapeutically effective amount of a compound provided herein, or a pharmaceutically acceptable derivative (e.g., salt or solvate) thereof. In one embodiment, the T cell lymphoma is peripheral T cell lymphoma (PTCL). In another embodiment, the T cell lymphoma is cutaneous T cell lymphoma (CTCL).

In one embodiment, the cancer or hematologic malignancy is Sézary syndrome. In a specific embodiment, provided herein is a method of treating or managing Sézary syndrome comprising administering to a patient a therapeutically effective amount of a compound provided herein, or a pharmaceutically acceptable derivative (e.g., salt or solvate) thereof. Also provided herein is a method of treating or lessening one or more of the symptoms associated with Sézary syndrome comprising administering to a patient a therapeutically effective amount of a compound provided herein, or a pharmaceutically acceptable derivative (e.g., salt or solvate) thereof. The symptoms associated with Sézary syndrome include, but are not limited to, epidermotropism by neoplastic CD4+ lymphocytes, Pautrier's microabscesses, erythroderma, lymphadenopathy, atypical T cells in the peripheral blood, and hepatosplenomegalyIn one embodiment, the therapeutically effective amount for treating or managing Sézary syndrome is from about 25 mg to 75 mg, administered twice daily. In other embodiments, the therapeutically effective amount is from about 50 mg to about 75 mg, from about 30 mg to about 65 mg, from about 45 mg to about 60 mg, from about 30 mg to about 50 mg, or from about 55 mg to about 65 mg, each of which is administered twice daily. In one embodiment, the effective amount is about 60 mg, administered twice daily.

In one embodiment, the cancer or hematologic malignancy is relapsed. In one embodiment, the cancer or hematologic malignancy is refractory. In certain embodiments, the cancer being treated or prevented is a specific sub-type of cancer described herein. In certain embodiments, the hematologic malignancy being treated or prevented is a specific sub-type of hematologic malignancy described herein. Certain classifications of type or sub-type of a cancer or hematologic malignancy provided herein is known in the art. Without being limited by a particular theory, it is believed that many of the cancers that become relapsed or refractory develop resistance to the particular prior therapy administered to treat the cancers. Thus, without being limited by a particular theory, a compound provided herein can provide a second line therapy by providing an alternative mechanism to treat cancers different from those mechanisms utilized by certain prior therapies. Accordingly, in one embodiment, provided herein is a method of treating or managing cancer or hematologic malignancy comprising administering to a patient a therapeutically effective amount of a compound provided herein, or a pharmaceutically acceptable derivative (e.g., salt or solvate) thereof, wherein the cancer or hematologic malignancy is relapsed after, or refractory to, a prior therapy.

In exemplary embodiments, the cancer or hematologic malignancy is refractory iNHL. In exemplary embodiments, the cancer or hematologic malignancy is refractory CLL. In exemplary embodiments, the cancer or hematologic malignancy is refractory SLL. In exemplary embodiments, the cancer or hematologic malignancy is refractory to rituximab therapy. In exemplary embodiments, the cancer or hematologic malignancy is refractory to chemotherapy. In exemplary embodiments, the cancer or hematologic malignancy is refractory to radioimmunotherapy (RIT). In exemplary embodiments, the cancer or hematologic malignancy is iNHL, FL, splenic marginal zone, nodal marginal zone, extranodal marginal zone, or SLL, the cancer or hematologic malignancy is refractory to rituximab therapy, chemotherapy, and/or RIT.

In another exemplary embodiment, the cancer or hematologic malignancy is lymphoma, and the cancer is relapsed after, or refractory to, the treatment by a BTK inhibitor such as, but not limited to, ibrutinib or ONO-4059. In another exemplary embodiment, the cancer or hematologic malignancy is CLL, and the cancer is relapsed after, or refractory to, the treatment by a BTK inhibitor such as, but not limited to, ibrutinib and AVL-292.

In certain embodiments, provided herein are methods of treating or preventing a solid tumor in a subject, comprising administering to the subject a therapeutically effective amount of a compound provided herein (e.g., a compound of any of Formulae (I"), (I'), (A'), (I), (A), (II), (III), (IV), (V), (VI), (VII), (IX), (X), (XI), (XII), (XIII), (XIV), (XV), (XVI), and (XVII), e.g., a selective PI3K-γ inhibitor, e.g., Compound 4), or a pharmaceutically acceptable form thereof.

In one embodiment, the solid tumor is selected from one or more of: a cancer of the pulmonary system, a brain cancer, a cancer of the gastrointestinal tract, a skin cancer, a genitourinary cancer, a pancreatic cancer, a lung cancer, a medullobastoma, a basal cell carcinoma, a glioma, a breast cancer, a prostate cancer, a testicular cancer, an esophageal cancer, a hepatocellular cancer, a gastric cancer, a gastrointestinal stromal tumor (GIST), a colon cancer, a colorectal cancer, an ovarian cancer, a melanoma, a neuroectodermal tumor, head and neck cancer, a sarcoma, a soft-tissue sarcoma, fibrosarcoma, myxosarcoma, liposarcoma, a chondrosarcoma, an osteogenic sarcoma, a chordoma, an angiosarcoma, an endotheliosarcoma, a lymphangiosarcoma, a lymphangioendotheliosarcoma, a synovioma, a mesothelioma, a leiomyosarcoma, a cervical cancer, a uterine cancer, an endometrial cancer, a carcinoma, a bladder carcinoma, an epithelial carcinoma, a squamous cell carcinoma, an adenocarcinoma, a bronchogenic carcinoma, a renal cell carcinoma, a hepatoma, a bile duct carcinoma, a neuroendocrine cancer, a carcinoid tumor, diffuse type giant cell tumor, and glioblastoma.

In one embodiment, the compound, or a pharmaceutically acceptable form thereof, is administered at a dose sufficient to cause a decrease in tumor growth of at least 10%, 20%, 30%, 40%, or 50% compared to a reference value, after administration of the compound.

In one embodiment, the method further comprises administering an immunomodulator to the subject. In one embodiment, the immunomodulator is a PDL-1 inhibitor or an anti-PDL-1 antibody.

In one embodiment, the method further comprises administering a PI3K-delta inhibitor to the subject.

In one embodiment, the compound, or a pharmaceutically acceptable form thereof, is administered at a dose such that the level of the compound in the subject is higher than the compound's IC50 of PI3K-gamma inhibition during at least 70%, 80%, 90%, 95%, 97%, 98%, or 99% of a selected time period, e.g., 6 hours, 12 hours, 24 hours, or 48 hours, immediately following the administration. In one embodiment, the compound, or a pharmaceutically acceptable form thereof, is administered at a dose such that the level of the compound in the subject is lower than the compound's IC50 of PI3K-delta inhibition during at least 70%, 80%, 90%, 95%, 97%, 98%, or 99% of a selected time period, e.g., 6 hours, 12 hours, 24 hours, or 48 hours, immediately following the administration. In one embodiment, the level of the compound is measured from the subject's plasma. In one embodiment, the level of the compound is measured from the subject's tissue.

In one embodiment, the subject has been previously treated with cyclophosphamide, docetaxel, paclitaxel, 5-FU, or temozolomide.

In one embodiment, the anti-tumor effect of the compound is maintained for a period of time after the discontinuation of treatment with the compound. In one embodiment, the period of time is at least 1 day, 2 days, 3 days, 4 days, 5 days, or 6 days.

Treatment of an Inflammatory Disorder

In one embodiment, provided herein is a method of treating an inflammation disorder, including autoimmune diseases in a subject. The method comprises administering to said subject a therapeutically effective amount of a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein. Examples of autoimmune diseases include but are not limited to acute disseminated encephalomyelitis (ADEM), Addison's disease, antiphospholipid antibody syndrome (APS), aplastic anemia, autoimmune hepatitis, autoimmune skin disease, coeliac disease, Crohn's disease, Diabetes mellitus (type 1), Goodpasture's syndrome, Graves' disease, Guillain-Barré syndrome (GBS), Hashimoto's disease, lupus erythematosus, multiple sclerosis, myasthenia gravis, opsoclonus myoclonus syndrome (OMS), optic neuritis, Ord's thyroiditis, oemphigus, polyarthritis, primary biliary cirrhosis, psoriasis, rheumatoid arthritis, Reiter's syndrome, Takayasu's arteritis, temporal arteritis (also known as "giant cell arteritis"), warm autoimmune hemolytic anemia, Wegener's granulomatosis, alopecia universalis (e.g., inflammatory alopecia), Chagas disease, chronic fatigue syndrome, dysautonomia, endometriosis, hidradenitis suppurativa, interstitial cystitis, neuromyotonia, sarcoidosis, scleroderma, ulcerative colitis, vitiligo, and vulvodynia. Other disorders include bone-resorption disorders and thrombosis.

Inflammation takes on many forms and includes, but is not limited to, acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative inflammation.

Exemplary inflammatory conditions include, but are not limited to, inflammation associated with acne, anemia (e.g., aplastic anemia, haemolytic autoimmune anaemia), asthma, arteritis (e.g., polyarteritis, temporal arteritis, periarteritis nodosa, Takayasu's arteritis), arthritis (e.g., crystalline arthritis, osteoarthritis, psoriatic arthritis, gout flare, gouty arthritis, reactive arthritis, rheumatoid arthritis and Reiter's arthritis), ankylosing spondylitis, amylosis, amyotrophic lateral sclerosis, autoimmune diseases, allergies or allergic reactions, atherosclerosis, bronchitis, bursitis, chronic prostatitis, conjunctivitis, Chagas disease, chronic obstructive pulmonary disease, cermatomyositis, diverticulitis, diabetes (e.g., type I diabetes mellitus, type 2 diabetes mellitus), a skin condition (e.g., psoriasis, eczema, burns, dermatitis, pruritus (itch)), endometriosis, Guillain-Barre syndrome, infection, ischaemic heart disease, Kawasaki disease, glomerulonephritis, gingivitis, hypersensitivity, headaches (e.g., migraine headaches, tension headaches), ileus (e.g., postoperative ileus and ileus during sepsis), idiopathic thrombocytopenic purpura, interstitial cystitis (painful bladder syndrome), gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), lupus, multiple sclerosis, morphea, myeasthenia gravis, myocardial ischemia, nephrotic syndrome, pemphigus vulgaris, pernicious aneaemia, peptic ulcers, polymyositis, primary biliary cirrhosis, neuroinflammation associated with brain disorders (e.g., Parkinson's disease, Huntington's disease, and Alzheimer's disease), prostatitis, chronic inflammation associated with cranial radiation injury, pelvic inflammatory disease, polymyalgia rheumatic, reperfusion injury, regional enteritis, rheumatic fever, systemic lupus erythematosus, scleroderma, scierodoma, sarcoidosis, spondyloarthopathies, Sjogren's syndrome, thyroiditis, transplantation rejection, tendonitis, trauma or injury (e.g., frostbite, chemical irritants, toxins, scarring, burns, physical injury), vasculitis, vitiligo and Wegener's granulomatosis. In certain embodiments, the inflammatory disorder is selected from arthritis (e.g., rheumatoid arthritis), inflammatory bowel disease, inflammatory bowel syndrome, asthma, psoriasis, endometriosis, interstitial cystitis and prostatisis. In certain embodiments, the inflammatory condition is an acute inflammatory condition (e.g., for example, inflammation resulting from infection). In certain embodiments, the inflammatory condition is a chronic inflammatory condition (e.g., conditions resulting from asthma, arthritis and inflammatory bowel disease). The compounds can also be useful in treating inflammation associated with trauma and non-inflammatory myalgia.

Immune disorders, such as auto-immune disorders, include, but are not limited to, arthritis (including rheumatoid arthritis, spondyloarthopathies, gouty arthritis, degenerative joint diseases such as osteoarthritis, systemic lupus erythematosus, Sjogren's syndrome, ankylosing spondylitis, undifferentiated spondylitis, Behcet's disease, haemolytic autoimmune anaemias, multiple sclerosis, amyotrophic lateral sclerosis, amylosis, acute painful shoulder, psoriatic, and juvenile arthritis), asthma, atherosclerosis, osteoporosis, bronchitis, tendonitis, bursitis, skin condition (e.g., psoriasis, eczema, burns, dermatitis, pruritus (itch)), enuresis, eosinophilic disease, gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), relapsing polychondritis (e.g., atrophic polychondritis and systemic polychondromalacia), and disorders ameliorated by a gastroprokinetic agent (e.g., ileus, postoperative ileus and ileus during sepsis; gastroesophageal reflux disease (GORD, or its synonym GERD); eosinophilic esophagitis, gastroparesis such as diabetic gastroparesis; food intolerances and food allergies and other functional bowel disorders, such as non-ulcerative dyspepsia (NUD) and non-cardiac chest pain (NCCP, including costo-chondritis)). In certain embodiments, a method of treating inflammatory or autoimmune diseases is provided comprising administering to a subject (e.g., a mammal) a therapeutically effective amount of a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, that selectively inhibits PI3K-δ and/or PI3K-γ as compared to all other type I PI3 kinases. Such selective inhibition of PI3K-δ and/or PI3K-γ can be advantageous for treating any of the diseases or conditions described herein. For example, selective inhibition of PI3K-δ and/or PI3K-γ can inhibit inflammatory responses associated with inflammatory diseases, autoimmune disease, or diseases related to an undesirable immune response including, but not limited to asthma, emphysema, allergy, dermatitis, rheumatoid arthritis, psoriasis, lupus erythematosus, anaphylaxsis, or graft versus host disease. Selective inhibition of PI3K-δ and/or PI3K-γ can further provide for a reduction in the inflammatory or undesirable immune response without a concomitant reduction in the ability to reduce a bacterial, viral, and/or fungal infection. Selective inhibition of both PI3K-δ and PI3K-γ can be advantageous for inhibiting the inflammatory response in the subject to a greater degree than that would be provided for by inhibitors that selectively inhibit PI3K-δ or PI3K-γ alone. In one aspect, one or more of the subject methods are effective in reducing antigen specific antibody production in vivo by about 2-fold, 3-fold, 4-fold, 5-fold, 7.5-fold, 10-fold, 25-fold, 50-fold, 100-fold, 250-fold, 500-fold, 750-fold, or about 1000-fold or more. In another aspect, one or more of the subject methods are effective in reducing antigen specific IgG3 and/or IgGM production in vivo by about 2-fold, 3-fold, 4-fold, 5-fold, 7.5-fold, 10-fold, 25-fold, 50-fold, 100-fold, 250-fold, 500-fold, 750-fold, or about 1000-fold or more.

In one aspect, one of more of the subject methods are effective in ameliorating symptoms associated with rheumatoid arthritis including, but not limited to a reduction in the swelling of joints, a reduction in serum anti-collagen levels, and/or a reduction in joint pathology such as bone resorption, cartilage damage, pannus, and/or inflammation. In another aspect, the subject methods are effective in reducing ankle inflammation by at least about 2%, 5%, 10%, 15%, 20%, 25%, 30%, 50%, or 60%, or about 75% to 90%. In another aspect, the subject methods are effective in reducing knee inflammation by at least about 2%, 5%, 10%, 15%, 20%, 25%, 30%, 50%, or 60%, or about 75% to 90% or more. In still another aspect, the subject methods are effective in reducing serum anti-type II collagen levels by at least about 10%, 12%, 15%, 20%, 24%, 25%, 30%, 35%, 50%, 60%, 75%, 80%, 86%, or 87%, or about 90% or more. In another aspect, the subject methods are effective in reducing ankle histopathology scores by about 5%, 10%, 15%, 20%, 25%, 30%, 40%, 50%, 60%, 75%, 80%, or 90%, or more. In still another aspect, the subject methods are effective in reducing knee histopathology scores by about 5%, 10%, 15%, 20%, 25%, 30%, 40%, 50%, 60%, 75%, 80%, or 90%, or more.

In certain embodiments, provided herein are methods of treating or preventing arthritis in a subject, comprising administering to the subject a therapeutically effective amount of a compound provided herein (e.g., a compound of any of Formulae (I"), (I'), (A'), (I), (A), (II), (III), (IV), (V), (VI), (VII), (IX), (X), (XI), (XII), (XIII), (XIV), (XV), (XVI), and (XVII), e.g., a selective PI3K-γ inhibitor, e.g., Compound 4), or a pharmaceutically acceptable form thereof. In one embodiment, the treatment results in reduction of periosteal bone formation in the subject. In one embodiment, the treatment results in at least 10%, 20%, 40%, 47%, 50%, 52%, 60%, 80%, or 82% reduction of periosteal bone formation in the subject, compared to a reference value. In one embodiment, the periosteal bone formation is measured by histopathology score or periosteal bone width. In one embodiment, the treatment results in at least 10%, 20%, 27%, 30%, 36%, 40%, 45%, 50%, or 57% reduction of inflammation, at least 10%, 20%, 28%, 30%, 40%, 44%, 50%, or 60%, 70%, or 71% reduction of pannus, at least 10%, 20%, 28%, 30%, 40%, 45%, 50%, or 59% reduction of cartilage damage, or at least 10%, 20%, 25%, 30%, 40%, 44%, 50%, 60%, or 65% reduction of bone resorption in the subject, compared to a reference value. In one embodiment, wherein the treatment results in reduction of joint swelling or anti-collagen level in the subject.

In some embodiments, provided herein are methods for treating disorders or conditions in which the δ isoform of PI3K is implicated to a greater extent than other PI3K isoforms such as PI3K-α and/or PI3K-β. In some embodiments, provided herein are methods for treating disorders or conditions in which the γ isoform of PI3K is implicated to a greater extent than other PI3K isoforms such as PI3K-α and/or PI3K-β. Selective inhibition of PI3K-δ and/or PI3K-γ can provide advantages over using less selective compounds which inhibit PI3K-α and/or PI3K-β, such as an improved side effects profile or lessened reduction in the ability to reduce a bacterial, viral, and/or fungal infection.

In other embodiments, provided herein are methods of using a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, to treat respiratory diseases including, but not limited to, diseases affecting the lobes of lung, pleural cavity, bronchial tubes, trachea, upper respiratory tract, or the nerves and muscle for breathing. For example, methods are provided to treat obstructive pulmonary disease. Chronic obstructive pulmonary disease (COPD) is an umbrella term for a group of respiratory tract diseases that are characterized by airflow obstruction or limitation. Conditions included in this umbrella term include, but are not limited to: chronic bronchitis, emphysema, and bronchiectasis.

In another embodiment, a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein is used for the treatment of asthma. Also, a compound provided herein, or a pharmaceutically acceptable form thereof, or a pharmaceutical composition described herein, can be used for the treatment of endotoxemia and sepsis. In one embodiment, the compounds or pharmaceutical compositions described herein are used to for the treatment of rheumatoid arthritis (RA). In yet another embodiment, the compounds or pharmaceutical compositions described herein is used for the treatment of contact or atopic dermatitis. Contact dermatitis includes irritant dermatitis, phototoxic dermatitis, allergic dermatitis, photoallergic dermatitis, contact urticaria, systemic contact-type dermatitis and the like. Irritant dermatitis can occur when too much of a substance is used on the skin of when the skin is sensitive to certain substance. Atopic dermatitis, sometimes called eczema, is a kind of dermatitis, an atopic skin disease.

In certain embodiments, provided herein are methods of reducing neutrophil migration or infiltration in a subject suffering from an inflammatory disease, comprising administering to the subject a therapeutically effective amount of a compound provided herein (e.g., a compound of any of Formulae (I"), (I'), (A'), (I), (A), (II), (III), (IV), (V), (VI), (VII), (IX), (X), (XI), (XII), (XIII), (XIV), (XV), (XVI), and (XVII), e.g., a selective PI3K-γ inhibitor, e.g., Compound 4), or a pharmaceutically acceptable form thereof. In one embodiment, the neutrophil migration or infiltration is reduced by at least about 10%, 20%, 40%, 60%, 80%, or 90% compared to a reference value, after administration of the compound. In one embodiment, the inflammatory disease is selected from the group consisting of COPD, arthritis, asthma, psoriasis, scleroderma, myositis, sarcoidosis, dermatomyositis, CREST syndrome, systemic lupus erythematosus, Sjorgren syndrome, encephalomyelitis, and inflammatory bowel disease (IBD). In one embodiment, the inflammatory disease is COPD or arthritis. In one embodiment, the subject is unresponsive or refractory to a PI3K-delta inhibitor treatment.

Treatment of Other Disorders or Conditions

In some embodiments, the disclosure provides a method of treating diseases related to vasculogenesis or angiogenesis in a subject that comprises administering to said subject a therapeutically effective amount of a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein. In some embodiments, said method is for treating a disease selected from tumor angiogenesis, chronic inflammatory disease such as rheumatoid arthritis and chronic inflammatory demyelinating polyneuropathy, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

In addition, the compounds described herein can be used for the treatment of arteriosclerosis, including atherosclerosis. Arteriosclerosis is a general term describing any hardening of medium or large arteries. Atherosclerosis is a hardening of an artery specifically due to an atheromatous plaque.

In some embodiments, provided herein is a method of treating a cardiovascular disease in a subject that comprises administering to said subject a therapeutically effective amount of a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein. Examples of cardiovascular conditions include, but are not limited to, atherosclerosis, restenosis, vascular occlusion and carotid obstructive disease.

In some embodiments, the disclosure relates to a method of treating diabetes in a subject that comprises administering to said subject a therapeutically effective amount of a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein.

In addition, a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, can be used to treat acne. In certain embodiments, the inflammatory condition and/or immune disorder is a skin condition. In some embodiments, the skin condition is pruritus (itch), psoriasis, eczema, burns or dermatitis. In certain embodiments, the skin condition is psoriasis. In certain embodiments, the skin condition is pruritis.

In certain embodiments, the inflammatory disorder and/or the immune disorder is a gastrointestinal disorder. In some embodiments, the gastrointestinal disorder is selected from gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)). In certain embodiments, the gastrointestinal disorder is inflammatory bowel disease (IBD).

Further, a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, can be used for the treatment of glomerulonephritis. Glomerulonephritis is a primary or secondary autoimmune renal disease characterized by inflammation of the glomeruli. It can be asymptomatic, or present with hematuria and/or proteinuria. There are many recognized types, divided in acute, subacute or chronic glomerulonephritis. Causes are infectious (bacterial, viral or parasitic pathogens), autoimmune or paraneoplastic.

In some embodiments, provided herein are compounds, or pharmaceutically acceptable forms (e.g., pharmaceutically acceptable salts, hydrates, solvates, isomers, prodrugs, and isotopically labeled derivatives) thereof, or pharmaceutical compositions as provided herein, for the treatment of multiorgan failure. Also provided herein are compounds, or pharmaceutically acceptable forms (e.g., pharmaceutically acceptable salts, hydrates, solvates, isomers, prodrugs, and isotopically labeled derivatives) thereof, or pharmaceutical compositions as provided herein, for the treatment of liver diseases (including diabetes), gall bladder disease (including gallstones), pancreatitis or kidney disease (including proliferative glomerulonephritis and diabetes-induced renal disease) or pain in a subject.

In some embodiments, provided herein are compounds, or pharmaceutically acceptable forms (e.g., pharmaceutically acceptable salts, hydrates, solvates, isomers, prodrugs, and isotopically labeled derivatives) thereof, or pharmaceutical compositions as provided herein, for the prevention of blastocyte implantation in a subject.

In some embodiments, provided herein are compounds, or pharmaceutically acceptable forms (e.g., pharmaceutically acceptable salts, hydrates, solvates, isomers, prodrugs, and isotopically labeled derivatives) thereof, or pharmaceutical compositions as provided herein, for the treatment of disorders involving platelet aggregation or platelet adhesion, including, but not limited to, Idiopathic thrombocytopenic purpura, Bernard-Soulier syndrome, Glanzmann's thrombasthenia, Scott's syndrome, von Willebrand disease, Hermansky-Pudlak Syndrome, and Gray platelet syndrome.

In some embodiments, provided herein are compounds, or pharmaceutically acceptable forms (e.g., pharmaceutically acceptable salts, hydrates, solvates, isomers, prodrugs, and isotopically labeled derivatives) thereof, or pharmaceutical compositions as provided herein, for the treatment of a disease which is skeletal muscle atrophy, skeletal or muscle hypertrophy. In some embodiments, provided herein are compounds, or pharmaceutically acceptable forms (e.g., pharmaceutically acceptable salts, hydrates, solvates, isomers, prodrugs, and isotopically labeled derivatives) thereof, or pharmaceutical compositions as provided herein, for the treatment of disorders that include, but are not limited to, cancers as discussed herein, transplantation-related disorders (e.g., lowering rejection rates, graft-versus-host disease, etc.), muscular sclerosis (MS), allergic disorders (e.g., arthritis, allergic encephalomyelitis) and other immunosuppressive-related disorders, metabolic disorders (e.g., diabetes), reducing intimal thickening following vascular injury, and misfolded protein disorders (e.g., Alzheimer's Disease, Gaucher's Disease, Parkinson's Disease, Huntington's Disease, cystic fibrosis, macular degeneration, retinitis pigmentosa, and prion disorders) (as mTOR inhibition can alleviate the effects of misfolded protein aggregates). The disorders also include hamartoma syndromes, such as tuberous sclerosis and Cowden Disease (also termed Cowden syndrome and multiple hamartoma syndrome).

Additionally, a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, can be used for the treatment of bursitis, lupus, acute disseminated encephalomyelitis (ADEM), Addison's disease, antiphospholipid antibody syndrome (APS), amyloidosis (including systemic and localized amyloidosis; and primary and secondary amyloidosis), aplastic anemia, autoimmune hepatitis, coeliac disease, crohn's disease, diabetes mellitus (type 1), eosinophilic gastroenterides, goodpasture's syndrome, graves' disease, guillain-barré syndrome (GBS), hashimoto's disease, inflammatory bowel disease, lupus erythematosus (including cutaneous lupus erythematosus and systemic lupus erythematosus), myasthenia gravis, opsoclonus myoclonus syndrome (OMS), optic neuritis, ord's thyroiditis, ostheoarthritis, uveoretinitis, pemphigus, polyarthritis, primary biliary cirrhosis, reiter's syndrome, takayasu's arteritis, temporal arteritis, warm autoimmune hemolytic anemia, wegener's granulomatosis, alopecia universalis, chagas' disease, chronic fatigue syndrome, dysautonomia, endometriosis, hidradenitis suppurativa, interstitial cystitis, neuromyotonia, sarcoidosis, scleroderma, ulcerative colitis, vitiligo, vulvodynia, appendicitis, arteritis, arthritis, blepharitis, bronchiolitis, bronchitis, cervicitis, cholangitis, cholecystitis, chorioamnionitis, colitis, conjunctivitis, cystitis, dacryoadenitis, dermatomyositis, endocarditis, endometritis, enteritis, enterocolitis, epicondylitis, epididymitis, fasciitis, fibrositis, gastritis, gastroenteritis, gingivitis, hepatitis, hidradenitis, ileitis, iritis, laryngitis, mastitis, meningitis, myelitis, myocarditis, myositis, nephritis, omphalitis, oophoritis, orchitis, osteitis, otitis, pancreatitis, parotitis, pericarditis, peritonitis, pharyngitis, pleuritis, phlebitis, pneumonitis, proctitis, prostatitis, pyelonephritis, rhinitis, salpingitis, sinusitis, stomatitis, synovitis, pigmented villonodular synovitis (also known as tenosynovial giant cell tumor), tendonitis, tonsillitis, uveitis (e.g., ocular uveitis), vaginitis, vasculitis, or vulvitis.

Further, the compounds provided herein may be used for the treatment of Perennial allergic rhinitis, Mesenteritis, Peritonitis, Acrodermatitis, Angiodermatitis, Atopic dermatitis, Contact dermatitis, Eczema, Erythema multiforme, Intertrigo, Stevens Johnson syndrome, Toxic epidermal necrolysis, Skin allergy, Severe allergic reaction/anaphylaxis, Allergic granulomatosis, Wegener granulomatosis, Allergic conjunctivitis, Chorioretinitis, Conjunctivitis, Infectious keratoconjunctivitis, Keratoconjunctivitis, Ophthalmia neonatorum, Trachoma, Uveitis, Ocular inflammation, ocular lymphoma, MALT lymphoma, Blepharoconjunctivitis, Mastitis, Gingivitis, Pericoronitis, Pharyngitis, Rhinopharyngitis, Sialadenitis, Musculoskeletal system inflammation, Adult onset Stills disease, Behcets disease, Bursitis, Chondrocalcinosis, Dactylitis, Felty syndrome, Gout, Infectious arthritis, Lyme disease, Inflammatory osteoarthritis, Periarthritis, Reiter syndrome, Ross River virus infection, Acute Respiratory, Distress Syndrome, Acute bronchitis, Acute sinusitis, Allergic rhinitis, Asthma, Severe refractory asthma, Pharyngitis, Pleurisy, Rhinopharyngitis, Seasonal allergic rhinitis, Sinusitis, Status asthmaticus, Tracheobronchitis, Rhinitis, Serositis, Meningitis, Neuromyelitis optica, Poliovirus infection, Alport syndrome, Balanitis, Epididymitis, Epididymo orchitis, Focal segmental, Glomerulosclerosis, Glomerulonephritis, IgA Nephropathy (Berger's Disease), Orchitis, Parametritis, Pelvic inflammatory disease, Prostatitis, Pyelitis, Pyelocystitis, Pyelonephritis, Wegener granulomatosis, Hyperuricemia, Aortitis, Arteritis, Chylopericarditis, Dressler syndrome, Endarteritis, Endocarditis, Extracranial temporal arteritis, HIV associated arteritis, Intracranial temporal arteritis, Kawasaki disease, Lymphangiophlebitis, Mondor disease, Periarteritis, or Pericarditis.

In other aspects, the compounds provided herein are used for the treatment of Autoimmune hepatitis, Jejunitis, Mesenteritis, Mucositis, Non alcoholic steatohepatitis, Non viral hepatitis, Autoimmune pancreatitis, Perihepatitis, Peritonitis, Pouchitis, Proctitis, Pseudomembranous colitis, Rectosigmoiditis, Salpingoperitonitis, Sigmoiditis, Steatohepatitis, Ulcerative colitis, Churg Strauss syndrome, Ulcerative proctitis, Irritable bowel syndrome, Gastrointestinal inflammation, Acute enterocolitis, Anusitis, Balser necrosis, Cholecystitis, Colitis, Crohns disease, Diverticulitis, Enteritis, Enterocolitis, Enterohepatitis, Eosinophilic esophagitis, Esophagitis, Gastritis, Hemorrhagic enteritis, Hepatitis, Hepatitis virus infection, Hepatocholangitis, Hypertrophic gastritis, Ileitis, Ileocecitis, Sarcoidosis, Inflammatory bowel disease, Ankylosing spondylitis, Rheumatoid arthritis, Juvenile rheumatoid arthritis, Psoriasis, Psoriatic arthritis, Lupus (cutaneous/systemic/nephritis), AIDS, Agammaglobulinemia, AIDS related complex, Brutons disease, Chediak Higashi syndrome, Common variable immunodeficiency, DiGeorge syndrome, Dysgammaglobulinemia, Immunoglobulindeficiency, Job syndrome, Nezelof syndrome, Phagocyte bactericidal disorder, Wiskott Aldrich syndrome, Asplenia, Elephantiasis, Hypersplenism, Kawasaki disease, Lymphadenopathy, Lymphedema, Lymphocele, Nonne Milroy Meige syndrome, Spleen disease, Splenomegaly, Thymoma, Thymus disease, Perivasculitis, Phlebitis, Pleuropericarditis, Polyarteritis nodosa, Vasculitis, Takayasus arteritis, Temporal arteritis, Thromboangiitis, Thromboangiitis obliterans, Thromboendocarditis, Thrombophlebitis, or COPD.

In another aspect, provided herein are methods of disrupting the function of a leukocyte or disrupting a function of an osteoclast. The method includes contacting the leukocyte or the osteoclast with a function disrupting amount of a compound provided herein.

In another aspect, provided herein are methods for the treatment of an ophthalmic disease by administering one or more of compounds provided herein, or pharmaceutically acceptable forms thereof, or pharmaceutical compositions as provided herein, to the eye of a subject.

Methods are further provided for administering the compounds provided herein via eye drop, intraocular injection, intravitreal injection, topically, or through the use of a drug eluting device, microcapsule, implant, or microfluidic device. In some cases, the compounds provided herein are administered with a carrier or excipient that increases the intraocular penetrance of the compound such as an oil and water emulsion with colloid particles having an oily core surrounded by an interfacial film.

In certain embodiments, provided herein are methods of treating, preventing, and/or managing a disease or a disorder using a compound, or a pharmaceutically acceptable form (e.g., pharmaceutically acceptable salts, hydrates, solvates, isomers, prodrugs, and isotopically labeled derivatives) thereof, or pharmaceutical compositions as provided herein, wherein the disease or disorder is: Crohn's disease; cutaneous lupus; multiple sclerosis; rheumatoid arthritis; and systemic lupus erythematosus.

In other embodiments, provided herein are methods of treating, preventing and/or managing a disease or a disorder using a compound, or a pharmaceutically acceptable form (e.g., pharmaceutically acceptable salts, hydrates, solvates, isomers, prodrugs, and isotopically labeled derivatives) thereof, or pharmaceutical compositions as provided herein, wherein the disease or disorder is: ankylosing spondylitis; chronic obstructive pulmonary disease; myasthenia gravis; ocular uveitis, psoriasis; and psoriatic arthritis.

In other embodiments, provided herein are methods of treating, preventing and/or managing a disease or a disorder using a compound, or a pharmaceutically acceptable form (e.g., pharmaceutically acceptable salts, hydrates, solvates, isomers, prodrugs, and isotopically labeled derivatives) thereof, or pharmaceutical compositions as provided herein, wherein the disease or disorder is: adult-onset Still's disease; inflammatory alopecia; amyloidosis; antiphospholipid syndrome; autoimmune hepatitis; autoimmune skin disease; Behcet's disease; chronic inflammatory demyelinating polyneuropathy; eosinophilic gastroenteritis; inflammatory myopathies, pemphigus, polymyalgia rheumatica; relapsing polychondritis; Sjorgen's syndrome; temporal arthritis; ulcerative colitis; vasculis; vitiligo, and Wegner's granulomatosis.

In other embodiments, provided herein are methods of treating, preventing and/or managing a disease or a disorder using a compound, or a pharmaceutically acceptable form (e.g., pharmaceutically acceptable salts, hydrates, solvates, isomers, prodrugs, and isotopically labeled derivatives) thereof, or pharmaceutical compositions as provided herein, wherein the disease or disorder is: gout flare; sacoidosis; and systemic sclerosis.

In certain embodiments, provided herein are methods of treating, preventing and/or managing a disease or a disorder using a compound, or a pharmaceutically acceptable form (e.g., pharmaceutically acceptable salts, hydrates, solvates, isomers, prodrugs, and isotopically labeled derivatives) thereof, or pharmaceutical compositions as provided herein, wherein the disease or disorder is: asthma; arthritis (e.g., rheumatoid arthritis and psoriatic arthritis); psoriasis; scleroderma; myositis (e.g., dermatomyositis); lupus (e.g., cutaneous lupus erythematosus ("CLE") or systemic lupus erythematosus ("SLE")); or Sjögren's syndrome.

Efficacy of a compound provided herein in treating, preventing and/or managing the disease or disorder can be tested using various animal models known in the art. For example: efficacy in treating, preventing and/or managing asthma can be assessed using ova induced asthma model described, for example, in Lee et al. (2006) *J Allergy Clin Immunol* 118(2):403-9; efficacy in treating, preventing and/or managing arthritis (e.g., rheumatoid or psoriatic arthritis) can be assessed using autoimmune animal models described, for example, in Williams et al. (2010) *Chem Biol*, 17(2): 123-34, WO 2009/088986, WO2009/088880, and WO 2011/008302; efficacy in treating, preventing and/or managing psoriasis can be assessed using transgenic or knockout mouse model with targeted mutations in epidermis, vasculature or immune cells, mouse model resulting from spontaneous mutations, and immuno-deficient mouse model with xenotransplantation of human skin or immune cells, all of which are described, for example, in Boehncke et al. (2007) *Clinics in Dermatology*, 25: 596-605; efficacy in treating, preventing and/or managing fibrosis or fibrotic condition can be assessed using the unilateral ureteral obstruction model of renal fibrosis (see Chevalier et al., *Kidney International* (2009) 75:1145-1152), the bleomycin induced model of pulmonary fibrosis (see Moore and Hogaboam, *Am. J. Physiol. Lung. Cell. Mol. Physiol.* (2008) 294:L152-L160), a variety of liver/biliary fibrosis models (see Chuang et al., *Clin Liver Dis* (2008) 12:333-347 and Omenetti, A. et al. (2007) *Laboratory Investigation* 87:499-514 (biliary duct-ligated model)), or a number of myelofibrosis mouse models (see Varicchio, L. et al. (2009) *Expert Rev. Hematol.* 2(3): 315-334); efficacy in treating, preventing and/or managing scleroderma can be assessed using mouse model induced by repeated local injections of bleomycin ("BLM") described, for example, in Yamamoto et al. (1999) *J Invest Dermatol* 112: 456-462; efficacy in treating, preventing and/or managing dermatomyositis can be assessed using myositis mouse model induced by immunization with rabbit myosin described, for example, in Phyanagi et al. (2009) *Arthritis & Rheumatism*, 60(10): 3118-3127; efficacy in treating, preventing and/or managing lupus (e.g., CLE or SLE) can be assessed using various animal models described, for example, in Ghoreishi et al. (2009) *Lupus*, 19: 1029-1035, Ohl et al. (2011) *Journal of Biomedicine and Biotechnology*, Article ID 432595 (14 pages), Xia et al. (2011) *Rheumatology*, 50:2187-2196, Pau et al. (2012) *PLoS ONE*, 7(5): e36761 (15 pages), Mustafa et al. (2011) *Toxicology*, 290: 156-168, Ichikawa et al. (2012) *Arthritis and Rheumatism*, 62(2): 493-503, Ouyang et al. (2012) *J Mol Med*, DOI 10.1007/s00109-012-0866-3 (10 pages), Rankin et al. (2012) *Journal of Immunology*, 188:1656-1667; and efficacy in treating, preventing and/or managing Sjögren's syndrome can be assessed using various mouse models described, for example, in Chiorini et al. (2009) *Journal of Autoimmunity*, 33: 190-196.

In one embodiment, provided herein is a method of treating, preventing and/or managing asthma. As used herein, "asthma" encompasses airway constriction regardless of the cause. Common triggers of asthma include, but are not limited to, exposure to an environmental stimulants (e.g., allergens), cold air, warm air, perfume, moist air, exercise or exertion, and emotional stress. Also provided herein is a method of treating, preventing and/or managing one or more symptoms associated with asthma. Examples of the symptoms include, but are not limited to, severe coughing, airway constriction and mucus production.

In one embodiment, provided herein is a method of treating, preventing and/or managing arthritis. As used herein, "arthritis" encompasses all types and manifestations of arthritis. Examples include, but are not limited to, crystalline arthritis, osteoarthritis, psoriatic arthritis, gouty arthritis, reactive arthritis, rheumatoid arthritis and Reiter's arthritis. In one embodiment, the disease or disorder is rheumatoid arthritis. In another embodiment, the disease or disorder is psoriatic arthritis. Also provided herein is a method of treating, preventing and/or managing one or more symptoms associated with arthritis. Examples of the symptoms include, but are not limited to, joint pain, which progresses into joint deformation, or damages in body organs such as in blood vessels, heart, lungs, skin, and muscles.

In one embodiment, provided herein is a method of treating, preventing and/or managing psoriasis. As used herein, "psoriasis" encompasses all types and manifestations of psoriasis. Examples include, but are not limited to, plaque psoriasis (e.g., chronic plaque psoriasis, moderate plaque psoriasis and severe plaque psoriasis), guttate psoriasis, inverse psoriasis, pustular psoriasis, pemphigus vulgaris, erythrodermic psoriasis, psoriasis associated with inflammatory bowel disease (IBD), and psoriasis associated with rheumatoid arthritis (RA). Also provided herein is a method of treating, preventing and/or managing one or more symptoms associated with psoriasis. Examples of the symptoms include, but are not limited to: red patches of skin covered with silvery scales; small scaling spots; dry, cracked skin that may bleed; itching; burning; soreness; thickened, pitted or ridged nails; and swollen and stiff joints.

In one embodiment, provided herein is a method of treating, preventing and/or managing fibrosis and fibrotic condition. As used herein, "fibrosis" or "fibrotic condition" encompasses all types and manifestations of fibrosis or fibrotic condition. Examples include, but are not limited to, formation or deposition of tissue fibrosis; reducing the size, cellularity (e.g., fibroblast or immune cell numbers), composition; or cellular content, of a fibrotic lesion; reducing the collagen or hydroxyproline content, of a fibrotic lesion; reducing expression or activity of a fibrogenic protein; reducing fibrosis associated with an inflammatory response; decreasing weight loss associated with fibrosis; or increasing survival.

In certain embodiments, the fibrotic condition is primary fibrosis. In one embodiment, the fibrotic condition is idiopathic. In other embodiments, the fibrotic condition is associated with (e.g., is secondary to) a disease (e.g., an infectious disease, an inflammatory disease, an autoimmune disease, a malignant or cancerous disease, and/or a connective disease); a toxin; an insult (e.g., an environmental hazard (e.g., asbestos, coal dust, polycyclic aromatic hydrocarbons), cigarette smoking, a wound); a medical treatment (e.g., surgical incision, chemotherapy or radiation), or a combination thereof.

In some embodiments, the fibrotic condition is associated with an autoimmune disease selected from scleroderma or lupus, e.g., systemic lupus erythematosus. In some embodiments, the fibrotic condition is systemic. In some embodiments, the fibrotic condition is systemic sclerosis (e.g., limited systemic sclerosis, diffuse systemic sclerosis, or systemic sclerosis sine scleroderma), nephrogenic systemic fibrosis, cystic fibrosis, chronic graft vs. host disease, or atherosclerosis.

In certain embodiments, the fibrotic condition is a fibrotic condition of the lung, a fibrotic condition of the liver, a fibrotic condition of the heart or vasculature, a fibrotic condition of the kidney, a fibrotic condition of the skin, a fibrotic condition of the gastrointestinal tract, a fibrotic condition of the bone marrow or a hematopoietic tissue, a fibrotic condition of the nervous system, a fibrotic condition of the eye, or a combination thereof.

In other embodiment, the fibrotic condition affects a tissue chosen from one or more of muscle, tendon, cartilage, skin (e.g., skin epidermis or endodermis), cardiac tissue, vascular tissue (e.g., artery, vein), pancreatic tissue, lung tissue, liver tissue, kidney tissue, uterine tissue, ovarian tissue, neural tissue, testicular tissue, peritoneal tissue, colon, small intestine, biliary tract, gut, bone marrow, hematopoietic tissue, or eye (e.g., retinal) tissue.

In some embodiments, the fibrotic condition is a fibrotic condition of the eye. In some embodiments, the fibrotic condition is glaucoma, macular degeneration (e.g., age-related macular degeneration), macular edema (e.g., diabetic macular edema), retinopathy (e.g., diabetic retinopathy), or dry eye disease.

In certain embodiments, the fibrotic condition is a fibrotic condition of the lung. In certain embodiments, the fibrotic condition of the lung is chosen from one or more of: pulmonary fibrosis, idiopathic pulmonary fibrosis (IPF), usual interstitial pneumonitis (UIP), interstitial lung disease, cryptogenic fibrosing alveolitis (CFA), bronchiectasis, and scleroderma lung disease. In one embodiment, the fibrosis of the lung is secondary to a disease, a toxin, an insult, a medical treatment, or a combination thereof. For example, the fibrosis of the lung can be associated with (e.g., secondary to) one or more of: a disease process such as asbestosis and silicosis; an occupational hazard; an environmental pollutant; cigarette smoking; an autoimmune connective tissue disorders (e.g., rheumatoid arthritis, scleroderma and systemic lupus erythematosus (SLE)); a connective tissue disorder such as sarcoidosis; an infectious disease, e.g., infection, particularly chronic infection; a medical treatment, including but not limited to, radiation therapy, and drug therapy, e.g., chemotherapy (e.g., treatment with as bleomycin, methotrexate, amiodarone, busulfan, and/or nitrofurantoin). In one embodiment, the fibrotic condition of the lung treated with the methods provided herein is associated with (e.g., secondary to) a cancer treatment, e.g., treatment of a cancer (e.g., squamous cell carcinoma, testicular cancer, Hodgkin's disease with bleomycin). In one embodiment, the fibrotic condition of the lung is associated with an autoimmune connective tissue disorder (e.g., scleroderma or lupus, e.g., SLE).

In certain embodiments, the fibrotic condition is a fibrotic condition of the liver. In certain embodiments, the fibrotic condition of the liver is chosen from one or more of: fatty liver disease, steatosis (e.g., nonalcoholic steatohepatitis (NASH), cholestatic liver disease (e.g., primary biliary cirrhosis (PBC)), cirrhosis, alcohol induced liver fibrosis, biliary duct injury, biliary fibrosis, or cholangiopathies. In other embodiments, hepatic or liver fibrosis includes, but is not limited to, hepatic fibrosis associated with alcoholism, viral infection, e.g., hepatitis (e.g., hepatitis C, B or D), autoimmune hepatitis, non-alcoholic fatty liver disease (NAFLD), progressive massive fibrosis, exposure to toxins or irritants (e.g., alcohol, pharmaceutical drugs and environmental toxins).

In certain embodiments, the fibrotic condition is a fibrotic condition of the heart. In certain embodiments, the fibrotic condition of the heart is myocardial fibrosis (e.g., myocardial fibrosis associated with radiation myocarditis, a surgical procedure complication (e.g., myocardial post-operative fibrosis), infectious diseases (e.g., Chagas disease, bacterial, trichinosis or fungal myocarditis)); granulomatous, metabolic storage disorders (e.g., cardiomyopathy, hemochromatosis); developmental disorders (e.g., endocardial fibroelastosis); arteriosclerotic, or exposure to toxins or irritants (e.g., drug induced cardiomyopathy, drug induced cardiotoxicity, alcoholic cardiomyopathy, cobalt poisoning or exposure). In certain embodiments, the myocardial fibrosis is associated with an inflammatory disorder of cardiac tissue (e.g., myocardial sarcoidosis). In some embodiments, the fibrotic condition is a fibrotic condition associated with a myocardial infarction. In some embodiments, the fibrotic condition is a fibrotic condition associated with congestive heart failure.

In certain embodiments, the fibrotic condition is a fibrotic condition of the kidney. In certain embodiments, the fibrotic condition of the kidney is chosen from one or more of: renal fibrosis (e.g., chronic kidney fibrosis), nephropathies associated with injury/fibrosis (e.g., chronic nephropathies associated with diabetes (e.g., diabetic nephropathy)), lupus, scleroderma of the kidney, glomerular nephritis, focal segmental glomerular sclerosis, IgA nephropathyrenal fibrosis associated with human chronic kidney disease (CKD), chronic progressive nephropathy (CPN), tubulointerstitial fibrosis, ureteral obstruction, chronic uremia, chronic interstitial nephritis, radiation nephropathy, glomerulosclerosis, progressive glomerulonephrosis (PGN), endothelial/thrombotic microangiopathy injury, HIV-associated nephropathy, or fibrosis associated with exposure to a toxin, an irritant, or a chemotherapeutic agent. In one embodiment, the fibrotic condition of the kidney is scleroderma of the kidney. In some embodiments, the fibrotic condition of the kidney is transplant nephropathy, diabetic nephropathy, lupus nephritis, or focal segmental glomerulosclerosis (FSGS).

In certain embodiments, the fibrotic condition is a fibrotic condition of the skin. In certain embodiments, the fibrotic condition of the skin is chosen from one or more of: skin fibrosis (e.g., hypertrophic scarring, keloid), scleroderma, nephrogenic systemic fibrosis (e.g., resulting after exposure to gadolinium (which is frequently used as a contrast substance for MRIs) in patients with severe kidney failure), and keloid.

In certain embodiments, the fibrotic condition is a fibrotic condition of the gastrointestinal tract. In certain embodiments, the fibrotic condition is chosen from one or more of: fibrosis associated with scleroderma; radiation induced gut fibrosis; fibrosis associated with a foregut inflammatory disorder such as Barrett's esophagus and chronic gastritis, and/or fibrosis associated with a hindgut inflammatory disorder, such as inflammatory bowel disease (IBD), ulcerative colitis and Crohn's disease. In some embodiments, the fibrotic condition of the gastrointestinal tract is fibrosis associated with scleroderma.

In certain embodiments, the fibrotic condition is a fibrotic condition of the bone marrow or a hematopoietic tissue. In certain embodiments, the fibrotic condition of the bone marrow is an intrinsic feature of a chronic myeloproliferative neoplasm of the bone marrow, such as primary myelofibrosis (also referred to herein as agnogenic myeloid metaplasia or chronic idiopathic myelofibrosis). In other embodiments, the bone marrow fibrosis is associated with (e.g., is secondary to) a malignant condition or a condition caused by a clonal proliferative disease. In other embodiments, the bone marrow fibrosis is associated with a hematologic disorder (e.g., a hematologic disorder chosen from one or more of polycythemia vera, essential thrombocythemia, myelodysplasia, hairy cell leukemia, lymphoma (e.g., Hodgkin or non-Hodgkin lymphoma), multiple myeloma or chronic myelogeneous leukemia (CML)). In yet other embodiments, the bone marrow fibrosis is associated with (e.g., secondary to) a non-hematologic disorder (e.g., a non-hematologic disorder chosen from solid tumor metastasis to bone marrow, an autoimmune disorder (e.g., systemic lupus erythematosus, scleroderma, mixed connective tissue disorder, or polymyositis), an infection (e.g., tuberculosis), or secondary hyperparathyroidism associated with vitamin D deficiency. In some embodiments, the fibrotic condition is idiopathic or drug-induced myelofibrosis. In some embodiments, the fibrotic condition of the bone marrow or hematopoietic tissue is associated with systemic lupus erythematosus or scleroderma.

In one embodiment, provided herein is a method of treating, preventing and/or managing scleroderma. Scleroderma is a group of diseases that involve hardening and tightening of the skin and/or other connective tissues. Scleroderma may be localized (e.g., affecting only the skin) or systemic (e.g., affecting other systems such as, e.g., blood vessels and/or internal organs). Common symptoms of scleroderma include Raynaud's phenomenon, gastroesophageal reflux disease, and skin changes (e.g., swollen fingers and hands, or thickened patches of skin). In some embodiments, the scleroderma is localized, e.g., morphea or linear scleroderma. In some embodiments, the condition is a systemic sclerosis, e.g., limited systemic sclerosis, diffuse systemic sclerosis, or systemic sclerosis sine scleroderma.

Localized scleroderma (localized cutaneous fibrosis) includes morphea and linear scleroderma. Morphea is typically characterized by oval-shaped thickened patches of skin that are white in the middle, with a purple border. Linear scleroderma is more common in children. Symptoms of linear scleroderma may appear mostly on one side of the body. In linear scleroderma, bands or streaks of hardened skin may develop on one or both arms or legs or on the forehead. En coup de sabre (frontal linear scleroderma or morphea en coup de sabre) is a type of localized scleroderma typically characterized by linear lesions of the scalp or face.

Systemic scleroderma (systemic sclerosis) includes, e.g., limited systemic sclerosis (also known as limited cutaneous systemic sclerosis, or CREST syndrome), diffuse systemic sclerosis (also known as diffuse cutaneous systemic sclerosis), and systemic sclerosis sine scleroderma. CREST stands for the following complications that may accompany limited scleroderma: calcinosis (e.g., of the digits), Raynaud's phenomenon, esophageal dysfunction, sclerodactyly, and telangiectasias. Typically, limited scleroderma involves cutaneous manifestations that mainly affect the hands, arms, and face. Limited and diffuse subtypes are distinguished based on the extent of skin involvement, with sparing of the proximal limbs and trunk in limited disease. See, e.g., Denton, C. P. et al. (2006), *Nature Clinical Practice Rheumatology*, 2(3):134-143. The limited subtype also typically involves a long previous history of Raynaud's phenomenon, whereas in the diffuse subtype, onset of Raynaud's phenomenon can be simultaneous with other manifestations or might occur later. Both limited and diffuse subtypes may involve internal organs. Typical visceral manifestations of limited systemic sclerosis include isolated pulmonary hypertension, severe bowel involvement, and pulmonary fibrosis. Typical visceral manifestations of diffuse systemic sclerosis include renal crisis, lung fibrosis, and cardiac disease. Diffuse systemic sclerosis typically progresses rapidly and affects a large area of the skin and one or more internal organs (e.g., kidneys, esophagus, heart, or lungs). Systemic sclerosis sine scleroderma is a rare disorder in which patients develop vascular and fibrotic damage to internal organs in the absence of cutaneous sclerosis.

In one embodiment, provided herein is a method of treating, preventing and/or managing inflammatory myopathies. As used herein, "inflammatory myopathies" encompass all types and manifestations of inflammatory myopathies. Examples include, but are not limited to, muscle weakness (e.g., proximal muscle weakness), skin rash, fatigue after walking or standing, tripping or falling, dysphagia, dysphonia, difficulty breathing, muscle pain, tender muscles, weight loss, low-grade fever, inflamed lungs, light sensitivity, calcium deposits (calcinosis) under the skin or in the muscle, as well as biological concomitants of inflammatory myopathies as disclosed herein or as known in the art. Biological concomitants of inflammatory myopathies (e.g., dermatomyositis) include, e.g., altered (e.g., increased) levels of cytokines (e.g., Type I interferons (e.g., IFN-α and/or IFN-β), interleukins (e.g., IL-6, IL-10, IL-15, IL-17 and IL-18), and TNF-α), TGF-β, B-cell activating factor (BAFF), overexpression of IFN inducible genes (e.g., Type I IFN inducible genes). Other biological concomitants of inflammatory myopathies can include, e.g., an increased erythrocyte sedimentation rate (ESR) and/or elevated level of creatine kinase. Further biological concomitants of inflammatory myopathies can include autoantibodies, e.g., anti-synthetase autoantibodies (e.g., anti-Jo1 antibodies), anti-signal recognition particle antibodies (anti-SRP), anti-Mi-2 antibodies, anti-p155 antibodies, anti-PM/Scl antibodies, and anti-RNP antibodies.

The inflammatory myopathy can be an acute inflammatory myopathy or a chronic inflammatory myopathy. In some embodiments, the inflammatory myopathy is a chronic inflammatory myopathy (e.g., dermatomyositis, polymyositis, or inclusion body myositis). In some embodiments, the inflammatory myopathy is caused by an allergic reaction, another disease (e.g., cancer or a connective tissue disease), exposure to a toxic substance, a medicine, or an infectious agent (e.g., a virus). In some embodiments, the inflammatory myopathy is associated with lupus, rheumatoid arthritis, or systemic sclerosis. In some embodiments, the inflammatory myopathy is idiopathic. In some embodiments, the inflammatory myopathy is selected from polymyositis, dermatomyositis, inclusion body myositis, and immune-mediated necrotizing myopathy. In some embodiments, the inflammatory myopathy is dermatomyositis.

In another embodiment, provided herein is a method of treating, preventing and/or managing a skin condition (e.g., a dermatitis). In some embodiments, the methods provided herein can reduce symptoms associated with a skin condition (e.g., itchiness and/or inflammation). In some such embodiments, the compound provided herein is administered topically (e.g., as a topical cream, eye-drop, nose drop or nasal spray). In some such embodiments, the compound is a PI3K delta inhibitor (e.g., a PI3K inhibitor that demonstrates greater inhibition of PI3K delta than of other PI3K isoforms). In some embodiments, the PI3K delta inhibitor prevents mast cell degranulation.

As used herein, "skin condition" includes any inflammatory condition of the skin (e.g., eczema or dermatitis, e.g., contact dermatitis, atopic dermatitis, dermatitis herpetiformis, seborrheic dermatitis, nummular dermatitis, stasis dermatitis, perioral dermatitis), as well as accompanying symptoms (e.g., skin rash, itchiness (pruritus), swelling (edema), hay fever, anaphalaxis). Frequently, such skin conditions are caused by an allergen. As used herein, a "skin condition" also includes, e.g., skin rashes (e.g., allergic rashes, e.g., rashes resulting from exposure to allergens such as poison ivy, poison oak, or poison sumac, or rashes caused by other diseases or conditions), insect bites, minor burns, sunburn, minor cuts, and scrapes. In some embodiments, the symptom associated with inflammatory myopathy, or the skin condition or symptom associated with the skin condition, is a skin rash or itchiness (pruritus) caused by a skin rash.

The skin condition (e.g., the skin rash) may be spontaneous, or it may be induced, e.g., by exposure to an allergen (e.g., poison ivy, poison oak, or poison sumac), drugs, food, insect bite, inhalants, emotional stress, exposure to heat, exposure to cold, or exercise. In some embodiments, the skin condition is a skin rash (e.g., a pruritic rash, e.g., utricaria). In some embodiments, the skin condition is an insect bite. In some embodiments, the skin condition is associated with another disease (e.g., an inflammatory myopathy, e.g., dermatomyositis).

In some embodiments, the subject (e.g., the subject in need of treatment for an inflammatory myopathy and/or a skin condition) exhibits an elevated level or elevated activity of IFN-α, TNF-α, IL-6, IL-8, IL-1, or a combination thereof. In certain embodiments, the subject exhibits an elevated level of IFN-α. In some embodiments, treating (e.g., decreasing or inhibiting) the inflammatory myopathy, or the skin condition, comprises inhibiting (e.g., decreasing a level of, or decreasing a biological activity of) one or more of IFN-α, TNF-α, IL-6, IL-8, or IL-1 in the subject or in a sample derived from the subject. In some embodiments, the method decreases a level of IFN-α, TNF-α, IL-6, IL-8, or IL-1 in the subject or in a sample derived from the subject. In some embodiments, the method decreases a level of IFN-α in the subject or in a sample derived from the subject. In some embodiments, the level of IFN-α, TNF-α, IL-6, IL-8, or IL-1 is the level assessed in a sample of whole blood or PBMCs. In some embodiments, the level of IFN-α, TNF-α, IL-6, IL-8, or IL-1 is the level assessed in a sample obtained by a skin biopsy or a muscle biopsy. In some embodiments, the sample is obtained by a skin biopsy.

In one embodiment, provided herein is a method of treating, preventing and/or managing myositis. As used herein, "myositis" encompasses all types and manifestations of myositis. Examples include, but are not limited to, myositis ossificans, fibromyositis, idiopathic inflammatory myopathies, dermatomyositis, juvenile dermatomyositis, polymyositis, inclusion body myositis and pyomyositis. In one embodiment, the disease or disorder is dermatomyositis. Also provided herein is a method of treating, preventing and/or managing one or more symptoms associated with myositis. Examples of the symptoms include, but are not limited to: muscle weakness; trouble lifting arms; trouble swallowing or breathing; muscle pain; muscle tenderness; fatigue; fever; lung problems; gastrointestinal ulcers; intestinal perforations; calcinosis under the skin; soreness; arthritis; weight loss; and rashes.

In one embodiment, provided herein is a method of treating, preventing and/or managing lupus. As used herein, "lupus" refers to all types and manifestations of lupus. Examples include, but are not limited to, systemic lupus erythematosus; lupus nephritis; cutaneous manifestations (e.g., manifestations seen in cutaneous lupus erythematosus, e.g., a skin lesion or rash); CNS lupus; cardiovascular, pulmonary, hepatic, hematological, gastrointestinal and musculoskeletal manifestations; neonatal lupus erythematosus; childhood systemic lupus erythematosus; drug-induced lupus erythematosus; anti-phospholipid syndrome; and complement deficiency syndromes resulting in lupus manifestations. In one embodiment, the lupus is systemic lupus erythematosus (SLE), cutaneous lupus erythematosus (CLE), drug-induced lupus, or neonatal lupus. In another embodiment, the lupus is a CLE, e.g., acute cutaneous lupus erythematosus (ACLE), subacute cutaneous lupus erythematosus (SCLE), intermittent cutaneous lupus erythematosus (also known as lupus erythematosus tumidus (LET)), or chronic cutaneous lupus. In some embodiments, the intermittent CLE is chronic discloid lupus erythematosus (CDLE) or lupus erythematosus profundus (LEP) (also known as lupus erythematosus panniculitis). Types, symptoms, and pathogenesis of CLE are described, for example, in Wenzel et al. (2010), *Lupus*, 19, 1020-1028.

In one embodiment, provided herein is a method of treating, preventing and/or managing Sjögren's syndrome. As used herein, "Sjögren's syndrome" refers to all types and manifestations of Sjögren's syndrome. Examples include, but are not limited to, primary and secondary Sjögren's syndrome. Also provided herein is a method of treating, preventing and/or managing one or more symptoms associated with Sjögren's syndrome. Examples of the symptoms include, but are not limited to: dry eyes; dry mouth; joint pain; swelling; stiffness; swollen salivary glands; skin rashes; dry skin; vaginal dryness; persistent dry cough; and prolonged fatigue.

In some embodiments, provided herein is a method of treating a bone disorder in a subject that comprises administering to said subject a therapeutically effective amount of a compound provided herein (e.g., a PI3K-γ selective compound provided herein), or a pharmaceutically acceptable form (e.g., pharmaceutically acceptable salts, hydrates, solvates, isomers, prodrugs, and isotopically labeled derivatives) thereof, or a pharmaceutical composition as provided herein. As used herein, "bone disorder" encompasses all types and manifestations of bone disorders. Exemplary bone disorders include, but are not limited to, bone cancer, bone metastases, osteoporosis, fracture repair, avascular necrosis (osteonecrosis), bone spur (osteophytes), craniosynostosis, Coffin-Lowry syndrome, fibrodysplasia ossificans progressive, fibrous dysplasia, Fong Disease (Nail-patella syndrome), Giant cell tumor of bone, Greenstick Fracture, hypophosphatasia, Klippel-Feil syndrome, metabolic bone disease, osteoarthritis, osteitis deformans (Paget's disease of bone), osteitis fibrosa cystica (osteitis fibrosa or Von Recklinghausen's disease of bone), osteitis pubis, condensing osteitis (osteitis condensas), osteochondritis dissecans, osteochondroma (bone tumor), osteogenesis imperfect, osteomalacia, osteomyelitis, osteopenia, osteopetrosis, porotic hyperostosis, primary hyperparathyroidism, renal osteodystrophy, Salter-Harris fractures, and water on the knee. In one embodiment, the bone disorder is a systemical bone disorder. In another embodiment, the bone disorder is a topical bone disorder. In one embodiment, the bone disorder is associated with excess bone formation. In another embodiment, the bone disorder is associated with excess bone resorption. In one embodiment, without being limited by a particular theory, a compound provided herein inhibits differentiation of osteoclasts from bone marrow macrophages.

In some embodiments, a symptom associated with the disease or disorder provided herein is reduced by at least 10%, at least 20%, at least 30%, at least 40%, at least 50%, at least 60%, at least 70%, at least 80%, at least 90%, or at least 95% relative to a control level. The control level includes any appropriate control as known in the art. For example, the control level can be the pre-treatment level in the sample or subject treated, or it can be the level in a control population (e.g., the level in subjects who do not have the disease or disorder or the level in samples derived from subjects who do not have the disease or disorder). In some embodiments, the decrease is statistically significant, for example, as assessed using an appropriate parametric or non-parametric statistical comparison.

Methods of Treatment, Prevention and/or Management for Pulmonary or Respiratory Disorders Without being limited by a particular theory, it was found that administering a compound provided herein (e.g., Compound 4) by inhalation can accord various therapeutic benefits as described herein in treating, preventing and/or managing pulmonary or respiratory diseases. Accordingly, in certain embodiments, provided herein is a method of treating, preventing, and/or managing a pulmonary or respiratory disease in a subject, comprising administering to a subject in need thereof by inhalation a therapeutically or prophylactically effective amount of a compound provided herein, or an enantiomer, a mixture of enantiomers, or a mixture of two or more diastereomers thereof, or a pharmaceutically acceptable form thereof.

In addition, without being limited by a particular theory, it was found that administering a compound provided herein by inhalation results in a prolonged retainment of the compound in patient's lung. Thus, in some embodiments, provided herein is a method of eliciting prolonged anti-inflammatory effect in lung in a subject suffering from a pulmonary or respiratory disease, comprising administering to the subject by inhalation a therapeutically or prophylactically effective amount of a compound provided herein, or an enantiomer, a mixture of enantiomers, or a mixture of two or more diastereomers thereof, or a pharmaceutically acceptable form thereof, wherein the compound is retained in lung for a prolonged period (e.g., a period longer than what is provided by oral administration).

In some embodiments, the compound is retained in lung for about hour, about 3 hours, about 6 hours, about 12 hours, about 24 hours, about 48 hours, or about 72 hours longer than what is provided by oral administration.

In some embodiments, more than 80%, more than 70%, more than 60%, more than 50%, more than 40%, more than 30%, or more than 20% of the amount of the compound as initially administered to patient remains in lung at 24 hours after administration by inhalation.

In some embodiments, the concentration of the compound in lung following administration by inhalation is about 100, about 200, about 500, about 1000, about 2000, about 3000, about 4000, about 5000, about 6000, about 7000, about 8000, about 9000, or about 10000 times higher than the plasma concentration of the compound at about 5 hours after the administration. In some embodiments, the concentration of the compound in lung following administration by inhalation is about 100, about 200, about 500, about 1000, about 2000, about 3000, about 4000, about 5000, about 6000, about 7000, about 8000, about 9000, or about 10000 times higher than the plasma concentration of the compound at about 12 hours after the administration. In some embodiments, the concentration of the compound in lung following administration by inhalation is about 100, about 200, about 500, about 1000, about 2000, about 3000, about 4000, about 5000, about 6000, about 7000, about 8000, about 9000, or about 10000 times higher than the plasma concentration of the compound at about 24 hours after the administration.

In some embodiments, the compound is administered at a dose of less than 0.01 µg/kg/day, less than 0.02 µg/kg/day, less than 0.05 µg/kg/day, less than 0.1 µg/kg/day, less than 0.2 µg/kg/day, less than 0.5 µg/kg/day, less than 1 µg/kg/day, less than 2 µg/kg/day, less than 5 µg/kg/day, less than 10 µg/kg/day, less than 20 µg/kg/day, less than 50 µg/kg/day, or less than 100 µg/kg/day. In some embodiments, the compound is administered at a dose of about 0.01 µg/kg/day, about 0.02 µg/kg/day, about 0.05 µg/kg/day, about 0.1 µg/kg/day, about 0.2 µg/kg/day, about 0.5 µg/kg/day, about 1 µg/kg/day, about 2 µg/kg/day, about 5 µg/kg/day, about 10 µg/kg/day, about 20 µg/kg/day, about 50 µg/kg/day, or about 100 µg/kg/day. In some embodiments, the compound is administered at a dose of from about 0.01 µg/kg/day to about 100 µg/kg/day, from about 0.01 µg/kg/day to about 50 µg/kg/day, from about 0.01 µg/kg/day to about 20 µg/kg/day, from about 0.01 µg/kg/day to about 10 µg/kg/day, from about 0.01 µg/kg/day to about 5 µg/kg/day, from about 0.01 µg/kg/day to about 1 µg/kg/day, from about 0.05 µg/kg/day to about 1 µg/kg/day, or from about 0.1 µg/kg/day to about 1 µg/kg/day.

In one embodiment, the compound is administered once daily (QD). In another embodiment, the compound is administered twice daily (BID). In another embodiment, the compound is administered three time daily (TID). In another embodiment, the compound is administered four times daily (QID).

In one embodiment, the subject is a mammal. In another embodiment, the subject is a human.

In one embodiment, provided herein is a method of treating, preventing, and/or managing a pulmonary or respiratory disease in a subject, comprising administering to a subject in need thereof by inhalation a therapeutically or prophylactically effective amount of a PI3Kγ inhibitor, or an enantiomer, a mixture of enantiomers, or a mixture of two or more diastereomers thereof, or a pharmaceutically acceptable form thereof. In some embodiments, the PI3Kγ inhibitor has a delta/gamma selectivity ratio of greater than about 1 to <10, greater than about 10 to <50, or greater than about 50 to <350. In some embodiments, the PI3Kγ inhibitor has a delta/gamma selectivity ratio of greater than about 1, greater than about 5, greater than about 10, greater than about 15, greater than about 20, greater than about 25, greater than about 50, greater than about 75, greater than about 100, greater than about 150, greater than about 200, greater than about 250, greater than about 300, greater than about 350, greater than about 500, or greater than about 1000.

In one embodiment, provided herein is a method of treating, preventing, and/or managing a pulmonary or respiratory disease in a subject, comprising administering to a subject in need thereof by inhalation a therapeutically or prophylactically effective amount of Compound 4, or an enantiomer, a mixture of enantiomers, or a mixture of two or more diastereomers thereof, or a pharmaceutically acceptable form thereof. In one embodiment, Compound 4 is a PI3Kγ inhibitor. In one embodiment, the compound, e.g., Compound 4 has a delta/gamma selectivity ratio of greater than about 1 to <10, greater than about 10 to <50, or greater than about 50 to <350. In one embodiment, the compound, e.g., Compound 4 has a delta/gamma selectivity ratio of greater than about 50 to <350. In one embodiment, the compound, e.g., Compound 4 has a delta/gamma selectivity ratio of greater than about 50 to <150. In one embodiment, the compound, e.g., Compound 4 has a delta/gamma selectivity ratio of greater than about 75 to <125. In one embodiment, the compound has a delta/gamma selectivity ratio of greater than about 100. In some embodiments, the compound has a delta/gamma selectivity ratio of greater than about 1, greater than about 5, greater than about 10, greater than about 15, greater than about 20, greater than about 25, greater than about 50, greater than about 75, greater than about 100, greater than about 150, greater than about 200, greater than about 250, greater than about 300, greater than about 350, greater than about 500, or greater than about 1000.

Administration by Inhalation

Many diseases of the respiratory tract are known to respond to treatment by the direct application of therapeutic agents by inhalation. Such administration can result in the better utilization of the medicament in that the drug is deposited directly at the desired site and where its action may be required. Therefore, without being limited by a particular theory, administration by inhalation can significantly reduce the dose required to achieve therapeutic efficacy, which, in turn can result in marked reduction of undesired side effects and cost of medicament. It is typically accepted in the industry that the bioavailability of the drug is optimum when the drug particles delivered to the respiratory tract are between 1 to 5 microns in size.

Various methods and devices can be used to deliver a compound provided herein by inhalation. The inhalable formulation can be administered via the mouth or nose ultimately for pulmonary delivery thereof. For example, dry powder inhalers (DPIs), which usually have a means for introducing the drug (active drug plus carrier) into a high velocity air stream, can be used to practice the methods provided herein. The high velocity air stream is used as the primary mechanism for breaking up the cluster of micronized particles or separating the drug particles from the carrier. Inhalation devices useful for dispensing powder forms of medicament such as those described in U.S. Pat. Nos. 3,507,277; 3,518,992; 3,635,219; 3,795,244; and 3,807,400, are encompassed by the current disclosure. In certain embodiments, such devices also include propeller means, which upon inhalation aid in dispensing the powder out of the capsule, so that it is not necessary to rely solely on the inhaled air to suction powder from the capsule. (See, e.g., U.S. Pat. Nos. 2,517,482; 3,831,606; 3,948,264; and 5,458, 135, all of which are incorporated herein by reference). In certain embodiments, utilization of vibration to facilitate suspension of power into an inhaled gas stream and which utilizes synthetic jetting to aerosolize drug powder from a blister pack is also provided herein. (See, e.g., U.S. Pat. Nos. 7,318,434 and 7,334,577, incorporated herein by reference). In some embodiments, controlled aliquots or doses of a medication or pre-packaged drug in a blister pack, which includes a frangible crowned top element which can be conical, conical with a rounded point, rounded, such as those described in U.S. Pat. No. 7,080,644, are also encompassed.

In certain embodiments, a compound provided herein is administered using metered dose inhalers (MDIs). MDIs typically have a pressurized canister filled with a liquid propellant. The drug is either suspended or dissolved in the propellant. The MDIs have a metering valve for metering out a known quantity of the propellant and hence the drug. When the canister is depressed against the MDI housing a known quantity of the propellant is discharged. The propellant evaporates leaving behind a fine aerosol of the drug suitable for inhalation by the patient. In certain embodiments, MDIs that contain a breath actuation mechanism a spacer are also encompassed herein.

In some embodiments, a compound provided herein is administered using nebulizers, such as the jet nebulizers. Nebulizers produce a fine aerosol mist/droplets which carry the drug either as a suspension or dissolved in the aqueous medium. The jet nebulizers use compressed air to atomize the aqueous solution. A drug can be administered to a patient with repetitive non-forced inhalation over a prolonged period of time.

Examples of devices suitable for such pulmonary delivery include, but are not limited to, air-jet, ultrasonic, or vibrating-mesh devices such as Pari LC Star, Aeroeclipse II, Prodose (HaloLite), Acorn II, T Up-draft II, Sidestream, AeroTech II, Mini heart, MisterNeb, Sonix 2000, MABIS-Mist II and other suitable aerosol systems. In some embodiments, the nebulizer is a vibrating-mesh nebulizer that could include an AERONEB PRO, AERONEB SOLO, AERONEB GO, AERONEB LAB, OMRON MICROAIR, PARI EFLOW, RESPIRONICS I-NEB, or other suitable devices.

Pulmonary or Respiratory Diseases

Provided herein is a method of treating, preventing, and/or managing pulmonary or respiratory disease using a compound provided herein. Examples of pulmonary or respiratory disease include, but are not limited to, lung inflammation, chronic obstructive pulmonary disease, asthma, pneumonia, hypersensitivity pneumonitis, pulmonary infiltrate with eosinophilia, environmental lung disease, pneumonia, bronchiectasis, cystic fibrosis, interstitial lung disease, post inflammatory pulmonary fibrosis, primary pulmonary hypertension, pulmonary thromboembolism, disorders of the pleura, disorders of the mediastinum, disorders of the diaphragm, disorders of the larynx, disorders of the trachea, acute lung injury, hypoventilation, hyperventilation, sleep apnea, acute respiratory distress syndrome, mesothelioma, sarcoma, graft rejection, graft versus host disease, lung cancer, allergic rhinitis, allergy, allergic bronchopulmonary aspergillosis, asbestosis, aspergilloma, aspergillosis, bronchiectasis, chronic bronchitis, emphysema, eosinophilic pneumonia, idiopathic pulmonary fibrosis, idiopathic interstitial pneumonia, non-specific interstitial pneumonia(NSIP), bronchiolitis obliterans with organizing pneumonia (BOOP, also called cryptogenic organizing pneumonia or COP), lymphocytic interstitial pneumonia (LIP), acute interstitial pneumonitis invasive pneumococcal disease, pneumococcal pneumonia, influenza, nontuberculous mycobacteria, pleural effusion, a pleural cavity disease, empyema, pleurisy, pneumoconiosis, pneumocytosis, respiratory viral infection, acute bronchitis, aspiration pneumonia, ventilator-associated pneumonia, pneumocystic jiroveci pneumonia, pneumonia, pulmonary actinomycosis, pulmonary alveolar proteinosis, pulmonary anthrax, pulmonary edema, pulmonary embolus, pulmonary embolism, acute chest syndrome, idiopathic pulmonary hemosiderosis, pulmonary hemorrhage, pulmonary hyperplasia, pulmonary inflammation, pulmonary histiocytosis X, eosinophilic granuloma, pulmonary Langerhan's cell histiocytosis, occupational lung disease, pneumopathy due to inhalation of dust, respiratory conditions due to chemical fumes and vapors, lipoid pneumonia, pulmonary hypertension, pulmonary arterial hypertension, pulmonary nocardiosis, pulmonary tuberculosis, pulmonary veno-occlusive disease, pulmonary vascular disease, rheumatoid lung disease, connective tissue disease-associated interstitial lung disease (e.g., systemic sclerosis (SSc or scleroderma)-associated interstitial lung disease, polymyositis-associated interstitial lung disease, dermatomyositis-associated interstitial lung disease, rheumatoid arthritis-associated interstitial lung disease, systemic lupus erythematosus-associated interstitial lung disease, interstitial lung disease associated with Sjögren's syndrome, mixed connective tissue disease-associated interstitial lung disease, and ankylosing spondylitis-associated interstitial lung disease), a restrictive lung disease, a respiratory tract infection (upper and lower), sarcoidosis, Wegener's granulomatosis (also known as granulomatosis with polyangiitis (GPA) or necrotizing granulomatous vasculitis (NGV)), Churg-Strauss Syndrome, microscopic polyangiitis (MPA), small cell lung carcinoma, non-small cell lung carcinoma, lymphangioleiomyomatosis (LAM), radiation-induced lung disease (also known as radiation pneumonitis), pulmonary vasculitis, viral pneumonia, pneumococcal pneumonia, bacterial pneumonia, bronchopneumonia, epithelial tumors, papillomas, adenomas, squamous cell carcinoma, small cell carcinoma, adenocarcinoma, large cell carcinoma, adenosquamous carcinoma, carcinoid tumor, carcinoma of salivary-gland type, soft tissue tumors, localized fibrous tumor, epithelioid hemangioendothelioma, pleuropulmonary blastoma, chondroma, calcifying fibrous pseudotumor of the pleura, congenital peribronchial myofibroblastic tumor, diffuse pulmonary lymphangiomatosis, desmoplastic small round cell tumor, mesothelial tumors, adenomatoid tumor, epithelioid mesothelioma, sarcomatoid mesothelioma, biphasic mesothelioma, hamartoma, sclerosing hemangioma, clear cell tumor, germ cell neoplasms, thymona, melanoma, and secondary tumor. In certain embodiments, provided herein is a method of treating, preventing, and/or managing a lymphoproliferative disease using a compound provided herein. Examples of lymphoproliferative disease include, but are not limited to, lymphoid interstitial pneumonia, nodular lymphoid hyperplasia, and lymphomatoid granulomatosis.

In certain embodiments, the pulmonary or respiratory disease to be treated, prevented and/or managed using a compound provided herein is an obstructive lung disease or disorder. In some embodiments, the obstructive lung disease is acute respiratory distress syndrome (ARDS), asthma, bronchiectasis, bronchiolectasis, bronchiolitis, bronchitis, chronic obstructive pulmonary disease (COPD), or emphysema.

In certain embodiments, in treating, preventing and/or managing a pulmonary or respiratory disease provided herein, a therapeutically or prophylactically effective amount of a compound provided herein (e.g., Compound 4), or an enantiomer, a mixture of enantiomers, or a mixture of two or more diastereomers thereof, or a pharmaceutically acceptable form thereof, is from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 50 mg per day, from about 0.5 to about 50 mg per day, from about 1 to about 50 mg per day, from about 2 to about 25 mg per day, or from about 5 to about 10 mg per day.

In certain embodiments, the therapeutically or prophylactically effective amount is about 0.1, about 0.2, about 0.5, about 1, about 2, about 5, about 10, about 15, about 20, about 25, about 30, about 40, about 45, about 50, about 60, about 70, about 80, about 90, about 100, or about 150 mg per day.

In one embodiment, the recommended daily dose range of a compound provided herein (e.g., Compound 4), or an enantiomer, a mixture of enantiomers, or a mixture of two or more diastereomers thereof, or a pharmaceutically acceptable form thereof, for the conditions described herein lie within the range of from about 0.5 mg to about 50 mg per day, in a single once-a-day dose or in divided doses throughout a day. In some embodiments, the dosage ranges from about 1 mg to about 50 mg per day. In some embodiments, the dosage ranges from about 0.5 to about 5 mg per day. Specific doses per day include 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 mg per day.

In one embodiment, a compound provided herein (e.g., Compound 4), or an enantiomer, a mixture of enantiomers, or a mixture of two or more diastereomers thereof, or a pharmaceutically acceptable form thereof, is administered at a dose of less than 0.1, about 0.1, less than 0.5, about 0.5, between about 0.1 and about 1.0, between about 0.5 and about 1.0, about 1, or about 2 mg per day.

In another embodiment, a compound provided herein (e.g., Compound 4), or an enantiomer, a mixture of enantiomers, or a mixture of two or more diastereomers thereof, or a pharmaceutically acceptable form thereof, is administered at a dose of less than 0.2, about 0.2, less than 1.0, about 1.0, between about 0.2 and about 2.0, between about 1.0 and about 2.0, about 2, or about 4 mg per day.

In one embodiment, the dose is less than 0.1 mg per day.
In another embodiment, the dose is about 0.1 mg per day.
In another embodiment, the dose is less than 0.5 mg per day.
In another embodiment, the dose is about 0.5 mg per day.
In another embodiment, the dose is between about 0.1 and about 1.0 mg per day.
In another embodiment, the dose is between about 0.5 and about 1.0 mg per day.
In another embodiment, the dose is about 1 mg per day.
In another embodiment, the dose is about 2 mg per day.
In another embodiment, the dose is less than 0.2 mg per day.
In another embodiment, the dose is about 0.2 mg per day.
In another embodiment, the dose is less than 1.0 mg per day.
In another embodiment, the dose is about 1.0 mg per day.
In another embodiment, the dose is between about 0.2 and about 2.0 mg per day.
In another embodiment, the dose is between about 1.0 and about 2.0 mg per day.
In another embodiment, the dose is about 2 mg per day.
In another embodiment, the dose is about 4 mg per day.

In a specific embodiment, the recommended starting dosage can be 0.5, 1, 2, 3, 4, 5, 10, 15, 20, 25 or 50 mg per day. In another embodiment, the recommended starting dosage can be 0.5, 1, 2, 3, 4, or 5 mg per day. The dose can be escalated to 15, 20, 25, 30, 35, 40, 45 and 50 mg/day.

In certain embodiments, the therapeutically or prophylactically effective amount is from about 0.001 to about 100 mg/kg/day, from about 0.01 to about 50 mg/kg/day, from about 0.01 to about 25 mg/kg/day, from about 0.01 to about 10 mg/kg/day, from about 0.01 to about 9 mg/kg/day, 0.01 to about 8 mg/kg/day, from about 0.01 to about 7 mg/kg/day, from about 0.01 to about 6 mg/kg/day, from about 0.01 to about 5 mg/kg/day, from about 0.01 to about 4 mg/kg/day, from about 0.01 to about 3 mg/kg/day, from about 0.01 to about 2 mg/kg/day, or from about 0.01 to about 1 mg/kg/day.

In certain embodiments, the therapeutically or prophylactically effective amount is from about 0.01 to about 25 mg/kg/day, from about 0.01 to about 20 mg/kg/day, from about 0.01 to about 15 mg/kg/day, from about 0.01 to about 10 mg/kg/day, from about 0.05 to about 25 mg/kg/day, from about 0.05 to about 20 mg/kg/day, from about 0.05 to about 15 mg/kg/day, or from about 0.05 to about 10 mg/kg/day.

The administered dose can also be expressed in units other than mg/kg/day. For example, doses for parenteral administration can be expressed as mg/m$^2$/day. One of ordinary skill in the art would readily know how to convert doses from mg/kg/day to mg/m$^2$/day to given either the height or weight of a subject or both (see, www.fda.gov/cder/cancer/animalframe.htm). For example, a dose of 1 mg/kg/day for a 65 kg human is approximately equal to 38 mg/m$^2$/day.

A compound provided herein (e.g., Compound 4), or an enantiomer, a mixture of enantiomers, or a mixture of two or more diastereomers thereof, or a pharmaceutically acceptable form thereof, can be administered once daily (QD), or divided into multiple daily doses such as twice daily (BID), three times daily (TID), and four times daily (QID). In addition, the administration can be continuous (i.e., daily for consecutive days or every day), intermittent, e.g., in cycles (i.e., including days, weeks, or months of rest without drug). As used herein, the term "daily" is intended to mean that a therapeutic compound, such as Compound 4, is administered once or more than once each day, for example, for a period of time. The term "continuous" is intended to mean that a therapeutic compound, such as Compound 4, is administered daily for an uninterrupted period of at least 10 days to 52 weeks. The term "intermittent" or "intermittently" as used herein is intended to mean stopping and starting at either regular or irregular intervals. For example, intermittent administration of Compound 4 is administration for one to six days per week, administration in cycles (e.g., daily administration for two to eight consecutive weeks, then a rest period with no administration for up to one week), or administration on alternate days. The term "cycling" as used herein is intended to mean that a therapeutic compound, such as Compound 4, is administered daily or continuously but with a rest period.

In some embodiments, the frequency of administration is in the range of about a daily dose to about a monthly dose. In certain embodiments, administration is once a day, twice a day, three times a day, four times a day, once every other day, twice a week, once every week, once every two weeks, once every three weeks, or once every four weeks. In one embodiment, the compound provided herein is administered once a day. In another embodiment, the compound provided herein is administered twice a day. In yet another embodiment, the compound provided herein is administered three times a day. In still another embodiment, the compound provided herein is administered four times a day.

In one embodiment, a compound provided herein (e.g., Compound 4), or an enantiomer, a mixture of enantiomers, or a mixture of two or more diastereomers thereof, or a pharmaceutically acceptable form thereof, is administered twice per day (BID). In one embodiment, the dose is about 0.1, 0.2, 0.25, 0.5, 1, 2, 2.5, 5, 10, 15, 20, 25, or 50 mg BID.

In one embodiment, a compound provided herein (e.g., Compound 4), or an enantiomer, a mixture of enantiomers, or a mixture of two or more diastereomers thereof, or a pharmaceutically acceptable form thereof, is administered at a dose of less than 0.1, about 0.1, less than 0.5, about 0.5, between about 0.1 and about 1.0, between about 0.5 and about 1.0, about 1, or about 2 mg BID.

In another embodiment, a compound provided herein (e.g., Compound 4), or an enantiomer, a mixture of enantiomers, or a mixture of two or more diastereomers thereof, or a pharmaceutically acceptable form thereof, is administered at a dose of less than 0.2, about 0.2, less than 1.0, about 1.0, between about 0.2 and about 2.0, between about 1.0 and about 2.0, about 2, or about 4 mg BID.

In one embodiment, the dose is less than 0.1 mg BID.
In another embodiment, the dose is about 0.1 mg BID.
In another embodiment, the dose is less than 0.5 mg BID.
In another embodiment, the dose is about 0.5 mg BID.
In another embodiment, the dose is between about 0.1 and about 1.0 mg BID.
In another embodiment, the dose is between about 0.5 and about 1.0 mg BID.
In another embodiment, the dose is about 1 mg BID.
In another embodiment, the dose is about 2 mg BID.
In another embodiment, the dose is less than 0.2 mg BID.
In another embodiment, the dose is about 0.2 mg BID.
In another embodiment, the dose is less than 1.0 mg BID.
In another embodiment, the dose is about 1.0 mg BID.
In another embodiment, the dose is between about 0.2 and about 2.0 mg BID.
In another embodiment, the dose is between about 1.0 and about 2.0 mg BID.
In another embodiment, the dose is about 2 mg BID.
In another embodiment, the dose is about 4 mg BID.

In one embodiment, a compound provided herein (e.g., Compound 4), or an enantiomer, a mixture of enantiomers, or a mixture of two or more diastereomers thereof, or a pharmaceutically acceptable form thereof, is administered once daily (QD). In one embodiment, the dose is about 0.1, 0.2, 0.25, 0.5, 1, 2, 2.5, 5, 10, 15, 20, 25, or 50 mg QD.

In one embodiment, a compound provided herein (e.g., Compound 4), or an enantiomer, a mixture of enantiomers, or a mixture of two or more diastereomers thereof, or a pharmaceutically acceptable form thereof, is administered at a dose of less than 0.1, about 0.1, less than 0.5, about 0.5, between about 0.1 and about 1.0, between about 0.5 and about 1.0, about 1, or about 2 mg QD.

In another embodiment, a compound provided herein (e.g., Compound 4), or an enantiomer, a mixture of enantiomers, or a mixture of two or more diastereomers thereof, or a pharmaceutically acceptable form thereof, is administered at a dose of less than 0.2, about 0.2, less than 1.0, about 1.0, between about 0.2 and about 2.0, between about 1.0 and about 2.0, about 2, or about 4 mg QD.

In one embodiment, the dose is less than 0.1 mg QD.
In another embodiment, the dose is about 0.1 mg QD.
In another embodiment, the dose is less than 0.5 mg QD.
In another embodiment, the dose is about 0.5 mg QD.

In another embodiment, the dose is between about 0.1 and about 1.0 mg QD.

In another embodiment, the dose is between about 0.5 and about 1.0 mg QD.

In another embodiment, the dose is about 1 mg QD.

In another embodiment, the dose is about 2 mg QD.

In another embodiment, the dose is less than 0.2 mg QD.

In another embodiment, the dose is about 0.2 mg QD.

In another embodiment, the dose is less than 1.0 mg QD.

In another embodiment, the dose is about 1.0 mg QD.

In another embodiment, the dose is between about 0.2 and about 2.0 mg QD.

In another embodiment, the dose is between about 1.0 and about 2.0 mg QD.

In another embodiment, the dose is about 2 mg QD.

In another embodiment, the dose is about 4 mg QD.

In one embodiment, the amount of the compound administered is sufficient to provide a lung concentration of the compound at steady state, ranging from about 0.005 to about 100 µM, from about 0.005 to about 10 µM, from about 0.01 to about 10 µM, from about 0.01 to about 5 µM, from about 0.005 to about 1 µM, from about 0.005 to about 0.5 µM, from about 0.005 to about 0.5 µM, from about 0.01 to about 0.2 µM, or from about 0.01 to about 0.1 µM. In one embodiment, the amount of the compound administered is sufficient to provide a lung concentration at steady state, of about 0.005 to about 100 µM. In another embodiment, the amount of the compound administered is sufficient to provide a lung concentration at steady state, of about 0.005 to about 10 µM. In yet another embodiment, the amount of the compound administered is sufficient to provide a lung concentration at steady state, of about 0.01 to about 10 µM. In yet another embodiment, the amount of the compound administered is sufficient to provide a lung concentration at steady state, of about 0.01 to about 5 µM. In yet another embodiment, the amount of the compound administered is sufficient to provide a lung concentration at steady state, of about 0.005 to about 1 µM. In yet another embodiment, the amount of the compound administered is sufficient to provide a lung concentration at steady state, of about 0.005 to about 0.5 µM. In yet another embodiment, the amount of the compound administered is sufficient to provide a lung concentration of the compound at steady state, of about 0.01 to about 0.2 µM. In still another embodiment, the amount of the compound administered is sufficient to provide a lung concentration of the compound at steady state, of about 0.01 to about 0.1 µM. As used herein, the term "lung concentration at steady state" is the concentration reached after a period of administration of a compound. Once steady state is reached, there are minor peaks and troughs on the time dependent curve of the lung concentration of the compound.

In one embodiment, the amount administered is sufficient to provide a maximum lung concentration (peak concentration) of the compound, ranging from about 0.005 to about 100 µM, from about 0.005 to about 10 µM, from about 0.01 to about 10 µM, from about 0.01 to about 5 µM, from about 0.005 to about 1 µM, from about 0.005 to about 0.5 µM, from about 0.01 to about 0.2 µM, or from about 0.01 to about 0.1 µM. In one embodiment, the amount of the compound administered is sufficient to provide a maximum lung concentration of the compound of about 0.005 to about 100 µM. In another embodiment, the amount of the compound administered is sufficient to provide a maximum lung concentration of the compound of about 0.005 to about 10 µM. In yet another embodiment, the amount of the compound administered is sufficient to provide a maximum lung concentration of the compound of about 0.01 to about 10 µM. In yet another embodiment, the amount of the compound administered is sufficient to provide a maximum lung concentration of the compound of about 0.01 to about 5 µM. In yet another embodiment, the amount of the compound administered is sufficient to provide a maximum lung concentration of the compound of about 0.005 to about 1 µM. In yet another embodiment, the amount of the compound administered is sufficient to provide a maximum lung concentration of the compound of about 0.005 to about 0.5 µM. In yet another embodiment, the amount of the compound administered is sufficient to provide a maximum lung concentration of the compound of about 0.01 to about 0.2 µM. In still another embodiment, the amount of the compound administered is sufficient to provide a maximum lung concentration of the compound of about 0.01 to about 0.1 µM.

In one embodiment, the amount administered is sufficient to provide a minimum lung concentration (trough concentration) of the compound, ranging from about 0.005 to about 100 µM, from about 0.005 to about 10 µM, from about 0.01 to about 10 µM, from about 0.01 to about 5 µM, from about 0.005 to about 1 µM, about 0.005 to about 0.5 µM, from about 0.01 to about 0.2 µM, or from about 0.01 to about 0.1 µM, when more than one doses are administered. In one embodiment, the amount of the compound administered is sufficient to provide a minimum lung concentration of the compound of about 0.005 to about 100 µM. In another embodiment, the amount of the compound administered is sufficient to provide a minimum lung concentration of the compound of about 0.005 to about 10 µM. In yet another embodiment, the amount of the compound administered is sufficient to provide a minimum lung concentration of the compound of about 0.01 to about 10 µM. In yet another embodiment, the amount of the compound administered is sufficient to provide a minimum lung concentration of the compound of about 0.01 to about 5 µM. In yet another embodiment, the amount of the compound administered is sufficient to provide a minimum lung concentration of the compound of about 0.005 to about 1 µM. In yet another embodiment, the amount of the compound administered is sufficient to provide a minimum lung concentration of the compound of about 0.005 to about 0.5 µM. In yet another embodiment, the amount of the compound administered is sufficient to provide a minimum lung concentration of the compound of about 0.01 to about 0.2 µM. In still another embodiment, the amount of the compound administered is sufficient to provide a minimum lung concentration of the compound of about 0.01 to about 0.1 µM.

In one embodiment, the amount administered is sufficient to provide an area under the curve (AUC) of the compound, ranging from about 50 to about 10,000 ng*hr/mL, about 100 to about 50,000 ng*hr/mL, from about 100 to 25,000 ng*hr/mL, or from about 10,000 to 25,000 ng*hr/mL. In certain embodiments, a compound provided herein (e.g., Compound 4), or an enantiomer, a mixture of enantiomers, or a mixture of two or more diastereomers thereof, or a pharmaceutically acceptable form thereof, is administered once per day from one day to six months, from one week to three months, from one week to four weeks, from one week to three weeks, or from one week to two weeks.

In certain embodiments, the compound provided herein is administered once per day for one week, two weeks, three weeks, or four weeks. In one embodiment, the compound provided herein is administered once per day for one week. In another embodiment, the compound provided herein is administered once per day for two weeks. In yet another embodiment, the compound provided herein is administered once per day for three weeks. In still another embodiment, the compound provided herein is administered once per day for four weeks.

In certain embodiments, a compound provided herein (e.g., Compound 4), or an enantiomer, a mixture of enantiomers, or a mixture of two or more diastereomers thereof, or a pharmaceutically acceptable form thereof, is administered twice per day from one day to six months, from one week to three months, from one week to four weeks, from one week to three weeks, or from one week to two weeks. In certain embodiments, the compound provided herein is administered twice per day for one week, two weeks, three weeks, or four weeks. In one embodiment, the compound provided herein is administered twice per day for one week. In another embodiment, the compound provided herein is administered twice per day for two weeks. In yet another embodiment, the compound provided herein is administered twice per day for three weeks. In still another embodiment, the compound provided herein is administered twice per day for four weeks.

The compound provided herein (e.g., Compound 4), or an enantiomer, a mixture of enantiomers, or a mixture of two or more diastereomers thereof, or a pharmaceutically acceptable form thereof, can be delivered as a single dose such as, e.g., a single bolus injection, or oral tablets or pills; or over time, such as, e.g., continuous infusion over time or divided bolus doses over time. The compound can be administered repeatedly if necessary, for example, until the patient experiences stable disease or regression, or until the patient experiences disease progression or unacceptable toxicity.

Chronic Obstructive Pulmonary Disease

In one embodiment, said obstructive lung disease or disorder is chronic obstructive pulmonary disease (COPD), e.g., as diagnosed by a forced expiratory air volume in 1 second ($FEV_1$) to forced vital capacity (FVC) ratio of less than 0.7. In another embodiment, administration of a compound provided herein results in a detectable rise in the $FEV_1$/FEC ratio above 0.7 after administration, e.g., a rise of 0.02, 0.03, 0.04, 0.05, 0.06, 0.07, 0.08, 0.09, 0.10, or more or more.

In one embodiment, provided herein is a method of reducing a COPD associated symptom in a subject, comprising administering a compound provided herein (e.g., Compound 4), or an enantiomer, a mixture of enantiomers, or a mixture of two or more diastereomers thereof, or a pharmaceutically acceptable form thereof, by inhalation in an amount sufficient to reduce the COPD associated symptom. In one embodiment, the subject is a mammalian subject, e.g., an animal model or as part of therapeutic protocol. In one embodiment, the compound is used as a single agent or in combination with another agent or therapeutic modality.

In one embodiment, provided herein is a method of treating, preventing, and/or managing COPD in a subject, comprising administering an effective amount of a compound provided herein (e.g., Compound 4), or an enantiomer, a mixture of enantiomers, or a mixture of two or more diastereomers thereof, or a pharmaceutically acceptable form thereof, to a subject in need thereof by inhalation. In one embodiment, the compound is administered as a single agent. In another embodiment, the compound is administered in combination with another agent or therapeutic modality.

As used herein, and unless otherwise specified, "COPD" or a "symptom" associated with COPD encompasses all types of manifestation of COPD as disclosed herein or as known in the art. Examples of COPD include, but are not limited to, emphysema, chronic bronchitis, and bronchiectasis. Examples of symptom of COPD include, but are not limited to, wheezing, coughing, chest tightness, shortness of breath, difficulty in breathing, coughing up mucus/phlegm, and use of accessory muscle. Symptoms are often worse at night or in the early morning, or in response to exercise or cold air. In one embodiment, the symptom of asthma is shortness of breath or difficulty in breathing.

As used herein, and unless otherwise specified, to "decrease," "ameliorate," "reduce," "inhibit," "treat" (or the like) COPD or a symptom associated with COPD includes reducing the severity and/or frequency of one or more symptoms of COPD, as well as preventing COPD and/or one or more symptoms of COPD (e.g., by reducing the severity and/or frequency of flares of symptoms).

In some embodiments, the symptom is reduced by at least about 2%, at least about 5%, at least about 10%, at least about 15%, at least about 20%, at least about 25%, at least about 30%, at least about 40%, at least about 50%, at least about 60%, at least about 70%, at least about 80%, at least about 90%, or at least about 95% relative to a control level. The control level includes any appropriate control as known in the art. For example, the control level can be the pre-treatment level in the sample or subject treated, or it can be the level in a control population (e.g., the level in subjects who do not have COPD or the level in samples derived from subjects who do not have COPD). In some embodiments, the decrease is statistically significant, for example, as assessed using an appropriate parametric or non-parametric statistical comparison.

In certain embodiments, the subject is an animal model of COPD, a human with COPD, or a subject (e.g., a human) at risk for developing COPD. In some embodiments, the subject is a human who has a family history of COPD, who carries a gene associated with COPD, who is positive for a biomarker associated with COPD, or a combination thereof. In some embodiments, the subject has been diagnosed with COPD. In some embodiments, the subject has one or more signs or symptoms associated with COPD. In some embodiments, the subject is at risk for developing COPD (e.g., the subject carries a gene that, individually, or in combination with other genes or environmental factors, is associated with development of COPD).

In one embodiment, the subject has been previously diagnosed of COPD or has episodic symptoms of airflow obstruction (e.g., shortness of breath, wheezing and/or chest tightness) for at least 1 week, 2 weeks, 1 month, 2 months, 3 months, 6 months, 9 months, 12 months before a compound provided herein (e.g., Compound 4), or an enantiomer, a mixture of enantiomers, or a mixture of two or more diastereomers thereof, or a pharmaceutically acceptable form thereof f, is administered. In one embodiment, the subject has been previously diagnosed of COPD or has episodic symptoms of airflow obstruction (e.g., wheezing and/or chest tightness) for at least 6 months before a compound provided herein (e.g., Compound 4), or an enantiomer or a mixture of enantiomers thereof, or a pharmaceutically acceptable salt, solvate, hydrate, co-crystal, clathrate, or polymorph thereof, is administered.

In some embodiments, the subject has been previously treated for COPD. In some embodiments, the subject has been previously treated for COPD but are non-responsive to standard therapies. In one embodiment, the standard therapy is steroid, e.g., corticosteroids. In some embodiments, the subject has developed steroid resistance, e.g., from previous treatment with steroids. In some embodiments, the subject can have inherent steroid resistance that is not a result of previous treatments. Steroid resistance can be overcome by a PI3K inhibitor, e.g., a compound provided herein (e.g., Compound 4). Thus, combination therapy with a compound provided herein and a steroid can be beneficial. In one embodiment, provided herein is a method of treating, preventing, and/or managing COPD in a subject, comprising administering an effective amount of a compound provided herein (e.g., Compound 4), or an enantiomer, a mixture of enantiomers, or a mixture of two or more diastereomers thereof, or a pharmaceutically acceptable form thereof, to a subject in need thereof, wherein the subject has been previously administered a therapy for COPD.

In some embodiments, the subject has not been previously treated for COPD.

In one embodiment, without being limited by any particular theory, administering an effective amount of a compound provided herein (e.g., Compound 4), or an enantiomer, a mixture of enantiomers, or a mixture of two or more diastereomers thereof, or a pharmaceutically acceptable form thereof, does not result in, or results in reduced, one or more common side effects of COPD treatment. The common side effects of COPD treatment include, but are not limited to: allergic reactions such as rashes, hives, swelling of the face, mouth and tongue, and breathing problems; sudden breathing problems; effects on heart such as increased blood pressure, fast and irregular heart beat, and chest pain; effects on nervous system such as tremor and nervousness; reduced adrenal function; changes in blood contents; weakened immune system and higher chance of infections; lower bone mineral density; eye problems such as glaucoma and cataracts; slowed growth in children; pneumonia; thrush in the mouth and throat; throat irritation; hoarseness and voice changes; viral respiratory infections; headache; and muscle and bone pain.

In some embodiments, the side effect is reduced by at least about 2%, at least about 5%, at least about 10%, at least about 15%, at least about 20%, at least about 25%, at least about 30%, at least about 40%, at least about 50%, at least about 60%, at least about 70%, at least about 80%, at least about 90%, or at least about 95% relative to a control level. The control level includes any appropriate control as known in the art. For example, the control level can be the side effect level in the subject treated with other COPD therapies (e.g., albuterol, levalbuterol, ipratropium, tiotropium, terbutaline, theophylline, formoterol, salmeterol, flucatisone, methylprednisone, and prednisone). In some embodiments, the decrease is statistically significant, for example, as assessed using an appropriate parametric or non-parametric statistical comparison.

Asthma

In another specific embodiment, said obstructive lung disease or disorder is asthma. In some embodiments, administration of a compound provided herein results in a detectable improvement in one or more symptoms of asthma, e.g., airway obstruction, as determined by spirometry or a peak flow meter.

In one embodiment, provided herein is a method of reducing an asthma associated symptom in a subject, comprising administering a compound provided herein (e.g., Compound 4), or an enantiomer, a mixture of enantiomers, or a mixture of two or more diastereomers thereof, or a pharmaceutically acceptable form thereof, by inhalation in an amount sufficient to reduce the asthma associated symptom. In one embodiment, the subject is a mammalian subject, e.g., an animal model or as part of therapeutic protocol. In one embodiment, the compound is used as a single agent or in combination with another agent or therapeutic modality.

In one embodiment, provided herein is a method of treating, preventing, and/or managing asthma in a subject, comprising administering an effective amount of a compound provided herein (e.g., Compound 4), or an enantiomer, a mixture of enantiomers, or a mixture of two or more diastereomers thereof, or a pharmaceutically acceptable form thereof to a subject in need thereof by inhalation. In one embodiment, the compound is administered as a single agent. In another embodiment, the compound is administered in combination with another agent or therapeutic modality.

As used herein, and unless otherwise specified, "asthma" or a "symptom" associated with asthma encompasses all types of manifestation of asthma as disclosed herein or as known in the art. Examples of asthma include, but are not limited to, severe and/or refractory asthma, atopic (extrinsic) asthma, non-atopic (intrinsic) asthma, type 1 brittle asthma, type 2 brittle asthma, asthma attack, status asthmaticus, exercise-induced asthma, or occupational asthma. In one embodiment, the asthma is severe or refractory asthma. Examples of symptom of asthma include, but are not limited to, wheezing, coughing, chest tightness, shortness of breath, and use of accessory muscle. Symptoms are often worse at night or in the early morning, or in response to exercise or cold air. Asthma is clinically classified according to the frequency of symptoms, forced expiratory volume in 1 second ($FEV_1$), and peak expiratory flow rate. In one embodiment, the symptom of asthma is wheezing or chest tightness.

As used herein, and unless otherwise specified, "asthma" or a "symptom" associated with asthma also encompasses biological concomitants of asthma as disclosed herein or as known in the art. Examples include, but are not limited to, immune complexes, elevated levels of cytokines (e.g., interferons (e.g., Type I interferons, e.g., IFN-α and/or IFN-β); interleukins (e.g., IL-6, IL-8, IL-1, and IL-18) and TNF-α), elevated levels of anti-dsDNA autoantibodies, overexpression of IFN-α and/or IFN-β inducible genes, elevated levels of IP-10, elevated levels of sCD40L, reduced levels of C3-derived C3b, reduced peripheral iNKT cell frequencies, defective B cell-mediated stimulation of iNKT cells, altered CD1d expression on B cells, reduced numbers of natural regulatory T cells (Treg), altered level of C-reactive protein, overexpression of mRNA for IL-4, overexpression of mRNA for IL-21, and elevated serum anti-collagen level. In some embodiments, the symptom is overexpression of IFN-α, TNF-α, IL-6, IL-8, or IL-1. In one embodiment, the symptom is overexpression of IFN-α. In one embodiment, the symptom is overexpression of IL-6. In some embodiments, the symptom is overexpression of mRNA for IL-4 or overexpression of mRNA for IL-21. In some embodiments, the symptom is elevated serum anti-collagen level.

As used herein, and unless otherwise specified, to "decrease," "ameliorate," "reduce," "inhibit," "treat" (or the like) asthma or a symptom associated with asthma includes reducing the severity and/or frequency of one or more symptoms of asthma, as well as preventing asthma and/or one or more symptoms of asthma (e.g., by reducing the severity and/or frequency of flares of symptoms).

In some embodiments, the symptom is reduced by at least about 2%, at least about 5%, at least about 10%, at least about 15%, at least about 20%, at least about 25%, at least about 30%, at least about 40%, at least about 50%, at least about 60%, at least about 70%, at least about 80%, at least about 90%, or at least about 95% relative to a control level. The control level includes any appropriate control as known in the art. For example, the control level can be the pre-treatment level in the sample or subject treated, or it can be the level in a control population (e.g., the level in subjects who do not have asthma or the level in samples derived from subjects who do not have asthma). In some embodiments, the decrease is statistically significant, for example, as assessed using an appropriate parametric or non-parametric statistical comparison.

In certain embodiments, the subject is an animal model of asthma, a human with asthma, or a subject (e.g., a human) at risk for developing asthma. In some embodiments, the subject is a human who has a family history of asthma, who carries a gene associated with asthma, who is positive for a biomarker associated with asthma, or a combination thereof. In some embodiments, the subject has been diagnosed with asthma. In some embodiments, the subject has one or more signs or symptoms associated with asthma. In some embodiments, the subject is at risk for developing asthma (e.g., the subject carries a gene that, individually, or in combination with other genes or environmental factors, is associated with development of asthma).

In one embodiment, the subject has been previously diagnosed of asthma or has episodic symptoms of airflow obstruction (e.g., wheezing and/or chest tightness) for at least 1 week, 2 weeks, 1 month, 2 months, 3 months, 6 months, 9 months, 12 months before a compound provided herein (e.g., Compound 4), or an enantiomer, a mixture of enantiomers, or a mixture of two or more diastereomers thereof, or a pharmaceutically acceptable form thereof, is administered. In one embodiment, the subject has been previously diagnosed of asthma or has episodic symptoms of airflow obstruction (e.g., wheezing and/or chest tightness) for at least 6 months before a compound provided herein (e.g., Compound 4), or an enantiomer, a mixture of enantiomers, or a mixture of two or more diastereomers thereof, or a pharmaceutically acceptable form thereof, is administered.

In one embodiment, the subject has a forced expiratory volume in one second ($FEV_1$) value of at least 95%, 90%, 85%, 80%, 75%, 70%, 65%, 60%, 55%, or 50% of a control value. In one embodiment, the subject has a forced expiratory volume in one second ($FEV_1$) value of at least 70% of a control value. In one embodiment, the control value may be calculated based on American Thoracic Society (ATS)/European Respiratory Society (ERS) standards.

In one embodiment, the subject has a positive response to a skin prick test to an allergen. In one embodiment, the positive response means that the induration of skin test wheal is larger in diameter (e.g., at least 2 mm larger) than the diameter of the control wheal. The allergen can be any allergen provided herein or known in the art that can be used in the diagnosis or determining status of asthma.

In one embodiment, the subject has an early-phase asthmatic response (EAR) of at least 5%, 10%, 15%, 20%, 25%, 30%, 35%, 40%, 45%, or 50% to an inhaled allergen challenge. In one embodiment, the subject has an early-phase asthmatic response of at least 20% to an inhaled allergen challenge. In one embodiment, the EAR response is a decrease from pre-challenge in $FEV_1$ on 2 consecutive occasions within 0 to <3 hours of last allergen challenge.

In one embodiment, the subject has a late-phase asthmatic response (LAR) of at least 5%, 10%, 15%, 20%, 25%, 30%, 35%, 40%, 45%, or 50% to an inhaled allergen challenge. In one embodiment, the subject has a late-phase asthmatic response of at least 15% to an inhaled allergen challenge. In one embodiment, the LAR response is a decrease from pre-challenge in $FEV_1$ on 2 consecutive occasions within 3 to 10 hours of last allergen challenge.

In one embodiment, the subject has an early-phase asthmatic response of at least 20% and a late-phase asthmatic response of at least 15% to an inhaled allergen challenge. The inhaled allergen can be any inhaled allergen provided herein or known in the art that can be used in the diagnosis or determining status of asthma.

In one embodiment, the subject exhibits an elevated level of C-reactive protein. In one embodiment, the subject exhibits an elevated level of C-reactive protein of at least 1.0 mg/L. In one embodiment, the subject exhibits an elevated level of C-reactive protein of at least 7 mg/L.

In some embodiments, the subject exhibits elevated levels of antinuclear antibodies (e.g., anti-Smith antibodies, anti-double stranded DNA (dsDNA) antibodies, anti-U1 RNP, SS-a (or anti-Ro), SS-b (or anti-La)), antiphospholipid antibodies, anti-ss DNA antibodies, anti-histone antibodies, or anticardiolipin antibodies. In some embodiments, the subject exhibits elevated levels of anti-dsDNA antibodies. In some embodiments, the subject exhibits elevated levels of anti-Sm antibodies.

In some embodiments, the subject exhibits autoantibodies against one or more antigens that are known to be associated with asthma or with asthma subtypes. In some embodiments, the subject exhibits autoantibodies against Sm/anti-RNP or Ro/La autoantigens.

The levels of antibodies associated with asthma can be assessed using any suitable method, e.g., methods known in the art, e.g., indirect immunofluorescence. In some embodiments, the methods disclosed herein reduce or prevent an increase in the levels of one or more of the foregoing antibodies.

In some embodiments, the subject exhibits elevated levels of IFN-α, TNF-α, IL-6, IL-8, or IL-1. In one embodiment, the subject exhibits an elevated level of IFN-α. In another embodiment, the subject exhibits an elevated level of IL-6. In another embodiment, the subject exhibits an elevated level of mRNA for IL-4 or IL-21.

In some embodiments, the subject has a mutation (e.g., an SNP) in a gene associated with asthma. In one embodiment, the gene is selected from STAT4, IRF5, BANK1, ITGAM, PD1, FAM167A-BLK, IRF5-TNP03, KIAA1542, TNFAIP3, XKR6, 1q25.1, PXK, ATG5, ICAl, XKR6, LYN and SCUB2 or a combination thereof. In some embodiments, the subject carries the DR3 and DQ2 variants, or the DR2 and DQ6 variants of HLA class II genes. In some embodiments, the subject has a deficiency in one or more complement proteins, e.g. a deficiency of a complement protein coded by the C4A or C2 genes on chromosome 6, or the C1r and C1s genes on chromosome 12.

In some embodiments, the subject exhibits excessive PI3K activity or abnormal activity (e.g., excessive or reduced activity) of one or more components of the PI3K signaling pathway (e.g., Akt (PKB), mTOR, a Tec kinase (e.g., Btk, Itk, Tec), phospholipase C, PDK1, PKCs, NFκB, Rac GEF (e.g., Vav-1), or Rac).

In some embodiments, the subject is an animal model of asthma provided herein or known in the art. Examples include, but are not limited to, the murine lipopolysaccharide (LPS) induced pulmonary inflammation model, and the murine ovalbumin-induced allergic airway inflammation model.

In some embodiments, the subject has been previously treated for asthma. In some embodiments, the subject has been previously treated for asthma but are non-responsive to standard therapies. Thus, in one embodiment, provided herein is a method of treating, preventing, and/or managing asthma in a subject, comprising administering an effective amount of a compound provided herein (e.g., Compound 4), or an enantiomer, a mixture of enantiomers, or a mixture of two or more diastereomers thereof, or a pharmaceutically acceptable form thereof, to a subject in need thereof, wherein the subject has been previously administered a therapy for asthma.

In some embodiments, the subject has not been previously treated for asthma.

In one embodiment, without being limited by any particular theory, administering an effective amount of a compound provided herein (e.g., Compound 4), or an enantiomer, a mixture of enantiomers, or a mixture of two or more diastereomers thereof, or a pharmaceutically acceptable form thereof, does not result in, or results in reduced, one or more common side effects of asthma treatment. The common side effects of asthma treatment include, but are not limited to, oral candidiasis, thrush, dysphonia (hoarseness), reflex cough, bronchospasm, poor growth, decreased bone density, disseminated varicella infection (chickenpox that spreads to organs), easy bruising, cataracts, glaucoma, adrenal gland suppression, stomach upset, headache, liver test abnormalities, skin rashes, Churg Strauss syndrome, bad taste in month, cough, itching, sore throat, sneezing, stuffy nose, shortness of breath, wheezing, viral illness, upper respiratory tract infections, sinusitis, feeling dizzy or faint, hives, changes in voice, swelling of the tongue, or difficulty in swallowing.

In some embodiments, the side effect is reduced by at least about 2%, at least about 5%, at least about 10%, at least about 15%, at least about 20%, at least about 25%, at least about 30%, at least about 40%, at least about 50%, at least about 60%, at least about 70%, at least about 80%, at least about 90%, or at least about 95% relative to a control level. The control level includes any appropriate control as known in the art. For example, the control level can be the side effect level in the subject treated with other asthma therapies (e.g., Xolair, Cromolyn Sodium, Nedocromil, Montelukast, and prednisone). In some embodiments, the decrease is statistically significant, for example, as assessed using an appropriate parametric or non-parametric statistical comparison.

In one embodiment, the regression of asthma is a decrease (e.g., at least 5%, 10%, 15%, 20%, 25%, 30%, 35%, 40%, 45%, 50% decrease) in the level of maximal decrease from pre-allergen challenge in $FEV_1$ following allergen challenge. The level of maximal decrease from pre-allergen challenge in $FEV_1$ following allergen challenge can be measured in EAR or LAR.

In one embodiment, the regression of asthma is a decrease (e.g., at least 5%, 10%, 15%, 20%, 25%, 30%, 35%, 40%, 45%, 50% decrease) in area under the curve (AUC) of $FEV_1$ following allergen challenge.

In one embodiment, the regression of asthma is an increase (e.g., at least 5%, 10%, 15%, 20%, 25%, 30%, 35%, 40%, 45%, 50% increase) in the amount of methacholine that is required to induce a 20% fall in $FEV_1$ ($PC_{20}$) following allergen challenge.

In one embodiment, the regression of asthma is a decrease (e.g., at least 5%, 10%, 15%, 20%, 25%, 30%, 35%, 40%, 45%, 50% decrease) in exhaled nitric oxide level of the subject.

In one embodiment, the regression of asthma is a decrease (e.g., at least 5%, 10%, 15%, 20%, 25%, 30%, 35%, 40%, 45%, 50% decrease) in the C-reactive protein (CRP) level of the subject.

In one embodiment, the regression of asthma is a decrease (e.g., at least 5%, 10%, 15%, 20%, 25%, 30%, 35%, 40%, 45%, 50% decrease) in white blood cell count and/or differential cell count in induced sputum of the subject after allergen challenge.

Combination Therapy

In some embodiments, provided herein are methods for combination therapies in which an agent known to modulate other pathways, or other components of the same pathway, or even overlapping sets of target enzymes are used in combination with a compound provided herein, or a pharmaceutically acceptable form (e.g., pharmaceutically acceptable salts, hydrates, solvates, isomers, prodrugs, and isotopically labeled derivatives) thereof. In one aspect, such therapy includes, but is not limited to, the combination of the subject compound with chemotherapeutic agents, therapeutic antibodies, and radiation treatment, to provide a synergistic or additive therapeutic effect.

By "in combination with," it is not intended to imply that the other therapy and the PI3K modulator must be administered at the same time and/or formulated for delivery together, although these methods of delivery are within the scope of this disclosure. The compound provided herein can be administered concurrently with, prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks before), or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks after), one or more other therapies (e.g., one or more other additional agents). In general, each therapeutic agent will be administered at a dose and/or on a time schedule determined for that particular agent. The other therapeutic agent can be administered with the compound provided herein in a single composition or separately in a different composition. Triple therapy is also contemplated herein.

In general, it is expected that additional therapeutic agents employed in combination be utilized at levels that do not exceed the levels at which they are utilized individually. In some embodiments, the levels utilized in combination will be lower than those utilized individually.

In some embodiments, the compound provided herein is a first line treatment for cancer or hematologic malignancy, i.e., it is used in a subject who has not been previously administered another drug or therapy intended to treat cancer or hematologic malignancy or one or more symptoms thereof.

In other embodiments, the compound provided herein is a second line treatment for cancer or hematologic malignancy, i.e., it is used in a subject who has been previously administered another drug or therapy intended to treat cancer or hematologic malignancy or one or more symptoms thereof.

In other embodiments, the compound provided herein is a third or fourth line treatment for cancer or hematologic malignancy, i.e., it is used in a subject who has been previously administered two or three other drugs or therapies intended to treat cancer or hematologic malignancy or one or more symptoms thereof.

In embodiments where two agents are administered, the agents can be administered in any order. For example, the two agents can be administered concurrently (i.e., essentially at the same time, or within the same treatment) or sequentially (i.e., one immediately following the other, or alternatively, with a gap in between administration of the two). In some embodiments, the compound provided herein is administered sequentially (i.e., after the first therapeutic).

In one aspect, a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, can present synergistic or additive efficacy when administered in combination with agents that inhibit IgE production or activity. Such combination can reduce the undesired effect of high level of IgE associated with the use of one or more PI3K-δ inhibitors, if such effect occurs. This can be particularly useful in treatment of autoimmune and inflammatory disorders (AIID) such as rheumatoid arthritis. Additionally, the administration of PI3K-δ, PI3K-γ, or PI3K-δ/γ inhibitors as provided herein in combination with inhibitors of mTOR can also exhibit synergy through enhanced inhibition of the PI3K pathway.

In a separate but related aspect, provided herein is a combination treatment of a disease associated with PI3K-δ comprising administering to a subject in need thereof a PI3K-δ inhibitor and an agent that inhibits IgE production or activity. Other exemplary PI3K-δ inhibitors are applicable for this combination and they are described in, e.g., U.S. Pat. No. 6,800,620, incorporated herein by reference. Such combination treatment is particularly useful for treating autoimmune and inflammatory diseases (AIID) including, but not limited to rheumatoid arthritis.

Agents that inhibit IgE production are known in the art and they include, but are not limited to, one or more of TEI-9874, 2-(4-(6-cyclohexyloxy-2-naphtyloxy)phenylacetamide)benzoic acid, rapamycin, rapamycin analogs (i.e., rapalogs), TORC1 inhibitors, TORC2 inhibitors, and any other compounds that inhibit mTORC1 and mTORC2. Agents that inhibit IgE activity include, for example, anti-IgE antibodies such as for example Omalizumab and TNX-901.

For treatment of autoimmune diseases, a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, can be used in combination with commonly prescribed drugs including, but not limited to, Enbrel®, Remicade®, Humira®, Avonex®, and Rebif®. For treatment of respiratory diseases, the subject compounds, or pharmaceutically acceptable forms thereof, or pharmaceutical compositions, can be administered in combination with commonly prescribed drugs including, but not limited to, Xolair®, Advair®, Singulair®, and Spiriva®.

The compounds as provided herein, or pharmaceutically acceptable forms (e.g., pharmaceutically acceptable salts, hydrates, solvates, isomers, prodrugs, and isotopically labeled derivatives) thereof, or pharmaceutical compositions as provided herein, can be formulated or administered in conjunction with other agents that act to relieve the symptoms of inflammatory conditions such as encephalomyelitis, asthma, and the other diseases described herein. These agents include non-steroidal anti-inflammatory drugs (NSAIDs), e.g., acetylsalicylic acid; ibuprofen; naproxen; indomethacin; nabumetone; tolmetin; etc. Corticosteroids are used to reduce inflammation and suppress activity of the immune system. An exemplary drug of this type is Prednisone. Chloroquine (Aralen) or hydroxychloroquine (Plaquenil) can also be used in some individuals with lupus. They can be prescribed for skin and joint symptoms of lupus. Azathioprine (Imuran) and cyclophosphamide (Cytoxan) suppress inflammation and tend to suppress the immune system. Other agents, e.g., methotrexate and cyclosporin are used to control the symptoms of lupus. Anticoagulants are employed to prevent blood from clotting rapidly. They range from aspirin at very low dose which prevents platelets from sticking, to heparin/coumadin. Other compounds used in the treatment of lupus include belimumab (Benlysta®).

In another aspect, provided herein is a pharmaceutical composition for inhibiting abnormal cell growth in a subject which comprises an amount of a compound provided herein, or a pharmaceutically acceptable form (e.g., pharmaceutically acceptable salts, hydrates, solvates, isomers, prodrugs, and isotopically labeled derivatives) thereof, in combination with an amount of an anti-cancer agent (e.g., a chemotherapeutic agent or a biotherapeutic agent). Many chemotherapeutics are presently known in the art and can be used in combination with a compound provided herein.

In some embodiments, the chemotherapeutic is selected from mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. Non-limiting examples are chemotherapeutic agents, cytotoxic agents, and non-peptide small molecules such as Gleevec® (imatinib mesylate), Velcade® (bortezomib), Casodex™ (bicalutamide), Iressa® (gefitinib), Tarceva® (erlotinib), and Adriamycin® (doxorubicin) as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphoramide and trimethylolomelamine; BTK inhibitors such as ibrutinib (PCI-32765), AVL-292, Dasatinib, LFM-A13, ONO-WG-307, and GDC-0834; HDAC inhibitors such as vorinostat, romidepsin, panobinostat, valproic acid, belinostat, mocetinostat, abrexinostat, entinostat, SB939, resminostat, givinostat, CUDC-101, AR-42, CHR-2845, CHR-3996, 4SC-202, CG200745, ACY-1215 and kevetrin; EZH2 inhibitors such as, but not limited to, EPZ-6438 (N-((4,6-dimethyl-2-oxo-1,2-dihydropyridin-3-yl)methyl)-5-(ethyl(tetrahydro-2H-pyran-4-yl)amino)-4-methyl-4'-(morpholinomethyl)-[1,1'-biphenyl]-3-carboxamide), GSK-126 ((S)-1-(sec-butyl)-N-((4,6-dimethyl-2-oxo-1,2-dihydropyridin-3-yl)methyl)-3-methyl-6-(6-(piperazin-1-yl)pyridin-3-yl)-1H-indole-4-carboxamide), GSK-343 (1-Isopropyl-N-((6-methyl-2-oxo-4-propyl-1,2-dihydropyridin-3-yl)methyl)-6-(2-(4-methylpiperazin-1-yl)pyridine-4-yl)-1H-indazole-4-carboxamide), Eli, 3-deazaneplanocin A (DNNep, 5R-(4-amino-1H-imidazo[4,5-c]pyridin-1-yl)-3-(hydroxymethyl)-3-cyclopentene-1S,2R-diol), small interfering RNA (siRNA) duplexes targeted against EZH2 (S. M. Elbashir et al., Nature 411:494-498 (2001)), isoliquiritigenin, and those provided in, for example, U.S. Publication Nos. 2009/0012031, 2009/0203010, 2010/0222420, 2011/0251216, 2011/0286990, 2012/0014962, 2012/0071418, 2013/0040906, and 2013/0195843, all of which are incorporated herein by reference; JAK/STAT inhibitors such as lestaurtinib, tofacitinib, ruxolitinib, pacritinib, CYT387, baricitinib, GLPG0636, TG101348, INCB16562, CP-690550, and AZD1480; PKC-β inhibitor such as Enzastaurin; SYK inhibitors such as, but not limited to, GS-9973, PRT 062607, R406, (S)-2-(2-(((3,5-dimethylphenyl)amino)pyrimidin-4-yl)-N-(1-hydroxypropan-2-yl)-4-methylthiazole-5-carboxamide, R112, GSK143, BAY61-3606, PP2, PRT 060318, R348, and those provided in, for example, U.S. Publication Nos. 2003/0113828, 2003/0158195, 2003/0229090, 2005/0075306, 2005/0232969, 2005/0267059, 2006/0205731, 2006/0247262, 2007/0219152, 2007/0219195, 2008/0114024, 2009/0171089, 2009/0306214, 2010/0048567, 2010/0152159, 2010/0152182, 2010/0316649, 2011/0053897, 2011/0112098, 2011/0245205, 2011/0275655, 2012/0027834, 2012/0093913, 2012/0101275, 2012/0130073, 2012/0142671, 2012/0184526, 2012/0220582, 2012/0277192, 2012/0309735, 2013/0040984, 2013/0090309, 2013/0116260, and 2013/0165431, all of which are incorporated herein by reference; SYK inhibitor such as R788 (fostamatinib); SYK/JAK dual inhibitor such as PRT2070; nitrogen mustards such as bendamustine, chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomycins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pralatrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; amsacrine; bestrabucil; bisantrene; edatrexate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK.R™; razoxane; sizofiran; spirogermanium; tenuazonic acid; triaziquone; 2,2',2"-trichlorotriethyla-mine; urethan; vindesine; dacarbazine; mannomustine; mitobronitol; mitolactol; pipobroman; gacytosine; arabinoside (Ara-C); cyclophosphamide; thiotepa; taxanes, e.g., paclitaxel (e.g., TAXOL™) and docetaxel (e.g., TAXOTERE™) and ABRAXANE® (paclitaxel protein-bound particles); retinoic acid; esperamicins; capecitabine; and pharmaceutically acceptable forms (e.g., pharmaceutically acceptable salts, hydrates, solvates, isomers, prodrugs, and isotopically labeled derivatives) of any of the above. Also included as suitable chemotherapeutic cell conditioners are anti-hormonal agents that act to regulate or inhibit hormone action on tumors such as anti-estrogens including for example tamoxifen (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylornithine (DMFO). Where desired, the compounds or pharmaceutical composition as provided herein can be used in combination with commonly prescribed anti-cancer drugs such as Herceptin®, Avastin®, Erbitux®, Rituxan®, Taxol®, Arimidex®, Taxotere®, ABVD, AVICINE, abagovomab, acridine carboxamide, adecatumumab, 17-N-allylamino-17-demethoxygeldanamycin, alpharadin, alvocidib, 3-aminopyridine-2-carboxaldehyde thiosemicarbazone, amonafide, anthracenedione, anti-CD22 immunotoxins, antineoplastic, antitumorigenic herbs, apaziquone, atiprimod, azathioprine, belotecan, bendamustine, BIBW 2992, biricodar, brostallicin, bryostatin, buthionine sulfoximine, CBV (chemotherapy), calyculin, crizotinib, cell-cycle nonspecific antineoplastic agents, dichloroacetic acid, discodermolide, elsamitrucin, enocitabine, epothilone, eribulin, everolimus, exatecan, exisulind, ferruginol, forodesine, fosfestrol, ICE chemotherapy regimen, IT-101, imexon, imiquimod, indolocarbazole, irofulven, laniquidar, larotaxel, lenalidomide, lucanthone, lurtotecan, mafosfamide, mitozolomide, nafoxidine, nedaplatin, olaparib, ortataxel, PAC-1, pawpaw, pixantrone, proteasome inhibitor, rebeccamycin, resiquimod, rubitecan, SN-38, salinosporamide A, sapacitabine, Stanford V, swainsonine, talaporfin, tariquidar, tegafur-uracil, temodar, tesetaxel, triplatin tetranitrate, tris(2-chloroethyl)amine, troxacitabine, uramustine, vadimezan, vinflunine, ZD6126, and zosuquidar.

In some embodiments, the chemotherapeutic is selected from hedgehog inhibitors including, but not limited to IPI-926 (See U.S. Pat. No. 7,812,164). Other suitable hedgehog inhibitors include, for example, those described and disclosed in U.S. Pat. No. 7,230,004, U.S. Patent Application Publication No. 2008/0293754, U.S. Patent Application Publication No. 2008/0287420, and U.S. Patent Application Publication No. 2008/0293755, the entire disclosures of which are incorporated by reference herein. Examples of other suitable hedgehog inhibitors include those described in U.S. Patent Application Publication Nos. US 2002/0006931, US 2007/0021493 and US 2007/0060546, and International Application Publication Nos. WO 2001/19800, WO 2001/26644, WO 2001/27135, WO 2001/49279, WO 2001/74344, WO 2003/011219, WO 2003/088970, WO 2004/020599, WO 2005/013800, WO 2005/033288, WO 2005/032343, WO 2005/042700, WO 2006/028958, WO 2006/050351, WO 2006/078283, WO 2007/054623, WO 2007/059157, WO 2007/120827, WO 2007/131201, WO 2008/070357, WO 2008/110611, WO 2008/112913, and WO 2008/131354, each incorporated herein by reference. Additional examples of hedgehog inhibitors include, but are not limited to, GDC-0449 (also known as RG3616 or vismodegib) described in, e.g., Von Hoff D. et al., N. Engl. J. Med. 2009; 361(12):1164-72; Robarge K. D. et al., Bioorg Med Chem Lett. 2009; 19(19):5576-81; Yauch, R. L. et al. (2009) Science 326: 572-574; Sciencexpress: 1-3 (10.1126/science.1179386); Rudin, C. et al. (2009) New England J of Medicine 361-366 (10.1056/nejma0902903); BMS-833923 (also known as XL139) described in, e.g., in Siu L. et al., J. Clin. Oncol. 2010; 28:15s (suppl; abstr 2501); and National Institute of Health Clinical Trial Identifier No.

NCT006701891; LDE-225 described, e.g., in Pan S. et al., *ACS Med. Chem. Lett.*, 2010; 1(3): 130-134; LEQ-506 described, e.g., in National Institute of Health Clinical Trial Identifier No. NCT01106508; PF-04449913 described, e.g., in National Institute of Health Clinical Trial Identifier No. NCT00953758; Hedgehog pathway antagonists disclosed in U.S. Patent Application Publication No. 2010/0286114; SMOi2-17 described, e.g., U.S. Patent Application Publication No. 2010/0093625; SANT-1 and SANT-2 described, e.g., in Rominger C. M. et al., *J. Pharmacol. Exp. Ther.* 2009; 329(3):995-1005; 1-piperazinyl-4-arylphthalazines or analogues thereof, described in Lucas B. S. et al., *Bioorg. Med. Chem. Lett.* 2010; 20(12):3618-22.

Other hormonal therapy and chemotherapeutic agents include, but are not limited to, anti-estrogens (e.g. tamoxifen, raloxifene, and megestrol acetate), LHRH agonists (e.g. goserelin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), *vinca* alkaloids (e.g. vincristine, vinblastine, vindesine, and vinorelbine), taxoids or taxanes (e.g. paclitaxel or a paclitaxel equivalent such as nanoparticle albumin-bound paclitaxel (Abraxane), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), anti-metabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonucleotide reductase inhibitors (e.g. hydroxyurea and deferoxamine), uracil analogs (e.g. 5-fluorouracil (5-FU), floxuridine, doxifluridine, raltitrexed, tegafur-uracil, capecitabine), cytosine analogs (e.g. cytarabine (ara C, cytosine arabinoside), and fludarabine), purine analogs (e.g. mercaptopurine and thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracyclines (e.g. daunorubicin, doxorubicin, pegylated liposomal doxorubicin, idarubicin, epirubicin, pirarubicin, zorubicin, mitoxantrone), MDR inhibitors (e.g. verapamil), Ca2+ ATPase inhibitors (e.g. thapsigargin), thalidomide, lenalidomide (REVLIMID®), tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (Velcade)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbazine, prednisolone, dexamethasone, camptothecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

Exemplary biotherapeutic agents include, but are not limited to, interferons, cytokines (e.g., tumor necrosis factor, interferon α, interferon γ), vaccines, hematopoietic growth factors, monoclonal serotherapy, immuno-stimulants and/or immuno-modulatory agents (e.g., IL-1, 2, 4, 6, 7, 12, 15, or 21), immune cell growth factors (e.g., GM-CSF) and antibodies (e.g. Herceptin (trastuzumab), T-DM1, AVASTIN (bevacizumab), ERBITUX (cetuximab), Vectibix (panitumumab), Rituxan (rituximab), Bexxar (tositumomab), or Perjeta (pertuzumab)).

In some embodiments, the biotherapeutic agent is an immunotherapeutic agent, e.g., a cancer vaccine e.g., a tumor vaccine. Exemplary cancer vaccines include Aduro (GVAX); Advaxis (ADXS11-001, ADXS31-001, ADXS31-164, ADXS31-142 (ADXS-PSA)); ALVAC-CEA vaccine; Avax Technologies (AC Vaccine); Amgen (talimogene laherparepvec); Biovest International (BiovaxID in phase III); Bavarian Nordic (PROSTVAC); Celldex Therapeutics (CDX110, CDX1307 and CDX1401); The Center of Molecular Immunology (CimaVax-EGF); CureVac develops mRNA-based cancer immunotherapies; CV9104; Dendreon Corp (Neuvenge); Galena Biopharma (NeuVax); Antigen Express (Ae-37); Geron Corporation (GRNVAC1); Globe-Immune (Tarmogens, GI-4000, GI-6207, GI-6301); Heat Biologics (ImPACT Therapy); Immatics biotechnologies (IMA901); Merck (Stimuvax); Panacela Labs, Inc. (MOBILAN Adenovirus-based treatment); Prima BioMed (Cvac); Scancell Holdings (SCIB1).

In embodiments, the biotherapeutic agent is a cellular therapy, e.g., dendritic cell therapy or a chimeric T cell therapy such as CART. Dendritic cell therapy can comprise loading dendritic cells with an antigen obtained from a patient's tumor, then administering the dendritic cells to the patient in order to sensitize the patient's own T cells to the tumor antigens. Chimeric antigen receptors (CARs) are engineered receptors that can be used to confer tumor specificity to a T cell. CARS have been generated with specificity for α-folate receptor, CAIX, CD19, CD20, CD22, CD30, CD33, CD44v7/8, CEA, EGP-2, EGP-40, erb-B2, erb-B 2,3,4, FBP, Fetal acetylcholine receptor, FD2, Her2/neu, IL13R-a2, KDR, k-light chain, LeY, L1 cell adhesion molecule, MAGE-A1, mesothelin, CMV-infected cells, MUC1, NKG2D ligands, oncofetal antigen h5T4, PSCA, PSMA, TAA, TAG-72, and VEGF-R$^2$.

In one embodiment, the biotherapeutic agent is an anti-CD37 antibody such as, but not limited to, IMGN529, K7153A and TRU-016. In another embodiment, the biotherapeutic agent is an anti-CD20 antibody such as, but not limited to, $^{131}$I tositumomab, $^{90}$Y ibritumomab, $^{111}$I ibritumomab, obinutuzumab (GAZYVA), and ofatumumab. In another embodiment, the biotherapeutic agent is an anti-CD52 antibody such as, but not limited to, alemtuzumab.

In some embodiments, the chemotherapeutic is selected from HSP90 inhibitors. The HSP90 inhibitor can be a geldanamycin derivative, e.g., a benzoquinone or hygroquinone ansamycin HSP90 inhibitor (e.g., IPI-493 and/or IPI-504). Non-limiting examples of HSP90 inhibitors include IPI-493, IPI-504, 17-AAG (also known as tanespimycin or CNF-1010), BIIB-021 (CNF-2024), BIIB-028, AUY-922 (also known as VER-49009), SNX-5422, STA-9090, AT-13387, XL-888, MPC-3100, CU-0305, 17-DMAG, CNF-1010, Macbecin (e.g., Macbecin I, Macbecin II), CCT-018159, CCT-129397, PU-H71, or PF-04928473 (SNX-2112).

In some embodiments, the chemotherapeutic is selected from PI3K inhibitors (e.g., including those PI3K inhibitors provided herein and those PI3K inhibitors not provided herein). In some embodiment, the PI3K inhibitor is an inhibitor of delta and gamma isoforms of PI3K. In some embodiment, the PI3K inhibitor is an inhibitor of delta isoform of PI3K. In some embodiment, the PI3K inhibitor is an inhibitor of gamma isoform of PI3K. In some embodiments, the PI3K inhibitor is an inhibitor of alpha isoform of PI3K. In other embodiments, the PI3K inhibitor is an inhibitor of one or more alpha, beta, delta and gamma isoforms of PI3K. Exemplary PI3K inhibitors that can be used in combination are described in, e.g., WO 09/088990, WO 09/088086, WO 2011/008302, WO 2010/036380, WO 2010/006086, WO 09/114870, WO 05/113556; US 2009/0312310, and US 2011/0046165, each incorporated herein by reference. Additional PI3K inhibitors that can be used in combination with the pharmaceutical compositions, include but are not limited to, RP-6530, TG 100-115, RV1729, AMG-319, GSK 2126458, GDC-0980, GDC-0941, Sanofi XL147, XL499, XL756, XL147, PF-4691502, BKM 120, CAL-101 (GS-1101), CAL 263, SF1126, PX-886, and a dual PI3K inhibitor (e.g., Novartis BEZ235). In one embodiment, the PI3K inhibitor is an isoquinolinone. In one embodiment, the PI3K inhibitor is RP-6530, which has the chemical name: (S)-2-(1-((9H-purin-6-yl)amino)propyl)-3-(3-fluorophenyl)-4H-chromen-4-one. In one embodiment, the PI3K inhibitor is TG 100-115, which has the chemical name: 6,7-Bis(3-hydroxyphenyl)pteridine-2,4-diamine. In one embodiment, the PI3K inhibitor is RV1729, which has the chemical name: 6-(2-((4-amino-3-(3-hydroxyphenyl)-1H-pyrazolo[3,4-d]pyrimidin-1-yl)methyl)-3-(2-chlorobenzyl)-4-oxo-3,4-dihydroquinazolin-5-yl)-N,N-bis(2-methoxyethyl)hex-5-ynamide.

Without being bound by any particular theory, it is believed that the role of each PI3K isoform is critically dependent on cell type and upstream initiating signals, and therefore pharmacologic inhibition of specific isoforms can lead to different physiologic outcomes. PI3K is a lipid kinase existing in multiple isoforms that have central roles in the regulation of important cellular processes, including cell growth and survival. Puri et al., Frontiers in Immunology. 2012, 3: 256. PI3K-δ and PI3K-γ are both expressed in CLL and NHL tumor cells. Signaling through PI3K is critical for supporting the growth and survival of these malignancies as they mediate intracellular BCR signaling and promote interactions between the tumor cells and their microenvironment. Puri et al., Frontiers in Immunology. 2012, 3: 256.

The specific functions of PI3K-δ in malignant B cells support the rationale for it to be a therapeutic target to control these diseases. PI3K-δ inhibition disrupts malignant cell interaction with the stromal microenvironment, thereby short-circuiting chemokine-mediated stimulation of CLL and other B-cell malignancies, priming cells for apoptosis by pharmacologic or natural stimuli. Pharmacologic inhibition of PI3K-δ reduces disease activity in various models of B-cell-derived malignancies, including CLL and B-cell lymphomas. PI3K-δ inhibition improves the therapeutic potential of other antitumor agents in various preclinical models of B-cell malignancy, including CLL. Lannutti et al., Blood. 2011, 117, 591-594.

The role of PI3K-γ in cells that maintain the malignant B-cell microenvironment creates potential for therapeutic inhibition of PI3K-γ to control these diseases. PI3K-γ plays a role in T-cell activation and migration and GPCR-associated chemokine signaling. Reif et al. J Immunol. 2004; 173:2236-2240. PI3K-γ also mediates adhesion and trafficking of tumor-associated macrophages (TAMs). Reif et al. J Immunol. 2004; 173:2236-2240. Hasan et al., Int Immunopharmacology. 2010, 10, 1017-1021; Laffargue et al., Immunity. 2002, 16, 441-451. There is dynamic interplay or "cross-talk" between PI3K-δ and PI3K-γ in essential cellular activities in malignant cells. In certain tumor types, PI3K-γ can promote tumorigenesis in the absence of PI3K-δ. Subramaniam et al., Cancer Cell. 2012, 21, 459-472.

In certain tumor types, dual isoform inhibition may be necessary for optimal tumor growth inhibition in preclinical models. Subramaniam et al., Cancer Cell. 2012, 21, 459-472. As shown in the examples, in some cell lines (e.g., NHL (e.g., follicular lymphoma), DLBCL, mantle cell, multiple myeloma, T-cell lymphoma), combined inhibition of PI3K-δ and PI3K-γ shows greater growth inhibition than inhibition of either isoform alone.

In certain embodiments, provided herein are pharmaceutical compositions comprising a PI3K gamma selective compound and a PI3K delta compound or a PI3K delta selective compound. In one embodiment, the composition is synergistic in treating or preventing a PI3K mediated disorder.

Also provided herein are methods of treating or preventing a PI3K mediated disorder in a subject, comprising administering to the subject a therapeutically effective amount of a PI3K gamma selective compound in combination with a PI3K delta compound or a PI3K delta selective compound. Also provided herein are methods of enhancing a PI3K delta compound treatment of a PI3K mediated disorder in a subject comprising administering a PI3K gamma selective compound in combination with the PI3K delta compound. In one embodiment, the administering the PI3K gamma selective compound in combination with the PI3K delta compound provides synergistic effect. In one embodiment, the administering the PI3K gamma selective compound in combination with the PI3K delta compound provides additive effect. In another embodiment, administering the PI3K gamma selective compound in combination with the PI3K delta compound provides a faster response time compared to administering a delta selective compound alone.

Also provided herein are methods for inhibiting migration of peripheral T-cells in a subject diagnosed with CLL comprising administering a PI3K gamma selective compound to the subject.

Also provided herein are methods of inhibiting growth of a cell comprising contacting the cell with a PI3K gamma selective compound in combination with a PI3K delta selective compound. In one embodiment, the cell is a cancer cell. In another embodiment, the cell is in a subject. In one embodiment, the subject is afflicted with a proliferative disease, cancer, autoimmune disease, or inflammatory disease.

In one embodiment, the PI3K gamma selective compound selectively inhibits PI3K gamma isoform over PI3K delta isoform. In one embodiment, the PI3K gamma selective compound has a delta/gamma selectivity ratio of greater than 1, greater than about 5, greater than about 10, greater than about 50, greater than about 100, greater than about 200, greater than about 400, greater than about 600, greater than about 800, greater than about 1000, greater than about 1500, greater than about 2000, greater than about 5000, greater than about 10,000, or greater than about 20,000. In one embodiment, the PI3K gamma selective compound has a delta/gamma selectivity ratio in the range of from greater than 1 to about 5, from about 5 to about 10, from about 10 to about 50, from about 50 to about 850, or greater than about 850. In one embodiment, the delta/gamma selectivity ratio is determined by dividing the compound's $IC_{50}$ against PI3K delta isoform by the compound's $IC_{50}$ against PI3K gamma isoform.

In one embodiment, the PI3K gamma selective compound is a compound provided herein, e.g., a compound of Formula (I'), (A'), (I), or (A), or a pharmaceutically acceptable form thereof. In one embodiment, the PI3K gamma selective compound is a compound of Formula (I'), (A'), (I), or (A), or a pharmaceutically acceptable form thereof, wherein $R^1$ is a heteroaryl (e.g., a 5-membered heteroaryl or a 6-membered heteroaryl), In one embodiment, the PI3K gamma selective compound is Compound 2, 4, 7, 9, 17, 19, 21, 26, 27, 30, 32, 35, 37, 38, 40, 41, 52, 60, 61, 63, 73, 75, 77, 79, 80, 81, or 88, or a pharmaceutically acceptable form thereof. In one embodiment, the PI3K gamma selective compound is Compound 4, 7, 9, 19, 27, 35, 37, 41, 52, 73, 80, or 88, or a pharmaceutically acceptable form thereof.

In one embodiment, the PI3K delta selective compound selectively inhibits PI3K delta isoform over PI3K gamma isoform. In one embodiment, the PI3K delta selective compound has a gamma/delta selectivity ratio of greater than 1, greater than about 5, greater than about 10, greater than about 50, greater than about 100, greater than about 200, greater than about 400, greater than about 600, greater than about 800, greater than about 1000, greater than about 1500, greater than about 2000, greater than about 5000, greater than about 10,000, or greater than about 20,000. In one embodiment, the PI3K delta selective compound has a gamma/delta selectivity ratio in the range of from greater than 1 to about 5, from about 5 to about 10, from about 10 to about 50, from about 50 to about 850, or greater than about 850. In one embodiment, the gamma/delta selectivity ratio is determined by dividing the inhibitor's $IC_{50}$ against PI3K gamma isoform by the inhibitor's $IC_{50}$ against PI3K delta isoform.

In certain embodiments, the PI3K inhibitor is a PI3K delta selective compound. In one embodiment, the PI3K delta selective compound selectively inhibits PI3K delta isoform over PI3K alpha isoform. In one embodiment, the PI3K delta selective compound has an alpha/delta selectivity ratio of greater than 1, greater than about 5, greater than about 10, greater than about 50, greater than about 100, greater than about 200, greater than about 400, greater than about 600, greater than about 800, greater than about 1000, greater than about 1500, greater than about 2000, greater than about 5000, greater than about 10,000, or greater than about 20,000. In one embodiment, the PI3K delta selective compound has an alpha/delta selectivity ratio in the range of from greater than 1 to about 5, from about 5 to about 10, from about 10 to about 50, from about 50 to about 850, or greater than about 850. In one embodiment, the alpha/delta selectivity ratio is determined by dividing the inhibitor's $IC_{50}$ against PI3K alpha isoform by the inhibitor's $IC_{50}$ against PI3K delta isoform.

In certain embodiments, the PI3K inhibitor is a PI3K delta selective compound. In one embodiment, the PI3K delta selective compound selectively inhibits PI3K delta isoform over PI3K beta isoform. In one embodiment, the PI3K delta selective compound has a beta/delta selectivity ratio of greater than 1, greater than about 5, greater than about 10, greater than about 50, greater than about 100, greater than about 200, greater than about 400, greater than about 600, greater than about 800, greater than about 1000, greater than about 1500, greater than about 2000, greater than about 5000, greater than about 10,000, or greater than about 20,000. In one embodiment, the PI3K delta selective compound has a beta/delta selectivity ratio in the range of from greater than 1 to about 5, from about 5 to about 10, from about 10 to about 50, from about 50 to about 850, or greater than about 850. In one embodiment, the beta/delta selectivity ratio is determined by dividing the compound's $IC_{50}$ against PI3K beta isoform by the compound's $IC_{50}$ against PI3K delta isoform.

In one embodiment, the PI3K delta selective compound is GSK-2269557 (2-(6-(1H-indol-4-yl)-1H-indazol-4-yl)-5-((4-isopropylpiperazin-1-yl)methyl)oxazole), GS9820 (CAL-120, (S)-2-(1-((9H-purin-6-yl)amino)ethyl)-6-fluoro-3-phenylquinazolin-4(3H)-one), GS-1101 (5-fluoro-3-phenyl-2-([S)]-1-[9H-purin-6-ylamino]-propyl)-3H-quinazolin-4-one), AMG319, or TGR-1202 ((S)-2-(1-(4-amino-3-(3-fluoro-4-isopropoxyphenyl)-H-pyrazolo[3,4-d]pyrimidin-1-yl)ethyl)-6-fluoro-3-(3-fluorophenyl)-4H-chromen-4-one), or a mixture thereof. In one embodiment, the PI3K delta selective compound is GS1101.

In one embodiment, the PI3K delta selective compound is a PI3K delta inhibitor as described in WO 2005/113556, the entirety of which is incorporated herein by reference. In one embodiment, the PI3K delta selective compound has an alpha/delta $IC_{50}$ ratio of greater than about 200, greater than about 250, greater than about 300, greater than about 500, greater than about 600, or greater than about 700. In one embodiment, the PI3K delta selective compound has a beta/delta $IC_{50}$ ratio of greater than about 50, greater than about 75, greater than about 80, greater than about 90, or greater than about 100. In one embodiment, the PI3K delta selective compound has a gamma/delta $IC_{50}$ ratio of greater than about 50, greater than about 75, greater than about 80, greater than about 100, greater than about 200, greater than about 300, greater than about 400, or greater than about 500. In one embodiment, the PI3K delta selective compound is Compound No. 113 or 107 as described in 2005/113556.

In one embodiment, the PI3K delta selective compound is a PI3K delta compound as described in WO2014/006572, the entirety of which is incorporated herein by reference. In one embodiment, the PI3K delta selective compound is a PI3K delta inhibitor has an alpha/delta selectivity ratio of greater than about 100, greater than about 250, greater than about 500, greater than about 750, or greater than about 1000. In one embodiment, the PI3K delta selective compound is a PI3K delta inhibitor has a beta/delta selectivity ratio of greater than about 10, greater than about 20, greater than about 30, greater than about 40, or greater than about 50. In one embodiment, the PI3K delta selective compound is a PI3K delta inhibitor has a gamma/delta selectivity ratio of greater than about 1, greater than about 10, greater than about 25, greater than about 30, or greater than about 50. In one embodiment, the PI3K delta selective compound is Compound Nos. A1, A2, B, B1 or B2 as described in WO2014/006572. In one embodiment, the PI3K delta selective compound is Compound No. B1 as described in WO2014/006572.

In one embodiment, the PI3K delta selective compound is a PI3K delta compound as described in WO 2013/032591, the entirety of which is incorporated herein by reference. In one embodiment, the PI3K delta selective compound is a compound of Formula (I) as described in WO 2013/032591. In one embodiment, the PI3K delta selective compound is a compound described in WO 2013/032591 with a $IC_{50}$ (nM) for the PI3K delta isoform of less than 100 nM and a $IC_{50}$ (nM) for the PI3K alpha, beta, or gamma of greater than about 100 nM, greater than about 1 μM, or greater than about 1 μM. In one embodiment, the PI3K delta selective compound has an alpha/delta selectivity ratio, a beta/delta selectivity ratio, or a gamma/delta selectivity ratio of greater than 1, greater than about 10, or greater than about 100. In one embodiment, the PI3K delta selective compound is Compound Nos. 13, 30, 41, 55, 57, 124, 167, 183, 185, 187, 191, 196, 226, 230, 232, 234, 235, 326, 327, 328, 333, 334, 336, 337, 338, 356, 359, 378, 439, 440, 443, or 455, as described in WO 2013/032591. In one embodiment, the PI3K delta selective compound is Compound Nos. 183, 230, 234, 235, 326, 333, 336, 337, 338, or 359, as described in WO 2013/032591. In one embodiment, the PI3K delta selective compound is Compound No. 359 as described in WO 2013/032591.

In one embodiment, provided herein are pharmaceutical compositions comprising a compound of Formula (I'), (A'), (I), or (A), or a pharmaceutically acceptable form thereof, and a PI3K delta selective compound, wherein the PI3K delta selective compound is GSK-2269557, GS-9820, GS-1101 (Cal-101 or idelalisib), AMG319, or TGR-1202, or a mixture thereof. In one embodiment, the PI3K delta selective compound is GS1101. In one embodiment, the composition is synergistic in treating or preventing a PI3K mediated disorder. In one embodiment, the PI3K delta selective compound is a compound described in WO2011/146882, the entirety of which is incorporated herein by reference. In one embodiment, the PI3K delta selective compound is a compound described in WO2011/146882 with a $IC_{50}$ (nM) for the PI3K delta isoform of less than 100 nM and a $IC_{50}$ (nM) for the PI3K alpha, beta, or gamma of greater than about 100 nM, greater than about 1 μM, or greater than about 1 μM. In one embodiment, the PI3K delta selective compound has an alpha/delta selectivity ratio, a beta/delta selectivity ratio, or a gamma/delta selectivity ratio of greater than 1, greater than about 10, or greater than about 100. In one embodiment, the PI3K delta selective compound is Compound No. 69 as described in WO2011/146882.

In one embodiment, the PI3K delta selective compound is a compound described in WO2013/012915, the entirety of which is incorporated herein by reference. In one embodiment, the PI3K delta selective compound is a compound described in WO2013/012915 with a $IC_{50}$ (nM) for the PI3K delta isoform of less than 100 nM and a $IC_{50}$ (nM) for the PI3K alpha, beta, or gamma of greater than about 100 nM, greater than about 1M, or greater than about 1 μM. In one embodiment, the PI3K delta selective compound has an alpha/delta selectivity ratio, a beta/delta selectivity ratio, or a gamma/delta selectivity ratio of greater than 1, greater than about 10, or greater than about 100. In one embodiment, the PI3K delta selective compound is Compound No. I-41 or I-106 as described in WO2013/012915.

In one embodiment, the PI3K delta selective compound is a compound described in WO2013/012918, the entirety of which is incorporated herein by reference. In one embodiment, the PI3K delta selective compound is a compound described in WO2013/012918 with a $IC_{50}$ (nM) for the PI3K delta isoform of less than 100 nM and a $IC_{50}$ (nM) for the PI3K alpha, beta, or gamma of greater than about 100 nM, greater than about 1M, or greater than about 1 μM. In one embodiment, the PI3K delta selective compound has an alpha/delta selectivity ratio, a beta/delta selectivity ratio, or a gamma/delta selectivity ratio of greater than 1, greater than about 10, or greater than about 100. In one embodiment, the PI3K delta selective compound is Compound No. 19, 28, 37, 38, 51, 59, 60, 89, 92, 103, 106, 107, 108, or 109 as described in WO2013/012918. In one embodiment, the PI3K delta selective compound is Compound No. 103 or 106 as described in WO2013/012918.

In one embodiment, provided herein are methods of treating or preventing a PI3K mediated disorder in a subject, comprising administering to the subject a therapeutically effective amount of a compound of Formula (I'), (A'), (I), or (A), or a pharmaceutically acceptable form thereof, in combination with a PI3K delta selective compound, wherein the PI3K delta selective compound is GSK-2269557, GS-9820, GS-1101 (Cal-101), AMG319, or TGR-1202, or a mixture thereof. In one embodiment, provided herein are methods of enhancing a PI3K delta selective compound treatment of a PI3K mediated disorder in a subject comprising administering a compound of Formula (I'), (A'), (I), or (A), or a pharmaceutically acceptable form thereof, in combination with the PI3K selective delta compound, wherein the PI3K delta selective compound is GSK-2269557, GS9-820, GS-1101 (Cal-101), AMG319, or TGR-1202, or a mixture thereof. In one embodiment, the PI3K delta selective compound is GS1101. In one embodiment, the administering a compound of Formula (I'), (A'), (I), or (A), or a pharmaceutically acceptable form thereof, in combination with the PI3K delta selective compound provides synergistic effect.

Also provided herein are methods of inhibiting growth of a cell comprising contacting the cell with a compound of Formula (I'), (A'), (I), or (A), or a pharmaceutically acceptable form thereof, in combination with a PI3K delta selective compound, wherein the PI3K delta selective compound is GSK-2269557, GS-9820, GS-1101 (Cal-101), AMG319, or TGR-1202, or a mixture thereof. In one embodiment, the PI3K delta selective compound is GS1101. In one embodiment, the cell is a cancer cell. In another embodiment, the cell is in a subject. In one embodiment, the subject is afflicted with a proliferative disease, cancer, autoimmune disease, or inflammatory disease.

In one embodiment, the PI3K delta selective compound is a compound selected from US Patent Publication Nos. 20140058103, 20140051699, 20140045825, 20140011819, 20130231356, 20130225557, 20120245144, 20100305084, 20100256167, 20100168139, 20100152211, and 20100029693. In one embodiment, the PI3K delta selective compound is a compound selected from U.S. Pat. Nos.

8,653,077, 8,637,533, 8,623,881, 8,586,597, 8,569,296, 8,563,540, 8,492,389, 8,440,651, 8,138,195, 7,932,260, and 6,949,535.

For example, a compound provided herein with a delta/gamma selectivity ratio of greater than 150 can be combined with a compound that has a gamma/delta selectivity ratio of 1000 at various amounts (e.g., a ratio of 10:1 or 40:1 of a gamma selective compound and a delta selective compound) to provide synergistic effect in cell lines (e.g., diffuse large B-cell lymphoma cell lines such as SU-DHL-4, TMD-8 and Farage).

The PI3K gamma selective compound and PI3K delta selective compound composition or combination therapy can provide synergistic effect in treating or preventing a PI3K mediated disorder. In one embodiment, the disorder is a cancer. In one embodiment, the cancer is diffuse large B-cell lymphoma (e.g., TMD-8 and Farage cell lines), B-cell lymphoma (e.g., karpas-422 cell line), T-cell lymphoma, non-Hodgkin's lymphoma, Hodgkin lymphoma, or anaplastic large cell lymphoma (e.g., HH cell line).

In some embodiments, the synergistic effect can be characterized by an isobologram. Potency shifting is usually shown using an isobologram which shows how much less a compound is required in combination to achieve a desired effect level, when compared to the single agent doses needed to reach that effect. The choice of effect level for the isobologram display and combination index calculations can either be manually or automatically selected in the Chalice Analyzer. Potency shifting is scored as the combination index (CI). Chou et al., Adv Enzyme Regul 1984; 22: 27-55. The CI is a rough estimate of how much a compound was needed in combination relative to the single agent doses required to achieve the chosen effect level, and a value of 0.1 means that only a tenth of equivalent amounts of the single agents were needed for the combination to reach the same effect level. Additive effect is CI=1.0. Synergistic effect is CI<1. Antagonistic effect is CI>1.0.

In some embodiment, the synergisitic effect is characterized by Synergy Score.

Different stimuli can be used to preferentially induce T-cell or CLL-cell migration. For example, CCL19 and CCL21 stimuli selectively induce migration of both CLL and T-cells. CXCL13 is CLL-cell specific, whereas CXCL12 is T-cell specific. As such, stimuli CXCL13 and CXCL12 can be used to induce CLL-cell and T-cell migrations, respectively. The PI3K gamma selective compounds provided herein can inhibit cancer-promoting cell migration, e.g., CXCL 12-induced T-cell migration. In some embodiments, elevated pAKT levels indicate that the CXCL12-induced migration machinery is activated. Consequently, in some embodiments, the PI3K gamma selective compound, e.g., Compound 4, interferes with AKT signaling and/or reduces pAKT levels in the T-cells. In one embodiment, the PI3K gamma selective compound is a compound that has a delta/gamma selectivity ratio of greater than about 50, such as Compound 4. In another embodiment, the PI3K delta selective compound is a compound that has a gamma/delta selectivity ratio of greater than about 50. The gamma selective compound can be more potent than a delta selective compound at inhibiting cancer-promoting cell migration, e.g., CXCL12-induced T cell migration in CLL PBMCs. The ability to inhibit the migration of cancer-promoting cells can stop the growth of cancers by blocking the migration of cells that promote cancer growth to the cancer cell niche. In another embodiment, gamma or delta selective compounds can inhibit the migration of cancer cells themselves and limit cancer cell dissemination. As such, the gamma selective compounds provided herein can be used to treat and/or prevent cancer, or slow down the progression of cancer or metastasis. Treatment with a combination of gamma and delta selective compounds can have an earlier response time compared to a delta selective compound alone, for example in B cell meditated cancers.

In one embodiment, a compound provided herein (e.g., a compound of any of Formulae (I"), (I'), (A'), (I), (A), (II), (III), (IV), (V), (VI), (VII), (IX), (X), (XI), (XII), (XIII), (XIV), (XV), (XVI), and (XVII), e.g., a selective PI3K-γ inhibitor, e.g., Compound 4), or a pharmaceutically acceptable form thereof, is administered in combination with a chemotherapy (e.g., temozolomide) for the treatment of a cancer. In one embodiment, the cancer is glioblastoma (e.g., glioblastoma multiforme). In one embodiment, provided herein is a method of treating glioblastoma in a subject, comprising administering to the subject a therapeutically effective amount of Compound 4, or a pharmaceutically acceptable form thereof, in combination with a chemotherapy. In one embodiment, the compound is administered subsequent to the chemotherapy. In one embodiment, the compound is administered concurrently to the chemotherapy. In one embodiment, the compound is administered prior to the chemotherapy.

In some embodiments, provided herein is a method for using a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, in combination with radiation therapy in inhibiting abnormal cell growth or treating the hyperproliferative disorder in the subject. Techniques for administering radiation therapy are known in the art, and these techniques can be used in the combination therapy described herein. The administration of a compound provided herein in this combination therapy can be determined as described herein.

In certain embodiments, provided herein are methods of treating a solid tumor in a subject, comprising administering to the subject a therapeutically effective amount of a compound provided herein (e.g., a compound of any of Formulae (I"), (I'), (A'), (I), (A), (II), (III), (IV), (V), (VI), (VII), (IX), (X), (XI), (XII), (XIII), (XIV), (XV), (XVI), and (XVII), e.g., a selective PI3K-γ inhibitor, e.g., Compound 4), or a pharmaceutically acceptable form thereof, in combination with a radiation therapy.

In one embodiment, the solid tumor is selected from one or more of a cancer of the pulmonary system, a brain cancer, a cancer of the gastrointestinal tract, a skin cancer, a genitourinary cancer, a pancreatic cancer, a lung cancer, a medullobastoma, a basal cell carcinoma, a glioma, a breast cancer (e.g., triple negative breast cancer), a prostate cancer, a testicular cancer, an esophageal cancer, a hepatocellular cancer, a gastric cancer, a gastrointestinal stromal tumor (GIST), a colon cancer, a colorectal cancer, an ovarian cancer, a melanoma, a neuroectodermal tumor, head and neck cancer, a sarcoma, a soft-tissue sarcoma, fibrosarcoma, myxosarcoma, liposarcoma, a chondrosarcoma, an osteogenic sarcoma, a chordoma, an angiosarcoma, an endotheliosarcoma, a lymphangiosarcoma, a lymphangioendotheliosarcoma, a synovioma, a mesothelioma, a leiomyosarcoma, a cervical cancer, a uterine cancer, an endometrial cancer, a carcinoma, a bladder carcinoma, an epithelial carcinoma, a squamous cell carcinoma, an adenocarcinoma, a bronchogenic carcinoma, a renal cell carcinoma, a hepatoma, a bile duct carcinoma, a neuroendocrine cancer, a carcinoid tumor, diffuse type giant cell tumor, andglioblastoma.

In one embodiment, the compound, or a pharmaceutically acceptable form thereof, is administered after the radiation therapy is administered. In one embodiment, the compound, or a pharmaceutically acceptable form thereof, is administered at the same time that radiation therapy is administered. In one embodiment, the compound, or a pharmaceutically acceptable form thereof, is administered alone after discontinuing the radiation therapy.

Radiation therapy can be administered through one of several methods, or a combination of methods, including without limitation, external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g., At-211, I-131, I-125, Y-90, Re-186, Re-188, Sm-153, Bi-212, P-32, and radioactive isotopes of Lu). Suitable radiation sources for use as a cell conditioner as provided herein include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Without being limited by any theory, a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, can render abnormal cells more sensitive to treatment with radiation for purposes of killing and/or inhibiting the growth of such cells. Accordingly, provided herein is a method for sensitizing abnormal cells in a subject to treatment with radiation which comprises administering to the subject an amount of a compound provided herein, or a pharmaceutically acceptable form (e.g., pharmaceutically acceptable salts, hydrates, solvates, isomers, prodrugs, and isotopically labeled derivatives) thereof, which amount is effective in sensitizing abnormal cells to treatment with radiation. The amount of the compound used in this method can be determined according to the means for ascertaining effective amounts of such compounds described herein.

In one embodiment, a compound as provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, can be used in combination with an amount of one or more substances selected from anti-angiogenesis agents, signal transduction inhibitors, and antiproliferative agents, glycolysis inhibitors, or autophagy inhibitors.

Other therapeutic agents, such as MMP-2 (matrix-metalloproteinase 2) inhibitors, MMP-9 (matrix-metalloproteinase 9) inhibitors, and COX-11 (cyclooxygenase 11) inhibitors, can be used in conjunction with a compound provided herein, or a pharmaceutically acceptable form thereof, or a pharmaceutical composition described herein. Such therapeutic agents include, for example, rapamycin, temsirolimus (CCI-779), everolimus (RAD001), sorafenib, sunitinib, and bevacizumab. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. In some embodiments, MMP-2 and MMP-9 inhibitors are those that have little or no activity inhibiting MMP-1. Other embodiments include those that selectively inhibit MMP-2 and/or AMP-9 relative to the other matrix-metalloproteinases (e.g., MAP-1, MMP-3, MMP-4, MMP-5, MMP-6, MMP-7, MMP-8, MMP-10, MMP-11, MMP-12, and MMP-13). Some non-limiting examples of MMP inhibitors are AG-3340, RO 32-3555, and RS 13-0830.

Autophagy inhibitors include, but are not limited to, chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNAs that inhibit expression of proteins including, but not limited to ATG5 (which are implicated in autophagy), can also be used.

In some embodiments, provided herein is a method of and/or a pharmaceutical composition for treating a cardiovascular disease in a subject which comprises an amount of a compound provided herein, or a pharmaceutically acceptable form (e.g., pharmaceutically acceptable salts, hydrates, solvates, isomers, prodrugs, and isotopically labeled derivatives) thereof, and an amount of one or more therapeutic agents use for the treatment of cardiovascular diseases.

Exemplary agents for use in cardiovascular disease applications are anti-thrombotic agents, e.g., prostacyclin and salicylates, thrombolytic agents, e.g., streptokinase, urokinase, tissue plasminogen activator (TPA) and anisoylated plasminogen-streptokinase activator complex (APSAC), anti-platelets agents, e.g., acetyl-salicylic acid (ASA) and clopidrogel, vasodilating agents, e.g., nitrates, calcium channel blocking drugs, anti-proliferative agents, e.g., colchicine and alkylating agents, intercalating agents, growth modulating factors such as interleukins, transformation growth factor-beta and congeners of platelet derived growth factor, monoclonal antibodies directed against growth factors, anti-inflammatory agents, both steroidal and non-steroidal, and other agents that can modulate vessel tone, function, arteriosclerosis, and the healing response to vessel or organ injury post intervention. Antibiotics can also be included in combinations or coatings. Moreover, a coating can be used to effect therapeutic delivery focally within the vessel wall. By incorporation of the active agent in a swellable polymer, the active agent will be released upon swelling of the polymer.

In one embodiment, a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, can be formulated or administered in conjunction with liquid or solid tissue barriers also known as lubricants. Examples of tissue barriers include, but are not limited to, polysaccharides, polyglycans, seprafilm, interceed and hyaluronic acid.

Medicaments which can be administered in conjunction with a compound provided herein, or a pharmaceutically acceptable form (e.g., pharmaceutically acceptable salts, hydrates, solvates, isomers, prodrugs, and isotopically labeled derivatives) thereof, include any suitable drugs usefully delivered by inhalation for example, analgesics, e.g., codeine, dihydromorphine, ergotamine, fentanyl or morphine; anginal preparations, e.g., diltiazem; antiallergics, e.g. cromoglycate, ketotifen or nedocromil; anti-infectives, e.g., cephalosporins, penicillins, streptomycin, sulphonamides, tetracyclines or pentamidine; antihistamines, e.g., methapyrilene; anti-inflammatories, e.g., beclomethasone, flunisolide, budesonide, tipredane, triamcinolone acetonide or fluticasone; antitussives, e.g., noscapine; bronchodilators, e.g., ephedrine, adrenaline, fenoterol, formoterol, isoprenaline, metaproterenol, phenylephrine, phenylpropanolamine, pirbuterol, reproterol, rimiterol, salbutamol, salmeterol, terbutalin, isoetharine, tulobuterol, orciprenaline or (−)-4-amino-3,5-dichloro-α-[[[6-[2-(2-pyridinyl)ethoxy]hexyl]-amino]methyl]benzenemethanol; diuretics, e.g., amiloride; anticholinergics e.g., ipratropium, atropine or oxitropium; hormones, e.g., cortisone, hydrocortisone or prednisolone; xanthines e.g., aminophylline, choline theophyllinate, lysine theophyllinate or theophylline; and therapeutic proteins and peptides, e.g., insulin or glucagon. It will be clear to a person skilled in the art that, where appropriate, the medicaments can be used in the form of salts (e.g., as alkali metal or amine salts or as acid addition salts) or as esters (e.g., lower alkyl esters) to optimize the activity and/or stability of the medicament.

Other exemplary therapeutic agents useful for a combination therapy include, but are not limited to, agents as described above, radiation therapy, hormone antagonists, hormones and their releasing factors, thyroid and antithyroid drugs, estrogens and progestins, androgens, adrenocorticotropic hormone; adrenocortical steroids and their synthetic analogs; inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, vitamins such as water-soluble vitamins, vitamin B complex, ascorbic acid, fat-soluble vitamins, vitamins A, K, and E, growth factors, cytokines, chemokines, muscarinic receptor agonists and antagonists; anticholinesterase agents; agents acting at the neuromuscular junction and/or autonomic ganglia; catecholamines, sympathomimetic drugs, and adrenergic receptor agonists or antagonists; and 5-hydroxytryptamine (5-HT, serotonin) receptor agonists and antagonists.

Therapeutic agents can also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, β-adrenergic agonists, ipratropium, glucocorticoids, methylxanthines, sodium channel blockers, opioid receptor agonists, calcium channel blockers, membrane stabilizers and leukotriene inhibitors.

Additional therapeutic agents contemplated herein include diuretics, vasopressin, agents affecting the renal conservation of water, rennin, angiotensin, agents useful in the treatment of myocardial ischemia, anti-hypertensive agents, angiotensin converting enzyme inhibitors, 0-adrenergic receptor antagonists, agents for the treatment of hypercholesterolemia, and agents for the treatment of dyslipidemia.

Other therapeutic agents contemplated herein include drugs used for control of gastric acidity, agents for the treatment of peptic ulcers, agents for the treatment of gastroesophageal reflux disease, prokinetic agents, antiemetics, agents used in irritable bowel syndrome, agents used for diarrhea, agents used for constipation, agents used for inflammatory bowel disease, agents used for biliary disease, agents used for pancreatic disease. Therapeutic agents include, but are not limited to, those used to treat protozoan infections, drugs used to treat Malaria, Amebiasis, Giardiasis, Trichomoniasis, Trypanosomiasis, and/or Leishmaniasis, and/or drugs used in the chemotherapy of helminthiasis. Other therapeutic agents include, but are not limited to, antimicrobial agents, sulfonamides, trimethoprim-sulfamethoxazole quinolones, and agents for urinary tract infections, penicillins, cephalosporins, and other, β-Lactam antibiotics, an agent containing an aminoglycoside, protein synthesis inhibitors, drugs used in the chemotherapy of tuberculosis, *Mycobacterium avium* complex disease, and leprosy, antifungal agents, antiviral agents including nonretroviral agents and antiretroviral agents.

Examples of therapeutic antibodies that can be combined with a compound provided herein include but are not limited to anti-receptor tyrosine kinase antibodies (cetuximab, panitumumab, trastuzumab), anti CD20 antibodies (rituximab, tositumomab), and other antibodies such as alemtuzumab, bevacizumab, and gemtuzumab.

Moreover, therapeutic agents used for immuno-modulation, such as immuno-modulators, immuno-suppressive agents, tolerogens, and immunostimulants are contemplated by the methods herein. In addition, therapeutic agents acting on the blood and the blood-forming organs, hematopoietic agents, growth factors, minerals, and vitamins, anticoagulant, thrombolytic, and anti-platelet drugs are also contemplated by the methods herein.

In exemplary embodiments, for treating renal carcinoma, one can combine a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, with sorafenib and/or avastin. For treating an endometrial disorder, one can combine a compound provided herein with doxorubincin, taxotere (taxol), and/or cisplatin (carboplatin). For treating ovarian cancer, one can combine a compound provided herein with cisplatin, carboplatin, docetaxel, doxorubincin, topotecan, and/or tamoxifen. For treating breast cancer, one can combine a compound provided herein with paclitaxel or docetaxel, gemcitabine, capecitabine, tamoxifen, letrozole, erlotinib, lapatinib, PD0325901, bevacizumab, trastuzumab, OSI-906, and/or OSI-930. For treating lung cancer, one can combine a compound as provided herein with paclitaxel, docetaxel, gemcitabine, cisplatin, pemetrexed, erlotinib, PD0325901, and/or bevacizumab.

In some embodiments, the disorder to be treated, prevented and/or managed is a hematological cancer, e.g., lymphoma (e.g., T-cell lymphoma; NHL), myeloma (e.g., multiple myeloma), and leukemia (e.g., CLL), and a compound provided herein is used in combination with: HDAC inhibitors such as vorinostat, romidepsin and ACY-1215; mTOR inhibitors such as everolimus; anti-folates such as pralatrexate; nitrogen mustard such as bendamustine; gemcitabine, optionally in further combination with oxaliplatin; rituximab-cyclophosphamide combination; PI3K inhibitors such as RP-6530, TG 100-115, RV1729, GS-1101, XL 499, GDC-0941, and AMG-319; angiogenesis inhibitors such as pomalidomide or BTK inhibitors such as ibrutinib, AVL-292, Dasatinib, LFM-AI3, ONO-WG-307, and GDC-0834. In some embodiments, the disorder to be treated, prevented and/or managed is DLBCL, and a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, is used in combination with HDAC inhibitors provided herein. In one particular embodiment, the HDAC inhibitor is ACY-1215.

In some embodiments, the disorder to be treated, prevented and/or managed is DLBCL, and a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, is used in combination with BTK inhibitors provided herein. In one particular embodiment, the BTK inhibitor is ibrutinib. In one embodiment, the BTK inhibitor is AVL-292.

In some embodiments, the disorder to be treated, prevented and/or managed is DLBCL, and a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, is used in combination with IRAK inhibitors provided herein. In one particular embodiment, the IRAK4 inhibitor is ND-2110 or ND-2158.

In some embodiments, the disorder to be treated, prevented and/or managed is WM, and a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, is used in combination with BTK inhibitors provided herein. In one particular embodiment, the BTK inhibitor is ibrutinib. In one embodiment, the BTK inhibitor is AVL-292.

In some embodiments, the disorder to be treated, prevented and/or managed is WM, and a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, is used in combination with IRAK4 inhibitors provided herein. In one particular embodiment, the IRAK4 inhibitor is ND-2110 or ND-2158.

In some embodiments, the disorder to be treated, prevented and/or managed is T-ALL, the subject/patient has a PTEN deficiency, and a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, is used in combination with doxorubicin and/or vincristine.

In certain embodiments, wherein inflammation (e.g., arthritis, asthma) is treated, prevented and/or managed, a compound provided herein can be combined with, for example: PI3K inhibitors such as RP-6530, TG 100-115, RV1729, GS-1101, XL 499, GDC-0941, and AMG-319; BTK inhibitors such as ibrutinib and AVL-292; JAK inhibitors such as tofacitinib and GLPG0636; SYK inhibitors such as fostamatinib.

In certain embodiments wherein asthma is treated, prevented and/or managed, a compound provided herein can be combined with, for example: beta 2-agonists such as, but not limited to, albuterol (Proventil®, or Ventolin®), salmeterol (Serevent®), formoterol (Foradil®), metaproterenol (Alupent®), pirbuterol (MaxAir®), and terbutaline sulfate; corticosteroids such as, but not limited to, budesonide (e.g., Pulmicort®), flunisolide (e.g., AeroBid Oral Aerosol Inhaler® or Nasalide Nasal Aerosol®), fluticasone (e.g., Flonase® or Flovent®) and triamcinolone (e.g., Azmacort®); mast cell stabilizers such as cromolyn sodium (e.g., Intal® or Nasalcrom®) and nedocromil (e.g., Tilade®); xanthine derivatives such as, but not limited to, theophylline (e.g., Aminophyllin®, Theo-24® or Theolair®); leukotriene receptor antagonists such as, but are not limited to, zafirlukast (Accolate®), montelukast (Singulair®), and zileuton (Zyflo®); and adrenergic agonists such as, but are not limited to, epinephrine (Adrenalin®, Bronitin®, EpiPen® or Primatene Mist®).

In certain embodiments wherein arthritis is treated, prevented and/or managed, a compound provided herein can be combined with, for example: TNF antagonist (e.g., a TNF antibody or fragment, a soluble TNF receptor or fragment, fusion proteins thereof, or a small molecule TNF antagonist); other biologic antirhheumatics (e.g., IL-6 antagonists, IL-1 antagonists, costimulatory modulators); an antirheumatic (e.g., methotrexate, auranofin, aurothioglucose, azathioprine, etanercept, gold sodium thiomalate, chrloroquine, hydroxychloroquine sulfate, leflunomide, sulfasalzine, penicillamine); a muscle relaxant; a narcotic; a non-steroid anti-inflammatory drug (NSAID); an analgesic; an anesthetic; a sedative; a local anesthetic; a neuromuscular blocker; an antimicrobial (e.g., an aminoglycoside, an antifungal, an antiparasitic, an antiviral, a carbapenem, cephalosporin, a fluoroquinolone, a macrolide, a penicillin, a sulfonamide, a tetracycline, another antimicrobial); an antipsoriatic; a corticosteroid; an anabolic steroid; a cytokine or a cytokine antagonist; a calcineurin inhibitor (e.g., cyclosporine, tacrolimus).

In some embodiments, a compound provided herein (e.g., a compound of Formula I (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or an enantiomer or a mixture of enantiomers thereof, or a pharmaceutically acceptable salt, solvate, hydrate, co-crystal, clathrate, or polymorph thereof) is administered in combination with an agent for the treatment of rheumatoid arthritis. Examples of agents for the treatment of rheumatoid arthritis include, but are not limited to, various NSAIDs, corticosteroids, sulfasalazine, auranofin, methotrexate, azathioprine, penicillamine, cyclosporine, Arava (leflunomide), TNF inhibitors (e.g., Enbrel (etanercept), Remicade (infliximab), Humira (adalimumab), Simponi (golimumab), and Cimzia (certolizumab)), IL-1 inhibitors (e.g., Kineret (anakinra)), T-cell costimulatory modulators (e.g., Orencia (abatacept)), Anti-CD20 (e.g., Rituxan (rituximab)), and IL-6 inhibitors (e.g., Actemra (tocilizumab)). In one embodiment, the agent is Cimzia (certolizumab). In another embodiment, the agent is Actemra (tocilizumab).

In some embodiments, a compound provided herein (e.g., a compound of Formula I (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or an enantiomer or a mixture of enantiomers thereof, or a pharmaceutically acceptable salt, solvate, hydrate, co-crystal, clathrate, or polymorph thereof) is administered in combination with an agent for rheumatology. Examples of agents for rheumatology include, but are not limited to, Rayos (prednisone), Stendra (avanafil), Actemra (tocilizumab), Duexis (ibuprofen and famotidine), Actemra (tocilizumab), Krystexxa (pegloticase), Vimovo (naproxen+esomeprazole), Cimzia (certolizumab pegol), Colcrys (colchicine), Pennsaid (diclofenac sodium topical solution), Simponi (golimumab), Uloric (febuxostat), Orencia (abatacept), Elaprase (idursulfase), Orencia (abatacept), Vioxx (rofecoxib), Enbrel (etanercept), Humira (adalimumab), Remicade (infliximab), Bextra, Kineret, Remicade (infliximab), Supartz, Mobic (meloxicam), Vivelle (estradiol transdermal system), Lodine XL (etodolac), Arava, Salagen, Arthrotec, Etodolac, Ketoprofen, Synvisc, Tolmetin Sodium, Azulfidine EN-tabs Tablets (sulfasalazine delayed release tablets, USP), and Naprelan (naproxen sodium).

In some embodiments, the second agent is selected from belimumab, AGS-009, rontalizumab, vitamin D3, sifalimumab, AMG 811, IFNα Kinoid, CEP33457, epratuzumab, LY2127399, Ocrelizumab, Atacicept, A-623, SBI-087, AMG557, laquinimod, rapamycin, cyclophosphamide, azathioprine, mycophenolate, leflunomide, methotrexate, CNTO 136, tamibarotene, N-acetylcysteine, CDP7657, hydroxychloroquine, rituximab, carfilzomib, bortezomib, ONX 0914, IMO-3100, DV1179, sulfasalazine, and chloroquine. In one embodiment, the second agent is methotrexate, sulfasalazine, chloroquine, or hydroxychloroquine. In one embodiment, the second agent is methotrexate.

In certain embodiments wherein psoriasis is treated, prevented and/or managed, a compound provided herein can be combined with, for example: budesonide, epidermal growth factor, corticosteroids, cyclosporine, sulfasalazine, aminosalicylates, 6-mercaptopurine, azathioprine, metronidazole, lipoxygenase inhibitors, mesalamine, olsalazine, balsalazide, antioxidants, thromboxane inhibitors, IL-1 receptor antagonists, anti-IL-1β monoclonal antibodies, anti-IL-6 monoclonal antibodies, growth factors, elastase inhibitors, pyridinyl-imidazole compounds, antibodies or agonists of TNF, LT, IL-1, IL-2, IL-6, IL-7, IL-8, IL-15, IL-16, IL-18, EMAP-II, GM-CSF, FGF, and PDGF, antibodies of CD2, CD3, CD4, CD8, CD25, CD28, CD30, CD40, CD45, CD69, CD90 or their ligands, methotrexate, cyclosporine, FK506, rapamycin, mycophenolate mofetil, leflunomide, NSAIDs, ibuprofen, corticosteroids, prednisolone, phosphodiesterase inhibitors, adenosine agonists, antithrombotic agents, complement inhibitors, adrenergic agents, IRAK, NIK, IKK, p38, MAP kinase inhibitors, IL-1β converting enzyme inhibitors, TNFα converting enzyme inhibitors, T-cell signaling inhibitors, metalloproteinase inhibitors, sulfasalazine, azathioprine, 6-mercaptopurines, angiotensin converting enzyme inhibitors, soluble cytokine receptors, soluble p55 TNF receptor, soluble p75 TNF receptor, sIL-1RI, sIL-1RII, sIL-6R, anti-inflammatory cytokines, IL-4, IL-10, IL-11, IL-13 and TGFβ.

In certain embodiments wherein fibrosis or fibrotic condition of the bone marrow is treated, prevented and/or managed, a compound provided herein can be combined with, for example, a Jak2 inhibitor (including, but not limited to, INCB018424, XL019, TG101348, or TG101209), an immuno-modulator, e.g., an IMID® (including, but not limited to thalidomide, lenalidomide, or panolinomide), hydroxyurea, an androgen, erythropoietic stimulating agents, prednisone, danazol, HDAC inhibitors, or other agents or therapeutic modalities (e.g., stem cell transplants, or radiation).

In certain embodiments wherein fibrosis or fibrotic condition of the heart is treated, prevented and/or managed, a compound provided herein can be combined with, for example, eplerenone, furosemide, pycnogenol, spironolactone, TcNC100692, torasemide (e.g., prolonged release form of torasemide), or combinations thereof.

In certain embodiments wherein fibrosis or fibrotic condition of the kidney is treated, prevented and/or managed, a compound provided herein can be combined with, for example, cyclosporine, cyclosporine A, daclizumab, everolimus, gadofoveset trisodium (ABLAVAR®), imatinib mesylate (GLEEVEC®), matinib mesylate, methotrexate, mycophenolate mofetil, prednisone, sirolimus, spironolactone, STX-100, tamoxifen, TheraCLEC™, or combinations thereof.

In certain embodiments wherein fibrosis or fibrotic condition of the skin is treated, prevented and/or managed, a compound provided herein can be combined with, for example, Bosentan (Tracleer), p144, pentoxifylline; pirfenidone; pravastatin, STI571, Vitamin E, or combinations thereof.

In certain embodiments wherein fibrosis or fibrotic condition of the gastrointestinal system is treated, prevented and/or managed, a compound provided herein can be combined with, for example, ALTU-135, bucelipase alfa (INN), DCI1020, EUR-1008 (ZENPEP™), ibuprofen, Lym-X-Sorb powder, pancrease MT, pancrelipase (e.g., pancrelipase delayed release), pentade canoic acid (PA), repaglinide, TheraCLEC™, triheptadecanoin (THA), ULTRASE MT20, ursodiol, or combinations thereof.

In certain embodiments wherein fibrosis or fibrotic condition of the lung is treated, prevented and/or managed, a compound provided herein can be combined with, for example, 18-FDG, AB0024, ACT-064992 (macitentan), aerosol interferon-gamma, aerosolized human plasma-derived alpha-1 antitrypsin, alphaI-proteinase inhibitor, ambrisentan, amikacin, amiloride, amitriptyline, anti-*pseudomonas* IgY gargle, ARIKACE™, AUREXIS® (tefibazumab), AZAPRED, azathioprine, azithromycin, azithromycin, AZLI, aztreonam lysine, BIBF1120, Bio-25 probiotic, bosentan, Bramitob® calfactant aerosol, captopril, CC-930, ceftazidime, ceftazidime, cholecalciferol (Vitamin D3), ciprofloxacin (CIPRO®, BAYQ3939), CNTO 888, colistin CF, combined Plasma Exchange (PEX), rituximab, and corticosteroids, cyclophosphamide, dapsone, dasatinib, denufosol tetrasodium (INS37217), domase alfa (PULMOZYME®), EPI-hNE4, erythromycin, etanercept, FG-3019, fluticasone, FTI, GC1008, GS-9411, hypertonic saline, ibuprofen, iloprost inhalation, imatinib mesylate (GLEEVEC®), inhaled sodium bicarbonate, inhaled sodium pyruvate, interferon gamma-1b, interferon-alpha lozenges, isotonic saline, IW001, KB001, losartan, lucinactant, mannitol, meropenem, meropenem infusion, miglustat, minocycline, Moli1901, MP-376 (levofloxacin solution for inhalation), mucoid exopolysaccharide *P. aeruginosa* immune globulin IV, mycophenolate mofetil, n-acetylcysteine, N-acetylcysteine (NAC), NaCl 6%, nitric oxide for inhalation, obramycin, octreotide, oligoG CF-5/20, Omalizumab, pioglitazone, piperacillin-tazobactam, pirfenidone, pomalidomide (CC-4047), prednisone, prevastatin, PRM-151, QAX576, rhDNAse, SB656933, SB-656933-AAA, sildenafil, tamoxifen, technetium [Tc-99m] sulfur colloid and Indium [In-111] DTPA, tetrathiomolybdate, thalidomide, ticarcillin-clavulanate, tiotropium bromide, tiotropium RESPIMAT® inhaler, tobramycin (GERNEBCIN®), treprostinil, uridine, valganciclovir (VALCYTE®), vardenafil, vitamin D3, xylitol, zileuton, or combinations thereof.

In certain embodiments wherein fibrosis or fibrotic condition of the liver is treated, prevented and/or managed, a compound provided herein can be combined with, for example, adefovir dipivoxil, candesartan, colchicine, combined ATG, mycophenolate mofetil, and tacrolimus, combined cyclosporine microemulsion and tacrolimus, elastometry, everolimus, FG-3019, Fuzheng Huayu, GI262570, glycyrrhizin (monoammonium glycyrrhizinate, glycine, L-cysteine monohydrochloride), interferon gamma-lb, irbesartan, losartan, oltipraz, ORAL IMPACT®, peginterferon alfa-2a, combined peginterferon alfa-2a and ribavirin, peginterferon alfa-2b (SCH 54031), combined peginterferon alpha-2b and ribavirin, praziquantel, prazosin, raltegravir, ribavirin (REBETOL®, SCH 18908), ritonavir-boosted protease inhibitor, pentoxyphilline, tacrolimus, tauroursodeoxycholic acid, tocopherol, ursodiol, warfarin, or combinations thereof.

In certain embodiments wherein cystic fibrosis is treated, prevented and/or managed, a compound provided herein can be combined with, for example, 552-02, 5-methyltetrahydrofolate and vitamin B12, Ad5-CB-CFTR, Adeno-associated virus-CFTR vector, albuterol, alendronate, alpha tocopherol plus ascorbic acid, amiloride HCl, aquADEK™, ataluren (PTC124), AZD1236, AZD9668, azithromycin, bevacizumab, biaxin (clarithromycin), BIIL 283 BS (amelubent), buprofen, calcium carbonate, ceftazidime, cholecalciferol, choline supplementation, CPX, cystic fibrosis transmembrane conductance regulator, DHA-rich supplement, digitoxin, cocosahexaenoic acid (DHA), doxycycline, ECGC, ecombinant human IGF-1, educed glutathione sodium salt, ergocalciferol (vitamin D2), fluorometholone, gadobutrol (GADOVIST, BAY86-4875), gentamicin, ghrelin, glargine, glutamine, growth hormone, GS-9411, H5.001CBCFTR, human recombinant growth hormone, hydroxychloroquine, hyperbaric oxygen, hypertonic saline, IH636 grape seed proanthocyanidin extract, insulin, interferon gamma-1b, IoGen (molecular iodine), iosartan potassium, isotonic saline, itraconazole, IV gallium nitrate (GANITE®) infusion, ketorolac acetate, lansoprazole, L-arginine, linezolid, lubiprostone, meropenem, miglustat, MP-376 (levofloxacin solution for inhalation), normal saline IV, Nutropin AQ, omega-3 triglycerides, pGM169/GL67A, pGT-1 gene lipid complex, pioglitazone, PTC124, QAU145, salmeterol, SB656933, SB656933, simvastatin, sitagliptin, sodium 4-phenylbutyrate, standardized turmeric root extract, tgAAVCF, TNF blocker, TOBI, tobramycin, tocotrienol, unconjugated Isoflavones 100, vitamin: choline bitartrate (2-hydroxyethyl) trimethylammonium salt 1:1, VX-770, VX-809, Zinc acetate, or combinations thereof.

In some embodiments, a compound provided herein is administered in combination with an agent that inhibits IgE production or activity. In some embodiments, the PI3K inhibitor (e.g., PI3Kδ inhibitor) is administered in combination with an inhibitor of mTOR. Agents that inhibit IgE production are known in the art and they include but are not limited to one or more of TEI-9874, 2-(4-(6-cyclohexyloxy-2-naphtyloxy)phenylacetamide)benzoic acid, rapamycin, rapamycin analogs (i.e. rapalogs), TORC1 inhibitors, TORC2 inhibitors, and any other compounds that inhibit mTORC1 and mTORC2. Agents that inhibit IgE activity include, for example, anti-IgE antibodies such as for example Omalizumab and TNX-901.

In certain embodiments wherein scleroderma is treated, prevented and/or managed, a compound provided herein can be combined with, for example: an immunosuppressant (e.g., methotrexate, azathioprine (Imuran®), cyclosporine, mycophenolate mofetil (Cellcept®), and cyclophosphamide (Cytoxan®)); T-cell-directed therapy (e.g., halofuginone, basiliximab, alemtuzumab, abatacept, rapamycin); B-cell directed therapy (e.g., rituximab); autologous hematopoietic stem cell transplantation; a chemokine ligand receptor antagonist (e.g., an agent that targets the CXCL12/CSCR4 axis (e.g., AMD3100)); a DNA methylation inhibitor (e.g., 5-azacytidine); a histone deacetylase inhibitor (e.g., trichostatin A); a statin (e.g., atorvastatin, simvastatin, pravastatin); an endothelin receptor antagonist (e.g., Bosentan®); a phosphodiesterase type V inhibitor (e.g., Sildenafil®); a prostacyclin analog (e.g., trepostinil); an inhibitor of cytokine synthesis and/or signaling (e.g., Imatinib mesylate, Rosiglitazone, rapamycin, antitransforming growth factor β1 (anti-TGFβ1) antibody, mycophenolate mofetil, an anti-IL-6 antibody (e.g., tocilizumab)); corticosteroids; nonsteroidal antiinflammatory drugs; light therapy; and blood pressure medications (e.g., ACE inhibitors).

In certain embodiments wherein inflammatory myopathies are treated, prevented and/or managed, a compound provided herein can be combined with, for example: topical creams or ointments (e.g., topical corticosteroids, tacrolimus, pimecrolimus); cyclosporine (e.g., topical cyclosporine); an anti-interferon therapy, e.g., AGS-009, Rontalizumab (rhuMAb IFNalpha), Vitamin D3, Sifalimumab (MEDI-545), AMG 811, IFNα Kinoid, or CEP33457. In some embodiments, the other therapy is an IFN-α therapy, e.g., AGS-009, Rontalizumab, Vitamin D3, Sifalimumab (MEDI-545) or IFNα Kinoid; corticosteroids such as prednisone (e.g., oral prednisone); immunosuppressive therapies such as methotrexate (Trexall®, Methotrexate®, Rheumatrex®), azathioprine (Azasan®, Imuran®), intravenous immunoglobulin, tacrolimus (Prograf®), pimecrolimus, cyclophosphamide (Cytoxan®), and cyclosporine (Gengraf®, Neoral®, Sandimmune®); anti-malarial agents such as hydroxychloroquine (Plaquenil®) and chloroquine (Aralen®); total body irradiation; rituximab (Rituxan®); TNF inhibitors (e.g., etanercept (Enbrel®), infliximab (Remicade®)); AGS-009; Rontalizumab (rhuMAb IFNalpha); Vitamin D3; Sifalimumab (MEDI-545); AMG 811; IFNα Kinoid; CEP33457; agents that inhibit IgE production such as TEI-9874, 2-(4-(6-cyclohexyloxy-2-naphtyloxy)phenylacetamide)benzoic acid, rapamycin, rapamycin analogs (i.e. rapalogs), TORC1 inhibitors, TORC2 inhibitors, and any other compounds that inhibit mTORC1 and mTORC2; agents that inhibit IgE activity such as anti-IgE antibodies (e.g., Omalizumab and TNX-90); and additional therapies such as physical therapy, exercise, rest, speech therapy, sun avoidance, heat therapy, and surgery.

In certain embodiments wherein myositis (e.g., dermatomysitis) is treated, prevented and/or managed, a compound provided herein can be combined with, for example: corticosteroids; corticosteroid sparing agents such as, but not limited to, azathioprine and methotrexate; intravenous immunoglobulin; immunosuppressive agents such as, but not limited to, tacrolimus, cyclophosphamide and cyclosporine; rituximab; TNFα inhibitors such as, but not limited to, etanercept and infliximab; growth hormone; growth hormone secretagogues such as, but not limited to, MK-0677, L-162752, L-163022, NN703 ipamorelin, hexarelin, GPA-748 (KPI02, GHRP-2), and LY444711 (Eli Lilly); other growth hormone release stimulators such as, but not limited to, Geref, GHRH (1-44), Somatorelin (GRF 1-44), ThGRF genotropin, L-DOPA, glucagon, and vasopressin; and insulin-like growth factor.

In certain embodiments wherein Sjögren's syndrome is treated, prevented and/or managed, a compound provided herein can be combined with, for example: pilocarpine; cevimeline; nonsteroidal anti-inflammatory drugs; arthritis medications; antifungal agents; cyclosporine; hydroxychloroquine; prednisone; azathioprine; and cyclophamide.

Further therapeutic agents that can be combined with a compound provided herein can be found in Goodman and Gilman's *"The Pharmacological Basis of Therapeutics"* Tenth Edition edited by Hardman, Limbird and Gilman or the Physician's Desk Reference, both of which are incorporated herein by reference in their entirety.

In one embodiment, the compounds described herein can be used in combination with the agents provided herein or other suitable agents, depending on the condition being treated. Hence, in some embodiments, a compound provided herein, or a pharmaceutically acceptable form thereof, will be co-administered with other agents as described above. When used in combination therapy, a compound described herein, or a pharmaceutically acceptable form thereof, can be administered with a second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound provided herein and any of the agents described above can be simultaneously administered, wherein both agents are present in separate formulations. In another alternative, a compound provided herein can be administered just followed by any of the agents described above, or vice versa. In the separate administration protocol, a compound provided herein and any of the agents described above can be administered a few minutes apart, or a few hours apart, or a few days apart.

Administration of a compound provided herein, or a pharmaceutically acceptable form thereof, can be effected by any method that enables delivery of the compound to the site of action. An effective amount of a compound provided herein, or a pharmaceutically acceptable form thereof, can be administered in either single or multiple doses by any of the accepted modes of administration of agents having similar utilities, including rectal, buccal, intranasal, and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

When a compound provided herein, or a pharmaceutically acceptable form thereof, is administered in a pharmaceutical composition that comprises one or more agents, and the agent has a shorter half-life than the compound provided herein, unit dose forms of the agent and the compound as provided herein can be adjusted accordingly.

In some embodiments, the compound provided herein and the second agent are administered as separate compositions, e.g., pharmaceutical compositions. In some embodiments, the PI3K modulator and the agent are administered separately, but via the same route (e.g., both orally or both intravenously). In other embodiments, the PI3K modulator and the agent are administered in the same composition, e.g., pharmaceutical composition.

In some embodiments, a compound provided herein (e.g., a compound of Formula I (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or an enantiomer or a mixture of enantiomers thereof, or a pharmaceutically acceptable salt, solvate, hydrate, co-crystal, clathrate, or polymorph thereof) is administered in combination with an agent for pulmonary or respiratory diseases. Examples of agents for pulmonary or respiratory diseases include, but are not limited to, Dymista (azelastine hydrochloride and fluticasone propionate), Kalydeco (ivacaftor), Qnasl (beclomethasone dipropionate) nasal aerosol, Rayos (prednisone) delayed-release tablets, Surfaxin (lucinactant), Tudorza Pressair (aclidinium bromide inhalation powder), Arcapta (indacaterol maleate inhalation powder), Daliresp (roflumilast), Xalkori (crizotinib), Cayston (aztreonam for inhalation solution), Dulera (mometasone furoate+formoterol fumarate dihydrate), Teflaro (ceftaroline fosamil), Adcirca (tadalafil), Tyvaso (treprostinil), Alvesco (ciclesonide), Patanase (olopatadine hydrochloride), Letairis (ambrisentan), Xyzal (levocetirizine dihydrochloride), Brovana (arformoterol tartrate), Tygacil (tigecycline), Ketek (telithromycin), Spiriva HandiHaler (tiotropium bromide), Aldurazyme (laronidase), Iressa (gefitinib), Xolair (omalizumab), Zemaira (alpha1-proteinase inhibitor), Clarinex, Qvar (beclomethasone dipropionate), Remodulin (treprostinil), Xopenex, Avelox I.V. (moxifloxacin hydrochloride), DuoNeb (albuterol sulfate and ipratropium bromide), Foradil Aerolizer (formoterol fumarate inhalation powder), Invanz, NasalCrom Nasal Spray, Tavist (clemastine fumarate), Tracleer (bosentan), Ventolin HFA (albuterol sulfate inhalation aerosol), Biaxin XL (clarithromycin extended-release tablets), Cefazolin and Dextrose USP, Tri-Nasal Spray (triamcinolone acetonide spray), Accolate, Cafcit Injection, Proventil HFA Inhalation Aerosol, Rhinocort Aqua Nasal Spray, Tequin, Tikosyn Capsules, Allegra-D, Clemastine fumarate syrup, Curosurf, Dynabac, Infasurf, Priftin, Pulmozyme (dornase alfa), Sclerosol Intrapleural Aerosol, Singulair, Synagis, Ceftin (cefuroxime axetil), Cipro (ciprofloxacin HCl), Claritin RediTabs (10 mg loratadine rapidly-disintegrating tablet), Flonase Nasal Spray, Flovent Rotadisk, Metaprotereol Sulfate Inhalation Solution (5%), Nasacort AQ (triamcinolone acetonide) Nasal Spray, Omnicef, Raxar (grepafloxacin), Serevent, Tilade (nedocromil sodium), Tobi, Vanceril 84 mcg Double Strength (beclomethasone dipropionate, 84 mcg) Inhalation Aerosol, Zagam (sparfloxacin) tablets, Zyflo (Zileuton), Accolate, Allegra (fexofenadine hydrochloride), Astelin nasal spray, Atrovent (ipratropium bromide), Augmentin (amoxicillin/clavulanate), Azmacort (triamcinolone acetonide) Inhalation Aerosol, Breathe Right, Claritin Syrup (loratadine), Claritin-D 24 Hour Extended Release Tablets (10 mg loratadine, 240 mg pseudoephedrine sulfate), Covera-HS (verapamil), Nasacort AQ (triamcinolone acetonide) Nasal Spray, OcuHist, Pulmozyme (dornase alfa), RespiGam (Respiratory Syncitial Virus Immune Globulin Intravenous), Tavist (clemastine fumarate), Tripedia (Diptheria and Tetanus Toxoids and Acellular Pertussis Vaccine Absorbed), Vancenase AQ 84 mcg Double Strength, Visipaque (iodixanol), Zosyn (sterile piperacillin sodium/tazobactam sodium), Cedax (ceftibuten), and Zyrtec (cetirizine HCl). In one embodiment, the agent for pulmonary or respiratory diseases is Arcapta, Daliresp, Dulera, Alvesco, Brovana, Spiriva HandiHaler, Xolair, Qvar, Xopenex, DuoNeb, Foradil Aerolizer, Accolate, Singulair, Flovent Rotadisk, Tilade, Vanceril, Zyflo, or Azmacort Inhalation Aerosol. In one embodiment, the agent for pulmonary or respiratory diseases is Spiriva HandiHaler.

In some embodiments, a compound provided herein (e.g., a compound of Formula I (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or an enantiomer or a mixture of enantiomers thereof, or a pharmaceutically acceptable salt, solvate, hydrate, co-crystal, clathrate, or polymorph thereof) is administered in combination with an agent for immunology or infectious diseases. Examples of agents for immunology or infectious diseases include, but are not limited to, Horizant (gabapentin enacarbil), Qnasl (beclomethasone dipropionate) nasal aerosol, Rayos (prednisone) delayed-release tablets, Stribild (elvitegravir, cobicistat, emtricitabine, tenofovir disoproxil fumarate), Tudorza Pressair (aclidinium bromide inhalation powder), Arcapta (indacaterol maleate inhalation powder), Benlysta (belimumab), Complera (emtricitabine/rilpivirine/tenofovir disoproxil fumarate), Daliresp (roflumilast), Dificid (fidaxomicin), Edurant (rilpivirine), Firazyr (icatibant), Gralise (gabapentin), Incivek (telaprevir), Nulojix (belatacept), Victrelis (boceprevir), Cayston (aztreonam for inhalation solution), Egrifta (tesamorelin for injection), Menveo (meningitis vaccine), Oravig (miconazole), Prevnar 13 (Pneumococcal 13-valent Conjugate Vaccine), Teflaro (ceftaroline fosamil), Zortress (everolimus), Zymaxid (gatifloxacin ophthalmic solution), Bepreve (bepotastine besilate ophthalmic solution), Berinert (C1 Esterase Inhibitor (Human)), Besivance (besifloxacin ophthalmic suspension), Cervarix [Human Papillomavirus Bivalent (Types 16 and 18) Vaccine, Recombinant], Coartem (artemether/lumefantrine), Hiberix (*Haemophilus* b Conjugate Vaccine; Tetanus Toxoid Conjugate), Ilaris (canakinumab), Ixiaro (Japanese Encephalitis Vaccine, Inactivated, Adsorbed), Kalbitor (ecallantide), Qutenza (capsaicin), Vibativ (telavancin), Zirgan (ganciclovir ophthalmic gel), Aptivus (tipranavir), Astepro (azelastine hydrochloride nasal spray), Cinryze (C1 Inhibitor (Human)), Intelence (etravirine), Moxatag (amoxicillin), Rotarix (Rotavirus Vaccine, Live, Oral), Tysabri (natalizumab), Viread (tenofovir disoproxil fumarate), Altabax (retapamulin), AzaSite (azithromycin), Doribax (doripenem), Extina (ketoconazole), Isentress (raltegravir), Selzentry (maraviroc), Veramyst (fluticasone furoate), Xyzal (levocetirizine dihydrochloride), Eraxis (anidulafungin), Gardasil (quadrivalent human papillomavirus (types 6, 11, 16, 18) recombinant vaccine), Noxafil (posaconazole), Prezista (darunavir), Rotateq (rotavirus vaccine, live oral pentavalent), Tyzeka (telbivudine), Veregen (kunecatechins), Aptivus (tipranavir), Baraclude (entecavir), Tygacil (tigecycline), Ketek (telithromycin), Tindamax, tinidazole, Xifaxan (rifaximin), Amevive (alefacept), FluMist (Influenza Virus Vaccine), Fuzeon (enfuvirtide), Lexiva (fosamprenavir calcium), Reyataz (atazanavir sulfate), Alinia (nitazoxanide), Clarinex, Daptacel, Fluzone Preservative-free, Hepsera (adefovir dipivoxil), Pediarix Vaccine, Pegasys (peginterferon alfa-2a), Restasis (cyclosporine ophthalmic emulsion), Sustiva, Vfend (voriconazole), Avelox I.V. (moxifloxacin hydrochloride), Cancidas, Peg-Intron (peginterferon alfa-2b), Rebetol (ribavirin), Spectracef, Twinrix, Valcyte (valganciclovir HCl), Viread (tenofovir disoproxil fumarate), Xigris (drotrecogin alfa [activated]), ABREVA (docosanol), Biaxin XL (clarithromycin extended-release tablets), Cefazolin and Dextrose USP, Children's Motrin Cold, Evoxac, Kaletra Capsules and Oral Solution, Lamisil (terbinafine hydrochloride) Solution (1%), Lotrisone (clotrimazole/betamethasone diproprionate) lotion, Malarone (atovaquone; proguanil hydrochloride) Tablet, Rapamune (sirolimus) Tablets, Rid Mousse, Tri-Nasal Spray (triamcinolone acetonide spray), Trivagizole 3 (clotrimazole) Vaginal Cream, Trizivir (abacavir sulfate; lamivudine; zidovudine AZT) Tablet, Agenerase (amprenavir), Cleocin (clindamycin phosphate), Famvir (famciclovir), Norvir (ritonavir), Panretin Gel, Rapamune (sirolimus) oral solution, Relenza, Synercid I.V., Tamiflu capsule, Vistide (cidofovir), Allegra-D, CellCept, Clemastine fumarate syrup, Cleocin (clindamycin phosphate), Dynabac, REBETRON™ Combination Therapy, Simulect, Timentin, Viroptic, INFANRIX (Diphtheria and Tetanus Toxoids and Acellular Pertussis Vaccine Adsorbed), Acyclovir Capsules, Aldara (imiquimod), Aphthasol, Combivir, Condylox Gel 0.5% (pokofilox), Famvir (famciclovir), Flagyl ER, Flonase Nasal Spray, Fortovase, INFERGEN (interferon alfacon-1), Intron A (interferon alfa-2b, recombinant), Norvir (ritonavir), Rescriptor Tablets (delavirdine mesylate tablets), SPORANOX (itraconazole), Stromectol (ivermectin), Taxol, Trovan, VIRACEPT (nelfinavir mesylate), Zerit (stavudine), Albenza (albendazole), Apthasol (Amlexanox), Carrington patch, Confide, Crixivan (Indinavir sulfate), Gastrocrom Oral Concentrate (cromolyn sodium), Havrix, Lamisil (terbinafine hydrochloride) Tablets, Leukine (sargramostim), Oral Cytovene, RespiGam (Respiratory Syncitial Virus Immune Globulin Intravenous), Videx (didanosine), Viramune (nevirapine), Vistide (cidofovir), Vitrasert Implant, Zithromax (azithromycin), Cedax (ceftibuten), Clarithromycin (Biaxin), Epivir (lamivudine), Intron A (Interferon alfa-2b, recombinant), Invirase (saquinavir), Valtrex (valacyclovir HCl), Western blot confirmatory device, Zerit (stavudine), and Zyrtec (cetirizine HCl).

In some embodiments, the second agent is an HDAC inhibitor, such as, e.g., belinostat, vorinostat, panobinostat, ACY-1215, or romidepsin.

In some embodiments, the second agent is an mTOR inhibitor, such as, e.g., everolimus (RAD 001).

In some embodiments, the second agent is a proteasome inhibitor, such as, e.g., bortezomib or carfilzomib.

In some embodiments, the second agent is a PKC-β inhibitor, such as, e.g., Enzastaurin (LY317615).

In some embodiments, the second agent is a JAK/STAT inhibitor, such as, e.g., INCB16562 or AZD1480.

In some embodiments, the second agent is an anti-folate, such as, e.g., pralatrexate.

In some embodiments, the second agent is a farnesyl transferase inhibitor, such as, e.g., tipifarnib.

In some embodiments, the second agent is an antibody or a biologic agent, such as, e.g., alemtuzumab, rituximab, ofatumumab, or brentuximab vedotin (SGN-035). In one embodiment, the second agent is rituximab. In one embodiment, the second agent is rituximab and the combination therapy is for treating, preventing, and/or managing iNHL, FL, splenic marginal zone, nodal marginal zone, extranodal marginal zone, and/or SLL.

In some embodiments, a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, is used in combination bendamustine and one additional active agent. In one embodiment, the cancer or hematological malignancy is iNHL.

In some embodiments, a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, is used in combination rituximab and one additional active agent. In one embodiment, the cancer or hematological malignancy is iNHL.

In some embodiments, a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, is used in combination bendamustine and rituximab. In one embodiment, the cancer or hematological malignancy is iNHL.

In some embodiments, a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, is used in combination fludarabine, cyclophosphamide, and rituximab. In one embodiment, the cancer or hematological malignancy is CLL.

In some embodiments, a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, is used in combination with an antibody or a biologic agent, such as, e.g., alemtuzumab, rituximab, ofatumumab, or brentuximab vedotin (SGN-035). In one embodiment, the second agent is rituximab. In one embodiment, the second agent is rituximab and the combination therapy is for treating, preventing, and/or managing iNHL, FL, splenic marginal zone, nodal marginal zone, extranodal marginal zone, and/or SLL.

In some embodiments, a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, is used in combination with an antibody-drug conjugate, such as, e.g., inotuzumab ozogamicin, or brentuximab vedotin.

In some embodiments, a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, is used in combination with a cytotoxic agent, such as, e.g., bendamustine, gemcitabine, oxaliplatin, cyclophosphamide, vincristine, vinblastine, anthracycline (e.g., daunorubicin or daunomycin, doxorubicin), actinomycin, dactinomycin, bleomycin, clofarabine, nelarabine, cladribine, asparaginase, methotrexate, or pralatrexate.

In some embodiments, a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, is used in combination with one or more other anti-cancer agents or chemotherapeutic agents, such as, e.g., fludarabine, ibrutinib, fostamatinib, lenalidomide, thalidomide, rituximab, cyclophosphamide, doxorubicin, vincristine, prednisone, or R-CHOP (Rituximab, Cyclophosphamide, Doxorubicin or Hydroxydaunomycin, Vincristine or Oncovin, Prednisone).

In some embodiments, a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, is used in combination with an antibody for a cytokine (e.g., an IL-15 antibody, an IL-21 antibody, an IL-4 antibody, an IL-7 antibody, an IL-2 antibody, an IL-9 antibody). In some embodiments, the second agent is a JAK1 inhibitor, a JAK3 inhibitor, a pan-JAK inhibitor, a BTK inhibitor, an SYK inhibitor, or a PI3K delta inhibitor. In some embodiments, the second agent is an antibody for a chemokine.

Without being limited to a particular theory, a targeted combination therapy described herein has reduced side effect and/or enhanced efficacy. For example, in one embodiment, provided herein is a combination therapy for treating CLL with a compound described herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, and a second active agent (e.g., IL-15 antibodies, IL-21 antibodies, IL-4 antibodies, IL-7 antibodies, IL-2 antibodies, IL-9 antibodies, JAK1 inhibitors, JAK3 inhibitors, pan-JAK inhibitors, BTK inhibitors, SYK inhibitors, and/or PI3K delta inhibitors).

Further without being limited by a particular theory, it was found that a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88) does not affect BTK or MEK pathway. Accordingly, in some embodiments, provided herein is a method of treating or managing cancer or hematological malignancy comprising administering to a patient a therapeutically effective amount of a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, in combination with a BTK inhibitor. In one embodiment, the BTK inhibitor is ibrutinib. In one embodiment, the BTK inhibitor is AVL-292. In one embodiment, the cancer or hematological malignancy is DLBCL. In another embodiment, the cancer or hematological malignancy is iNHL. In another embodiment, the cancer or hematological malignancy is CLL.

In other embodiments, provided herein is a method of treating or managing cancer or hematological malignancy comprising administering to a patient a therapeutically effective amount of a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, in combination with a MEK inhibitor. In one embodiment, the MEK inhibitor is trametinib/GSK1120212 (N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-1(2H)-yl}phenyl)acetamide), selumetinob (6-(4-bromo-2-chloroanilino)-7-fluoro-N-(2-hydroxyethoxy)-3-methylbenzimidazole-5-carboxamide), pimasertib/AS703026/MSC1935369 ((S)—N-(2,3-dihydroxypropyl)-3-((2-fluoro-4-iodophenyl)amino)isonicotinamide), XL-518/GDC-0973 (1-({3,4-difluoro-2-[(2-fluoro-4-iodophenyl)amino]phenyl}carbonyl)-3-[(2S)-piperidin-2-yl]azetidin-3-ol), refametinib/BAY869766/RDEA119 (N-(3,4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2,3-Dihydroxypropoxy]-3,4-difluoro-2-[(2-fluoro-4-iodophenyl)amino]-benzamide), TAK733 ((R)-3-(2,3-Dihydroxypropyl)-6-fluoro-5-(2-fluoro-4-iodophenylamino)-8-methylpyrido[2,3-d]pyrimidine-4,7(3H,8H)-dione), MEK162/ARRY438162 (5-[(4-Bromo-2-fluorophenyl)amino]-4-fluoro-N-(2-hydroxyethoxy)-1-methyl-1H-benzimidazole-6-carboxamide), RO5126766 (3-[[3-Fluoro-2-(methylsulfamoylamino)-4-pyridyl]methyl]-4-methyl-7-pyrimidin-2-yloxychromen-2-one), WX-554, RO4987655/CH4987655 (3,4-difluoro-2-((2-fluoro-4-iodophenyl)amino)-N-(2-hydroxyethoxy)-5-((3-oxo-1,2-oxazinan-2-yl)methyl)benzamide), or AZD8330 (2-((2-fluoro-4-iodophenyl)amino)-N-(2-hydroxyethoxy)-1,5-dimethyl-6-oxo-1,6-dihydropyridine-3-carboxamide). In one embodiment, the cancer or hematological malignancy is DLBCL. In another embodiment, the cancer or hematological malignancy is ALL. In another embodiment, the cancer or hematological malignancy is CTCL.

In other embodiments, provided herein is a method of treating or managing cancer or hematological malignancy comprising administering to a patient a therapeutically effective amount of a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, in combination with an EZH2 inhibitor. In one embodiment, the EZH2 inhibitor is EPZ-6438, GSK-126, GSK-343, Ell, or 3-deazaneplanocin A (DNNep). In one embodiment, the cancer or hematological malignancy is DLBCL. In another embodiment, the cancer or hematological malignancy is iNHL. In another embodiment, the cancer or hematological malignancy is ALL. In another embodiment, the cancer or hematological malignancy is CTCL.

In other embodiments, provided herein is a method of treating or managing cancer or hematological malignancy comprising administering to a patient a therapeutically effective amount of a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, in combination with a bcl-2 inhibitor. In one embodiment, the BCL2 inhibitor is ABT-199 (4-[4-[[2-(4-Chlorophenyl)-4,4-dimethylcyclohex-1-en-1-yl]methyl]piperazin-1-yl]-N-[[3-nitro-4-[[(tetrahydro-2H-pyran-4-yl)methyl]amino]phenyl]sulfonyl]-2-[(1H-pyrrolo[2,3-b]pyridin-5-yl)oxy]benzamide), ABT-737 (4-[4-[[2-(4-chlorophenyl)phenyl]methyl]piperazin-1-yl]-N-[4-[[(2R)-4-(dimethylamino)-1-phenylsulfanylbutan-2-yl]amino]-3-nitrophenyl]sulfonylbenzamide), ABT-263 ((R)-4-(4-((4'-chloro-4,4-dimethyl-3,4,5,6-tetrahydro-[1,1'-biphenyl]-2-yl)methyl)piperazin-1-yl)-N-((4-((4-morpholino-1-(phenylthio)butan-2-yl)amino)-3((trifluoromethyl)sulfonyl)phenyl)sulfonyl)benzamide), GX15-070 (obatoclax mesylate, (2Z)-2-[(5Z)-5-[(3,5-dimethyl-1H-pyrrol-2-yl)methylidene]-4-methoxypyrrol-2-ylidene]indole; methanesulfonic acid))), or G3139 (Oblimersen). In one embodiment, the cancer or hematological malignancy is DLBCL. In another embodiment, the cancer or hematological malignancy is iNHL. In another embodiment, the cancer or hematological malignancy is CLL. In another embodiment, the cancer or hematological malignancy is ALL. In another embodiment, the cancer or hematological malignancy is CTCL.

In other embodiments, provided herein is a method of treating or managing iNHL comprising administering to a patient a therapeutically effective amount of a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, in combination with rituximab. In one embodiment, the patient is an elderly patient. In another embodiment, iNHL is relapsed or refractory.

In other embodiments, provided herein is a method of treating or managing iNHL comprising administering to a patient a therapeutically effective amount of a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, in combination with bendamustine. In one embodiment, iNHL is relapsed or refractory.

In other embodiments, provided herein is a method of treating or managing iNHL comprising administering to a patient a therapeutically effective amount of a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, in combination with rituximab, and in further combination with bendamustine. In one embodiment, iNHL is relapsed or refractory.

In other embodiments, provided herein is a method of treating or managing iNHL comprising administering to a patient a therapeutically effective amount of a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, in combination with lenalidomide. In one embodiment, iNHL is relapsed or refractory.

In other embodiments, provided herein is a method of treating or managing CLL comprising administering to a patient a therapeutically effective amount of a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, in combination with rituximab. In one embodiment, the patient is an elderly patient. In another embodiment, CLL is relapsed or refractory.

In other embodiments, provided herein is a method of treating or managing CLL comprising administering to a patient a therapeutically effective amount of a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, in combination with bendamustine. In one embodiment, CLL is relapsed or refractory.

In other embodiments, provided herein is a method of treating or managing CLL comprising administering to a patient a therapeutically effective amount of a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, in combination with rituximab, and in further combination with bendamustine. In one embodiment, CLL is relapsed or refractory.

In other embodiments, provided herein is a method of treating or managing CLL comprising administering to a patient a therapeutically effective amount of a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, in combination with lenalidomide. In one embodiment, CLL is relapsed or refractory.

In other embodiments, provided herein is a method of treating or managing DLBCL comprising administering to a patient a therapeutically effective amount of a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, in combination with rituximab.

In one embodiment, the patient is an elderly patient. In another embodiment, DLBCL is relapsed or refractory.

In other embodiments, provided herein is a method of treating or managing DLBCL comprising administering to a patient a therapeutically effective amount of a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, in combination with bendamustine. In one embodiment, DLBCL is relapsed or refractory.

In other embodiments, provided herein is a method of treating or managing DLBCL comprising administering to a patient a therapeutically effective amount of a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, in combination with rituximab, and in further combination with bendamustine. In one embodiment, DLBCL is relapsed or refractory.

In other embodiments, provided herein is a method of treating or managing DLBCL comprising administering to a patient a therapeutically effective amount of a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, in combination with R-GDP (rituximab, cyclophosphamide, vincristine and prednisone). In one embodiment, DLBCL is relapsed or refractory. In another embodiment, the treatment is done subsequent to treatment by R-CHOP.

In other embodiments, provided herein is a method of treating or managing DLBCL comprising administering to a patient a therapeutically effective amount of a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, in combination with ibrutinib. In one embodiment, DLBCL is relapsed or refractory.

In other embodiments, provided herein is a method of treating or managing T-cell lymphoma (PTCL or CTCL) comprising administering to a patient a therapeutically effective amount of a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, in combination with rituximab. In one embodiment, T-cell lymphoma is relapsed or refractory.

In other embodiments, provided herein is a method of treating or managing T-cell lymphoma (PTCL or CTCL) comprising administering to a patient a therapeutically effective amount of a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, in combination with bendamustine. In one embodiment, T-cell lymphoma is relapsed or refractory.

In other embodiments, provided herein is a method of treating or managing T-cell lymphoma (PTCL or CTCL) comprising administering to a patient a therapeutically effective amount of a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, in combination with rituximab, and in further combination with bendamustine. In one embodiment, T-cell lymphoma is relapsed or refractory.

In other embodiments, provided herein is a method of treating or managing T-cell lymphoma (PTCL or CTCL) comprising administering to a patient a therapeutically effective amount of a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, in combination with romidepsin. In one embodiment, T-cell lymphoma is relapsed or refractory.

In other embodiments, provided herein is a method of treating or managing mantle cell lymphoma comprising administering to a patient a therapeutically effective amount of a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, in combination with rituximab. In one embodiment, mantle cell lymphoma is relapsed or refractory.

In other embodiments, provided herein is a method of treating or managing mantle cell lymphoma comprising administering to a patient a therapeutically effective amount of a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, in combination with bendamustine. In one embodiment, mantle cell lymphoma is relapsed or refractory.

In other embodiments, provided herein is a method of treating or managing mantle cell lymphoma comprising administering to a patient a therapeutically effective amount of a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, in combination with rituximab, an din further combination with bendamustine. In one embodiment, mantle cell lymphoma is relapsed or refractory.

In other embodiments, provided herein is a method of treating or managing mantle cell lymphoma comprising administering to a patient a therapeutically effective amount of a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, in combination with ibrutinib. In one embodiment, mantle cell lymphoma is relapsed or refractory.

Further, without being limited by a particular theory, it was found that cancer cells exhibit differential sensitivity profiles to doxorubicin and compounds provided herein. Thus, provided herein is a method of treating or managing cancer or hematological malignancy comprising administering to a patient a therapeutically effective amount of a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, in combination with a doxorubicin. In one embodiment, the cancer or hematological malignancy is ALL.

In some embodiments, provided herein is a method of treating or managing cancer or hematological malignancy comprising administering to a patient a therapeutically effective amount of a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, in combination with a AraC. In one embodiment, the cancer or hematological malignancy is AML.

In specific embodiments, compounds 2, 4, 7, 9, 17, 19, 21, 26, 27, 30, 32, 35, 37, 38, 40, 41, 52, 60, 61, 63, 73, 75, 77, 79, 80, 81, and 88 or a pharmaceutically acceptable form thereof, is used in combination with one or more second agent or second therapy provided herein.

In some embodiments, the second agent is an antibody-drug conjugate, such as, e.g., inotuzumab ozogamicin, or brentuximab vedotin.

In some embodiments, the second agent is a cytotoxic agent, such as, e.g., bendamustine, gemcitabine, oxaliplatin, cyclophosphamide, vincristine, vinblastine, anthracycline (e.g., daunorubicin or daunomycin, doxorubicin), actinomycin, dactinomycin, bleomycin, clofarabine, nelarabine, cladribine, asparaginase, methotrexate, or pralatrexate.

In some embodiments, the second agent is one or more other anti-cancer agents or chemotherapeutic agents, such as, e.g., fludarabine, ibrutinib, fostamatinib, lenalidomide, thalidomide, rituximab, cyclophosphamide, doxorubicin, vincristine, prednisone, or R-CHOP (Rituximab, Cyclophosphamide, Doxorubicin or Hydroxydaunomycin, Vincristine or Oncovin, Prednisone).

In some embodiments, the second agent is an antibody for a cytokine (e.g., an IL-15 antibody, an IL-21 antibody, an IL-4 antibody, an IL-7 antibody, an IL-2 antibody, an IL-9 antibody). In some embodiments, the second agent is a JAK1 inhibitor, a JAK3 inhibitor, a pan-JAK inhibitor, a BTK inhibitor, an SYK inhibitor, or a PI3K delta inhibitor. In some embodiments, the second agent is an antibody for a chemokine.

Without being limited to a particular theory, a targeted combination therapy described herein has reduced side effect and/or enhanced efficacy. For example, in one embodiment, provided herein is a combination therapy for treating CLL with a compound described herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88) and a second active agent (e.g., IL-15 antibodies, IL-21 antibodies, IL-4 antibodies, IL-7 antibodies, IL-2 antibodies, IL-9 antibodies, JAK1 inhibitors, JAK3 inhibitors, pan-JAK inhibitors, BTK inhibitors, SYK inhibitors, and/or PI3K delta inhibitors).

Further without being limited by a particular theory, it was found that a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88) does not affect BTK or MEK pathway. Accordingly, in some embodiments, provided herein is a method of treating or managing cancer or hematological malignancy comprising administering to a patient a therapeutically effective amount of a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, in combination with a BTK inhibitor. In one embodiment, the BTK inhibitor is ibrutinib. In one embodiment, the BTK inhibitor is AVL-292. In one embodiment, the cancer or hematological malignancy is DLBCL. In another embodiment, the cancer or hematological malignancy is CLL.

In other embodiments, provided herein is a method of treating or managing cancer or hematological malignancy comprising administering to a patient a therapeutically effective amount of a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, in combination with a MEK inhibitor. In one embodiment, the MEK inhibitor is tametinib, selumetinob, AS703026/MSC1935369, XL-518/GDC-0973, BAY869766/RDEA119, GSK1120212 (trametinib), pimasertib, refametinib, PD-0325901, TAK733, MEK162/ARRY438162, RO5126766, WX-554, RO4987655/CH4987655 or AZD8330. In one embodiment, the cancer or hematological malignancy is DLBCL. In another embodiment, the cancer or hematological malignancy is ALL. In another embodiment, the cancer or hematological malignancy is CTCL.

In other embodiments, provided herein is a method of treating or managing cancer or hematological malignancy comprising administering to a patient a therapeutically effective amount of a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, in combination with a bcl-2 inhibitor. In one embodiment, the BCL2 inhibitor is ABT-199, ABT-737, ABT-263, GX15-070 (obatoclax mesylate) or G3139 (Genasense). In one embodiment, the cancer or hematological malignancy is DLBCL. In another embodiment, the cancer or hematological malignancy is ALL. In another embodiment, the cancer or hematological malignancy is CTCL.

Further, without being limited by a particular theory, it was found that cancer cells exhibit differential sensitivity profiles to doxorubicin and compounds provided herein. Thus, provided herein is a method of treating or managing cancer or hematological malignancy comprising administering to a patient a therapeutically effective amount of a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, in combination with a doxorubicin. In one embodiment, the cancer or hematological malignancy is ALL.

In some embodiments, provided herein is a method of treating or managing cancer or hematological malignancy comprising administering to a patient a therapeutically effective amount of a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, in combination with a AraC. In one embodiment, the cancer or hematological malignancy is AML.

In specific embodiments, compounds 2, 4, 7, 9, 17, 19, 21, 26, 27, 30, 32, 35, 37, 38, 40, 41, 52, 60, 61, 63, 73, 75, 77, 79, 80, 81, and 88 or a pharmaceutically acceptable form thereof, is used in combination with one or more second agent or second therapy provided herein.

In certain embodiments, provided herein are pharmaceutical composition comprising a therapeutically effective amount of a compound provided herein (e.g., a compound of any of Formulae (I"), (I'), (A'), (I), (A), (II), (III), (IV), (V), (VI), (VII), (IX), (X), (XI), (XII), (XIII), (XIV), (XV), (XVI), and (XVII), e.g., a selective PI3K-γ inhibitor, e.g., Compound 4), or a pharmaceutically acceptable form thereof, and a PI3K-delta inhibitor.

In one embodiment, the PI3K-delta inhibitor is a PI3K-delta selective inhibitor. In one embodiment, the PI3K-delta inhibitor is GS-1101 (Cal-101), GSK-2269557, GS-9820, AMG319, or TGR-1202, or a mixture thereof. In one embodiment, the PI3K-delta inhibitor is of the formula:

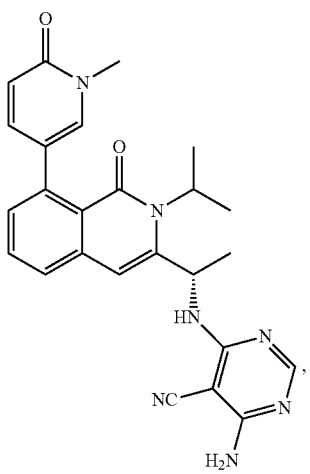 [SMILES: CC(C)n1c([C@H](C)Nc2ncnc(N)c2C#N)cc2cccc(-c3ccc(=O)n(C)c3)c2c1=O]

or a pharmaceutically acceptable form thereof.

In one embodiment, the molar ratio of the compound, or a pharmaceutically acceptable form thereof, to the PI3K-delta inhibitor is in the range of from about 10000:1 to about 1:10000. In one embodiment, the molar ratio of the compound, or a pharmaceutically acceptable form thereof, to the PI3K-delta inhibitor is in the range of from about 10:1 to about 1:10. In one embodiment, the composition comprises the compound, or a pharmaceutically acceptable form thereof, at an amount of in the range of from about 0.01 mg to about 75 mg and the PI3K-delta inhibitor at an amount of in the range of from about 0.01 mg to about 1100 mg. In one embodiment, the compound, or a pharmaceutically acceptable form thereof, and the PI3K-delta inhibitor are the only therapeutically active ingredients.

In one embodiment, the compound, or pharmaceutically acceptable form thereof, and the PI3K-delta inhibitor are in a single dosage form. In one embodiment, the compound, or pharmaceutically acceptable form thereof, and the PI3K-delta inhibitor are in separate dosage forms. In one embodiment, the composition further comprising a pharmaceutically acceptable excipient.

In one embodiment, the composition is synergistic in treating a cancer, inflammatory disease, or autoimmune disease.

In one embodiment, provided herein is a method of treating a PI3K-mediated disorder in a subject, comprising administering to the subject a therapeutically effective amount of the composition.

In certain embodiments, provided herein are methods treating a PI3K-mediated disorder in a subject, comprising administering to the subject a therapeutically effective amount of a compound provided herein (e.g., a compound of any of Formulae (I''), (I'), (A'), (I), (A), (II), (III), (IV), (V), (VI), (VII), (IX), (X), (XI), (XII), (XIII), (XIV), (XV), (XVI), and (XVII), e.g., a selective PI3K-γ inhibitor, e.g., Compound 4), or a pharmaceutically acceptable form thereof, in combination with a PI3K-delta inhibitor.

In one embodiment, the compound, or a pharmaceutically acceptable form thereof, is administered concurrently with the PI3K-delta inhibitor. In one embodiment, the compound, or a pharmaceutically acceptable form thereof, is administered subsequent to the PI3K-delta inhibitor. In one embodiment, the compound, or a pharmaceutically acceptable form thereof, is administered prior to the PI3K-delta inhibitor. In one embodiment, the compound, or a pharmaceutically acceptable form thereof, is administered alone after discontinuing the administration of the PI3K-delta inhibitor.

In one embodiment, the PI3K-mediated disorder is a cancer, autoimmune disease, or inflammatory disease. In one embodiment, the cancer is of hematopoietic origin. In one embodiment, the cancer is a leukemia or lymphoma. In one embodiment, the leukemia or lymphoma is a B-cell lymphoma, T-cell lymphoma, non-Hodgkin lymphoma, Hodgkin lymphoma, or anaplastic large cell lymphoma.

In one embodiment, the cancer is a solid tumor. In one embodiment, the cancer is selected from one or more of: a cancer of the pulmonary system, a brain cancer, a cancer of the gastrointestinal tract, a skin cancer, a genitourinary cancer, a pancreatic cancer, a lung cancer, a medullobastoma, a basal cell carcinoma, a glioma, a breast cancer, a prostate cancer, a testicular cancer, an esophageal cancer, a hepatocellular cancer, a gastric cancer, a gastrointestinal stromal tumor (GIST), a colon cancer, a colorectal cancer, an ovarian cancer, a melanoma, a neuroectodermal tumor, head and neck cancer, a sarcoma, a soft-tissue sarcoma, fibrosarcoma, myxosarcoma, liposarcoma, a chondrosarcoma, an osteogenic sarcoma, a chordoma, an angiosarcoma, an endotheliosarcoma, a lymphangiosarcoma, a lymphangioendotheliosarcoma, a synovioma, a mesothelioma, a leiomyosarcoma, a cervical cancer, a uterine cancer, an endometrial cancer, a carcinoma, a bladder carcinoma, an epithelial carcinoma, a squamous cell carcinoma, an adenocarcinoma, a bronchogenic carcinoma, a renal cell carcinoma, a hepatoma, a bile duct carcinoma, a neuroendocrine cancer, a carcinoid tumor, diffuse type giant cell tumor, and glioblastoma.

In one embodiment, the PI3K-delta inhibitor is a PI3K-delta selective inhibitor. In one embodiment, the PI3K-delta inhibitor is of the formula:

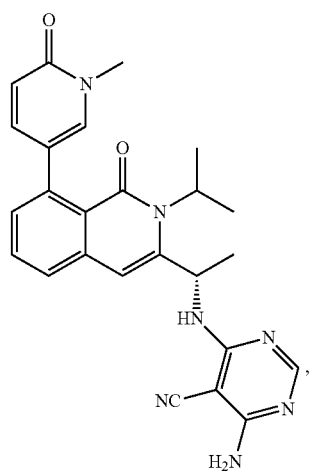 [SMILES: CC(C)n1c([C@H](C)Nc2ncnc(N)c2C#N)cc2cccc(-c3ccc(=O)n(C)c3)c2c1=O]

or a pharmaceutically acceptable form thereof.

In one embodiment, the compound, or a pharmaceutically acceptable form thereof, and the PI3K-delta inhibitor are in a single dosage form. In one embodiment, the compound, or a pharmaceutically acceptable form thereof, and the PI3K-delta inhibitor are in separate dosage forms.

In one embodiment, the concentration of the compound that is required to achieve 50% inhibition is at least 20%, 30%, 40%, or 50% lower when the compound is administered in combination with the PI3K-delta inhibitor than when the compound is administered individually. In one embodiment, the concentration of the PI3K-delta inhibitor that is required to achieve 50% inhibition is at least 20%, 30%, 40%, or 50% lower when the PI3K-delta inhibitor is administered in combination with the compound than when the PI3K-delta inhibitor is administered individually. In one embodiment, the dose of the compound that is required to achieve 50% inhibition is at least 20%, 30%, 40%, or 50% lower when the compound is administered in combination with the PI3K-delta inhibitor than when the compound is administered individually. In one embodiment, the dose of the PI3K-delta inhibitor that is required to achieve 50% inhibition is at least 20%, 30%, 40%, or 50% lower when the PI3K-delta inhibitor is administered in combination with the compound than when the PI3K-delta inhibitor is administered individually.

In one embodiment, the combination is synergistic as indicated by a combination index value that is less than 0.7, 0.5, or 0.1 for the combination of the compound and the PI3K-delta inhibitor. In one embodiment, the combination index value is assessed at 50% inhibition. In one embodiment, the combination index value is assessed at 50% growth inhibition. In one embodiment, the combination is synergistic as indicated by a Synergy Score that is greater than 1, 2, or 3 for the combination of the Compound 4 and the PI3K-delta inhibitor. In one embodiment, the combination is synergistic as indicated by a Synergy Score that is greater than 1, 2, or 3, for the combination of the compound and the PI3K-delta inhibitor for inhibition or growth inhibition.

In one embodiment, the PI3K-mediated disorder is cancer, and the anti-cancer effect provided by the combination is at least 2 fold greater, at least 3 fold greater, at least 5 fold greater, or at least 10 fold greater than the anti-cancer effect provided by Compound 4, or pharmaceutically acceptable form thereof, alone. In one embodiment, the PI3K-mediated disorder is cancer, and the anti-cancer effect provided by the combination is at least 2 fold greater, at least 3 fold greater, at least 5 fold greater, or at least 10 fold greater than the anti-cancer effect provided by the PI3K-delta inhibitor alone.

In one embodiment, wherein one or more side effects associated with administration of the compound, or a pharmaceutically acceptable form thereof, alone is reduced when the combination is administered at a dose that achieves the same therapeutic effect. In one embodiment, one or more side effects associated with administration of the PI3K-delta inhibitor alone is reduced when the combination is administered at a dose that achieves the same therapeutic effect.

Combinations with Immune Modulators

While not wishing to be bound by theory, it is believed that tumor growth is influenced by at least two classes of immune cells in the tumor microenvironment: effector cells (including cytotoxic cells and M1 macrophages) which have anti-tumor activity, and tumor associated suppressor cells (including M2 macrophages, MDSC, Tregs, and regulatory dendritic cells) which have pro-tumor activity because they inhibit the effector cells or provide direct growth stimulation to the tumor cells or tumor vasculature. An abundance of suppressor cells can lead to tumor immune tolerance, and enhancement of tumor growth. A combination cancer therapy can be designed taking this mechanism into consideration.

For example, in embodiments, a PI3K-γ inhibitor as described herein (or a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88)) is administered in combination with a second therapeutic that blocks homeostatic down-regulation of a T cell response in an effector T cell. This second agent may be an immune checkpoint therapy as described below. As another example, in embodiments, a PI3K-γ inhibitor as described herein is administered in combination with a second therapeutic that reduces or eliminates suppressive cells in the tumor microenvironment, e.g., may deplete MDSCs, TAMs or M2 macrophages, or any combination thereof. This agent could comprise, e.g., a CSF1R inhibitor, a CCL2 inhibitor, a CXCR4 inhibitor, a MEK inhibitor, or an MTOR inhibitor, or any combination thereof. In some embodiments, the second agent is an immunotherapy such as a tumor vaccine, e.g., a tumor vaccine described herein. In some embodiments, the second agent is a cell therapy, e.g., a dendritic cell or a chimeric T cell, e.g., as described herein. In some embodiments, the second agent is an interleukin, e.g., IL7, IL12, IL15, or IL21. According to non-limiting theory, some interleukins exert an anti-cancer effect by stimulating the growth of immune cell populations.

In another embodiment, a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88) is administered in combination with a vaccine, e.g., a cancer vaccine, (e.g., a dendritic cell renal carcinoma (DC-RCC) vaccine). In certain embodiments, the combination of compound and the DC-RCC vaccine is used to treat a cancer, e.g., a cancer as described herein (e.g., a renal carcinoma, e.g., metastatic renal cell carcinoma (RCC) or clear cell renal cell carcinoma (CCRCC)).

In some embodiments, a compound provided herein, or a pharmaceutically acceptable derivative (e.g., salt or solvate) thereof, is administered in combination with one or more immune checkpoint therapies. In some embodiments, provided herein is a method of treating a cancer in a subject, comprising administering to the subject a PI3K gamma inhibitor or a compound as described herein (e.g., a compound of any of Formulae (I″), (I′), (A′), (I), (A), (II), (III), (IV), (V), (VI), (VII), (IX), (X), (XI), (XII), (XIII), (XIV), (XV), (XVI), and (XVII), e.g., Compound 4, as described herein) in combination with one or more immune checkpoint therapies (e.g., PD-1 or PD-L1 inhibitors). In some embodiments, provided herein is a method of treating a solid cancer in a subject, comprising administering to the subject Compound 4, or a pharmaceutically acceptable form thereof, in combination with one or more of PD-1 or PD-L1 inhibitors. In one embodiment, the cancer is melanoma, bladder cancer, head and neck cancer, lung cancer (e.g., non-small cell lung cancer), or renal cell carcinoma. In one embodiment, the cancer is melanoma. In one embodiment, the cancer is bladder cancer. In one embodiment, the cancer is lung cancer. In one embodiment, the cancer is non-small cell lung cancer. In one embodiment, the cancer is renal cell carcinamo. In one embodiment, the cancer is head and neck cancer. In one embodiment, the cancer is breast cancer. In one embodiment, the cancer is triple-negative breast cancer. In one embodiment, the cancer is colon cancer. In one embodiment, the cancer is glioblastoma. In one embodiment, the cancer is ovarian cancer.

In some embodiments, the subject is naive to immunotherapy treatment. In some embodiments, the subject is naive to radiation therapy treatment. In some embodiments, the subject is naive to chemotherapy treatment.

In some embodiments, the subject has been pre-treated or previously treated with one or more immunotherapy treatments. In one embodiment, the subject is responsive to the pre-treatment or previous treatment with the immunotherapy. In one embodiment, the immunotherapy treatment is a checkpoint treatment such as a PD-1 or PD-L1 inhibitor. In one embodiment, the subject is a smoker.

In one embodiment, the cancer is melanoma, and the subject has been pre-treated or previously treated with one or more immunotherapy treatments. In one embodiment, the subject has been pre-treated or previously treated with two or more immunotherapy treatments.

In one embodiment, the cancer is head and neck cancer, lung cancer (e.g., non-small cell lung cancer), renal cell carcinoma, or bladder cancer, and the subject has been pre-treated or previously treated with one immunotherapy treatment.

In one embodiment, the cancer is breast cancer (e.g., triple-negative breast cancer), ovarian cancer, glioblastoma, or colon cancer, and the subject is naive to immunotherapy treatment.

In some embodiments, the immune checkpoint therapy inhibits CTLA-4, PD-1, or PD-L1, or any combination thereof. The immune checkpoint therapy may be, e.g., a small molecule or an antibody. In some embodiments, the immune checkpoint therapy is an antibody that inhibits programmed cell death 1 (also known as PD-1). In another embodiment, the immune checkpoint therapy is nivolumab (also known as Opdivo). In some embodiments, the immune checkpoint therapy is anti-PD-L1 (programmed cell death ligand 1, also known as cluster of differentiation 274 (CD274)), anti-PDL2, or anti-CTLA-4 (cytotoxic T-lymphocyte antigen 4, also known as cluster of differentiation (CD152)) antibody. Certain anti-PD-1, anti-PD-L1, and anti-CTLA-4 antibodies have activity in preclinical and clinical tumor models. Cancer Res; 73(12) Jun. 15, 2013; Curran M A et al. PNAS 2010; 107:4275-4280; Topalian et al. N Engl J Med 2012; 366:2443-2454; Wolchok et al., 2013. NEJM 369.

There are two main types of immune checkpoint therapies: an activator of a costimulatory molecule, and an inhibitor of an immune checkpoint molecule.

When the immune checkpoint therapy is an activator of a costimulatory molecule, it may be, e.g., chosen from an agonist (e.g., an agonistic antibody or antigen-binding fragment thereof, or a soluble fusion) of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand. In certain embodiments, the immune checkpoint therapy is an inhibitor of OX40 or anti-OX40 ab.

In the second situation, the immune checkpoint therapy is an inhibitor of an immune checkpoint molecule, for instance, an inhibitor of PD-1, PD-L1, PD-L2, CTLA4, TIM3, LAG3, VISTA, BTLA, TIGIT, LAIR1, CD160, 2B4 and/or TGFR beta. For instance, the inhibitor of an immune checkpoint molecule may inhibit PD-1, PD-L1, LAG-3, TIM-3 or CTLA4, or any combination thereof.

Inhibition of an inhibitory molecule can be performed at the DNA, RNA or protein level. For example, an inhibitory nucleic acid (e.g., a dsRNA, siRNA or shRNA), can be used to inhibit expression of an inhibitory molecule. In other embodiments, the inhibitor of an inhibitory signal is, a polypeptide e.g., a soluble ligand (e.g., PD-1-Ig or CTLA-4 Ig), or an antibody or antigen-binding fragment thereof, that binds to the inhibitory molecule; e.g., an antibody or fragment thereof (also referred to herein as "an antibody molecule") that binds to PD-1, PD-L1, PD-L2, CTLA4, TIM3, LAG3, VISTA, BTLA, TIGIT, LAIR1, CD160, 2B4 and/or TGFR beta, or a combination thereof. The antibody molecule may be, e.g., a full antibody or fragment thereof (e.g., a Fab, F(ab')$_2$, Fv, or a single chain Fv fragment (scFv)). The antibody molecule may be, e.g., in the form of a bispecific antibody molecule. In one embodiment, the bispecific antibody molecule has a first binding specificity to PD-1 or PD-L1 and a second binding specifity, e.g., a second binding specificity to TIM-3, LAG-3, or PD-L2. In certain embodiments, the antibody molecule is administered by injection (e.g., subcutaneously or intravenously) at a dose of about 1 to 30 mg/kg, e.g., about 5 to 25 mg/kg, about 10 to 20 mg/kg, about 1 to 5 mg/kg, or about 3 mg/kg. The dosing schedule can vary from e.g., once a week to once every 2, 3, or 4 weeks.

In certain embodiments, the immune checkpoint therapy is an inhibitor of PD-1, e.g., human PD-1. In another embodiment, the immune checkpoint therapy is an inhibitor of PD-L1, e.g., human PD-L1. In one embodiment, the inhibitor of PD-1 or PD-L1 is an antibody molecule to PD-1 or PD-L1. The PD-1 or PD-L1 inhibitor can be administered alone, or in combination with other immune checkpoint therapies, e.g., in combination with an inhibitor of LAG-3, TIM-3 or CTLA4. In some embodiments, the inhibitor of PD-1 or PD-L1, e.g., the anti-PD-1 or PD-L1 antibody molecule, is administered in combination with a LAG-3 inhibitor, e.g., an anti-LAG-3 antibody molecule. In another embodiment, the inhibitor of PD-1 or PD-L1, e.g., the anti-PD-1 or PD-L1 antibody molecule, is administered in combination with a TIM-3 inhibitor, e.g., an anti-TIM-3 antibody molecule. In yet other embodiments, the inhibitor of PD-1 or PD-L1, e.g., the anti-PD-1 antibody molecule, is administered in combination with a LAG-3 inhibitor, e.g., an anti-LAG-3 antibody molecule, and a TIM-3 inhibitor, e.g., an anti-TIM-3 antibody molecule. Other combinations of immune checkpoint therapies with a PD-1 inhibitor (e.g., one or more of PD-L2, CTLA4, TIM3, LAG3, VISTA, BTLA, TIGIT, LAIR1, CD160, 2B4 and/or TGFR) are also within the present invention. Any of the PI3K inhibitor molecules known in the art or disclosed herein can be used in the aforesaid combinations of inhibitors of checkpoint molecule.

In some embodiments, the anti-PD-1 antibody is Nivolumab. Alternative names for Nivolumab include MDX-1106, MDX-1106-04, ONO-4538, or BMS-936558. In some embodiments, the anti-PD-1 antibody is Nivolumab (CAS Registry Number: 946414-94-4). Nivolumab is a fully human IgG4 monoclonal antibody which specifically blocks PD1. Nivolumab (clone 5C4) and other human monoclonal antibodies that specifically bind to PD1 are disclosed in U.S. Pat. No. 8,008,449 and WO2006/121168.

In other embodiments, the anti-PD-1 antibody is Pembrolizumab. Pembrolizumab (Trade name KEYTRUDA formerly Lambrolizumab, also known as Merck 3745, MK-3475 or SCH-900475) is a humanized IgG4 monoclonal antibody that binds to PD1. Pembrolizumab is disclosed, e.g., in Hamid, O. et al. (2013) *New England Journal of Medicine* 369 (2): 134-44, WO2009/114335, and U.S. Pat. No. 8,354,509.

In some embodiments, the anti-PD-1 antibody is Pidilizumab. Pidilizumab (CT-011; Cure Tech) is a humanized IgG1k monoclonal antibody that binds to PD1. Pidilizumab and other humanized anti-PD-1 monoclonal antibodies are disclosed in WO2009/101611. Other anti-PD1 antibodies are disclosed in U.S. Pat. No. 8,609,089, US 2010028330, and/or US 20120114649. Other anti-PD1 antibodies include AMP 514 (Amplimmune).

In some embodiments, the PD-1 inhibitor is an immunoadhesin (e.g., an immunoadhesin comprising an extracellular or PD-1 binding portion of PD-L1 or PD-L2 fused to a constant region (e.g., an Fc region of an immunoglobulin sequence)). In some embodiments, the PD-1 inhibitor is AMP-224. In some embodiments, a PI3K inhibitor, e.g., a PI3K-γ inhibitor as described herein (e.g., Compound 4), is administered together with an immunoadhesin (e.g., an immunoadhesin comprising an extracellular or PD-1 binding portion of PD-L1 or PD-L2 fused to a constant region (e.g., an Fc region of an immunoglobulin sequence)). In some embodiments, the combination therapy is used in a method of treating a cancer, as described herein.

In some embodiments, the PD-L1 inhibitor is anti-PD-L antibody. In some embodiments, the anti-PD-L1 inhibitor is chosen from YW243.55.S70, MPDL3280A, MEDI-4736, MSB-0010718C, or MDX-1105.

In one embodiment, the PD-L1 inhibitor is MDX-1105. MDX-1105, also known as BMS-936559, is an anti-PD-L1 antibody described in WO2007/005874.

In one embodiment, the PD-L1 inhibitor is YW243.55.S70. The YW243.55.S70 antibody is an anti-PD-L1 described in WO 2010/077634 (heavy and light chain variable region sequences shown in SEQ ID Nos. 20 and 21, respectively).

In one embodiment, the PD-L1 inhibitor is MDPL3280A (Genentech/Roche). MDPL3280A is a human Fc optimized IgG1 monoclonal antibody that binds to PD-L1. MDPL3280A and other human monoclonal antibodies to PD-L1 are disclosed in U.S. Pat. No. 7,943,743 and U.S Publication No.: 20120039906.

In other embodiments, the PD-L2 inhibitor is AMP-224. AMP-224 is a PD-L2 Fc fusion soluble receptor that blocks the interaction between PD1 and B7-H1 (B7-DCIg; Amplimmune; e.g., disclosed in WO2010/027827 and WO2011/066342).

In one embodiment, the LAG-3 inhibitor is an anti-LAG-3 antibody molecule. In one embodiment, the LAG-3 inhibitor is BMS-986016.

In some embodiments, the anti-PD-L1 binding antagonist is chosen from YW243.55.S70, MPDL3280A, MEDI-4736, MSB-0010718C, or MDX-1105. MDX-1105, also known as BMS-936559, is an anti-PD-L1 antibody described in WO2007/005874. Antibody YW243.55.S70 (heavy and light chain variable region sequences shown in SEQ ID Nos. 20 and 21, respectively) is an anti-PD-L described in WO 2010/077634.

In some embodiments, the anti-PD-1 antibody is Nivolumab. Alternative names for Nivolumab include MDX-1106, MDX-1106-04, ONO-4538, or BMS-936558. In some embodiments, the anti-PD-1 antibody is Nivolumab (CAS Registry Number: 946414-94-4). Nivolumab (also referred to as BMS-936558 or MDX1106; Bristol-Myers Squibb) is a fully human IgG4 monoclonal antibody which specifically blocks PD-1. Nivolumab (clone 5C4) and other human monoclonal antibodies that specifically bind to PD-1 are disclosed in U.S. Pat. No. 8,008,449, EP2161336 and WO2006/121168.

In some embodiments, the anti-PD-1 antibody is Pembrolizumab. Pembrolizumab (also referred to as Lambrolizumab, MK-3475, MK03475, SCH-900475 or KEYTRUDA®; Merck) is a humanized IgG4 monoclonal antibody that binds to PD-1. Pembrolizumab and other humanized anti-PD-1 antibodies are disclosed in Hamid, O. et al. (2013) *New England Journal of Medicine* 369 (2): 134-44, U.S. Pat. No. 8,354,509 and WO2009/114335.

Pidilizumab (CT-011; Cure Tech) is a humanized IgG1k monoclonal antibody that binds to PD1. Pidilizumab and other humanized anti-PD-1 monoclonal antibodies are disclosed in WO2009/101611.

Other anti-PD1 antibodies include AMP 514 (Amplimmune), among others, e.g., anti-PD1 antibodies disclosed in U.S. Pat. No. 8,609,089, US 2010028330, and/or US 20120114649.

In some embodiments, the anti-PD-L1 antibody is MSB0010718C. MSB0010718C (also referred to as A09-246-2; Merck Serono) is a monoclonal antibody that binds to PD-L1. Pembrolizumab and other humanized anti-PD-L1 antibodies are disclosed in WO2013/079174.

MDPL3280A (Genentech/Roche) is a human Fc optimized IgG1 monoclonal antibody that binds to PD-L1. MDPL3280A and other human monoclonal antibodies to PD-L1 are disclosed in U.S. Pat. No. 7,943,743 and U.S Publication No.: 20120039906. Other anti-PD-L1 binding agents include YW243.55.S70 (heavy and light chain variable regions are shown in SEQ ID NOs 20 and 21 in WO2010/077634) and MDX-1105 (also referred to as BMS-936559, and, e.g., anti-PD-L1 binding agents disclosed in WO2007/005874).

AMP-224 (B7-DCIg; Amplimmune; e.g., disclosed in WO2010/027827 and WO2011/066342), is a PD-L2 Fc fusion soluble receptor that blocks the interaction between PD1 and B7-H1.

In some embodiments, the anti-LAG-3 antibody is BMS-986016. BMS-986016 (also referred to as BMS986016; Bristol-Myers Squibb) is a monoclonal antibody that binds to LAG-3. BMS-986016 and other humanized anti-LAG-3 antibodies are disclosed in US 2011/0150892, WO2010/019570, and WO2014/008218.

In certain embodiments, the combination therapies disclosed herein include a modulator of a costimulatory molecule or an inhibitory molecule, e.g., a co-inhibitory ligand or receptor.

In one embodiment, the costimulatory modulator, e.g., agonist, of a costimulatory molecule is chosen from an agonist (e.g., an agonistic antibody or antigen-binding fragment thereof, or soluble fusion) of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand.

In another embodiment, the combination therapies disclosed herein include a costimulatory molecule, e.g., an agonist associated with a positive signal that includes a costimulatory domain of CD28, CD27, ICOS and GITR.

Exemplary GITR agonists include, e.g., GITR fusion proteins and anti-GITR antibodies (e.g., bivalent anti-GITR antibodies), such as, a GITR fusion protein described in U.S. Pat. No. 6,111,090, European Patent No.: 090505B1, U.S. Pat. No. 8,586,023, PCT Publication Nos.: WO 2010/003118 and 2011/090754, or an anti-GITR antibody described, e.g., in U.S. Pat. No. 7,025,962, European Patent No.: 1947183B1, U.S. Pat. Nos. 7,812,135, 8,388,967, 8,591,886, European Patent No.: EP 1866339, PCT Publication No.: WO 2011/028683, PCT Publication No.:WO 2013/039954, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, PCT Publication No.: WO2006/083289, PCT Publication No.: WO 2005/115451, U.S. Pat. No. 7,618,632, and PCT Publication No.: WO 2011/051726.

In one embodiment, the inhibitor is a soluble ligand (e.g., a CTLA-4-Ig), or an antibody or antibody fragment that binds to PD-L1, PD-L2 or CTLA4. For example, a compound disclosed herein, e.g., Compound 4, can be administered in combination with an anti-CTLA-4 antibody, e.g., ipilimumab, for example, to treat a cancer (e.g., a cancer chosen from: a melanoma, e.g., a metastatic melanoma; a lung cancer, e.g., a non-small cell lung carcinoma; or a prostate cancer). Exemplary anti-CTLA4 antibodies include Tremelimumab (IgG2 monoclonal antibody available from Pfizer, formerly known as ticilimumab, CP-675,206); and Ipilimumab (CTLA-4 antibody, also known as MDX-010, Yervoy, CAS No. 477202-00-9). In some embodiments, a compound provided herein is administered in combination with an anti-PD-L1 inhibitor (e.g., nivolumab) and a CTLA-4 antibody (e.g., ipilimumab). In some embodiments, a compound provided herein is administered in combination with nivolumab and ipilimumab.

In some embodiments, a compound provided herein, or a pharmaceutically acceptable derivative (e.g., salt or solvate) thereof, is administered in combination with an anti-PD-L1 or anti-CTLA-4 antibody. In some embodiments, a compound provided herein, or a pharmaceutically acceptable derivative (e.g., salt or solvate) thereof, is administered in combination with an anti-PD-L1 antibody. In another embodiment, a compound provided herein, or a pharmaceutically acceptable derivative (e.g., salt or solvate) thereof, is administered in combination with anti-CTLA-4 antibody. In some embodiments, the anti-PD-L1 antibody is selected from BMS-936559, MPDL3280A, and MDX-1105. In some embodiments, the anti-CTLA-4 antibody is selected from ipilimumab and tremelimumab.

In some embodiments, provided herein is a method of treating breast cancer, colon cancer, pancreatic cancer, melanoma, glioblastoma, or lung cancer comprising administering to a patient a therapeutically effective amount of a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88), or a pharmaceutically acceptable derivative (e.g., salt or solvate) thereof, in combination with an anti-PD-L1 or an anti-CTLA-4 antibody. In another embodiment, the cancer is chosen form a carcinoma (e.g., advanced or metastatic carcinoma), melanoma or a lung carcinoma, e.g., a non-small cell lung carcinoma. In one embodiment, the cancer is a lung cancer, e.g., a non-small cell lung cancer. In one embodiment, the cancer is a melanoma, e.g., an advanced melanoma. In one embodiment, the cancer is an advanced or unresectable melanoma that does not respond to other therapies. In other embodiments, the cancer is a melanoma with a BRAF mutation (e.g., a BRAF V600E mutation). In another embodiment, the cancer is a hepatocarcinoma, e.g., an advanced hepatocarcinoma, with or without a viral infection, e.g., a chronic viral hepatitis. In another embodiment, the cancer is a prostate cancer, e.g., an advanced prostate cancer. In yet another embodiment, the cancer is a myeloma, e.g., multiple myeloma. In yet another embodiment, the cancer is a renal cancer, e.g., a renal cell carcinoma (RCC) (e.g., a metastatic RCC or clear cell renal cell carcinoma (CCRCC)).

For example, a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88) can be administered in combination with an anti-CTLA-4 antibody, e.g., ipilimumab, for example, to treat a cancer (e.g., a cancer chosen from: a melanoma, e.g., a metastatic melanoma; a lung cancer, e.g., a non-small cell lung carcinoma; or a prostate cancer). In one embodiment, a compound provided herein (e.g., compounds 2, 4, 7, 9, 17, 19, 21, 26, 27, 30, 32, 35, 37, 38, 40, 41, 52, 60, 61, 63, 73, 75, 77, 79, 80, 81, and 88) is administered after treatment with an anti-CTLA4 antibody (e.g., ipilimumab) with or without a BRAF inhibitor (e.g., vemurafenib or dabrafenib).

In some embodiments, the immune checkpoint therapy is a costimulatory ligand. In some embodiments, the costimulatory ligand is OX40L, 41BBL, CD153, ICOSL, or CD40L.

In some embodiments, the immune checkpoint therapy is a MCSF/CSF-1R inhibitor. An anti-CSF-1R can deplete TAMs, resulting in tumor growth inhibition. Cancer Cell 25, 1-14, Jun. 16, 2014. In some embodiments, the CSF-1R inhibitor is BLZ945, GW2850, RO5509554, or PLX3397. In some embodiments, the CSF-1R inhibitor is BLZ945 or GW2850. In some embodiments, the CSF-1R inhibitor is PLX3397.

In some embodiments, the immune checkpoint therapy is an immunostimulant. In some embodiments, the immunostimulant is GMCSF, TLR ligands, 41BBL, or ICOSL.

In some embodiments, the immune checkpoint therapy is a CXCR4/CXCL12 inhibitor. In some embodiments, the CXCR4/CXCL12 inhibitor is AMD3100, AMD11070, AMD12118, AMD11814, or AMD13073. In some embodiments, the CXCR4/CXCL12 inhibitor is AMD3100.

In some embodiments, the immunotherapy is a CCL2 and/or CCR2 antagonist. In some embodiments, the antagonist of CCL2 and/or CCR2 is an anti-CCL2 or CCR2 antibody. CCL2 is a chemokine and CCR2 is a chemokine receptor. CCL2 and CCR2, according to non-limiting theory, play a role in MDSC migration.

In some embodiments, a PI3K-γ inhibitor disclosed herein, e.g., Compound 4, is administered in combination with a BTK inhibitor. In one embodiment, the BTK inhibitor is BTK inhibitors such as ibrutinib, AVL-292, Dasatinib, LFM-A13, ONO-WG-307, and GDC-0834.

In some embodiments, a PI3K-γ inhibitor disclosed herein, e.g., Compound 4, is administered in combination with an IDO (indoleamine 2,3-dioxygenase) inhibitor or an TDO (tryptophan 2,3-dioxygenase) inhibitor. In one embodiment, the IDO inhibitor is indoximod, NLG919, INCB024360, F001287, norharmane, rosmarinic acid, or alpha-methyl-tryptophan. Although IDO inhibitors act within the TME, they do not specifically target MDSCs. The overexpression of IDO by dendritic cells creates an immunosuppressive tumor microenvironment.

In some embodiments, a PI3K-γ inhibitor disclosed herein, e.g., Compound 4, is administered in combination with an inhibitor of one or more members of TAM family, a receptor tyrosine kinase (RTK) subfamily comprising Tyro-3 (also called Sky), Axl and Mer. In one embodiment, the TAM inhibitor is BGB324 (R428), S49076, TP0903, CEP-40783, ONO-9330547, bosutinib (SKI606, PF5208763), cabozantinib (XL184), sunitinib (SU11248), foretinib (XL880, GSK1363089), MGCD265, BMS777607 (ASLAN002), LY2801653, SG17079, amuvatinib (SGI-0470-02, MP470), SNS314, PF-02341066, diaminopyrimidine, spiroindoline, UNC569, UNC1062, UNC1666, UNC2025, or LDC1267. Additional TAM inhibitors include those described in Mollard et al., Med. Chem. Lett. 2011, 2, 907-912 and Feneyrolles et al., Mol. Cancer Ther. 13(9), Published OnlineFirst Aug. 19, 2014, the entireties of which are incorporated by reference herein.

In some embodiment, a PI3K-γ inhibitor disclosed herein, e.g., Compound 4, is administered to a subject concurrent or prior to the administration of immune checkpoint therapy. In some embodiment, an immunostimulant is administered to a subject concurrent or prior to the administration of immune checkpoint therapy. In some embodiment, chemotherapy (e.g., carboplatin, oxaliplatin, or radiation) is administered to a subject concurrent or prior to the administration of immune checkpoint therapy.

In some embodiments, a PI3K-γ inhibitor disclosed herein, e.g., Compound 4, is administered in combination with an ARG1 inhibitor. While not wishing to be bound by theory, it has been reported that tumor associated myeloid cells establish an immunosuppressive microenvironment in tumors through the expression of Arginase-1, which depletes the tumor microenvironment of arginine, thereby the death or inhibition of anti-tumor immune cells. Schmid et al., Proceedings: AACR 103rd Annual Meeting 2012, Cancer Research: Apr. 15, 2012; Volume 72, Issue 8, Supplement 1. It has been reported that suppression of PI3Kgamma or Arginase-1 expression blocked myeloid cell induced death of T cells in vitro. Id. According to the non-limiting theory, PI3Kgamma inhibition blocks Arginase-1 expression, thereby increasing the number of CD8+ T cells in tumors, stimulating T cell-mediated cytotoxicity of tumor cells, and suppressing growth and metastasis of tumors. Combination therapies can be designed in accordance with this mechanism.

For instance, in some embodiments, a PI3K-γ inhibitor disclosed herein, e.g., Compound 4, is administered in combination with an ARG1 inhibitor. The ARG1 inhibitor may be, e.g., an inhibitory nucleic acid such as a siRNA, an inhibitory anti-ARG-1 antibody, or an analog of arginine. Other exemplary inhibitors of ARG1 include N-hydroxy-guanidinium or N-hydroxy-nor-1-arginine, and boronic acid derivatives, such as, 2(S)-amino-6-boronohexanoic acid, and S-(2-boronoethyl)-1-cysteine, α-α-disubstituted amino acid based arginase inhibitors [such as (R)-2-amino-6-borono-2-(2-(piperidin-1-yl)ethyl)hexanoic acid], and piceatannol-3'-O-β-d-glucopyranoside (PG). Steppan et al., "Development of novel arginase inhibitors for therapy of endothelial dysfunction.", Front Immunol. 2013 Sep. 17; 4:278. doi: 10.3389/fimmu.2013.00278.

The PI3K γ inhibitors disclosed herein can have minimal effects on T-cell activation when compared to the suppressive effect of a PI3K δ inhibitor on T-cell activation. Lewis lung carcinoma tumor growth can be reduced in PI3K γ knockout mice and can have decreased tumor associated suppressive myeloid cell infiltrates. Tumor associated suppressive myeloid cells can include e.g., myeloid derived suppressor cells (MDSCs) and tumor associated macrophages (TAMs). PI3K γ knockout mice have TAMs where the M2 phenotype is lost. M2 cells are immunosuppressive and support tumor growth. PI3K inhibitors provided herein can block M2 phenotype (e.g., in an in vitro differentiation system), and thus can slow tumor growth.

For example, the effect of PI3K γ inhibitors and PI3K δ inhibitors on T cell activation as measured by inhibition of IFN-γ in response to ConA has shown that PI3K-δ is plays a role in mediating T cell activation, while PI3K-γ has minimal effects on T-cell activation. The $IC_{50}$ for a PI3K δ inhibitor in this assay is 3 nM, and the $IC_{50}$ for a PI3K γ inhibitor is 2500 nM. Administration of PI3K-γ inhibitors can lead to impaired T-cell migration but may have reduced effects on T-cell proliferation or activation.

In some embodiments, the PI3K γ inhibitors disclosed herein can have potent effects on tumor associated suppressive myeloid cells without inhibiting the effector T-cell. The PI3K γ inhibitors disclosed herein can have potent effects on tumor associated suppressive myeloid cells without blocking anti-tumor T-cell effects and thus can increase T cell activity. In one embodiment, this effect can be enhanced by administering CTLA4 antagonists and/or PD-1 and PDL1 antagonists. The PI3K γ inhibitors disclosed herein can increase T cell activation and proliferation. In some embodiments, provided herein is a method of blocking tumor associated suppressive myeloid cells without inhibiting the effects on anti-tumor T-cells comprising administering an effective amount of a PI3K γ inhibitor disclosed herein or a pharmaceutically acceptable salt thereof to a subject. In some embodiments, provided herein is a method of blocking tumor associated suppressive myeloid cells without inhibiting the effects on anti-tumor T-cells comprising administering an effective amount of a compound disclosed herein or a pharmaceutically acceptable salt thereof to a subject. In some embodiments, the subject has lung cancer, breast cancer, glioblastoma, or lymphoma (e.g., non-Hodgkin's lymphoma).

Further provided herein are methods of modulating kinase activity by contacting a kinase with an amount of a compound provided herein sufficient to modulate the activity of the kinase. Modulate can be inhibiting or activating kinase activity. In some embodiments, provided herein are methods of inhibiting kinase activity by contacting a kinase with an amount of a compound provided herein sufficient to inhibit the activity of the kinase. In some embodiments, provided herein are methods of inhibiting kinase activity in a solution by contacting said solution with an amount of a compound provided herein sufficient to inhibit the activity of the kinase in said solution. In some embodiments, provided herein are methods of inhibiting kinase activity in a cell by contacting said cell with an amount of a compound provided herein sufficient to inhibit the activity of the kinase in said cell. In some embodiments, provided herein are methods of inhibiting kinase activity in a tissue by contacting said tissue with an amount of a compound provided herein sufficient to inhibit the activity of the kinase in said tissue. In some embodiments, provided herein are methods of inhibiting kinase activity in an organism by contacting said organism with an amount of a compound provided herein sufficient to inhibit the activity of the kinase in said organism. In some embodiments, provided herein are methods of inhibiting kinase activity in an animal by contacting said animal with an amount of a compound provided herein sufficient to inhibit the activity of the kinase in said animal. In some embodiments, provided herein are methods of inhibiting kinase activity in a mammal by contacting said mammal with an amount of a compound provided herein sufficient to inhibit the activity of the kinase in said mammal. In some embodiments, provided herein are methods of inhibiting kinase activity in a human by contacting said human with an amount of a compound provided herein sufficient to inhibit the activity of the kinase in said human. In some embodiments, the % of kinase activity after contacting a kinase with a compound provided herein is less than 1, 5, 10, 20, 30, 40, 50, 60, 70, 80 90, 95, or 99% of the kinase activity in the absence of said contacting step.

In certain embodiments, provided herein are pharmaceutical composition comprising a therapeutically effective amount of a compound provided herein (e.g., a compound of any of Formulae (I"), (I'), (A'), (I), (A), (II), (III), (IV), (V), (VI), (VII), (IX), (X), (XI), (XII), (XIII), (XIV), (XV), (XVI), and (XVII), e.g., a selective PI3K-γ inhibitor, e.g., Compound 4), or a pharmaceutically acceptable form thereof, and an immunomodulator.

In one embodiment, the immunomodulator is an inhibitor of PD-1, PD-L1, LD-L2, CTLA-4, TIM3, LAG3, VISTA, BTLA, TIGIT, LAIR1, CD160, 2B4, TGFR-beta, or IDO/TDO, or a combination thereof. In one embodiment, the immunomodulator is an inhibitor of PD-L1. In one embodiment, the immunomodulator is an antibody or fragment thereof, an inhibitory nucleic acid, a soluble ligand, or a fusion of a PD-1 ligand with a Fc region of an immunoglobulin. In one embodiment, the immunomodulator is a costimulatory ligand, a MCSF/CSF-1R inhibitor, an immunostimulant, a CXCR4/CXCL12 inhibitor, a CCL2 inhibitor, or a CCR2 inhibitor. In one embodiment, the immunomodulator is cyclophosphamide, docetaxel, paclitaxel, 5-FU, or temozolomide.

In one embodiment, provided herein is a method of treating a PI3K-mediated disorder in a subject, comprising administering to the subject a therapeutically effective amount of the composition.

Combination Therapy for Pulmonary and Respiratory Diseases

In some embodiments, the compound provided herein is administered in combination with one or more other therapies. Such therapies include therapeutic agents as well as other medical interventions, behavioral therapies (e.g., avoidance of sunlight), and the like.

By "in combination with," it is not intended to imply that the other therapy and the compound provided herein must be administered at the same time and/or formulated for delivery together, although these methods of delivery are within the scope of this disclosure. The compound provided herein can be administered concurrently with, prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks before), or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks after), one or more other therapies (e.g., one or more other additional agents). In general, each therapeutic agent will be administered at a dose and/or on a time schedule determined for that particular agent. The other therapeutic agent can be administered with the compound provided herein in a single composition or separately in a different composition. Triple therapy is also contemplated herein.

In general, it is expected that additional therapeutic agents employed in combination be utilized at levels that do not exceed the levels at which they are utilized individually. In some embodiments, the levels utilized in combination will be lower than those utilized individually.

In some embodiments, the compound provided herein is a first line treatment for a pulmonary or respiratory disease, i.e., it is used in a subject who has not been previously administered another drug intended to treat a pulmonary or respiratory disease, or one or more symptoms of the disease.

In some embodiments, the compound provided herein is a second line treatment for a pulmonary or respiratory disease, i.e., it is used in a subject who has been previously administered another drug intended to treat a pulmonary or respiratory disease, or one or more symptoms of the disease.

In some embodiments, the compound provided herein is a third or fourth line treatment for a pulmonary or respiratory disease, i.e., it is used in a subject who has been previously administered two or three other drugs intended to treat a pulmonary or respiratory disease, or one or more symptoms of the disease.

In embodiments where two agents are administered, the agents can be administered in any order. For example, the two agents can be administered concurrently (i.e., essentially at the same time, or within the same treatment) or sequentially (i.e., one immediately following the other, or alternatively, with a gap in between administration of the two). In some embodiments, the compound provided herein is administered sequentially (i.e., after the first therapeutic).

In some embodiments, the compound provided herein and the second agent are administered as separate compositions, e.g., pharmaceutical compositions. In some embodiments, the compound provided herein and the agent are administered separately, but via the same route (e.g., both by inhalation). In some embodiments, the compound provided herein and the agent are administered in the same composition, e.g., pharmaceutical composition.

In some embodiments, the compound provided herein (e.g., PI3Kδ inhibitor or PI3Kγ inhibitor) is administered in combination with an agent that inhibits IgE production or activity. In some embodiments, the compound provided herein (e.g., PI3Kδ inhibitor or PI3Kγ inhibitor) is administered in combination with an inhibitor of mTOR. Agents that inhibit IgE production are known in the art and they include but are not limited to one or more of TEI-9874, 2-(4-(6-cyclohexyloxy-2-naphtyloxy)phenylacetamide)benzoic acid, rapamycin, rapamycin analogs (i.e., rapalogs), TORC1 inhibitors, TORC2 inhibitors, and any other compounds that inhibit mTORC1 and mTORC2. Agents that inhibit IgE activity include, for example, anti-IgE antibodies such as for example Omalizumab and TNX-901.

In certain embodiments, wherein inflammation (e.g., COPD, asthma) is treated, prevented and/or managed, a compound provided herein can be combined with, for example: PI3K inhibitors such as RP-6530, TG 100-115, RV1729, GS-1101, XL 499, GDC-0941, and AMG-319; BTK inhibitors such as ibrutinib and AVL-292; JAK inhibitors such as tofacitinib and GLPG0636; SYK inhibitors such as fostamatinib.

In some embodiments, a compound provided herein can be combined with other agents that act to relieve the symptoms of inflammatory conditions, such as COPD, asthma, and the other diseases described herein. These agents include, but are not limited to, non-steroidal anti-inflammatory drugs (NSAIDs), e.g., acetylsalicylic acid; ibuprofen; naproxen; indomethacin; nabumetone; and tolmetin. In some embodiments, corticosteroids are used to reduce inflammation and suppress activity of the immune system.

In some embodiments, a compound provided herein (e.g., Compound 4), or an enantiomer, a mixture of enantiomers, or a mixture of two or more diastereomers thereof, or a pharmaceutically acceptable form thereof, is administered in combination with an agent for pulmonary or respiratory diseases. Examples of agents for pulmonary or respiratory diseases include, but are not limited to, Abraxane (paclitaxel protein-bound particles for injectable suspension), Adempas (riociguat), Anoro Ellipta (umeclidinium and vilanterol inhalation powder), Breo Ellipta (fluticasone furoate and vilanterol inhalation powder), Opsumit (macitentan), Qnasl (beclomethasone dipropionate) nasal aerosol, Sirturo (bedaquiline), Dymista (azelastine hydrochloride and fluticasone propionate), Kalydeco (ivacaftor), Qnasl (beclomethasone dipropionate) nasal aerosol, Rayos (prednisone) delayed-release tablets, Surfaxin (lucinactant), Tudorza Pressair (aclidinium bromide inhalation powder), Arcapta (indacaterol maleate inhalation powder), Daliresp (roflumilast), Xalkori (crizotinib), Cayston (aztreonam for inhalation solution), Dulera (mometasone furoate+formoterol fumarate dihydrate), Teflaro (ceftaroline fosamil), Adcirca (tadalafil), Tyvaso (treprostinil), Alvesco (ciclesonide), Patanase (olopatadine hydrochloride), Letairis (ambrisentan), Xyzal (levocetirizine dihydrochloride), Brovana (arformoterol tartrate), Tygacil (tigecycline), Ketek (telithromycin), Spiriva HandiHaler (tiotropium bromide), Aldurazyme (laronidase), Iressa (gefitinib), Xolair (omalizumab), Zemaira (alpha1- proteinase inhibitor), Clarinex, Qvar (beclomethasone dipropionate), Remodulin (treprostinil), Xopenex (levalbuterol), Avelox I.V. (moxifloxacin hydrochloride), DuoNeb (albuterol sulfate and ipratropium bromide), Foradil Aerolizer (formoterol fumarate inhalation powder), Invanz, NasalCrom Nasal Spray, Tavist (clemastine fumarate), Tracleer (bosentan), Ventolin HFA (albuterol sulfate inhalation aerosol), Biaxin XL (clarithromycin extended-release tablets), Cefazolin and Dextrose USP, Tri-Nasal Spray (triamcinolone acetonide spray), Accolate (zafirlukast), Cafcit Injection, Proventil HFA Inhalation Aerosol, Rhinocort Aqua Nasal Spray, Tequin, Tikosyn Capsules, Allegra-D, Clemastine fumarate syrup, Curosurf, Dynabac, Infasurf, Priftin, Pulmozyme (domase alfa), Sclerosol Intrapleural Aerosol, Singulair (montelukast sodium), Synagis, Ceftin (cefuroxime axetil), Cipro (ciprofloxacin HCl), Claritin RediTabs (10 mg loratadine rapidly-disintegrating tablet), Flonase Nasal Spray, Flovent Rotadisk, Metaprotereol Sulfate Inhalation Solution (5%), Nasacort AQ (triamcinolone acetonide) Nasal Spray, Omnicef, Raxar (grepafloxacin), Serevent, Tilade (nedocromil sodium), Tobi, Vanceril 84 mcg Double Strength (beclomethasone dipropionate, 84 mcg) Inhalation Aerosol, Zagam (sparfloxacin) tablets, Zyflo (Zileuton), Allegra (fexofenadine hydrochloride), Astelin nasal spray, Atrovent (ipratropium bromide), Augmentin (amoxicillin/clavulanate), Azmacort (triamcinolone acetonide) Inhalation Aerosol, Breathe Right, Claritin Syrup (loratadine), Claritin-D 24 Hour Extended Release Tablets (10 mg loratadine, 240 mg pseudoephedrine sulfate), Covera-HS (verapamil), OcuHist, RespiGam (Respiratory Syncitial Virus Immune Globulin Intravenous), Tripedia (Diptheria and Tetanus Toxoids and Acellular Pertussis Vaccine Absorbed), Vancenase AQ 84 mcg Double Strength, Visipaque (iodixanol), Zosyn (sterile piperacillin sodium/tazobactam sodium), Cedax (ceftibuten), and Zyrtec (cetirizine HCl). In one embodiment, the agent for pulmonary or respiratory diseases is Arcapta (indacaterol maleate inhalation powder), Daliresp (roflumilast), Dulera (mometasone furoate+formoterol fumarate dihydrate), Alvesco (ciclesonide), Brovana (arformoterol tartrate), Spiriva HandiHaler (tiotropium bromide), Xolair (omalizumab), Qvar (beclomethasone dipropionate), Xopenex (levalbuterol), DuoNeb (albuterol sulfate and ipratropium bromide), Foradil Aerolizer (formoterol fumarate inhalation powder), Accolate (zafirlukast), Singulair (montelukast sodium), Flovent Rotadisk (fluticasone propionate inhalation powder), Tilade (nedocromil sodium), Vanceril (beclomethasone dipropionate, 84 mcg), Zyflo (Zileuton), and Azmacort (triamcinolone acetonide) Inhalation Aerosol. In one embodiment, the agent for pulmonary or respiratory diseases is Spiriva HandiHaler (tiotropium bromide).

Examples of agents for pulmonary or respiratory diseases include, but are not limited to, acetylcysteine (mucomyst) selected from Tudorza Pressair (aclidinium bromide), Atrovent (ipratropium), and Spiriva (tiotropium).

Examples of agents for pulmonary or respiratory diseases include, but are not limited to, beta2 agonists selected from short-acting beta2 agonists and long acting beta2 agonists. Short acting beta2 agonists include, but are not limited to, Proventil (albuterol), Tornalate (bitolterol), Xopenex (levalbuterol), Maxair (pirbuterol), and Alupent (metaproterenol). Long acting beta2 agonists include, but are not limited to, Brovana (arformoterol tartrate), Foradil (formoterol), Arcapta Neohaler (indacaterol maleate), and Serevent (salmeterol).

Examples of agents for pulmonary or respiratory diseases include, but are not limited to, combination of two agents. In one embodiment, the combination is administered through inhalation. The combination of two agents includes, but is not limited to a beta2 agonist and an anticholinergi selected from Combivent (albuterol and ipratropium) and Anoro Ellipta (umeclidinium and vilanterol inhalation powder). The combination of two agents include, but are not limited to a beta2 agonist and a corticosteroid selected from Advair (fluticasone and salmeterol), Breo Ellipta (fluticasone furoate and vilanterol inhalation powder), Dulera (mometasone furoate and formoterol fumarate), and Symbicort (budesonide and formoterol).

Examples of agents for pulmonary or respiratory diseases include, but are not limited to, corticosteroids selected from Vanceril Beclovent (beclomethasone), Pulmicort (budesonide), Alvesco (ciclesonide), Aerobid (flunisolide), Flovent (fluticasone), Asmanex (mometasone furoate), and Azmacort (triamcinolone).

Examples of agents for pulmonary or respiratory diseases include, but are not limited to, leukotriene inhibitors selected from Singulair (montelukast), Accolate (zafirlukast), and Zyflo (zileuton).

Examples of agents for pulmonary or respiratory diseases include, but are not limited to, mast cell stabilizers selected from Intal (cromolyn sodium) and Tilade (nedocromil).

Examples of agents for pulmonary or respiratory diseases include, but are not limited to, phosphodiesterase 4 (PDE4) inhibitors selected from Daliresp (roflumilast).

In some embodiments, a compound provided herein (e.g., Compound 4), or an enantiomer, a mixture of enantiomers, or a mixture of two or more diastereomers thereof, or a pharmaceutically acceptable form thereof, is administered in combination with an agent for immunology or infectious diseases. Examples of agents for immunology or infectious diseases include, but are not limited to, Kineret (anakinra), Lovenox (enoxaparin sodium) Injection, Makena (hydroxyprogesterone caproate injection), Myalept (metreleptin for injection), Qnasl (beclomethasone dipropionate) nasal aerosol, Simponi (golimumab), Sitavig (acyclovir) buccal tablets, Tecfidera (dimethyl fumarate), Tivicay (dolutegravir), VariZIG, Varicella Zoster Immune Globulin (Human), Flublok (seasonal influenza vaccine), Flucelvax (influenza virus vaccine), Fulyzaq (crofelemer), Horizant (gabapentin enacarbil), Qnasl (beclomethasone dipropionate) nasal aerosol, Rayos (prednisone) delayed-release tablets, Stribild (elvitegravir, cobicistat, emtricitabine, tenofovir disoproxil fumarate), Tudorza Pressair (aclidinium bromide inhalation powder), Arcapta (indacaterol maleate inhalation powder), Benlysta (belimumab), Complera (emtricitabine/rilpivirine/tenofovir disoproxil fumarate), Daliresp (roflumilast), Dificid (fidaxomicin), Edurant (rilpivirine), Firazyr (icatibant), Gralise (gabapentin), Incivek (telaprevir), Nulojix (belatacept), Victrelis (boceprevir), Cayston (aztreonam for inhalation solution), Egrifta (tesamorelin for injection), Menveo (meningitis vaccine), Oravig (miconazole), Prevnar 13 (Pneumococcal 13-valent Conjugate Vaccine), Teflaro (ceftaroline fosamil), Zortress (everolimus), Zymaxid (gatifloxacin ophthalmic solution), Bepreve (bepotastine besilate ophthalmic solution), Berinert (C1 Esterase Inhibitor (Human)), Besivance (besifloxacin ophthalmic suspension), Cervarix [Human Papillomavirus Bivalent (Types 16 and 18) Vaccine, Recombinant], Coartem (artemether/lumefantrine), Hiberix (*Haemophilus* b Conjugate Vaccine; Tetanus Toxoid Conjugate), Ilaris (canakinumab), Ixiaro (Japanese Encephalitis Vaccine, Inactivated, Adsorbed), Kalbitor (ecallantide), Qutenza (capsaicin), Vibativ (telavancin), Zirgan (ganciclovir ophthalmic gel), Aptivus (tipranavir), Astepro (azelastine hydrochloride nasal spray), Cinryze (C1

Inhibitor (Human)), Intelence (etravirine), Moxatag (amoxicillin), Rotarix (Rotavirus Vaccine, Live, Oral), Tysabri (natalizumab), Viread (tenofovir disoproxil fumarate), Altabax (retapamulin), AzaSite (azithromycin), Doribax (doripenem), Extina (ketoconazole), Isentress (raltegravir), Selzentry (maraviroc), Veramyst (fluticasone furoate), Xyzal (levocetirizine dihydrochloride), Eraxis (anidulafungin), Gardasil (quadrivalent human papillomavirus (types 6, 11, 16, 18) recombinant vaccine), Noxafil (posaconazole), Prezista (darunavir), Rotateq (rotavirus vaccine, live oral pentavalent), Tyzeka (telbivudine), Veregen (kunecatechins), Baraclude (entecavir), Tygacil (tigecycline), Ketek (telithromycin), Tindamax, tinidazole, Xifaxan (rifaximin), Amevive (alefacept), FluMist (Influenza Virus Vaccine), Fuzeon (enfuvirtide), Lexiva (fosamprenavir calcium), Reyataz (atazanavir sulfate), Alinia (nitazoxanide), Clarinex, Daptacel, Fluzone Preservative-free, Hepsera (adefovir dipivoxil), Pediarix Vaccine, Pegasys (peginterferon alfa-2a), Restasis (cyclosporine ophthalmic emulsion), Sustiva, Vfend (voriconazole), Avelox I.V. (moxifloxacin hydrochloride), Cancidas, Peg-Intron (peginterferon alfa-2b), Rebetol (ribavirin), Spectracef, Twinrix, Valcyte (valganciclovir HCl), Xigris (drotrecogin alfa [activated]), ABREVA (docosanol), Biaxin XL (clarithromycin extended-release tablets), Cefazolin and Dextrose USP, Children's Motrin Cold, Evoxac, Kaletra Capsules and Oral Solution, Lamisil (terbinafine hydrochloride) Solution (1%), Lotrisone (clotrimazole/betamethasone diproprionate) lotion, Malarone (atovaquone; proguanil hydrochloride) Tablet, Rapamune (sirolimus) Tablets, Rid Mousse, Tri-Nasal Spray (triamcinolone acetonide spray), Trivagizole 3 (clotrimazole) Vaginal Cream, Trizivir (abacavir sulfate; lamivudine; zidovudine AZT) Tablet, Agenerase (amprenavir), Cleocin (clindamycin phosphate), Famvir (famciclovir), Norvir (ritonavir), Panretin Gel, Rapamune (sirolimus) oral solution, Relenza, Synercid IV., Tamiflu capsule, Vistide (cidofovir), Allegra-D, CellCept, Clemastine fumarate syrup, Dynabac, REBETRON™ Combination Therapy, Simulect, Timentin, Viroptic, INFANRIX (Diphtheria and Tetanus Toxoids and Acellular Pertussis Vaccine Adsorbed), Acyclovir Capsules, Aldara (imiquimod), Aphthasol, Combivir, Condylox Gel 0.5% (pokofilox), Flagyl ER, Flonase Nasal Spray, Fortovase, INFERGEN (interferon alfacon-1), Intron A (interferon alfa-2b, recombinant), Rescriptor Tablets (delavirdine mesylate tablets), SPORANOX (itraconazole), Stromectol (ivermectin), Taxol, Trovan, VIRACEPT (nelfinavir mesylate), Zerit (stavudine), Albenza (albendazole), Apthasol (Amlexanox), Carrington patch, Confide, Crixivan (Indinavir sulfate), Gastrocrom Oral Concentrate (cromolyn sodium), Havrix, Lamisil (terbinafine hydrochloride) Tablets, Leukine (sargramostim), Oral Cytovene, RespiGam (Respiratory Syncitial Virus Immune Globulin Intravenous), Videx (didanosine), Viramune (nevirapine), Vitrasert Implant, Zithromax (azithromycin), Cedax (ceftibuten), Clarithromycin (Biaxin), Epivir (lamivudine), Invirase (saquinavir), Valtrex (valacyclovir HCl), and Zyrtec (cetirizine HCl).

The examples and preparations provided below further illustrate and exemplify the compounds as provided herein and methods of preparing such compounds. It is to be understood that the scope of the present disclosure is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers can be obtained by methods known to those skilled in the art.

Synthesis of Compounds

In some embodiments, compounds of provided herein may be prepared according to methods known in the art. For example, the compounds provided herein can be synthesized according to the schemes below. Scheme 1, shows the synthesis of amine A-30, F-50, X-40, and H50. Scheme 2 shows the synthesis of amide D-20 and formula I.

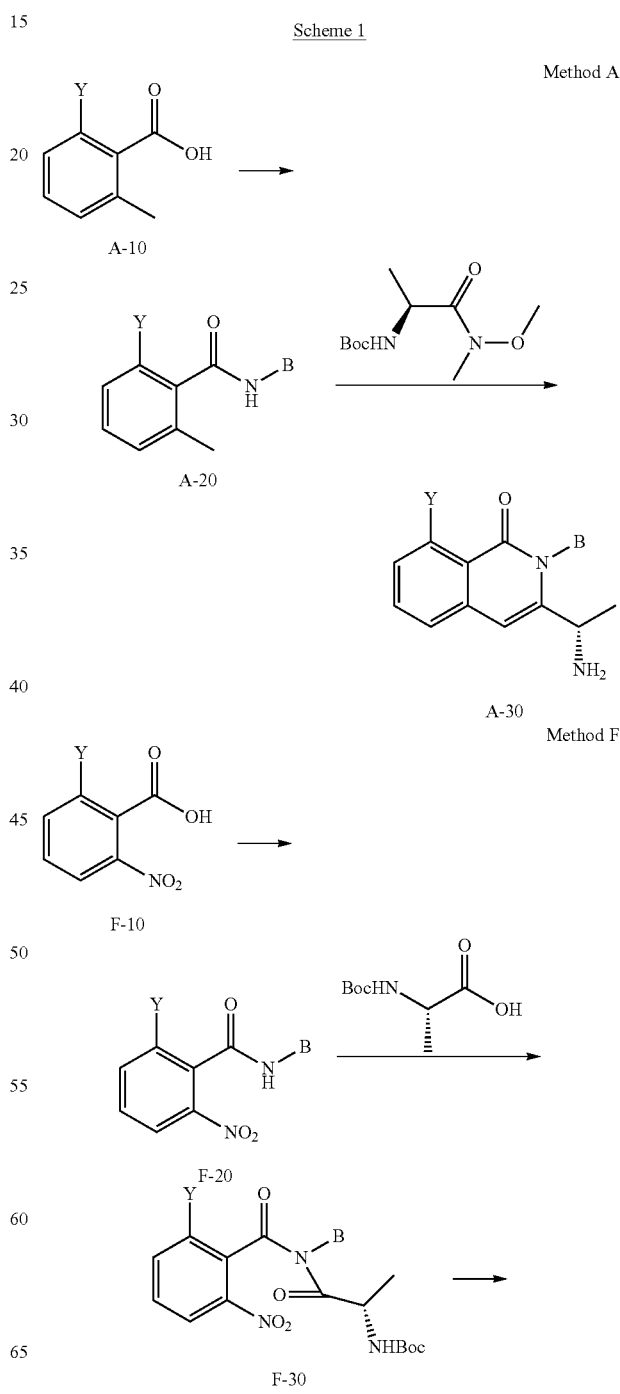

Scheme 1

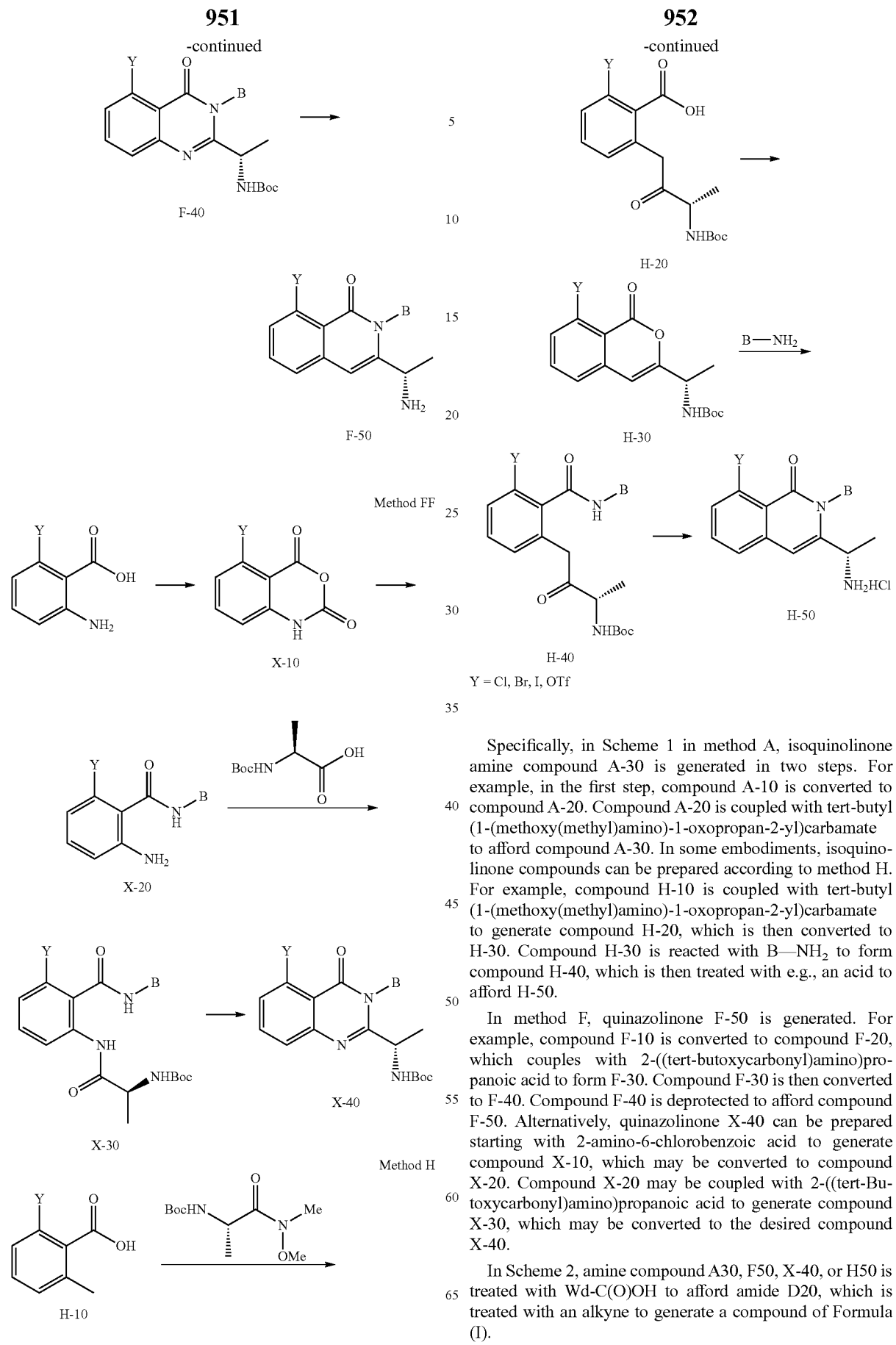

Specifically, in Scheme 1 in method A, isoquinolinone amine compound A-30 is generated in two steps. For example, in the first step, compound A-10 is converted to compound A-20. Compound A-20 is coupled with tert-butyl (1-(methoxy(methyl)amino)-1-oxopropan-2-yl)carbamate to afford compound A-30. In some embodiments, isoquinolinone compounds can be prepared according to method H. For example, compound H-10 is coupled with tert-butyl (1-(methoxy(methyl)amino)-1-oxopropan-2-yl)carbamate to generate compound H-20, which is then converted to H-30. Compound H-30 is reacted with B—NH₂ to form compound H-40, which is then treated with e.g., an acid to afford H-50.

In method F, quinazolinone F-50 is generated. For example, compound F-10 is converted to compound F-20, which couples with 2-((tert-butoxycarbonyl)amino)propanoic acid to form F-30. Compound F-30 is then converted to F-40. Compound F-40 is deprotected to afford compound F-50. Alternatively, quinazolinone X-40 can be prepared starting with 2-amino-6-chlorobenzoic acid to generate compound X-10, which may be converted to compound X-20. Compound X-20 may be coupled with 2-((tert-Butoxycarbonyl)amino)propanoic acid to generate compound X-30, which may be converted to the desired compound X-40.

In Scheme 2, amine compound A30, F50, X-40, or H50 is treated with Wd-C(O)OH to afford amide D20, which is treated with an alkyne to generate a compound of Formula (I).

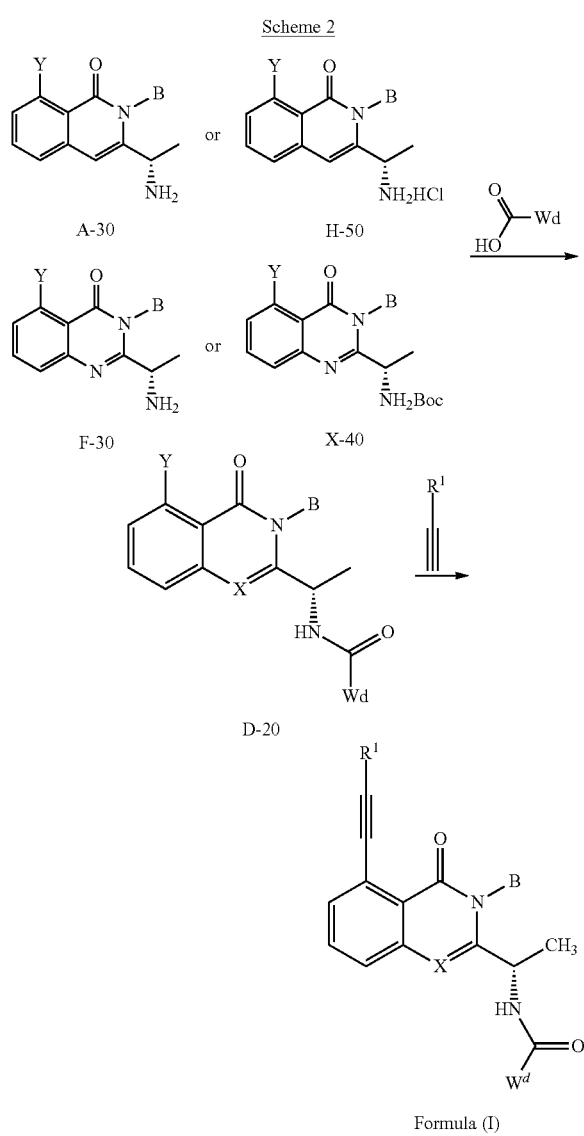

Scheme 2

Formula (I)

EXAMPLES

Chemical Examples

The chemical entities described herein can be synthesized according to one or more illustrative schemes herein and/or techniques well known in the art.

Unless specified to the contrary, the reactions described herein take place at atmospheric pressure, generally within a temperature range from −10° C. to 200° C. Further, except as otherwise specified, reaction times and conditions are intended to be approximate, e.g., taking place at about atmospheric pressure within a temperature range of about −10° C. to about 110° C. over a period that is, for example, about 1 to about 24 hours; reactions left to run overnight in some embodiments can average a period of about 16 hours.

The terms "solvent," "organic solvent," and "inert solvent" each mean a solvent inert under the conditions of the reaction being described in conjunction therewith including, for example, benzene, toluene, acetonitrile, tetrahydrofuran ("THF"), dimethylformamide ("DMF"), chloroform, methylene chloride (or dichloromethane), diethyl ether, methanol, N-methylpyrrolidone ("NMP"), pyridine, and the like. Unless specified to the contrary, the solvents used in the reactions described herein are inert organic solvents. Unless specified to the contrary, for each gram of the limiting reagent, one cc (or mL) of solvent constitutes a volume equivalent.

Isolation and purification of the chemical entities and intermediates described herein can be effected, if desired, by any suitable separation or purification procedure, such as, for example, filtration, extraction, crystallization, column chromatography, thin-layer chromatography, or thick-layer chromatography, or a combination of these procedures. Specific illustrations of suitable separation and isolation procedures are given by reference to the examples herein below. However, other equivalent separation or isolation procedures can also be used.

When desired, the (R)- and (S)-isomers of the non-limiting exemplary compounds, if present, can be resolved by methods known to those skilled in the art, for example by formation of diastereoisomeric salts or complexes which can be separated, for example, by crystallization; via formation of diastereoisomeric derivatives which can be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer can be synthesized by asymmetric synthesis using optically active reagents, substrates, catalysts or solvents, or by converting one enantiomer to the other by asymmetric transformation. Further, atropisomers (i.e., stereoisomers from hindered rotation about single bonds) of compounds provided herein can be resolved or isolated by methods known to those skilled in the art. For example, certain B substituents with ortho or meta substituted phenyl may form atropisomers, where they may be separated and isolated.

The compounds described herein can be optionally contacted with a pharmaceutically acceptable acid to form the corresponding acid addition salts. Also, the compounds described herein can be optionally contacted with a pharmaceutically acceptable base to form the corresponding basic addition salts.

In some embodiments, compounds provided herein can generally be synthesized by an appropriate combination of generally well known synthetic methods. Techniques useful in synthesizing these chemical entities are both readily apparent and accessible to those of skill in the relevant art, based on the instant disclosure. Many of the optionally substituted starting compounds and other reactants are commercially available, e.g., from Aldrich Chemical Company (Milwaukee, Wis.) or can be readily prepared by those skilled in the art using commonly employed synthetic methodology.

The discussion below is offered to illustrate certain of the diverse methods available for use in making the compounds and is not intended to limit the scope of reactions or reaction sequences that can be used in preparing the compounds provided herein.

General Synthetic Methods

The compounds herein being generally described, it will be more readily understood by reference to the following examples, which are included merely for purposes of illustration of certain aspects and embodiments, and are not intended to limit these aspects and embodiments.

(i) General Method for the Synthesis of Amine Cores:

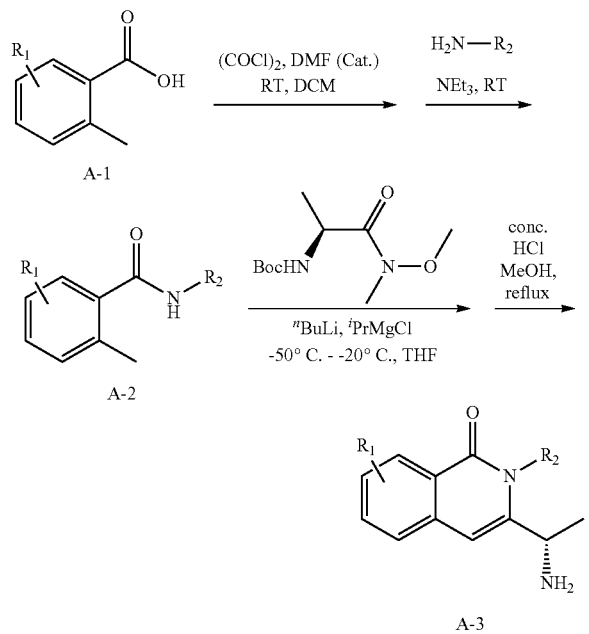

Method A

General conditions for the preparation of (S)-3-(1-amino-ethyl)-isoquinolin-1(2H)-ones:

To a stirred mixture of a given o-methylbenzoic acid (A-1) (1 eq, e.g., 1.5 mol) and DMF (catalytic, e.g., 2 mL) in DCM (1.2 M, e.g., 1275 mL) at RT, oxalyl chloride (1.1 eq, e.g., 1.65 mol) is added over 5 min and the resulting mixture is stirred at RT for 2 h. The mixture is then concentrated in vacuo. The residue is dissolved in DCM (150 mL) and the resulting solution (solution A) is used directly in the next step.

To a stirred mixture of aniline (1.05 eq, e.g., 1.58 mol) and triethylamine (2.1 eq, e.g., 3.15 mol) in DCM (1.2 M, e.g., 1350 mL), the above solution A (e.g., 150 mL) is added dropwise while the reaction temperature is maintained between 25° C. to 40° C. by an ice-water bath. The resulting mixture is stirred at RT for 2 h and then water (e.g., 1000 mL) is added. The organic layers are separated and washed with water (2× e.g., 1000 mL), dried over $Na_2SO_4$ and filtered. The filtrate is concentrated in vacuo. The product is suspended in n-heptanes (e.g., 1000 mL) and stirred at RT for 30 min. The precipitate is collected by filtration, rinsed with heptanes (e.g., 500 mL) and further dried in vacuo to afford the amide (A-2).

To a stirred mixture of amide (A-2) (1 eq, e.g., 173 mmol) in anhydrous THF (e.g., 250 mL) at −30° C. under an argon atmosphere, a solution of n-butyllithium in hexanes (2.5 eq, 2.5 M, e.g., 432 mol) is added dropwise over 30 min while keeping the inner temperature between −30° C. and −10° C. The resulting mixture is then stirred at −30° C. for 30 min.

To a stirred mixture of (S)-tert-butyl 1-(methoxy(methyl) amino)-1-oxopropan-2-ylcarbamate (1.5 eq, e.g., 260 mmol) in anhydrous THF (e.g., 250 mL) at −30° C. under an argon atmosphere, a solution of isopropylmagnesium chloride in THF (1.65 eq, 1 M, e.g., 286 mmol) is added dropwise over 30 min while keeping inner temperature between −30° C. and −10° C. The resulting mixture is stirred at −30° C. for 30 min. This solution is then slowly added to above reaction mixture while keeping inner temperature between −30° C. and −10° C. The resulting mixture is stirred at −15° C. for 1 h. The reaction mixture is quenched with water (e.g., 50 mL) and then acidified with conc. HCl at −10° C. to 0° C. to adjust the pH to 1-3. The mixture is allowed to warm to RT and concentrated in vacuo. The residue is dissolved in MeOH (e.g., 480 mL), and then conc. HCl (e.g., 240 mL) is added quickly at RT. The resulting mixture is stirred at reflux for 1 h. The reaction mixture is concentrated in vacuo to reduce the volume to about 450 mL. The residue is extracted with a 2:1 mixture of heptane and ethyl acetate (e.g., 2×500 mL). The aqueous layer is basified with concentrated ammonium hydroxide to adjust the pH value to 9-10 while keeping the inner temperature between −10° C. and 0° C. The mixture is then extracted with DCM (e.g., 3×300 mL), washed with brine, dried over $MgSO_4$ and filtered. The filtrate is concentrated in vacuo and the residue is dissolved in MeOH (e.g., 1200 mL) at RT. To this solution, D-(−)-tartaric acid (0.8 eq, e.g., 21 g, 140 mmol) is added in one portion at RT. After stirring at RT for 30 min, a white solid precipitates and the mixture is slurried at RT for 10 h. The solid is collected by filtration and rinsed with MeOH (e.g., 3×50 mL). The collected solid is suspended in water (e.g., 500 mL) and then neutralized with concentrated ammonium hydroxide solution at RT to adjust the pH to 9-10. The mixture is extracted with DCM (e.g., 3×200 mL). The combined organic layers are washed with brine, dried over $MgSO_4$ and filtered. The filtrate is concentrated in vacuo to afford the (S)-3-(1-aminoethyl)-isoquinolin-1(2H)-ones(A-3).

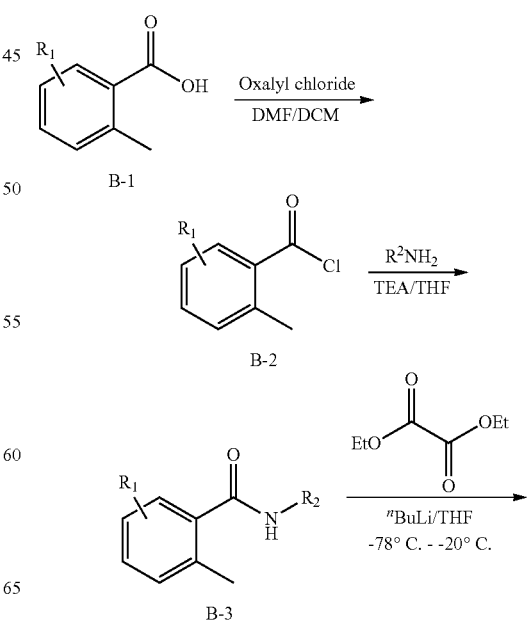

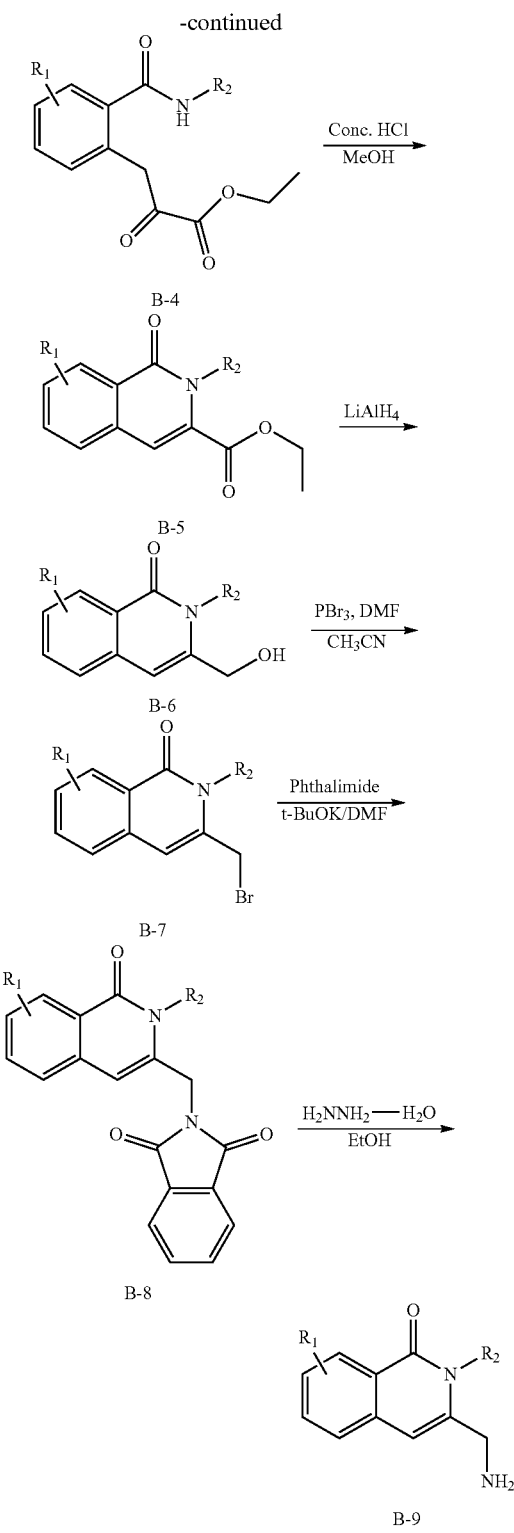

Method B

General Conditions for the Preparation of 3-(aminomethyl)-isoquinolin-1(2H)-ones A mixture of benzoic acid (B-1) (1 eq, e.g., 400 mmol), oxalyl chloride (2 eq, e.g., 101 g, 800 mmol) and DMF (catalytic, e.g., 0.2 ml) in DCM (1M, e.g., 400 mL) is stirred at RT for 2 h. The mixture is concentrated in vacuo to afford the acid chloride (B-2). The product obtained is used directly in the next step without further purification.

A mixture of $R_2NH_2$ amine (1.05 eq, e.g., 420 mmol) and triethylamine (1.7, e.g., 700 mmol) in DCM (1.4 M, e.g., 300 mL) is stirred at RT for 10 min. To this mixture, acid chloride (B-2) (1 eq, e.g., 400 mmol) is added dropwise, and the resulting mixture is stirred at RT for 30 min. The reaction mixture is poured into water (e.g., 300 mL) and extracted with DCM (e.g., 3×200 mL), dried over anhydrous $Na_2SO_4$ and filtered. The filtrate is concentrated in vacuo to afford the product. The product is suspended in isopropyl ether (e.g., 300 mL), stirred at reflux for 30 min, and then cooled to 0-5° C. The precipitate is collected by filtration and further dried in vacuo to afford the product amide (B-3).

To a stirred solution of amide (B-3) (1.0 eq, e.g., 0.1 mol) in anhydrous THF (0.4 M, e.g., 225 mL) at −78° C. under an argon atmosphere, a solution of n-butyllithium in hexanes (2.5 M, 3 eq, e.g., 120 mL, 0.3 mol) is added dropwise over 1 h period of time while keeping inner temperature between −78° C. to −50° C. The resulting mixture is stirred at −70° C. for 1 h, and then diethyl oxalate (1.2 eq, e.g., 17.5 g, 0.12 mol) is quickly added (with an increase in temperature to −20° C. upon addition). The mixture is stirred at −50° C. for 10 min, and then quenched with water (e.g., 100 mL). The inorganic salt is removed by filtration, and the filtrate is washed with ethyl acetate (e.g., 2×100 mL). The combined organic layers are washed with brine (e.g., 100 mL), dried over $MgSO_4$ and filtered. The filtrate is concentrated in vacuo to afford the product as a semi-solid. The product is slurried in isopropyl ether (e.g., 100 mL) at RT for 10 min. The solid is collected by filtration and further dried in vacuo to afford the product (B-4). The product obtained is used directly in the next step.

Compound (B-4) (1 eq, e.g., 88 mmol) is dissolved at 0.9 M with HCl/MeOH (100 mL, e.g., 10 M), and the resulting mixture is stirred at reflux for 1 h. The reaction mixture is concentrated in vacuo, and the residue is slurried in ethyl acetate (100 mL) at RT for 30 min. The solid is collected by filtration, rinsed with ethyl acetate (3×50 mL), and further dried in vacuo to afford the product (B-5).

To a stirred suspension of lithium aluminum hydride (3 eq., e.g., 15.6 g, 410 mmol) in anhydrous THF (0.3 M, e.g., 500 mL) at −78° C. under a nitrogen atmosphere, (B-5) (1 eq, e.g., 137 mmol) is slowly added over a 10 min period of time. The resulting mixture is allowed to warm to −30° C. and stirred for 30 min. The mixture is then cooled to −78° C., and quenched carefully with water (e.g., 100 mL). The mixture is allowed to warm to RT, filtered through silica gel (e.g., 20 g), and the filtrate is concentrated in vacuo. The product mixture is poured into $H_2O$ (e.g., 200 mL) and extracted with ethyl acetate (e.g., 3×200 mL). The combined organic layers are washed with brine (e.g., 100 mL), dried over $Na_2SO_4$ and filtered. The filtrate is concentrated in vacuo. The product is suspended in ethyl acetate (e.g., 30 mL) and stirred for 10 min. The solid is collected by filtration and further dried in vacuo to afford the product (B-6).

Phosphorus tribromide (1.2 eq, e.g., 3.42 g, 12.6 mmol) and DMF (2.0 eq, e.g., 1.6 g, 21.0 mmol) is dissolved in $CH_3CN$ (0.13 M, e.g., 100 mL) and the resulting mixture is stirred at −10° C. for 10 min. To this mixture, alcohol (B-6) (1.0 eq, 10.5 mmol) is added in portions. The resulting mixture is allowed to warm to RT and stirred for an additional 30 min. The reaction mixture is neutralized with saturated aqueous $NaHCO_3$ solution at 0-5° C. and then filtered. The filtrate is extracted with ethyl acetate (e.g., 3×100 mL). The combined organic layers are washed with brine, dried over $Na_2SO_4$ and filtered. The filtrate is concentrated in vacuo and the residue is purified by flash column chromatography on silica gel (20% ethyl acetate-petroleum ether) to afford the product bromide (B-7).

To a stirred mixture of phthalimide (1.1 eq, e.g., 6.93 mmol) in DMF (e.g., 20 mL) at RT, potassium-tert-butoxide (1.5 eq, e.g., 1.1 g, 9.45 mmol) is added in portions over 10 min and then bromide (B-7) (1.0 eq, e.g., 6.3 mmol) is added. The resulting mixture is stirred at 100° C. for 2 h. The reaction mixture is allowed to cool to RT and then poured into ice-water (e.g., 30 mL). The mixture is extracted with ethyl acetate (e.g., 3×20 mL). The combined organic layers are washed with brine, dried over $Na_2SO_4$ and filtered. The filtrate is concentrated in vacuo and the residue is purified by flash column chromatography on silica gel (e.g., 16% ethyl acetate-petroleum ether) to afford the product dione (B-8).

Dione (B-8) (1.0 eq, e.g., 1.5 mmol) and hydrazine hydrate (e.g., 8.0 eq, 600 mg, 12 mmol) are dissolved in EtOH (e.g., 20 mL) and the resulting mixture is stirred at reflux for 1 h. The mixture is allowed to cool to RT and then filtered. The filter cake is washed with EtOH (e.g., 10 mL). The combined filtrate is concentrated in vacuo and the residue is purified by flash column chromatography on silica gel (e.g., 2.5% MeOH-DCM) to afford the amine (B-9).

(ii) General Methods for Amide Synthesis:

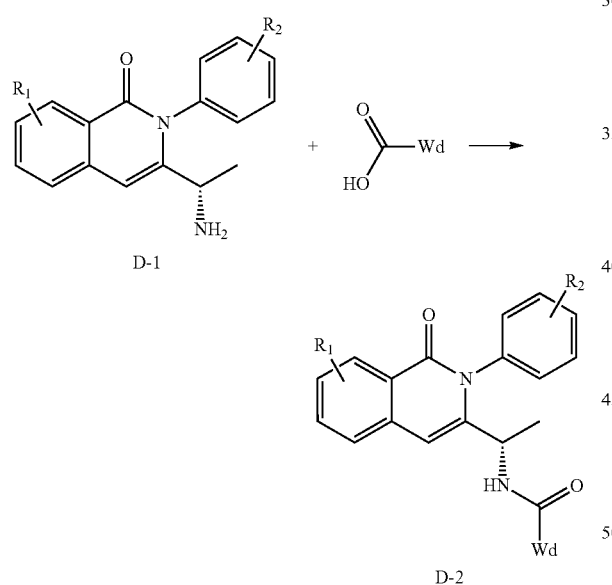

Method D

To a mixture of amine (D-1) (1.0 eq, e.g., 0.5 mmol), $W_d$—COOH carboxylic acid (1.1 eq, e.g., 0.55 mmol), and N,N-diisopropylethylamine (2.0 eq, e.g., 0.17 mL, 1.0 mmol) in anhydrous DMF (e.g., 5 mL), 1-hydroxybenzotriazole hydrate (1.3 eq, e.g., 0.65 mmol) and EDC hydrochloride (1.3 eq, e.g., 0.65 mmol,) are added sequentially and the resulting mixture is stirred at RT for 2-16 h. Ice-water or saturated sodium carbonate solution is added to the reaction mixture and then stirred for 10 min. The precipitate is collected by filtration, rinsed with water and dried in vacuo. The solid collected is further purified by flash column chromatography on silica gel (e.g., 0-10% MeOH-DCM) to afford the product amide (D-2).

Method E

A solution of amine (D-1) (1 eq, e.g., 0.25 mmol), $W_d$—COOH carboxylic acid (1.1 eq), and 1-hydroxybenzotriazole hydrate (1.3 eq) in dimethylformamide (0.1 M) is treated with diisopropylethylamine (2 eq) and then EDC hydrochloride (1.3 eq, e.g., 63 mg). The reaction mixture is stirred at ambient temperature overnight. The reaction mixture is diluted with water (5× solvent) and acetic acid (1.5 eq) is added, then the mixture is stirred in an ice bath for 40 min. The resulting precipitate is collected by filtration, and washed with water (e.g., 3×3 mL). The collected solid is dried in vacuo to afford amide (D-2).

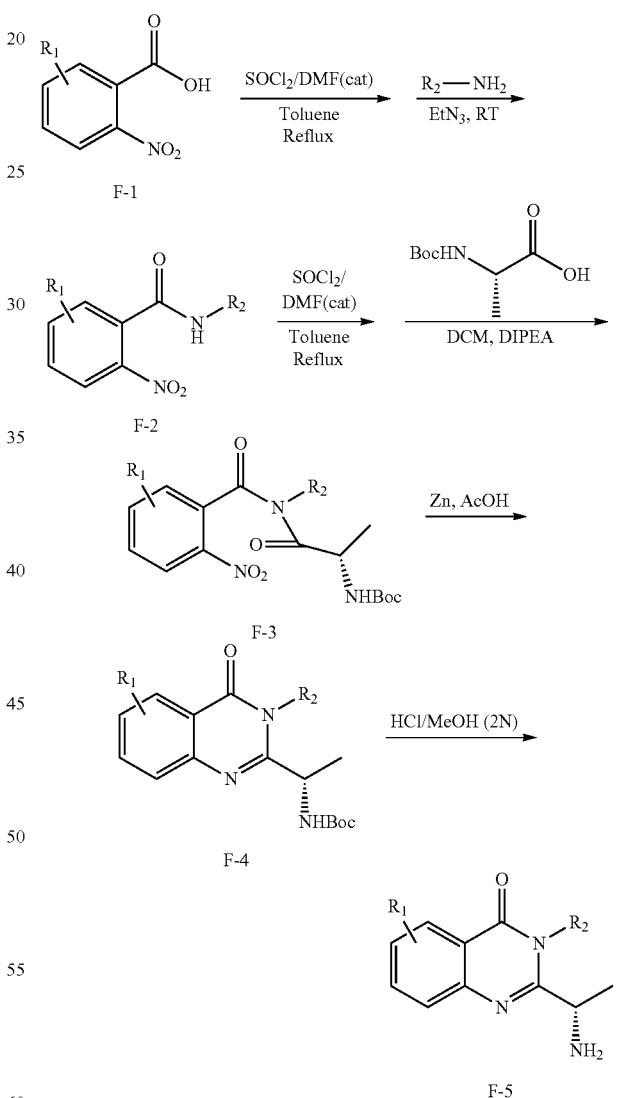

Method F

To a stirred mixture of nitrobenzoic acid (F-1) (1.0 eq, 1.0 mol) and DMF (e.g., 2.0 mL) in toluene (e.g., 800 mL), thionyl chloride (4.0 eq, e.g., 292 mL, 1.0 mol) is added dropwise (over 15 min) and the resulting mixture is stirred at reflux for 1.5 h. The mixture is allowed to cool to RT and then concentrated in vacuo. The residue is dissolved in DCM (e.g., 100 mL) to form solution A, which is used directly in the next step.

To a stirred mixture of a given amine $R_2$—$NH_2$ (1.1 eq, e.g., 102.4 g, 1.1 mol) and triethylamine (2.0 eq, e.g., 280 mL, 2.0 mol) in DCM (1.6 M, e.g., 700 mL), solution A is added dropwise while keeping the reaction temperature below 10° C. The resulting mixture is allowed to warm to RT and then stirred at RT overnight. The reaction mixture is diluted with ice-water (e.g., 1.0 L) and stirred for 15 min. The precipitate is collected by filtration, rinsed with isopropyl ether (e.g., 3×100 mL) and petroleum ether (e.g., 3×100 mL), and then dried in vacuo to afford product amide (F-2).

A mixture of nitro-benzamide (F-2) (1.0 eq, e.g., 20.0 mmol,) and DMF (cat.) in toluene (0.3 M, e.g., 60 mL) at RT, thionyl chloride (8.2 eq, e.g., 12 mL, 164 mmol) is added dropwise (over 5 min) and the resulting mixture is stirred at reflux for 2 h. The mixture is allowed to cool to RT and then concentrated in vacuo. The residue is dissolved in DCM (e.g., 10 mL) to form solution B, which is used directly in the next step.

To a stirred mixture of N-(tert-butoxycarbonyl)-L-alanine (0.8 eq, e.g., 16.0 mmol) and N,N-diisopropylethylamine (1.5 eq, e.g., 4.0 g, 31.0 mol) in DCM (0.8 M, e.g., 20 mL), solution B is added dropwise while keeping the reaction temperature between 0-10° C. The resulting mixture is stirred at this temperature for 1 h and then stirred at RT overnight. The reaction mixture is quenched with ice-water (e.g., 100 mL). The organic layer is separated and the aqueous layer is extracted with DCM (e.g., 2×80 mL). The combined organic layers are washed with brine, dried over $Na_2SO_4$ and filtered. The filtrate is concentrated in vacuo and the residue is slurried in isopropyl ether (e.g., 100 mL) for 15 min. The solid is collected by filtration and dried in vacuo to afford product (F-3).

To a suspension of zinc dust (10.0 eq, e.g., 7.2 g, 110 mmol) in glacial acetic acid (2.8 M, e.g., 40 mL) at 15° C., a solution of (F-3) (1.0 eq, e.g., 11.0 mmol) in glacial acetic acid (0.3 M, e.g., 40 mL) is added and the resulting mixture is stirred at RT for 4 h. The mixture is poured into ice-water (e.g., 200 mL) and neutralized with saturated aqueous $NaHCO_3$ solution to adjust the pH to 8. The resulting mixture is extracted with DCM (e.g., 3×150 mL). The combined organic layers are washed with brine, dried over $Na_2SO_4$ and filtered. The filtrate is concentrated in vacuo and the residue is purified by flash chromatography on silica gel (7% ethyl acetate-petroleum ether) to afford product (F-4).

Compound (F-4) (1.0 eq, e.g., 0.5 mmol) is dissolved in hydrochloric methanol solution (8 eq, e.g., 2N, 20 mL) and the resulting mixture is stirred at RT for 2 h. The mixture is concentrated in vacuo. The residue is diluted with water (30 mL) and then neutralized with saturated aqueous $NaHCO_3$ to adjust the pH to 8 while keeping the temperature below 5° C. The resulting mixture is extracted with DCM (e.g., 3×30 mL). The combined organic layers are washed with brine, dried over $Na_2SO_4$ and filtered. The filtrate is concentrated in vacuo and the residue is slurried in petroleum ether (e.g., 10 mL). The solid is collected by filtration and dried in vacuo to afford product (F-5).

The quinazolinone (F-5) can be used to synthesize compounds described herein using, for example, Method D to couple the amine to $W_d$ groups.

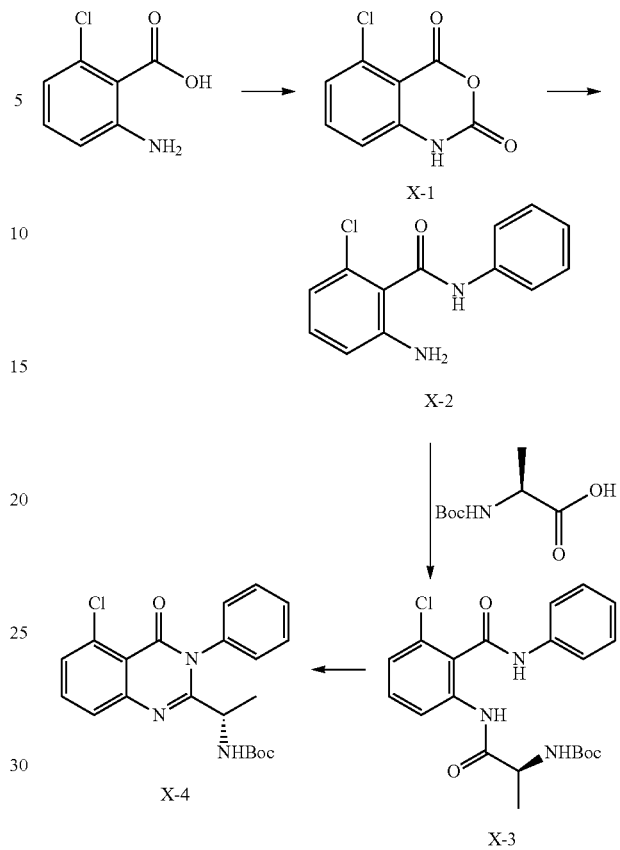

Method FF

Alternatively, compounds with a quinazolinone core can be prepared according to the procedures in PCT publication no. WO2013082540.

In Method FF, 2-Amino-6-chlorobenzoic acid (63 mmol, 1.0 equiv) is dissolved in acetonitrile (60 mL) in a 250 mL round bottomed-flask, placed under an atmosphere of Ar and heated to 50° C. Pyridine (2.0 equiv) is added followed by dropwise the addition of a solution of triphosgene (0.34 equiv in 30 mL acetonitrile) while maintaining the internal temperature below 60° C. The mixture is then stirred at 50° C. for 2 h after which the solvent is removed under vacuum. The remaining residue is dispersed in 50 mL of water and filtered. The resulting solid is washed with a minimal amount of acetonitrile to remove discoloration and then dried to provide desired anhydride X-1.

Anhydride X-1 (25.5 mmol, 1.0 equiv) is suspended in dioxane (40 mL) under an atmosphere of Ar in a 200 mL round bottomed-flask. Aniline (1.0 equiv) is added dropwise. Heating is started at 40° C. and gradually increased to 100° C. After 4 h, the majority of starting material is consumed after which the reaction is allowed to cool. The solvent is then removed under vacuum to provide an oil which is redissolved in toluene followed by the addition of hexanes until the solvent appears close to portioning. The mixture is stirred for 14 h after which a solid appeared in the flask. This solid is isolated via vacuum filtration and washed with hexanes to provide the desired amide X-2 in high yield.

(S)-2-((tert-Butoxycarbonyl)amino)propanoic acid (33.0 mmol, 2.0 equiv) is dissolved in dry tetrahydrofuran (70 mL) under an atmosphere of Ar after which N-methylmorpholine (2.2 equiv) is added dropwise. The mixture is then cooled to −17° C. in an acetone/dry ice bath after which a solution of isobutyl chloroformate (2.0 equiv in 10 mL of dry tetrahydrofuran) is added dropwise to the mixture followed by stirring for 30 min. A solution of amine X-2 (10 equiv in 10 mL of dry tetrahydrofuran) is then added. The dry ice bath is then removed and the mixture is stirred at RT for 90 min. It is then heated to 60° C. for another 2 h after which it is allowed to cool. MTBE (150 mL) and water (150 mL) are then successively added with strong stirring. The phases are separated and the organic phase is washed with water (2×50 mL) and brine (50 mL) and dried over sodium sulfate. The solution is then concentrated under reduced pressure and the crude reside is purified using flash silica gel chromatography (gradient 5-30 ethyl acetate/hexanes) X-3 as the coupled product.

Compound X-3 (4.9 mmol, 1.0 equiv) is then suspended in acetonitrile (100 mL). Triethylamine (48 equiv) is then added with stirring followed by the dropwise addition of chlorotrimethylsilane (15 equiv). The flask is then sealed and heated to 90° C. for 3 d. The reaction is allowed to cool after which the solvent is removed under vacuum. The residue is then dissolved in ethyl acetate (120 mL) and successively washed with saturated sodium carbonate (1×100 mL), water (1×100 mL) and brine (1×100 mL). The organic layer is then dried over anhydrous sodium sulfate and concentrated under reduced pressure to provide cyclized product X-4. The product can either be used directly in subsequent reactions or purified using flash silica gel chromatography.

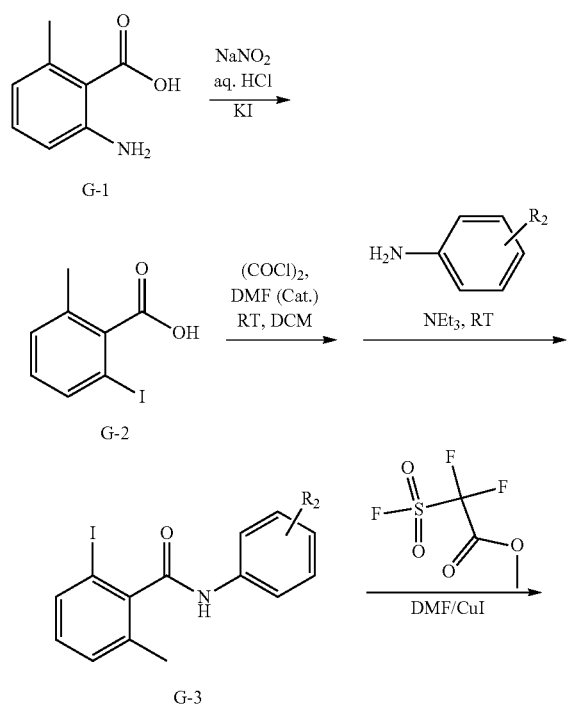

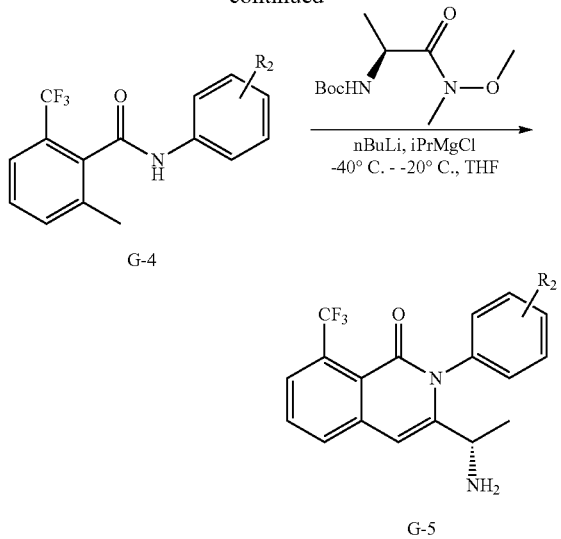

Method G

General Conditions for the Preparation of (S)-3-(1-aminoethyl)1-8-(trifluoromethyl)isoquinolin-1(2H)-ones To a suspension of 2-amino-6-methylbenzoic acid (G-1) (20.0 g, 132.0 mmol, 1.0 eq) in $H_2O$ (55 mL) at 0-5° C., conc. HCl (36.5%, 64 mL, 749 mmol, 5.7 eq) is added slowly. After stirring for 15 min, the mixture is added dropwise to a solution of sodium nitrite (12.02 g, 174.0 mmol, 1.32 eq) in $H_2O$ (36 mL) at 0-5° C., and the resulting mixture is stirred for 1 h. The resulting solution is then added to a solution of KI (60.5 g, 364.5 mmol, 2.76 eq) in $H_2O$ (150 mL) at 0-5° C. The reaction mixture is allowed to warm to RT and stirred at RT overnight. The mixture is extracted with ethyl acetate (3×100 mL). The combined organic layers are washed with water (2×100 mL), dried over anhydrous $Na_2SO_4$ and filtered. The filtrate is concentrated in vacuo and the residue is purified by flash column chromatography on silica gel (0-20% ethyl acetate-petro ether) to afford the product, 2-iodo-6-methylbenzoic acid (G-2).

To a stirred mixture of 2-iodo-6-methylbenzoic acid (G-2) (305.3 mmol, 1.0 eq) and DMF (0.3 mL) in DCM (350 mL) at RT, oxalyl chloride (466.4 mmol, 1.5 eq) is added dropwise. The resulting mixture is stirred at RT for 3 h and then concentrated in vacuo. The residue is dissolved in DCM (50 mL) and the resulting solution (solution A) is used directly in the next step.

To a stirred mixture of $R_3$-substituted aniline (335.7 mmol, 1.1 eq) and triethylamine (915.0 mmol, 3.0 eq) in DCM (350 mL), solution A (150 mL) is added dropwise while the reaction temperature is controlled below 30° C. by an ice-water bath. The reaction mixture is stirred at RT for 1 h and then quenched with water (200 mL). The organic layer is separated, washed with water (2×200 mL), dried over anhydrous $Na_2SO_4$ and filtered. The filtrate is concentrated in vacuo. The product is rinsed with isopropyl ether and dried in vacuo to afford the product amide (G-3).

A mixture of amide (G-3) (18.0 mmol, 1.0 eq), methyl 2,2-difluoro-2-(fluorosulfonyl)acetate (72.9 mmol, 4.0 eq) and CuI (3.63 mmol, 0.2 eq) in DMF (130 mL) is stirred at 70° C. under an argon atmosphere overnight. The mixture is allowed to cool to RT and then concentrated in vacuo to remove the solvent. The resulting residue is partitioned between ethyl acetate (60 mL) and water (60 mL), and the aqueous layer is extracted with ethyl acetate (2×60 mL). The combined organic layers are washed with water (2×60 mL), dried over anhydrous $Na_2SO_4$ and filtered. The filtrate is concentrated in vacuo and the residue is purified by flash column chromatography on silica gel to afford the product, trifluoromethyl amide (G-4).

To a stirred mixture of amide (G-4) (10.1 mmol, 1.0 eq) in anhydrous THF (25 mL) at −40° C. under an argon atmosphere, a solution of n-butyllithium in THF (2.5 M, 25.3 mmol, 2.5 eq) is added dropwise (over 15 min) and the inner temperature is controlled between −30° C. and −20° C. during the addition. The resulting mixture is stirred at −30° C. for an additional 1 h. To a stirred mixture of (S)-tert-butyl 1-(methoxy(methyl)amino)-1-oxopropan-2-ylcarbamate (11.1 mmol, 1.1 eq) in anhydrous THF (20 mL) at −30° C. under an argon atmosphere, a solution of isopropylmagnesium chloride in THF (12.6 mmol, 1.25 eq) is added dropwise (over 15 min) and the inner temperature is controlled below −20° C. during the addition. The resulting mixture is stirred at −15° C. for 1 h. This solution is then slowly added to above reaction mixture at −30° C. (over 10 min), and the resulting mixture is stirred at −30° C. for an additional 30 min. The reaction mixture is quenched with water (50 mL) and then acidified with conc. HCl at −5° C. to adjust the pH to 5. The mixture is allowed to warm to RT and concentrated in vacuo. The residue is dissolved in MeOH (10 mL), and then conc. HCl (10 mL) is added quickly at RT. The resulting mixture is stirred at reflux for 2 h, cooled to RT and then concentrated in vacuo. The residue is suspended in water (15 mL), basified with concentrated ammonium hydroxide to adjust the pH to 9-10 while keeping the inner temperature below 5° C. and then extracted with DCM (3×15 mL). The combined organic layers are washed with brine, dried over $MgSO_4$ and filtered. The filtrate is concentrated in vacuo and the residue is dissolved in MeOH (70 mL). To this solution, D-(−)-tartaric acid (8.1 mmol, 0.8 eq) is added in one portion at RT. After stirring at RT for 30 min, a solid precipitates and the mixture is slurried at RT for 10 h. The precipitate is collected by filtration and rinsed with MeOH (3×4.0 mL). The collected solid is suspended in water (30 mL) and then neutralized with concentrated ammonium hydroxide solution at RT to adjust the pH to 9-10. The mixture is extracted with DCM (3×15 mL). The combined organic layers are washed with brine, dried over anhydrous $MgSO_4$ and filtered. The filtrate is concentrated in vacuo to afford the product, (S)-3-(1-aminoethyl)-8-(trifluoromethyl)isoquinolin-1(2H)-one(G-5).

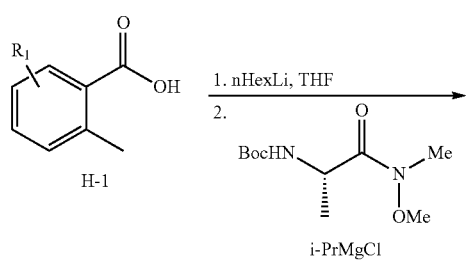

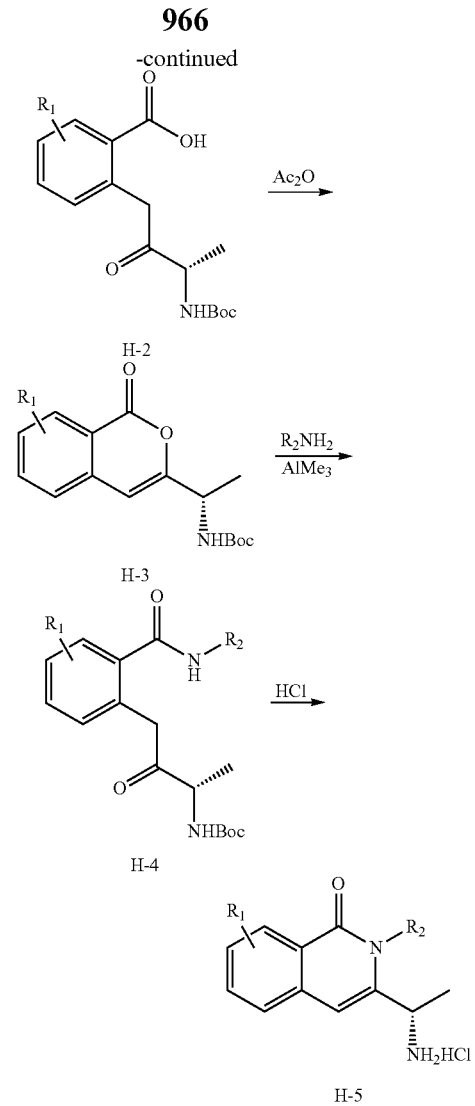

Method H

General Conditions for the Preparation of (S)-3-(1-aminoethyl)-isoquinolin-1(2H)-ones An o-methylbenzoic acid (H-1) (1 eq, e.g., 46.9 mmol) in a flame-dried round bottom flask under nitrogen is dissolved in THF (1 M, e.g., 50 mL). The resulting homogeneous yellow solution is cooled to −25° C. and n-hexyllithium (4.3 eq, e.g., 202 mmol; 2.3 M in hexanes) is slowly added, after which the solution becomes dark red and is stirred at −20° C. for 20 min.

(S)-Tert-butyl 1-(methoxy(methyl)amino)-1-oxopropan-2-ylcarbamate (1.3 eq, e.g., 61.0 mmol) is charged into a second dry round bottom flask under $N_2$ and suspended in 70 mL of dry THF and cooled to −10° C. Isopropyl magnesium chloride (2 M, 2.7 eq, e.g., 127 mmol) is slowly added resulting in a clear yellow solution. This solution is then slowly cannulated dropwise into the first round bottom flask. After addition is complete, the dark solution is slowly warmed to RT and stirred at RT for 2 h. The reaction mixture is then recooled to −10° C. and quickly cannulated into another flask fitted with ethyl acetate (e.g., 15 mL) and isobutyric acid (e.g., 10 mL) at −10° C. under $N_2$. During this time the mixture goes from orange and cloudy to clear and homogeneous. After addition, the mixture is stirred for 5 min after which water (e.g., 10 mL) is rapidly added and it is stirred vigorously for 10 min at RT.

The mixture is then transferred to a separation funnel, and water (e.g., 200 mL) is added to dissolve salts (pH ~9). The water layer is extracted with EtOAc (e.g., 3×400 mL). The aqueous layer is then acidified with HCl (2 M) to pH 3, and then extracted with EtOAc (e.g., 3×500 mL), dried over sodium sulfate and concentrated to provide crude material which is filtered under vacuum through a pad of silica gel using a MeOH/DCM (gradient of 2-10% MeOH) to provide the acid H-2 after concentration.

A 50 mL round bottom flask with a stir bar is filled with benzoic acid H-2 (1 eq., e.g., 14.63 mmol) in acetic anhydride (1.5 M, e.g., 10 mL) and then stirred at 70° C. for 2.5 hours until complete conversion to the product is indicated by LC/MS. The acetic anhydride is evaporated under reduced pressure and the crude residue is purified with combiflash (gradient of EtOAc/hexanes) to give the lactone H-3.

A 50 mL dry round bottom flask with a stir bar is filled with amine $R_2NH_2$ (5.1 eq, e.g., 1.54 mmol) in 2 mL of DCM (0.8 M) after which trimethylaluminum (5.1 eq, e.g., 1.54 mmol) is added to the solution and stirred for 15 min. A solution of lactone H-3 (1.0 eq, e.g., 0.31 mmol) in DCM (1.5 M, e.g., 2 mL) is then added. The mixture is then stirred at RT for 3 h until LC/MS analysis showed complete formation of the desired product. The reaction mixture is quenched with 10 mL of Rochelle's salt and stirred for 2 h. The mixture is then diluted with DCM, washed with brine, dried with over sodium sulfate and evaporated to give a yellow sticky liquid H-4 which is used directly in next step.

To the amide H-4 (1 eq, e.g., 0.31 mmol) in isopropanol (0.06 M, e.g., 5 mL) was added 3 mL of concentrated HCl (300 eq). The mixture is then heated in an oil bath at 65° C. for 3 h until LC/MS shows no remaining starting material. The flask is then removed from heat and the solvents are evaporated under reduced pressure to provide a yellow solid H-5 which is used directly in subsequent transformations.

(iii) General Methods for Alkyne Synthesis:

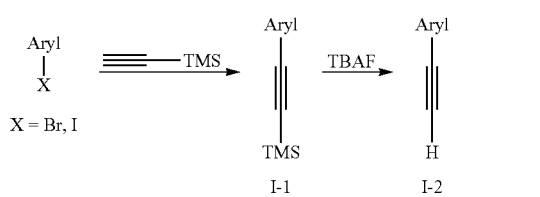

Method I

A sealed vessled is chared with $PdCl_2(MeCN)_2$ and X-Phos (3:1 ratio of X-Phos to $PdCl_2(MeCN)_2$, 5-15 mol % catalyst), cesium carbonate (1.5-3.0 equiv) and propionitrile (0.5 M). The mixture is stirred for 5 min after which the aryl bromide or aryl iodide substrate was added. After another 5 minutes of stirring TMS-acetylene (3.0 equiv) is added and the flask is sealed and heated at RT for 10 min followed by 1 h of heating at 95° C. The reaction is allowed to cool after which it is concentrated directly onto silica gel and purified using flash silica gel chromatography (gradient of ethyl acetate/hexanes) to provide alkyne I-1.

Alkyne I-1 (1.0 equiv) is then dissolved in tetrahydrofuran (0.13 M) and charged with TBAF (1.1 equiv, 1.0 M in tetrahydrofuran). The resulting mixture is stirred at RT for 6 h after which it is poured into saturated bicarbonate solution and extracted with ethyl acetate. The organic layer is washed with brine and concentrated onto silica gel where it is purified directly by flash silica gel chromatography (gradient of ethyl acetate/hexanes) to provide aryl alkyne I-2.

Method J

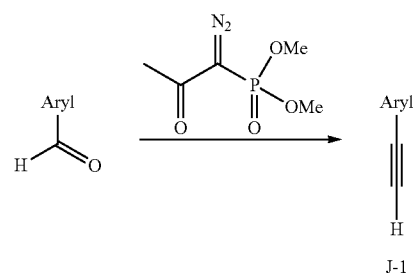

Aldehyde (1.0 equiv) was a dissolved in anhydrous methanol (0.2-0.5 mM) and charged with cesium carbonate (1.0 equiv) and cooled to 0-5° C. Dimethyl (1-diazo-2-oxopropyl)phosphonate (1.0 equiv) was added dropwise after which the reaction was allowed to stir for 1-18 h after which the crude mixture was concentrated onto silica gel and purified directly by flash silica gel chromatography to provide the desired alkyne J-1.

Method K

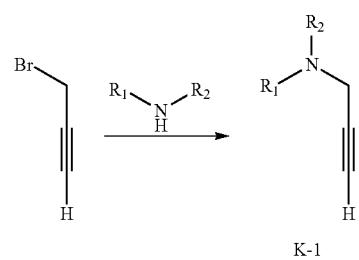

A secondary amine (1.0 equiv) is dissolved in acetonitrile (0.42 M) and potassium carbonate (1.1 equiv) was added. The white suspension was stirred at 0-5° C. for 5 min after which point propargyl bromide (1.01 equiv) was added dropwise over 3 min. The reaction was then stirred for an additional 15 min at 0-5° C. and then at room temperature for 15 h. The heterogeneous mixture was then filtered. The filtrate was concentrated under reduced pressure, diluted with MTBE and washed with water (2×), brine (1×), dried over sodium sulfate and then filtered through celite. The resulting filtrate was concentrated and purified using flash silica gel chromatography to provide the desired alkyne K-1.

Example 1

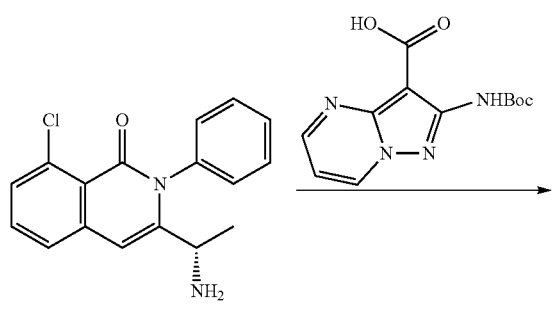

A

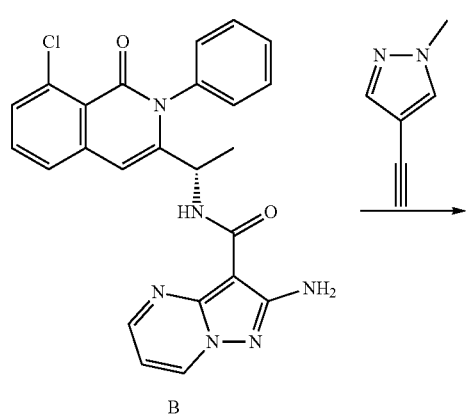

B

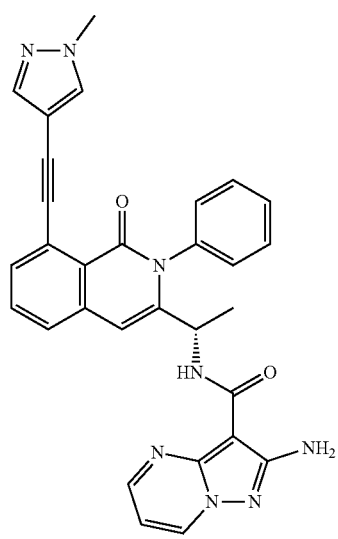

4

Compound 4 was prepared in 3 steps from compound A according to the following procedures: Compound A was prepared according to Method A. It was coupled to 2-((tert-butoxycarbonyl)amino)pyrazolo[1,5-a]pyrimidine-3-carboxylic acid according to the following procedure: Compound A (27.4 mmol, 1.0 equiv), HOBt hydrate (1.2 equiv), 2-((tert-butoxycarbonyl)amino)pyrazolo[1,5-a]pyrimidine-3-carboxylic acid (1.05 equiv) and EDC (1.25 equiv) were added to a 200 mL round bottomed flask with a stir bar. N,N-Dimethylformamide (50 mL) was added and the suspension was stirred at RT for 2 min. Hunig's base (4.0 equiv) was added and after which the suspension became homogeneous and was stirred for 22 h resulting in the formation of a solid cake in the reaction flask. The solid mixture was added to water (600 mL) and stirred for 3 h. The resulting cream colored solid was filtered and washed with water (2×100 mL) and dried. The solid was then dissolved in methylene chloride (40 mL) after which trifluoroacetic acid (10 equiv, 20 mL) was added and the reaction was stirred for 30 min at RT after which there is no more starting material by LC/MS analysis. The solution was then concentrated and coevaporated with a mixture of methylene chloride/ethanol (1:1 v/v) and then dried under high vacuum overnight. The resulting solid was triturated with 60 mL of ethanol for 1 h and then collected via vacuum filtration. The beige solid was then neutralized with sodium carbonate solution (100 mL) and then transferred to a separatory funnel with methylene chloride (350 mL). The water layer was extracted with an additional 100 mL of methylene chloride. The combined organic layers were dried over sodium sulfate, filtered and concentrated under vacuum to provide a pale yellow solid that was purified using flash silica gel chromatography (Combiflash, 24 g column, gradient of 0-5% methanol/methylene chloride) to provide amide B. ESI-MS m/z: 459.4 [M+H]+.

Amide B was placed in a sealed tube (0.67 mmol, 1.0 equiv) followed by dichlorobis(acetonitrile)palladium (15 mol %), X-Phos (45 mol %), and cesium carbonate (3.0 equiv) Propionitrile (5 mL) was added and the mixture was bubbled with Ar for 1 min. 4-Ethynyl-1-methyl-1H-pyrazole (1.24 equiv) was added and the resulting orange mixture was sealed and stirred in an oil bath at 85° C. for 1.5 h. The resulting brownish-black mixture was allowed to cool at which point there was no more SM by LC/MS analysis. The mixture was then filtered through a short plug of cotton using acetonitrile and methylene chloride. The combined filtrates were concentrated onto silica gel and purified using flash silica gel chromatography (Combiflash, 4 g column, gradient of 0-5% methylene chloride/methanol). The resulting material was further purified by reverse phase HPLC (15-90% acetonitrile with 0.1% formic acid/water with 0.1% formic water) to provide desired compound 4. ESI-MS m/z: 529.5 [M+H]+.

The following compounds were prepared in analogous fashion. The alkynes were either commercially available or prepared using Method I, J, or K as described herein.

| Compound no. | Structure | Alkyne | ESI-MS m/z |
|---|---|---|---|
| Compound 2 | (structure) | (isopropyl alkyne) | 491.1 [M + H]+ |
| Compound 5 | (structure) | (phenylacetylene) | 525.5 [M + H]+ |
| Compound 6 | (structure) | (5-ethynyl-2-methoxypyridine) | 556.3 [M + H]+ |

-continued

| Compound no. | Structure | Alkyne | ESI-MS m/z |
| --- | --- | --- | --- |
| Compound 7 | 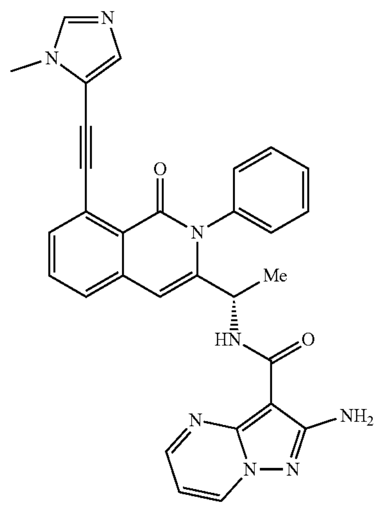 [SMILES: C[C@H](NC(=O)c1c(N)nn2cccnc12)c1cc2cccc(C#Cc3cncn3C)c2c(=O)n1-c1ccccc1] | | 529.5 [M + H]+ |
| Compound 8 | 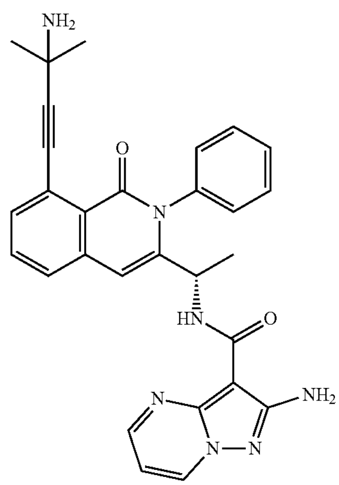 [SMILES: C[C@H](NC(=O)c1c(N)nn2cccnc12)c1cc2cccc(C#CC(C)(C)N)c2c(=O)n1-c1ccccc1] | | 506.1 [M + H]+ |
| Compound 9 | 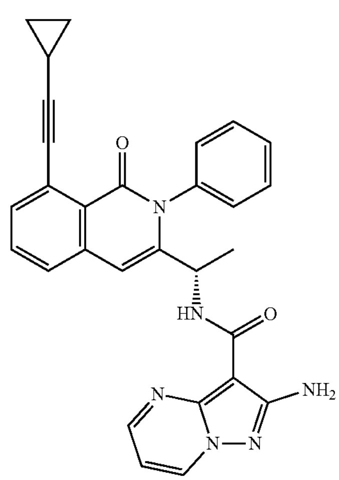 [SMILES: C[C@H](NC(=O)c1c(N)nn2cccnc12)c1cc2cccc(C#CC3CC3)c2c(=O)n1-c1ccccc1] | | 489.4 [M + H]+ |

-continued

| Compound no. | Structure | Alkyne | ESI-MS m/z |
| --- | --- | --- | --- |
| Compound 10 | 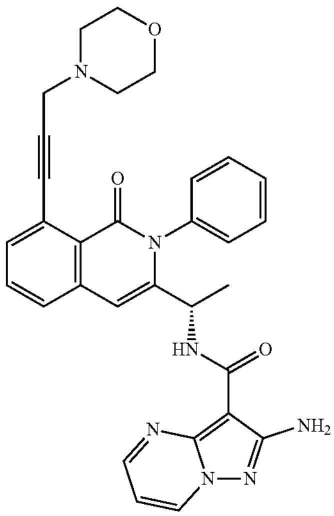 [SMILES: C[C@H](NC(=O)c1c(N)nn2cccnc12)c1cc2cccc(C#CCN3CCOCC3)c2c(=O)n1-c1ccccc1] | Synthesized according to Method K | 548.6 [M + H]+ |
| Compound 11 | 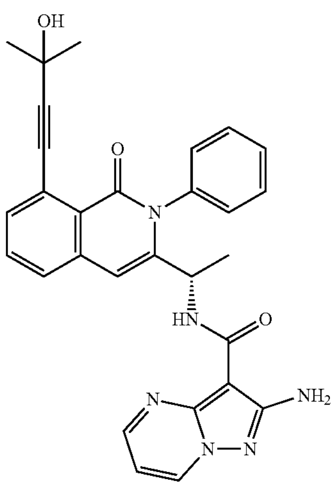 [SMILES: C[C@H](NC(=O)c1c(N)nn2cccnc12)c1cc2cccc(C#CC(C)(C)O)c2c(=O)n1-c1ccccc1] | | 507.1 [M + H]+ |
| Compound 12 | 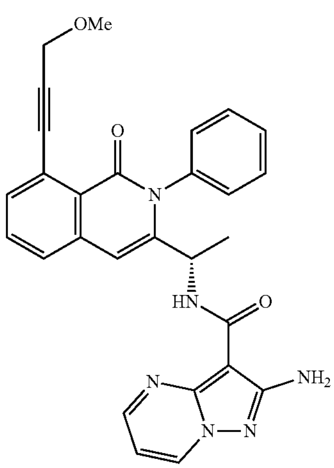 [SMILES: COCC#Cc1cccc2cc([C@H](C)NC(=O)c3c(N)nn4cccnc34)n(-c3ccccc3)c(=O)c12] | | 493.1 [M + H]+ |

-continued
| Compound no. | Structure | Alkyne | ESI-MS m/z |
|---|---|---|---|
| Compound 13 | 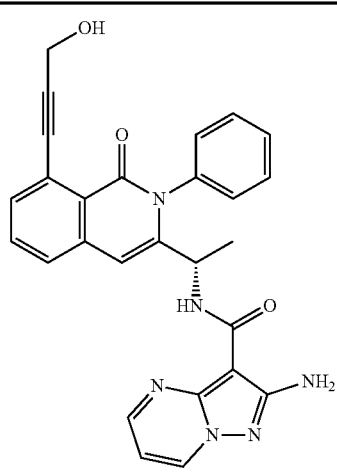 | 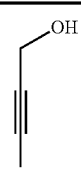 | 479.1 [M + H]⁺ |
| Compound 14 | 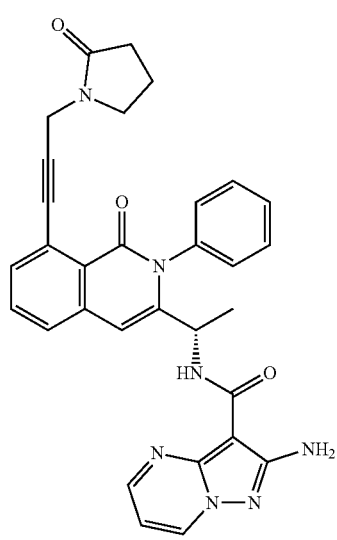 [SMILES: C[C@H](NC(=O)c1c(N)nn2cccnc12)c1cc2cccc(C#CCN3CCCC3=O)c2c(=O)n1-c1ccccc1] | 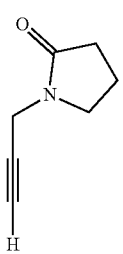 | 546.5 [M + H]⁺ |
| Compound 15 | 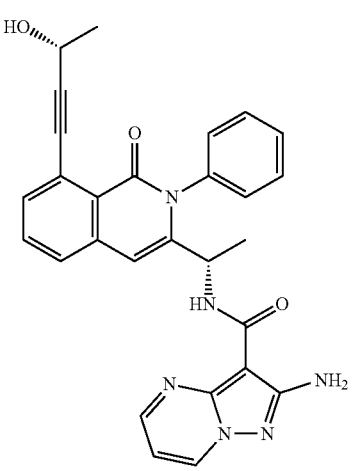 [SMILES: C[C@H](NC(=O)c1c(N)nn2cccnc12)c1cc2cccc(C#C[C@@H](C)O)c2c(=O)n1-c1ccccc1] | 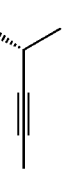 | 493.4 [M + H]⁺ |

-continued

| Compound no. | Structure | Alkyne | ESI-MS m/z |
|---|---|---|---|
| Compound 16 | (structure) | (alkyne) | 493.4 [M + H]⁺ |
| Compound 17 | (structure) | (alkyne) | 526.5 [M + H]⁺ |
| Compound 18 | (structure) | (alkyne) Synthesized according to Method I | 557.1 [M + H]⁺ |

-continued

| Compound no. | Structure | Alkyne | ESI-MS m/z |
|---|---|---|---|
| Compound 19 | 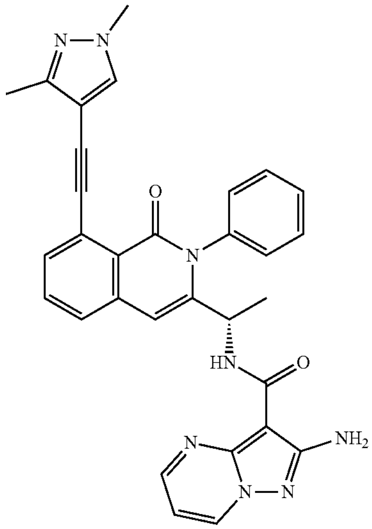 [SMILES: Cc1nn(C)cc1C#Cc1cccc2cc([C@H](C)NC(=O)c3c(N)nn4cccnc34)n(-c3ccccc3)c(=O)c12] | | 543.2 |
| | | Synthesized according to Method I | |
| Compound 20 | 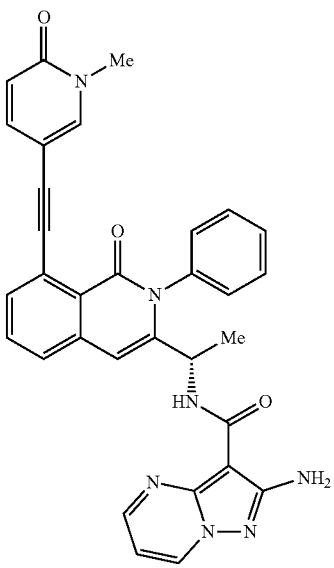 [SMILES: C[C@H](NC(=O)c1c(N)nn2cccnc12)c1cc2cccc(C#Cc3ccc(=O)n(C)c3)c2c(=O)n1-c1ccccc1] | | 556.2 [M + H]⁺ |
| | | Synthesized according to Method I | |
| Compound 26 | 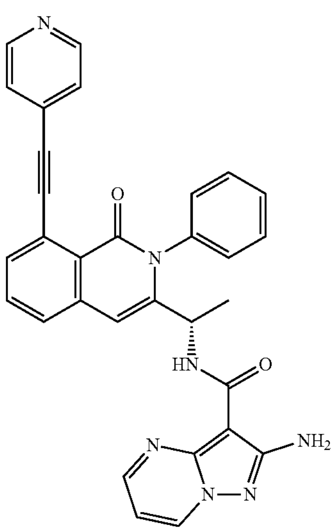 [SMILES: C[C@H](NC(=O)c1c(N)nn2cccnc12)c1cc2cccc(C#Cc3ccncc3)c2c(=O)n1-c1ccccc1] | | 526.3 [M + H]⁺ |

-continued

| Compound no. | Structure | Alkyne | ESI-MS m/z |
|---|---|---|---|
| Compound 28 | (structure shown) | (2-methoxypyridin-4-yl)ethyne; Synthesized according to Method J | 556.3 [M + H]⁺ |
| Compound 30 | (structure shown) | (1-methyl-1H-pyrazol-3-yl)ethyne; Synthesized according to Method J | 529.4 [M + H]⁺ |
| Compound 32 | (structure shown) | 2-ethynylpyridine | 526.4 [M + H]⁺ |

-continued

| Compound no. | Structure | Alkyne | ESI-MS m/z |
|---|---|---|---|
| Compound 34 | 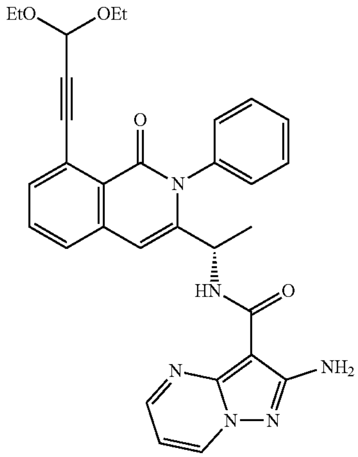 | | 505.3 [M + H(−OEt)]+ |
| Compound 35 | 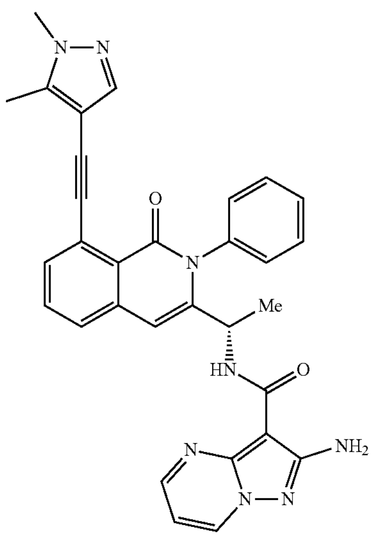 [SMILES: Cc1c(C#Cc2cccc3cc([C@H](C)NC(=O)c4c(N)nn5cccnc45)n(-c4ccccc4)c(=O)c23)cnn1C] | Synthesized according to Method J | 543.4 [M + H]+ |
| Compound 37 | 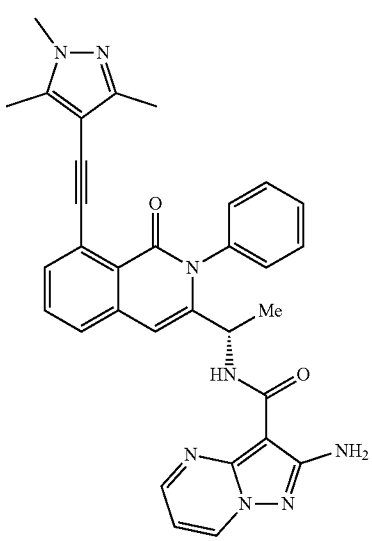 [SMILES: Cc1nn(C)c(C)c1C#Cc1cccc2cc([C@H](C)NC(=O)c3c(N)nn4cccnc34)n(-c3ccccc3)c(=O)c12] | Synthesized according to Method J | 557.4 [M + H]+ |

-continued
| Compound no. | Structure | Alkyne | ESI-MS m/z |
|---|---|---|---|
| Compound 38 | 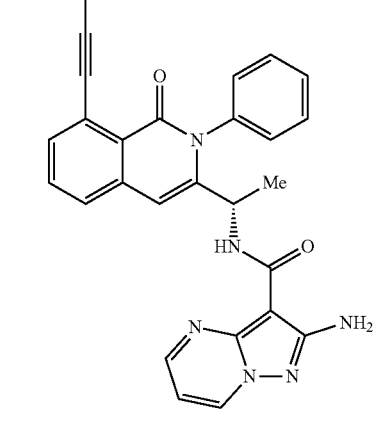 | 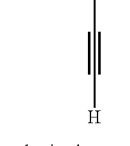<br>Synthesized according to Method J | 543.4 [M + H]⁺ |
| Compound 40 | 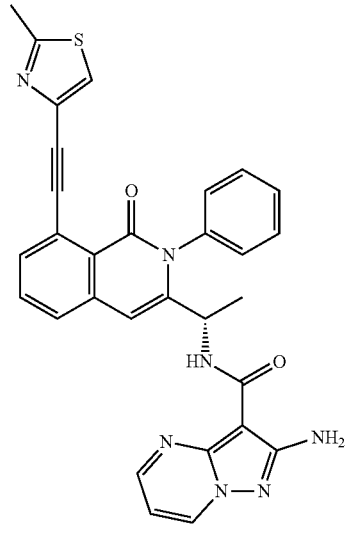 [SMILES: Cc1nc(C#Cc2cccc3cc([C@H](C)NC(=O)c4c(N)nn5cccnc45)n(-c4ccccc4)c(=O)c23)cs1] | 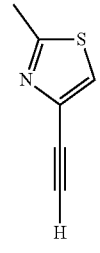<br>Synthesized according to Method J | 546.6 [M + H]⁺ |
| Compound 41 | 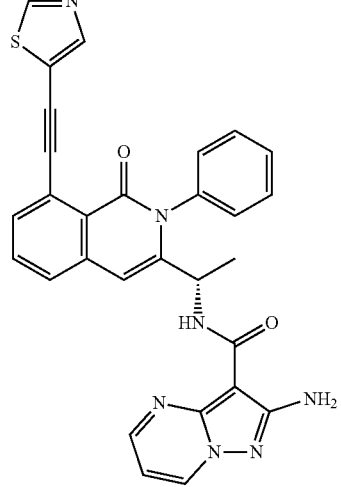 | 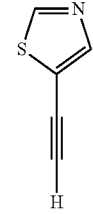<br>Synthesized according to Method J | 532.6 [M + H]⁺ |

-continued

| Compound no. | Structure | Alkyne | ESI-MS m/z |
|---|---|---|---|
| Compound 54 | 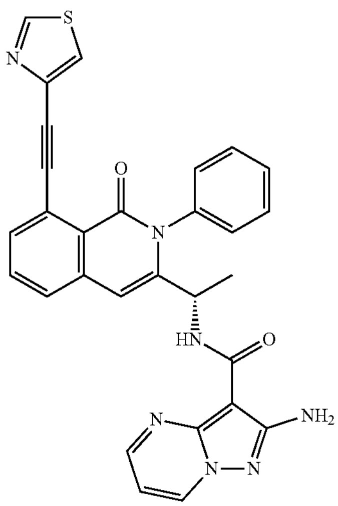 | Synthesized according to Method J | 532.6 [M + H]⁺ |
| Compound 56 | 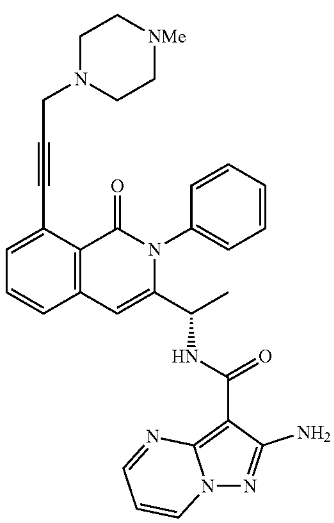 [SMILES: C[C@H](NC(=O)c1c(N)nn2cccnc12)c1cc2cccc(C#CCN3CCN(C)CC3)c2c(=O)n1-c1ccccc1] | Synthesized according to Method K | 561.7 [M + H]⁺ |
| Compound 57 | 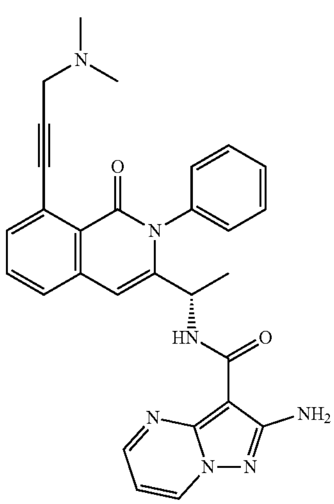 [SMILES: C[C@H](NC(=O)c1c(N)nn2cccnc12)c1cc2cccc(C#CCN(C)C)c2c(=O)n1-c1ccccc1] | | 506.6 [M + H]⁺ |

-continued

| Compound no. | Structure | Alkyne | ESI-MS m/z |
|---|---|---|---|
| Compound 59 | (structure) | (thiazol-2-yl ethyne), Synthesized according to Method J | 532.5 [M + H]⁺ |
| Compound 60 | (structure) | (4-methylthiazol-2-yl ethyne), Synthesized according to Method J | 545.6 [M + H]⁺ |
| Compound 61 | (structure) | (4-methylpyridin-3-yl ethyne), Synthesized according to Method J | 540.3 [M + H]⁺ |

-continued

| Compound no. | Structure | Alkyne | ESI-MS m/z |
|---|---|---|---|
| Compound 64 | 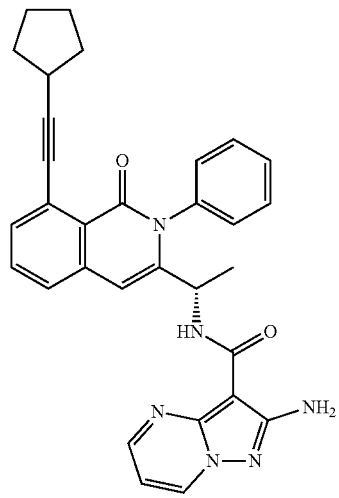 [SMILES: C[C@H](NC(=O)c1c(N)nn2cccnc12)c1cc2cccc(C#CC3CCCC3)c2c(=O)n1-c1ccccc1] | | 517.6 [M + H]+ |
| Compound 65 | 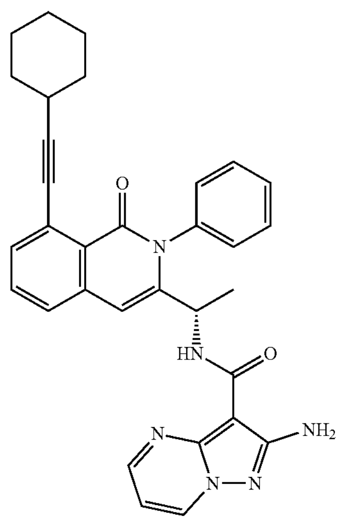 [SMILES: C[C@H](NC(=O)c1c(N)nn2cccnc12)c1cc2cccc(C#CC3CCCCC3)c2c(=O)n1-c1ccccc1] | | 531.6 [M + H]+ |
| Compound 66 | 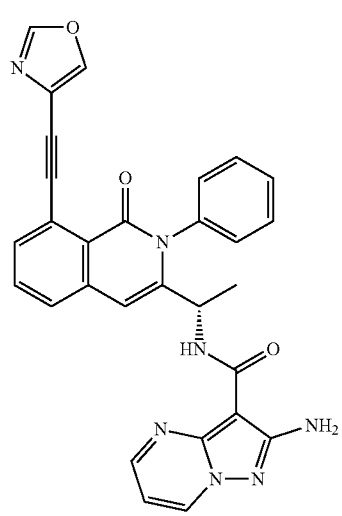 [SMILES: C[C@H](NC(=O)c1c(N)nn2cccnc12)c1cc2cccc(C#Cc3cocn3)c2c(=O)n1-c1ccccc1] | Synthesized according to Method J | 516.5 [M + H]+ |

-continued

| Compound no. | Structure | Alkyne | ESI-MS m/z |
|---|---|---|---|
| Compound 67 | 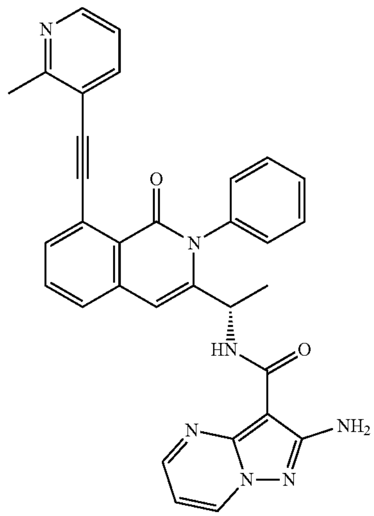 [SMILES: Cc1ncccc1C#Cc1cccc2cc([C@H](C)NC(=O)c3c(N)nn4cccnc34)n(-c3ccccc3)c(=O)c12] | Synthesized according to Method J | 540.3 [M + H]+ |
| Compound 27 | 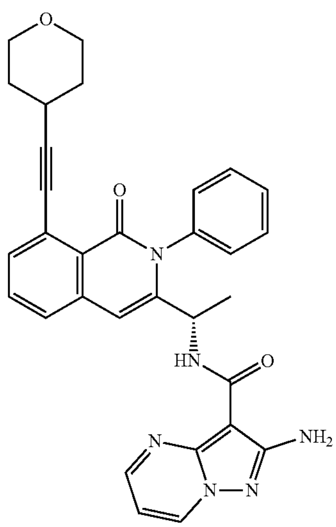 [SMILES: C[C@H](NC(=O)c1c(N)nn2cccnc12)c1cc2cccc(C#CC3CCOCC3)c2c(=O)n1-c1ccccc1] | | 533.5 [M + H]+ |
| Compound 69 | 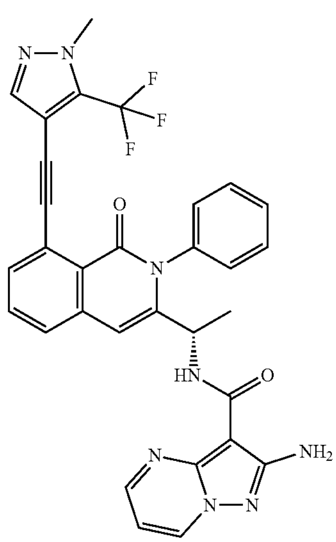 [SMILES: C[C@H](NC(=O)c1c(N)nn2cccnc12)c1cc2cccc(C#Cc3cnn(C)c3C(F)(F)F)c2c(=O)n1-c1ccccc1] | Synthesized according to Method J | 597.2 [M + H]+ |

-continued

| Compound no. | Structure | Alkyne | ESI-MS m/z |
|---|---|---|---|
| Compound 73 | 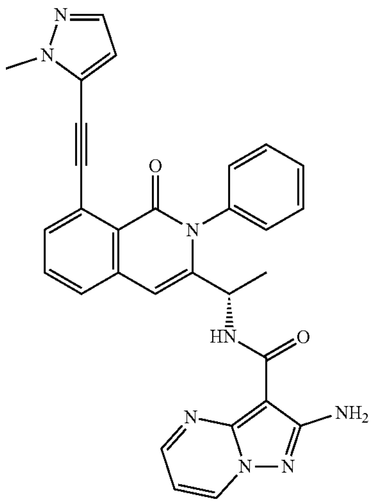 [SMILES: C[C@H](NC(=O)c1c(N)nn2cccnc12)c1cc2cccc(C#Cc3ccnn3C)c2c(=O)n1-c1ccccc1] | | 529.2 [M + H]+ |
| | | Synthesized according to Method J | |
| Compound 75 | 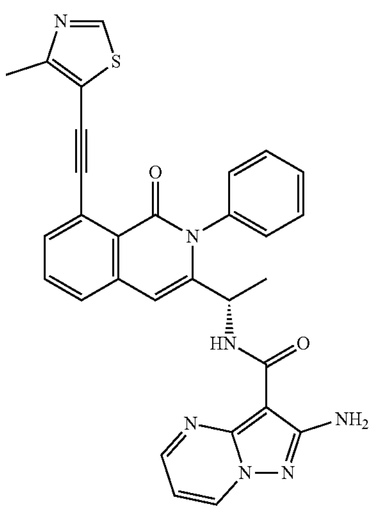 [SMILES: Cc1ncsc1C#Cc1cccc2cc([C@H](C)NC(=O)c3c(N)nn4cccnc34)n(-c3ccccc3)c(=O)c12] | | 546.2 [M + H]+ |
| | | Synthesized according to Method J | |
| Compound 76 | 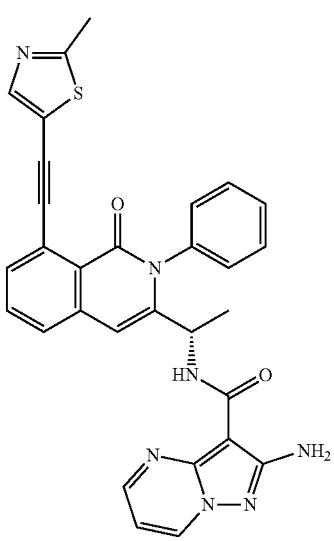 [SMILES: Cc1ncc(C#Cc2cccc3cc([C@H](C)NC(=O)c4c(N)nn5cccnc45)n(-c4ccccc4)c(=O)c23)s1] | | 546.2 [M + H]+ |
| | | Synthesized according to Method J | |

-continued

| Compound no. | Structure | Alkyne | ESI-MS m/z |
|---|---|---|---|
| Compound 77 | 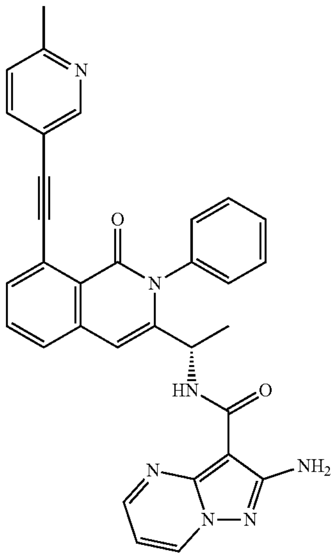 [SMILES: Cc1ccc(C#Cc2cccc3cc([C@H](C)NC(=O)c4c(N)nn5cccnc45)n(-c4ccccc4)c(=O)c23)cn1] | Synthesized according to Method J | 540.3 [M + H]+ |
| Compound 78 | 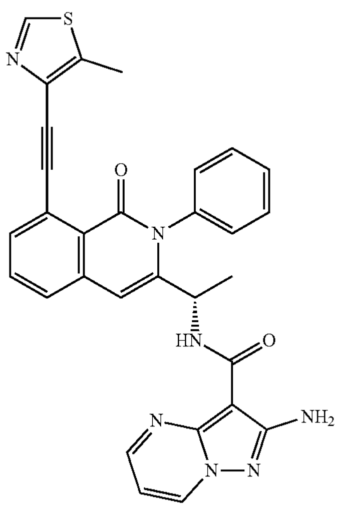 [SMILES: Cc1scnc1C#Cc1cccc2cc([C@H](C)NC(=O)c3c(N)nn4cccnc34)n(-c3ccccc3)c(=O)c12] | Synthesized according to Method J | 546.2 [M + H]+ |
| Compound 79 | 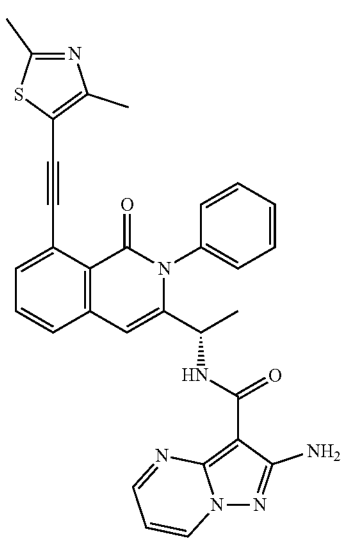 [SMILES: Cc1nc(C)c(C#Cc2cccc3cc([C@H](C)NC(=O)c4c(N)nn5cccnc45)n(-c4ccccc4)c(=O)c23)s1] | Synthesized according to Method J | 560.1 [M + H]+ |

-continued

| Compound no. | Structure | Alkyne | ESI-MS m/z |
|---|---|---|---|
| Compound 81 | 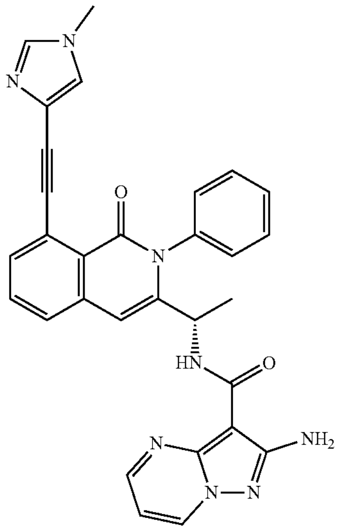 [SMILES: C[C@H](NC(=O)c1c(N)nn2cccnc12)c1cc2cccc(C#Cc3cn(C)cn3)c2c(=O)n1-c1ccccc1] | Synthesized according to Method J | 529.0 [M + H]+ |
| Compound 84 | 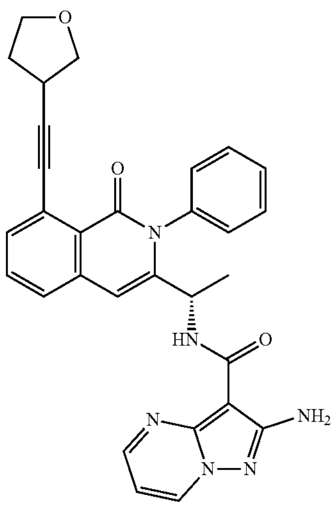 [SMILES: C[C@H](NC(=O)c1c(N)nn2cccnc12)c1cc2cccc(C#CC3CCOC3)c2c(=O)n1-c1ccccc1] | | 519.4 [M + H]+ |
| Compound 85 | 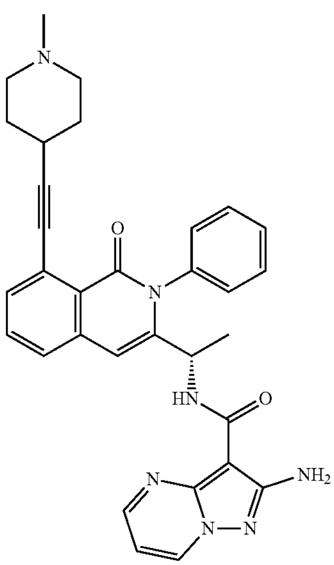 [SMILES: C[C@H](NC(=O)c1c(N)nn2cccnc12)c1cc2cccc(C#CC3CCN(C)CC3)c2c(=O)n1-c1ccccc1] | Synthesized according to Method J | 546.5 [M + H]+ |

1003
-continued
| Compound no. | Structure | Alkyne | ESI-MS m/z |
|---|---|---|---|
| Compound 86 | 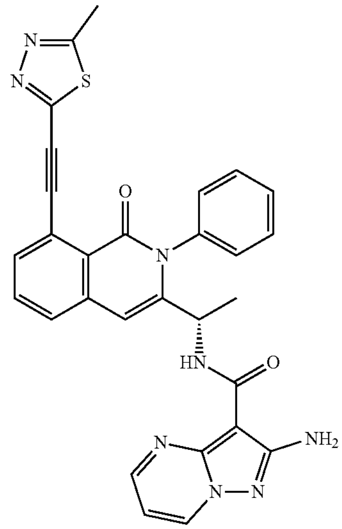 [SMILES: Cc1nnc(C#Cc2cccc3cc([C@H](C)NC(=O)c4c(N)nn5cccnc45)n(-c4ccccc4)c(=O)c23)s1] | | 547.0 [M + H]+ |
| | | Synthesized according to Method J | |
Example 2
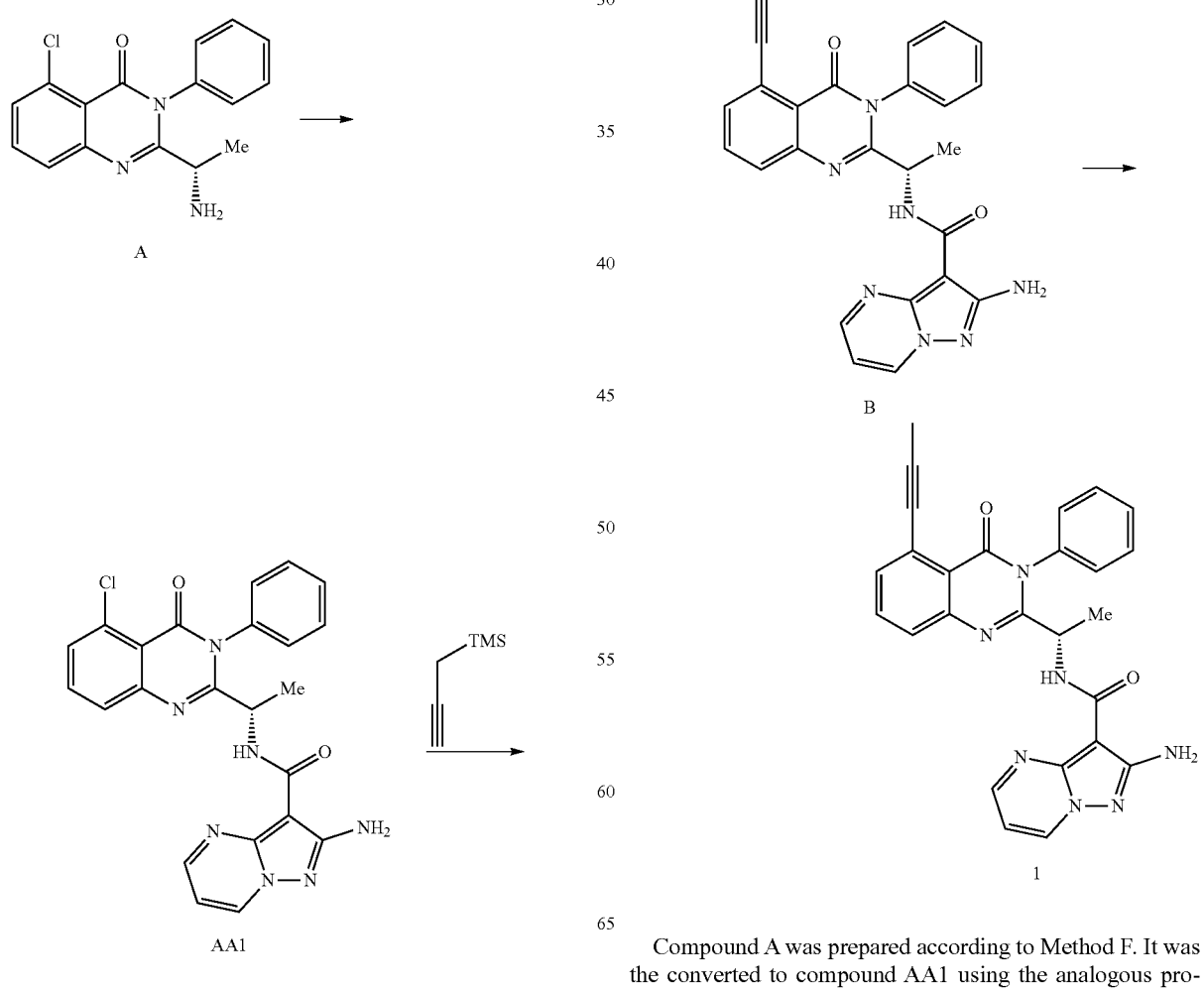
Compound A was prepared according to Method F. It was the converted to compound AA1 using the analogous procedure for compound B in Example 1. Compound 1 was then prepared from compound AA1 in two steps according to the following procedures: Compound AA1 (0.55 mmol, 1.0 equiv), PdCl$_2$(MeCN)$_2$ (10 mol %), X-Phos (30 mol %) and cesium carbonate (2.6 equiv) were suspended in proprionitrile (4 mL). The mixture was bubbled with Ar for 25 min after which trimethyl(propargyl)silane (1.3 equiv) was added and the reaction was sealed and heated to 90° C. The mixture was allowed to heat for 4.5 h after which it was cooled and partitioned between ethyl acetate and water. The layers were separated and the aqueous layer was extracted with ethyl acetate (2×). The organic layers were combined, dried over sodium sulfate and concentrated onto silica gel (2 g). The crude material was then purified using flash silica gel chromatography (ISCO Combiflash Si-12 g, gradient of 10-55% acetone/methylene chloride) to provide a mixture of compound B and deprotected compound 1.

The mixture (0.23 mmol, 1.0 equiv) was redissolved in anhydrous tetrahydrofuran (6 mL). TBAF in THF (1.0 M, 1.2 equiv) was added and the resulting mixture was stirred at RT for 45 min until complete conversion to compound 1 by TLC analysis. The reaction was then concentrated onto silica gel (1 g) and purified by flash silica gel chromatography (Interchim Si-25 g HP silicycle, gradient of 14-45% acetone/methylene chloride) to provide compound 1. ESI-MS m/z: 464.1 [M+H]$^+$.

Example 3

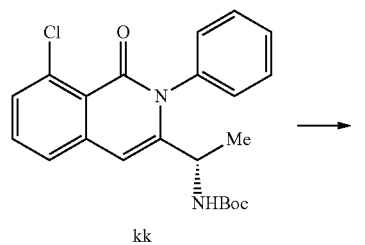

kk

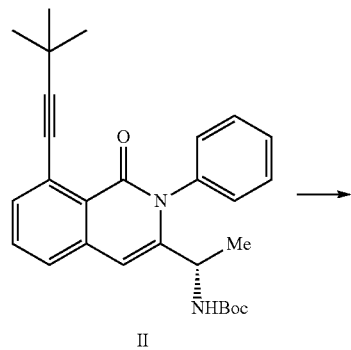

II

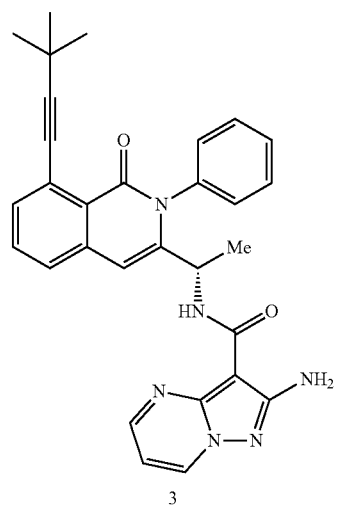

3

Compound kk was prepared from compound A (example 2) under standard Boc protection conditions. It was then converted to compound II using the analogous coupling procedure for compound B in Example 2 except that 3,3-dimethylbut-1-yne was used in place of triethylsilylacetylene to provide compound II Compound II (0.094 mmol, 1.0 equiv) was dissolved in anhydrous methylene chloride (2 mL). Trifluoroacetic acid (400 uL, 55 equiv) was added and the reaction was allowed to stir at RT for 2 h until at which point there was no more SM by LC/MS analysis. The reaction was carefully quenched with sodium bicarbonate solution and the aqueous layer was extracted with methylene chloride (2×). The combined organic layers were dried with sodium sulfate and concentrated. The crude material was purified using reverse phase chromatography (Interchim, gradient of acetonitrile and water with 0.1% formic acid) to provide the free amine which was then coupled to 2-((tert-butoxycarbonyl)amino) pyrazolo[1,5-a]pyrimidine-3-carboxylic acid using Method D followed by Boc-deprotection again using the analogous conditions from Example 11 to provide the desired compound 3. ESI-MS m/z: 505.1 [M+H]$^+$.

Example 4

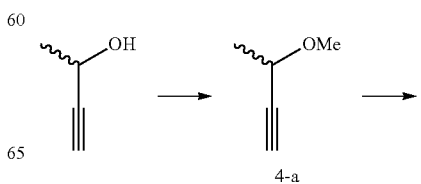

4-a

1007

-continued

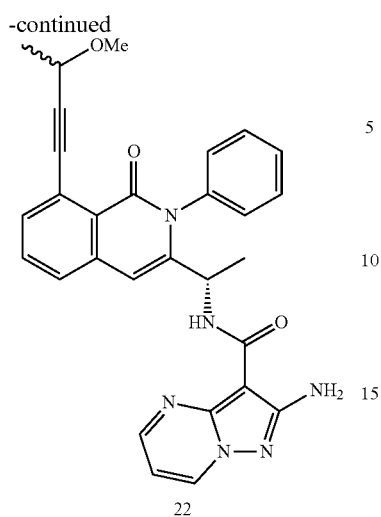

22

A solution of 3-butyn-2-ol (10 mL, 128 mmol) in N,N-dimethylformamide (20 mL) was added over 30 minutes to a stirred slurry of sodium hydride (60% dispersion in mineral oil, (7.65 g, 2.5 equiv) in N,N-dimethylformamide (100 mL) at 0° C. under an argon atmosphere. After 30 min, dimethyl sulfate (1.5 equiv) was added over 30 min at 0° C. The mixture was then stirred for 30 min at 0° C. after which acetic acid was slowly added (1.05 equiv) and the reaction was allowed to warm to room temperature while stirring for an additional 2 h. The product was isolated from fractional distillation directly from the reaction mixture (58-63° C.) to provided ether 4-a that was used directly in the next step. Compound 4-a was then coupled to compound A using analogous Sonogashira conditions as in to Example 1 to generate compound 22. ESI-MS m/z: 507.5 [M+H]$^+$.

Example 5

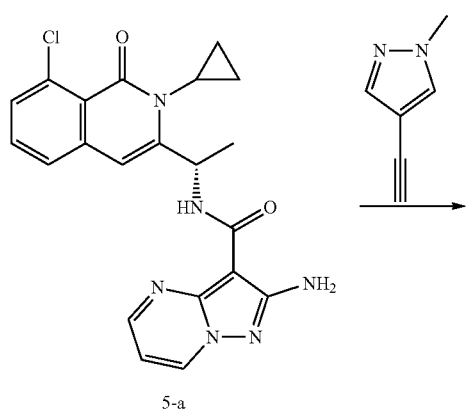

5-a

1008

-continued

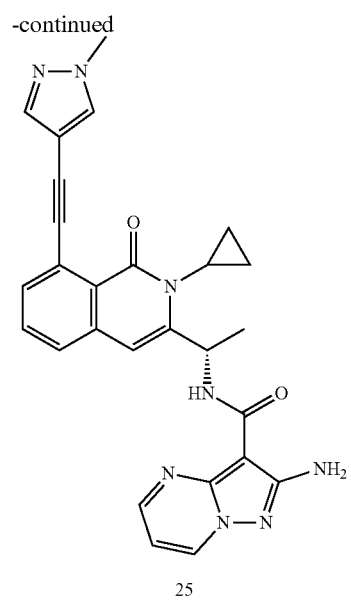

25

Compound 25 was prepared in analogous fashion to compound B in Example 1. It was then coupled to 4-ethynyl-1-methyl-1H-pyrazole using the Sonogashira conditions in Example 1 to provide compound 25. ESI-MS m/z: 493.4 [M+H]$^+$.

Example 6

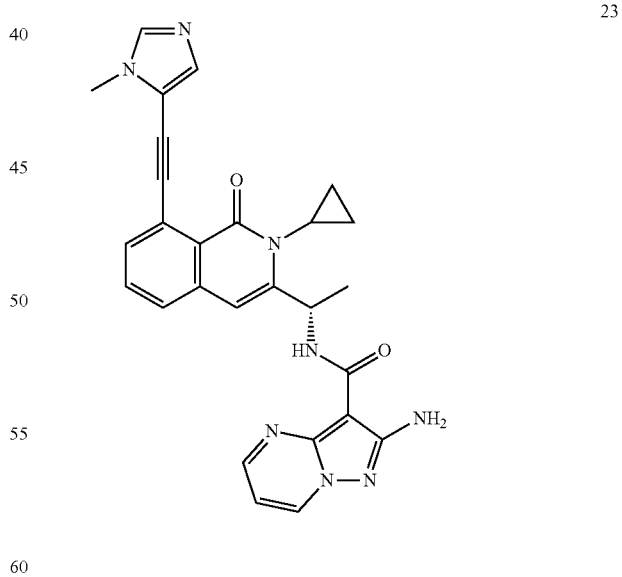

23

Compound 23 was prepared in analogous fashion to compound 25 in Example 5 except that 5-ethynyl-1-methyl-1H-imidazole was used in place of 4-ethynyl-1-methyl-1H-pyrazole. ESI-MS m/z: 493.4 [M+H]$^+$.

Example 7

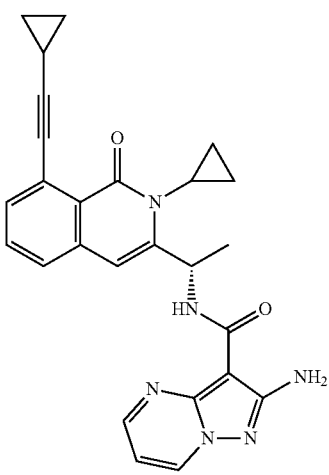

24

Compound 24 was prepared in analogous fashion to compound 25 in Example 5 except that ethynylcyclopropane was used in place of 4-ethynyl-1-methyl-1H-pyrazole. ESI-MS m/z: 453.4 [M+H]$^+$.

Example 8

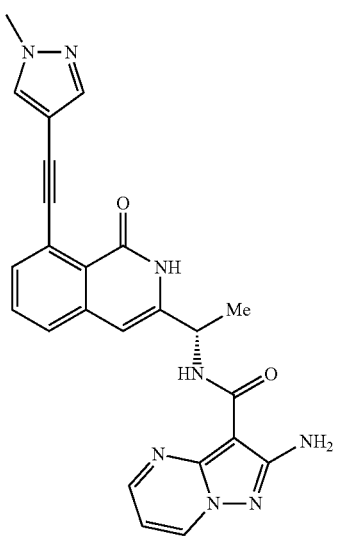

44

Compound 44 was isolated as a byproduct from Example 5. ESI-MS m/z: 453.4 [M+H]$^+$.

Example 9

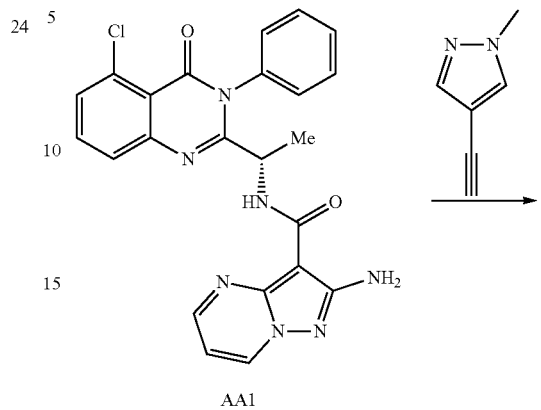

AA1

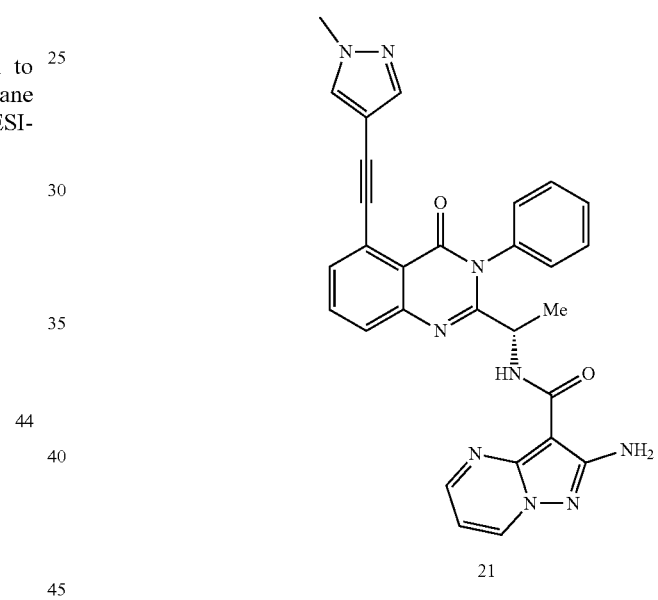

21

Compound 21 was prepared from compound AA1 using analogous coupling conditions for the preparation of compound 4 in Example 1. ESI-MS m/z: 530.2 [M+H]$^+$.

Example 10

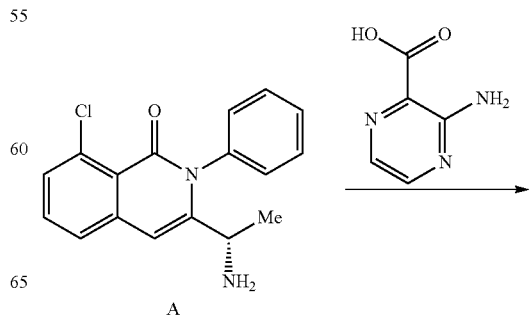

A

1011

-continued

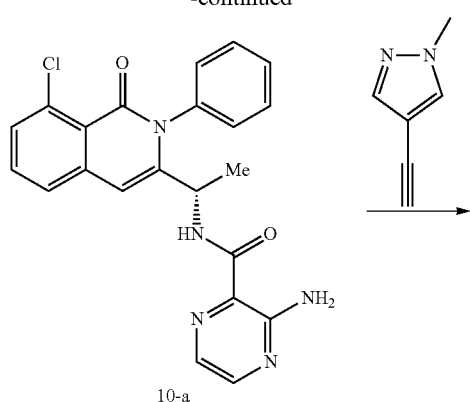

10-a

1012

-continued

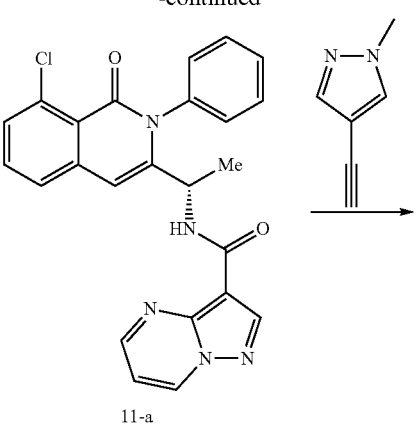

11-a

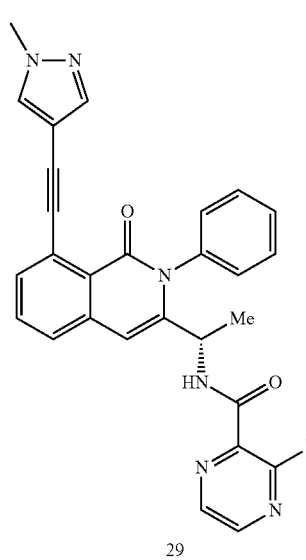

29

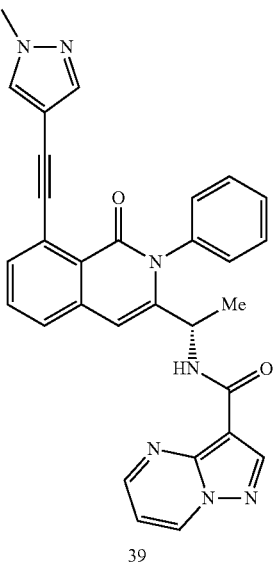

39

3-Aminopyrazine-2-carboxylic acid was coupled to compound A using Method D to provide compound 10-a. It was then converted to compound 29 using analogous coupling conditions for the preparation of compound 4 in Example 1. ESI-MS m/z: 490.3 [M+H]⁺.

Example 11

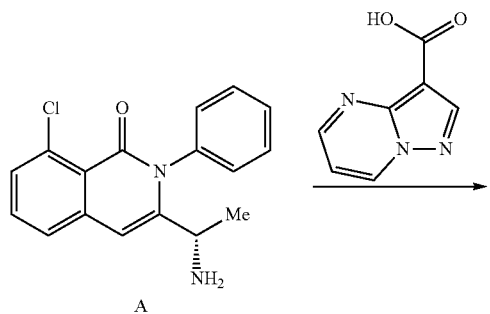

Pyrazolo[1,5-a]pyrimidine-3-carboxylic acid was coupled to compound A using Method D to provide compound 11-a. It was then converted to compound 39 using analogous coupling conditions for the preparation of compound 4 in Example 1. ESI-MS m/z: 514.4 [M+H]⁺.

Example 12

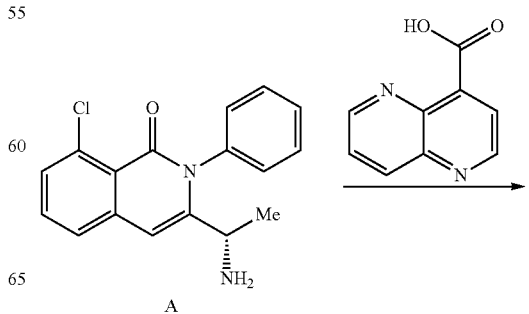

1013
-continued

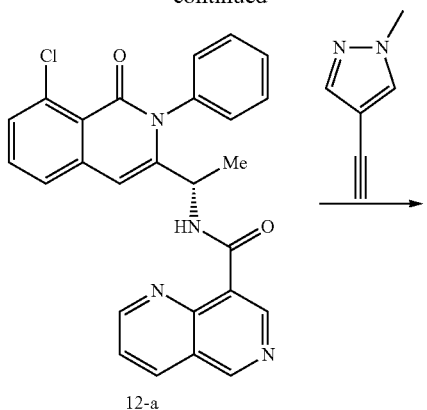
12-a

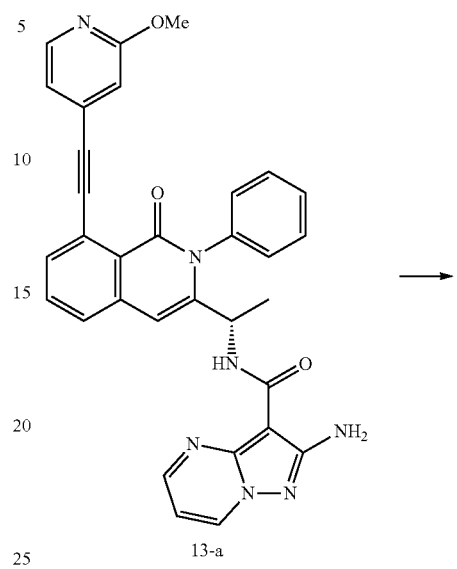

Example 13

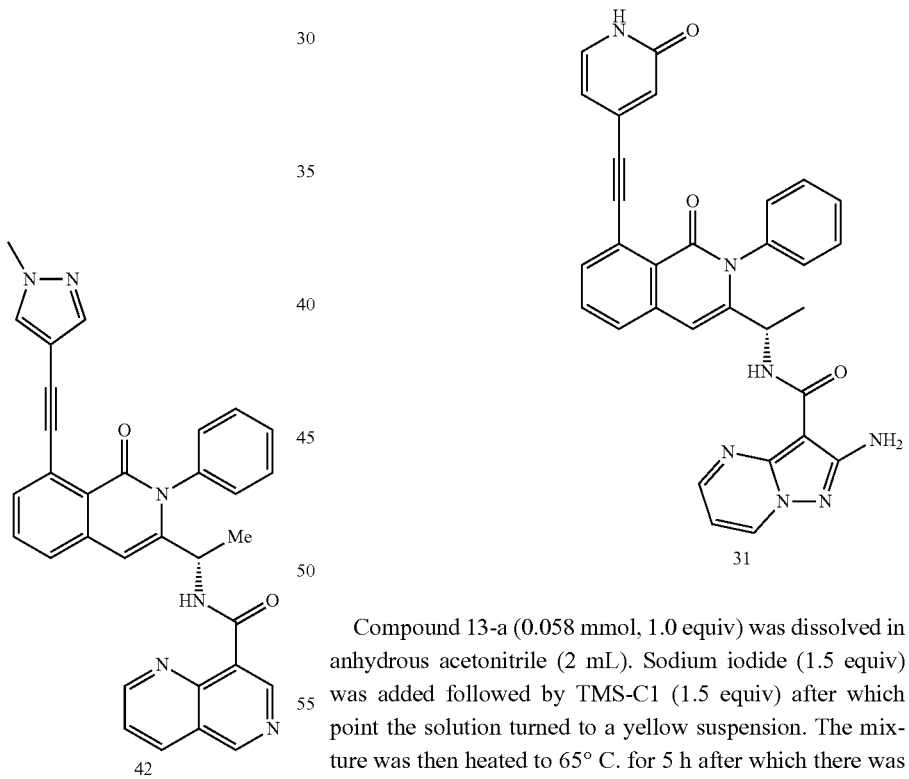

1,5-Naphthyridine-4-carboxylic acid was coupled to compound A using Method D to provide compound 12a. It was then converted to compound 42 using analogous coupling conditions for the preparation of compound 4 in Example 1. ESI-MS m/z: 525.3 [M+H]⁺.

Compound 13-a (0.058 mmol, 1.0 equiv) was dissolved in anhydrous acetonitrile (2 mL). Sodium iodide (1.5 equiv) was added followed by TMS-Cl (1.5 equiv) after which point the solution turned to a yellow suspension. The mixture was then heated to 65° C. for 5 h after which there was no more starting material by LC/MS analysis. The reaction was allowed to cool and poured into water (4 mL) and stirred for 15 min after which it was partitioned between water and methylene chloride. The organic layer was when dried and concentrated. The crude material was purified using reverse phase HPLC (Interchim, gradient of 10-90% acetonitrile/water with 0.1% formic acid) to provide desired compound 31. ESI-MS m/z: 542.4 [M+H]⁺.

Example 14

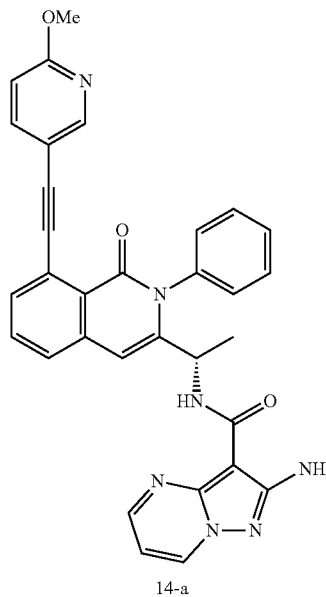

14-a

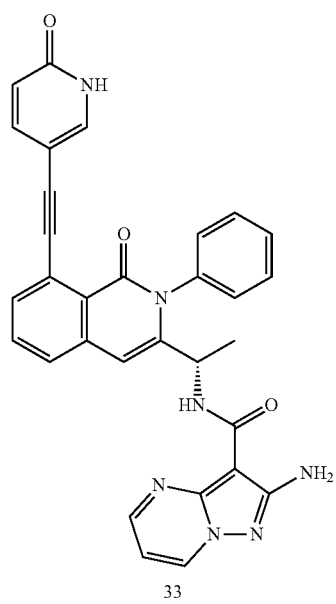

33

Compound 33 was prepared from compound 14-a using the analogous conditions as in Example 13. ESI-MS m/z: 542.4 [M+H]+.

Example 15

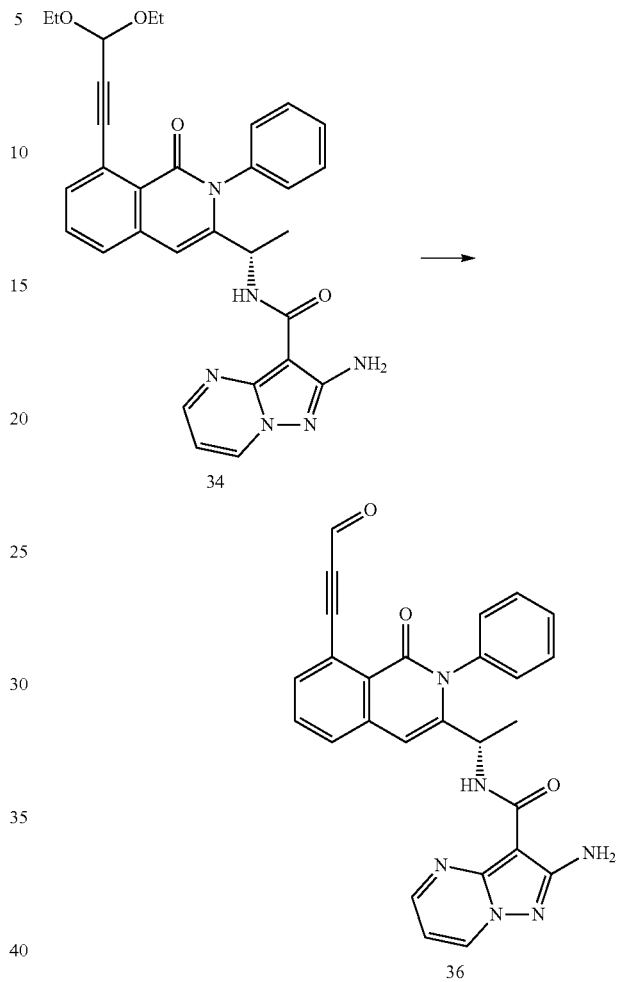

Compound 34 was (0.47 mmol, 1.0 equiv) was dissolved in acetone (5 mL) and water (4 mL). p-Toluene sulfonic acid (25 mol %) was added and the cloudy mixture was heated to 50° C. The mixture was then allowed to cool after which most of the solvent was removed under vacuum. The residue was then partitioned between methylene chloride and saturated sodium bicarbonate. The organic layer was separated and adsorbed onto SiO₂ (3 g) after which it was purified by flash silica gel chromatography (ISCO, 24 g Si column, gradient of 25-100% ethyl acetate/hexanes) to provide the desired aldehyde 36. ESI-MS m/z: 477.2 [M+H]+.

Example 16

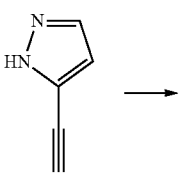

1017
-continued

Example 17

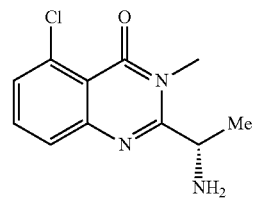

17-a

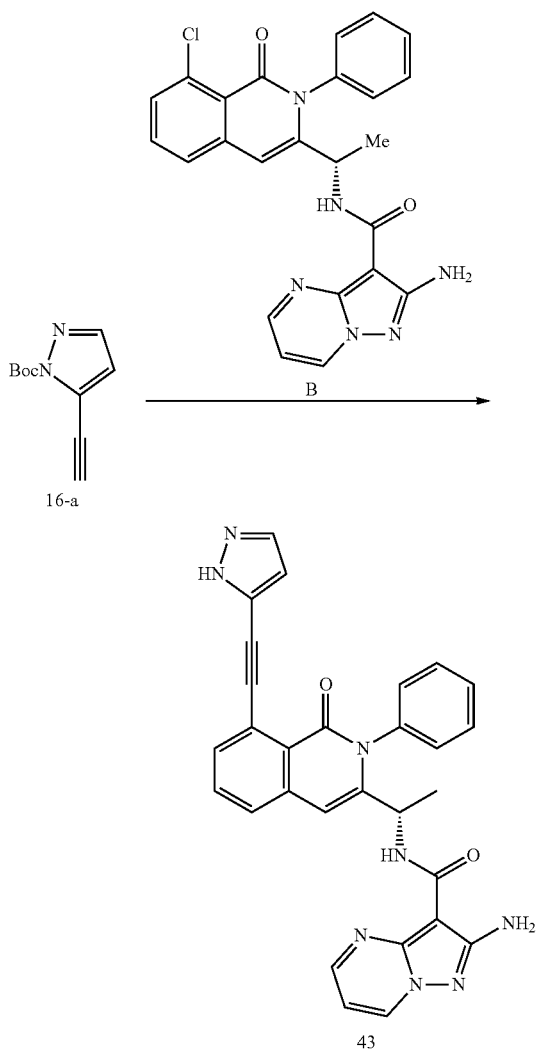

43

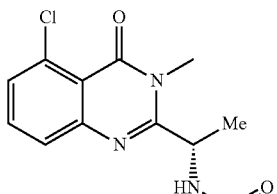

17-b

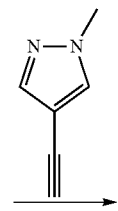

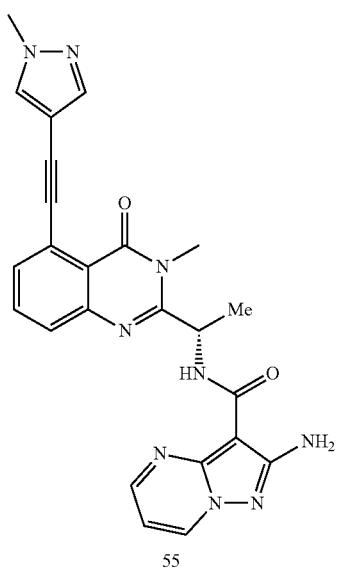

55

5-Ethynyl-1H-pyrazole (1.1 mmol, 1.0 equiv) was dissolved in methylene chloride (10 mL). Triethylamine (3.0 equiv) and Boc anhydride (1.0 equiv) were then added and the reaction was allowed to stir for 2 h. Water (100 mL) was added and the mixture was transferred to a separatory funnel. The layers were separated and the water layer was washed with water (2×20 mL). The organic layers were dried over MgSO4 and concentrated to provide alkyne 16-a which was used directly in the next step.

A pressure flask (15 mL) was charged with compound B (0.22 mmol, 1.0 equiv), X-Phos (45 mol %), dichlorobis(acetonitrile)Pd (15 mol %), and cesium carbonate (1.1 equiv) under a flow of $N_2$. Propionitrile (3 mL) was added and the solution was bubble with Ar for 1 min. Alkyne 16-a (2.5 equiv) was then added followed by Boc anhydride (1.0 equiv) and the reaction was sealed and heated to 100° C. for 1.h. The reaction was then filtered and concentrated. The residue was redissolved in methylene chloride (3 mL) after which trifluoroacetic acid (800 uL) was added and the mixture was stirred for 1 h. The reaction was then concentrated onto silica gel and purified by flash silica gel chromatography (gradient 0-30% methanol/methylene chloride) to provide compound 43. ESI-MS m/z: 515.4 [M+H]$^+$.

Compound 17-a was prepared according to Method F. It was then converted to Compound 55 in analogous fashion to compound 21 in Example 9. ESI-MS m/z: 468.3 [M+H]$^+$.

Example 18

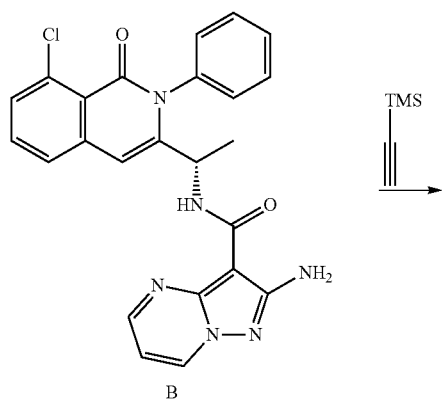

B

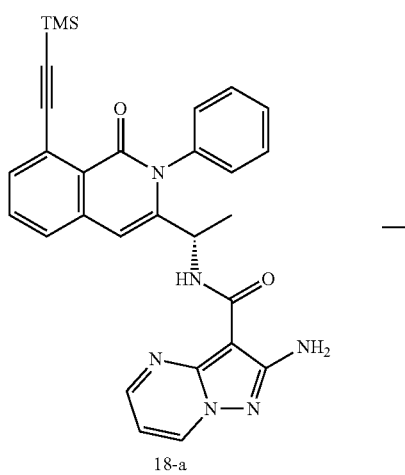

18-a

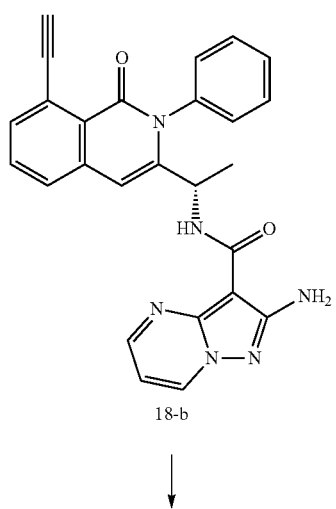

18-b

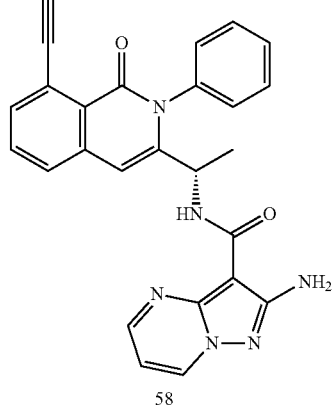

58

A sealed tube (30 mL) was charged with compound B (0.69 mmol, 1.0 equiv), dichlorobis(acetonitrile)palladium (10 mol %), X-Phos (30 mol %) and cesium carbonate (1.5 equiv). Acetonitrile (10 mL) was added followed by the additional of ethynyltrimethylsilane (0.4 mL) and the mixture was purged with Ar for 1 min. The reaction was then sealed and heated in an oil bath to 85° C. After 45 min, an additional aliquot of ethynyltrimethylsilane (1.0 mL) was added and reheated to 75° C. for 14 h after which there was no more starting material by LC/MS analysis. The mixture was filtered and concentrated onto silica gel and purified by flash silica gel chromatography (Combiflash, 12 g column, gradient of 0-5% methanol/methylene chloride) to provide compound 18-a.

Compound 18-a (0.57 mmol, 1.0 equiv) was the dissolved in tetrahydrofuran (4 mL). A solution of TBAF in tetrahydrofuran (0.8 mL, 1.0 M) was added and the mixture was stirred at RT for 1 h at which point the deprotected product was observed as the desired peak by LC/MS analysis. The solution was concentrated onto silica gel and purified using flash silica gel chromatography (Combiflash, 12 g column, gradient of 0-5% methanol/methylene chloride) to provide compound 18-b.

An oven dried RBF with a stir bar was charged with CuI (0.34 mmol, 1.0 equiv), 1,10-phenanthroline (1.0 equiv) and KF (1.0 equiv). Dry N,N-dimethylformamide (2 mL) was added and the mixture was stirred for 15 min under an atmosphere of air. Trimethyl(trifluoromethyl)silane (5.0 equiv) was then added and the mixture was heated to 100° C. under an air atmosphere. A solution of compound 18-b (1.0 equiv in 2 mL N,N-dimethylformamide) was added over the course of 4 h using a syringe pump. Following the completion of compound 18-b addition, the reaction was stirred for an additional 1.5 h at 100° C. At this point the reaction was allowed to cool after which water (100 mL) was added and the mixture was extracted with methylene chloride (3×). The combined organics were washed with water, dried over sodium sulfate and concentrated onto silica gel after which the material was purified by flash silica gel chromatography (Combiflash, 4 g column, gradient of 0-10% methanol/methylene chloride). The crude material was further purified by reverse phase HPLC (Interchim, gradient of 0-10% acetonitrile:water with 0.1% formic acid to provide the desired alkyne 58. ESI-MS m/z: 517.5 [M+H]$^+$.

Example 19

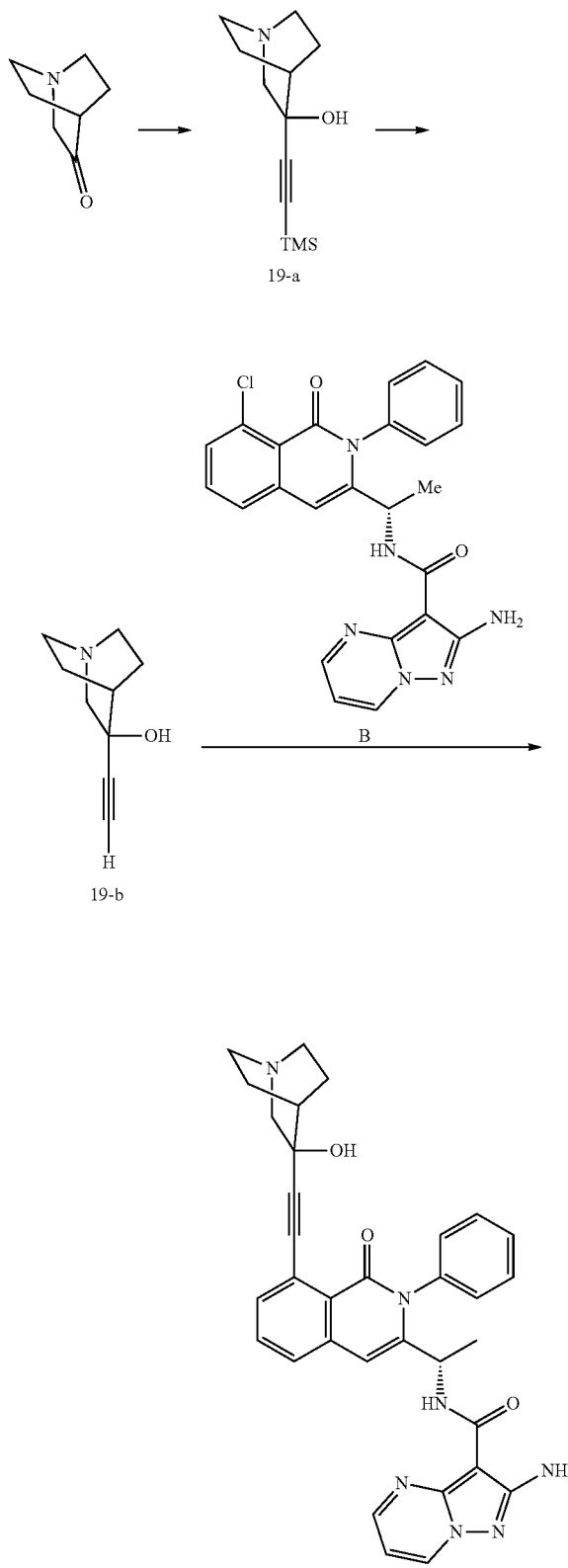

3-Quinuclidone hydrochloride (9.6 mmol, 1.0 equiv) was suspended in methylene chloride (30 mL) and potassium carbonate solution was added (1.0 M, 16 ml). The mixture was stirred for 30 min after which the organic later was collected and the aqueous layer was washed with methylene chloride (3×20 mL), dried over sodium sulfate, filtered and concentrated to provide the corresponding free base.

A solution of ethynyltrimethylsilane (10.6 mmol, 1.1 equiv) in tetrahydrofuran (10 mL) was cooled to −10° C. n-Butyl lithium (2.5 M in THF, 1.15 equiv) was added over 7 min. The reaction was stirred at −10° C. for 30 min after which it was cooled to −78° C. 3-Quinuclidone (1.0 equiv in 20 mLTHF) was added to the flask over a period of 20 min, stirred for 15 additional min after which the cooling bath was removed and the reaction was allowed to stir at 23° C. for 15 h. The mixture was then quenched with saturated ammonium chloride (50 mL) and extracted with ethyl acetate (5×25 mL). The combined organic layers were then washed with water (1×20 mL) and brine (1×20 mL), dried over sodium sulfate and concentrated under reduced pressure to provide alkyne 19-a which was used directly in the next step.

Compound 19-a (7.7 mmol, 1.0 equiv) was dissolved in methanol (17 mL) and treated with potassium carbonate (1.05 equiv). The reaction was allowed to stir at room temperature for 4 h after which it was filtered through celite, washing with 10% methanol in methylene chloride. The filtrates were concentrated under reduced pressure to half the volume and filtered again after which they were concentrated completely under reduced pressure. The material was then redissolved in chloroform (30 mL) and washed with 50% saturated brine (10 mL). The aqueous layer was extracted with chloroform (3×20 mL). The combined organic layers were then washed with brine (5 mL), dried over sodium sulfate and concentrated under reduced pressure to provide compound 19-b.

An oven dried sealed tube was charged with dichlorobis (acetonitrile)palladium (15 mol %), X-Phos (45 mol %), and cesium carbonate (1.2 equiv) followed by propionitrile (5 mL). Compound B (0.22 mmol, 1.0 equiv) was added and the reaction was degassed with Ar for 15 min. Alkyne 19-b (3.0 equiv) was added as a solid and the mixture was purged for an additional 1 min with Ar. The flask was then sealed and heated to 100° C. for 2.5 h after which there was no more starting material by LC/MS analysis. The mixture was filtered through celite and the filtrate was concentrated under reduced pressure and adsorbed onto a 1:4 ratio of Si-Triamine and silica gel (1.5 g) after which it was purified using flash silica gel chromatography (Interchim, 12 g Si column, gradient of 0-20% 1M ammonia in methanol/methylene chloride) to provide the desired compound 62. ESI-MS m/z: 574.6 [M+H]$^+$.

Example 20

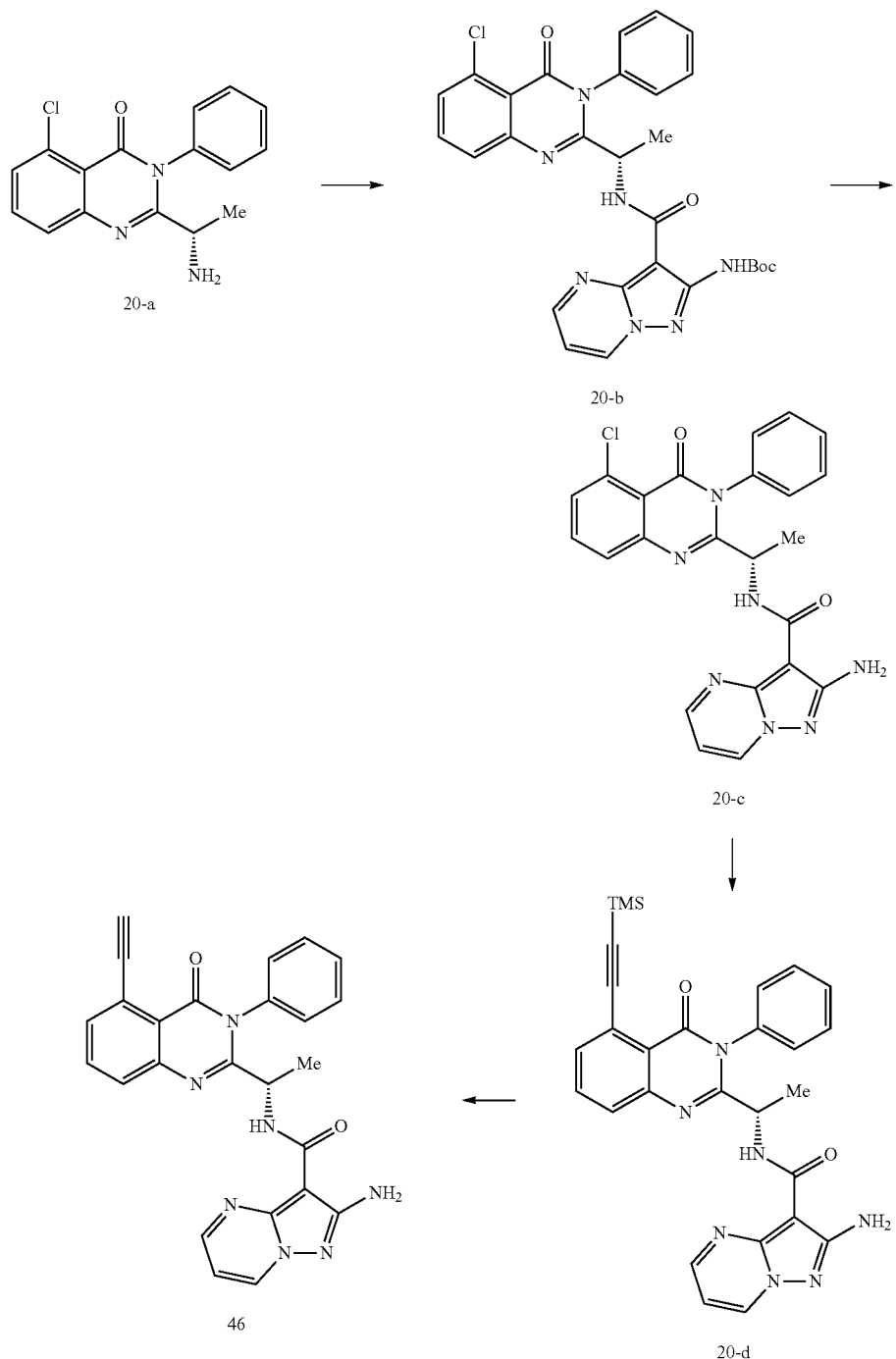

Compound 20-a was prepared according to Method F. It was then coupled to 2-((tert-butoxycarbonyl)amino)pyrazolo[1,5-a]pyrimidine-3-carboxylic acid according to Method D to provide compound 20-b. The Boc group was deprotected under standard conditions using trifluoroacetic acid according to the following procedure: Compound 20-b was dissolved in 0.06 M methylene chloride. Trifluoroacetic acid (40 equiv) was then added and the reaction was allowed to stir at room temperature for 30 min. The mixture was then poured into saturated sodium bicarbonate solution and extracted with methylene chloride (2×). The combined organic layers were dried over $Na_2SO_4$, and concentrated to provide compound 20-c which was used directly in the next step.

A vial was then charged with compound 20-c (0.25 mmol, 1.0 equiv), cesium carbonate (3.0 equiv), $PdCl_2(CH_3CN)_2$ (30 mol %), X-Phos (15 mol %), propionitrile (3 mL) and DMSO (0.5 mL). The mixture was bubbled with Argon for 10 min after which TMS-acetylene (4.0 equiv) was added and the reaction was sealed and heated to 100° C. for 2 h until there was no more starting material as indicated by LC/MS analysis. The reaction was then partitioned between ethyl acetate and brine. The water layer was washed with ethyl acetate (1×). The combined organics were dried over Na₂SO₄ and concentrated to provide crude compound 20-d which was used directly in the next step.

Compound 20-d (0.25 mmol, 1.0 equiv) was dissolved in tetrahydrofuran (10 mL) after which 1M TBAF in tetrahydrofuran (4.0 equiv, 989 uL). Ater 15 min there was no more SM by HPLC analysis. The crude reaction is then partioned between methylene chloride and water. The aqueous layer was first extracted with methylene chloride (2×) and then diluted with 1N HCl and extracted with ethyl acetate (2×). All the organic layers were dried over Na₂SO₄ and concentrated to provide crude material which was first purified by flash silica gel chromatography (Interchim Si-25 g HP silicycle, gradient of 30-100 ethyl acetate/hexanes) to provide material which was further purified by HPLC (30-90% methanol/0.1% trifluoroacetic acid in water) to provide compound 46. ESI-MS m/z: 450.3 [M+H]⁺.

Example 21

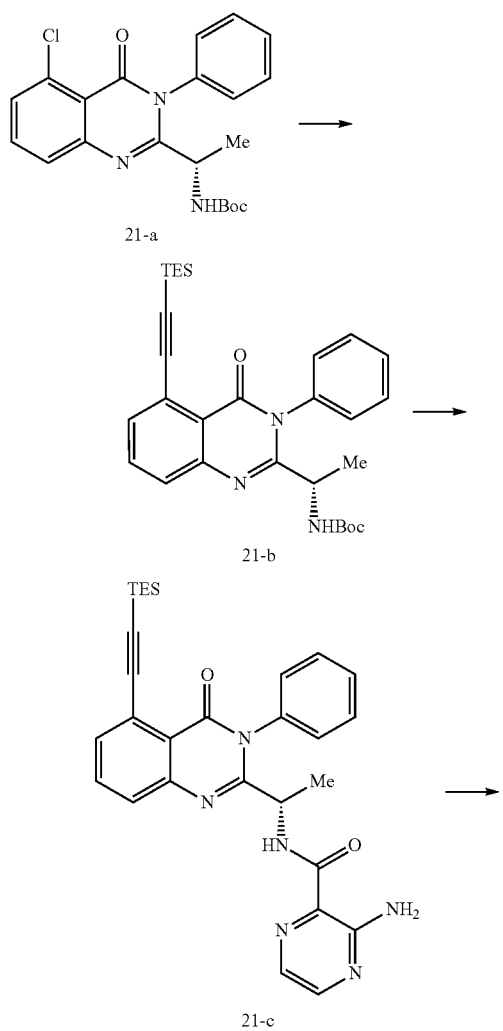

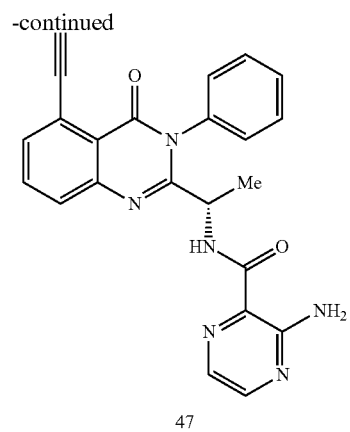

Compound 21-a was prepared according to Method F. It was then coupled to TES-acetylene according to the following procedure: A vial was then charged with compound 21-a (0.48 mmol, 1.0 equiv), cesium carbonate (2.6 equiv), PdCl₂(CH₃CN)₂ (10 mol %), X-Phos (30 mol %) and acetonitrile (2 mL). The mixture was bubbled with Argon for 10 min after which TES-acetylene (1.3 equiv) was added and the reaction was sealed and heated to 90° C. for 2 h until there was no more starting material as indicated by LC/MS analysis. The reaction was then partitioned between ethyl acetate and brine. The water layer was washed with ethyl acetate (1×). The combined organics were dried over Na₂SO₄ and concentrated provide crude compound 21-b which purified using flash silica gel chromatography (Interchim Si-25 g HP silicycle, gradient of 30-100 ethyl acetate/hexanes).

Compound 21-b was then Boc-deprotected and coupled to 3-amino-pyrazine-2-carboxylic acid using Method D to provide compound 21-c. Compound 21-c (0.11 mmol, 1.0 equiv) was dissolved in tetrahydrofuran (4 mL) and treated with 1M TBAF in tetrahydrofuran (3.0 equiv, 320 uL). After 35 min there was no more starting material by LC/MS analysis. The crude mixture was concentrated, pre-adsorbed onto silica gel and purified using flash silica gel chromatography (Interchim Si-12 g HP silicycle, gradient of 40-100 ethyl acetate/hexanes) to provide compound 47 as the desired product. ESI-MS m/z: 411.3 [M+H]⁺.

Example 22

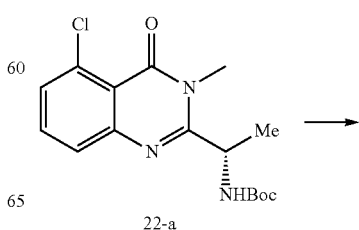

1027

-continued

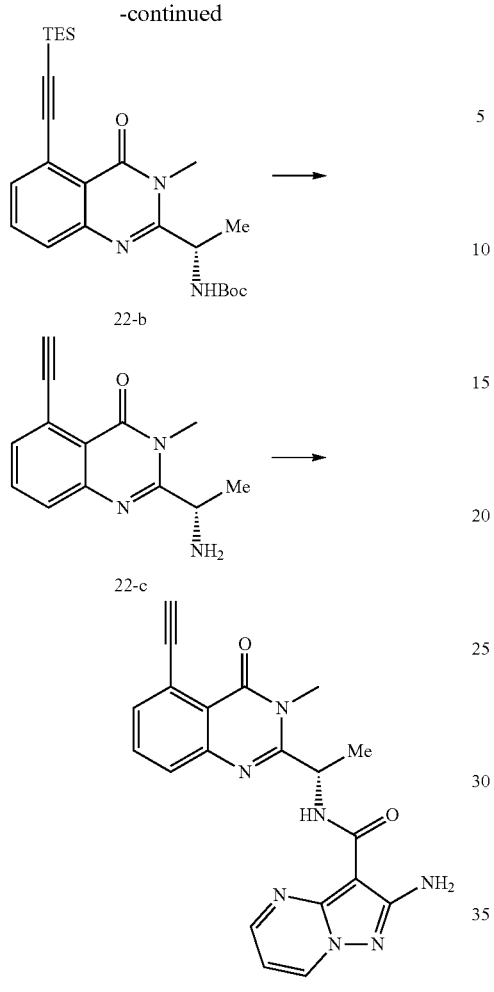

Compound 22-a was prepared according to Method F. A 2 dram vial was then charged with compound 22-a (0.59 mmol, 1.0 equiv), cesium carbonate (2.6 equiv), PdCl$_2$(CH$_3$CN)$_2$ (10 mol %) X-Phos (30 mol %) and propionitrile (2 mL). The mixture was bubbled with Argon for 25 min after which TES-acetylene (2.0 equiv) was added and the reaction was sealed and heated to 90° C. for 3 h until there was no more starting material as indicated by LC/MS analysis. The reaction was then partitioned between ethyl acetate and brine. The water layer was washed with ethyl acetate (1×). The combined organics were dried over Na$_2$SO$_4$ and concentrated provide crude compound 32 which purified using flash silica gel chromatography (Interchim Si-25 g HP silicycle, gradient of 0-30 ethyl acetate/hexanes) to provide the desired material.

The TES group was removed and then Boc-deprotected provide amine 22-b. This was then coupled to 2-((tert-butoxycarbonyl)amino)pyrazolo[1,5-a]pyrimidine-3-carboxylic acid using Method D followed by Boc-deprotection to provide the desired compound 48. ESI-MS m/z: 388.0 [M+H]$^+$.

1028

Example 23

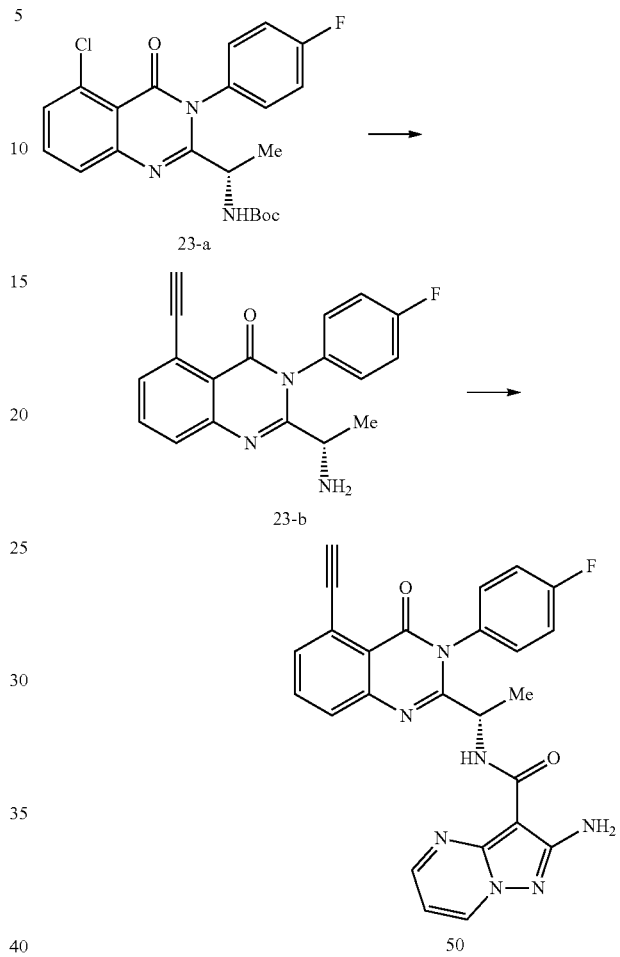

Compound 23-a was prepare according to Method F. It was then converted to amine. This was then coupled to 2-((tert-butoxycarbonyl)amino)pyrazolo[1,5-a]pyrimidine-3-carboxylic acid using Method D followed by Boc-deprotection to provide the desired compound 50. ESI-MS m/z: 478.0 [M+H]$^+$.

Example 24

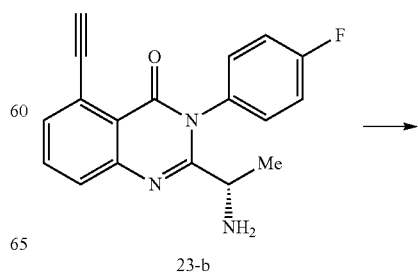

23-b

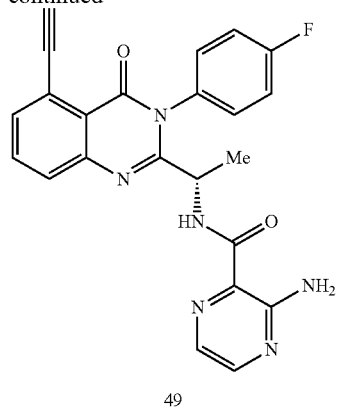
49
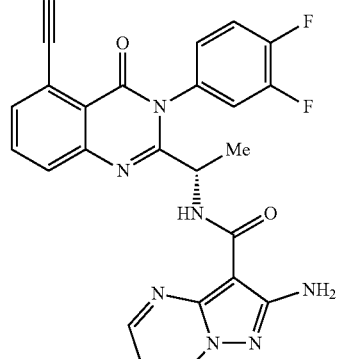
45
Compound 23-b was coupled to 3-amino-pyrazine-2-carboxylic using Method D to prepare compound 49. ESI-MS m/z: 429.0 [M+H]$^+$.
Example 25
Compound 45 was prepared in analogous fashion as compound 49, using 3,4-difluoroaniline instead of 4-fluoroaniline and using 2-aminopyrazolo[1,5-a]pyrimidine-3-carboxylic acid instead of 3-amino-pyrazine-2-carboxylic acid. ESI-MS m/z: 486.1 [M+H]$^+$.
Example 26
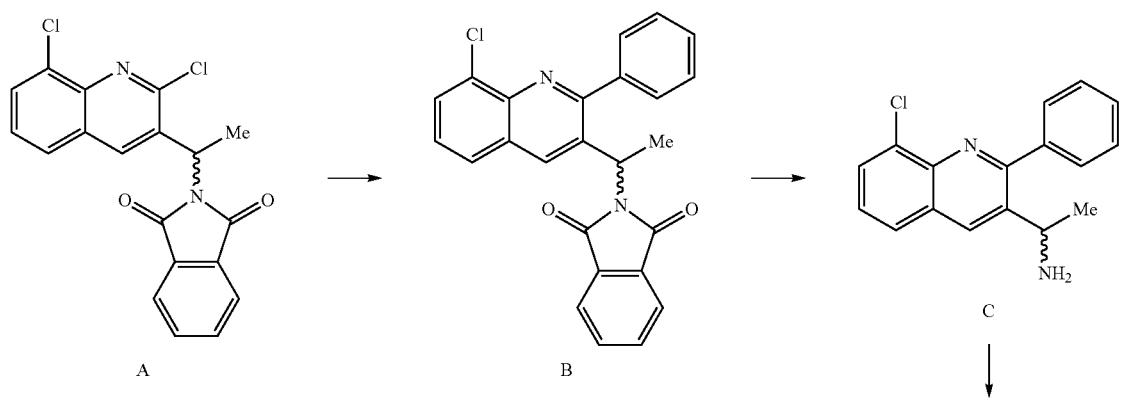
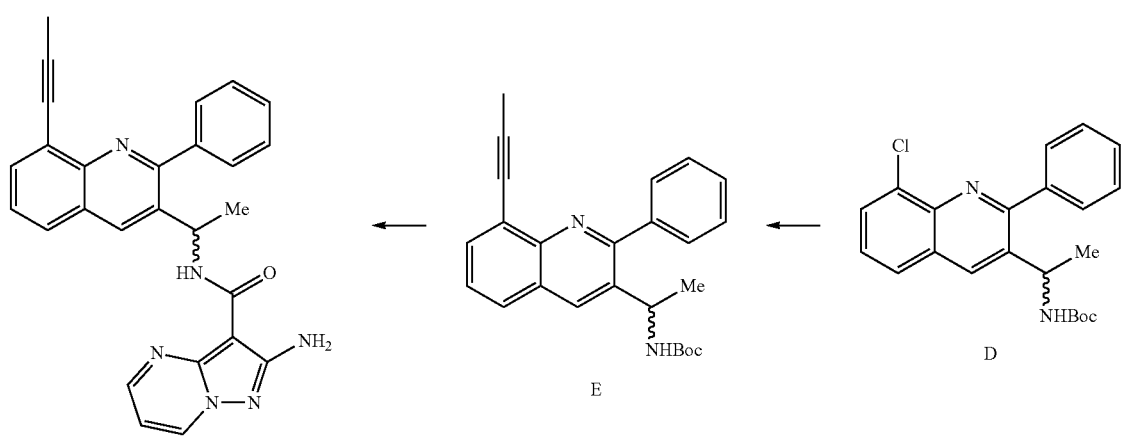

Compound A was prepared according to WO 2008118468.

A mixture of chloride A (0.93 mmol, 1.0 equiv), phenylboronic acid (1.5 equiv), Pd(PPh$_3$)$_4$ (5 mol %) and sodium carbonate (2 equiv) in dioxane/water (4/1 v/v, 65 mL) was then degassed with Ar for 10 min. The resulting mixture was heated to 85° C. and stirred for 3 hr. The resulting suspension was cooled to RT, partitioned between ethyl acetate and a saturated aqueous sodium chloride solution. The organic phase was separated, dried with sodium sulfate, pre-adsorbed on silica gel and purified using silica gel chromatography with ethyl acetate and hexanes to afford compound B. ESI-MS m/z: 413.3 [M+H]$^+$.

A mixture of phthalimide B (0.56 mmol, 1.0 equiv) and hydrazine (20 equiv) in methanol (10 mL) was heated to 75° C. and stirred for 1 hr. The resulting mixture was concentrated, re-suspended in methylene chloride and filtered. The filtrate was concentrated to dryness to afford compound C. ESI-MS m/z: 283.3 [M+H]$^+$.

Compound C (1.3 mmol, 1.0 equiv) was dissolved in N,N-dimethylformamide (5 mL) and charged with Hunig's base (2.0 equiv) and Boc anhydride (1.1 equiv). The mixture was stirred at RT for 1 h after which there was no more starting material by HPLC analysis. The reaction was then poured into brine and extracted with ethyl acetate. The organic layer as washed with brine, dried over sodium sulfate and pre-adsorbed onto silica gel (2 g). The residue was then purified using flash silica gel chromatography (Interchim, Si-25 g, gradient of 10-30% ethyl acetate/hexanes) to provide compound D. ESI-MS m/z: 383.1 [M+H]$^+$.

Compound D (0.52 mmol, 1.0 equiv) was added to a 25 mL RBF containing a suspension of PdCl$_2$(MeCN)$_2$ (15 mol %), X-Phos (45 mol %) and cesium carbonate (3.0 equiv) in propionitrile (5 mL). The mixture was stirred for 1 min after which TMS-propargylsilane (3.0 equiv) was added. The mixture was then stirred at RT for 30 min followed by heating to 95° C. for 1 h. LC/MS analysis showed conversion of the starting material to primarily compound E after which the reaction was allowed to cool. It was then partitioned between ethyl acetate and water in a separatory funnel. The layers were separated and the aqueous layer was extracted with ethyl acetate (1×). The combined organic layers were dried with sodium sulfate and pre-adsorbed onto silica gel (2 g). The resulting material was purified using flash silica gel chromatography (ISCO, 25 g column, gradient of 10-30% ethyl acetate/hexanes) to provide alkyne E. ESI-MS m/z: 387.1 [M+H]$^+$.

Compound E was then Boc deprotected according to the following procedure: Compound E (0.19 mmol, 1.0 equiv) was dissolved in methylene chloride (4 mL) followed by the addition of trifluoroacetic acid (1 mL). The reaction was allowed to stir at RT for 90 min after which there was complete conversion of starting material by HPLC analysis. The reaction was quenched with saturated sodium bicarbonate solution and extracted with methylene chloride. The organic layer was concentrated over sodium sulfate and concentrated. The resulting amine was then converted to compound 51 using the analogous procedures for the conversion of compound A to B in Example 1. ESI-MS m/z: 447.1 [M+H]$^+$.

Example 27

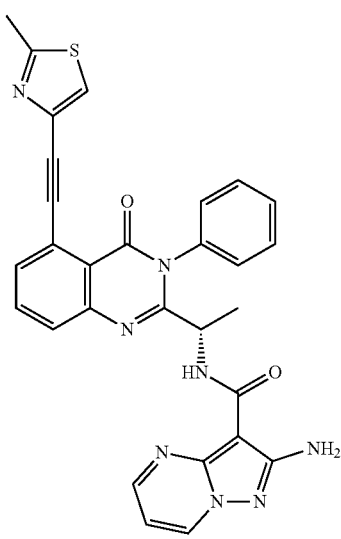

Compound 63 was prepared in analogous fashion to compound 4 in Example 1 except that compound AA1 was used as starting material. ESI-MS m/z: 547.2 [M+H]$^+$.

Example 28

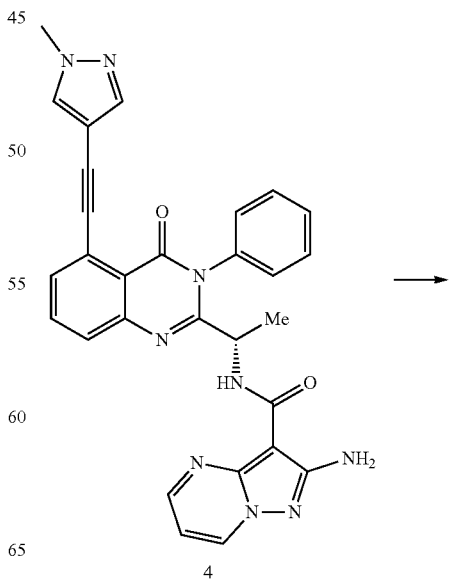

4

1033
-continued

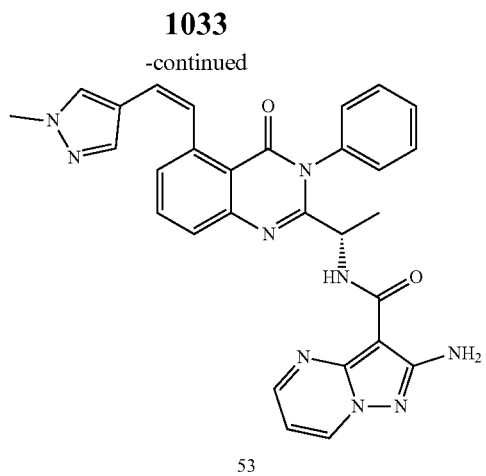

53

Compound 4 (0.12 mmol, 1.0 equiv) was dissolved in a mixture of ethanol and ethyl acetate (20 mL, 3:1 v/v). Palladium on carbon (19 mg, 10% Pd) was added and the reaction was placed under an atmosphere of $H_2$. The mixture was stirred at RT for 41 h after which it was filtered through a filter disk, concentrated and purified by flash silica gel chromatography (Combiflash, 4 g Si column, gradient of 0-5% methanol/methylene chloride) to provide alkene 53. ESI-MS m/z: 531.6 $[M+H]^+$.

Example 29

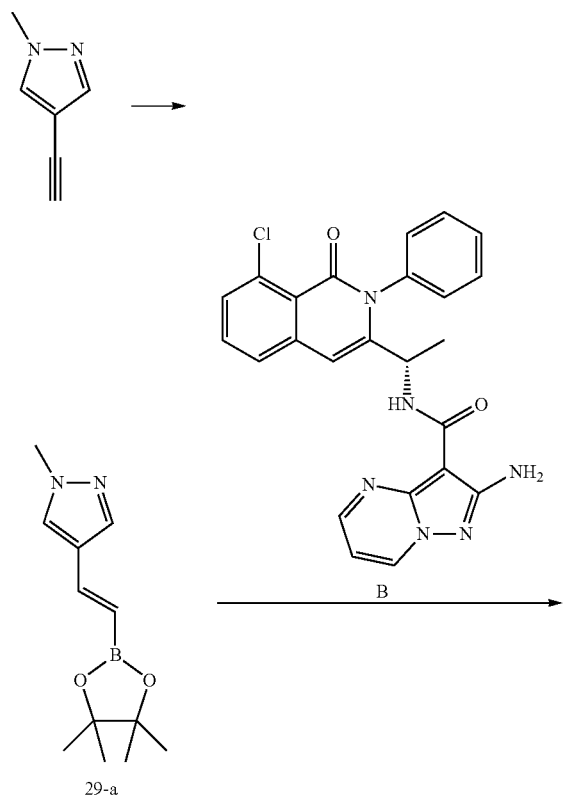

1034
-continued

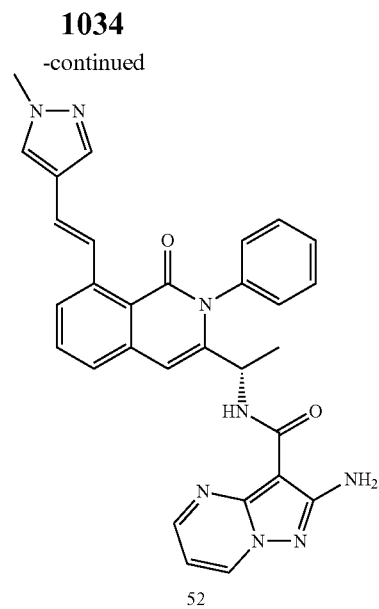

52

4-Ethynyl-1-methyl-1H-pyrazole (1.8 mmol, 1.0 equiv) and pinacolborane (5.0 equiv) were combined in toluene (8 mL) in a RBF under Ar. Carbonylchlorohydridotris(triphenylphosphine) ruthenium(II) (10 mol %) was added and the reaction was heated to 50° C. for 1.5 h after which there was no more starting material by LC/MS analysis. The solvent was evaporated and the crude residue was transferred to a separatory funnel with ethyl acetate (10 mL) and washed with saturated sodium bicarbonate (10 mL), water (10 mL) and brine (10 mL). The organic layer was dried over magnesium sulfate, concentrated and purified using flash silica gel chromatography (gradient 10-40% ethyl acetate/hexanes) to provide alkene 29-a.

Compound B (0.22 mmol, 1.0 equiv), $PdCl_2(Amphos)_2$ (10 mol %) and sodium carbonate (2.0 equiv) were charged to a 4 mL vial under an Ar atmosphere. A solution of compound 29-a in dioxane/water (1.5 equiv, 2 mL solvent, 4:1 v/v) was added and the reaction was stirred at RT for 5 min under Ar before heating to 85° C. for 1 h. The reaction was then allowed to cool, diluted with methylene chloride (15 mL) and washed with water (15 mL). The aqueous layer was then washed with additional methylene chloride (2×15 mL). The organic layers were combined and then washed with water (30 mL), brine (20 mL), dried over sodium sulfate and concentrated to provide crude material which was first purified by flash silica gel chromatography (Interchim Si-12 g, gradient of 0-5% methanol/methylene chloride) followed by purification using reverse phase HPLC (Interchim C18-Sunfire column, acetonitrile/water/0.1% formic acid) to provide compound 52. ESI-MS m/z: 531.4 $[M+H]^+$.

Example 30

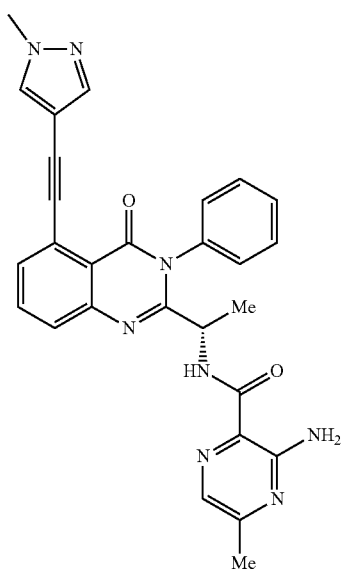 [SMILES: Cc1cnc(C(=O)N[C@@H](C)c2nc3cccc(C#Cc4cnn(C)c4)c3c(=O)n2-c2ccccc2)c(N)n1]

Compound 68 is prepared according to the methods described herein. ESI-MS m/z: 504.2 [M+H]$^+$.

Example 31

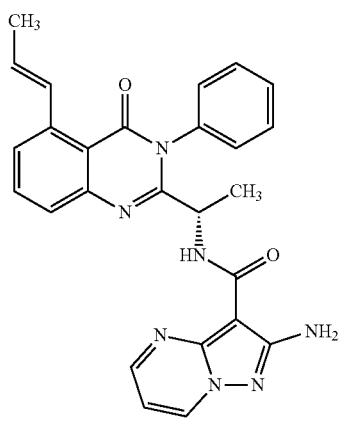 [SMILES: C/C=C/c1cccc2nc([C@H](C)NC(=O)c3c(N)nn4cccnc34)n(-c3ccccc3)c(=O)c12]

Compound B and trans-1-propen-1-ylboronic acid were coupled using the analogous Suzuki coupling conditions in Example 29 to provide Compound 70. ESI-MS m/z: 465.2 [M+H]$^+$.

Example 32

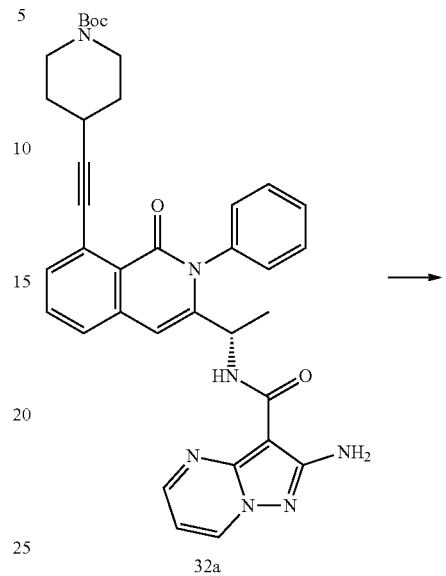

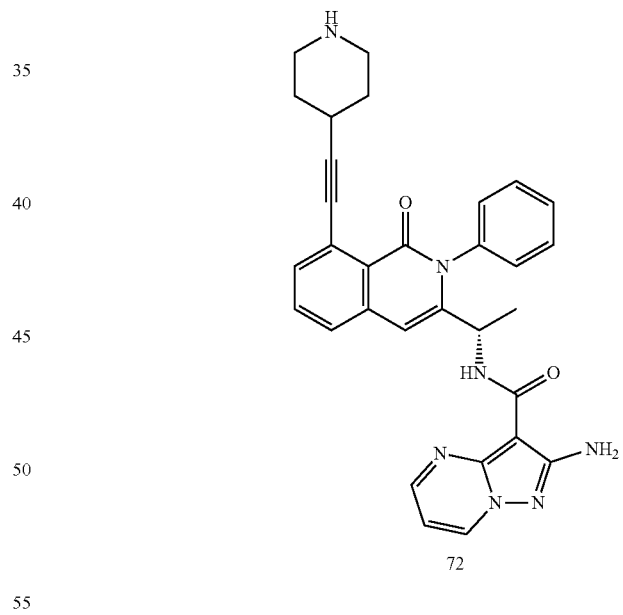

Compound B and 4-ethynylpiperidine-1-carboxylic acid tert-butyl ester were coupled using the Sonogashira coupling conditions in Example 1 to provide compound 32a. Compound 32a was then dissolved in methylene chloride (0.007 M) followed by the addition of trifluoroacetic acid (10 equiv). The reaction was allowed to stir for 2 h at RT after which it was concentrated under vacuum. The residue was treated with excess saturated sodium bicarbonate. The resulting residue was isolated via vacuum filtration and washed with excess water to provide Compound 72. ESI-MS m/z: 532.6 [M+H]$^+$.

Example 33
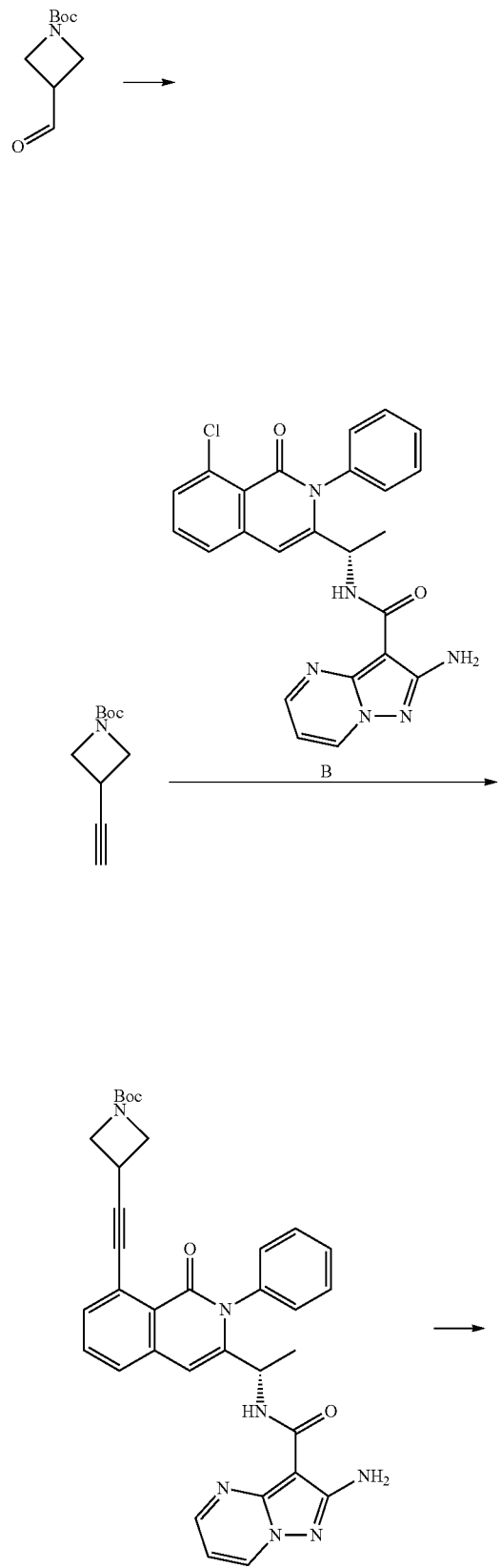
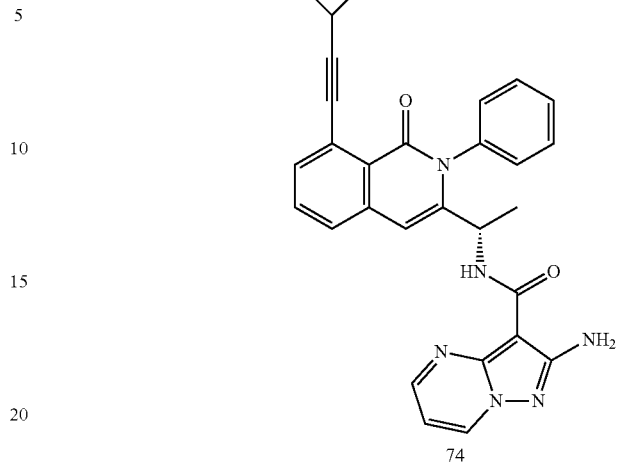
Compound 74 was prepared in 3 steps according to the following procedures: tert-Butyl 3-formylazetidine-1-carboxylate was converted to tert-butyl 3-ethynylazetidine-1-carboxylate according to Method J. It was then coupled to compound B and subsequently deprotected in analogous fashion to the synthesis of Compound 72 in Example 32. ESI-MS m/z: 504.5 [M+H]$^+$.
Example 34
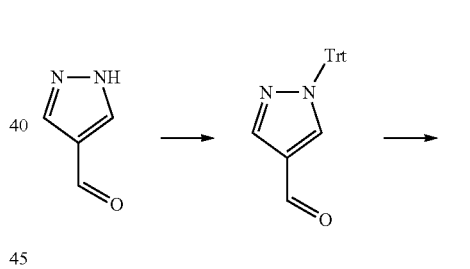
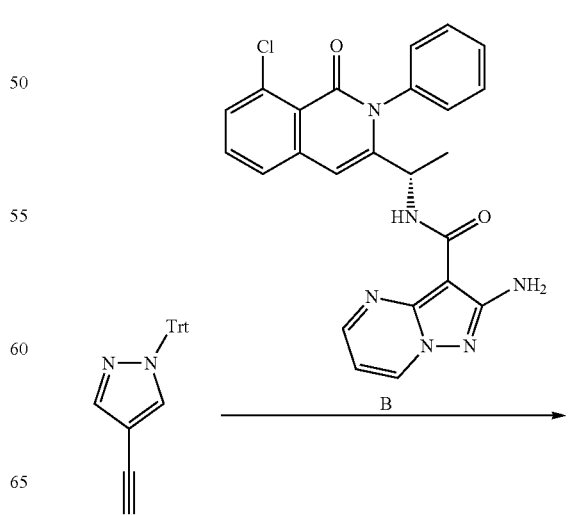

1039

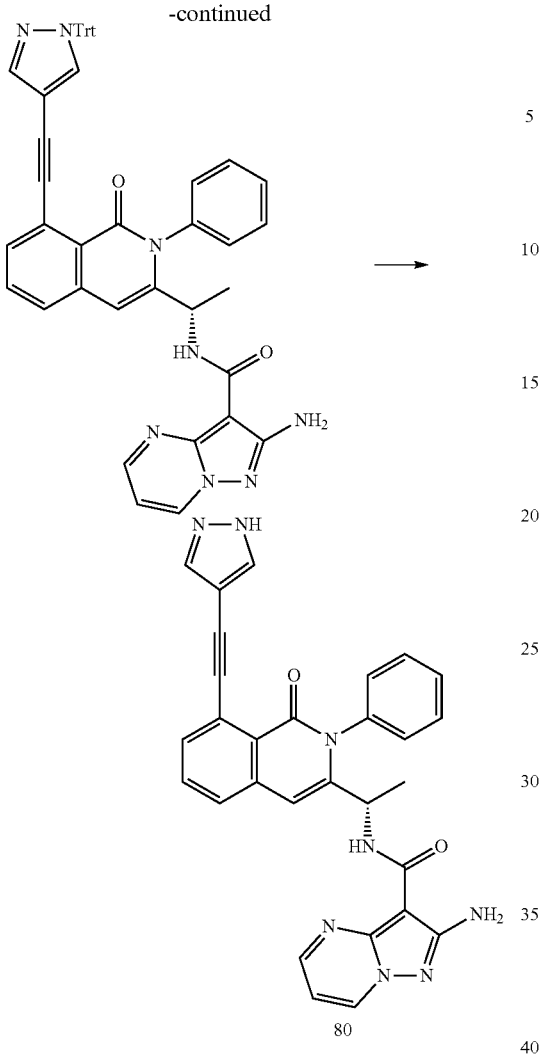

80

Compound 80 was prepared in 4 steps from 1H-pyrazole-4-carbaldehyde according to the following procedures: 1H-pyrazole-4-carbaldehyde (2.1 mmol, 1.0 equiv) was dissolved in 20 mL methylene chloride followed by the addition of triethylamine (3.0 equiv) and trityl chloride (1.0 equiv). The reaction was stirred at RT for 1 h after it was quenched with water (1 mL) and extracted with methylene chloride. The organic layers were concentrated and purified using flash silica gel chromatography (gradient 0-30% methanol/methylene chloride with 0.5% triethylamine). 1-Trity-1H-pyrazole-4-carbaldehyde was then converted to it's corresponding alkyne using Method J after which it was coupled to compound B using the analogous coupling conditions in Example 1. The resulting compound was then deprotected under standard triflouroacetic acid in methylene chloride deprotection conditions after which it was concentrated and purified using flash silica gel chromatography (ISCO, gradient 0-5% methanol/methylene chloride with 0.05% triethylamine and then repurified using reverse-phase HPLC (Interchim C18-Sunfire column, gradient of acetonitrile/water with 0.01% formic acid) to provide compound 80. ESI-MS m/z: 515.0 [M+H]$^+$.

1040

Example 35

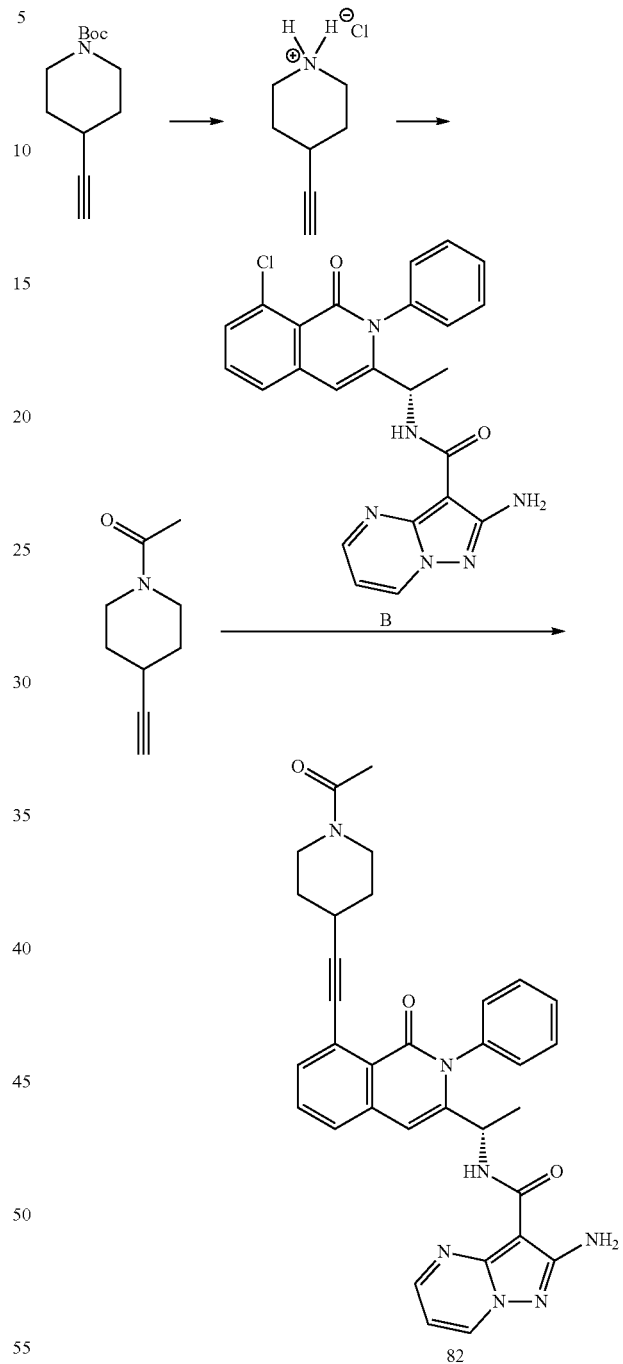

82

Compound 82 was prepared in 3 steps according to the following procedures: N-Boc-4-ethynylpiperidine (3.8 mmol) was dissolved in dioxane (10 mL) and HCl in dioxane (4M, 5.0 equiv) was added. The reaction was allowed to stir at RT for 22 h. The mixture was concentrated under reduced pressure, diluted with 10 mL dioxane and reevaporated under reduced pressure. Diethylether (20 mL) was then added and the mixture was reevaporated to provide the HCl salt that was used directly in the next step. A suspension of the HCl salt (1.05 mmol, 1.0 equiv) in methylene chloride (1 mL) was cooled to 0-5° C. in an ice bath. Hunig's base (3.0 equiv) was added and then after a minute of stirring acetic anhydride (2.0 equiv) was added. The mixture was allowed to stir for 1 h after which there was no more starting material by TLC analysis. The reaction was then diluted with methylene chloride (5 mL), washed with 5% citric acid (1×2 mL), water (1×2 mL) dried over sodium sulfate, and evaporated under reduced pressure. The crude residue was purified using flash silica gel chromatography (ISCO, 4 g column, 0-50% ethyl acetate in methylene chloride) to provide N-acetyl-4-ethynylpiperidine which was coupled directly to compound B using the analogous Sonogashira coupling conditions in example 1 to provide compound 82. ESI-MS m/z: 574.5 [M+H]+.

Example 36

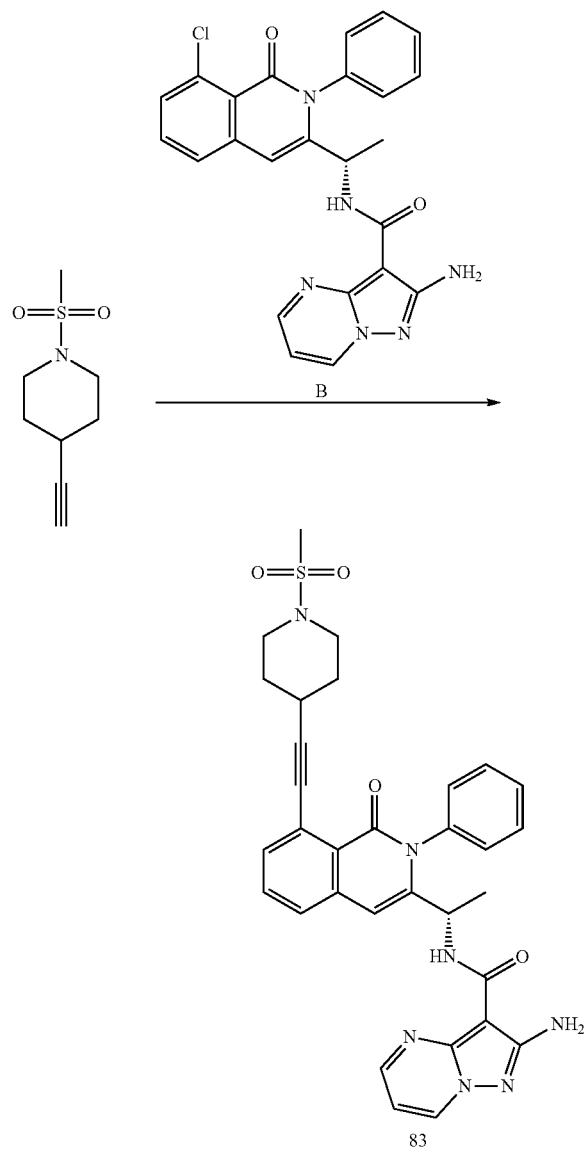

A suspension of 4-ethynyl piperidine HCl(1.1 mmol, 1.0 equiv) was suspended in methylene chloride (1 mL) and cooled to 0-5° C. in an ice bath. Hunig's base (3.0 equiv) was added and then after a minute of stirring methanesulfonyl chloride (2.0 equiv) was added and the reaction was allowed to stir for 1 h after which there was no more starting material by LC/MS analysis. The mixture was then diluted with methylene chloride (5 mL) washed with 5% citric acid (1×2 mL), water (1×2 mL), dried over sodium sulfate and concentrated. The crude residue was purified using flash silica gel chromatography (ISCO, 12 g Si column, gradient of 0-10% ethyl acetate/methylene chloride) to provide N-methanesulfonamide-4-ethynylpiperidine which was coupled directly to compound B using the analogous Sonogashira coupling conditions in example 1 to provide compound 83. ESI-MS m/z: 610.6 [M+H]+.

Example 37

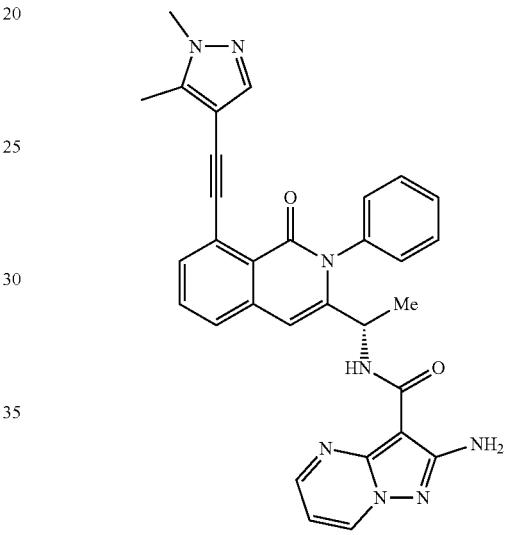

Compound 88 was prepared in analogous fashion as compound 21 in example 9 except that 4-ethynyl-1,5-dimethyl-1H-pyrazole was used in place of 4-ethynyl-1-methyl-1H-pyrazole. A suspension of (S)-2-amino-N-(1-(5-chloro-4-oxo-3-phenyl-3,4-dihydroquinazolin-2-yl)ethyl)pyrazolo[1,5-a]pyrimidine-3-carboxamide (146 mg, 0.317 mmol), Cesium carbonate (198 mg, 0.608 mmol, 2 eq.), Dichlorobis(acetonitrile)palladium (II) (15 mg, 0.058 mmol, 0.2 eq.) and Xphos (87 mg, 0.182, 0.6 eq.) in propionitrile (2 mL) was bubbled with argon for 5 minutes. The mixture was charged with 4-ethynyl-1,5-dimethyl-H-pyrazole (73 mg, 0.6 mmol, 2 eq.), heated to 95° C. and stirred for 2 hr. The resulting mixture was cooled to RT, partitioned between Ethyl acetate and water. The organic phase was separated, washed with saturated aqueous sodium chloride solution, dried with sodium sulfate and concentrated. The residue was purified with silica gel chromatography using a gradient of DCM and MeOH to afford (S)-2-amino-N-(1-(5-((1,5-dimethyl-1H-pyrazol-4-yl)ethynyl)-4-oxo-3-phenyl-3,4-dihydroquinazolin-2-yl)ethyl)pyrazolo[1,5-a]pyrimidine-3-carboxamide. ESI-MS m/z: 544.2 [M+H]+.

Example 38

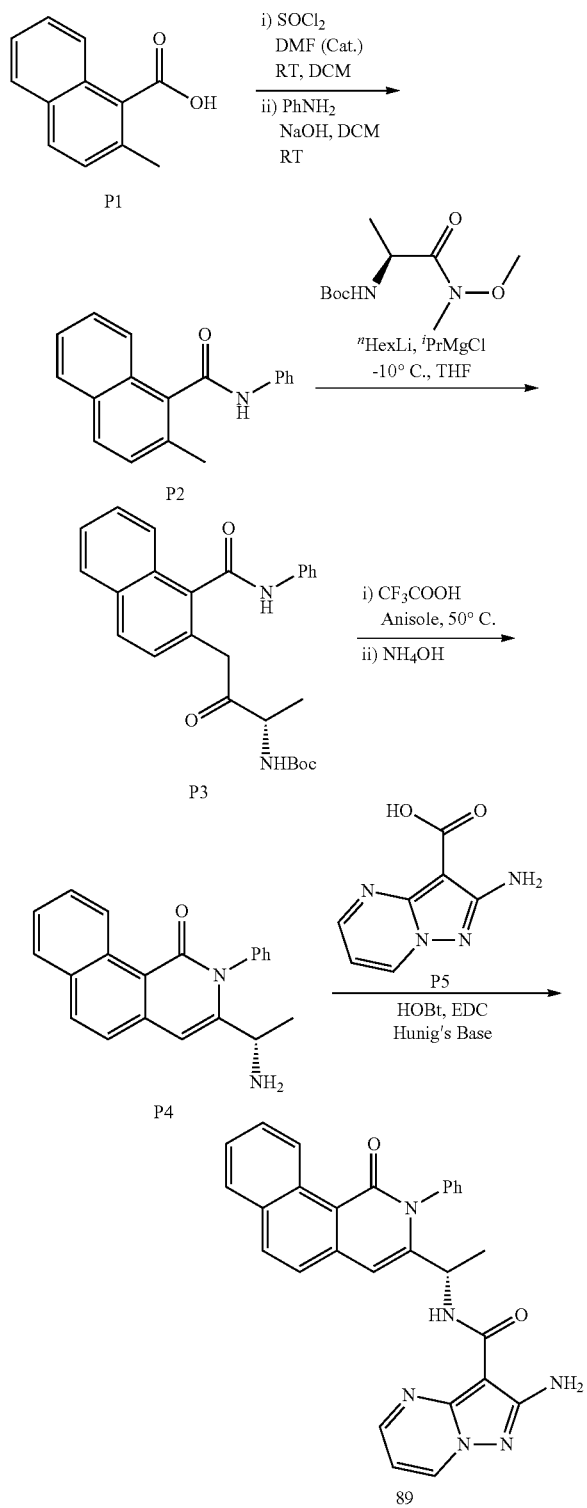

To a stirred mixture of 2-Methyl-1-naphthoic acid 1 (2.5 g, 13.4 mmols) and DMF (0.67 mL) in anhydrous chloroform was added thionyl chloride (1 mL, 13.6 mmols) and the mixture was heated at reflux for 1 h. The solvents were evaporated, dissolved in 10 mL DCM and added to a biphasic mixture of aniline (2.5 mL, 27 mmols) in 40 mL DCM and 40 mL 1M aqueous sodium hydroxide solution. The mixture was stirred for 30 min, the aqueous layer was extracted with DCM (3×20 mL), washed with cold 1M HCl (20 mL), water (3×20 mL), brine (20 mL), dried and the solvents were evaporated under reduced pressure and the crude solid (3.68 g, 92%) was recrystallized from DCM-hexanes to give 1.57 g of pure amide P2. M+H 262.23; M−H 260.23. To a stirred mixture of amide P2 (1.05 g, 1 mmol, 1 eq) in anhydrous THF (8 mL) at −10° C. under an argon atmosphere, a solution of hexyllithium in hexanes (3.93 mL, 9.04 mols, 2.25 eq) was added drop wise over 8 min while keeping the internal temperature between −10° C. and −7° C. The resulting mixture is then stirred at −10° C. for 30 min.

To a stirred mixture of (S)-tert-butyl 1-(methoxy(methyl)amino)-1-oxopropan-2-ylcarbamate (1.12 g, 4.82 mmols, 1.2 eq) in anhydrous THF (8 mL) at −10° C. under an argon atmosphere, a solution of isopropylmagnesium chloride in THF (2.53 mL, 5.06 mmols, 1.26 eq) was added drop wise over 7 min while keeping inner temperature between −10° C. and −7° C. The resulting mixture was stirred at −10° C. for 30 min. This solution was then slowly added to above reaction mixture while keeping inner temperature between −10° C. and −13° C. The resulting mixture is stirred at −10° C. for 1 h and then allowed to warm to room temp over a period of 1 h. The reaction mixture was added into a biphasic mixture of 20 mL 1M citric acid and 30 mL ethyl acetate at −5° C. to 0° C. The aqueous layer was extracted with ethyl acetate (3×20 mL), washed with water and brine (20 mL), dried over sodium sulfate, the solvents were removed in vacuo and the residue was purified by chromatography on silica gel (40 g, 0-50% EtOAc-Hexanes) to give 1.353 g of P3 as a solid. M+H 432.42; M−H 431.43.

A solution of 3 (1.1 g, 2.54 mmols) in 9 mL anisole was treated with trifluoroacetic acid (1.52 mL, 20.3 mmols) and the mixture was heated at 50 C for 18 h. The mixture was cooled, treated with 25 mL MTBE, the precipitated solids were filtered, washed with MTBE (3×10 mL) and dried to give 1.07 g (2.5 mmols) the TFA salt of P4 as a solid.

200 mg of the TFA salt of 4 (0.467 mmols) was suspended in 6 mL DCM, treated with aqueous ammonium hydroxide solution (2 mL, ~6%) for 30 min. The mixture was diluted with water (10 mL), extracted with DCM (2×5 mL), washed with water (5 mL), dried and the solvents were evaporated in vacuo to give 149 mg (0.467 mmols) of crude P4. The crude P4 (120 mg, 0.382 mmols), 2-Aminopyrazolo[1,5-a]pyrimidinecarboxylic acid (75 mg, 0.42 mmols), HOBt (70 mg, 0.46 mmols), EDC (91 mg, 0.48 mmols) and Hunig's base (0.27 mL, 1.53 mmols) in 3 mL DMF was stirred for 19 h. The mixture was slowly diluted with 6 mL methanol, heated to 50 C and cooled to room temperature. The precipitated solids was collected, washed with methanol and dried to give 89 as a solid (154 mg). ESI-MS m/z: 475.46 [M+H]⁺.

Example 39

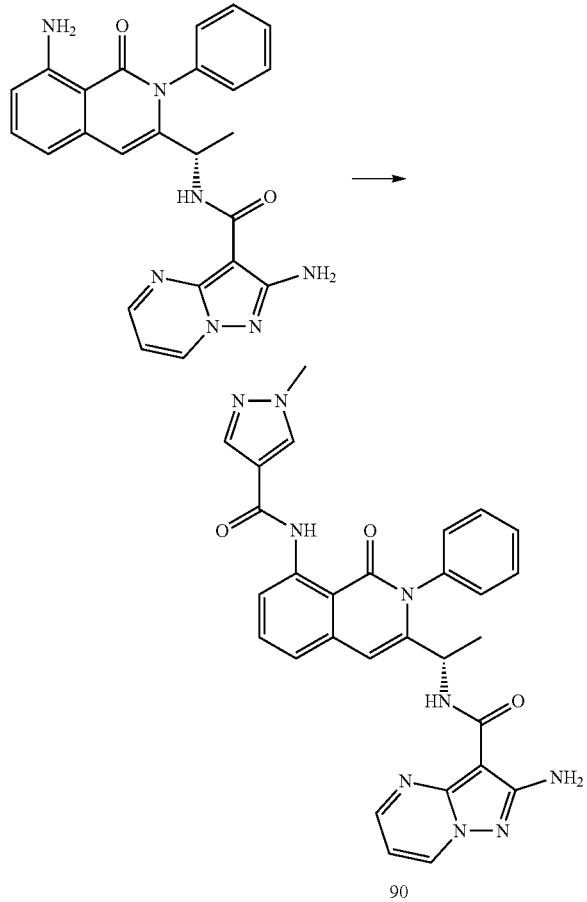

Compound 90 was prepared according to amide formation methods generally known in the art. ESI-MS m/z: 548.31 [M+H]⁺.

Example 40

Compounds 91 and 92 were prepared.

| Compound no. | Structure | ESI-MS m/z |
|---|---|---|
| Compound 91 | 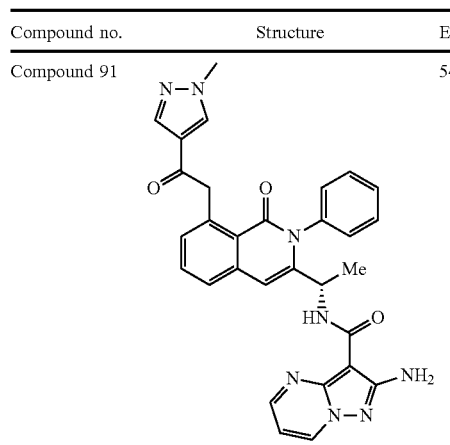 | 547.25 [M + H]⁺ |
| Compound 92 | 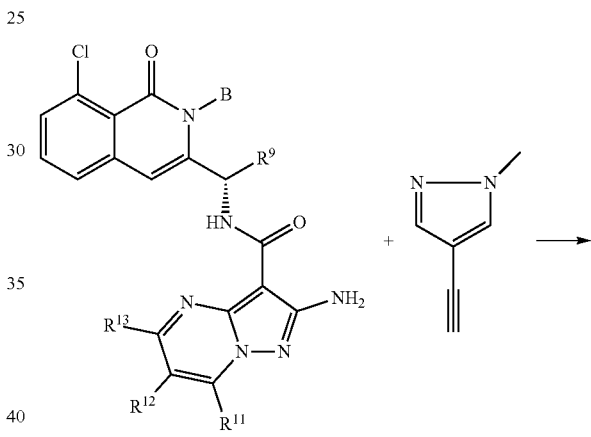 | 531.31 [M + H]⁺ |

Example 41

Compounds 93-108 were prepared according to the procedure below.

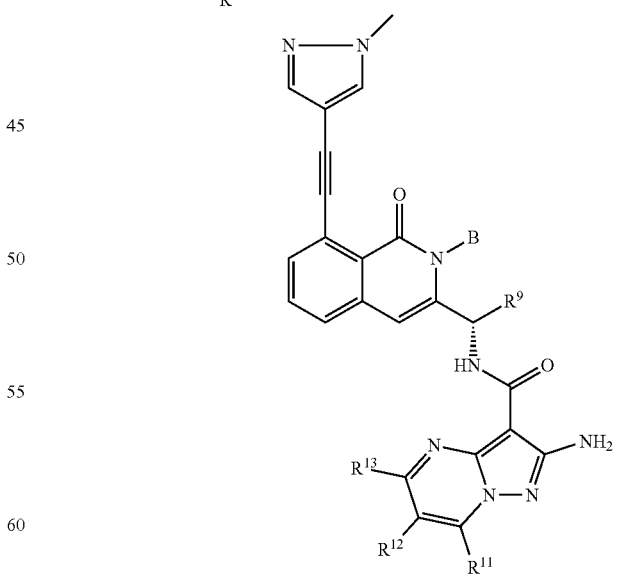

A suspension of aryl chloride (0.03-0.06 mmol), cesium carbonate (1.2 eq.), dichlorobis(acetonitrile)palladium (II) (0.05 eq.) and Xphos (0.15 eq.) in acetonitrile (2 mL) was bubbled with argon for 5 minutes. The mixture was charged with 4-ethynyl-1-methyl-1H-pyrazole (2 eq.), heated to 75° C. and stirred for 6 hr. The resulting mixture was cooled to RT, partitioned between ethyl acetate and water. The organic phase was separated, washed with saturated aqueous sodium chloride solution, dried with sodium sulfate and concentrated. The residue was purified on semi-prep HPLC (C-18) using a gradient of ACN/Water/Formic acid (9.9/90/0.1% to 49.9/50/0.1%) to afford the desired compound (confirmed by LCMS).

| Compound no | Structure | ESI-MS m/z [M + H]+ |
|---|---|---|
| 93 | | 547.2 |
| 94 | | 467.2 |
| 95 | 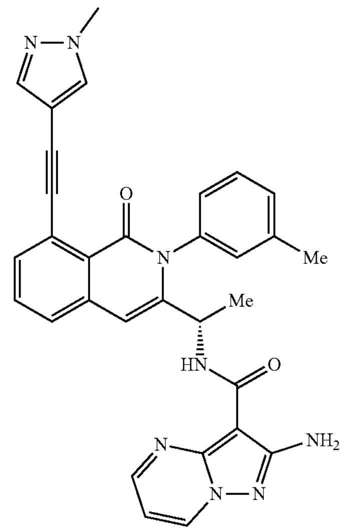 [SMILES: Cc1cccc(-n2c([C@H](C)NC(=O)c3c(N)nn4cccnc34)cc3cccc(C#Cc4cnn(C)c4)c3c2=O)c1] | 543.2 |
| 96 | 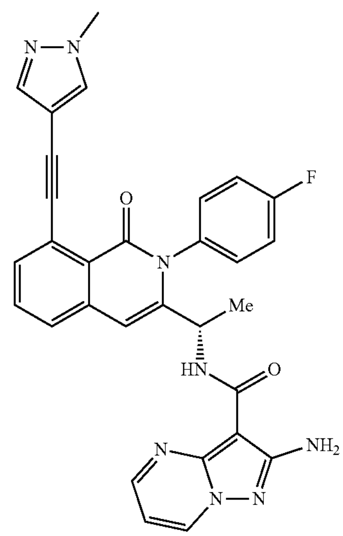 [SMILES: C[C@H](NC(=O)c1c(N)nn2cccnc12)c1cc2cccc(C#Cc3cnn(C)c3)c2c(=O)n1-c1ccc(F)cc1] | 547.2 |
| 97 | 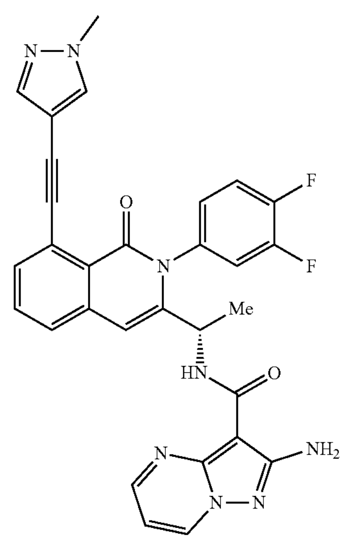 [SMILES: C[C@H](NC(=O)c1c(N)nn2cccnc12)c1cc2cccc(C#Cc3cnn(C)c3)c2c(=O)n1-c1ccc(F)c(F)c1] | 565.2 |

-continued
| Compound no | Structure | ESI-MS m/z [M + H]+ |
|---|---|---|
| 98 | 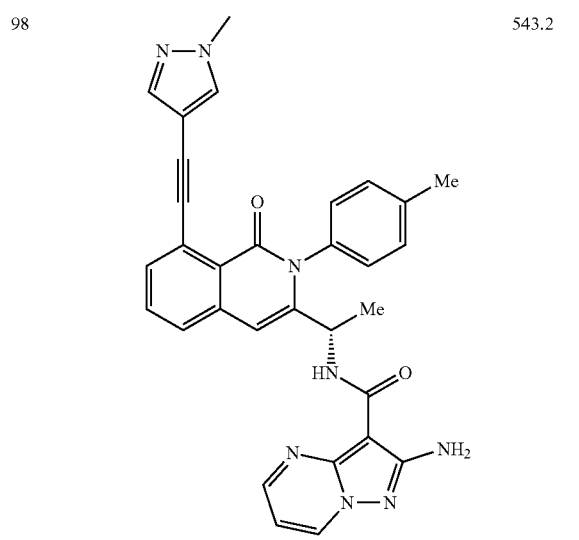 | 543.2 |
| 99 | 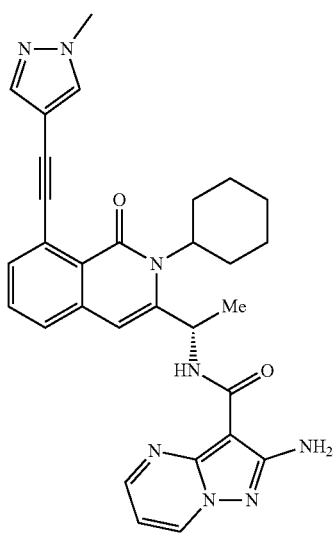 [SMILES: C[C@H](NC(=O)c1c(N)nn2cccnc12)c1cc2cccc(C#Cc3cnn(C)c3)c2c(=O)n1C1CCCCC1] | 535.3 |
-continued
| Compound no | Structure | ESI-MS m/z [M + H]+ |
|---|---|---|
| 100 | 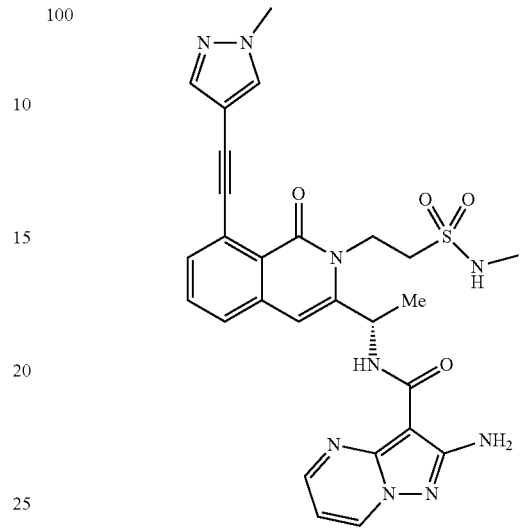 | 574.2 |
| 101 | 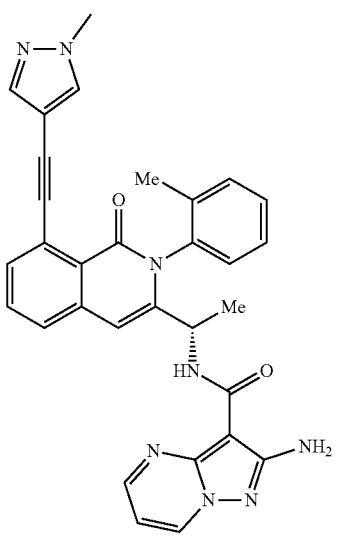 [SMILES: Cc1ccccc1-n1c([C@H](C)NC(=O)c2c(N)nn3cccnc23)cc2cccc(C#Cc3cnn(C)c3)c2c1=O] | 543.2 |

-continued

| Compound no | Structure | ESI-MS m/z [M + H]+ |
|---|---|---|
| 102 | | 543.2 |
| 103 | | 495.2 |
| 104 | 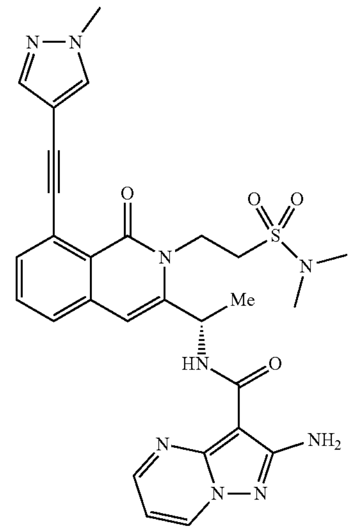 [SMILES: C[C@H](NC(=O)c1c(N)nn2cccnc12)c1cc2cccc(C#Cc3cnn(C)c3)c2c(=O)n1CCS(=O)(=O)N(C)C] | 588.2 |
| 105 | 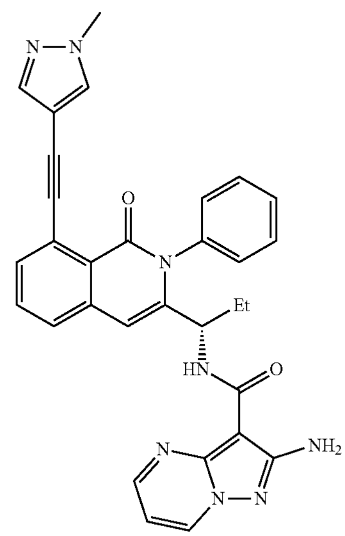 [SMILES: CC[C@H](NC(=O)c1c(N)nn2cccnc12)c1cc2cccc(C#Cc3cnn(C)c3)c2c(=O)n1-c1ccccc1] | 543.3 |
| 106 | 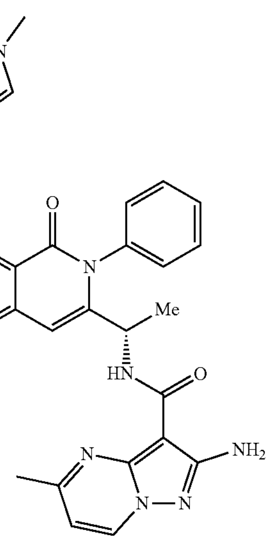 | 543.3 |

1053 -continued
| Compound no | Structure | ESI-MS m/z [M + H]+ |
|---|---|---|
| 107 | 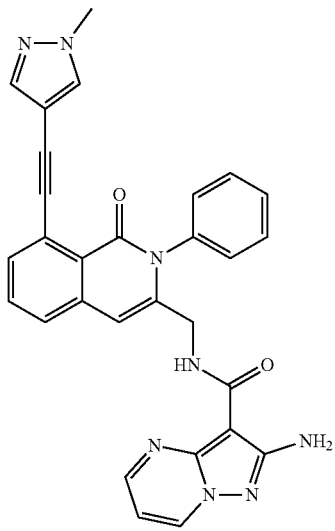 [SMILES: Cn1cc(C#Cc2cccc3cc(CNC(=O)c4c(N)nn5cccnc45)n(-c4ccccc4)c(=O)c23)cn1] | 515.2 |
| 108 | 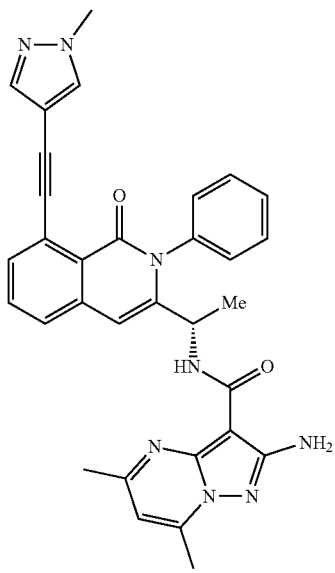 [SMILES: Cc1cc(C)n2nc(N)c(C(=O)N[C@@H](C)c3cc4cccc(C#Cc5cnn(C)c5)c4c(=O)n3-c3ccccc3)c2n1] | 557.3 |
1054 -continued
| Compound no | Structure | ESI-MS m/z [M + H]+ |
|---|---|---|
| 110 | 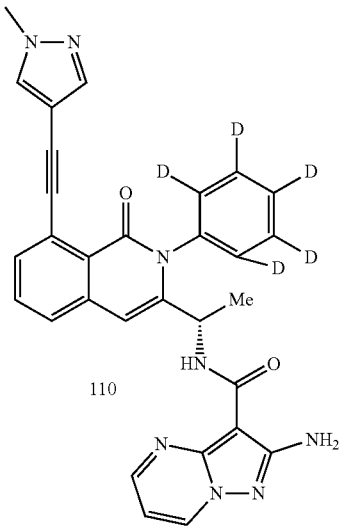 [SMILES: [2H]c1c([2H])c([2H])c(-n2c([C@H](C)NC(=O)c3c(N)nn4cccnc34)cc3cccc(C#Cc4cnn(C)c4)c3c2=O)c([2H])c1[2H]] | 534.2 |
Example 42
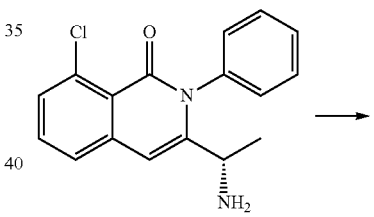
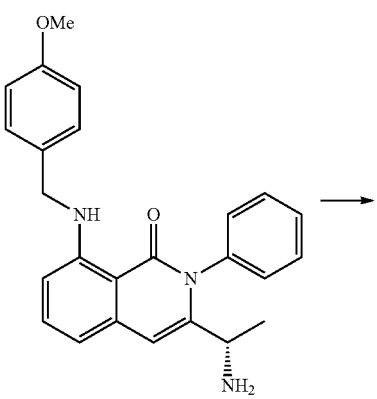

-continued

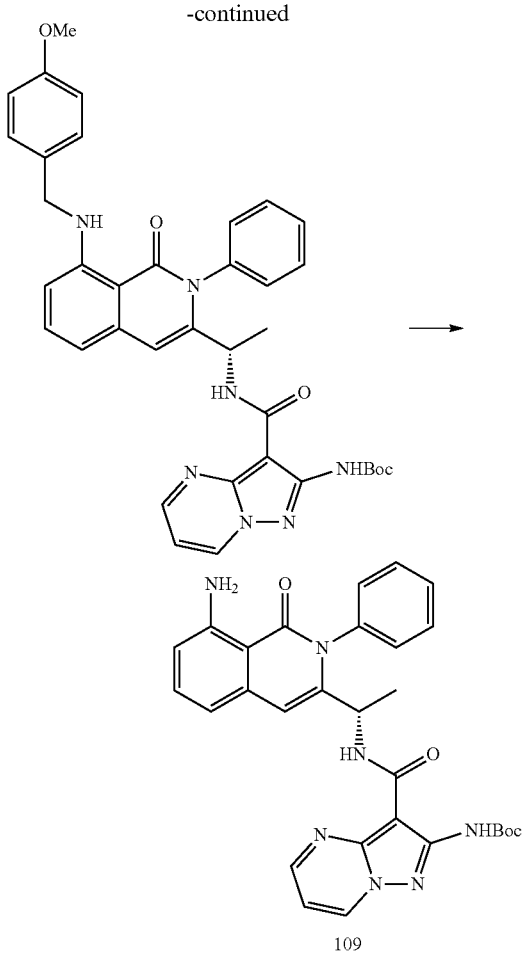

109

In a MW compatible vial, (S)-3-(1-aminoethyl)-8-chloro-2-phenylisoquinolin-1(2H)-one (700 mg, 2.343 mmol), (4-methoxyphenyl)methanamine (3.2 g, 23.4 mmol, 20 eq.) and diisopropylethylamine (1.6 mL, 9.4 mmol, 4 eq.) were dissolved in NMP (12 mL). The vial was sealed and heated to 180° C. in a under MW irradiation and stirred for 6 hr. The reaction mixture was cooled to RT, partitioned between Ethyl acetate and water. The organic phase was separated, washed with saturated aqueous sodium chloride solution, dried with sodium sulfate and concentrated. The residue was purified with silica gel chromatography using a gradient of DCM and MeOH to afford (S)-3-(1-aminoethyl)-8-((4-methoxybenzyl)amino)-2-phenylisoquinolin-1(2H)-one. ESI-MS m/z: 400.1 [M+H]⁺. (S)-3-(1-aminoethyl)-8-((4-methoxybenzyl)amino)-2-phenylisoquinolin-1(2H)-one (720 mg, 1.8 mmol), 2-((tert-butoxycarbonyl)amino)pyrazolo[1,5-a]pyrimidine-3-carboxylic acid (1.2 g, 4.31 mmol, 2.4 eq.), HOBt (700 mg, 4.57 mmol, 2.5 eq.) and EDC (800 mg, 4.17 mmol, 2.3 eq.) were suspended in DMF (30 mL). The reaction mixture was charged with diisopropylethylamine (2 mL, 11.45 mmol, 6.4 eq.) and stirred at RT for 1 hr. The reaction mixture was partitioned between Ethyl acetate and water. The organic phase was separated, washed with saturated aqueous sodium chloride solution, dried with sodium sulfate and concentrated. The residue was purified with silica gel chromatography using a gradient of Ethyl acetate and hexanes and triturated with MeOH to afford (S)-tert-butyl (3-((1-(8-((4-methoxybenzyl)amino)-1-oxo-2-phenyl-1,2-dihydroisoquinolin-3-yl)ethyl)carbamoyl)pyrazolo[1,5-a]pyrimidin-2-yl)carbamate. ESI-MS m/z: 660.3 [M+H]⁺. (S)-tert-butyl (3-((1-(8-((4-methoxybenzyl)amino)-1-oxo-2-phenyl-1,2-dihydroisoquinolin-3-yl)ethyl)carbamoyl)pyrazolo[1,5-a]pyrimidin-2-yl)carbamate (360 mg, 0.546 mmol) and anisole (238 μL, 2.183 mmol, 4 eq.) was dissolved TFA (2 mL) and stirred at 60° C. for 1 hr. The reaction mixture was poured in a saturated aqueous bicarbonate solution. The organic phase was dried with sodium sulfate and concentrated. The residue was purified with silica gel chromatography using a gradient of DCM. The residue was purified on semi-prep HPLC (C-18) using a gradient of ACN/Water/Formic acid to afford (S)-2-amino-N-(1-(8-amino-1-oxo-2-phenyl-1,2-dihydroisoquinolin-3-yl)ethyl)pyrazolo[1,5-a]pyrimidine-3-carboxamide. ESI-MS m/z: 440.2 [M+H]⁺.

Biological Activity Assessment

TABLE 15

In Vitro IC$_{50}$ data for selected compounds.

| Compound no. | PI3K α IC$_{50}$ | PI3K β IC$_{50}$ | PI3K δ IC$_{50}$ | PI3K γ IC$_{50}$ | RAJI p110 δ assay IC$_{50}$ | Raw264.7 p110 γ assay IC$_{50}$ | PI3K δ/ PI3K γ IC$_{50}$ (selectivity) | RAJI δ/ Raw264.7 γ IC$_{50}$ (selectivity) |
|---|---|---|---|---|---|---|---|---|
| 1 | D2 | C2 | B2 | A3 | A4 | A5 | X | X |
| 2 | D2 | D2 | D2 | C3 | C4 | A5 | X | Y |
| 3 | D2 | D2 | D2 | D3 | D4 | B5 | W | X |
| 4 | C2 | C2 | D2 | A3 | B4 | A5 | Y | Y |
| 5 | D2 | D2 | A2 | D3 | A4 | A5 | V | W |
| 6 | D2 | D2 | D2 | B3 | C4 | A5 | Y | X |
| 7 | D2 | D2 | D2 | B3 | C4 | A5 | Y | Y |
| 8 | D2 | D2 | D2 | C3 | D4 | C5 | X | W |
| 9 | C2 | C2 | C2 | B3 | B4 | A5 | X | Y |
| 10 | D2 | D2 | D2 | B3 | D4 | A5 | X | X |
| 11 | D2 | D2 | D2 | B3 | D4 | B5 | X | X |
| 12 | D2 | C2 | C2 | A3 | B4 | A5 | X | X |
| 13 | D2 | C2 | B2 | A3 | A4 | A5 | X | W |
| 14 | C2 | C2 | A2 | A3 | A4 | A5 | X | W |
| 15 | D2 | D2 | B2 | A3 | B4 | A5 | X | W |
| 16 | D2 | C2 | C2 | A3 | B4 | A5 | Y | X |
| 17 | D2 | D2 | D2 | B3 | B4 | A5 | Y | Y |
| 18 | D2 | D2 | D2 | B3 | B4 | A5 | Y | X |
| 19 | D2 | D2 | D2 | B3 | C4 | A5 | Y | Y |
| 20 | D2 | D2 | C2 | A3 | B4 | A5 | X | X |

TABLE 15-continued

In Vitro IC$_{50}$ data for selected compounds.

| Compound no. | PI3K α IC$_{50}$ | PI3K β IC$_{50}$ | PI3K δ IC$_{50}$ | PI3K γ IC$_{50}$ | RAJI p110 δ assay IC$_{50}$ | Raw264.7 p110 γ assay IC$_{50}$ | PI3K δ/ PI3K γ IC$_{50}$ (selectivity) | RAJI δ/ Raw264.7 γ IC$_{50}$ (selectivity) |
|---|---|---|---|---|---|---|---|---|
| 21 | D2 | D2 | D2 | A3 | B4 | A5 | Y | Y |
| 22 | D2 | D2 | D2 | B3 | D4 | A5 | X | X |
| 23 | C2 | C2 | D2 | D3 | B4 | A5 | W | W |
| 24 | C2 | C2 | C2 | D3 | B4 | A5 | W | W |
| 25 | C2 | C2 | D2 | C3 | B4 | A5 | X | X |
| 26 | D2 | D2 | D2 | B3 | B4 | A5 | X | Y |
| 27 | D2 | D2 | D2 | B3 | A4 | A5 | X | Y |
| 28 | D2 | D2 | D2 | D3 | B4 | A5 | W | X |
| 29 | D2 | C2 | C2 | B3 | A4 | A5 | X | W |
| 30 | D2 | D2 | D2 | B3 | B4 | A5 | Y | Y |
| 31 | D2 | D2 | D2 | B3 | B4 | B5 | X | W |
| 32 | D2 | D2 | D2 | B3 | C4 | A5 | Y | Y |
| 33 | D2 | D2 | D2 | A3 | B4 | A5 | Y | W |
| 34 | D2 | D2 | D2 | C3 | C4 | B5 | X | X |
| 35 | D2 | D2 | D2 | B3 | C4 | A5 | Y | Y |
| 36 | C2 | A2 | C2 | A3 | B4 | C5 | X | W |
| 37 | D2 | D2 | D2 | D3 | D4 | A5 | W | Y |
| 38 | D2 | D2 | D2 | A3 | C4 | A5 | Y | Y |
| 39 | D2 | D2 | D2 | B3 | D4 | B5 | X | X |
| 40 | C2 | D2 | D2 | A3 | B4 | A5 | Y | Y |
| 41 | D2 | D2 | D2 | B3 | B4 | A5 | Y | Y |
| 42 | D2 | D2 | D2 | B3 | C4 | A5 | X | X |
| 43 | D2 | D2 | D2 | B3 | B4 | A5 | Y | X |
| 44 | D2 | C2 | C2 | D3 | A4 | B5 | W | V |
| 45 | D2 | D2 | D2 | B3 | B4 | A5 | Y | W |
| 46 | D2 | C2 | C2 | A3 | A4 | A5 | Y | W |
| 47 | C2 | A2 | A2 | A3 | ND | ND | V | ND |
| 48 | C2 | B2 | C2 | C3 | A4 | A5 | W | V |
| 49 | D2 | C2 | C2 | A3 | A4 | A5 | X | V |
| 50 | D2 | D2 | C2 | A3 | A4 | A5 | Y | W |
| 51 | D2 | C2 | C2 | B3 | A4 | A5 | W | W |
| 52 | D2 | D2 | D2 | B3 | C4 | A5 | Y | Y |
| 53 | D2 | D2 | D2 | D3 | C4 | B5 | W | X |
| 54 | C2 | C2 | C2 | A3 | B4 | A5 | Y | W |
| 55 | C2 | C2 | D2 | D3 | C4 | A5 | W | X |
| 56 | D2 | D2 | D2 | B3 | B4 | C5 | X | V |
| 57 | D2 | D2 | D2 | C3 | B4 | B5 | W | W |
| 58 | D2 | D2 | D2 | D3 | C4 | C5 | W | V |
| 59 | D2 | D2 | D2 | B3 | B4 | A5 | X | X |
| 60 | D2 | D2 | D2 | B3 | B4 | A5 | X | Y |
| 61 | D2 | D2 | D2 | C3 | D4 | A5 | X | Y |
| 62 | D2 | D2 | D2 | C3 | D4 | C5 | X | V |
| 63 | D2 | D2 | D2 | A3 | C4 | A5 | Y | Y |
| 64 | D2 | D2 | D2 | D3 | D4 | C5 | W | X |
| 65 | D2 | D2 | D2 | D3 | D4 | C5 | W | X |
| 66 | D2 | C2 | C2 | A3 | B4 | A5 | X | X |
| 67 | D2 | D2 | D2 | D3 | D4 | C5 | W | X |
| 68 | D2 | D2 | D2 | D3 | D4 | C5 | W | W |
| 69 | D2 | D2 | D2 | D3 | ND | C5 | W | ND |
| 70 | D2 | D2 | D2 | B3 | A4 | A5 | X | X |
| 71 | D2 | D2 | D2 | E3 | D4 | ND | V | ND |
| 72 | D2 | D2 | D2 | C3 | D4 | C5 | X | W |
| 73 | D2 | D2 | D2 | B3 | C4 | A5 | X | Y |
| 74 | D2 | D2 | C2 | C3 | D4 | C5 | W | W |
| 75 | D2 | D2 | D2 | D3 | D4 | A5 | W | Y |
| 76 | D2 | D2 | D2 | B3 | B4 | A5 | Y | X |
| 77 | D2 | D2 | D2 | A3 | C4 | A5 | Y | Y |
| 78 | D2 | D2 | D2 | B3 | B4 | A5 | X | X |
| 79 | D2 | D2 | D2 | C3 | D4 | A5 | X | Y |
| 80 | C2 | D2 | D2 | A3 | B4 | A5 | Y | Y |
| 81 | C2 | C2 | C2 | A3 | ND | ND | Y | ND |
| 82 | D2 | D2 | D2 | B3 | C4 | A5 | X | X |
| 83 | D2 | D2 | D2 | C3 | C4 | A5 | X | X |
| 84 | D2 | D2 | D2 | A3 | B4 | A5 | Y | X |
| 85 | D2 | D2 | D2 | C3 | ND | ND | X | ND |
| 86 | D2 | C2 | C2 | B3 | ND | ND | X | ND |
| 87 | D2 | D2 | D2 | E3 | ND | ND | V | ND |
| 88 | D2 | D2 | D2 | B3 | B4 | A5 | X | Y |
| 89 | D2 | D2 | D2 | C3 | D4 | A5 | X | Y |
| 90 | D2 | D2 | D2 | D3 | D4 | C5 | W | X |
| 91 | D2 | D2 | D2 | C3 | B4 | C5 | W | W |
| 92 | D2 | D2 | C2 | C3 | B4 | C5 | W | V |
| 93 | D2 | D2 | D2 | A3 | ND | ND | Y | ND |

TABLE 15-continued

In Vitro IC$_{50}$ data for selected compounds.

| Compound no. | PI3K α IC$_{50}$ | PI3K β IC$_{50}$ | PI3K δ IC$_{50}$ | PI3K γ IC$_{50}$ | RAJI p110 δ assay IC$_{50}$ | Raw264.7 p110 γ assay IC$_{50}$ | PI3K δ/ PI3K γ IC$_{50}$ (selectivity) | RAJI δ/ Raw264.7 γ IC$_{50}$ (selectivity) |
|---|---|---|---|---|---|---|---|---|
| 94 | C2 | B2 | D2 | B3 | ND | ND | X | ND |
| 95 | D2 | D2 | D2 | B3 | ND | ND | X | ND |
| 96 | C2 | D2 | D2 | A3 | ND | ND | Y | ND |
| 97 | D2 | D2 | D2 | B3 | ND | ND | X | ND |
| 98 | D2 | D2 | D2 | B3 | ND | ND | X | ND |
| 99 | D2 | D2 | D2 | D3 | ND | ND | X | ND |
| 100 | C2 | C2 | D2 | A3 | ND | ND | Y | ND |
| 101 | D2 | D2 | D2 | A3 | ND | ND | Y | ND |
| 102 | D2 | D2 | D2 | B3 | ND | ND | X | ND |
| 103 | D2 | D2 | D2 | C3 | ND | ND | X | ND |
| 104 | C2 | C2 | D2 | A3 | ND | ND | Y | ND |
| 105 | C2 | D2 | D2 | A3 | ND | ND | Y | ND |
| 106 | D2 | C2 | D2 | A3 | ND | ND | Y | ND |
| 107 | D2 | D2 | D2 | D3 | ND | ND | X | ND |
| 108 | D2 | D2 | D2 | B3 | ND | ND | X | ND |
| 109 | D2 | C2 | C2 | A3 | ND | ND | X | ND |
| 110 | D2 | D2 | D2 | A3 | ND | ND | Y | ND |

The data in Table 15 are coded as follows.

| For PI3K α, β, and δ IC$_{50}$: | For PI3K γ IC$_{50}$: | RAJI p110 δ assay IC$_{50}$ | Raw264.7 p110 γ assay IC$_{50}$ |
|---|---|---|---|
| A2 = 1 to <500 nM | A3 = 1 to <100 nM | A4 = 1 to <100 nM | A5 = 1 to <50 nM |
| B2 = 500 to <1000 nM | B3 = 100 to <500 nM | B4 = 100 to <500 nM | B5 = 50 to <100 nM |
| C2 = 1000 to <5000 nM | C3 = 500 to <1000 nM | C4 = 500 to <1000 nM | C5 = 100 to <10000 nM |
| D2 = 5000 to 10000 nM | D3 = 1000 to 5000 nM | D4 = 1000 to 10000 nM | |
| | E3 = >5000 nM | | |

δ/γ IC$_{50}$ selectivity:
ND = not determined
V = 0.1 to 1
W = >1 to <10
X = 10 to <50
Y = 50 to <850

Example 222: PI3-Kinase HTRF™ Assay

A PI3-Kinase HTRF® assay kit (cat No. 33-016) purchased from Millipore Corporation was used to screen compounds provided herein. This assay used specific, high affinity binding of the GRP1 pleckstrin homology (PH) domain to PIP3, the product of a Class 1A or 1B PI3 Kinase acting on its physiological substrate PIP2. During the detection phase of the assay, a complex was generated between the GST-tagged PH domain and biotinylated short chain PIP3. The biotinylated PIP3 and the GST-tagged PH domain recruited fluorophores (Streptavidin-Allophycocyanin and Europium-labeled anti-GST respectively) to form the fluorescence resonance energy transfer (FRET) architecture, generating a stable time-resolved FRET signal. The FRET complex was disrupted in a competitive manner by non-biotinylated PIP3, a product formed in the PI3 Kinase assay.

PI3 Kinase α, β, γ or δ activity was assayed using the PI3 Kinase HTRF® assay kit (catalogue No. 33-016) purchased from Millipore Corporation. Purified recombinant PI3Kα (catalogue No. 14-602-K), PI3Kβ (catalogue No. 14-603-K), PI3Kγ (catalogue No. 14-558-K), and PI3Kδ (catalogue No. 14-604-K) were obtained from Millipore Corporation.

Purified recombinant PI3K enzyme was used to catalyze the phosphorylation of phosphatidylinositol 4,5-bisphosphate (PIP2 at 10 µM) to phosphatidylinositol 3,4,5-trisphosphate (PIP3) in the presence of 10 µM ATP. The assay was carried out in 384-well format and detected using a Perkin Elmer EnVision Xcite Multilabel Reader. Emission ratios were converted into percent inhibitions and imported into Graph-Pad Prism software. The concentration necessary to achieve inhibition of enzyme activity by 50% (IC$_{50}$) was calculated using concentrations ranging from 20 µM to 0.1 nM (12-point curve). IC$_{50}$ values were determined using a nonlinear regression model available in GraphPad Prism 5.

Example 223: Chemical Stability

The chemical stability of one or more subject compounds is determined according to standard procedures known in the art. The following details an exemplary procedure for ascertaining chemical stability of a subject compound. The default buffer used for the chemical stability assay is phosphate-buffered saline (PBS) at pH 7.4; other suitable buffers can be used. A subject compound is added from a 100 µM stock solution to an aliquot of PBS (in duplicate) to give a final assay volume of 400 µL, containing 5 µM test compound and 1% DMSO (for half-life determination a total sample volume of 700 µL is prepared). Reactions are incubated, with shaking, for 24 hours at 37° C.; for half-life determination samples are incubated for 0, 2, 4, 6, and 24 hours. Reactions are stopped by adding immediately 100 µL of the incubation mixture to 100 µL of acetonitrile and vortexing for 5 minutes. The samples are then stored at −20° C. until analysis by HPLC-MS/MS. Where desired, a control compound or a reference compound such as chlorambucil (5 µM) is tested simultaneously with a subject compound of interest, as this compound is largely hydrolyzed over the course of 24 hours. Samples are analyzed via (RP)HPLC-MS/MS using selected reaction monitoring (SRM). The HPLC conditions consist of a binary LC pump with autosampler, a mixed-mode, C12, 2×20 mm column, and a gradient program. Peak areas corresponding to the analytes are recorded by HPLC-MS/MS. The ratio of the parent compound remaining after 24 hours relative to the amount remaining at time zero, expressed as percent, is reported as chemical stability. In case of half-life determination, the half-life is estimated from the slope of the initial linear range of the logarithmic curve of compound remaining (%) vs. time, assuming first order kinetics.

Example 224: Expression and Inhibition Assays of p110α/p85α, p110β/p85α, p110δ/p85α, and p110γ

Class I PI3-Ks can be either purchased (p110α/p85α, p110β/p85α, p110δ/p85α from Upstate, and p110γ from Sigma) or expressed as previously described (Knight et al., 2004). $IC_{50}$ values are measured using either a standard TLC assay for lipid kinase activity (described below) or a high-throughput membrane capture assay. Kinase reactions are performed by preparing a reaction mixture containing kinase, inhibitor (2% DMSO final concentration), buffer (25 mM HEPES, pH 7.4, 10 mM $MgCl_2$), and freshly sonicated phosphatidylinositol (100 μg/ml). Reactions are initiated by the addition of ATP containing 10 μCi of γ-32P-ATP to a final concentration of 10 or 100 μM and allowed to proceed for 5 minutes at room temperature. For TLC analysis, reactions are then terminated by the addition of 105 μL 1N HCl followed by 160 μL $CHCl_3$:MeOH (1:1). The biphasic mixture is vortexed, briefly centrifuged, and the organic phase is transferred to a new tube using a gel loading pipette tip precoated with $CHCl_3$. This extract is spotted on TLC plates and developed for 3-4 hours in a 65:35 solution of n-propanol:1M acetic acid. The TLC plates are then dried, exposed to a phosphorimager screen (Storm, Amersham), and quantitated. For each compound, kinase activity is measured at 10-12 inhibitor concentrations representing two-fold dilutions from the highest concentration tested (typically, 200 μM). For compounds showing significant activity, $IC_{50}$ determinations are repeated two to four times, and the reported value is the average of these independent measurements.

Other commercial kits or systems for assaying PI3-K activities are available. The commercially available kits or systems can be used to screen for inhibitors and/or agonists of PI3-Ks including, but not limited to, PI 3-Kinase α, β, δ, and γ. An exemplary system is PI 3-Kinase (human) HTRF™ Assay from Upstate. The assay can be carried out according to the procedures suggested by the manufacturer. Briefly, the assay is a time resolved FRET assay that indirectly measures PIP3 product formed by the activity of a PI3-K. The kinase reaction is performed in a microtiter plate (e.g., a 384 well microtiter plate). The total reaction volume is approximately 20 μL per well. In the first step, each well receives 2 μL of test compound in 20% dimethylsulphoxide resulting in a 2% DMSO final concentration. Next, approximately 14.5 μL of a kinase/PIP2 mixture (diluted in 1× reaction buffer) is added per well for a final concentration of 0.25-0.3 μg/mL kinase and 10 μM PIP2. The plate is sealed and incubated for 15 minutes at room temperature. To start the reaction, 3.5 μL of ATP (diluted in 1× reaction buffer) is added per well for a final concentration of 10 μM ATP. The plate is sealed and incubated for 1 hour at room temperature. The reaction is stopped by adding 5 μL of Stop Solution per well and then 5 μL of Detection Mix is added per well. The plate is sealed, incubated for 1 hour at room temperature, and then read on an appropriate plate reader. Data is analyzed and $IC_{50}$s are generated using GraphPad Prism 5.

Example 225: B Cell Activation and Proliferation Assay

The ability of one or more subject compounds to inhibit B cell activation and proliferation is determined according to standard procedures known in the art. For example, an in vitro cellular proliferation assay is established that measures the metabolic activity of live cells. The assay is performed in a 96 well microtiter plate using Alamar Blue reduction. Balb/c splenic B cells are purified over a Ficoll-Paque™ PLUS gradient followed by magnetic cell separation using a MACS B cell Isolation Kit (Miletenyi). Cells are plated in 90 μL at 50,000 cells/well in B Cell Media (RPMI+10% FBS+Penn/Strep+50 μM bME+5 mM HEPES). A compound provided herein is diluted in B Cell Media and added in a 10 μL volume. Plates are incubated for 30 min at 37° C. and 5% $CO_2$ (0.2% DMSO final concentration). A 50 μL B cell stimulation cocktail is then added containing either 10 μg/mL LPS or 5 μg/mL F(ab')2 Donkey anti-mouse IgM plus 2 ng/mL recombinant mouse IL4 in B Cell Media. Plates are incubated for 72 hours at 37° C. and 5% $CO_2$. A volume of 15 μL of Alamar Blue reagent is added to each well and plates are incubated for 5 hours at 37° C. and 5% $CO_2$. Alamar Blue fluoresce is read at 560Ex/590Em, and $IC_{50}$ or $EC_{50}$ values are calculated using GraphPad Prism 5.

Example 226: Tumor Cell Line Proliferation Assay

The ability of one or more subject compounds to inhibit tumor cell line proliferation can be determined according to standard procedures known in the art. For instance, an in vitro cellular proliferation assay can be performed to measure the metabolic activity of live cells. The assay is performed in a 96-well microtiter plate using Alamar Blue reduction. Human tumor cell lines are obtained from ATCC (e.g., MCF7, U-87 MG, MDA-MB-468, PC-3), grown to confluency in T75 flasks, trypsinized with 0.25% trypsin, washed one time with Tumor Cell Media (DMEM+10% FBS), and plated in 90 μL at 5,000 cells/well in Tumor Cell Media. A compound provided herein is diluted in Tumor Cell Media and added in a 10 μL volume. Plates are incubated for 72 hours at 37° C. and 5% $CO_2$. A volume of 10 μL of Alamar Blue reagent is added to each well and plates are incubated for 3 hours at 37° C. and 5% $CO_2$. Alamar Blue fluoresce is read at 560Ex/590Em, and $IC_{50}$ values are calculated using GraphPad Prism 5.

Example 227: Antitumor Activity In Vivo

The compounds described herein can be evaluated in a panel of human and murine tumor models. In one aspect, compounds provided herein may be evaluated in the following models according to methods known in the art. The dosage and schedule of administration may be varied depending on the model. The results may be evaluated with those of selective delta inhibitors, and combinations of delta and gamma inhibitors, and/or with antibodies that block specific inhibitory receptors.

Paclitaxel-Refractory Tumor Models

1. Clinically-Derived Ovarian Carcinoma Model.

This tumor model is established from a tumor biopsy of an ovarian cancer patient. Tumor biopsy is taken from the patient. The compounds described herein are administered to nude mice bearing staged tumors using an every 2 days x 5 schedule.

2. A2780Tax Human Ovarian Carcinoma Xenograft (Mutated Tubulin).

A2780Tax is a paclitaxel-resistant human ovarian carcinoma model. It is derived from the sensitive parent A2780 line by co-incubation of cells with paclitaxel and verapamil, an MDR-reversal agent. Its resistance mechanism has been shown to be non-MDR related and is attributed to a mutation in the gene encoding the beta-tubulin protein. The compounds described herein can be administered to mice bearing staged tumors on an every 2 days x 5 schedule.

3. HCT116/VM46 Human Colon Carcinoma Xenograft (Multi-Drug Resistant).

HCT116/VM46 is an MDR-resistant colon carcinoma developed from the sensitive HCT116 parent line. In vivo, grown in nude mice, HCT116/VM46 has consistently demonstrated high resistance to paclitaxel. The compounds described herein can be administered to mice bearing staged tumors on an every 2 days x 5 schedule.

One or more compounds as provided herein can be used in combination with other therapeutic agents in vivo in the multidrug resistant human colon carcinoma xenografts HCT/VM46 or any other model known in the art including those described herein.

4. M5076 Murine Sarcoma Model

M5076 is a mouse fibrosarcoma that is inherently refractory to paclitaxel in vivo. The compounds described herein can be administered to mice bearing staged tumors on an every 2 days x 5 schedule.

Pancreatic Models

KPC model is a transgenic mouse model of pancreatic ductal adenocarcinoma (PDA), in which there is conditional expression of both mutant KrasG12D and p53R172H alleles in pancreatic cells. Tumors develop spontaneously in this mouse over a period of 3-6 months, and can be used to study prophylactic, as well as therapeutic efficacy with novel agents. Cells from these KPC tumors can also be adoptively transferred into syngeneic B6.129 hybrid mice, creating a model with a shorter latency period and allowing large number of animals with tumors to be synchronously established. See e.g., Cancer Cell 7:468 (2005). In some embodiments, compounds provided herein can be administered alone or in combination with anti-PD-L1.

Pan02 model: The murine pancreatic adenocarcinoma cell line Pan02 is a nonmetastatic tumor line, syngeneic to C57BL/6. It can be studied following s.c. injection into flank, or orthotopically following injection directly into the pancreas. See e.g., Cancer Res. 44: 717-726 (1984).

Lung Models

LLC Lewis Lung carcinoma model: LLC cells are derived from a spontaneous lung tumor from a C57BL/6 mouse and can be studied as a s.c. tumor when injected in the flank, or as an orthotopic tumor if injected i.v., following which it localizes to the lung.

LLC cells have also been modified to express a peptide from ovalbumin (LL2-OVA cells). Use of these cells, following either s.c. or i.v. injection, allows the tracking of OVA-specific CD8+ lymphocyctes and measurement of effects of therapy on the adaptive immune response against the tumor. See e.g., Science 330:827 (2010).

Breast Model

The 4T1 mammary carcinoma is a transplantable tumor cell line that grows in syngeneic BALB/c mice. It is highly tumorigenic and invasive and, unlike most tumor models, can spontaneously metastasize from the primary tumor in the mammary gland to multiple distant sites including lymph nodes, blood, liver, lung, brain, and bone. See e.g., Current Protocols in Immunology Unit 20.2 (2000). The parental 4T1 cell line has been modified to constitutively express luciferase (4T1-luc). 4T1-Luc cell line can be introduced orthotopically into the mammary fat pad of Balb/c mice. When introduced orthotopically the 4T-luc model grows rapidly at the primary site and forms metastases at distal sites over a period of 3-6 weeks. The rapid and efficient metastasis to organs affected in human breast cancer makes this an excellent mouse model for the study of metastatic progression of breast cancer in humans. Because the model is syngeneic to Balb/c mice, it can be used to study the role of the immune system in tumor growth and metastasis. See e.g., Cancer Res. 1992 Mar. 15; 52(6):1399-405. For example, the cancer cells of the 4T1 model can metastasize to the lung. 4T1 tumor cells are 6-thioguanine-resistant, and the metastatic cells can be detected and quantified by explanting organs, plating dissociated cells in medium supplemented with 6-thioguanine, and counting the number of 6-TG-resistant clonogenic tumor cells. The 4T1 model can be a model of lung metastasis. See e.g., Current Protocols in Immunology Unit 20.2 (2000); and Kerbel, R. S., The Breast 22 (2013), S57-S65.

4T1-Luc, luciferin-expressing 4T1 cell line is cultured in filtered RPMI-1640 supplemented with 10% heat inactivated fetal bovine serum at 37° C. in 5% $CO_2$ atmospheric air. 5000 4T1-Luc cells in 50 uL phosphate buffered saline are implanted orthotopically into the mammary fat pad of 6-8 week old Balb/c female mice. When tumors reach approximately 50-100 $mm^3$, mice are randomized into treatment groups. Mice are orally administered vehicle or an exemplary PI3Kγ inhibitor disclosed herein that has a delta/gamma selectivity ratio of greater than about 50. For example, the PI3Kγ inhibitor is orally administered 3 mg/kg once daily for 21 consecutive days alone or in combination with anti-PD-L1 (200 ug) or Isotype control (Rat IgG2b κ; 200 ug) antibodies that are administered intraperitonal once every 3 days for a total of 5 doses. Tumor and body weight measurements are taken 3 times a week. Luciferin measurements will be taken twice a week imaged using the IVIS 200. At the end of the study, mice are euthanized and tumor will be harvested for evaluating pathway inhibition and immune response of constant PI3Kγ pathway suppression. Plasma is collected for pharmokinetic (PK) analysis. Efficacy is determined, for example, by tumor volume measurements.

Another breast model is described as follows. Prior to injection, PyMT 8119 cells are cultured in F12K supplemented with 5% Fetal Clone II, 50 ug/ml gentamycin, 2.5 ug/ml fugizone, and 1 ul/ml MITO. PyMT 8119 cells are injected subcutaneously or orthotopically in to the mammary fatpad (1×10^6 cells/mouse) into C57B16 or nude mice. Tumor measurements are recorded 3 times a week starting at d7 post injection and tumor volumes are calculated using the formula: (length×width×width)/2=volume where length denotes the longest dimension measured and width denotes the shortest dimension.

Lymphoma Model

EL4 is a C57BL/6 T thymoma and EG7 is an OVA-expressing subclone of EL4. The parental EL4 line has been modified to constitutively express luciferase, which allows non-invasive imaging of tumor growth throughout the animal using the Xenogen imaging platform.

A20 is a Balb/c B cell lymphoma cell line derived from a spontaneous neoplasm found in an old Balb/cAnN mouse, expressing MHC class I and class II H-2d molecules. The parental A20 cell line has been modified to constitutively express luciferase(A20-Luc). A20-Luc, a luciferase-expressing cell line is derived from the parental A20 cell line can be implanted into Balb/c mice subcutaneously or intravenously. The systemic i.v. syngeneic model can be used to study the role of the immune system in tumor growth and metastasis. See e.g., J. Clin Invest. 2013; 123(6):2447-2463.

Melanoma Model

B16 murine melanoma cells are syngeneic with C57BL/6 mice and can be studied after s.c., i.d. (inter dermal), or i.v. injection. Placement at either site will result in metastases to lung and other organs. This model has been extensively studied in terms of the role that inhibitory receptors play in the anti-tumor immune response. See e.g., PNAS 107:4275 (2010).

The B16-F10 luc tagged tumor model allows evaluation of efficacy and pharmacodynamic effects of PI3K-γ inhibitors and other anti-tumor agents. The model can be used as follows. C57 BLK mice (male) are ordered at 5-6 weeks from Jackson Labs, n=40. Mice are dosed QD with a PI3K-γ inhibitor. PDL-1 dose E3D or vehicle is dosed QD. Tumor measurements and bodyweights are taken 3×/week. Tumors are harvested on the last day or if the vehicle reached approximately 2000 mm$^3$. Tumors are cut in half One half is cut in half again with ½ fixed in 10% NBF the other frozen in OCT for frozen sections. The remaining half is processed to single cell suspension and evaluated by FACS using two panels. Dosing is listed in Table 16 below. Vaccination of this model can enhance response to treatment. See e.g., Duraiswamy, J. et al., Cancer Res, 73(12), 2013, 3591; Curran, M. A., et al., PNAS, 107(9), 2010, 4275.

TABLE 16

| Grp # | N | Compound | Dose (mg/kg) | Route | Frequency | Dose vol (ml/kg) | Drug conc (mg/ml) |
|---|---|---|---|---|---|---|---|
| 1 | 12 | Vehicle | 0 | PO/IP | QD | 5/10 | 0 |
| 2 | 12 | Compound 4 | 15 | PO | QD | 5 | 3 |
| 4 | 12 | PDL-1 | 200 uL/mouse | IP | Q3D | 10 | — |

Melanoma is known to be sensitive to immunotherapies, and data linking a poor prognosis to high TAM cell counts in these tumors have been reported. Without being limited by a particular theory, a compound provided herein (e.g., Compound 4) can affect TAM cell counts in the tumor microenvironment, and can be tested in one or more melanoma model known in the art.

Colon Cancer Model

CT26 is an N-nitroso-N-methylurethane-(NNMU) induced, undifferentiated mouse colon carcinoma cell line. It is cloned to generate the cell line designated CT26.WT (ATCC CRL-2638). The syngeneic CT26 colon cancer model is established by subcutaneous implantation of CT26 cells into BALB/c mice. This model has been extensively used to study the anti-tumor activity of immunotherapies (Yu et al., Clinical Cancer Research, 2010; Daraiswamy et al., Cancer Research, 2013). This model can be used to demonstrate the effects of PI3K inhibitors disclosed herein. In some embodiments, a compound provided herein can be administered alone or in combination with an anti-PD-L1.

Another colon cancer model is the CR C57BL/6 mice. Female CR C57BL/6 mice are set up with 1×106 MC38 tumor cells in 0% Matrigel sc in flank. The cell injection volume is 0.05 ml per mouse. When tumors reached an average size of 80-100 mm, a pair match is made and treatment with a compound provided herein begins.

Glioblastoma Model

Nude mouse xenograft model of human glioma can be used to study the effects of compounds provided herein in glioblastoma. Tumors are generated in athymic nude mice (Taconic Laboratories). The animals are injected subcutaneously on the right flank with 5×10$^6$ U87 human glioma cells in 0.1 ml of PBS supplemented with 0.1% glucose. Tumors are measured using an external caliper, every day of treatment, and volume is calculated. When tumors reaches a volume of 200 mm$^3$, mice are randomly distributed into different experimental groups and treated daily with vehicle of the control compound or with blank or a compound provided herein at various doses and schedule. Mice are monitored daily for health status and for tumor volumes. After certain days of treatment mice are sacrificed and tumors are removed, measured and weighed. See e.g., Dolores Hernan Perez de la Ossa, et al., PLOS ONE, 2013, vol. 8 (1), e54795.

In some cases, the GL261 glioblastoma model is used. This is a syngeneic glioblastoma multiform model run subcutaneously or orthotopically, and is described in more detail in the examples provided herein. In some embodiments, the model has previously been treated with radiation therapy but there is a recurrence of the cancer. Compounds provided herein can be administered to models with a recurrence or relapse of cancer after prior treatment.

Example 228: Microsome Stability Assay

The stability of one or more subject compounds is determined according to standard procedures known in the art. For example, stability of one or more subject compounds is established by an in vitro assay. For example, an in vitro microsome stability assay is established that measures stability of one or more subject compounds when reacting with mouse, rat or human microsomes from liver. The microsome reaction with compounds is performed in 1.5 mL Eppendorf tube. Each tube contains 0.1 μL of 10.0 mg/mL NADPH; 75 μL of 20.0 mg/mL mouse, rat or human liver microsome; 0.4 μL of 0.2 M phosphate buffer, and 425 μL of ddH$_2$O. Negative control (without NADPH) tube contains 75 μL of 20.0 mg/mL mouse, rat or human liver microsome; 0.4 μL of 0.2 M phosphate buffer, and 525 μL of ddH$_2$O. The reaction is started by adding 1.0 μL of 10.0 mM tested compound. The reaction tubes are incubated at 37° C. 100 μL sample is collected into new Eppendorf tube containing 300 μL cold methanol at 0, 5, 10, 15, 30 and 60 minutes of reaction. Samples are centrifuged at 15,000 rpm to remove protein. Supernatant of centrifuged sample is transferred to new tube. Concentration of stable compound after reaction with microsome in the supernatant is measured by Liquid Chromatography/Mass Spectrometry (LC-MS).

Example 229: Plasma Stability Assay

The stability of one or more subject compounds in plasma is determined according to standard procedures known in the art. See, e.g., *Rapid Commun. Mass Spectrom.*, 10: 1019-1026. The following procedure is an HPLC-MS/MS assay using human plasma; other species including monkey, dog, rat, and mouse are also available. Frozen, heparinized human plasma is thawed in a cold water bath and spun for 10 minutes at 2000 rpm at 4° C. prior to use. A subject compound is added from a 400 μM stock solution to an aliquot of pre-warmed plasma to give a final assay volume of 400 μL (or 800 μL for half-life determination), containing 5 μM test compound and 0.5% DMSO. Reactions are incubated, with shaking, for 0 minutes and 60 minutes at 37 C, or for 0, 15, 30, 45 and 60 minutes at 37 C for half life determination. Reactions are stopped by transferring 50 μL of the incubation mixture to 200 μL of ice-cold acetonitrile and mixed by shaking for 5 minutes. The samples are centrifuged at 6000×g for 15 minutes at 4° C. and 120 μL of supernatant removed into clean tubes. The samples are then evaporated to dryness and submitted for analysis by HPLC-MS/MS.

In one embodiment, one or more control or reference compounds (5 µM) are tested simultaneously with the test compounds: one compound, propoxycaine, with low plasma stability and another compound, propantheline, with intermediate plasma stability.

Samples are reconstituted in acetonitrile/methanol/water (1/1/2, v/v/v) and analyzed via (RP)HPLC-MS/MS using selected reaction monitoring (SRM). The HPLC conditions consist of a binary LC pump with autosampler, a mixed-mode, C12, 2×20 mm column, and a gradient program. Peak areas corresponding to the analytes are recorded by HPLC-MS/MS. The ratio of the parent compound remaining after 60 minutes relative to the amount remaining at time zero, expressed as percent, is reported as plasma stability. In case of half-life determination, the half-life is estimated from the slope of the initial linear range of the logarithmic curve of compound remaining (%) vs. time, assuming first order kinetics.

Example 230: Kinase Signaling in Blood

PI3K/Akt/mTOR signaling is measured in blood cells using the phosflow method (*Methods Enzymol.* (2007) 434: 131-54). This method is by nature a single cell assay so that cellular heterogeneity can be detected rather than population averages. This allows concurrent distinction of signaling states in different populations defined by other markers. Phosflow is also highly quantitative. To test the effects of one or more compounds provided herein, unfractionated splenocytes, or peripheral blood mononuclear cells are stimulated with anti-CD3 to initiate T-cell receptor signaling. The cells are then fixed and stained for surface markers and intracellular phosphoproteins. Certain inhibitors provided herein, e.g., PI3K-δ inhibitors, inhibit anti-CD3 mediated phosphorylation of Akt-S473 and S6, whereas rapamycin inhibits S6 phosphorylation and enhances Akt phosphorylation under the conditions tested. Certain inhibitors provided herein, e.g., PI3K-γ inhibitors, act on GPCR ligand (e.g., CCL2, CXCL12, or IL8) stimulation of phospho AKT in blood cells. Accordingly, to test the effect of one or more compounds provided herein, unfractionated splenocytes, or peripheral blood mononuclear cells are contacted with a GPCR ligand. The cells are then fixed and stained for surface markers and intracellular phosphoproteins.

Similarly, aliquots of whole blood are incubated for 15 minutes with vehicle (e.g., 0.1% DMSO) or kinase inhibitors at various concentrations, before addition of stimuli to crosslink the T cell receptor (TCR) (e.g., anti-CD3 with secondary antibody) or the B cell receptor (BCR) using anti-kappa light chain antibody (Fab'2 fragments). After approximately 5 and 15 minutes, samples are fixed (e.g., with cold 4% paraformaldehyde) and used for phosflow. Surface staining is used to distinguish T and B cells using antibodies directed to cell surface markers that are known to the art. The level of phosphorylation of kinase substrates such as Akt and S6 are then measured by incubating the fixed cells with labeled antibodies specific to the phosphorylated isoforms of these proteins. The population of cells are then analyzed by flow cytometry.

Example 231: Colony Formation Assay

Murine bone marrow cells freshly transformed with a p190 BCR-Abl retrovirus (herein referred to as p190 transduced cells) are plated in the presence of various drug combinations in M3630 methylcellulose media for about 7 days with recombinant human IL-7 in about 30% serum, and the number of colonies formed is counted by visual examination under a microscope.

Alternatively, human peripheral blood mononuclear cells are obtained from Philadelphia chromosome positive (Ph+) and negative (Ph−) patients upon initial diagnosis or relapse. Live cells are isolated and enriched for CD19+CD34+ B cell progenitors. After overnight liquid culture, cells are plated in methocult GF+H4435 (Stem Cell Technologies), supplemented with cytokines (IL-3, IL-6, IL-7, G-CSF, GM-CSF, CF, Flt3 ligand, and erythropoietin) and various concentrations of known chemotherapeutic agents in combination with compounds of the present disclosure. Colonies are counted by microscopy 12-14 days later. This method can be used to test for evidence of additive or synergistic activity.

Example 232: In Vivo Effect of Kinase Inhibitors on Leukemic Cells

Female recipient mice are lethally irradiated from a γ source in two doses about 4 hr apart, with approximately 5 Gy each. About 1 hr after the second radiation dose, mice are injected i.v. with about $1 \times 10^6$ leukemic cells (e.g., Ph+ human or murine cells, or p190 transduced bone marrow cells). These cells are administered together with a radio-protective dose of about $5 \times 10^6$ normal bone marrow cells from 3-5 week old donor mice. Recipients are given antibiotics in the water and monitored daily. Mice who become sick after about 14 days are euthanized and lymphoid organs are harvested for analysis. Kinase inhibitor treatment begins about 10 days after leukemic cell injection and continues daily until the mice become sick or a maximum of approximately 35 days post-transplant. Inhibitors are given by oral lavage.

Peripheral blood cells are collected approximately on day 10 (pre-treatment) and upon euthanization (post treatment), contacted with labeled anti-hCD4 antibodies and counted by flow cytometry. This method can be used to demonstrate that the synergistic effect of one or more compounds provided herein in combination with known chemotherapeutic agents can reduce leukemic blood cell counts as compared to treatment with known chemotherapeutic agents (e.g., Gleevec) alone under the conditions tested.

Example 233: Treatment of Lupus Disease Model Mice

Mice lacking the inhibitory receptor FcγRIIb that opposes PI3K signaling in B cells develop lupus with high penetrance. FcγRIIb knockout mice (R2KO, Jackson Labs) are considered a valid model of the human disease as some lupus patients show decreased expression or function of FcγRIIb (S. Bolland and J. V. Ravtech 2000. *Immunity* 12:277-285).

The R2KO mice develop lupus-like disease with anti-nuclear antibodies, glomerulonephritis and proteinurea within about 4-6 months of age. For these experiments, the rapamycin analogue RAD001 (available from LC Laboratories) is used as a benchmark compound, and administered orally. This compound has been shown to ameliorate lupus symptoms in the B6.Sle1z.Sle3z model (T. Wu et al. *J. Clin Invest.* 117:2186-2196).

The NZB/W F1 mice that spontaneously develop a systemic autoimmune disease is a model of lupus. The murine NZB/W F1 lupus model has many features of human lupus, and is characterized by elevated levels of anti-nuclear and anti-dsDNA autoantibodies; a critical role for plasmacytoid dendritic cells and IFN-α; T-cell, B-cell, macrophage involvement; pheymolytic anemia; progressive immune complex glomerulonephritis; proteinurea; severity and incidence more pronounced in females; and decreased survival. Treatment with a compound provided herein can be determined by evaluation of urine protein scores, organ weights, plasma anti-dsDNA IgG levels, and histopathology of the kidneys. The mice are treated starting at 20 weeks of age for a profilactic model and at 23 weeks of age for a therapeutic model. Blood and urine samples are obtained throughout the testing period, and tested for antinuclear antibodies (in dilutions of serum) or protein concentration (in urine). Serum is also tested for anti-ssDNA and anti-dsDNA antibodies by ELISA. Glomerulonephritis is assessed in kidney sections stained with H&E at the end of the study, or survival can be an endpoint. For example, the proteozome inhibitor Bortezimib is effective at blocking disease in the NZB/W model in both the profilactic and therapeutic model with reductions in auto-antibody production, kidney damage, and improvements in survival (*Nature Medicine* 14, 748-755 (2008)).

Lupus disease model mice such as R2KO, BXSB or MLR/lpr are treated at about 2 months old, approximately for about two months. Mice are given doses of: vehicle, RAD001 at about 10 mg/kg, or compounds provided herein at approximately 1 mg/kg to about 500 mg/kg. Blood and urine samples are obtained throughout the testing period, and tested for antinuclear antibodies (in dilutions of serum) or protein concentration (in urine). Serum is also tested for anti-ssDNA and anti-dsDNA antibodies by ELISA. Animals are euthanized at day 60 and tissues harvested for measuring spleen weight and kidney disease. Glomerulonephritis is assessed in kidney sections stained with H&E. Other animals are studied for about two months after cessation of treatment, using the same endpoints.

This established art model can be employed to demonstrate that the kinase inhibitors provided herein can suppress or delay the onset of lupus symptoms in lupus disease model mice.

Example 234: Murine Bone Marrow Transplant Assay

Female recipient mice are lethally irradiated from a γ ray source. About 1 hr after the radiation dose, mice are injected with about 1×10⁶ leukemic cells from early passage p190 transduced cultures (e.g., as described in *Cancer Genet Cytogenet*. 2005 August; 161(1):51-6). These cells are administered together with a radioprotective dose of approximately 5×10⁶ normal bone marrow cells from 3-5 wk old donor mice. Recipients are given antibiotics in the water and monitored daily. Mice who become sick after about 14 days are euthanized and lymphoid organs harvested for flow cytometry and/or magnetic enrichment. Treatment begins on approximately day 10 and continues daily until mice become sick, or after a maximum of about 35 days post-transplant. Drugs are given by oral gavage (p.o.). In a pilot experiment, a dose of chemotherapeutic that is not curative but delays leukemia onset by about one week or less is identified; controls are vehicle-treated or treated with chemotherapeutic agent, previously shown to delay but not cure leukemogenesis in this model (e.g., imatinib at about 70 mg/kg twice daily). For the first phase, p190 cells that express eGFP are used, and postmortem analysis is limited to enumeration of the percentage of leukemic cells in bone marrow, spleen and lymph node (LN) by flow cytometry. In the second phase, p190 cells that express a tailless form of human CD4 are used and the postmortem analysis includes magnetic sorting of hCD4+ cells from spleen followed by immunoblot analysis of key signaling endpoints: p Akt-T308 and S473; pS6 and p4EBP-1. As controls for immunoblot detection, sorted cells are incubated in the presence or absence of kinase inhibitors of the present disclosure inhibitors before lysis. Optionally, "phosflow" is used to detect p Akt-S473 and pS6-S235/236 in hCD4-gated cells without prior sorting. These signaling studies are particularly useful if, for example, drug-treated mice have not developed clinical leukemia at the 35 day time point. Kaplan-Meier plots of survival are generated and statistical analysis done according to methods known in the art. Results from p190 cells are analyzed separated as well as cumulatively.

Samples of peripheral blood (100-200 μL) are obtained weekly from all mice, starting on day 10 immediately prior to commencing treatment. Plasma is used for measuring drug concentrations, and cells are analyzed for leukemia markers (eGFP or hCD4) and signaling biomarkers as described herein.

This general assay known in the art can be used to demonstrate that effective therapeutic doses of the compounds provided herein can be used for inhibiting the proliferation of leukemic cells.

Example 235: Matrigel Plug Angiogenesis Assay

Matrigel containing test compounds are injected subcutaneously or intraocularly, where it solidifies to form a plug. The plug is recovered after 7-21 days in the animal and examined histologically to determine the extent to which blood vessels have entered it. Angiogenesis is measured by quantification of the vessels in histologic sections. Alternatively, fluorescence measurement of plasma volume is performed using fluorescein isothiocyanate (FITC)-labeled dextran 150. The results are expected to indicate one or more compounds provided herein that inhibit angiogenesis and are thus expected to be useful in treating ocular disorders related to aberrant angiogenesis and/or vascular permeability.

Example 236: Corneal Angiogenesis Assay

A pocket is made in the cornea, and a plug containing an angiogenesis inducing formulation (e.g., VEGF, FGF, or tumor cells), when introduced into this pocket, elicits the ingrowth of new vessels from the peripheral limbal vasculature. Slow-release materials such as ELVAX (ethylene vinyl copolymer) or Hydron are used to introduce angiogenesis inducing substances into the corneal pocket. Alternatively, a sponge material is used.

The effect of putative inhibitors on the locally induced (e.g., sponge implant) angiogenic reaction in the cornea (e.g., by FGF, VEGF, or tumor cells). The test compound is administered orally, systemically, or directly to the eye. Systemic administration is by bolus injection or, more effectively, by use of a sustained-release method such as implantation of osmotic pumps loaded with the test inhibitor. Administration to the eye is by any of the methods described herein including, but not limited to eye drops, topical administration of a cream, emulsion, or gel, intravitreal injection.

The vascular response is monitored by direct observation throughout the course of the experiment using a stereomicroscope in mice. Definitive visualization of the corneal vasculature is achieved by administration of fluorochrome-labeled high-molecular weight dextran. Quantification is performed by measuring the area of vessel penetration, the progress of vessels toward the angiogenic stimulus over time, or in the case of fluorescence, histogram analysis or pixel counts above a specific (background) threshold.

The results can indicate one or more compounds provided herein inhibit angiogenesis and thus can be useful in treating ocular disorders related to aberrant angiogenesis and/or vascular permeability.

Example 237: Microtiter-Plate Angiogenesis Assay

The assay plate is prepared by placing a collagen plug in the bottom of each well with 5-10 cell spheroids per collagen plug each spheroid containing 400-500 cells. Each collagen plug is covered with 1100 µL of storage medium per well and stored for future use (1-3 days at 37° C., 5% $CO_2$). The plate is sealed with sealing. Test compounds are dissolved in 200 µL assay medium with at least one well including a VEGF positive control and at least one well without VEGF or test compound as a negative control. The assay plate is removed from the incubator and storage medium is carefully pipetted away. Assay medium containing the test compounds are pipetted onto the collagen plug. The plug is placed in a humidified incubator for (37° C., 5% $CO_2$) 24-48 hours. Angiogenesis is quantified by counting the number of sprouts, measuring average sprout length, or determining cumulative sprout length. The assay can be preserved for later analysis by removing the assay medium, adding 1 mL of 10% paraformaldehyde in Hanks BSS per well, and storing at 4° C. The results are expected to identify compounds that inhibit angiogenesis in various cell types tested, including cells of ocular origin.

Example 238: Combination Use of PI3K-δ Inhibitors and Agents that Inhibit IgE Production or Activity The compounds as provided herein can present synergistic or additive efficacy when administered in combination with agents that inhibit IgE production or activity. Agents that inhibit IgE production include, for example, one or more of TEI-9874, 2-(4-(6-cyclohexyloxy-2-naphtyloxy) phenylacetamide)benzoic acid, rapamycin, rapamycin analogs (i.e., rapalogs), TORC1 inhibitors, TORC2 inhibitors, and any other compounds that inhibit mTORC1 and mTORC2. Agents that inhibit IgE activity include, for example, anti-IgE antibodies such as Omalizumab and TNX-901.

One or more of the subject compounds capable of inhibiting PI3K-δ can be efficacious in treatment of autoimmune and inflammatory disorders (AIID), for example, rheumatoid arthritis. If any of the compounds causes an undesired level of IgE production, one can choose to administer it in combination with an agent that inhibits IgE production or IgE activity. Additionally, the administration of PI3K-δ or PI3K-δ/γ inhibitors as provided herein in combination with inhibitors of mTOR can also exhibit synergy through enhanced inhibition of the PI3K pathway. Various in vivo and in vitro models can be used to establish the effect of such combination treatment on AIID including, but not limited to: (a) in vitro B-cell antibody production assay, (b) in vivo TNP assay, and (c) rodent collagen induced arthritis model.

(a) B-Cell Assay

Mice are euthanized, and the spleens are removed and dispersed through a nylon mesh to generate a single-cell suspension. The splenocytes are washed (following removal of erythrocytes by osmotic shock) and incubated with anti-CD43 and anti-Mac-1 antibody-conjugated microbeads (Miltenyi Biotec). The bead-bound cells are separated from unbound cells using a magnetic cell sorter. The magnetized column retains the unwanted cells and the resting B cells are collected in the flow-through. Purified B-cells are stimulated with lipopolysaccharide or an anti-CD40 antibody and interleukin 4. Stimulated B-cells are treated with vehicle alone or with PI3K-δ inhibitors as provided herein with and without mTOR inhibitors such as rapamycin, rapalogs, or mTORC1/C2 inhibitors. The results are expected to show that in the presence of mTOR inhibitors (e.g., rapamycin) alone, there is little to no substantial effect on IgG and IgE response. However, in the presence of PI3K-δ and mTOR inhibitors, the B-cells are expected to exhibit a decreased IgG response as compared to the B-cells treated with vehicle alone, and the B-cells are expected to exhibit a decreased IgE response as compared to the response from B-cells treated with PI3K-δ inhibitors alone.

(b) TNP Assay

Mice are immunized with TNP-Ficoll or TNP-KHL and treated with: vehicle, a PI3K-δ inhibitor, an mTOR inhibitor, for example rapamycin, or a PI3K-δ inhibitor in combination with an mTOR inhibitor such as rapamycin. Antigen-specific serum IgE is measured by ELISA using TNP-BSA coated plates and isotype specific labeled antibodies. It is expected that mice treated with an mTOR inhibitor alone exhibit little or no substantial effect on antigen specific IgG3 response and no statistically significant elevation in IgE response as compared to the vehicle control. It is also expected that mice treated with both PI3K-δ inhibitor and mTOR inhibitor exhibit a reduction in antigen specific IgG3 response as compared to the mice treated with vehicle alone. Additionally, the mice treated with both PI3K-δ inhibitor and mTOR inhibitor exhibit a decrease in IgE response as compared to the mice treated with PI3K-δ inhibitor alone.

(c) Rat Collagen Induced Arthritis Model

Female Lewis rats are anesthetized and given collagen injections prepared and administered as described previously on day 0. On day 6, animals are anesthetized and given a second collagen injection. Caliper measurements of normal (pre-disease) right and left ankle joints are performed on day 9. On days 10-11, arthritis typically occurs and rats are randomized into treatment groups. Randomization is performed after ankle joint swelling is obviously established and there is good evidence of bilateral disease.

After an animal is selected for enrollment in the study, treatment is initiated. Animals are given vehicle, PI3K-δ inhibitor, or PI3K-δ inhibitor in combination with rapamycin. Dosing is administered on days 1-6. Rats are weighed on days 1-7 following establishment of arthritis and caliper measurements of ankles taken every day. Final body weights are taken on day 7 and animals are euthanized.

The combination treatment using a compound as provided herein and rapamycin can provide greater efficacy than treatment with PI3K-δ inhibitor alone.

Example 239: Delayed Type Hypersensitivity Model

DTH is induced by sensitizing 60 BALB/c male mice on day 0 and day 1 with a solution of 0.05% 2,4 dinitrofluorobenzene (DNFB) in a 4:1 acetone/olive oil mixture. Mice are gently restrained while 20 µL of solution is applied to the hind foot pads of each mouse. The hind foot pads of the mice are used as they represent an anatomical site that can be easily isolated and immobilized without anesthesia. On day 5, mice are administered a single dose of vehicle, a compound provided herein at 10, 3, 1, or 0.3 mg/kg, or dexamethasone at a dose of 5 mg/kg by oral gavage. Thirty minutes later mice are anaesthetized, and a solution of 0.25% DNFB in a 4:1 acetone/olive oil solution is applied to the left inner and outer ear surface. This application results in the induction of swelling to the left ear and under these conditions, all animals responded to this treatment with ear swelling. A vehicle control solution of 4:1 acetone/olive oil is applied to the right inner and outer ear. Twenty four hours later, mice are anaesthetized, and measurements of the left and right ear are taken using a digital micrometer. The difference between the two ears is recorded as the amount of swelling induced by the challenge of DNFB. Drug treatment groups are compared to vehicle control to generate the percent reduction in ear swelling. Dexamethasone is routinely used as a positive control as it has broad anti-inflammatory activity.

Example 240: Peptidoglycan-Polysaccharide Rat Arthritic Model (a) Systemic Arthritis Model All injections are performed under anesthesia. 60 female Lewis rats (150-170) are anesthetized by inhalation isoflurane using a small animal anesthesia machine. The animals are placed in the induction chamber until anesthetized by delivery of 4-5% isoflurane in $O_2$ and then held in that state using a nose cone on the procedure table. Maintenance level of isoflurane is at 1-2%. Animals are injected intraperitoneally (i.p.) with a single injection of purified PG-PS 10S Group A, D58 strain (concentration 25 µg/g of bodyweight) suspended in sterile 0.85% saline. Each animal receives a total volume of 500 microliters administered in the lower left quadrant of the abdomen using a 1 milliliter syringe with a 23 gauge needle. Placement of the needle is critical to avoid injecting the PG-PS 10S into either the stomach or caecum. Animals are under continuous observation until fully recovered from anesthesia and moving about the cage. An acute response of a sharp increase in ankle measurement, typically 20% above baseline measurement can peak in 3-5 days post injection. Treatment with test compounds can be PO, SC, IV or IP. Rats are dosed no more than two times in a 24 hour time span. Treatment can begin on day 0 or any day after that through day 30. The animals are weighed on days 0, 1, 2, 3, 4, 5, 6, 7 and beginning again on day 12-30 or until the study is terminated. Paw/ankle diameter is measured with a digital caliper on the left and right side on day 0 prior to injection and again on day 1, 2, 3, 4, 5, 6 and 7. On day 12, measurements begin again and continue on through day 30. At this time, animals can be anesthetized with isoflurane, as described above, and terminal blood samples can be obtained by tail vein draws for the evaluation of the compound blood levels, clinical chemistry or hematology parameters. Animals are then euthanized with carbon dioxide overdose. A thoracotomy can be conducted as a means of death verification.

(b) Monoarticular Arthritis Model

All injections are performed under anesthesia. 60 female Lewis rats (150-170) are anesthetized by inhalation isoflurane using a small animal anesthesia machine. The animals are placed in the induction chamber until anesthetized by delivery of 4-5% isoflurane in $O_2$ and then held in that state using a nose cone on the procedure table. Maintenance level of isoflurane is at 1-2%. Animals are injected intra-articular (i.a.) with a single injection of purified PG-PS 100P Group A, D58 strain (concentration 500 µg/mL) suspended in sterile 0.85% saline. Each rat receives a total volume of 10 microliters administered into the tibiotalar joint space using a 1 milliliter syringe with a 27 gauge needle. Animals are under continuous observation until fully recovered from anesthesia and moving about the cage. Animals that respond 2-3 days later with a sharp increase in ankle measurement, typically 20% above baseline measurement on the initial i.a. injection, are included in the study. On day 14, all responders are anesthetized again using the procedure previously described. Animals receive an intravenous (IV.) injection of PG-PS (concentration 250 µL/mL). Each rat receives a total volume of 400 microliters administered slowly into the lateral tail vein using a 1 milliliter syringe with a 27 gauge needle. Baseline ankle measurements are measured prior to IV injection and continue through the course of inflammation or out to day 10. Treatment with test compounds will be PO, SC, IV or IP. Rats are dosed no more than two times in a 24 hour time span. Treatment can begin on day 0 or any day after that through day 24. The animals are weighed on days 0, 1, 2, 3, 4, 5, and beginning again on day 14-24 or until the study is terminated. Paw/ankle diameter is measured with a digital caliper on the left and right side on day 0 prior to injection and again on day 1, 2, 3, 4, 5, and beginning again on day 14-24 or until the study is terminated. At this time, animals can be anesthetized with isoflurane, as described above, and terminal blood samples can be obtained by tail vein draws for the evaluation of the compound blood levels, clinical chemistry or hematology parameters. Animals are them euthanized with carbon dioxide overdose. A thoracotomy can be conducted as a means of death verification.

Example 241: Mice Models for Asthma

Efficacy of a compound provided herein in treating, preventing and/or managing asthma can be assessed using an conventional animal models including various mice models described in, for example, Nials et al., *Dis Model Mech.* 1(4-5): 213-220 (2008).

(a) Acute Allergen Challenge Models

Several models are known in the art and any of such models can be used. Although various allergens can be used to induce asthma-like conditions, the principle is consistent throughout the methods. Briefly, asthma-like conditions are induced through multiple systemic administration of the allergen (e.g., ova, house dust mite extracts and cockroach extracts) in the presence of an adjuvant such as aluminum hydroxide. Alternatively, an adjuvant-free system can be used, but it usually requires a higher number of exposures to achieve suitable sensitization. Once induced, animals exhibit many key features of clinical asthma such as: elevated levels of IgE; airway inflammation; goblet cell hyperplasia; epithelial hypertrophy; AHR ro specific stimuli; and early and late phase bronchoconstriction. Potential efficacy of a compound thus can be assessed by determining whether one or more of these clinical features are reversed or mitigated.

(b) Chronic Allergen Challenge Models

Chronic allergen challenge models aim to reproduce more of the features of the clinical asthma, such as airway remodeling and persistent AHR, than acute challenge models. While allergens similar to those used in acute allergen challenge models can be used, in chronic allergen challenge models, animals are subjected to repeated exposure of the airways to low levels of allergen for a period of up to 12 weeks. Once induced, animals exhibit key features of human asthma such as: allergen-dependent sensitization; a Th2-dependent allergic inflammation characterized by eosinophillic influx into the airway mucosa; AHR; and airway remodeling as evidenced by goblet cell hyperplasia, epithelial hypertrophy, subepithelial or peribronchiolar fibrosis. Potential efficacy of a compound thus can be assessed by determining whether one or more of these clinical features are reversed or mitigated.

Example 242: Models for Psoriasis

Efficacy of a compound provided herein in treating, preventing and/or managing psoriasis can be assessed using an conventional animal models including various animal models described in, for example, Boehncke et al., *Clinics in Dermatology*, 25: 596-605 (2007).

As an example, the mouse model based on adoptive transfer of CD4$^+$CD45RB$^{hi}$ T cells described in Hong et al., *J. Immunol.*, 162: 7480-7491 (1999) can be made. Briefly, female BALB/cBY (donor) and C.B.-17/Prkdc scid/scid (recipient) mice are housed in a specific pathogen-free environment and are used between 6 and 8 weeks of age. CD4$^+$ T cells are enriched from BALB/cBy splenocytes using a mouse CD4 enrichment kit. The cells are then labeled with PE-conjugated anti-CD4, FITC-conjugated anti-CD45RB, and APC-conjugated anti-CD25 antibodies. Cells are sorted using a cell sorter. CD4$^+$CD45RB$^{hi}$CD25 cells are collected. Cells are resuspended in saline and 4×10$^8$ cells/mouse are injected i.p. into C.B.-17/Prkdc scid/scid mice. Mice may be dosed with LPS, cytokines, or antibodies as necessary. Mice are monitored for external signs of skin lesions twice each week. After the termination, ear, back skin, lymph nodes and spleen may be collected for further ex vivo studies.

Example 243: Models for Scleroderma

A compound's efficacy in treating scleroderma can be tested using animal models. An exemplary animal model is a mouse model for scleroderma induced by repeated local injections of bleomycin ("BLM") described, for example, in Yamamoto et al., *J Invest Dermatol* 112: 456-462 (1999), the entirety of which is incorporated herein by reference. This mouse model provides dermal sclerosis that closely resembles systemic sclerosis both histologically and biochemically. The sclerotic changes observed in the model include, but are not limited to: thickened and homogenous collagen bundles and cellular filtrates; gradual increase in number of mast cells; degranulation of mast cells; elevated histamine release; increase in hydroxyproline in skin; presence of anti-nuclear antibody in serum; and strong expression of transforming growth factor β-2 mRNA. Therefore, efficacy of a compound in treating scleroderma can be assessed by monitoring the lessening of one or more of these changes.

Briefly, the following exemplary procedures can be used to generate the mouse model for scleroderma: Specific pathogen-free, female BALB/C mice and C3H mice of 6 weeks old, weighing about 20 g, are purchased and maintained with food and water ad libitum. BLM is dissolved in PBS at differing concentrations and sterilized with filtration. Aliquots of each concentration of BLM or PBS are injected subcutaneously into the shaved back of the mice daily for 1-4 weeks with a needle. Alternatively, mice are injected every other day.

Histopathological and biochemical changes induced can be assessed using any methods commonly practiced in the field. For example, histopathological changes can be assessed using a standard avidine-biotin peroxidase technique with anti-L3T4 monoclonal antibody, anti-Lyt2 monoclonal antibody, anti-mouse pan-tissue-fixed macrophage antibody, anti-stem cell factor monoclonal antibody, anti-transforming growth factor-β polyclonal antibody, and anti-decorin antibody. Cytokine expression of cellular infiltrates can be assessed by using several anti-cytokine antibodies. Hydroxyproline level can be assessed by hydrolyzing skin pieces with hydrochloric acid, neutralizing with sodium hydroxide, and colorimetrically assessing the hydrolates at 560 nm with p-dimethylaminobenzaldehyde. Pepsin-resistant collagen can be assessed by treating collagen sample extracted from biopsied tissues and analyzing by polyacrylamide stacking gel electrophoresis. Mast cells can be identified by toluidine blue, and cells containing matachromatic granules can be counted under high magnification of a light microscope. Serum levels of various cytokines can be assessed by enzyme-linked immunosorbent assay, and mRNA levels of the cytokines can be assessed by reverse-transcriptase polymerase chain reaction. Autoantibodies in serum can be detected using 3T3 fibroblasts as the substrate for the screening.

Example 244: Models for Myositis

A compound's efficacy in treating myositis (e.g., dermatomyositis) can be tested using animal models known in the art. One such example is the familial canine dermatomyositis model described in Hargis et al., *AJP* 120(2): 323-325 (1985). Another example is the rabbit myosin induced mouse model described in Phyanagi et al., *Arthritis & Rheumatism*, 60(10): 3118-3127 (2009).

Briefly, 5-week old male SJL/J mice are used. Purified myosin from rabbit skeletal muscle (6.6 mg/ml) is emulsified with an equal amount of Freund's complete adjuvant and 3.3 mg/ml *Mycobacterium butyricum*. The mice are immunized repeatedly with emulsified rabbit myosin. Once myositis is induced, inflammatory cell filtration and necrotic muscle fiber should be evident in the model. In the muscles of animals, CD4$^+$ T cells are mainly located in the perimysum and CD8$^+$ T cells are mainly located in the endomysium and surround non-necrotic muscle fibers. TNFα, IFNγ and perforin are up-regulated and intercellular adhesion molecule 1 is increased in the muscles.

To assess the efficacy of a compound, following administration of the compound through adequate route at specified dose, the mice are killed and muscle tissues are harvested. The muscle tissue is immediately frozen in chilled isopentane precooled in liquid nitrogen, and then cryostat sections are prepared. The sections are stained with hematoxylin and eosin for counting of number of infiltrated cells. Three sections from each mouse are prepared and photomicrographs are obtained. For immunohistochemical tests, cryostat sections of muscle are dried and fixed in cold acetone at −20° C. The slides are rehydrated in PBS, and then endogeneous peroxidase activity is blocked by incubation in 1% hydrogen peroxide. The sections are incubated overnight with rat anti-mouse CD4 monoclonal antibody, rat anti-mouse CD8 monoclonal antibody, rat anti-mouse F4/80 monoclonal antibody or normal rat IgG in antibody diluent. The samples are washed with PBS and incubated with biotin-conjugated rabbit anti-rat IgG pretreated with 5% normal mouse serum. After washing with PBS, the samples are incubated with streptavidin-horseradish peroxidase. After washing PBS, diaminobenzidine is used for visualization.

Example 245: Models for Sjögren Syndrome

A compound's efficacy in treating Sjögren's syndrome can be tested using animal models known in the art, for example, those described in Chiorini et al., *Journal of Autoimmunity* 33: 190-196 (2009). Examples include: mouse model spontaneously developed in first filial generation of NZB mice crossed to NZW mice (see, e.g., Jonsson et al., *Clin Immunol Immunopathol* 42: 93-101 (1987); mouse model induced by i.p. injection of incomplete Freund's adjuvant (id.; Deshmukh et al., *J Oral Pathol Med* 38: 42-27 (2009)); NOD mouse models wherein Sjögren's phenotype is developed by specific genotypes (see, e.g., Cha et al., *Arthritis Rheum* 46: 1390-1398 (2002); Kong et al., *Clin Exp Rheumatol* 16: 675-681 (1998); Podolin et al., *J Exp Med* 178: 793-803 (1993); and Rasooly et al., *Clin Immunol Immunopathol* 81: 287-292 (1996)); mouse model developed in spontaneous lpr mutation; mouse model developed in Id3 knock-out mice (see, e.g., Li et al., *Immunity* 21: 551-560 (2004)); mouse model developed in PI3K knock-out mice (see, e.g., Oak et al., *Proc Natl Acad Sci USA* 103: 16882-16887 (2006)); mouse model developed in BAFF over-expressing transgenic mice (see, e.g., Groom et al., *J Clin Invest* 109: 59-68 (2002)); mouse model induced by injection of Ro antigen into BALB/c mice (see, e.g., Oh-Hora et al., *Nat. Immunol* 9: 432-443 (2008)); mouse model induced by injection of carbonic anhydrase II (see, e.g., Nishimori et al., *J Immunol* 154: 4865-4873 (1995); mouse model developed in IL-14 over-expressing transgenic mice (see, e.g., Shen et al., *J Immunol* 177: 5676-5686 (2006)); and mouse model developed in IL-12 expressing transgenic mice (see, e.g., McGrath-Morrow et al., *Am J Physiol Lung Cell Mol Physiol* 291: L837-846 (2006)).

Example 246: Models for Immune Complex Mediated Disease

The Arthus reaction is a type 3 immune response to immune complexes, and thus, can be a mechanistic model supporting therapeutic hypothesis for immune complex mediated diseases such as rheumatoid arthritis, lupus and other autoimmune diseases. For example, PI3Kγ and δ deficient mice can be used as experimental models of the Arthus reaction and provide assessment of therapeutic potential of a compound as to the treatment of immune complex mediated diseases. The Arthus reaction can be induced using the following exemplary procedures as described in Konrad et al., *Journal of Biological Chemistry* (2008 283(48): 33296-33303.

PI3Kγ- and PI3Kδ-deficient mice are maintained under dry barrier conditions. Mice are anesthetized with ketamine and xylazine, and the trachea is cannulated. Appropriate amount of protein G-purified anti-OVA IgG Ab is applied, and appropriate amount of OVA antigen is given intravenously. For PI3K blocking experiments, wortmanin is given intratracheally together with the application of anti-OVA igG. Mice are killed at 2-4 hours after initiation of inflammation, and desired follow up assessments can be performed using methods known in the art.

Example 247: PI3-Kinase Promega™ Assay

Promega ADP-Glo Max assay kit (Cat. No. V7002) was utilized to determine $IC_{50}$ values for α, β, δ and γ isoforms of human Class I PI3 kinases (Millipore). Samples of kinase (20 nM α or δ, 40 nM β or γ isoform) were incubated with compound for 15 minutes at room temperature in reaction buffer (15 mM HEPES pH 7.4, 20 mM NaCl, 1 mM EGTA, 0.02% Tween 20, 10 mM $MgCl_2$, 0.2 mg/mL bovine-γ-globulins) followed by addition of ATP/diC8-PtdInsP mixture to give final concentrations of 3 mM ATP and 500 uM $diC_8$-PtdInsP. Reactions were incubated at room temperature for 2 hours followed by addition of 25 uL of stop solution. After a 40-minute incubation at room temperature, 50 uL of Promega detection mix was added followed by incubation for 1 hour at room temperature. Plates were then read on Envision plate reader in luminescence mode. Data was converted to % inhibition using the following equation below:

$$\% \text{ inhibition} = 100 - \left(\left[\frac{S - Pos}{Neg - Pos}\right] * 100\right)$$

where S is the sample luminescence, Pos is a positive control without added PI3K, Neg is the negative control without added compound. Data was then plotted as % inhibition vs compound concentration. Data fit to 4 parameter logistic equation to determine $IC_{50}$ values:

$$\% \text{ inhibition} = \frac{\max - \min}{1 - \left(\frac{IC_{50}^h}{[I]^h}\right)}$$

Certain compounds provided herein were tested in PI3-Kinase Promega Assay using procedures as described above to determine $IC_{50}$ values for α, β, δ and/or γ isoforms. The $IC_{50}$ values are summarized in Table 15.

Example 248: Isoform-Selective Cellular Assays (a) PI3K-δ Selective Assay

A compound's ability in selectively inhibiting PI3K-δ can be assessed using RAJI cells, i.e., B lymphocyte cells derived from lymphoma patients. Briefly, serum-starved RAJI cells are stimulated with anti-human IgM, thereby causing signaling through the B-cell receptors, as described in, for example, He et al., *Leukemia Research* (2009) 33: 798-802. B-cell receptor signaling is important for the activation, differentiation, and survival of B cells and certain B-cell derived cancers. Reduction of phospho-AKT is indicative of compounds that may inhibit B-cell proliferation and function in certain diseases. By monitoring the reduction of phospho-AKT in stimulated RAJI cells (using for example, phospho-AKT antibodies), a compound's potential efficacy in selectively inhibiting PI3Kδ can be assessed.

Certain compounds provided herein were tested in RAJI cell model using procedures as described above. The $IC_{50}$ values for phospho-AKT are summarized in Table 15.

(b) PI3K-γ Selective Assay

A compound's ability in selectively inhibiting PI3K-γ can be assessed using RAW264.7 macrophages. Briefly, serum-starved RAW264.7 cells are stimulated with a known GPCR agonist C5a. See, e.g., Camps et al., *Nature Medicine* (2005) 11(9):936-943. Cells can be treated with test compounds prior to, simultaneously with, or subsequent to the stimulation by C5a. RAW 264.7 cells respond to the complement component fragment C5a through activation of the C5a receptor, and the C5a receptor activates macrophages and induces cell migration. Test compounds' ability to inhibit C5a-mediated AKT phosphorylation is indicative of selective inhibition of PI3K-γ. Thus, by monitoring the reduction of phospho-AKT in stimulated RAW 264.7 cells (using for example, phospho-AKT antibodies), a compound's potential efficacy in selectively inhibiting PI3Kγ can be assessed.

Certain compounds provided herein were tested in RAW 264.7 cell model using procedures as described above. The $IC_{50}$ values for phospho-AKT are summarized in Table 15.

(c) PI3K-α Selective Assay

A compound's ability in selectively inhibiting PI3K-α can be assessed using SKOV-3 cells, i.e., human ovarian carcinoma cell line. Briefly, SKOV-3 cells, in which mutant PI3Kα is constitutively active, can be treated with test compounds. Test compounds' ability to inhibit AKT phosphorylation in SKOV-3 cells, therefore, is indicative of selective inhibition of PI3Kα. Thus, by monitoring the reduction of phospho-AKT in SKOV-3 cells (using for example, phospho-AKT antibodies), a compound's potential efficacy in selectively inhibiting PI3Kα can be assessed.

(d) PI3K-β Selective Assay

A compound's ability in selectively inhibiting PI3K-β can be assessed using 786-O cells, i.e., human kidney carcinoma cell line. Briefly, 786-O cells, in which PI3K is constitutively active, can be treated with test compounds. Test compounds' ability to inhibit AKT phosphorylation in 786-O cells, therefore, is indicative of selective inhibition of PI3Kβ. Thus, by monitoring the reduction of phospho-AKT in 786-O cells (using for example, phospho-AKT antibodies), a compound's potential efficacy in selectively inhibiting PI3Kβ can be assessed.

Example 249: Models for Chronic Lymphocytic Leukemia

The TCL-1 transgenic mouse model is a model of chronic lymphocytic leukemia (CLL) that is generated by introducing the human TCL1 gene under control of a B cell-specific Ig promoter. TCL1 transgenic mice develop a monoclonal B-cell lymphocytosis that is very similar to human CLL in immunophenotypic and clinical features. Leukemic splenocytes from diseased mice can also be adoptively transferred into syngeneic C57BL/6 mice, creating a model allowing for a large number of animals with synchronously established disease. See e.g., Johnson, A. J., et al., Blood 108(4):1334-8 (2006).

Placement of tcl-1 under the control of a B-cell-specific IgVH promoter and IgH-E enhancer results in a similar B-cell phenotype in which mice develop normally into adulthood, but then develop enlarged spleens, livers, and lymph nodes associated with high blood lymphocyte counts. The transformed lymphocytes from the TCL-1 mice are G0-1 arrested, clonal, and express CD19+/CD5+/IgM+, as seen in human CLL. One transgenic leukemic spleen is harvested from a previously implanted C57BL/6 mouse. Under aseptic conditions, the spleen is dissociated and red blood cells are removed. $2\times10^6$ TCL1 leukemic spleen lymphocytes are transplanted intravenously into 6-8 week old female C57BL/6 recipient mice. Starting two weeks post engraftment, mice are bled by submandibular bleed twice weekly to check peripheral blood for percent leukemia. Blood samples are evaluated by flow cytometry for coexpression of CD5 and CD19 and disease is reported as a percentage of double positive cells of the parent CD45+ population. Once the animal has reached 10-20% double positive staining in peripheral blood, it is assigned to a treatment group. Animals are weighed twice a week and palpated for splenomegaly. At the end of the study, animals are euthanized and tissues are harvested for measuring spleen weight and systemic organ disease. Organ disease is assessed in tissue sections stained with H&E. In exemplary studies, a compound provided herein is administered alone or in combination with a PI3Kδ inhibitor. In one exemplary study, a compound provided herein is a PI3Kγ inhibitor. In another exemplary study, the PI3Kδ inhibitor has a gamma/delta selectivity ratio of greater than about 50. In yet another exemplary study, the PI3Kγ inhibitor has a delta/gamma selectivity ratio of greater than about 50.

Example 250: Effect on the Collagen Induced Arthritis Model

Rat collagen arthritis is an experimental model of polyarthritis that has been widely used for preclinical testing of numerous anti-arthritic agents that are either under preclinical or clinical investigation or are currently used as therapeutics in this disease. The hallmarks of this model are reliable onset and progression of robust, easily measurable, polyarticular inflammation, marked cartilage destruction in association with pannus formation and mild to moderate bone resorption and periosteal bone proliferation.

Compound BB (PI3K gamma selective compound disclosed here) was administered to rats model of collagen induced arthritis (CIA). Compound BB is an exemplary PI3K gamma selective compound provided herein that has a delta/gamma selectivity ratio of greater than about 50. Compound BB was administered at 0.5 mg/kg, 1.5 mg/kg, and 5 mg/kg in groups as identified below:

TABLE 17

| Group | Treatment | N |
| --- | --- | --- |
| 1 | veh | 15 |
| 2 | Compound BB at 5 mg/kg | 11 |
| 3 | Compound BB at 1.5 mg/kg | 11 |
| 4 | Compound BB at 1 mg | 11 |
| 5 | naive | 5 |

Scoring of Joints: collagen arthritic ankles are given scores of 0-5 according to the following criteria:

For inflammation, 0=Normal; 0.5=Minimal focal inflammation; 1=Minimal infiltration of inflammatory cells in synovium/periarticular tissue; 2=Mild infiltration; 3=Moderate infiltration with moderate edema; 4=Marked infiltration with marked edema; and 5=Severe infiltration with severe edema.

For pannus, 0=Normal; 0.5=Minimal infiltration of pannus in cartilage and subchondral bone, affects only marginal zones and affects only a few joints; 1=Minimal infiltration of pannus in cartilage and subchondral bone, primarily affects marginal zones; 2=Mild infiltration (<¼ of tibia or tarsals at marginal zones); 3=Moderate infiltration (¼ to ⅓ of tibia or small tarsals affected at marginal zones); 4=Marked infiltration (½-¾ of tibia or tarsals affected at marginal zones); and 5=Severe infiltration (>¾ of tibia or tarsals affected at marginal zones, severe distortion of overall architecture).

For cartilage damage (emphasis on small tarsals), 0=Normal; 0.5=Minimal decrease in T blue staining, affects only marginal zones and affects only a few joints; 1=Minimal=minimal to mild loss of toluidine blue staining with no obvious chondrocyte loss or collagen disruption; 2=Mild=mild loss of toluidine blue staining with focal mild (superficial) chondrocyte loss and/or collagen disruption; 3=Moderate=moderate loss of toluidine blue staining with multifocal moderate (depth to middle zone) chondrocyte loss and/or collagen disruption, smaller tarsals affected to ½-¾ depth with rare areas of full thickness loss; 4=Marked=marked loss of toluidine blue staining with multifocal marked (depth to deep zone) chondrocyte loss and/or collagen disruption, 1 or 2 small tarsals surfaces have full thickness loss of cartilage; and 5=Severe=severe diffuse loss of toluidine blue staining with multifocal severe (depth to tide mark) chondrocyte loss and/or collagen disruption affecting more than 2 cartilage surfaces.

For bone resorption, 0=Normal; 0.5=Minimal resorption affects only marginal zones and affects only a few joints; 1=Minimal, small areas of resorption, not readily apparent on low magnification, rare osteoclasts; 2=Mild, more numerous areas of resorption, not readily apparent on low magnification, osteoclasts more numerous, <1/4 of tibia or tarsals at marginal zones resorbed; 3=Moderate, obvious resorption of medullary trabecular and cortical bone without full thickness defects in cortex, loss of some medullary trabeculae, lesion apparent on low magnification, osteoclasts more numerous, 1/4 to 1/3 of tibia or tarsals affected at marginal zones; 4=Marked, full thickness defects in cortical bone, often with distortion of profile of remaining cortical surface, marked loss of medullary bone, numerous osteoclasts, 1/2-3/4 of tibia or tarsals affected at marginal zones; 5=Severe, full thickness defects in cortical bone, often with distortion of profile of remaining cortical surface, marked loss of medullary bone, numerous osteoclasts, >3/4 of tibia or tarsals affected at marginal zones, severe distortion of overall architecture.

Periosteal New Bone Formation (measure on 16×): Studies that go beyond the acute inflammatory stage often show varying degrees of periosteal new bone formation. In order to convey the degree of periosteal new bone formation the following scores are applied based on the distribution of periosteal bone proliferation and a measurement of width of periosteal new bone formation at the widest location. 0=Normal, no periosteal proliferation; 0.5=Minimal focal or multifocal proliferation, measures less than 127 µm width (1-2) at any location; 1.0=Minimal multifocal proliferation, width at any location measures 127 µm-252 µm (3-4 units); 2.0=Mild multifocal on tarsals, diffuse in some locations, width at any location 253 µm-441 µm (5-7 units); 3.0=Moderate multifocal on tarsals, diffuse in most other locations, width at any location measures 442 µm-630 µm (8-10 units); 4.0=Marked multifocal on tarsals, diffuse at most other locations, width at any location measures 630 µm-819 µm (11-13 units); 5.0=Severe, multifocal on tarsals, diffuse at most other locations, width at any location measures >819 µm (>13 units).

Data was analyzed using a one-way ANOVA or Kruskal-Wallis (non-parametricANOVA) test, along with an appropriate multiple comparisons post-test. Unless indicated, Bolder BioPATH, Inc. performs statistical analysis on raw (untransformed) data only. Statistical tests make certain assumptions regarding the data's normality and homogeneity of variance, and further analysis may be required if testing resulted in violations of these assumptions. Significance for all tests was set at $p<0.05$.

Figure 2:
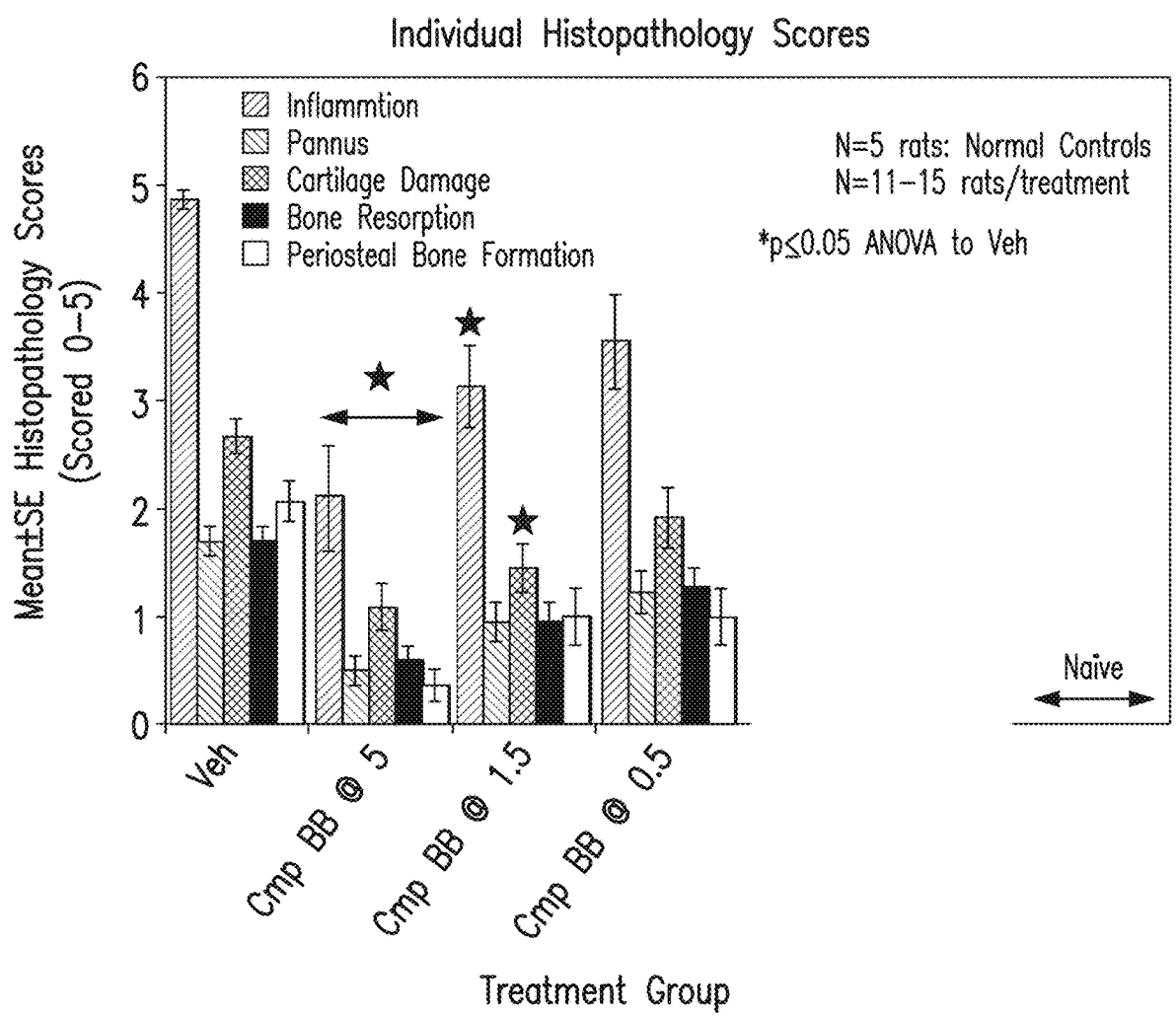
FIG. 2 shows the effect of Compound BB in the collagen induced arthritis rat model as measured by the individual histopathology scores for inflammation, pannus, cartilage damage, bone resorption, and periosteal bone formation.
Figure 3:
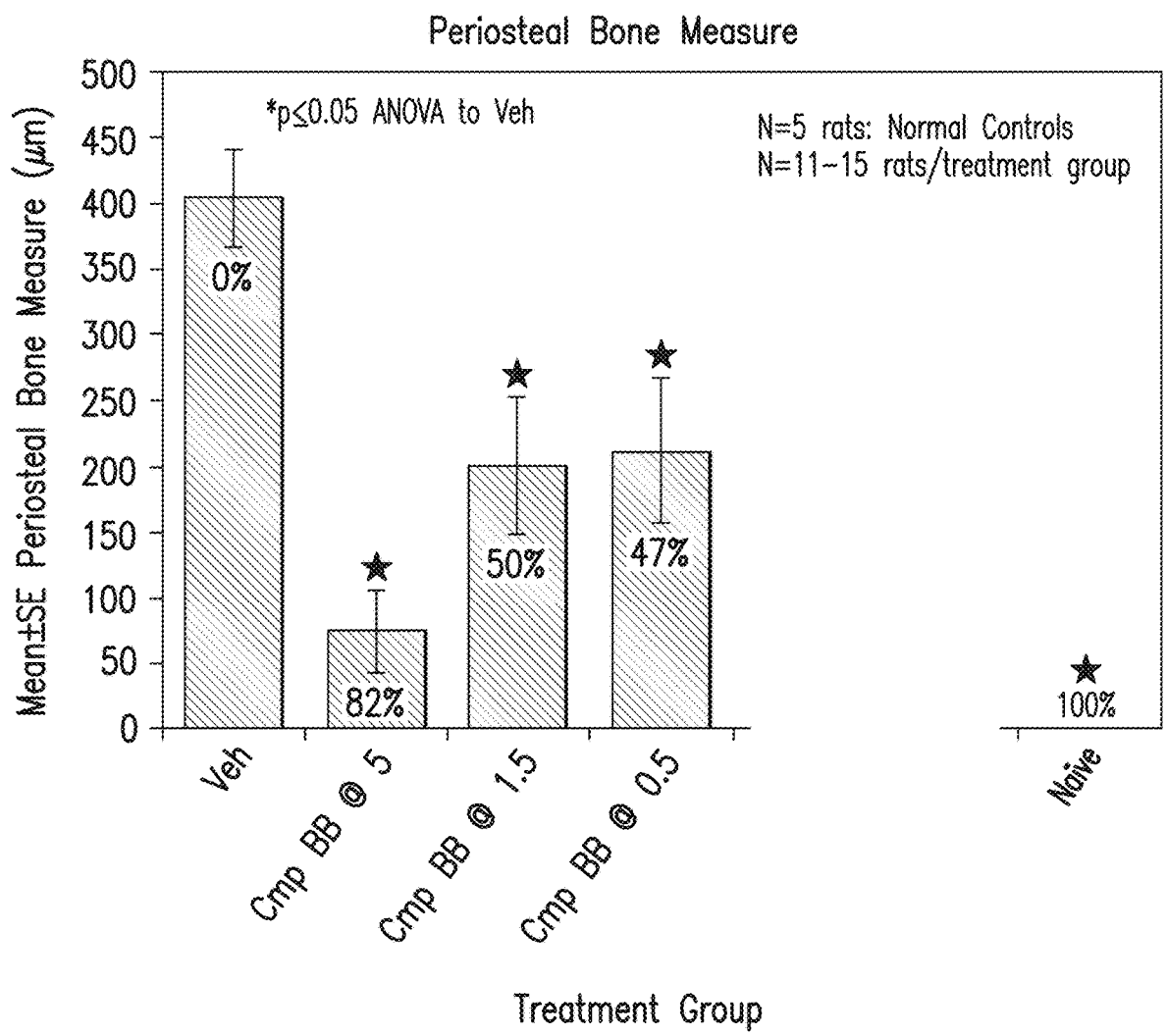
FIG. 3 shows the effect of Compound BB in the collagen induced arthritis rat model as measured by periosteal bone measure.

FIG. 1 shows that Compound BB has therapeutic effects in the CIA rat model where the mean ankle diameter in inches is measured from day 9 to day 17. FIG. 2 shows the individual histopathology scores for inflammation, pannus, cartilage damage, bone resorption, and periosteal bone formation. More particularly, in the experiment shown in FIG. 2, inflammation was reduced by 57%, 36%, and 27% when the animals were treated with Compound BB at 5, 1.5, and 0.5 mg/kg, respectively. Pannus was reduced by 71%, 44%, and 28% when the animals were treated with Compound BB at 5, 1.5, and 0.5 mg/kg, respectively. Cartilage damage was reduced by 59%, 45%, and 28% when the animals were treated with Compound BB at 5, 1.5, and 0.5 mg/kg, respectively. Bone resorption was reduced by 65%, 44%, and 25% when the animals were treated with Compound BB at 5, 1.5, and 0.5 mg/kg, respectively. Periosteal bone formation was reduced by 82%, 52%, and 52% when the animals were treated with Compound BB at 5, 1.5, and 0.5 mg/kg, respectively. FIG. 3 shows the periosteal bone measure. Animals treated with 5 mg/kg of Compound BB had significant 57-82% reductions in all scores resulting in a significant 64% reduction in summed scores. Periosteal bone widths were also significantly reduced by 82%. Animals treated with 1.5 mg/kg of Compound BB had significantly reduced inflammation and cartilage damage (45%) scores, contributing to a significant 42% reduction in summed scores. Although periosteal bone scores were not significantly reduced, periosteal bone widths were significantly reduced by 50%. Animals treated with 0.5 mg/kg of Compound BB had significantly reduced periosteal bone widths (47%). Scored parameters were non-significantly reduced by 27-52%, with a 31% non-significant reduction in summed scores. Results of this study indicate that treatment with Compound BB had beneficial effects on lesions of collagen-induced arthritis in rats that were generally significant at 1.5 mg/kg and above. The $ED_{50}$ value for this treatment was 2.132 mg/kg. All doses of Compound BB tested significantly reduced periosteal bone formation.

Example 251: Effect on the IL-8 Driven Murine Air Pouch Model

The purpose is to study the dose response evaluation of the effect of infiltrating neutrophils in mouse air pouches stimulated with recombinant hIL-8 after treatment with Compound BB or Compound AA. Compound AA is a PI3K delta selective compound that has a gamma/delta selectivity ratio of greater than about 50. Compound BB is a PI3K gamma selective compound described herein that has a delta/gamma selectivity ratio of greater than about 50. Balb/c male mice (Stock 000651) were ordered at 6 weeks of age from Jackson Labs/n=60.

Model/Procedure:

The air pouch model is used as a pseudo-synovial space to investigate the role of specific cytokines and/or effect of compounds on inflammatory mediated events. The pouches are stimulated with recombinant human IL-8, which is a proinflammatory CXC chemokine that can signal through the CXCR1 and CXCR2 receptors. IL-8 chemoattracts and activates neutrophils.

Pouches are developed by anesthetizing mice using isoflurane at a 34% flow. Air pouches are produced by administration of a subcutaneous injection of 5 mL of sterile air. This can be done by using a 5 mL syringe with a 22 microfilter attached and a 25G5/8" needle attached to the filter. 5 mLs of air will be drawn into the syringe, the filter with needle will be placed onto the syringe. The intrascapular area of the back may be swabbed with a 70% alcohol pad. Grabbing the skin between the intrascapular area, a tent will be created by which to insert the needle subcutaneously between the shoulders of the mouse. Air is injected slowly, using ones left hand to guide the air to form a long cylindrical pouch (approximately 10 sec), taking precaution not to have the air slip down the arms or over the head of the mouse. After all 5 mL has been administered, the needle is withdrawn and the injection site is pinched for approximately 5 sec. Mice are then returned to their cages and monitored for up to an hour during recovery. Mice are checked throughout the day on the day pouches are formed and checked daily for the next 3 days. On Day 3, mice will be re-injected with 3 ml of sterile air, following the procedure listed above, using a 3 ml syringe with 25G needle.

On Day 6, mice are weighed and assigned to a group and compound will be then be administered. One hour post dose, mice are bled via submandibular bleed. Approximately 150 uL of blood is collected into a microtainer with EDTA. Blood samples are placed on ice, centrifuged for 10 min 10,000 RMP at 4 degree. Plasma is placed in an eppendorf tube and stored in the −80 until analyzed by the PK group. Immediately following blood collection, mice are anesthetized and 1 mL of cold IL-8 stimulant or PBS is injected into the pouch using a 1 mL syringe with a 25G needle. The pouch is then massaged gently to ensure the entire lining of the pouch has been exposed to the solution.

Sample Collection:

Four hours post stimulation, mice are euthanized by $CO_2$. Mice are bled via cardiac puncture and blood is collected in the same manner stated above. Pouch exudates are then collected in the following manner-3 mls of cold endotoxin free PBS w/1 mM EDTA is injected into the pouch using a 3 ml syringe with 20G needle. Pouches are massaged to adequately suspend the cells in the pouch, making sure the needle is kept in the pouch to avoid leakage. 2 mL of lavage fluid is drawn out of the pouch and placed in a 5 mL BD Falcon round bottom tube and set on ice until analysis. Lavage fluid will be analyzed on the Cell Dyn and cell differential results will be plotted, with the focus being on total neutrophil counts from each lavage sample.

Example time line of experimental procedure is listed in the table below:

TABLE 18

| Day 0 | Day 1 | Day 2 | Day 3 | Day 4 | Day 5 | Day 6 |
|---|---|---|---|---|---|---|
| Animals weighed Animals receive 1st injection of air | Daily monitoring | Daily monitoring | Animals weighed Animals receive 2nd injection of air | Daily monitoring | Daily monitoring | Animals weighed Injection of test compounds 1 h post dose PK blood draws Administration of stimulant 4 hours post stimulation animals euthanized Collect terminal PK sample, wash and collect lavage fluid |

For the pouch injections, no stimulation models are injected 1 mL endotoxin free PBS; and stimulation models are injected 10 ug IL-8 in 1 mL of endotoxin free PBS. The reagents are Recombinant Human CXCL8/IL-8-R&D Systems, Cat #208-IL-050/CF Lot #BA3313051; Endotoxin free PBS-Teknova, Cat #P0300; and EDTA (0.5M)-Sigma, Cat #E-7889EDTA (0.5M)-Sigma, Cat #E-7889. Each vial contains 100 ug of IL-8-6 may be used for this experiment. Stock is reconstituted to 0.1 mg/mL by adding 1 mL of endotoxin free PBS, 10 ug/pouch (5.5 mL stock+50 mL PBS). EDTA is prepared using a stock solution concentration of 0.5M and adding 500 ul of stock solution to 250 mL PBS for final concentration of 1 mM EDTA.

Figure 4:
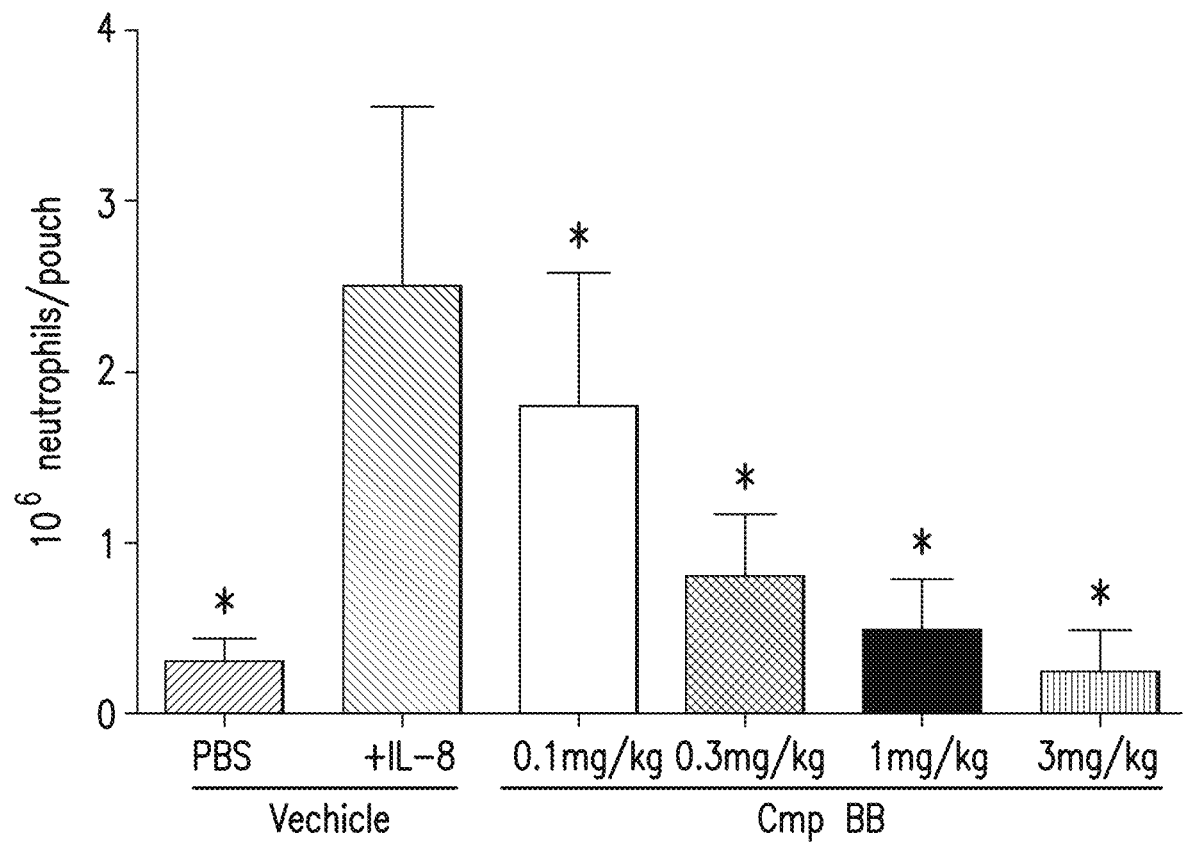
FIG. 4 shows the effect of Compound BB on IL-8 induced neutrophil migration in a mouse air pouch model.
Figure 5:
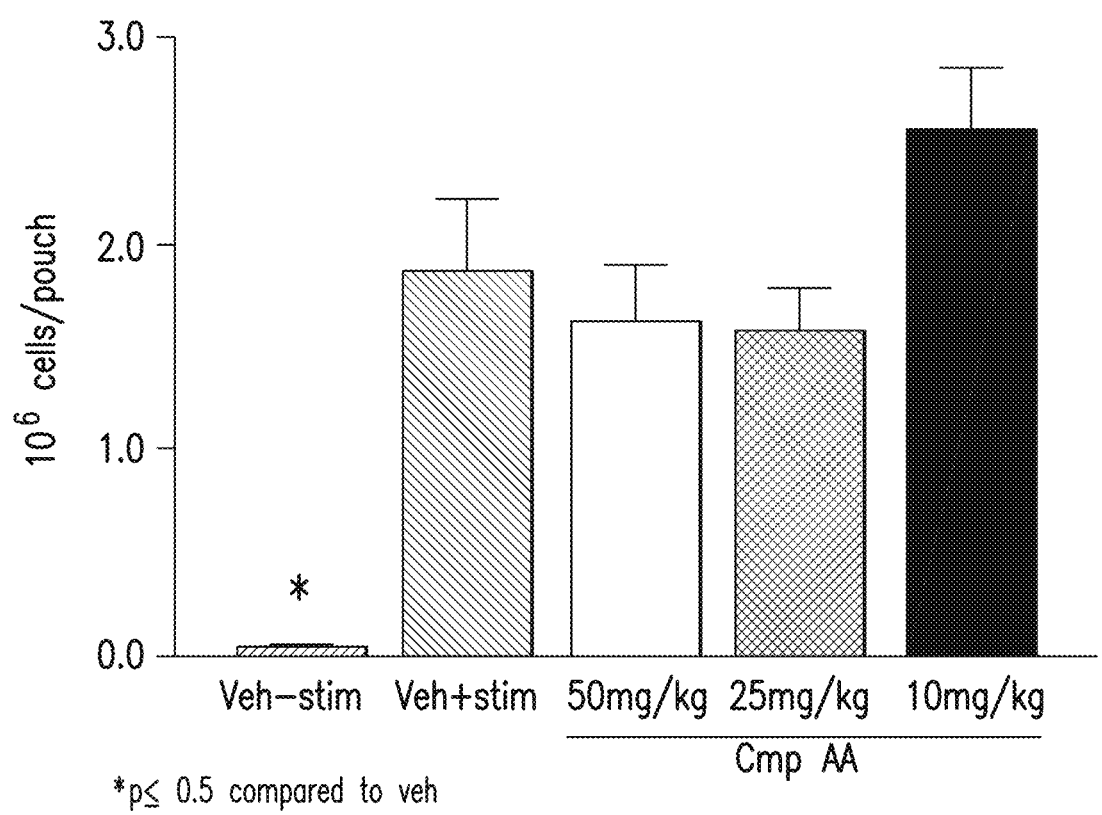
FIG. 5 shows the effect of Compound AA on IL-8 induced neutrophil migration in a mouse air pouch model.

Compound BB and Compound AA were tested in the murine air pouch model according to the procedures described above. Compound BB (PI3K gamma-selective compound) was administered to IL-8 induced neutrophil model at 0.1 mg/kg, 0.3 mg/kg, 1 mg/kg, and 3 mg/kg. Compound AA (PI3K delta-selective compound) was administered to the IL-8 induced neutrophil model at 10 mg/kg, 25 mg/kg, and about 50 mg/kg. The results were compared to the vehicle. FIG. 4 shows that Compound BB (PI3K gamma-selective compound) blocks IL-8 induced neutrophil migration, and FIG. 5 shows that Compound AA (PI3K delta-selective compound) does not inhibit IL-8 induced neutrophil migration. This example demonstrates that PI3K gamma selective compounds provided herein can be used to reduce and/or prevent inflammation.

Example 252: Gamma Selective Compounds Exhibit Synergy with Delta Selective Compounds The purpose of this study is to evaluate the anti-cancer effects of combinations of PI3K gamma selective compounds provided herein and PI3K delta selective compounds. PI3K gamma selective compounds provided herein are combined with a compound that selectively inhibits the PI3K delta isoform over the gamma isoform (e.g. delta selective compounds) to provide synergy. Specifically, compounds provided herein that have a delta/gamma selectivity ratio of greater than about 1 to <10, greater than about 10 to <50, or greater than about 50 to <350 are combined with a compound that has a gamma/delta selectivity ratio of greater than a factor of about 1, greater than a factor of about 2, greater than a factor of about 3, greater than a factor of about 5, greater than a factor of about 10, greater than a factor of about 50, greater than a factor of about 100, greater than a factor of about 200, greater than a factor of about 400, greater than a factor of about 600, greater than a factor of about 800, greater than a factor of about 1000, greater than a factor of about 1500, greater than a factor of about 2000, greater than a factor of about 5000, greater than a factor of about 10,000, or greater than a factor of about 20,000.

Procedures: Cells are thawed from a liquid nitrogen preserved state. Once cells have been expanded and divide at their expected doubling times, screening begins. Cells are seeded in growth media in either black 1536-well or 384-well tissue culture treated plates. Cells are then equilibrated in assay plates via centrifugation and placed in incubators attached to the Dosing Modules at 37° C. for 24 hours before treatment. At the time of treatment, a set of assay plates (which do not receive treatment) are collected and ATP levels are measured by adding ATPLite (Perkin Elmer). These Tzero ($T_0$) plates are read using ultra-sensitive luminescence on Envision plate readers (Perkin Elmer). Treated assay plates are incubated with compound for 72 hours. After 72 hours, plates are developed for endpoint analysis using ATPLite. All data points are collected via automated processes, quality controlled and analyzed using Zalicus software. Assay plates are accepted if they pass the following quality control standards: relative luciferase values are consistent throughout the entire experiment, Z-factor scores are greater than 0.6, untreated/vehicle controls behave consistently on the plate.

Growth Inhibition (GI) is used as a measure of cell viability. The cell viability of vehicle is measured at the time of dosing (T0) and after 72 hours (T72). A GI reading of 0% represents no growth inhibition—T72 compound-treated and T72 vehicle signals are matched. A GI reading of 100% represents complete growth inhibition—T72 compound-treated and T0 vehicle signals are matched. Cell numbers have not increased during the treatment period in wells with GI 100% and may suggest a cytostatic effect for compounds reaching a plateau at this effect level. A GI reading of 200% represents complete death of all cells in the culture well. Compounds reaching an activity plateau of GI 200% are considered cytotoxic. GI is calculated by applying the following test and equation:

$$\text{If } T < V_0: 100 * \left(1 - \frac{T - V_0}{V_0}\right)$$

$$\text{If } T \geq V_0: 100 * \left(1 - \frac{T - V_0}{V - V_0}\right)$$

where T is the signal measure for a test article, V is the vehicle-treated control measure, and Vo is the vehicle control measure at time zero. This formula is derived from the Growth Inhibition calculation used in the National Cancer Institute's NCI-60 high-throughput screen.

Inhibition (I) is defined as $$I = (1 - T/V) * 100\%$$

where T is treated cell count and V is untreated (vehicle) cell count (at 72 hours). I ranges from 0% (when T=V) to 100% (when T=0). The $IC_{50}$ value is defined as the drug concentration needed to inhibit 50% of the cell growth compared to growth of the vehicle treated cells (the drug concentration which gives I=50%). The measure of effect in the experiment can be the inhibition of cellular response relative to the untreated level (vehicle alone). For untreated vehicle and treated levels V and T, a fractional inhibition I=1-T/V is calculated. The inhibition ranges from 0% at the untreated level to 100% when T=0. Inhibition levels are negative for agents that actually increase levels. Other effect measures, such as an activity ratio r=T/V may be more appropriate for some assays. When activity ratios (e.g, fold increase over stimulated control) are being used, the effect can be measured using an induction I=ln(T/V). With this definition, all effect expressions are the same as for inhibition.

Combination analysis data are collected in a 6×6 dose matrix. Synergy is calculated by comparing a combination's response to those of its single compound, against the drug-with-itself dose-additive reference model. Deviations from dose additivity may be assessed visually on an isobologram or numerically with a Combination Index (CI). See Table 3 below for CI at 50% inhibition and CI at 50% growth inhibition. A combination provides additive effect when CI=1.0; synergistic effect when CI<1.0; and antagonistic effect when CI>1.0.

Potency shifting is evaluated using an isobologram, which demonstrates how much less drug is required in combination to achieve a desired effect level, when compared to the single agent doses needed to reach that effect. The isobologram is drawn by identifying the locus of concentrations that correspond to crossing the indicated inhibition level. This is done by finding the crossing point for each single agent concentration in a dose matrix across the concentrations of the other single agent. Practically, each vertical concentration $C_Y$ is held fixed while a bisection algorithm is used to identify the horizontal concentration $C_X$ in combination with that vertical dose that gives the chosen effect level in the response surface $Z(C_X, C_Y)$. These concentrations are then connected by linear interpolation to generate the isobologram display. For synergistic interactions, the isobologram contour fall below the additivity threshold and approaches the origin, and an antagonistic interaction would lie above the additivity threshold. The error bars represent the uncertainty arising from the individual data points used to generate the isobologram. The uncertainty for each crossing point is estimated from the response errors using bisection to find the concentrations where $Z - \sigma_Z(C_X, C_Y)$ and $Z + \sigma_Z(C_X, C_Y)$ cross $I_{cut}$, where $\sigma_Z$ is the standard deviation of the residual error on the effect scale.

To measure combination effects in excess of Loewe additivity, a scalar measure to characterize the strength of synergistic interaction termed the Synergy Score is devised. The Synergy Score is calculated as:

Synergy Score=$\log f_X \log f_Y \Sigma \max(0, I_{data})(I_{data} - I_{Loewe})$ The fractional inhibition for each component agent and combination point in the matrix is calculated relative to the median of all vehicle-treated control wells. The Synergy Score equation integrates the experimentally-observed activity volume at each point in the matrix in excess of a model surface numerically derived from the activity of the component agents using the Loewe model for additivity. Additional terms in the Synergy Score equation (above) are used to normalize for various dilution factors used for individual agents and to allow for comparison of synergy scores across an entire experiment. The inclusion of positive inhibition gating or an $I_{data}$ multiplier removes noise near the zero effect level, and biases results for synergistic interactions at that occur at high activity levels.

The Synergy Score measure is used for the self-cross analysis. Synergy Scores of self-crosses are expected to be additive by definition and, therefore, maintain a synergy score of zero. However, while some self-cross synergy scores are near zero, many are greater suggesting that experimental noise or non-optimal curve fitting of the single agent dose responses are contributing to the slight perturbations in the score. This strategy is cell line-centric, focusing on self-cross behavior in each cell line versus a global review of cell line panel activity. Additivity should maintain a synergy score of zero, and synergy score of 2 or 3 standard deviations indicate that the combination is synergistic at statistically significant levels of 95% and 99%, respectively.

Loewe Volume (Loewe Vol) is used to assess the overall magnitude of the combination interaction in excess of the Loewe additivity model. Loewe Volume is particularly useful when distinguishing synergistic increases in a phenotypic activity (positive Loewe Volume) versus synergistic antagonisms (negative Loewe Volume). When antagonisms are observed, the Loewe Volume should be assessed to examine if there is any correlation between antagonism and a particular drug target-activity or cellular genotype. This model defines additivity as a non-synergistic combination interaction where the combination dose matrix surface should be indistinguishable from either drug crossed with itself. The calculation for Loewe additivity is:

$I_{Loewe}$ that satisfies $(X/X_1) + (Y/Y_1) = 1$ where XI and YI are the single agent effective concentrations for the observed combination effect I. For example, if 50% inhibition is achieved separately by 1 µM of drug A or 1 µM of drug B, a combination of 0.5 µM of A and 0.5 µM of B should also inhibit by 50%.

Figure 6:
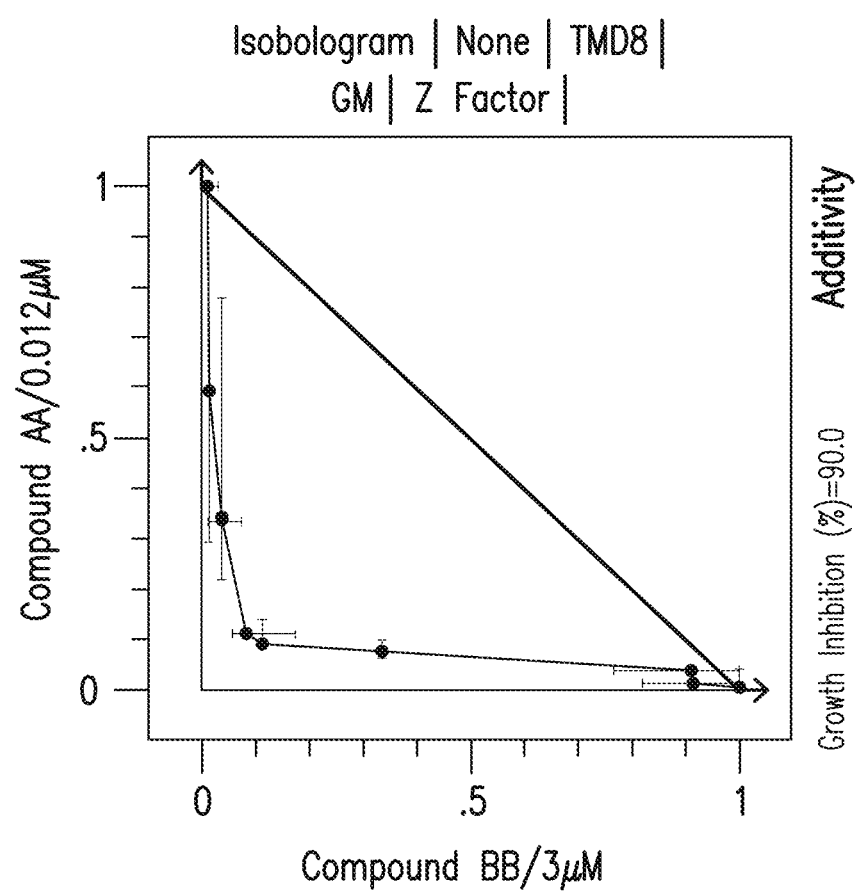
FIG. 6 shows an isobologram depicting the synergistic effect of the combination of a PI3K delta-selective compound, Compound AA, and a PI3K gamma selective compound, Compound BB, in TMD8 cell line.
Figure 7:
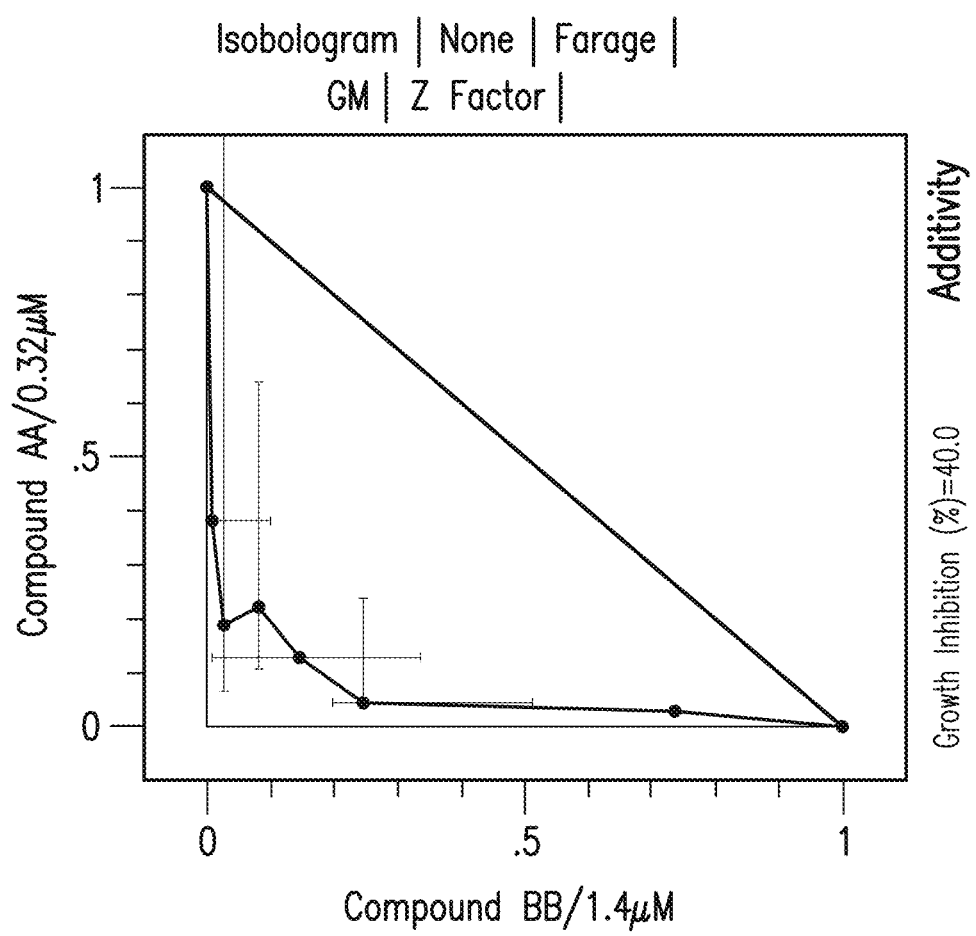
FIG. 7 shows an isobologram depicting the synergistic effect of the combination of a PI3K delta-selective compound, Compound AA and a PI3K gamma selective compound, Compound BB, in Farage cell line.

Exemplary combinations of PI3K gamma-selective and delta-selective compounds were tested according to the procedures described above. In one exemplary study, the combination effects of Compound AA with Compound BB at various concentrations were studied in various cell lines and the results are listed in Table 19 below. Compound AA is a PI3Kδ inhibitor (e.g., delta-selective compound) that has a gamma/delta selectivity ratio of greater than about 50. Compound BB is a PI3Kγ inhibitor (e.g., gamma-selective compound) described herein that has a delta/gamma selectivity ratio of greater than about 50. The gamma/delta selectivity ratio is determined by dividing the inhibitor's $IC_{50}$ against PI3K gamma isoform by the inhibitor's IC50 against PI3K delta isoform. The delta/gamma selectivity ratio is determined by dividing the inhibitor's $IC_{50}$ against PI3K delta isoform by the inhibitor's IC50 against PI3K gamma isoform. For illustrative purposes, the isobolograms of FIG. 6 (at 90% growth inhibition) and FIG. 7 (at 40% growth inhibition) show that a combination of Compound AA and Compound BB provides synergy in diffuse large B-cell lymphoma (DLBCL) in TMD8 and Farage cell lines. Isobolograms of a combination of Compound AA and Compound BB also demonstrate synergistic effects in a B-cell lymphoma cell line (Karpas-422 cell line), and in a T-cell lymphoma, non-Hodgkin's lymphoma, Hodgkin lymphoma, and anaplastic large cell lymphoma cell line (HH cell line) (isobolograms not shown).

The $CI_{50}$ values for growth inhibition and inhibition in Table 19 are categorized as follows: S=0.1 to <0.5, T=0.5 to <0.7, U=0.7 to <1, W=>1. The synergy score values for growth inhibition and inhibition are categorized as follows: A 1=0.01 to <1, A2=1 to <3, and A3=>3. The types of cell lines tested are diffuse large B-cell lymphoma (DBCL) activated B-cell-like (ABC), DBCL germinal center B-cell-like (GCB), follicular lymphoma, mantle cell lymphoma, multiple myeloma, and T-cell lymphoma. Data show that a combination of a gamma-selective and a delta-selective compound provides a synergistic effect in various types of cancer cell lines.

TABLE 19

| Cell Line | type of cell line | $CI_{50}$ growth inhibition | Synergy Score growth inhibition | $CI_{50}$ inhibition | Synergy Score inhibition |
|---|---|---|---|---|---|
| HBL-1 | DLBCL ABC | T | A2 | W | A1 |
| OCT-Ly3 | DLBCL ABC | U | A2 | | A1 |
| U-2932 | DLBCL ABC | T | A2 | W | A1 |
| TMD8 | DLBCL ABC | W | A3 | U | A3 |
| OCI-Ly7 | DLBCL GCB | W | A1 | | A1 |
| SU-DHL-10-epst | DLBCL GCB | U | A3 | U | A2 |
| SU-DHL-4-epst | DLBCL GCB | T | A3 | T | A2 |
| DOHH-2 | DLBCL GCB | S | A3 | S | A2 |
| Farage | DLBCL GCB | S | A3 | S | A3 |
| RL | Follicular lymphoma | W | A1 | | A1 |
| KARPAS-422 | Follicular lymphoma | T | A2 | T | A1 |
| WSU-NHL | Follicular lymphoma | U | A3 | U | A2 |
| GRANTA-519 | Mantle cell lymphoma | T | A1 | W | A1 |
| Jeko-1 | Mantle cell lymphoma | U | A1 | T | A1 |
| Mino | Mantle cell lymphoma | T | A2 | T | A2 |
| RPMI-8226 | Multiple myeloma | W | A1 | W | A1 |
| OPM-2 | Multiple myeloma | W | A1 | | A1 |
| NCI-H929 | Multiple myeloma | S | A3 | T | A2 |
| HH | T-cell lymphoma | S | A2 | S | A1 |
| KARPAS-299 | T-cell lymphoma | | A1 | | A1 |

Example 253: PI3K Gamma Selective Compounds Inhibit CXCL12-Induced T-Cell Migration in Malignant B-Cell In Vitro Model The PI3K gamma selective compounds provided herein can inhibit CXCL12-induced T-cell migration. Specifically, the material used were media (RPMI+0.5% Fetal Bovine Serum+Pen/Strep), total CLL PBMCs (AllCells), CoStar 24-transwell plates (5 uM insert) #3421, BD Cytofix Fixation Buffer (#554655), BD FBS Stain Buffer (BD Biosciences, 554656), Deep 96-well plate (Axygen, P-2ML-SQ-C), rhCXCL12 (R&D, 350-NS-050), CD-19 APC Cy7 (BD #348794 1:20), CD3-PerCPCy5.5 (BD #560835, 1:20), CD5-PE (Biolegend #300608, 1:5), CD4-FITC (BD #561842, 1:20), and CD8-APC (BD #561953, 1:20).

Total CLL human PBMCs were preincubated with Compound AA or BB in media for 45 minutes at 37° C. 600 uL of either basal or media containing 300 ng/mL CXCL12+/− DMSO or Compound AA or Compound BB was placed in the lower chamber of transwell insert. After the 45 minutes of compound preincubation, 500-750K CLL PBMCs were placed in the upper chamber of the transwell insert in a total volume of 100 uL. The cells were allowed to migrate for 2-4 hours at 37° C. The inserts were removed, and 550 uL media from lower chamber were transferred into a deep 96-well plate. The cells were spun at 1280 rpm for 5 minutes and flick media. The cells were resuspended in 400 uL BD Cytofixation buffer and incubated at RT for 10 minutes. 1 mL BD FBS stain buffer was added. The cells were spun at 1280 rpm and fixation buffer was disposed. The cells were resuspended in 100 uL of CD3,4,8,5,19 antibody cocktail made up in BD FBS stain buffer, which was then incubated at room temperature in the dark for 30-60 minutes. 1 mL BD FBS stain buffer was added to each well, which was then spun and flicked. The cells were resuspended in 150 uL FBS stain buffer and transferred to FACS tubes already containing 150 uL FBS stain buffer. Each sample was read on the FACS for 25 seconds. Gate on CD3, 4, 8 and CD19/5 subpopulations individually and calculate average migration index from triplicate samples. See e.g., Borge et al., haematologica 2010, 95(5): 768-775; de Rooij et al., Blood 2012, 119: 2590-2594.

Figure 8:
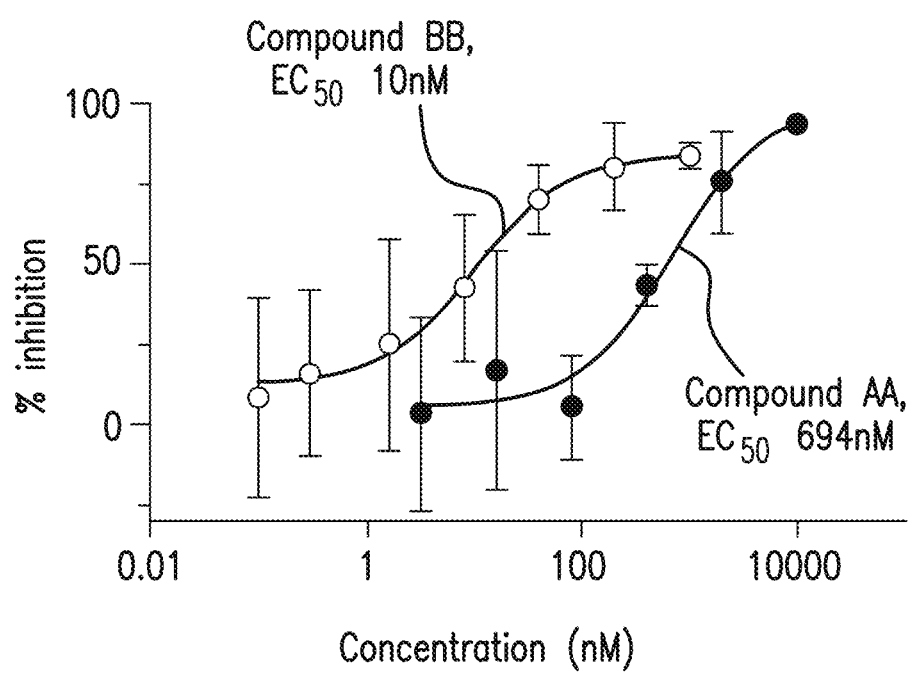
FIG. 8 shows the effects of a PI3K delta selective compound, Compound AA, and a PI3K selective compound, Compound BB, on migration of chronic lymphocytic leukemia (CLL) associated peripheral T-cells.

Compound AA is a PI3K delta selective compound described herein that has a gamma/delta selectivity ratio of greater than about 50. Compound BB is a PI3K gamma selective compound described herein that has a delta/gamma selectivity ratio of greater than about 50. FIG. 8 shows the percent cell inhibition of CXCL12-induced CD3+ T cell migration at various concentrations of Compound AA ($EC_{50}$=694 nM) and Compound BB ($EC_{50}$=10 nM). In a similar experiment, the $EC_{50}$ was determined for three subsets of T-cells for a PI3K-δ inhibitor (Compound AA) and a PI3K-γ inhibitor (Compound BB). The results are shown in the following Table. Compound BB is a potent inhibitor of CXCL12 induced T-cell migration.

TABLE 20

| T-cell subset | AVG Cmpd AA $EC_{50}$ (nM) | Cmpd BB $EC_{50}$ (nM) |
|---|---|---|
| CD3+ | 630 ± 71 | 17 ± 17 |
| CD4+ | 726 ± 230 | 20 ± 21 |
| CD8+ | 423 ± 290 | 13 ± 15 |

The data demonstrate that Compound BB (a gamma selective compound) is more potent than Compound AA (a delta selective compound) at inhibiting CXCL12-induced CD3+ T cell migration in CLL PBMCs. Gamma selective compounds can be used to block the migration of growth promoting T-cells into the B-cell tumor niche slowing down the progression of the disease. This could translate to increased progression free survival or deeper responses in the clinic with respect to B cell malignancies.

Figure 9:
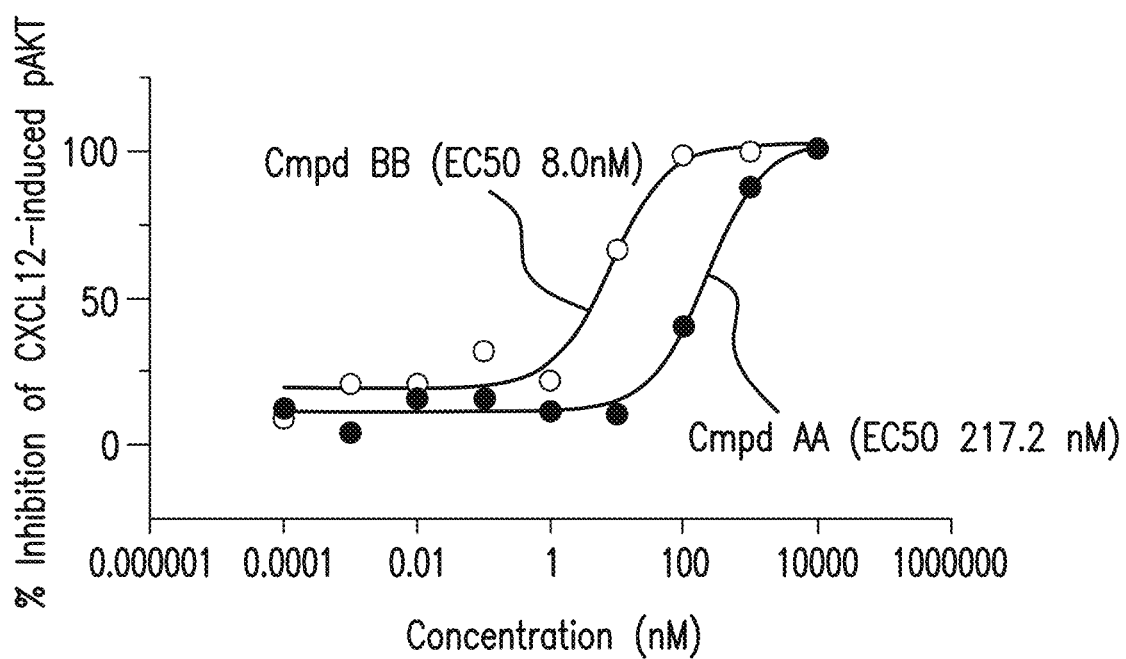
FIG. 9 shows that CXCL12 induced pAKT in T-cells is PI3K-γ dependent.

The mechanism of Compound BB's inhibition of migration was studied. It was found that Compound BB inhibited CXCL12-induced pAKT in T-cells more strongly than a PI3K-δ inhibitor (Compound AA) (FIG. 9). There was a tight correlation between the $EC_{50}$s observed in the CXCL12-induced pAKT assay and the T-cell migration assay. This result suggests that a PI3K-γ inhibitor interferes with T cell migration in CLL patient PBMCs by blocking pAKT signaling. While PI3K inhibition does not abrogate IL4-induced CLL survival (data not shown), PI3K-γ-dependent inhibition of T-cell migration to CLL lymph node microenvironments may indirectly prevent T-cell derived cytokines (e.g., IL-4) from providing PI3K independent CLL survival signals.

Without being bound by a particular theory, the data suggest the following model in B cell malignancies. Malignant B-cells receive growth and pro-survival signals from BCR activation and mesenchymal cells, transmitted via the PI3K-δ, and -γ pathways. Malignant B-cell growth and survival is also supported by T-cells and myeloid cells via PI3K-dependent and -independent mechanisms. Inhibition of PI3K-δ reduces the proliferation of malignant B-cells; however, other PI3K-independent signals may potentiate tumor cell survival. Inhibition of PI3K-γ, e.g., by Compound BB, may block migration and/or differentiation of accessory T-cells and myeloid cells and abolish these key support cells within the tumor microenvironment. The lack of key support cells within the tumor microenvironment as a result of PI3K-γ inhibition may thus more completely block malignant B-cell growth and survival. Without being bound by a particular theory, Compound BB may act to inhibit tumor growth and/or survival at any of the above-mentioned steps.

Example 254: Inflammatory Bowel Disease (IBD) Model

A study can be conducted to evaluate the potential efficacy of a compound provided herein in female SCID mice with CD4+ inflammatory bowel disease. In this murine model, female C.B-17 SCID mice are injected intraperitoneally (IP) with CD45RB$^{high}$ cells, a subset of CD4+ T cells obtained from normal BALB/c mice, to induce spontaneous chronic inflammation in the large intestine. Gross and histopathologic changes resulting from this treatment resemble those occurring in Crohn's disease and ulcerative colitis in humans. See Leach et al., Inflammatory Bowel Disease in C.B-17 scid Mice Reconstituted with the CD45RB$^{high}$ Subset of CD4+ T Cells, *American Journal of Pathology*, 1996, 148 (5), 1503-1515.

On study day 0, Balb/C mice are terminated, and spleens are obtained for CD45RB$^{high}$ cell isolation per the SCID IBD cell separation protocol. SCID mice are weighed and received intraperitoneal (IP) injections of the sorted cells (approx. 4×10$^6$ cells/ml, 100 l/mouse injections). On study day 21, mice are weighed and randomized by body weight loss into treatment groups, and daily (QD), oral (PO) dosing is initiated. Dosing continued through study day 41, and mice are terminated on day 42. The mice can be divided into various groups. Group 1 can be the normal control; group 2 can be the vehicle control (0.5% CMC, 0.05% Tween80 in $H_2O$); and various amounts of a compound provided herein can be administered to different groups as comparison.

For each animal, the entire colon (proximal and distal) is trimmed into 8 equally spaced pieces for processing and embedding. Sections are stained with hemotoxylin and eosin (H&E). For each H&E stained section, submucosal edema is quantitated by measuring the distance from the muscularis mucosa to the internal border of the outer muscle layer in a non tangential area thought to most represent the severity of this change. Mucosal thickness is also measured in a non-tangential area of the section that best represented the overall mucosal thickness. This parameter is indicative of gland elongation and mucosal hyperplasia. In order to incorporate this parameter into the summed score, a hyperplasia score is derived from the measurement as follows: 0=<250 μm; 1=250-349 μm; 2=350-449 μm; 3=450-599 μm; 4=600-699 μm; and 5=>700 μm.

The extent of inflammation (foamy macrophage, lymphocyte and PMN infiltrate) is assigned severity scores according to the following criteria:
Normal=0
Minimal=1 (generally focal affecting 1-10% of mucosa or if diffuse then minimal)
Mild=2 (generally focal affecting 11-25% of mucosa or if diffuse then mild)
Moderate=3 (26-50% of mucosa affected with areas of gland loss replaced by inflammatory cell infiltrate, milder in remaining areas of mucosa)
Marked=4 (51-75% of mucosa affected with areas of gland loss replaced by inflammatory cell infiltrate, milder in remaining areas of mucosa)
Severe=5 (76-100% of mucosa affected with areas of gland loss replaced by inflammatory cell infiltrate, milder in remaining areas of mucosa)

The parameters reflecting epithelial cell loss/damage are scored individually using a percent area involved scoring method: None=0; 1-10% of the mucosa affected=1; 11-25% of the mucosa affected=2; 26-50% of the mucosa affected=3; 51-75% of the mucosa affected=4; and 76-100% of the mucosa affected=5.

Parameters that are scored using percent involvement included: (1) Colon glandular epithelial loss—this includes crypt epithelial as well as remaining gland epithelial loss; and (2) Colon Erosion—this reflects loss of surface epithelium and generally is associated with mucosal hemorrhage (reflective of the bleeding seen clinically and at necropsy).

The 4 important scored parameters (inflammation, glandular epithelial loss, erosion, hyperplasia) are ultimately summed to arrive at a sum of histopathology scores, which indicates the overall damage and would have a maximum score of 20.

Inflammatory cell infiltrates in the colonic mucosa are evaluated for approximate % of neutrophils in the total infiltrate using the criteria below. The approximate % of total is then multiplied by the 0-5 inflammation score in an attempt to semiquantify relative PMN infiltration across sections and animals: 0=approx 0%; 10=approx 10%; 25=approx 25%; 50=approx 50%; and 75=75% or greater. This value is then multiplied by the inflammation score in an attempt to semiquantify relative PMN infiltration across sections and animals.

Example 255: Autoimmune Encephalomyelitis (EAE) Model

Effects of a compound provided herein on treating inflammation can be tested in a 28 day semi-therapeutic mouse EAE model. EAE can be induced in 60 mice using Hooke Kit™ $MOG_{35-55}$/CFA Emulsion PTX (Hooke Laboratories, Lawrence Mass.), catalog number EK-0110, lot number 0104, per manufacturer's recommended protocol.

Mice are injected subcutaneously, at two sites in the back, with the emulsion component of the kit (containing $MOG_{35-55}$). One site of injection is in the area of the upper back, approximately 1 cm caudal of the neck line. The second site is in the area of the lower back, approximately 2 cm cranial of the base of the tail. Injection volume is 0.1 mL at each site. Within 2 hours of the injection of emulsion, and then again 24 hours after the injection of emulsion, the pertussis toxin component of the kit is administered intraperitoneally. Volume of each injection is 0.1 mL.

EAE is induced in certain mices, which can be divided into various groups e.g., a group of negative control and groups treated with various amounts of a compound provided herein.

Readouts are EAE scores and changes in body weight. Mice are scored daily. EAE is scored on scale 0 to 5:
0—No obvious changes in motor functions of the mouse in comparison to non-immunized mice. When picked up by the tail, the tail has tension and is erect. Hind legs are usually spread apart. When the mouse is walking, there is no gait or head tilting.
1—Limp tail. When the mouse is picked up by the tail, instead of being erect, the whole tail drapes over finger.
2—Limp tail and weakness of hind legs. When mouse is picked up by tail, legs are not spread apart, but held closer together. When the mouse is observed walking, it has a clearly apparent wobbly walk.
3—Limp tail and complete paralysis of hind legs (most common); or limp tail with paralysis of one front and one hind leg; or all of: severe head tilting, walking only along the edges of the cage, pushing against the cage wall, and spinning when picked up by the tail.
4—Limp tail, complete hind leg and partial front leg paralysis. Mouse is minimally moving around the cage but appears alert and feeding. Usually, euthanasia is recommended after the mouse scores level 4 for 2 days. When the mouse is euthanized because of severe paralysis, score of 5 is entered for that mouse for the rest of the experiment.
5—Complete hind and complete front leg paralysis, no movement around the cage; or mouse is spontaneously rolling in the cage; or mouse is found dead due to paralysis.

At the end of the study, the following tissues can be collected and analyzed, e.g., collection of plasma for PK, collection of serum, collection of spines for histological analysis, histological analysis of spines, count of inflammatory foci, estimation of demyelination area, or count of apoptotic cells.

Example 256: Pharmacokinetics and Reduction of LPS-Induced Neutrophilia-Oral Administration To evaluate the effect of Compound BB (PI3Kγ inhibitor (e.g., gamma-selective compound provided herein)) and Compound AA (PI3Kδ inhibitor (e.g., delta-selective compound)) on the LPS induced inflammatory parameters, Compound BB and Compound AA were administered orally. Compound AA has a gamma/delta selectivity ratio of greater than about 50. Compound BB has a delta/gamma selectivity ratio of greater than about 50.

This study also includes assessment of the exposure to the compounds in plasma and lung tissues. The groups and details of the administration are provided in the table below.

TABLE 21

| Groups | LPS delivered intra-tracheally (i.t.) (mg/kg) | Number of rats |
|---|---|---|
| 1. vehicle/saline | i.t. volume 0.25 mL/rat | 6 |
| 2. vehicle/LPS | i.t. 1 ug LPS/rat | 10 |
| 3. Compound AA (p.o.) | 0.2 mg/kg | 7 |
| 4. Compound AA (p.o.) | 1 mg/kg | 7 |
| 5. Compound AA (p.o.) | 5 mg/kg | 7 |
| 6. Compound BB (p.o.) | 0.5 mg/kg | 7 |
| 7. Compound BB (p.o.) | 1.5 mg/kg | 7 |
| 8. Compound BB (p.o.) | 5 mg/kg | 7 |
| 9. Ref A (p.o.) | 3 mg/kg | 7 |

Reference A = budesonide.
p.o. vehicle for Compound AA and Compound BB is 5% NMP and 95% PEG 400. Ref C is budesonide p.o. The compound was administered p.o. and about 1 hour later, LPS was administered intra-tracheally and plasma was collected. After about 5 hours, plasma and bronchoalveolar lavage samples were collected.

The oral PK summary of Compound AA and Compound BB in the rat LPS studies is provided in the table below.

TABLE 22

| | | Free Plasma Conc (nM) | | Cellular $IC_{50}$ (nM) | | | |
|---|---|---|---|---|---|---|---|
| | Dose (mg/kg) | 1.5 h* | 5.5 h** | δ | γ | β | α |
| Compound BB | 0.5 | 2.1 | 2.6 | 197 | 1 | 189 | 873 |
| | 1.5 | 5.2 | 5.4 | | | | |
| | 5 | 22.6 | 24.7 | | | | |
| Compound AA | 0.2 | BLQ | BLQ | 0.1 | 418 | 102 | 1900 |
| | 1 | 1.8 | 1.1 | | | | |
| | 5 | 17.8 | 4.6 | | | | |

*= free plasma concentration at time of LPS challenge.
**= free plasma concentration approximately 4 hours post LPS challenge.

Figure 10:
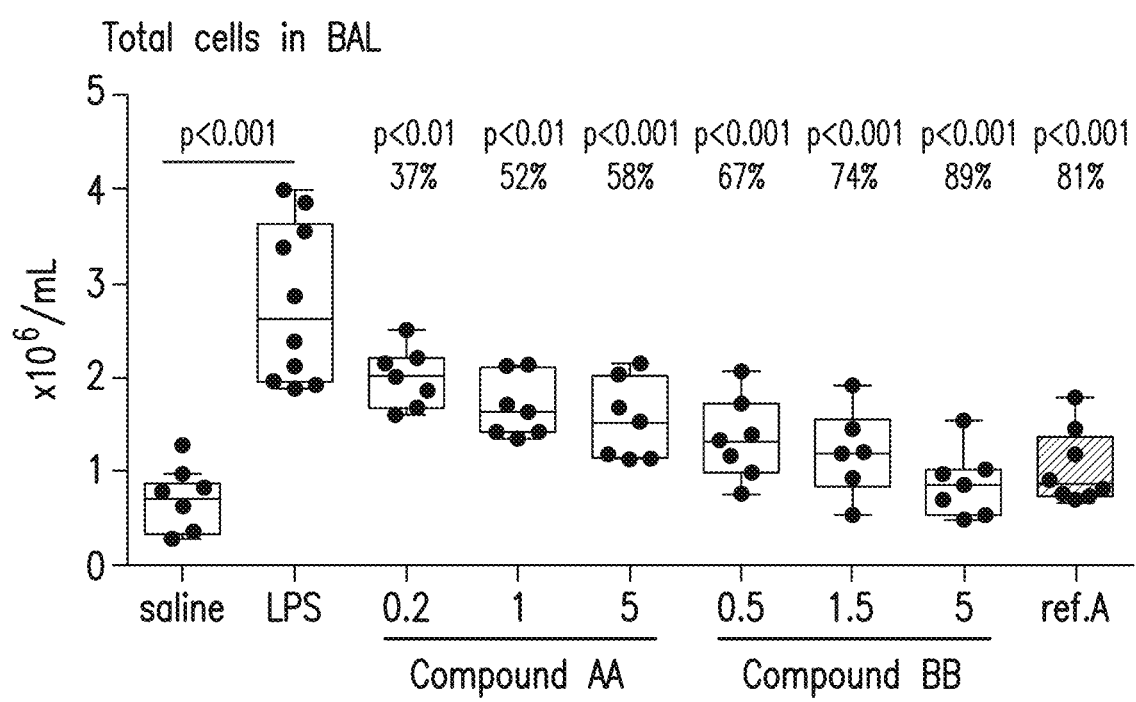
FIG. 10 is a graph showing the total cell counts per milliliter in a bronchoalveolar lavage (BAL) sample when the lipopolysaccharide (LPS) induced inflammatory rat model is exposed to Compound AA or Compound BB.
Figure 11:
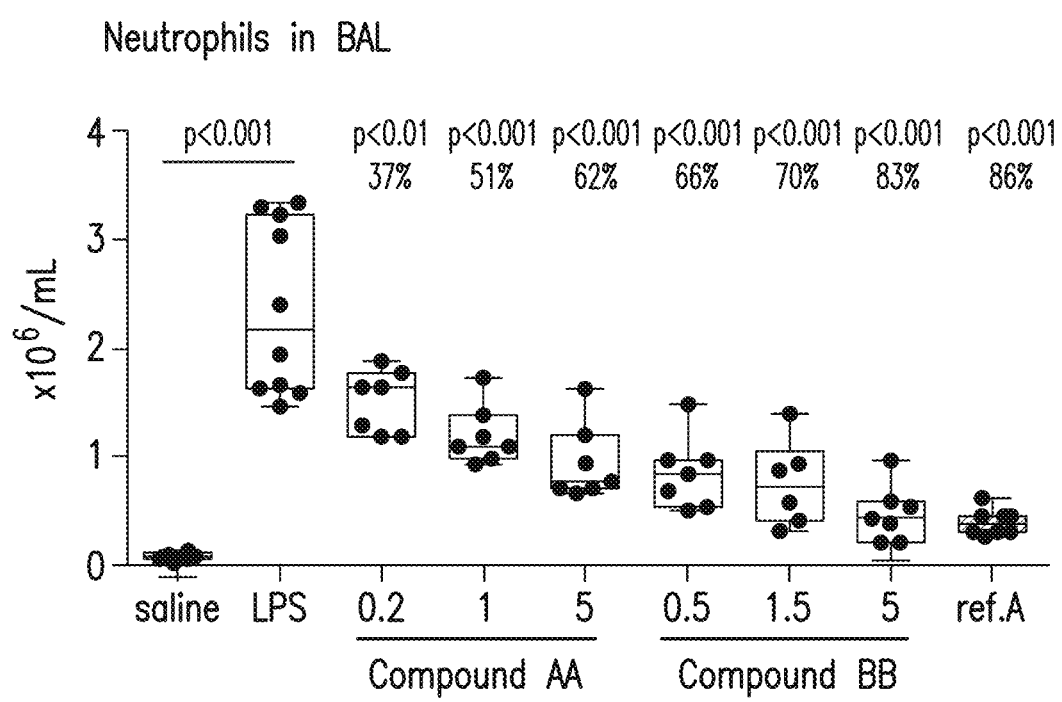
FIG. 11 is a graph showing the neutrophil counts per milliliter in a bronchoalveolar lavage (BAL) sample when the lipopolysaccharide (LPS) induced inflammatory rat model is exposed to Compound AA or Compound BB.
Figure 12:
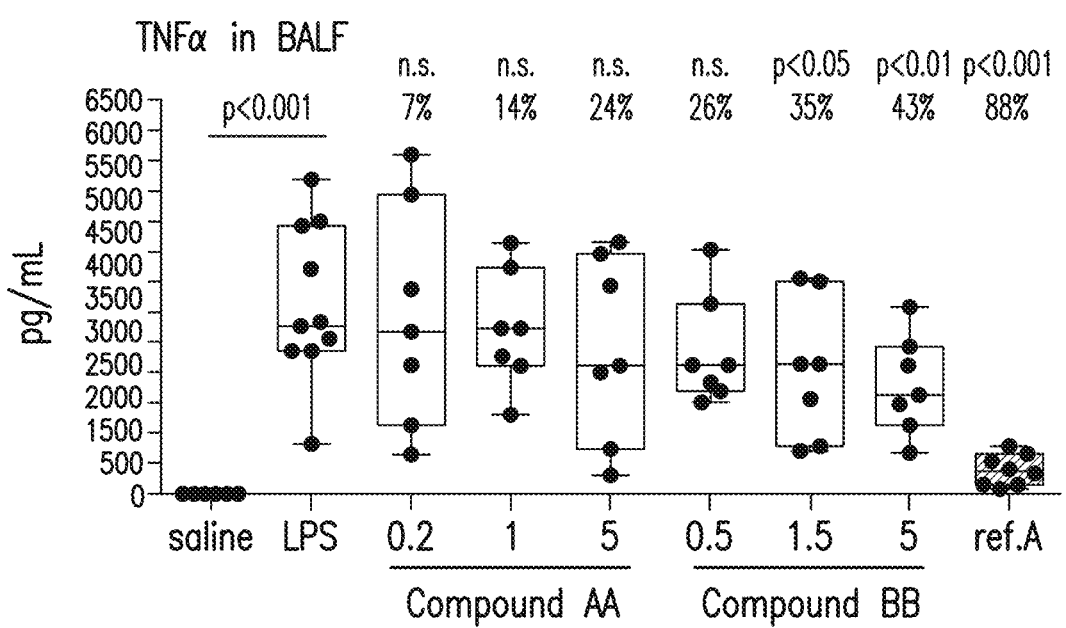
FIG. 12 is a graph showing TNFα pictogram per milliliter in a bronchoalveolar lavage (BAL) sample when the lipopolysaccharide (LPS) induced inflammatory rat model is exposed to Compound AA or Compound BB.

Compound BB and Compound AA (p.o.) reduced neutrophil in bronchoalveolar lavage fluid (BALF) 4 hours post-LPS challenge in a dose dependent manner. Compound BB had a more profound effect on neutrophil influx compared Compound AA (FIG. 10, FIG. 11 and FIG. 12 (mean with SEM, p-value is from t-test; groups are individually compared to the LPS-group)). These data show that PI3K-γ is involved in infiltration of neutrophils into the lung, a key pathologic cell type in chronic obstructive pulmonary disease (COPD).

PK results showed free plasma levels of both Compound BB and Compound AA at the highest dose levels were equal or greater than the $IC_{90}$ for gamma and delta, respectively, and yet well below the $IC_{50}$ for the next closest PI3K isoforms for each compound.

In another exemplary study, it was found out that the increase in CXCL12-induced p-AKT in CD3+ T cells was mediated by PI3K-γ. In yet another exemplary study, it was found out that, within the malignant B-cell population, the increase in CXCL12-induced p-AKT was PI3K-δ dependent, suggesting that CXCL12 signals through different PI3K isoforms in these varying cell types.

Example 257: Effects on CXCL12 Induced p-AKT Induction in Differentiated Macrophages Myeloid-derived cells and mesenchymal stromal cells can support CLL cell survival as components of the tumor microenvironment (TME). Recent reports suggest that CLL cytoprotective nurse-like cells may have an M2 polarization and be similar to the immunosuppressive tumor associated myeloid cells found in solid tumors. Giannoni et al., Haematologica 2014, 99(6), 1078-88. A purpose of this study is to model these TME components and to evaluate the effects of PI3K isoform selective inhibitors on CXCL12 induced p-AKT induction in differentiated macrophages. Compound AA is a PI3K delta selective compound that has a gamma/delta selectivity ratio of greater than about 50. Compound BB is a PI3K gamma selective compound described herein that has a delta/gamma selectivity ratio of greater than about 50.

Macrophage Differentiation and Polarization:

Long bones from young C57B6 mice were harvested and bone marrow was extruded by gentle lavage of the bone marrow cavities with a 28 guage needle. Red blood cells were removed using red blood cell lysis buffer (Sigma). Bone marrow cells were differentiated to macrophages using MCSF for 6 days (RPMI and 20% FCS) with one media change (with removal of all non-adherent cells) at day 3. Macrophages were polarized into M0 (MCSF), M1 (MCSF, IFNγ, and LPS for 1 day), or M2 (MCSF, IL4 for 2 days).

CXCL12-induced p-AKT induction assay: Polarized macrophages were lifted with Acutase, and plated at 0.5M cells per well (0.5 ml) in a deep well (2 ml) non adherent plate in polarization media for 1 hour. DMSO or tested compound in DMSO (0.1% final DMSO concentration, Compound AA or Compound BB) was added for 40 minutes. CXCL12 was added, and the cells were mixed on a plate shaker for 2 minutes. 1 ml of 37 degree FACS Lyse/fix buffer (BD bioscience) was added and the plate was mixed for 1 minute. The plates were spun and decanted and frozen at −80° C. Phospho AKT staining with anti Phospho AKT 473 PERCP labeled (Cell Signaling Technologies) was performed and measured by flow cytometry. Total cell MFI was used to calculate the effect of tested compound on CXCL12 induction of phospho AKT.

Figure 13:
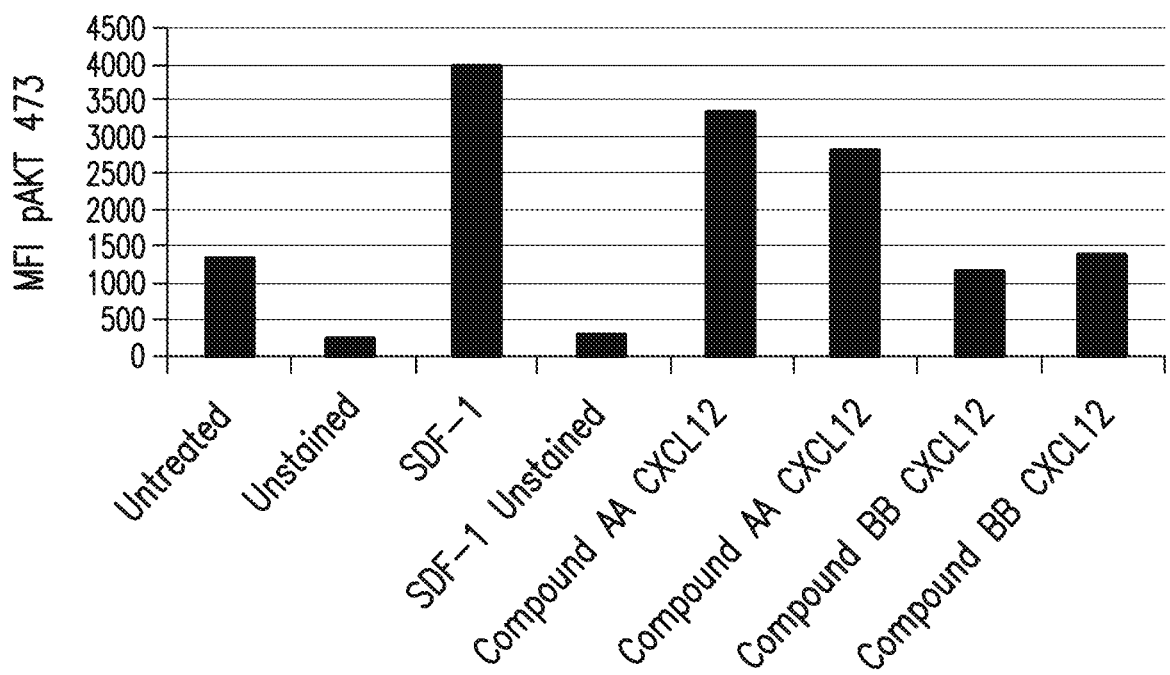
FIG. 13 shows the effects of Compound AA and Compound BB on CXCL12 (SDF-1a) induced p-AKT in M2 phenotype macrophage.

Results:

Compound BB inhibited CXCL12 induced p-AKT in differentiated and M1 polarized macrophage with an $IC_{50}$ value of about 14 nM. Compound BB inhibited CXCL12 induced p-AKT in differentiated and M2 polarized macrophage with an $IC_{50}$ value of about 8.4 nM. Compound AA did not significantly inhibit CXCL12-induced p-AKT in differentiated and M1 or M2 polarized macrophages. FIG. 13 shows the p-AKT staining result for M2 phenotype. The results of this study show that CXCL12 mediated-M2 activation is dependent upon PI3K-γ as it is more potently inhibited by the PI3K-γ selective inhibitor (Compound BB) than the PI3K-δ selective inhibitor (Compound AA).

Example 258: CLL Co-Culture with M2 Macrophage Cells

Figure 14:
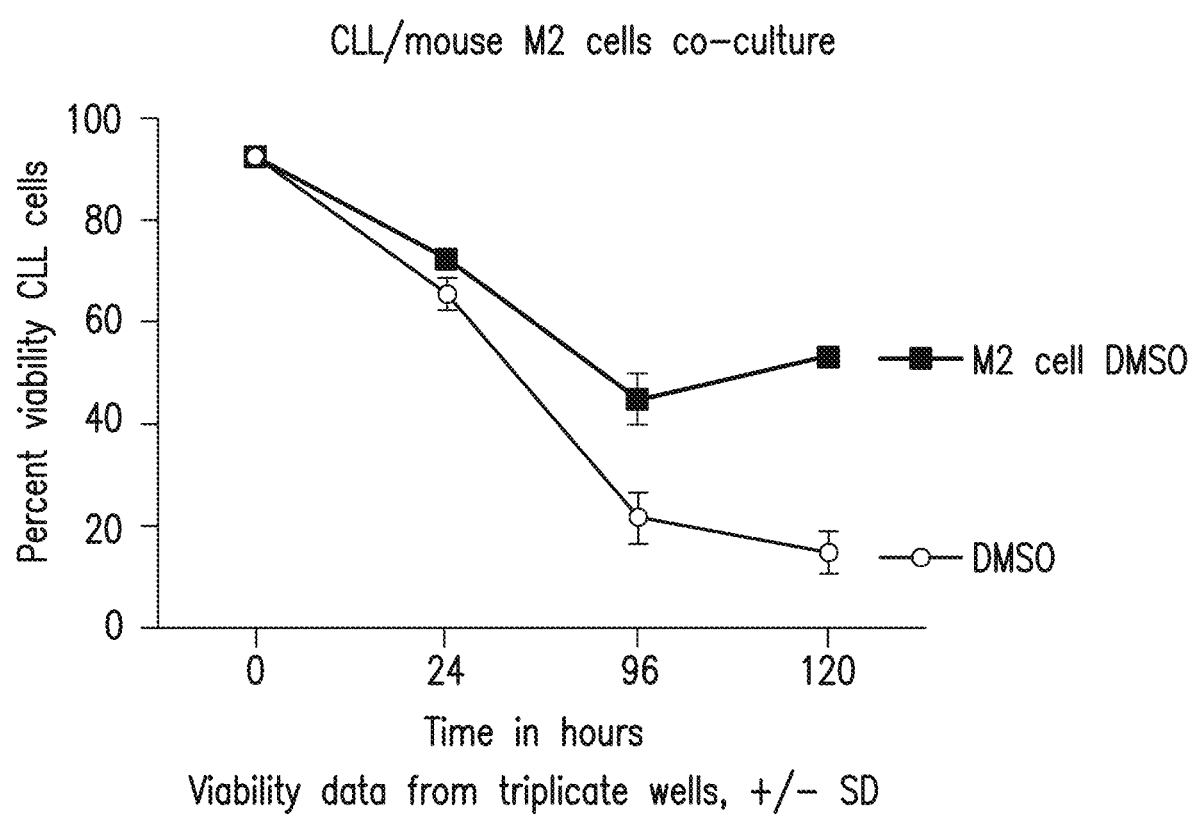
FIG. 14 shows that co-cultures of M2 macrophages with CLL cells led to extended CLL cell survival.

Frozen purified CLL cells were obtained from a commercial vendor (All Cells). Macrophages were polarized into M0 (MCSF) or M2 (MCSF, IL4 for 2 days). M0 or M2 polarized macrophages were plated into a 96 well tissue culture plate at the stated density in RPMI+10% FCS with their respective polarization factors. The CLL cells were plated in the tissue culture plate at 150 thousand cells per well with media or M0 or M2 macrophages. CLL cell viability over time was measured by Guava viacount (Millipore). Co-cultures of M2 macrophages with CLL cells led to extended CLL cell survival (FIG. 14). The result shows that M2 macrophage cells have an ability to protect CLL cells from cell death, that is enhanced over the protective effects of the M0 cells at 120 hours (data not shown).

Figure 15:
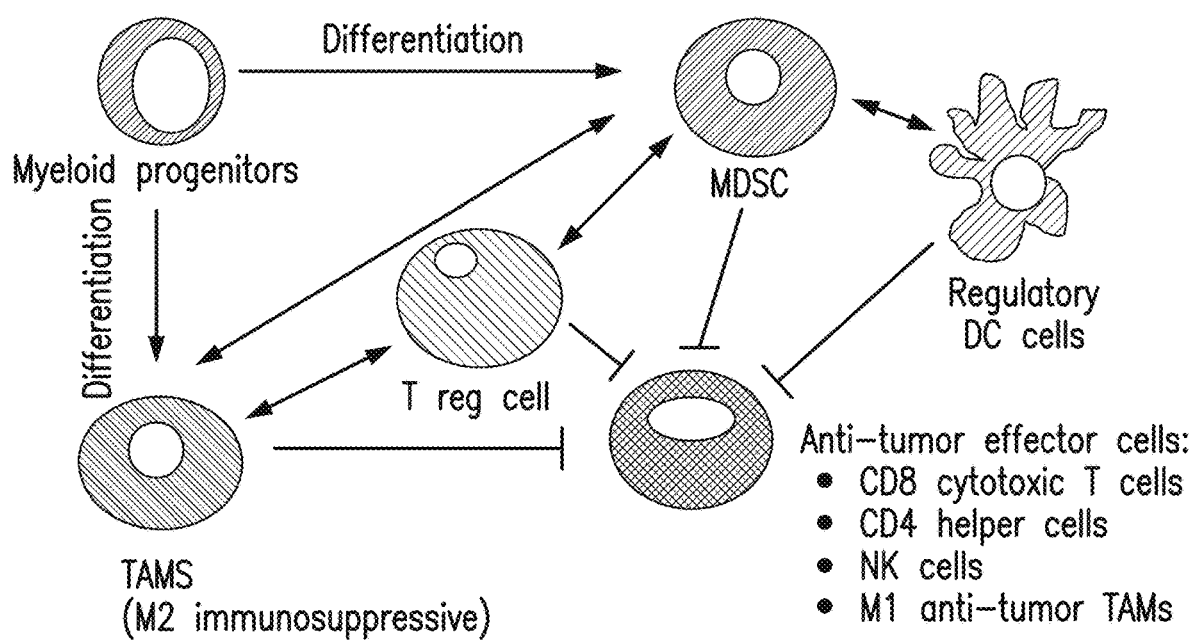
FIG. 15 is a schematic of the differentiation of myeloid progenitor cells and interactions between certain T cells.
Figure 16:
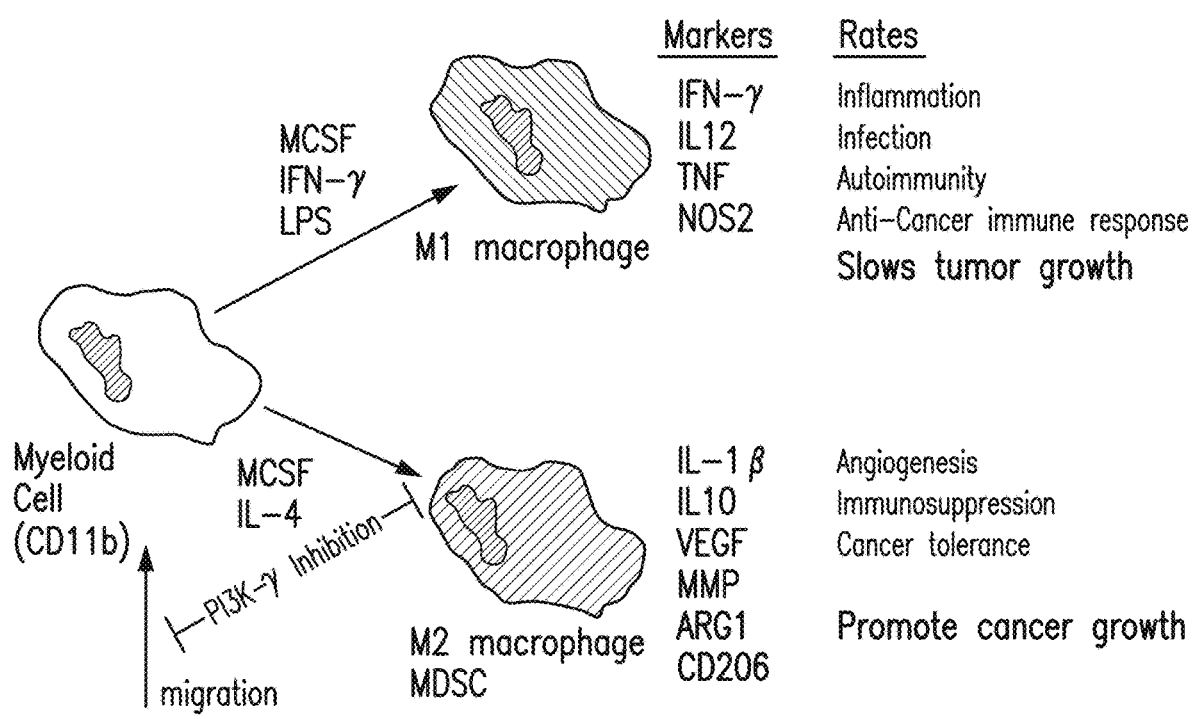
FIG. 16 illustrates differentiation of a myeloid cell into an M1 macrophage or M2 macrophage.

The results indicate that PI3K-γ selective compounds can be used to treat CLL by potently inhibiting M2 activation and reducing survival of CLL cells. FIG. 15 is a schematic of the differentiation of myeloid progenitor cells and interactions between certain T cells. FIG. 16 illustrates differentiation of a myeloid cell into an M1 macrophage or M2 macrophage.

Example 259: Effect on Macrophage Differentiation into Osteoclasts

Recent reports suggest that PI3K-γ knockout mice have normal osteoblast activity, but are deficient in osteoclast activity, which leads to an increase in bone formation. Osteoclast differentiation from bone marrow cells is deficient in these PI3K-γ knockout mice. Kang et al., Proc Natl Acad Sci USA. 2010, 107(29): 12901-12906. A purpose of this study is to evaluate PI3K-γ selective inhibitor on differentiation of osteoclasts from bone marrow macrophages. Compound BB is a PI3K gamma selective compound described herein that has a delta/gamma selectivity ratio of greater than about 50.

Bone Marrow Derived Macrophages as Osteoclast Progenitors:

Long bones from young C57B6 mice were harvested and bone marrow was extruded by gentle lavage of the bone marrow cavities with a 28 gage needle. The cells were screened, and red blood cells were removed using red blood cell lysis buffer (Sigma). Bone marrow cells were differentiated to macrophages using 20 ng/ml mouse MCSF (RnD systems) for 3 days (RPMI and 20% FCS). The cell were washed with PBS, and lifted with Accutase for 10 minutes.

Osteoclast Differentiation Assay:

The bone marrow macrophage cells were plated at 150,000 cells per well in a 96 well plate in a MEM 10% FCS. The cells were treated with DMSO or Compound BB in DMSO for 40 minutes prior to cytokine addition. Then 25 ng/ml mouse MCSF with or without mouse RANKL (100 ng/ml, RnD systems) was added for 6 days. Media changes (including drugs) were done at day 3 and day 5. The cells were then fixed and stained with the tartrate resistant acid phosphatase (TRAP) assay kit from Sigma according to the manufactures instructions. TRAP positive cells (osteoclasts and cells undergoing an osteoclastic differentiation) in a transect of the triplicate wells (at 20× concentration) were manually counted by going through the widest part of each well.

Figure 17:
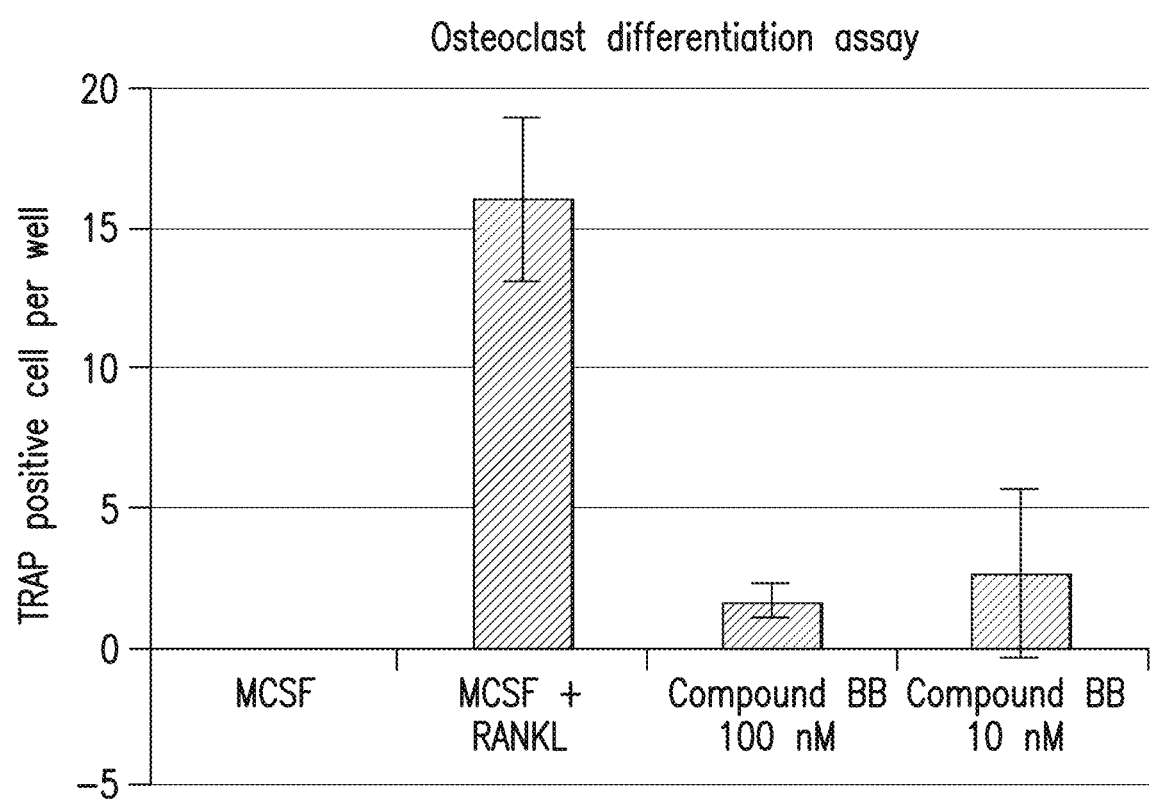
FIG. 17 shows that Compound BB prevents RANKL driven differentiation of osteoclasts from bone marrow macrophages.

Results:

The results are depicted in FIG. 17, which shows that Compound BB prevents RANKL driven differentiation of osteoclasts from bone marrow macrophages. The results indicate that PI3K-γ selective compounds can be used for treatment of osteoclast driven bone diseases.

Example 260: Pharmacokinetics

The purpose of the study is to evaluate the pharmacokinetics of Compound BB following a single and a repeat dose administration in CB6F1 female mice. Compound BB was orally administered at 2, 7.5 and 15 mg/kg once daily for 3 consecutive days to female mice (Female CB6F1 mice, n=72 (5-6 weeks old). The animals were divided into three dosing groups: Compound BB @ 2 mg/kg, PO in 5% NMP, 95% PEG400; Compound BB @ 7.5 mg/kg, PO in 5% NMP, 95% PEG400; and Compound BB @15 mg/kg, PO in 5% NMP, 95% PEG400.

Compound BB was administered orally once a day for a total of three days at a dosing volume of 10 mL/kg based on the most recent body weight. Animals were weighed daily prior to dosing. On the day of the first dose animals were closely monitored over the 1st hour following administration, animals were observed at least twice during the 4 hours following dose administration, and at the end of the day. On subsequent dosing days, the animals' condition was noted prior to dosing; the animals were observed within 4 hours of dosing, and at the end of the day. Increased monitoring can occur if the animals are exhibiting clinical signs. If an animal is exhibiting mild to moderate clinical signs of toxicity, dosing may be held, in consultation with the study director, to allow for recovery.

Samples were collected at pre-dose 0.25, 0.5, 1, 2, 4, 6 and 24 h following the first dose on day 1 and pre-dose (trough), 0.25, 0.5, 1, 2, 4, 6 and 24 h following the final dose on day 3. Animals received a single oral dose daily for 3 consecutive days. Blood was collected by retro-orbital bleeding for all time points on day 1. All other blood sampling was collected by a cardiac puncture. Blood was collected into K2EDTA tubes and placed on wet ice. Within 15 min of collection, the sample was centrifuged at 10,000 rpm at 4° C. for 10 min in a bench top centrifuge and the plasma transferred to a new microcentrifuge tube.

Figure 18:
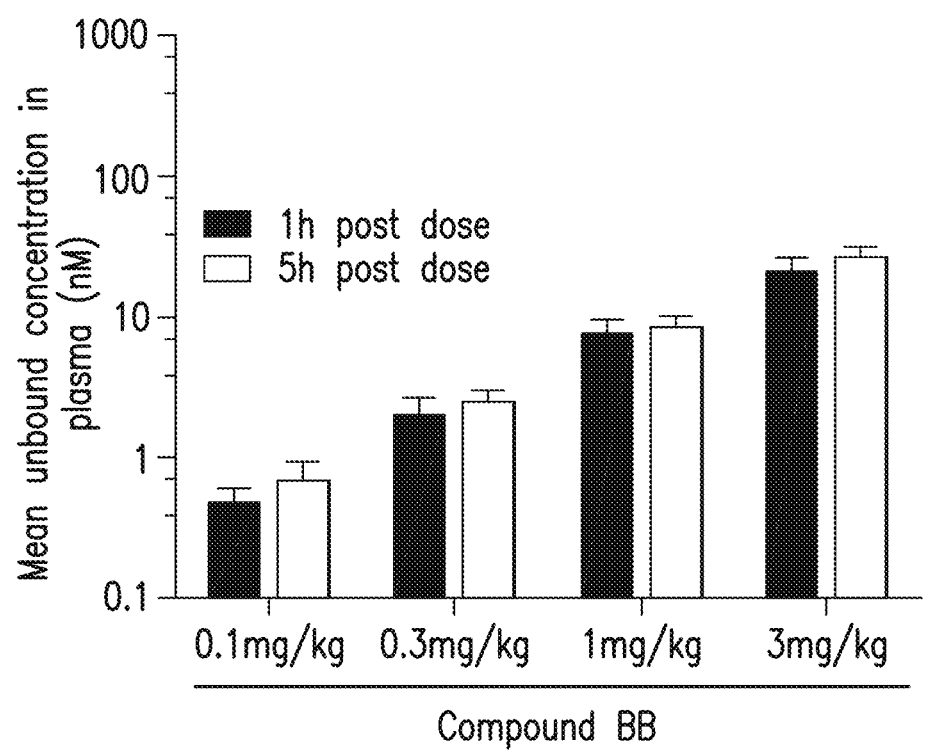
FIG. 18 shows the mean unbound concentration of Compound BB in plasma, 1 or 5 hours after dosing.
Figure 19:
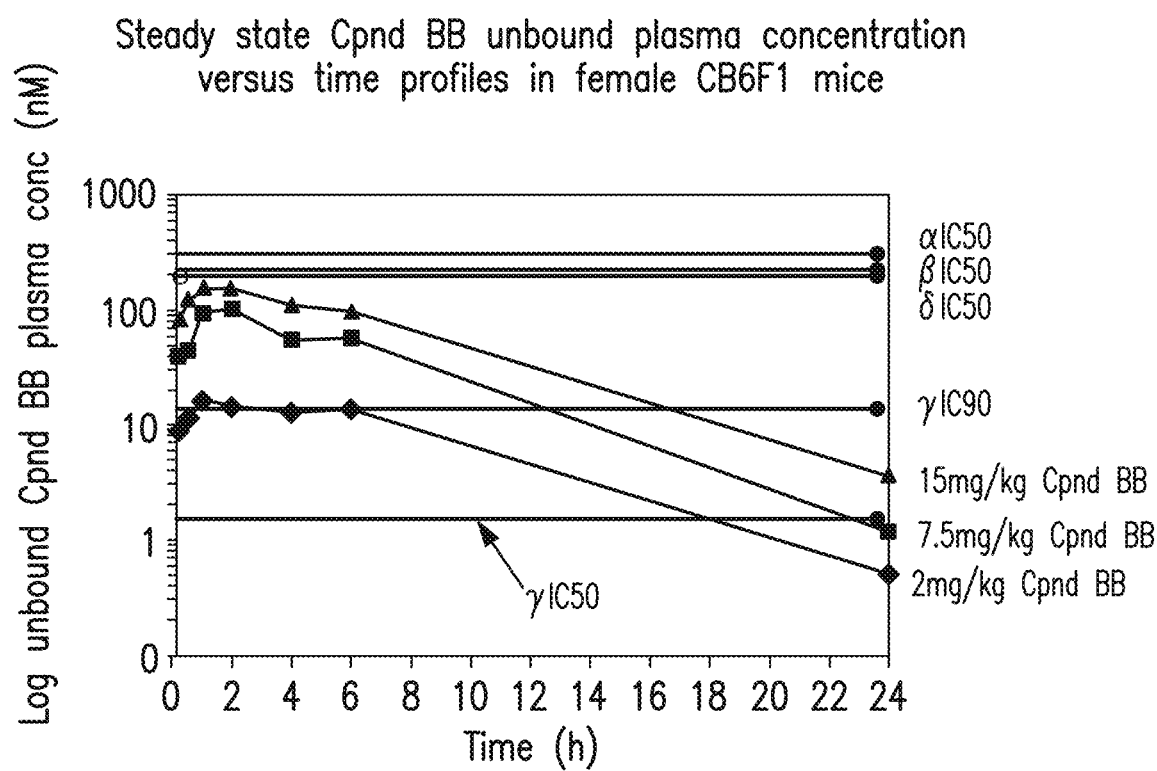
FIG. 19 shows a 24-hour time course of unbound plasma concentration of Compound BB. The five horizontal lines represent the $IC_{50}$s (and one $IC_{90}$) of four PI3K isoforms. From top to bottom, the horizontal lines correspond to the $IC_{50}$ for PI3K-α, $IC_{50}$ for PI3K-β, $IC_{50}$ for PI3K-δ, $IC_{90}$ for PI3K-γ, and $IC_{50}$ for PI3K-γ.

FIG. 18 shows the mean unbound concentration of Compound BB in plasma, 1 or 5 hours after dosing. FIG. 19 shows the results of the study above, for measuring a 24-hour time course of unbound plasma concentration of Compound BB. This experiment indicates that Compound BB has good stability in serum and is suitable for administration, e.g., once per day.

Figure 20:
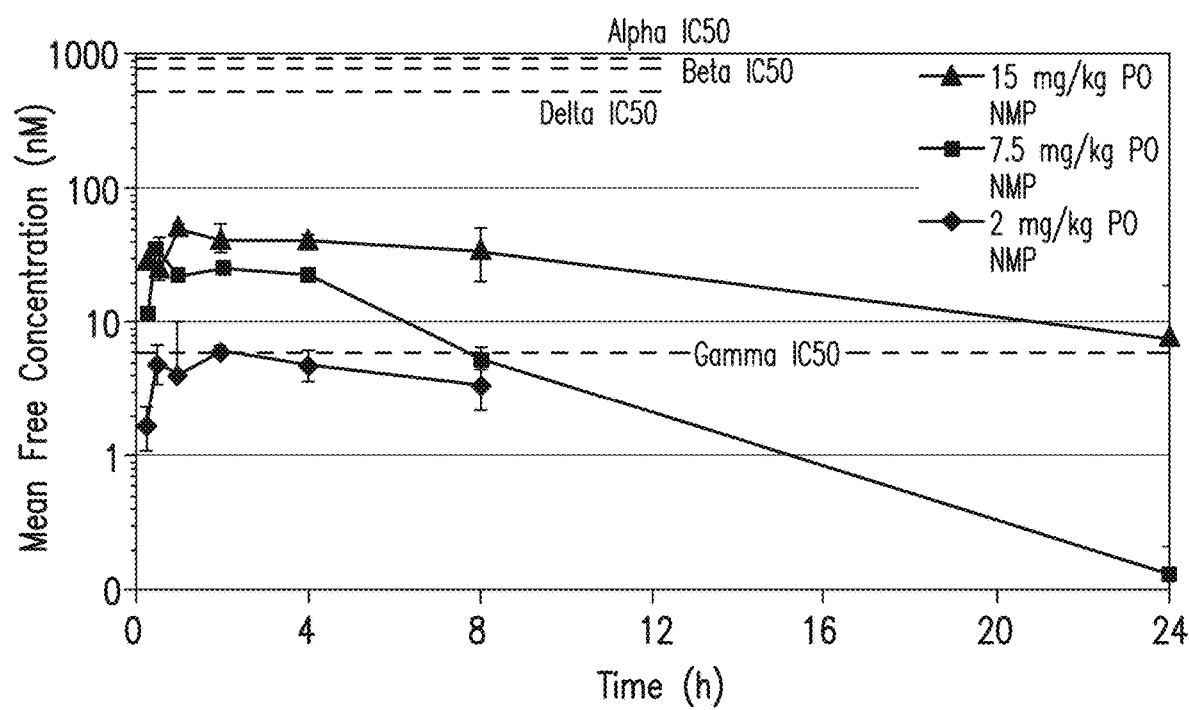
FIG. 20 shows the mean plasma unbound Compound 88 concentration-time profiles for female C57 mice administered 2, 7.5 or 15 mg/kg PO.

A similar study was carried out using Compound 88. FIG. 20 shows the mean plasma unbound Compound 88 concentration-time profiles for female C57 mice administered 2, 7.5 or 15 mg/kg PO. Below is a table that details the results for Compound 88:

| | $C_{max}$ (ng/mL) | $t_{max}$ (h) | $t_{last}$ (h) | $AUC_{last}$ (ng*h/mL) | $AUC_{0\text{-}INF}$ (ng*h/mL) | $AUC_{0\text{-}8}$ (ng*h/mL) | $t_{1/2}$ (h) |
|---|---|---|---|---|---|---|---|
| 2 mg/kg PO NMP | 654 | 2 | 8 | 3891 | N/A | 3891 | N/A |
| 7.5 mg/kg PO NMP | 3705 | 1 | 24 | 20625 | 20684 | 15819 | 2.8 |
| 15 mg/kg PO NMP | 5705 | 1 | 24 | 71746 | 81234 | 34591 | 7.9 |

N/A = Not applicable due to insufficient data points in terminal phase

This shows that Compound 88 also has good stability in serum and is suitable for administration.

Example 261: Effects of Compound BB on T Cell Activation

The purpose of this study is to evaluate the effect of various antigens (Con-A) in T cell activation in Human Whole Blood vs. 1:1 Diluted Blood using test compounds at 24 hour time-point.

T-cell Activation Media includes RPMI-1000 ml, MEM NEAA-10 ml, Sodium Pyruvate (100 mM)-10 ml, Pen Strep-10 ml, 2-Mercaptoethanol-1 ml, and FBS-100 ml. 100 ul of whole blood were plated in 96 well plate. Used only the 60 inside wells and filled the outside with media or PBS. Diluted human whole blood with 5% Serum RPMI 1640 1:1 and plate 100 ul in 96 well plate. Used only the 60 inside wells and filled the outside with media or PBS. The samples were allowed to rest for 45 minutes in the incubator, and then they were treated with Compound BB for 45 minutes.

The compound was diluted using DMSO (Sigma hybrid-max). For 1000 nM highest concentration starting from a 10 mM stock, added 300 ul of DMSO into deep well plates. To the highest concentration add 10 ul of 10 mM compound stock. See table below.

| | DMSO (200 ul) | DMSO (200 ul) + Compound stock | DMSO (200 ul) (50 ul from previous well) | DMSO (200 ul) (50 ul from previous well) | DMSO (200 ul) (50 ul from previous well) | DMSO (200 ul) (50 ul from previous well) | DMSO (200 ul) (50 ul from previous well) | DMSO (200 ul) (50 ul from previous well) | DMSO (200 ul) (50 ul from previous well) | DMSO (200 ul) (50 ul from previous well) |
|---|---|---|---|---|---|---|---|---|---|---|
| compound | | 10 ul | | | | | | | | |

A media plate was prepared from DMSO plate by taking 100 ul and go into 900 ul media in new deep well plate, taping plate, and putting on mixer for 5 minutes.

The rested cell plates were removed from incubator. Added 12 uL of diluted compound from media plate (final DMSO is 1%), and incubated for 45 minutes.

Con-A was prepared as follows: 200 ul stock into 1 ml Media, 100 ul of that into 1 ml Media, 100 ul of that into 1 ml Media. Used highest concentration. This was analyzed after 24 Hours.

10× stock in media, added 12 ul per well. Incubated at 37° C. degree in humidity chamber for 24 hours at 5% $CO_2$. Analyzed with multiplex elisa from MSD. Human Pro-Inflammatory Panel 1 IFNg V-Plex Kit.

| Media | CON-A | CON-A | CON-A | CON-A | CON-A | CON-A | CON-A | CON-A | CON-A |
|---|---|---|---|---|---|---|---|---|---|
| Media | CON-A | CON-A | CON-A | CON-A | CON-A | CON-A | CON-A | CON-A | CON-A |

-continued

| Media | CON-A | CON-A | CON-A | CON-A | CON-A | CON-A | CON-A | CON-A | CON-A |
| CON-A | CON-A | CON-A | CON-A | CON-A | CON-A | CON-A | CON-A | CON-A | CON-A |
| CON-A | CON-A | CON-A | CON-A | CON-A | CON-A | CON-A | CON-A | CON-A | CON-A |
| CON-A | CON-A | CON-A | CON-A | CON-A | CON-A | CON-A | CON-A | CON-A | CON-A |

Figure 21:
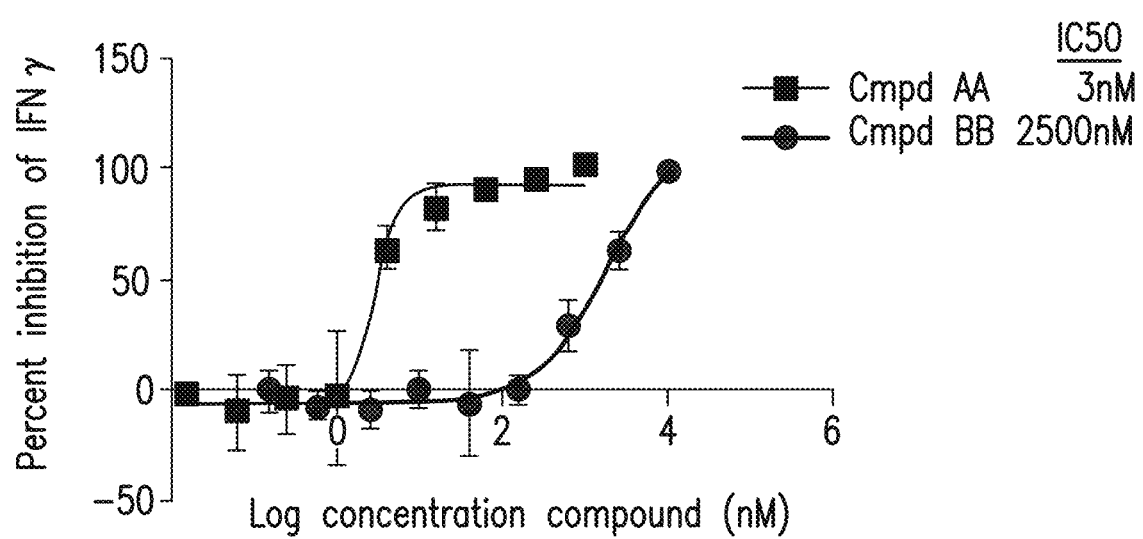
FIG. 21 shows that Compound AA is a highly selective inhibitor of IFN-γ in a Concanavalin A-induced model for activation of human T cells. Compound BB has little to no effect in this assay at isoform selective concentrations.

FIG. 21 shows the effects of Compound BB and Compound AA on T cell activation, as measured by inhibition of IFN-γ. Since compound BB is highly selective for PI3K-γ and Compound AA is highly selective for PI3K-δ, the compounds' very different $IC_{50}$s in this assay (3 nM for Compound AA and 2500 nM for Compound BB) indicate that PI3K-δ is important for T cell activation, and PI3K-γ less so.

Example 262: Effects of Compound BB on Murine M2 TAM Differentiation

Figure 22A:
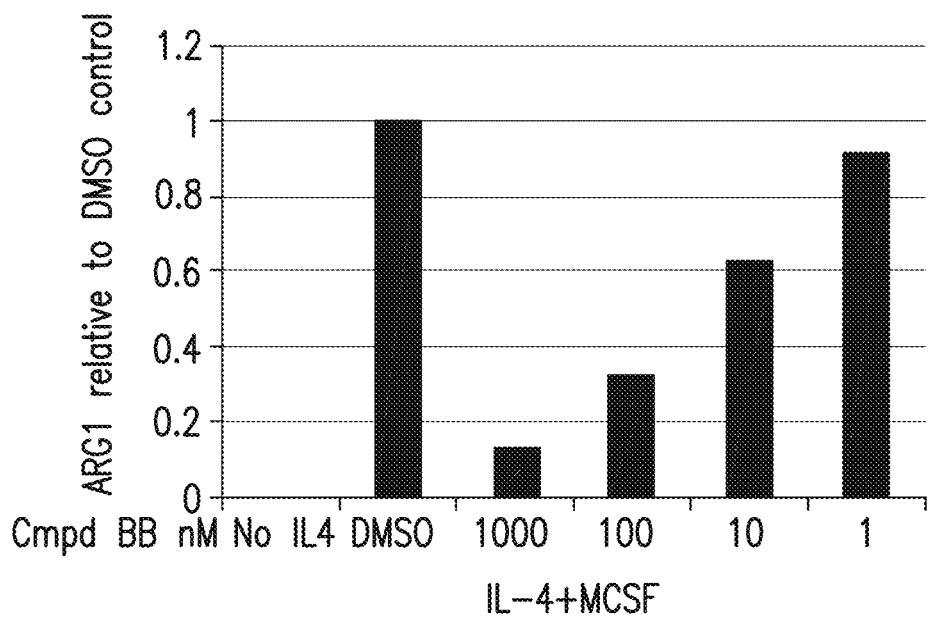
FIGS. 22A and 22B show the level of ARG1 (Arginase-1) in murine macrophages polarized to M2 phenotype in response to different doses of Compound BB and Compound AA, respectively.
Figure 22B:
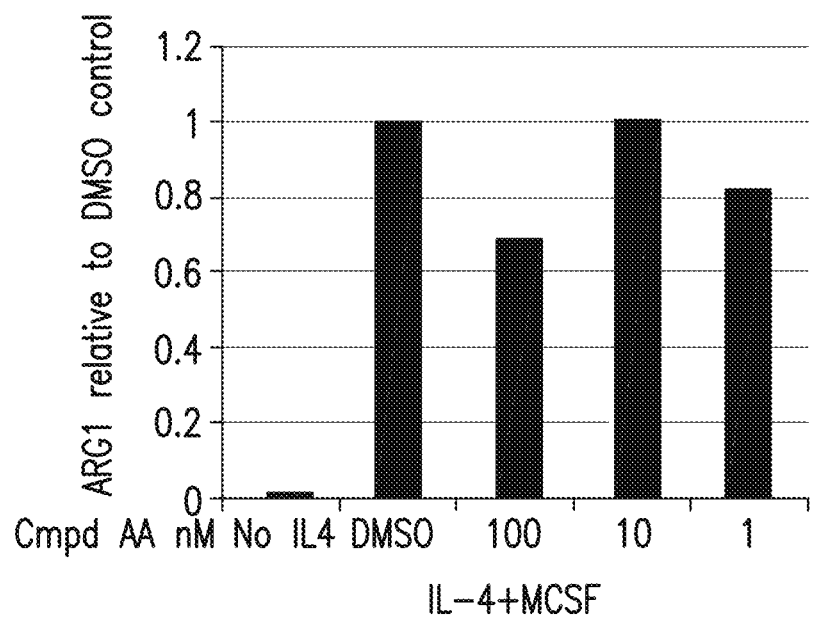
Figure 23:
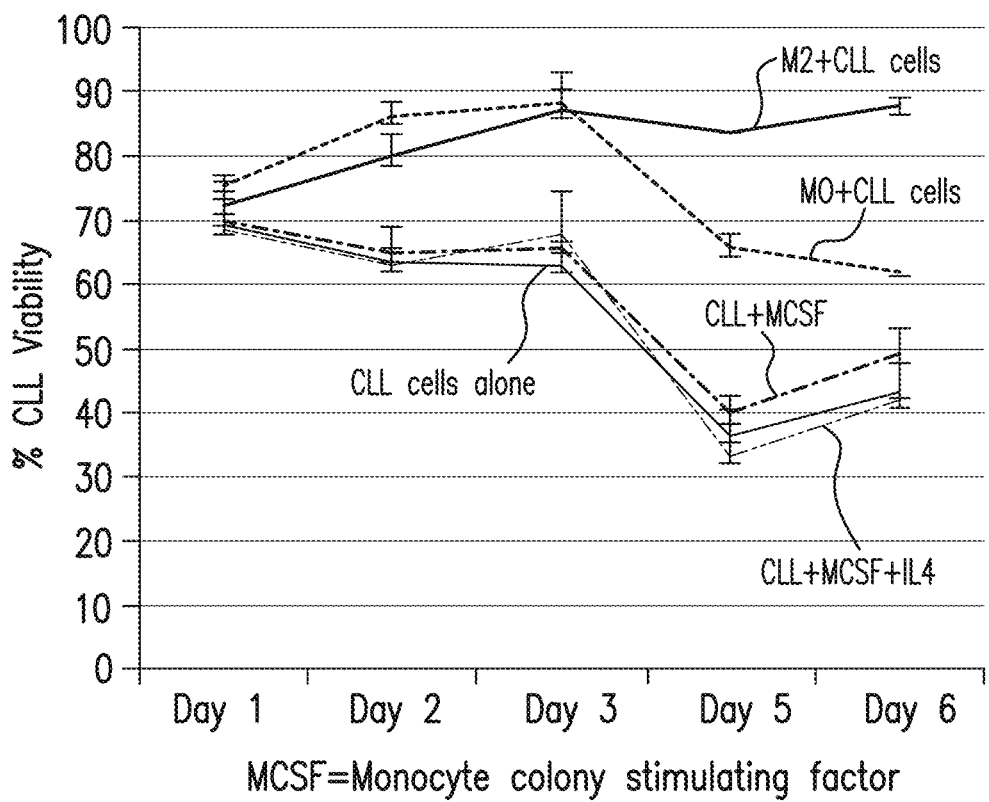
FIG. 23 shows that CLL cell survival is enhanced upon M2 macrophage co-culture. The x-axis corresponds to time, and the y-axis corresponds to % CLL viability.

Compound BB, which selectively inhibits PI3K-γ, and Compound AA, which is highly selective for PI3K-δ, were tested for their ability to block differentiation of myeloid cells into M2 TAMs, and the results are shown in FIG. 22A and FIG. 22B, respectively. High ARG1 (Arginase-1) levels indicate that myeloid cells are differentiating into M2 macrophages, so lower ARG1 levels relative to a control indicate interference with differentiation into M2 macrophages. Expression of Arginase-1 depletes the tumor microenvironment of arginine, thereby promoting T cell death and NK cell inhibition. Schmid et. al., Proceedings: AACR 103rd Annual Meeting 2012, Cancer Research: Apr. 15, 2012; Volume 72, Issue 8, Supplement 1. Compound BB inhibited M2 TAM differentiation much more effectively than PI3K-δ inhibitor. M2 TAMs promote cancer cell survival (FIG. 23). Because Compound BB prevents differentiation to pro-tumor M2 cells, this experiment indicates that Compound BB is expected to increase a subject's anti-tumor immune response.

Figures 24A, 24B:
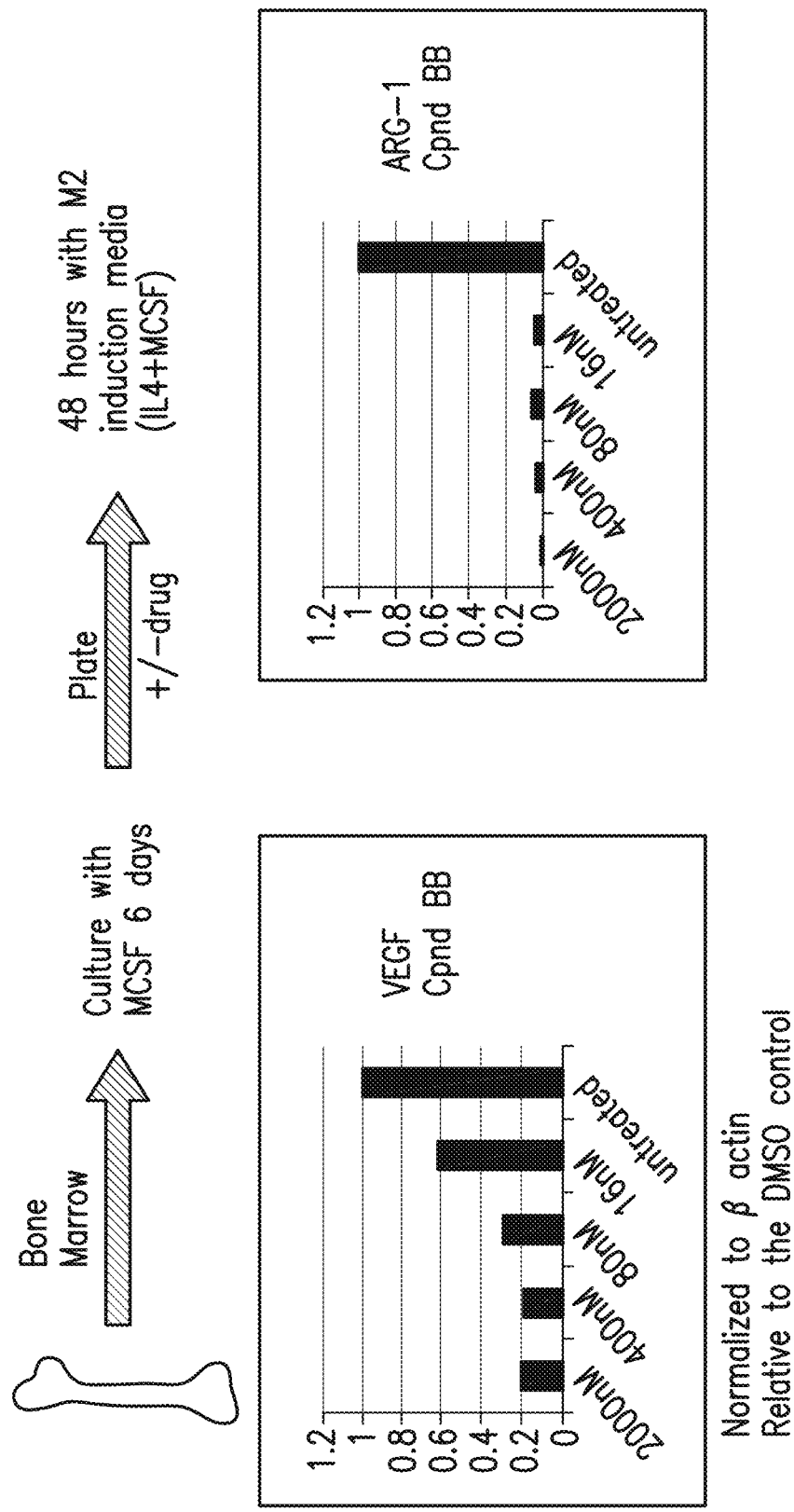
FIGS. 24A and 24B show that Compound BB suppresses VEGF and ARG1 in an Myeloid Derived Suppressor Cell differentiation assay, respectively.

A similar experiment was performed on bone marrow cells differentiating into MDSCs. Compound BB suppressed both VEGF (FIG. 24A) and ARG1 (FIG. 24B) in an Myeloid Derived Suppressor Cell differentiation assay.

A similar experiment was performed on M1 differentiation. Compound BB did not have an observable effect on M1 macrophage differentiation (data not shown). Accordingly, Compound BB is not expected to interfere with the anti-tumor activities of M1 macrophages.

Example 263: Single Agent Activity of Compound BB in the Lewis Lung Carcinoma Model Compound BB was tested in the Lewis Lung Carcinoma model, which is known in the art and briefly described hereinabove.

LLC tumor brei model was prepared and injected subcutaneously into a mouse in the hind flank region. The tumor brei was prepared as follows. LL2-Luc tumor cells were grown in culture in DMEM+10% FBS. Cells were implanted @ $1 \times 10^6$ cells/100 uL SC in the flank of C57 Albino mice (male) When tumors reached 1000 mm3, tumors were harvested. Only the white, living tissue was harvested. Any material containing visable blood or necrotic area was isolated away from the tumor tissue. Tumor tissue was placed in a Dounce tissue homoginized with 5 mLs of warm DMEM (no FBS). About 1-2 grams of tumor tissue was collected, homogenized, pooled into 50 mL falcon tube, and cells were counted. Cells were spinned @ 12,000 RPM, and FBS was pooled off Cells were resuspended to equal $1 \times 10^7$ cells/mL with sterile PBS. 100 uL of cells/mouse SC at the hind flank region were implanted. This process was repeated one more time before conducting brei tumor efficacy study.

Figure 25A:
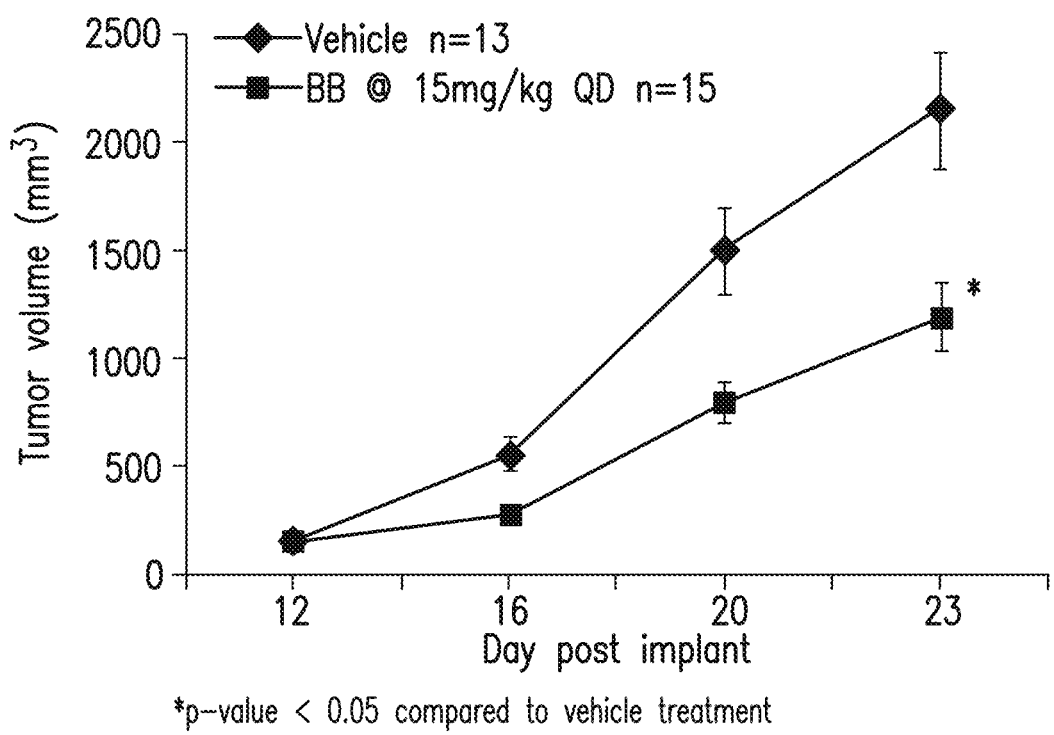
FIGS. 25A and 25B show that Compound BB demonstrates single agent activity in the Lewis Lung Carcinoma model.
Figure 25B:
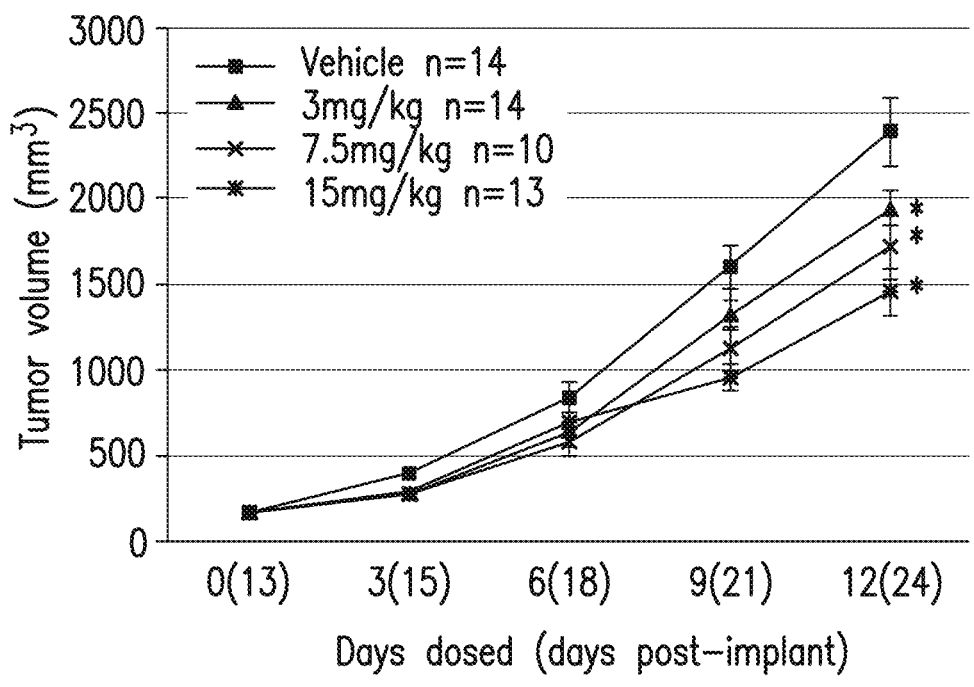
Figure 26:
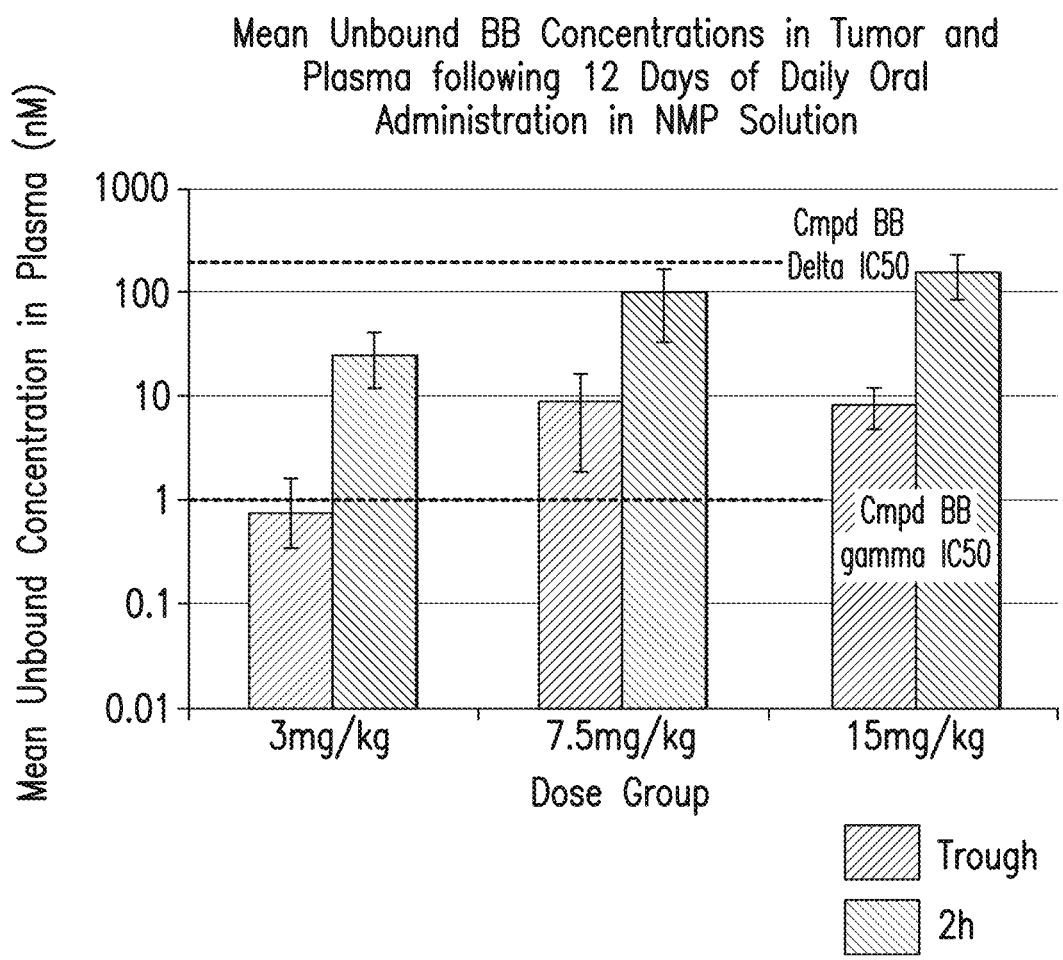
FIG. 26. shows the mean unbound Compound BB concentrations in tumor and plasma following 12 days of daily oral administration in NMP solution.

FIGS. 25A and 25B show that Compound BB demonstrated single agent activity in the Lewis Lung Carcinoma model. FIG. 26 shows the mean unbound Compound BB concentrations in tumor and plasma following 12 days of daily oral administration in NMP solution. Below is a table of details:

| Tissue | Dose Group | Time (h) | Free Conc (nM) | SD Free Conc |
|---|---|---|---|---|
| Plasma | 3 mg/kg | Trough | 0.75 | 0.408 |
| | | 2 h | 25.9 | 14.0 |
| | 7.5 mg/kg | Trough | 8.99 | 7.21 |
| | | 2 h | 99.0 | 66.3 |
| | 15 mg/kg | Trough | 8.39 | 3.67 |
| | | 2 h | 157 | 72.2 |

The results indicate that exposure increased with increase in dose. At 2 h, Compound BB levels are above cellular gamma $IC_{50}$ in all groups. For 7.5 mg/kg and 15 mg/kg groups, they are above the gamma $IC_{50}$ at 24 h.

Example 264: Effects of Compound BB on Tumor Growth in CT26 and MC38 Colon Cancer Models The purpose of this study is to determine the efficacy of Compound BB as a single agent and in combination with anti-PD-L1 in the CT26 allograft model of mouse colon cancer. CT26 is an N-nitroso-N-methylurethane-(NNMU) induced, undifferentiated colon carcinoma cell line. It was cloned to generate the cell line designated CT26.WT (ATCC catalog number CRL-2638). 5-6 week old female, Balb/c mice (Jackson Labs) were implanted subcutaneously with $5 \times 10^5$ CT26 cells in 200 µl PBS. CT26 cells were cultured in DMEM supplemented with 10% FBS. Dosing commenced when tumors reached an average volume of ~100 mm³. Administration of the compounds was performed according to the following Table:

TABLE 23

| Group | # mice/ group (n) | Cpnd BB PO QD mg/kg | α-PD-L1 IP Q3D µg/mouse |
|---|---|---|---|
| 1 | 15 | 0 | 0 |
| 2 | 15 | 6 | 0 |
| 3 | 15 | 0 | 200 |
| 4 | 15 | 6 | 200 |

Compound BB vehicle: 5% NMP/95% PEG400
Compound BB prepared at 0.6 mg/ml in 5% NMP/95% PEG400
Isotype control (Ultra-LEAF purified rat IgG2b, k isotype control, clone RTK4530, Lot B180477, Biolegend, Cat #70640)

Anti-PD-L1 antibody (Ultra-LEAF purified anti-mouse CD274-B7H1, PD-L1-, clone 10F9G2, Lot B178331, Biolegend, Cat #124318)

Dosing Regimen:
Compound BB: QD for 3 weeks at a volume of 5 ml/kg
Anti-PD-L1: every third day for a total of 4 doses
Body weights and tumor volumes were measured three times per week.

Figure 27A:
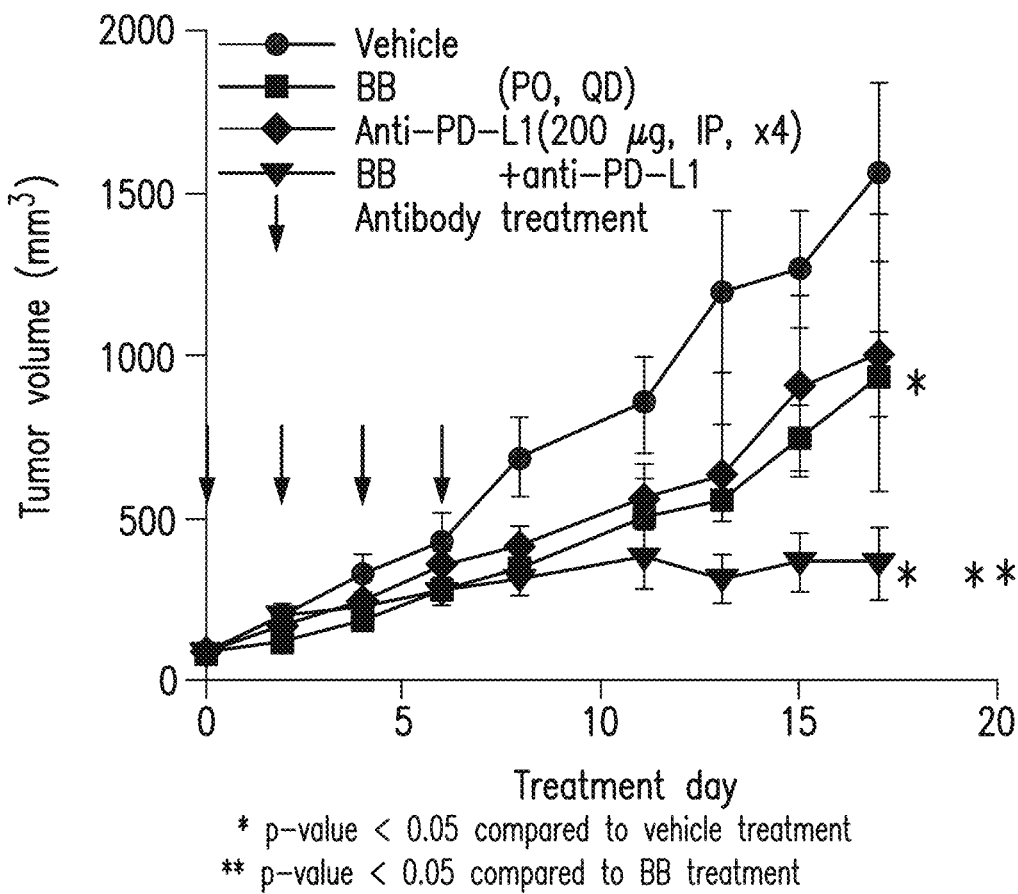
FIGS. 27A and 27B show the effect of Compound BB administered together with an anti-PD-L1 checkpoint inhibitor in the CT26 colon cancer model.
Figure 27B:
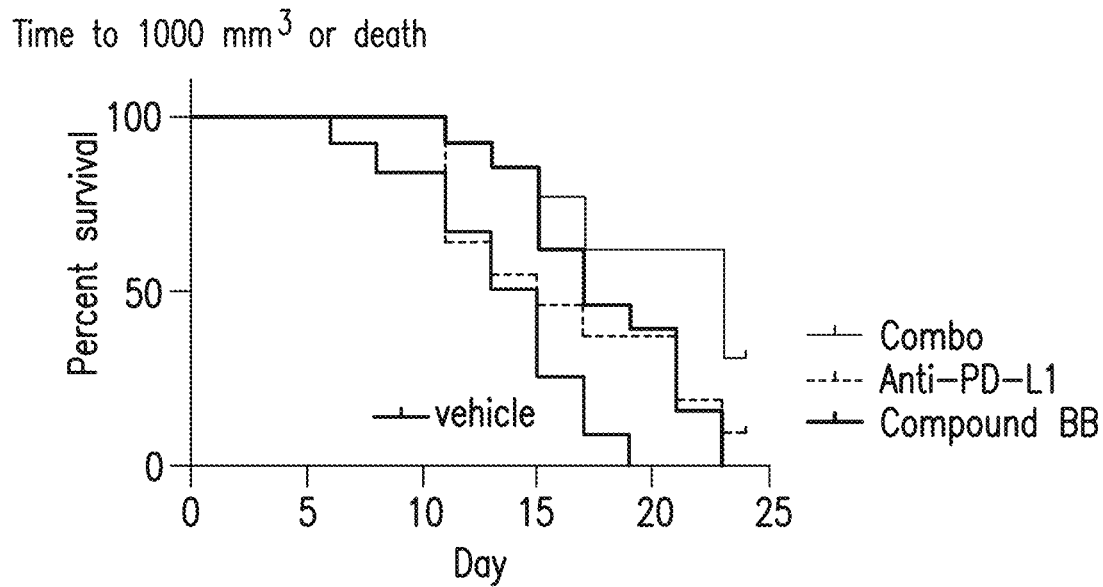

FIG. 27A and FIG. 27B show Compound BB administered together with an anti-PD-L1 checkpoint inhibitor in the CT26 model. FIG. 27A shows the effect on tumor volume over time. FIG. 27B shows the percent survival over time.

Figure 28:
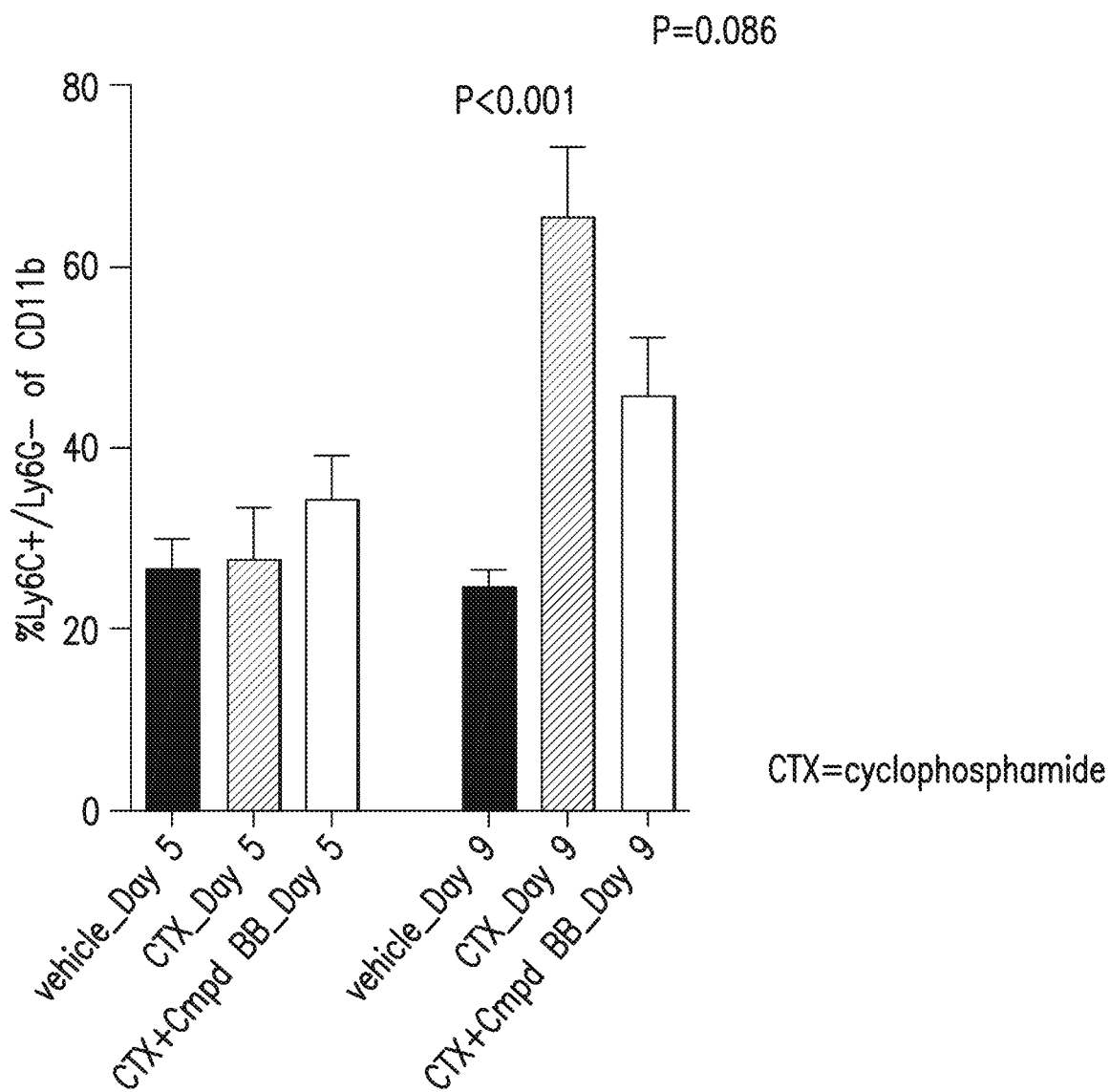
FIG. 28 shows that MDSC expansion after cyclophosphamide treatment is decreased by Compound BB in the CT26 colon cancer model.

FIG. 28 shows that MDSC expansion after cyclophosphamide treatment occurs within the 5-9 day time frame and that this expansion is decreased by Compound BB in the CT26 model.

A second model for colon cancer, the M38 model, was used to further evaluate the effects of Compound BB. In this model, a syngeneic colon cancer cell line is run subcutaneously. The experimental setup was as follows.

Female CR C57BL/6 mice were set up with 1×106 MC38 tumor cells in 0% Matrigel sc in flank. The cell injection volume was 0.05 ml per mouse. When tumors reached an average size of 80-100 mm, a pair match was made and treatment began. The tumor was measured by caliper biweekly.

The dosing and formulations were as follows: 5-FU in D5W; Compound BB in 5% NMP/95% PEG. The dosing volume was 5 mL/kg.

For all animals, blood was collected by terminal cardiac puncture under isoflurane anesthesia. The blood was processed for plasma. In addition, tumor samples were collected.

Figure 29A:
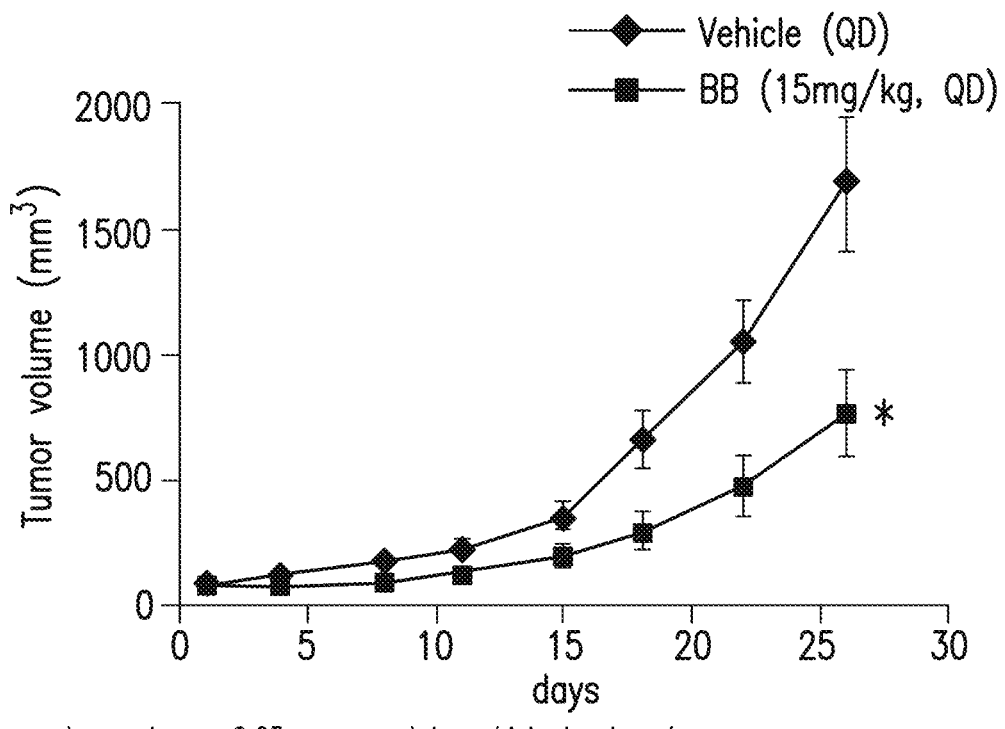
FIGS. 29A and 29B show the efficacy of Compound BB alone and in combination with 5-FU, respectively, in the MC38 colon cancer model. The x-axis represents time and the y-axis represents tumor size in $mm^3$.
Figure 29B:
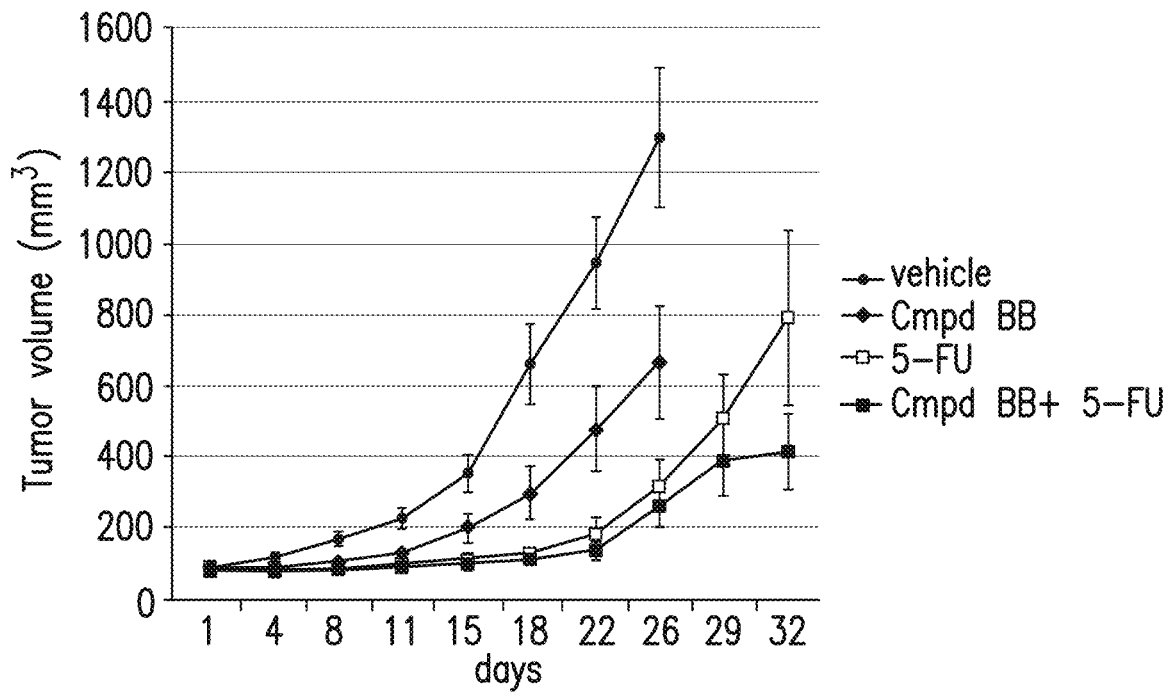

FIG. 29A shows that Compound BB monotherapy significantly inhibited tumor growth in the MC38 colon cancer model. FIG. 29B shows the effects of Compound BB and 5-FU used separately and in combination in the MC38 model.

Figure 30:
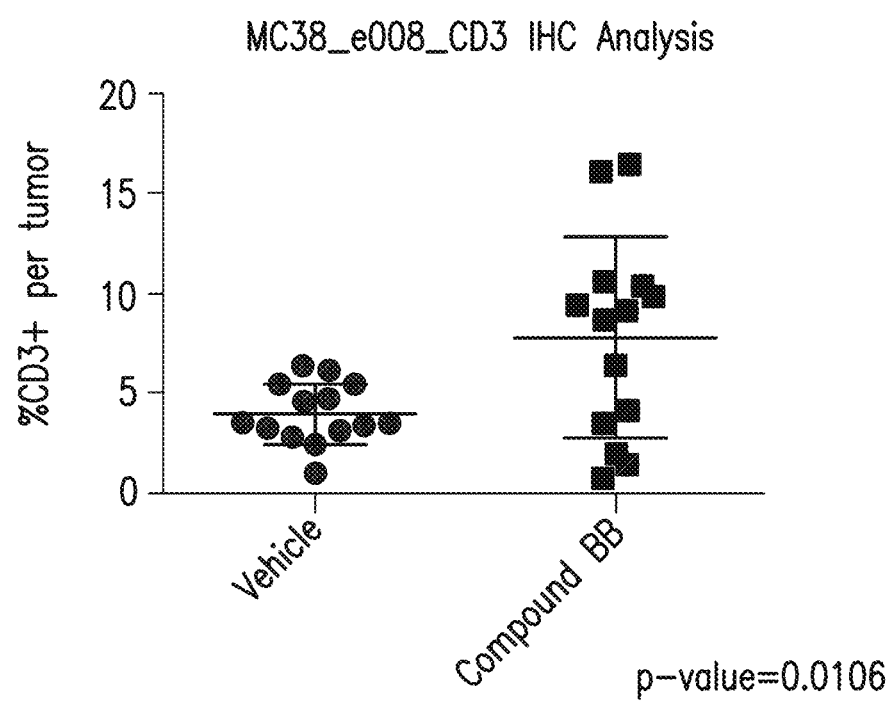
FIG. 30 shows CD3 IHC analysis after treatment with Compound BB in MC38 tumors.
Figure 31A:
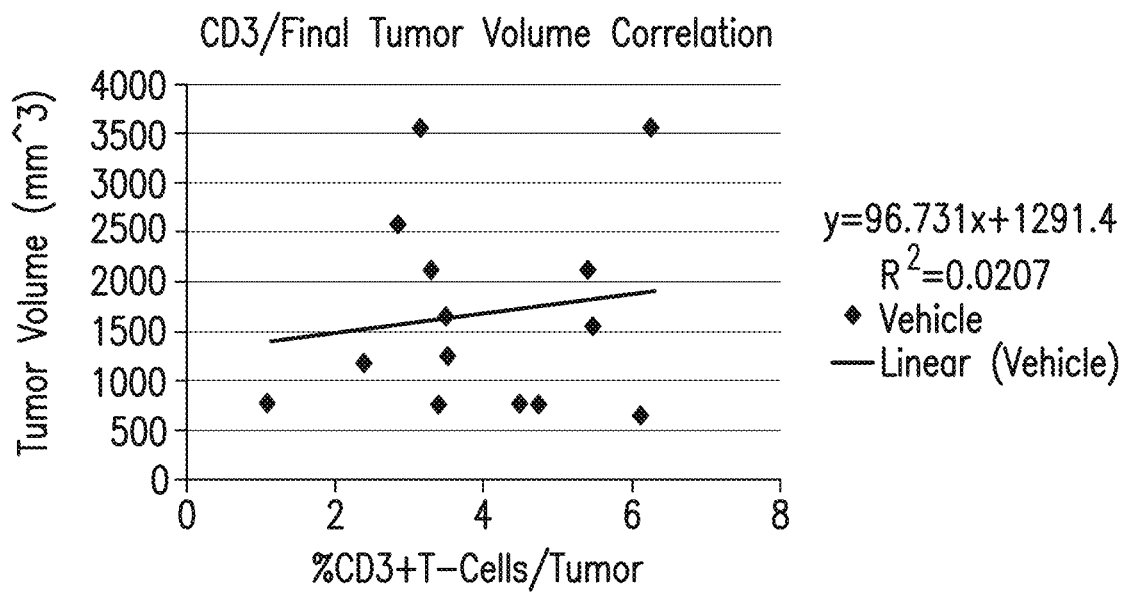
FIG. 31A shows the CD3 and tumor volume correlation for vehicle.
Figure 31B:
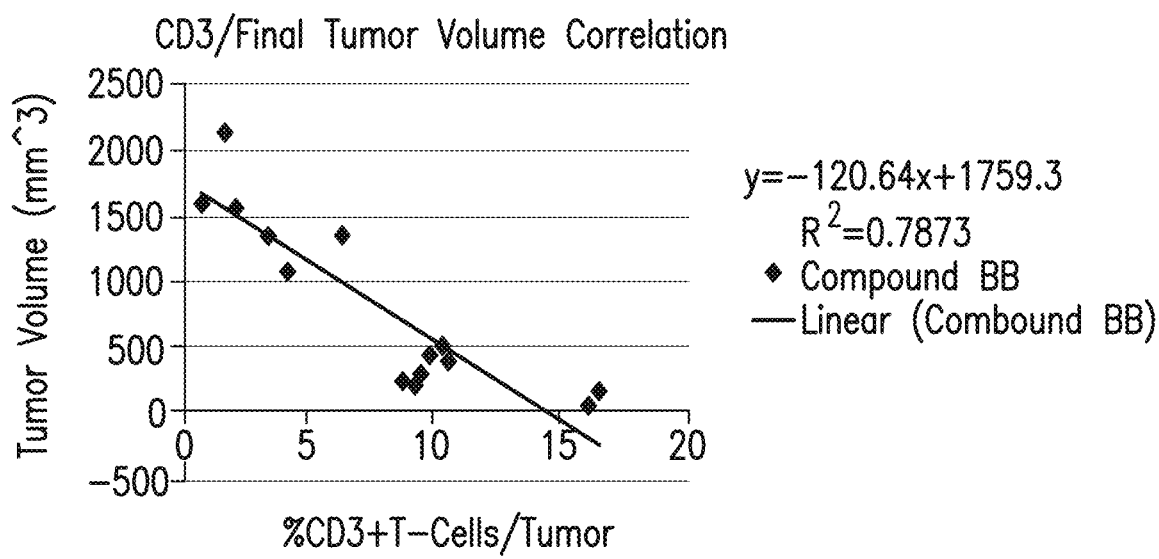
FIG. 31B shows the CD3 and tumor volume correlation for Compound BB.

At study end, tumors were isolated, fixed in 10% neutral buffered formalin and embedded in paraffin for histologic analysis. Tumor sections from both vehicle and Compound BB monotherapy were cut for immunohistochemical analysis. T-cells within the tumor sections were identified utilizing a CD3-specific antibody via automated immunohistochemistry equipment (Ventana). Once stained, slides were digitalized via Aperio slide scanning equipment. Next, stained tumor sections were quantified via Definians software to assess the percentage of CD3 positive cells within each tumor. FIG. 30 shows that MC38 tumors treated with Compound BB have significantly more intratumoral CD3+ T cells when compared to vehicle. Final tumor volume was plotted as a function of percent CD3+ T-cells in vehicle sample (FIG. 31A) and Compound BB monotherapy sample (FIG. 31B), respectively. A trendline was added to the vehicle and Compound BB monotherapy graphs. The vehicle final tumor volumes did not correlate with percent CD3+ T-cells whereas in the cohort of Compound BB monotherapy final tumor volumes strongly correlated with intratumoral percent CD3+ T-cells (R2=0.7873). The results indicate that significant influx of CD3+ T-cells upon PI3K-gamma inhibition leads to decreases in tumor size.

Example 265: Effect of Compound BB in the DoHH2 Human Follicular B Cell Lymphoma Model The purpose of this study is to evaluate the anti-tumor activity of Compound AA and Compound BB alone and in combination in the DoHH2 human transformed folicullar B cell lymphoma subcutaneous model in female CB17.SCID mice. DoHH2, a human folicular B cell lymphoma cell line, was grown in tissue culture (filtered RPMI-1640 supplemented with 10% fetal bovine serum) and implanted (5×10$^6$ cells in 100 uL RPMI-1640 media and 100 uL matrigel (LDV free)) subcutaneously into the hind flank of female CB17.SCID mice. Treatment began when tumors reached 100 mm$^3$ in volume. In dosing groups of 15 mice per group, drug was administered as follows: 1. Vehicle (5% NMP 95% PEG400)+Vehicle; 2. Compound AA (10 mg/kg)+Vehicle; 3. Compound BB (15 mg/kg)+Vehicle; 4. Compound AA+Compound BB. Animals were dosed for 21 consecutive days. Efficacy comparisons were determined by tumor caliper measurements, three times per week.

Figure 32A:
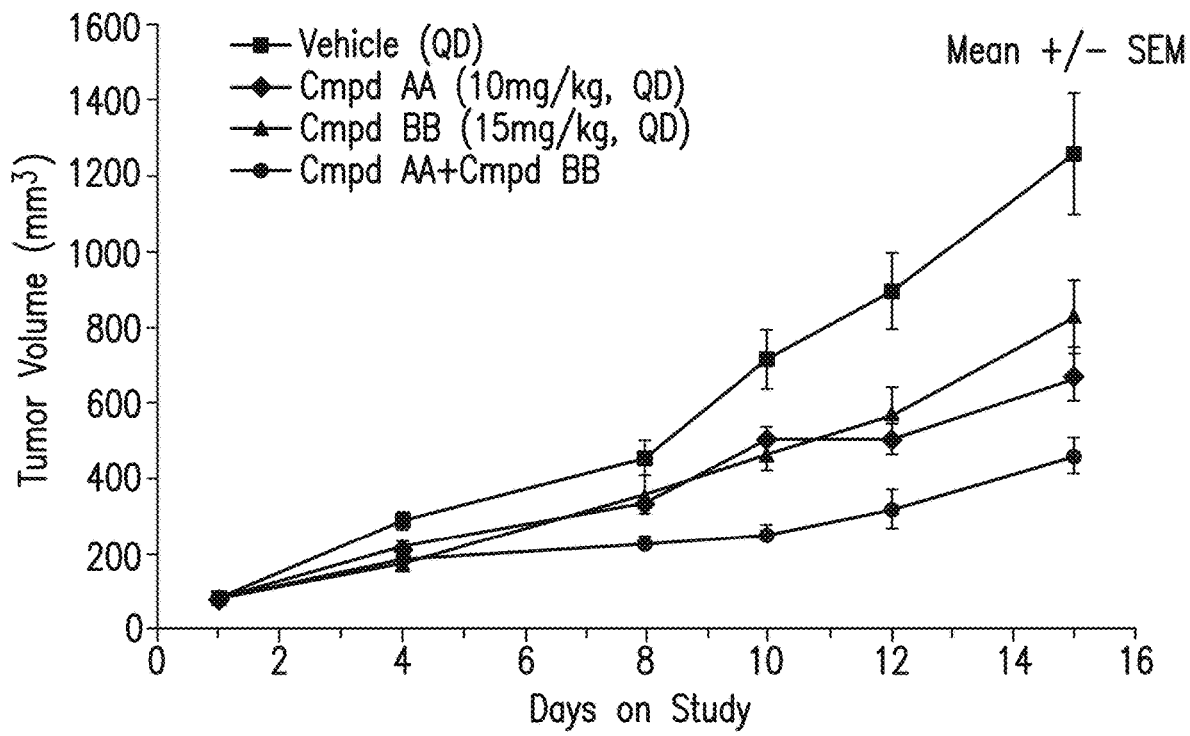
FIGS. 32A and 32B show the effects of Compound BB and/or Compound AA in the DoHH2 human follicular B cell lymphoma model.
Figure 32B:
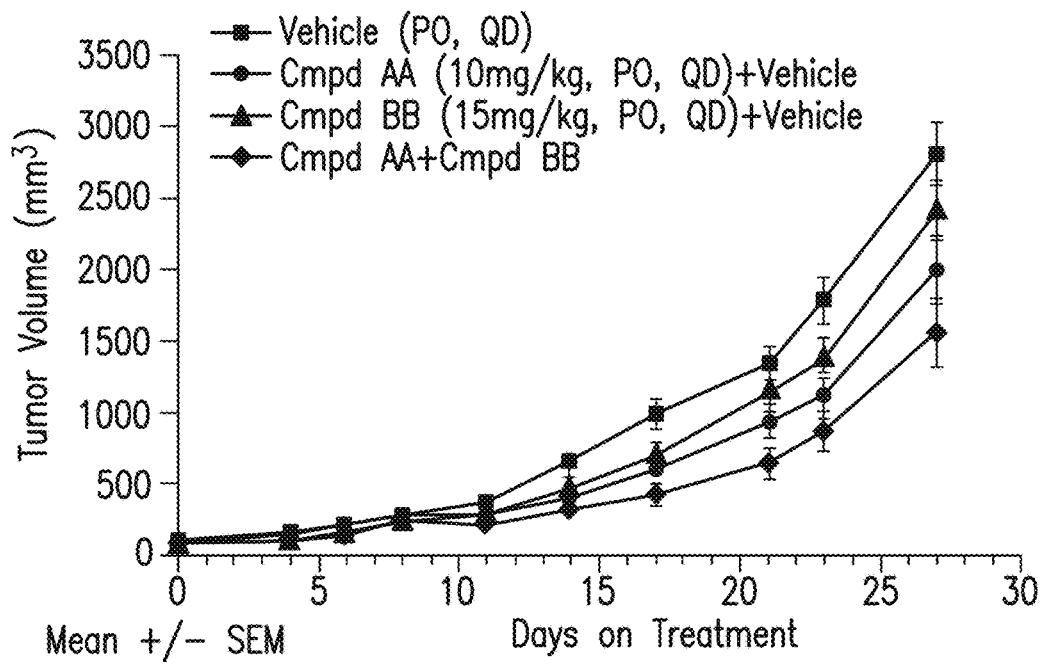

FIGS. 32A and 32B show the result of inhibiting PI3K-γ (Compound BB) and/or PI3K-δ (Compound AA) in the DoHH2 model. FIG. 32B is a repeat study. Dual inhibition of PI3K-δ and PI3K-γ is superior to inhibition of either isoform alone.

Example 266: Effects of Compound BB and/or PDL-1 Inhibition on Tumor Growth in Orthotopic 4T1 Breast Cancer Model The PI3K-γ selective inhibitor, Compound BB, and the immune checkpoint therapy, PDL-1, were assayed separately and together for effects on tumor growth in the 4T1 breast cancer model. This model system is described in more detail in Example 227. Briefly, in this study, treatment was initiated when tumors reached approximately 100 mm$^3$. Compound BB or vehicle was orally administered once daily for 3 weeks. Anti-PD-L1 or isotype control antibodies were adminstered intraperitoneal once every 3 days for a total of 5 doses. In a sample of 15 mice, dosing groups were as follows. 1. Vehicle+Isotype control (Rat IgG2b κ, 200 ug); 2. Compound BB (7.5 mg/kg), PO+Isotype control (200 ug); 3. Vehicle+anti-PD-L1 (200 ug); 4. Compound BB (7.5 mg/kg), PO+anti-PD-L1 (200 ug). During the experiment, tumor luciferin flux was measured twice a week. Efficacy comparisons were determined by tumor caliper measurements.

Figures 33A, 33B:
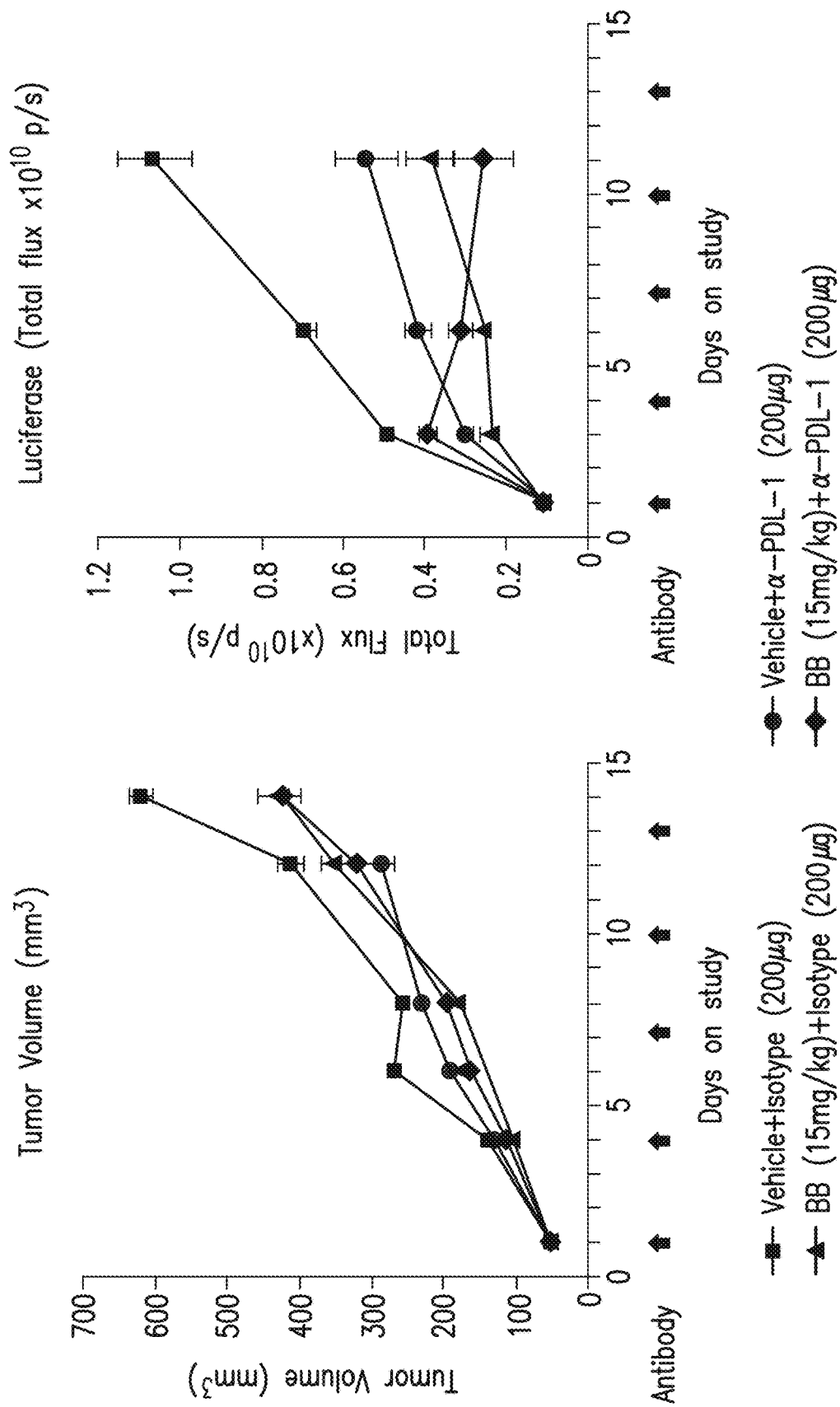
FIG. 33A shows reduced tumor growth with Compound BB and/or PDL-1 inhibition in orthotopic 4T1 breast cancer model.
FIG. 33B shows reduced total luciferase flux with Compound BB and/or PDL-1 inhibition in orthotopic 4T1 breast cancer model.
Figure 34:
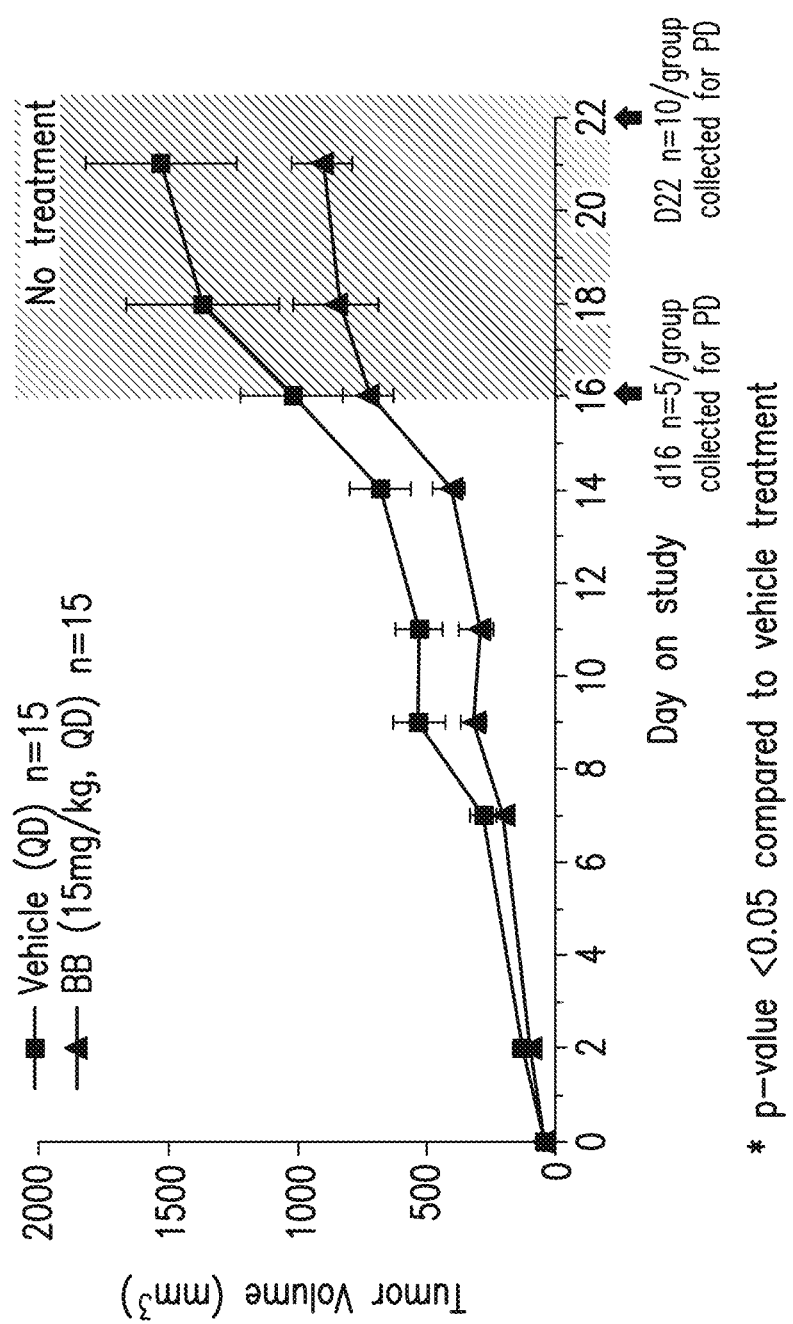
FIG. 34 shows that Compound BB demonstrates single agent activity in subcutaneous 4T1 breast cancer model.

FIG. 33A shows reduced tumor growth with Compound BB and/or PDL-1 inhibition in orthotopic 4T1 breast cancer model. FIG. 33B shows reduced total luciferase flux with Compound BB and/or PDL-1 inhibition in orthotopic 4T1 breast cancer model. FIG. 34 shows that Compound BB demonstrated single agent activity in subcutaneous 4T1 breast cancer model and that the anti-tumor effect of Compound BB was maintained for at least 6 days after the discontinuation of treatment with Compound BB.

The 4T1 model was also used to determine the anti-cancer activity of Compound BB and 5-FU, docetaxel, or paclitaxel. Briefly, treatment began when tumors reached ~50 mm$^3$ in volume. Compound BB or vehicle was orally administered once daily at 15 mg/kg in the NMP formulation to balb/c female mice for 2 weeks. Docetaxel 33 mg/kg Q7Dx2, paclitaxel 10 mg/kg Q5Dx3, 5-FU 50 mg/kg QODx7 or saline was adminstered intraperitoneal. Efficacy was determined by tumor volume and luciferin measurements. Tumor measurements and body weights were taken three times a week. Luciferin measurements were taken twice a week.

Figure 35:
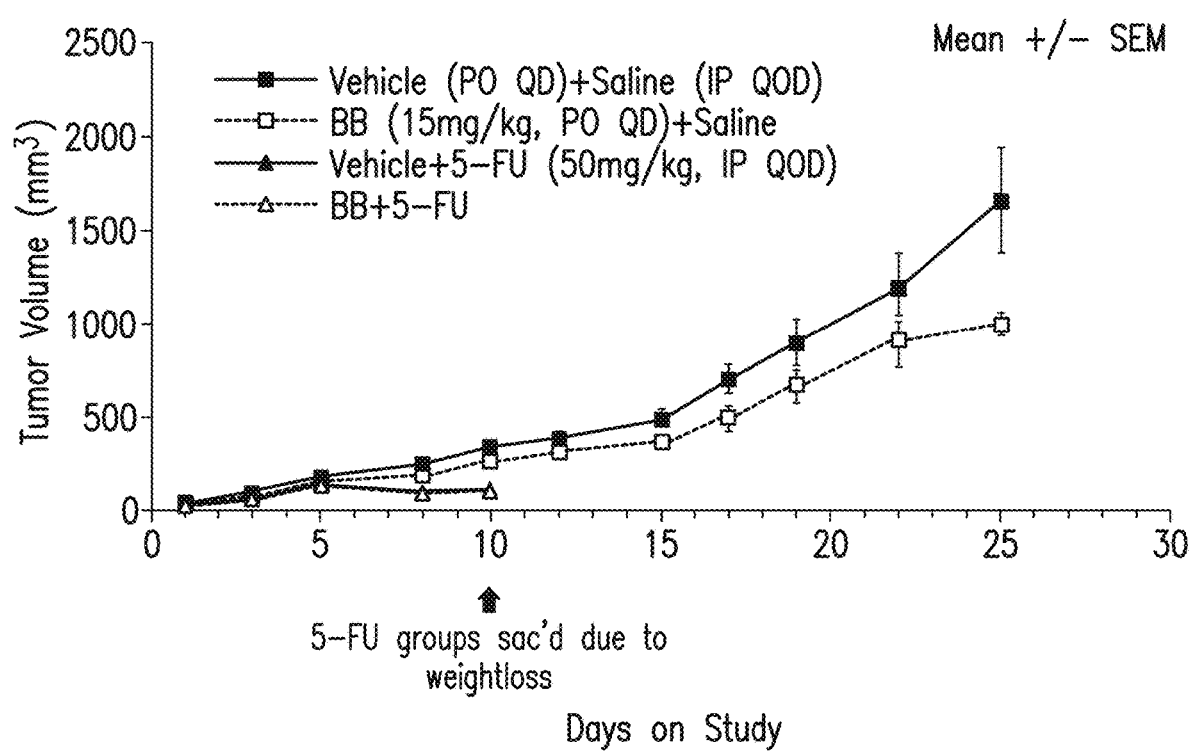
FIG. 35 shows that Compound BB alone achieves a reduction in tumor growth, while co-administration of Compound BB and 5-FU achieves a further reduction.
Figure 36:
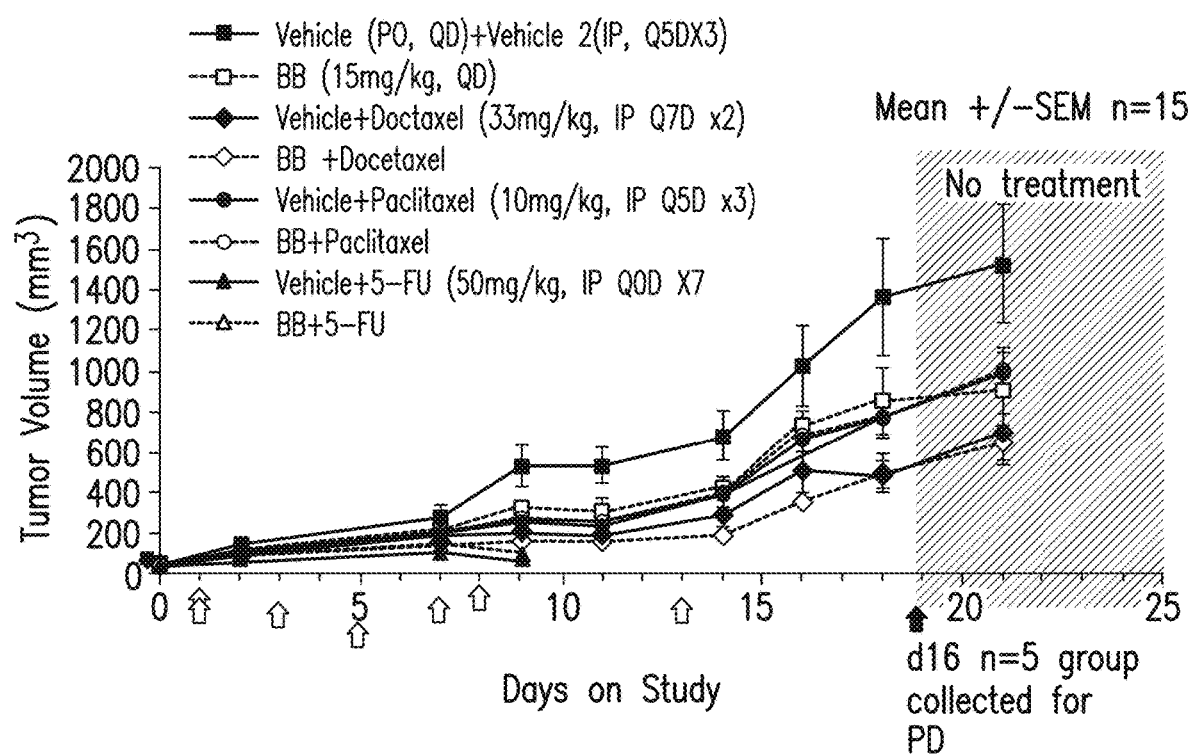
FIG. 36 shows that Compound BB demonstrated single agent activity in subcutaneous 4T1 breast cancer model, while co-administration with docetaxel, paclitaxel, or 5-FU achieved a further reduction in tumor growth.

FIG. 35 shows that Compound BB alone achieved a reduction in tumor growth, while co-administration of Compound BB and 5-FU achieved a further reduction. FIG. 36 shows that Compound BB demonstrated single agent activity in subcutaneous 4T1 breast cancer model, while co-administration with docetaxel, paclitaxel, or 5-FU achieved a further reduction in tumor growth.

In some cases, a tumor being treated with an immune therapy may undergo a transient increase in size, see 2008 ASCO Abstract #3120 Wolchok. However, this increase in size is not necessarily due to cancer cell growth. Instead, it can be due to tumor infiltration by anti-tumor lymphocytes.

To summarize, Compound BB showed activity in models for breast cancer, lung cancer, colon cancer, and glioblastoma.

Example 267: Pharmacodynamic Studies in Murine Syngeneic Breast, Lung, Colon Models The effect of Compound BB on solid tumor immune infiltrates was characterized.

Immunohistochemistry was performed to determine the distribution of immune cells within the tumor. In particular, CD11b myeloid cells were examined, as were regulatory vs. effector T cells (CD3, CD4, CD8, FoxP3). Briefly, IHC for CD11b or CD68+ was performed as follows. CD11b antibodies were available from Abcam, clone I-70, Catalog #ab 8878. CD68 antibodies were available from Abcam, clone FA-11, catalog #ab 53444. Tissues were fixed in cold methanol, air-dried, and then stained using a Res IHC Omni-UltraMap HRP XT protocol.

Figures 37A, 37B:
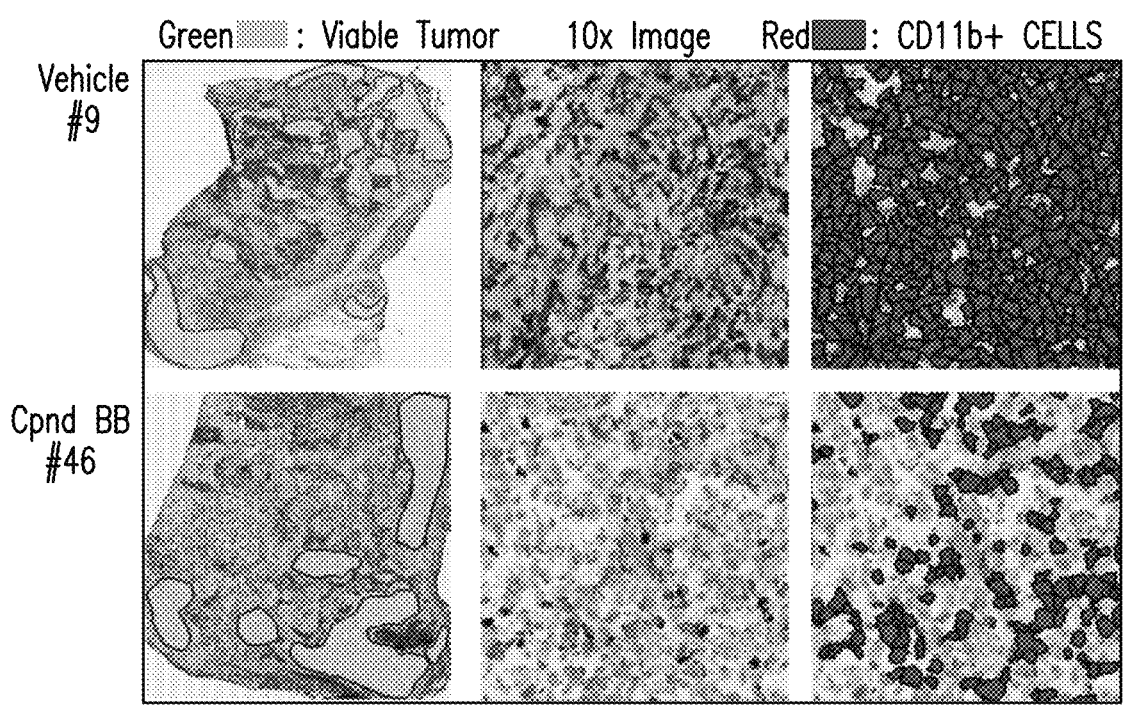
FIGS. 37A, 37B, 37C, 37D, 37E, 37F, 37G, and 37H show CD11b+ or CD68+ myeloid cell quantities in cancer tissue from Compound BB-treated or control mice.
Figure 37C:
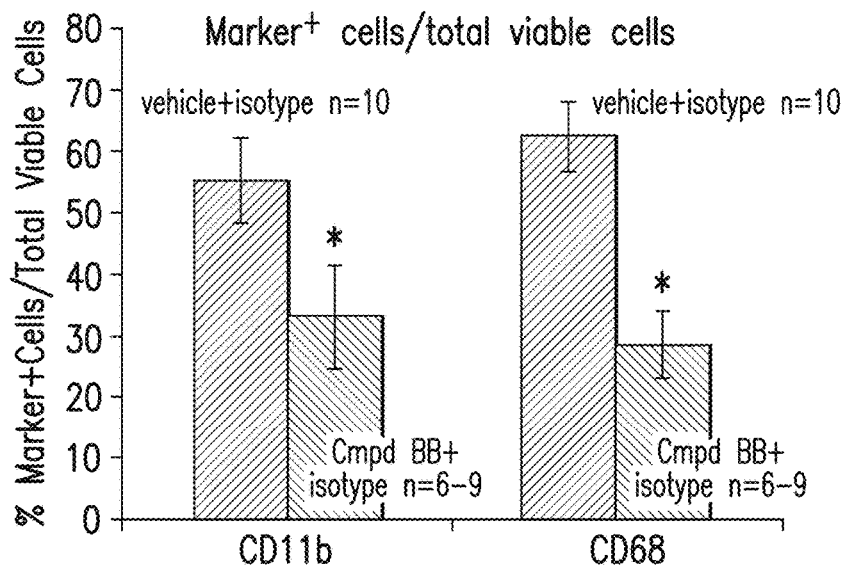
Figure 37D:
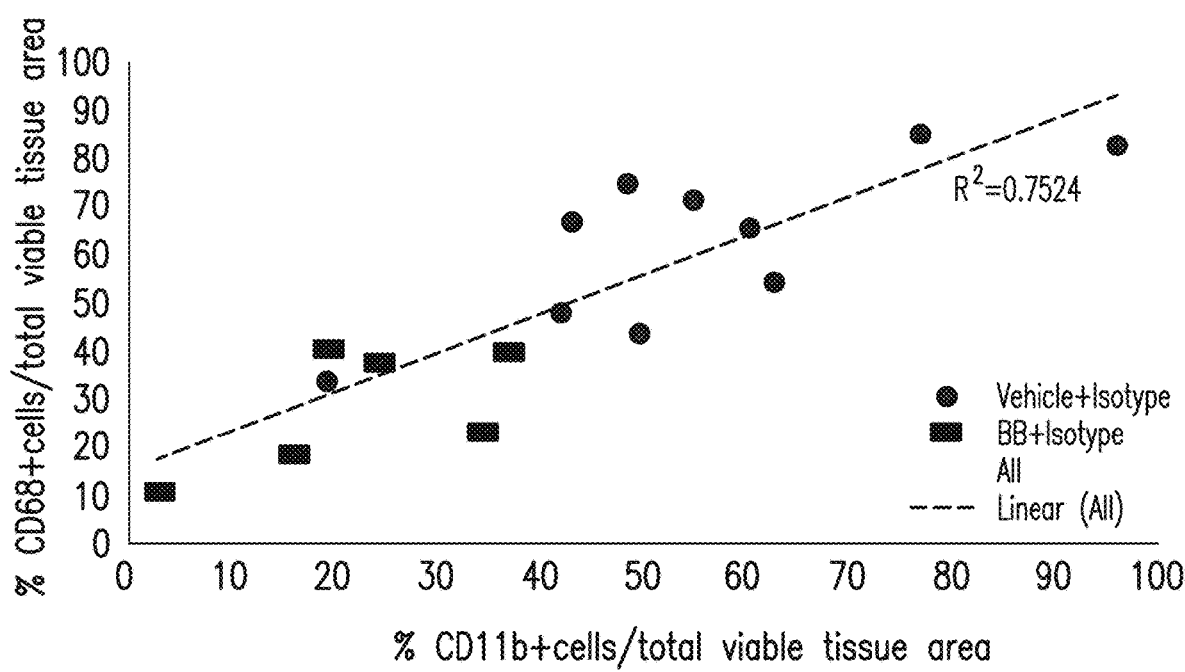
Figure 37E:
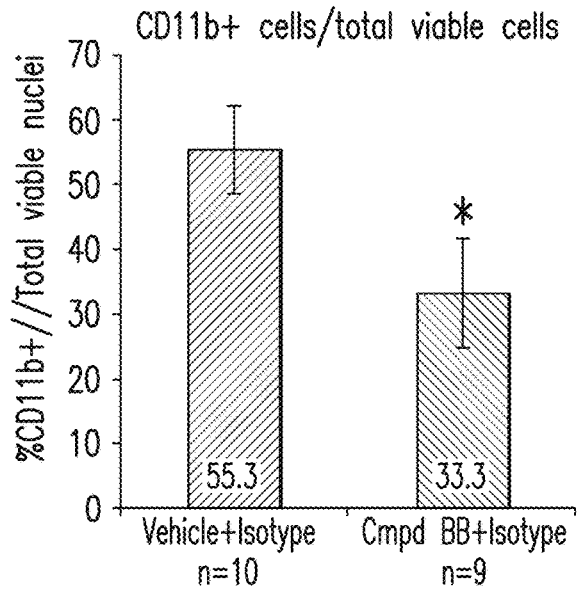
Figure 37F:
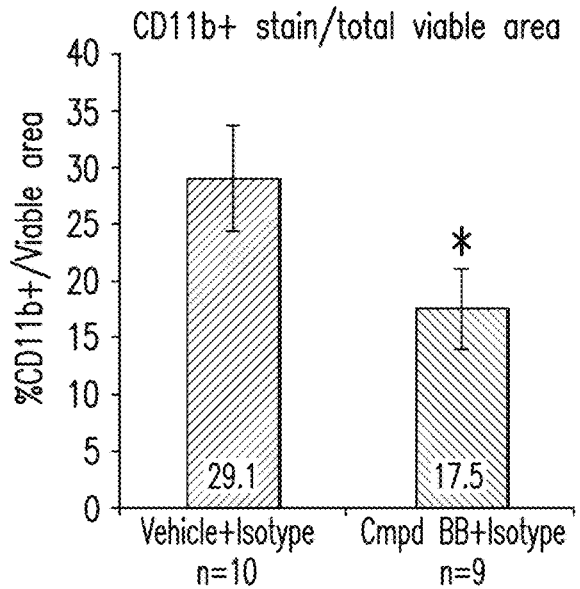
Figure 37G:
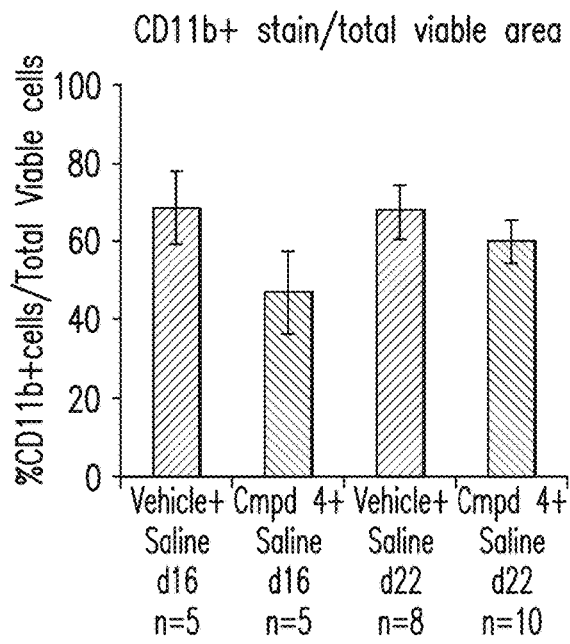
Figure 37H:
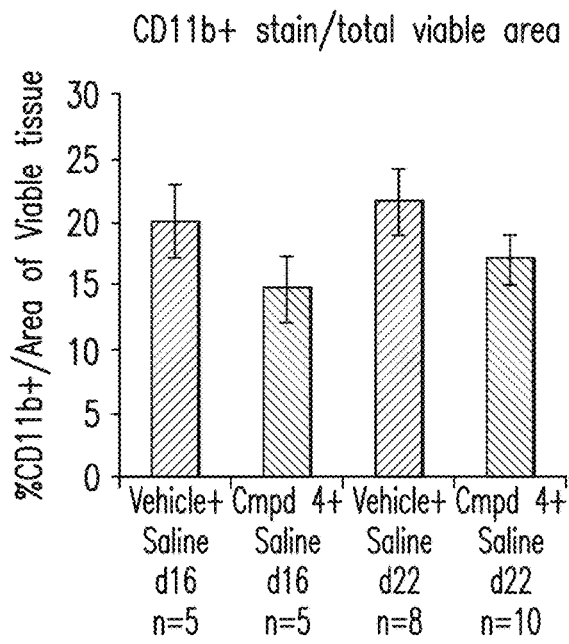

As a baseline, untreated murine breast cancer cells showed moderate levels of CD11b+ myeloid cells (data not shown). FIG. 37A shows that upon treatment with Compound BB, there was a decrease in CD11b+ myeloid cell staining in viable regions of 4T1 tumors treated with Compound BB compared to vehicle, on day 13 of study. Without being bound by a particular theory, the decrease in the pro-tumorigenic tumor associated myeloid cells can result in activation of cytotoxic T-cells and anti-tumor immunity. FIG. 37B shows image analysis of tumor tissue treated with Compound BB or vehicle, where Compound BB resulted in a decrease of CD11b+ cells in the tumor. FIG. 37C shows quantification of the percentage of CD11b+ cells or CD68+ cells in tumor tissue treated with Compound BB or vehicle. FIG. 37E and FIG. 37F show quantification of CD11b levels by IHC on tumor cells from 4T1-luc mammary fat pad tumors; Compound BB reduces the percentage of tumor cells observed. When the images were quantified as CD11b+ cells per total viable cells (FIG. 37E), a Student t-Test p-value of 0.0355 was obtained when comparing the Compound BB-treated cells to controls. When the images were quantified as CD11b+ stained area per total visible area (FIG. 37F), a Student t-Test p-value of 0.0441 was obtained when comparing the Compound BB-treated cells to controls. Thus, Compound BB causes a statistically significant reduction in CD11b+ cells in this assay. FIG. 37G and FIG. 37H show further IHC analysis showing how Compound BB affects the percentage of CD11b-stained cells. When the images were quantified as CD11b+ cells per total viable cells (FIG. 37G), a Student t-Test p-value of 0.0864 (d16) or 0.3967 (d22) was obtained when comparing the Compound BB-treated cells to controls. When the images were quantified as CD11b+ stained area per total visible area (FIG. 37H), a Student t-Test p-value of 0.2074 (d16) or 0.1538 (d22) was obtained when comparing the Compound BB-treated cells to controls. As FIG. 37D indicates, there is a strong correlation between CD11b+ and CD68+ myeloid cells in Compound BB-treated 4T1 tumors.

Flow cytometry was performed to obtain a more extensive cellular subset analysis. In particular, the study examined T cell vs. Myeloid cells, Myeloid cell subsets, Regulatory vs. effector T cells, and Tumor markers vs. WBC (e.g., PD-L1 expression on tumor).

Figure 38A:
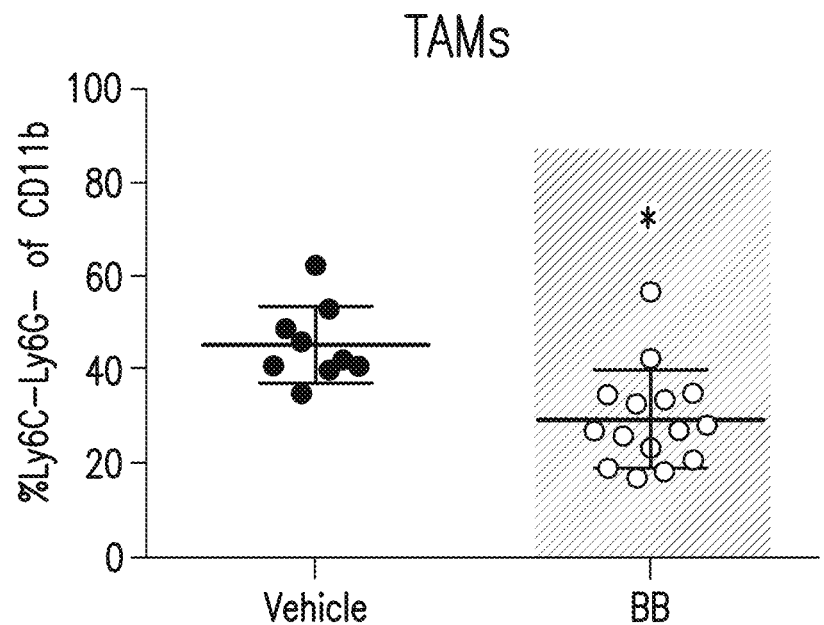
FIGS. 38A and 38B show the levels of different immune cells in treated and untreated tumors. Specifically.
Figure 38B:
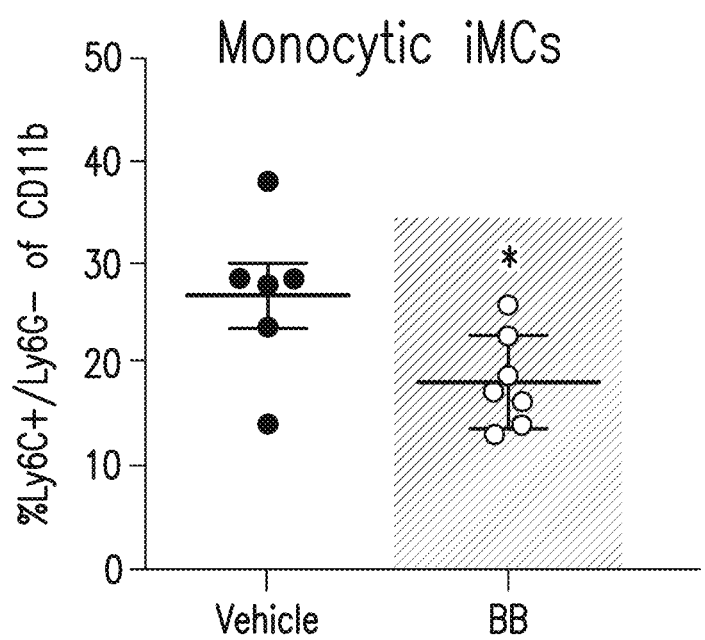
Figure 39:
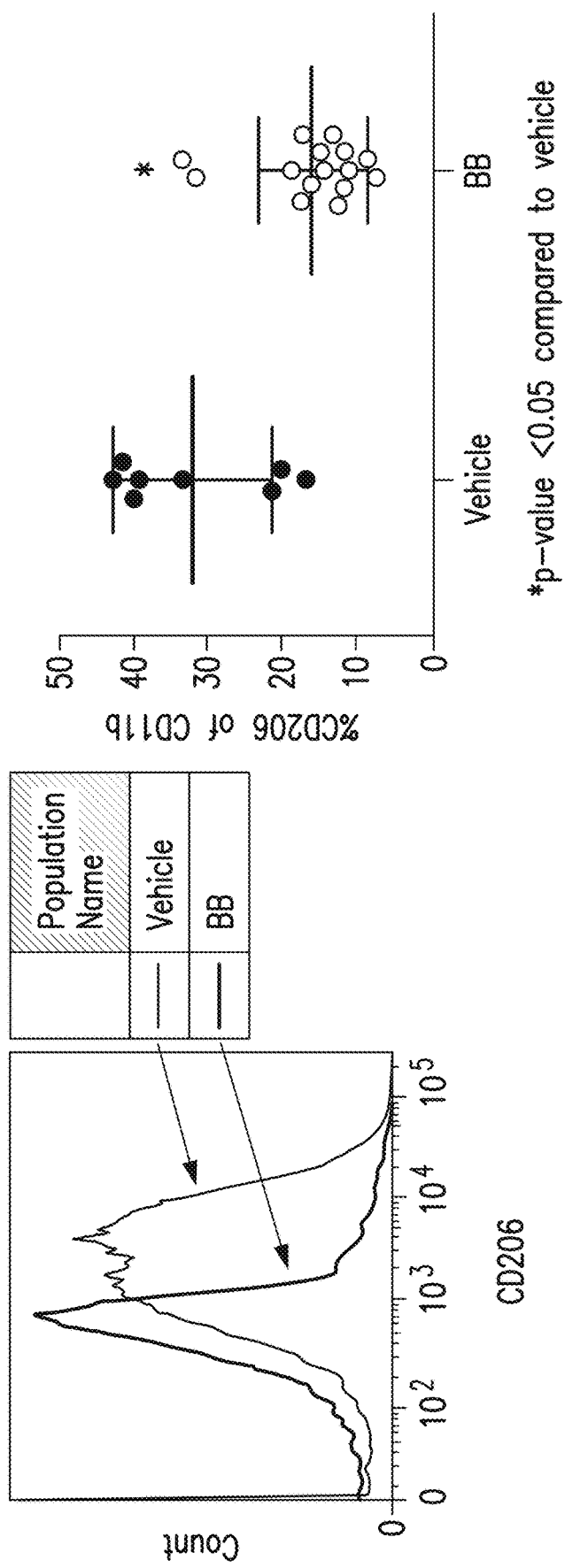
FIG. 39 shows that Compound BB reduces CD206+M2 polarized suppressive macrophages in LLC tumor brei model.

Different populations of tumor-associated myeloid cells can be identified by flow cytometry, e.g., monocytic immature myeloid cells (iMC),Granulocytic iMCs/Neutrophils, Tumor Associated Macrophages (TAMs), and Granulocytic MDSCs. The different populations, and panels for detecting MDSCs, are described in Cancer Discovery 2011; 1:54-67. Tumors may vary in their myeloid cell composition. In LLC tumor brei models treated with Compound BB, the number of infiltrating TAMs was decreased, as shown in FIG. 38A. This experiment indicates that Compound BB successfully reduced a type of immunosuppressive cells in the tumor microenvironment, supporting the model that Compound BB treats cancer by blocking immunosuppression at or near the tumor site. In a colon cancer model (CT26 subcutaneous tumors) monocytic iMCs were decreased by Compound BB as shown in FIG. 38B. FIG. 39 shows that Compound BB reduced M2 polarized suppressive macrophages. CD206 is characteristic of (pro-tumor) M2 macrophages or MDSCs, and CD206 staining was reduced in LLC tumor brei samples upon treatment with Compound BB, compared to a control.

In conclusion, Compound BB shows a pharmacodynamic effect on myeloid cells that is consistent with an anti-tumor activity. This effect was observed in 4T1-luc breast cancer cells, LLC-luc lung cancer cells, and CT26 colon cancer cells.

In addition RNA profiling was performed to determine the M1 vs. M2 status of differentiated macrophages, as well as broader immunosuppressive vs. inflammatory panel in whole tumors.

M2 macrophages can be produced as follows. Sacrifice mouse and collect femur and tibias. Immerse the bones on a petri dish in 70% ethanol for 1-2 min, then remove the bones and let the ethanol dry off for 3-4 min. Cut off a very small portion of the end of the bones to make an easy access for needle insert. Using a 27 g needle filled will media containing DMEM+10% FBS+1% Pen/Strep (complete DMEM), expel the bone marrow from both ends of the bones into a 15 ml petri dish. Pipette the bone marrow to dissociate the bone marrow cells. Centrifuge and add 1× Red Cell lysis buffer to the pellet. Let RBC lyse for 2 min then add equal amount of complete DMEM and centrifuge. The bone marrow from one mouse can be divided into 2 petri dishes containing 7 ml of BMM media (DMEM+20% FBS+1% Pen/Strep+50 ng/ml M-CSF). The day that the cells are plated onto petri dishes is day One. On day four add 3 ml BMM media to each plate. Add the M-CSF right before culturing. The cells are ready for polarization on day 6.

Next, the cells can be polarized. To harvest cells, remove the supernatant and wash once with 1×PBS. Add 4 ml Accutase detachment solution per petri dish. Leave for 5-10 min and collect cells and wash the petri dish with complete DMEM to obtain all the cells on the dish. A longer harvest time can increase yield. At this point cells can be plated for experiments.

1. Add DMEM+10% FBS+1% Pen/Strep to the cell pellets.
2. Plate cells into 12 well plates (1×10^6 cells/2 ml media per well) in complete DMEM containing 20 ng/ml M-CSF.
3. For M1 polarization add: 20 ng/ml IFNg+100 ng/ml LPS for 24 hrs
4. For M2 polarization add: 20 ng/ml IL-4 ng/ml for 48 hrs
5. Add the treatments/inhibitors at the same time.

6. Add test drug (for example test concentrations of Compound BB and +/−DMSO controls)

7. Harvest RNA.

RNA quantity and quality can be evaluated to normalize prior to RT PCR. qRT PCR is performed according to the manufactures recommendations using the RNA to CT one step kit from ABI and ABI taqman primer kits for relevant genes. If the cells are being analyzed by FACS, the differentiated cells are lysed/fixed (bd) after harvest, and frozen. Staining for mouse CD206 (Biolegend 161707) and ARG 1 (R and D systems IC5868F) is done in BD stain buffer with BSA.

RNA expression profiling was performed for immunophenotyping with a Tagman low density array (TLDA). Table 24 below shows a panel of genes that can be used to determine the phenotype of immunoinfiltrates.

TABLE 24

Genes that can be used to determine the phenotype of immunoinfiltrates

| Cell population | Inflammatory tumor killing | T-cell activation | Immunosuppressive | Tumor microenvironment & angiogenesis |
|---|---|---|---|---|
| CD45 | TNFa | IL6R | FOXP3 | PDGF |
| CD11c | IFNγ | CD62L | CTLA4 | VEGF |
| CD11b | IL12b | CD25 | INOS | VEGFR1 |
| CD3 | Granzyme B | CD80 | IDO | VEGFR2 |
| CD4 | | CD86 | TGFb | SMA1a |
| CD8 | | CD83 | IL10r | |
| CD68 | | CD137L | PD-1 | |
| | | GITRL | ARG1 | |
| | | CD40 | PDL1 | |
| | | OX40L | BACH2 | |
| | | OX40 | ADM | |

KPC Pancreatic Cancer cells were implanted into syngeneic animals which were subsequently treated with vehicle (n=13), Compound BB at 3 mg/kg (n=7), anti-PDL1 (n=9), or a combination of Compound BB and anti-PDL-1 (n=8). For mouse tumors, snap frozen samples were powdered with a Genogrinder at liquid nitrogen temperatures and RNA was isolated with Trizol. Next, the sample was cleaned-up using Qiashredder, and then using a RNeasy kit.

Data was analyzed as follows. CT values were used for analysis. For each sample Si and each gene, the following values were calculated:

$$dCT(Si, gene) = CT(Si, gene) - CT(Si, ACTB)$$

$$ddCT(Si, gene) = dCT(Si, gene) - median(dCT(vehicle\ treated\ samples, gene))$$

$$RQ(Si, gene) = 2^{\wedge}(-ddCT(Si, gene))$$

This produced a matrix of RQ values: 48 genes (rows)×39 samples (cols).

Figure 40:
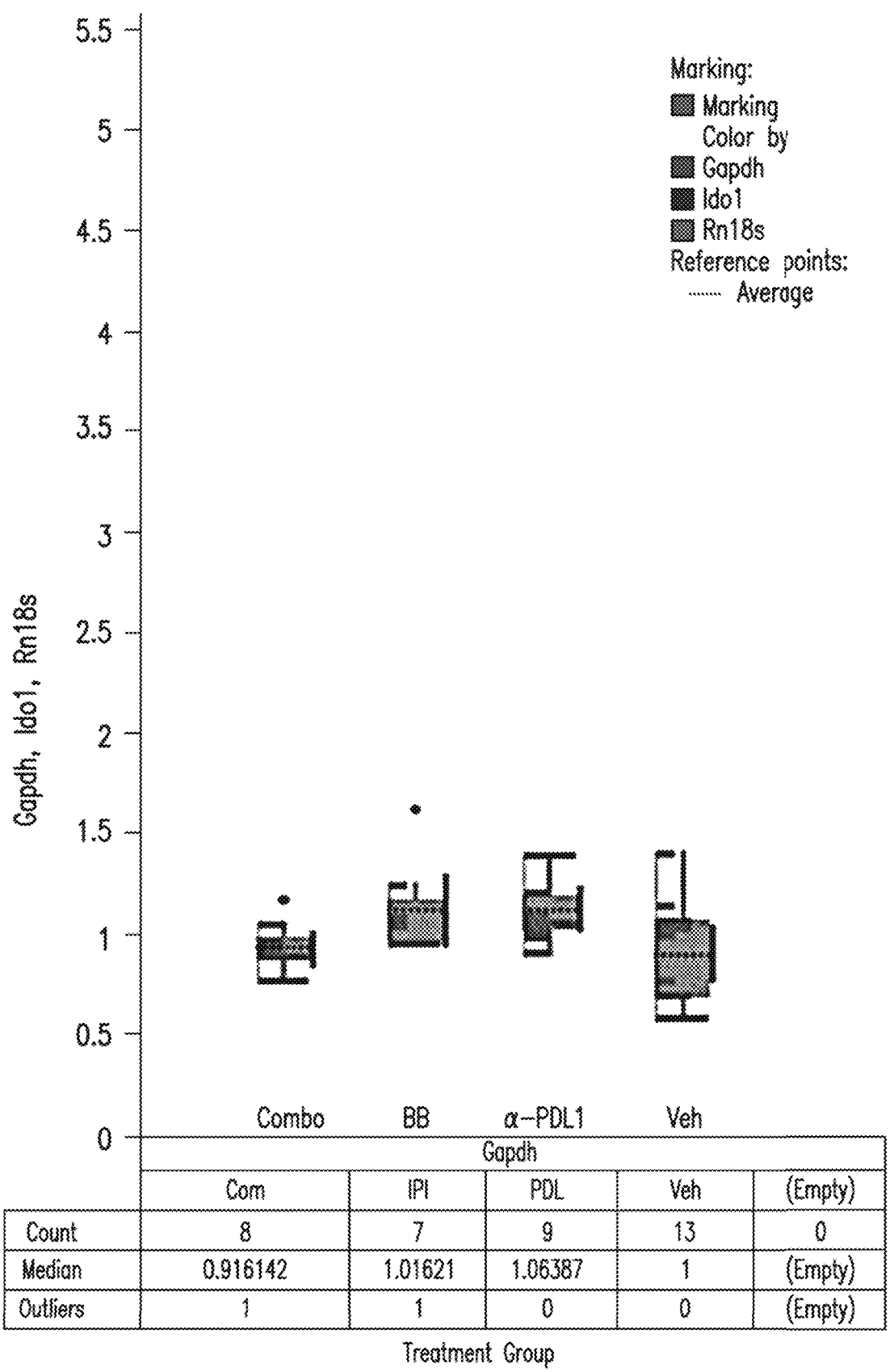
FIG. 40 shows normalization to β-actin gives stable expression of GAPDH and 18S genes.
Figure 40:
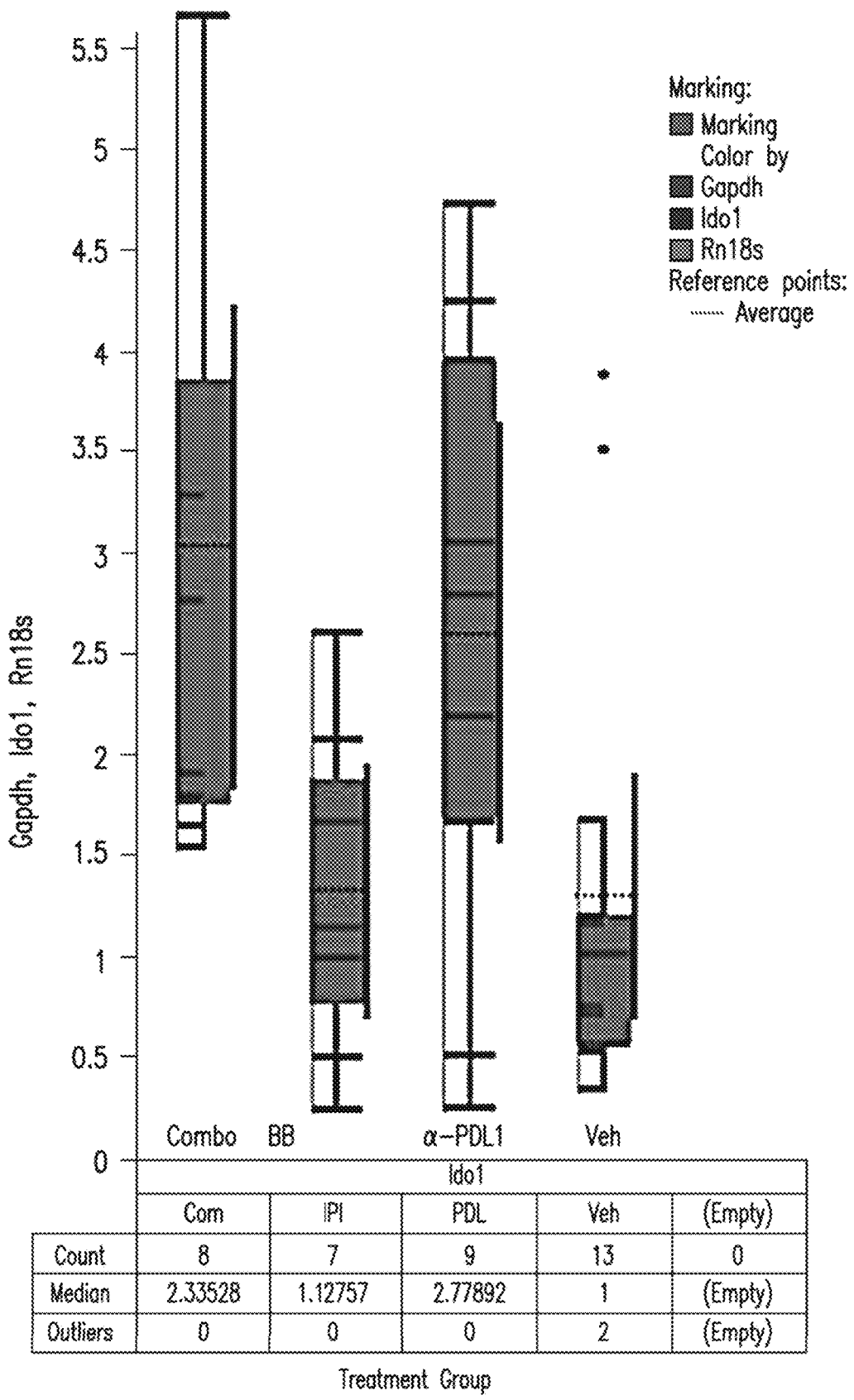
Figure 40:
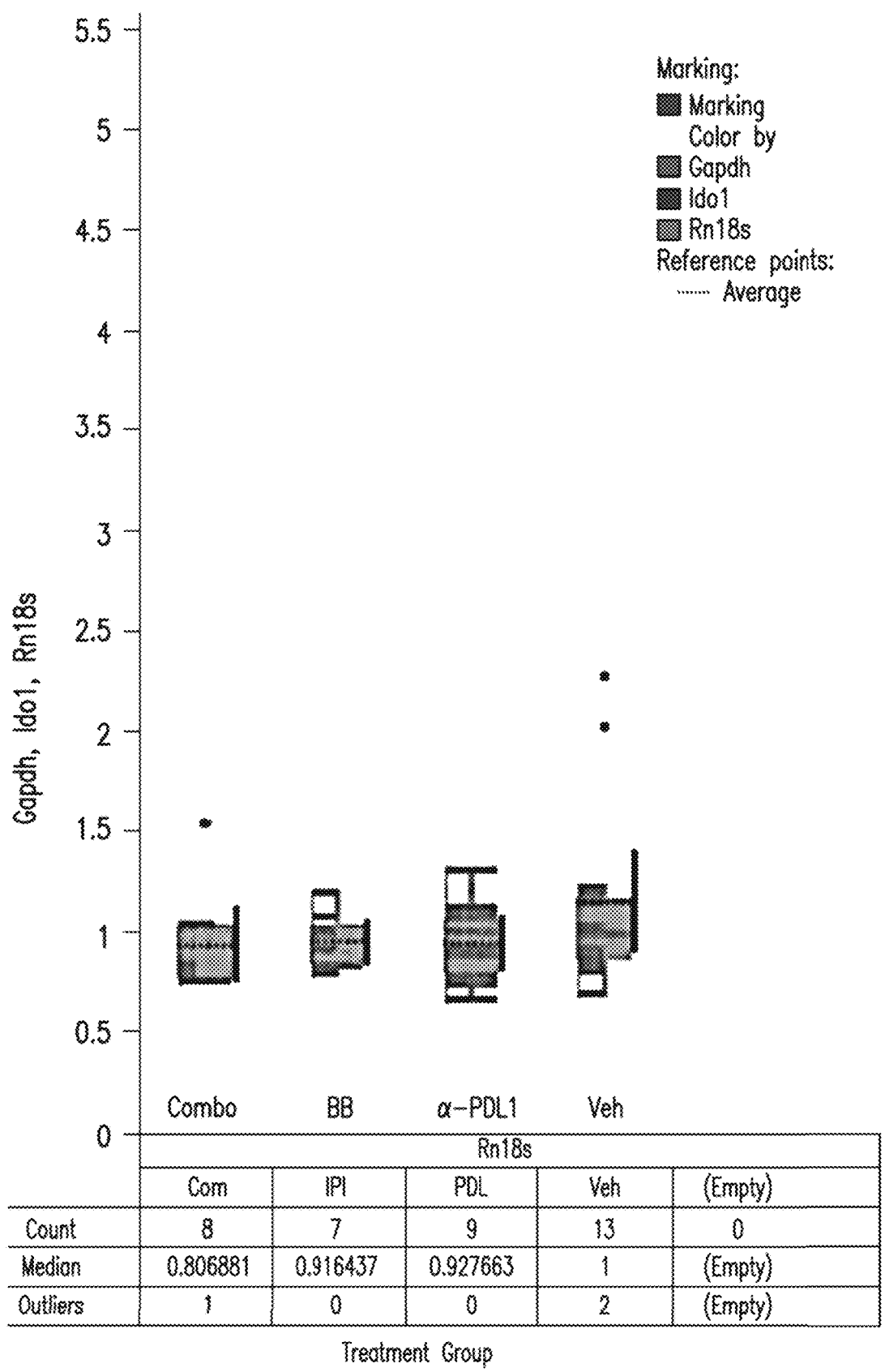

Four rows were added to the RQ matrix to represent the treatment with vehicle, Compound BB, anti-PDL1, or a combination of Compound BB and anti-PDL-1. The analysis used R package Non-negative Matrix Factorization (NMF) with rank=3 and the "lee" algorithm. FIG. 40 shows normalization to β-actin gives stable expression of GAPDH and 18S genes.

The analysis shows that M2 macrophage markers VEGF and ARG-1 trended towards reduction by Compound BB with or without PDL-1 antibody. This result is consistent with Compound BB inhibiting the differentiation or migration of M2 macrophages.

Figure 41:
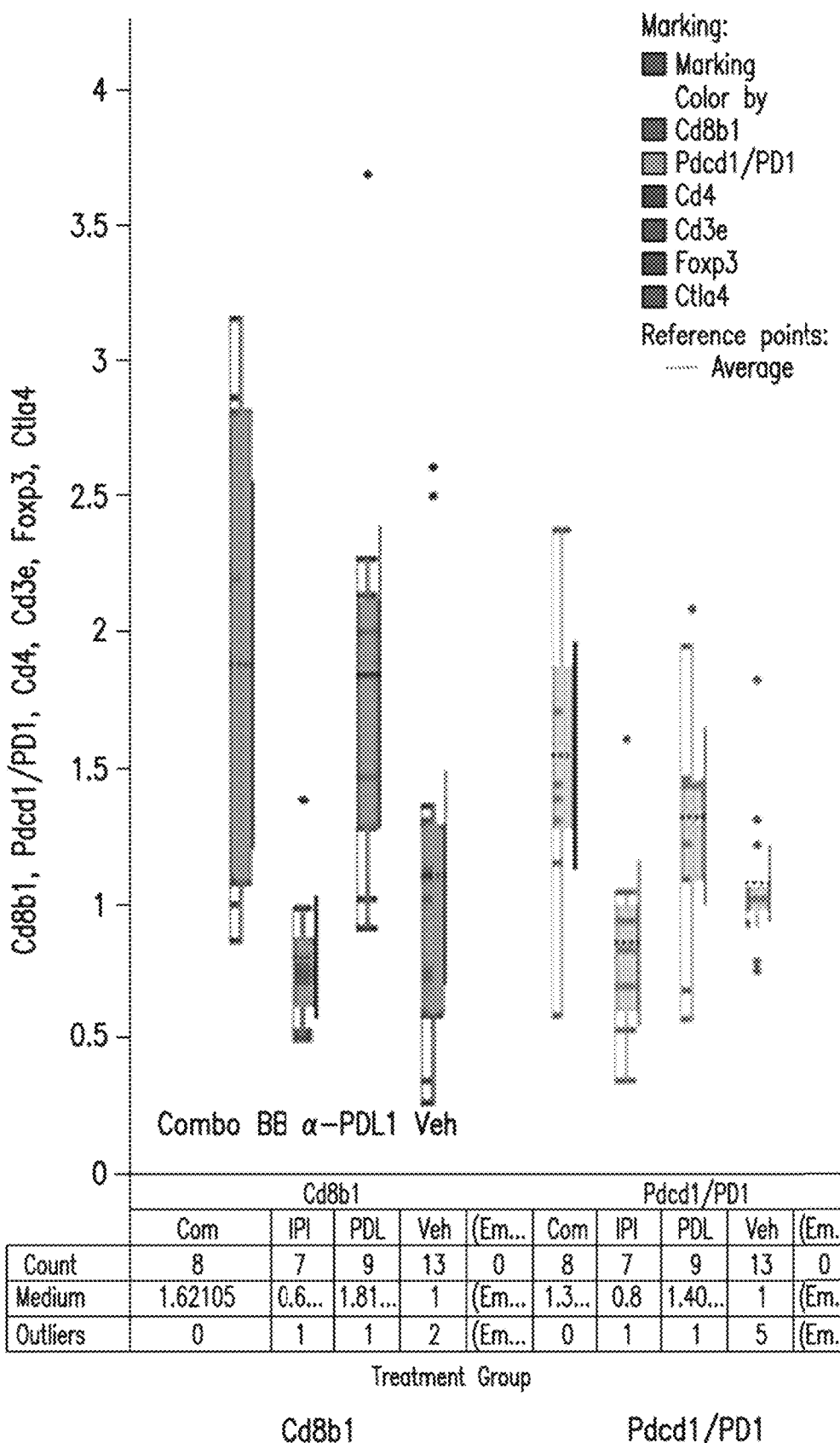
FIG. 41 shows the effect of Compound BB on markers Cd8b1, Pdcd1/PD1, Cd4, Cd3e, Foxp3, and Clla4 with or without PDL-1 antibody.
Figure 41:
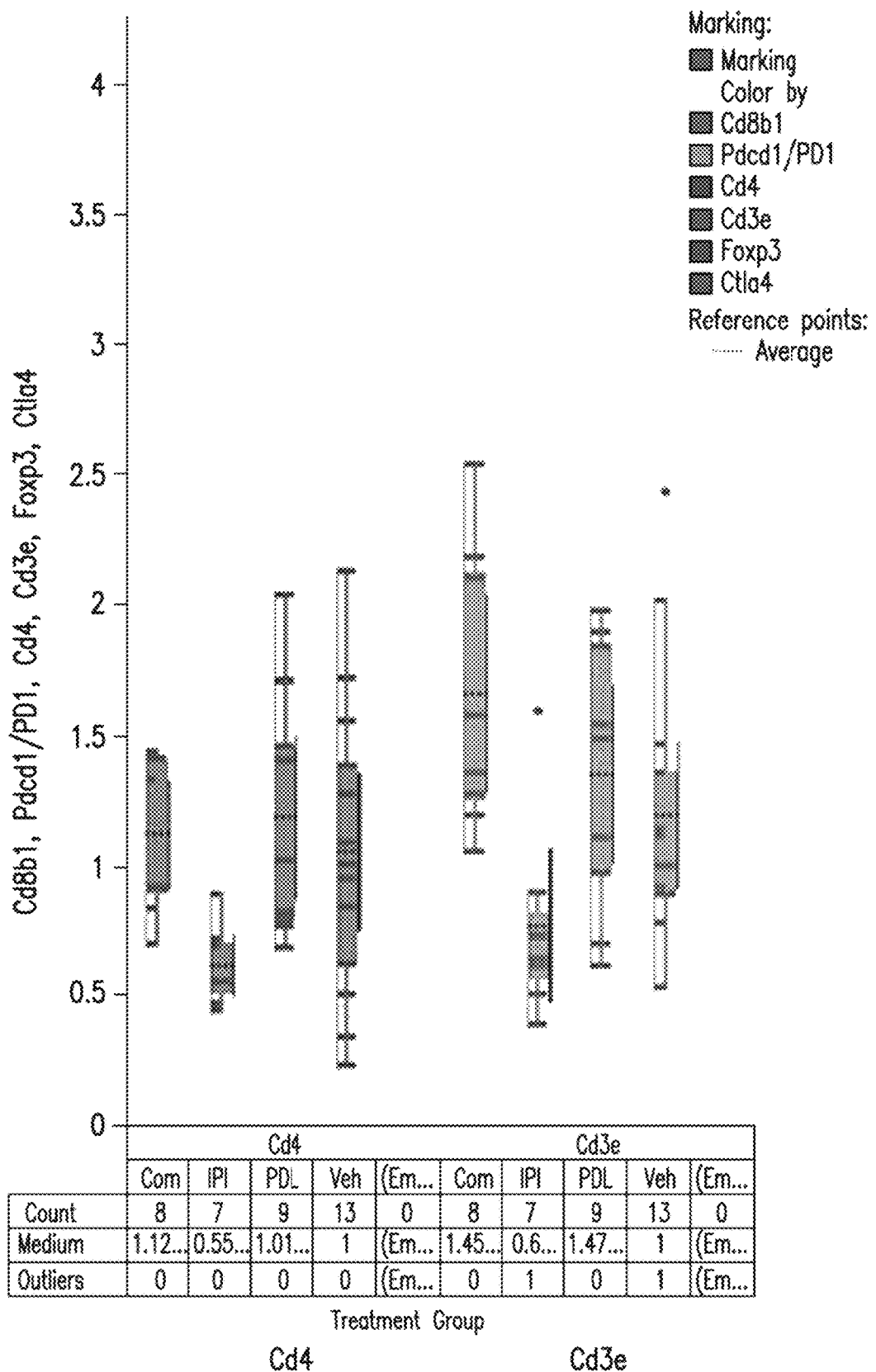
Figure 41:
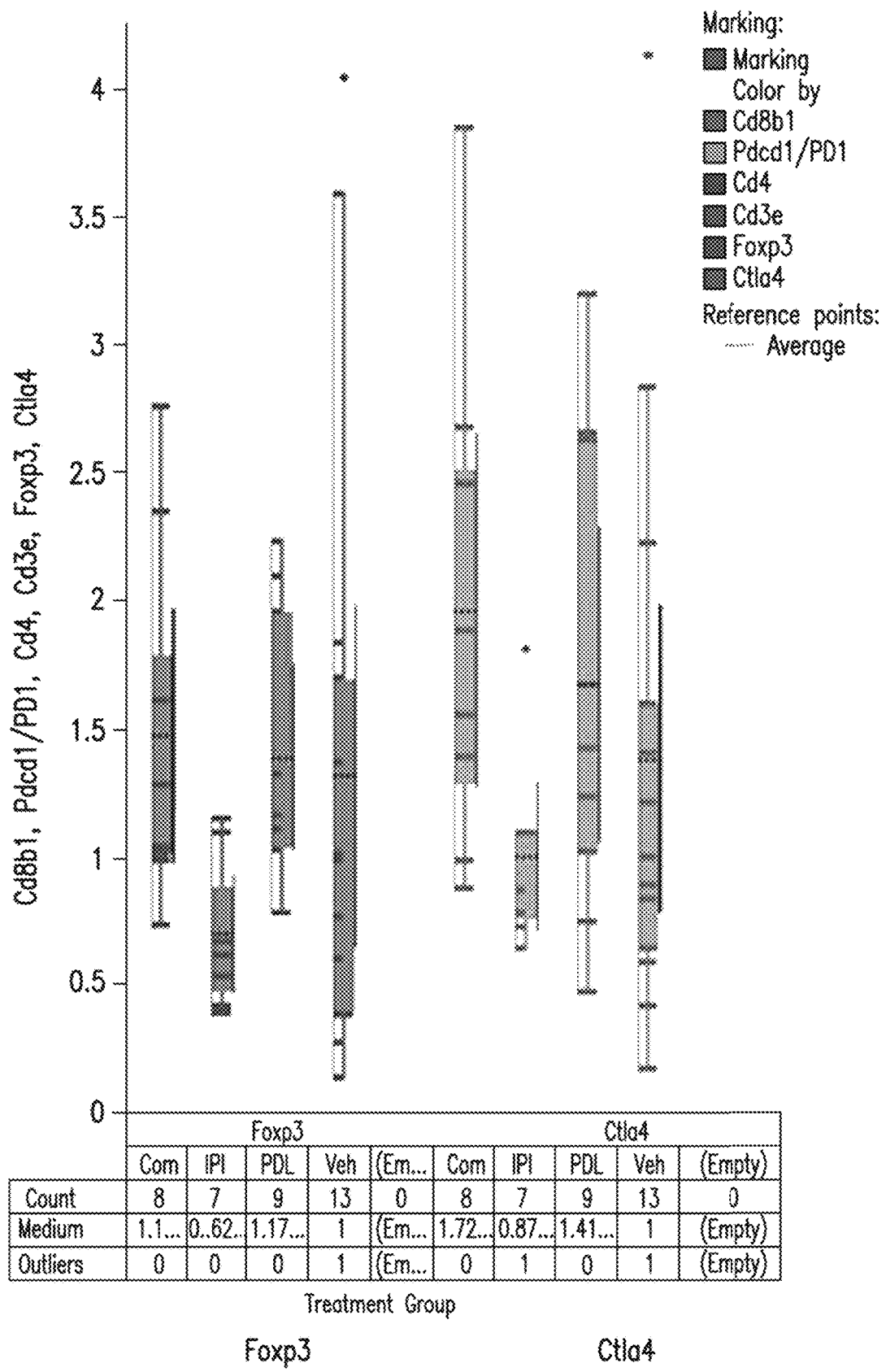
Figure 42A:
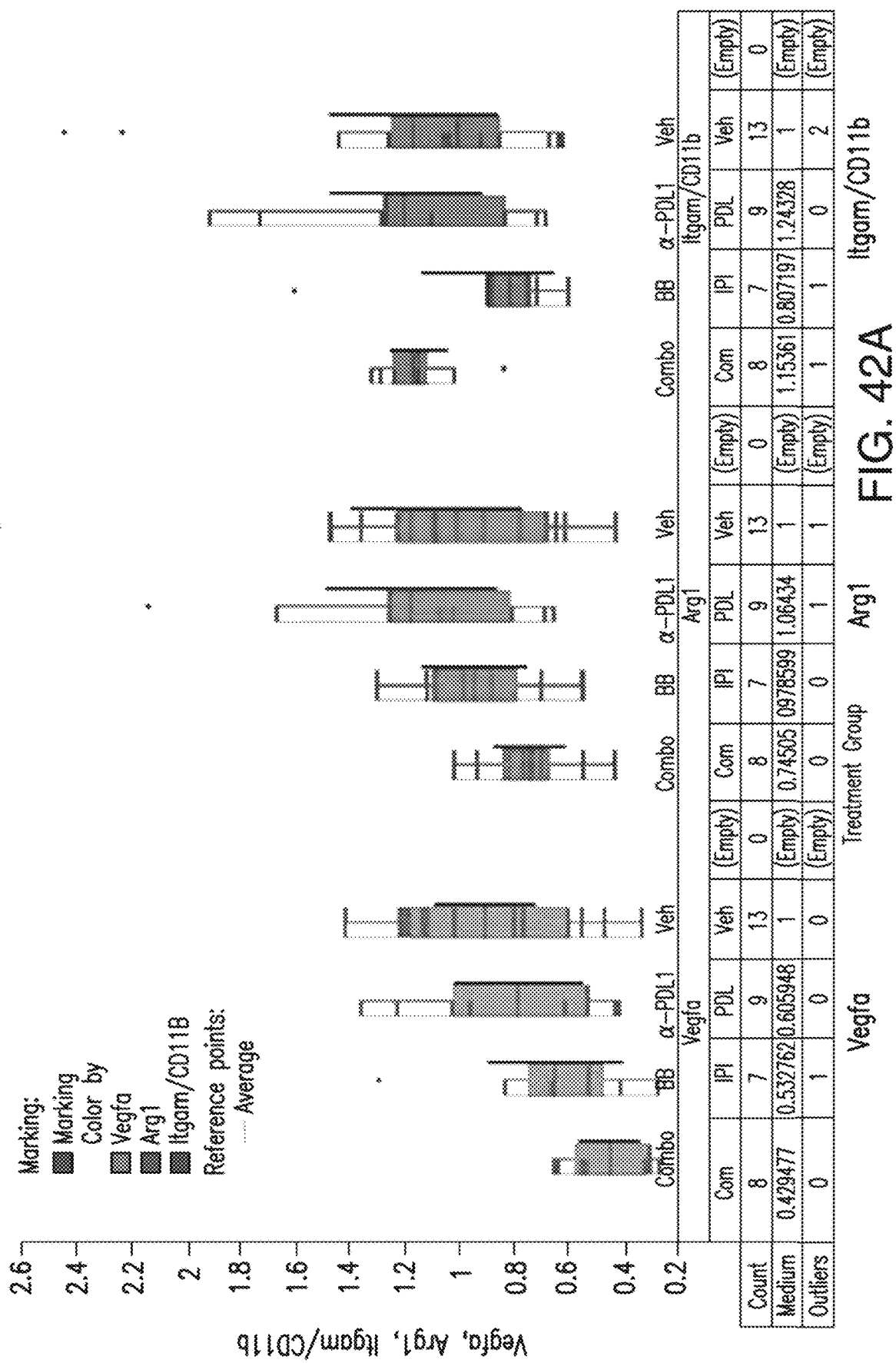
FIG. 42A shows M2 macrophage markers VEGF and ARG-1 are reduced by Compound BB with or without PDL-1 antibody.
Figure 42B:
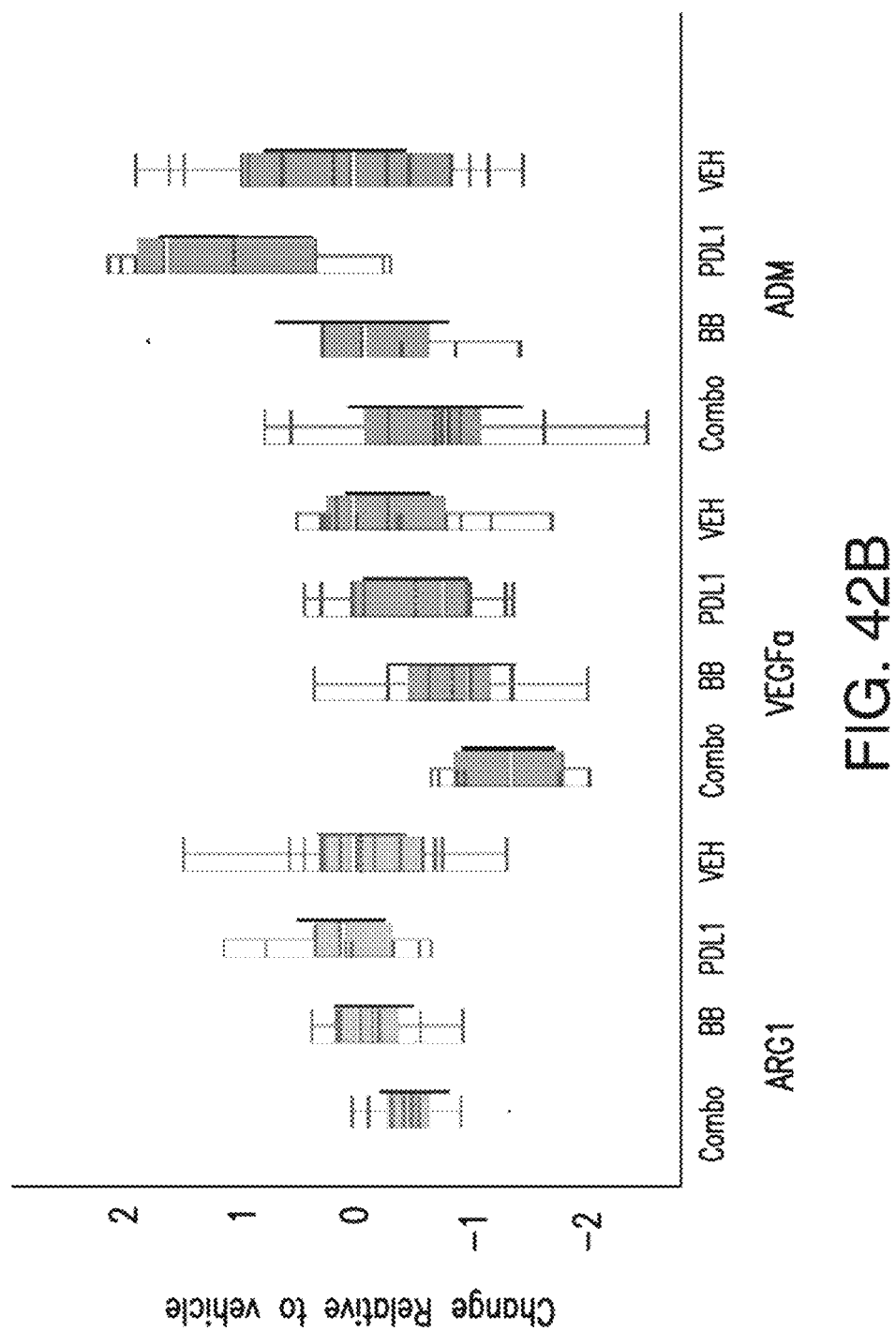
FIG. 42B shows the effect of Compound BB with or without PDL-1 antibody on M2 macrophage markers ARG1, VEGFa and ADM.

The analysis indicates that Compound BB alone resulted in a trend in lower T regulatory and T effector genes, and a decrease in Dentritic cell activation markers. A PDL1 antibody in combination with Compound BB did not exhibit these effects. It also indicates that Compound BB alone or in combination with PDL1 antibody yielded a decrease in the M2 genes ARG-1, VEGF, i.e., Compound BB seems to reduce the level of M2 cells in the sample, for example, by blocking differentiation of bone marrow cells into M2 cells. As a control, PDL-1 antibody resulted in the expected induction of pro-inflammatory genes. FIG. 41 shows the effect of Compound BB on markers Cd8b1, Pdcd1/PD1, Cd4, Cd3e, Foxp3, and Clla4 with or without PDL-1 antibody. FIG. 42A shows M2 macrophage markers VEGF and ARG-1 are reduced by Compound BB with or without PDL-1 antibody. FIG. 42B shows the effect of Compound BB with or without PDL-1 antibody on M2 macrophage markers ARG1, VEGFa and ADM.

Example 268: Physical and Pharmacokinetic Properties of Compound BB

The phyiscochemical properties of Compound BB are drug-like, and suitable for use of the compound as a drug. For instance, Compound BB has a molecular weight of 528.6 Da, a c Log P of 4.0, a stability in 38° simulated gastric fluid of >4 hours, and a pKa that shows no ionization from pH 3-10.

ADME characteristics of Compound BB were examined, and are shown below in Table 25.

TABLE 25

ADME characteristics of Compound BB

| | |
|---|---|
| Papp [10-6 cm/s] @ 10 uM | High |
| PGP efflux @ 10 uM | No |
| PGP Inhibition @10 uM | 98% (IC$_{50}$ < 1 uM) |
| PPB % free @ 1 uM | 1.0-5% (all species) |
| M, C, D, H Mic (t$_{1/2}$ min) | >120 all (incl rat) |
| M, C, D, H Hep (t$_{1/2}$, min) | >240 all (incl rat) |
| GSH Adduct Formation | Neg |
| Human hep viability IC$_{50}$ | 10-25 uM |
| Rev Cyp Inhibition IC$_{50}$ | All Cyps >10 uM |
| Time dep Cyp Inhibition @ 10 uM | Neg |
| Cyp Induction @ 10 uM | Neg (activity and mRNA) |
| Mouse PK AUC$_{last}$ @ 10 mg/kg in NMP solution (ng*h/mL) | 83742 |

Compound BB exhibits high cellular membrane permeability. In addition, the compound does not substantially inhibit CYP. Compound BB achieves high oral bioavailability in rodent and non-rodent animal species. Compound BB achieves a high volume of distribution and appears to readily distribute into cells/tissues. It also has high metabolic stability. This stability translates to low clearance and a long half-life in vivo. These properties indicate the compound's suitability for in vivo administration.

Compound BB appears to be an inhibitor of P-GP (P-glycoprotein 1). In some embodiments, a PI3K-γ inhibitor such a Compound BB is administered to a patient in combination with a second therapeutic that is a P-gp substrate. Without being bound by a particular theory, the P-gp inhibitor could help maintain levels of the P-gp substrate in tumors overexpressing the P-gp transporter.

The oral half-life of Compound BB is about 3.3 hours in rat, about 7.1 hours in dog, and about 10.2 hours in monkey. Based on this data, the oral half-life in humans is expected to be 10-13 hours.

There is low potential for reversible inhibition of main Cytochrome P450 isoforms. Compound BB is not expected to form reactive metabolites.

Figure 43:
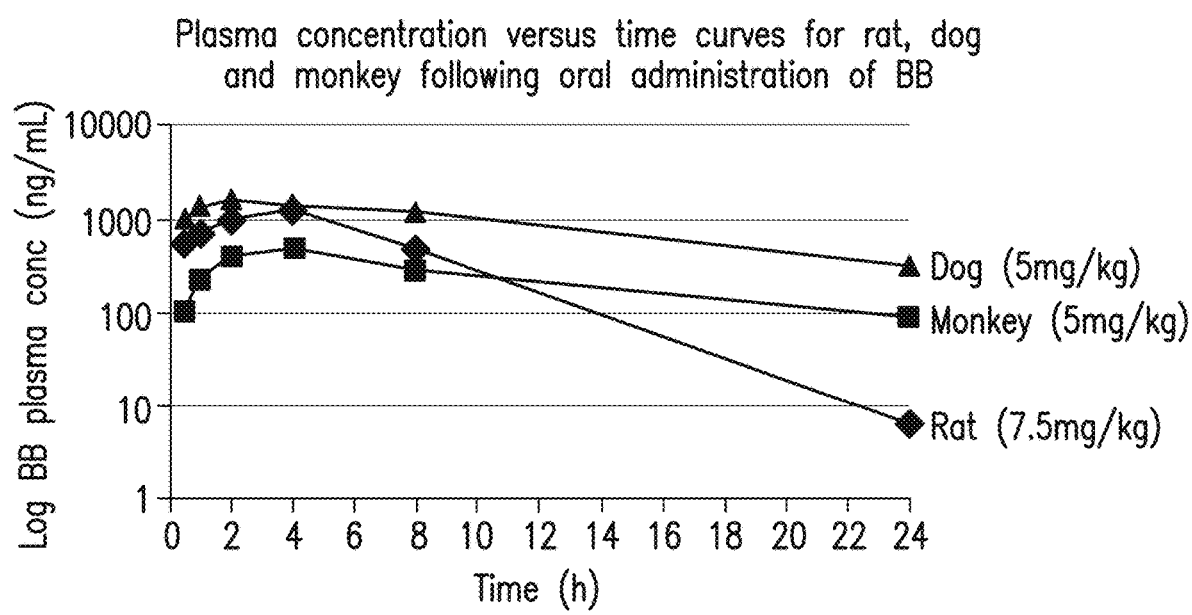
FIG. 43 shows that Compound BB oral exposure is high in the rat, dog and monkey.

In one exemplary study, the plasma concentrations of Compound BB within 24 hours following oral administration in rat (7.5 mg/kg), dog (5 mg/kg), and monkey (5 mg/kg) were measured and the results are shown in FIG. 43. Compound BB's oral exposure is high in rat, dog and monkey. Good oral bioavailability and low clearance in rodent and non-rodent animal species results in high oral exposure.

Figure 44:
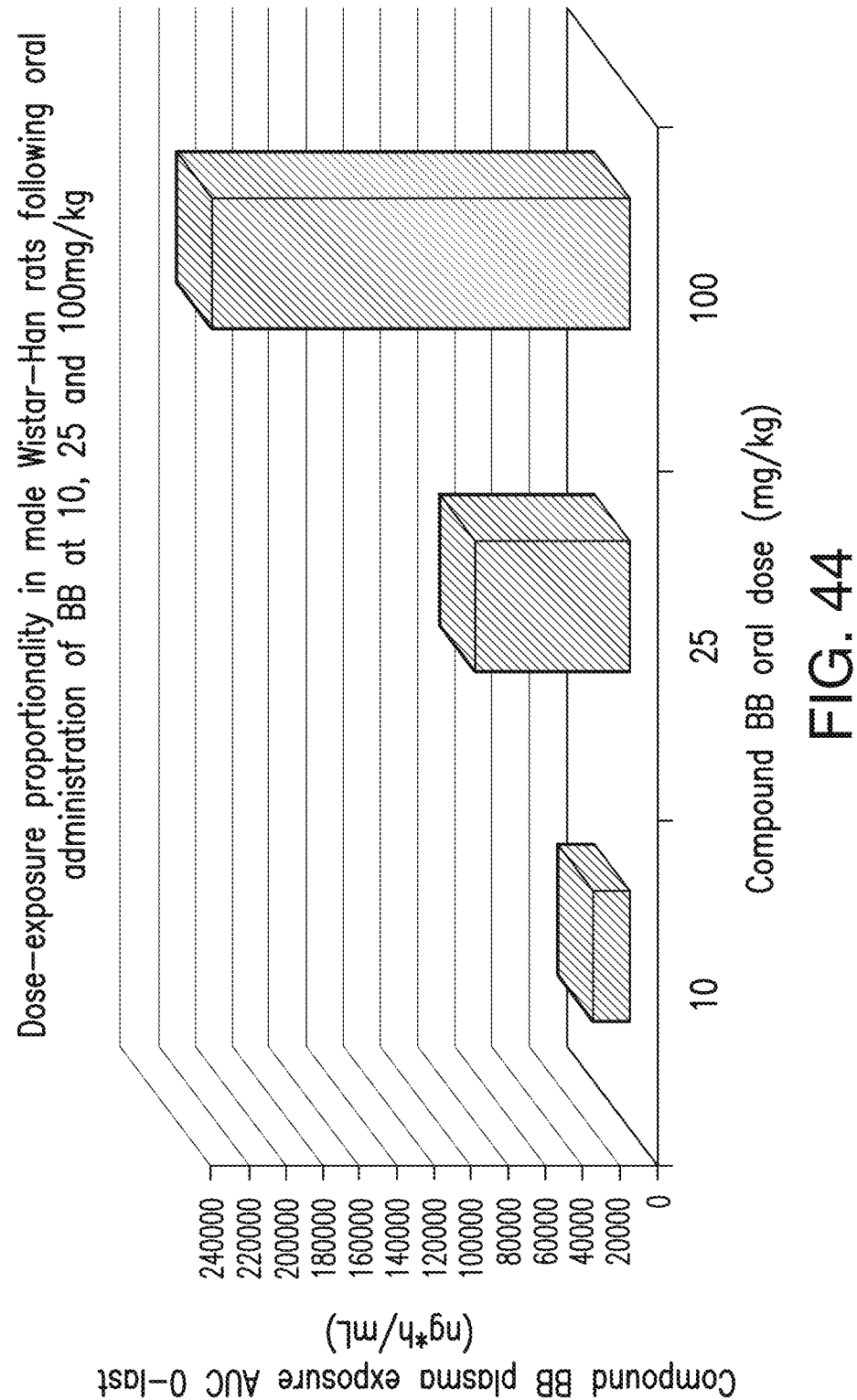
FIG. 44 shows that Compound BB exhibits dose-exposure proportionality.

In another exemplary study, the plasma exposures of Compound BB in rats following oral administration at 10, 25, and 100 mg/kg were measured (by AUC 0-last) and the results are shown in FIG. 44. The increase in exposure of Compound BB is greater than or equal to the increase in dose. Thus, the compound exhibits good dose-exposure proportionality.

Example 269: Toxicology Studies of Compound BB

In vitro toxicology studies of Compound BB showed that the compound is expected to have very low toxicity. A target organ toxicity (TOT) study was performed in rats. The rats were dosed orally with Compound BB for 10 days. This study assessed clinical observations/mortality, body weights, clinical pathology, toxicokinetics, and histopathology of select tissues. The tissues studied were: Adrenal gland, Bone marrow (femur), Brain, Small Intestine (including GALT), Heart, Large Intestine, Kidney, Stomach, Liver, Pancreas, Spleen, Testis, and Thymus. Doses were selected based on repeat-dose tolerability study, PK and plasma protein binding, and cellular $IC_{50}$s for PI3K isoforms. The doses selected were: high-dose: 50 mg/kg/day, expected to inhibit α, β, δ, and γ PI3K isoforms; Mid-high dose: 20 mg/kg/day, expected to inhibit β, δ, and γ PI3K isoforms; Mid-low dose: 7.5 mg/kg, expected to inhibit γ PI3K isoform only; and Low-dose: 1 mg/kg/day, expected to inhibit γ PI3K isoform only. The formulation used was Formulation: 0.5% CMC, 0.05% Tween in water with Compound BB.

The TOT study indicated that Compound BB was well-tolerated for 10 days. No mortality or clinical signs were observed at any dose level. There was a minimal decrease in body weights of high dose animals (5-8%) compared to vehicle. As to clinical pathology, minimal changes in neutrophils, lymphocytes, and fibrinogen, (primarily in 20 and 50 mg/kg/day groups) were observed. In terms of histopathology, no significant gross changes were observed. In the spleen, there was minimal/mild lymphoid depletion of the marginal zone and periarteriolar lymphoid sheaths (PALS) primarily at doses ≥20 mg/kg/day, and in the thymus, there was minimal/mild lymphoid depletion in males treated at ≥7.5 mg/kg/day and in females at 50 mg/kg/day.

Figure 45:
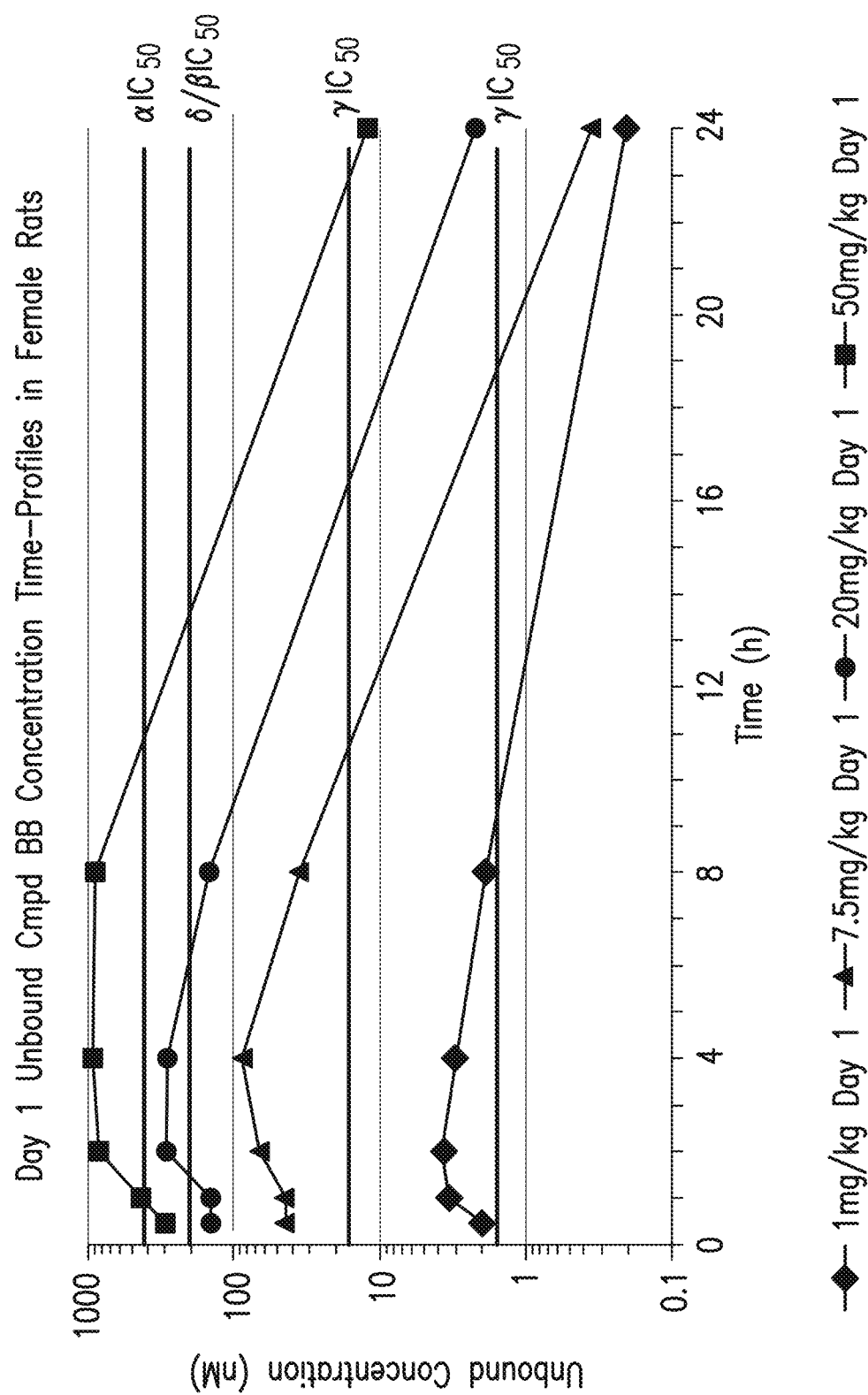
FIG. 45 shows the concentrations of unbound Compound BB in a toxicity study.

FIG. 45 shows the concentrations of unbound Compound BB, in a TOT study. Free Compound BB reaches concentrations that are expected to inhibit PI3K isoforms. Evaluation of the PI3K isoform inhibition data relative to free plasma concentrations demonstrates that the doses that were administered inhibited the desired isoforms. Specifically, the 1 and 7.5 mg/kg/doses achieved high enough concentrations to selectively inhibit PI3K γ without substantially inhibiting PI3K α, β, or δ.

Example 270: Effect of the Tumor Microenvironment on Cancer Cell Survival

Figure 46:
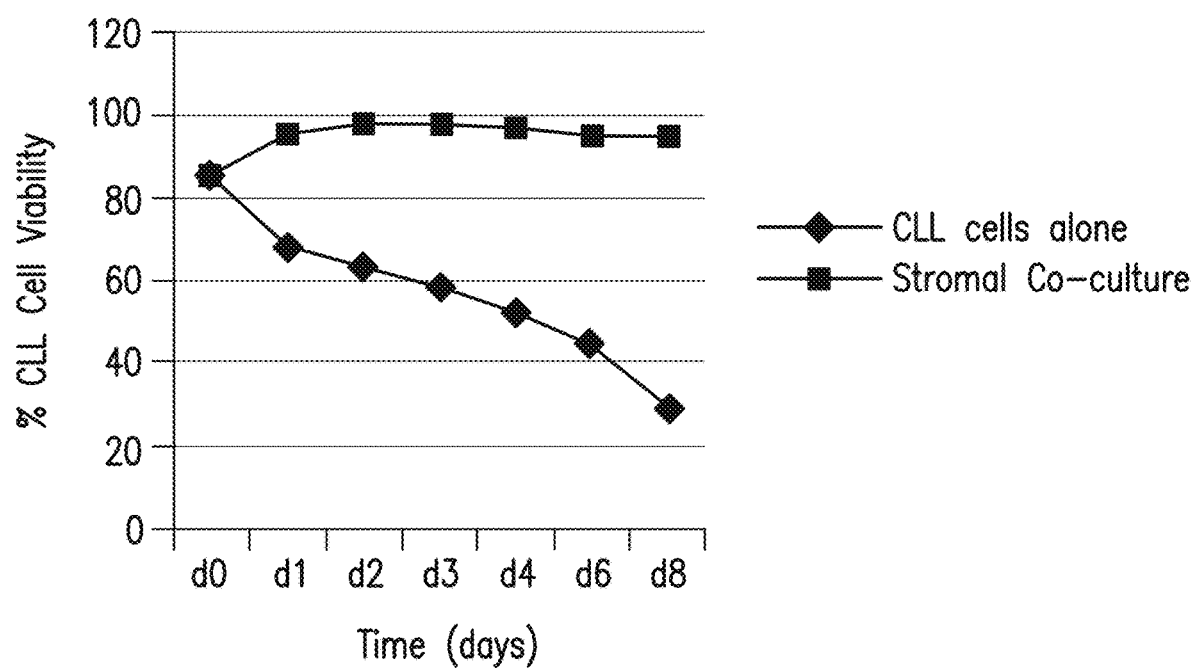
FIG. 46 shows the survival of primary human CLL cells with and without co-cultured stromal cells.

Bone marrow stromal cells protect CLL cells from spontaneous apoptosis in vitro. This is shown in an experiment where CLL cells were added to confluent stroma, and then CLL viability was assessed over time. FIG. 46 shows that CLL cells have a higher survival rate when co-cultured with stromal cells. This experiment suggests that stromal cells send pro-survival signals to CLL cells, and these signals are mediated by PI3K. Experiments with selective inhibitors for PI3K-δ and PI3K-γ indicates that TME-induced CLL proliferation is dependent on PI3K-δ (data not shown).

This signaling also seems to occur in vivo, as there is an increase in PI3K signaling in proliferation centers of human CLL lymph nodes, as measured by high levels of pS6. Balakrishnan et al., ASH 2013. In addition to pS6, which is an indicator of AKT activation, these proliferation centers have high levels of T-cells, as indicated by CD3 staining (data not shown). High levels of proliferation are indicated by the presence of Ki-67.

Example 271: Developing a Panel of Genes for Identifying MDSCs

The goal of this study is to develop a myeloid cell panel for dissociated tumor cells to measure infiltrates for TAMs and MDSCs. 4T1 tumors were assayed by FACS for the presence of various immune cells. The study quantified the level of Ly6C and Ly6G in the population. The study indicated that 4T1 cells are much more enriched for granulocytic (Ly6C+, Ly6G+) than LLC tumor brei models (data not shown). FACS analysis also showed that In vitro differentiated M2 (or M1) cells have an "TAM" MDSC phenotype (data not shown).

Potential markers for a myeloid cell panel for M1 cells includes: M1 CD68 MHCII, CD68 iNOS (PLoS One, 2013; 8(12): e79769).

Potential markers for a myeloid cell panel for M2 cells includes: CD68+CD163+ or CD68+ VEGF+ (PLoS One, 2013; 8(12): e79769).

Potential markers for a myeloid cell panel for myocytes includes CD14 and CD16, with attention paid to the ratio between the two, e.g., CD14+CD16—is the classical pattern, while CD14 low CD16 bright is non classical.

CSF1R is another potential marker (Cancer Cell 25, 1-14, Jun. 16, 2014 ᵃ2014 Elsevier Inc.). The Cancer Cell publication describes a biomarker trial in solid tumors.

Other potential markers for a panel include CD11b F4/80; CD11b LY6C/G; ARG1, CD206, and MHC expression, which can differentiate between M1 and M2 cells in mouse); and VEGF (which is highly expressed in a subset of TAMs).

Example 272: Efficacy of Compound BB in a Glioblastoma Model

The purpose of this study is to evaluate the anti-tumor activity and immune modulatory effects of Compound BB in the GL261-Luc murine glioblastoma subcutaneous model. GL261-luc was a murine luciferase expressing brain derived cell line which was stably transfected with firefly luciferase gene. GL261-Luc adherent cells were grown in tissue culture, in filtered DMEM medium supplemented with 10% fetal bovine serum and 1% pen/step. Tumor innoculum was prepared at a concentration of 1×107 cells in 100 uL of sterile PBS+matrigel. Cells were implanted subcutaneously in the right hind flank area to C57BL/6 Albino male mice (stock #000058-age 6 weeks) from Jackson Laboratories. Treatment begins when tumors reach ~100-200 mm³ in volume. Compound BB or vehicle was orally administered once daily at 15 mg/kg in the NMP formulation. Efficacy was determined by tumor volume and luciferin measurements. Tumor measurements and body weights were taken two to three times a week. Luciferin measurements were taken twice a week. At the end of the study, tumor cells were harvested and prepared for analysis by FACS, IHC, RNA analysis, or other analysis.

Figure 47A:
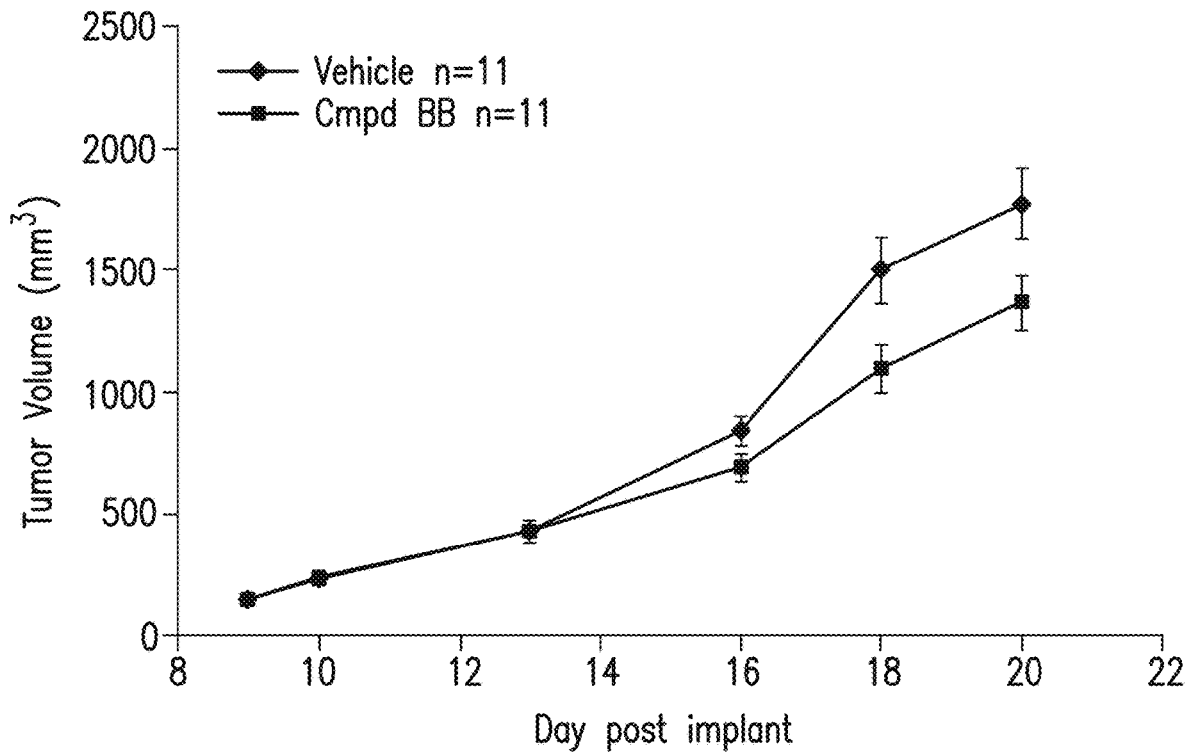
FIG. 47A and FIG. 47B show the effects of Compound BB QD on tumor volume from day 9 to day 20 after implant and total luciferase flux in the GL-261 syngeneic glioma model.
Figure 47B:
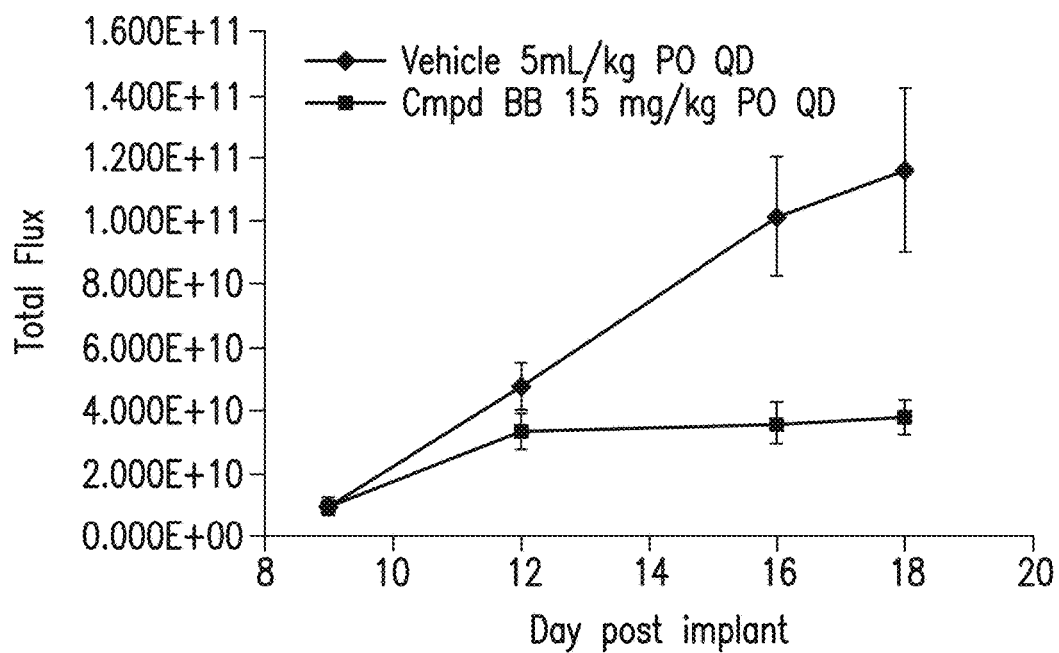
Figure 47C:
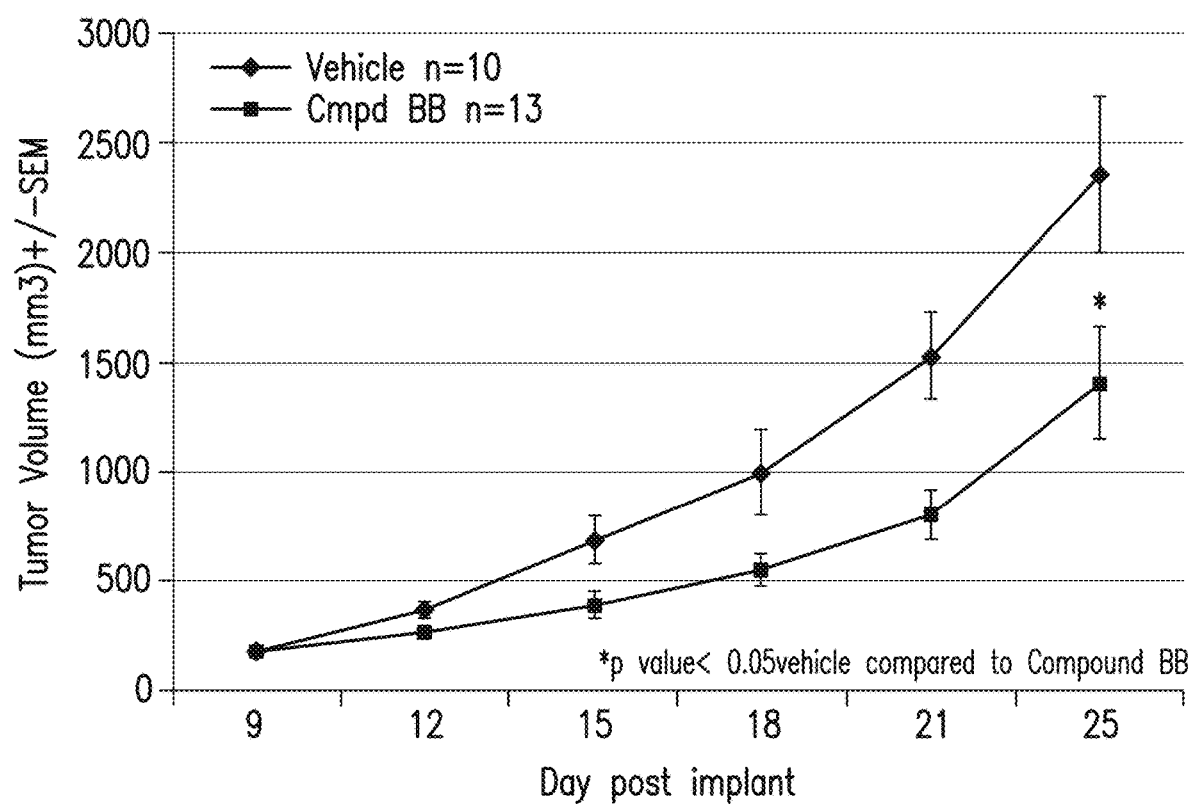
FIG. 47C is a repeat study that shows the effects of Compound BB QD on tumor volume from day 9 to day 25 after implant.

FIG. 47A shows that Compound BB reduced tumor volume in the GL-261 syngeneic glioma model at 15 mg/kg QD, PO. FIG. 47B shows that Compound BB reduced the total flux in the same model. FIG. 47C is a repeat study of the same model that shows the effects of Compound BB QD on tumor volume from day 9 to day 25 after implant.

Example 273: Efficacy of Compound BB with or without Cyclophosphamide in an LLC Model The purpose of this study is to evaluate the combination effect of Compound BB+/−cyclophosphamide in the LLC-tumor brei model. In this experiment, treatment began when tumors reached approx. 150 mm$^3$—around day 12. Caliper and xenogen images were monitored. Treatment groups n=13-15/group. The following doses and formulations were used: Vehicle (5% NMP/95% PEG 400/PBS) PO/IP; Compound BB @ 15 mg/kg QD, PO; Cyclophosphamide @ 50 mg/kg EOD IP; Combination (Compound BB+Cyclo). Samples for FACs analysis were collected on day 23 post implant. Using FACS, cells were assayed for the level of CD11b and Gr-1. Gr1+CD11b+ myeloid cells are the most prevalent inflammatory cells found in tumors, where they directly promote tumor angiogenesis and immunosuppression. Hardamon et. al., Proceedings: AACR 103rd Annual Meeting 2012, Cancer Research: Apr. 15, 2012; Volume 72, Issue 8, Supplement 1.

Figure 48:
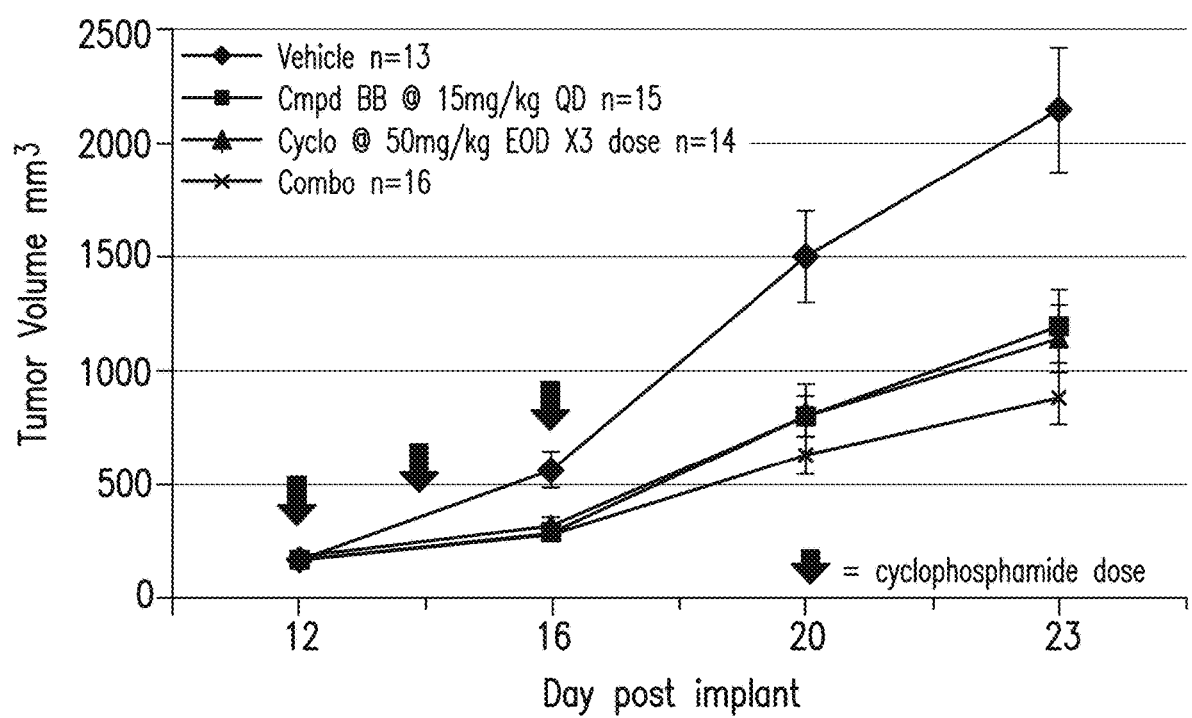
FIG. 48 shows tumor growth after treatment with Compound BB+/– cyclophosphamide in the LLC tumor brei model.

FIG. 48 shows the results of this experiment. Compound BB alone and cyclophosphamide alone each reduced tumor growth by about the same amount. When both compounds were administered together, tumor growth was further slowed. FIGS. 49A, 49B, 49C, 49D, and 49E show CD11b/Gr-1 plots when Compound BB was administered at 15 mg/kg and Cyclophosphamide at 50 mg/kg. FIG. 49A shows the percentage of cells that are CD3 relative to CD45+. FIG. 49B shows the percentage of cells that are CD11b+Gr-1− relative to CD45+. FIG. 49C shows the percentage of cells that are CD11b+Gr-1+ relative to CD45+. FIG. 49D shows the percentage of cells that are CD11b-Gr-1-relative to CD45+. FIG. 49E shows the percentage of cells that are CD11b-Gr-1+ relative to CD45+.

Figure 50B:
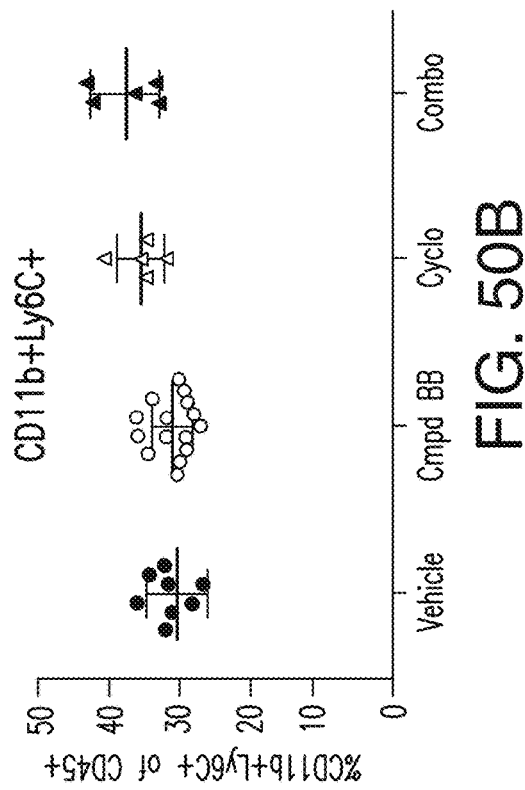
FIGS. 50A, 50B, 50C, and 50D show MDSC panel CD11b/Ly6C/Ly6G after treatment with Compound BB+/– cyclophosphamide in the LLC tumor brei model.
Figure 50D:
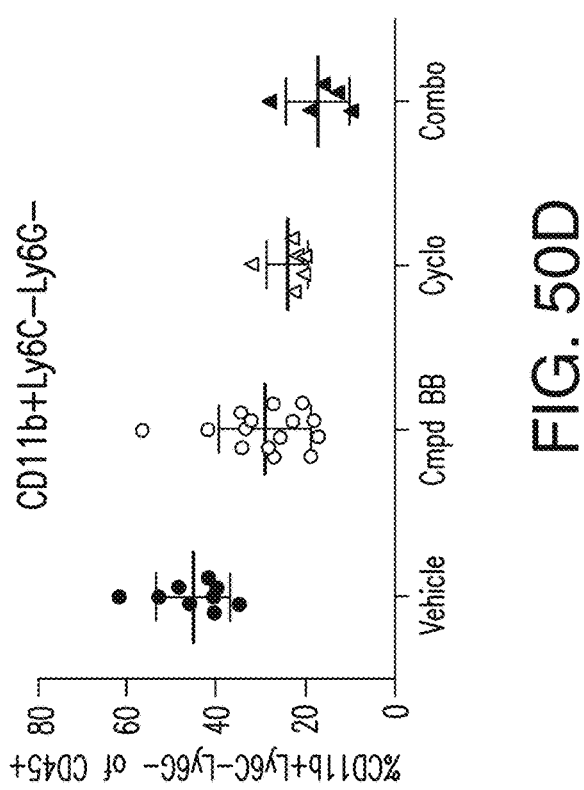
Figure 50A:
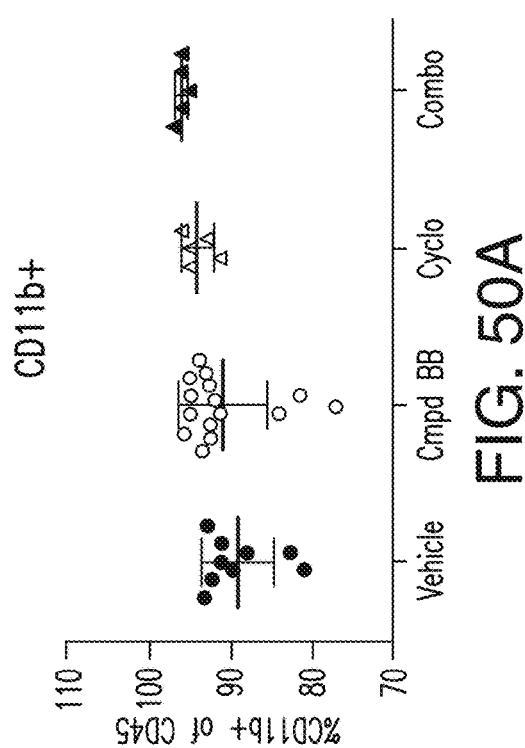
Figure 50C:
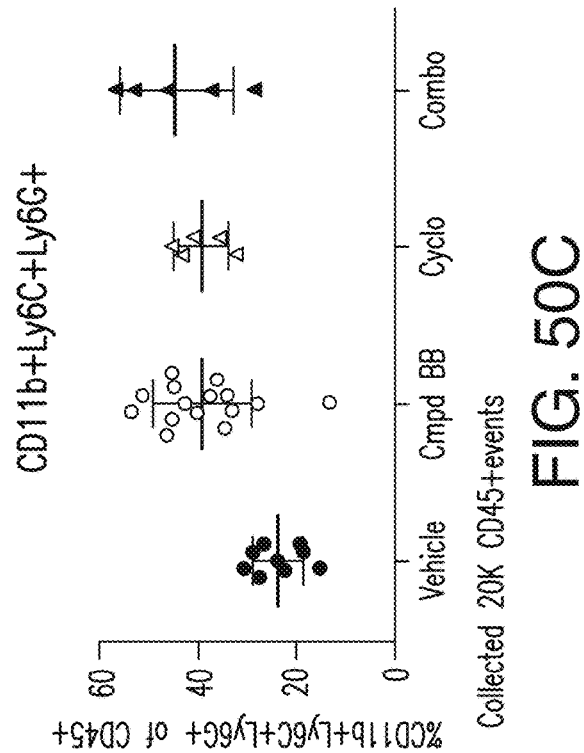

FIGS. 50A, 50B, 50C, and 50D show MDSC panel CD11b/Ly6C/Ly6G when Compound BB was administered at 15 mg/kg and Cyclophosphamide at 50 mg/kg. FIG. 50A shows the percentage of cells that are CD11b+ relative to CD45. FIG. 50B shows the percentage of cells that are CD11b+Ly6C+ relative to CD45+. FIG. 50C shows the percentage of cells that are CD11b+Ly6C+Ly6G+ relative to CD45+. FIG. 50D shows the percentage of cells that are CD11b+Ly6C-Ly6G− relative to CD45+.

Figure 51A:
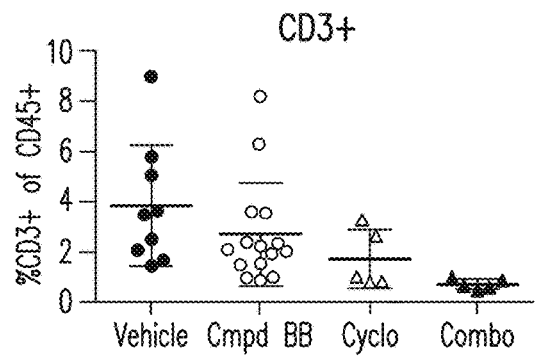
FIGS. 51A, 51B, 51C, 51D, and 51E show CD3/CD4/CD8 plots after treatment with Compound BB+/– cyclophosphamide in the LLC tumor brei model.
Figure 51B:
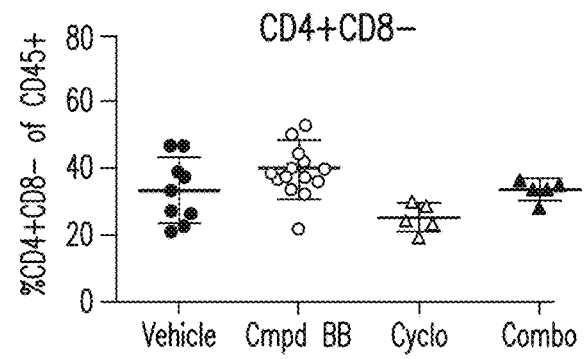
Figure 51C:
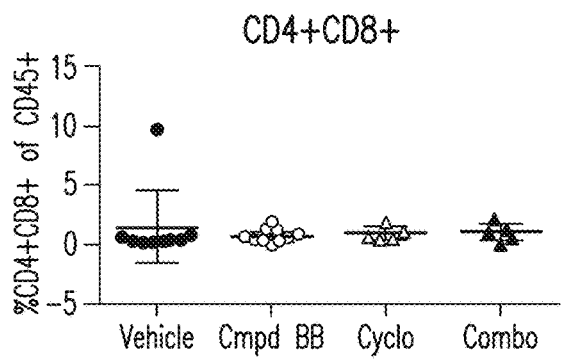
Figure 51D:
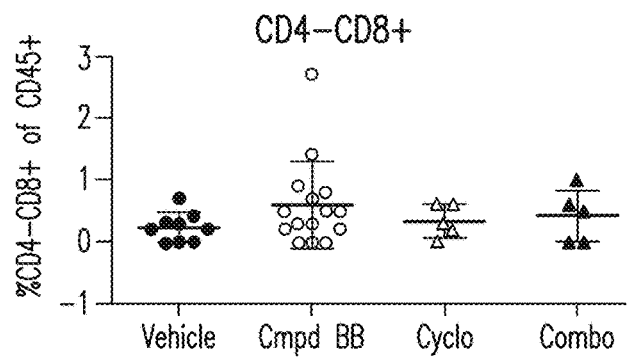
Figure 51E:
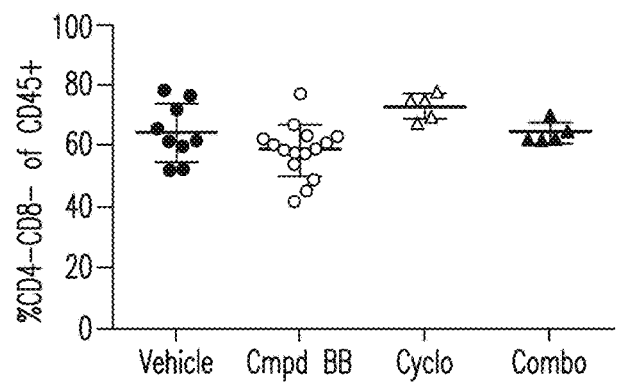
Figure 53A:
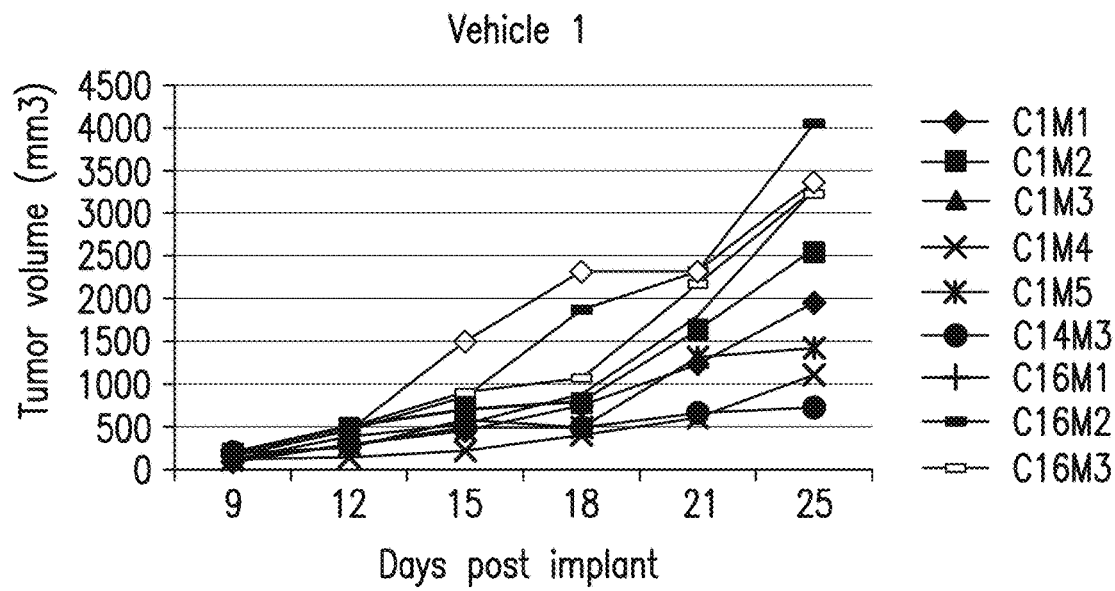
FIGS. 53A, 53B, 53C, 53D, and 53E show the effect of Compound BB following temozolomide treatment on GL-261 tumors.
Figure 53B:
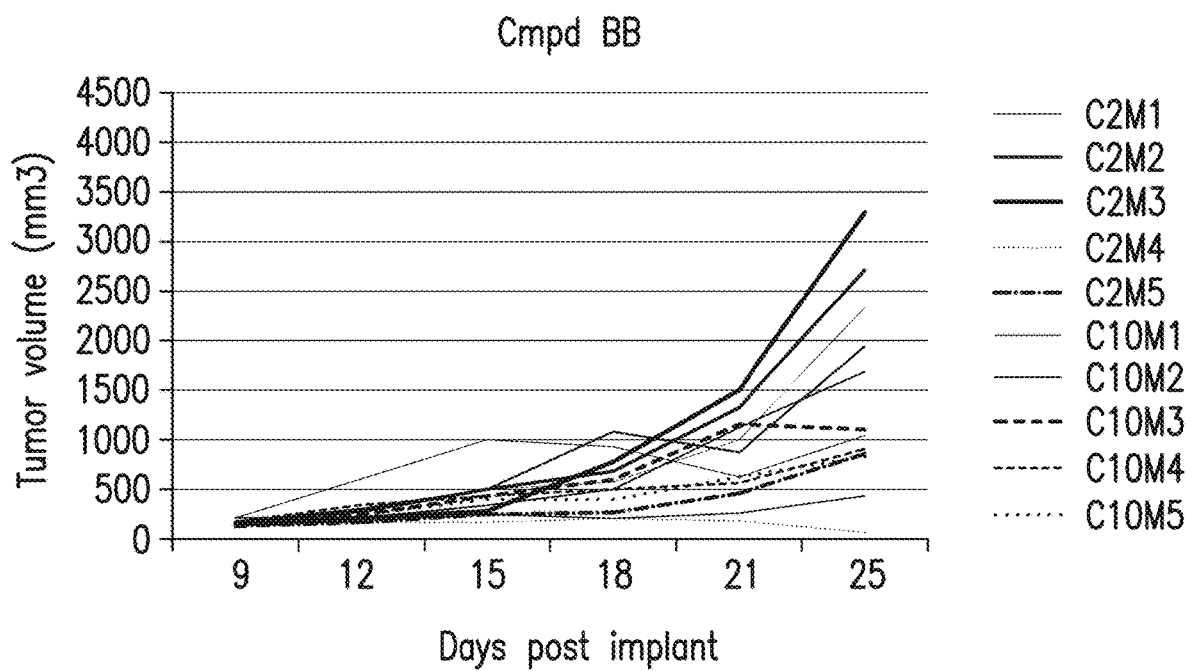
Figure 53C:
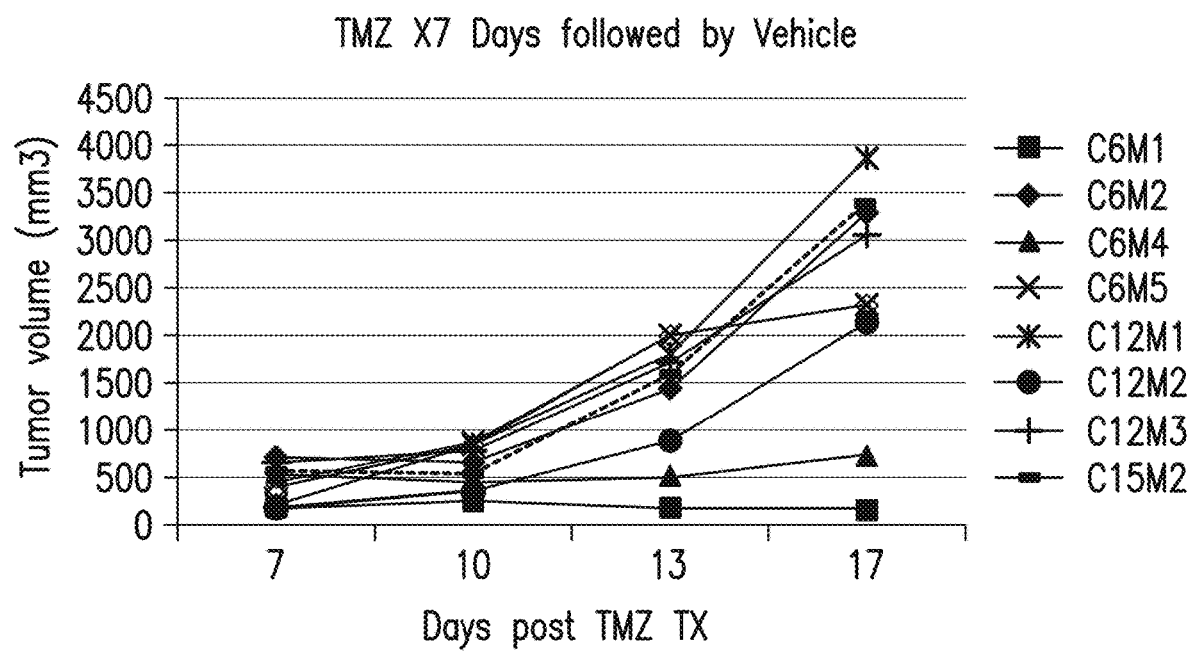
Figure 53D:
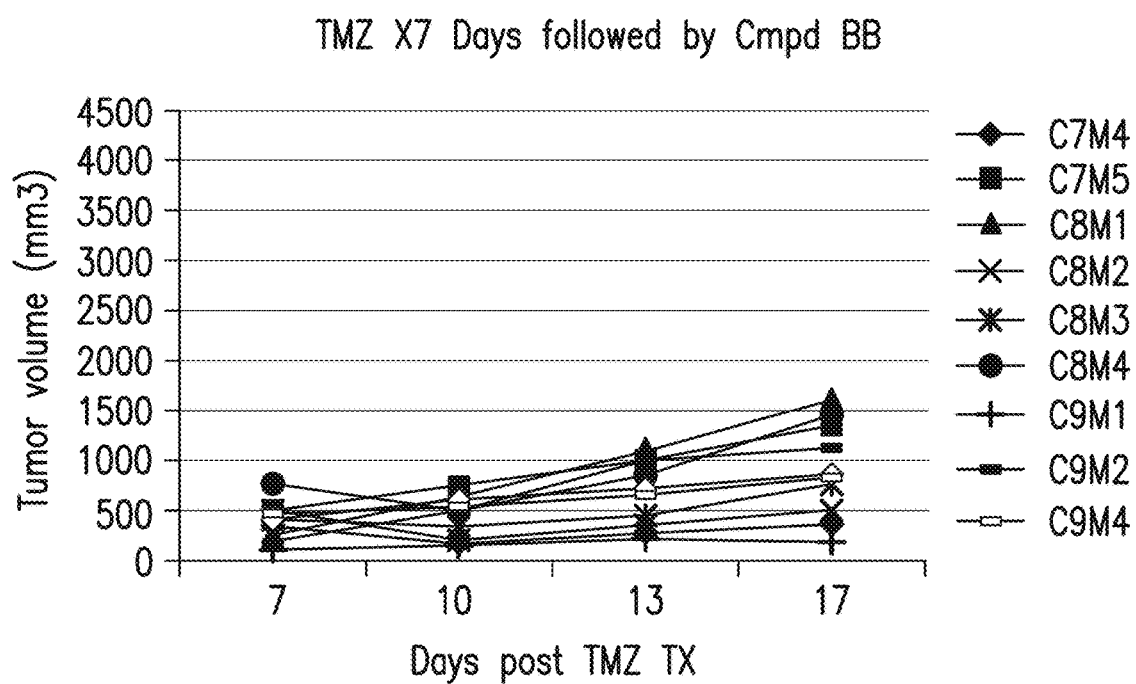
Figure 53E:
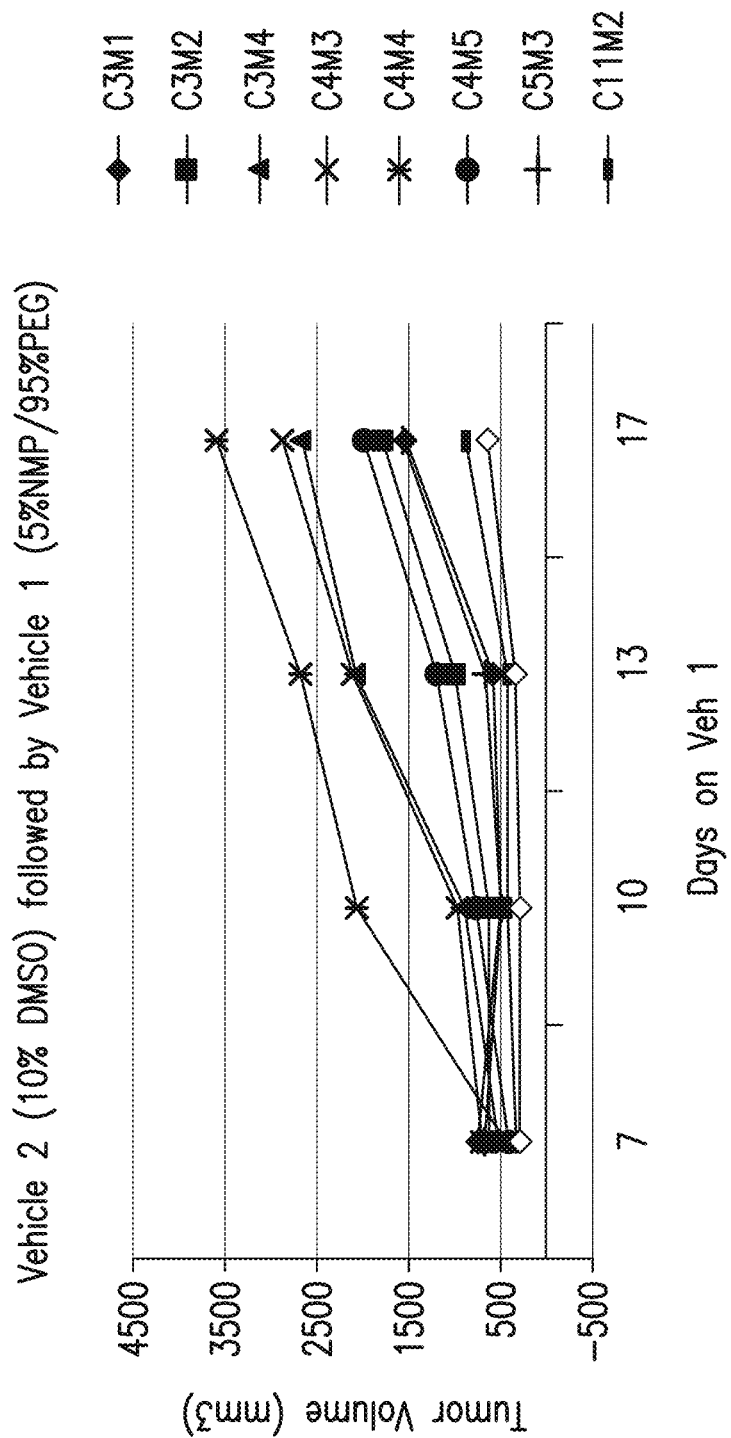

FIGS. 51A, 51B, 51C, 51D, and 51E show CD3/CD4/CD8 plots when Compound BB was administered at 15 mg/kg and Cyclophosphamide at 50 mg/kg. FIG. 51A shows the percentage of cells that are CD3+ relative to CD45+. FIG. 51B shows the percentage of cells that are CD4+CD8− relative to CD45+. FIG. 51C shows the percentage of cells that are CD4+CD8+ relative to CD45+. FIG. 51D shows the percentage of cells that are CD4-CD8+ relative to CD45+. FIG. 51E shows the percentage of cells that are CD4-CD8− relative to CD45+.

Example 274: The Effect of Compound BB on CD206 Levels of Macrophages in LLC Tumors The purpose of this study is to evaluate the effects of Compound BB dosed PO, QD along or in combination with cyclophosphamide. C57 Albino mice were dosed QD with Compound BB. Cyclophosphamide was dosed EOD IP. Tumor measurements and bodyweights were taken 2x/week. Tumors were harvested on the last day or if the vehicles reached approx. 3000 mm$^3$. Tumors were cut in half. One half was cut in half again with ½ fixed in 10% NBF, and the other was frozen in OCT for frozen sections. The remaining half was processed to single cell suspension and evaluated by FACS using two panels.

Antibodies used for staining for FACS were as follows.
Staining with CD4 and CD8a: CD45-AF700 (BDB560510) at 1.25 ug/ml; CD3-FITC (BDB555274) at 1 ug/ml; CD4-PE (BDB553049) at 2.5 ug/ml; and CD8a-PerCP (BDB553036) at 5 ug/ml.

Staining with CD11b and GR-1: CD45-AF700 (BDB560510) at 1.25 ug/ml; CD3-FITC (BDB555274) at 1 ug/ml; CD11b-APC (BDB553312) at 2.5 ug/ml; and GR-1-PE-CY7 (BDB552985) at 0.5 ug/ml.

Staining with CD206 panel: CD45-AF700 (BDB560510) at 1.25 ug/ml; CD11b PE at 2.5 ug/ml; and CD206 APC at 25 ug/ml.

Staining with MDSC panel: CD45-AF700 (BDB560510) at 1.25 ug/ml; CD11b PE at 2.5 ug/ml; Ly6C APC at 2.5 ug/ml; and Ly6G FITC at 2.5 ug/ml.

FIGS. 52A, 52B, 52C, 52D, and 52E show the percentage of cells that are CD45+, CD11b+, or CD206+, expressed as a percent of total cells, in LLC tumor brei model treated with Compound BB+/− cyclophosphamide. FIG. 52A shows the percentage of cells that are CD45+ expressed as a percent of total cells. FIG. 52B shows the percentage of cells that are CD11b expressed as a percent of total cells. FIG. 52C shows the percentage of cells that are CD206 expressed as a percent of total cells. FIG. 52D shows the percentage of cells that are CD11b expressed as a percent of total cells. FIG. 52E shows the percentage of cells that are CD206 expressed as a percent of total cells.

There appears to be a decrease in the CD206 population with both Compound BB administered alone and in combination with cyclophosphamide. Compound BB therefore reduces the number of M2 macrophages in the tumor, either by preventing them from migrating into the tumor or by preventing immature myeloid cells from differentiating into M2 cells, or both.

Example 275: Pharmacokinetics and Reduction of LPS-Induced Neutrophilia-Intratracheal Administration The study of intratracheal (i.t.) administration of Compound BB on LPS-induced neutrophilia model is carried out using methods known in the art. For example, Compound BB is administered intratracheally to rats at an amount of e.g., 1 g/kg, 10 g/kg or 100 g/kg. The administration of the controls is performed as e.g.: (1) oral administration of Compound BB at 10 mg/kg; (2) intratracheal administration of saline (vehicle) at 0.25 mL/rat; (3) intratracheal administration of LSP (vehicle) at 1 g LPS/rat; and (4) intratracheal administration of budenoside at 0.3 mg/kg. At one hour post-administration, neutrophilia is induced by treatment with LPS, and the samples are collected by bronchoalveolar lavage (BAL) at varying hours post-administration and subjected to further examination. Compound BB is a PI3Kγ inhibitor that has a delta/gamma selectivity ratio of greater than about 50. As a comparison, similar procedures are carried out using a PI3K-δ inhibitor, which has a gamma/delta selectivity ratio of greater than about 50.

The levels of Compound BB in lung, bronchoalveolar lavage fluid (BALF), and plasma are determined using methods known in the art.

Example 276: Studies with Smoking Mouse Model of Chronic Obstructive Pulmonary Disease (COPD)

Studies of the effect of the compounds provided herein on smoking mouse model of COPD can be conducted using methods known in the art.

A. Provided below is an illustrative example of such method. The mice are exposed to cigarette smoke for 4 days in a whole body exposure box. Whole body exposure is conducted for a certain amount of time in a custom made cylindrical 32 L Perspex box (e.g., Boehringer Ingelheim Pharma GmbH & Co. KG, Biberach, Germany) before each cigarette smoke exposure or before lung function measurement. Animals are separated by stainless steel spacers. The floor of the box is additionally heated (e.g., 38° C.) to maintain the physiological body temperature of the animals. Control animals receive solvent as placebo. On day one and two, mice are exposed to the mainstream smoke of cigarettes. Exposure to the smoke of each cigarette lasts for about 15 min followed by an 8 min exposure with fresh room air. Every second cigarette an additional break of 24 min with exposure to fresh room air is conducted. A semi-automatic cigarette lighter and smoke generator with an electronic timer is used to control the cigarette exposure (e.g., Boehringer Ingelheim Pharma GmbH&Co. KG, Biberach, Germany). Cigarette smoke particle concentration is monitored by a real time ambient particle monitor (e.g., MicroDustPro, Casella, Amherst, N.H., USA). Control animals are exposed to room air. See e.g., L. Wollin, et al., Pulmonary Pharmacology & Therapeutics 23 (2010) 345-354.

Compounds provided herein are administered orally or intra-tracheally (i.t.) using, e.g., methods know in the art. For example, a compound provided herein is administered orally as a solid or a solution. Alternatively, a compound provided herein is administered intra-tracheally by aerosolizing a solution of the compound with a jet nebulizer. A compound provided herein is administered at various concentration and schedules. For example, whole body exposure of a compound provided herein is administered for 5 min and 1 h prior to exposure to cigarette smoke.

Differential cell counts are determined in the bronchoalveolar lavage fluid (BALF). For example, the total BAL cell counts and the amount of neutrophils in the samples are used to evaluate the efficacy of a compound provided herein. Models of cigarette-smoke induced pulmonary inflammation have an increased BAL total cell count and also the amount of neutrophils. As such, a decrease of BAL total cell count and the amount of neutrophil in models administered with a compound provided herein as compared to a control model (without administration of a compound provided herein) illustrates the effectiveness of a compound provided herein in the treatment of pulmonary inflammation. See e.g., L. Wollin, et al., Pulmonary Pharmacology & Therapeutics 23 (2010) 345-354.

Further, lung sections stained with e.g., H&E or AB/PAS of the control models (e.g., models without administration of a compound provided herein) are compared with lung sections of models administered with a compound provided herein. H&E staining shows inflammation and alveolar infiltrates in the lungs. AB/PAS staining shows the mucus content in the goblet cells of the large airway. See e.g., L. Wollin, et al., Pulmonary Pharmacology & Therapeutics 23 (2010) 345-354.

B. Provided below is an example for a COPD 10 days cigarette smoke model. The goal of this study is to determine whether treatment with a compound provided herein can prevent the steroid resistant pulmonary inflammation induced by exposing mice for 10 days to cigarette smoke. Mice are first exposed for 5 days to cigarette smoke to induce glucocorticosteroid resistance. Thereafter, the animals are exposed for an additional 5 days to cigarette smoke together with the administration of the test compounds to investigate whether the glucocorticosteroid resistance can be diminished.

Specifically, Balb/c by J mice (weight 24-26 gr; 10-12 weeks old) are exposed to standard air or cigarette smoke for 10 days ("whole body exposure"). Mice are exposed when they are sitting together in one Perspex box. The cigarettes used are special research cigarettes standardized from Kentucky University: 3R4F without filter. Dose and time are increased starting at the $1^{st}$ till the $10^{th}$ day of exposure (twice a day (=2 runs); interval exposure is 5 hours):

1st day: run 1=2 pairs of cigarettes and run 2=3 pairs of cigarettes. The smoke exposure dose and time=10-15 min. (CO dose=150-300 ppm; $O_2$ concentration=20.8% measured by Baccharach PCA3-analyzer);

2nd day: run 1=4 pairs of cigarettes and run 2=5 pairs of cigarettes. The smoke exposure dose and time=20-25 min. (CO dose=150-300 ppm; $O_2$ concentration=20.8%

3rd day: run 1=6 pairs of cigarettes and run 2=7 pairs of cigarettes. The smoke exposure dose and time=0-35 min. (CO dose=150-300 ppm; $O_2$ concentration=20.8%;

4th day till the 10th day: run 1=7 pairs of cigarettes and run 2=7 pairs of cigarettes. The smoke exposure dose and time=35 min. (CO dose=150-300 ppm; $O_2$ concentration=20.8%.

Animals are treated with a compound provided or Vehicle solution 1 or 2 orally daily from day 6 till 10. Dexamethasone (5 mg/kg) is administered daily intraperitoneally (IP) from day 6 till 10. Body weight of the individual animals is monitored daily from day 1 till day 11.

Mice are sacrificed 1 day after the last exposure to air or CS(day 10). Blood is collected via a heart puncture and the isolated serum is collected and stored at −30° C. Lungs are lavaged, BAL cells are isolated counted and differentiated. BAL fluid is stored for determination of cytokines/chemokines.

Below are tables of the experimental setup:

| Day | Treatment |
|---|---|
| 1 till 10 | Balb/c byJ mice (weight 24-26 gr; 10-12 weeks old) are exposed to standard air or cigarette smoke. |
| 6 till 10 | Animals are treated with a compound provided herein or Vehicle solution 1 or 2 orally daily from day 6 till 10. Dexamethasone (5 mg/kg) is administered daily intraperitoneally (IP) from day 6 till 10. |
| 1 till 11 | Body weight of each individual mouse is noted once a day. |
| 11 | The animals are sacrificed. Blood is isolated. Serum is stored for cytokine/chemokine profiling (optional). Lungs are lavaged, BAL cells are isolated, counted, and differentiated. BAL fluid is stored for determination of cytokines/chemokines (optional). |

| group | Model | Veh 1 | Veh 2 | Dex | TC 1 | TC2 | TC3 | N = |
|---|---|---|---|---|---|---|---|---|
| 1 | Air | X | X | | | | | 10 |
| 2 | Cigarette Smoke | X | X | | | | | 10 |
| 3 | Cigarette Smoke | X | | X | | | | 10 |
| 4 | Cigarette Smoke | | X | | X | | | 10 |
| 5 | Cigarette Smoke | | X | | | X | | 10 |
| 6 | Cigarette Smoke | | X | | | | X | 10 |
| 7 | Cigarette Smoke | | | | X | X | | 10 |
| 8 | Cigarette Smoke | | | | X | | X | 10 |
| 9 | Cigarette Smoke | | | | X | | X | 10 |
| Total | | | | | | | | 90 |

C. Provided below is a murine smoking model. See e.g., Yasuo, T., et al., Am J Respir Crit Care Med 2010; 182: 897-904; Sato T, et al., Am J Respir Crit Care Med 2006; 174:530-537; and Kasagi S, et al., Am J Physiol Lung Cell Mol Physiol 2006; 290: 396-404.

Inhalation of tobacco smoke is performed utilizing unfiltered research cigarette 1R1 (Tobacco Health Research Institute, Kentucky Univ., Lexington, Ky.) and the Tobacco Smoke Inhalation Experiment System for Small Animals (model SIS-CS; Shibata Scientific Technology, Tokyo, Japan). Model SIS-CS consisted of both a tobacco smoke generator (model SG-200) and an inhalation chamber. The smoke generator is controlled by a laptop computer and automatically generated tobacco smoke by setting a volume of syringe pump (10-50 cm$^3$/puff) and a number of puffs/min (1-12 puffs).

The tobacco smoke generated is delivered to the inhalation chamber, to which the mouse body holders are set (maximum 12 body holders can be set at a time), and mice inhale tobacco smoke through their noses. Tobacco smoke can be diluted to a desired concentration at the blender, where tobacco smoke and compressed air are combined, before delivery to the inhalation chamber. At 12 wk of age, mice are subjected to the experiment of chronic inhalation of tobacco smoke. The experimental settings are as follows: 15 ml of stroke volume and 12 puffs/min to generate tobacco smoke, 1.5% tobacco smoke diluted by compressed air. The mass concentration of total particulate matter (TPM) in 1.5% tobacco smoke is determined by gravimetric analysis of filter samples taken during exposure periods and is 23.9 mg of TPM/m$^3$.

First, mice are trained to be set into a body holder for 30 min/day without smoking for 5 days, followed by exposure to 1.5% tobacco smoke for 15 min/day for 5 days. After this induction period, mice continue to inhale 1.5% tobacco for 30 min/day, 5 days/wk, and for 8 wk. As a control for the inhalation of tobacco smoke, mice are subjected to the same experimental procedure with the same conditions described above, but air was delivered instead of tobacco smoke.

Example 277: Lung Inflammation Assay

Compounds provided herein can be tested using one or both of the LPS-induced lung inflammation assay and the ovalbumin-induced lung inflammation assay.

To perform the LPS-induced lung inflammation assay, compounds are dosed orally. A group is dosed with vehicle only and dexamethasone is used in another group as positive control. Pulmonary inflammation is determined 6 h after intranasal instillation of LPS. The following parameters can be evaluated: total number of leukocytes and number of neutrophils in bronchoalveolar lavage (BAL).

In the ovalbumin-induced lung inflammation assay, compounds are dosed orally. A group is dosed with vehicle only and dexamethasone is used in another group as positive control. Pulmonary inflammation is determined 4 days after 4 consecutive daily intranasal instillation of ovalbumin. Compounds are given by gavage 30 min before each challenge (4 challenges) at the indicated doses. The following parameters can be evaluated: total number of leukocytes and number of eosinophils in bronchoalveolar lavage (BAL).

Example 278: Efficacy of Compound BB with or without Temozolomide in Glioma Model The purpose of this model is to evaluate the GL-261 glioma model treated continuously with Compound BB or with temoloamide (TMZ) followed by vehicle or Compound BB. TMZ was dosed IP 1x/day for 7 days. The group then were randomized to receive Compound BB @ 15 mg/kg QD dosed PO or vehicle to evaluate the delay in tumor regrowth.

Animals: C57 Albino mice (male) from Jackson Labs, n=80. Parameters Evaluated:

In life: Mice were dosed QD with Compound BB. Temozolomide was dosed QD IP, for 7 days. Tumor measurements and bodyweights were taken 2x/week, but caliper and xenogen measurements.

End point analysis: Tumors were cut in half. One half was cut in half again with ½ fixed in 10% NBF the other was frozen in OCT for frozen sections. The remaining half was processed to single cell suspension and evaluated by FACS.

PD satellite group—8 mice from the TMZ treated mice and 8 mice from the vehicle treated mice were sacrificed on day 7 post treatment. Tumors were processed to single cell suspension and evaluated by FACS.

The study overview is shown in the following Table 26:

TABLE 26

| Grp # | N | Compound | Dose (mg/kg) | Route | Frequency | Dose vol (ml/kg) | Drug conc (mg/ml) |
|---|---|---|---|---|---|---|---|
| 1 | 12 | Vehicle | 0 | PO/IP | QD | 5/10 | 0 |
| 2 | 12 | Compound BB | 15 | PO | QD | 5 | 3 |
| 3 | 20 | Compound BB | 15 | PO | QD | 5 | 3 |
| 4 | 40 | Temozolomide | 1 | IP | | 10 | 5 |
| 4 - PD | 8 | Vehicle | 0 | PO/IP | QD | 5/10 | 0 |
| 4 - PD | 8 | Temozolomide | 1 | IP | QD | 5/10 | 0 |

Figure 54A:
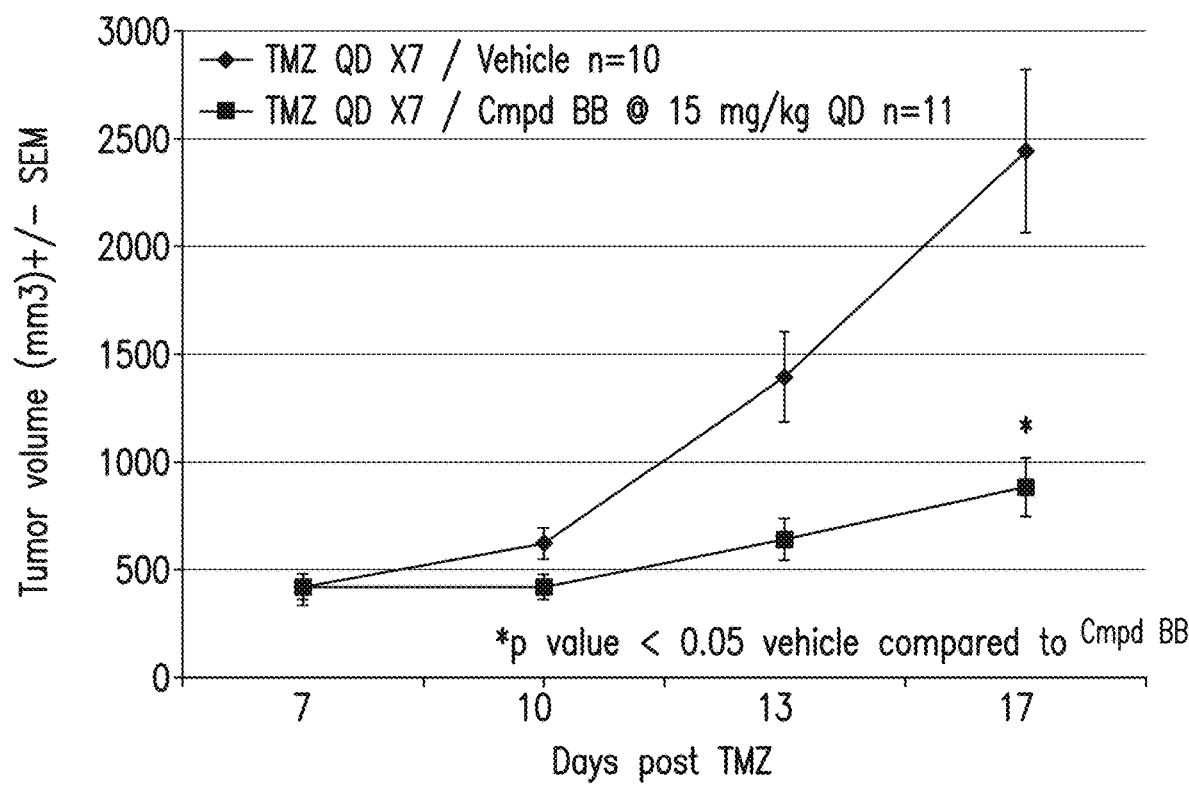
FIG. 54A shows the effect of TMZ treatment versus vehicle.
Figure 54B:
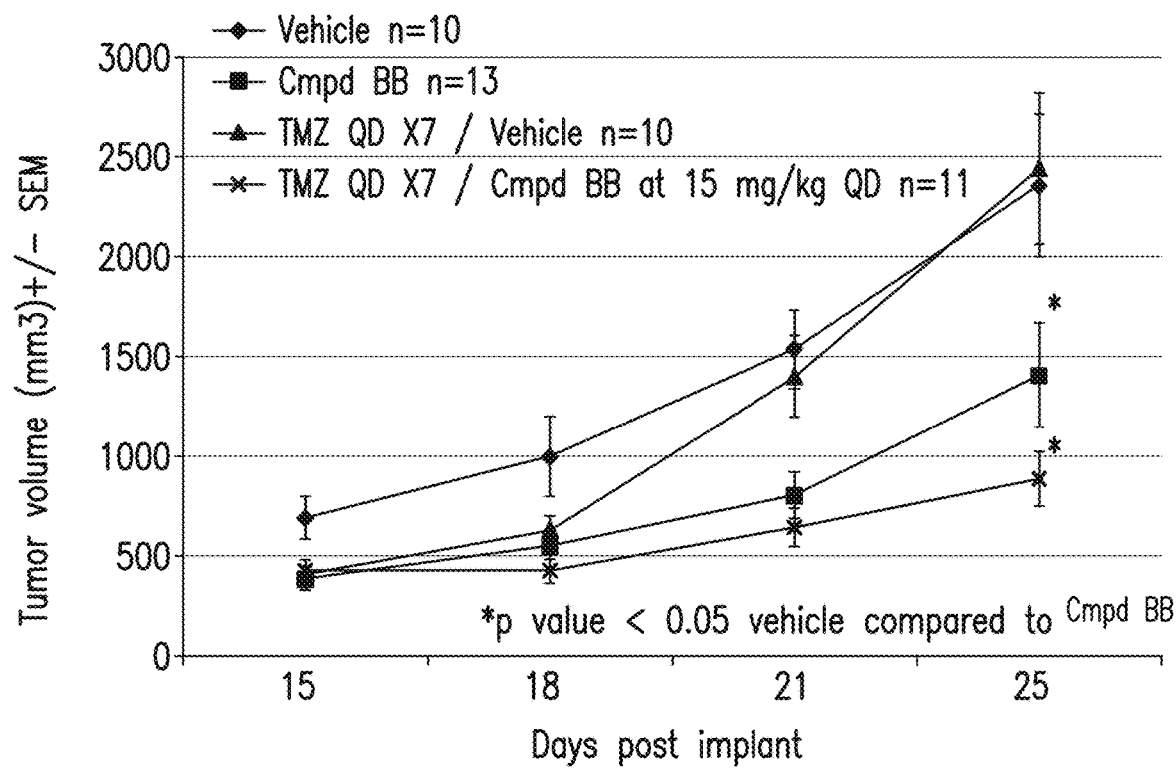
FIG. 54B show the effects of Compound BB on tumor volume post TMZ treatment.

FIGS. 53A, 53B, 53C, 53D, and 53E show the effect of Compound BB following temozolomide treatment on GL-261 tumors. FIG. 54A shows the effect of TMZ treatment versus vehicle and FIG. 54B shows the effects of Compound BB on tumor volume post TMZ treatment. Compound BB is effective in reducing the tumor volume in GL-261 tumors following the treatment of temozolomide.

Treatment with TMZ @ 1 mg/kg followed by treatment with Compound BB resulted in significant reduction in tumor volume as compared to vehicle treated mice. Mice treated with Compound BB from the start of treat also resulted in a significant reduction in tumor volume as compared to vehicle treated mice. The two groups were not significant from one another but with longer treatment and monitoring this may result in a significantly bigger window.

Example 279: Effect of Compound BB and Anti-PDL-1 on T Cell Proliferation with CT26 Tumors The goal of this study is to evaluate the effect of Compound BB on T cell proliferation with CT26 tumors. CT26 was an N-nitroso-N-methylurethane-(NNMU) induced, undifferentiated colon carcinoma cell line. It was cloned to generate the cell line designated CT26.WT (ATCC CRL-2638).

The duration of the study was 1 week under treatment. 5-6 week old female, Balb/c mice (Jackson Labs) implanted subcutaneously with $5 \times 10^5$ CT26 cells in 100 µl PBS. CT26 cells were cultured in RPMI supplemented with 10% FBS. Dosing commenced when tumors reached an average volume of 500-600 mm$^3$.

The groups were treated as follows:

| Group | # mice/ group (n) | Vehicle PO QD mg/kg | Compound BB PO QD mg/kg | αPD-L1 IP X1 mg/kg |
|---|---|---|---|---|
| 1 | 10 | 0 | 0 | 0 |
| 2 | 10 | 0 | 15 | 0 |
| 3 | 10 | 0 | 0 | RTU* |

Group 1: Vehicle (5% NMP/95% PEG)
Group 2: Compound BB prepared at 10 mg/ml
Group 3: *aPD-L1 antibody comes ready to use (RTU) (1 mg/ml) dosed with 200 ug, once. Supplied by BioLegend (Cat #124318, lot #B179643), clone 10F.9G2

For groups 1 and 2 (vehicle and compound BB, respectively), the mice were dosed QD, PO for 5 days at a volume of 5 ml/kg. For group 3 (αPD-L1), the mice were dosed once, IP, 200 ug (200 uL from 1 mg/ml stock).

Mice were monitored daily for adverse clinical effects. Body weights and tumor luminescent were measured two times per week. At the end of the study, tumors were harvested and cut into 3 parts; one piece for CTL killing assay, one piece for CSFE proliferation assay and one piece (split into two) for OCT/FFPE.

Spleens from 3 vehicle treated tumor bearing mice were physically dissociated in T cell media and passed through a 70 micron filter. After red cell lysis, the cells were pooled, brought up in PBS and stained with CFSE (invitrogen). After washing, these cells were brought up in 20 ml T cell media. Half the cells received Dynal mouse activator beads (CD3/CD28 crosslinking at a 1:1 concentration). CD3/CD28 beads induce proliferation in splenocytes from tumor bearing mouse (data not shown).

Tumors from vehicle treated, Compound BB treated, and anti-PDL1 treated mice were minced, treated with collagenase and Dnase for 30 minutes at 37 degrees ° C., and cells were isolated by passing the digested tumor though a 70 micron filter. The cells were treated with red cell lysis buffer, washed, and re-suspended in 10 ml T cell media. 2 mls of the each tumor cell suspension were plated into each of two 12 well plates. To one of the plates, Dynal bead activated CSFE labeled splenocytes were added and un-activated CSFE labeled splenocytes were added to the other. CSFE labeled splenocytes were also added to wells that had T cell media without tumor cells.

After four days, the cells were harvested from the wells and stained with antibodies for CD3, CD4, and CD8. Analysis was by FACS, measuring the percentage of cells that remained in an un-proliferated state (CSFE stain undiluted) after 4 days. Measurements of splenocyte proliferation, either activated or un-activated, from the wells without the tumor cells provided the positive and negative controls for proliferation.

Figure 55A:
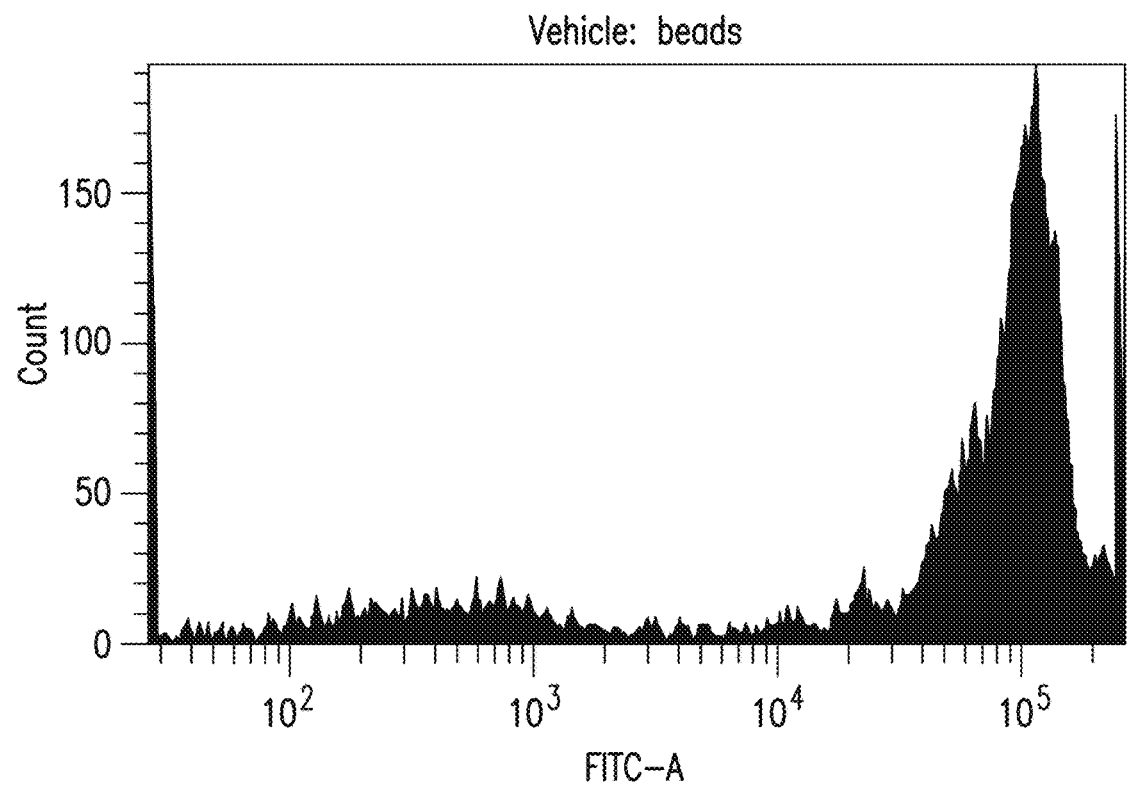
FIGS. 55A, 55B, and 55C show the effect of Compound BB and anti PDL-1 on tumor-derived cell mediated inhibition of T cell proliferation versus vehicle.
Figure 55B:
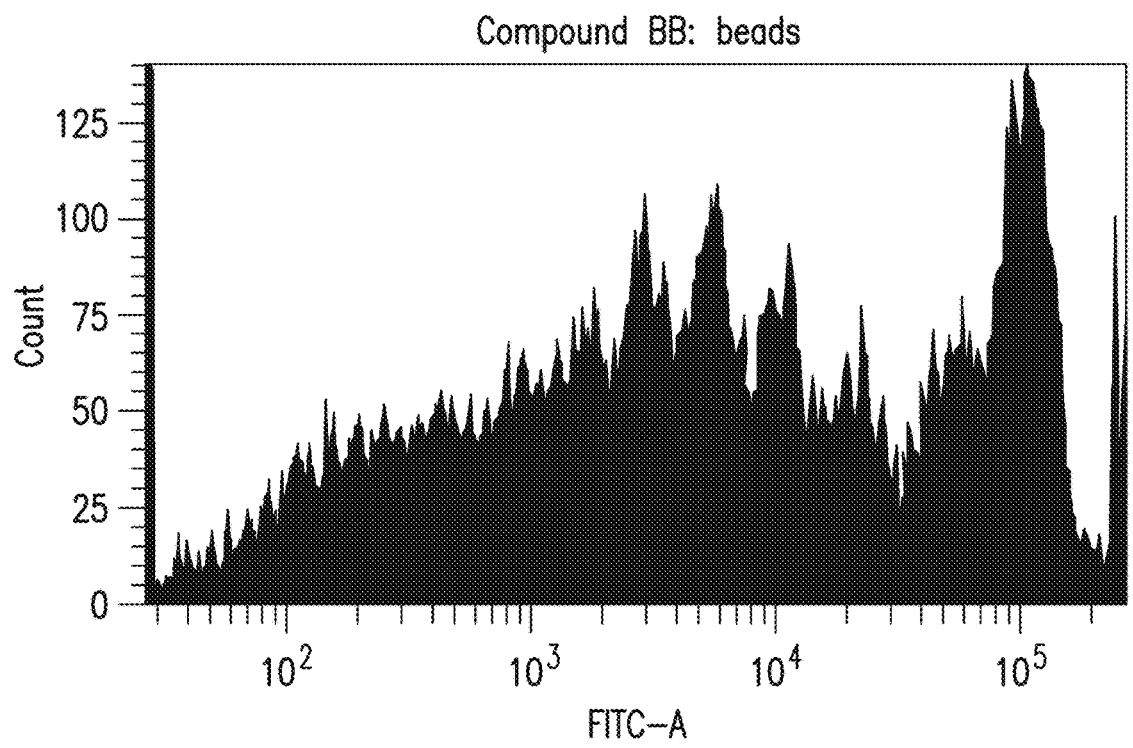
Figure 55C:
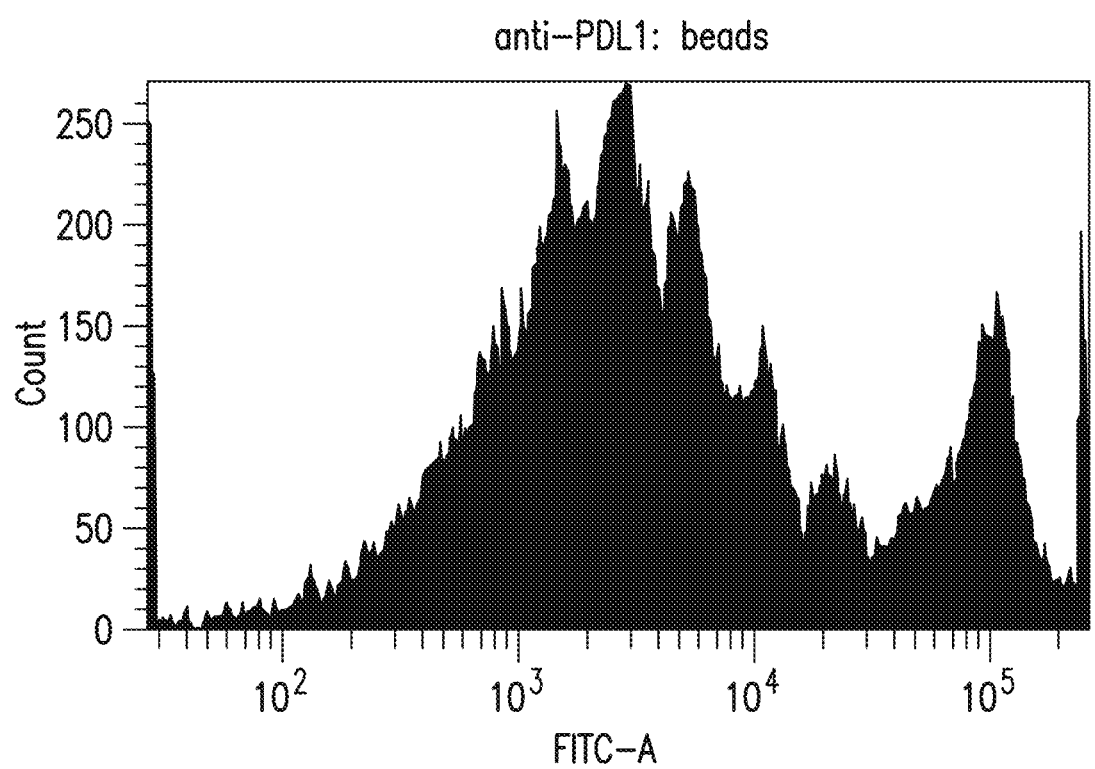
Figure 56A:
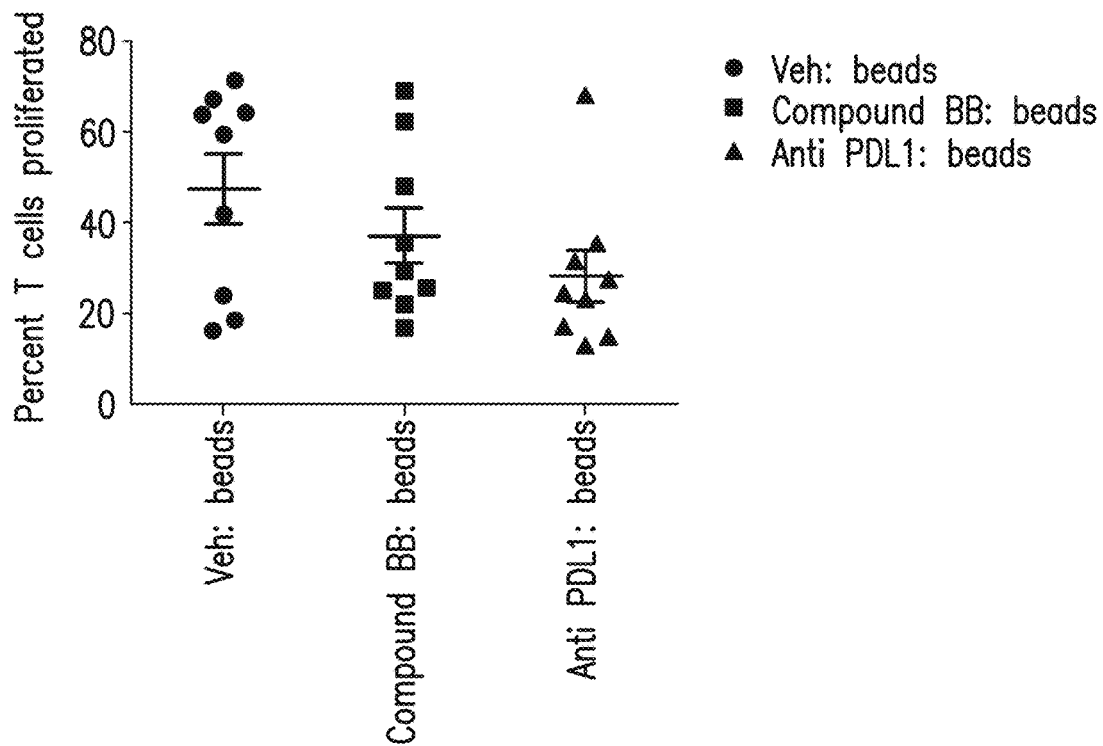
FIGS. 56A and 56B show that cells isolated from tumors from Compound BB and anti-PDL-1 treated mice are less inhibitory of spleen T cell proliferation as compared to tumor derived cells from vehicle treated mice.
Figure 56B:
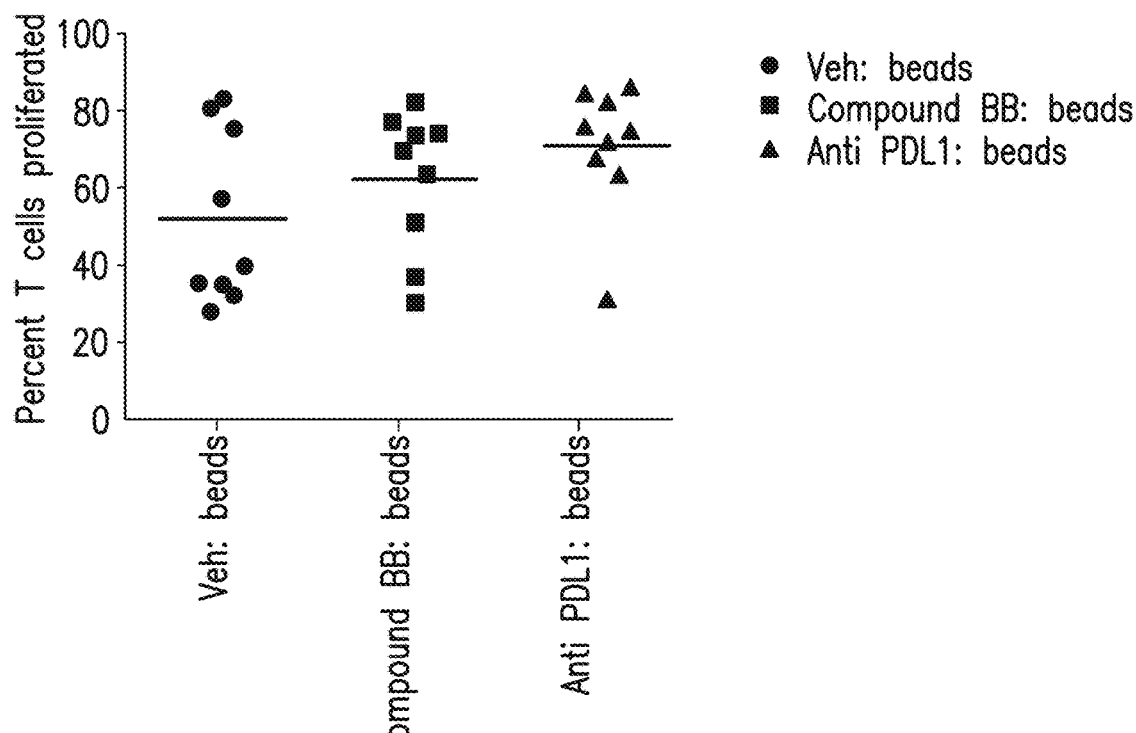

FIGS. 55A, 55B, and 55C show the effect of Compound BB and anti PDL-1 on tumor cells inhibition of T cell proliferation versus vehicle. FIG. 55A shows the effect of tumor cells from vehicle treated mice. FIG. 55B shows the effect of tumor cells from Compound BB treated mice. FIG. 55C shows the effect of tumor cells from anti PDL-1 treated mice. FIG. 56A and FIG. 56B show that tumor cells from Compound BB and anti-PDL-1 treated mice are less inhibitory of spleen T cell proliferation as compared to tumor cells from vehicle treated mice.

Figure 57:
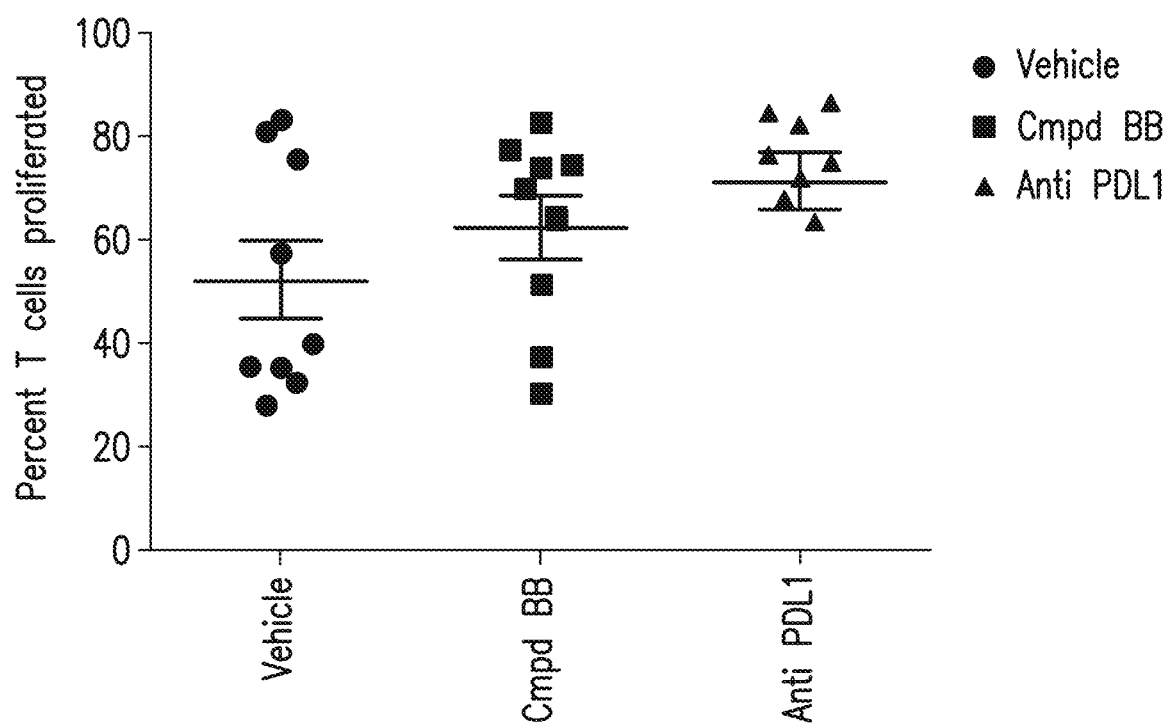
FIG. 57 shows Compound BB reduces immune suppressive environment via an ex vivo T-cell proliferation assay.

FIG. 57 shows Compound BB reduces immune suppressive environment via an ex vivo T-cell proliferation assay.

In summary, T cell proliferation can be suppressed by cells derived from CT26 mouse tumors, but treatment with either Compound BB or anti-PDL1 can release the suppression.

Example 280: Compound BB Inhibits the Ex Vivo Whole Blood Stimulation of Phospho-AKT in T Cells and Monocytes by CXCL12

C57 BL/6 Albino mice were implanted with $1 \times 10^6$ cells in a SC injection in the hind flank. The cell implant material was generated from brei that was passaged from mouse to mouse. Treatment started when tumors were between 160-180 mm$^3$. Mice were dosed for 12 days, QD, PO with vehicle, 15, 7.5 or 3 mg/kg. On day 12 mice were dosed and terminal blood was collected 2 h post dose by cardiac stick collection. Blood was placed in EDTA K2 collection tube and stored at room temp for PD analysis.

Figure 58:
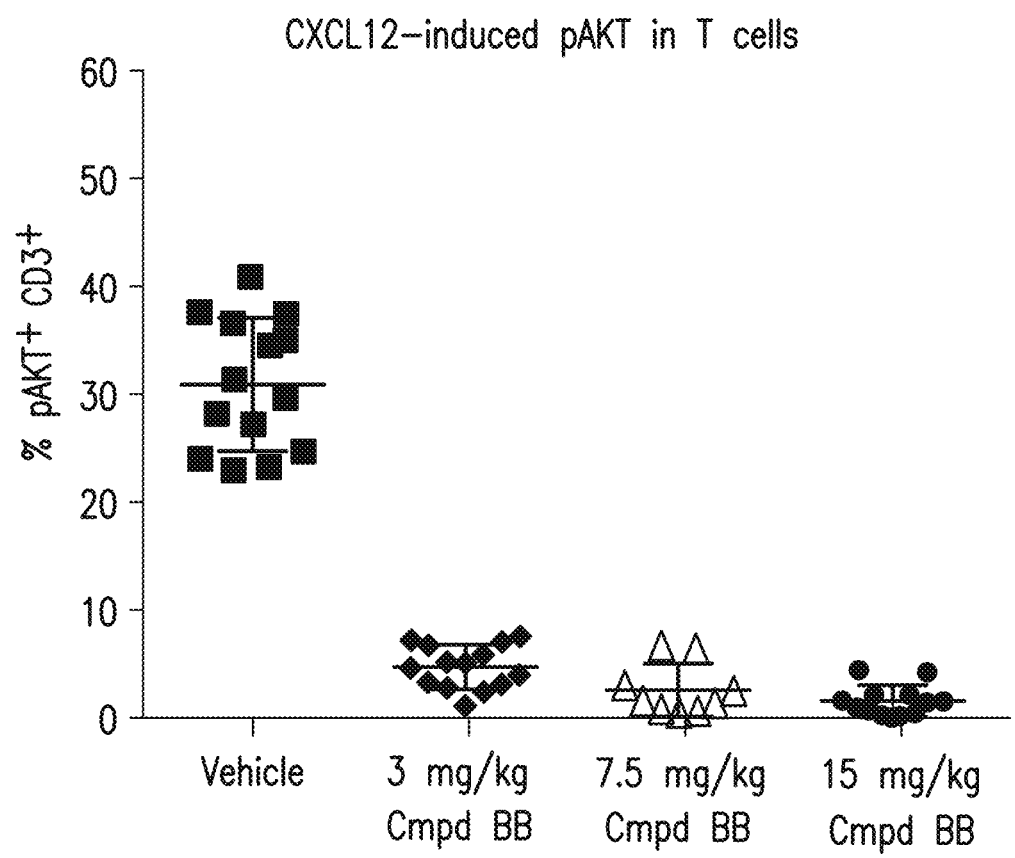
FIG. 58 shows LLC-bearing mice treated with Compound BB inhibits the ex vivo whole blood stimulation of phospho-AKT in T cells.
Figure 59:
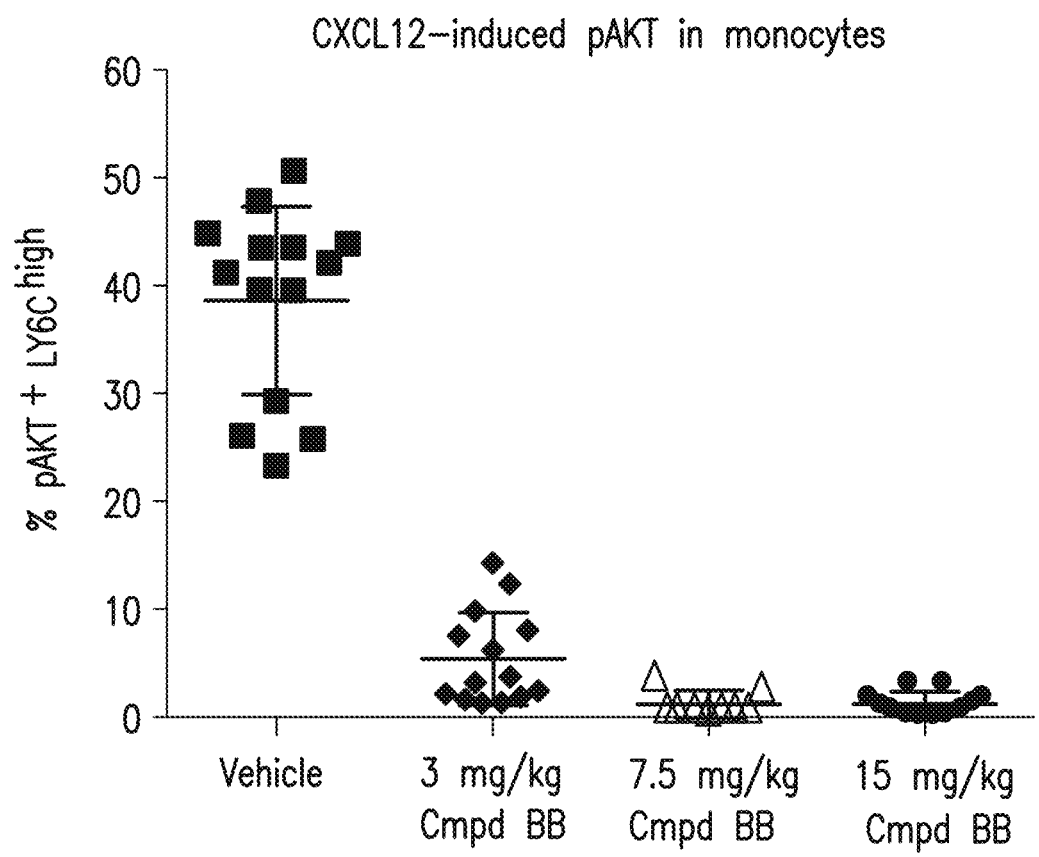
FIG. 59 shows LLC-bearing mice treated with Compound BB inhibits the ex vivo whole blood stimulation of phospho-AKT in monocytes.
Figure 60:
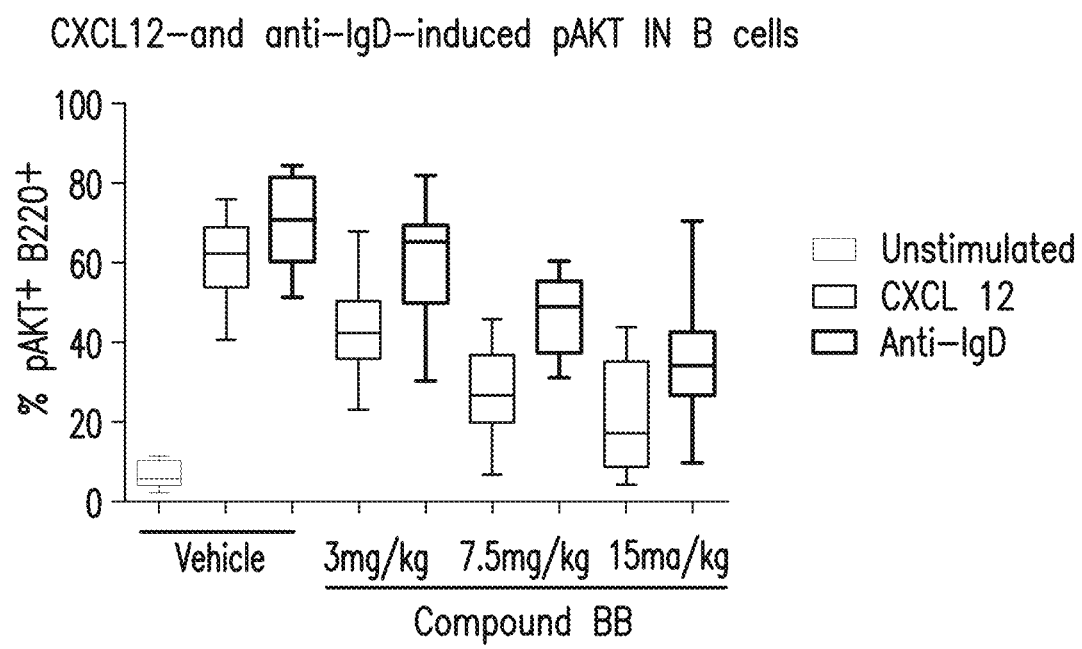
FIG. 60 shows the effect of Compound BB on CXCL12- or anti-IgD-induced pAKT in B cells.

Blood from each animal was aliquotted into 2 plates and warmed to 37° C. degrees. PBS was added to one plate as an unstimulated control. Murine CXCL12/SDF-1 was added to the second plate to a final concentration of 800 ng/mL and plate was returned to the 37° C. degree block. After 2 minutes of incubation, blood was lysed and fixed using paraformaldehyde. Samples were washed and frozen until flow cytometric analysis. T cells were gated using an antibody to CD3 and monocytes were gated as LY6G$^-$ LY6C$^{high}$. Intracellular pAKT S473 was measured and percent positive was used for graphing. FIG. 58 shows LLC-bearing mice treated with Compound BB inhibits the ex vivo whole blood stimulation of phosphor-AKT in T cells. FIG. 59 shows LLC-bearing mice treated with Compound BB inhibits the ex vivo whole blood stimulation of phosphor-AKT in monocytes. FIG. 60 shows the effect of Compound BB on CXCL12- or anti-IgD-induced pAKT in B cells.

Example 281: Single Dose Dog PK of Compound BB

Figure 61:
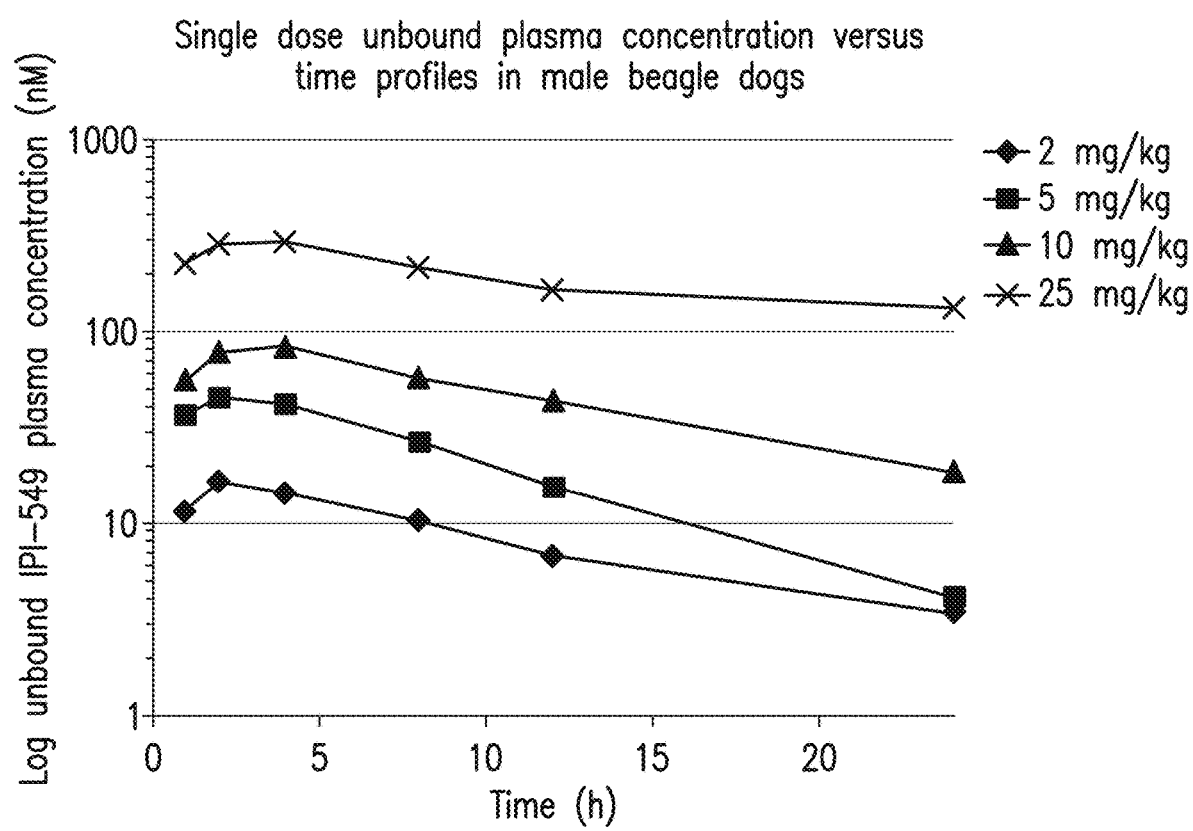
FIG. 61 shows the single dose unbound plasma concentration of Compound BB versus time profiles in male beagle dogs.

The PK of Compound BB in male beagle dog was measured at four different dosage: 2 mg/kg, 5 mg/kg, 10 mg/kg, and 25 mg/kg. FIG. 61 shows the single dose unbound plasma concentration of Compound BB versus time profiles in male beagle dogs.

Example 282: Bone Marrow Derived Macrophages (BMDMs) Migration Assay

BMDMs are obtained from bone marrow isolated from femurs and tibias of C57Bl/6J mice. Bone marrow cells are cultured in a petri plate in the presence of RPMI additioned with 30% L-cell conditioned medium (supernatant of 5 days culture of L929 cells), 20% FBS and penicillin and streptomycin. After about 10 days, almost all cells become attached BMDM. For the migration assay, BMDMs are pretreated with 6 different concentrations of a compound provided herein and migration assay is performed by using a Boyden chamber toward C5a chemokine (50 nM) or CXCL12. Migrating BMDM, attached to the polycarbonate of the Boyden chamber, are counted at the microscope (5 fields/sample) and % of migrating cells is calculated by relating the number of the treated cells with the control vehicle. All values are plotted in a dose response curve and the $EC_{50}$ is defined by using nonlinear regression analysis (GraphPad Prism program). Compound BB can be tested for its effect on migration of the BMDMs to C5a or CXCL12.

Example 283: Combination with Temazolamide and Radiation Therapy in the Evaluation of Orthotopic Tumor Growth of GL-261 Cells in C57Bl/6 Mice The purpose of this study is to evaluate the effect of compound provide herein in combination with temazolamide and radiation therapy in orthotopic tumor growth of GL-261 Cells in C57Bl/6 mice.

Sixty (60) 4-6 week old C57Bl/6 male mice are anesthetized with xylazine (5 mg/kg) and ketamine (100 mg/kg) given by intraperitoneal injection and the surgical area of the skull prepped with alcohol and Betadine. A diagonal incision is made from behind the eye to the posterior of the head. The bregma is exposed and the cells implanted 2 mm to the right and 1 mm anterior to the bregma using a small drill to generate the hole followed by a Hamilton Syringe to administer $1 \times 10^5$ cells in a total volume of 10 µL a rate of 1 µL per minute. The skin is sutured and the mice are recovered on a heating pad then returned to their cages. All animals receive post-operative pain medication every 12 hours for 72 hours.

Animals are IVIS imaged 5 days after surgery to determine the total flux per animal for randomization. After randomization, animals in Group 1 are dosed with Vehicle (route/schedule TBD) and animals in Group 2 are dosed with compound provided herein, e.g., Compound BB at 15 mg/kg. Animals in Group 3 are dosed with compound provided herein, e.g., Compound BB, and 3 fractions of radiation of 2 Gy each focused to the area of the brain tumor. Animals in Group 4 receive treatment with 25 mg/kg Temazolamide (i.p.) 5 times per week on a schedule of Day 0, 1, 3, 5 and 6 and are given three (3) 2 Gy fractions of focused radiation to the tumor on Days 0, 2 and 4 in addition to a compound provided herein e.g., Compound BB at 15 mg/kg. Animals in Groups 5 and 6 receive 25 mg/kg Temazolamide (i.p.) 5 times per week on a schedule of Day 0, 1, 3, 5 and 6 and are given three (3) 2 Gy or 4 Gy fractions of focused radiation to the tumor on Days 0, 2 and 4.

For focused radiation, a lead shield containing a thin window cut out of the top is placed over the animal exposing only the top of the head in the area of the tumor. On days where mice are receiving radiation, they are anesthetized using xylazine (5 mg/kg) and ketamine (100 mg/kg) given by intraperitoneal injection. The mice are placed on a 4-mm polymethyl methacrylate plate. Radiation is generated by a 160 kVp (15-ma) X-ray source at a focal distance of 25 cm, hardened with a 0.35 mm Cu filtration system at a rate of 1 Gy/minute. Animals are weighed and monitored for general health daily and assigned a body condition score. Tumors are measured via IVIS imaging twice weekly beginning on Day 5 and total flux is determined for each animal. Experimental details are summarized below in table below:

| Group | Number of Animals | Tumor Cells | Treatment (i.p.) | Dose/ Frequency | Temazolamide (i.p.) Day 0, 1, 3, 5 & 6 | Fractionated Radiation | Radiation Frequency |
|---|---|---|---|---|---|---|---|
| 1 | 10 | GL-261 $1 \times 10^5$ | Vehicle | — | — | None | — |
| 2 | 10 | GL-261 $1 \times 10^5$ | Compound provided herein | QD 15 mg/kg | — | — | — |
| 3 | 10 | GL-261 $1 \times 10^5$ | Compound provided herein | QD 15 mg/kg | TMZ 25 mg/kg | 2 Gy | Day 0, 2 and 4 |
| 4 | 10 | GL-261 $1 \times 10^5$ | Compound provided herein | QD 15 mg/kg | TMZ 25 mg/kg | 4 Gy | Day 0, 2 and 4 |
| 5 | 10 | GL-261 $1 \times 10^5$ | — | — | TMZ 25 mg/kg | 2 Gy | Day 0, 2 and 4 |
| 6 | 10 | GL-261 $1 \times 10^5$ | — | — | TMZ 25 mg/kg | 4 Gy | Day 0, 2 and 4 |

GL-261 cells are cultured at subconfluence in DMEM growth medium containing 10% FBS. Cells are administered via intracranial inoculation by first generating a hole in the skull using a small drill followed by injection of cells 3 mm into the cranium using a Hamilton Syringe at $1 \times 10^5$ cells in a 10 µL volume of serum free media at a rate of 1 µL per minute.

Mice are anesthetized using xylazine (5 mg/kg) and ketamine (100 mg/kg) given by intraperitoneal injection. The mice are placed on a 4-mm polymethyl methacrylate plate. A lead shield containing a thin window cut out of the top is placed over the animal exposing only the area of the cranium to be irradiated. The tumors are directly irradiated with 2 or 4 Gy of radiation on Days 0, 2 and 4. Radiation will be generated by a 160 kVp (15-ma) X-ray source at a focal distance of 25 cm, hardened with a 0.35 mm Cu filtration system at a rate of 1.0 Gy/minute.

Tumor progression is evaluated in life twice weekly by IVIS imaging. Mice are injected via intraperitoneal injection with 0.1 ml/20 g body weight of 15 mg/ml D-luciferin-K$^+$ bioluminescent substrate in PBS. Ten (10) minutes following injection, mice are anesthetized under isoflurane and placed in the IVIS® Lumina at maximum sensitivity for up to 5 minutes exposure to detect bioluminescence with an open emission filter. Saved images are loaded into Living Image® analysis software and color scales matched based on maximum and minimum radiance (photons/second/cm$^2$/steradian). Identical regions of interest are drawn around each animal and total flux is determined in terms of photons/second for each region of interest.

In addition to measuring tumors in the animals in-life, animals are assigned a body condition score 3 times each week. Animals with a body condition of lower than BC2 is sacrificed. The conditions are categorized as follows:

BC5: The animal is obese, smooth and bulky. One is unable to identify its bone structure under the flesh and fat. Often mice in this condition cannot groom well and hair coat may appear oily and stained.

BC4: The animal is over-conditioned and vertebrae are only palpable with firm pressure.

BC3: The animal is well-conditioned. Vertebrae and pelvis are palpable.

BC2: The animal is under-conditioned. Segmentation of the vertebral column is evident and pelvis is palpable.

BC1: The animal is emaciated, skeletal structure very prominent with little flesh cover. Vertebrae are distinctly segmented.

All animals are weighed daily throughout this study. Group weight change is expressed as a mean percent weight change. Animal deaths in this model generally occur as a consequence of anesthesia overdose or drug toxicity. Animals are monitored on a daily basis and those exhibiting weight loss greater than 30%, are unable to ambulate, achieve food and water, and/or appear moribund are euthanized. If the tumors appear to be ulcerated, the animal is euthanized. Any adverse effects or unanticipated deaths are reported to the veterinarian immediately.

Statistical differences between treatment groups are determined using appropriate statistical techniques. A one-way ANOVA or ANOVA on ranks are used to evaluate the area-under the curve for weight gain and tumor radiance.

Example 284: Role of T Cells in Tumor Growth Suppression

The purpose is to study the role of T cells on the tumor growth suppression after treatment with a compound provided herein (e.g., Compound BB).

Method A: Tumors cells are implanted into RAG-/-mice. These mice are defective in their ability to produced either T or B cells and cannot achieve immunological memory. Tumor cells are implanted into WT or RAG-/-mice on the appropriate strain background (for CT26 colon tumor cells, BALB/C). The tumor bearing animals are randomized into vehicle and those treated with a compound provided herein (e.g., Compound BB) groups for both WT and RAG-/-mice. Efficacy is evaluated by comparing tumor growth kinetics in the WT compared to RAG-/-mice.

Method B: This method uses antibodies against the T cell markers CD4 and CD8 to deplete T cell subsets. LLC-Brie, CT26 colon cancer or MC38 cells is implanted into the appropriate host strain of mice. Mice with established tumors will be randomized into treatment groups as described below.

CD4 and CD8 Depletion Antibodies aCD4/CD8 Isotype Control: Rat IgG2b Isotype (BioXcell Clone: LTF-2 Cat: BE0090-R005 Lot: TBFO)

aCD4: Diluted to 1 mg/ml in Endotoxin-Free PBS (BioXcell Clone: GK1.5 Cat: BE0003-1 Lot: TBFO)

aCD8: Diluted to 1 mg/ml in Endotoxin-Free PBS (BioXcell Clone: YTS 169.4 Cat: BE0117 Lot: TBFO)

Dosing Regimen

αCD4/aCD8 therapies will be delivered i.p. every 3 days (100 ug each)

Study Design

Vehicle; Vehicle+anti CD4; Vehicle+anti CD8; Vehicle+anti CD4/CD8;

compound provided herein (e.g., Compound BB);

compound provided herein (e.g., Compound BB)+anti CD4;

compound provided herein (e.g., Compound BB)+anti CD8;

compound provided herein (e.g., Compound BB)+anti CD4/8.

Example 285: Osteolytic Bone Cancer in Bone Cancer Model

To evaluate the effect of compound provided herein (e.g., Compound BB) on osteoclast development and whether it would prevent bone damage in the NCTC-2472 model. The NCTC-2472 tumor cell line was propagated in cell culture and harvested while in logarithmic growth. 100,000 cells were implanted directly into the medullary cavity of the distal femur on study day 0.

On study day 0 the mice was weighed and randomized by body weight into treatment groups. Mice were anesthetized with isoflurane and right knee arthrotomy performed. Cells were injected in 20 ul with a 29 gage needle. The entry hole in the bone was filled with bone wax to prevent tumor cell extravasation.

On Day 2 through 22 drug treatment was done in the following groups: Vehicle, Compound BB (15 mg/kg), and Resendronate as a control. Weight was taken twice weekly. On study Day 22 the mice was exsanguinated under isoflurane and femur samples were taken for X ray and histopathology analysis. The relevant endpoints include bone erosion and abnormal bone formation.

The present invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims. Various publications, patents and patent applications are cited herein, the disclosures of which are incorporated by reference in their entireties.

What is claimed is:

1. A method of treating a solid tumor in a subject, comprising administering to the subject a therapeutically effective amount a compound of the formula:

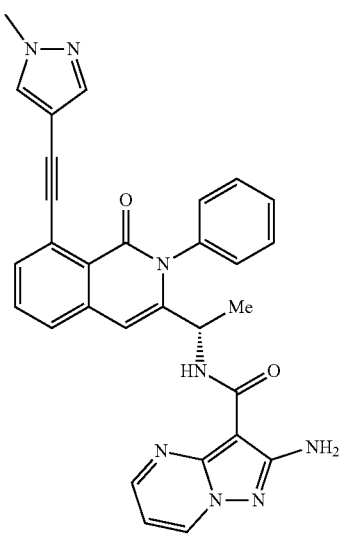 [SMILES: C[C@H](NC(=O)c1c(N)nn2cccnc12)c1cc2cccc(C#Cc3cnn(C)c3)c2c(=O)n1-c1ccccc1]

or a pharmaceutically acceptable salt thereof, in combination with an anti-PD-L1 antibody, wherein the solid tumor is breast cancer or colon cancer.

2. The method of claim 1, wherein the anti-PD-L1 antibody is YW243.55.S70, MPDL3280A, MSB0010718C, MDX-1105, or MEDI-4736.

3. The method of claim 2, wherein the anti-PD-L1 antibody is MPDL3280A.

4. The method of claim 1, wherein the solid tumor is colon cancer.

5. The method of claim 1, wherein the solid tumor is breast cancer.

6. The method of claim 5, wherein the breast cancer is metastatic.

7. The method of claim 5, further comprising administering to the subject paclitaxel.

8. The method of claim 5, further comprising administering to the subject nanoparticle albumin-bound paclitaxel.

9. The method of claim 1, wherein the compound is administered at a dose of about 20, about 30, or about 40 mg once daily.

10. The method of claim 1, wherein the subject has a high number of MDSC, compared to a reference value.

11. A method of treating triple negative breast cancer in a subject, comprising administering to the subject a therapeutically effective amount a compound of the formula:

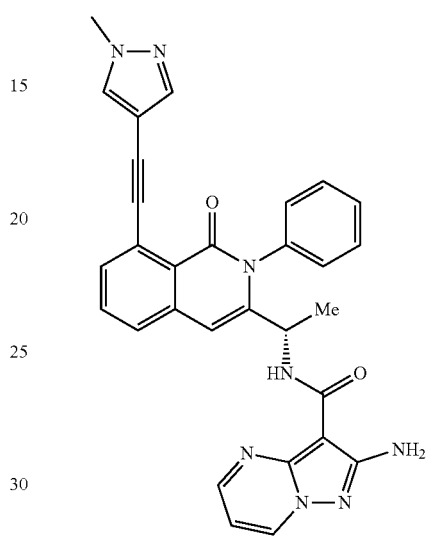

or a pharmaceutically acceptable salt thereof, in combination with MPDL3280A and nanoparticle albumin-bound paclitaxel.

* * * * *